US011597927B2

(12) United States Patent
Vargeese et al.

(10) Patent No.: US 11,597,927 B2
(45) Date of Patent: Mar. 7, 2023

(54) OLIGONUCLEOTIDE COMPOSITIONS AND METHODS OF USE THEREOF

(71) Applicant: WAVE LIFE SCIENCES LTD., Singapore (SG)

(72) Inventors: Chandra Vargeese, Schwenksville, PA (US); Naoki Iwamoto, Brighton, MA (US); David Charles Donnell Butler, Medford, MA (US); Subramanian Marappan, Acton, MA (US); Genliang Lu, Winchester, MA (US); Jason Jingxin Zhang, Walpole, MA (US); Vinod Vathipadiekal, Stoneham, MA (US); Luciano Henrique Apponi, Chelsea, MA (US); Hanna Maria Wisniewska, Providence, RI (US); Xiayun Cheng, Old Saybrook, CT (US); Young Jin Cho, Belmont, MA (US)

(73) Assignee: WAVE LIFE SCIENCES LTD., Singapore (SG)

( * ) Notice: Subject to any disclaimer, the term of this patent is extended or adjusted under 35 U.S.C. 154(b) by 127 days.

(21) Appl. No.: 16/618,001

(22) PCT Filed: Jun. 1, 2018

(86) PCT No.: PCT/US2018/035721
§ 371 (c)(1),
(2) Date: Nov. 27, 2019

(87) PCT Pub. No.: WO2018/223081
PCT Pub. Date: Dec. 6, 2018

(65) Prior Publication Data
US 2020/0190515 A1    Jun. 18, 2020

Related U.S. Application Data

(60) Provisional application No. 62/670,698, filed on May 11, 2018, provisional application No. 62/514,769, filed on Jun. 2, 2017.

(51) Int. Cl.
| | | |
|---|---|---|
| C12N 15/113 | (2010.01) | |
| A61K 47/54 | (2017.01) | |
| A61K 47/55 | (2017.01) | |
| A61K 45/06 | (2006.01) | |

(52) U.S. Cl.
CPC .......... *C12N 15/113* (2013.01); *A61K 45/06* (2013.01); *A61K 47/54* (2017.08); *A61K 47/545* (2017.08); *A61K 47/548* (2017.08); *A61K 47/549* (2017.08); *A61K 47/55* (2017.08); *C12N 2310/14* (2013.01); *C12N 2310/315* (2013.01); *C12N 2310/32* (2013.01); *C12N 2310/33* (2013.01); *C12N 2310/352* (2013.01)

(58) Field of Classification Search
None
See application file for complete search history.

(56) References Cited

U.S. PATENT DOCUMENTS

| | | |
|---|---|---|
| 5,270,468 A | 12/1993 | Khanna et al. |
| 8,470,987 B2 | 6/2013 | Wada et al. |
| 8,729,036 B2 | 5/2014 | Zamore et al. |
| 8,822,671 B2 | 9/2014 | Shimizu et al. |
| 8,859,755 B2 | 10/2014 | Wada et al. |
| 8,927,513 B2 | 1/2015 | Manoharan et al. |
| 9,394,333 B2 | 7/2016 | Wada et al. |
| 9,476,044 B2 | 10/2016 | Tuschl et al. |
| 9,598,458 B2 | 3/2017 | Shimizu et al. |
| 9,605,019 B2 | 3/2017 | Verdine et al. |
| 9,617,547 B2 | 4/2017 | Gemba |
| 9,695,211 B2 | 7/2017 | Wada et al. |

(Continued)

FOREIGN PATENT DOCUMENTS

| | | |
|---|---|---|
| WO | WO-2003/002587 A2 | 1/2003 |
| WO | WO-2004/007718 A2 | 1/2004 |

(Continued)

OTHER PUBLICATIONS

U.S. Appl. No. 16/618,003, filed Nov. 27, 2019, Vargeese et al.
U.S. Appl. No. 16/624,896, filed Dec. 19, 2019, Butler et al.
U.S. Appl. No. 16/636,900, filed Feb. 5, 2020, Dodart et al.
U.S. Appl. No. 16/636,902, filed Feb. 5, 2020, Vargeese et al.
U.S. Appl. No. 16/648,146, filed Mar. 17, 2020, Bowman et al.
U.S. Appl. No. 16/717,986, filed Dec. 17, 2019, Butler et al.
U.S. Appl. No. 16/755,544, filed Apr. 10, 2020, Zhang et al.
U.S. Appl. No. 16/782,021, filed Feb. 4, 2020, Frank-Kamenetsky et al.

(Continued)

*Primary Examiner* — Tracy Vivlemore
(74) *Attorney, Agent, or Firm* — Choate, Hall & Stewart LLP; Brenda Herschbach Jarrell; Xiaodong Li

(57) ABSTRACT

Among other things, the present disclosure provides designed PNPLA3 oligonucleotides, compositions, and methods thereof. In some embodiments, provided oligonucleotide compositions provide improved single-stranded RNA interference and/or RNase H-mediated knockdown. Among other things, the present disclosure encompasses the recognition that structural elements of oligonucleotides, such as base sequence, chemical modifications (e.g., modifications of sugar, base, and/or internucleotidic linkages) or N patterns thereof, conjugation with additional chemical moieties, and/or stereochemistry [e.g., stereochemistry of backbone chiral centers (chiral internucleotidic linkages)], and/or patterns thereof, can have significant impact on oligonucleotide properties and activities, e.g., RNA interference (RNAi) activity, stability, delivery, etc. In some embodiments, the present disclosure provides methods for treatment of diseases using provided oligonucleotide compositions, for example, in RNA interference and/or RNase H-mediated knockdown.

15 Claims, 15 Drawing Sheets
Specification includes a Sequence Listing.

(56) References Cited

U.S. PATENT DOCUMENTS

| | | | |
|---|---|---|---|
| 9,744,183 B2 | 8/2017 | Verdine et al. | |
| 9,982,257 B2 | 5/2018 | Butler et al. | |
| 10,144,933 B2 | 12/2018 | Gemba et al. | |
| 10,149,905 B2 | 12/2018 | Gemba et al. | |
| 10,160,969 B2 | 12/2018 | Meena et al. | |
| 10,167,309 B2 | 1/2019 | Shimizu et al. | |
| 10,280,192 B2 | 5/2019 | Verdine et al. | |
| 10,307,434 B2 | 6/2019 | Verdine et al. | |
| 10,322,173 B2 | 6/2019 | Gemba et al. | |
| 10,329,318 B2 | 6/2019 | Wada et al. | |
| 10,428,019 B2 | 10/2019 | Wada et al. | |
| 10,450,568 B2 | 10/2019 | Butler et al. | |
| 10,479,995 B2 | 11/2019 | Vargeese et al. | |
| 10,590,413 B2 | 3/2020 | Butler et al. | |
| 10,696,711 B2 | 6/2020 | Shimizu et al. | |
| 10,724,035 B2 | 7/2020 | Vargeese et al. | |
| 10,815,482 B2 | 10/2020 | Meena et al. | |
| 11,013,757 B2 | 5/2021 | Zhang et al. | |
| 11,034,958 B2 | 6/2021 | Fitzgerald et al. | |
| 11,136,346 B2 | 10/2021 | Shimizu et al. | |
| 11,208,430 B2 | 12/2021 | Stetsenko et al. | |
| 2008/0200409 A1 | 8/2008 | Wilson et al. | |
| 2009/0023675 A1 | 1/2009 | McSwiggen et al. | |
| 2013/0178612 A1 | 7/2013 | Wada et al. | |
| 2014/0323709 A1 | 10/2014 | Obika et al. | |
| 2015/0211006 A1* | 7/2015 | Butler | C12N 15/11 514/44 A |
| 2016/0331835 A1 | 11/2016 | Gemba et al. | |
| 2016/0331836 A1 | 11/2016 | Gemba et al. | |
| 2016/0333349 A1 | 11/2016 | Gemba et al. | |
| 2016/0355808 A1 | 12/2016 | Khvorova et al. | |
| 2017/0340661 A1* | 11/2017 | Fitzgerald | C12P 19/34 |
| 2018/0216107 A1 | 8/2018 | Frank-Kamenetsky et al. | |
| 2019/0077817 A1 | 3/2019 | Butler et al. | |
| 2019/0106696 A1 | 4/2019 | Meena et al. | |
| 2019/0127733 A1 | 5/2019 | Butler et al. | |
| 2019/0177357 A1 | 6/2019 | Shimizu et al. | |
| 2019/0209604 A1 | 7/2019 | Zhang et al. | |
| 2019/0249173 A1 | 8/2019 | Vargeese et al. | |
| 2019/0264267 A1 | 8/2019 | Yang et al. | |
| 2019/0375774 A1 | 12/2019 | Butler et al. | |
| 2019/0390197 A1 | 12/2019 | Butler et al. | |
| 2020/0056173 A1 | 2/2020 | Vargeese et al. | |
| 2020/0157545 A1 | 5/2020 | Vargeese et al. | |
| 2020/0231620 A1 | 7/2020 | Bowman et al. | |
| 2020/0299692 A1 | 9/2020 | Frank-Kamenetsky et al. | |
| 2020/0362337 A1 | 11/2020 | Dodart et al. | |
| 2020/0385420 A1 | 12/2020 | Shimizu et al. | |
| 2021/0032620 A1 | 2/2021 | Vargeese et al. | |
| 2021/0115444 A1 | 4/2021 | Meena et al. | |
| 2021/0130821 A1 | 5/2021 | Butler et al. | |
| 2021/0198305 A1 | 7/2021 | Vargeese et al. | |
| 2021/0228615 A1 | 7/2021 | Zhang et al. | |
| 2021/0254062 A1 | 8/2021 | Zhang et al. | |
| 2022/0098585 A1 | 3/2022 | Brown et al. | |
| 2022/0127301 A1 | 4/2022 | Shimizu et al. | |
| 2022/0145300 A1 | 5/2022 | Liu et al. | |
| 2022/0162598 A1 | 5/2022 | Vargeese et al. | |
| 2022/0186217 A1 | 6/2022 | Zhang et al. | |
| 2022/0195429 A1 | 6/2022 | Vargeese et al. | |

FOREIGN PATENT DOCUMENTS

| | | | |
|---|---|---|---|
| WO | WO-2005/014609 A2 | 2/2005 | |
| WO | WO-2005/023828 A1 | 3/2005 | |
| WO | WO-2005/028494 A1 | 3/2005 | |
| WO | WO-2005/070859 A1 | 8/2005 | |
| WO | WO-2005/085272 A1 | 9/2005 | |
| WO | WO-2005/092909 A1 | 10/2005 | |
| WO | WO-2006/023880 A2 | 3/2006 | |
| WO | WO-2007/059816 A1 | 5/2007 | |
| WO | WO-2008/128686 A1 | 10/2008 | |
| WO | WO-2010/048549 A2 | 4/2010 | |
| WO | WO-2010/048585 A2 | 4/2010 | |
| WO | WO-2010/064146 A2 | 6/2010 | |
| WO | WO-2011/005761 A1 | 1/2011 | |
| WO | WO-2011/109427 A2 | 9/2011 | |
| WO | WO-2011/139911 A2 | 11/2011 | |
| WO | WO-2012/039448 A1 | 3/2012 | |
| WO | WO-2012037254 A1 * | 3/2012 | ............ A61P 31/20 |
| WO | WO-2013/009735 A1 | 1/2013 | |
| WO | WO-2013/012758 A1 | 1/2013 | |
| WO | WO-2014/010250 A1 | 1/2014 | |
| WO | WO-2014/012081 A2 | 1/2014 | |
| WO | WO-2015/107425 A2 | 7/2015 | |
| WO | WO-2015/108046 A1 | 7/2015 | |
| WO | WO-2015/108047 A1 | 7/2015 | |
| WO | WO-2015/108048 A1 | 7/2015 | |
| WO | WO-2016/130806 A2 | 8/2016 | |
| WO | WO-2017/015555 A1 | 1/2017 | |
| WO | WO-2017/015575 A1 | 1/2017 | |
| WO | WO-2017/048620 A1 | 3/2017 | |
| WO | WO-2017/062862 A2 | 4/2017 | |
| WO | WO-2017/160741 A1 | 9/2017 | |
| WO | WO-2017/192664 A1 | 11/2017 | |
| WO | WO-2017/192679 A1 | 11/2017 | |
| WO | WO-2017/205880 A1 | 11/2017 | |
| WO | WO-2017/210647 A1 | 12/2017 | |
| WO | WO-2018/022473 A1 | 2/2018 | |
| WO | WO-2018/067973 A1 | 4/2018 | |
| WO | WO-2018/098264 A1 | 5/2018 | |
| WO | WO-2018/223056 A1 | 12/2018 | |
| WO | WO-2018/223073 A1 | 12/2018 | |
| WO | WO-2018/223081 A1 | 12/2018 | |
| WO | WO-2018/237194 A1 | 12/2018 | |
| WO | WO-2019/002237 A1 | 1/2019 | |
| WO | WO-2019/032607 A1 | 2/2019 | |
| WO | WO-2019/032612 A1 | 2/2019 | |
| WO | WO-2019/055951 A1 | 3/2019 | |
| WO | WO-2019/071028 A1 | 4/2019 | |
| WO | WO-2019/075357 A1 | 4/2019 | |
| WO | WO-2019/118638 A2 | 6/2019 | |
| WO | WO-2019/200185 A1 | 10/2019 | |
| WO | WO-2019/217784 A1 | 11/2019 | |
| WO | WO-2020/061200 A1 | 3/2020 | |
| WO | WO-2020/118246 A1 | 6/2020 | |
| WO | WO-2020/160336 A1 | 8/2020 | |
| WO | WO-2020/191252 A1 | 9/2020 | |
| WO | WO-2020/196662 A1 | 10/2020 | |
| WO | WO-2020/219981 A2 | 10/2020 | |
| WO | WO-2020/219983 A2 | 10/2020 | |
| WO | WO-2020/227691 A2 | 11/2020 | |
| WO | WO-2021/071788 A2 | 4/2021 | |
| WO | WO-2021/071858 A1 | 4/2021 | |
| WO | WO-2021/126734 A1 | 6/2021 | |
| WO | WO-2021/178237 A2 | 9/2021 | |
| WO | WO-2021/195467 A2 | 9/2021 | |
| WO | WO-2021/237223 A1 | 11/2021 | |
| WO | WO-2022/046667 A1 | 3/2022 | |
| WO | WO-2022/046723 A1 | 3/2022 | |
| WO | WO-2022/099159 A1 | 5/2022 | |

OTHER PUBLICATIONS

U.S. Appl. No. 16/869,126, filed May 7, 2020, Vargeese et al.
U.S. Appl. No. 16/878,461, filed May 19, 2020, Shimizu et al.
International Search Report for PCT/US2018/035721, 5 pages (dated Oct. 18, 2018).
Written Opinion for PCT/US2018/035721, 10 pages (dated Oct. 18, 2018).
U.S. Appl. No. 17/442,663, filed Sep. 24, 2021, Yokota et al.
U.S. Appl. No. 17/766,677, filed Apr. 5, 2022, Monlan et al.
U.S. Appl. No. 17/766,680, filed Apr. 5, 2022, Liu et al.
Kandasamy, P. et al., Control of backbone chemistry and chirality boost oligonucleotide splice switching activity, Nucleic Acids Research, 50(10):5443-5466 (2022).
Koch, T., LNA Therapeutics—update, Navigate the phosphorothioate diastereoisomer space, Roche pRED RNA Therapeutics Research, EuroTIDES, PostillionConventionCenter, Amsterdam, Netherlands (Nov. 6-9, 2018).
Stetsenko, D.A. and Pyshnyi, D.V., Ex Siberia Semper Novi: Siberia Always Brings Us Something New, Phosphoryl Guanidines: New

(56) References Cited

OTHER PUBLICATIONS

Chemical Analogues of Nucleic Acids, Science First Hand, N2(41): 2 pages (Aug. 30, 2015). URL: https://scfh.ru/en/papers/phosphoryl-guanidines-new-chemical-analogues-of-nucleic-acids-/.
Vergeese, C., Exploring new oligonucleotide backbone chemistries and their deployment to improve the properties of stereopure oligonucleotides, Wave Life Sciences, presented at TIDES USA on Sep. 22, 2021.
WAVE Life Sciences, Analyst & Investor Research Webcast (Aug. 2020), 64 pages.
U.S. Appl. No. 17/046,752, filed Oct. 9, 2020, Zhang et al.
U.S. Appl. No. 17/054,452, filed Nov. 10, 2020, Zhang et al.
U.S. Appl. No. 17/177,111, filed Feb. 16, 2021, Zhang et al.
U.S. Appl. No. 17/311,285, filed Jun. 4, 2021, Zhang et al.
U.S. Appl. No. 17/375,658, filed Jul. 14, 2021, Vargeese et al.
U.S. Appl. No. 17/426,511, filed Jul. 28, 2021, Brown et al.
U.S. Appl. No. 17/439,755, filed Sep. 15, 2021, Kandasamy et al.
U.S. Appl. No. 17/465,238, filed Feb. 9, 2021, Shimizu et al.
U.S. Appl. No. 17/605,997, filed Oct. 22, 2021, Byrne et al.
U.S. Appl. No. 17/605,998, filed Oct. 22, 2021, Byrne et al.
U.S. Appl. No. 17/609,330, filed Nov. 5, 2021, Liu et al.
Anderson, B. A. et al., Towards next generation antisense oligonucleotides: mesylphosphoramidate modification improves therapeutic index and duration of effect of gapmer antisense oligonucleotides, Nucl. Acids. Res., 49(16):9026-9041 (2021).
Belikova, A. M., et al., Synthesis of Ribonucleosides and Diribonucleoside phosphates containing 2-chloro-ethylamine and Nitrogen Mustard Residues, Terahedron Letters, 37:3557-3562 (1967).
Jäger, A. et al., Oligonucleotide N-alkylphosphoramidates: synthesis and binding to polynucleotides, Biochemistry, 27(19):7237-46 (1988).
Kozarski, M. et al., 7-Methylguanosine monophosphate analogues with 5'-(1,2,3-triazoyl) moiety: Synthesis and evaluation as the inhibitors of cNIIIB nucleotidase, Bioorg. Med. Chem., 26(1):191-199 (2018).
Kurata, C. et al., Characterization of high molecular weight impurities in synthetic phosphorothioate oligonucleotides, Bioorg. Med. Chem. Lett., 16:607-614 (2006).
Lebedeva, N. et al., Design of a New Fluorescent Oligonucleotide-Based Assay for a Highly Specific Real-Time Detection of Apurinic/Apyrimidinic Site Cleavage by Tyrosyl-DNA Phosphodiesterase 1, Bioconjugate Chem., 26(10):2046-2053 (2015).
Lee, M. Y. et al., Synthesis and SAR of sulfonyl- and phosphoryl amidine compounds as anti-resorptive agents, Bioorg. Med. Chem. Lett., 20:541-545 (2010).
Ohkubo, A. et al., A new strategy for the synthesis of oligodeoxynucleotides directed towards perfect O-selective internucleotidic bond formation without base protection, Tetrahedron Letters, 45:363-366 (2004).
Ohkubo, A. et al., O-Selectivity and Utility of Phosphorylation Mediated by Phosphite Triester Intermediates in the N-Unprotected Phosphoramidite Method, J. Am. Chem., 126:10884-10896 (2004).
Prakash, T. P. et al., Identification of metabolically stable 5'-phosphate analogs that support single-stranded siRNA activity, Nucleic Acids Research, 43(6):2993-3011 (2015).
PubChem SID: 226629328, 9 pages, date available: Feb. 2, 2015.
PubChem SID: 316086382, 8 pages, date available: Aug. 2, 2016, date modified: Jun. 20, 2019.
PubChem SID: 355354479, 7 pages, date available: Apr. 8, 2018.
PubChem SID: 368967557, 7 pages, date available: May 25, 2018.
Rigo, F. et al., Synthetic oligonucleotides recruit ILF2/3 to RNA transcripts to modulate splicing, Nat. Chem. Bio., 8:555-562 (2012).
Sekine, M. et al., Proton-Block Strategy for the Synthesis of Oligodeoxynucleotides without Base Protection, Capping Reaction, and P—N Bond Cleavage Reaction, J. Org. Chem., 68:5478-5492 (2003).
Shen, W. et al., Acute hepatotoxicity of 2' fluoro-modified 5-10-5 gapmer phosphorothioate oligonucleotides in mice correlates with intracellular protein binding and the loss of DBHS proteins, Nucl. Acids Res., 46(5):2204-2217 (2018).
Skaric, V. and Raza, Z., The Homologation of 1-(2,3-Dihydroxypropyl)- into 1-(2,4-Dihydroxybutyl)-thymine, Croatica Chemica Acta, 52(1):51-59 (1979).
Skaric, V. et al., Aliphatic Thymidine and Deoxyuridine Analogs, Croatica Chemica Acta, 52(3):281-292 (1979).
Skvortsova, Y. V., et al., A new Antisense Phosphoryl Guanidine Oligo-2'-O-Methylribonucleotide Penetrates Into Intracellular Mycobacteria and Suppresses Target Gene Expression, 10:1-9 (2019).
Stetsenko, D. A., Phosphoryl Guanidines: New Chemical Analogues of Nucleic Acids, 4 pages (Aug. 2015), <https://scfh.ru/en/papers/phosphoryl-guanidines-new-chemical-analogues-of-nucleic-acids-/>. Retrieved Sep. 15, 2020.
WAVE Life Sciences Press Release, WAVE Life Sciences Announces Discontinuation of Suvodirsen Development for Duchenne Muscular Dystrophy, 2 pages (Dec. 16, 2019).

\* cited by examiner

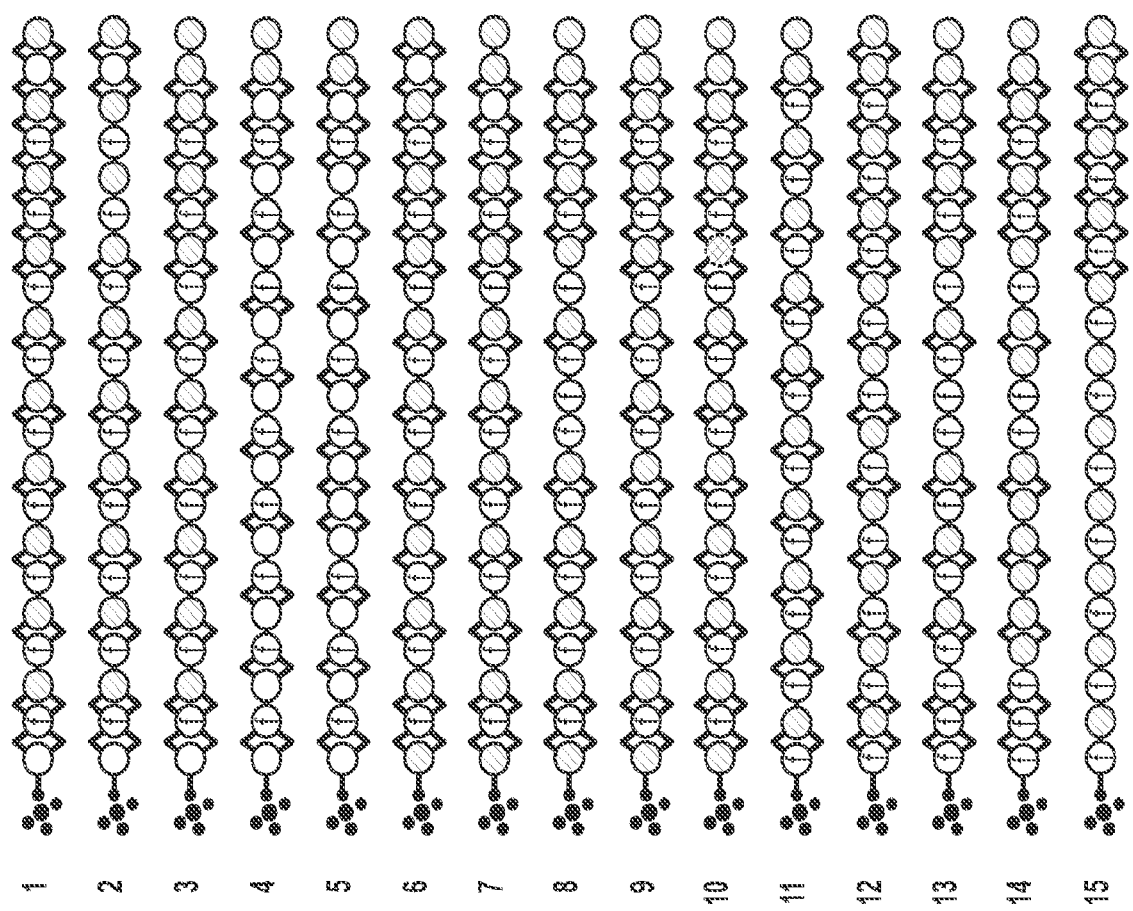

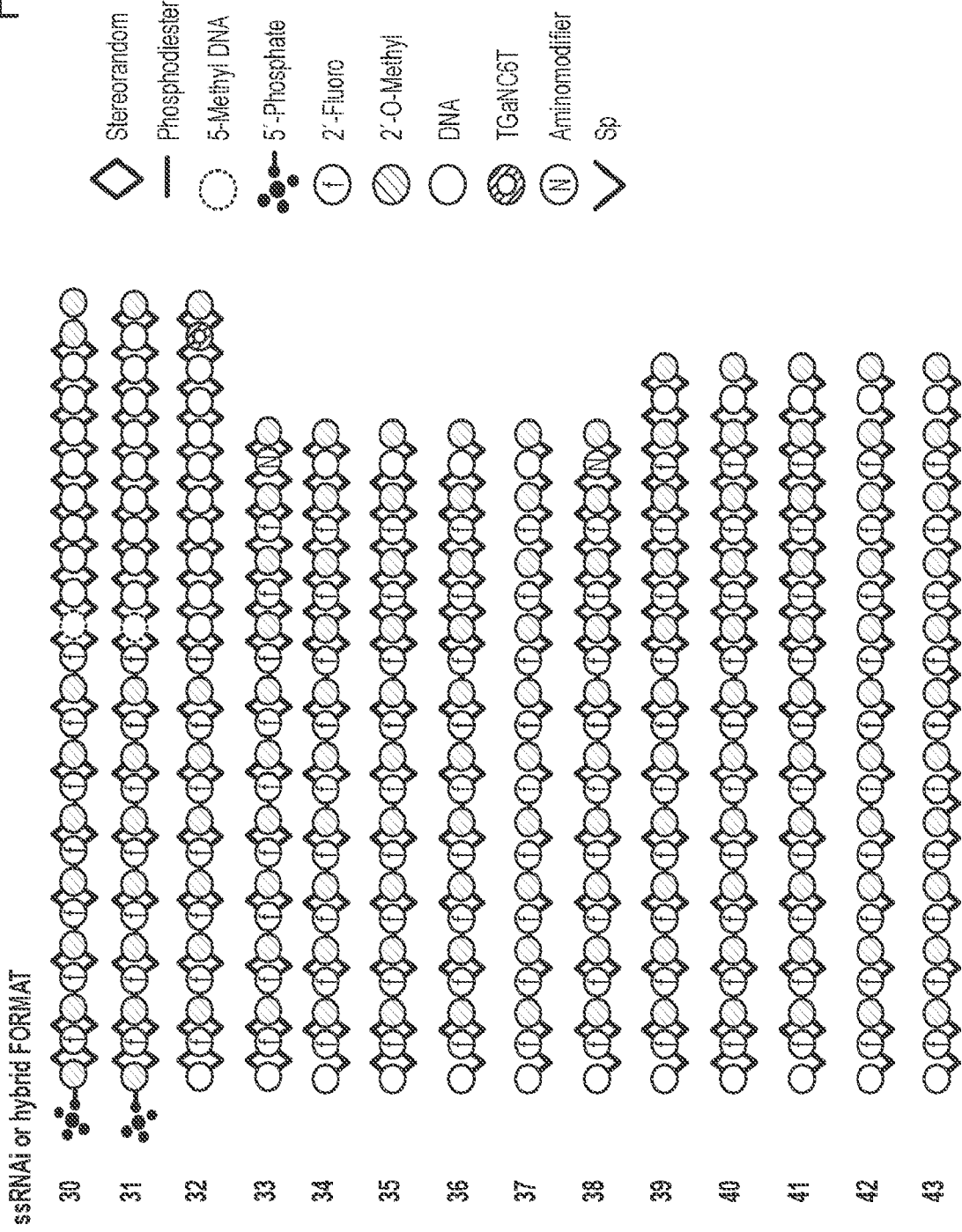

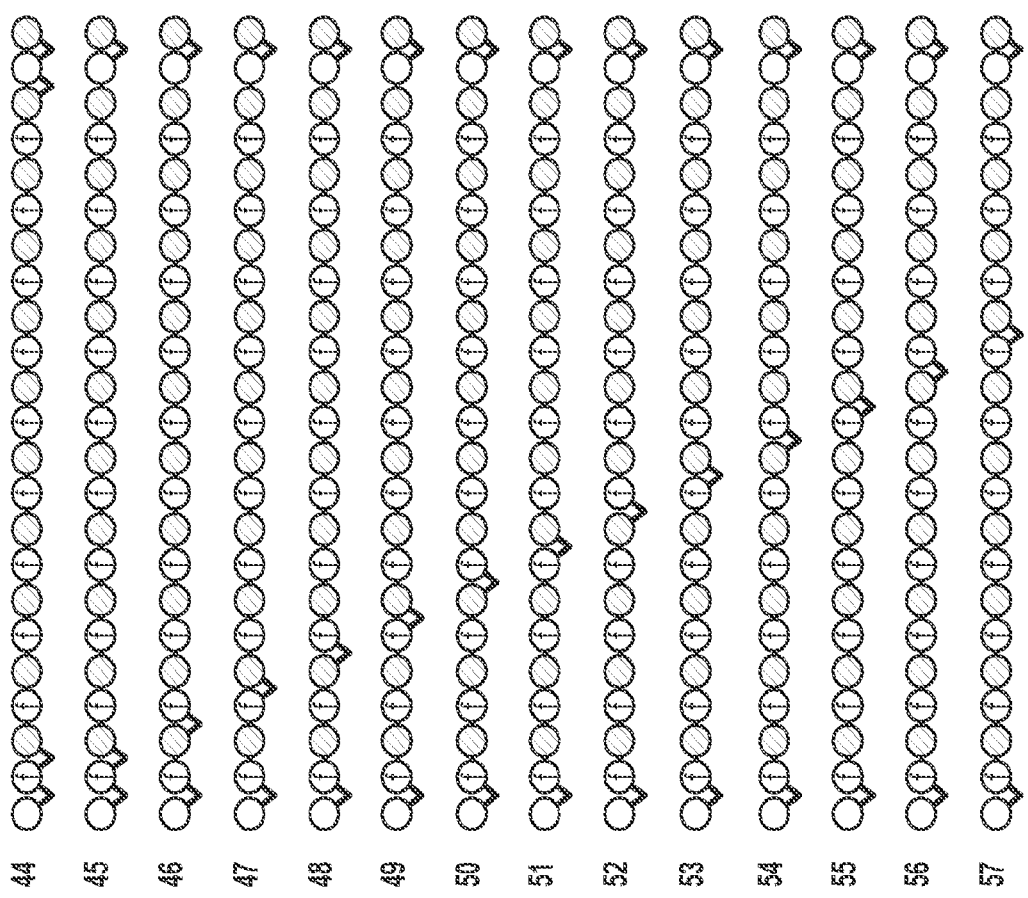

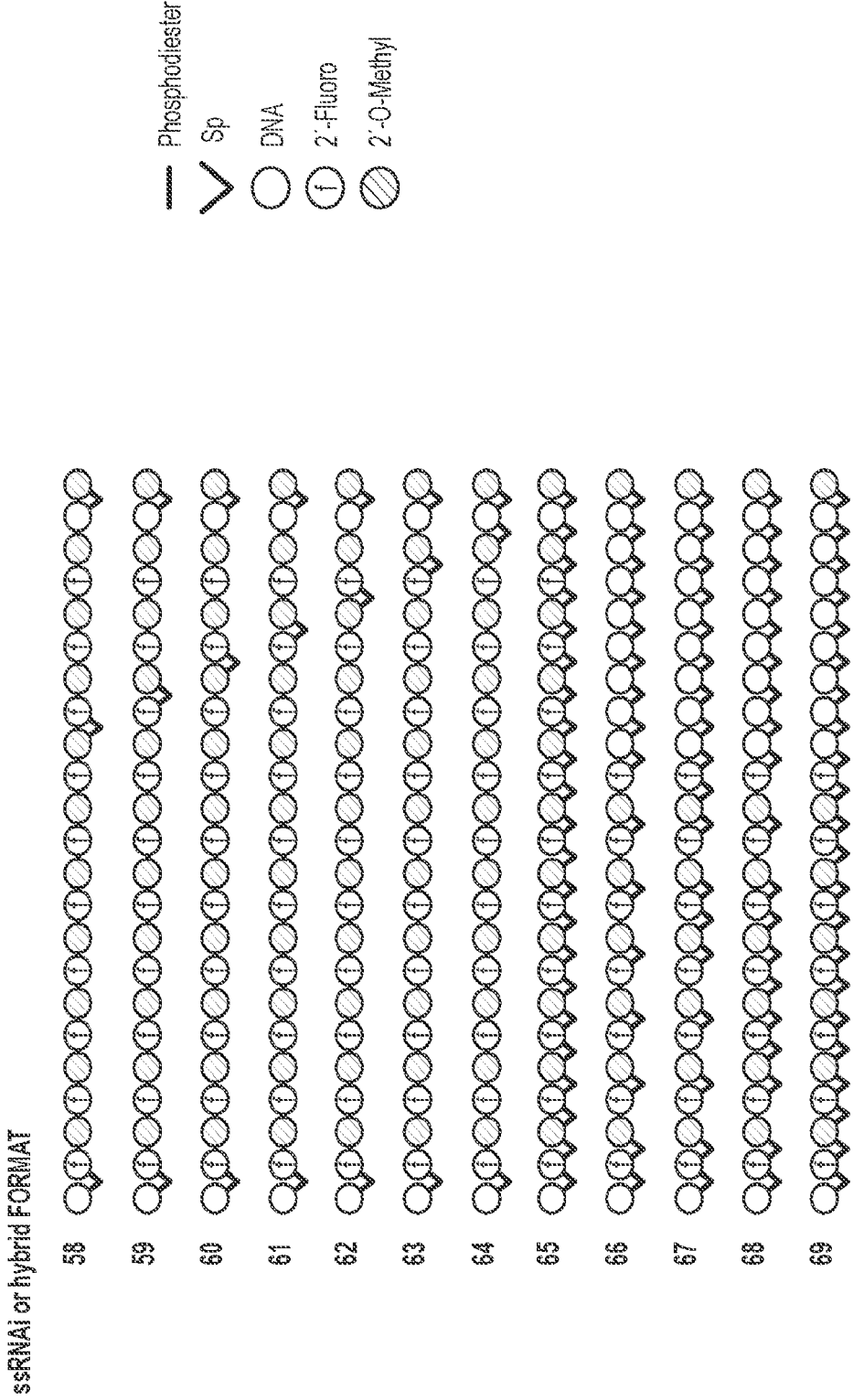

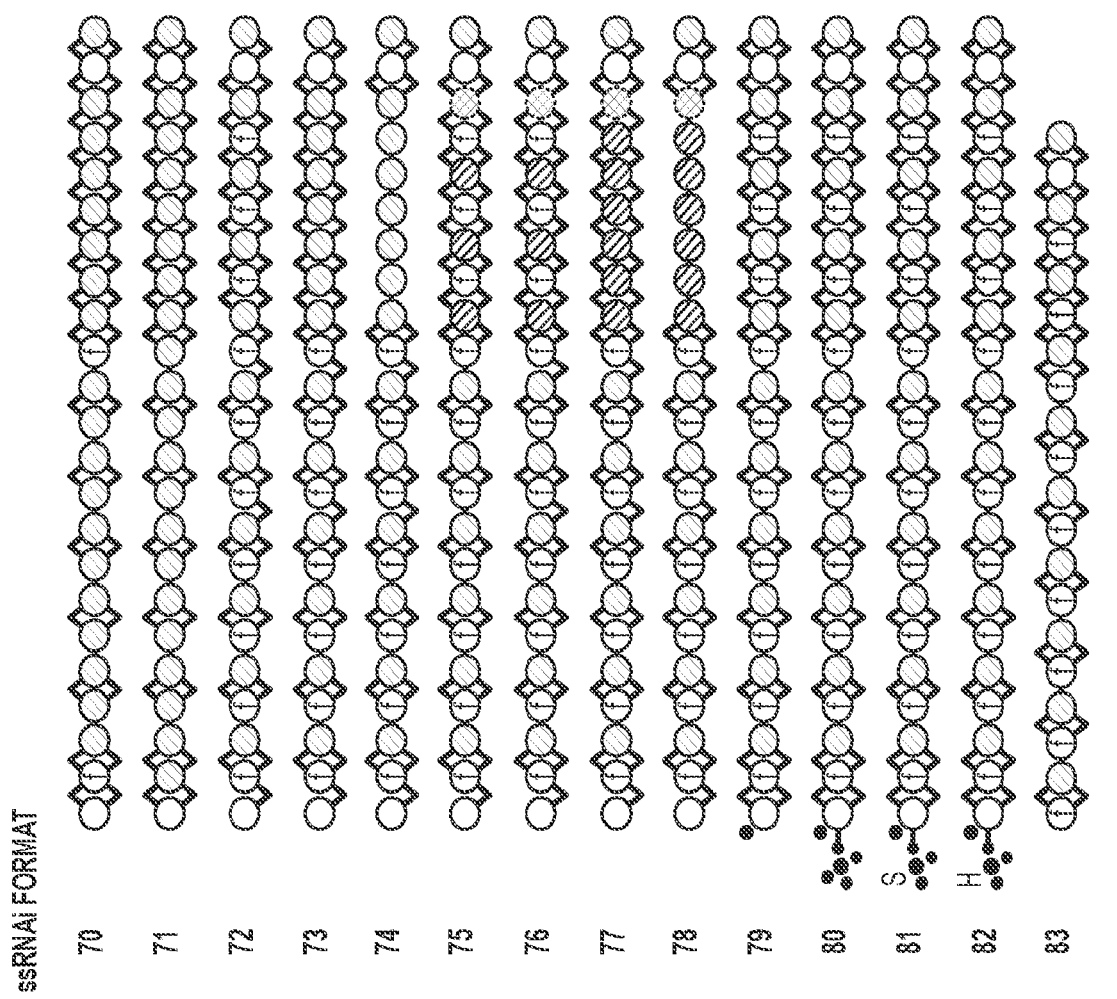

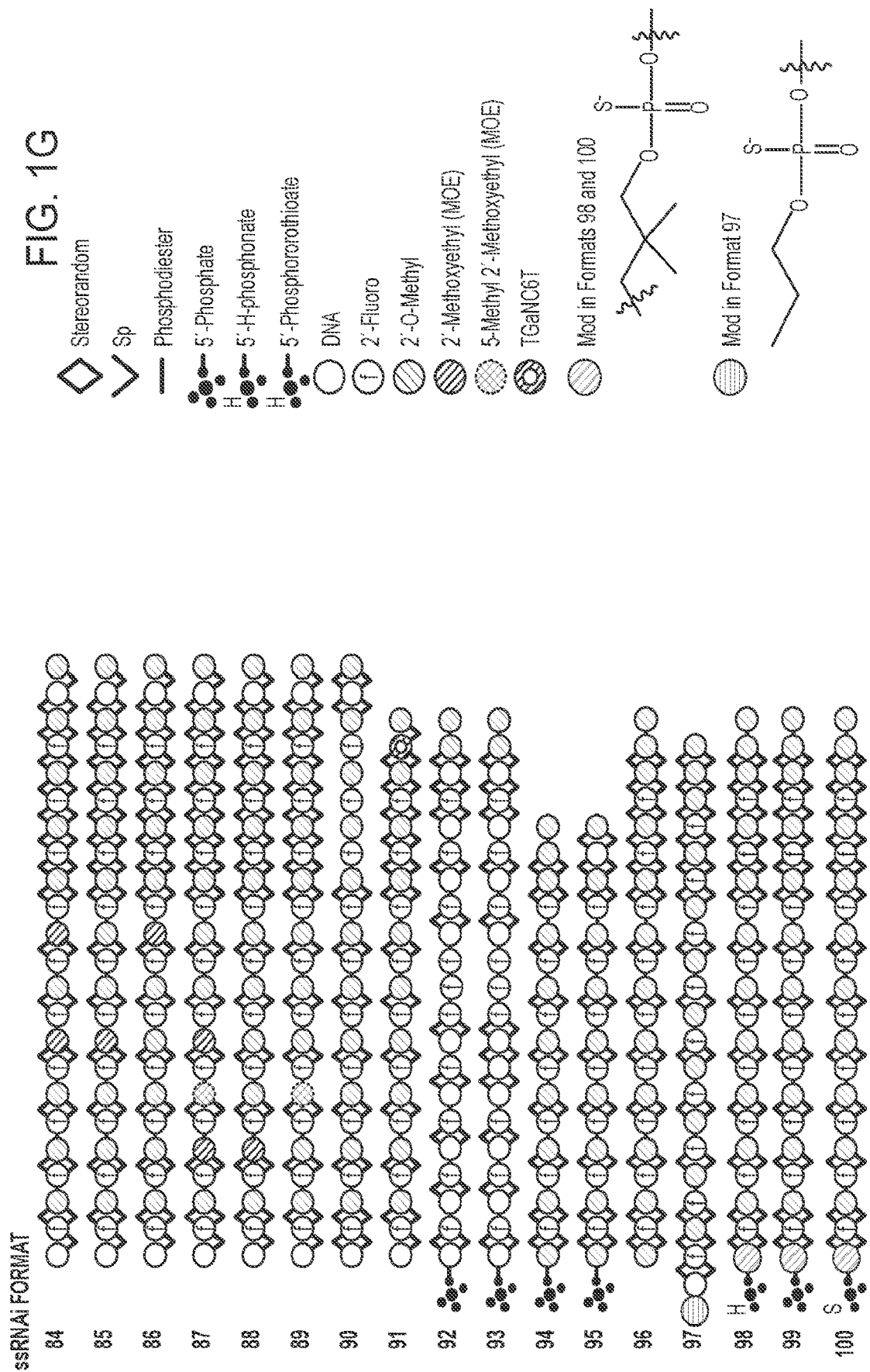

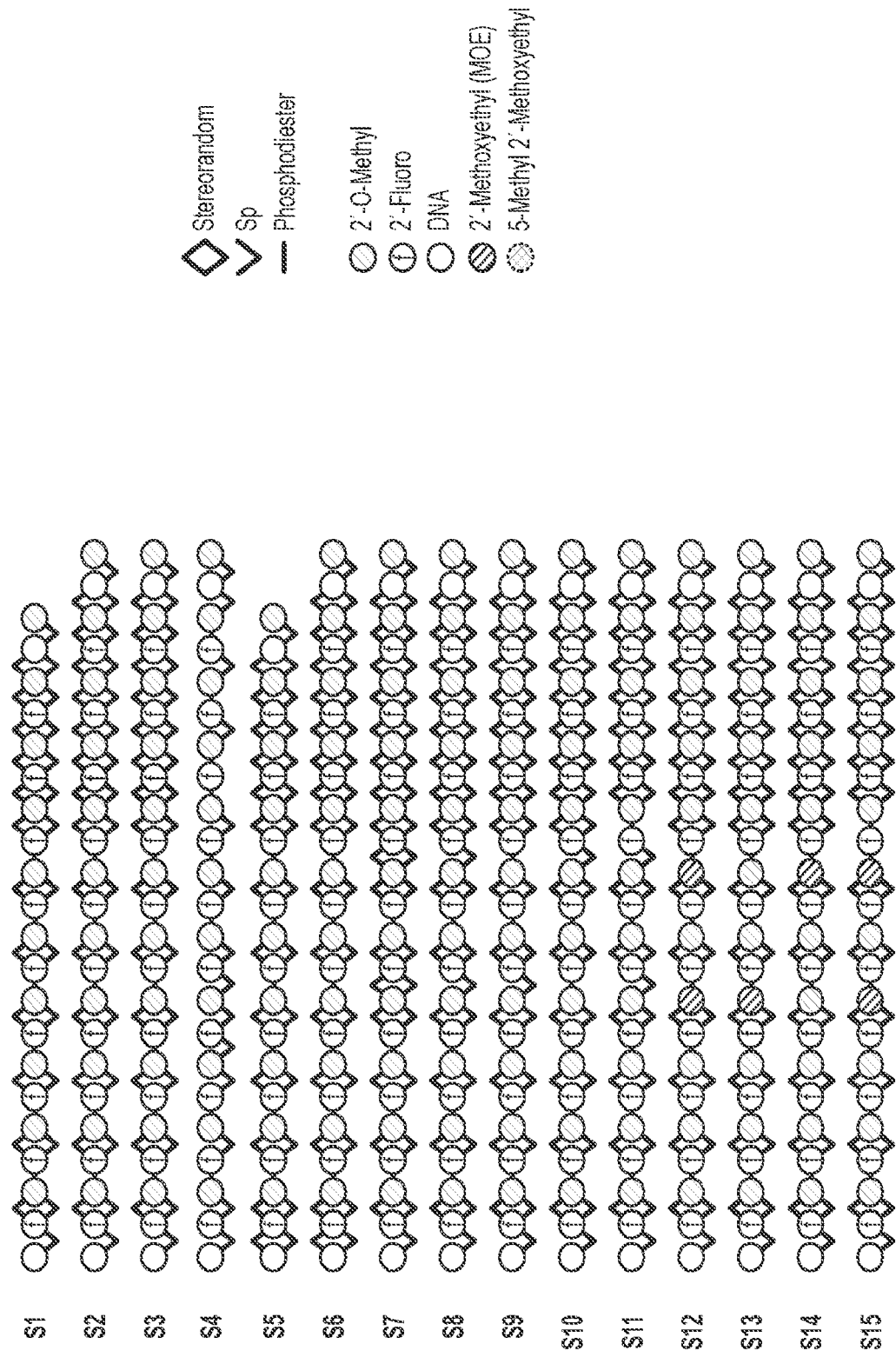

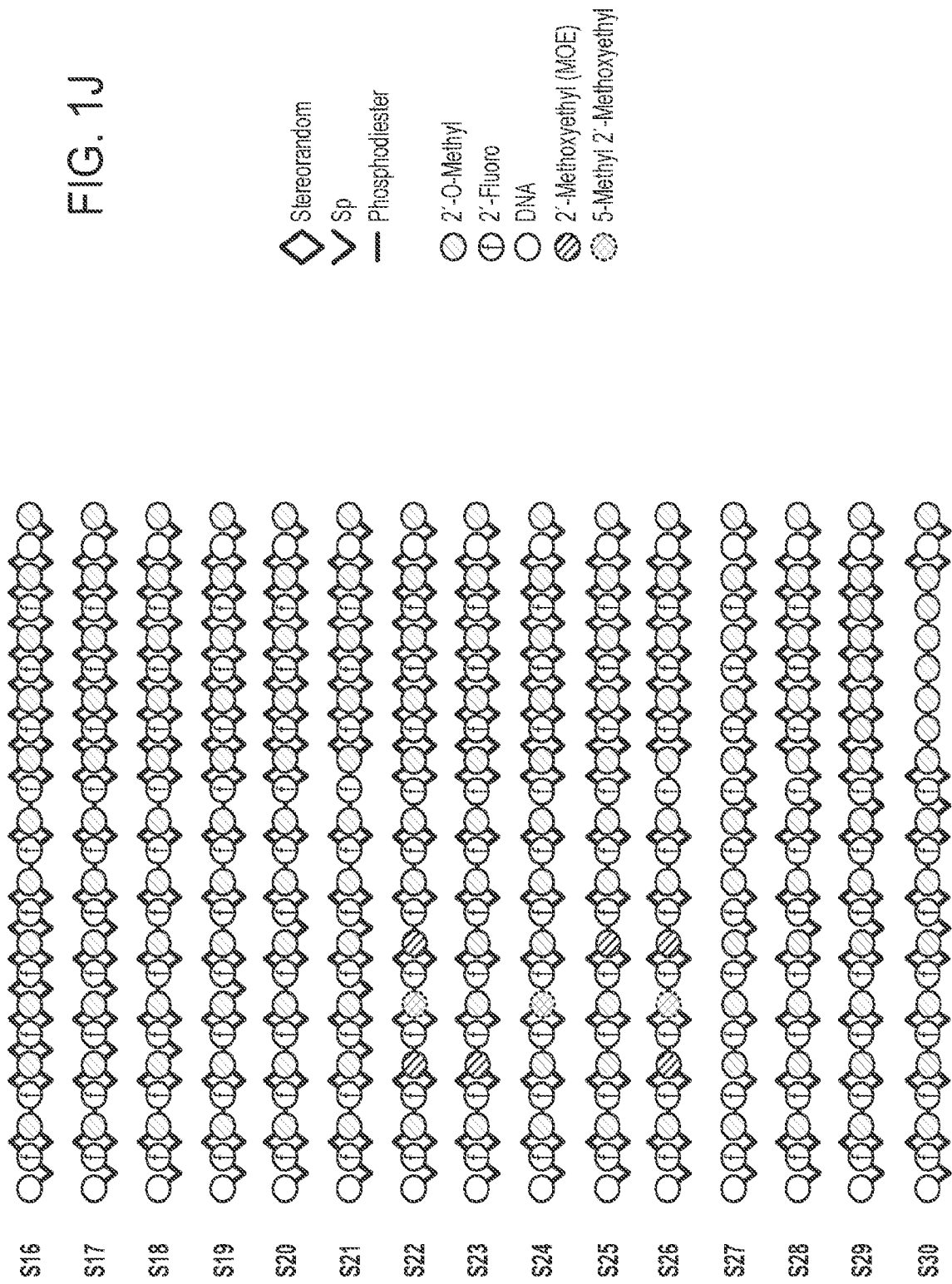

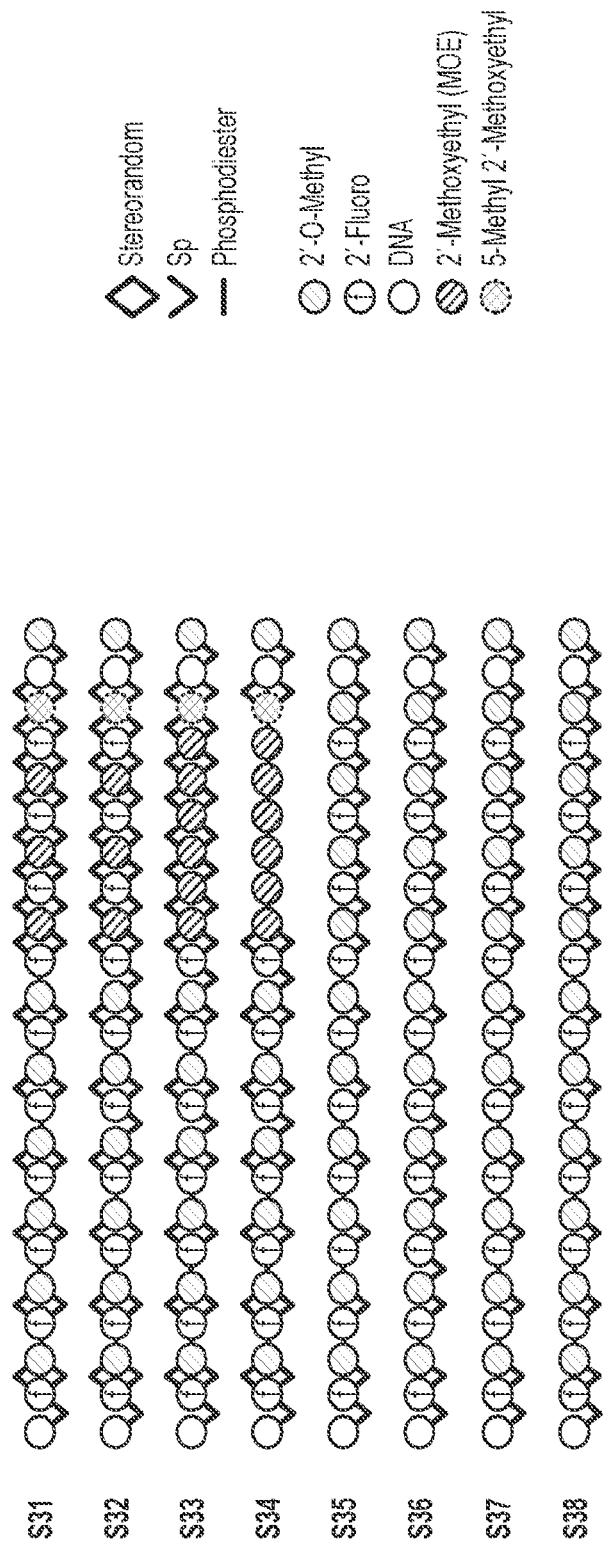

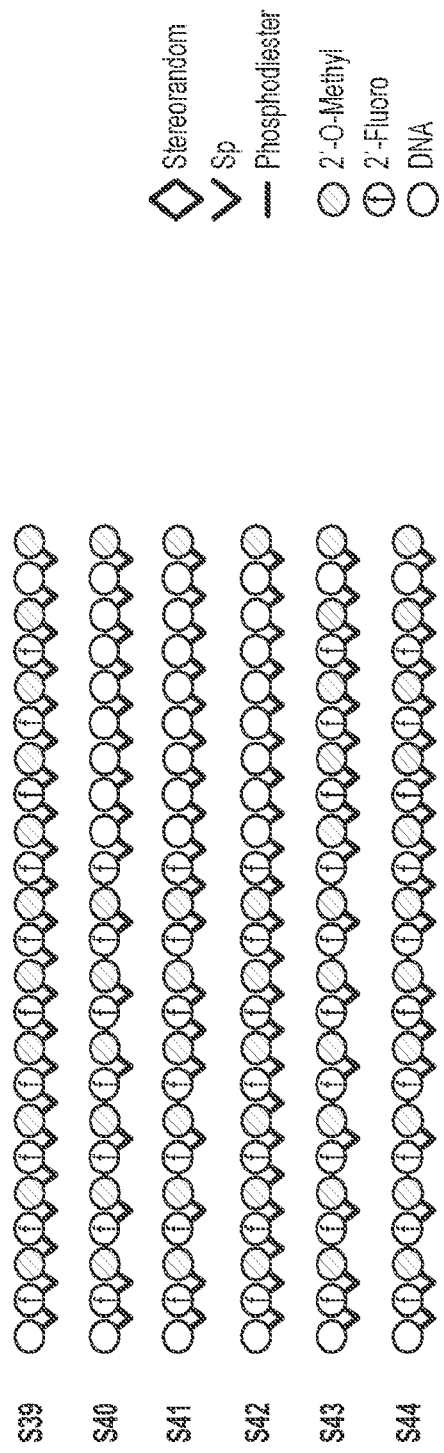

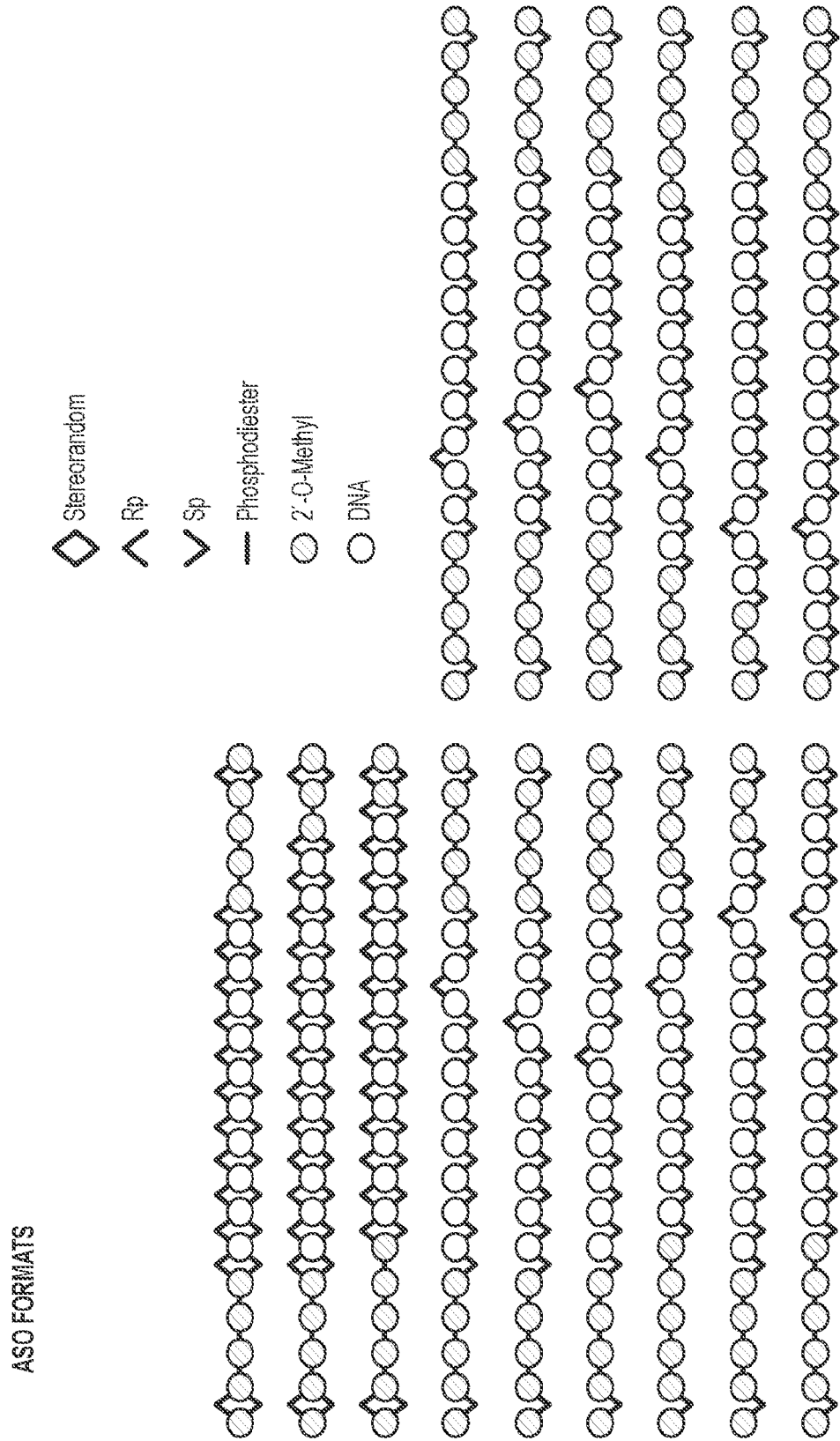

SEQUENCE LISTING

```
<160> NUMBER OF SEQ ID NOS: 1142

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
gcauagcgag cgagggaaaa c                                                 21

<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2 guuucccuc gcucgcuaug c                                                  21

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
gcauagcgag cgagggaaaa c                                                 21

<210> SEQ ID NO 4
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
tuuuucccuc gcucgcuaut u                                              21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
aagggcatga agcaggaaca                                                20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaagggcatg aagcaggaac                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
agaagggcat gaagcaggaa                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
uagaagggca tgaagcagga                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 9
guagaagggc atgaagcagg                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
uguagaaggg catgaagcag                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
cuguagaagg gcatgaagca                                              20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 12
acuguagaag ggcatgaagc                                              20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 13
cacugtagaa gggcaugaag                                              20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 14
ccacugtaga agggcaugaa                                                20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
uuccgactcc tggccuuccg                                                20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
uccgactcct ggcctuccgc                                                20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
ccgactcctg gccttccgca                                                20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
accugaggat ggaccgcggg                                                20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 19
ugugcuuggc uccugccugg                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
cuggaccuga ggauggaccg                                           20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 21
uguuccgacu ccuggccuuc                                           20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 22
guuccgacuc cuggccuucc                                           20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 23
cgacuccugg ccuuccgcac                                           20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 24
ccugctgtgc ttggcuccug                                           20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 25
ucuugttacc cccgccaugg                                           20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 26
ccugcctcag tgtctcggcc                                           20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 27
cccugcctca gtgtcucggc                                           20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 28 uuaccccgc catggagacg                                            20

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 29 accccccgcca tggagacguu                                                    20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 30
gaccugagga tggaccgcgg                                                     20

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggacctgagg atggaccgcg                                                     20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 32 uaccccgcc atggagacgu                                                      20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 33
gggaccctct gcactgggcu                                                     20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 34
ccugggcgag agggtgucca                                               20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 35
cccccgccat ggagacguuu                                               20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 36
ucugctggac agcccuuggg                                               20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 37
cugcactggg cttccuggug                                               20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 38
uccugctgtg cttggcuccu                                               20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 39
cuccugcugt gcuuggcucc                                          20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 40
uggaccugag gauggaccgc                                          20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 41
uaccctgcct cagtgucucg                                          20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 42
agggaccctc tgcacugggc                                          20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
cucaggcagc gggtcgcccc                                          20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 44
ccucagtgtc tcggccaggg                                       20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 45
auuugggacc tggaggcggg                                       20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 46
cuugutaccc ccgccaugga                                       20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 47
acaugggcca gcctacccccc                                      20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 48
ugcugtgctt ggctccugcc                                       20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 49
accugtgagg tcacccacug                                                    20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 50
auguuccgac tcctggccuu                                                    20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 51
cucugctgga cagcccuugg                                                    20

<210> SEQ ID NO 52
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
gccugggcga gaggugucc                                                     20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 53
cugguggaca ttggccggga                                                    20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 54
cugcuccagc gggataccgg                                        20

<210> SEQ ID NO 55
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uuguuacccc cgccauggag                                        20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 56
uguuaccccc gccatggaga                                        20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 57
agcgctctct accctgccuc                                        20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58
ugggcgagag ggtgtccagg                                        20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 59
```
aggcugggat ccuccacguc                                                  20

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 60
ugguggacat tggccgggag                                                  20

<210> SEQ ID NO 61
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61
agaggcuggg atccuccacg                                                  20

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 62
gcuggtggac attggccggg                                                  20

<210> SEQ ID NO 63
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 63
ucugcuccag cgggauaccg                                                  20

<210> SEQ ID NO 64
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 64
ucugcacugg gcuuccuggu                                                  20

<210> SEQ ID NO 65
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 65
gcgcuctcta ccctgccuca           20

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 66
cugcctcagt gtctcggcca           20

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 67
gacucctggc cttccgcaca           20

<210> SEQ ID NO 68
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 68
cgacctcagg atccaucccu           20

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 69
ggcugggauc ucccacguca        20

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 70
ucugcuagac ucgccuccuc        20

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 71
aucuuguuac ccccgccaug        20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 72
ugcacugggc uuccuggugu        20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 73
ugcagagacc cugucggagg        20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 74

```
cccagcacct tgagauccgg                                          20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 75 ccgugaggt cacccacugc                                           20

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 76
cugggcatgg cgaccucagg                                          20

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
cgaactgcac cccttcccac                                          20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
agcgagcctg ggcgagaggg                                          20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 79
ggguggcctc tgcttugguc                                          20

<210> SEQ ID NO 80
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 80
ugcuccagcg ggataccgga                                              20

<210> SEQ ID NO 81
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 81
aagggaccct ctgcacuggg                                              20

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 82
cugcugtgct tggctccugc                                              20

<210> SEQ ID NO 83
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 83
gacgaactgc accccuuccc                                              20

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 84
ugcugtagcg agcctgggcg                                              20
```

```
<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 85
caccccttcc cacagcaugg                                                   20

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 86
gaccctctgc actgggcuuc                                                   20

<210> SEQ ID NO 87
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 87
agcuggtgga cattggccgg                                                   20

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
ucucggccag ggcatuccca                                                   20

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
ggucuctgct ggacagcccu                                                   20
```

<210> SEQ ID NO 90
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
cggccagggc attcccagcg                                              20

<210> SEQ ID NO 91
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 91
ugggatcctc cacgtcacag                                              20

<210> SEQ ID NO 92
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 92
ccugutggct gctcacuggc                                              20

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 93
gccugttggc tgctcacugg                                              20

<210> SEQ ID NO 94
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
ccagcacctt gagatccggg                                              20

<210> SEQ ID NO 95
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 95
gggaggcctg ttggcugcuc                                               20

<210> SEQ ID NO 96
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 96
cucagaggct gggatccucc                                               20

<210> SEQ ID NO 97
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 97
gccucagtgt ctcggccagg                                               20

<210> SEQ ID NO 98
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 98
cacaugggcc agcctacccc                                               20

<210> SEQ ID NO 99
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 99
gguggcctct gctttggucu                                               20

<210> SEQ ID NO 100
<211> LENGTH: 20
<212> TYPE: DNA
```

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 100
acguugtcac tcactccucc					20

<210> SEQ ID NO 101
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 101
uagaaaggca tgaagcagga					20

<210> SEQ ID NO 102
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 102
guagaaaggc atgaagcagg					20

<210> SEQ ID NO 103
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 103
uguagaaagg catgaagcag					20

<210> SEQ ID NO 104
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 104
cuguagaaag gcatgaagca					20

<210> SEQ ID NO 105
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 105
acuguagaaa ggcatgaagc                                                    20

<210> SEQ ID NO 106
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 106
cacugtagaa aggcaugaag                                                    20

<210> SEQ ID NO 107
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 107
ccacugtaga aaggcaugaa                                                    20

<210> SEQ ID NO 108
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 108
uagaaaggca tgaagcagga acaua                                              25

<210> SEQ ID NO 109
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 109
guagaaaggc atgaagcagg aacau                                              25

<210> SEQ ID NO 110
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 110
uguagaaagg catgaagcag gaaca                                            25

<210> SEQ ID NO 111
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 111
cuguagaaag gcatgaagca ggaac                                            25

<210> SEQ ID NO 112
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 112
acuguagaaa ggcatgaagc aggaa                                            25

<210> SEQ ID NO 113
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 113
cacugtagaa aggcatgaag cagga                                            25

<210> SEQ ID NO 114
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 114
ccacugtaga aaggcatgaa gcagg                                            25
```

```
<210> SEQ ID NO 115
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
gccactgtag aaaggcatga agcag                                         25

<210> SEQ ID NO 116
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
ggccactgta gaaaggcatg aagca                                         25

<210> SEQ ID NO 117
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aggccactgt agaaaggcat gaagc                                         25

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 118
aaggccactg tagaaaggca ugaag                                         25

<210> SEQ ID NO 119
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 119
uaaggccact gtagaaaggc augaa                                         25

<210> SEQ ID NO 120
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 120
tcugaggaug gaccgcgggt u                                                  21

<210> SEQ ID NO 121
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 121
tcugaggaug gaccgcgggt u                                                  21

<210> SEQ ID NO 122
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 122
tcugaggaug gaccgcgggt u                                                  21

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 123
taccugagga uggaccgcgt u                                                  21

<210> SEQ ID NO 124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 124
taccugagga uggaccgcgt u                                                  21

<210> SEQ ID NO 125
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide -continued

```
<220> FEATURE:
<223> OTHER INFORMATION: Description of Combined DNA/RNA Molecule:
      Synthetic oligonucleotide

<400> SEQUENCE: 125
tgaccugagg auggaccgct u                                              21

<210> SEQ ID NO 126
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 126
tgaccugagg auggaccgct u                                              21

<210> SEQ ID NO 127
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 127
tuuguuaccc ccgccauggt u                                              21

<210> SEQ ID NO 128
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 128
tuuguuaccc ccgccauggt u                                              21

<210> SEQ ID NO 129
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 129
tccccgccau ggagacguut u                                              21

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 130
tccccgccau ggagacguut u                                              21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 131 taccccgcc auggagacgt u                                               21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 132 taccccgcc auggagacgt u                                               21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 133
tcccccgcca uggagacgut u                                              21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 134
tcccccgcca uggagacgut u                                              21

<210> SEQ ID NO 135
<211> LENGTH: 21
<212> TYPE: DNA
<213> ORGANISM: Artificial Sequence
<220> FEATURE:

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 135
tgcucggccu ccaguuccat u                                              21

<210> SEQ ID NO 136
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 136
tgcucggccu ccaguuccat u                                              21

<210> SEQ ID NO 137
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 137
tggacccucu gcacugggct u                                              21

<210> SEQ ID NO 138
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 138
tggacccucu gcacugggct u                                              21

<210> SEQ ID NO 139
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 139
tgacccucug cacugggcut u                                              21

<210> SEQ ID NO 140
<211> LENGTH: 21
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 140
tgacccucug cacugggcut u                                          21

<210> SEQ ID NO 141
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 141
tcaugaagca ggaacauact u                                          21

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 142
tgcaugaagc aggaacauat u                                          21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 143
tggcaugaag caggaacaut u                                          21

<210> SEQ ID NO 144
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 144
taggcaugaa gcaggaacat u                                          21

<210> SEQ ID NO 145
<211> LENGTH: 21
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 145
taaggcauga agcaggaact u                                              21

<210> SEQ ID NO 146
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 146
taaaggcaug aagcaggaat u                                              21

<210> SEQ ID NO 147
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 147
tgaaaggcau gaagcaggat u                                              21

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 148
tagaaaggca ugaagcaggt u                                              21

<210> SEQ ID NO 149
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 149
tuagaaaggc augaagcagt u                                              21

<210> SEQ ID NO 150
<211> LENGTH: 21
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 150
tguagaaagg caugaagcat u                                             21

<210> SEQ ID NO 151
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 151
tuguagaaag gcaugaagct u                                             21

<210> SEQ ID NO 152
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 152
tcuguagaaa ggcaugaagt u                                             21

<210> SEQ ID NO 153
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 153
tacuguagaa aggcaugaat u                                             21

<210> SEQ ID NO 154
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 154
tcacuguaga aaggcaugat u                                             21

<210> SEQ ID NO 155
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 155
tccacuguag aaaggcaugt u                                          21

<210> SEQ ID NO 156
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 156
tgccacugua gaaaggcaut u                                          21

<210> SEQ ID NO 157
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 157
tggccacugu agaaaggcat u                                          21

<210> SEQ ID NO 158
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 158
taggccacug uagaaaggct u                                          21

<210> SEQ ID NO 159
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 159
taaggccacu guagaaaggt u                                          21
```

```
<210> SEQ ID NO 160
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 160
tuaaggccac uguagaaagt u                                              21

<210> SEQ ID NO 161
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 161
tauaaggcca cuguagaaat u                                              21

<210> SEQ ID NO 162
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 162
tcaugaagca ggaacauact u                                              21

<210> SEQ ID NO 163
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 163
tgcaugaagc aggaacauat u                                              21

<210> SEQ ID NO 164
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 164
tggcaugaag caggaacaut u                                              21
```

```
<210> SEQ ID NO 165
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 165
taggcaugaa gcaggaacat u                                              21

<210> SEQ ID NO 166
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 166
taaggcauga agcaggaact u                                              21

<210> SEQ ID NO 167
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 167
taaaggcaug aagcaggaat u                                              21

<210> SEQ ID NO 168
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 168
tgaaaggcau gaagcaggat u                                              21

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 169
tagaaaggca ugaagcaggt u                                              21
```

<210> SEQ ID NO 170
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 170
tuagaaaggc augaagcagt u                                              21

<210> SEQ ID NO 171
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 171
tguagaaagg caugaagcat u                                              21

<210> SEQ ID NO 172
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 172
tuguagaaag gcaugaagct u                                              21

<210> SEQ ID NO 173
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 173
tcuguagaaa ggcaugaagt u                                              21

<210> SEQ ID NO 174
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 174
tacuguagaa aggcaugaat u                                              21

<210> SEQ ID NO 175
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 175
tcacuguaga aaggcaugat u                                              21

<210> SEQ ID NO 176
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 176
tccacuguag aaaggcaugt u                                              21

<210> SEQ ID NO 177
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 177
tgccacugua gaaaggcaut u                                              21

<210> SEQ ID NO 178
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 178
tggccacugu agaaaggcat u                                              21

<210> SEQ ID NO 179
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 179

-continued

```
taggccacug uagaaaggct u                                          21

<210> SEQ ID NO 180
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 180
taaggccacu guagaaaggt u                                          21

<210> SEQ ID NO 181
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 181
tuaaggccac uguagaaagt u                                          21

<210> SEQ ID NO 182
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 182
tauaaggcca cuguagaaat u                                          21

<210> SEQ ID NO 183
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 183
tcaugaagca ggaacauacc atu                                        23

<210> SEQ ID NO 184
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 184
tgcaugaagc aggaacauac ctu                                        23

<210> SEQ ID NO 185
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 185
tggcaugaag caggaacaua ctu                                        23

<210> SEQ ID NO 186
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 186
taggcaugaa gcaggaacau atu                                        23

<210> SEQ ID NO 187
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 187
taaggcauga agcaggaaca utu                                        23

<210> SEQ ID NO 188
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 188
taaaggcaug aagcaggaac atu                                        23

<210> SEQ ID NO 189
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 189
tgaaaggcau gaagcaggaa ctu                                            23

<210> SEQ ID NO 190
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 190
tagaaaggca ugaagcagga atu                                            23

<210> SEQ ID NO 191
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 191
tuagaaaggc augaagcagg atu                                            23

<210> SEQ ID NO 192
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 192
tguagaaagg caugaagcag gtu                                            23

<210> SEQ ID NO 193
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 193
tuguagaaag gcaugaagca gtu                                            23

<210> SEQ ID NO 194
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 194
tcuguagaaa ggcaugaagc atu                               23

<210> SEQ ID NO 195
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 195
tacuguagaa aggcaugaag ctu                               23

<210> SEQ ID NO 196
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 196
tcacuguaga aaggcaugaa gtu                               23

<210> SEQ ID NO 197
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 197
tccacuguag aaaggcauga atu                               23

<210> SEQ ID NO 198
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 198
tgccacugua gaaaggcaug atu                               23

<210> SEQ ID NO 199
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 199
tggccacugu agaaaggcau gtu                                             23

<210> SEQ ID NO 200
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 200
taggccacug uagaaaggca utu                                             23

<210> SEQ ID NO 201
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 201
taaggccacu guagaaaggc atu                                             23

<210> SEQ ID NO 202
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 202
tuaaggccac uguagaaagg ctu                                             23

<210> SEQ ID NO 203
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 203
tauaaggcca cuguagaaag gtu                                             23

<210> SEQ ID NO 204
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 204
tgauaaggcc acuguagaaa gtu                                            23

<210> SEQ ID NO 205
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 205
tggauaaggc cacuguagaa atu                                            23

<210> SEQ ID NO 206
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 206
tcaugaagca ggaacauacc atu                                            23

<210> SEQ ID NO 207
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 207
tgcaugaagc aggaacauac ctu                                            23

<210> SEQ ID NO 208
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 208
tggcaugaag caggaacaua ctu                                            23

<210> SEQ ID NO 209
<211> LENGTH: 23
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 209
taggcaugaa gcaggaacau atu                                             23

<210> SEQ ID NO 210
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 210
taaggcauga agcaggaaca utu                                             23

<210> SEQ ID NO 211
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 211
taaaggcaug aagcaggaac atu                                             23

<210> SEQ ID NO 212
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 212
tgaaaggcau gaagcaggaa ctu                                             23

<210> SEQ ID NO 213
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 213
tagaaaggca ugaagcagga atu                                             23

<210> SEQ ID NO 214
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 214
tuagaaaggc augaagcagg atu                                              23

<210> SEQ ID NO 215
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 215
tguagaaagg caugaagcag gtu                                              23

<210> SEQ ID NO 216
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 216
tuguagaaag gcaugaagca gtu                                              23

<210> SEQ ID NO 217
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 217
tcuguagaaa ggcaugaagc atu                                              23

<210> SEQ ID NO 218
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 218
tacuguagaa aggcaugaag ctu                                              23

<210> SEQ ID NO 219
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 219
tcacuguaga aaggcaugaa gtu                                           23

<210> SEQ ID NO 220
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 220
tccacuguag aaaggcauga atu                                           23

<210> SEQ ID NO 221
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 221
tgccacugua gaaaggcaug atu                                           23

<210> SEQ ID NO 222
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 222
tggccacugu agaaaggcau gtu                                           23

<210> SEQ ID NO 223
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 223
taggccacug uagaaaggca utu                                           23

<210> SEQ ID NO 224
<211> LENGTH: 23
<212> TYPE: DNA
```

<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 224
taaggccacu guagaaaggc atu                                          23

<210> SEQ ID NO 225
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 225
tuaaggccac uguagaaagg ctu                                          23

<210> SEQ ID NO 226
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 226
tauaaggcca cuguagaaag gtu                                          23

<210> SEQ ID NO 227
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 227
tgauaaggcc acuguagaaa gtu                                          23

<210> SEQ ID NO 228
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 228
tggauaaggc cacuguagaa atu                                          23

<210> SEQ ID NO 229
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 229
tgccacugua gaaaggcaug atu                                              23

<210> SEQ ID NO 230
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 230
tgccacugua gaaaggcaug atu                                              23

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 231
tgccacugua gaaaggcaug atu                                              23

<210> SEQ ID NO 232
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 232
tgccacugua gaaaggcaug atu                                              23

<210> SEQ ID NO 233
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 233
tgccacugua gaaaggcaug atu                                              23

<210> SEQ ID NO 234
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 234
tgccacugua gaaaggcaug atu                                              23

<210> SEQ ID NO 235
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 235
tgccacugua gaaaggcaug atu                                              23

<210> SEQ ID NO 236
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 236
tgccacugua gaaaggcaug atu                                              23

<210> SEQ ID NO 237
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 237
tgccacugua gaaaggcaug atu                                              23

<210> SEQ ID NO 238
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 238
tgccacugua gaaaggcaug atu                                              23
```

```
<210> SEQ ID NO 239
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 239
tgccacugua gaaaggcaut u                                                 21

<210> SEQ ID NO 240
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 240
tgccacugua gaaaggcaut u                                                 21

<210> SEQ ID NO 241
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 241
tgccacugua gaaaggcaut u                                                 21

<210> SEQ ID NO 242
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 242
tgccacugua gaaaggcaut u                                                 21

<210> SEQ ID NO 243
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 243
tgccacugua gaaaggcaut u                                                 21
```

<210> SEQ ID NO 244
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 244
tgccacugua gaaaggcaut u                                                 21

<210> SEQ ID NO 245
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 245
tgccacugua gaaaggcaut u                                                 21

<210> SEQ ID NO 246
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 246
tgccacugua gaaaggcaut u                                                 21

<210> SEQ ID NO 247
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 247
tgccacugua gaaaggcaut u                                                 21

<210> SEQ ID NO 248
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 248
tgccacugua gaaaggcaut u                                                 21

<210> SEQ ID NO 249
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 249
taggcaugaa gcaggaacat u                                              21

<210> SEQ ID NO 250
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 250
taggcaugaa gcaggaacau atu                                            23

<210> SEQ ID NO 251
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 251
tccugaggau ggaccgcggg gtu                                            23

<210> SEQ ID NO 252
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 252
tgugcuuggc uccugccugg gtu                                            23

<210> SEQ ID NO 253
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 253
tcuuguuacc cccgccaugg atu                                               23

<210> SEQ ID NO 254
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 254 tuaccccgc cauggagacg utu                                                23

<210> SEQ ID NO 255
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 255
tcccccgcca uggagacguu utu                                               23

<210> SEQ ID NO 256
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 256
taccugagga uggaccgcgg gtu                                               23

<210> SEQ ID NO 257
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 257
tgaccugagg auggaccgcg gtu                                               23

<210> SEQ ID NO 258
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 258

-continued tacccccgcc auggagacgu utu				23

<210> SEQ ID NO 259
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 259 tggaccccucu gcacgggcu utu				23

<210> SEQ ID NO 260
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 260
tcugcuggac agcccuuggg gtu				23

<210> SEQ ID NO 261
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 261
tugcacuggg cuuccuggug utu				23

<210> SEQ ID NO 262
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 262
tggaccugag gauggaccgc gtu				23

<210> SEQ ID NO 263
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 263
tgggacccuc ugcacugggc utu                                              23

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 264
tuuguuaccc ccgccaugga gtu                                              23

<210> SEQ ID NO 265
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 265
tccugugagg ucacccacug ctu                                              23

<210> SEQ ID NO 266
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 266
tucugcugga cagcccuugg gtu                                              23

<210> SEQ ID NO 267
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 267
tugcuccagc gggauaccgg atu                                              23

<210> SEQ ID NO 268
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 268
tggcugggau ccuccacguc atu                                          23

<210> SEQ ID NO 269
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 269
tucuuguuac ccccgccaug gtu                                          23

<210> SEQ ID NO 270
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 270
tagggacccu cugcacuggg ctu                                          23

<210> SEQ ID NO 271
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 271
tcuguuggcu gcucacuggc atu                                          23

<210> SEQ ID NO 272
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 272
tccugaggau ggaccgcggg gtu                                          23

<210> SEQ ID NO 273
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 273
tgugcuuggc uccugccugg gtu                                          23

<210> SEQ ID NO 274
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 274
tcuuguuacc cccgccaugg atu                                          23

<210> SEQ ID NO 275
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 275 tuaccccgc cauggagacg utu                                           23

<210> SEQ ID NO 276
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 276
tcccccgcca uggagacguu utu                                          23

<210> SEQ ID NO 277
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 277
taccugagga uggaccgcgg gtu                                          23

<210> SEQ ID NO 278
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 278
tgaccugagg auggaccgcg gtu                                             23

<210> SEQ ID NO 279
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 279 taccccccgcc auggagacgu utu                                            23

<210> SEQ ID NO 280
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 280
tggacccucu gcacugggcu utu                                             23

<210> SEQ ID NO 281
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 281
tcugcuggac agcccuuggg gtu                                             23

<210> SEQ ID NO 282
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 282
tugcacuggg cuuccuggug utu                                             23

<210> SEQ ID NO 283
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 283
tggaccugag gauggaccgc gtu                                              23

<210> SEQ ID NO 284
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 284
tgggacccuc ugcacugggc utu                                              23

<210> SEQ ID NO 285
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 285
tuuguuaccc ccgccaugga gtu                                              23

<210> SEQ ID NO 286
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 286
tccugugagg ucacccacug ctu                                              23

<210> SEQ ID NO 287
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 287
tucugcugga cagcccuugg gtu                                              23

<210> SEQ ID NO 288
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 288
tugcuccagc gggauaccgg atu                                           23

<210> SEQ ID NO 289
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 289
tggcugggau ccuccacguc atu                                           23

<210> SEQ ID NO 290
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 290
tucuuguuac ccccgccaug gtu                                           23

<210> SEQ ID NO 291
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 291
tagggacccu cugcacuggg ctu                                           23

<210> SEQ ID NO 292
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 292
tcuguuggcu gcucacuggc atu                                           23

<210> SEQ ID NO 293
<211> LENGTH: 27
<212> TYPE: RNA
<213> ORGANISM: Artificial Sequence
<220> FEATURE:
```

```
<223> OTHER INFORMATION: Description of Artificial Sequence: Synthetic
      oligonucleotide

<400> SEQUENCE: 293
accccgcggu ccauccucag guccagc                                              27

<210> SEQ ID NO 294
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 294
augacaccag gaagcccagu gcagagg                                              27

<210> SEQ ID NO 295
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 295
gaagcccagu gcagaggguc ccuuacu                                              27

<210> SEQ ID NO 296
<211> LENGTH: 27
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 296
aacgucucca uggcgggggu aacaaga                                              27

<210> SEQ ID NO 297
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 297
tgccacugua gaaggaaug atu                                                   23

<210> SEQ ID NO 298
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 298
tgccacugua gaagggaug atu                                                   23
```

```
<210> SEQ ID NO 299
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 299
tgccacugua gaaagguaug atu                                            23

<210> SEQ ID NO 300
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 300
tgccacugua gaagggcaug atu                                            23

<210> SEQ ID NO 301
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 301
tgccacugua gaacggcaug atu                                            23

<210> SEQ ID NO 302
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 302
tgccacugua gaauggcaug atu                                            23

<210> SEQ ID NO 303
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 303
tgccacugua gaaggggaug atu                                            23
```

```
<210> SEQ ID NO 304
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 304
tgccacugua gaaaggcaug aagtu                                          25

<210> SEQ ID NO 305
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 305
tgccacugua gaaaggcaug aatu                                           24

<210> SEQ ID NO 306
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 306
tgccacugua gaaaggcaug tu                                             22

<210> SEQ ID NO 307
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 307
tgccacugua gaaaggcatu                                                20

<210> SEQ ID NO 308
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 308
tgccacugua gaaaggctu                                                 19
```

<210> SEQ ID NO 309
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 309
tgccacugua gaaaggcagg                                                    20

<210> SEQ ID NO 310
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 310
tgccacugua gaaaggcgg                                                     19

<210> SEQ ID NO 311
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 311
tgccacugua gaaaggcaug atu                                                23

<210> SEQ ID NO 312
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 312
tgccacugua gaaaggcaug atu                                                23

<210> SEQ ID NO 313
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 313
tgccacugua gaaaggcaug atu                                              23

<210> SEQ ID NO 314
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 314
tgccacugua gaaaggcaug atu                                              23

<210> SEQ ID NO 315
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 315
tgccacugua gaaaggcaug atu                                              23

<210> SEQ ID NO 316
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 316
tgccacugua gaaaggcaug atu                                              23

<210> SEQ ID NO 317
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 317
tgccacugua gaaaggcaug atu                                              23

<210> SEQ ID NO 318
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 318
tgccacugua gaaaggcaug atu                                          23

<210> SEQ ID NO 319
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 319
tgccacugua gaaaggcaug atu                                          23

<210> SEQ ID NO 320
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 320
tgccacugua gaaaggcaug atu                                          23

<210> SEQ ID NO 321
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 321
tgccacugua gaaaggcaug atu                                          23

<210> SEQ ID NO 322
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 322
tgccacugua gaaaggcaug atu                                          23

<210> SEQ ID NO 323
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

```
<400> SEQUENCE: 323
tgccacugua gaaaggcaug atu                                              23

<210> SEQ ID NO 324
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 324
tgccacugua gaaaggcaug atu                                              23

<210> SEQ ID NO 325
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 325
tgccacugua gaaaggcaug atu                                              23

<210> SEQ ID NO 326
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 326
tgccacugua gaaaggcaug atu                                              23

<210> SEQ ID NO 327
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 327
tgccacugua gaaaggcaug atu                                              23

<210> SEQ ID NO 328
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 328
tgccacugua gaaaggcaug atu                                              23

<210> SEQ ID NO 329
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 329
tgccacugua gaaaggcaug atu                                              23

<210> SEQ ID NO 330
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 330
tgccacugua gaaaggcaug atu                                              23

<210> SEQ ID NO 331
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 331
tgccacugua gaaaggcaug atu                                              23

<210> SEQ ID NO 332
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 332
tgccacugua gaaaggcaug atu                                              23

<210> SEQ ID NO 333
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 333
tgccacugua gaaaggcaug atu                                           23

<210> SEQ ID NO 334
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 334
tgccacugua gaaaggcaug ata                                           23

<210> SEQ ID NO 335
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 335
tgccacugua gaaaggcaug atg                                           23

<210> SEQ ID NO 336
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 336
tgccacugua gaaaggcaug atc                                           23

<210> SEQ ID NO 337
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 337
tgccacugua gaaaggcaut a                                             21

<210> SEQ ID NO 338
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 338
tgccacugua gaaaggcaut g                                              21

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 339
tgccacugua gaaaggcaut c                                              21

<210> SEQ ID NO 340
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 340
tgccacugua gaaaggcaug atu                                            23

<210> SEQ ID NO 341
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 341
tgccacugua gaaaggcaug atu                                            23

<210> SEQ ID NO 342
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 342
tgccacugua gaaaggcaug atu                                            23

<210> SEQ ID NO 343
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 343
tgccacugua gaaaggcaug atu                                               23

<210> SEQ ID NO 344
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 344
tgccacugua gaaaggcaug atu                                               23

<210> SEQ ID NO 345
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 345
tgccacugua gaaaggcaug atu                                               23

<210> SEQ ID NO 346
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 346
tgccacugua gaaaggcaug atu                                               23

<210> SEQ ID NO 347
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 347
tgccacugua gaaaggcaug atu                                               23

<210> SEQ ID NO 348
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                            oligonucleotide
<220> FEATURE:
<223> OTHER INFORMATION: Description of Combined DNA/RNA Molecule:
      Synthetic oligonucleotide

<400> SEQUENCE: 348
tgccacugua gaaaggcaug atu                                            23

<210> SEQ ID NO 349
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 349
tgccacugua gaaaggcaug atu                                            23

<210> SEQ ID NO 350
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 350
tgccacugua gaaaggcaug atu                                            23

<210> SEQ ID NO 351
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 351
tgccacugua gaaaggcaug atu                                            23

<210> SEQ ID NO 352
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 352
tgccacugua gaaaggcaug atu                                            23

<210> SEQ ID NO 353
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 353
tgccacugua gaaaggcaug atu                                               23

<210> SEQ ID NO 354
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 354
tgccacugua gaaaggcaug atu                                               23

<210> SEQ ID NO 355
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 355
tgccacugua gaaaggcaug atu                                               23

<210> SEQ ID NO 356
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 356
tgccacugua gaaaggcaug atu                                               23

<210> SEQ ID NO 357
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 357
tgccacugua gaaaggcaug atu                                               23

<210> SEQ ID NO 358
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 358
tgccacugua gaaaggcaug atu                                           23

<210> SEQ ID NO 359
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 359
tgccacugua gaaaggcaug atu                                           23

<210> SEQ ID NO 360
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 360
tgccacugua gaaaggcaug atu                                           23

<210> SEQ ID NO 361
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 361
tgccacugua gaaaggcaug atu                                           23

<210> SEQ ID NO 362
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 362
tgccacugua gaaaggcaug atu                                           23

<210> SEQ ID NO 363
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 363
tgccacugua gaaaggcaug atu                                              23

<210> SEQ ID NO 364
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 364
ugccacugua gaaaggcaug atu                                              23

<210> SEQ ID NO 365
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 365
agccacugua gaaaggcaug atu                                              23

<210> SEQ ID NO 366
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 366
ggccacugua gaaaggcaug atu                                              23

<210> SEQ ID NO 367
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 367
cgccacugua gaaaggcaug atu                                              23

<210> SEQ ID NO 368
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 368
ugccacugua gaaaggcaug atu                                              23

<210> SEQ ID NO 369
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 369
agccacugua gaaaggcaug atu                                              23

<210> SEQ ID NO 370
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 370
ggccacugua gaaaggcaug atu                                              23

<210> SEQ ID NO 371
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 371
cgccacugua gaaaggcaug atu                                              23

<210> SEQ ID NO 372
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 372
tgccacugua gaaaggcaug atu                                              23

<210> SEQ ID NO 373
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 373
tgccacugua gaaaggcaug atu                                             23

<210> SEQ ID NO 374
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 374
tgccacugua gaaaggcaug atu                                             23

<210> SEQ ID NO 375
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 375
tgccacugua gaaaggcaug atu                                             23

<210> SEQ ID NO 376
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 376
tgccacugua gaaaggcaug atu                                             23

<210> SEQ ID NO 377
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 377
tgccacugua gaaaggcaug atu                                             23
```

```
<210> SEQ ID NO 378
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 378
tgccactgua gaaaggcaug atu                                              23

<210> SEQ ID NO 379
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 379
tgccacugua gaaaggcaug atu                                              23

<210> SEQ ID NO 380
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 380
tgccacugta gaaaggcaug atu                                              23

<210> SEQ ID NO 381
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 381
tgccacugua gaaaggcaug atu                                              23

<210> SEQ ID NO 382
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 382
tgccacugua gaaaggcaug atu                                              23
```

<210> SEQ ID NO 383
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 383
tgccacugua gaaaggcaug atu                                              23

<210> SEQ ID NO 384
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 384
tgccacugua gaaaggcaug atu                                              23

<210> SEQ ID NO 385
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 385
tgccacugua gaaaggcaug atu                                              23

<210> SEQ ID NO 386
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 386
tgccacugua gaaaggcaug atu                                              23

<210> SEQ ID NO 387
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 387
tgccacugua gaaaggcaug atu                                              23

<210> SEQ ID NO 388
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 388
tgccacugua gaaaggcaug atu                                          23

<210> SEQ ID NO 389
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 389
tgccacugua gaaaggcaug atu                                          23

<210> SEQ ID NO 390
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 390
tgccacugua gaaaggcatg atu                                          23

<210> SEQ ID NO 391
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 391
tgccacugua gaaaggcaug atu                                          23

<210> SEQ ID NO 392
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 392
tgccacugua gaaaggcaug atu                                          23

<210> SEQ ID NO 393
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 393
tgccacugua gaaaggcaug atu                                          23

<210> SEQ ID NO 394
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 394
tgccactgua gaaaggcaug atu                                          23

<210> SEQ ID NO 395
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 395
tgccactgua gaaaggcaug atu                                          23

<210> SEQ ID NO 396
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 396
tgccactgua gaaaggcaug atu                                          23

<210> SEQ ID NO 397
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 397
tgccacugua gaaaggcaug atu                                           23

<210> SEQ ID NO 398
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 398
agccacugua gaaaggcaug atu                                           23

<210> SEQ ID NO 399
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 399
ggccacugua gaaaggcaug atu                                           23

<210> SEQ ID NO 400
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 400
cgccacugua gaaaggcaug atu                                           23

<210> SEQ ID NO 401
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 401
tgccacugua gaaaggcaug atu                                           23

<210> SEQ ID NO 402
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 402
tgccacugua gaaaggcaug atu                                          23

<210> SEQ ID NO 403
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 403
tgccacugua gaaaggcaug atu                                          23

<210> SEQ ID NO 404
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 404
tgccacugua gaaaggcaug atu                                          23

<210> SEQ ID NO 405
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 405
tgccacugua gaaaggcaug atu                                          23

<210> SEQ ID NO 406
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 406
tgccactgua gaaaggcaug atu                                          23

<210> SEQ ID NO 407
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 407
tgccacugua gaaaggcaug atu					23

<210> SEQ ID NO 408
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 408
tgccacugta gaaaggcaug atu					23

<210> SEQ ID NO 409
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 409
tgccacugua gaaaggcaug atu					23

<210> SEQ ID NO 410
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 410
tgccacugua gaaaggcaug atu					23

<210> SEQ ID NO 411
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 411
tgccacugua gaaaggcaug atu					23

<210> SEQ ID NO 412
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

-continued

Synthetic oligonucleotide

<400> SEQUENCE: 412
tgccacugua gaaaggcaug atu                          23

<210> SEQ ID NO 413
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 413
tgccacugua gaaaggcaug atu                          23

<210> SEQ ID NO 414
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 414
tgccacugua gaaaggcaug atu                          23

<210> SEQ ID NO 415
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 415
tgccacugua gaaaggcaug atu                          23

<210> SEQ ID NO 416
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 416
tgccacugua gaaaggcaug atu                          23

<210> SEQ ID NO 417
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 417
tgccacugua gaaaggcaug atu                                              23

<210> SEQ ID NO 418
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 418
tgccacugua gaaaggcatg atu                                              23

<210> SEQ ID NO 419
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 419
tgccacugua gaaaggcaug atu                                              23

<210> SEQ ID NO 420
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 420
tgccacugua gaaaggcaug atu                                              23

<210> SEQ ID NO 421
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 421
tgccacugua gaaaggcaug atu                                              23

<210> SEQ ID NO 422
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 422
agccacugua gaaaggcaug atu                                              23

<210> SEQ ID NO 423
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 423
ggccacugua gaaaggcaug atu                                              23

<210> SEQ ID NO 424
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 424
cgccacugua gaaaggcaug atu                                              23

<210> SEQ ID NO 425
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 425
tgccacugua gaaaggcaug atu                                              23

<210> SEQ ID NO 426
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 426
tgccactgua gaaaggcaug atu                                              23

<210> SEQ ID NO 427
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 427
tgccactgua gaaaggcaug atu                                            23

<210> SEQ ID NO 428
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 428
tgccactgua gaaaggcaug atu                                            23

<210> SEQ ID NO 429
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 429
tgccacugua gaaaggcaug atu                                            23

<210> SEQ ID NO 430
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 430
tgccacugua gaaaggcaug atu                                            23

<210> SEQ ID NO 431
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 431
tgccacugua gaaaggcaug atu                                            23

<210> SEQ ID NO 432
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 432
tgccactgua gaaaggcaug atu                                            23

<210> SEQ ID NO 433
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 433
tgccacugta gaaaggcaug atu                                            23

<210> SEQ ID NO 434
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 434
tgccacugua gaaaggcaug atu                                            23

<210> SEQ ID NO 435
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 435
tgccacugua gaaaggcaug atu                                            23

<210> SEQ ID NO 436
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 436
tgccacugua gaaaggcaug atu                                            23

<210> SEQ ID NO 437
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 437
tgccacugua gaaaggcaug atu                                            23

<210> SEQ ID NO 438
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 438
tgccacugua gaaaggcaug atu                                            23

<210> SEQ ID NO 439
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 439
tgccacugua gaaaggcaug atu                                            23

<210> SEQ ID NO 440
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 440
tgccacugua gaaaggcaug atu                                            23

<210> SEQ ID NO 441
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 441
tgccacugua gaaaggcaug atu                                            23

<210> SEQ ID NO 442
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 442
tgccacugua gaaaggcaug atu                                              23

<210> SEQ ID NO 443
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 443
tgccacugua gaaaggcatg atu                                              23

<210> SEQ ID NO 444
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 444
tgccacugua gaaaggcaug atu                                              23

<210> SEQ ID NO 445
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 445
tgccacugua gaaaggcaug atu                                              23

<210> SEQ ID NO 446
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 446
agccacugua gaaaggcaug atu                                              23

<210> SEQ ID NO 447
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 447
ggccacugua gaaaggcaug atu                                              23

<210> SEQ ID NO 448
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 448
cgccacugua gaaaggcaug atu                                              23

<210> SEQ ID NO 449
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 449
tgccacugua gaaaggcaug atu                                              23

<210> SEQ ID NO 450
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 450
tgccactgua gaaaggcaug atu                                              23

<210> SEQ ID NO 451
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 451
tgccactgua gaaaggcaug atu                                              23

<210> SEQ ID NO 452
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 452
tgccactgua gaaaggcaug atu                                              23

<210> SEQ ID NO 453
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 453
tgccacugua gaaaggcatg atu                                              23

<210> SEQ ID NO 454
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 454
tgccacugua gaaaggcatg atu                                              23

<210> SEQ ID NO 455
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 455
tgucacugua gaaaggcaug atu                                              23

<210> SEQ ID NO 456
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 456
tgcuacugua gaaaggcaug atu                                              23
```

```
<210> SEQ ID NO 457
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 457
tgccgcugua gaaaggcaug atu                                             23

<210> SEQ ID NO 458
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 458
tgccauugua gaaaggcaug atu                                             23

<210> SEQ ID NO 459
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 459
tgccacugug gaaaggcaug atu                                             23

<210> SEQ ID NO 460
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 460
tgccacugua ggaaggcaug atu                                             23

<210> SEQ ID NO 461
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 461
tgccacugua gagaggcaug atu                                             23
```

```
<210> SEQ ID NO 462
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 462
tgccacugua gaagggcaug atu                                              23

<210> SEQ ID NO 463
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 463
tgccacugua gaaagguaug atu                                              23

<210> SEQ ID NO 464
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 464
tgccacugua gaaaggcgug atu                                              23

<210> SEQ ID NO 465
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 465
tgccacugua gaaaggcaug gtu                                              23

<210> SEQ ID NO 466
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 466
accugaggat ggaccgcggg                                                  20
```

```
<210> SEQ ID NO 467
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 467
acctgaggat ggaccgcggg                                              20

<210> SEQ ID NO 468
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 468
ggacctgagg atggaccgcg                                              20

<210> SEQ ID NO 469
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 469
ggacctgagg atggaccgcg                                              20

<210> SEQ ID NO 470
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 470
accugaggat ggaccgcggg                                              20

<210> SEQ ID NO 471
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 471
acctgaggat ggaccgcggg                                              20

<210> SEQ ID NO 472
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 472
```
ggacctgagg atggaccgcg                                              20

<210> SEQ ID NO 473
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 473
ggacctgagg atggaccgcg                                              20

<210> SEQ ID NO 474
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 474
accugaggat ggaccgcggg                                              20

<210> SEQ ID NO 475
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 475
acctgaggat ggaccgcggg                                              20

<210> SEQ ID NO 476
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 476
ggacctgagg atggaccgcg                                              20

<210> SEQ ID NO 477
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 477
ggacctgagg atggaccgcg                                              20

<210> SEQ ID NO 478
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide <220> FEATURE:
<223> OTHER INFORMATION: Description of Combined DNA/RNA Molecule:
     Synthetic oligonucleotide

<400> SEQUENCE: 478
tgccacugua gaaaggcaug atu                                              23

<210> SEQ ID NO 479
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 479
tgccacugua gaaaggcaug atu                                              23

<210> SEQ ID NO 480
<211> LENGTH: 27
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 480
cccccaggca ggagccaagc acagcag                                          27

<210> SEQ ID NO 481
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 481
tgccacugua gaaaggcaug atu                                              23

<210> SEQ ID NO 482
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide

<400> SEQUENCE: 482
tgccacugua gaaaggcaug atu                                              23

<210> SEQ ID NO 483
<211> LENGTH: 23
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:

Synthetic oligonucleotide

<400> SEQUENCE: 483
tgccacugua gaaaggcaug atu                                              23

<210> SEQ ID NO 484
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 484
tgccacugua gaaaggcaug atu                                              23

<210> SEQ ID NO 485
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 485
tgccacugua gaaaggcaug atu                                              23

<210> SEQ ID NO 486
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 486
tgccacugua gaaaggcaug atu                                              23

<210> SEQ ID NO 487
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 487
tgccacugua gaaaggcaug atu                                              23

<210> SEQ ID NO 488
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 488
tgccacugua gaaaggcaug atu                                            23

<210> SEQ ID NO 489
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 489
tgccacugua gaaaggcaug atu                                            23

<210> SEQ ID NO 490
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 490
tgccacugua gaaaggcaug atu                                            23

<210> SEQ ID NO 491
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 491
tgccacugua gaaaggcaug atu                                            23

<210> SEQ ID NO 492
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 492
tgccacugua gaaaggcaug atu                                            23

<210> SEQ ID NO 493
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 493
tgccacugua gaaaggcaug atu                                              23

<210> SEQ ID NO 494
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 494
tgccacugua gaaaggcaug atu                                              23

<210> SEQ ID NO 495
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 495
tgccacugua gaaaggcaug atu                                              23

<210> SEQ ID NO 496
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 496
tgccacugua gaaaggcaug atu                                              23

<210> SEQ ID NO 497
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 497
tgccacugua gaaaggcaug atu                                              23

<210> SEQ ID NO 498
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 498
tgccacugua gaaaggcaug atu                                              23

<210> SEQ ID NO 499
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 499
tgccacugua gaaaggcaug atu                                              23

<210> SEQ ID NO 500
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 500
tgccacugua gaaaggcaug atu                                              23

<210> SEQ ID NO 501
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 501
tgccacugua gaaaggcaug atu                                              23

<210> SEQ ID NO 502
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 502
tgccacugua gaaaggcaug atu                                              23

<210> SEQ ID NO 503
<211> LENGTH: 23
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 503
tgccacugua gaaaggcaug atu                                                23

<210> SEQ ID NO 504
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 504
tgccacugua gaaaggcaug atu                                                23

<210> SEQ ID NO 505
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 505
tgccacugua gaaaggcaug atu                                                23

<210> SEQ ID NO 506
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 506
tgccacugua gaaaggcaug atu                                                23

<210> SEQ ID NO 507
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 507
tgccacugua gaaaggcaug atu                                                23

<210> SEQ ID NO 508
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 508
tgccacugua gaaaggcaug atu                                            23

<210> SEQ ID NO 509
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 509
tgccacugua gaaaggcaut u                                              21

<210> SEQ ID NO 510
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 510
tgccacugua gaaaggcaut u                                              21

<210> SEQ ID NO 511
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 511
tgccacugua gaaaggcaut u                                              21

<210> SEQ ID NO 512
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 512
tgccacugua gaauggcaut u                                              21

<210> SEQ ID NO 513
<211> LENGTH: 21
<212> TYPE: DNA
```

<210> SEQ ID NO 513
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 513
tgccacugua gaaacgcaut u                                              21

<210> SEQ ID NO 514
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 514
tgccacugua gaaagccaut u                                              21

<210> SEQ ID NO 515
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 515
tgccacugua gaaagggaut u                                              21

<210> SEQ ID NO 516
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 516
tgccacugua gaaaggcuut u                                              21

<210> SEQ ID NO 517
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule: Synthetic oligonucleotide

<400> SEQUENCE: 517
tgccacugua gaaaggcaat u                                              21

<210> SEQ ID NO 518
<211> LENGTH: 23

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 518
tgccacugua gaaacgcaug atu                                             23

<210> SEQ ID NO 519
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 519
tgccacugua gaaagccaug atu                                             23

<210> SEQ ID NO 520
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 520
tgccacugua gaaaggcuug atu                                             23

<210> SEQ ID NO 521
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 521
tgccacugua gaaaggcaag atu                                             23

<210> SEQ ID NO 522
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 522
tgccacugua gaaaggcauc atu                                             23

<210> SEQ ID NO 523
```

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 523
tgccacugua gaaaggcaug utu                                              23

<210> SEQ ID NO 524
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 524
ugugcttggc tcctgccugg                                                  20

<210> SEQ ID NO 525
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 525
ucuugttacc cccgccaugg                                                  20

<210> SEQ ID NO 526
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 526
acccccgcca tggagacguu                                                  20

<210> SEQ ID NO 527
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 527
uacccccgcc atggagacgu                                                  20
```

```
<210> SEQ ID NO 528
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 528
cugcactggg cttccuggug                                                   20

<210> SEQ ID NO 529
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 529
uggacctgag gatggaccgc                                                   20

<210> SEQ ID NO 530
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 530
agggaccctc tgcacugggc                                                   20

<210> SEQ ID NO 531
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 531
cuugutaccc ccgccaugga                                                   20

<210> SEQ ID NO 532
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 532
aggcugggat cctccacguc                                                   20
```

<210> SEQ ID NO 533
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 533
aagggaccct ctgcacuggg                                               20

<210> SEQ ID NO 534
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 534
tgtgcttggc tcctgcctgg                                               20

<210> SEQ ID NO 535
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 535
tcttgttacc cccgccatgg                                               20

<210> SEQ ID NO 536
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 536
acccccgcca tggagacgtt                                               20

<210> SEQ ID NO 537
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 537 taccccgcc atggagacgt                                                20

<210> SEQ ID NO 538
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 538

-continued

```
ctgcactggg cttcctggtg                                        20

<210> SEQ ID NO 539
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 539
tggacctgag gatggaccgc                                        20

<210> SEQ ID NO 540
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 540
agggaccctc tgcactgggc                                        20

<210> SEQ ID NO 541
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 541
cttgttaccc ccgccatgga                                        20

<210> SEQ ID NO 542
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 542
aggctgggat cctccacgtc                                        20

<210> SEQ ID NO 543
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 543
aagggaccct ctgcactggg                                        20

<210> SEQ ID NO 544
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 544
ugugcuuggc uccugccugg                                              20

<210> SEQ ID NO 545
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 545
ucuuguuacc cccgccaugg                                              20

<210> SEQ ID NO 546
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 546 accccccgcca tggagacguu                                             20

<210> SEQ ID NO 547
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 547 uaccccccgcc atggagacgu                                             20

<210> SEQ ID NO 548
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 548
cugcactggg cuuccuggug                                              20

<210> SEQ ID NO 549
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 549
uggacctgag gatggaccgc                                              20

<210> SEQ ID NO 550
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 550
agggaccctc tgcacugggc                                              20

<210> SEQ ID NO 551
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 551
cuugutaccc ccgccaugga                                              20

<210> SEQ ID NO 552
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 552
aggcugggat cctccacguc                                              20

<210> SEQ ID NO 553
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 553
aagggaccct ctgcacuggg                                              20

<210> SEQ ID NO 554
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 554
```

```
tgtgcttggc tcctgcctgg                                               20

<210> SEQ ID NO 555
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 555
tcttgttacc cccgccatgg                                               20

<210> SEQ ID NO 556
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 556
acccccgcca tggagacgtt                                               20

<210> SEQ ID NO 557
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 557 taccccgcc atggagacgt                                                20

<210> SEQ ID NO 558
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 558
ctgcactggg cttcctggtg                                               20

<210> SEQ ID NO 559
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 559
tggacctgag gatggaccgc                                               20

<210> SEQ ID NO 560
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 560
```
agggaccctc tgcactgggc                                              20

<210> SEQ ID NO 561
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 561
cttgttaccc ccgccatgga                                              20

<210> SEQ ID NO 562
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 562
aggctgggat cctccacgtc                                              20

<210> SEQ ID NO 563
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 563
aagggaccct ctgcactggg                                              20

<210> SEQ ID NO 564
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 564
tgccacugua gaaaggcaug atu                                          23

<210> SEQ ID NO 565
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 565
tgccacugua gaaaggcaug atu                                          23

<210> SEQ ID NO 566
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 566
tgccacugua gaaaggcaug atu                                                23

<210> SEQ ID NO 567
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 567
tgccacugua gaaaggcatt u                                                  21

<210> SEQ ID NO 568
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 568
tgccacugua gaaaggcatg atu                                                23

<210> SEQ ID NO 569
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 569
caugaagcag gaacauacca                                                    20

<210> SEQ ID NO 570
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 570
gcaugaagca ggaacauacc                                                    20

<210> SEQ ID NO 571
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 571
```

```
ggcaugaagc aggaacauac                                                   20

<210> SEQ ID NO 572
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 572
aggcatgaag caggaacaua                                                   20

<210> SEQ ID NO 573
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 573
aaggcatgaa gcaggaacau                                                   20

<210> SEQ ID NO 574
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 574
aaaggcatga agcaggaaca                                                   20

<210> SEQ ID NO 575
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 575
gaaaggcatg aagcaggaac                                                   20

<210> SEQ ID NO 576
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 576
agaaaggcat gaagcaggaa                                                   20

<210> SEQ ID NO 577
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 577
gccactgtag aaaggcauga                                                     20

<210> SEQ ID NO 578
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 578
ggccactgta gaaaggcaug                                                     20

<210> SEQ ID NO 579
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 579
aggccactgt agaaaggcau                                                     20

<210> SEQ ID NO 580
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 580
aaggccactg tagaaaggca                                                     20

<210> SEQ ID NO 581
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 581
uaaggccact gtagaaaggc                                                     20

<210> SEQ ID NO 582
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 582
auaaggccac tgtagaaagg                                                   20

<210> SEQ ID NO 583
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 583
gauaaggcca ctgtagaaag                                                   20

<210> SEQ ID NO 584
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 584
ggauaaggcc actgtagaaa                                                   20

<210> SEQ ID NO 585
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 585
catgaagcag gaacatacca                                                   20

<210> SEQ ID NO 586
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 586
gcatgaagca ggaacatacc                                                   20

<210> SEQ ID NO 587
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 587
ggcatgaagc aggaacatac                                                   20
```

```
<210> SEQ ID NO 588
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 588
aggcatgaag caggaacata                                               20

<210> SEQ ID NO 589
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 589
aaggcatgaa gcaggaacat                                               20

<210> SEQ ID NO 590
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 590
aaaggcatga agcaggaaca                                               20

<210> SEQ ID NO 591
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 591
gaaaggcatg aagcaggaac                                               20

<210> SEQ ID NO 592
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 592
agaaaggcat gaagcaggaa                                               20

<210> SEQ ID NO 593
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 593
tagaaaggca tgaagcagga                                               20
```

```
<210> SEQ ID NO 594
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 594
gtagaaaggc atgaagcagg                                                     20

<210> SEQ ID NO 595
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 595
tgtagaaagg catgaagcag                                                     20

<210> SEQ ID NO 596
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 596
ctgtagaaag gcatgaagca                                                     20

<210> SEQ ID NO 597
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 597
actgtagaaa ggcatgaagc                                                     20

<210> SEQ ID NO 598
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 598
cactgtagaa aggcatgaag                                                     20

<210> SEQ ID NO 599
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 599
ccactgtaga aaggcatgaa                                                     20

<210> SEQ ID NO 600
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 600
gccactgtag aaaggcatga                                               20

<210> SEQ ID NO 601
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 601
ggccactgta gaaaggcatg                                               20

<210> SEQ ID NO 602
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 602
aggccactgt agaaaggcat                                               20

<210> SEQ ID NO 603
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 603
aaggccactg tagaaaggca                                               20

<210> SEQ ID NO 604
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 604
taaggccact gtagaaaggc                                               20

<210> SEQ ID NO 605
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 605
ataaggccac tgtagaaagg                                               20

<210> SEQ ID NO 606
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 606
gataaggcca ctgtagaaag                                             20

<210> SEQ ID NO 607
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 607
ggataaggcc actgtagaaa                                             20

<210> SEQ ID NO 608
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 608
caugaagcag gaacauacca                                             20

<210> SEQ ID NO 609
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 609
gcaugaagca ggaacauacc                                             20

<210> SEQ ID NO 610
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 610
ggcaugaagc aggaacauac                                             20

<210> SEQ ID NO 611
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 611
aggcatgaag caggaacaua                                             20
```

```
<210> SEQ ID NO 612
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 612
aaggcatgaa gcaggaacat                                                      20

<210> SEQ ID NO 613
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 613
aaaggcatga agcaggaaca                                                      20

<210> SEQ ID NO 614
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 614
gaaaggcatg aagcaggaac                                                      20

<210> SEQ ID NO 615
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 615
agaaaggcat gaagcaggaa                                                      20

<210> SEQ ID NO 616
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 616
tagaaaggca tgaagcagga                                                      20

<210> SEQ ID NO 617
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 617
guagaaaggc atgaagcagg                                                      20
```

<210> SEQ ID NO 618
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 618
tguagaaagg catgaagcag                                              20

<210> SEQ ID NO 619
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 619
cuguagaaag gcatgaagca                                              20

<210> SEQ ID NO 620
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 620
acuguagaaa ggcatgaagc                                              20

<210> SEQ ID NO 621
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 621
cacugtagaa aggcaugaag                                              20

<210> SEQ ID NO 622
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 622

```
ccacugtaga aaggcaugaa                                              20

<210> SEQ ID NO 623
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 623
gccactgtag aaaggcauga                                              20

<210> SEQ ID NO 624
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 624
ggccactgta gaaaggcaug                                              20

<210> SEQ ID NO 625
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 625
aggccactgt agaaaggcat                                              20

<210> SEQ ID NO 626
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 626
aaggccactg tagaaaggca                                              20

<210> SEQ ID NO 627
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 627
taaggccact gtagaaaggc                                              20

<210> SEQ ID NO 628
<211> LENGTH: 20
<212> TYPE: DNA
<213> ORGANISM: Artificial Sequence
<220> FEATURE:
```

<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 628
auaaggccac tgtagaaagg                                              20

<210> SEQ ID NO 629
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 629
gauaaggcca ctgtagaaag                                              20

<210> SEQ ID NO 630
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 630
ggauaaggcc actgtagaaa                                              20

<210> SEQ ID NO 631
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 631
catgaagcag gaacatacca                                              20

<210> SEQ ID NO 632
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 632
gcatgaagca ggaacatacc                                              20

<210> SEQ ID NO 633
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 633
ggcatgaagc aggaacatac 20

<210> SEQ ID NO 634
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 634
aggcatgaag caggaacata 20

<210> SEQ ID NO 635
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 635
aaggcatgaa gcaggaacat 20

<210> SEQ ID NO 636
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 636
aaaggcatga agcaggaaca 20

<210> SEQ ID NO 637
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 637
gaaaggcatg aagcaggaac 20

<210> SEQ ID NO 638
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 638
agaaaggcat gaagcaggaa 20

<210> SEQ ID NO 639
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 639
tagaaaggca tgaagcagga 20

<210> SEQ ID NO 640
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 640
gtagaaaggc atgaagcagg                                              20

<210> SEQ ID NO 641
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 641
tgtagaaagg catgaagcag                                              20

<210> SEQ ID NO 642
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 642
ctgtagaaag gcatgaagca                                              20

<210> SEQ ID NO 643
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 643
actgtagaaa ggcatgaagc                                              20

<210> SEQ ID NO 644
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 644
cactgtagaa aggcatgaag                                              20

<210> SEQ ID NO 645
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 645
ccactgtaga aaggcatgaa                                              20

<210> SEQ ID NO 646
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 646
gccactgtag aaaggcatga                                           20

<210> SEQ ID NO 647
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 647
ggccactgta gaaaggcatg                                           20

<210> SEQ ID NO 648
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 648
aggccactgt agaaaggcat                                           20

<210> SEQ ID NO 649
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 649
aaggccactg tagaaaggca                                           20

<210> SEQ ID NO 650
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 650
taaggccact gtagaaaggc                                           20

<210> SEQ ID NO 651
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 651
ataaggccac tgtagaaagg                                           20

```
<210> SEQ ID NO 652
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 652
gataaggcca ctgtagaaag                                              20

<210> SEQ ID NO 653
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 653
ggataaggcc actgtagaaa                                              20

<210> SEQ ID NO 654
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 654
ggacctgagg atggaccgcg                                              20

<210> SEQ ID NO 655
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 655
ggacctgagg atggaccgcg                                              20

<210> SEQ ID NO 656
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 656
tgccacugua gaaaggcaug atu                                          23

<210> SEQ ID NO 657
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 657
ggacctgagg atggaccgcg                                              20
```

<210> SEQ ID NO 658
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 658
ggacctgagg atggaccgcg                                               20

<210> SEQ ID NO 659
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 659
ggacctgagg atggaccgcg                                               20

<210> SEQ ID NO 660
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 660
ggacctgagg atggaccgcg                                               20

<210> SEQ ID NO 661
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 661
ggacctgagg atggaccgcg                                               20

<210> SEQ ID NO 662
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 662
ggacctgagg atggaccgcg                                               20

<210> SEQ ID NO 663
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 663
ggacctgagg atggaccgcg                                               20

```
<210> SEQ ID NO 664
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 664
ggacctgagg atggaccgcg                                                     20

<210> SEQ ID NO 665
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 665
ggacctgagg atggaccgcg                                                     20

<210> SEQ ID NO 666
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 666
ggacctgagg atggaccgcg                                                     20

<210> SEQ ID NO 667
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 667
ggacctgagg atggaccgcg                                                     20

<210> SEQ ID NO 668
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 668
ggacctgagg atggaccgcg                                                     20

<210> SEQ ID NO 669
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 669
ggacctgagg atggaccgcg                                                     20
```

```
<210> SEQ ID NO 670
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 670
ggacctgagg atggaccgcg                                                   20

<210> SEQ ID NO 671
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 671
ggacctgagg atggaccgcg                                                   20

<210> SEQ ID NO 672
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 672
ggacctgagg atggaccgcg                                                   20

<210> SEQ ID NO 673
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 673
tgccacugua gaaaggcaug atu                                               23

<210> SEQ ID NO 674
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 674
tgccacugua gaaaggcatg atu                                               23

<210> SEQ ID NO 675
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
    Synthetic oligonucleotide

<400> SEQUENCE: 675
tgccacugua gaaaggcatg atu                                               23

<210> SEQ ID NO 676
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 676
tgccacugua gaaaggcatg atu                                               23

<210> SEQ ID NO 677
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 677
tgccacugua gaaaggcatg atu                                               23

<210> SEQ ID NO 678
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 678
tgccacugua gaaaggcaug atu                                               23

<210> SEQ ID NO 679
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 679
tgccacugua gaaaggcaug atu                                               23

<210> SEQ ID NO 680
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide

```
<220> FEATURE:
<223> OTHER INFORMATION: Description of Combined DNA/RNA Molecule:
      Synthetic oligonucleotide

<400> SEQUENCE: 680
tgccacugua gaaaggcatg atu                                              23

<210> SEQ ID NO 681
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 681
tgccacugua gaaaggcatg atu                                              23

<210> SEQ ID NO 682
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 682
tgccacugua gaaaggcatg atu                                              23

<210> SEQ ID NO 683
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 683
tgccacugua gaaaggcatg atu                                              23

<210> SEQ ID NO 684
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 684
tgccacugua gaaaggcaug atu                                              23

<210> SEQ ID NO 685
<211> LENGTH: 23
<212> TYPE: DNA
<213> ORGANISM: Artificial Sequence
<220> FEATURE:
<223> OTHER INFORMATION: Description of Artificial Sequence: Synthetic
```

```
                oligonucleotide
<220> FEATURE:
<223> OTHER INFORMATION: Description of Combined DNA/RNA Molecule:
      Synthetic oligonucleotide

<400> SEQUENCE: 685
tgccacugua gaaaggcaug atu                                              23

<210> SEQ ID NO 686
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 686
tgccacugua gaaaggcaut uttttttggta atccactttc agagg                     45

<210> SEQ ID NO 687
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 687
tgccacugua gaaaggcaut uttttttggta atccactttc agagg                     45

<210> SEQ ID NO 688
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 688
tgccacugua gaaaggcaut uttttttggta atccactttc agagg                     45

<210> SEQ ID NO 689
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 689
tgccacugua gaaaggcaut uttttttggta atccactttc agagg                     45

<210> SEQ ID NO 690
<211> LENGTH: 45
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 690
tgccacugua gaaaggcaut utttttggta atccactttc agagg            45

<210> SEQ ID NO 691
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 691
ggacctgagg atggaccgcg                                        20

<210> SEQ ID NO 692
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 692
ggacctgagg atggaccgcg                                        20

<210> SEQ ID NO 693
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 693
ggacctgagg atggaccgcg                                        20

<210> SEQ ID NO 694
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 694
tgccacugua gaaaggcaug atu                                    23

<210> SEQ ID NO 695
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 695
```
tgccacugua gaaaggcaug atu                                                23

<210> SEQ ID NO 696
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 696
tgccacugua gaaaggcatg atu                                                23

<210> SEQ ID NO 697
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 697
tgccacugua gaaaggcatg atu                                                23

<210> SEQ ID NO 698
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 698
tgccacugua gaaaggcatg atu                                                23

<210> SEQ ID NO 699
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 699
tgccacugua gaaaggcatg atu                                                23

<210> SEQ ID NO 700
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 700
tgccacugua gaaaggcaug atu                                              23

<210> SEQ ID NO 701
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 701
ggacctgagg atggaccgcg                                                  20

<210> SEQ ID NO 702
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 702
ggacctgagg atggaccgcg                                                  20

<210> SEQ ID NO 703
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 703
ggacctgagg atggaccgcg                                                  20

<210> SEQ ID NO 704
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 704
ggacctgagg atggaccgcg                                                  20

<210> SEQ ID NO 705
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 705
ggacctgagg atggaccgcg                                                  20

<210> SEQ ID NO 706
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 706

```
ggacctgagg atggaccgcg                                              20

<210> SEQ ID NO 707
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 707
ggacctgagg atggaccgcg                                              20

<210> SEQ ID NO 708
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 708
ggacctgagg atggaccgcg                                              20

<210> SEQ ID NO 709
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 709
ggacctgagg atggaccgcg                                              20

<210> SEQ ID NO 710
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 710
ggacctgagg atggaccgcg                                              20

<210> SEQ ID NO 711
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 711
ggacctgagg atggaccgcg                                              20

<210> SEQ ID NO 712
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 712
ggacctgagg atggaccgcg                                              20
```

<210> SEQ ID NO 713
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 713
tgccacugua gaaaggcaug atu                                             23

<210> SEQ ID NO 714
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide

<400> SEQUENCE: 714
tgccacugua gaaaggcaug atu                                             23

<210> SEQ ID NO 715
<211> LENGTH: 27
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 715
cugugacgug gaggauccca gccucug                                         27

<210> SEQ ID NO 716
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 716
ggacctgagg atggaccgcg                                                 20

<210> SEQ ID NO 717
<211> LENGTH: 20
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 717
ggacctgagg atggaccgcg                                                 20

<210> SEQ ID NO 718
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 718
ctgtagaaag gcatgaagca                                              20

<210> SEQ ID NO 719
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 719
ctgtagaaag gcatgaagca                                              20

<210> SEQ ID NO 720
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 720
ccactgtaga aaggcatgaa                                              20

<210> SEQ ID NO 721
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 721
ccactgtaga aaggcatgaa                                              20

<210> SEQ ID NO 722
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 722
ctgtagaaag gcatgaagca                                              20

<210> SEQ ID NO 723
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 723
ctgtagaaag gcatgaagca                                              20

<210> SEQ ID NO 724
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 724
caugaagcag gaacauacca                                              20

<210> SEQ ID NO 725
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 725
gcaugaagca ggaacauacc                                              20

<210> SEQ ID NO 726
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 726
ggcaugaagc aggaacauac                                              20

<210> SEQ ID NO 727
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 727
aggcatgaag caggaacaua                                              20

<210> SEQ ID NO 728
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 728
aaggcatgaa gcaggaacau                                              20

<210> SEQ ID NO 729
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 729
aaaggcatga agcaggaaca                                              20

<210> SEQ ID NO 730
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 730
gaaaggcatg aagcaggaac                                                   20

<210> SEQ ID NO 731
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 731
agaaaggcat gaagcaggaa                                                   20

<210> SEQ ID NO 732
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 732
uagaaaggca tgaagcagga                                                   20

<210> SEQ ID NO 733
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 733
guagaaaggc atgaagcagg                                                   20

<210> SEQ ID NO 734
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 734
uguagaaagg catgaagcag                                                   20

<210> SEQ ID NO 735
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 735
cuguagaaag gcatgaagca                                              20

<210> SEQ ID NO 736
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 736
acuguagaaa ggcatgaagc                                              20

<210> SEQ ID NO 737
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 737
cacugtagaa aggcaugaag                                              20

<210> SEQ ID NO 738
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 738
ccacugtaga aaggcaugaa                                              20

<210> SEQ ID NO 739
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 739
gccactgtag aaaggcauga                                              20

<210> SEQ ID NO 740
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<223> OTHER INFORMATION: Description of Combined DNA/RNA Molecule:
      Synthetic oligonucleotide

<400> SEQUENCE: 740
ggccactgta gaaaggcaug                                                    20

<210> SEQ ID NO 741
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 741
aggccactgt agaaaggcau                                                    20

<210> SEQ ID NO 742
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 742
aaggccactg tagaaaggca                                                    20

<210> SEQ ID NO 743
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 743
uaaggccact gtagaaaggc                                                    20

<210> SEQ ID NO 744
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 744
auaaggccac tgtagaaagg                                                    20

<210> SEQ ID NO 745
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

```
<223> OTHER INFORMATION: Description of Combined DNA/RNA Molecule:
      Synthetic oligonucleotide

<400> SEQUENCE: 745
gauaaggcca ctgtagaaag                                              20

<210> SEQ ID NO 746
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 746
ggauaaggcc actgtagaaa                                              20

<210> SEQ ID NO 747
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 747
catgaagcag gaacatacca                                              20

<210> SEQ ID NO 748
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 748
gcatgaagca ggaacatacc                                              20

<210> SEQ ID NO 749
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 749
ggcatgaagc aggaacatac                                              20

<210> SEQ ID NO 750
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 750
aggcatgaag caggaacata                                              20

<210> SEQ ID NO 751
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 751
aaggcatgaa gcaggaacat                                                      20

<210> SEQ ID NO 752
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 752
aaaggcatga agcaggaaca                                                      20

<210> SEQ ID NO 753
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 753
gaaaggcatg aagcaggaac                                                      20

<210> SEQ ID NO 754
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 754
agaaaggcat gaagcaggaa                                                      20

<210> SEQ ID NO 755
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 755
tagaaaggca tgaagcagga                                                      20

<210> SEQ ID NO 756
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 756
gtagaaaggc atgaagcagg                                                      20

<210> SEQ ID NO 757
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 757
tgtagaaagg catgaagcag                                                   20

<210> SEQ ID NO 758
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 758
ctgtagaaag gcatgaagca                                                   20

<210> SEQ ID NO 759
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 759
actgtagaaa ggcatgaagc                                                   20

<210> SEQ ID NO 760
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 760
cactgtagaa aggcatgaag                                                   20

<210> SEQ ID NO 761
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 761
ccactgtaga aaggcatgaa                                                   20

<210> SEQ ID NO 762
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 762
gccactgtag aaaggcatga                                                   20

<210> SEQ ID NO 763
<211> LENGTH: 20
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 763
ggccactgta gaaaggcatg                                                    20

<210> SEQ ID NO 764
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 764
aggccactgt agaaaggcat                                                    20

<210> SEQ ID NO 765
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 765
aaggccactg tagaaaggca                                                    20

<210> SEQ ID NO 766
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 766
taaggccact gtagaaaggc                                                    20

<210> SEQ ID NO 767
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 767
ataaggccac tgtagaaagg                                                    20

<210> SEQ ID NO 768
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 768
gataaggcca ctgtagaaag                                                    20

<210> SEQ ID NO 769
<211> LENGTH: 20
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 769
ggataaggcc actgtagaaa                                           20

<210> SEQ ID NO 770
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 770
caugaagcag gaacauacca                                           20

<210> SEQ ID NO 771
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 771
gcaugaagca ggaacauacc                                           20

<210> SEQ ID NO 772
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 772
ggcaugaagc aggaacauac                                           20

<210> SEQ ID NO 773
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 773
aggcatgaag caggaacaua                                           20

<210> SEQ ID NO 774
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 774
aaggcatgaa gcaggaacat                                           20

<210> SEQ ID NO 775
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 775
aaaggcatga agcaggaaca                                                     20

<210> SEQ ID NO 776
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 776
gaaaggcatg aagcaggaac                                                     20

<210> SEQ ID NO 777
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 777
agaaaggcat gaagcaggaa                                                     20

<210> SEQ ID NO 778
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 778
tagaaaggca tgaagcagga                                                     20

<210> SEQ ID NO 779
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 779
guagaaaggc atgaagcagg                                                     20

<210> SEQ ID NO 780
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 780
tguagaaagg catgaagcag                                                     20
```

```
<210> SEQ ID NO 781
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 781
cuguagaaag gcatgaagca                                                    20

<210> SEQ ID NO 782
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 782
acuguagaaa ggcatgaagc                                                    20

<210> SEQ ID NO 783
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 783
cacugtagaa aggcaugaag                                                    20

<210> SEQ ID NO 784
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 784
ccacugtaga aaggcaugaa                                                    20

<210> SEQ ID NO 785
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 785
gccactgtag aaaggcauga                                                    20
```

<210> SEQ ID NO 786
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 786
ggccactgta gaaaggcaug                                               20

<210> SEQ ID NO 787
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 787
aggccactgt agaaaggcat                                               20

<210> SEQ ID NO 788
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 788
aaggccactg tagaaaggca                                               20

<210> SEQ ID NO 789
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 789
taaggccact gtagaaaggc                                               20

<210> SEQ ID NO 790
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 790
auaaggccac tgtagaaagg                                               20

<210> SEQ ID NO 791
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Description of Combined DNA/RNA Molecule:
      Synthetic oligonucleotide

<400> SEQUENCE: 791
gauaaggcca ctgtagaaag                                          20

<210> SEQ ID NO 792
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 792
ggauaaggcc actgtagaaa                                          20

<210> SEQ ID NO 793
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 793
catgaagcag gaacatacca                                          20

<210> SEQ ID NO 794
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 794
gcatgaagca ggaacatacc                                          20

<210> SEQ ID NO 795
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 795
ggcatgaagc aggaacatac                                          20

<210> SEQ ID NO 796
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 796
aggcatgaag caggaacata                                          20

<210> SEQ ID NO 797

```
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 797
aaggcatgaa gcaggaacat                                                    20

<210> SEQ ID NO 798
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 798
aaaggcatga agcaggaaca                                                    20

<210> SEQ ID NO 799
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 799
gaaaggcatg aagcaggaac                                                    20

<210> SEQ ID NO 800
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 800
agaaaggcat gaagcaggaa                                                    20

<210> SEQ ID NO 801
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 801
tagaaaggca tgaagcagga                                                    20

<210> SEQ ID NO 802
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 802
gtagaaaggc atgaagcagg                                                    20

<210> SEQ ID NO 803
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 803
tgtagaaagg catgaagcag                                                20

<210> SEQ ID NO 804
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 804
ctgtagaaag gcatgaagca                                                20

<210> SEQ ID NO 805
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 805
actgtagaaa ggcatgaagc                                                20

<210> SEQ ID NO 806
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 806
cactgtagaa aggcatgaag                                                20

<210> SEQ ID NO 807
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 807
ccactgtaga aaggcatgaa                                                20

<210> SEQ ID NO 808
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 808
gccactgtag aaaggcatga                                                20

<210> SEQ ID NO 809
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 809
ggccactgta gaaaggcatg                                              20

<210> SEQ ID NO 810
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 810
aggccactgt agaaaggcat                                              20

<210> SEQ ID NO 811
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 811
aaggccactg tagaaaggca                                              20

<210> SEQ ID NO 812
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 812
taaggccact gtagaaaggc                                              20

<210> SEQ ID NO 813
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 813
ataaggccac tgtagaaagg                                              20

<210> SEQ ID NO 814
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 814
gataaggcca ctgtagaaag                                              20

<210> SEQ ID NO 815
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 815
ggataaggcc actgtagaaa                                                   20

<210> SEQ ID NO 816
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 816
tgccacugua gaaaggcaut uttttggta atccactttc agagg                        45

<210> SEQ ID NO 817
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 817
tgccacugua gaaaggcaut uttttggta atccactttc agagg                        45

<210> SEQ ID NO 818
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 818
tgccacugua gaaaggcaut uttttggta atccactttc agagg                        45

<210> SEQ ID NO 819
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 819
tgccacugua gaaaggcaut uttttggta atccactttc agagg                        45

<210> SEQ ID NO 820
<211> LENGTH: 45
<212> TYPE: DNA
<213> ORGANISM: Artificial Sequence
<220> FEATURE:
<223> OTHER INFORMATION: Description of Artificial Sequence: Synthetic
```

```
      oligonucleotide
<220> FEATURE:
<223> OTHER INFORMATION: Description of Combined DNA/RNA Molecule:
      Synthetic oligonucleotide

<400> SEQUENCE: 820
tgccacugua gaaaggcaut utttttggta atccactttc agagg              45

<210> SEQ ID NO 821
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 821
uugguauguu ccugcuucau gccuucuac aguggccuua uccc                44

<210> SEQ ID NO 822
<211> LENGTH: 44
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 822
uugguauguu ccugcuucau ccccuucuac aguggccuua uccc                44

<210> SEQ ID NO 823
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 823
ctgtagaaag gcatgaagca                                          20

<210> SEQ ID NO 824
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 824
ctgtagaaag gcatgaagca                                          20

<210> SEQ ID NO 825
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 825
ccactgtaga aaggcatgaa                                          20

<210> SEQ ID NO 826
<211> LENGTH: 20
<212> TYPE: DNA
<213> ORGANISM: Artificial Sequence
```

<220> FEATURE:
<223> OTHER INFORMATION: Description of Artificial Sequence: Synthetic
      oligonucleotide

<400> SEQUENCE: 826
ccactgtaga aaggcatgaa                                                    20

<210> SEQ ID NO 827
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 827
ctgtagaaag gcatgaagca                                                    20

<210> SEQ ID NO 828
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 828
ctgtagaaag gcatgaagca                                                    20

<210> SEQ ID NO 829
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 829
ccuucccuga agguuccucc                                                    20

<210> SEQ ID NO 830
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 830
tgccacugua gaaaggcaug atu                                                23

<210> SEQ ID NO 831
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 831
ctgtagaaag gcatgaagca                                                    20

<210> SEQ ID NO 832
<211> LENGTH: 20

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 832
ctgtagaaag gcatgaagca                                                   20

<210> SEQ ID NO 833
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 833
ctgtagaaag gcatgaagca                                                   20

<210> SEQ ID NO 834
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 834
ctgtagaaag gcatgaagca                                                   20

<210> SEQ ID NO 835
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 835
ccacugtaga aaggcatgaa                                                   20

<210> SEQ ID NO 836
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 836
ccactgtaga aaggcatgaa                                                   20

<210> SEQ ID NO 837
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 837
```
ccacugtaga aaggcatgaa                                          20

<210> SEQ ID NO 838
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 838
ccactgtaga aaggcatgaa                                          20

<210> SEQ ID NO 839
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 839
ctgtagaaag gcatgaagca                                          20

<210> SEQ ID NO 840
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 840
ccactgtaga aaggcatgaa                                          20

<210> SEQ ID NO 841
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 841
tgccacugua gaaaggcaut uttttttggta atccactttc agagg             45

<210> SEQ ID NO 842
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 842
ggacctgagg atggaccgcg                                          20

<210> SEQ ID NO 843
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 843
ggacctgagg atggaccgcg                                              20

<210> SEQ ID NO 844
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 844
ggacctgagg atggaccgcg                                              20

<210> SEQ ID NO 845
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 845
ggacctgagg atggaccgcg                                              20

<210> SEQ ID NO 846
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 846
tgccacugua gaaaggcaug atu                                          23

<210> SEQ ID NO 847
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 847
tgccacugua gaaaggcaut u                                            21

<210> SEQ ID NO 848
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 848
tgccacugua gaaaggcaut u                                            21
```

```
<210> SEQ ID NO 849
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 849
tgccacugua gaaaggcaut u                                            21

<210> SEQ ID NO 850
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 850
tgccacugua gaaaggcaut u                                            21

<210> SEQ ID NO 851
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 851
tgccacugua gaaaggcaut u                                            21

<210> SEQ ID NO 852
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 852
tgccacugua gaaaggcaut u                                            21

<210> SEQ ID NO 853
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 853
tgccacugua gaaaggcaut u                                            21
```

<210> SEQ ID NO 854
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 854
tgccacugua gaaaggcaut u                                              21

<210> SEQ ID NO 855
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 855
tgccacugua gaaaggcaug atu                                            23

<210> SEQ ID NO 856
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 856
tgccacugua gaaaggcaug atu                                            23

<210> SEQ ID NO 857
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 857
tgccacugua gaaaggcaug atu                                            23

<210> SEQ ID NO 858
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 858
tgccacugua gaaaggcaug atu                                            23

<210> SEQ ID NO 859
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 859
tgccacugua gaaaggcaug atu                                              23

<210> SEQ ID NO 860
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 860
tgccacugua gaaaggcaug atu                                              23

<210> SEQ ID NO 861
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 861
tgccacugua gaaaggcaug atu                                              23

<210> SEQ ID NO 862
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 862
tgccacugua gaaaggcaug atu                                              23

<210> SEQ ID NO 863
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 863
ccactgtaga aaggcatgaa                                                  20

-continued

```
<210> SEQ ID NO 864
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 864
ccactgtaga aaggcatgaa                                                   20

<210> SEQ ID NO 865
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 865
ccactgtaga aaggcatgaa                                                   20

<210> SEQ ID NO 866
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 866
ccactgtaga aaggcatgaa                                                   20

<210> SEQ ID NO 867
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 867
tgccacugua gaaaggcaut u                                                 21

<210> SEQ ID NO 868
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 868
tgccacugua gaaaggcaug atu                                               23

<210> SEQ ID NO 869
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

<223> OTHER INFORMATION: Description of Combined DNA/RNA Molecule:
      Synthetic oligonucleotide

<400> SEQUENCE: 869
tgccacugua gaaaggcaut u                                              21

<210> SEQ ID NO 870
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 870
tgccacugua gaaaggcaug atu                                            23

<210> SEQ ID NO 871
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 871
tgccacugua gaaaggcaut u                                              21

<210> SEQ ID NO 872
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 872
tgccacugua gaaaggcaug atu                                            23

<210> SEQ ID NO 873
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 873
tgccacugua gaaaggcaut u                                              21

<210> SEQ ID NO 874
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 874
tgccacugua gaaaggcaug atu                                              23

<210> SEQ ID NO 875
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 875
ctgtagaaag gcatgaagca                                                  20

<210> SEQ ID NO 876
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 876
ccactgtaga aaggcatgaa                                                  20

<210> SEQ ID NO 877
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 877
ctgtagaaag gcatgaagca                                                  20

<210> SEQ ID NO 878
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 878
ccactgtaga aaggcaugaa                                                  20

<210> SEQ ID NO 879
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 879
ctgtagaaag gcatgaagca                                                  20

<210> SEQ ID NO 880
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 880
ccacugtaga aaggcatgaa                                                   20

<210> SEQ ID NO 881
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 881
ctgtagaaag gcatgaagca                                                   20

<210> SEQ ID NO 882
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 882
ccacugtaga aaggcaugaa                                                   20

<210> SEQ ID NO 883
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 883
ctgtagaaag gcatgaagca                                                   20

<210> SEQ ID NO 884
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 884
ccactgtaga aaggcatgaa                                                   20

<210> SEQ ID NO 885
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 885
```
ctgtagaaag gcatgaagca                                                    20

<210> SEQ ID NO 886
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 886
ctgtagaaag gcatgaagca                                                    20

<210> SEQ ID NO 887
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 887
ctgtagaaag gcatgaagca                                                    20

<210> SEQ ID NO 888
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 888
ctgtagaaag gcatgaagca                                                    20

<210> SEQ ID NO 889
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 889
ctgtagaaag gcatgaagca                                                    20

<210> SEQ ID NO 890
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 890
ctgtagaaag gcatgaagca                                                    20

<210> SEQ ID NO 891
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide -continued

```
<400> SEQUENCE: 891
ccacugtaga aaggcaugaa                                                   20

<210> SEQ ID NO 892
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 892
ctgtagaaag gcatgaagca                                                   20

<210> SEQ ID NO 893
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 893
ccactgtaga aaggcatgaa                                                   20

<210> SEQ ID NO 894
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 894
ctgtagaaag gcatgaagca                                                   20

<210> SEQ ID NO 895
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 895
ctgtagaaag gcatgaagca                                                   20

<210> SEQ ID NO 896
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 896
ctgtagaaag gcatgaagca                                                   20

<210> SEQ ID NO 897
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 897
```
ctgtagaaag gcatgaagca                                          20

<210> SEQ ID NO 898
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 898
ctgtagaaag gcatgaagca                                          20

<210> SEQ ID NO 899
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 899
ctgtagaaag gcatgaagca                                          20

<210> SEQ ID NO 900
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 900
ccacugtaga aaggcaugaa                                          20

<210> SEQ ID NO 901
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 901
ctgtagaaag gcatgaagca                                          20

<210> SEQ ID NO 902
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 902
ccactgtaga aaggcatgaa                                          20

<210> SEQ ID NO 903
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 903
ctgtagaaag gcatgaagca                                                    20

<210> SEQ ID NO 904
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 904
ctgtagaaag gcatgaagca                                                    20

<210> SEQ ID NO 905
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 905
ctgtagaaag gcatgaagca                                                    20

<210> SEQ ID NO 906
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 906
ctgtagaaag gcatgaagca                                                    20

<210> SEQ ID NO 907
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 907
ctgtagaaag gcatgaagca                                                    20

<210> SEQ ID NO 908
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 908
ccacugtaga aaggcaugaa                                                    20

<210> SEQ ID NO 909
<211> LENGTH: 20
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 909
ccacugtaga aaggcaugaa                                              20

<210> SEQ ID NO 910
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 910
ccacugtaga aaggcaugaa                                              20

<210> SEQ ID NO 911
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 911
tgccacugua gaaaggcaug atu                                          23

<210> SEQ ID NO 912
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 912
tgccacugua gaaaggcaug atu                                          23

<210> SEQ ID NO 913
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 913
tgccacugua gaaaggcaug atu                                          23

<210> SEQ ID NO 914
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 914
tgccacugua gaaaggcaug atu                                              23

<210> SEQ ID NO 915
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 915
cugcuucaug ccuuucuaca gugg                                             24

<210> SEQ ID NO 916
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 916
cugcuucauc cccuucuaca gugg                                             24

<210> SEQ ID NO 917
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 917
ugtagaaagg catgaagcag                                                  20

<210> SEQ ID NO 918
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 918
uguagaaagg catgaagcag                                                  20

<210> SEQ ID NO 919
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 919
```
tgtagaaagg catgaagcag                                          20

<210> SEQ ID NO 920
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 920
uguagaaagg catgaagcag                                          20

<210> SEQ ID NO 921
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 921
cuguagaaag gcatgaagca                                          20

<210> SEQ ID NO 922
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 922
ctgtagaaag gcatgaagca                                          20

<210> SEQ ID NO 923
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 923
cuguagaaag gcatgaagca                                          20

<210> SEQ ID NO 924
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 924
actguagaaa ggcatgaagc                                          20

<210> SEQ ID NO 925
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 925
acuguagaaa ggcatgaagc                                               20

<210> SEQ ID NO 926
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 926
actgtagaaa ggcatgaagc                                               20

<210> SEQ ID NO 927
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 927
acuguagaaa ggcatgaagc                                               20

<210> SEQ ID NO 928
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 928
cactgtagaa aggcaugaag                                               20

<210> SEQ ID NO 929
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 929
cacugtagaa aggcaugaag                                               20

```
<210> SEQ ID NO 930
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 930
cactgtagaa aggcaugaag                                              20

<210> SEQ ID NO 931
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 931
cacugtagaa aggcatgaag                                              20

<210> SEQ ID NO 932
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 932
ccacugtaga aaggcatgaa                                              20

<210> SEQ ID NO 933
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 933
ccactgtaga aaggcaugaa                                              20

<210> SEQ ID NO 934
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 934
ccacugtaga aaggcatgaa                                              20
```

```
<210> SEQ ID NO 935
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 935
tgccacugua gaaaggcaug atu                                             23

<210> SEQ ID NO 936
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 936
tgccacugua gaaaggcaug atu                                             23

<210> SEQ ID NO 937
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 937
tgccacugua gaaaggcaug atu                                             23

<210> SEQ ID NO 938
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 938
tgccacugua gaaaggcaug atu                                             23

<210> SEQ ID NO 939
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 939
tgccacugua gaaaggcaug atu                                             23
```

<210> SEQ ID NO 940
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 940
tgccacugua gaaaggcaug atu                                              23

<210> SEQ ID NO 941
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 941
tgccacugua gaaaggcaug atu                                              23

<210> SEQ ID NO 942
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 942
tgccacugua gaaaggcaug atu                                              23

<210> SEQ ID NO 943
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 943
tgtagaaagg gatgaagcag                                                  20

<210> SEQ ID NO 944
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 944
ctgtagaaag ggatgaagca                                                  20

<210> SEQ ID NO 945
<211> LENGTH: 20
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 945
actgtagaaa gggatgaagc                                                 20

<210> SEQ ID NO 946
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 946
cactgtagaa agggatgaag                                                 20

<210> SEQ ID NO 947
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 947
ccactgtaga aagggatgaa                                                 20

<210> SEQ ID NO 948
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 948
tgtagaaagg gatgaagcag                                                 20

<210> SEQ ID NO 949
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 949
ctgtagaaag ggatgaagca                                                 20

<210> SEQ ID NO 950
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 950
actgtagaaa gggatgaagc                                                 20

<210> SEQ ID NO 951
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 951
cactgtagaa agggatgaag                                                    20

<210> SEQ ID NO 952
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 952
ccactgtaga aagggatgaa                                                    20

<210> SEQ ID NO 953
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 953
ugtagaaagg gatgaagcag                                                    20

<210> SEQ ID NO 954
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 954
ctgtagaaag ggatgaagca                                                    20

<210> SEQ ID NO 955
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 955
actguagaaa gggatgaagc                                                    20

<210> SEQ ID NO 956
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 956
```

```
cactgtagaa agggaugaag                                            20

<210> SEQ ID NO 957
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 957
ccacugtaga aagggaugaa                                            20

<210> SEQ ID NO 958
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 958
tgccacugua gaaaggcaug atu                                        23

<210> SEQ ID NO 959
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 959
tgccacugua gaaaggcaug atu                                        23

<210> SEQ ID NO 960
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 960
tgccacugua gaaaggcaug atu                                        23

<210> SEQ ID NO 961
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

```
<400> SEQUENCE: 961
tgccacugua gaaaggcaug atu                                              23

<210> SEQ ID NO 962
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 962
tgccacugua gaaaggcaug atu                                              23

<210> SEQ ID NO 963
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 963
tgccacugua gaaaggcaug atu                                              23

<210> SEQ ID NO 964
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 964
tgccacugua gaaaggcaug atu                                              23

<210> SEQ ID NO 965
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 965
tgccacugua gaaaggcaug atu                                              23

<210> SEQ ID NO 966
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
```

<400> SEQUENCE: 966
tgccacugua gaaaggcaug atu         23

<210> SEQ ID NO 967
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 967
tgccacugua gaaaggcaug atu         23

<210> SEQ ID NO 968
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 968
tgccacugua gaaaggcaug atu         23

<210> SEQ ID NO 969
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 969
tgccacugua gaaaggcaug atu         23

<210> SEQ ID NO 970
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 970
tgccacugua gaaaggcaug atu         23

<210> SEQ ID NO 971
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

Synthetic oligonucleotide

<400> SEQUENCE: 971
tgccacugua gaaaggcaug atu                                           23

<210> SEQ ID NO 972
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 972
tgccacugua gaaaggcaug atu                                           23

<210> SEQ ID NO 973
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 973
ctgtagaaag gcatgaagca                                               20

<210> SEQ ID NO 974
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 974
ctgtagaaag gcatgaagca                                               20

<210> SEQ ID NO 975
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 975
ctgtagaaag gcatgaagca                                               20

<210> SEQ ID NO 976
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 976
ctgtagaaag gcatgaagca                                               20

<210> SEQ ID NO 977
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 977
ctgtagaaag gcatgaagca                                                    20

<210> SEQ ID NO 978
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 978
ctgtagaaag gcatgaagca                                                    20

<210> SEQ ID NO 979
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 979
ctgtagaaag gcatgaagca                                                    20

<210> SEQ ID NO 980
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 980
tgccacugua gaaaggcaug atu                                                23

<210> SEQ ID NO 981
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 981
tgccacugua gaaaggcaug atu                                                23

<210> SEQ ID NO 982
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 982
ctgtagaaag gcatgaagca                                                    20
```

```
<210> SEQ ID NO 983
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 983
ctgtagaaag gcatgaagca                                                    20

<210> SEQ ID NO 984
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 984
ctgtagaaag gcatgaagca                                                    20

<210> SEQ ID NO 985
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 985
tgccacugua gaaaggcaug atu                                                23

<210> SEQ ID NO 986
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 986
tgccacugua gaaaggcaug atu                                                23

<210> SEQ ID NO 987
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 987
ctgtagaaag gcatgaagca                                                    20

<210> SEQ ID NO 988
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 988
ctgtagaaag gcatgaagca                                               20

<210> SEQ ID NO 989
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 989
ctgtagaaag gcatgaagca                                               20

<210> SEQ ID NO 990
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 990
ctgtagaaag gcatgaagca                                               20

<210> SEQ ID NO 991
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 991
ctgtagaaag gcatgaagca                                               20

<210> SEQ ID NO 992
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 992
ctgtagaaag gcatgaagca                                               20

<210> SEQ ID NO 993
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 993
ctgtagaaag gcatgaagca                                               20

<210> SEQ ID NO 994
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 994
ctgtagaaag gcatgaagca                                              20

<210> SEQ ID NO 995
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 995
ctgtagaaag gcatgaagca                                              20

<210> SEQ ID NO 996
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 996
ctgtagaaag gcatgaagca                                              20

<210> SEQ ID NO 997
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 997
ctgtagaaag gcatgaagca                                              20

<210> SEQ ID NO 998
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 998
ctgtagaaag gcatgaagca                                              20

<210> SEQ ID NO 999
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 999
ctgtagaaag gcatgaagca                                              20

<210> SEQ ID NO 1000
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1000
```

```
ctgtagaaag gcatgaagca                                                   20

<210> SEQ ID NO 1001
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1001
ctgtagaaag gcatgaagca                                                   20

<210> SEQ ID NO 1002
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1002
ctgtagaaag gcatgaagca                                                   20

<210> SEQ ID NO 1003
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1003
tccuucccug aagguuccuc ctu                                               23

<210> SEQ ID NO 1004
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1004
tccuucccug aagguuccuc ctu                                               23

<210> SEQ ID NO 1005
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1005
tccuucccug aagguuccuc ctu                                               23

<210> SEQ ID NO 1006
```

```
<210> SEQ ID NO 1006
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1006
tccuucccug aagguuccuc ctu                                             23

<210> SEQ ID NO 1007
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1007
tccuucccug aagguuccuc ctu                                             23

<210> SEQ ID NO 1008
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1008
tccuucccug aagguuccuc ctu                                             23

<210> SEQ ID NO 1009
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1009
tccuucccug aagguuccuc ctu                                             23

<210> SEQ ID NO 1010
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1010
tccuucccug aagguuccuc ctu                                             23
```

```
<210> SEQ ID NO 1011
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1011
tgccacugua gaaaggcaug atu                                              23

<210> SEQ ID NO 1012
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1012
tgccacugua gaaaggcaug atu                                              23

<210> SEQ ID NO 1013
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1013
tgccacugua gaaaggcaug atu                                              23

<210> SEQ ID NO 1014
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1014
tgccacugua gaaaggcaug atu                                              23

<210> SEQ ID NO 1015
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1015
ctgtagaaag gcatgaagca                                                  20

<210> SEQ ID NO 1016
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1016
ctgtagaaag gcatgaagca                                                  20

<210> SEQ ID NO 1017
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1017
ctgtagaaag gcatgaagca                                                  20

<210> SEQ ID NO 1018
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1018
ctgtagaaag gcatgaagca                                                  20

<210> SEQ ID NO 1019
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1019
ctgtagaaag gcatgaagca                                                  20

<210> SEQ ID NO 1020
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1020
ctgtagaaag gcatgaagca                                                  20

<210> SEQ ID NO 1021
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1021
tgccacugua gaaaggcaug atu                                              23
```

```
<210> SEQ ID NO 1022
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1022
tgccacugua gaaaggcaug atu                                              23

<210> SEQ ID NO 1023
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1023
tgccacugua gaaaggcaug atu                                              23

<210> SEQ ID NO 1024
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1024
tgccacugua gaaaggcaug atu                                              23

<210> SEQ ID NO 1025
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1025
cactgtagaa aggcatgaag cagg                                             24

<210> SEQ ID NO 1026
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1026
cactgtagaa aggcatgaag cagg                                             24

<210> SEQ ID NO 1027
<211> LENGTH: 24
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 1027
cactgtagaa aggcatgaag cagg                                              24

<210> SEQ ID NO 1028
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1028
cactgtagaa aggcatgaag cagg                                              24

<210> SEQ ID NO 1029
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1029
cactgtagaa aggcatgaag cagg                                              24

<210> SEQ ID NO 1030
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1030
cactgtagaa aggcatgaag cagg                                              24

<210> SEQ ID NO 1031
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1031
cactgtagaa aggcatgaag cagg                                              24

<210> SEQ ID NO 1032
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1032
cactgtagaa aggcatgaag cagg                                              24

<210> SEQ ID NO 1033
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1033
cactgtagaa aggcatgaag cagg                                          24

<210> SEQ ID NO 1034
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1034
cactgtagaa aggcatgaag cagg                                          24

<210> SEQ ID NO 1035
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1035
cactgtagaa aggcatgaag cagg                                          24

<210> SEQ ID NO 1036
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1036
cactgtagaa aggcatgaag cagg                                          24

<210> SEQ ID NO 1037
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1037
tgccacugua gaaaggcaug auu                                           23

<210> SEQ ID NO 1038
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1038
tgccacugua gaaaggcaug auu                                           23

<210> SEQ ID NO 1039

-continued

```
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1039
tgccacugua gaaaggcaug auu                                              23

<210> SEQ ID NO 1040
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1040
tgccacugua gaaaggcaug auu                                              23

<210> SEQ ID NO 1041
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1041
tgccacugua gaaaggcaug auu                                              23

<210> SEQ ID NO 1042
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1042
tgccacugua gaaaggcaug auu                                              23

<210> SEQ ID NO 1043
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1043
tgccacugua gaaaggcaug auu                                              23
```

```
<210> SEQ ID NO 1044
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1044
tgccacugua gaaaggcaug auu                                              23

<210> SEQ ID NO 1045
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1045
tgccacugua gaaaggcaug atu                                              23

<210> SEQ ID NO 1046
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1046
tgccacugua gaaaggcaug atu                                              23

<210> SEQ ID NO 1047
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1047
tgccacugua gaaaggcaug atu                                              23

<210> SEQ ID NO 1048
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1048
tgccacugua gaaaggcaug atu                                              23
```

<210> SEQ ID NO 1049
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1049
ccugcuucau gccuuucuac agug                                           24

<210> SEQ ID NO 1050
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1050
ccugcuucau ccccuucuac agug                                           24

<210> SEQ ID NO 1051
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1051
tgccacugua gaaaggcaug atu                                            23

<210> SEQ ID NO 1052
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1052
tgccacugua gaaaggcaug atu                                            23

<210> SEQ ID NO 1053
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1053
cuucaugccu uucuacagug gccu                                           24

<210> SEQ ID NO 1054
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

```
<400> SEQUENCE: 1054
cuucaucccc uucuacagug gccu                                          24

<210> SEQ ID NO 1055
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1055
gccacuguag aaaggcauga tu                                            22

<210> SEQ ID NO 1056
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1056
tccacuguag aaaggcauga tu                                            22

<210> SEQ ID NO 1057
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1057
tgcacuguag aaaggcauga tu                                            22

<210> SEQ ID NO 1058
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1058
tgcacuguag aaaggcauga tu                                            22

<210> SEQ ID NO 1059
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
```

Synthetic oligonucleotide

<400> SEQUENCE: 1059
tgcccuguag aaaggcauga tu                                              22

<210> SEQ ID NO 1060
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1060
tgccauguag aaaggcauga tu                                              22

<210> SEQ ID NO 1061
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1061
tgccacguag aaaggcauga tu                                              22

<210> SEQ ID NO 1062
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1062
tgccacuuag aaaggcauga tu                                              22

<210> SEQ ID NO 1063
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1063
tgccacugag aaaggcauga tu                                              22

<210> SEQ ID NO 1064
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:

<223> OTHER INFORMATION: Description of Combined DNA/RNA Molecule:
      Synthetic oligonucleotide

<400> SEQUENCE: 1064
tgccacugug aaaggcauga tu                                                  22

<210> SEQ ID NO 1065
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1065
tgccacugua aaaggcauga tu                                                  22

<210> SEQ ID NO 1066
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1066
tgccacugua gaaggcauga tu                                                  22

<210> SEQ ID NO 1067
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1067
gccacuguag aaaggcauga tu                                                  22

<210> SEQ ID NO 1068
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1068
tccacuguag aaaggcauga tu                                                  22

<210> SEQ ID NO 1069
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

```
<220> FEATURE:
<223> OTHER INFORMATION: Description of Combined DNA/RNA Molecule:
      Synthetic oligonucleotide

<400> SEQUENCE: 1069
tgcacuguag aaaggcauga tu                                                   22

<210> SEQ ID NO 1070
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1070
tgcacuguag aaaggcauga tu                                                   22

<210> SEQ ID NO 1071
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1071
tgcccuguag aaaggcauga tu                                                   22

<210> SEQ ID NO 1072
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1072
tgccauguag aaaggcauga tu                                                   22

<210> SEQ ID NO 1073
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1073
tgccacguag aaaggcauga tu                                                   22

<210> SEQ ID NO 1074
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
            oligonucleotide
<220> FEATURE:
<223> OTHER INFORMATION: Description of Combined DNA/RNA Molecule:
      Synthetic oligonucleotide

<400> SEQUENCE: 1074
tgccacuuag aaaggcauga tu                                              22

<210> SEQ ID NO 1075
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1075
tgccacugag aaaggcauga tu                                              22

<210> SEQ ID NO 1076
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1076
tgccacugug aaaggcauga tu                                              22

<210> SEQ ID NO 1077
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1077
tgccacugua aaaggcauga tu                                              22

<210> SEQ ID NO 1078
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1078
tgccacugua gaaggcauga tu                                              22

<210> SEQ ID NO 1079
<211> LENGTH: 23
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1079
tgccacugua gaaaggcaug atu                                           23

<210> SEQ ID NO 1080
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1080
cactgtagaa aggcatgaag cagg                                          24

<210> SEQ ID NO 1081
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1081
cactgtagaa aggcatgaag cagg                                          24

<210> SEQ ID NO 1082
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1082
cactgtagaa aggcatgaag cagg                                          24

<210> SEQ ID NO 1083
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1083
cactgtagaa aggcatgaag cagg                                          24

<210> SEQ ID NO 1084
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1084
cactgtagaa aggcatgaag cagg                                          24

<210> SEQ ID NO 1085
<211> LENGTH: 24
<212> TYPE: DNA
```

<210> SEQ ID NO 1085
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1085
cactgtagaa aggcatgaag cagg        24

<210> SEQ ID NO 1086
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1086
cactgtagaa aggcatgaag cagg        24

<210> SEQ ID NO 1087
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1087
cactgtagaa aggcatgaag cagg        24

<210> SEQ ID NO 1088
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1088
cactgtagaa aggcatgaag cagg        24

<210> SEQ ID NO 1089
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1089
cactgtagaa aggcatgaag cagg        24

<210> SEQ ID NO 1090
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1090
cactgtagaa aggcatgaag cagg        24

<210> SEQ ID NO 1091
<211> LENGTH: 24
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1091
cactgtagaa aggcatgaag cagg                                          24

<210> SEQ ID NO 1092
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1092
cactgtagaa aggcatgaag cagg                                          24

<210> SEQ ID NO 1093
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1093
cactgtagaa aggcatgaag cagg                                          24

<210> SEQ ID NO 1094
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1094
cactgtagaa aggcatgaag cagg                                          24

<210> SEQ ID NO 1095
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1095
tgccacugua gaaaggcaug atu                                           23

<210> SEQ ID NO 1096
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1096
tgccacugua gaaaggcaug atu                                           23
```

<210> SEQ ID NO 1097
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1097
tgccacugua gaaaggcaug atu                                             23

<210> SEQ ID NO 1098
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1098
tgccacugua gaaaggcaug atu                                             23

<210> SEQ ID NO 1099
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1099
tgccacugua gaaaggcaug atu                                             23

<210> SEQ ID NO 1100
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1100
tgccacugua gaaaggcaug atu                                             23

<210> SEQ ID NO 1101
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1101
actgtagaaa ggcatgaagc ag                                              22

<210> SEQ ID NO 1102

```
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1102
actgtagaaa ggcatgaagc ag                                              22

<210> SEQ ID NO 1103
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1103
actgtagaaa ggcatgaagc ag                                              22

<210> SEQ ID NO 1104
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1104
actgtagaaa ggcatgaagc ag                                              22

<210> SEQ ID NO 1105
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1105
actgtagaaa ggcatgaagc ag                                              22

<210> SEQ ID NO 1106
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1106
actgtagaaa ggcatgaagc ag                                              22

<210> SEQ ID NO 1107
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1107
actgtagaaa ggcatgaagc ag                                              22

<210> SEQ ID NO 1108
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1108
actgtagaaa ggcatgaagc ag                                              22

<210> SEQ ID NO 1109
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1109
actgtagaaa ggcatgaagc ag                                              22

<210> SEQ ID NO 1110
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1110
actgtagaaa ggcatgaagc ag                                              22

<210> SEQ ID NO 1111
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1111
actgtagaaa ggcatgaagc ag                                              22

<210> SEQ ID NO 1112
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1112
actgtagaaa ggcatgaagc ag                                              22

<210> SEQ ID NO 1113
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1113
actgtagaaa ggcatgaagc ag                                              22

<210> SEQ ID NO 1114
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 1114
actgtagaaa ggcatgaagc ag                                              22

<210> SEQ ID NO 1115
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1115
actgtagaaa ggcatgaagc ag                                              22

<210> SEQ ID NO 1116
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1116
ctgtagaaag gcatgaagca                                                 20

<210> SEQ ID NO 1117
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1117
ctgtagaaag gcatgaagca                                                 20

<210> SEQ ID NO 1118
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1118
ctgtagaaag gcatgaagca                                                 20

<210> SEQ ID NO 1119
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1119
gcuucaugcc uuucuacagu ggccu                                           25

<210> SEQ ID NO 1120
<211> LENGTH: 25
<212> TYPE: RNA
<213> ORGANISM: Artificial Sequence
```

<220> FEATURE:
<223> OTHER INFORMATION: Description of Artificial Sequence: Synthetic
      oligonucleotide

<400> SEQUENCE: 1120
gcuucauccc cuucuacagu ggccu                                       25

<210> SEQ ID NO 1121
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1121
tgccacugua gaaaggcaug atu                                         23

<210> SEQ ID NO 1122
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1122
tgccacugua gaaaggcaug atu                                         23

<210> SEQ ID NO 1123
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1123
tgccacugua gaaaggcaut u                                           21

<210> SEQ ID NO 1124
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 1124
tgccacugua gaaaggcaut u                                           21

<210> SEQ ID NO 1125
<211> LENGTH: 21
<212> TYPE: DNA
<213> ORGANISM: Artificial Sequence
<220> FEATURE:
<223> OTHER INFORMATION: Description of Artificial Sequence: Synthetic

```
       oligonucleotide
<220>  FEATURE:
<223>  OTHER INFORMATION: Description of Combined DNA/RNA Molecule:
       Synthetic oligonucleotide

<400> SEQUENCE: 1125
tgccacugua gaaaggcaut u                                                   21

<210>  SEQ ID NO 1126
<211>  LENGTH: 21
<212>  TYPE: DNA
<213>  ORGANISM: Artificial Sequence
<220>  FEATURE:
<223>  OTHER INFORMATION: Description of Artificial Sequence: Synthetic
       oligonucleotide
<220>  FEATURE:
<223>  OTHER INFORMATION: Description of Combined DNA/RNA Molecule:
       Synthetic oligonucleotide

<400> SEQUENCE: 1126
tgccacugua gaaaggcaut u                                                   21

<210>  SEQ ID NO 1127
<211>  LENGTH: 21
<212>  TYPE: DNA
<213>  ORGANISM: Artificial Sequence
<220>  FEATURE:
<223>  OTHER INFORMATION: Description of Artificial Sequence: Synthetic
       oligonucleotide
<220>  FEATURE:
<223>  OTHER INFORMATION: Description of Combined DNA/RNA Molecule:
       Synthetic oligonucleotide

<400> SEQUENCE: 1127
tgccacugua gaaaggcaut u                                                   21

<210>  SEQ ID NO 1128
<211>  LENGTH: 21
<212>  TYPE: DNA
<213>  ORGANISM: Artificial Sequence
<220>  FEATURE:
<223>  OTHER INFORMATION: Description of Artificial Sequence: Synthetic
       oligonucleotide
<220>  FEATURE:
<223>  OTHER INFORMATION: Description of Combined DNA/RNA Molecule:
       Synthetic oligonucleotide

<400> SEQUENCE: 1128
tgccacugua gaaaggcaut u                                                   21

<210>  SEQ ID NO 1129
<211>  LENGTH: 25
<212>  TYPE: RNA
<213>  ORGANISM: Artificial Sequence
<220>  FEATURE:
<223>  OTHER INFORMATION: Description of Artificial Sequence: Synthetic
       oligonucleotide

<400> SEQUENCE: 1129
gcuggccucc caauaaagcu ggaca                                               25

<210>  SEQ ID NO 1130
<211>  LENGTH: 25
<212>  TYPE: RNA
<213>  ORGANISM: Artificial Sequence
<220>  FEATURE:
<223>  OTHER INFORMATION: Description of Artificial Sequence: Synthetic
       oligonucleotide
```

```
<400> SEQUENCE: 1130
gcuggccucc caauaaagcu ggaca                                           25

<210> SEQ ID NO 1131
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1131
tggtaatcca ctttcagagg                                                 20

<210> SEQ ID NO 1132
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1132
tggtaatcca ctttcagagg                                                 20

<210> SEQ ID NO 1133
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1133
tggtaatcca ctttcagagg                                                 20

<210> SEQ ID NO 1134
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1134
tggtaatcca ctttcagagg                                                 20

<210> SEQ ID NO 1135
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1135
tggtaatcca ctttcagagg                                                 20

<210> SEQ ID NO 1136
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1136
```
agcttcttgt ccagctttat                                        20

<210> SEQ ID NO 1137
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1137
agcttcttgt ccagctttat                                        20

<210> SEQ ID NO 1138
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1138
agcttcttgt ccagctttat                                        20

<210> SEQ ID NO 1139
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1139
agcttcttgt ccagctttat                                        20

<210> SEQ ID NO 1140
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1140
agcttcttgt ccagctttat                                        20

<210> SEQ ID NO 1141
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1141
agcttcttgt ccagctttat                                        20

<210> SEQ ID NO 1142
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 1142
agcttcttgt ccagctttat                                          20
```

OLIGONUCLEOTIDE COMPOSITIONS AND METHODS OF USE THEREOF

CROSS-REFERENCE TO RELATED APPLICATIONS

This application is a National Stage Entry of International Application No. PCT/US18/35721, filed Jun. 1, 2018, which claims priority to U.S. Provisional Application Nos. 62/514,769, filed Jun. 2, 2017, and 62/670,698, filed May 11, 2018, the entirety of each of which is incorporated herein by reference.

SEQUENCE LISTING

The instant application contains a Sequence Listing which has been submitted electronically in ASCII format and is hereby incorporated by reference in its entirety. Said ASCII copy, created on Mar. 9, 2022, is named SequenceListing.txt and is 339,734 bytes in size.

BACKGROUND

Oligonucleotides which target PNPLA3 (PNPLA3 oligonucleotides) are useful in various applications, e.g., therapeutic applications. The use of naturally-occurring nucleic acids (e.g., unmodified DNA or RNA) can be limited, for example, by their susceptibility to endo- and exo-nucleases.

SUMMARY

Among other things, the present disclosure encompasses the recognition that controlling structural elements of PNPLA3 oligonucleotides, such as chemical modifications (e.g., modifications of a sugar, base and/or internucleotidic linkage) or patterns thereof, alterations in stereochemistry (e.g., stereochemistry of a backbone chiral internucleotidic linkage) or patterns thereof, and/or conjugation with an additional chemical moiety (e.g., a lipid moiety, a targeting moiety, carbohydrate moiety, a moiety that binds to a asialoglycoprotein receptor or ASGPR, e.g., a GalNAc moiety, etc.) can have a significant impact on PNPLA3 oligonucleotide properties and/or activities. In some embodiments, the properties and/or activities include, but are not limited to, participation in, direction of a decrease in expression, activity or level of a PNPLA3 gene or a gene product thereof, mediated, for example, by RNA interference (RNAi interference), single-stranded RNA interference (ssRNAi), RNase H-mediated knockdown, steric hindrance of translation, etc.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of exemplary embodiments of the invention and the examples included therein.

It is to be understood that this invention is not limited to specific synthetic methods of making that may of course vary. It is also to be understood that the terminology used herein is for the purpose of describing particular embodiments only and is not intended to be limiting.

In some embodiments, the present disclosure encompasses the recognition that stereochemistry, particularly stereochemistry of backbone chiral centers, can unexpectedly improve properties of PNPLA3 oligonucleotides. In contrast to many prior observations that some structural elements that increase stability can also lower activity, for example, RNA interference, the present disclosure demonstrates that control of stereochemistry can, surprisingly, increase stability while not significantly decreasing activity.

In some embodiments, the present disclosure provides oligonucleotides having certain 5'-end structures.

In some embodiments, the present disclosure provides 5'-end structures that, when used in accordance with the present disclosure, can provided oligonucleotides with high biological activities, e.g., RNAi activity.

In some embodiments, the present disclosure encompasses the recognition that various additional chemical moieties, such as lipid moieties and/or carbohydrate moieties, when incorporated into oligonucleotides, can improve one or more PNPLA3 oligonucleotide properties, such as knock down of the PNPLA3 target gene or a gene product thereof. In some embodiments, an additional chemical moiety is optional. In some embodiments, a PNPLA3 oligonucleotide can comprise more than one additional chemical moiety. In some embodiments, a PNPLA3 oligonucleotide can comprise two or more additional chemical moieties, wherein the additional chemical moieties are identical or non-identical, or of the same category (e.g., targeting moiety, carbohydrate moiety, a moiety that binds to ASPGR, lipid moiety, etc.) or not of the same category. In some embodiments, certain additional chemical moieties facilitate delivery of oligonucleotides to desired cells, tissues and/or organs. In some embodiments, certain additional chemical moieties facilitate internalization of oligonucleotides and/or increase oligonucleotide stability.

In some embodiments, the present disclosure provides PNPLA3 oligonucleotide compositions that achieve allele-specific suppression, wherein transcripts from one allele of a particular target gene is selectively knocked down relative to at least one other allele of the same gene.

In some embodiments, the present disclosure demonstrates that certain provided structural elements, technologies and/or features are particularly useful for PNPLA3 oligonucleotides that participate in and/or direct RNAi mechanisms (e.g., RNAi agents). Regardless, however, the teachings of the present disclosure are not limited to oligonucleotides that participate in or operate via any particular mechanism. In some embodiments, the present disclosure pertains to any oligonucleotide which operates through any mechanism, and which comprises any sequence, structure or format (or portion thereof) described herein. In some embodiments, the present disclosure provides a PNPLA3 oligonucleotide which operates through any mechanism, and which comprises any sequence, structure or format (or portion thereof) described herein, including, but not limited to, any 5'-end structure; 5'-end region; a first region (including but not limited to, a seed region); a second region (including, but not limited to, a post-seed region); and a 3'-end region (which can be a 3'-terminal dinucleotide and/or a 3'-end cap); an optional additional chemical moiety (including but not limited to a targeting moiety, a carbohydrate moiety, a moiety that binds APGR, and a lipid moiety); stereochemistry or patterns of stereochemistry; modification or pattern of modification; internucleotidic linkage or pattern of internucleotidic linkages; modification of sugar(s) or pattern of modifications of sugars; modification of base(s) or patterns of modifications of bases. In some embodiments, provided oligonucleotides may participate in (e.g., direct) RNAi mechanisms. In some embodiments, provided oligonucleotides may participate in RNase H (ribonuclease H) mechanisms. In some embodiments, provided oligonucleotides may act as translational inhibitors (e.g., may provide steric blocks of translation). In some embodiments, provided oligonucleotides may be therapeutic. In some embodiments, provided oligonucleotides are useful in therapeutic, diagnostic, research and/or nanomaterials applications. In some embodiments, a target is a specific allele with respect to which expression and/or activity of one or more products (e.g., RNA and/or protein products) are intended to be altered. In many embodiments, a target allele is one whose presence and/or expression is associated (e.g., correlated) with presence, incidence, and/or severity, of one or more diseases and/or conditions. Alternatively or additionally, in some embodiments, a target allele is one for which alteration of level and/or activity of one or more gene products correlates with improvement (e.g., delay of onset, reduction of severity, responsiveness to other therapy, etc) in one or more aspects of a disease and/or condition.

In some embodiments, where presence and/or activity of a particular allele (a disease-associated allele) is associated (e.g., correlated) with presence, incidence and/or severity of one or more disorders, diseases and/or conditions, a different allele of the same gene exists and is not so associated, or is associated to a lesser extent (e.g., shows less significant, or statistically insignificant correlation). In some such embodiments, oligonucleotides and methods thereof as described herein may preferentially or specifically target the associated allele relative to the one or more less-associated/unassociated allele(s), thus mediating allele-specific suppression.

In some embodiments, a PNPLA3 target sequence is a sequence to which a PNPLA3 oligonucleotide as described herein binds. In many embodiments, a target sequence is identical to, or is an exact complement of, a sequence of a provided oligonucleotide, or of consecutive residues therein (e.g., a provided oligonucleotide includes a target-binding sequence that is identical to, or an exact complement of, a target sequence). In some embodiments, a target-binding sequence is an exact complement of a target sequence of a transcript (e.g., pre-mRNA, mRNA, etc.). A target-binding sequence/target sequence can be of various lengths to provided oligonucleotides with desired activities and/or properties. In some embodiments, a target binding sequence/target sequence comprises 5-50 bases. In some embodiments, a small number of differences/mismatches is tolerated between (a relevant portion of) an PNPLA3 oligonucleotide and its target sequence, including but not limited to the 5' and/or 3'-end regions of the target and/or oligonucleotide sequence. In many embodiments, a target sequence is present within a transcript (e.g., an mRNA and/or a pre-mRNA) produced from a target gene.

In some embodiments, a target sequence includes one or more allelic sites (i.e., positions within a target gene at which allelic variation occurs). In some embodiments, an allelic site is a mutation. In some embodiments, an allelic site is a SNP. In some such embodiments, a provided oligonucleotide binds to one allele preferentially or specifically relative to one or more other alleles. In some embodiments, a provided oligonucleotide binds preferentially to a disease-associated allele. For example, in some embodiments, a PNPLA3 oligonucleotide (or a target-binding sequence portion thereof) provided herein has a sequence that is, at least in part, identical to, or an exact complement of a particular allelic version of a target sequence.

Unless otherwise noted, all sequences (including, but not limited to base sequences and patterns of chemistry, modification, and/or stereochemistry) are presented in 5' to 3' order.

In some embodiments, the present disclosure provides compositions and methods related to a PNPLA3 oligonucleotide which is specific to a target and which has or comprises the base sequence of any oligonucleotide disclosed herein, or a region of at least 15 contiguous nucleotides of the base sequence of any oligonucleotide disclosed herein, wherein the first nucleotide of the base sequence or the first nucleotide of the at least 15 contiguous nucleotides can be optionally replaced by T or DNA T. In some embodiments, the oligonucleotide is capable of directing ssRNAi.

In some embodiments, the present disclosure provides a PNPLA3 oligonucleotide composition comprising a first plurality of oligonucleotides which have a common base sequence and comprise one or more internucleotidic linkage, sugar, and/or base modifications.

In some embodiments, a nucleotide is a natural nucleotide. In some embodiments, a nucleotide is a modified nucleotide. In some embodiments, a nucleotide is a nucleotide analog. In some embodiments, a base is a modified base. In some embodiments, a base is protected nucleobase, such as a protected nucleobase used in oligonucleotide synthesis. In some embodiments, a base is a base analog. In some embodiments, a sugar is a modified sugar. In some embodiments, a sugar is a sugar analog. In some embodiments, an internucleotidic linkage is a modified internucleotidic linkage. In some embodiments, a nucleotide comprises a base, a sugar, and an internucleotidic linkage, wherein each of the base, the sugar, and the internucleotidic linkage is independently and optionally naturally-occurring or non-naturally occurring. In some embodiments, a nucleoside comprises a base and a sugar, wherein each of the base and the sugar is independently and optionally naturally-occurring or non-naturally occurring. Non-limiting examples of nucleotides include DNA (2'-deoxy) and RNA (2'-OH) nucleotides; and those which comprise one or more modifications at the base, sugar and/or internucleotidic linkage. Non-limiting examples of sugars include ribose and deoxyribose; and ribose and deoxyribose with 2'-modifications, including but not limited to 2'-F, LNA, 2'-OMe, and 2'-MOE modifications. In some embodiments, an internucleotidic linkage can have a structure of Formula I as described in the present disclosure. In some embodiments, an internucleotidic linkage is a moiety which does not a comprise a phosphorus but serves to link two natural or non-natural sugars.

In some embodiments, the present disclosure provides a chirally controlled PNPLA3 oligonucleotide composition that directs a greater decrease of the expression, activity and/or level of a PNPLA3 gene or a gene product thereof, single-stranded RNA interference and/or RNase H-mediated knockdown, when compared to a reference condition, e.g., absence of the composition, or presence of a reference composition (e.g., a stereorandom composition of oligonucleotides having the same base sequence and chemical modifications).

In some embodiments, an PNPLA3 oligonucleotide composition comprising a plurality of oligonucleotides is stereorandom in that oligonucleotides of the plurality do not share a common stereochemistry at any chiral internucleotidic linkage. In some embodiments, an PNPLA3 oligonucleotide composition comprising a plurality of oligonucleotides is chirally controlled in that oligonucleotides of the plurality share a common stereochemistry at one or more chiral internucleotidic linkages. In some embodiments, an PNPLA3 oligonucleotide composition comprising a first plurality of oligonucleotides which is chirally controlled has a decreased susceptibility to endo- and exo-nucleases relative to an PNPLA3 oligonucleotide composition comprising a first plurality of oligonucleotides which is stereorandom.

In some embodiments, a composition comprises a multimer of two or more of any: PNPLA3 oligonucleotides of a first plurality and/or oligonucleotides of a second plurality, wherein the oligonucleotides of the first and second plurality can independently direct knockdown of the same or different targets independently via RNA interference and/or RNase H-mediated knockdown.

In some embodiments, an PNPLA3 oligonucleotide composition comprising a plurality of oligonucleotides (e.g., a first plurality of oligonucleotides) is chirally controlled in that oligonucleotides of the plurality share a common stereochemistry independently at one or more chiral internucleotidic linkages. In some embodiments, oligonucleotides of the plurality share a common stereochemistry configuration at 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 or more chiral internucleotidic linkages, each of which is independently Rp or Sp In some embodiments, oligonucleotides of the plurality share a common stereochemistry configuration at each chiral internucleotidic linkages. In some embodiments, a chiral internucleotidic linkage where a predetermined level of oligonucleotides of a composition share a common stereochemistry configuration (independently Rp or Sp) is referred to as a chirally controlled internucleotidic linkage.

In some embodiments, at least 5 internucleotidic linkages are chirally controlled; in some embodiments, at least 10 internucleotidic linkages are chirally controlled; in some embodiments, at least 15 internucleotidic linkages are chirally controlled; in some embodiments, each chiral internucleotidic linkage is chirally controlled.

In some embodiments, the present disclosure provides an PNPLA3 oligonucleotide composition comprising a first plurality of PNPLA3 oligonucleotides which share:

1) a common base sequence;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, the common pattern of backbone chiral centers comprises at least one internucleotidic linkage comprising a chirally controlled chiral center.

In some embodiments, levels of oligonucleotides and/or diastereopurity can be determined by analytical methods, e.g., chromatographic, spectrometric, spectroscopic methods or any combinations thereof.

Among other things, the present disclosure encompasses the recognition that stereorandom PNPLA3 oligonucleotide preparations contain a plurality of distinct chemical entities that differ from one another, e.g., in the stereochemical structure (or stereochemistry) of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence and/or chemical modifications, they are different chemical entities at least due to their different backbone stereochemistry, and they can have, as demonstrated herein, different properties, e.g., sensitivity to nucleases, activities, distribution, etc. In some embodiments, a particular stereoisomer may be defined, for example, by its base sequence, its length, its pattern of backbone linkages, and its pattern of backbone chiral centers. In some embodiments, the present disclosure demonstrates that improvements in properties and activities achieved through control of stereochemistry within a PNPLA3 oligonucleotide can be comparable to, or even better than those achieved through use of chemical modification.

In some embodiments, a PNPLA3 oligonucleotide comprises, in 5' to 3' order, a 5'-end region, a seed region, a post-seed region, and a 3'-end region, optionally further comprising an additional chemical moiety.

In some embodiments, a 5'-end region is the entire portion of a PNPLA3 oligonucleotide which is 5' to the seed region. In some embodiments, a 3'-end region is the entire portion of a PNPLA3 oligonucleotide which is 3' to the post-seed region.

In some embodiments, a 5'-end structure is a 5'-end group.

In some embodiments, a 5'-end structure comprises a 5'-end group.

In some embodiments, a provided oligonucleotide can comprise a 5'-end region, 5'-end structure, 5'-end group, 5'-end nucleoside, or 5'-end nucleotide described herein or known in the art.

In some embodiments, a 5'-end structure, a 5'-end region, 5' nucleotide moiety, seed region, post-seed region, 3'-terminal dinucleotide and/or 3'-end cap independently have any structure described herein or known in the art. In some embodiments, any structure for a 5'-end described herein or known in the art and/or any structure for a 5' nucleotide moiety described herein or known in the art and/or any structure for a seed region described herein or known in the art and/or any structure for a post-seed region described herein or known in the art and/or any structure for a 3'-terminal dinucleotide described herein or known in the art and/or any structure for a 3'-end cap described herein or known in the art can be combined.

In some embodiments, a provided oligonucleotide comprises one or more blocks. In some embodiments, a provided oligonucleotide comprise one or more blocks, wherein a block comprises one or more consecutive nucleosides, and/or nucleotides, and/or sugars, or bases, and/or internucleotidic linkages. In some embodiments, a block encompasses an entire seed region or a portion thereof. In some embodiments, a block encompasses an entire post-seed region or a portion thereof.

In some embodiments, provided oligonucleotides are blockmers.

In some embodiments, provided oligonucleotides are altmers comprising alternating blocks. In some embodiments, a blockmer or an altmer can be defined by chemical modifications (including presence or absence), e.g., base modifications, sugar modification, internucleotidic linkage modifications, stereochemistry, etc., or patterns thereof.

In some embodiments, provided oligonucleotides comprise one or more sugar modifications. In some embodiments, a sugar modification is at the 2'-position. In some embodiments, a sugar modification is selected from: 2'-F, 2'-OMe, and 2'-MOE. 2'-F is also designated 2' Fluoro. 2'-OMe is also designated 2'-O-Methyl. 2'-MOE is also designated 2'-Methoxyethyl or MOE.

In some embodiments, an PNPLA3 oligonucleotide comprises only two 2'-F. In some embodiments, a PNPLA3 oligonucleotide comprises only two 2'-F, wherein the two nucleotides are at the 2nd and 14th positions.

In some embodiments, a PNPLA3 oligonucleotide comprises only two 2'-F, wherein the two nucleotides are at the 2nd and 14th positions, and wherein the first nucleotide is 2'-deoxy.

In some embodiments, a PNPLA3 oligonucleotide comprises only two 2'-F, wherein the two nucleotides are at the 2nd and 14th positions, and wherein the first nucleotide is 2'-deoxy T.

In some embodiments, a PNPLA3 oligonucleotide comprises only two 2'-F, wherein the two nucleotides are at the 2nd and 14th positions, and wherein the first nucleotide is 2'-deoxy, and the 5'-end structure is —OH.

In some embodiments, a PNPLA3 oligonucleotide comprises only two 2'-F, wherein the two nucleotides are at the 2nd and 14th positions, and wherein the first nucleotide is 2'-deoxy T, and the 5'-end structure is —OH.

In some embodiments herein, in reference to a PNPLA3 oligonucleotide, "first" (e.g., first nucleotide) refers to the 5' end of the oligonucleotide, and "last" or "end" (e.g., last nucleotide or end nucleotide) refers to the 3' end.

In some embodiments, provided oligonucleotides comprise sugars with a particular modification which alternate with sugars with no modification or a different modification. In some embodiments, sugars with a particular modification appear in one or more blocks.

In some embodiments, provided oligonucleotides comprise one or more blocks comprising sugars with a particular 2' modification which alternate with sugars which independently have no modification or have a different modification. In some embodiments, provided oligonucleotides comprise one or more blocks comprising sugars with a 2'-F modification which alternate with sugars which independently have no modification or have a different modification. In some embodiments, provided oligonucleotides comprise one or more blocks comprising sugars with a 2'-OMe modification which alternate with sugars which independently have no modification or a different modification. In some embodiments, provided oligonucleotides one or more blocks comprising sugars with a 2'-OMe modification which alternate with sugars with a 2'-F modification.

In some embodiments, a block of sugars has or comprises a pattern of 2'-modifications of any of: ff, fffm, fffmm, fffmmm, fffmmmm, fffmmmmm, fffmmmmmm, fffmmmmmmm, fffmmmmmmmf, fffmmmmmmff, fffmmmmmmffm, fffmmmmmmffmm, fffmmmmmmffmmf, fffmmmmmmffmm, fffmmmmmmffmmfm, fffmmmmmmffmmfmf, fffmmmmmmffmmfmfm, fffmmmmmmffmmfmfmf, fffmmmmmmfffmmfmfmfm, fffmmmmmmffmmfmfmfmm, fffmmmmmmffmmfmfmfmmm, fffmmffmm, ffmmmmmm-fmmfmfmfmmm, fmfmfmfmfmfmfm, fmfmfmfmfmfmfmf, fmfmfmfmfmfmfmfm, fmfmfmfmfmfmfmfmf, fmfmfm-fmfmfmfmfmfm, fmfmfmfmfmfmfmfmf, fmfmfm-fmfmfmfmfmfn, fmfmfmfmfmfmfmfmfmm, fmfmfmfm-fmfmfmfmfmm, fmfmfmfmfmfmfmfmm, fmfmfmfm-fmfmfmm, fmfmfmfmfmfmmm, fmmffmm, fmmm-mmmffmmfmfmfmmm, mff, mffm, mffmf, mffmff, mffmffm, mffmmffmm, mfmfm, mfmfmfmfm-fffmfmfmfmmm, mfmfmfmfmfmfm, mfmfmfmfm-fmfmfmfmfmm, mfmfmfmfmfmfmfmmm, mfmfm-fmfmfmfmfmfmm, mfmfmfmfmfmfmm, mfmfmfmfm-fmfmm, mfmfmfmfmfmmm, mfmfmfmfmfmmm, mfmfmfmfmfmmmfm, mfmfmfmfmfmmmm, mfmfm- fmfmmm, mfmfmfmfmmmfmfm, mfmfmfmfmmmfmmm, mfmfmfmfmmmmmfm, mfmfmfmmm, mfmfmfmmm-fmfmfm, mfmfmfmmmfmfmmm, mfmfmfmmmfmmmfm, mfmfmfmmmmmfmfm, mfmfmmmm, mfmfmmm-fmfmfm, mfmfmmmfmfmmm, mfmfmmmfmmmfm, mfmfmmmmmfmfm, mfmfmmm, mfmfmmm-fmfmfmfm, mfmfmmmfmfmmm, mfmfmmmfm-fmmmfm, mfmfmmmmfmfmmm, mfmfmmmfmfmfmfm, mfmmm, mfmmmfmfmfmfm, mfmmmfmfmfmfmmm, mfmmmfmfmfmmmfm, mfmmmfmfmmmfmfm, mf-mmmfmmmmfmfmfm mfmmmfmmmfmfmfm, mfmm-mmmfmfmfmfm, mmffm, mmffmm, mmffmm, mmffmmf, mmffmmff, mmffmmffm, mmffmmffmm, mmffm-mfmfmfmmm, mmm, mmmffmmfmfmfmmm, mmm-fmfmfmfmfm, mmmfmfmfmfmmm, mmmfmfm-fmfmmmfm, mmmfmfmfmmmfm, mmmfmfmmmfm-fmfm, mmmfmmmfmfmfm, mmmmffmmfmfmfmmm, mmm, mmmm, mmmmm, mmmmmffmmfmfmfmmm, mmmmmfmfmfmfmfm, mmmmmmm, mmmmmmmffmm-fmfmfmmm, mfmf, mfmf, mfmfmf, fmfm, fmfmfm, fmfmfmf, dfdf, dfdfdf, dfdfdfdf, fdfd, fdfdfd, fdfdfdfd, dfdfmfmf, dfmfmf, mfdfmf, or dfmfdf, wherein m indicates a 2'-OMe, f indicates a 2'-F, and d indicates no substitution at 2'-position. In some embodiments, a seed region and/or post-seed region can comprise a block of sugar modifications.

In some embodiments, a block is a stereochemistry block. In some embodiments, a block is an Rp block in that each internucleotidic linkage of the block is Rp. In some embodiments, a seed region-block is an Rp block. In some embodiments, a post-seed region-block is an Rp block. In some embodiments, a block is an Sp block in that each internucleotidic linkage of the block is Sp. In some embodiments, a seed region-block is an Sp block. In some embodiments, a post-seed region-block is an Sp block. In some embodiments, provided oligonucleotides comprise both Rp and Sp blocks. In some embodiments, provided oligonucleotides comprise one or more Rp but no Sp blocks. In some embodiments, provided oligonucleotides comprise one or more Sp but no Rp blocks. In some embodiments, provided oligonucleotides comprise one or more PO blocks wherein each internucleotidic linkage of the block is a natural phosphate linkage.

In some embodiments, a seed region-block is an Sp block wherein each sugar moiety comprises a 2'-F modification. In some embodiments, a seed region-block is an Sp block wherein each of internucleotidic linkage is a modified internucleotidic linkage and each sugar moiety comprises a 2'-F modification. In some embodiments, a seed region-block is an Sp block wherein each of internucleotidic linkage is a phosphorothioate linkage and each sugar moiety comprises a 2'-F modification. In some embodiments, a seed region-block comprises 4 or more nucleoside units. In some embodiments, a nucleoside unit is a nucleoside. In some embodiments, a seed region-block comprises 5 or more nucleoside units. In some embodiments, a seed region-block comprises 6 or more nucleoside units. In some embodiments, a seed region-block comprises 7 or more nucleoside units. In some embodiments, a post-seed region-block is an Sp block wherein each sugar moiety comprises a 2'-F modification. In some embodiments, a post-seed region-block is an Sp block wherein each of internucleotidic linkage is a modified internucleotidic linkage and each sugar moiety comprises a 2'-F modification. In some embodiments, a post-seed region-block is an Sp block wherein each of internucleotidic linkage is a phosphorothioate linkage and each sugar moiety comprises a 2'-F modification. In some embodiments, a post-seed region-block comprises 4 or more nucleoside units. In some embodiments, a post-seed region-block comprises 5 or more nucleoside units. In some embodiments, a post-seed region-block comprises 6 or more nucleoside units. In some embodiments, a post-seed region-block comprises 7 or more nucleoside units. In some embodiments, a seed region and/or post-seed region can comprise a block. In some embodiments, a seed region and/or post-seed region comprises a stereochemistry block.

In some embodiments, the present disclosure provides an PNPLA3 oligonucleotide composition comprising a first plurality of oligonucleotides which:

1) have a common base sequence; and
2) comprise one or more modified sugar moieties and modified internucleotidic linkages.

In some embodiments, the present disclosure provides an PNPLA3 oligonucleotide composition comprising a first plurality of oligonucleotides capable of directing single-stranded RNA interference which:

1) have a common base sequence complementary to a target sequence in a transcript; and
2) comprise one or more modified sugar moieties and modified internucleotidic linkages.

In some embodiments, a reference condition is absence of the composition. In some embodiments, a reference condition is presence of a reference composition. Example reference compositions comprising a reference plurality of oligonucleotides are extensively described in this disclosure. In some embodiments, oligonucleotides of the reference plurality have a different structural elements (chemical modifications, stereochemistry, etc.) compared with oligonucleotides of the first plurality in a provided composition. In some embodiments, a provided oligonucleotide composition comprising a first plurality of oligonucleotide is chirally controlled in that the first plurality of oligonucleotides comprise one or more chirally controlled internucleotidic linkages. In some embodiments, a provided oligonucleotide composition comprising a first plurality of oligonucleotide is chirally controlled in that the first plurality of oligonucleotides comprise 1-20 chirally controlled internucleotidic linkages. In some embodiments, the first plurality of oligonucleotides comprise 2, 3, 4, 5, 6, 7, 8, 9, 10, 11, 12, 13, 14, or 15 chirally controlled internucleotidic linkages. In some embodiments, a reference composition is a stereorandom preparation of oligonucleotides having the same chemical modifications. In some embodiments, a reference composition is a mixture of stereoisomers while a provided composition is a single-stranded RNAi agent of one stereoisomer. In some embodiments, oligonucleotides of the reference plurality have the same base sequence as oligonucleotide of the first plurality in a provided composition. In some embodiments, oligonucleotides of the reference plurality have the same chemical modifications as oligonucleotide of the first plurality in a provided composition. In some embodiments, oligonucleotides of the reference plurality have the same sugar modifications as oligonucleotide of the first plurality in a provided composition. In some embodiments, oligonucleotides of the reference plurality have the same base modifications as oligonucleotide of the first plurality in a provided composition. In some embodiments, oligonucleotides of the reference plurality have the same internucleotidic linkage modifications as oligonucleotide of the first plurality in a provided composition. In some embodiments, oligonucleotides of the reference plurality have the same base sequence and the same chemical modifications as oligonucleotide of the first plurality in a provided composition. In some embodiments, oligonucleotides of the reference plurality have the same stereochemistry as oligonucleotide of the first plurality in a provided composition but different chemical modifications, e.g., base modification, sugar modification, internucleotidic linkage modifications, etc.

In some embodiments, the present disclosure provides a composition comprising an PNPLA3 oligonucleotide, wherein the oligonucleotide is complementary or substantially complementary to a target RNA sequence, has a length of about 15 to about 49 total nucleotides, wherein the oligonucleotide comprises at least one non-natural base, sugar and/or internucleotidic linkage.

In some embodiments, the present disclosure provides a PNPLA3 oligonucleotide composition comprising a single-stranded RNAi agent, wherein the single-stranded RNAi agent is complementary or substantially complementary to a target RNA sequence, has a length of about 15 to about 49 total nucleotides, and is capable of directing target-specific RNA interference, wherein the single-stranded RNAi agent comprises at least one non-natural base, sugar and/or internucleotidic linkage.

In some embodiments, the length is 15 to 49, about 17 to about 49, 17 to 49, about 19 to about 29, 19 to 29, about 19 to about 25, 19 to 25, about 19 to about 23, or 19 to 23 total nucleotides.

In some embodiments, the present disclosure provides a PNPLA3 oligonucleotide composition comprising a first plurality of oligonucleotides which:

1) have a common base sequence complementary or substantially complementary to a target sequence in a transcript; and
2) comprise one or more modified sugar moieties and modified internucleotidic linkages, the oligonucleotide composition being characterized in that, when it is contacted with the transcript, knockdown of the transcript is improved relative to that observed under reference conditions selected from the group consisting of absence of the composition, presence of a reference composition, and combinations thereof.

In some embodiments, the present disclosure provides a PNPLA3 oligonucleotide composition comprising a first plurality of oligonucleotides capable of directing single-stranded RNA interference which:

1) have a common base sequence complementary to a target sequence in a transcript; and
2) comprise one or more modified sugar moieties and modified internucleotidic linkages, the oligonucleotide composition being characterized in that, when it is contacted with the transcript in a RNA interference system, RNAi-mediated knockdown of the transcript is improved relative to that observed under reference conditions selected from the group consisting of absence of the composition, presence of a reference composition, and combinations thereof.

In some embodiments, the present disclosure provides a PNPLA3 oligonucleotide composition comprising a first plurality of oligonucleotides, wherein oligonucleotides of the first plurality are of a particular oligonucleotide type defined by:

1) base sequence;
2) pattern of backbone linkages;
3) pattern of backbone chiral centers; and
4) pattern of backbone phosphorus modifications.

In some embodiments, the present disclosure provides a PNPLA3 oligonucleotide composition comprising a first plurality of oligonucleotides capable of directing single-stranded RNA interference, wherein oligonucleotides of the first plurality are of a particular oligonucleotide type defined by:
  1) base sequence;
  2) pattern of backbone linkages;
  3) pattern of backbone chiral centers; and
  4) pattern of backbone phosphorus modifications.

In some embodiments, the present disclosure provides an PNPLA3 oligonucleotide composition comprising a first plurality of oligonucleotides of a PNPLA3 oligonucleotide type, wherein the oligonucleotide type is defined by:
  1) base sequence;
  2) pattern of backbone linkages;
  3) pattern of backbone chiral centers; and
  4) pattern of backbone phosphorus modifications, which composition is chirally controlled in that it is enriched, relative to a substantially racemic preparation of oligonucleotides having the same base sequence, for oligonucleotides of the particular oligonucleotide type,
  the oligonucleotide composition being characterized in that, when it is contacted with the transcript, knockdown of the transcript is improved relative to that observed under reference conditions selected from the group consisting of absence of the composition, presence of a reference composition, and combinations thereof.

In some embodiments, the present disclosure provides a PNPLA3 oligonucleotide composition comprising a first plurality of oligonucleotides which are capable of directing single-stranded RNA interference and are of a PNPLA3 oligonucleotide type, wherein the oligonucleotide type is defined by:
  1) base sequence;
  2) pattern of backbone linkages;
  3) pattern of backbone chiral centers; and
  4) pattern of backbone phosphorus modifications,
which composition is chirally controlled in that it is enriched, relative to a substantially racemic preparation of oligonucleotides having the same base sequence, for oligonucleotides of the particular oligonucleotide type,
  the oligonucleotide composition being characterized in that, when it is contacted with the transcript in a RNA interference system, RNAi-mediated knockdown of the transcript is improved relative to that observed under reference conditions selected from the group consisting of absence of the composition, presence of a reference composition, and combinations thereof.

In some embodiments, a provided oligonucleotide has any of the Formats illustrated in FIG. 1, or any structural element illustrated in any of the Formats illustrated in FIG. 1.

In some embodiments, a provided single-stranded RNAi agent has any of the Formats illustrated in FIG. 1, or any structural element illustrated in any of the Formats illustrated in FIG. 1.

Among other things, the present disclosure presents data showing that various oligonucleotides of the disclosed Formats are capable of directing a decrease in the expression and/or level of a target gene or its gene product, when targeted against any of several different sequences, in any of several different genes. In some embodiments, the present disclosure presents data showing that various RNAi agents of the disclosed Formats are capable of directing RNA interference against any of many different sequences, in any of many different genes.

In some embodiments, an PNPLA3 oligonucleotide having any of the structures described and/or illustrated herein is capable of directing RNA interference. In some embodiments, a PNPLA3 oligonucleotide having any of the structures described and/or illustrated herein is capable of directing RNase H-mediated knockdown. In some embodiments, a PNPLA3 oligonucleotide having any of the structures described and/or illustrated herein is capable of directing RNA interference and/or RNase H-mediated knockdown. In some embodiments, a PNPLA3 oligonucleotide comprises any structural element of any oligonucleotide described herein, or any Format described herein or illustrated in FIG. 1. In some embodiments, a PNPLA3 oligonucleotide comprises any structural element of any oligonucleotide described herein, or any Format described herein or illustrated in FIG. 1 and is capable of directing RNA interference. In some embodiments, a PNPLA3 oligonucleotide comprises any structural element of any oligonucleotide described herein, or any Format described herein or illustrated in FIG. 1 and is capable of directing RNase H-mediated knockdown. In some embodiments, a PNPLA3 oligonucleotide comprises any structural element of any oligonucleotide described herein, or any Format described herein or illustrated in FIG. 1 and is capable of directing RNA interference and/or RNase H-mediated knockdown.

In some embodiments, a RNAi agent comprises any one or more of: a 5'-end structure, a 5'-end region, a seed region, a post-seed region, and a 3'-end region, and an optional additional chemical moiety. In some embodiments, a seed region is any seed region described herein or known in the art. In some embodiments, a post-seed region can be any region between a seed region and a 3'-end region described herein or known in the art. In some embodiments, a 3'-end region can be any 3'-end region described herein or known in the art. In some embodiments, any optional additional chemical moiety can be any optional additional chemical moiety described herein or known in the art. Any individual 5'-end structure, 5'-end region, seed region, post-seed region, 3'-end region, and optional additional chemical moiety described herein or known in the art can be combined, independently, with any other 5'-end structure, 5'-end region, seed region, post-seed region, 3'-end region, and optional additional chemical moiety described herein or known in the art. In some embodiments, as non-limiting examples, a region of a single-stranded RNAi agent is a 5'-end structure, a 5'-end region, a seed region, a post-seed region, a portion of a seed region, a portion of a post-seed region, or a 3'-terminal dinucleotide.

In some embodiments, the base sequence of a provided oligonucleotide consists of the base sequence of any oligonucleotide disclosed herein. In some embodiments, the base sequence of a provided oligonucleotide comprises the base sequence of any oligonucleotide disclosed herein. In some embodiments, the base sequence of a provided oligonucleotide comprises a sequence comprising the sequence of 15 contiguous bases of the base sequence of any oligonucleotide disclosed herein. In some embodiments, the base sequence of a provided oligonucleotide comprises a sequence comprising the sequence of 20 contiguous bases, with up to 5 mismatches, of the base sequence of any oligonucleotide disclosed herein.

In some embodiments, a provided oligonucleotide is capable of directing a decrease in the expression and/or level of a target gene or its gene product. In some embodiments, a provided oligonucleotide is capable of directing single-stranded RNAi interference. In some embodiments, a provided oligonucleotide is capable of directing RNase H-mediated knockdown. In some embodiments, a provided oligonucleotide is capable of directing single-stranded RNA interference and RNase H-mediated knockdown. In some embodiments, a oligonucleotide comprises a sequence which targets any transcript or gene targeted by a oligonucleotide disclosed herein.

In some embodiments, provided oligonucleotides target PNPLA3.

In some embodiments, provided oligonucleotides can be used to decrease or inhibit the activity, level and/or expression of a PNPLA3 gene or its gene product. In some embodiments, provided oligonucleotides can be used to decrease or inhibit the activity, level and/or expression of a gene or its gene product, wherein abnormal or excessive activity, level and/or expression of, a deleterious mutation in, or abnormal tissue or inter- or intracellular distribution of a gene or its gene product is related to, causes and/or is associated with a disorder. In some embodiments, provided oligonucleotides can be used to treat a disorder and/or to manufacture a medicament for the treatment of a disorder related to, caused and/or associated with the abnormal or excessive activity, level and/or expression or abnormal distribution of a gene or its gene product.

In some embodiments, the present disclosure pertains to methods of using oligonucleotides disclosed herein which are capable of targeting PNPLA3 and useful for treating and/or manufacturing a treatment for a PNPLA3-related disorder.

In some embodiments, a PNPLA3 oligonucleotide capable of targeting a gene comprises a base sequence which is a portion of or complementary or substantially complementary to a portion of the base sequence of the target gene. In some embodiments, a portion is at least 15 bases long. In some embodiments, a base sequence of a single-stranded RNAi agent can comprise or consist of a base sequence which has a specified maximum number of mismatches from a specified base sequence.

In some embodiments, a mismatch is a difference between the base sequence or length when two sequences are maximally aligned and compared. As a non-limiting example, a mismatch is counted if a difference exists between the base at a particular location in one sequence and the base at the corresponding position in another sequence. Thus, a mismatch is counted, for example, if a position in one sequence has a particular base (e.g., A), and the corresponding position on the other sequence has a different base (e.g., G, C or U). A mismatch is also counted, e.g., if a position in one sequence has a base (e.g., A), and the corresponding position on the other sequence has no base (e.g., that position is an abasic nucleotide which comprises a phosphate-sugar backbone but no base) or that position is skipped. A single-stranded nick in either sequence (or in the sense or antisense strand) may not be counted as mismatch, for example, no mismatch would be counted if one sequence comprises the sequence 5'-AG-3', but the other sequence comprises the sequence 5'-AG-3' with a single-stranded nick between the A and the G. A base modification is generally not considered a mismatch, for example, if one sequence comprises a C, and the other sequence comprises a modified C (e.g., 5mC) at the same position, no mismatch may be counted. In some embodiments, for purposes of counting mismatches, substitution of a T for U or vice versa is not considered a mismatch.

In some embodiments, an PNPLA3 oligonucleotide is complementary or totally or 100% complementary to a target sequence (e.g., a RNA, such as a mRNA), meaning that the base sequence of the oligonucleotide has no mismatches with a sequence which is fully complementary (e.g., base-pairs via Watson-Crick basepairing) to the target sequence. Without wishing to be bound by any particular theory, the disclosure notes that, for a single-stranded RNAi agent, it is not necessary for the 5'-end nucleotide moiety or the 3'-terminal dinucleotide to base-pair with the target. These may be mismatches. In addition, an antisense oligonucleotide or single-stranded RNAi agent can have a small number of internal mismatches and still direct a decrease in the expression and/or level of a target gene or its gene product and/or direct RNase H-mediated knockdown and/or RNA interference. If a first base sequence of a PNPLA3 oligonucleotide, (e.g., antisense oligonucleotide or single-stranded RNAi agent) has a small number of mismatches from a reference base sequence which is 100% complementary to a target sequence, then the first base sequence is substantially complementary to the target sequence. In some embodiments, a PNPLA3 oligonucleotide, (e.g., antisense oligonucleotide or single-stranded RNAi agent) can have a base sequence which is complementary or substantially complementary to a target sequence. In some embodiments, complementarity is determined based on Watson-Crick base pairs (guanine-cytosine and adenine-thymine/uracil), wherein guanine, cytosine, adenine, thymine, uracil may be optionally and independently modified but maintains their pairing hydrogen-bonding patters as unmodified. In some embodiments, a sequence complementary to another sequence comprises at least 5, 6, 7, 8, 9, 10, 11, 12, 13, 14, 15, 16, 17, 18, 19, 20 bases.

In some embodiments, a PNPLA3 oligonucleotide, oligonucleotide composition or oligonucleotide type has a common pattern of backbone linkages. In some embodiments, a common pattern of backbone linkages comprises at least 10 modified internucleotidic linkages.

In some embodiments, a common pattern of backbone linkages comprises at least 10 phosphorothioate linkages. In some embodiments, a PNPLA3 oligonucleotide, oligonucleotide composition or oligonucleotide type has a common pattern of backbone chiral centers. In some embodiments, a common pattern of backbone chiral centers comprises at least 1 internucleotidic linkage in the Sp configuration. In some embodiments, a common pattern of backbone chiral centers comprises at least 1 internucleotidic linkage which is phosphorothioate in the Sp configuration. In some embodiments, oligonucleotides in provided compositions have a common pattern of backbone phosphorus modifications. In some embodiments, a provided composition is a PNPLA3 oligonucleotide composition that is chirally controlled in that the composition contains a predetermined level of oligonucleotides of an individual oligonucleotide type, wherein a PNPLA3 oligonucleotide type is defined by:

1) base sequence;
2) pattern of backbone linkages;
3) pattern of backbone chiral centers; and
4) pattern of backbone phosphorus modifications.

As noted above and understood in the art, in some embodiments, base sequence of a PNPLA3 oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, a particular oligonucleotide type may be defined by
 1A) base identity;
 1B) pattern of base modification;
 1C) pattern of sugar modification;
 2) pattern of backbone linkages;

3) pattern of backbone chiral centers; and
4) pattern of backbone phosphorus modifications.

Thus, in some embodiments, oligonucleotides of a particular type may share identical bases but differ in their pattern of base modifications and/or sugar modifications. In some embodiments, oligonucleotides of a particular type may share identical bases and pattern of base modifications (including, e.g., absence of base modification), but differ in pattern of sugar modifications.

In some embodiments, oligonucleotides of a particular type are chemically identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S⁻, and -L-R¹ of Formula I).

Among other things, the present disclosure provides oligonucleotide compositions and technologies for optimizing properties, e.g., improved single-stranded RNA interference, RNase H-mediated knockdown, etc. In some embodiments, the present disclosure provides methods for lowering immune response associated with administration of oligonucleotides and compositions thereof (i.e., of administering oligonucleotide compositions so that undesirable immune responses to oligonucleotides in the compositions are reduced, for example relative to those observed with a reference composition of nucleotides of comparable or identical nucleotide sequence). In some embodiments, the present disclosure provides methods for increasing binding to certain proteins by oligonucleotides and compositions thereof. In some embodiments, the present disclosure provides methods for increasing binding to certain proteins by oligonucleotides and compositions thereof. In some embodiments, the present disclosure provides methods for enhancing delivery of oligonucleotides and compositions thereof. Among other things, the present disclosure encompasses the recognition that optimal delivery of oligonucleotides to their targets, in some embodiments, involves balance of oligonucleotides binding to certain proteins so that oligonucleotides can be transported to the desired locations, and oligonucleotide release so that oligonucleotides can be properly released from certain proteins to perform their desired functions, for example, hybridization with their targets, cleavage of their targets, inhibition of translation, modulation of transcript processing, etc. As exemplified in this disclosure, the present disclosure recognizes, among other things, that improvement of oligonucleotide properties can be achieved through chemical modifications and/or stereochemistry.

In some embodiments, the present disclosure provides a method for treating or preventing a disease, comprising administering to a subject a PNPLA3 oligonucleotide composition described herein.

In some embodiments, a disease is one in which, after administering a provided composition, knocking down a target nucleic acid via single-stranded RNA interference can repair, restore or introduce a new beneficial function.

In some embodiments, a common sequence comprises a sequence selected from Table 1A. In some embodiments, a common sequence is a sequence selected from Table 1A. In some embodiments, a pattern of backbone chiral centers is selected from those described in Table 1A.

In some embodiments, the present disclosure provides a method comprising administering a composition comprising a first plurality of oligonucleotides, which composition displays improved delivery as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition.

In some embodiments, the present disclosure provides a method of administering a PNPLA3 oligonucleotide composition comprising a first plurality of oligonucleotides capable of directing a decrease in the expression and/or level of a target gene or its gene product and having a common nucleotide sequence, the improvement that comprises:

administering a PNPLA3 oligonucleotide comprising a first plurality of oligonucleotides that is characterized by improved delivery relative to a reference oligonucleotide composition of the same common nucleotide sequence.

In some embodiments, the present disclosure provides a method of administering a PNPLA3 oligonucleotide composition comprising a first plurality of oligonucleotides capable of directing single-stranded RNA interference and having a common nucleotide sequence, the improvement that comprises:

administering a PNPLA3 oligonucleotide comprising a first plurality of oligonucleotides that is characterized by improved delivery relative to a reference oligonucleotide composition of the same common nucleotide sequence.

In some embodiments, the present disclosure provides a single-stranded RNAi agent of a PNPLA3 oligonucleotide selected from any of the Tables, including but not limited to Table 1A, or otherwise disclosed herein. In some embodiments, the present disclosure provides a single-stranded RNAi agent of a PNPLA3 oligonucleotide selected from any of the Tables, including but not limited to Table 1A, or otherwise disclosed herein, wherein the oligonucleotide is conjugated to a lipid moiety.

In some embodiments, a provided oligonucleotide comprises a lipid moiety. In some embodiments, a lipid moiety is incorporated by conjugation with a lipid. In some embodiments, a lipid moiety is a fatty acid. In some embodiments, a PNPLA3 oligonucleotide is conjugated to a fatty acid. In some embodiments, a provided single-stranded RNAi agent further comprises a lipid. In some embodiments, a provided single-stranded RNAi agent comprises a lipid moiety conjugated at the 9$^{th}$ or 11$^{th}$ nucleotide (counting from the 5'-end). In some embodiments, a PNPLA3 oligonucleotide is conjugated at the base to a fatty acid. In some embodiments, a provided single-stranded RNAi agent comprises a lipid moiety. In some embodiments, a provided single-stranded RNAi agent comprises a lipid moiety conjugated at the base at the 9$^{th}$ or 11$^{th}$ nucleotide (counting from the 5'-end).

In some embodiments, a single-stranded RNAi agent is any one of the preceding compositions, further comprising one or more additional components.

In some embodiments, a provided oligonucleotide is capable of degrading a target transcript, e.g., RNA, through both a RNase H mechanism and a RNAi mechanism.

In some embodiments, conjugation of a lipid moiety to an PNPLA3 oligonucleotide improves at least one property of the oligonucleotide. In some embodiments, improved properties include increased activity (e.g., increased ability to direct a decrease in the expression and/or level of a target gene or its gene product and/or direct single-stranded RNA interference and/or direct RNase H-mediated knockdown) and/or improved distribution to a tissue. In some embodiments, a tissue is muscle tissue. In some embodiments, a tissue is skeletal muscle, gastrocnemius, triceps, heart or diaphragm. In some embodiments, improved properties include reduced hTLR9 agonist activity. In some embodiments, improved properties include hTLR9 antagonist activity. In some embodiments, improved properties include increased hTLR9 antagonist activity.

In general, properties of oligonucleotide compositions as described herein can be assessed using any appropriate assay.

Those of skill in the art will be aware of and/or will readily be able to develop appropriate assays for particular oligonucleotide compositions.

Definitions

As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001.

As used herein in the specification, "a" or "an" may mean one or more. As used herein in the claim(s), when used in conjunction with the word "comprising", the words "a" or "an" may mean one or more than one. As used herein "another" may mean at least a second or more.

The term "about" refers to a relative term denoting an approximation of plus or minus 10% of the nominal value to which it refers, or in one embodiment, of plus or minus 5%, or, in another embodiment, of plus or minus 2%. For the field of this disclosure, this level of approximation is appropriate unless the value is specifically stated to require a tighter range.

Aliphatic: As used herein, "aliphatic" means a straight-chain (i.e., unbranched) or branched, substituted or unsubstituted hydrocarbon chain that is completely saturated or that contains one or more units of unsaturation, or a substituted or unsubstituted monocyclic, bicyclic, or polycyclic hydrocarbon ring that is completely saturated or that contains one or more units of unsaturation (but not aromatic), or combinations thereof. In some embodiments, aliphatic groups contain 1-50 aliphatic carbon atoms. In some embodiments, aliphatic groups contain 1-20 aliphatic carbon atoms. In other embodiments, aliphatic groups contain 1-10 aliphatic carbon atoms. In other embodiments, aliphatic groups contain 1-9 aliphatic carbon atoms. In other embodiments, aliphatic groups contain 1-8 aliphatic carbon atoms. In other embodiments, aliphatic groups contain 1-7 aliphatic carbon atoms. In other embodiments, aliphatic groups contain 1-6 aliphatic carbon atoms. In still other embodiments, aliphatic groups contain 1-5 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

Alkenyl: As used herein, the term "alkenyl" refers to an alkyl group, as defined herein, having one or more double bonds.

Alkyl: As used herein, the term "alkyl" is given its ordinary meaning in the art and may include saturated aliphatic groups, including straight-chain alkyl groups, branched-chain alkyl groups, cycloalkyl (alicyclic) groups, alkyl substituted cycloalkyl groups, and cycloalkyl substituted alkyl groups. In some embodiments, an alkyl has 1-100 carbon atoms. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10. In some embodiments, cycloalkyl rings have from about 3-10 carbon atoms in their ring structure where such rings are monocyclic, bicyclic, or polycyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

Alkynyl: As used herein, the term "alkynyl" refers to an alkyl group, as defined herein, having one or more triple bonds.

Antisense: The term "Antisense", as used herein, refers to a characteristic of an oligonucleotide or other nucleic acid having a base sequence complementary or substantially complementary to a target nucleic acid to which it is capable of hybridizing. In some embodiments, a target nucleic acid is a target gene mRNA. In some embodiments, hybridization is required for or results in at one activity, e.g., a decrease in the level, expression or activity of the target nucleic acid or a gene product thereof. The term "antisense oligonucleotide", as used herein, refers to an oligonucleotide complementary to a target nucleic acid. In some embodiments, an antisense oligonucleotide is capable of directing a decrease in the level, expression or activity of the target nucleic acid or a gene product thereof. In some embodiments, an antisense oligonucleotide is capable of directing a decrease in the level, expression or activity of the target nucleic acid or a gene product thereof, via a mechanism that involves RNaseH, steric hindrance and/or RNA interference.

Approximately: As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). In some embodiments, use of the term "about" in reference to dosages means ±5 mg/kg/day.

Aryl: The term "aryl", as used herein, used alone or as part of a larger moiety as in "aralkyl," "aralkoxy," or "aryloxyalkyl," refers to monocyclic, bicyclic or polycyclic ring systems having a total of five to thirty ring members, wherein at least one ring in the system is aromatic. In some embodiments, an aryl group is a monocyclic, bicyclic or polycyclic ring system having a total of five to fourteen ring members, wherein at least one ring in the system is aromatic, and wherein each ring in the system contains 3 to 7 ring members. In some embodiments, an aryl group is a biaryl group. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

Characteristic portion: As used herein, the phrase a "characteristic portion" of a protein or polypeptide is one that contains a continuous stretch of amino acids, or a collection of continuous stretches of amino acids, that together are characteristic of a protein or polypeptide. Each such continuous stretch generally will contain at least two amino acids. In general, a characteristic portion is one that, in addition to the sequence identity specified above, shares at least one functional characteristic with the relevant intact protein.

Characteristic structural element: The term "characteristic structural element" or "structural element" refers to a distinctive structural element that is found in all members of a family of polypeptides, small molecules, or nucleic acids, and therefore can be used by those of ordinary skill in the art to define members of the family. In some embodiments, a structural element of a single-stranded RNAi agent includes, but is not limited to: a 5'-end structure, a 5'-end region, a 5' nucleotide moiety, a seed region, a post-seed region, a 3'-end region, a 3'-terminal dinucleotide, a 3' cap, a pattern of modifications, a pattern of stereochemistry in the backbone, additional chemical moieties, etc.

Comparable: The term "comparable" is used herein to describe two (or more) sets of conditions or circumstances that are sufficiently similar to one another to permit comparison of results obtained or phenomena observed. In some embodiments, comparable sets of conditions or circumstances are characterized by a plurality of substantially identical features and one or a small number of varied features. Those of ordinary skill in the art will appreciate that sets of conditions are comparable to one another when characterized by a sufficient number and type of substantially identical features to warrant a reasonable conclusion that differences in results obtained or phenomena observed under the different sets of conditions or circumstances are caused by or indicative of the variation in those features that are varied.

Cycloaliphatic: The term "cycloaliphatic," "carbocycle," "carbocyclyl," "carbocyclic radical," and "carbocyclic ring," are used interchangeably, and as used herein, refer to saturated or partially unsaturated, but non-aromatic, cyclic aliphatic monocyclic, bicyclic, or polycyclic ring systems, as described herein, having, unless otherwise specified, from 3 to 30 ring members. Cycloaliphatic groups include, without limitation, cyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, a cycloaliphatic group has 3-6 carbons. In some embodiments, a cycloaliphatic group is saturated and is cycloalkyl. The term "cycloaliphatic" may also include aliphatic rings that are fused to one or more aromatic or nonaromatic rings, such as decahydronaphthyl or tetrahydronaphthyl. In some embodiments, a cycloaliphatic group is bicyclic. In some embodiments, a cycloaliphatic group is tricyclic. In some embodiments, a cycloaliphatic group is polycyclic. In some embodiments, "cycloaliphatic" refers to $C_3$-$C_6$ monocyclic hydrocarbon, or $C_8$-$C_{10}$ bicyclic or polycyclic hydrocarbon, that is completely saturated or that contains one or more units of unsaturation, but which is not aromatic, that has a single point of attachment to the rest of the molecule, or a $C_9$-$C_{16}$ polycyclic hydrocarbon that is completely saturated or that contains one or more units of unsaturation, but which is not aromatic, that has a single point of attachment to the rest of the molecule.

Heteroaliphatic: The term "heteroaliphatic", as used herein, is given its ordinary meaning in the art and refers to aliphatic groups as described herein in which one or more carbon atoms are independently replaced with one or more heteroatoms (e.g., oxygen, nitrogen, sulfur, silicon, phosphorus, and the like). In some embodiments, one or more units selected from C, CH, $CH_2$, and $CH_3$ are independently replaced by one or more heteroatoms (including oxidized and/or substituted form thereof). In some embodiments, a heteroaliphatic group is heteroalkyl. In some embodiments, a heteroaliphatic group is heteroalkenyl.

Heteroalkyl: The term "heteroalkyl", as used herein, is given its ordinary meaning in the art and refers to alkyl groups as described herein in which one or more carbon atoms are independently replaced with one or more heteroatoms (e.g., oxygen, nitrogen, sulfur, silicon, phosphorus, and the like). Examples of heteroalkyl groups include, but are not limited to, alkoxy, poly(ethylene glycol)-, alkyl-substituted amino, tetrahydrofuranyl, piperidinyl, morpholinyl, etc.

Heteroaryl: The terms "heteroaryl" and "heteroar-", as used herein, used alone or as part of a larger moiety, e.g., "heteroaralkyl," or "heteroaralkoxy," refer to monocyclic, bicyclic or polycyclic ring systems having a total of five to thirty ring members, wherein at least one ring in the system is aromatic and at least one aromatic ring atom is a heteroatom. In some embodiments, a heteroaryl group is a group having 5 to 10 ring atoms (i.e., monocyclic, bicyclic or polycyclic), in some embodiments 5, 6, 9, or 10 ring atoms. In some embodiments, a heteroaryl group has 6, 10, or 14 π electrons shared in a cyclic array; and having, in addition to carbon atoms, from one to five heteroatoms. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic or polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl group, wherein the alkyl and heteroaryl portions independently are optionally substituted.

Heteroatom: The term "heteroatom", as used herein, means an atom that is not carbon or hydrogen. In some embodiments, a heteroatom is oxygen, sulfur, nitrogen, phosphorus, or silicon (including any oxidized form of nitrogen, sulfur, phosphorus, or silicon; the quaternized form of any basic nitrogen or a substitutable nitrogen of a heterocyclic ring (for example, N as in 3,4-dihydro-2H-pyrrolyl), NH (as in pyrrolidinyl) or NR+ (as in N-substituted pyrrolidinyl); etc.).

Heterocycle: As used herein, the terms "heterocycle," "heterocyclyl," "heterocyclic radical," and "heterocyclic ring", as used herein, are used interchangeably and refer to a monocyclic, bicyclic or polycyclic ring moiety (e.g., 3-30 membered) that is saturated or partially unsaturated and has one or more heteroatom ring atoms. In some embodiments, a heterocyclyl group is a stable 5- to 7-membered monocyclic or 7- to 10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes substituted nitrogen. As an example, in a saturated or partially unsaturated ring having 0-3 heteroatoms selected from oxygen, sulfur and nitrogen, the nitrogen may be N (as in 3,4-dihydro-2H-pyrrolyl), NH (as in pyrrolidinyl), or +NR (as in N-substituted pyrrolidinyl). A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothienyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic or polycyclic. The term "heterocyclylalkyl" refers to an alkyl group substituted by a heterocyclyl, wherein the alkyl and heterocyclyl portions independently are optionally substituted.

Lower alkyl: The term "lower alkyl" refers to a $C_{1-4}$ straight or branched alkyl group. Example lower alkyl groups are methyl, ethyl, propyl, isopropyl, butyl, isobutyl, and tert-butyl.

Lower haloalkyl: The term "lower haloalkyl" refers to a $C_{1-4}$ straight or branched alkyl group that is substituted with one or more halogen atoms.

Optionally Substituted: As described herein, compounds, e.g., oligonucleotides, of the disclosure may contain optionally substituted and/or substituted moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. In some embodiments, an optionally substituted group is unsubstituted. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable atom, e.g., a suitable carbon atom, are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\beta$; —$(CH_2)_{0-4}CH(OR^\circ)_2$; —$(CH_2)_{0-4}Ph$, which may be substituted with $R^\circ$; —$(CH_2)_{0-4}O(CH_2)_{0-1}Ph$ which may be substituted with $R^\beta$; —CH=CHPh, which may be substituted with $R^\circ$; —$(CH_2)_{0-4}O(CH_2)_{0-1}$-pyridyl which may be substituted with $R^\beta$; —$NO_2$; —CN; —$N_3$; —$(CH_2)_{0-4}N(R^\circ)_2$; —$(CH_2)_{0-4}N(R^\circ)C(O)R^\beta$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$, —$SC(S)SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$SC(S)SR^\circ$, —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$Si(R^\circ)_3$; —$OSi(R^\circ)_3$; —$B(R^\circ)_2$; —$OB(R^\circ)_2$; —$OB(OR^\circ)_2$; —$P(R^\circ)_2$; —$P(OR^\circ)_2$; —$OP(R^\circ)_2$; —$OP(OR^\circ)_2$; —$P(O)(R^\circ)_2$; —$P(O)(OR^\circ)_2$; —$OP(O)(R^\circ)_2$; —$OP(O)(OR^\circ)_2$; —$OP(O)(OR^\circ)(SR^\circ)$; —$SP(O)(R^\circ)_2$; —$SP(O)(OR^\circ)_2$; —$N(R^\circ)P(O)(R^\circ)_2$; —$N(R^\circ)P(O)(OR^\circ)_2$; —$P(R^\circ)_2[B(R^\circ)_3]$; —$P(OR^\circ)_2[B(R^\circ)_3]$; —$OP(IV)_2[B(R^\circ)_3]$; —$OP(OR^\circ_2[B(R^\circ_3]$; —$(C_{1-4}$ straight or branched)alkylene)O—$N(R^\circ)_2$; or —$(C_{1-4}$ straight or branched)alkylene)C(O)O—$N(R^\circ)_2$, wherein each $R^\circ$ may be substituted as defined below and is independently hydrogen, $C_{1-20}$ aliphatic, $C_{1-20}$ heteroaliphatic having 1-5 heteroatoms independently selected from nitrogen, oxygen, sulfur, silicon and phosphorus, —$CH_2$—$(C_{6-14}$ aryl), —$O(CH_2)_{0-1}(C_{6-14}$ aryl), —$CH_2$-(5-14 membered heteroaryl ring), a 5-20 membered, monocyclic, bicyclic, or polycyclic, saturated, partially unsaturated or aryl ring having 0-5 heteroatoms independently selected from nitrogen, oxygen, sulfur, silicon and phosphorus, or, notwithstanding the definition above, two independent occurrences of $R^\circ$, taken together with their intervening atom(s), form a 5-20 membered, monocyclic, bicyclic, or polycyclic, saturated, partially unsaturated or aryl ring having 0-5 heteroatoms independently selected from nitrogen, oxygen, sulfur, silicon and phosphorus, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(haloR$^\bullet$), —$(CH_2)_{0-2}OH$, —$(CH_2)_{0-2}OR^\bullet$, —$(CH_2)_{0-2}CH(OR^\circ)_2$; -(haloR$^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$C(O)SR^\bullet$, —$(C_{1-4}$ straight or branched alkylene)C(O)OR$^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, and a 5-6-membered saturated, partially unsaturated, or aryl ring having 0-4 heteroatoms independently selected from nitrogen, oxygen, and sulfur. Suitable divalent substituents on a saturated carbon atom of $R^\circ$ include =O and =S.

Suitable divalent substituents, e.g., on a suitable carbon atom, are independently the following: =O, =S, =$NNR^*_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, and an unsubstituted 5-6-membered saturated, partially unsaturated, or aryl ring having 0-4 heteroatoms independently selected from nitrogen, oxygen, and sulfur.

Suitable substituents on the aliphatic group of R* are independently halogen, —R˙, -(haloR˙), —OH, —OR˙, —O(haloR˙), —CN, —C(O)OH, —C(O)OR˙, —NH$_2$, —NHR˙, —NR˙$_2$, or —NO$_2$, wherein each R˙ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, and sulfur.

Partially unsaturated: As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

RNA interference: As used herein, the terms "RNA interference" or "RNAi" refer to a post-transcriptional, targeted gene-silencing process involving the RISC (RNA-induced silencing complex). A process of RNAi reportedly naturally occurs when ribonuclease III (Dicer) cleaves a longer dsRNA into shorter fragments called siRNAs. A naturally-produced siRNA (small interfering RNA) is typically about 21 to 23 nucleotides long with an about 19 basepair duplex and two single-stranded overhangs and is typically RNA. These RNA segments then reportedly direct the degradation of the target nucleic acid, such as a mRNA or pre-mRNA. Dicer has reportedly also been implicated in the excision of 21- and 22-nucleotide small temporal RNAs (stRNAs) from precursor RNA of conserved structure that are implicated in translational control. Hutvagner et al. 2001, Science, 293, 834. Those skilled in the art are aware that RNAi can be mediated by a single-stranded or a double-stranded oligonucleotide that includes a sequence complementary or substantially complementary to a target sequence (e.g., in a target mRNA). Thus, in some embodiments of the present disclosure, a single-stranded oligonucleotide as described herein may act as an RNAi agent; in some embodiments, a double-stranded oligonucleotide as described herein may act as an RNAi agent. In some embodiments, an RNAi response involves an endonuclease complex, commonly referred to as an RNA-induced silencing complex (RISC), which directs cleavage of single-stranded mRNA complementary to the antisense strand of the siRNA. In some embodiments, RISC directs cleavage of target RNA complementary to provided oligonucleotides which can function as single-stranded RNAi agent. In some embodiments, cleavage of a target RNA takes place in the middle of the region complementary to the antisense strand of a siRNA duplex or single-stranded RNAi agent. In some embodiments, RNA interference is directed by a single-stranded oligonucleotide which acts as a single-stranded RNAi agent that can direct RNA interference in a mechanism involving the RISC pathway.

RNAi agent: As used herein, the term "RNAi agent," "iRNA agent", and the like, refer to a PNPLA3 oligonucleotide that, when administered to a system in which a target gene product (e.g., a transcript, such as a pre-mRNA or a mRNA, of a target gene) is being or has been expressed, reduces level and/or activity (e.g., translation) of that target gene product. In some embodiments, an RNAi agent may be or comprise a single-stranded oligonucleotide or a double-stranded oligonucleotide. In some embodiments, an RNAi agent may have a structure recognized in the art as a siRNA (short inhibitory RNA), shRNA (short or small hairpin RNA), dsRNA (double-stranded RNA), microRNA, etc. In some embodiments, an RNAi agent may specifically bind to a RNA target (e.g., a transcript of a target gene). In some embodiments, upon binding to its target, and RNAi agent is loaded to the RISC (RNA-induced silencing complex). In some embodiments, an RNAi agent directs degradation of, and/or inhibits translation of, its target, in some embodiments via a mechanism involving the RISC (RNA-induced silencing complex) pathway. In some embodiments, an RNAi agent is a PNPLA3 oligonucleotide that activates the RISC complex/pathway. In some embodiments, an RNAi agent comprises an antisense strand sequence. In some embodiments, an RNAi agent includes only one oligonucleotide strand (e.g., is a single-stranded oligonucleotide). In some embodiments, a single-stranded RNAi agent oligonucleotide can be or comprise a sense or antisense strand sequence, as described by Sioud 2005 J. Mol. Biol. 348: 1079-1090. In some embodiments, a RNAi agent is a compound capable of directing RNA interference. In some embodiments, a RNAi agent may have a structure or format as is found in "canonical" siRNA structure). In some embodiments, an RNAi agent may have a structure that differs from a "canonical" siRNA structure. To give but a few examples, in some embodiments, an RNAi agent can be longer or shorter than the canonical, can be blunt-ended, and/or can comprise one or more modifications, mismatches, gaps and/or nucleotide replacements. In some embodiments, an RNAi agent contains a 3'-end cap as described in the present disclosure. Without wishing to be bound by any particular theory, Applicant proposes that, in some embodiments, a 3'-end cap can allow both of two functions: (1) allowing RNA interference; and (2) increasing duration of activity and/or biological half-life, which may be accomplished, for example, by increased binding to the PAZ domain of Dicer and/or one or more Ago proteins and/or reducing or preventing degradation of the RNAi agent (e.g., by nucleases such as those in the serum or intestinal fluid). In some embodiments, a RNAi agent of the present disclosure targets (e.g., binds to, anneals to, etc.) a target mRNA. In some embodiments, exposure of a RNAi agent to its target results in a decrease of activity, level and/or expression, e.g., a "knock-down" or "knock-out" of the target. Particularly, in some embodiments, in the case of a disease, disorder and/or condition characterized by over-expression and/or hyperactivity of a target gene, administration of a RNAi agent to a cell, tissue, or subject knocks down the target gene enough to restore a normal level of activity, or to reduce activity to a level that can alleviate, ameliorate, relieve, inhibit, prevent, delay onset of, reduce severity of, and/or reduce incidence of one or more symptoms or features of a disease, disorder, and/or condition of the disease, disorder, and/or condition. In some embodiments, a RNAi agent is double-stranded comprising an antisense strand which is a single-stranded RNAi agent as described herein, which, in combination with a sense strand, can direct RNA interference.

Single-stranded RNA interference: As used herein, the phrases "single-stranded RNAi" or "single-stranded RNA interference" or the like refer to a process or method of gene silencing directed at least in part by administration of a single-stranded RNAi agent to a system (e.g., cells, tissues, organs, subjects, etc.) where RNAi is to be directed by the agent, and which requires the RISC pathway. The terms may be utilized herein in certain instances to distinguish from "double-stranded RNAi" or "double-stranded RNA interference", in which a double-stranded RNAi agent is administered to a system, and may be further processed, for example so that one of its two strands is loaded to RISC to, e.g., suppress translation, cleave target RNA, etc.

Single-stranded RNAi agent: As used herein, the phrase "single-stranded RNAi agent" refers to a single-stranded oligonucleotide that can direct single-stranded RNA interference (RNAi or iRNA) or gene silencing via the RISC pathway. A single-stranded RNAi agent can comprise a polymer of one or more single-stranded nucleotides.

Subject: As used herein, the term "subject" or "test subject" refers to any organism to which a provided compound or composition is administered in accordance with the present disclosure e.g., for experimental, diagnostic, prophylactic and/or therapeutic purposes. Typical subjects include animals (e.g., mammals such as mice, rats, rabbits, non-human primates, and humans; insects; worms; etc.) and plants. In some embodiments, a subject may be suffering from and/or susceptible to a disease, disorder and/or condition.

Substantially: As used herein, the term "substantially" refers to the qualitative condition of exhibiting total or near-total extent or degree of a characteristic or property of interest. A base sequence which is substantially complementary to a second sequence is not identical to the second sequence, but is mostly or nearly identical to the second sequence. In addition, one of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and/or chemical phenomena.

Suffering from: An individual who is "suffering from" a disease, disorder and/or condition has been diagnosed with and/or displays one or more symptoms of a disease, disorder and/or condition.

Susceptible to: An individual who is "susceptible to" a disease, disorder and/or condition is one who has a higher risk of developing the disease, disorder and/or condition than does a member of the general public. In some embodiments, an individual who is susceptible to a disease, disorder and/or condition may not have been diagnosed with the disease, disorder and/or condition. In some embodiments, an individual who is susceptible to a disease, disorder and/or condition may exhibit symptoms of the disease, disorder and/or condition. In some embodiments, an individual who is susceptible to a disease, disorder and/or condition may not exhibit symptoms of the disease, disorder and/or condition. In some embodiments, an individual who is susceptible to a disease, disorder, and/or condition will develop the disease, disorder, and/or condition. In some embodiments, an individual who is susceptible to a disease, disorder and/or condition will not develop the disease, disorder and/or condition.

Systemic: The phrases "systemic administration," "administered systemically," "peripheral administration," and "administered peripherally" as used herein have their art-understood meaning referring to administration of a compound or composition such that it enters the recipient's system.

Therapeutic agent: As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

Therapeutically effective amount: As used herein, the term "therapeutically effective amount" means an amount of a substance (e.g., a therapeutic agent, composition, and/or formulation) that elicits a desired biological response when administered as part of a therapeutic regimen. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of compound in a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition. In some embodiments, a therapeutically effective amount is administered in a single dose; in some embodiments, multiple unit doses are required to deliver a therapeutically effective amount.

Treat: As used herein, the term "treat," "treatment," or "treating" refers to any method used to partially or completely alleviate, ameliorate, relieve, inhibit, prevent, delay onset of, reduce severity of, and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition, for example for the purpose of decreasing the risk of developing pathology associated with the disease, disorder, and/or condition.

Unsaturated: The term "unsaturated," as used herein, means that a moiety has one or more units of unsaturation.

Wild-type: As used herein, the term "wild-type" has its art-understood meaning that refers to an entity having a structure and/or activity as found in nature in a "normal" (as contrasted with mutant, diseased, altered, etc) state or context. Those of ordinary skill in the art will appreciate that wild type genes and polypeptides often exist in multiple different forms (e.g., alleles).

Nucleic acid: The term "nucleic acid", as used herein, includes any nucleotides and polymers thereof. The term "polynucleotide", as used herein, refers to a polymeric form of nucleotides of any length, either ribonucleotides (RNA) or deoxyribonucleotides (DNA). These terms refer to the primary structure of the molecules and, thus, include double- and single-stranded DNA, and double- and single-stranded RNA. These terms include, as equivalents, analogs of either RNA or DNA made from modified nucleotides and/or modified polynucleotides, such as, though not limited to, methylated, protected and/or capped nucleotides or polynucleotides. The terms encompass poly- or oligo-ribonucleotides (RNA) and poly- or oligo-deoxyribonucleotides (DNA); RNA or DNA derived from N-glycosides or C-glycosides of nucleobases and/or modified nucleobases; nucleic acids derived from sugars and/or modified sugars; and nucleic acids derived from phosphate bridges and/or modified internucleotide linkages. The term encompasses nucleic acids containing any combinations of nucleobases, modified nucleobases, sugars, modified sugars, phosphate bridges or modified internucleotidic linkages. Examples include, and are not limited to, nucleic acids containing ribose moieties, nucleic acids containing deoxy-ribose moieties, nucleic acids containing both ribose and deoxyribose moieties, nucleic acids containing ribose and modified ribose moieties. Unless otherwise specified, the prefix poly- refers to a nucleic acid containing 2 to about 10,000 nucleotide monomer units and wherein the prefix oligo- refers to a nucleic acid containing 2 to about 200 nucleotide monomer units.

Nucleotide: The term "nucleotide" as used herein refers to a monomeric unit of a polynucleotide that consists of a heterocyclic base, a sugar, and one or more internucleotidic linkages. The naturally occurring bases (guanine, (G), adenine, (A), cytosine, (C), thymine, (T), and uracil (U)) are derivatives of purine or pyrimidine, though it should be understood that naturally and non-naturally occurring base analogs are also included. The naturally occurring sugar is the pentose (five-carbon sugar) deoxyribose (which forms DNA) or ribose (which forms RNA), though it should be understood that naturally and non-naturally occurring sugar analogs are also included. Nucleotides are linked via internucleotidic linkages to form nucleic acids, or polynucleotides. Many internucleotidic linkages are known in the art (such as, though not limited to, phosphate, phosphorothioates, boranophosphates and the like). Artificial nucleic acids include PNAs (peptide nucleic acids), phosphotriesters, phosphorothionates, H-phosphonates, phosphoramidates, boranophosphates, methylphosphonates, phosphonoacetates, thiophosphonoacetates and other variants of the phosphate backbone of native nucleic acids, such as those described herein. In some embodiments, a natural nucleotide comprises a naturally occurring base, sugar and internucleotidic linkage. As used herein, the term "nucleotide" also encompasses structural analogs used in lieu of natural or naturally-occurring nucleotides, such as modified nucleotides and nucleotide analogs.

Modified nucleotide: The term "modified nucleotide" includes any chemical moiety which differs structurally from a natural nucleotide but is capable of performing at least one function of a natural nucleotide. In some embodiments, a modified nucleotide comprises a modification at a sugar, base and/or internucleotidic linkage. In some embodiments, a modified nucleotide comprises a modified sugar, modified nucleobase and/or modified internucleotidic linkage. In some embodiments, a modified nucleotide is capable of at least one function of a nucleotide, e.g., forming a subunit in a polymer capable of base-pairing to a nucleic acid comprising an at least complementary sequence of bases.

Analog: The term "analog" means any functional analog wherein a chemical moiety which differs structurally from a reference chemical moiety or class of moieties, but which is capable of performing at least one function of such a reference chemical moiety or class of moieties. As non-limiting examples, a nucleotide analog differs structurally from a nucleotide but performs at least one function of a nucleotide; a nucleobase analog differs structurally from a nucleobase but performs at least one function of a nucleobase; etc.

Nucleoside: The term "nucleoside" refers to a moiety wherein a nucleobase or a modified nucleobase is covalently bound to a sugar or modified sugar.

Modified nucleoside: The term "modified nucleoside" refers to a moiety derived from or chemically similar to a natural nucleoside, but which comprises a chemical modification which differentiates it from a natural nucleoside. Non-limiting examples of modified nucleosides include those which comprise a modification at the base and/or the sugar. Non-limiting examples of modified nucleosides include those with a 2' modification at a sugar. Non-limiting examples of modified nucleosides also include abasic nucleosides (which lack a nucleobase). In some embodiments, a modified nucleoside is capable of at least one function of a nucleoside, e.g., forming a moiety in a polymer capable of base-pairing to a nucleic acid comprising an at least complementary sequence of bases.

Nucleoside analog: The term "nucleoside analog" refers to a chemical moiety which is chemically distinct from a natural nucleoside, but which is capable of performing at least one function of a nucleoside. In some embodiments, a nucleoside analog comprises an analog of a sugar and/or an analog of a nucleobase. In some embodiments, a modified nucleoside is capable of at least one function of a nucleoside, e.g., forming a moiety in a polymer capable of base-pairing to a nucleic acid comprising a complementary sequence of bases.

Sugar: The term "sugar" refers to a monosaccharide or polysaccharide in closed and/or open form. In some embodiments, sugars are monosaccharides. In some embodiments, sugars are polysaccharides. Sugars include, but are not limited to, ribose, deoxyribose, pentofuranose, pentopyranose, and hexopyranose moieties. As used herein, the term "sugar" also encompasses structural analogs used in lieu of conventional sugar molecules, such as glycol, polymer of which forms the backbone of the nucleic acid analog, glycol nucleic acid ("GNA"), etc. As used herein, the term "sugar" also encompasses structural analogs used in lieu of natural or naturally-occurring nucleotides, such as modified sugars and nucleotide sugars.

Modified sugar: The term "modified sugar" refers to a moiety that can replace a sugar. A modified sugar mimics the spatial arrangement, electronic properties, or some other physicochemical property of a sugar.

Nucleobase: The term "nucleobase" refers to the parts of nucleic acids that are involved in the hydrogen-bonding that binds one nucleic acid strand to another complementary strand in a sequence specific manner. The most common naturally-occurring nucleobases are adenine (A), guanine (G), uracil (U), cytosine (C), and thymine (T). In some embodiments, the naturally-occurring nucleobases are modified adenine, guanine, uracil, cytosine, or thymine. In some embodiments, the naturally-occurring nucleobases are methylated adenine, guanine, uracil, cytosine, or thymine. In some embodiments, a nucleobase is a "modified nucleobase," e.g., a nucleobase other than adenine (A), guanine (G), uracil (U), cytosine (C), and thymine (T). In some embodiments, the modified nucleobases are methylated adenine, guanine, uracil, cytosine, or thymine. In some embodiments, the modified nucleobase mimics the spatial arrangement, electronic properties, or some other physicochemical property of the nucleobase and retains the property of hydrogen-bonding that binds one nucleic acid strand to another in a sequence specific manner. In some embodiments, a modified nucleobase can pair with all of the five naturally occurring bases (uracil, thymine, adenine, cytosine, or guanine) without substantially affecting the melting behavior, recognition by intracellular enzymes or activity of the oligonucleotide duplex. As used herein, the term "nucleobase" also encompasses structural analogs used in lieu of natural or naturally-occurring nucleotides, such as modified nucleobases and nucleobase analogs.

Modified nucleobase: The terms "modified nucleobase", "modified base" and the like refer to a chemical moiety which is chemically distinct from a nucleobase, but which is capable of performing at least one function of a nucleobase. In some embodiments, a modified nucleobase is a nucleobase which comprises a modification. In some embodiments, a modified nucleobase is capable of at least one function of a nucleobase, e.g., forming a moiety in a polymer capable of base-pairing to a nucleic acid comprising an at least complementary sequence of bases.

3'-end cap: The term "3'-end cap" refers to a non-nucleotidic chemical moiety bound to the 3'-end of a PNPLA3 oligonucleotide, e.g., a RNAi agent. In some embodiments, a 3'-end cap replaces a 3'-terminal dinucleotide. In some embodiments, a 3'-end cap of a PNPLA3 oligonucleotide performs at least one of the following functions: allowing RNA interference directed by the oligonucleotide, protecting the oligonucleotide from degradation or reducing the amount or rate of degradation of the oligonucleotide (e.g., by nucleases), reducing the off-target effects of a sense strand, or increasing the activity, duration or efficacy of RNA interference directed by the oligonucleotide. By describing a 3'-end cap as "non-nucleotidic", it is meant that a 3'-end cap is not a nucleotidic moiety, or oligonucleotide moiety, connected to a sugar moiety of the rest of an PNPLA3 oligonucleotide as it would do if it is part of a PNPLA3 oligonucleotide chain. Certain example 3'-end caps are described herein. A person having ordinary skill understands that others 3'-end caps known in the art can be utilized in accordance in the present disclosure.

Blocking group: The term "blocking group" refers to a group that masks the reactivity of a functional group. The functional group can be subsequently unmasked by removal of the blocking group. In some embodiments, a blocking group is a protecting group.

Moiety: The term "moiety" refers to a specific segment or functional group of a molecule. Chemical moieties are often recognized chemical entities embedded in or appended to a molecule.

Solid support: The term "solid support" refers to any support which enables synthesis of nucleic acids. In some embodiments, the term refers to a glass or a polymer, that is insoluble in the media employed in the reaction steps performed to synthesize nucleic acids, and is derivatized to comprise reactive groups. In some embodiments, the solid support is Highly Cross-linked Polystyrene (HCP) or Controlled Pore Glass (CPG). In some embodiments, the solid support is Controlled Pore Glass (CPG). In some embodiments, the solid support is hybrid support of Controlled Pore Glass (CPG) and Highly Cross-linked Polystyrene (HCP).

Linker or Linking moiety: The terms "linker", "linking moiety" and the like refer to any chemical moiety which connects one chemical moiety to another. In some embodiments, a linker is a moiety which connects one oligonucleotide to another oligonucleotide in a multimer. In some embodiments, a linker is a moiety optionally positioned between the terminal nucleoside and the solid support or between the terminal nucleoside and another nucleoside, nucleotide, or nucleic acid.

Gene: The terms "gene," "recombinant gene" and "gene construct" as used herein, refer to a DNA molecule, or portion of a DNA molecule, that encodes a protein or a portion thereof. The DNA molecule can contain an open reading frame encoding the protein (as exon sequences) and can further include intron sequences. The term "intron" as used herein, refers to a DNA sequence present in a given gene which is not translated into protein and is found in some, but not all cases, between exons. It can be desirable for the gene to be operably linked to, (or it can comprise), one or more promoters, enhancers, repressors and/or other regulatory sequences to modulate the activity or expression of the gene, as is well known in the art.

Complementary DNA: As used herein, a "complementary DNA" or "cDNA" includes recombinant polynucleotides synthesized by reverse transcription of mRNA and from which intervening sequences (introns) have been removed.

Oligonucleotide: The term "oligonucleotide" refers to a polymer or oligomer of nucleotides, and may contain any combination of natural and non-natural nucleobases, sugars, and internucleotidic linkages.

Oligonucleotides can be single-stranded or double-stranded. As used herein, the term "oligonucleotide strand" encompasses a single-stranded oligonucleotide. A single-stranded oligonucleotide can have double-stranded regions (formed by two portions of the single-stranded oligonucleotide) and a double-stranded oligonucleotide, which comprises two oligonucleotide chains, can have single-stranded regions for example, at regions where the two oligonucleotide chains are not complementary to each other. In some embodiments, oligonucleotides are capable of directing a decrease in the expression and/or level of a target gene or its gene product. In some embodiments, oligonucleotides are capable of directing a decrease in the expression and/or level of a target gene or its gene product via RNA interference. In some embodiments, oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, oligonucleotides are capable of directing a decrease in the expression and/or level of a target gene or its gene product via RNA interference and/or RNase H-mediated knockdown. Example oligonucleotides include, but are not limited to structural genes, genes including control and termination regions, self-replicating systems such as viral or plasmid DNA, single-stranded and double-stranded RNAi agents and other RNA interference reagents (RNAi agents or iRNA agents), shRNA, antisense oligonucleotides, ribozymes, microRNAs, microRNA mimics, supermirs, aptamers, antimirs, antagomirs, UI adaptors, triplex-forming oligonucleotides, G-quadruplex oligonucleotides, RNA activators, immunostimulatory oligonucleotides, and decoy oligonucleotides.

Double-stranded and single-stranded oligonucleotides that are effective in inducing RNA interference are also referred to as a RNAi agent or iRNA agent, herein. In some embodiments, these RNA interference inducing oligonucleotides associate with a cytoplasmic multi-protein complex known as RNAi-induced silencing complex (RISC). In many embodiments, double-stranded RNAi agents are sufficiently long that they can be cleaved by an endogenous molecule, e.g., by Dicer, to produce smaller oligonucleotides that can enter the RISC machinery and participate in RISC mediated cleavage and/or translation suppression of a target sequence, e.g. a target mRNA sequence.

Oligonucleotides of the present disclosure can be of various lengths. In particular embodiments, oligonucleotides can range from about 2 to about 200 nucleotides in length. In various related embodiments, oligonucleotides, single-stranded, double-stranded, and triple-stranded, can range in length from about 4 to about 10 nucleotides, from about 10 to about 50 nucleotides, from about 20 to about 50 nucleotides, from about 15 to about 30 nucleotides, or from about 20 to about 30 nucleotides in length. In some embodiments, a PNPLA3 oligonucleotide is from about 10 to about 40 nucleotides in length. In some embodiments, a PNPLA3 oligonucleotide is from about 9 to about 39 nucleotides in length. In some embodiments, the oligonucleotide is at least 4 nucleotides in length. In some embodiments, the oligonucleotide is at least 5 nucleotides in length. In some embodiments, the oligonucleotide is at least 6 nucleotides in length. In some embodiments, the oligonucleotide is at least 7 nucleotides in length. In some embodiments, the oligonucleotide is at least 8 nucleotides in length. In some embodiments, the oligonucleotide is at least 9 nucleotides in length. In some embodiments, the oligonucleotide is at least 10 nucleotides in length. In some embodiments, the oligonucleotide is at least 11 nucleotides in length. In some embodiments, the oligonucleotide is at least 12 nucleotides in length. In some embodiments, the oligonucleotide is at least 15 nucleotides in length. In some embodiments, the oligonucleotide is at least 20 nucleotides in length. In some embodiments, the oligonucleotide is at least 25 nucleotides in length. In some embodiments, the oligonucleotide is at least 30 nucleotides in length. In some embodiments, the oligonucleotide is a duplex of complementary strands of at least 18 nucleotides in length. In some embodiments, the oligonucleotide is a duplex of complementary strands of at least 21 nucleotides in length. In some embodiments, each nucleotide counted in a length independently comprises an optionally substituted nucleobase selected from adenine, cytosine, guanosine, thymine, and uracil.

Internucleotidic linkage: As used herein, the phrase "internucleotidic linkage" refers generally to a linkage linking nucleoside units of a PNPLA3 oligonucleotide or a nucleic acid. In some embodiments, an internucleotidic linkage is a phosphodiester linkage, as found in naturally occurring DNA and RNA molecules (natural phosphate linkage). In some embodiments, the term "internucleotidic linkage" includes a modified internucleotidic linkage. In some embodiments, an internucleotidic linkage is a "modified internucleotidic linkage" wherein each oxygen atom of the phosphodiester linkage is optionally and independently replaced by an organic or inorganic moiety. In some embodiments, such an organic or inorganic moiety is selected from but not limited to =S, =Se, =NR', —SR', —SeR', —N(R')$_2$, B(R')$_3$, —S—, —Se—, and —N(R')—, wherein each R' is independently as defined and described in the present disclosure. In some embodiments, an internucleotidic linkage is a phosphotriester linkage, phosphorothioate diester linkage

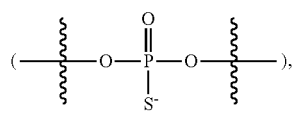 [SMILES: *OP(=O)([S-])O*]

or modified phosphorothioate triester linkage.

It is understood by a person of ordinary skill in the art that an internucleotidic linkage may exist as an anion or cation at a given pH due to the existence of acid or base moieties in the linkage.

In some embodiments, "All-(Rp)" or "All-(Sp)" is used to indicate that all chiral linkage phosphorus atoms in oligonucleotide have the same Rp or Sp configuration, respectively.

Oligonucleotide type: As used herein, the phrase "oligonucleotide type" is used to define a PNPLA3 oligonucleotide that has a particular base sequence, pattern of backbone linkages (i.e., pattern of internucleotidic linkage types, for example, phosphate, phosphorothioate, etc.), pattern of backbone chiral centers (i.e. pattern of linkage phosphorus stereochemistry (Rp/Sp)), and pattern of backbone phosphorus modifications (e.g., pattern of "—XLR$^1$" groups in formula I). In some embodiments, oligonucleotides of a common designated "type" are structurally identical to one another.

One of skill in the art will appreciate that synthetic methods of the present disclosure provide for a degree of control during the synthesis of a PNPLA3 oligonucleotide strand such that each nucleotide unit of the oligonucleotide strand can be designed and/or selected in advance to have a particular stereochemistry at the linkage phosphorus and/or a particular modification at the linkage phosphorus, and/or a particular base, and/or a particular sugar. In some embodiments, a PNPLA3 oligonucleotide strand is designed and/or selected in advance to have a particular combination of stereocenters at the linkage phosphorus. In some embodiments, an PNPLA3 oligonucleotide strand is designed and/ or determined to have a particular combination of modifications at the linkage phosphorus. In some embodiments, a PNPLA3 oligonucleotide strand is designed and/or selected to have a particular combination of bases. In some embodiments, a PNPLA3 oligonucleotide strand is designed and/or selected to have a particular combination of one or more of the above structural characteristics. In some embodiments, the present disclosure provides compositions comprising or consisting of a plurality of oligonucleotide molecules (e.g., chirally controlled oligonucleotide compositions). In some embodiments, all such molecules are of the same type (i.e., are structurally identical to one another). In many embodiments, however, provided compositions comprise a plurality of oligonucleotides of different types, typically in pre-determined relative amounts.

Chiral control: As used herein, "chiral control" refers to control of the stereochemical designation of a chiral linkage phosphorus in a chiral internucleotidic linkage within a PNPLA3 oligonucleotide. In some embodiments, a control is achieved through a chiral element that is absent from the sugar and base moieties of a PNPLA3 oligonucleotide, for example, in some embodiments, a control is achieved through use of one or more chiral auxiliaries during oligonucleotide preparation as exemplified in the present disclosure, which chiral auxiliaries often are part of chiral phosphoramidites used during oligonucleotide preparation. In contrast to chiral control, a person having ordinary skill in the art appreciates that conventional oligonucleotide synthesis which does not use chiral auxiliaries cannot control stereochemistry at a chiral internucleotidic linkage if such conventional oligonucleotide synthesis is used to form the chiral internucleotidic linkage. In some embodiments, the stereochemical designation of each chiral linkage phosphorus in a chiral internucleotidic linkage within a PNPLA3 oligonucleotide is controlled.

Chirally controlled oligonucleotide composition: The terms "chirally controlled oligonucleotide composition", "chirally controlled nucleic acid composition", and the like, as used herein, refers to a composition that comprises a plurality of oligonucleotides (or nucleic acids) which share 1) a common base sequence, 2) a common pattern of backbone linkages, and 3) a common pattern of backbone phosphorus modifications, wherein the plurality of oligonucleotides (or nucleic acids) share the same stereochemistry at one or more chiral internucleotidic linkages (chirally controlled internucleotidic linkages), and the level of the plurality of oligonucleotides (or nucleic acids) in the composition is pre-determined (e.g., through chirally controlled oligonucleotide preparation to form one or more chiral internucleotidic linkages). In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence are oligonucleotides of the plurality. In some embodiments, about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a chirally controlled oligonucleotide composition that share the common base sequence, the common pattern of backbone linkages, and the common pattern of backbone phosphorus modifications are oligonucleotides of the plurality. In some embodiments, a predetermined level is be about 1%-100%, (e.g., about 5%-100%, 10%-100%, 20%-100%, 30%-100%, 40%-100%, 50%-100%, 60%-100%, 70%-100%, 80-100%, 90-100%, 95-100%, 50%-90%, or about 5%, 10%, 20%, 30%, 40%, 50%, 60%, 70%, 80%, 85%, 90%, 91%, 92%, 93%, 94%, 95%, 96%, 97%, 98%, or 99%, or at least 5%, 10%, 20%, 30%, 40%, 50%, 60%, 70%, 80%, 85%, 90%, 91%, 92%, 93%, 94%, 95%, 96%, 97%, 98%, or 99%) of all oligonucleotides in a composition, or of all oligonucleotides in a composition that share a common base sequence (e.g., of a plurality of oligonucleotide or a PNPLA3 oligonucleotide type), or of all oligonucleotides in a composition that share a common base sequence, a common pattern of backbone linkages, and a common pattern of backbone phosphorus modifications are oligonucleotides of the plurality, or of all oligonucleotides in a composition that share a common base sequence, a common patter of base modifications, a common pattern of sugar modifications, a common pattern of internucleotidic linkage types, and/or a common pattern of internucleotidic linkage modifications.

In some embodiments, the plurality of oligonucleotides share the same stereochemistry at about 1-50 (e.g., about 1-10, 1-20, 5-10, 5-20, 10-15, 10-20, 10-25, 10-30, or about 1, 2, 3, 4, 5, 6, 7, 8, 9, 10, 11, 12, 13, 14, 15, 16, 17, 18, 19, or 20, or at least 1, 2, 3, 4, 5, 6, 7, 8, 9, 10, 11, 12, 13, 14, 15, 16, 17, 18, 19, or 20) chiral internucleotidic linkages. In some embodiments, the plurality of oligonucleotides share the same stereochemistry at about 1%-100% (e.g., about 5%-100%, 10%-100%, 20%-100%, 30%-100%, 40%-100%, 50%-100%, 60%-100%, 70%-100%, 80-100%, 90-100%, 95-100%, 50%-90%, about 5%, 10%, 15%, 20%, 25%, 30%, 35%, 40%, 45%, 50%, 55%, 60%, 65%, 70%, 75%, 80%, 85%, 90%, 95%, or 100%, or at least 5%, 10%, 15%, 20%, 25%, 30%, 35%, 40%, 45%, 50%, 55%, 60%, 65%, 70%, 75%, 80%, 85%, 90%, 95%, or 99%) of chiral internucleotidic linkages. In some embodiments, each chiral internucleotidic linkage is a chiral controlled internucleotidic linkage, and the composition is a completely chirally controlled oligonucleotide composition. In some embodiments, not all chiral internucleotidic linkages are chiral controlled internucleotidic linkages, and the composition is a partially chirally controlled oligonucleotide composition. In some embodiments, a chirally controlled oligonucleotide composition comprises predetermined levels of individual oligonucleotide or nucleic acids types. For instance, in some embodiments a chirally controlled oligonucleotide composition comprises one oligonucleotide type. In some embodiments, a chirally controlled oligonucleotide composition comprises more than one oligonucleotide type. In some embodiments, a chirally controlled oligonucleotide composition comprises multiple oligonucleotide types. In some embodiments, a chirally controlled oligonucleotide composition is a composition of oligonucleotides of a oligonucleotide type, which composition comprises a predetermined level of a plurality of oligonucleotides of the oligonucleotide type.

Chirally pure: as used herein, the phrase "chirally pure" is used to describe the relative amount of a PNPLA3 oligonucleotide, e.g., a single-stranded RNAi agent, in which all of the oligonucleotides exist in a single diastereomeric form with respect to the linkage phosphorus.

Chirally uniform: as used herein, the phrase "chirally uniform" is used to describe a PNPLA3 oligonucleotide molecule or type in which all nucleotide units have the same stereochemistry at the linkage phosphorus. For instance, a PNPLA3 oligonucleotide whose nucleotide units all have Rp stereochemistry at the linkage phosphorus is chirally uniform. Likewise, an PNPLA3 oligonucleotide whose nucleotide units all have Sp stereochemistry at the linkage phosphorus is chirally uniform.

Predetermined: By predetermined (or pre-determined) is meant deliberately selected, for example as opposed to randomly occurring or achieved without control. Those of ordinary skill in the art, reading the present specification, will appreciate that the present disclosure provides technologies that permit selection of particular chemistry and/or stereochemistry features to be incorporated into oligonucleotide compositions, and further permits controlled preparation of oligonucleotide compositions having such chemistry and/or stereochemistry features. Such provided compositions are "predetermined" as described herein. Compositions that may contain certain oligonucleotides because they happen to have been generated through a process that are not controlled to intentionally generate the particular chemistry and/or stereochemistry features is not a "predetermined" composition. In some embodiments, a predetermined composition is one that can be intentionally reproduced (e.g., through repetition of a controlled process). In some embodiments, a predetermined level of a plurality of oligonucleotides in a composition means that the absolute amount, and/or the relative amount (ratio, percentage, etc.) of the plurality of oligonucleotides in the composition is controlled. In some embodiments, a predetermined level of a plurality of oligonucleotides in a composition is achieved through chirally controlled oligonucleotide preparation.

Linkage phosphorus: as defined herein, the phrase "linkage phosphorus" is used to indicate that the particular phosphorus atom being referred to is the phosphorus atom present in the internucleotidic linkage, which phosphorus atom corresponds to the phosphorus atom of a phosphodiester of an internucleotidic linkage as occurs in naturally occurring DNA and RNA. In some embodiments, a linkage phosphorus atom is in a modified internucleotidic linkage, wherein each oxygen atom of a phosphodiester linkage is optionally and independently replaced by an organic or inorganic moiety. In some embodiments, a linkage phosphorus atom is $P^L$ of Formula I. In some embodiments, a linkage phosphorus atom is chiral.

P-modification: as used herein, the term "P-modification" refers to any modification at the linkage phosphorus other than a stereochemical modification. In some embodiments, a P-modification comprises addition, substitution, or removal of a pendant moiety covalently attached to a linkage phosphorus. In some embodiments, the "P-modification" is —X-L-$R^1$ wherein each of X, L and $R^1$ is independently as defined and described in the present disclosure.

For purposes of this disclosure, the chemical elements are identified in accordance with the Periodic Table of the Elements, CAS version, *Handbook of Chemistry and Physics,* 67th Ed., 1986-87, inside cover.

The methods and structures described herein relating to compounds and compositions of the disclosure also apply to the pharmaceutically acceptable acid or base addition salts and all stereoisomeric forms of these compounds and compositions.

BRIEF DESCRIPTION OF THE DRAWINGS

FIG. 1, including FIG. 1A to 1L, presents cartoons of various ssRNAi formats and hybrid formats.

FIG. 2 presents cartoons of various antisense oligonucleotide formats.

FIG. 3A shows example multimer formats. Oligonucleotides can be joined directly and/or through linkers. As illustrated, a multimer can comprise oligonucleotide monomers of the same or different structures/types. In some embodiments, a monomer of a multimer is an ssRNAi agent. In some embodiments, a monomer of a multimer is a RNase H-dependent antisense oligonucleotide (ASO). Monomers can be joined through various positions, for example, the 5'-end, the 3'-end, or positions in between.

DETAILED DESCRIPTION OF CERTAIN EMBODIMENTS

Figure 1B:
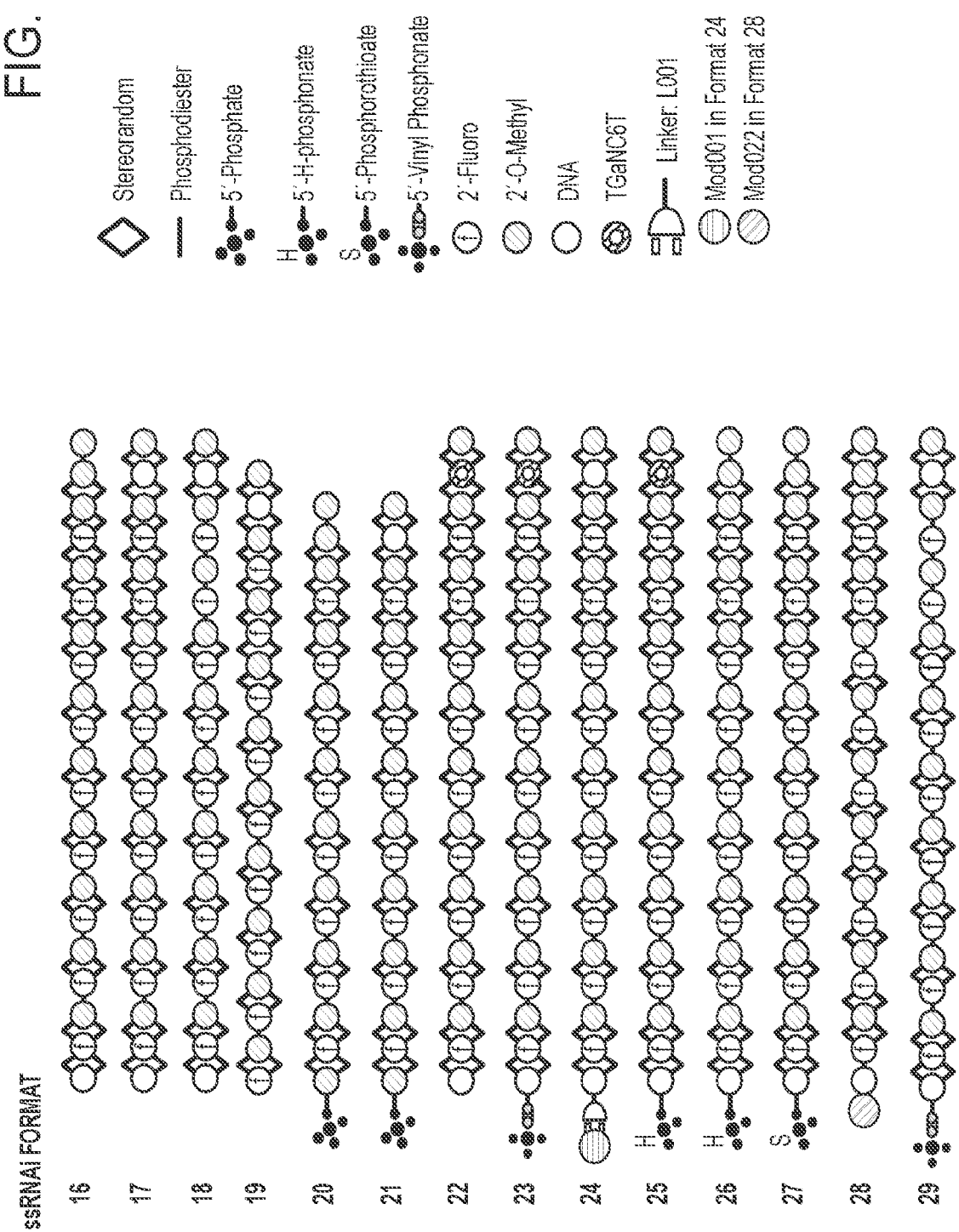

Synthetic oligonucleotides provide useful molecular tools in a wide variety of applications. For example, oligonucleotides are useful in therapeutic, diagnostic, research, and new nanomaterials applications. The use of naturally occurring nucleic acids (e.g., unmodified DNA or RNA) is limited, for example, by their susceptibility to endo- and exo-nucleases. As such, various synthetic counterparts have been developed to circumvent these shortcomings. These include synthetic oligonucleotides that contain chemical modifications, e.g., base modifications, sugar modifications, backbone modifications, etc., which, among other things, render these molecules less susceptible to degradation and improve other properties of oligonucleotides. From a structural point of view, modifications to internucleotide phosphate linkages can introduce chirality, and certain properties of oligonucleotides may be affected by configurations of phosphorus atoms that form the backbone of oligonucleotides. For example, in vitro studies have shown that properties of antisense oligonucleotides, such as binding affinity, sequence specific binding to complementary RNA, stability to nucleases, are affected by, inter alia, chirality of backbone phosphorus atoms.

Among other things, the present disclosure encompasses the recognition that structural elements of oligonucleotides, such as chemical modifications (e.g., modifications of sugar, base, and/or internucleotidic linkages) or patterns thereof, conjugation to lipids or other moieties, and/or stereochemistry [e.g., stereochemistry of backbone chiral centers (chiral internucleotidic linkages), and/or patterns thereof], can have significant impact on properties and activities (e.g., stability, specificity, selectivity, activities to reduce levels of products (transcripts and/or protein) of target genes, etc.). In some embodiments, oligonucleotide properties can be adjusted by optimizing chemical modifications (modifications of base, sugar, and/or internucleotidic linkage moieties), patterns of chemical modifications, stereochemistry and/or patterns of stereochemistry.

In some embodiments, the present disclosure demonstrates that oligonucleotide compositions comprising oligonucleotides with controlled structural elements, e.g., controlled chemical modifications and/or controlled backbone stereochemistry patterns, provide unexpected properties and activities, including but not limited to those described herein. In some embodiments, provided compositions comprising oligonucleotides having chemical modifications (e.g., base modifications, sugar modification, internucleotidic linkage modifications, etc.) or patterns thereof have improved properties and activities. Non-limiting examples of such improved properties include: directing a decrease in the expression and/or level of a target gene or its gene product; and/or directing RNA interference; and/or directing RNase H-mediated knockdown. In some embodiments, the present disclosure provides technologies (e.g., oligonucleotides, compositions, methods, etc.) for single-stranded RNAi. In some embodiments, a provided oligonucleotide is a ssRNAi agent.

In some embodiments, RNA interference is reportedly a post-transcriptional, targeted gene-silencing technique that uses an RNAi agent to target a RNA, e.g., a gene transcript such as a messenger RNA (mRNA), comprising a sequence complementary to the RNAi agent, for cleavage mediated by the RISC (RNA-induced silencing complex) pathway. In nature, a type of RNAi reportedly occurs when ribonuclease III (Dicer) cleaves a long dsRNA (double-stranded RNA) (e.g., a foreign dsRNA introduced into a mammalian cell) into shorter fragments called siRNAs. siRNAs (small interfering RNAs or short inhibitory RNAs) are typically about 21 to 23 nucleotides long and comprise about 19 base pair duplexes. The smaller RNA segments then reportedly mediate the degradation of the target mRNA. The RNAi response also reportedly features an endonuclease complex, commonly referred to as an RNA-induced silencing complex (RISC), which directs cleavage of single-stranded mRNA complementary to the antisense strand of the siRNA. Cleavage of the target RNA reportedly takes place in the middle of the region complementary to the antisense strand of the siRNA duplex. The use of the RNAi agent to a target transcript reportedly results in a decrease of gene activity, level and/or expression, e.g., a "knock-down" or "knockout" of the target gene or target sequence. Artificial siRNAs are useful both as therapeutics and for experimental use.

In one aspect, an RNA interference agent includes a single stranded RNA that interacts with a target RNA sequence to direct the cleavage of the target RNA. Without wishing to be bound by theory, long double stranded RNA introduced into plants and invertebrate cells is reportedly broken down into siRNA by a Type III endonuclease known as Dicer (Sharp et al., Genes Dev. 2001, 15:485). Dicer, a ribonuclease-III-like enzyme, reportedly processes the dsRNA into 19-23 base pair short interfering RNAs with characteristic two base 3' overhangs (Bernstein, et al., (2001) Nature 409:363). The siRNAs are reportedly then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleaves the target to induce silencing (Elbashir, et al., (2001) Genes Dev. 15: 188). Thus, in one aspect the disclosure relates to a single stranded RNA that promotes the formation of a RISC complex to effect silencing of a target gene.

In some embodiments, a suitable RNAi agent can be selected by any processes known in the art or conceivable by one of ordinary skill in the art in accordance with the present disclosure. For example, the selection criteria can include one or more of the following steps: initial analysis of the target gene sequence and design of RNAi agents; this design can take into consideration sequence similarity across species (human, cynomolgus, mouse, etc.) and dissimilarity to other (non-target) genes; screening of RNAi agents in vitro (e.g., at 10 nM in cells expressing the target transcript); determination of EC50 or IC50 in cells; determination of viability of cells treated with RNAi agents, wherein it is desired, in some embodiments, that the RNAi agent to the target not inhibit the viability of these cells; testing with human PBMC (peripheral blood mononuclear cells), e.g., to test levels of TNF-alpha to estimate immunogenicity, wherein immunostimulatory sequences are usually less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein immunostimulatory sequences are usually less desired; determination of gene knockdown in vivo using cells or tumors in test animals; and optimization of specific modifications of the RNAi agents.

The so-called canonical siRNA structure is reportedly a double-stranded RNA molecule, wherein each strand is about 21 nucleotides long. The two strands are reportedly an antisense (or "guide") strand, which recognizes and binds to a complementary sequence in the target transcript, and a sense (or "passenger") strand, which is complementary to the antisense strand. The sense and antisense strands are reportedly largely complementary, typically forming two 3' overhangs of 2 nucleotides on both ends.

While a canonical siRNA structure is reportedly double-stranded, RNAi agent can also be single-stranded. In some embodiments, a single-stranded RNAi agent corresponds to an antisense strand of a double-stranded siRNA, and the single-stranded RNAi agent lacks a corresponding passenger strand.

However, it has been reported that not all tested structural elements for single-stranded RNAi agents are effective; introduction of some structural elements into a PNPLA3 oligonucleotide can reportedly interference with single-stranded RNA interference activity.

In some embodiments, the present disclosure provides oligonucleotides and compositions useful as RNAi agent. In some embodiments, the present disclosure provides oligonucleotides and compositions useful as single-stranded RNAi agent. The present disclosure, among other things, provides novel structures of single-stranded oligonucleotides capable of directing RNA interference. Without wishing to be bound by any particular theory, this disclosure notes that single-stranded RNAi agents have advantages over double-stranded RNAi agents. For example, single-stranded RNAi agents have a lower cost of goods, as the construction of only one strand is required. Additionally or alternatively, only one strand (the antisense strand) is administered to target a target transcript. A source of off-target effects directed by dsRNA is loading of the sense strand into RISC and binding to and knockdown of undesired targets (Jackson et al. 2003 Nat. Biotech. 21: 635-637), a single-stranded RNAi agent can elicit fewer off-target effects than a corresponding double-stranded RNAi agent. In addition, some single-stranded RNAi agents, including some disclosed herein, can target particular sequences which have not previously been successfully targeted with double-stranded RNAi agents (for example, they can reduce levels of the sequences, and/or products (transcripts and/or proteins) of the sequences, significantly more than double-stranded RNAi agents). The present disclosure, among other things, provides novel formats (modifications, stereochemistry, combinations thereof, etc.) for oligonucleotides which can direct single-stranded RNA interference.

Oligonucleotides

In some embodiments, provided oligonucleotides can direct a decrease in the expression and/or level of a target gene or its gene product. In some embodiments, provided oligonucleotides can direct a decrease in levels of target products. In some embodiments, provided oligonucleotide can reduce levels of transcripts of target genes. In some embodiments, provided oligonucleotide can reduce levels of mRNA of target genes. In some embodiments, provided oligonucleotide can reduce levels of proteins encoded by target genes. In some embodiments, provided oligonucleotides can direct a decrease in the expression and/or level of a target gene or its gene product via RNA interference. In some embodiments, provided oligonucleotides can direct a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides can direct a decrease in the expression and/or level of a target gene or its gene product via RNA interference and/or RNase H-mediated knockdown. In some embodiments, provided oligonucleotides can direct a decrease in the expression and/or level of a target gene or its gene product by sterically blocking translation after binding to a target gene mRNA, and/or by altering or interfering with mRNA splicing and/or exon inclusion or exclusion. In some embodiments, provided oligonucleotides comprise one or more structural elements described herein or known in the art in accordance with the present disclosure, e.g., base sequences; modifications; stereochemistry; patterns of internucleotidic linkages; patterns of backbone linkages; patterns of backbone chiral centers; patterns of backbone phosphorus modifications; additional chemical moieties, including but not limited to, one or more targeting moieties, lipid moieties, and/or carbohydrate moieties, etc.; seed regions; post-seed regions; 5'-end structures; 5'-end regions; 5' nucleotide moieties; 3'-end regions; 3'-terminal dinucleotides; 3'-end caps; etc. In some embodiments, a seed region of a PNPLA3 oligonucleotide is or comprises the second to eighth, second to seventh, second to sixth, third to eighth, third to seventh, third to seven, or fourth to eighth or fourth to seventh nucleotides, counting from the 5' end; and the post-seed region of the oligonucleotide is the region immediately 3' to the seed region, and interposed between the seed region and the 3' end region.

In some embodiments, a provided composition comprises a PNPLA3 oligonucleotide. In some embodiments, a provided composition comprises one or more lipid moieties, one or more carbohydrate moieties (unless otherwise specified, other than sugar moieties of nucleoside units that form oligonucleotide chain with internucleotidic linkages), and/or one or more targeting components.

In some embodiments, where presence and/or activity of a particular allele (and/or its one or more products (e.g., RNA and/or protein products)) (a disease-associated allele) is associated (e.g., correlated) with presence, incidence and/or severity of one or more diseases and/or conditions, a different allele of the same sequence (e.g. gene) exists and is not so associated, or is associated to a lesser extent (e.g., shows less significant, or statistically insignificant correlation). In some such embodiments, oligonucleotides and methods thereof as described herein may preferentially or specifically target the associated allele relative to the one or more less-associated/unassociated allele(s).

In some embodiments, a target sequence is a sequence to which a PNPLA3 oligonucleotide as described herein binds. In many embodiments, a target sequence is identical to, or is an exact complement of, a sequence of a provided oligonucleotide, or of consecutive residues therein (e.g., a provided oligonucleotide includes a target-binding sequence that is identical to, or an exact complement of, a target sequence). In some embodiments, a small number of differences/mismatches is tolerated between (a relevant portion of) a PNPLA3 oligonucleotide and its target sequence. In many embodiments, a target sequence is present within a target gene. In many embodiments, a target sequence is present within a transcript (e.g., an mRNA and/or a pre-mRNA) produced from a target gene.

In some embodiments, a target sequence includes one or more allelic sites (i.e., positions within a target gene at which allelic variation occurs). In some such embodiments, a provided oligonucleotide binds to one allele preferentially or specifically relative to one or more other alleles. In some embodiments, a target-binding sequence is identical to, or is an exact complement of, a target sequence of one allele. In some embodiments, a target-binding sequence is identical to a target sequence of one allele. In some embodiments, a target-binding sequence is an exact complement of a target sequence of one allele. In some embodiments, a provided oligonucleotide binds preferentially to a disease-associated allele. In some embodiments, a provided oligonucleotide binds preferentially to a disease-associated allele, and comprises a target-binding sequence which is identical to, or is an exact complement of, a target sequence of a disease-associated allele but not other allele(s). For example, in some embodiments, a PNPLA3 oligonucleotide (or a target-binding sequence portion thereof) provided herein has a sequence that is identical to, or an exact complement of a particular allelic version of a target sequence. In some embodiments, a target sequence is a sequence of a particular allele. In some embodiments, a PNPLA3 oligonucleotide (or a target-binding sequence portion thereof) provided herein has a sequence that is identical to, or an exact complement of an allelic site of a disease-associated allele.

As appreciated by those skilled in the art, various allelic sites can be included in a target sequence in accordance with the present disclosure. In some embodiments, a target sequence comprises a SNP. In some embodiments, a target sequence comprises a mutation. In some embodiments, a SNP is a SNP in PNPLA3.

Various linker, lipid moieties, carbohydrate moieties and targeting moieties, including many known in the art, can be utilized in accordance with the present disclosure. In some embodiments, a lipid moiety is a targeting moiety. In some embodiments, a carbohydrate moiety is a targeting moiety. In some embodiments, a targeting moiety is a lipid moiety. In some embodiments, a targeting moiety is a carbohydrate moiety. As readily appreciated by those skilled in the art, various linkers, including those described in the present disclosure, can be utilized in accordance with the present disclosure to link two moieties, for example, a lipid/carbohydrate/targeting component with an PNPLA3 oligonucleotide moiety. As readily appreciated by those skilled in the art, linkers described for linking two moieties can also be used to link other moieties, for example, linkers for linking a lipid and a PNPLA3 oligonucleotide moiety can also be used to link a carbohydrate or target moiety with a PNPLA3 oligonucleotide moiety and vice versa.

In some embodiments, the present disclosure provides oligonucleotides and oligonucleotide compositions that are chirally controlled. For instance, in some embodiments, a provided composition contains predetermined levels of one or more individual oligonucleotide types, wherein a PNPLA3 oligonucleotide type is defined by: 1) base sequence; 2) pattern of backbone linkages; 3) pattern of backbone chiral centers; and 4) pattern of backbone P-modifications. In some embodiments, a particular oligonucleotide type may be defined by 1A) base identity; 1B) pattern of base modification; 1C) pattern of sugar modification; 2) pattern of backbone linkages; 3) pattern of backbone chiral centers; and 4) pattern of backbone P-modifications. In some embodiments, oligonucleotides of the same oligonucleotide type are identical. In some embodiments, the present disclosure provides chirally controlled oligonucleotide compositions of oligonucleotides, wherein the composition comprises a predetermined level of a plurality of oligonucleotides, wherein oligonucleotides of the plurality share a common base sequence, and comprise the same configuration of linkage phosphorus at at least 1, 2, 3, 4, 5, 6, 7, 8, 9, 10, 11, 12, 13, 14, 15, 16, 17, 18, 19, 20, 21, 22, 23, 24, or 25 chiral internucleotidic linkages (chirally controlled internucleotidic linkages).

In some embodiments, provided oligonucleotides comprise 2-30 chirally controlled internucleotidic linkages. In some embodiments, provided oligonucleotides comprise 5-30 chirally controlled internucleotidic linkages. In some embodiments, provided oligonucleotides comprise 10-30 chirally controlled internucleotidic linkages. In some embodiments, provided oligonucleotides comprise 1 chirally controlled internucleotidic linkage. In some embodiments, provided oligonucleotides comprise 2 chirally controlled internucleotidic linkages. In some embodiments, provided oligonucleotides comprise 3 chirally controlled internucleotidic linkages. In some embodiments, provided oligonucleotides comprise 4 chirally controlled internucleotidic linkages. In some embodiments, provided oligonucleotides comprise 5 chirally controlled internucleotidic linkages. In some embodiments, provided oligonucleotides comprise 6 chirally controlled internucleotidic linkages. In some embodiments, provided oligonucleotides comprise 7 chirally controlled internucleotidic linkages. In some embodiments, provided oligonucleotides comprise 8 chirally controlled internucleotidic linkages. In some embodiments, provided oligonucleotides comprise 9 chirally controlled internucleotidic linkages. In some embodiments, provided oligonucleotides comprise 10 chirally controlled internucleotidic linkages. In some embodiments, provided oligonucleotides comprise 11 chirally controlled internucleotidic linkages. In some embodiments, provided oligonucleotides comprise 12 chirally controlled internucleotidic linkages. In some embodiments, provided oligonucleotides comprise 13 chirally controlled internucleotidic linkages. In some embodiments, provided oligonucleotides comprise 14 chirally controlled internucleotidic linkages. In some embodiments, provided oligonucleotides have 15 chirally controlled internucleotidic linkages. In some embodiments, provided oligonucleotides have 16 chirally controlled internucleotidic linkages. In some embodiments, provided oligonucleotides have 17 chirally controlled internucleotidic linkages. In some embodiments, provided oligonucleotides have 18 chirally controlled internucleotidic linkages. In some embodiments, provided oligonucleotides have 19 chirally controlled internucleotidic linkages. In some embodiments, provided oligonucleotides have 20 chirally controlled internucleotidic linkages.

In some embodiments, a provided oligonucleotide is a unimer. In some embodiments, a provided oligonucleotide is a P-modification unimer. In some embodiments, a provided oligonucleotide is a stereounimer. In some embodiments, a provided oligonucleotide is a stereounimer of configuration Rp. In some embodiments, a provided oligonucleotide is a stereounimer of configuration Sp.

In some embodiments, a provided oligonucleotide is an altmer. In some embodiments, a provided oligonucleotide is a P-modification altmer. In some embodiments, a provided oligonucleotide is a stereoaltmer.

In some embodiments, a provided oligonucleotide is a blockmer. In some embodiments, a provided oligonucleotide is a P-modification blockmer. In some embodiments, a provided oligonucleotide is a stereoblockmer.

In some embodiments, a provided oligonucleotide is a gapmer.

In some embodiments, a provided oligonucleotide is a skipmer.

In some embodiments, a provided oligonucleotide is a hemimer. In some embodiments, a hemimer is an PNPLA3 oligonucleotide wherein the 5'-end or the 3'-end region has a sequence that possesses a structure feature that the rest of the oligonucleotide does not have. In some embodiments, the 5'-end or the 3'-end region has or comprises 2 to 20 nucleotides. In some embodiments, a structural feature is a base modification. In some embodiments, a structural feature is a sugar modification. In some embodiments, a structural feature is a P-modification. In some embodiments, a structural feature is stereochemistry of the chiral internucleotidic linkage. In some embodiments, a structural feature is or comprises a base modification, a sugar modification, a P-modification, or stereochemistry of the chiral internucleotidic linkage, or combinations thereof. In some embodiments, a hemimer is an PNPLA3 oligonucleotide in which each sugar moiety of the 5'-end region shares a common modification. In some embodiments, a hemimer is an PNPLA3 oligonucleotide in which each sugar moiety of the 3'-end region shares a common modification. In some embodiments, a common sugar modification of the 5' or 3'-end region is not shared by any other sugar moieties in the oligonucleotide. In some embodiments, an example hemimer is a PNPLA3 oligonucleotide comprising a sequence of substituted or unsubstituted 2'-O-alkyl sugar modified nucleosides, bicyclic sugar modified nucleosides, β-D-ribonucleosides or β-D-deoxyribonucleosides (for example 2'-MOE modified nucleosides, and LNA™ or ENA™ bicyclic sugar modified nucleosides) at one terminus region and a sequence of nucleosides with a different sugar moiety (such as a substituted or unsubstituted 2'-O-alkyl sugar modified nucleosides, bicyclic sugar modified nucleosides or natural ones) at the other terminus region. In some embodiments, a provided oligonucleotide is a combination of one or more of unimer, altmer, blockmer, gapmer, hemimer and skipmer. In some embodiments, a provided oligonucleotide is a combination of one or more of unimer, altmer, blockmer, gapmer, and skipmer. For instance, in some embodiments, a provided oligonucleotide is both an altmer and a gapmer. In some embodiments, a provided nucleotide is both a gapmer and a skipmer. One of skill in the chemical and synthetic arts will recognize that numerous other combinations of patterns are available and are limited only by the commercial availability and/or synthetic accessibility of constituent parts required to synthesize a provided oligonucleotide in accordance with methods of the present disclosure. In some embodiments, a hemimer structure provides advantageous benefits. In some embodiments, provided oligonucleotides are 5'-hemimers that comprises modified sugar moieties in a 5'-end sequence. In some embodiments, provided oligonucleotides are 5'-hemimers that comprises modified 2'-sugar moieties in a 5'-end sequence.

In some embodiments, a provided oligonucleotide comprises one or more optionally substituted nucleotides. In some embodiments, a provided oligonucleotide comprises one or more modified nucleotides. In some embodiments, a provided oligonucleotide comprises one or more optionally substituted nucleosides. In some embodiments, a provided oligonucleotide comprises one or more modified nucleosides. In some embodiments, a provided oligonucleotide comprises one or more optionally substituted LNAs.

In some embodiments, a provided oligonucleotide comprises one or more optionally substituted nucleobases. In some embodiments, a provided oligonucleotide comprises one or more optionally substituted natural nucleobases. In some embodiments, a provided oligonucleotide comprises one or more optionally substituted modified nucleobases. In some embodiments, a provided oligonucleotide comprises one or more 5-methylcytidine; 5-hydroxymethylcytidine, 5-formylcytosine, or 5-carboxylcytosine. In some embodiments, a provided oligonucleotide comprises one or more 5-methylcytidine.

In some embodiments, each base (BA) is independently an optionally substituted or protected nucleobase of adenine, cytosine, guanosine, thymine, or uracil. As appreciated by those skilled in the art, various protected nucleobases, including those widely known in the art, for example, those used in oligonucleotide preparation (e.g., protected nucleobases of WO/2010/064146, WO/2011/005761, WO/2013/012758, WO/2014/010250, US2013/0178612, WO/2014/012081, WO/2015/107425, WO2017/015555, and WO2017/062862, protected nucleobases of each of which are incorporated herein by reference), and can be utilized in accordance with the present disclosure.

In some embodiments, a provided oligonucleotide comprises one or more optionally substituted sugars. In some embodiments, a provided oligonucleotide comprises one or more optionally substituted sugars found in naturally occurring DNA and RNA. In some embodiments, a provided oligonucleotide comprises one or more optionally substituted ribose or deoxyribose. In some embodiments, a provided oligonucleotide comprises one or more optionally substituted ribose or deoxyribose, wherein one or more hydroxyl groups of the ribose or deoxyribose moiety is optionally and independently replaced by halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen, R', —N(R')$_2$, —OR', or —SR', wherein each R' is independently as defined above and described herein. In some embodiments, a provided oligonucleotide comprises one or more optionally substituted deoxyribose, wherein the 2' position of the deoxyribose is optionally and independently substituted with halogen. In some embodiments, a provided oligonucleotide comprises one or more optionally substituted deoxyribose, wherein the 2' position of the deoxyribose is optionally and independently substituted with one or more —F. halogen. In some embodiments, a provided oligonucleotide comprises one or more optionally substituted deoxyribose, wherein the 2' position of the deoxyribose is optionally and independently substituted with —OR', wherein each R' is independently as defined above and described herein. In some embodiments, a provided oligonucleotide comprises one or more optionally substituted deoxyribose, wherein the 2' position of the deoxyribose is optionally and independently substituted with —OR', wherein each $R^1$ is independently an optionally substituted $C_1$-$C_6$ aliphatic. In some embodiments, a provided oligonucleotide comprises one or more optionally substituted deoxyribose, wherein the 2' position of the deoxyribose is optionally and independently substituted with —OR', wherein each $R^1$ is independently an optionally substituted $C_1$-$C_6$ alkyl. In some embodiments, a provided oligonucleotide comprises one or more optionally substituted deoxyribose, wherein the 2' position of the deoxyribose is optionally and independently substituted with —OMe. In some embodiments, a provided oligonucleotide comprises one or more optionally substituted deoxyribose, wherein the 2' position of the deoxyribose is optionally and independently substituted with —O-methoxyethyl.

In some embodiments, a provided oligonucleotide is a hybridized oligonucleotide strand. In certain embodiments, a provided oligonucleotide is a partially hybridized oligonucleotide strand. In certain embodiments, a provided oligonucleotide is a completely hybridized oligonucleotide strand. In certain embodiments, a provided oligonucleotide is a double-stranded oligonucleotide. In certain embodiments, a provided oligonucleotide is a triple-stranded oligonucleotide (e.g., a triplex).

In some embodiments, any one of the structures comprising a PNPLA3 oligonucleotide depicted in WO2012/030683 can be modified in accordance with methods of the present disclosure to provide chirally controlled compositions thereof. For example, in some embodiments, chirally controlled composition comprises a stereochemical control at any one or more of chiral linkage phosphorus atoms, optionally through incorporation of one or more P-modifications described in WO2012/030683 or the present disclosure. For example, in some embodiments, a particular nucleotide unit of a PNPLA3 oligonucleotide of WO2012/030683 is preselected to be provided with chiral control at the linkage phosphorus of that nucleotide unit and/or to be P-modified with chiral control at the linkage phosphorus of that nucleotide unit.

In some embodiments, a provided oligonucleotide comprises a nucleic acid analog, e.g., GNA, LNA, PNA, TNA, F-HNA (F-THP or 3'-fluoro tetrahydropyran), MNA (mannitol nucleic acid, e.g., Leumann 2002 Bioorg. Med. Chem. 10: 841-854), ANA (anitol nucleic acid), and Morpholino.

In some embodiments, a provided oligonucleotide is characterized as having the ability to indirectly or directly increase or decrease activity of a protein or inhibition or promotion of the expression of a protein. In some embodiments, a provided oligonucleotide is characterized in that it is useful in the control of cell proliferation, viral replication, and/or any other cell signaling process.

In some embodiments, the 5'-end and/or the 3'-end of a provided oligonucleotide is modified. In some embodiments, the 5'-end and/or the 3'-end of a provided oligonucleotide is modified with a terminal cap moiety. Examples of such modifications, including terminal cap moieties are extensively described herein and in the art, for example but not limited to those described in US Patent Application Publication US 2009/0023675A1.

In some embodiments, oligonucleotides of a PNPLA3 oligonucleotide type characterized by 1) a common base sequence and length, 2) a common pattern of backbone linkages, and 3) a common pattern of backbone chiral centers, have the same chemical structure. For example, they have the same base sequence, the same pattern of nucleoside modifications, the same pattern of backbone linkages (i.e., pattern of internucleotidic linkage types, for example, phosphate, phosphorothioate, etc), the same pattern of backbone chiral centers (i.e. pattern of linkage phosphorus stereochemistry (Rp/Sp)), and the same pattern of backbone phosphorus modifications (e.g., pattern of "—XLR$^1$" groups in Formula I).

Single-Stranded RNAi Agents and Antisense Oligonucleotides

In some embodiments, the present disclosure provides oligonucleotides. In some embodiments, the present disclosure provides oligonucleotides which decrease the expression and/or level of a target gene or its gene product. Those of ordinary skill in the art, reading the present disclosure, will appreciate that, in some embodiments, provided oligonucleotides may act as RNAi agents. Alternatively or additionally, in some embodiments, provided oligonucleotides may act via an RNase H-dependent mechanism and/or another biochemical mechanism that does not involve RNA interference.

Among other things, the present disclosure defines certain structural attributes that may be particularly desirable and/or effective in an PNPLA3 oligonucleotide. Among other things, the present disclosure defines certain structural attributes that may be particularly desirable and/or effective in a PNPLA3 oligonucleotide that acts as an RNAi agent. In some embodiments, the present disclosure defines certain structural attributes that may be particularly desirable and/or effective in a PNPLA3 oligonucleotide that acts via an RNase H-dependent mechanism and/or other biochemical mechanism. In some embodiments, the present disclosure defines certain structural attributes that may be particularly desirable and/or effective in a single-stranded ssRNAi agent (ssRNAi or ssRNAi agent); in some such embodiments, as described further herein below, such structural attributes may be distinct from those that are particularly desirable and/or effective in a corresponding strand of a double-stranded RNAi agent (dsRNAi or dsRNAi agent). In some embodiments, provided oligonucleotides are single-stranded RNAi agents (e.g., which can be loaded into RISC and/or can direct or enhance RISC-mediated target). In some embodiments, provided oligonucleotides are antisense oligonucleotides (e.g., which can be loaded into RNase H and/or direct or enhance RNase-H-mediated cleavage of a target and/or operate via a different biochemical mechanism).

In some embodiments (including in some single-stranded oligonucleotide embodiments), oligonucleotides that act as RNAi agents may have one or more different structural attributes and/or functional properties from those oligonucleotides that act via an RNase H-dependent mechanism. In some embodiments, a PNPLA3 oligonucleotide can direct a decrease in the expression and/or level of a target gene or its gene product by sterically blocking translation after binding to a target gene mRNA, and/or by altering or interfering with mRNA splicing and/or exon inclusion or exclusion (e.g., skipping). In some embodiments, a PNPLA3 oligonucleotide can perform a function, or a significant percentage of a function (for example, 10-100%, no less than 10%, 20%, 30%, 40%, 50%, 60%, 70%, 80%, 90% percent or more) independent of RNA interference or RISC.

In some embodiments, a provided oligonucleotide is an antisense oligonucleotide (ASO) which directs cleavage of a target RNA mediated by RNase H and not RISC (RNA interference silencing complex).

In some embodiments, a provided oligonucleotide is a single-stranded RNAi (ssRNAi) agent which directs cleavage of a target mRNA mediated by the RISC (RNA interference silencing complex) and not the enzyme RNase H. In some embodiments, a PNPLA3 oligonucleotide can perform a function, or a significant percentage of a function (for example, 10-100%, no less than 10%, 20%, 30%, 40%, 50%, 60%, 70%, 80%, 90% percent or more) independent of RNase H.

A double-stranded RNAi agent can also direct cleavage of a target mRNA using RISC and not the enzyme RNase H. In some embodiments, a single-stranded RNAi agent differs from a double-stranded RNAi agent in that a ssRNAi agent includes only a single oligonucleotide strand and generally does not comprise a double-stranded region of significant length, and a dsRNAi agent comprises a double stranded region of significant length (e.g., at least about 15 bp, or about 19 bp in a "canonical" siRNA). In some embodiments, a dsRNAi comprises two separate, complementary strands (which are not covalently linked) which form a double-stranded region (e.g., in a "canonical" siRNA), or a long single strand which comprises two complementary sequences which together form a double-stranded region (e.g., in a shRNA or short hairpin RNA). In some embodiments of a dsRNAi, the passenger strand has a single-stranded nick, forming two strands. In some embodiments, the present disclosure demonstrates that sequences and/or structural elements (chemical modifications, stereochemistry, etc.) required for efficacious single-stranded RNAi agents may differ from those required for efficacious double-stranded RNAi agents.

Among other things, the present disclosure encompasses the recognition that certain designs (e.g., sequences and/or structural elements) which may be suitable for double-stranded RNAi agents may not be suitable for single-stranded RNAi agents (including single-stranded RNAi agents of provided formats described herein), and vice versa. In some embodiments, the present disclosure provides designs for effective ssRNAi. In some embodiments, the present disclosure demonstrates that certain base sequences, when combined with structural elements (modifications, stereochemistry, additional chemical moiety or moieties, etc.) in accordance with the present disclosure, can provided oligonucleotides having unexpectedly high activities, for example, when administered as ssRNAi agents, particularly in comparison with oligonucleotides comprising the same sequences but double-stranded and administered as dsRNAi agents. In some embodiments, the present disclosure demonstrates that certain base sequences, when combined with structural elements (modifications, stereochemistry, additional chemical moiety or moieties, etc.) in accordance with the present disclosure, can provided oligonucleotides having unexpectedly high activities, for example, the ability to decrease the expression and/or level of a target gene or its gene product.

Structural and functional differences between single-stranded RNAi (ssRNAi) agents, double-stranded RNAi (dsRNAi) agents, and RNase H-dependent antisense oligonucleotides (ASOs)

In some embodiments, single-stranded RNAi (ssRNAi) agents, double-stranded RNAi (dsRNAi) agents and RNase H-dependent antisense oligonucleotides (ASOs) all involve binding of an agent or oligonucleotide (or portion thereof) to a complementary (or substantially complementary) target RNA (e.g., a mRNA or pre-mRNA), followed by cleavage of the target RNA and/or a decrease the expression and/or level of a target gene or its gene product. In some embodiments, RNAi agents, whether double- or single-stranded, employ the RISC, or RNA interference silencing complex, which includes the enzyme Ago-2 (Argonaute-2). In some embodiments, RNase H-dependent antisense oligonucleotides are single-stranded and employ a different enzyme, RNase H. RNAse H is reportedly a cellular endonuclease which cleaves the RNA strand of an RNA:DNA duplex; see U.S. Pat. No. 7,919,472. See also, Saetrom (2004 Bioinformatics 20: 3055-3063); Kretschmer-Kazemi Far et al. (2003 Nucleic Acids 31: 4417-4424); Bertrand et al. (2002) Biochem. Biophys. Res. Comm. 296: 1000-1004); Vickers et al. (2003 J. Biol. Chem. 278: 7108). In some embodiments, oligonucleotides that can direct RNase H-mediated knockdown include, but are not limited to, those consisting of or comprising a region of consecutive 2'-deoxy nucleotide units which contain no 2'-modifications. In some embodiments, oligonucleotides that can direct RNase H-mediated knockdown are gap-widened oligonucleotides or gapmers. In some embodiments, a gapmer comprises an internal region comprises a plurality of nucleotides that supports RNase H cleavage and is positioned between external regions having a plurality of nucleotides that are chemically distinct from the nucleosides of the internal region. In some embodiments, a gapmer comprise a span of 2'-deoxy nucleotides containing no 2'-modifications, flanked or adjacent to one or two wings. In some embodiments, a gap directs RNase H cleavage of the corresponding RNA target. In some embodiments, the wings do not direct or act as substrates for RNase H cleavage. The wings can be of varying lengths (including, but not limited to, 1 to 8 nt) and can comprise various modifications or analogs (including, but not limited to, 2'-modifications, including, but not limited to, 2'-OMe and 2'-MOE). See, as non-limiting examples, U.S. Pat. Nos. 9,550,988; 7,919,472; 5,013,830; 5,149,797; 5,220,007; 5,256,775; 5,366,878; 5,403,711; 5,491,133; 5,565,350; 5,623,065; 5,652,355; 5,652,356; and 5,700,922. In some embodiments, presence of one or more such modifications or analogs may correlate with modified (e.g., increased, reduced, or altered) RNase H cleavage of a target.

In some embodiments, double-stranded RNAi agents, even the antisense strand thereof, differ structurally from a RNase H-dependent antisense oligonucleotide. In some embodiments, RNase H-dependent antisense oligonucleotides and siRNA oligonucleotides seem to have completely opposite characteristics, both regarding 5'-end structures and overall duplex stability.

Double-stranded RNAi agents can reportedly be naturally-produced in a cell by the Dicer enzyme, which cleaves larger RNA molecules, such as double-stranded RNA from invading viruses, into a dsRNA. The canonical structure of a dsRNA agent comprises two strands of RNA, each about 19 to 23 nt long, which are annealed to form an about 19-21 bp double-stranded region and two 3' dinucleotide overhangs. For a double-stranded RNAi agent, the sense strand is reportedly unwound from the duplex before the antisense strand is incorporated into RISC. Aside from the natural separation of a double-stranded RNAi agent into antisense and sense strands, single-stranded RNAi agents have not been reported to be naturally produced in a human cell.

Among other things, the present disclosure provides the teaching that, in many cases, a single-stranded RNAi agent is not simply an isolated antisense strand of a double-stranded RNAi agent in that, for example, an antisense strand of an effective dsRNAi agent may be much less effective than the dsRNAi agent, and a ssRNAi agent, when formulated as a dsRNAi agent (for example, by annealing with a sense strand), may be much less effective than the ssRNAi agent. In some embodiments, double-stranded and single-stranded RNAi agents differ in many significant ways. Structural parameters of double-stranded RNAi agents are not necessarily reflected in single-stranded RNAi agents.

In some embodiments, the present disclosure teaches that target sequences which are suitable for double-stranded RNAi agents may not be suitable for single-stranded RNAi agents, and vice versa. For example, in at least some cases, single-stranded versions of double-stranded RNAi agents may not be efficacious. As a non-limiting example, Table 46A shows that several ssRNAi agents were constructed with sequences derived from dsRNAi. These ssRNAi based on dsRNAi were generally less efficacious than the corresponding dsRNAi.

In some embodiments, double-stranded and single-stranded RNAi agents also differ in their sensitivity to incorporation of chirally controlled internucleotidic linkages. For example, Matranga et al. (2005 Cell 123: 607-620) reported that introduction of a single Sp internucleotidic linkage (e.g., a single Sp PS) into the sense strand of a double-stranded RNAi agent greatly decreased RISC assembly and RNA interference activity. In contrast, in some embodiments, data shown herein demonstrate that, surprisingly, incorporation of a Sp internucleotidic linkage)(e.g., Sp PS) can perform two functions for a single-stranded RNAi agent: (a) it increases stability against nucleases; and (b) does not interfere with RNA interference activity. Many example oligonucleotides can perform as efficacious single-stranded RNAi agents comprising one or more chirally controlled internucleotidic linkages (e.g., Sp internucleotidic linkages, or Sp PS (phosphorothioate) are shown herein).

Alternatively or additionally, double-stranded and single-stranded RNAi agents can differ in immunogenicity. In some embodiments, some single-stranded RNAi agents are reportedly more immunogenic than double-stranded RNAi agents. Sioud J. Mol. Biol. (2005) 348, 1079-1090. In some embodiments, several double-stranded RNAi agents reportedly did not induce an immune response, whereas corresponding single-stranded RNAi agents did. In some embodiments, the present disclosure provides oligonucleotides with low immunogenicity. In some embodiments, such oligonucleotides can be utilized as ssRNAi reagent.

Among other things, the present disclosure encompasses the recognition that certain conventional designs of single-stranded RNAi agents, which derive single-stranded RNAi agents, including base sequences, from double-stranded RNAi agents, often fail to provide effective single-stranded RNAi agents. In some embodiments, the present disclosure demonstrates that, surprisingly, ssRNAi agents derived from base sequences of effective RNase H-dependent ASOs can produce efficacious ssRNAi agents (see Table 46A).

In some embodiments, the present disclosure provides oligonucleotides which can be utilized as efficacious RNase-H dependent ASOs, which comprise regions of 2'-deoxy nucleotides without 2'-modifications, and which are complementary or substantially complementary to RNA sequences or portions thereof. In some embodiments, a region can be, for example, a core sequence of about 10 nt flanked on one or both sides by wings, wherein the wings differ from the core in chemistry and can comprise, as non-limiting examples, 2'-modifications or internucleotidic linkage modifications.

Oligonucleotides

In some embodiments, provided oligonucleotides can direct a decrease in the expression and/or level of a target gene or its gene product. In some embodiments, provided oligonucleotides can direct a decrease in the expression and/or level of a target gene or its gene product via RNA interference. In some embodiments, provided oligonucleotides can direct a decrease in the expression and/or level of a target gene or its gene product via a biochemical mechanism which does not involve RNA interference or RISC (including, but not limited to, RNaseH-mediated knock-down or steric hindrance of gene expression). In some embodiments, provided oligonucleotides can direct a decrease in the expression and/or level of a target gene or its gene product via RNA interference and/or RNase H-mediated knockdown. In some embodiments, provided oligonucleotides can direct a decrease in the expression and/or level of a target gene or its gene product by sterically blocking translation after binding to a target gene mRNA, and/or by altering or interfering with mRNA splicing and/or exon inclusion or exclusion.

In some embodiments, a provided oligonucleotide has a structural element or format or portion thereof described herein.

In some embodiments, a provided oligonucleotide capable of directing a decrease in the expression and/or level of a target gene or its gene product has a structural element or format or portion thereof described herein.

In some embodiments, a provided oligonucleotide capable of directing a decrease in the expression and/or level of a target gene or its gene product has the format of any oligonucleotide disclosed herein, e.g., in Table 1A, or in the Figures or Tables, or otherwise disclosed herein.

Figure 1H:
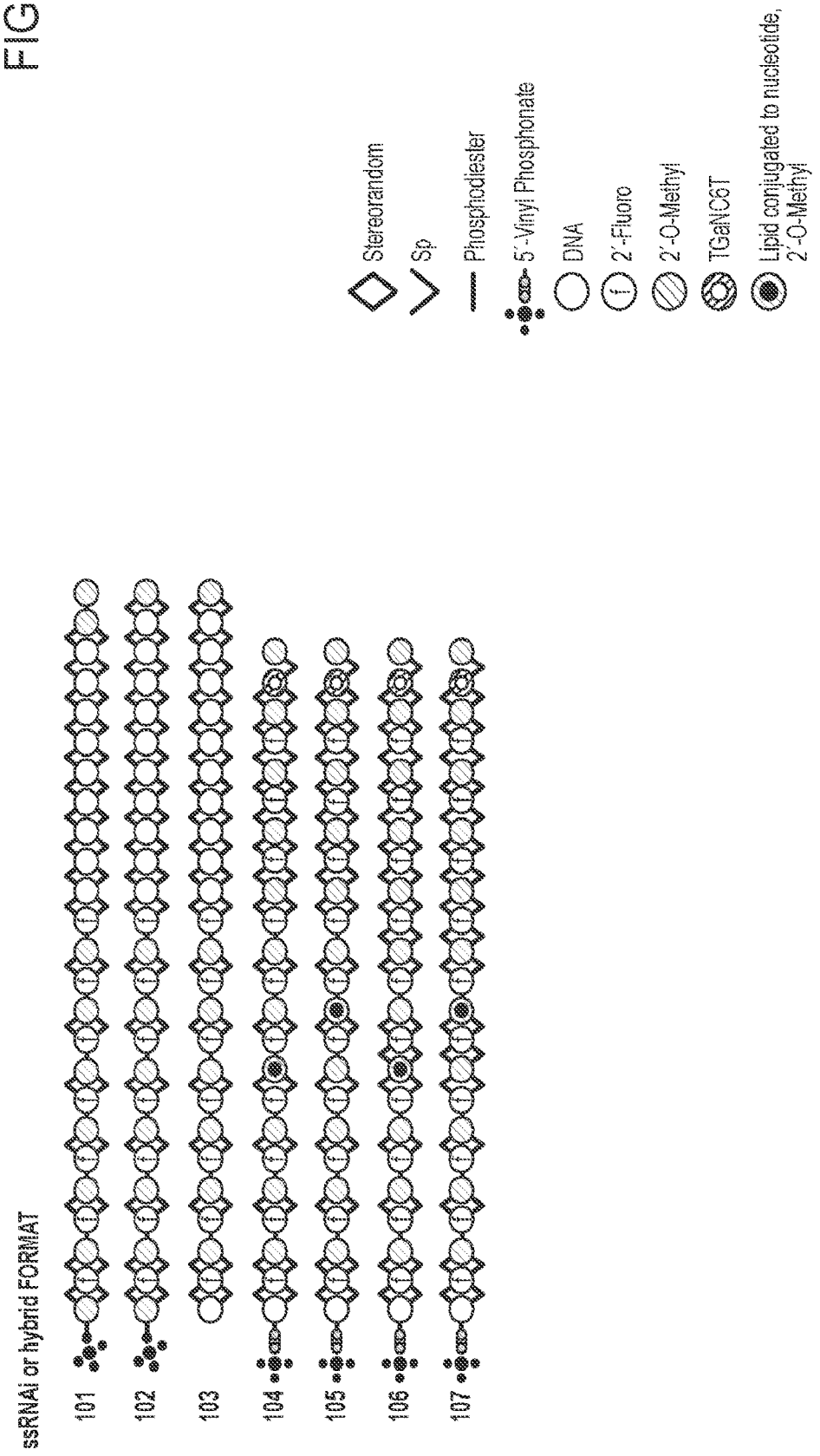

In some embodiments, a provided oligonucleotide has any of Formats illustrated in FIG. 1.

The present disclosure presents data showing that various oligonucleotides of various formats are capable of directing a decrease in the expression and/or level of a target gene or its gene product targeted against any of multiple different sequences, in multiple different genes, in multiple different species; additional data was generated supporting the efficacy of ssRNAi agents of the disclosed Formats and not shown.

In some embodiments, a provided oligonucleotide capable of directing RNase H-mediated knockdown has a structural element or format or portion thereof described herein.

In some embodiments, a provided oligonucleotide capable of directing RNase H-mediated knockdown has the format of any oligonucleotide disclosed herein, e.g., in Table 1A or in the Figures or Tables, or otherwise disclosed herein.

In some embodiments, a provided oligonucleotide has any of Formats illustrated in FIG. 1.

The present disclosure presents data showing that various oligonucleotides of various formats are capable of directing RNase H-mediated knockdown against any of multiple different sequences, in multiple different genes, in multiple different species; additional data was generated supporting the efficacy of ssRNAi agents of the disclosed Formats and not shown.

In some embodiments, a provided oligonucleotide capable of directing single-stranded RNA interference has a structural element or format or portion thereof described herein.

In some embodiments, a provided oligonucleotide capable of directing single-stranded RNA interference has the format of any oligonucleotide disclosed herein, e.g., in Table 1A or in the Figures or Tables, or otherwise disclosed herein.

In some embodiments, a provided single-stranded RNAi agent has any of the Formats illustrated in FIG. 1.

The present disclosure presents data showing that various RNAi agents of various formats are capable of directing RNA interference against any of multiple different sequences, in any of multiple different genes; additional data was generated supporting the efficacy of ssRNAi agents of the disclosed Formats and not shown.

In some embodiments, a target of RNAi is a transcript. In some embodiments, a transcript is pre-mRNA. In some embodiments, a transcript is mature RNA. In some embodiments, a transcript is mRNA. In some embodiments, a transcript comprises a mutation. In some embodiments, a mutation is a frameshift. In some embodiments, a transcript comprises a premature termination codon. In some embodiments, a target of RNAi is a RNA which is not a mRNA. In some embodiments, a target of RNAi is a non-coding RNA. In some embodiments, a target of RNAi is a long non-coding RNA. In some embodiments, provided oligonucleotides in provided compositions, e.g., oligonucleotides of a first plurality, comprise base modifications, sugar modifications, and/or internucleotidic linkage modifications. In some embodiments, provided oligonucleotides comprise base modifications and sugar modifications. In some embodiments, provided oligonucleotides comprise base modifications and internucleotidic linkage modifications. In some embodiments, provided oligonucleotides comprise sugar modifications and internucleotidic modifications. In some embodiments, provided compositions comprise base modifications, sugar modifications, and internucleotidic linkage modifications. Example chemical modifications, such as base modifications, sugar modifications, internucleotidic linkage modifications, etc. are widely known in the art including but not limited to those described in this disclosure. In some embodiments, a modified base is substituted A, T, C, G or U. In some embodiments, a sugar modification is 2'-modification. In some embodiments, a 2'-modification is 2-F modification. In some embodiments, a 2'-modification is 2'-OR'. In some embodiments, a 2'-modification is 2'-OR', wherein $R^1$ is optionally substituted alkyl. In some embodiments, a 2'-modification is 2'-OMe. In some embodiments, a 2'-modification is 2'-MOE. In some embodiments, a modified sugar moiety is a bridged bicyclic or polycyclic ring. In some embodiments, a modified sugar moiety is a bridged bicyclic or polycyclic ring having 5-20 ring atoms wherein one or more ring atoms are optionally and independently heteroatoms. Example ring structures are widely known in the art, such as those found in BNA, LNA, etc. In some embodiments, provided oligonucleotides comprise both one or more modified internucleotidic linkages and one or more natural phosphate linkages. In some embodiments, oligonucleotides comprising both modified internucleotidic linkage and natural phosphate linkage and compositions thereof provide improved properties, e.g., activities, etc. In some embodiments, a modified internucleotidic linkage is a chiral internucleotidic linkage. In some embodiments, a modified internucleotidic linkage is a phosphorothioate linkage. In some embodiments, a modified internucleotidic linkage is a substituted phosphorothioate linkage.

Among other things, the present disclosure encompasses the recognition that stereorandom oligonucleotide preparations contain a plurality of distinct chemical entities that differ from one another, e.g., in the stereochemical structure of individual backbone chiral centers within the oligonucleotide chain. Without control of stereochemistry of backbone chiral centers, stereorandom oligonucleotide preparations provide uncontrolled compositions comprising undetermined levels of oligonucleotide stereoisomers. Even though these stereoisomers may have the same base sequence, they are different chemical entities at least due to their different backbone stereochemistry, and they can have, as demonstrated herein, different properties, e.g., activities, etc. Among other things, the present disclosure provides new compositions that are or contain particular stereoisomers of oligonucleotides of interest. In some embodiments, a particular stereoisomer may be defined, for example, by its base sequence, its length, its pattern of backbone linkages, and its pattern of backbone chiral centers. As is understood in the art, in some embodiments, base sequence may refer to the identity and/or modification status of nucleoside residues (e.g., of sugar and/or base components, relative to standard naturally occurring nucleotides such as adenine, cytosine, guanosine, thymine, and uracil) in a PNPLA3 oligonucleotide and/or to the hybridization character (i.e., the ability to hybridize with particular complementary residues) of such residues. In some embodiments, the present disclosure provide an PNPLA3 oligonucleotide composition comprising a predetermined level of oligonucleotides of an individual oligonucleotide type which are chemically identical, e.g. they have the same base sequence, the same pattern of nucleoside modifications (modifications to sugar and base moieties, if any), the same pattern of backbone chiral centers, and the same pattern of backbone phosphorus modifications. The present disclosure demonstrates, among other things, that individual stereoisomers of a particular oligonucleotide can show different stability and/or activity from each other. In some embodiments, property improvements achieved through inclusion and/or location of particular chiral structures within a PNPLA3 oligonucleotide can be comparable to, or even better than those achieved through use of particular backbone linkages, residue modifications, etc. (e.g., through use of certain types of modified phosphates [e.g., phosphorothioate, substituted phosphorothioate, etc.], sugar modifications [e.g., 2'-modifications, etc.], and/or base modifications [e.g., methylation, etc.]). Among other things, the present disclosure recognizes that, in some embodiments, properties (e.g., activities, etc.) of an PNPLA3 oligonucleotide can be adjusted by optimizing its pattern of backbone chiral centers, optionally in combination with adjustment/optimization of one or more other features (e.g., linkage pattern, nucleoside modification pattern, etc.) of the oligonucleotide. As exemplified by various examples in the present disclosure, provided chirally controlled oligonucleotide compositions can demonstrate improved properties, e.g., improved single-stranded RNA interference activity, RNase H-mediated knockdown, improved delivery, etc.

In some embodiments, oligonucleotide properties can be adjusted by optimizing stereochemistry (pattern of backbone chiral centers) and chemical modifications (modifications of base, sugar, and/or internucleotidic linkage) or patterns thereof.

In some embodiments, a common pattern of backbone chiral centers (e.g., a pattern of backbone chiral centers in a single-stranded RNAi agent) comprises a pattern of OSOSO, OSSSO, OSSSOS, SOSO, SOSO, SOSOS, SOSOS, SOSOSOS, SOSSSO, SSOSSSOSS, SSSOSOSSS, SSSSOSOSSSS, SSSSS, SSSSSS, SSSSSSS, SSSSSSSS, SSSSSSSSS, or RRR, wherein S represents a phosphorothioate in the Sp configuration, and O represents a phosphodiester. wherein R represents a phosphorothioate in the Rp configuration.

In some embodiments, the non-chiral center is a phosphodiester linkage. In some embodiments, the chiral center in a Sp configuration is a phosphorothioate linkage. In some embodiments, the non-chiral center is a phosphodiester linkage. In some embodiments, the chiral center in a Sp configuration is a phosphorothioate linkage.

In some embodiments, a provided oligonucleotide comprises any pattern of stereochemistry described herein. In some embodiments, a provided oligonucleotide comprises any pattern of stereochemistry described herein and is capable of directing RNA interference. In some embodiments, a provided oligonucleotide comprises any pattern of stereochemistry described herein and is capable of directing RNase H-mediated knockdown. In some embodiments, a provided oligonucleotide comprises any pattern of stereochemistry described herein and is capable of directing RNA interference and RNase H-mediated knockdown. In some embodiments, a provided oligonucleotide comprises any pattern of stereochemistry described herein and is capable of directing RNA interference, wherein the pattern of stereochemistry is in the seed and/or post-seed region. In some embodiments, a provided oligonucleotide comprises any pattern of stereochemistry described herein and is capable of directing RNA interference and RNase H-mediated knockdown, wherein the pattern of stereochemistry is in the seed and/or post-seed region.

In some embodiments, a provided oligonucleotide comprises any modification or pattern of modification described herein. In some embodiments, a provided oligonucleotide comprises any modification or pattern of modification described herein and is capable of directing RNA interference. In some embodiments, a provided oligonucleotide comprises any pattern of modification described herein and is capable of directing RNase H-mediated knockdown. In some embodiments, a provided oligonucleotide comprises any pattern of modification described herein and is capable of directing RNA interference and RNase H-mediated knockdown. In some embodiments, a provided oligonucleotide comprises any pattern of modification described herein and is capable of directing RNA interference, wherein the pattern of modification is in the seed and/or post-seed region. In some embodiments, a provided oligonucleotide comprises any pattern of modification described herein and is capable of directing RNA interference and RNase H-mediated knockdown, wherein the pattern of modification is in the seed and/or post-seed region. In some embodiments, a modification or pattern of modification is a modification or pattern of modifications at the 2' position of a sugar. In some embodiments, a modification or pattern of modification is a modification or pattern of modifications of sugars, e.g., at the 2' position of a sugar, including but not limited to, 2'-deoxy, 2'-F, 2'-OMe, 2'-MOE, and 2'-OR1, wherein R1 is optionally substituted $C_{1-6}$ alkyl.

In some embodiments, the present disclosure demonstrates that 2'-F modifications, among other things, can improve single-stranded RNA interference. In some embodiments, the present disclosure demonstrates that Sp internucleotidic linkages, among other things, at the 5'- and 3'-ends can improve oligonucleotide stability. In some embodiments, the present disclosure demonstrates that, among other things, natural phosphate linkages and/or Rp internucleotidic linkages can improve removal of oligonucleotides from a system. As appreciated by a person having ordinary skill in the art, various assays known in the art can be utilized to assess such properties in accordance with the present disclosure.

In some embodiments, provided oligonucleotides capable of directing single-stranded RNA interference comprise one or more modified sugar moieties. In some embodiments, 5% or more of the sugar moieties of provided oligonucleotides are modified.

In some embodiments, the present disclosure provides an PNPLA3 oligonucleotide composition comprising a first plurality of oligonucleotides, wherein:

oligonucleotides of the first plurality have the same base sequence; and oligonucleotides of the first plurality comprise one or more modified sugar moieties, or comprise one or more natural phosphate linkages and one or more modified internucleotidic linkages.

In some embodiments, oligonucleotides of the first plurality comprise one or more modified sugar moieties. In some embodiments, provided oligonucleotides comprise one or more modified sugar moieties.

In some embodiments, provided compositions alter transcript single-stranded RNA interference so that an undesired target and/or biological function are suppressed. In some embodiments, in such cases provided composition can also induce cleavage of the transcript after hybridization.

In some embodiments, each oligonucleotide of the first plurality comprises one or more modified sugar moieties and/or one or more modified internucleotidic linkages. In some embodiments, each oligonucleotide of the first plurality comprises no more than about 95% unmodified sugar moieties. In some embodiments, each oligonucleotide of the first plurality comprises no more than about 50% unmodified sugar moieties. In some embodiments, each oligonucleotide of the first plurality comprises no more than about 5% unmodified sugar moieties. In some embodiments, each sugar moiety of the oligonucleotides of the first plurality is independently modified.

In some embodiments, each oligonucleotide of the first plurality comprises two or more modified internucleotidic linkages. In some embodiments, each oligonucleotide of the first plurality comprises three or more modified internucleotidic linkages. In some embodiments, each oligonucleotide of the first plurality comprises four or more modified internucleotidic linkages. In some embodiments, each oligonucleotide of the first plurality comprises five or more modified internucleotidic linkages. In some embodiments, each oligonucleotide of the first plurality comprises ten or more modified internucleotidic linkages.

In some embodiments, each oligonucleotide of the first plurality comprises no more than about 30% natural phosphate linkages. In some embodiments, each oligonucleotide of the first plurality comprises no more than about 20% natural phosphate linkages. In some embodiments, each oligonucleotide of the first plurality comprises no more than about 10% natural phosphate linkages. In some embodiments, each oligonucleotide of the first plurality comprises no more than about 5% natural phosphate linkages.

In some embodiments, provided oligonucleotides contain increased levels of one or more isotopes. In some embodiments, provided oligonucleotides are labeled, e.g., by one or more isotopes of one or more elements, e.g., hydrogen, carbon, nitrogen, etc. In some embodiments, provided oligonucleotides in provided compositions, e.g., oligonucleotides of a first plurality, comprise base modifications, sugar modifications, and/or internucleotidic linkage modifications, wherein the oligonucleotides contain an enriched level of deuterium. In some embodiments, provided oligonucleotides are labeled with deuterium (replacing —$^1$H with —$^2$H) at one or more positions. In some embodiments, one or more $^1$H of a PNPLA3 oligonucleotide or any moiety conjugated to the oligonucleotide (e.g., a targeting moiety, lipid moiety, etc.) is substituted with $^2$H. Such oligonucleotides can be used in any composition or method described herein.

The present invention includes all pharmaceutically acceptable isotopically-labelled compounds wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I, $^{124}$I, and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of Formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Tomography (PET) studies for examining substrate receptor occupancy.

Isotopically-labelled compounds can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may contain asymmetric or chiral centers, and, therefore, exist in different stereoisomeric forms. Unless specified otherwise, it is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Chiral compounds of the invention (and chiral precursors thereof) may be obtained in enantiomerically-enriched form using chromatography, typically high pressure liquid chromatography (HPLC) or supercritical fluid chromatography (SFC), on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine (DEA) or isopropylamine. Concentration of the eluent affords the enriched mixture.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereoisomers and converting (e.g. hydrolyzing) the individual diastereoisomers to the corresponding pure enantiomers. Enantiomers can also be separated by use of a chiral HPLC column. Alternatively, the specific stereoisomers may be synthesized by using an optically active starting material, by asymmetric synthesis using optically active reagents, substrates, catalysts or solvents, or by converting one stereoisomer into the other by asymmetric transformation.

In some embodiments, controlling structural elements of oligonucleotides, such as chemical modifications (e.g., modifications of a sugar, base and/or internucleotidic linkage) or patterns thereof, alterations in stereochemistry (e.g., stereochemistry of a backbone chiral internucleotidic linkage) or patterns thereof, substitution of an atom with an isotope of the same element, and/or conjugation with an additional chemical moiety (e.g., a lipid moiety, targeting moiety, etc.) can have a significant impact on a desired biological effect. In some embodiments, a desired biological effect is enhanced by more than 2 fold.

In some embodiments, a desired biological effect is directing a decrease in the expression and/or level of a target gene or its gene product. In some embodiments, a desired biological effect is improved single-stranded RNA interference. In some embodiments, a desired biological effect is improved RNase H-mediated knockdown. In some embodiments, a desired biological effect is improved single-stranded RNA interference and/or RNase H-mediated knockdown.

In some embodiments, the present disclosure provides an PNPLA3 oligonucleotide composition comprising a first plurality of oligonucleotides which:

1) have a common base sequence complementary to a target sequence in a transcript; and 2) comprise one or more modified sugar moieties and modified internucleotidic linkages.

In some embodiments, a provided oligonucleotide composition is characterized in that, when it is contacted with the transcript in a single-stranded RNA interference system, RNAi-mediated knockdown of the transcript is improved relative to that observed under reference conditions selected from the group consisting of absence of the composition, presence of a reference composition, and combinations thereof.

In some embodiments, the present disclosure provides an PNPLA3 oligonucleotide composition comprising a first plurality of oligonucleotides capable of directing single-stranded RNA interference, wherein a PNPLA3 oligonucleotides type is defined by:
1) base sequence;
2) pattern of backbone linkages;
3) pattern of backbone chiral centers; and
4) pattern of backbone phosphorus modifications,
which composition is chirally controlled in that it is enriched, relative to a substantially racemic preparation of oligonucleotides having the same base sequence, for oligonucleotides of the particular oligonucleotide type, the oligonucleotide composition being characterized in that, when it is contacted with the transcript in a single-stranded RNA interference system, RNAi-mediated knockdown of the transcript is improved relative to that observed under reference conditions selected from the group consisting of absence of the composition, presence of a reference composition, and combinations thereof.

In some embodiments, each of the consecutive nucleoside units is independently preceded and/or followed by a modified internucleotidic linkage. In some embodiments, each of the consecutive nucleoside units is independently preceded and/or followed by a phosphorothioate linkage. In some embodiments, each of the consecutive nucleoside units is independently preceded and/or followed by a chirally controlled modified internucleotidic linkage. In some embodiments, each of the consecutive nucleoside units is independently preceded and/or followed by a chirally controlled phosphorothioate linkage. In some embodiments, a modified internucleotidic linkage has a structure of Formula I. In some embodiments, a modified internucleotidic linkage has a structure of Formula I-a.

In some embodiments, the present disclosure provides a single-stranded RNAi agent comprising a predetermined level of a first plurality of oligonucleotides, wherein:
oligonucleotides of the first plurality have the same base sequence;
oligonucleotides of the first plurality comprise a seed region comprising 2, 3, 4, 5, 6, 7 or more consecutive Sp modified internucleotidic linkages, a post-seed region comprising 2, 3, 4, 5, 6, 7, 8, 9, 10 or more consecutive Sp modified internucleotidic linkages.

In some embodiments, a seed region comprises 2 or more consecutive Sp modified internucleotidic linkages.

In some embodiments, a modified internucleotidic linkage has a structure of Formula I. In some embodiments, a modified internucleotidic linkage has a structure of Formula I-a.

As demonstrated in the present disclosure, in some embodiments, a provided oligonucleotide composition is characterized in that, when it is contacted with the transcript in a single-stranded RNA interference system, RNAi-mediated knockdown of the transcript is improved relative to that observed under reference conditions selected from the group consisting of absence of the composition, presence of a reference composition, and combinations thereof.

In some embodiments, the present disclosure provides a PNPLA3 oligonucleotide composition comprising a first plurality of oligonucleotides defined by having:
1) a common base sequence and length;
2) a common pattern of backbone linkages; and
3) a common pattern of backbone chiral centers, which composition is a substantially pure preparation of a single oligonucleotide in that a predetermined level of the oligonucleotides in the composition have the common base sequence and length, the common pattern of backbone linkages, and the common pattern of backbone chiral centers.

In some embodiments, a common base sequence and length may be referred to as a common base sequence. In some embodiments, oligonucleotides having a common base sequence may have the same pattern of nucleoside modifications, e.g. sugar modifications, base modifications, etc. In some embodiments, a pattern of nucleoside modifications may be represented by a combination of locations and modifications. In some embodiments, a pattern of backbone linkages comprises locations and types (e.g., phosphate, phosphorothioate, substituted phosphorothioate, etc.) of each internucleotidic linkages. A pattern of backbone chiral centers of a PNPLA3 oligonucleotide can be designated by a combination of linkage phosphorus stereochemistry (Rp/Sp) from 5' to 3'. As exemplified above, locations of non-chiral linkages may be obtained, for example, from pattern of backbone linkages.

As understood by a person having ordinary skill in the art, a stereorandom or racemic preparation of oligonucleotides is prepared by non-stereoselective and/or low-stereoselective coupling of nucleotide monomers, typically without using any chiral auxiliaries, chiral modification reagents, and/or chiral catalysts. In some embodiments, in a substantially racemic (or chirally uncontrolled) preparation of oligonucleotides, all or most coupling steps are not chirally controlled in that the coupling steps are not specifically conducted to provide enhanced stereoselectivity. An example substantially racemic preparation of oligonucleotides is the preparation of phosphorothioate oligonucleotides through sulfurizing phosphite triesters from commonly used phosphoramidite oligonucleotide synthesis with either tetraethylthiuram disulfide or (TETD) or 3H-1, 2-bensodithiol-3-one 1, 1-dioxide (BDTD), a well-known process in the art. In some embodiments, substantially racemic preparation of oligonucleotides provides substantially racemic oligonucleotide compositions (or chirally uncontrolled oligonucleotide compositions).

As understood by a person having ordinary skill in the art, in some embodiments, diastereoselectivity of a coupling or a linkage can be assessed through the diastereoselectivity of a dimer formation under the same or comparable conditions, wherein the dimer has the same 5'- and 3'-nucleosides and internucleotidic linkage.

In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type. In some embodiments, the present disclosure provides chirally controlled oligonucleotide composition of a first plurality of oligonucleotides in that the composition is enriched, relative to a substantially racemic preparation of the same oligonucleotides, for oligonucleotides of a single oligonucleotide type that share:
1) a common base sequence and length;
2) a common pattern of backbone linkages; and
3) a common pattern of backbone chiral centers.

In some embodiments, the present disclosure provides a PNPLA3 oligonucleotide composition comprising a first plurality of oligonucleotides capable of directing single-stranded RNA interference, wherein oligonucleotides are of a particular oligonucleotide type characterized by:

1) a common base sequence and length;
2) a common pattern of backbone linkages; and
3) a common pattern of backbone chiral centers;

which composition is chirally controlled in that it is enriched, relative to a substantially racemic preparation of oligonucleotides having the same base sequence and length, for oligonucleotides of the particular oligonucleotide type.

In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have identical structures.

In some embodiments, oligonucleotides of a PNPLA3 oligonucleotide type have a common pattern of backbone phosphorus modifications and a common pattern of sugar modifications. In some embodiments, oligonucleotides of a PNPLA3 oligonucleotide type have a common pattern of backbone phosphorus modifications and a common pattern of base modifications. In some embodiments, oligonucleotides of a PNPLA3 oligonucleotide type have a common pattern of backbone phosphorus modifications and a common pattern of nucleoside modifications. In some embodiments, oligonucleotides of an PNPLA3 oligonucleotide type are identical.

In some embodiments, oligonucleotides having a common base sequence and length, a common pattern of backbone linkages, and a common pattern of backbone chiral centers have a common pattern of backbone phosphorus modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers have a common pattern of backbone phosphorus modifications and a common pattern of sugar modifications. In some embodiments, oligonucleotides having a common base sequence and length, a common pattern of backbone linkages, and a common pattern of backbone chiral centers have a common pattern of backbone phosphorus modifications and a common pattern of base modifications. In some embodiments, oligonucleotides having a common base sequence and length, a common pattern of backbone linkages, and a common pattern of backbone chiral centers have a common pattern of backbone phosphorus modifications and a common pattern of nucleoside modifications. In some embodiments, oligonucleotides having a common base sequence and length, a common pattern of backbone linkages, and a common pattern of backbone chiral centers are identical.

In some embodiments, oligonucleotides in provided compositions have a common pattern of backbone phosphorus modifications. In some embodiments, a common base sequence is a base sequence of an PNPLA3 oligonucleotide type. In some embodiments, a provided composition is an PNPLA3 oligonucleotide composition that is chirally controlled in that the composition contains a predetermined level of a first plurality of oligonucleotides of an individual oligonucleotide type, wherein a PNPLA3 oligonucleotide type is defined by:

1) base sequence;
2) pattern of backbone linkages;
3) pattern of backbone chiral centers; and
4) pattern of backbone phosphorus modifications.

As noted above and understood in the art, in some embodiments, the base sequence of a PNPLA3 oligonucleotide may refer to the identity and/or modification status of nucleoside residues (e.g., of sugar and/or base components, relative to standard naturally occurring nucleotides such as adenine, cytosine, guanosine, thymine, and uracil) in the oligonucleotide and/or to the hybridization character (i.e., the ability to hybridize with particular complementary residues) of such residues.

In some embodiments, oligonucleotides of a particular type are identical in that they have the same base sequence (including length), the same pattern of chemical modifications to sugar and base moieties, the same pattern of backbone linkages (e.g., pattern of natural phosphate linkages, phosphorothioate linkages, phosphorothioate triester linkages, and combinations thereof), the same pattern of backbone chiral centers (e.g., pattern of stereochemistry (Rp/Sp) of chiral internucleotidic linkages), and the same pattern of backbone phosphorus modifications (e.g., pattern of modifications on the internucleotidic phosphorus atom, such as —S$^-$, and -L-R$^1$ of Formula I).

Among other things, the present disclosure recognizes that combinations of oligonucleotide structural elements (e.g., patterns of chemical modifications, backbone linkages, backbone chiral centers, and/or backbone phosphorus modifications) can provide surprisingly improved properties such as bioactivities.

In some embodiments, provided chirally controlled (and/or stereochemically pure) preparations are RNAi agent oligonucleotides.

In some embodiments, provided chirally controlled (and/or stereochemically pure) preparations are of oligonucleotides that include one or more modified backbone linkages, bases, and/or sugars.

In some embodiments, provided compositions comprise oligonucleotides containing one or more residues which are modified at the sugar moiety. In some embodiments, provided compositions comprise oligonucleotides containing one or more residues which are modified at the 2' position of the sugar moiety (referred to herein as a "2'-modification"). Examples of such modifications are described above and herein and include, but are not limited to, 2'-OMe, 2'-MOE, 2'-LNA, 2'-F, FRNA, FANA, S-cEt, etc. In some embodiments, provided compositions comprise oligonucleotides containing one or more residues which are 2'-modified. For example, in some embodiments, provided oligonucleotides contain one or more residues which are 2'-O-methoxyethyl (2'-MOE)-modified residues. In some embodiments, provided compositions comprise oligonucleotides which do not contain any 2'-modifications. In some embodiments, provided compositions are oligonucleotides which do not contain any 2'-MOE residues. That is, in some embodiments, provided oligonucleotides are not MOE-modified. Additional example sugar modifications are described in the present disclosure.

In some embodiments, one or more is one. In some embodiments, one or more is two. In some embodiments, one or more is three. In some embodiments, one or more is four. In some embodiments, one or more is five. In some embodiments, one or more is six. In some embodiments, one or more is seven. In some embodiments, one or more is eight. In some embodiments, one or more is nine. In some embodiments, one or more is ten. In some embodiments, one or more is at least one. In some embodiments, one or more is at least two. In some embodiments, one or more is at least three. In some embodiments, one or more is at least four. In some embodiments, one or more is at least five. In some embodiments, one or more is at least six. In some embodiments, one or more is at least seven. In some embodiments, one or more is at least eight. In some embodiments, one or more is at least nine. In some embodiments, one or more is at least ten.

In some embodiments, a sugar moiety without a 2'-modification is a sugar moiety found in a natural DNA nucleoside.

A person of ordinary skill in the art understands that various regions of a target transcript can be targeted by provided compositions and methods. In some embodiments, a base sequence of provided oligonucleotides comprises an intron sequence. In some embodiments, a base sequence of provided oligonucleotides comprises an exon sequence. In some embodiments, a base sequence of provided oligonucleotides comprises an intron and an exon sequence.

As understood by a person having ordinary skill in the art, provided oligonucleotides and compositions, among other things, can target a great number of nucleic acid polymers. For instance, in some embodiments, provided oligonucleotides and compositions may target a transcript of a nucleic acid sequence, wherein a common base sequence of oligonucleotides (e.g., a base sequence of a PNPLA3 oligonucleotide type) comprises or is a sequence complementary to a sequence of the transcript. In some embodiments, a common base sequence comprises a sequence complimentary to a sequence of a target. In some embodiments, a common base sequence is a sequence complimentary to a sequence of a target. In some embodiments, a common base sequence comprises or is a sequence 100% complimentary to a sequence of a target. In some embodiments, a common base sequence comprises a sequence 100% complimentary to a sequence of a target. In some embodiments, a common base sequence is a sequence 100% complimentary to a sequence of a target.

I

In some embodiments, a common base sequence comprises or is a sequence complementary to a characteristic sequence element. In some embodiments, a common base sequence comprises a sequence complementary to a characteristic sequence element. In some embodiments, a common base sequence is a sequence complementary to a characteristic sequence element. In some embodiments, a common base sequence comprises or is a sequence 100% complementary to a characteristic sequence element. In some embodiments, a common base sequence comprises a sequence 100% complementary to a characteristic sequence element. In some embodiments, a common base sequence is a sequence 100% complementary to a characteristic sequence element. In some embodiments herein, a characteristic sequence element is, as non-limiting examples, a seed region, a post-seed region or a portion of a seed region, or a portion of a post-seed region or a 3'-terminal dinucleotide.

In some embodiments, a characteristic sequence element comprises or is a mutation. In some embodiments, a characteristic sequence element comprises a mutation. In some embodiments, a characteristic sequence element is a mutation. In some embodiments, a characteristic sequence element comprises or is a point mutation. In some embodiments, a characteristic sequence element comprises a point mutation. In some embodiments, a characteristic sequence element is a point mutation. In some embodiments, a characteristic sequence element comprises or is an SNP. In some embodiments, a characteristic sequence element comprises an SNP. In some embodiments, a characteristic sequence element is an SNP.

In some embodiments, a common base sequence 100% matches a target sequence, which it does not 100% match a similar sequence of the target sequence.

For example, in some embodiments, a common base sequence matches a mutation in the disease-causing copy or allele of a target nucleic acid sequence, but does not match a non-disease-causing copy or allele at the mutation site; in some other embodiments, a common base sequence matches an SNP in the disease-causing allele of a target nucleic acid sequence, but does not match a non-disease-causing allele at the corresponding site.

Among other things, the present disclosure recognizes that a base sequence may have impact on oligonucleotide properties. In some embodiments, a base sequence may have impact on cleavage pattern of a target when oligonucleotides having the base sequence are utilized for suppressing a target, e.g., through a pathway involving RNase H: for example, structurally similar (all phosphorothioate linkages, all stereorandom) oligonucleotides have different sequences may have different cleavage patterns.

In some embodiments, a common base sequence is a base sequence that comprises a SNP.

As a person having ordinary skill in the art understands, provided oligonucleotide compositions and methods have various uses as known by a person having ordinary skill in the art. Methods for assessing provided compositions, and properties and uses thereof, are also widely known and practiced by a person having ordinary skill in the art. Example properties, uses, and/or methods include but are not limited to those described in WO/2014/012081 and WO/2015/107425.

In some embodiments, a chiral internucleotidic linkage has the structure of Formula I. In some embodiments, a chiral internucleotidic linkage is phosphorothioate. In some embodiments, each chiral internucleotidic linkage in a single oligonucleotide of a provided composition independently has the structure of Formula I. In some embodiments, each chiral internucleotidic linkage in a single oligonucleotide of a provided composition is a phosphorothioate.

In some embodiments, oligonucleotides of the present disclosure comprise one or more modified sugar moieties. In some embodiments, oligonucleotides of the present disclosure comprise one or more modified base moieties. As known by a person of ordinary skill in the art and described in the disclosure, various modifications can be introduced to a sugar and/or moiety. For example, in some embodiments, a modification is a modification described in U.S. Pat. No. 9,006,198, WO2014/012081 and WO/2015/107425, the sugar and base modifications of each of which are incorporated herein by reference.

In some embodiments, a sugar modification is a 2'-modification. Commonly used 2'-modifications include but are not limited to 2'-OR', wherein $R^1$ is not hydrogen. In some embodiments, a modification is 2'-OR, wherein R is optionally substituted aliphatic. In some embodiments, a modification is 2'-OMe. In some embodiments, a modification is 2'-O-MOE. In some embodiments, the present disclosure demonstrates that inclusion and/or location of particular chirally pure internucleotidic linkages can provide stability improvements comparable to or better than those achieved through use of modified backbone linkages, bases, and/or sugars. In some embodiments, a provided single oligonucleotide of a provided composition has no modifications on the sugars. In some embodiments, a provided single oligonucleotide of a provided composition has no modifications on 2'-positions of the sugars (i.e., the two groups at the 2'-position are either —H/—H or —H/—OH). In some embodiments, a provided single oligonucleotide of a provided composition does not have any 2'-MOE modifications.

In some embodiments, a 2'-modification is —O-L- or -L- which connects the 2'-carbon of a sugar moiety to another carbon of a sugar moiety. In some embodiments, a 2'-modification is —O-L- or -L- which connects the 2'-carbon of a sugar moiety to the 4'-carbon of a sugar moiety. In some embodiments, a 2'-modification is S-cEt. In some embodiments, a modified sugar moiety is an LNA moiety.

In some embodiments, a 2'-modification is —F. In some embodiments, a 2'-modification is FANA. In some embodiments, a 2'-modification is FRNA.

In some embodiments, a sugar modification is a 5'-modification, e.g., R-5'-Me, S-5'-Me, etc.

In some embodiments, a sugar modification changes the size of the sugar ring. In some embodiments, a sugar modification is the sugar moiety in FHNA.

In some embodiments, a sugar modification replaces a sugar moiety with another cyclic or acyclic moiety. Examples of such moieties are widely known in the art, including but not limited to those used in morpholino (optionally with its phosphorodiamidate linkage), glycol nucleic acids, etc.

In some embodiments, an ssRNAi agent is or comprises a PNPLA3 oligonucleotide selected from the group consisting of any ssRNAi of any format described in FIG. 1 or otherwise herein. Those skilled in the art, reading the present specification, will appreciate that the present disclosure specifically does not exclude the possibility that any oligonucleotide described herein which is labeled as a ssRNAi agent may also or alternatively operate through another mechanism (e.g., as an antisense oligonucleotide; mediating knock-down via a RNaseH mechanism; sterically hindering translation; or any other biochemical mechanism).

In some embodiments, an antisense oligonucleotide (ASO) is or comprises a PNPLA3 oligonucleotide selected from the group consisting of any oligonucleotide of any format described in FIG. 2. Those skilled in the art, reading the present specification, will appreciate that the present disclosure specifically does not exclude the possibility that any oligonucleotide described herein which is labeled as an antisense oligonucleotide (ASO) may also or alternatively operate through another mechanism (e.g., as a ssRNAi utilizing RISC); the disclosure also notes that various ASOs may operate via different mechanisms (utilizing RNaseH, sterically blocking translation or other post-transcriptional processes, changing the conformation of a target nucleic acid, etc.).

In some embodiments, a hybrid oligonucleotide is or comprises a PNPLA3 oligonucleotide selected from the group consisting of: WV-2111, WV-2113, WV-2114, WV-2148, WV-2149, WV-2152, WV-2153, WV-2156, WV-2157, WV-2387, WV-3069, WV-7523, WV-7524, WV-7525, WV-7526, WV-7527, WV-7528, and any oligonucleotide of any of Formats S40 to S42 of FIG. 1L; or Formats 30-32, 66-69 or 101-103 of FIG. 1. Those skilled in the art, reading the present specification, will appreciate that the present disclosure specifically does not exclude the possibility that any oligonucleotide described herein which is labeled as a hybrid oligonucleotide may also or alternatively operate through another mechanism (e.g., as an antisense oligonucleotide; mediating knock-down via a RNaseH mechanism; sterically hindering translation; or any other biochemical mechanism).

Chirally Controlled Oligonucleotides and Chirally Controlled Oligonucleotide Compositions In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides are chirally controlled.

The present disclosure provides chirally controlled oligonucleotides, and chirally controlled oligonucleotide compositions which are of high crude purity and of high diastereomeric purity. In some embodiments, the present disclosure provides chirally controlled oligonucleotides, and chirally controlled oligonucleotide compositions which are of high crude purity. In some embodiments, the present disclosure provides chirally controlled oligonucleotides, and chirally controlled oligonucleotide compositions which are of high diastereomeric purity.

In some embodiments, a single-stranded RNAi agent is a substantially pure preparation of an PNPLA3 oligonucleotide type in that oligonucleotides in the composition that are not of the oligonucleotide type are impurities form the preparation process of said oligonucleotide type, in some case, after certain purification procedures.

In some embodiments, the present disclosure provides oligonucleotides comprising one or more diastereomerically pure internucleotidic linkages with respect to the chiral linkage phosphorus. In some embodiments, the present disclosure provides oligonucleotides comprising one or more diastereomerically pure internucleotidic linkages having the structure of Formula I. In some embodiments, the present disclosure provides oligonucleotides comprising one or more diastereomerically pure internucleotidic linkages with respect to the chiral linkage phosphorus, and one or more phosphate diester linkages. In some embodiments, the present disclosure provides oligonucleotides comprising one or more diastereomerically pure internucleotidic linkages having the structure of Formula I, and one or more phosphate diester linkages. In some embodiments, the present disclosure provides oligonucleotides comprising one or more diastereomerically pure internucleotidic linkages having the structure of Formula I-c, and one or more phosphate diester linkages. In some embodiments, such oligonucleotides are prepared by using stereoselective oligonucleotide synthesis, as described in this application, to form pre-designed diastereomerically pure internucleotidic linkages with respect to the chiral linkage phosphorus. Example internucleotidic linkages, including those having structures of Formula I, are further described below.

In some embodiments, the present disclosure provides a chirally controlled oligonucleotide, wherein at least two of the individual internucleotidic linkages within the oligonucleotide have different stereochemistry and/or different P-modifications relative to one another.

Internucleotidic Linkages

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides comprise any internucleotidic linkage described herein or known in the art.

In some embodiments, an PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any internucleotidic linkage described herein or known in the art.

A non-limiting example of an internucleotidic linkage or unmodified internucleotidic linkage is a phosphodiester; non-limiting examples of modified internucleotidic linkages include those in which one or more oxygen of a phosphodiester has been replaced by, as non-limiting examples, sulfur (as in a phosphorothioate), H, alkyl, or another moiety or element which is not oxygen. A non-limiting example of an internucleotidic linkage is a moiety which does not a comprise a phosphorus but serves to link two sugars. A non-limiting example of an internucleotidic linkage is a moiety which does not a comprise a phosphorus but serves to link two sugars in the backbone of a PNPLA3 oligonucleotide. Disclosed herein are additional non-limiting examples of nucleotides, modified nucleotides, nucleotide analogs, internucleotidic linkages, modified internucleotidic linkages, bases, modified bases, and base analogs, sugars, modified sugars, and sugar analogs, and nucleosides, modified nucleosides, and nucleoside analogs.

In certain embodiments, a internucleotidic linkage has the structure of Formula I:

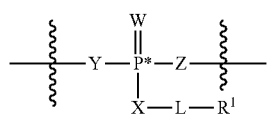

(I)

wherein each variable is as defined and described below. In some embodiments, a linkage of Formula I is chiral. In some embodiments, the present disclosure provides a chirally controlled oligonucleotide comprising one or more modified internucleotidic linkages of Formula I. In some embodiments, the present disclosure provides a chirally controlled oligonucleotide comprising one or more modified internucleotidic linkages of Formula I, and wherein individual internucleotidic linkages of Formula I within the oligonucleotide have different P-modifications relative to one another. In some embodiments, the present disclosure provides a chirally controlled oligonucleotide comprising one or more modified internucleotidic linkages of Formula I, and wherein individual internucleotidic linkages of Formula I within the oligonucleotide have different —X-L-$R^1$ relative to one another. In some embodiments, the present disclosure provides a chirally controlled oligonucleotide comprising one or more modified internucleotidic linkages of Formula I, and wherein individual internucleotidic linkages of Formula I within the oligonucleotide have different X relative to one another. In some embodiments, the present disclosure provides a chirally controlled oligonucleotide comprising one or more modified internucleotidic linkages of Formula I, and wherein individual internucleotidic linkages of Formula I within the oligonucleotide have different -L-$R^1$ relative to one another. In some embodiments, a chirally controlled oligonucleotide is a PNPLA3 oligonucleotide in a provided composition that is of the particular oligonucleotide type. In some embodiments, a chirally controlled oligonucleotide is a PNPLA3 oligonucleotide in a provided composition that has the common base sequence and length, the common pattern of backbone linkages, and the common pattern of backbone chiral centers. In some embodiments, a chirally controlled oligonucleotide is an PNPLA3 oligonucleotide in a chirally controlled composition that is of the particular oligonucleotide type, and the chirally controlled oligonucleotide is of the type. In some embodiments, a chirally controlled oligonucleotide is a PNPLA3 oligonucleotide in a provided composition that comprises a predetermined level of a plurality of oligonucleotides that share a common base sequence, a common pattern of backbone linkages, and a common pattern of backbone chiral centers, and the chirally controlled oligonucleotide shares the common base sequence, the common pattern of backbone linkages, and the common pattern of backbone chiral centers.

In some embodiments, a chirally controlled oligonucleotide comprises different internucleotidic phosphorus linkages.

In some embodiments, a phosphorothioate triester linkage comprises a chiral auxiliary, which, for example, is used to control the stereoselectivity of a reaction. In some embodiments, a phosphorothioate triester linkage does not comprise a chiral auxiliary. In some embodiments, a phosphorothioate triester linkage is intentionally maintained until and/or during the administration to a subject.

In some embodiments, a chirally controlled oligonucleotide is linked to a solid support. In some embodiments, a chirally controlled oligonucleotide is cleaved from a solid support.

In some embodiments, a chirally controlled oligonucleotide comprises at least one phosphate diester internucleotidic linkage and at least two consecutive modified internucleotidic linkages. In some embodiments, a chirally controlled oligonucleotide comprises at least one phosphate diester internucleotidic linkage and at least two consecutive phosphorothioate triester internucleotidic linkages.

In some embodiments, the present disclosure provides compositions comprising or consisting of a plurality of provided oligonucleotides (e.g., chirally controlled oligonucleotide compositions). In some embodiments, all such provided oligonucleotides are of the same type, i.e., all have the same base sequence, pattern of backbone linkages (i.e., pattern of internucleotidic linkage types, for example, phosphate, phosphorothioate, etc), pattern of backbone chiral centers (i.e. pattern of linkage phosphorus stereochemistry (Rp/Sp)), and pattern of backbone phosphorus modifications (e.g., pattern of "—XLR$^1$" groups in Formula I, disclosed herein). In some embodiments, all oligonucleotides of the same type are identical. In many embodiments, however, provided compositions comprise a plurality of oligonucleotides types, typically in pre-determined relative amounts.

In some embodiments, a PNPLA3 oligonucleotide, a PNPLA3 oligonucleotide that directs RNA interference, a PNPLA3 oligonucleotide that directs RNase H-mediated knockdown, or an PNPLA3 oligonucleotide that directs both RNA interference and RNase H-mediated knockdown can comprise any internucleotidic linkage described herein or known in the art. In some embodiments, a moiety that binds ASPGR is, for example, a GalNAc moiety is any GalNAc, or variant or modification thereof, as described herein or known in the art. In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any internucleotidic linkage described herein or known in the art in combination with any other structural element or modification described herein, including but not limited to, base sequence or portion thereof, sugar, base (nucleobase); stereochemistry or pattern thereof; additional chemical moiety, including but not limited to, a targeting moiety, a lipid moiety, a carbohydrate moiety, etc.; seed region; post-seed region; 5'-end structure; 5'-end region; 5' nucleotide moiety; 3'-end region; 3'-terminal dinucleotide; 3'-end cap; length; additional chemical moiety, including but not limited to, a targeting moiety, lipid moiety, a GalNAc, etc.; format or any structural element thereof, and/or any other structural element or modification described herein; and in some embodiments, the present disclosure pertains to multimers of any such oligonucleotides.

In some embodiments, a chirally controlled oligonucleotide comprises one or more modified internucleotidic phosphorus linkages. In some embodiments, a chirally controlled oligonucleotide comprises, e.g., a phosphorothioate or a phosphorothioate triester linkage.

In some embodiments, a modified internucleotidic linkage is phosphorothioate. In some embodiments, a modified internucleotidic linkage is selected from those described in, for example: US 20110294124, US 20120316224, US 20140194610, US 20150211006, US 20150197540, WO 2015107425, PCT/US2016/043542, and PCT/US2016/043598, Whittaker et al. 2008 Tetrahedron Letters 49: 6984-6987.

Non-limiting examples of internucleotidic linkages also include those described in the art, including, but not limited to, those described in any of: Gryaznov, S.; Chen, J.-K. J. Am. Chem. Soc. 1994, 116, 3143, Jones et al. J. Org. Chem. 1993, 58, 2983, Koshkin et al. 1998 Tetrahedron 54: 3607-3630, Lauritsen et al. 2002 Chem. Comm. 5: 530-531, Lauritsen et al. 2003 Bioo. Med. Chem. Lett. 13: 253-256, Mesmaeker et al. Angew. Chem., Int. Ed. Engl. 1994, 33, 226, Petersen et al. 2003 TRENDS Biotech. 21: 74-81, Schultz et al. 1996 Nucleic Acids Res. 24: 2966, Ts'o et al. Ann. N. Y. Acad. Sci. 1988, 507, 220, and Vasseur et al. J. Am. Chem. Soc. 1992, 114, 4006.

In some embodiments, the present disclosure provides a chirally controlled oligonucleotide comprising a sequence found in any oligonucleotide disclosed herein. In some embodiments, the present disclosure provides a chirally controlled oligonucleotide comprising a sequence found in any oligonucleotide disclosed herein, wherein one or more U is replaced with T. In some embodiments, the present disclosure provides a chirally controlled oligonucleotide comprising a sequence found in any oligonucleotide disclosed herein, wherein the said sequence has over 50% identity with the sequence of any oligonucleotide disclosed herein.

In some embodiments, the present disclosure provides a chirally controlled oligonucleotide comprising the sequence of any oligonucleotide disclosed herein. In some embodiments, the present disclosure provides a chirally controlled oligonucleotide having the sequence of any oligonucleotide disclosed herein. In some embodiments, the present disclosure provides a chirally controlled oligonucleotide comprising a sequence found in any oligonucleotide disclosed herein, wherein the oligonucleotides have a pattern of backbone linkages, pattern of backbone chiral centers, and/or pattern of backbone phosphorus modifications described herein.

In some embodiments, the present disclosure provides a chirally controlled oligonucleotide comprising a sequence found in any oligonucleotide disclosed herein. In some embodiments, the present disclosure provides a chirally controlled oligonucleotide comprising a sequence found in any oligonucleotide disclosed herein, wherein one or more T is substituted with U. In some embodiments, the present disclosure provides a chirally controlled oligonucleotide comprising a sequence found in any oligonucleotide disclosed herein, wherein the said sequence has over 50% identity with the sequence of any oligonucleotide disclosed herein. In some embodiments, the present disclosure provides a chirally controlled oligonucleotide comprising a sequence found in any oligonucleotide disclosed herein, wherein the said sequence has over 60% identity with the sequence of any oligonucleotide disclosed herein. In some embodiments, the present disclosure provides a chirally controlled oligonucleotide comprising a sequence found in any oligonucleotide disclosed herein, wherein the said sequence has over 70% identity with the sequence of any oligonucleotide disclosed herein. In some embodiments, the present disclosure provides a chirally controlled oligonucleotide comprising a sequence found in any oligonucleotide disclosed herein, wherein the said sequence has over 80% identity with the sequence of any oligonucleotide disclosed herein. In some embodiments, the present disclosure provides a chirally controlled oligonucleotide comprising a sequence found in any oligonucleotide disclosed herein, wherein the said sequence has over 90% identity with the sequence of any oligonucleotide disclosed herein. In some embodiments, the present disclosure provides a chirally controlled oligonucleotide comprising a sequence found in any oligonucleotide disclosed herein, wherein the said sequence has over 95% identity with the sequence of any oligonucleotide disclosed herein. In some embodiments, the present disclosure provides a chirally controlled oligonucleotide comprising the sequence of any oligonucleotide disclosed herein. In some embodiments, the present disclosure provides a chirally controlled oligonucleotide having the sequence of any oligonucleotide disclosed herein.

In some embodiments, the present disclosure provides a chirally controlled oligonucleotide comprising the sequence of any oligonucleotide disclosed herein, wherein at least one internucleotidic linkage is

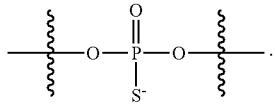 [SMILES: *OP(=O)([S-])O*]

In some embodiments, the present disclosure provides a chirally controlled oligonucleotide comprising the sequence of any oligonucleotide disclosed herein, wherein each internucleotidic linkage is

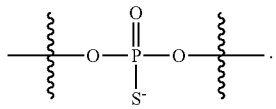

In some embodiments, the present disclosure provides a chirally controlled oligonucleotide having the sequence of any oligonucleotide disclosed herein, wherein at least one internucleotidic linkage is

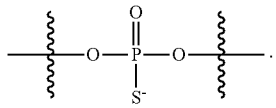 [SMILES: *OP(=O)([S-])O*]

In some embodiments, the present disclosure provides a chirally controlled oligonucleotide having the sequence of any oligonucleotide disclosed herein, wherein each internucleotidic linkage is

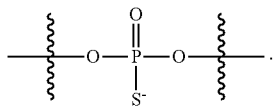 [SMILES: *OP(=O)([S-])O*]

In some embodiments, the present disclosure provides a chirally controlled oligonucleotide having the sequence of any oligonucleotide disclosed herein, wherein each cytosine is optionally and independently replaced by 5-methylcytosine. In some embodiments, the present disclosure provides a chirally controlled oligonucleotide having the sequence of any oligonucleotide disclosed herein, wherein at least one cytosine is optionally and independently replaced by 5-methylcytosine. In some embodiments, the present disclosure provides a chirally controlled oligonucleotide having the sequence of any oligonucleotide disclosed herein, wherein each cytosine is optionally and independently replaced by 5-methylcytosine.

Bases (Nucleobases)

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides comprise any nucleobase described herein or known in the art.

In some embodiments, a nucleobase present in a provided oligonucleotide is a natural nucleobase or a modified nucleobase derived from a natural nucleobase. Examples include, but are not limited to, uracil, thymine, adenine, cytosine, and guanine having their respective amino groups protected by acyl protecting groups, 2-fluorouracil, 2-fluorocytosine, 5-bromouracil, 5-iodouracil, 2,6-diaminopurine, azacytosine, pyrimidine analogs such as pseudoisocytosine and pseudouracil and other modified nucleobases such as 8-substituted purines, xanthine, or hypoxanthine (the latter two being the natural degradation products). Example modified nucleobases are disclosed in Chiu and Rana, *RNA,* 2003, 9, 1034-1048, Limbach et al. *Nucleic Acids Research,* 1994, 22, 2183-2196 and Revankar and Rao, *Comprehensive Natural Products Chemistry*, vol. 7, 313. In some embodiments, a modified nucleobase is substituted uracil, thymine, adenine, cytosine, or guanine. In some embodiments, a modified nucleobase is a functional replacement, e.g., in terms of hydrogen bonding and/or base pairing, of uracil, thymine, adenine, cytosine, or guanine. In some embodiments, a nucleobase is optionally substituted uracil, thymine, adenine, cytosine, 5-methylcytosine, or guanine. In some embodiments, a nucleobase is uracil, thymine, adenine, cytosine, 5-methylcytosine, or guanine.

In some embodiments, a modified base is optionally substituted adenine, cytosine, guanine, thymine, or uracil. In some embodiments, a modified nucleobase is independently adenine, cytosine, guanine, thymine or uracil, modified by one or more modifications by which:

(1) a nucleobase is modified by one or more optionally substituted groups independently selected from acyl, halogen, amino, azide, alkyl, alkenyl, alkynyl, aryl, heteroalkyl, heteroalkenyl, heteroalkynyl, heterocyclyl, heteroaryl, carboxyl, hydroxyl, biotin, avidin, streptavidin, substituted silyl, and combinations thereof;

(2) one or more atoms of a nucleobase are independently replaced with a different atom selected from carbon, nitrogen and sulfur;

(3) one or more double bonds in a nucleobase are independently hydrogenated; or (4) one or more aryl or heteroaryl rings are independently inserted into a nucleobase.

Various additional nucleobases are described in the art.

Sugars

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides comprise any sugar described herein or known in the art.

In some embodiments, provided oligonucleotides capable of directing single-stranded RNA interference comprise one or more modified sugar moieties beside the natural sugar moieties.

The most common naturally occurring nucleotides are comprised of ribose sugars linked to the nucleobases adenosine (A), cytosine (C), guanine (G), and thymine (T) or uracil (U). Also contemplated are modified nucleotides wherein a phosphate group or linkage phosphorus in the nucleotides can be linked to various positions of a sugar or modified sugar. As non-limiting examples, the phosphate group or linkage phosphorus can be linked to the 2", 3", 4" or 5" hydroxyl moiety of a sugar or modified sugar. Nucleotides that incorporate modified nucleobases as described herein are also contemplated in this context. In some embodiments, nucleotides or modified nucleotides comprising an unprotected —OH moiety are used in accordance with methods of the present disclosure.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base (nucleobase), modified base or base analog described herein or known in the art. In some embodiments, a PNPLA3 oligonucleotide, a PNPLA3 oligonucleotide that directs RNA interference, an PNPLA3 oligonucleotide that directs RNase H-mediated knockdown, or a PNPLA3 oligonucleotide that directs both RNA interference and RNase H-mediated knockdown can comprise any base described herein or known in the art in combination with any other structural element or modification described herein, including but not limited to, base sequence or portion thereof, sugar; internucleotidic linkage; stereochemistry or pattern thereof; additional chemical moiety, including but not limited to, a targeting moiety, lipid moiety, a GalNAc moiety, etc.; 5'-end structure; 5'-end region; 5' nucleotide moiety; seed region; post-seed region; 3'-end region; 3'-terminal dinucleotide; 3'-end cap; pattern of modifications of sugars, bases or internucleotidic linkages; format or any structural element thereof, and/or any other structural element or modification described herein; and in some embodiments, the present disclosure pertains to multimers of any such oligonucleotides.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any sugar.

Various additional sugars are described in the art.

Base Sequence of a PNPLA3 Oligonucleotide

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can comprise any base sequence or portion thereof, described herein, wherein a portion is a span of at least 15 contiguous bases, or a span of at least 15 contiguous bases with 1-5 mismatches.

In some embodiments, a PNPLA3 oligonucleotide, a PNPLA3 oligonucleotide that directs RNA interference, a PNPLA3 oligonucleotide that directs RNase H-mediated knockdown, or an PNPLA3 oligonucleotide that directs both RNA interference and RNase H-mediated knockdown can comprise any base sequence described herein. In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base sequence or portion thereof, described herein. In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base sequence or portion thereof, described herein, wherein a portion is a span of 15 contiguous bases, or a span of 15 contiguous bases with 1-5 mismatches.

The sequence of a single-stranded RNAi agent has a sufficient length and identity to a transcript target to mediate target-specific RNA interference. In some embodiments, the RNAi agent is complementary to a portion of a transcript target sequence.

The base sequence of a single-stranded RNAi agent is complementary to that of a target transcript. As used herein, "target transcript sequence," "target sequence", "target gene", and the like, refer to a contiguous portion of the nucleotide sequence of an mRNA molecule formed during the transcription of a gene, e.g., a target gene, including mRNA that is a product of RNA processing of a primary transcription product.

The terms "complementary," "fully complementary" and "substantially complementary" herein may be used with respect to the base matching between the strand of a single-stranded RNAi agent and a target sequence or between an antisense oligonucleotide and a target sequence, as will be understood from the context of their use. A strand of a single-stranded RNAi agent or antisense oligonucleotide or other oligonucleotide is complementary to that of a target sequence when each base of the single-stranded RNAi agent, antisense oligonucleotide or other oligonucleotide is capable of base-pairing with a sequential base on the target strand, when maximally aligned. As a non-limiting example, if a target sequence has, for example, a base sequence of 5'-GCAUAGCGAGCGAGGGAAAAC-3' (SEQ ID NO: 1), a PNPLA3 oligonucleotide with a base sequence of 5'GUUUUCCCUCGCUCGCUAUGC-3' (SEQ ID NO: 2) is complementary or fully complementary to such a target sequence. It is noted, of course, that substitution of T for U, or vice versa, does not alter the amount of complementarity.

As used herein, a polynucleotide that is "substantially complementary" to a target sequence is largely or mostly complementary but not 100% complementary. In some embodiments, a sequence (e.g., a strand of a single-stranded RNAi agent or an antisense oligonucleotide) which is substantially complementary has 1, 2, 3, 4 or 5 mismatches from a sequence which is 100% complementary to the target sequence. In the case of a single-stranded RNAi agent, this disclosure notes that the 5' terminal nucleotide (N1) in many cases has a mismatch from the complement of a target sequence. Similarly, in a single-stranded RNAi agent, the 3'-terminal dinucleotide, if present, can be a mismatch from the complement of the target sequence. As a non-limiting example, if a target sequence has, for example, a base sequence of 5'-GCAUAGCGAGCGAGGGAAAAC-3' (SEQ ID NO: 3), a single-stranded RNAi agent with a base sequence of 5'TUUUUCCCUCGCUCGCUAUTU-3' (SEQ ID NO: 4) is substantially complementary to such a target sequence.

The present disclosure presents, in Table 1A and elsewhere, various single-stranded RNAi agents and antisense oligonucleotides and other oligonucleotides, each of which has a defined base sequence. In some embodiments, the disclosure encompasses any oligonucleotide having a base sequence which is, comprises, or comprises a portion of the base sequence of any various single-stranded RNAi agent, antisense oligonucleotide and other oligonucleotide disclosed herein. In some embodiments, the disclosure encompasses any oligonucleotide having a base sequence which is, comprises, or comprises a portion of the base sequence of any various single-stranded RNAi agent, antisense oligonucleotide and other oligonucleotide disclosed herein, which has any chemical modification, stereochemistry, format, structural feature (e.g., if the oligonucleotide is a single-stranded RNAi agent, the 5'-end structure, 5'-end region, 5' nucleotide moiety, seed region, post-seed region, 3'-end region, 3'-terminal dinucleotide, 3'-end cap, or any structure, pattern or portion thereof), and/or any other modification described herein (e.g., conjugation with another moiety, such as a targeting moiety, carbohydrate moiety, a GalNAc moiety, lipid moiety, etc.; and/or multimerization).

In some embodiments, a PNPLA3 oligonucleotide has a base sequence which is, comprises or comprises a portion of the base sequence of any oligonucleotide disclosed herein.

In some embodiments, the present disclosure discloses an PNPLA3 oligonucleotide of a sequence recited herein. In some embodiments, the present disclosure discloses an PNPLA3 oligonucleotide of a sequence recited herein, wherein the oligonucleotide is capable of directing a decrease in the expression and/or level of a target gene or its gene product. In some embodiments, an PNPLA3 oligonucleotide of a recited sequence is a single-stranded RNAi agent. In some embodiments, a PNPLA3 oligonucleotide of a recited sequence is an antisense oligonucleotide which directs RNase H-mediated knockdown. In some embodiments, a PNPLA3 oligonucleotide of a recited sequence directs both RNA interference and RNase H-mediated knockdown. In some embodiments, a PNPLA3 oligonucleotide of a recited sequence comprises any structure described herein (e.g., any 5'-end structure, 5'-end region, 5' nucleotide moiety, seed region, post-seed region, 3'-terminal dinucleotide, 3'-end cap, or any portion of any of these structures, or any chemistry, stereochemistry, additional chemical moiety, etc., described herein). If the oligonucleotide is a ssRNAi agent, the sequence can be preceded by a T (as a non-limiting example, a 2'-deoxy T, 5'-(R)-Me OH T, 5'-(R)-Me PO T, 5'-(R)-Me PS T, 5'-(R)-Me PH T, 5'-(S)-Me OH T, 5'-(S)-Me PO T, 5'-(S)-Me PS T, or 5'-(S)-PH T) or the first nucleobase is replaced by a T (as a non-limiting example, a 2'-deoxy T, 5'-(R)-Me OH T, 5'-(R)-Me PO T, 5'-(R)-Me PS T, 5'-(R)-Me PH T, 5'-(S)-Me OH T, 5'-(S)-Me PO T, 5'-(S)-Me PS T, or 5'-(S)-PH T) and/or followed by a 3'-terminal dinucleotide (e.g., as non-limiting examples: TT, UU, TU, etc.). In various sequences, U can be replaced by T or vice versa, or a sequence can comprise a mixture of U and T. In some embodiments, a PNPLA3 oligonucleotide has a length of no more than about 49, 45, 40, 30, 35, 25, 23 total nucleotides. In some embodiments, a portion is a span of at least 15, 16, 17, 18, 19, 20, 21, 22, 23, 24, or 25 total nucleotides with 0-3 mismatches. In some embodiments, a portion is a span of at least 15, 16, 17, 18, 19, 20, 21, 22, 23, 24, or 25 total nucleotides with 0-3 mismatches, wherein a span with 0 mismatches is complementary and a span with 1 or more mismatches is a non-limiting example of substantial complementarity. In some embodiments, wherein the sequence recited above starts with a U at the 5'-end, the U can be deleted and/or replaced by another base. In some embodiments, the disclosure encompasses any oligonucleotide having a base sequence which is or comprises or comprises a portion of the base sequence of any oligonucleotide disclosed herein, which has a format or a portion of a format disclosed herein.

In some embodiments, a PNPLA3 oligonucleotide, an PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base sequence described herein. In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base sequence or portion thereof, described herein. In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any base sequence or portion thereof, described herein, wherein a portion is a span of 15 contiguous bases, or a span of 15 contiguous bases with 1-5 mismatches. In some embodiments, a PNPLA3 oligonucleotide, an PNPLA3 oligonucleotide that directs RNA interference, an PNPLA3 oligonucleotide that directs RNase H-mediated knockdown, or an PNPLA3 oligonucleotide that directs both RNA interference and RNase H-mediated knockdown can comprise any base sequence or portion thereof described herein in combination with any other structural element or modification described herein, including but not limited to, sugar, base; internucleotidic linkage; stereochemistry or pattern thereof; additional chemical moiety, including but not limited to, a targeting moiety, lipid moiety, a GalNAc moiety, etc.; 5'-end structure; 5'-end region; 5' nucleotide moiety; seed region; post-seed region; 3'-end region; 3'-terminal dinucleotide; 3'-end cap; pattern of modifications of sugars, bases or internucleotidic linkages; format or any structural element thereof, and/or any other structural element or modification described herein; and in some embodiments, the present disclosure pertains to multimers of any such oligonucleotides.

Non-limiting examples of oligonucleotides having various base sequences are disclosed in Table 1A, below.

TABLE 1A

Oligonucleotides.
PNPLA3 oligonucleotides.

| WAVE ID | Naked Sequence | SEQ ID NO: | Sequence | Stereochemistry |
|---|---|---|---|---|
| WV-3367 | AAGGGCATGAAGCAGGAACA | 5 | mA*mAmGmGmG*C*A*T*G*A*A*G*C*A*G* mGmAmAmC*mA | XOOOXXXXXXXXXXXXXOOOX |
| WV-3368 | GAAGGGCATGAAGCAGGAAC | 6 | mG*mAmAmGmG*C*A*T*G*A*A*G*C*A* mGmGmAmA*mC | XOOOXXXXXXXXXXXXXOOOX |
| WV-3369 | AGAAGGGCATGAAGCAGGAA | 7 | mA*mGmAmAmG*G*G*C*A*T*G*A*A*G*C* mAmGmGmA*mA | XOOOXXXXXXXXXXXXXOOOX |
| WV-3370 | UAGAAGGGCATGAAGCAGGA | 8 | mU*mAmGmAmA*G*G*G*C*A*T*G*A*A*G* mCmAmGmG*mA | XOOOXXXXXXXXXXXXXOOOX |
| WV-3371 | GUAGAAGGGCATGAAGCAGG | 9 | mG*mUmAmGmA*A*G*G*C*A*T*G*A*A* mGmCmAmG*mG | XOOOXXXXXXXXXXXXXOOOX |
| WV-3372 | UGUAGAAGGGCATGAAGCAG | 10 | mU*mGmUmAmG*A*A*G*G*G*C*A*T*G*A* mAmGmCmA*mG | XOOOXXXXXXXXXXXXXOOOX |
| WV-3373 | CUGUAGAAGGGCATGAAGCA | 11 | mC*mUmGmUmA*G*A*A*G*G*G*C*A*T*G* mAmAmGmC*mA | XOOOXXXXXXXXXXXXXOOOX |
| WV-3374 | ACUGUAGAAGGGCATGAAGC | 12 | mA*mCmUmGmU*A*G*A*A*G*G*G*C*A*T* mGmAmAmG*mC | XOOOXXXXXXXXXXXXXOOOX |
| WV-3375 | CACUGUAGAAGGGCATGAAG | 13 | mC*mAmCmUmG*T*A*G*A*A*G*G*G*C*A* mTmGmAmA*mG | XOOOXXXXXXXXXXXXXOOOX |
| WV-3376 | CCACUGUAGAAGGGCATGAA | 14 | mC*mCmAmCmU*G*T*A*G*A*A*G*G*G*C* mAmTmGmA*mA | XOOOXXXXXXXXXXXXXOOOX |
| WV-3377 | UUCCGACTCCTGGCCUUCCG | 15 | mU*mUmCmCmG*A*C*T*C*C*T*G*G*C*C* mUmUmCmC*mG | XOOOXXXXXXXXXXXXXOOOX |
| WV-3378 | UCCGACTCCTGGCCUUCCGC | 16 | mU*mCmCmGmA*C*T*C*C*T*G*G*C*C*T* mUmCmCmG*mC | XOOOXXXXXXXXXXXXXOOOX |
| WV-3379 | CCGACTCCTGGCCUUCCGCA | 17 | mC*mCmGmAmC*T*C*C*T*G*G*C*C*T*T* mCmCmGmC*mA | XOOOXXXXXXXXXXXXXOOOX |
| WV-3380 | ACCUGAGGATGGACCGCGGG | 18 | mA*mCmCmUmG*A*G*G*A*T*G*G*A*C*C* mGmCmGmG*mG | XOOOXXXXXXXXXXXXXOOOX |
| WV-3381 | UGUGCUUGGCTCCTGCCUGG | 19 | mU*mGmUmGmC*T*T*G*C*T*C*C*T*G* mCmCmUmG*mG | XOOOXXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3382 | CUGGACCUGAGGAUGACCG | 20 | mC*mUmGmGmA*C*C*T*G*A*G*G*A*T*G* mGmAmCmC*mG | XOOOXXXXXXXXXXXXXOOOX |
| WV-3383 | UGUUCCCGACUCCUGGCCUUC | 21 | mU*mGmUmCmC*C*G*A*C*T*C*C*T*G*G* mCmCmUmU*mC | XOOOXXXXXXXXXXXXXOOOX |
| WV-3384 | GUUCCGACUCCUGGCCUUCC | 22 | mG*mUmUmCmC*G*A*C*T*C*C*T*G*G*C* mCmUmUmC*mC | XOOOXXXXXXXXXXXXXOOOX |
| WV-3385 | CGACUCCUGGCCUUCCGCAC | 23 | mC*mGmAmCmU*C*C*T*G*G*C*C*T*T*C* mCmGmCmA*mC | XOOOXXXXXXXXXXXXXOOOX |
| WV-3386 | CCUGCUGUGCUUGGCUCCUG | 24 | mC*mCmUmGmC*T*G*T*G*C*T*T*G*G*C* mUmCmCmU*mG | XOOOXXXXXXXXXXXXXOOOX |
| WV-3387 | UCUUGUUACCCCGCCAUGG | 25 | mU*mCmUmUmG*T*T*A*C*C*C*C*G*C*C* mCmAmUmG*mG | XOOOXXXXXXXXXXXXXOOOX |
| WV-3388 | CCUGCCUCAGUGUCUCGGCC | 26 | mC*mCmUmGmC*C*T*C*A*G*T*G*T*C*T* mCmGmGmC*mC | XOOOXXXXXXXXXXXXXOOOX |
| WV-3389 | CCCUGCCUCAGUGUCUCGGC | 27 | mC*mCmCmUmG*C*C*T*C*A*G*T*G*T*C* mUmCmGmG*mC | XOOOXXXXXXXXXXXXXOOOX |
| WV-3390 | UUACCCCGCCAUGAGAGACG | 28 | mU*mUmAmCmC*C*C*G*C*C*A*T*G*G* mAmGmAmC*mG | XOOOXXXXXXXXXXXXXOOOX |
| WV-3391 | ACCCCGCCAUGGAGACGUU | 29 | mA*mCmCmCmC*G*C*C*A*T*G*G*A*G* mAmCmGmU*mU | XOOOXXXXXXXXXXXXXOOOX |
| WV-3392 | GACCUGAGGAUGACCGCGG | 30 | mG*mAmCmCmU*G*A*G*G*A*T*G*A*C* mCmGmCmG*mG | XOOOXXXXXXXXXXXXXOOOX |
| WV-3393 | GGACCUGAGGAUGACCGCG | 31 | mG*mGmAmCmC*T*G*A*G*G*A*T*G*A* mCmCmGmC*mG | XOOOXXXXXXXXXXXXXOOOX |
| WV-3394 | UACCCCGCCAUGGAGACGU | 32 | mU*mUmAmCmC*C*C*G*C*C*A*T*G*G* mAmGmAmC*mG | XOOOXXXXXXXXXXXXXOOOX |
| WV-3395 | GGGACCCUCUGCACUGGGCU | 33 | mG*mGmGmAmC*C*C*T*C*T*G*C*A*C*T* mGmGmGmC*mU | XOOOXXXXXXXXXXXXXOOOX |
| WV-3396 | CCUGGGCGAGAGGGUGUCCA | 34 | mC*mCmUmGmG*G*C*G*A*G*A*G*G*T* mGmUmCmC*mA | XOOOXXXXXXXXXXXXXOOOX |
| WV-3397 | CCCCCGCCAUGGAGACGUUU | 35 | mC*mCmCmCmC*G*C*C*A*T*G*G*A*G*A* mCmGmUmU*mU | XOOOXXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3398 | UCUGCUGGACAGCCCUUGGG | 36 | mU*mCmUmGmC*T*G*A*C*A*G*C*C*C* mUmGmG*mG | XOOOXXXXXXXXXXXOOOX |
| WV-3399 | CUGACUGGGCUUCCUGGUG | 37 | mC*mUmGmCmA*C*T*G*G*C*T*T*C*C* mUmGmGmU*mG | XOOOXXXXXXXXXXXOOOX |
| WV-3400 | UCCUGCUGUGCUUGGCUCCU | 38 | mU*mCmCmUmG*C*T*G*T*G*C*T*T*G*G* mCmUmCmC*mU | XOOOXXXXXXXXXXXOOOX |
| WV-3401 | CUCCUGCUGUGCUUGGCUCC | 39 | mC*mUmCmCmU*G*C*T*G*T*G*C*T*T*G* mGmCmUmC*mC | XOOOXXXXXXXXXXXOOOX |
| WV-3402 | UGGACCUGAGGAUGGACCGC | 40 | mU*mGmGmAmC*C*T*G*A*G*G*A*T*G*G* mAmCmCmG*mC | XOOOXXXXXXXXXXXOOOX |
| WV-3403 | UACCCUGCCUCAGUGUCUCG | 41 | mU*mAmCmCmC*T*G*C*C*T*C*A*G*T*G* mUmCmUmC*mG | XOOOXXXXXXXXXXXOOOX |
| WV-3404 | AGGGACCCUCUGCACUGGGC | 42 | mA*mGmGmGmA*C*C*C*T*C*T*G*C*A*C* mUmGmGmG*mC | XOOOXXXXXXXXXXXOOOX |
| WV-3405 | CUCAGGCAGCGGGUCGCCCC | 43 | mC*mUmCmAmG*G*C*A*G*C*G*G*G*T*C* mGmCmCmC*mC | XOOOXXXXXXXXXXXOOOX |
| WV-3406 | CCUCAGUGUCUCGGCCAGGG | 44 | mC*mCmUmCmA*G*T*G*T*C*T*C*G*G*C* mCmAmGmG*mG | XOOOXXXXXXXXXXXOOOX |
| WV-3407 | AUUUGGGACCUGAGGCGGGG | 45 | mA*mUmUmUmG*G*G*A*C*C*T*G*A*G*G* mCmGmGmG*mG | XOOOXXXXXXXXXXXOOOX |
| WV-3408 | CUUGUUACCCCGCCAUGGA | 46 | mC*mUmUmGmU*T*A*C*C*C*C*G*C*C* mAmUmGmG*mA | XOOOXXXXXXXXXXXOOOX |
| WV-3409 | ACAUGGGCCAGCCUACCCCC | 47 | mA*mCmAmUmG*G*G*C*C*A*G*C*C*T*A* mCmCmCmC*mC | XOOOXXXXXXXXXXXOOOX |
| WV-3410 | UGCUGUCUUGGCUUCCUGCC | 48 | mU*mGmCmUmG*T*C*T*T*G*G*C*T*T*C* mCmUmGmC*mC | XOOOXXXXXXXXXXXOOOX |
| WV-3411 | ACCUGUGAGGUCACCCACUG | 49 | mA*mCmCmUmG*T*G*A*G*G*T*C*A*C*C* mCmAmCmU*mG | XOOOXXXXXXXXXXXOOOX |
| WV-3412 | AUGUUCCGACUCCUGGCCUU | 50 | mA*mUmGmUmU*C*C*G*A*C*T*C*C*T*G* mGmCmCmU*mU | XOOOXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3413 | CUCUGCUGGACAGCCCUUGG | 51 | mC*mUmCmUmG*C*T*G*A*C*A*G*C*C* mCmUmUmG*mG | XOOOXXXXXXXXXXXXXOOOX |
| WV-3414 | GCCUGGGCGAGAGGGUGUCC | 52 | mG*mCmCmUmG*G*C*G*A*G*A*G*G*G* mUmGmUmC*mC | XOOOXXXXXXXXXXXXXOOOX |
| WV-3415 | CUGGUGGACAUUGGCCGGGA | 53 | mC*mUmGmGmU*G*G*A*C*A*T*T*G*C* mCmGmGmG*mA | XOOOXXXXXXXXXXXXXOOOX |
| WV-3416 | CUGUCCAGCGGGAUACCGG | 54 | mC*mUmGmUmCmU*C*C*A*G*C*G*G*A*T* mAmCmCmG*mG | XOOOXXXXXXXXXXXXXOOOX |
| WV-3417 | UUGUUACCCCGCCAUGGAG | 55 | mU*mUmGmUmUmU*A*C*C*C*C*G*C*C*A* mUmGmGmA*mG | XOOOXXXXXXXXXXXXXOOOX |
| WV-3418 | UGUUACCCCGCCAUGGAGA | 56 | mU*mGmUmUmA*C*C*C*C*G*C*C*A*T* mGmGmAmG*mA | XOOOXXXXXXXXXXXXXOOOX |
| WV-3419 | AGCGCUCUCUACCCUGCCUC | 57 | mA*mGmCmGmC*T*C*T*C*T*A*C*C*C*T* mGmCmCmU*mC | XOOOXXXXXXXXXXXXXOOOX |
| WV-3420 | UGGGCGAGAGGGUGUCCAGG | 58 | mU*mGmGmGmC*G*A*G*A*G*G*G*T*G* mUmCmAmG*mG | XOOOXXXXXXXXXXXXXOOOX |
| WV-3421 | AGGCUGGAUCCUCCACGUC | 59 | mA*mGmGmCmU*G*G*A*T*C*C*T*C*C* mAmCmGmU*mC | XOOOXXXXXXXXXXXXXOOOX |
| WV-3422 | UGGUGGACAUUGGCCGGGAG | 60 | mU*mGmGmUmG*G*A*C*A*T*T*G*G*C*C* mGmGmGmA*mG | XOOOXXXXXXXXXXXXXOOOX |
| WV-3423 | AGAGGCUGGGAUCCUCCACG | 61 | mA*mGmAmGmG*C*T*G*G*A*T*C*C*T* mCmCmAmC*mG | XOOOXXXXXXXXXXXXXOOOX |
| WV-3424 | GCUGGUGGACAUUGGCCGGG | 62 | mG*mCmUmGmG*T*G*G*A*C*A*T*T*G*G* mCmCmGmG*mG | XOOOXXXXXXXXXXXXXOOOX |
| WV-3425 | UCUGCUCCAGCGGGAUACCG | 63 | mU*mCmUmGmC*T*C*C*A*G*C*G*G*G*A* mUmAmCmC*mG | XOOOXXXXXXXXXXXXXOOOX |
| WV-3426 | UCUGCACUGGGCUUCCUGGU | 64 | mU*mCmUmGmC*A*C*T*G*G*G*C*T*T*C* mCmUmGmG*mU | XOOOXXXXXXXXXXXXXOOOX |
| WV-3427 | GCGCUCUCUACCCUGCCUCA | 65 | mG*mCmGmCmU*C*T*C*T*A*C*C*C*T*G* mCmCmUmC*mA | XOOOXXXXXXXXXXXXXOOOX |
| WV-3428 | CUGCCUCAGUGUCUCGGCCA | 66 | mC*mUmGmCmC*T*C*A*G*T*G*T*C*T*C* mGmGmCmC*mA | XOOOXXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3429 | GACUCCUGGCCUUCCGCACA | 67 | mG*mAmCmUmC*C*T*G*C*C*T*T*C*C*mGmCmAmC*mA | XOOOXXXXXXXXXXXOOOX |
| WV-3430 | CGACCUCAGGAUCCAUCCCU | 68 | mC*mGmAmCmC*T*C*A*G*G*A*T*C*C*A*mUmCmCmC*mU | XOOOXXXXXXXXXXXXOOOX |
| WV-3431 | GGCUGGGAUCCUCCACGUCA | 69 | mG*mGmCmUmG*G*G*A*T*C*C*T*C*C*A*mCmGmUmC*mA | XOOOXXXXXXXXXXXXOOOX |
| WV-3432 | UCUGCUAGACUCGCUCCUC | 70 | mU*mCmUmGmC*T*A*G*A*C*T*C*G*C*C*mUmCmCmU*mC | XOOOXXXXXXXXXXXXOOOX |
| WV-3433 | AUCUUGUUACCCCGCCAUG | 71 | mA*mUmCmUmU*G*T*T*A*C*C*C*C*G*mCmCmAmU*mG | XOOOXXXXXXXXXXXXOOOX |
| WV-3434 | UGCACUGGGCUUCCUGGUGU | 72 | mU*mGmCmAmC*T*G*G*G*C*T*T*C*C*T*mGmGmUmG*mU | XOOOXXXXXXXXXXXXOOOX |
| WV-3435 | UGCAGAGACCCUGUCGGAGG | 73 | mU*mGmCmAmG*A*G*A*C*C*C*T*G*T*C*mGmGmAmG*mG | XOOOXXXXXXXXXXXXOOOX |
| WV-3436 | CCCAGCACCUUGAGAUCCGG | 74 | mC*mCmCmAmG*C*A*C*C*T*T*G*A*G*A*mUmCmCmG*mG | XOOOXXXXXXXXXXXXOOOX |
| WV-3437 | CCUGUGAGGUCACCCACUGC | 75 | mC*mCmUmGmU*G*A*G*G*T*C*A*C*C*C*mAmCmUmG*mC | XOOOXXXXXXXXXXXXOOOX |
| WV-3438 | CUGGGCAUGGCGACCUCAGG | 76 | mC*mUmGmGmG*C*A*T*G*G*C*G*A*C*C*mUmCmAmG*mG | XOOOXXXXXXXXXXXXOOOX |
| WV-3439 | CGAACUGCACCCUUCCCAC | 77 | mC*mGmAmAmC*T*G*C*A*C*C*C*C*T*T*mCmCmCmA*mC | XOOOXXXXXXXXXXXXOOOX |
| WV-3440 | AGCGAGCCUGGGCGAGAGGG | 78 | mA*mGmCmGmA*G*C*C*T*G*G*G*C*G*A*mGmAmGmG*mG | XOOOXXXXXXXXXXXXOOOX |
| WV-3441 | GGGUGGCCUCUGCUUGGUC | 79 | mG*mGmGmUmG*G*C*C*T*C*T*G*C*T*T*mGmUmGmU*mC | XOOOXXXXXXXXXXXXOOOX |
| WV-3442 | UGCUCCAGCGGGAUACCGGA | 80 | mU*mGmCmUmC*C*A*G*C*G*G*G*A*T*A*mCmCmGmG*mA | XOOOXXXXXXXXXXXXOOOX |
| WV-3443 | AAGGGACCCUCUGACUGGG | 81 | mA*mAmGmGmG*A*C*C*C*T*C*T*G*C*A*mCmUmGmG*mG | XOOOXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3444 | CUGCUGTGCTTGGCTCCUGC | 82 | mC*mUmGmCmU*G*T*G*C*T*T*G*C*T*mCmCmUmG*mC | XOOOXXXXXXXXXXXXOOOX |
| WV-3445 | GACGAACTGCACCCCUUCCC | 83 | mG*mAmCmGmA*A*C*T*G*C*A*C*C*C*C*mUmUmCmC*mC | XOOOXXXXXXXXXXXXOOOX |
| WV-3446 | UGCUGUAGCGAGCCTGGGCG | 84 | mU*mGmCmUmG*T*A*G*C*G*A*G*C*C*T*mGmGmGmC*mG | XOOOXXXXXXXXXXXXOOOX |
| WV-3447 | CACCCCUUCCCACAGCAUGG | 85 | mC*mAmCmCmC*C*T*T*C*C*C*A*C*A*G*mCmAmUmG*mG | XOOOXXXXXXXXXXXXOOOX |
| WV-3448 | GACCCUCUCUGCACTGGGCUUC | 86 | mG*mAmCmCmC*T*C*T*C*T*G*C*A*C*T*mGmGmCmU*mU | XOOOXXXXXXXXXXXXOOOX |
| WV-3449 | AGCUGGUGGACATTGGCCGG | 87 | mA*mGmCmUmG*G*T*G*G*A*C*A*T*T*G*mGmCmCmG*mG | XOOOXXXXXXXXXXXXOOOX |
| WV-3450 | UCUCGGCCAGGGCATUCCCA | 88 | mU*mCmUmCmG*G*C*C*A*G*G*G*C*A*T*mUmCmCmC*mA | XOOOXXXXXXXXXXXXOOOX |
| WV-3451 | GGUCUCUGCTGGACAGCCCU | 89 | mG*mGmUmCmU*C*T*G*C*T*G*G*A*C*A*mGmCmCmC*mU | XOOOXXXXXXXXXXXXOOOX |
| WV-3452 | CGGCCAGGGCATTCCCAGCG | 90 | mC*mGmGmCmC*A*G*G*G*C*A*T*T*C*C*mCmAmGmC*mG | XOOOXXXXXXXXXXXXOOOX |
| WV-3453 | UGGGATCCTCCACGTCACAG | 91 | mU*mGmGmGmA*T*C*C*T*C*C*A*C*G*T*mCmAmCmA*mG | XOOOXXXXXXXXXXXXOOOX |
| WV-3454 | CCUGUTGGCTGCTCACUGGC | 92 | mC*mCmUmGmU*T*G*G*C*T*G*C*T*C*A*mCmUmGmG*mC | XOOOXXXXXXXXXXXXOOOX |
| WV-3455 | GCCUGUTGGCTGCTCACUGG | 93 | mG*mCmCmUmG*T*T*G*G*C*T*G*C*T*C*mAmCmUmG*mG | XOOOXXXXXXXXXXXXOOOX |
| WV-3456 | CCAGCACCTTGAGATCCGGG | 94 | mC*mCmAmGmC*A*C*C*T*T*G*A*G*A*T*mCmCmGmG*mG | XOOOXXXXXXXXXXXXOOOX |
| WV-3457 | GGGAGGCCTGTTGGCTGCUC | 95 | mG*mGmGmAmG*G*C*C*T*G*T*T*G*G*C*mUmGmCmU*mC | XOOOXXXXXXXXXXXXOOOX |
| WV-3458 | CUCAGAGGCTGGGATCCUCC | 96 | mC*mUmCmAmG*A*G*G*C*T*G*G*G*A*T*mCmCmUmC*mC | XOOOXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3459 | GCCUCAGTGTCTCGGCCAGG | 97 | mG*mCmCmUmC*A*G*T*G*T*C*T*C*G*G* mCmCmAmG*mG | XOOOXXXXXXXXXXXXOOOX |
| WV-3460 | CACAUGGGCCAGCCTACCCC | 98 | mC*mAmCmAmU*G*G*C*C*A*G*C*C*T* mAmCmCmC*mC | XOOOXXXXXXXXXXXXOOOX |
| WV-3461 | GGUGGCCCTCTGCTTTGGUCU | 99 | mG*mGmUmGmG*C*C*T*C*T*G*C*T*T*T* mGmGmUmC*mU | XOOOXXXXXXXXXXXXOOOX |
| WV-3462 | ACGUGTCACTCACTCCUCC | 100 | mA*mCmGmUmU*G*T*C*A*C*T*C*A*C*T* mCmCmUmC*mC | XOOOXXXXXXXXXXXXOOOX |
| WV-3858 | UAGAAAGGCATGAAGCAGGA | 101 | mU*mAmGmAmA*A*G*G*C*A*T*G*A*A*G* mCmAmGmG*mA | XOOOXXXXXXXXXXXXOOOX |
| WV-3859 | GUAGAAAGGCATGAAGCAGG | 102 | mG*mUmAmGmA*A*A*A*G*G*C*A*T*G*A*A* mGmCmAmG*mG | XOOOXXXXXXXXXXXXOOOX |
| WV-3860 | UGUAGAAAGGCATGAAGCAG | 103 | mU*mGmUmAmG*A*A*A*A*G*G*C*A*T*G*A* mAmGmCmA*mG | XOOOXXXXXXXXXXXXOOOX |
| WV-3861 | CUGUAGAAAGGCATGAAGCA | 104 | mC*mUmGmUmA*G*A*A*A*A*G*G*C*A*T*G* mAmAmGmC*mA | XOOOXXXXXXXXXXXXOOOX |
| WV-3862 | ACUGUAGAAAGGCATGAAGC | 105 | mA*mCmUmGmU*A*G*A*A*A*A*G*G*C*A*T* mGmAmAmG*mC | XOOOXXXXXXXXXXXXOOOX |
| WV-3863 | CACUGUAGAAAGGCAUGAAG | 106 | mC*mAmCmUmG*T*A*G*A*A*A*A*G*G*C*A* mUmGmAmA*mG | XOOOXXXXXXXXXXXXOOOX |
| WV-3864 | CCACUGUAGAAAGGCAUGAA | 107 | mC*mCmAmCmU*G*T*A*G*A*A*A*A*G*G*C* mAmUmGmA*mA | XOOOXXXXXXXXXXXXOOOX |
| WV-3865 | UAGAAAGGCA TGAAGCAGGAACAUA | 108 | mU*mAmGmAmA*A*G*C*A*T*G*A*A*G* C*A*G*G*A*mAmCmAmU*mA | XOOOXXXXXXXXXXXXXXXXX XOOOX |
| WV-3866 | GUAGAAAGGC ATGAAGCAGGAACAU | 109 | mG*mUmAmGmA*A*A*G*G*C*A*T*G*A*A* G*C*A*G*G*mAmAmCmA*mU | XOOOXXXXXXXXXXXXXXXXX XOOOX |
| WV-3867 | UGUAGAAAGG CATGAAGCAGGAACA | 110 | mU*mGmUmAmG*A*A*A*A*G*G*C*A*T*G*A* A*G*C*A*G*mGmAmAmC*mA | XOOOXXXXXXXXXXXXXXXXX XOOOX |
| WV-3868 | CUGUAGAAAG GCATGAAGCAGGAAC | 111 | mC*mUmGmUmA*G*A*A*A*A*G*G*C*A*T*G* A*A*G*C*A*mGmGmAmA*mC | XOOOXXXXXXXXXXXXXXXXX XOOOX |
| WV-3869 | ACUGUAGAAA GGCATGAAGCAGGAA | 112 | mA*mCmUmGmU*A*G*A*A*A*A*G*G*C*A*T* G*A*A*G*C*mAmGmGmA*mA | XOOOXXXXXXXXXXXXXXXXX XOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3870 | CACUGTAGAA AGGCATGAAGCAGGA | 113 | mC*mAmCmUmG*T*A*G*A*A*A*G*C*A* T*G*A*A*G*mCmAmGmG*mA | XOOOXXXXXXXXXXXXXXXX XOOOX |
| WV-3871 | CCACUGTAGA AAGGCATGAAGCAG | 114 | mC*mCmAmCmU*G*T*A*G*A*A*A*A*G*G*C* A*T*G*A*A*mGmCmAmG*mG | XOOOXXXXXXXXXXXXXXXX XOOOX |
| WV-3872 | GCCACTGTAG AAAGGCATGAAGCAG | 115 | mG*mCmCmAmC*T*G*T*A*G*A*A*A*A*G*G* C*A*T*G*A*mAmGmCmA*mG | XOOOXXXXXXXXXXXXXXXX XOOOX |
| WV-3873 | GGCCACTGTA GAAAGGCATGAAGCA | 116 | mG*mGmCmCmA*C*T*G*T*A*G*T*A*G*A*A*A*G* G*C*A*T*G*mAmAmGmC*mA | XOOOXXXXXXXXXXXXXXXX XOOOX |
| WV-3874 | AGGCCACTGT AGAAAGGCATGAAGC | 117 | mA*mGmGmCmC*A*C*T*G*T*A*G*A*A*A* G*G*C*A*T*mGmAmAmG*mC | XOOOXXXXXXXXXXXXXXXX XOOOX |
| WV-3875 | AAGGCCACTG TAGAAAGGCATGAAG | 118 | mA*mAmGmGmC*C*A*C*T*G*T*A*G*A*A* A*G*G*C*A*mUmGmAmA*mG | XOOOXXXXXXXXXXXXXXXX XOOOX |
| WV-3876 | UAAGGCCACT GTAGAAAGGCATGAA | 119 | mU*mAmAmGmG*C*C*A*C*T*G*T*A*G*A* A*A*G*G*C*mAmUmGmA*mA | XOOOXXXXXXXXXXXXXXXX OOOX |
| WV-3986 | TCUGAGGAUGGACCGCGGGTU | 120 | T*fC*mUfG*mAfG*mGfA*mUfG*mCfC*mG *fC*mG*fG*mG*T*mU | XXOXOXOXOXOXOXOXXXXXX |
| WV-3987 | TCUGAGGAUGGACCGCGGGTU | 121 | T*fC*mUfG*mAfG*mGfA*mUfG*mGfA*mCfC* mGfCmGfGmG*T*mU | XXOXOXOXOXOXOXOXOOOXXX |
| WV-3988 | TCUGAGGAUGGACCGCGGGTU | 122 | POT*fC*mUfG*mAfG*mGfA*mUfG*mGfA*mCfC* mG*fC*mG*fG*mG*T*mU | XXOXOXOXOXOXOXOXXXXXX |
| WV-3989 | TACCUGAGGAUGGACCGCGTU | 123 | T*fA*mCfC*mUfG*mAfG*mGfA*mUfG*mGfA*mC *fC*mG*fC*mG*T*mU | XXOXOXOXOXOXOXOXXXXXX |
| WV-3990 | TACCUGAGGAUGGACCGCGTU | 124 | T*fA*mCfC*mUfG*mAfG*mGfA*mUfG*mGfA* mCfCmGfCmG*T*mU | XXOXOXOXOXOXOXOOOOXXX |
| WV-3991 | TGACCUGAGGAUGGACCGCTU | 125 | T*fG*mAfC*mCfU*mGfA*mGfG*mAfU*mGfG*mA *fC*mC*fG*mC*T*mU | XXOXOXOXOXOXOXOXXXXXX |
| WV-3992 | TGACCUGAGGAUGGACCGCTU | 126 | T*fG*mAfC*mCfU*mGfA*mGfG*mAfU*mGfG*mA *fC*mC*fG*mC*T*mU | XXOXOXOXOXOXOXOXXXXXX |
| WV-3993 | TUUGUUACCCCGCCAUGGTU | 127 | T*fU*mUfG*mUfU*mAfC*mCfC*mCfC*mGfC*mC *fA*mU*fG*mG*T*mU | XXOXOXOXOXOXOXOXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-3994 | TUUGUUACCCCGCCAUGGTU | 128 | T*fU*mUfG*mUfU*mAfC*mCfC*mCfC*mGfC*mCfAmUfGmG*T*mU | XXOXOXOXOXOXOOOOXX |
| WV-3995 | TCCCCGCCAUGGAGACGUUTU | 129 | T*fC*mCfC*mCfG*mCfC*mAfU*mGfG*mAfG*mA*fC*mG*fU*mU*T*mU | XXOXOXOXOXOXOXXXXXX |
| WV-3996 | TCCCCGCCAUGGAGACGUUTU | 130 | T*fC*mCfC*mCfG*mCfC*mAfU*mGfG*mAfG*mAfCmGfUmU*T*mU | XXOXOXOXOXOXOXOOOXX |
| WV-3997 | TACCCCGCCAUGGAGACGUTU | 131 | T*fA*mCfC*mCfC*mCfG*mCfC*mAfU*mGfG*mA*fG*mA*fC*mG*T*mU | XXOXOXOXOXOXOXXXXXX |
| WV-3998 | TACCCCGCCAUGGAGACGUTU | 132 | T*fA*mCfC*mCfC*mCfG*mCfC*mAfU*mGfG*mAfGmAfCmG*T*mU | XXOXOXOXOXOXOOOOXX |
| WV-3999 | TCCCCCGCCAUGGAGACGUTU | 133 | T*fC*mCfC*mCfC*mCfG*mCfC*mAfU*mGfG*mA*fU*mG*fA*mG | XXOXOXOXOXOXOXXXXXX |
| WV-4000 | TCCCCCGCCAUGGAGACGUTU | 134 | T*fC*mCfC*mCfC*mCfG*mCfC*mGfC*mCfA*mUfG*mGfA* mGfAmCfGmU*T*mU | XXOXOXOXOXOXOXOOOXX |
| WV-4001 | TGCUCGGCCUCCAGUUCCATU | 135 | T*fG*mCfU*mCfG*mGfC*mCfU*mCfC*mAfG*mU*fU*mC*fC*mA*T*mU | XXOXOXOXOXOXOXXXXXX |
| WV-4002 | TGCUCGGCCUCCAGUUCCATU | 136 | T*fG*mCfU*mCfG*mGfC*mCfU*mCfC*mAfG*mUfUmCfCmA*T*mU | XXOXOXOXOXOXOOOOXX |
| WV-4003 | TGGACCCUCUGCACUGGGCTU | 137 | T*fG*mGfA*mCfC*mCfU*mCfU*mGfC*mAfC*mU*fG*mG*fG*mC*T*mU | XXOXOXOXOXOXOXXXXXX |
| WV-4004 | TGGACCCUCUGCACUGGGCTU | 138 | T*fG*mGfA*mCfC*mCfU*mCfU*mGfC*mAfC*mUfGmGfGmC*T*mU | XXOXOXOXOXOXOOOOXX |
| WV-4005 | TGACCCUCUGCACUGGGCUTU | 139 | T*fG*mAfC*mCfC*mUfC*mUfG*mCfA*mCfU*mG*fG*mG*fC*mU*T*mU | XXOXOXOXOXOXOXXXXXX |
| WV-4006 | TGACCCUCUGCACUGGGCUTU | 140 | T*fG*mAfC*mCfC*mUfC*mUfG*mCfA*mCfU*mGfGmGfCmU*T*mU | XXOXOXOXOXOXOOOOXX |
| WV-4018 | TCAUGAAGCAGGAACAUACTU | 141 | T*fC*mAfU*mGfA*mAfG*mCfA*mGfG*mAfA*mC*fA*mU*fA*mC*T*mU | XXOXOXOXOXOXOXXXXXX |
| WV-4019 | TGCAUGAAGCAGGAACAUATU | 142 | T*fG*mCfA*mUfG*mAfA*mGfC*mAfG*mGfA*mA*fC*mA*fU*mA*T*mU | XXOXOXOXOXOXOXXXXXX |
| WV-4020 | TGGCAUGAAGCAGGAACAUTU | 143 | T*fG*mGfC*mAfU*mGfA*mAfG*mCfA*mGfG*mA*fA*mC*fA*mU*T*mU | XXOXOXOXOXOXOXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4021 | TAGGCAUGAAGCAGGAACAUU | 144 | T*fA*mGfG*mCfA*mUfG*mAfA*mGfC*mAfG*mG*fA*mA*fC*mA*T*mU | XXOXOXOXOXOXOXXXXXX |
| WV-4022 | TAAGGCAUGAAGCAGGAACUU | 145 | T*fA*mAfG*mGfC*mAfU*mGfA*mAfG*mCfA*mG*fG*mA*fA*mC*T*mU | XXOXOXOXOXOXOXXXXXX |
| WV-4023 | TAAAGGCAUGAAGCAGGAAUU | 146 | T*fA*mAfA*mGfG*mCfA*mUfG*mAfA*mGfC*mA*fG*mG*fA*mA*T*mU | XXOXOXOXOXOXOXXXXXX |
| WV-4024 | TGAAAGGCAUGAAGCAGGAUU | 147 | T*fG*mAfA*mAfG*mGfC*mAfU*mGfA*mAfG*mC*fA*mG*fG*mA*T*mU | XXOXOXOXOXOXOXXXXXX |
| WV-4025 | TAGAAAGGCAUGAAGCAGGUU | 148 | T*fA*mGfA*mAfA*mGfG*mCfA*mUfG*mAfA*mG*fC*mA*fG*mG*T*mU | XXOXOXOXOXOXOXXXXXX |
| WV-4026 | TUAGAAAGGCAUGAAGCAGUU | 149 | T*fU*mAfG*mAfA*mAfG*mGfC*mAfU*mGfA*mA*fG*mC*fA*mG*T*mU | XXOXOXOXOXOXOXXXXXX |
| WV-4027 | TGUAGAAAGGCAUGAAGCAUU | 150 | T*fG*mUfA*mGfA*mAfA*mGfG*mCfA*mUfG*mA*fA*mG*fC*mA*T*mU | XXOXOXOXOXOXOXXXXXX |
| WV-4028 | TUGUAGAAAGGCAUGAAGCUU | 151 | T*fU*mGfU*mAfG*mAfA*mAfG*mGfC*mAfU*mG*fA*mA*fG*mC*T*mU | XXOXOXOXOXOXOXXXXXX |
| WV-4029 | TCUGUAGAAAGGCAUGAAGUU | 152 | T*fC*mUfG*mUfA*mGfA*mAfA*mGfG*mCfA*mU*fG*mA*fA*mG*T*mU | XXOXOXOXOXOXOXXXXXX |
| WV-4030 | TACUGUAGAAAGGCAUGAAUU | 153 | T*fA*mCfU*mGfU*mAfG*mAfA*mAfG*mGfC*mA*fU*mG*fA*mA*T*mU | XXOXOXOXOXOXOXXXXXX |
| WV-4031 | TCACUGUAGAAAGGCAUGAUU | 154 | T*fC*mAfC*mUfG*mUfA*mGfA*mAfA*mGfG*mC*fA*mU*fG*mA*T*mU | XXOXOXOXOXOXOXXXXXX |
| WV-4032 | TCCACUGUAGAAAGGCAUGUU | 155 | T*fC*mCfA*mCfU*mGfU*mAfG*mAfA*mAfG*mG*fC*mA*fU*mG*T*mU | XXOXOXOXOXOXOXXXXXX |
| WV-4033 | TGCCACUGUAGAAAGGCAUUU | 156 | T*fG*mCfC*mAfC*mUfG*mUfA*mGfA*mAfA*mG*fG*mC*fA*mU*T*mU | XXOXOXOXOXOXOXXXXXX |
| WV-4034 | TGGCCACUGUAGAAAGGCAUU | 157 | T*fG*mGfC*mCfA*mCfU*mGfU*mAfG*mAfA*mA*fG*mG*fC*mA*T*mU | XXOXOXOXOXOXOXXXXXX |
| WV-4035 | TAGGCCACUGUAGAAAGGCUU | 158 | T*fA*mGfG*mCfC*mAfC*mUfG*mUfA*mGfA*mA*fA*mG*fG*mC*T*mU | XXOXOXOXOXOXOXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4036 | TAAGGCCACUGUAGAAAGGTU | 159 | T*fA*mAfG*mGfC*mCfA*mCfU*mGfU*mGfA*mAfG*mA*fA*mA*fG*mG*T*mU | XXOXOXOXOXOXOXXXXXX |
| WV-4037 | TUAAGGCCACUGUAGAAAGTU | 160 | T*fU*mAfA*mGfG*mCfC*mAfC*mUfG*mUfA*mG*fA*mA*fA*mG*T*mU | XXOXOXOXOXOXOXXXXXX |
| WV-4038 | TAUAAGGCCACUGUAGAAATU | 161 | T*fA*mUfA*mAfG*mGfC*mCfA*mCfU*mGfU*mA*fG*mA*fA*mA*T*mU | XXOXOXOXOXOXOXXXXXX |
| WV-4039 | TCAUGAAGCAGGAACAUACTU | 162 | T*fC*mAfU*mGfA*mAfG*mCfA*mGfG*mAfA*mCfAmUfAmC*T*mU | XXOXOXOXOXOXOXOOOXX |
| WV-4040 | TGCAUGAAGCAGGAACAUATU | 163 | T*fG*mCfA*mUfG*mAfA*mGfC*mAfG*mGfA*mAfCmAfUmA*T*mU | XXOXOXOXOXOXOXOOOXX |
| WV-4041 | TGGCAUGAAGCAGGAACAUTU | 164 | T*fG*mGfC*mAfU*mGfA*mAfG*mCfA*mGfG*mAfAmCfAmU*T*mU | XXOXOXOXOXOXOXOOOXX |
| WV-4042 | TAGGCAUGAAGCAGGAACATU | 165 | T*fA*mGfG*mCfA*mUfG*mAfA*mGfC*mAfG*mGfA*mAfCmA*T*mU | XXOXOXOXOXOXOXOOOXX |
| WV-4043 | TAAGGCAUGAAGCAGGAACTU | 166 | T*fA*mAfG*mGfC*mAfU*mGfA*mAfG*mCfA*mGfG*mAfAmC*T*mU | XXOXOXOXOXOXOXOOOXX |
| WV-4044 | TAAAGGCAUGAAGCAGGAATU | 167 | T*fA*mAfA*mGfG*mCfA*mUfG*mAfA*mGfC*mAfG*mGfAmA*T*mU | XXOXOXOXOXOXOXOOOXX |
| WV-4045 | TGAAAGGCAUGAAGCAGGATU | 168 | T*fG*mAfA*mAfG*mGfC*mAfU*mGfA*mAfG*mCfAmGfGmA*T*mU | XXOXOXOXOXOXOXOOOXX |
| WV-4046 | TAGAAAGGCAUGAAGCAGGTU | 169 | T*fA*mGfA*mAfA*mGfG*mCfA*mUfG*mAfA*mGfCmAfGmG*T*mU | XXOXOXOXOXOXOXOOOXX |
| WV-4047 | TUAGAAAGGCAUGAAGCAGTU | 170 | T*fU*mAfG*mAfA*mAfG*mGfC*mAfU*mGfA*mAfGmCfAmG*T*mU | XXOXOXOXOXOXOXOOOXX |
| WV-4048 | TGUAGAAAGGCAUGAAGCATU | 171 | T*fG*mUfA*mGfA*mAfA*mGfG*mCfA*mUfG*mAfAmGfCmA*T*mU | XXOXOXOXOXOXOXOOOXX |
| WV-4049 | TUGUAGAAAGGCAUGAAGCTU | 172 | T*fU*mGfU*mAfG*mAfA*mAfG*mGfC*mAfU*mGfAmAfGmC*T*mU | XXOXOXOXOXOXOXOOOXX |
| WV-4050 | TCUGUAGAAAGGCAUGAAGTU | 173 | T*fC*mUfG*mUfA*mGfA*mAfA*mGfG*mCfA*mUfGmAfAmG*T*mU | XXOXOXOXOXOXOXOOOXX |
| WV-4051 | TACUGUAGAAAGGCAUGAATU | 174 | T*fA*mCfU*mGfU*mAfG*mAfA*mAfG*mGfC*mAfUmGfAmA*T*mU | XXOXOXOXOXOXOXOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4052 | TCACUGUAGAAGGCAUGAUU | 175 | T*fC*mAfC*mUfG*mUfA*mGfA*mAfA*mGfG* mCfAmUfGmA*T*mU | XXOXOXOXOXOXOXOOOXX |
| WV-4053 | TCCACUGUAGAAGGCAUGUU | 176 | T*fC*mCfA*mCfU*mGfU*mAfA*mAfA*mAfG* mGfCmAfUmG*T*mU | XXOXOXOXOXOXOXOOOXX |
| WV-4054 | TGCCACUGUAGAAGGCAUUU | 177 | T*fG*mCfC*mAfC*mUfG*mUfA*mGfA*mAfA* mGfGmCfAmU*T*mU | XXOXOXOXOXOXOXOOOXX |
| WV-4055 | TGGCCACUGUAGAAGGCAUU | 178 | T*fG*mGfC*mCfA*mCfU*mGfU*mAfG*mAfA* mAfGmGfCmA*T*mU | XXOXOXOXOXOXOXOOOXX |
| WV-4056 | TAGGCCACUGUAGAAGGCUU | 179 | T*fA*mGfG*mCfC*mAfC*mUfG*mUfA*mGfA* mAfAmGfGmC*T*mU | XXOXOXOXOXOXOXOOOXX |
| WV-4057 | TAAGGCCACUGUAGAAGGUU | 180 | T*fA*mAfG*mGfC*mCfA*mCfU*mGfU*mAfG* mAfAmAfGmG*T*mU | XXOXOXOXOXOXOXOOOXX |
| WV-4058 | TUAAGGCCACUGUAGAAGUU | 181 | T*fU*mAfA*mGfG*mCfC*mAfC*mUfG*mUfA* mGfAmAfAmG*T*mU | XXOXOXOXOXOXOXOOOXX |
| WV-4059 | TAUAAGGCCACUGUAGAAUU | 182 | T*fA*mUfA*mAfG*mGfC*mCfA*mCfU*mGfU* mAfGmA fAmA*T*mU | XXOXOXOXOXOXOXOOOXX |
| WV-4060 | TCAUGAAGCAGGAACAUACCAUU | 183 | T*fC*mAfU*mGfA*mAfG*mCfA*mGfG*mAfA*mC *fA*mU*fA*mC*fC*mA*T*mU | XXOXOXOXOXOXOXOXXXXXX XX |
| WV-4061 | TGCAUGAAGCAGGAACAUACCU | 184 | T*fG*mCfA*mUfG*mAfA*mGfC*mAfG*mGfA*mA *fC*mA*fU*mA*fC*mC*T*mU | XXOXOXOXOXOXOXOXXXXXX XX |
| WV-4062 | TGGCAUGAAGCAGGAACAUACU | 185 | T*fG*mGfC*mAfU*mGfA*mAfG*mCfA*mGfG*mA *fA*mC*fA*mU*fA*mC*T*mU | XXOXOXOXOXOXOXOXXXXXX XX |
| WV-4063 | TAGGCAUGAAGCAGGAACAUAU | 186 | T*fA*mGfG*mCfA*mUfG*mAfA*mGfC*mAfG*mG *fA*mA*fC*mA*fU*mA*T*mU | XXOXOXOXOXOXOXOXXXXXX XX |
| WV-4064 | TAAGGCAUGAAGCAGGAACAUU | 187 | T*fA*mAfG*mGfC*mAfU*mGfA*mAfG*mCfA*mG *fG*mA*fA*mC*fA*mU*T*mU | XXOXOXOXOXOXOXOXXXXXX XX |
| WV-4065 | TAAAGGCAUGAAGCAGGAACAU | 188 | T*fA*mAfA*mGfG*mCfA*mUfG*mAfA*mGfC*mA *fG*mG*fA*mA*fC*mA*T*mU | XXOXOXOXOXOXOXOXXXXXX XX |
| WV-4066 | TGAAAGGCAUGAAGCAGGAACU | 189 | T*fG*mAfA*mAfG*mGfC*mAfU*mGfA*mAfG*mC *fA*mG*fG*mA*fA*mC*T*mU | XXOXOXOXOXOXOXOXXXXXX XX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4067 | TAGAAAGGCAUGAAGCAGGAAU | 190 | T*fA*mGfA*mAfA*mGfG*mCfA*mUfG*mAfA*mG*fC*mA*fG*mG*fA*mA*T*mU | XXOXOXOXOXOXOXOXXXXXXX XX |
| WV-4068 | TUAGAAAGGCAUGAAGCAGGAU | 191 | T*fU*mAfG*mAfA*mAfG*mGfC*mAfU*mGfA*mA*fG*mC*fA*fG*mG*fA*mA*T*mU | XXOXOXOXOXOXOXOXXXXXXX XX |
| WV-4069 | TGUAGAAAGGCAUGAAGCAGGU | 192 | T*fG*mUfA*mGfA*mAfA*mGfG*mCfA*mUfG*mA*fA*mG*fC*mA*fG*mG*T*mU | XXOXOXOXOXOXOXOXXXXXXX XX |
| WV-4070 | TUGUAGAAAGGCAUGAAGCAGU | 193 | T*fU*mGfU*mAfG*mAfA*mAfG*mGfC*mAfU*mG*fA*mA*fG*mC*fA*mG*T*mU | XXOXOXOXOXOXOXOXXXXXXX XX |
| WV-4071 | TCUGUAGAAAGGCAUGAAGCAU | 194 | T*fC*mUfG*mUfA*mGfA*mAfA*mGfG*mCfA*mU*fG*mA*fA*mG*fC*mA*T*mU | XXOXOXOXOXOXOXOXXXXXXX XX |
| WV-4072 | TACUGUAGAAAGGCAUGAAGCU | 195 | T*fA*mCfU*mGfU*mAfG*mAfA*mAfG*mGfC*mA*fU*mG*fA*mA*fG*mC*T*mU | XXOXOXOXOXOXOXOXXXXXXX XX |
| WV-4073 | TCACUGUAGAAAGGCAUGAAGU | 196 | T*fC*mAfC*mUfG*mUfA*mGfA*mAfA*mGfG*mC*fA*mU*fG*mA*fA*mG*T*mU | XXOXOXOXOXOXOXOXXXXXXX XX |
| WV-4074 | TCCACUGUAGAAAGGCAUGAAU | 197 | T*fC*mCfA*mCfU*mGfU*mAfG*mAfA*mAfG*mG*fC*mA*fU*mG*fA*mA*T*mU | XXOXOXOXOXOXOXOXXXXXXX XX |
| WV-4075 | TGCCACUGUAGAAAGGCAUGAU | 198 | T*fG*mCfC*mAfC*mUfG*mUfA*mGfA*mAfA*mG*fG*mC*fA*mU*fG*mA*T*mU | XXOXOXOXOXOXOXOXXXXXXX XX |
| WV-4076 | TGGCCACUGUAGAAAGGCAUGU | 199 | T*fG*mGfC*mCfA*mCfU*mGfU*mAfG*mAfA*mA*fG*mG*fC*mA*fU*mG*T*mU | XXOXOXOXOXOXOXOXXXXXXXXX |
| WV-4077 | TAGGCCACUGUAGAAAGGCAUT | 200 | T*fA*mGfG*mCfC*mAfC*mUfG*mUfA*mGfA*mA*fA*mG*fG*mC*fA*mU*T*mU | XXOXOXOXOXOXOXOXXXXXXXXX |
| WV-4078 | TAAGGCCACUGUAGAAAGGCAU | 201 | T*fA*mAfG*mGfC*mCfA*mCfU*mGfU*mAfG*mA*fA*mA*fG*mG*fC*mA*T*mU | XXOXOXOXOXOXOXOXXXXXXXXX |
| WV-4079 | TUAAGGCCACUGUAGAAAGGCU | 202 | T*fU*mAfA*mGfG*mCfC*mAfC*mUfG*mUfA*mG*fA*mA*fA*mG*fG*mC*T*mU | XXOXOXOXOXOXOXOXXXXXXXXX |
| WV-4080 | TAUAAGGCCACUGUAGAAAGGU | 203 | T*fA*mUfA*mAfG*mGfC*mCfA*mCfU*mGfU*mA*fG*mA*fA*mA*fG*mG*T*mU | XXOXOXOXOXOXOXOXXXXXXXXX |
| WV-4081 | TGAUAAGGCCACUGUAGAAAGU | 204 | T*fG*mAfU*mAfA*mGfG*mCfC*mAfC*mUfG*mU*fA*mG*fA*mA*fA*mG*T*mU | XXOXOXOXOXOXOXOXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4082 | TGGAUAAGGCCACUGUAGAAAU | 205 | T*fG*mGfA*mUfA*mAfG*mGfC*mCfA*mCfU*mG*fU*mA*fG*mA*fA*mA*T*mU | XXOXOXOXOXOXOXXXXXXXX |
| WV-4083 | TCAUGAAGCAGGAACAUACCAUU | 206 | T*fC*mAfU*mGfA*mAfG*mCfA*mGfG*mAfA* mCfAmUfAmCfCmA*T*mU | XXOXOXOXOXOXOXOOOOOOX X |
| WV-4084 | TGCAUGAAGCAGGAACAUACCU | 207 | T*fG*mCfA*mUfG*mAfA*mGfC*mAfG*mGfA* mAfCmAfUmAfCmC*T*mU | XXOXOXOXOXOXOXOOOOOOX X |
| WV-4085 | TGGCAUGAAGCAGGAACAUACU | 208 | T*fG*mGfC*mAfU*mGfA*mAfG*mCfA*mGfG* mAfAmCfAmUfAmC*T*mU | XXOXOXOXOXOXOXOOOOOOX X |
| WV-4086 | TAGGCAUGAAGCAGGAACAUAU | 209 | T*fA*mGfG*mCfA*mUfG*mAfA*mGfC*mAfG* mGfAmAfCmAfUmA*T*mU | XXOXOXOXOXOXOXOOOOOOX X |
| WV-4087 | TAAGGCAUGAAGCAGGAACAUU | 210 | T*fA*mAfG*mGfC*mAfU*mGfA*mAfG*mCfA* mGfGmAfAmCfAmU*T*mU | XXOXOXOXOXOXOXOOOOOOX X |
| WV-4088 | TAAAGGCAUGAAGCAGGAACAU | 211 | T*fA*mAfA*mGfG*mCfA*mUfG*mAfA*mGfC* mAfGmGfAmAfCmA*T*mU | XXOXOXOXOXOXOXOOOOOOX X |
| WV-4089 | TGAAAGGCAUGAAGCAGGAACU | 212 | T*fG*mAfA*mAfG*mGfC*mAfU*mGfA*mAfG* mCfAmGfGmAfAmC*T*mU | XXOXOXOXOXOXOXOOOOOOX X |
| WV-4090 | TAGAAAGGCAUGAAGCAGGAAU | 213 | T*fA*mGfA*mAfA*mGfG*mCfA*mUfG*mAfA* mGfCmAfGmGfAmA*T*mU | XXOXOXOXOXOXOXOOOOOOX X |
| WV-4091 | TUAGAAAGGCAUGAAGCAGGAU | 214 | T*fU*mAfG*mAfA*mAfG*mGfC*mAfU*mGfA* mAfGmCfAmGfGmA*T*mU | XXOXOXOXOXOXOXOOOOOOX X |
| WV-4092 | TGUAGAAAGGCAUGAAGCAGGU | 215 | T*fG*mUfA*mGfA*mAfA*mGfG*mCfA*mUfG* mAfAmGfCmAfGmG*T*mU | XXOXOXOXOXOXOXOOOOOOX X |
| WV-4093 | TUGUAGAAAGGCAUGAAGCAGU | 216 | T*fU*mGfU*mAfG*mAfA*mAfG*mGfC*mAfU* mGfAmAfGmCfAmG*T*mU | XXOXOXOXOXOXOXOOOOOOX X |
| WV-4094 | TCUGUAGAAAGGCAUGAAGCAU | 217 | T*fC*mUfG*mUfA*mGfA*mAfA*mGfG*mCfA* mUfGmAfAmGfCmA*T*mU | XXOXOXOXOXOXOXOOOOOOX X |
| WV-4095 | TACUGUAGAAAGGCAUGAAGCU | 218 | T*fA*mCfU*mGfU*mAfG*mAfA*mAfG*mGfC* mAfUmGfAmAfGmC*T*mU | XXOXOXOXOXOXOXOOOOOOX X |
| WV-4096 | TCACUGUAGAAAGGCAUGAAGU | 219 | T*fC*mAfC*mUfG*mUfA*mGfA*mAfA*mGfG* mCfAmUfGmAfAmG*T*mU | XXOXOXOXOXOXOXOOOOOOX X |
| WV-4097 | TCCACUGUAGAAAGGCAUGAAU | 220 | T*fC*mCfA*mCfU*mGfU*mAfG*mAfA*mAfG* mGfCmAfUmGfAmA*T*mU | XXOXOXOXOXOXOXOOOOOOX X |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-4098 | TGCCACUGUAGAAGGCAUGAT U | 221 | T*fG*mCfC*mAfC*mUfG*mUfA*mGfA*mAfA* mGfGmCfAmUfGmA*T*mU | XXOXOXOXOXOXOXOOOOOOX X |
| WV-4099 | TGGCCACUGUAGAAGGCAUGT U | 222 | T*fG*mCfC*mCfA*mCfU*mGfU*mUfA*mAfA* mAfGmGfCmAfUmG*T*mU | XXOXOXOXOXOXOXOOOOOOX X |
| WV-4100 | TAGGCCACUGUAGAAGGCAUT U | 223 | T*fA*mGfG*mCfC*mAfC*mUfG*mUfA*mGfA* mAfAmGfGmCfAmU*T*mU | XXOXOXOXOXOXOXOOOOOOX X |
| WV-4101 | TAAGGCCACUGUAGAAGGCAT U | 224 | T*fA*mAfG*mGfC*mCfA*mCfU*mGfU*mAfG* mAfAmGfGmCfA*T*mU | XXOXOXOXOXOXOXOOOOOOX X |
| WV-4102 | TUAAGGCCACUGUAGAAGGCT U | 225 | T*fU*mAfA*mGfG*mCfC*mAfC*mUfG*mUfA* mGfAmAfGmGfGmC*T*mU | XXOXOXOXOXOXOXOOOOOOX X |
| WV-4103 | TAUAAGGCCACUGUAGAAGGT U | 226 | T*fA*mUfA*mAfG*mGfC*mCfA*mCfU*mGfU* mAfGmAfAmGfGmG*T*mU | XXOXOXOXOXOXOXOOOOOOX X |
| WV-4104 | TGAUAAGGCCACUGUAGAAGT U | 227 | T*fG*mAfU*mAfA*mGfG*mCfC*mAfC*mUfG* mUfAmGfAmAfAmG*T*mU | XXOXOXOXOXOXOXOOOOOOX X |
| WV-4105 | TGGAUAAGGCCACUGUAGAAT U | 228 | T*fG*mGfA*mUfA*mAfG*mGfC*mCfA*mCfU* mGfUmAfGmAfAmA*T*mU | XXOXOXOXOXOXOXOOOOOOX X |
| WV-5305 | TGCCACUGUAGAAGGCAUGAT U | 229 | T*fG*mCfC*mAfC*mUfG*mUfA*mGfA* mAfAmGfGmCfAmUfGmA*T*mU | XXOXOXOXOXOXOXOOOOOOX X |
| WV-5306 | TGCCACUGUAGAAGGCAUGAT U | 230 | T*fG*mCfC*mAfC*mUfG*mUfA* mGfAmAfGmGfGmCfAmUfGmA*T*mU | XXOXOXOXOXOXOOOOOOOOOO XX |
| WV-5307 | TGCCACUGUAGAAGGCAUGAT U | 231 | T*fG*mCfC*mAfC*mUfG* mUfAmGfAmAfGmGfGmCfAmUfGmA*T*mU | XXOXOXOXOXOOOOOOOOOOO XX |
| WV-5308 | TGCCACUGUAGAAGGCAUGAT U | 232 | T*fG*mCfC*mAfC* mUfGmUfAmGfAmAfGmGfGmCfAmUfGmA*T*mU | XXOXOXOXOOOOOOOOOOOOO XX |
| WV-5309 | TGCCACUGUAGAAGGCAUGAT U | 233 | T*fG*mCfC*mAfCmUfGmUfAmGfAmAfAmGfGmCfA mUfGmA*T*mU | XXOXOXOOOOOOOOOOOOOOO XX |
| WV-5310 | TGCCACUGUAGAAGGCAUGAT U | 234 | T*fG*mCfCmAfCmUfGmUfAmGfAmAfAmGfGmC fAmUfGmA*T*mU | XXOXOOOOOOOOOOOOOOOOO OXX |
| WV-5311 | TGCCACUGUAGAAGGCAUGAT U | 235 | T*fG*mCC*mAC*mUG*mUfA*mGfA*mAfA* mGfGmCfAmUfGmA*T*mU | XXOXOXOXOXOXOXOOOOOOX X |

TABLE 1A-continued oligonucleotides.
PNPLA3 oligonucleotides.

| WAVE ID | Naked Sequence | SEQ ID NO: | Sequence | Stereochemistry |
|---------|----------------|------------|----------|-----------------|
| WV-5312 | TGCCACUGUAGAAAGGCAUGAU | 236 | T*fG*mCC*mAfC*mUfG*mUfA*mGfA*mAfA*mGfGmCfAmUfGmA*T*mU | XXOXOXOXOXOXOXOOOOOOXX |
| WV-5313 | TGCCACUGUAGAAAGGCAUGAU | 237 | T*fG*mCfC*mAC*mUfG*mUfA*mGfA*mAfA*mGfGmCfAmUfGmA*T*mU | XXOXOXOXOXOXOXOOOOOOXX |
| WV-5314 | TGCCACUGUAGAAAGGCAUGAU | 238 | T*fG*mCfC*mAfC*mUfG*mUfA*mGfA*mAfA*mGfGmCfAmUfGmA*T*mU | XXOXOXOXOXOXOXOOOOOOXX |
| WV-5315 | TGCCACUGUAGAAAGGCAUUU | 239 | T*fG*mCfC*mAfC*mUfG*mUfA*mGfA*mAfAmGfGmCfAmU*T*mU | XXOXOXOXOXOOOOOOOOOXX |
| WV-5316 | TGCCACUGUAGAAAGGCAUUU | 240 | T*fG*mCfC*mAfC*mUfG*mUfG*mUfA*mGfA*mGfAmAfAmGfGmCfAmU*T*mU | XXOXOXOXOXOOOOOOOOOXX |
| WV-5317 | TGCCACUGUAGAAAGGCAUUU | 241 | T*fG*mCfC*mAfC*mUfG* mUfAmGfAmAfAmGfGmCfAmU*T*mU | XXOXOXOXOOOOOOOOOOOXX |
| WV-5318 | TGCCACUGUAGAAAGGCAUUU | 242 | T*fG*mCfC*mAfC*mUfG*mUfGmUfAmGfA mAfAmGfGmCfAmU*T*mU | XXOXOXOOOOOOOOOOOOOXX |
| WV-5319 | TGCCACUGUAGAAAGGCAUUU | 243 | T*fG*mCfC*mAfCmUfGmUfAmGfA mAfAmGfGmCfAmU*T*mU | XXOXOOOOOOOOOOOOOOOXX |
| WV-5320 | TGCCACUGUAGAAAGGCAUUU | 244 | T*fG*mCfCmAfCmUfGmUfAmGfAmAfAmGfGmCfAmU*T*mU | XXOOOOOOOOOOOOOOOOOXX |
| WV-5321 | TGCCACUGUAGAAAGGCAUUU | 245 | T*fG*mCC*mAC*mUG*mUfA*mGfA*mAfA*mGfGmCfAmU*T*mU | XXOXOXOXOXOOOOOOOOOXX |
| WV-5322 | TGCCACUGUAGAAAGGCAUUU | 246 | T*fG*mCC*mAfC*mUfG*mUfA*mGfA*mAfA*mGfGmCfAmU*T*mU | XXOXOXOXOXOOOOOOOOOXX |
| WV-5323 | TGCCACUGUAGAAAGGCAUUU | 247 | T*fG*mCfC*mAC*mUfG*mUfA*mGfA*mAfA*mGfGmCfAmU*T*mU | XXOXOXOXOXOOOOOOOOOXX |
| WV-5324 | TGCCACUGUAGAAAGGCAUUU | 248 | T*fG*mCfC*mAfC*mUG*mUfA*mGfA*mAfA*mGfGmCfAmU*T*mU | XXOXOXOXOXOOOOOOOOOXX |
| WV-5325 | TAGGCAUGAAGCAGGAACAUU | 249 | T*fA*mGfG*mCfA*mUfG*mAfA*mGfC* mAfGmGfAmAfCmA*T*mU | XXOXOXOXOXOOOOOOOOOXX |
| WV-5326 | TAGGCAUGAAGCAGGAACAUAU | 250 | T*fA*mGfG*mCfA*mUfG*mAfA*mGfC* mAfGmGfAmAfCmAfUmA*T*mU | XXOXOXOXOXOXOOOOOOOXX |
| WV-6153 | TCCUGAGGAUGGACCGCGGGU | 251 | T*fC*mCfU*mGfA*mGfG*mAfU*mGfG*mAfC*mC *fG*mC*fG*mG*fG*mG*T*mU | XXOXOXOXOXOXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6154 | TGUGCUUGCUCCUGCCUGGGT U | 252 | T*fG*mUfG*mCfU*mUfG*mGfC*mUfC*mCfU*mG*fC*mC*fU*mG*fG*mG*T*mU | XXOXOXOXOXOXOXXXXXXX |
| WV-6155 | TCUUGUUACCCCGCCAUGGAT U | 253 | T*fC*mUfU*mGfU*mUfA*mCfC*mCfC*mCfG*mC*fC*mA*fU*mG*fG*mA*T*mU | XXOXOXOXOXOXOXXXXXXX |
| WV-6156 | TUACCCCCGCCAUGGAGACGUTU | 254 | T*fU*mAfC*mCfC*mCfC*mGfC*mCfA*mUfG*mG*fA*mG*fA*mC*fG*mU*T*mU | XXOXOXOXOXOXOXXXXXXX |
| WV-6157 | TCCCCCGCCAUGGAGACGUUUT U | 255 | T*fC*mCfC*mCfC*mGfC*mCfA*mUfG*mGfA*mG*fA*mC*fG*mU*fU*mU*T*mU | XXOXOXOXOXOXOXXXXXXX |
| WV-6158 | TACCUGAGGAUGGACCGCGGGT U | 256 | T*fA*mCfC*mUfG*mAfG*mGfA*mUfG*mGfA*mC*fC*mG*fC*mG*fG*mG*T*mU | XXOXOXOXOXOXOXXXXXXX |
| WV-6159 | TGACCUGAGGAUGGACCGCGT U | 257 | T*fG*mAfC*mCfU*mGfA*mGfG*mAfU*mGfG*mA*fC*mC*fG*mC*fG*mU*T*mU | XXOXOXOXOXOXOXXXXXXX |
| WV-6160 | TACCCCCGCCAUGGAGACGUUTU | 258 | T*fA*mCfC*mCfC*mCfG*mCfC*mAfU*mGfG*mA*fG*mA*fC*mG*fU*mU*T*mU | XXOXOXOXOXOXOXXXXXXX |
| WV-6161 | TGGACCCUCGCACGGGCUUT U | 259 | T*fG*mGfA*mCfC*mCfU*mCfG*mCfA*mCfG*mG*fG*mC*fU*mU*fU*mU*T*mU | XXOXOXOXOXOXOXXXXXXX |
| WV-6162 | TCUGCUGGACAGCCCUUGGGGT U | 260 | T*fC*mUfG*mCfU*mGfG*mAfC*mAfG*mCfC*mC*fU*mU*fG*mG*fG*mG*T*mU | XXOXOXOXOXOXOXXXXXXX |
| WV-6163 | TUGCACUGGGCUUCCUGUGUT U | 261 | T*fU*mGfC*mAfC*mUfG*mGfG*mCfU*mUfC*mC*fU*mG*fU*mG*fU*mU*T*mU | XXOXOXOXOXOXOXXXXXXX |
| WV-6164 | TGGACCUGAGGAUGGACCGCGT U | 262 | T*fG*mGfA*mCfC*mUfG*mAfG*mGfA*mUfG*mG*fA*mC*fC*mG*fG*mG*T*mU | XXOXOXOXOXOXOXXXXXXX |
| WV-6165 | TGGGACCCUCUGCACUGGGCUT U | 263 | T*fG*mGfG*mAfC*mCfC*mUfC*mUfG*mCfA*mC*fU*mG*fG*mG*fG*mA*T*mU | XXOXOXOXOXOXOXXXXXXX |
| WV-6166 | TUUGUUACCCCGCCAUGGAGT U | 264 | T*fU*mUfG*mUfU*mAfC*mCfC*mCfC*mGfC*mC*fA*mU*fG*mG*fA*mG*T*mU | XXOXOXOXOXOXOXXXXXXX |
| WV-6167 | TCCUGUGAGGUCACCCACUGCT U | 265 | T*fC*mCfU*mGfU*mGfA*mGfG*mUfC*mAfC*mC*fC*mA*fC*mU*fG*mC*T*mU | XXOXOXOXOXOXOXXXXXXX |
| WV-6168 | TCUGCUGGACAGCCCUUGGGGT U | 266 | T*fU*mCfU*mGfC*mUfG*mGfA*mCfA*mGfC*mC*fC*mU*fU*mG*fG*mG*T*mU | XXOXOXOXOXOXOXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6169 | TUGCUCCAGCGGGAUACCGGAU | 267 | T*fU*mGfC*mUfC*mCfA*mGfG*mGfA*mU*fA*mC*fC*mG*fG*mA*T*mU | XXOXOXOXOXOXOXXXXXXX |
| WV-6170 | TGGCUGGGAUCCUCCACGUCAU | 268 | T*fG*mGfC*mUfG*mGfG*mAfU*mCfC*mUfC*mC*fA*mC*fG*mU*fC*mA*T*mU | XXOXOXOXOXOXOXXXXXXX |
| WV-6171 | TUCUUGUUACCCCCGCCAUGGU | 269 | T*fU*mCfU*mUfG*mUfU*mAfC*mCfC*mCfC*mG*fC*mC*fA*mU*fG*mG*T*mU | XXOXOXOXOXOXOXXXXXXX |
| WV-6172 | TAGGGACCCUGCACUGGGGCU | 270 | T*fA*mGfG*mGfA*mCfC*mCfU*mGfC*mA*fC*mU*fG*mG*fG*mC*T*mU | XXOXOXOXOXOXOXXXXXXX |
| WV-6173 | TCUGUUGGCUGCUCACUGGCAU | 271 | T*fC*mUfG*mUfU*mGfG*mCfU*mGfC*mUfC*mA*fC*mU*fG*mG*fC*mA*T*mU | XXOXOXOXOXOXOXXXXXXX |
| WV-6174 | TCCUGAGGAUGGACCGCGGGU | 272 | T*fC*mCfU*mGfA*mGfG*mAfU*mGfG*mAfC*mCfG*mC*fG*mG*fG*mG*T*mU | XXOXOXOXOXOXOXXXXXXX |
| WV-6175 | TGUGCUUGGCUCUCUGCCUGGU | 273 | T*fG*mUfG*mCfU*mUfG*mGfC*mUfC*mUfC*mUfG*mC*fC*mU*fG*mG*T*mU | XXOXOXOXOXOXOXXXXXXX |
| WV-6176 | TCUUGUUACCCCCGCCAUGGAU | 274 | T*fC*mUfU*mGfU*mUfA*mCfC*mCfC*mCfC*mG*fC*mC*fA*mU*fG*mG*T*mU | XXOXOXOXOXOXOXXXXXXX |
| WV-6177 | TUACCCCCGCCAUGGAGAGACGUTU | 275 | T*fU*mAfC*mCfC*mCfC*mGfC*mCfA*mUfG*mGmG*fA*mC*fA*mC*fU*mU*T*mU | XXOXOXOXOXOXOXXXXXXX |
| WV-6178 | TCCCCCGCCAUGGAGACGUUUT | 276 | T*fC*mCfC*mCfC*mGfC*mCfA*mUfG*mGfA*mGfA*mC*fG*mU*fU*mU*T*mU | XXOXOXOXOXOXOXXXXXXX |
| WV-6179 | TACCUGAGGAUGGACCGCGGGU | 277 | T*fA*mCfC*mUfG*mAfG*mGfA*mUfG*mGfA*mC*fC*mG*fC*mG*fG*mG*T*mU | XXOXOXOXOXOXOXXXXXXX |
| WV-6180 | TGACCUGAGGAUGGACCGCGCGU | 278 | T*fG*mAfC*mCfU*mGfA*mGfG*mAfU*mGfG*mAfC*mC*fG*mC*fG*mC*T*mU | XXOXOXOXOXOXOXXXXXXX |
| WV-6181 | TACCCCCGCCAUGGAGAGACGUUTU | 279 | T*fA*mCfC*mCfC*mCfC*mGfC*mCfA*mUfG*mGfA*mGfA*mC*fG*mU*fU*mU*T*mU | XXOXOXOXOXOXOXXXXXXX |
| WV-6182 | TGGACCCUGCACUGGGGCUUT | 280 | T*fG*mGfA*mCfC*mCfU*mGfC*mAfC*mUfG*mG*fG*mG*fC*mU*fU*mU*T*mU | XXOXOXOXOXOXOXXXXXXX |
| WV-6183 | TCUGCUGGACAGCCCUUGGGGU | 281 | T*fC*mUfG*mCfU*mGfG*mAfC*mAfG*mC*fC*mC*fU*mU*fG*mG*T*mU | XXOXOXOXOXOXOXXXXXXX |
| WV-6184 | TUGCACUGGCUUCCUGGUGUT | 282 | T*fU*mGfC*mAfC*mUfG*mGfC*mUfU*mC*fC*mU*fG*mG*fU*mG*T*mU | XXOXOXOXOXOXOXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6185 | TGGACCTUGAGGAUGGACCGCGT U | 283 | T*fG*mGfA*mCfC*mUfG*mAfG*mGfA*mUfGmG* fA*mC*fC*mG*fC*mG*T*mU | XXOXOXOXOXOXOOXXXXXXX |
| WV-6186 | TGGGACCCUCUGCACUGGGCUT U | 284 | T*fG*mGfG*mAfC*mCfC*mUfC*mUfG*mGfGmC* fU*mG*fG*mC*fC*mU*T*mU | XXOXOXOXOXOXOOXXXXXXX |
| WV-6187 | TUUGUUACCCCGCCAUGGAGU U | 285 | T*fU*mUfG*mUfU*mAfC*mCfC*mCfC*mGfCmC* fA*mU*fG*mG*fA*mG*T*mU | XXOXOXOXOXOXOOXXXXXXX |
| WV-6188 | TCCUGAGGUCACCACUGCT U | 286 | T*fC*mCfU*mGfA*mGfG*mUfC*mAfC*mCfAmC* fC*mA*fC*mU*fG*mC*T*mU | XXOXOXOXOXOXOOXXXXXXX |
| WV-6189 | TCUGCUGGACAGCCCUUGGGT U | 287 | T*fU*mCfU*mGfC*mUfG*mGfA*mCfA*mGfCmC* fC*mU*fU*mG*fG*mG*T*mU | XXOXOXOXOXOXOOXXXXXXX |
| WV-6190 | TUGCCAGCGGGAUACCGAT U | 288 | T*fU*mGfC*mCfA*mGfC*mGfG*mGfA*mUfAmC* fC*mG*fA*mU*T*mU | XXOXOXOXOXOXOOXXXXXXX |
| WV-6191 | TGGCUGGGAUCCUCCACGUCAT U | 289 | T*fG*mGfC*mUfG*mGfG*mAfU*mCfC*mUfCmC* fA*mC*fG*mU*fC*mA*T*mU | XXOXOXOXOXOXOOXXXXXXX |
| WV-6192 | TUCUUGUUACCCCGCCAUGGT U | 290 | T*fU*mCfU*mUfG*mUfU*mAfC*mCfC*mCfGmC* fC*mA*fU*mG*fG*mG*T*mU | XXOXOXOXOXOXOOXXXXXXX |
| WV-6193 | TAGGGACCCUCUGCACUGGGCT U | 291 | T*fA*mGfG*mGfA*mCfC*mCfU*mCfU*mGfCmA* fC*mU*fG*mG*fG*mC*T*mU | XXOXOXOXOXOXOOXXXXXXX |
| WV-6194 | TCUGUUGGCUGCUCACUGGCAT U | 292 | T*fC*mUfU*mGfG*mCfU*mGfC*mUfC*mAfCmU* fG*mG*fC*mA*T*mU | XXOXOXOXOXOXOOXXXXXXX |
| WV-6574 | ACCCCGCGGU CCAUCCCUCAGGUCCAGC | 293 | rArCrCrCrCrGrCrGrGrUrCrCrArUrCrCrCrUrCrA rGrGrUrCrCrArGrC | OOOOOOOOOOOOOOOO OOOOOOOOOOOO |
| WV-6575 | AUGACACCAG GAAGCCCAGUGCAGAGG | 294 | rArUrGrArCrArCrCrArGrG rArArGrCrCrCrArGrUrGrCrArGrArGrG | OOOOOOOOOOOOOOOO OOOOOOOOOOOO |
| WV-6576 | GAAGCCCAGU GCAGAGGGUCCCUUACU | 295 | rGrArArGrCrCrCrArGrUrG rCrArGrArGrGrGrUrCrCrCrUrUrArCrU | OOOOOOOOOOOOOOOO OOOOOOOOOOOO |
| WV-6577 | AACGUCUCCA UGGCGGGGUAACAAGA | 296 | rArArCrGrUrCrUrCrCrArU rGrGrCrGrGrGrGrUrArArCrArArGrA | OOOOOOOOOOOOOOOO OOOOOOOOOOOO |
| WV-6585 | TGCCACUGUAGAAAGGAAUGAT U | 297 | T*fG*mCfC*mAfC*mUfG*mUfA*mGfA*mAfA* mGfGmA*fAmUfGmA*T*mU | XXOXOXOXOXOXOOOOOOOX X |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6586 | TGCCACUGUAGAAAGGGAUGAU | 298 | T*fG*mCfC*mAfC*mUfUG*mUfUA*mGfA*mAfA*mGfGmGfAmUfGmA*T*mU | XXOXOXOXOXOXOXOOOOOOXX |
| WV-6587 | TGCCACUGUAGAAGGUAUGAU | 299 | T*fG*mCfC*mAfC*mUfUG*mUfUA*mGfA*mAfA*mGfGmCfAmUfGmA*T*mU | XXOXOXOXOXOXOXOOOOOOXX |
| WV-6588 | TGCCACUGUAGAAGGCAUGAU | 300 | T*fG*mCfC*mAfC*mUfUG*mUfUA*mGfA*mAfG*mGfGmCfAmUfGmA*T*mU | XXOXOXOXOXOXOXOOOOOOXX |
| WV-6589 | TGCCACUGUAGAACCGCAUGAU | 301 | T*fG*mCfC*mAfC*mUfUG*mUfUA*mGfA*mAfC*mGfGmCfAmUfGmA*T*mU | XXOXOXOXOXOXOXOOOOOOXX |
| WV-6590 | TGCCACUGUAGAAUGGCAUGAU | 302 | T*fG*mCfC*mAfC*mUfUG*mUfUA*mGfA*mAfU*mGfGmCfAmUfGmA*T*mU | XXOXOXOXOXOXOXOOOOOOXX |
| WV-6591 | TGCCACUGUAGAAGGGGAUGAU | 303 | T*fG*mCfC*mAfC*mUfUG*mUfUA*mGfA*mAfG*mGfGmGfAmUfGmA*T*mU | XXOXOXOXOXOXOXOOOOOOXX |
| WV-6592 | TGCCACUGUAGAAAGGCAUGU | 304 | T*fG*mCfC*mAfC*mUfUG*mUfUA*mGfA*mAfA*mGfGmCfAmUfGmAfAmG*T*mU | XXOXOXOXOXOXOXOOOOOOOOXX |
| WV-6593 | TGCCACUGUAGAAAGGCAUGAAT | 305 | T*fG*mCfC*mAfC*mUfUG*mUfUA*mGfA*mAfA*mGfGmCfAmUfGmAfAmGfA*T*mU | XXOXOXOXOXOXOXOOOOOOOOXX |
| WV-6594 | TGCCACUGUAGAAAGGCAUGAU | 306 | T*fG*mCfC*mAfC*mUfUG*mUfUA*mGfA*mAfA*mGfGmCfAmUfG*T*mU | XXOXOXOXOXOXOXOOOOXXX |
| WV-6595 | TGCCACUGUAGAAAGGCAUU | 307 | T*fG*mCfC*mAfC*mUfUG*mUfUA*mGfA*mAfA*mGfGmCfA*T*mU | XXOXOXOXOXOXOXOOOXX |
| WV-6596 | TGCCACUGUAGAAAGGCTU | 308 | T*fG*mCfC*mAfC*mUfUG*mUfUA*mGfA*mAfA*mGfGmC*T*mU | XXOXOXOXOXOXOXOXOOXX |
| WV-6597 | TGCCACUGUAGAAAGGCAGG | 309 | T*fG*mCfC*mAfC*mUfUG*mUfUA*mGfA*mAfA*mGfGmCfA*G*mG | XXOXOXOXOXOXOXOOOXX |
| WV-6598 | TGCCACUGUAGAAAGGCGG | 310 | T*fG*mCfC*mAfC*mUfUG*mUfUA*mGfA*mAfA*mGfGmC*G*mG | XXOXOXOXOXOXOXOOXX |
| WV-6599 | TGCCACUGUAGAAAGGCAUGAU | 311 | T*fG*mC*fC*mA*fC*mU*fG*mU*fG*mU*fA*mG*fA* mA*fA*mG*fG*mC*fA*mU*fG*mA*T*mU | XXXXXXXXXXXXXXXXXXXXXX |
| WV-6600 | TGCCACUGUAGAAAGGCAUGAU | 312 | T*fGmCfCmAfCmUfGmUfA mGfAmAfAmGfGmCfAmUfGmAT*mU | XOOOOOOOOOOOOOOOOOOOX |
| WV-6601 | TGCCACUGUAGAAAGGCAUGAU | 313 | T*fG*mCfC*mAfC*mUfUG*mUfUA*mGfA*mAfA*mGfG*mCfA*mUfG*mA*T*mU | XXOXOXOXOXOXOXOXOXOXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6602 | TGCCACUGUAGAAAGGCAUGAU | 314 | T*fG*mC*fCmA*fCmU*fGmU*fAmA*fAmG*fGmC*fAmU*fGmA*T*mU | XXXXOXOXOXOXOXOXOXOX |
| WV-6603 | TGCCACUGUAGAAAGGCAUGAU | 315 | TfG*mCfC*mAfC*mUfG*mUfA*mGfA*mAfA*mGfGmCfAmUfGmA*T*mU | OXOXOXOXOXOXOXOOOOOOX |
| WV-6604 | TGCCACUGUAGAAAGGCAUGAU | 316 | T*fGmCfC*mAfC*mUfG*mUfA*mGfA*mAfA*mGfGmCfAmUfGmA*T*mU | XOOXOXOXOXOXOXOOOOOOX |
| WV-6605 | TGCCACUGUAGAAAGGCAUGAU | 317 | T*fG*mC*fC*mAfC*mUfG*mUfA*mGfA*mAfA*mGfGmCfAmUfGmA*T*mU | XXXXOXOXOXOXOXOOOOOOX |
| WV-6606 | TGCCACUGUAGAAAGGCAUGAU | 318 | T*fG*mCfCmAfC*mUfG*mUfA*mGfA*mAfA*mGfGmCfAmUfGmA*T*mU | XXOOXOXOXOXOXOOOOOOX |
| WV-6607 | TGCCACUGUAGAAAGGCAUGAU | 319 | T*fG*mCfC*mA*fC*mUfG*mUfA*mGfA*mAfA*mGfGmCfAmUfGmA*T*mU | XXXOXXOXOXOXOXOOOOOOX |
| WV-6608 | TGCCACUGUAGAAAGGCAUGAU | 320 | T*fG*mCfC*mAfCmUfG*mUfA*mGfA*mAfA*mGfGmCfAmUfGmA*T*mU | XXXOXOOXOXOXOXOOOOOOX |
| WV-6609 | TGCCACUGUAGAAAGGCAUGAU | 321 | T*fG*mCfC*mAfC*mU*fG*mUfA*mGfA*mAfA*mGfGmCfAmUfGmA*T*mU | XXXOXOXXOXOXOXOOOOOOX |
| WV-6610 | TGCCACUGUAGAAAGGCAUGAU | 322 | T*fG*mCfC*mAfC*mUfGmUfA*mGfA*mAfA*mGfGmCfAmUfGmA*T*mU | XXXOXOXOOXOXOXOOOOOOX |
| WV-6611 | TGCCACUGUAGAAAGGCAUGAU | 323 | T*fG*mCfC*mAfC*mUfG*mU*fA*mGfA*mAfA*mGfGmCfAmUfGmA*T*mU | XXXOXOXOXXOXOXOOOOOOX |
| WV-6612 | TGCCACUGUAGAAAGGCAUGAU | 324 | T*fG*mCfC*mAfC*mUfG*mUfAmGfA*mAfA*mGfGmCfAmUfGmA*T*mU | XXXOXOXOXOOXOXOOOOOOX |
| WV-6613 | TGCCACUGUAGAAAGGCAUGAU | 325 | T*fG*mCfC*mAfC*mUfG*mUfA*mG*fA*mAfA*mGfGmCfAmUfGmA*T*mU | XXXOXOXOXOXXOXOOOOOOX |
| WV-6614 | TGCCACUGUAGAAAGGCAUGAU | 326 | T*fG*mCfC*mAfC*mUfG*mUfA*mGfAmAfA*mGfGmCfAmUfGmA*T*mU | XXXOXOXOXOXOOXOOOOOOX |
| WV-6615 | TGCCACUGUAGAAAGGCAUGAU | 327 | T*fG*mCfC*mAfC*mUfG*mUfA*mGfA*mA*fA*mGfGmCfAmUfGmA*T*mU | XXXOXOXOXOXOXXOOOOOOX |
| WV-6616 | TGCCACUGUAGAAAGGCAUGAU | 328 | T*fG*mCfC*mAfC*mUfG*mUfA*mGfA*mAfA*mG*fGmCfAmUfGmA*T*mU | XXXOXOXOXOXOXOXOOOOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6617 | TGCCACUGUAGAAAGGCAUGAU | 329 | T*fG*mCfC*mAfC*mUfG*mUfA*mGfA*mAfA*mGfG*mCfAmUfGmA*T*mU | XXOXOXOXOXOXOXOXOOXOOX X |
| WV-6618 | TGCCACUGUAGAAAGGCAUGAU | 330 | T*fG*mCfC*mAfC*mUfG*mUfA*mGfA*mAfA*mGfGmC*fAmUfGmA*T*mU | XXOXOXOXOXOXOXOXOOOXOX X |
| WV-6619 | TGCCACUGUAGAAAGGCAUGAU | 331 | T*fG*mCfC*mAfC*mUfG*mUfA*mGfA*mAfA*mGfGmCfA*mUfGmA*T*mU | XXOXOXOXOXOXOXOOXOOXOX X |
| WV-6620 | TGCCACUGUAGAAAGGCAUGAU | 332 | T*fG*mCfC*mAfC*mUfG*mUfA*mGfA*mAfA*mGfGmCfAmU*fGmA*T*mU | XXOXOXOXOXOXOXOXOOOXOX X |
| WV-6621 | TGCCACUGUAGAAAGGCAUGAU | 333 | T*fG*mCfC*mAfC*mUfG*mUfA*mGfA*mAfA*mGfGmCfAmUfG*mA*T*mU | XXOXOXOXOXOXOXOXOOOOXX X |
| WV-6622 | TGCCACUGUAGAAAGGCAUGAA | 334 | T*fG*mCfC*mAfC*mUfG*mUfA*mGfA*mAfA*mGfGmCfAmUfGmA*T*mA | XXOXOXOXOXOXOXOOOOOOOX X |
| WV-6623 | TGCCACUGUAGAAAGGCAUGAG | 335 | T*fG*mCfC*mAfC*mUfG*mUfA*mGfA*mAfA*mGfGmCfAmUfGmA*T*mG | XXOXOXOXOXOXOXOOOOOOOX X |
| WV-6624 | TGCCACUGUAGAAAGGCAUGAC | 336 | T*fG*mCfC*mAfC*mUfG*mUfA*mGfA*mAfA*mGfGmCfAmUfGmA*T*mC | XXOXOXOXOXOXOXOOOOOOOX X |
| WV-6625 | TGCCACUGUAGAAAGGCAUUA | 337 | T*fG*mCfC*mAfC*mUfG*mUfA*mGfA*mAfA*mGfGmCfAmU*T*mA | XXOXOXOXOXOXOXOOOOOXX |
| WV-6626 | TGCCACUGUAGAAAGGCAUUG | 338 | T*fG*mCfC*mAfC*mUfG*mUfA*mGfA*mAfA*mGfGmCfAmU*T*mG | XXOXOXOXOXOXOXOOOOOXX |
| WV-6627 | TGCCACUGUAGAAAGGCAUUC | 339 | T*fG*mCfC*mAfC*mUfG*mUfA*mGfA*mAfA*mGfGmCfAmU*T*mC | XXOXOXOXOXOXOXOOOOOXX |
| WV-6628 | TGCCACUGUAGAAAGGCAUGAU | 340 | T*fG*mCmC*mAmC*mUmG*mUmA*mGmA*mAmA*mGmCmAmUmGmA*T*mU | XXOXOXOXOXOXOXOOOOOOXX X |
| WV-6629 | TGCCACUGUAGAAAGGCAUGAU | 341 | T*fG*mCmC*mAfC*mUmG*mUmA*mGmA*mAmA*mGfGmCmAmUmGmA*T*mU | XXOXOXOXOXOXOXOOOOOOXX X |
| WV-6630 | TGCCACUGUAGAAAGGCAUGAU | 342 | T*fG*mCmC*mAfC*mUfG*fUmA*mGmA*mAmA*mGfGmCmAmUmGmA*T*mU | XXOXOXOXOXOXOXOOOOOOXX X |
| WV-6631 | TGCCACUGUAGAAAGGCAUGAU | 343 | T*fG*mCmC*mAfC*mUfG*mUfA*mGmA*mAmA*mGfGmCfAmUmGmA*T*mU | XXOXOXOXOXOXOXOOOOOOXX X |
| WV-6632 | TGCCACUGUAGAAAGGCAUGAU | 344 | T*mG*mCfC*mAfC*mUfG*mUfA*mGfA*mAfA*mGfGmCfAmUfGmA*T*mU | XXOXOXOXOXOXOXOOOOOOXX X |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6633 | TGCCACUGUAGAAAGGCAUGAU | 345 | T*fG*fCfC*mAfC*mUfG*mUfA*mGfA*mAfA*mGfGmCfAmUfGmA*T*mU | XXOXOXOXOXOXOXOXOOOOOOXX |
| WV-6634 | TGCCACUGUAGAAAGGCAUGAU | 346 | T*fG*mCmC*mAfC*mUfG*mUfA*mGfA*mAfA*mGfGmCfAmUfGmA*T*mU | XXOXOXOXOXOXOXOXOOOOOOXX |
| WV-6635 | TGCCACUGUAGAAAGGCAUGAU | 347 | T*fG*mCfC*fAfC*mUfG*mUfA*mGfA*mAfA*mGfGmCfAmUfGmA*T*mU | XXOXOXOXOXOXOXOXOOOOOOXX |
| WV-6636 | TGCCACUGUAGAAAGGCAUGAU | 348 | T*fG*mCfC*mAmC*mUfG*mUfA*mGfA*mAfA*mGfGmCfAmUfGmA*T*mU | XXOXOXOXOXOXOXOXOOOOOOXX |
| WV-6637 | TGCCACUGUAGAAAGGCAUGAU | 349 | T*fG*mCfC*mAfC*fUfG*mUfA*mGfA*mAfA*mGfGmCfAmUfGmA*T*mU | XXOXOXOXOXOXOXOXOOOOOOXX |
| WV-6638 | TGCCACUGUAGAAAGGCAUGAU | 350 | T*fG*mCfC*mAfC*mUmG*mUfA*mGfA*mAfA*mGfGmCfAmUfGmA*T*mU | XXOXOXOXOXOXOXOXOOOOOOXX |
| WV-6639 | TGCCACUGUAGAAAGGCAUGAU | 351 | T*fG*mCfC*mAfC*mUfG*fUfA*mGfA*mAfA*mGfGmCfAmUfGmA*T*mU | XXOXOXOXOXOXOXOXOOOOOOXX |
| WV-6640 | TGCCACUGUAGAAAGGCAUGAU | 352 | T*fG*mCfC*mAfC*mUfG*mUmA*mGfA*mAfA*mGfGmCfAmUfGmA*T*mU | XXOXOXOXOXOXOXOXOOOOOOXX |
| WV-6641 | TGCCACUGUAGAAAGGCAUGAU | 353 | T*fG*mCfC*mAfC*mUfG*mUfA*fGfA*mAfA*mGfGmCfAmUfGmA*T*mU | XXOXOXOXOXOXOXOXOOOOOOXX |
| WV-6642 | TGCCACUGUAGAAAGGCAUGAU | 354 | T*fG*mCfC*mAfC*mUfG*mUfA*mGmA*mAfA*mGfGmCfAmUfGmA*T*mU | XXOXOXOXOXOXOXOXOOOOOOXX |
| WV-6643 | TGCCACUGUAGAAAGGCAUGAU | 355 | T*fG*mCfC*mAfC*mUfG*mUfA*mGfA*fAfA*mGfGmCfAmUfGmA*T*mU | XXOXOXOXOXOXOXOXOOOOOOXX |
| WV-6644 | TGCCACUGUAGAAAGGCAUGAU | 356 | T*fG*mCfC*mAfC*mUfG*mUfA*mGfA*mAmA*mGfGmCfAmUfGmA*T*mU | XXOXOXOXOXOXOXOXOOOOOOXX |
| WV-6645 | TGCCACUGUAGAAAGGCAUGAU | 357 | T*fG*mCfC*mAfC*mUfG*mUfA*mGfA*mAfA*fGfGmCfAmUfGmA*T*mU | XXOXOXOXOXOXOXOXOOOOOOXX |
| WV-6646 | TGCCACUGUAGAAAGGCAUGAU | 358 | T*fG*mCfC*mAfC*mUfG*mUfA*mGfA*mAfA*mGmGmCfAmUfGmA*T*mU | XXOXOXOXOXOXOXOXOOOOOOXX |
| WV-6647 | TGCCACUGUAGAAAGGCAUGAU | 359 | T*fG*mCfC*mAfC*mUfG*mUfA*mGfA*mAfA*mGfGfCfAmUfGmA*T*mU | XXOXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6648 | TGCCACUGUAGAAAGGCAUGAU | 360 | T*fG*mCfC*mAfC*mUfG*mUfA*mGfA*mAfA* mGfGmCfAmUfGmA*T*mU | XXOXOXOXOXOXOXOOOOOOXX |
| WV-6649 | TGCCACUGUAGAAAGGCAUGAU | 361 | T*fG*mCfC*mAfC*mUfG*mUfA*mGfA*mAfA* mGfGmCfAfUfGmA*T*mU | XXOXOXOXOXOXOXOOOOOOXX |
| WV-6650 | TGCCACUGUAGAAAGGCAUGAU | 362 | T*fG*mCfC*mAfC*mUfG*mUfA*mGfA*mAfA* mGfGmCfAmUmGmA*T*mU | XXOXOXOXOXOXOXOOOOOOXX |
| WV-6651 | TGCCACUGUAGAAAGGCAUGAU | 363 | T*fG*mCfC*mAfC*mUfG*mUfA*mGfA*mAfA* mGfGmCfAmUfGfAT*mU | XXOXOXOXOXOXOXOOOOOOXX |
| WV-6652 | UGCCACUGUAGAAAGGCAUGAU | 364 | fU*fG*mCfC*mAfC*mUfG*mUfA*mGfA*mAfA* mGfGmCfAmUfGmA*T*mU | XXOXOXOXOXOXOXOOOOOOXX |
| WV-6653 | AGCCACUGUAGAAAGGCAUGAU | 365 | fA*fG*mCfC*mAfC*mUfG*mUfA*mGfA*mAfA* mGfGmCfAmUfGmA*T*mU | XXOXOXOXOXOXOXOOOOOOXX |
| WV-6654 | GGCCACUGUAGAAAGGCAUGAU | 366 | fG*fG*mCfC*mAfC*mUfG*mUfA*mGfA*mAfA* mGfGmCfAmUfGmA*T*mU | XXOXOXOXOXOXOXOOOOOOXX |
| WV-6655 | CGCCACUGUAGAAAGGCAUGAU | 367 | fC*fG*mCfC*mAfC*mUfG*mUfA*mGfA*mAfA* mGfGmCfAmUfGmA*T*mU | XXOXOXOXOXOXOXOOOOOOXX |
| WV-6656 | UGCCACUGUAGAAAGGCAUGAU | 368 | mU*fG*mCfC*mAfC*mUfG*mUfA*mGfA*mAfA* mGfGmCfAmUfGmA*T*mU | XXOXOXOXOXOXOXOOOOOOXX |
| WV-6657 | AGCCACUGUAGAAAGGCAUGAU | 369 | mA*fG*mCfC*mAfC*mUfG*mUfA*mGfA*mAfA* mGfGmCfAmUfGmA*T*mU | XXOXOXOXOXOXOXOOOOOOXX |
| WV-6658 | GGCCACUGUAGAAAGGCAUGAU | 370 | mG*fG*mCfC*mAfC*mUfG*mUfA*mGfA*mAfA* mGfGmCfAmUfGmA*T*mU | XXOXOXOXOXOXOXOOOOOOXX |
| WV-6659 | CGCCACUGUAGAAAGGCAUGAU | 371 | mC*fG*mCfC*mAfC*mUfG*mUfA*mGfA*mAfA* mGfGmCfAmUfGmA*T*mU | XXOXOXOXOXOXOXOOOOOOXX |
| WV-6660 | TGCCACUGUAGAAAGGCAUGAU | 372 | T*fG*mCfC*mAfC*mUfG*mUfA*mGfA*mAfA* mGfGfCfAmUfGmA*T*mU | XXOXOXOXOXOXOXOOOOOOXX |
| WV-6661 | TGCCACUGUAGAAAGGCAUGAU | 373 | T*Geo*mCfC*mAfC*mUfG*mUfA*mGfA*mAfA* mGfGmCfAmUfGmA*T*mU | XXOXOXOXOXOXOXOOOOOOXX |
| WV-6662 | TGCCACUGUAGAAAGGCAUGAU | 374 | T*fG*mCm5Ceofc*mAfC*mUfG*mUfA*mGfA*mAfA* mGfGmCfAmUfGmA*T*mU | XXOXOXOXOXOXOXOOOOOOXX |
| WV-6663 | TGCCACUGUAGAAAGGCAUGAU | 375 | T*fG*mCm5Ceo*mAfC*mUfG*mUfA*mGfA*mAfA *mGfGmCfAmUfGmA*T*mU | XXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6664 | TGCCACUGUAGAAAGGGCAUGAU | 376 | T*fG*mCfC*AeofC*mUfG*mUfA*mGfA*mAfA*mGfGmCfAmUfGmA*T*mU | XXOXOXOXOXOXOXOXOOOOOOXX |
| WV-6665 | TGCCACUGUAGAAAGGGCAUGAU | 377 | T*fG*mCfC*mAn5Ceo*mUfG*mUfA*mGfA*mAfA*mGfGmCfAmUfGmA*T*mU | XXOXOXOXOXOXOXOXOOOOOOXX |
| WV-6666 | TGCCACTGUAGAAAGGGCAUGAU | 378 | T*fG*mCfC*mAfC*TeofG*mUfA*mGfA*mAfA*mGfGmCfAmUfGmA*T*mU | XXOXOXOXOXOXOXOXOOOOOOXX |
| WV-6667 | TGCCACUGUAGAAAGGGCAUGAU | 379 | T*fG*mCfC*mAfC*mUGeo*mUfA*mGfA*mAfA*mGfGmCfAmUfGmA*T*mU | XXOXOXOXOXOXOXOXOOOOOOXX |
| WV-6668 | TGCCACUGUAGAAAGGGCAUGAU | 380 | T*fG*mCfC*mAfC*mUfG*TeofA*mGfA*mAfA*mGfGmCfAmUfGmA*T*mU | XXOXOXOXOXOXOXOXOOOOOOXX |
| WV-6669 | TGCCACUGUAGAAAGGGCAUGAU | 381 | T*fG*mCfC*mAfC*mUfG*mUAeo*mGfA*mAfA*mGfGmCfAmUfGmA*T*mU | XXOXOXOXOXOXOXOXOOOOOOXX |
| WV-6670 | TGCCACUGUAGAAAGGGCAUGAU | 382 | T*fG*mCfC*mAfC*mUfG*mUfA*GeofA*mAfA*mGfGmCfAmUfGmA*T*mU | XXOXOXOXOXOXOXOXOOOOOOXX |
| WV-6671 | TGCCACUGUAGAAAGGGCAUGAU | 383 | T*fG*mCfC*mAfC*mUfG*mUfA*mGAeo*mAfA*mGfGmCfAmUfGmA*T*mU | XXOXOXOXOXOXOXOXOOOOOOXX |
| WV-6672 | TGCCACUGUAGAAAGGGCAUGAU | 384 | T*fG*mCfC*mAfC*mUfG*mUfA*mGfA*Aeofa*mGfGmCfAmUfGmA*T*mU | XXOXOXOXOXOXOXOXOOOOOOXX |
| WV-6673 | TGCCACUGUAGAAAGGGCAUGAU | 385 | T*fG*mCfC*mAfC*mUfG*mUfA*mGfA*mAAeo*mGfGmCfAmUfGmA*T*mU | XXOXOXOXOXOXOXOXOOOOOOXX |
| WV-6674 | TGCCACUGUAGAAAGGGCAUGAU | 386 | T*fG*mCfC*mAfC*mUfG*mUfA*mGfA*mAfA*GeofGmCfAmUfGmA*T*mU | XXOXOXOXOXOXOXOXOOOOOOXX |
| WV-6675 | TGCCACUGUAGAAAGGGCAUGAU | 387 | T*fG*mCfC*mAfC*mUfG*mUfA*mGfA*mAfA*mGeomCfAmUfGmA*T*mU | XXOXOXOXOXOXOXOXOOOOOOXX |
| WV-6676 | TGCCACUGUAGAAAGGGCAUGAU | 388 | T*fG*mCfC*mAfC*mUfG*mUfA*mGfA*mAfA*mGfGm5CeofAmUfGmA*T*mU | XXOXOXOXOXOXOXOXOOOOOOXX |
| WV-6677 | TGCCACUGUAGAAAGGGCAUGAU | 389 | T*fG*mCfC*mAfC*mUfG*mUfA*mGfA*mAfA*mGfGmCAeomUfGmA*T*mU | XXOXOXOXOXOXOXOXOOOOOOXX |
| WV-6678 | TGCCACUGUAGAAAGGGCAUGAU | 390 | T*fG*mCfC*mAfC*mUfG*mUfA*mGfA*mAfA*mGfGmCfATeofGmA*T*mU | XXOXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6679 | TGCCACUGUAGAAAGGCAUGAU | 391 | T*fG*mCfC*mAfC*mUfG*mUfA*mGfA*mAfA*mGfGmCfAmUGeomA*T*mU | XXOXOXOXOXOXOXOOOOOOXX |
| WV-6680 | TGCCACUGUAGAAAGGCAUGAU | 392 | T*fG*mCfC*mAfC*mUfG*mUfA*mGfA*mAfA*mGfGmCfAmUfGAeo*T*mU | XXOXOXOXOXOXOXOOOOOOXX |
| WV-6681 | TGCCACUGUAGAAAGGCAUGAU | 393 | T*fG*m5Ceofc*Aeofc*mUfG*mUfA*mGfA*mAfA*mGfGmCfAmUfGmA*T*mU | XXOXOXOXOXOXOXOOOOOOXX |
| WV-6682 | TGCCACUGUAGAAAGGCAUGAU | 394 | T*fG*mCfC*AeofC*TeofG*mUfA*mGfA*mAfA*mGfGmCfAmUfGmA*T*mU | XXOXOXOXOXOXOXOOOOOOXX |
| WV-6683 | TGCCACUGUAGAAAGGCAUGAU | 395 | T*fG*m5CeofC*mAfC*TeofG*mUfA*mGfA*mAfA*mGfGmCfAmUfGmA*T*mU | XXOXOXOXOXOXOXOOOOOOXX |
| WV-6684 | TGCCACUGUAGAAAGGCAUGAU | 396 | T*fG*m5CeofC*AeofC*TeofG*mUfA*mGfA*mAfA*mGfGmCfAmUfGmA*T*mU | XXOXOXOXOXOXOXOOOOOOXX |
| WV-6685 | TGCCACUGUAGAAAGGCAUGAU | 397 | Teo*fG*mCfC*mAfC*mUfG*mUfA*mGfA*mAfA*mGfGmCfAmUfGmA*T*mU | XXOXOXOXOXOXOXOOOOOOXX |
| WV-6686 | AGCCACUGUAGAAAGGCAUGAU | 398 | Aeo*fG*mCfC*mAfC*mUfG*mUfA*mGfA*mAfA*mGfGmCfAmUfGmA*T*mU | XXOXOXOXOXOXOXOOOOOOXX |
| WV-6687 | GGCCACUGUAGAAAGGCAUGAU | 399 | Geo*fG*mCfC*mAfC*mUfG*mUfA*mGfA*mAfA*mGfGmCfAmUfGmA*T*mU | XXOXOXOXOXOXOXOOOOOOXX |
| WV-6688 | CGCCACUGUAGAAAGGCAUGAU | 400 | m5Ceo*fG*mCfC*mAfC*mUfG*mUfA*mGfA*mAfA*mGfGmCfAmUfGmA*T*mU | XXOXOXOXOXOXOXOOOOOOXX |
| WV-6689 | TGCCACUGUAGAAAGGCAUGAU | 401 | T*fG*mCfC*mAfC*mUfG*mUfA*mGfA*mAfA*mGfGmCfAmUfGmA*T*mU | XXOXOXOXOXOXOXOOOOOOXX |
| WV-6690 | TGCCACUGUAGAAAGGCAUGAU | 402 | T*fG*m5ICfC*mAfC*mUfG*mUfA*mGfA*mAfA*mGfGmCfAmUfGmA*T*mU | XXOXOXOXOXOXOXOOOOOOXX |
| WV-6691 | TGCCACUGUAGAAAGGCAUGAU | 403 | T*fG*mCm5IC*mAfC*mUfG*mUfA*mGfA*mAfA*mGfGmCfAmUfGmA*T*mU | XXOXOXOXOXOXOXOOOOOOXX |
| WV-6692 | TGCCACUGUAGAAAGGCAUGAU | 404 | T*fG*mCfC*IAfC*mUfG*mUfA*mGfA*mAfA*mGfGmCfAmUfGmA*T*mU | XXOXOXOXOXOXOXOOOOOOXX |
| WV-6693 | TGCCACUGUAGAAAGGCAUGAU | 405 | T*fG*mCfC*mAm5IC*mUfG*mUfA*mGfA*mAfA*mGfGmCfAmUfGmA*T*mU | XXOXOXOXOXOXOXOOOOOOXX |
| WV-6694 | TGCCACUGUAGAAAGGCAUGAU | 406 | T*fG*mCfC*mAfC*ITfG*mUfA*mGfA*mAfA*mGfGmCfAmUfGmA*T*mU | XXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6695 | TGCCACUGUAGAAAGGCAUGAU | 407 | T*fG*mCfC*mAfC*mUfG*mUfA*mGfA*mAfA*mGfGmCfAmUfGmA*T*mU | XXOXOXOXOXOXOXOXOOOOOOXX |
| WV-6696 | TGCCACUGUAGAAAGGCAUGAU | 408 | T*fG*mCfC*mAfC*mUfG*ITfA*mGfA*mAfA*mGfGmCfAmUfGmA*T*mU | XXOXOXOXOXOXOXOXOOOOOOXX |
| WV-6697 | TGCCACUGUAGAAAGGCAUGAU | 409 | T*fG*mCfC*mAfC*mUfG*mUfA*mGfA*mAfA*mGfGmCfAmUfGmA*T*mU | XXOXOXOXOXOXOXOXOOOOOOXX |
| WV-6698 | TGCCACUGUAGAAAGGCAUGAU | 410 | T*fG*mCfC*mAfC*mUfG*mUfA*IGfA*mAfA*mGfGmCfAmUfGmA*T*mU | XXOXOXOXOXOXOXOXOOOOOOXX |
| WV-6699 | TGCCACUGUAGAAAGGCAUGAU | 411 | T*fG*mCfC*mAfC*mUfG*mUfA*mGfA*mAfA*mGfGmCfAmUfGmA*T*mU | XXOXOXOXOXOXOXOXOOOOOOXX |
| WV-6700 | TGCCACUGUAGAAAGGCAUGAU | 412 | T*fG*mCfC*mAfC*mUfG*mUfA*mGfA*IAfA*mGfGmCfAmUfGmA*T*mU | XXOXOXOXOXOXOXOXOOOOOOXX |
| WV-6701 | TGCCACUGUAGAAAGGCAUGAU | 413 | T*fG*mCfC*mAfC*mUfG*mUfA*mGfA*mAIA*mGfGmCfAmUfGmA*T*mU | XXOXOXOXOXOXOXOXOOOOOOXX |
| WV-6702 | TGCCACUGUAGAAAGGCAUGAU | 414 | T*fG*mCfC*mAfC*mUfG*mUfA*mGfA*mAfA*IGfGmCfAmUfGmA*T*mU | XXOXOXOXOXOXOXOXOOOOOOXX |
| WV-6703 | TGCCACUGUAGAAAGGCAUGAU | 415 | T*fG*mCfC*mAfC*mUfG*mUfA*mGfA*mAfA*mGIGmCfAmUfGmA*T*mU | XXOXOXOXOXOXOXOXOOOOOOXX |
| WV-6704 | TGCCACUGUAGAAAGGCAUGAU | 416 | T*fG*mCfC*mAfC*mUfG*mUfA*mGfA*mAfA*mGfGm5ICfAmUfGmA*T*mU | XXOXOXOXOXOXOXOXOOOOOOXX |
| WV-6705 | TGCCACUGUAGAAAGGCAUGAU | 417 | T*fG*mCfC*mAfC*mUfG*mUfA*mGfA*mAfA*mGfGmCIAmUfGmA*T*mU | XXOXOXOXOXOXOXOXOOOOOOXX |
| WV-6706 | TGCCACUGUAGAAAGGCAUGAU | 418 | T*fG*mCfC*mAfC*mUfG*mUfA*mGfA*mAfA*mGfGmCfAITfGmA*T*mU | XXOXOXOXOXOXOXOXOOOOOOXX |
| WV-6707 | TGCCACUGUAGAAAGGCAUGAU | 419 | T*fG*mCfC*mAfC*mUfG*mUfA*mGfA*mAfA*mGfGmCfAmUIGmA*T*mU | XXOXOXOXOXOXOXOXOOOOOOXX |
| WV-6708 | TGCCACUGUAGAAAGGCAUGAU | 420 | T*fG*mCfC*mAfC*mUfG*mUfA*mGfA*mAfA*mGfGmCfAmUfGIA*T*mU | XXOXOXOXOXOXOXOXOOOOOOXX |
| WV-6709 | TGCCACUGUAGAAAGGCAUGAU | 421 | IT*fG*mCfC*mAfC*mUfG*mUfA*mGfA*mAfA*mGfGmCfAmUfGmA*T*mU | XXOXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6710 | AGCCACUGUAGAAAGGCAUGAU | 422 | IA*fG*mCfC*mAfC*IAfC*mUfG*mUfA*mGfA*mAfA* mGfGmCfAmUfGmA*T*mU | XXOXOXOXOXOXOXOOOOOOXX |
| WV-6711 | GGCCACUGUAGAAAGGCAUGAU | 423 | IG*fG*mCfC*mAfC*IAfC*mUfG*mUfA*mGfA*mAfA* mGfGmCfAmUfGmA*T*mU | XXOXOXOXOXOXOXOOOOOOXX |
| WV-6712 | CGCCACUGUAGAAAGGCAUGAU | 424 | m5IC*fG*mCfC*mAfC*IAfC*mUfG*mUfA*mGfA*mAfA* mGfGmCfAmUfGmA*T*mU | XXOXOXOXOXOXOXOOOOOOXX |
| WV-6713 | TGCCACUGUAGAAAGGCAUGAU | 425 | T*fG*m5ICfC*IAfC*mUfG*mUfA*mGfA*mAfA* mGfGmCfAmUfGmA*T*mU | XXOXOXOXOXOXOXOOOOOOXX |
| WV-6714 | TGCCACTGUAGAAAGGCAUGAU | 426 | T*fG*mCfC*IAfC*ITfG*mUfA*mGfA*mAfA* mGfGmCfAmUfGmA*T*mU | XXOXOXOXOXOXOXOOOOOOXX |
| WV-6715 | TGCCACTGUAGAAAGGCAUGAU | 427 | T*fG*m5ICfC*mAfC*ITfG*mUfA*mGfA*mAfA* mGfGmCfAmUfGmA*T*mU | XXOXOXOXOXOXOXOOOOOOXX |
| WV-6716 | TGCCACUGUAGAAAGGCAUGAU | 428 | T*fG*m5ICfC*IAfC*ITfG*mUfA*mGfA*mAfA* mGfGmCfAmUfGmA*T*mU | XXOXOXOXOXOXOXOOOOOOXX |
| WV-6717 | TGCCACUGUAGAAAGGCAUGAU | 429 | T*G*mCfC*mAfC*mUfG*mUfA*mGfA*mAfA* mGfGmCfAmUfGmA*T*mU | XXOXOXOXOXOXOXOOOOOOXX |
| WV-6718 | TGCCACUGUAGAAAGGCAUGAU | 430 | T*fG*CfC*mAfC*mUfG*mUfA*mGfA*mAfA* mGfGmCfAmUfGmA*T*mU | XXOXOXOXOXOXOXOOOOOOXX |
| WV-6719 | TGCCACUGUAGAAAGGCAUGAU | 431 | T*fG*mCfC*AfC*mUfG*mUfA*mGfA*mAfA* mGfGmCfAmUfGmA*T*mU | XXOXOXOXOXOXOXOOOOOOXX |
| WV-6720 | TGCCACTGUAGAAAGGCAUGAU | 432 | T*fG*mCfC*mAfC*TfG*mUfA*mGfA*mAfA* mGfGmCfAmUfGmA*T*mU | XXOXOXOXOXOXOXOOOOOOXX |
| WV-6721 | TGCCACUGUAGAAAGGCAUGAU | 433 | T*fG*mCfC*mAfC*mUfG*TfA*mGfA*mAfA* mGfGmCfAmUfGmA*T*mU | XXOXOXOXOXOXOXOOOOOOXX |
| WV-6722 | TGCCACUGUAGAAAGGCAUGAU | 434 | T*fG*mCfC*mAfC*mUfG*mUA*mGfA*mAfA* mGfGmCfAmUfGmA*T*mU | XXOXOXOXOXOXOXOOOOOOXX |
| WV-6723 | TGCCACUGUAGAAAGGCAUGAU | 435 | T*fG*mCfC*mAfC*mUfG*mUfA*GfA*mAfA* mGfGmCfAmUfGmA*T*mU | XXOXOXOXOXOXOXOOOOOOXX |
| WV-6724 | TGCCACUGUAGAAAGGCAUGAU | 436 | T*fG*mCfC*mAfC*mUfG*mUfA*mGA*mAfA* mGfGmCfAmUfGmA*T*mU | XXOXOXOXOXOXOXOOOOOOXX |
| WV-6725 | TGCCACUGUAGAAAGGCAUGAU | 437 | T*fG*mCfC*mAfC*mUfG*mUfA*mGfA*AfA* mGfGmCfAmUfGmA*T*mU | XXOXOXOXOXOXOXOOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6726 | TGCCACUGUAGAAAGGCAUGAT U | 438 | T*fG*mCfC*mAfC*mUfG*mUfA*mGfA*mAA* mGfGmCfAmUfGmA*T*mU | XXOXOXOXOXOXOXOXOOOOOOX X |
| WV-6727 | TGCCACUGUAGAAAGGCAUGAT U | 439 | T*fG*mCfC*mAfC*mUfG*mUfA*mGfA*mAfA* GfGmCfAmUfGmA*T*mU | XXOXOXOXOXOXOXOXOOOOOOX X |
| WV-6728 | TGCCACUGUAGAAAGGCAUGAT U | 440 | T*fG*mCfC*mAfC*mUfG*mUfA*mGfA*mAfA* mGGmCfAmUfGmA*T*mU | XXOXOXOXOXOXOXOXOOOOOOX X |
| WV-6729 | TGCCACUGUAGAAAGGCAUGAT U | 441 | T*fG*mCfC*mAfC*mUfG*mUfA*mGfA*mAfA* mGfGCfAmUfGmA*T*mU | XXOXOXOXOXOXOXOXOOOOOOX X |
| WV-6730 | TGCCACUGUAGAAAGGCAUGAT U | 442 | T*fG*mCfC*mAfC*mUfG*mUfA*mGfA*mAfA* mGfGmCAmUfGmA*T*mU | XXOXOXOXOXOXOXOXOOOOOOX X |
| WV-6731 | TGCCACUGUAGAAAGGCAUGAT U | 443 | T*fG*mCfC*mAfC*mUfG*mUfA*mGfA*mAfA* mGfGmCfATfGmA*T*mU | XXOXOXOXOXOXOXOXOOOOOOX X |
| WV-6732 | TGCCACUGUAGAAAGGCAUGAT U | 444 | T*fG*mCfC*mAfC*mUfG*mUfA*mGfA*mAfA* mGfGmCfAmUGmA*T*mU | XXOXOXOXOXOXOXOXOOOOOOX X |
| WV-6733 | TGCCACUGUAGAAAGGCAUGAT U | 445 | T*fG*mCfC*mAfC*mUfG*mUfA*mGfA*mAfA* mGfGmCfAmUfGA*T*mU | XXOXOXOXOXOXOXOXOOOOOOX X |
| WV-6734 | AGCCACUGUAGAAAGGCAUGAT U | 446 | A*fG*mCfC*mAfC*mUfG*mUfA*mGfA*mAfA* mGfGmCfAmUfGmA*T*mU | XXOXOXOXOXOXOXOXOOOOOOX X |
| WV-6735 | GGCCACUGUAGAAAGGCAUGAT U | 447 | G*fG*mCfC*mAfC*mUfG*mUfA*mGfA*mAfA* mGfGmCfAmUfGmA*T*mU | XXOXOXOXOXOXOXOXOOOOOOX X |
| WV-6736 | CGCCACUGUAGAAAGGCAUGAT U | 448 | C*fG*mCfC*mAfC*mUfG*mUfA*mGfA*mAfA* mGfGmCfAmUfGmA*T*mU | XXOXOXOXOXOXOXOXOOOOOOX X |
| WV-6737 | TGCCACUGUAGAAAGGCAUGAT U | 449 | T*fG*mCfC*AfC*mUfG*mUfA*mGfA*mAfA* mGfGmCfAmUfGmA*T*mU | XXOXOXOXOXOXOXOXOOOOOOX X |
| WV-6738 | TGCCACUGUAGAAAGGCAUGAT U | 450 | T*fG*mCfC*AfC*TfG*mUfA*mGfA*mAfA* mGfGmCfAmUfGmA*T*mU | XXOXOXOXOXOXOXOXOOOOOOX X |
| WV-6739 | TGCCACTGUAGAAAGGCAUGAT U | 451 | T*fG*CfC*mAfC*TfG*mUfA*mGfA*mAfA* mGfGmCfAmUfGmA*T*mU | XXOXOXOXOXOXOXOXOOOOOOX X |
| WV-6740 | TGCCACTGUAGAAAGGCAUGAT U | 452 | T*fG*CfC*AfC*TfG*mUfA*mGfA*mAfA* mGfGmCfAmUfGmA*T*mU | XXOXOXOXOXOXOXOXOOOOOOX X |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6741 | TGCCACUGUAGAAAGGCAUGAU | 453 | T*fG*mCfC*mAfC*mUfG*mUfA*mGfA*mAfA*mGfGmCA*T*G*A*T*mU | XXXOXOXOXOXOXOOOXXXX |
| WV-6742 | TGCCACUGUAGAAAGGCAUGAU | 454 | T*fG*mCfC*mAfC*mUfG*mUfA*mGfA*mAfA*G*mGfGmCA*T*G*A*T*mU | XXXOXOXOXOXOXOXXXXXXX |
| WV-6743 | TGUCACUGUAGAAAGGCAUGAU | 455 | T*fG*mUfC*mAfC*mUfG*mUfA*mGfA*mAfA*mGfGmCfAmUfGmA*T*mU | XXXOXOXOXOXOXOOOOOOOX |
| WV-6744 | TGCUACUGUAGAAAGGCAUGAU | 456 | T*fG*mCfU*mAfC*mUfG*mUfA*mGfA*mAfA*mGfGmCfAmUfGmA*T*mU | XXXOXOXOXOXOXOOOOOOOX |
| WV-6745 | TGCCCGCUGUAGAAAGGCAUGAU | 457 | T*fG*mCfC*mGfC*mUfG*mUfA*mGfA*mAfA*mGfGmCfAmUfGmA*T*mU | XXXOXOXOXOXOXOOOOOOOX |
| WV-6746 | TGCCAUUGUAGAAAGGCAUGAU | 458 | T*fG*mCfC*mAfU*mUfG*mUfA*mGfA*mAfA*mGfGmCfAmUfGmA*T*mU | XXXOXOXOXOXOXOOOOOOOX |
| WV-6747 | TGCCACUGUGGAAAGGCAUGAU | 459 | T*fG*mCfC*mAfC*mUfG*mUfG*mGfA*mAfA*mGfGmCfAmUfGmA*T*mU | XXXOXOXOXOXOXOOOOOOOX |
| WV-6748 | TGCCACUGUAGAAGGCAUGAU | 460 | T*fG*mCfC*mAfC*mUfG*mUfA*mGfA*mAfG*mGfGmCfAmUfGmA*T*mU | XXXOXOXOXOXOXOOOOOOOX |
| WV-6749 | TGCCACUGUAGAGGGCAUGAU | 461 | T*fG*mCfC*mAfC*mUfG*mUfA*mGfA*mGfG*mGfGmCfAmUfGmA*T*mU | XXXOXOXOXOXOXOOOOOOOX |
| WV-6750 | TGCCACUGUAGAAAGGCAUGAU | 462 | T*fG*mCfC*mAfC*mUfG*mUfA*mGfA*mAfA*mGfGmCfAmUfGmA*T*mU | XXXOXOXOXOXOXOOOOOOOX |
| WV-6751 | TGCCACUGUAGAAAGGCAUGAU | 463 | T*fG*mCfC*mAfC*mUfG*mUfA*mGfA*mAfA*mAfG*mGfGmCfAmUfGmA*T*mU | XXXOXOXOXOXOXOOOOOOOX |
| WV-6752 | TGCCACUGUAGAAAGGCGUGAU | 464 | T*fG*mCfC*mAfC*mUfG*mUfA*mGfA*mAfA*mGfGmCfGmUfGmA*T*mU | XXXOXOXOXOXOXOOOOOOOX |
| WV-6753 | TGCCACUGUAGAAAGGCAUGGU | 465 | T*fG*mCfC*mAfC*mUfG*mUfA*mGfA*mAfA*mGfGmCfAmUfGmG*T*mU | XXXOXOXOXOXOXOOOOOOOX |
| WV-6818 | ACCUGAGGAUGGACCGCGGG | 466 | mA*mC*mC*mU*mG*A*G*A*T*G*A*C*C*mG*mC*mG*mG*mG | XXXXXXXXXXXXXXXXXXXX |
| WV-6819 | ACCUGAGGAUGGACCGCGGG | 467 | Aeo*m5Ceo*m5Ceo*Teo*Geo*A*G*G*A*T*G*G*A*C*C*Geo*m5Ceo*Geo*Geo*Geo | XXXXXXXXXXXXXXXXXXXX |
| WV-6820 | GGACCUGAGGAUGGACCGCG | 468 | mG*mG*mA*mC*mC*T*G*A*G*G*A*T*G*G*A*mC*mC*mG*mC*mG | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-6821 | GGACCTGAGGATGGACCGCG | 469 | Geo*Geo*Aeo*m5Ceo*m5Ceo*T*G*A*G*A*T*G*A*m5Ceo*m5Ceo*Geo*m5Ceo*Geo | XXXXXXXXXXXXXXXXXXXX |
| WV-6822 | ACCTGAGGATGGACCGCGGG | 470 | Mod001L001mA*mC*mC*mU*mG*A*G*A*T*G*G*A*C*C*mG*mC*mG*mG | OXXXXXXXXXXXXXXXXXXX |
| WV-6823 | ACCTGAGGATGGACCGCGGG | 471 | Mod001L001Aeo*m5Ceo*m5Ceo*Teo*Geo*A*G*G*A*T*G*G*A*C*C*Geo*m5Ceo*Geo*Geo*Geo | OXXXXXXXXXXXXXXXXXXX |
| WV-6824 | GGACCTGAGGATGGACCGCG | 472 | Mod001L001mG*mG*mA*mC*mC*T*G*A*G*G*A*T*G*G*A*m5Ceo*m5Ceo*Geo*m5Ceo*Geo*Geo | OXXXXXXXXXXXXXXXXXXX |
| WV-6825 | ACCTGAGGATGGACCGCGGG | 473 | Mod001L001Geo*Aeo*m5Ceo*m5Ceo*T*G*A*G*G*A*T*G*G*A*m5Ceo*m5Ceo*Geo*m5Ceo*Geo | OXXXXXXXXXXXXXXXXXXX |
| WV-7113 | ACCTGAGGATGGACCGCGGG | 474 | L001mA*mC*mC*mU*mG*A*G*A*T*G*G*A*C*C*mG*mC*mG*mG | OXXXXXXXXXXXXXXXXXXX |
| WV-7114 | ACCTGAGGATGGACCGCGGG | 475 | L001Aeo*m5Ceo*m5Ceo*Teo*Geo*A*G*G*A*T*G*G*A*C*C*Geo*m5Ceo*Geo*Geo*Geo | OXXXXXXXXXXXXXXXXXXX |
| WV-7115 | GGACCTGAGGATGGACCGCG | 476 | L001mG*mG*mA*mC*mC*T*G*A*G*G*A*T*G*G*A*m5Ceo*m5Ceo*Geo*m5Ceo*Geo*Geo | OXXXXXXXXXXXXXXXXXXX |
| WV-7116 | GGACCTGAGGATGGACCGCG | 477 | L001Geo*Geo*Aeo*m5Ceo*m5Ceo*T*G*A*G*G*A*T*G*G*A*m5Ceo*m5Ceo*Geo*m5Ceo*Geo | OXXXXXXXXXXXXXXXXXXX |
| WV-7316 | TGCCACUGUAGAAAGGCAUGAU | 478 | T*fG*mCfC*mAfC*mU*fG*mU*fA*mGfA*mAfA*mGfGmC*fAmU*fGmA*T*mU | XXXOXOXXXXOXOXOOXOXOXX |
| WV-7317 | TGCCACUGUAGAAAGGCAUGAU | 479 | VPT*fG*mCfC*mAfC*mU*fG*mU*fA*mGfA*mAfA*mGfGmC*fAmU*fGmA*T*mU | XXXOXOXXXXOXOXOOXOXOXX |
| WV-7403 | CCCCCAGGCA GGAGCCAAGCACAGCAG | 480 | rCrCrCrCrCrArGrGrCrArGrGrArGrCrCrArArGrCrArCrArGrCrArG | OOOOOOOOOO OOOOOOOOOOOOOOOO |
| WV-7462 | TGCCACUGUAGAAAGGCAUGAU | 481 | T*fG*mCfC*mAfC*mU*fG*mU*fA*mGfA*mAfA*mGfGmC*fAmUfGmA*T*mU | XXXOXOXXXXOXOXOOOOOXOXX |
| WV-7463 | TGCCACUGUAGAAAGGCAUGAU | 482 | T*fG*mCfC*mAfC*mUfG*mU*fA*mGfA*mAfA*mGfGmC*fAmU*fGmA*T*mU | XXXOXOXOXOXOXOXOXOXOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7464 | TGCCACUGUAGAAAGGCAUGAU | 483 | T*SfG*SmCfC*SmAfC*SmUfG*SmUfA*SmGfA*SmAfA*SmGfGmCfAmUfGmA*ST*SmU | SSOSOSOSOSOSO-SOOOOOSS |
| WV-7465 U | TGCCACUGUAGAAAGGCAUGAU | 484 | T*SfG*SmCfC*SmAfC*SmUfG*SmUfA*SmGfA*SmAfA*SmG*SfG*SmC*SfA*SmU*SfG*SmA*ST*SmU | SSOSOSOSOSOSOSSSSSSSS |
| WV-7466 U | TGCCACUGUAGAAAGGCAUGAU | 485 | T*SfG*SmCfC*SmAfC*SmUfG*SmU*SfA*SmGfA*SmAfA*SmGfGmC*SfAmU*SfGmA*ST*SmU | SSOSOSSSSOSO-SOOSOSOSS |
| WV-7467 U | TGCCACUGUAGAAAGGCAUGAU | 486 | T*SfG*SmCfC*SmAfC*SmUfG*SmU*SfA*SmGfA*SmAfA*SmGfGmCfAmUfGmA*ST*SmU | SSOSOSSSSOSO-SOOOOOSS |
| WV-7468 U | TGCCACUGUAGAAAGGCAUGAU | 487 | T*SfG*SmCfC*SmAfC*SmUfG*SmUfA*SmGfA*SmAfA*SmGfGmC*SfAmU*SfGmA*ST*SmU | SSOSOSOSOSOSO-SOOSOSSS |
| WV-7469 U | TGCCACUGUAGAAAGGCAUGAU | 488 | T*SfG*mCfC*mAfC*mUfG*mUfA*mGfA*mAfA*mGfGmCfAmUfGmA*T*SmU | SXOXOXOXOXOXOOOOOOXS |
| WV-7470 U | TGCCACUGUAGAAAGGCAUGAU | 489 | T*SfG*SmCfC*mAfC*mUfG*mUfA*mGfA*mAfA*mGfGmCfAmUfGmA*T*SmU | SSOXOXOXOXOXOXOOOOOOXS |
| WV-7471 U | TGCCACUGUAGAAAGGCAUGAU | 490 | T*SfG*mC*SfC*mAfC*mUfG*mUfA*mGfA*mAfA*mGfGmCfAmUfGmA*T*SmU | SXSXOXOXOXOXOXOOOOOOXS |
| WV-7472 U | TGCCACUGUAGAAAGGCAUGAU | 491 | T*SfG*mCfC*mAfC*mUfG*mUfA*mGfA*mAfA*mGfGmCfAmUfGmA*T*SmU | SXOXOXOXOXOXOXOOOOOOX |
| WV-7473 U | TGCCACUGUAGAAAGGCAUGAU | 492 | T*SfG*mCfC*mA*SfC*mUfG*mUfA*mGfA*mAfA*mGfGmCfAmUfGmA*T*SmU | SXOXSXOXOXOXOXOOOOOOXS |
| WV-7474 U | TGCCACUGUAGAAAGGCAUGAU | 493 | T*SfG*mCfC*mAfC*SmUfG*mUfA*mGfA*mAfA*mGfGmCfAmUfGmA*T*SmU | SXOXOXSXOXOXOXOOOOOOX |
| WV-7475 U | TGCCACUGUAGAAAGGCAUGAU | 494 | T*SfG*mCfC*mAfC*mU*SfG*mUfA*mGfA*mAfA*mGfGmCfAmUfGmA*T*SmU | SXOXOXOXSXOXOXOOOOOOX |
| WV-7476 U | TGCCACUGUAGAAAGGCAUGAU | 495 | T*SfG*mCfC*mAfC*mUfG*SmUfA*mGfA*mAfA*mGfGmCfAmUfGmA*T*SmU | SXOXOXOXOXOXOXOOOOOOX |
| WV-7477 U | TGCCACUGUAGAAAGGCAUGAU | 496 | T*SfG*mCfC*mAfC*mUfG*mU*SfA*mGfA*mAfA*mGfGmCfAmUfGmA*T*SmU | SXOXOXOXOXSXOXOOOOOOXS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7478 | TGCCACUGUAGAAAGGCAUGAT U | 497 | T*SfG*mCfC*mAfC*mUfG*mUfA*SmGfA*mAfA* mGfGmCfAmUfGmA*T*SmU | SXOXOXOXOSOXOXOOOOOXS |
| WV-7479 | TGCCACUGUAGAAAGGCAUGAT U | 498 | T*SfG*mCfC*mAfC*mUfG*mUfA*mG*SfA*mAfA* mGfGmCfAmUfGmA*T*SmU | SXOXOXOXSXOXOXOOOOOXS |
| WV-7480 | TGCCACUGUAGAAAGGCAUGAT U | 499 | T*SfG*mCfC*mAfC*mUfG*mUfA*mGfA*SmGfA* mGfGmCfAmUfGmA*T*SmU | SXOXOXOXOXSXOXOOOOOX S |
| WV-7481 | TGCCACUGUAGAAAGGCAUGAT U | 500 | T*SfG*mCfC*mAfC*mUfG*mUfA*mGfA*mA*SfA* mGfGmCfAmUfGmA*T*SmU | SXOXOXOXOXOXSXOOOOOXS |
| WV-7482 | TGCCACUGUAGAAAGGCAUGAT U | 501 | T*SfG*mCfC*mAfC*mUfG*mUfA*mGfA*mAfA* SmGfGmCfAmUfGmA*T*SmU | SXOXOXOXOXOXOSOOOOOX S |
| WV-7483 | TGCCACUGUAGAAAGGCAUGAT U | 502 | T*SfG*mCfC*mAfC*mUfG*mUfA*mGfA*mAfA* mG*SfGmCfAmUfGmA*T*SmU | SXOXOXOXOXOXOX-SOOOOOXS |
| WV-7484 | TGCCACUGUAGAAAGGCAUGAT U | 503 | T*SfG*mCfC*mAfC*mUfG*mUfA*mGfA*mAfA* mGfG*SmCfAmUfGmA*T*SmU | SXOXOXOXOXOXOXO-SOOOOXS |
| WV-7485 | TGCCACUGUAGAAAGGCAUGAT U | 504 | T*SfG*mCfC*mAfC*mUfG*mUfA*mGfA*mAfA* mGfGmC*SfAmUfGmA*T*SmU | SXOXOXOXOXOXOXOO-SOOOXS |
| WV-7486 | TGCCACUGUAGAAAGGCAUGAT U | 505 | T*SfG*mCfC*mAfC*mUfG*mUfA*mGfA*mAfA* mGfGmCfA*SmUfGmA*T*SmU | SXOXOXOXOXOXOXOOO-SOOXS |
| WV-7487 | TGCCACUGUAGAAAGGCAUGAT U | 506 | T*SfG*mCfC*mAfC*mUfG*mUfA*mGfA*mAfA* mGfGmCfAmU*SfGmA*T*SmU | SXOXOXOXOXOXOXOOOOSOXS |
| WV-7488 | TGCCACUGUAGAAAGGCAUGAT U | 507 | T*SfG*mCfC*mAfC*mUfG*mUfA*mGfA*mAfA* mGfGmCfAmUfG*SmA*T*SmU | SXOXOXOXOXOXOXOOOOOSXS |
| WV-7489 | TGCCACUGUAGAAAGGCAUGAT U | 508 | T*SfG*mCfC*mAfC*mUfG*mUfA*mGfA*mAfA* mGfGmCfAmUfGmA*ST*SmU | SXOXOXOXOXOXOXOOOOOOS S |
| WV-7509 | TGCCACUGUAGAAAGGCAUTU | 509 | T*SfG*SmCfC*SmAfC*SmUfG*SmUfA*SmGfA* SmAfA*SmGfGmCfAmU*ST*SmU | SSOSOSOSOSOSOSOOOOSS |
| WV-7510 | TGCCACUGUAGAAAGGCAUTU | 510 | T*SfG*SmCfC*SmAfC*SmUfG*SmUfA*SmGfA* SmAfA*SmGfGmC*SfAmU*ST*SmU | SSOSOSOSOSOSOSOSOSOSS |
| WV-7511 | TGCCACUGUAGAAAGGCAUTU | 511 | T*SfG*SmCfC*SmA*SfC*SmU*SfG*SmU*SfA* SmGfA*SmAfA*SmGfGmC*SfAmU*ST*SmU | SSOSSSSSSOSOSOSOSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7545 | TGCCACUGUAGAAUGGCAUUU | 512 | T*fG*mCfC*mAfC*mUfG*mUfA*mGfA*mAfU* mGfGmCfAmU*T*mU | XXOXOXOXOXOXOXOOOOXX |
| WV-7546 | TGCCACUGUAGAAACGCAUUU | 513 | T*fG*mCfC*mAfC*mUfG*mUfA*mGfA*mAfA* mCfGmCfAmU*T*mU | XXOXOXOXOXOXOXOOOOXX |
| WV-7547 | TGCCACUGUAGAAAGCCAUUU | 514 | T*fG*mCfC*mAfC*mUfG*mUfA*mGfA*mAfA* mGfCmCfAmU*T*mU | XXOXOXOXOXOXOXOOOOXX |
| WV-7548 | TGCCACUGUAGAAGGGAUUU | 515 | T*fG*mCfC*mAfC*mUfG*mUfA*mGfA*mAfA* mGfGmGfAmU*T*mU | XXOXOXOXOXOXOXOOOOXX |
| WV-7549 | TGCCACUGUAGAAAGGCUUUU | 516 | T*fG*mCfC*mAfC*mUfG*mUfA*mGfA*mAfA* mGfGmCfUmU*T*mU | XXOXOXOXOXOXOXOOOOXX |
| WV-7550 | TGCCACUGUAGAAAGGCAAUU | 517 | T*fG*mCfC*mAfC*mUfG*mUfA*mGfA*mAfA* mGfGmCfAmA*T*mU | XXOXOXOXOXOXOXOOOOXX |
| WV-7551 | TGCCACUGUAGAAACGCAUGAU | 518 | T*fG*mCfC*mAfC*mUfG*mUfA*mGfA*mAfA* mCfGmCfAmUfGmA*T*mU | XXOXOXOXOXOXOXOOOOOXX |
| WV-7552 | TGCCACUGUAGAAAGCCAUGAU | 519 | T*fG*mCfC*mAfC*mUfG*mUfA*mGfA*mAfA* mGfCmCfAmUfGmA*T*mU | XXOXOXOXOXOXOXOOOOOXX |
| WV-7553 | TGCCACUGUAGAAAGGCUUGAU | 520 | T*fG*mCfC*mAfC*mUfG*mUfA*mGfA*mAfA* mGfGmCfUmUfGmA*T*mU | XXOXOXOXOXOXOXOOOOOXX |
| WV-7554 | TGCCACUGUAGAAAGGCAAGAU | 521 | T*fG*mCfC*mAfC*mUfG*mUfA*mGfA*mAfA* mGfGmCfAmAfGmA*T*mU | XXOXOXOXOXOXOXOOOOOXX |
| WV-7555 | TGCCACUGUAGAAAGGCAUCAU | 522 | T*fG*mCfC*mAfC*mUfG*mUfA*mGfA*mAfA* mGfGmCfAmUfCmA*T*mU | XXOXOXOXOXOXOXOOOOOXX |
| WV-7556 | TGCCACUGUAGAAAGGCAUGUU | 523 | T*fG*mCfC*mAfC*mUfG*mUfA*mGfA*mAfA* mGfGmCfAmUfGmU*T*mU | XXOXOXOXOXOXOXOOOOOXX |
| WV-7576 | UGUGCUUGGCUCCUGCCUGG | 524 | Mod001L001mU*mG*mU*mG*mC*T*mG*C *T*C*C*T*G*mC*mC*mU*mG*mG | OXXXXXXXXXXXXXXXXXXX |
| WV-7577 | UCUUGUUACCCCCGCCAUGG | 525 | Mod001L001mU*mC*mU*mU*mG*T*T*A*C*C* C*C*m5C*G*C*mC*mA*mU*mG*mG | OXXXXXXXXXXXXXXXXXXX |
| WV-7578 | ACCCCCGCCAUGGAGACGUU | 526 | Mod001L001mA*mC*mC*mC*mC*mC*G*C*C* A*T*G*A*G*mA*mC*mG*mU*mU | OXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7579 | UACCCCCGCCAUGGAGACGU | 527 | Mod001L001mU*mA*mC*mC*mC*mC*G*C*C*A*T*G*G*A*mG*mA*mC*mG*mU | OXXXXXXXXXXXXXXXXXXX |
| WV-7580 | CUGCACUGGGCUUCCUGGUG | 528 | Mod001L001mC*mU*mG*mC*mA*C*T*G*G*G*C*T*T*C*C*mU*mG*mG*mU*mG | OXXXXXXXXXXXXXXXXXXX |
| WV-7581 | UGGACCUGAGGAUGACCGC | 529 | Mod001L001mU*mG*mG*mA*mC*C*T*G*A*G*G*A*T*G*mA*mC*mC*mG*mC | OXXXXXXXXXXXXXXXXXXX |
| WV-7582 | AGGGACCCUCUGCACUGGGC | 530 | Mod001L001mA*mG*mG*mG*mA*C*C*C*T*C*T*G*C*A*C*mU*mG*mG*mG*mC | OXXXXXXXXXXXXXXXXXXX |
| WV-7583 | CUUGUTACCCCGCCAUGGA | 531 | Mod001L001mC*mU*mU*mG*mU*T*A*C*C*C*C*m5C*G*C*C*mA*mU*mG*mG*mA | OXXXXXXXXXXXXXXXXXXX |
| WV-7584 | AGGCUGGAUCCUCCACGUC | 532 | Mod001L001mA*mG*mG*mC*mU*G*G*A*T*C*C*T*C*C*mA*mC*mG*mU*mC | OXXXXXXXXXXXXXXXXXXX |
| WV-7585 | AAGGGACCCUCUGCACUGGG | 533 | Mod001L001mA*mA*mG*mG*mG*A*C*C*C*T*C*T*G*C*A*mC*mU*mG*mG*mG | OXXXXXXXXXXXXXXXXXXX |
| WV-7586 | TGTGCUUGGCUCCUGCCUGG | 534 | Mod001L001Teo*Geo*Teo*Geo*m5Ceo*T*T*G*G*C*T*C*C*T*G*m5Ceo*m5Ceo*Teo*Geo*Geo | OXXXXXXXXXXXXXXXXXXX |
| WV-7587 | TCTTGTTACCCCGCCATGG | 535 | Mod001L001Teo*m5Ceo*Teo*Teo*Geo*T*T*A*C*C*C*C*m5C*G*C*m5Ceo*Aeo*Teo*Geo*Geo | OXXXXXXXXXXXXXXXXXXX |
| WV-7588 | ACCCCCGCCATGGAGACGTT | 536 | Mod001L001Aeo*m5Ceo*m5Ceo*m5Ceo*m5Ceo*m5Ceo*G*C*C*A*T*G*G*A*G*A*m5Ceo*Geo*Teo*Teo | OXXXXXXXXXXXXXXXXXXX |
| WV-7589 | TACCCCCGCCATGGAGACGT | 537 | Mod001L001Teo*Aeo*m5Ceo*m5Ceo*m5Ceo*m5Ceo*m5Ceo*G*C*C*A*T*G*G*A*G*A*m5Ceo*Geo*Teo | OXXXXXXXXXXXXXXXXXXX |
| WV-7590 | CTGCACTGGGCTTCCTGGTG | 538 | Mod001L001m5Ceo*Teo*Geo*m5Ceo*Aeo*C*T*G*G*G*C*T*T*C*C*Teo*Geo*Geo*Teo*Geo | OXXXXXXXXXXXXXXXXXXX |
| WV-7591 | TGGACCTGAGGATGACCGC | 539 | Mod001L001Teo*Geo*Geo*Aeo*m5Ceo*C*T*G*A*G*G*A*T*G*A*Aeo*m5Ceo*m5Ceo*Geo*m5Ceo | OXXXXXXXXXXXXXXXXXXX |
| WV-7592 | AGGGACCCTCTGCACTGGGC | 540 | Mod001L001Aeo*Geo*Geo*Geo*Aeo*C*C*C*T*C*T*G*C*A*C*Teo*Geo*Geo*Geo*m5Ceo | OXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7593 | CTTGTTACCCCGCCATGGA | 541 | Mod001L001m5Ceo*Teo*Teo*Geo*Teo*T*A*C*C*C*m5C*G*C*C*Aeo*Teo*Geo*Aeo | OXXXXXXXXXXXXXXXXXX |
| WV-7594 | AGGCTGGGATCCTCCACGTC | 542 | Mod001L001Aeo*Geo*Geo*m5Ceo*Teo*G*G*G*A*T*C*C*T*C*C*Aeo*m5Ceo*Geo*Teo*m5Ceo | OXXXXXXXXXXXXXXXXXXX |
| WV-7595 | AAGGGACCCTCTGCACTGGG | 543 | Mod001L001Aeo*Aeo*Geo*Geo*Geo*A*C*C*C*T*C*T*G*C*A*m5Ceo*Teo*Geo*Geo*Geo | OXXXXXXXXXXXXXXXXXXX |
| WV-7615 | UGUGCTTGGCTCCTGCCUGG | 544 | L001mU*mG*mU*mG*mC*mT*T*G*C*T*C*C*T*G*mC*mC*mU*mG*mG | OXXXXXXXXXXXXXXXXXX |
| WV-7616 | UCUUGTTACCCCGCCAUGG | 545 | L001mU*mC*mU*mU*mG*T*T*A*C*C*C*C*m5C*G*C*mC*mA*mU*mG*mG | OXXXXXXXXXXXXXXXXXX |
| WV-7617 | ACCCCGCCATGGAGACGUU | 546 | L001mA*mC*mC*mC*mC*m5C*G*C*C*A*T*G*G*A*G*mA*mC*mG*mU*mU | OXXXXXXXXXXXXXXXXXX |
| WV-7618 | UACCCCGCCATGGAGACGU | 547 | L001mU*mA*mC*mC*mC*C*m5C*G*C*C*A*T*G*G*A*mG*mA*mC*mG*mU | OXXXXXXXXXXXXXXXXXX |
| WV-7619 | CUGCACTGGGCTTCCUGGUG | 548 | L001mC*mU*mG*mC*mA*C*T*G*G*G*C*T*T*C*C*mU*mG*mG*mU*mG | OXXXXXXXXXXXXXXXXXX |
| WV-7620 | UGGACCTGAGGATGACCGC | 549 | L001mU*mG*mG*mA*mC*C*T*G*A*G*G*A*T*G*A*mC*mC*mG*mC | OXXXXXXXXXXXXXXXXXX |
| WV-7621 | AGGGACCCCTCTGCACUGGGC | 550 | L001mA*mG*mG*mG*mA*C*C*C*T*C*T*G*C*A*C*mU*mG*mG*mG*mC | OXXXXXXXXXXXXXXXXXX |
| WV-7622 | CUUGUTACCCCGCCAUGGA | 551 | L001mC*mU*mU*mG*mU*T*A*C*C*C*C*mA*mU*mG*mG*mA | OXXXXXXXXXXXXXXXXXX |
| WV-7623 | AGGCTGGGATCCTCCACGUC | 552 | L001mA*mG*mG*mC*mU*G*G*G*A*T*C*C*T*C*mC*mA*mC*mG*mU*mC | OXXXXXXXXXXXXXXXXXX |
| WV-7624 | AAGGGACCCTCTGCACUGGG | 553 | L001mA*mA*mG*mG*mG*A*C*C*C*T*C*T*G*C*A*mC*mU*mG*mG*mG | OXXXXXXXXXXXXXXXXXX |
| WV-7625 | TGTGCTTGGCTCCTGCCTGG | 554 | L001Teo*Geo*Teo*Geo*m5Ceo*T*T*G*C*T*C*C*T*G*m5Ceo*m5Ceo*Teo*Geo*Geo | OXXXXXXXXXXXXXXXXXX |
| WV-7626 | TCTTGTTACCCCGCCATGG | 555 | L001Teo*m5Ceo*Teo*Teo*Geo*T*T*A*C*C*C*C*m5C*G*C*m5Ceo*Aeo*Teo*Geo*Geo | OXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7627 | ACCCCCGCCATGGAGACGTT | 556 | L001Aeo*m5Ceo*m5Ceo*m5Ceo*m5Ceo*m5C*G*C*C*A*T*G*G*A*G*Aeo*m5Ceo*Geo*Teo*Teo | OXXXXXXXXXXXXXXXXXXX |
| WV-7628 | TACCCCGCCATGGAGACGT | 557 | L001Teo*Aeo*m5Ceo*m5Ceo*m5Ceo*m5C*G*C*C*A*T*G*G*A*Geo*Aeo*m5Ceo*Geo*Teo | OXXXXXXXXXXXXXXXXXXX |
| WV-7629 | CTGCACTGGGCTTCCTGGTG | 558 | L001m5Ceo*Teo*Geo*m5Ceo*Aeo*m5Ceo*T*G*G*G*C*T*T*C*C*Teo*Geo*Geo*Teo*Geo | OXXXXXXXXXXXXXXXXXXX |
| WV-7630 | TGGACCTGAGGATGGACCGC | 559 | L001Teo*Geo*Geo*Aeo*m5Ceo*m5Ceo*T*G*A*G*G*A*T*G*G*Aeo*m5Ceo*m5Ceo*Geo*m5Ceo | OXXXXXXXXXXXXXXXXXXX |
| WV-7631 | AGGGACCCTCGCACTGGGC | 560 | L001Aeo*Geo*Geo*Geo*Aeo*C*C*C*T*C*T*G*C*A*C*Teo*Geo*Geo*m5Ceo | OXXXXXXXXXXXXXXXXXXX |
| WV-7632 | CTTGTTACCCCGCCATGGA | 561 | L001m5Ceo*Teo*Teo*Geo*Teo*T*A*C*C*C*m5C*G*C*C*Aeo*Teo*Geo*Geo*Aeo | OXXXXXXXXXXXXXXXXXXX |
| WV-7633 | AGGCTGGGATCCTCCACGTC | 562 | L001Aeo*Geo*Geo*m5Ceo*Teo*G*G*G*A*T*C*C*T*C*C*Aeo*m5Ceo*Geo*Teo*m5Ceo | OXXXXXXXXXXXXXXXXXXX |
| WV-7634 | AAGGGACCCTCTGCACTGGG | 563 | L001Aeo*Aeo*Geo*Geo*Geo*A*C*C*C*T*C*T*G*C*A*m5Ceo*Teo*Geo*Geo*Geo | OXXXXXXXXXXXXXXXXXXX |
| WV-7674 | TGCCACUGUAGAAAGGCAUGAU | 564 | T*SfG*mCfC*mAfC*mUfG*mUfA*mGfA*mAfA*mGfGmCfAmUmG*SmA*T*SmU | SXOXOXOXOXOOOOOSXS |
| WV-7675 | TGCCACUGUAGAAAGGCAUGAU | 565 | T*SfG*SmCfC*SmAfC*SmUfG*SmUfA*SmGfA*SmAfA*SmGfG*SmCfA*SmUfG*SmAT*SmU | SOSOSOSOSOSOSOSOSOS |
| WV-7676 | TGCCACUGUAGAAAGGCAUGAU | 566 | T*SfGmC*SfCmA*SfCmU*SfGmU*SfAmG*SfAmA*SfAmG*SfGmC*SfAmU*SfGmA*ST*SmU | SOSOSOSOSOSOSOSOSS |
| WV-7776 | TGCCACUGUAGAAAGGCAUUU | 567 | T*fG*mCfC*mAfC*mUfG*mUfA*mGfA*mAfA*GeoGeom5CeoAeoTeo*T*mU | XXXOXOXOXOXOOOOXX |
| WV-7777 | TGCCACUGUAGAAAGGCAUGAU | 568 | T*fG*mCfC*mAfC*mUfG*mUfA*mGfA*mAfA*GeoGeom5CeoAeoTeoGeoAeo*T*mU | XXXOXOXOXOXOOOOOX X |
| WV-7778 | CAUGAAGCAGGAACAUACCA | 569 | mC*mAmUmGmA*A*G*C*A*G*G*A*A*C*A*mUmAmCmC*mA | XOOOXXXXXXXXXOOOX |
| WV-7779 | GCAUGAAGCAGGAACAUACC | 570 | mG*mCmAmUmG*A*A*G*C*A*G*G*A*A*C*A*mAmUmAmC*mC | XOOOXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7780 | GGCAUGAAGCAGGAACAUAC | 571 | mG*mGmCmAmU*G*A*A*G*C*A*G*G*A*A*mCmAmUmA*mC | XOOOXXXXXXXXXXXXOOOX |
| WV-7781 | AGGCATGAAGCAGGAACAUA | 572 | mA*mGmGmCmA*T*G*A*A*G*C*A*G*G*A*mAmCmAmU*mA | XOOOXXXXXXXXXXXXOOOX |
| WV-7782 | AAGGCATGAAGCAGGAACAU | 573 | mA*mAmGmGmC*A*T*G*A*A*G*C*A*G*G*mAmAmCmA*mU | XOOOXXXXXXXXXXXXOOOX |
| WV-7783 | AAAGGCATGAAGCAGGAACA | 574 | mA*mAmAmGmG*C*A*T*G*A*A*G*C*A*G*mGmAmAmC*mA | XOOOXXXXXXXXXXXXOOOX |
| WV-7784 | GAAAGGCATGAAGCAGGAAC | 575 | mG*mAmAmAmG*G*C*A*T*G*A*A*G*C*A*mGmGmAmA*mC | XOOOXXXXXXXXXXXXOOOX |
| WV-7785 | AGAAAGGCATGAAGCAGGAA | 576 | mA*mGmAmAmA*G*C*A*T*G*A*A*G*C*A*mGmGmAmA*mA | XOOOXXXXXXXXXXXXOOOX |
| WV-7786 | GCCACTGTAGAAAGGCAUGA | 577 | mG*mCmCmAmC*T*G*T*A*G*A*A*A*G*G*mCmAmUmG*mA | XOOOXXXXXXXXXXXXOOOX |
| WV-7787 | GGCCACTGTGAAAGGCAUG | 578 | mG*mGmCmCmA*C*T*G*T*A*G*A*A*A*G*mGmCmAmU*mG | XOOOXXXXXXXXXXXXOOOX |
| WV-7788 | AGGCCACTGTAGAAAGGCAU | 579 | mA*mGmGmCmC*A*C*T*G*T*A*G*A*A*A*mGmGmCmA*mU | XOOOXXXXXXXXXXXXOOOX |
| WV-7789 | AAGGCCACTGTAGAAAGGCA | 580 | mA*mAmGmGmC*C*A*C*T*G*T*A*G*A*A*mAmGmGmC*mA | XOOOXXXXXXXXXXXXOOOX |
| WV-7790 | UAAGGCCACTGTAGAAAGGC | 581 | mU*mAmAmGmG*C*C*A*C*T*G*T*A*G*A*mAmGmGmC | XOOOXXXXXXXXXXXXOOOX |
| WV-7791 | AUAAGGCCACTGTGAAAAGG | 582 | mA*mUmAmAmG*G*C*C*A*C*T*G*T*A*G*mAmAmAmG*mG | XOOOXXXXXXXXXXXXOOOX |
| WV-7792 | GAUAAGGCCACTGTAGAAAG | 583 | mG*mAmUmAmA*G*G*C*C*A*C*T*G*T*A*mGmAmAmA*mG | XOOOXXXXXXXXXXXXOOOX |
| WV-7793 | GGAUAAGGCCACTGTAGAAA | 584 | mG*mGmAmUmA*A*G*G*C*C*A*C*T*G*T*mAmGmAmA*mA | XOOOXXXXXXXXXXXXOOOX |
| WV-7794 | CATGAAGCAGGAACATACCA | 585 | m5Ceo*AeoTeoGeoAeo*A*G*C*A*G*G*A*A*C*A*TeoAeom5Ceom5Ceo*Aeo | XOOOXXXXXXXXXXXXOOOX |
| WV-7795 | GCATGAAGCAGGAACATACC | 586 | Geo*m5CeoAeoTeoGeo*A*A*G*C*A*G*G*A*A*C*AeoTeoAeom5Ceo*m5Ceo | XOOOXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7796 | GGCATGAAGCAGGAACATAC | 587 | Geo*Geom5CeoAeoTeo*G*A*A*G*C*A*G*A*m5CeoAeoTeoAeo*m5Ceo | XOOOXXXXXXXXXXXXOOOX |
| WV-7797 | AGGCATGAAGCAGGAACATA | 588 | Aeo*GeoGeom5CeoAeo*T*G*A*A*G*C*A*G*A*Aeom5CeoAeoTeo*Aeo | XOOOXXXXXXXXXXXXOOOX |
| WV-7798 | AAGGCATGAAGCAGGAACAT | 589 | Aeo*AeoGeoGeom5Ceo*A*T*G*A*A*G*C*A*G*A*G*AeoAeom5CeoAeo*Teo | XOOOXXXXXXXXXXXXOOOX |
| WV-7799 | AAAGGCATGAAGCAGGAACA | 590 | Aeo*AeoAeoGeoGeo*C*A*T*G*A*A*G*C*A*G*GeoAeoAeom5Ceo*Aeo | XOOOXXXXXXXXXXXXOOOX |
| WV-7800 | GAAAGGCATGAAGCAGGAAC | 591 | Geo*AeoAeoAeoGeo*G*C*A*T*G*A*A*G*C*A*GeoGeoAeoAeo*m5Ceo | XOOOXXXXXXXXXXXXOOOX |
| WV-7801 | AGAAAGGCATGAAGCAGGAA | 592 | Aeo*GeoAeoAeoAeo*G*G*C*A*T*G*A*A*G*C*AeoGeoGeoAeo*Aeo | XOOOXXXXXXXXXXXXOOOX |
| WV-7802 | TAGAAAGGCATGAAGCAGGA | 593 | Teo*AeoGeoAeoAeo*A*G*G*C*A*T*G*A*A*G*m5CeoAeoGeoGeo*Aeo | XOOOXXXXXXXXXXXXOOOX |
| WV-7803 | GTAGAAAGGCATGAAGCAGG | 594 | Geo*TeoAeoGeoAeo*A*A*G*G*C*A*T*G*A*A*Geom5CeoAeoGeo*Geo | XOOOXXXXXXXXXXXXOOOX |
| WV-7804 | TGTAGAAAGGCATGAAGCAG | 595 | Teo*GeoTeoAeoGeo*A*A*A*G*G*C*A*T*G*A*AeoGeom5CeoAeo*Geo | XOOOXXXXXXXXXXXXOOOX |
| WV-7805 | CTGTAGAAAGGCATGAAGCA | 596 | m5Ceo*TeoGeoTeoAeo*G*A*A*A*G*G*C*A*T*G*AeoAeoGeom5Ceo*Aeo | XOOOXXXXXXXXXXXXOOOX |
| WV-7806 | ACTGTAGAAAGGCATGAAGC | 597 | Aeo*m5CeoTeoGeoTeo*A*G*A*A*A*G*G*C*A*T*GeoAeoAeoGeo*m5Ceo | XOOOXXXXXXXXXXXXOOOX |
| WV-7807 | CACTGTAGAAAGGCATGAAG | 598 | m5Ceo*Aeom5CeoTeoGeo*T*A*G*A*A*A*G*G*C*A*TeoGeoAeoAeo*Geo | XOOOXXXXXXXXXXXXOOOX |
| WV-7808 | CCACTGTAGAAAGGCATGAA | 599 | m5Ceo*m5CeoAeom5CeoTeo*G*T*A*G*A*A*A*G*G*C*AeoTeoGeoAeo*Aeo | XOOOXXXXXXXXXXXXOOOX |
| WV-7809 | GCCACTGTAGAAAGGCATGA | 600 | Geo*m5Ceom5CeoAeo*C*T*G*T*A*G*A*A*A*G*G*m5CeoAeoTeoGeo*Aeo | XOOOXXXXXXXXXXXXOOOX |
| WV-7810 | GGCCACTGTAGAAAGGCATG | 601 | Geo*Geom5Ceom5CeoAeo*C*T*G*T*A*G*A*A*A*G*Geom5CeoAeoTeo*Geo | XOOOXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7811 | AGGCCACTGTAGAAAGGCAT | 602 | Aeo*GeoGeom5Ceom5Ceo*A*C*T*G*T*A*G*A*A*A*GeoGeom5CeoAeo*Teo | XOOOXXXXXXXXXXXXOOOX |
| WV-7812 | AAGGCCACTGTAGAAAGGCA | 603 | Aeo*AeoGeoGeom5Ceo*C*A*C*T*G*T*A*G*A*A*AeoGeoGeom5Ceo*Aeo | XOOOXXXXXXXXXXXXOOOX |
| WV-7813 | TAAGGCCACTGTAGAAAGGC | 604 | Teo*AeoAeoGeoGeo*C*C*A*C*T*G*T*A*G*A*AeoAeoGeoGeo*m5Ceo | XOOOXXXXXXXXXXXXOOOX |
| WV-7814 | ATAAGGCCACTGTAGAAAGG | 605 | Aeo*TeoAeoAeoGeo*G*C*C*A*C*T*G*T*A*G*AeoAeoGeoGeo*Geo | XOOOXXXXXXXXXXXXOOOX |
| WV-7815 | GATAAGGCCACTGTAGAAAG | 606 | Geo*AeoTeoAeoAeo*G*G*C*C*A*C*T*G*T*A*GeoAeoAeoAeo*Geo | XOOOXXXXXXXXXXXXOOOX |
| WV-7816 | GGATAAGGCCACTGTAGAAA | 607 | Geo*GeoAeoTeoAeo*A*G*G*C*C*A*C*T*G*T*AeoGeoAeoAeo*Aeo | XOOOXXXXXXXXXXXXOOOX |
| WV-7817 | CAUGAAGCAGGAACAUACCA | 608 | m5IC*mAmUmGmA*A*G*C*A*G*G*A*A*C*A*mUmAmCmC*IA | XOOOXXXXXXXXXXXXOOOX |
| WV-7818 | GCAUGAAGCAGGAACAUACC | 609 | IG*mCmAmUmG*A*A*G*C*A*G*G*A*A*C*mAmUmAmC*m5IC | XOOOXXXXXXXXXXXXOOOX |
| WV-7819 | GGCAUGAAGCAGGAACAUAC | 610 | IG*mGmCmAmU*G*A*A*G*C*A*G*G*A*A*mCmAmUmA*m5IC | XOOOXXXXXXXXXXXXOOOX |
| WV-7820 | AGGCAUGAAGCAGGAACAUA | 611 | IA*mGmGmCmA*T*G*A*A*G*C*A*G*G*A*mAmCmAmU*IA | XOOOXXXXXXXXXXXXOOOX |
| WV-7821 | AAGGCAUGAAGCAGGAACAU | 612 | IA*mAmGmGmC*A*T*G*A*A*G*C*A*G*G*mAmAmCmA*IT | XOOOXXXXXXXXXXXXOOOX |
| WV-7822 | AAAGGCAUGAAGCAGGAACA | 613 | IA*mAmAmGmG*C*A*T*G*A*A*G*C*A*G*mGmAmCmC*IA | XOOOXXXXXXXXXXXXOOOX |
| WV-7823 | GAAAGGCAUGAAGCAGGAAC | 614 | IG*mAmAmAmG*G*C*A*T*G*A*A*G*C*A*mGmGmAmA*m5IC | XOOOXXXXXXXXXXXXOOOX |
| WV-7824 | AGAAAGGCAUGAAGCAGGAA | 615 | IA*mGmAmAmA*G*G*C*A*T*G*A*A*G*C*mAmGmGmA*IA | XOOOXXXXXXXXXXXXOOOX |
| WV-7825 | TAGAAAGGCAUGAAGCAGGA | 616 | IT*mAmGmAmA*A*G*G*C*A*T*G*A*A*G*mCmAmGmG*IA | XOOOXXXXXXXXXXXXOOOX |
| WV-7826 | GUAGAAAGGCAUGAAGCAGG | 617 | IG*mUmAmGmA*A*A*G*G*C*A*T*G*A*A*mGmCmAmG*IG | XOOOXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7827 | TGUAGAAAGGCATGAAGCAG | 618 | IT*mGmUmAmG*A*A*A*G*G*C*A*T*G*A*mAmGmCmA*IG | XOOOXXXXXXXXXXOOOX |
| WV-7828 | CUGUAGAAAGGCATGAAGCA | 619 | m5IC*mUmGmUmA*G*A*A*A*G*G*C*A*T*G*mAmAmGmC*IA | XOOOXXXXXXXXXXOOOX |
| WV-7829 | ACUGUAGAAAGGCATGAAGC | 620 | IA*mCmUmGmU*A*G*A*A*A*G*G*C*A*T*mGmAmAmG*m5IC | XOOOXXXXXXXXXXOOOX |
| WV-7830 | CACUGUAGAAAGGCATGAAG | 621 | m5IC*mAmCmUmG*T*A*G*A*A*A*G*G*C*A*mUmGmAmA*IG | XOOOXXXXXXXXXXOOOX |
| WV-7831 | CCACUGUAGAAAGGCAUGAA | 622 | m5IC*mCmAmCmU*G*T*A*G*A*A*A*G*G*C*mAmUmGmA*IA | XOOOXXXXXXXXXXOOOX |
| WV-7832 | GCCACTGTAGAAAGGCAUGA | 623 | IG*mCmCmAmC*T*G*T*A*G*A*A*A*G*G*mCmAmUmG*IA | XOOOXXXXXXXXXXOOOX |
| WV-7833 | GGCCACTGTAGAAAGGCAUG | 624 | IG*mGmCmCmA*C*T*G*T*A*G*A*A*A*G*mGmCmAmU*IG | XOOOXXXXXXXXXXOOOX |
| WV-7834 | AGGCCACTGTAGAAAGGCAT | 625 | IA*mGmGmCmC*A*C*T*G*T*A*G*A*A*A*mGmGmCmA*IT | XOOOXXXXXXXXXXOOOX |
| WV-7835 | AAGGCCACTGTAGAAAGGCA | 626 | IA*mAmGmGmC*C*A*C*T*G*T*A*G*A*A*mAmGmGmC*IA | XOOOXXXXXXXXXXOOOX |
| WV-7836 | TAAGGCCACTGTAGAAAGGC | 627 | IT*mTmAmAmGmG*C*C*A*C*T*G*T*A*G*A*mAmGmGmC*m5IC | XOOOXXXXXXXXXXOOOX |
| WV-7837 | AUAAGGCCACTGTAGAAAGG | 628 | IA*mUmAmAmG*G*C*C*A*C*T*G*T*A*G*mAmAmAmG*IG | XOOOXXXXXXXXXXOOOX |
| WV-7838 | GAUAAGGCCACTGTAGAAAG | 629 | IG*mAmUmAmA*G*G*C*C*A*C*T*G*T*A*mGmAmAmA*IG | XOOOXXXXXXXXXXOOOX |
| WV-7839 | GGAUAAGGCCACTGTAGAAA | 630 | IG*mGmAmUmA*A*G*G*C*C*A*C*T*G*T*mAmGmAmA*IA | XOOOXXXXXXXXXXOOOX |
| WV-7840 | CATGAAGCAGGAACATACCA | 631 | m5IC*AeoTeoGeoAeo*A*A*G*C*A*G*G*A*A*C*A*TeoAeom5Ceom5Ceo*IA | XOOOXXXXXXXXXXOOOX |
| WV-7841 | GCATGAAGCAGGAACATACC | 632 | IG*m5CeoAeoTeoGeo*A*A*G*C*A*G*G*A*A*C*AeoTeoAeom5Ceo*m5IC | XOOOXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7842 | GGCATGAAGCAGGAACATAC | 633 | IG*Geom5CeoAeoTeo*G*A*A*G*C*A*G*G*A*m5CeoAeoTeoAeo*m5IC | XOOOXXXXXXXXXXXXXOOOX |
| WV-7843 | AGGCATGAAGCAGGAACATA | 634 | IA*GeoGeom5CeoAeo*T*G*A*A*G*C*A*G*G*A*A*Aeom5CeoAeoTeo*IA | XOOOXXXXXXXXXXXXXOOOX |
| WV-7844 | AAGGCATGAAGCAGGAACAT | 635 | IA*AeoGeoGeom5Ceo*A*T*G*A*A*G*C*A*G*G*A*Aeom5CeoAeo*IT | XOOOXXXXXXXXXXXXXOOOX |
| WV-7845 | AAAGGCATGAAGCAGGAACA | 636 | IA*AeoAeoGeoGeo*C*A*T*G*A*A*G*C*A*G*GeoAeoAeom5Ceo*IA | XOOOXXXXXXXXXXXXXOOOX |
| WV-7846 | GAAAGGCATGAAGCAGGAAC | 637 | IG*AeoAeoAeoGeo*G*C*A*T*G*A*A*G*C*A*GeoGeoAeoAeo*m5IC | XOOOXXXXXXXXXXXXXOOOX |
| WV-7847 | AGAAAGGCATGAAGCAGGAA | 638 | IA*AeoGeoAeoAeo*G*G*C*A*T*G*A*A*G*C*AeoGeoGeoAeo*IA | XOOOXXXXXXXXXXXXXOOOX |
| WV-7848 | TAGAAAGGCATGAAGCAGGA | 639 | IT*AeoGeoAeoAeo*A*G*G*C*A*T*G*A*A*G*C*m5CeoAeoGeoGeo*IA | XOOOXXXXXXXXXXXXXOOOX |
| WV-7849 | GTAGAAAGGCATGAAGCAGG | 640 | IG*TeoAeoGeoAeo*A*A*G*G*C*A*T*G*A*A*Geom5CeoAeoGeo*IG | XOOOXXXXXXXXXXXXXOOOX |
| WV-7850 | TGTAGAAAGGCATGAAGCAG | 641 | IT*GeoTeoAeoGeo*A*A*A*G*G*C*A*T*G*A*AeoGeom5CeoAeo*IG | XOOOXXXXXXXXXXXXXOOOX |
| WV-7851 | CTGTAGAAAGGCATGAAGCA | 642 | m5IC*TeoGeoTeoAeo*G*A*A*A*G*G*C*A*T*G*AeoAeoGeom5Ceo*IA | XOOOXXXXXXXXXXXXXOOOX |
| WV-7852 | ACTGTAGAAAGGCATGAAGC | 643 | IA*m5CeoTeoGeoTeo*A*G*A*A*A*G*G*C*A*T*GeoAeoAeoGeo*m5IC | XOOOXXXXXXXXXXXXXOOOX |
| WV-7853 | CACTGTAGAAAGGCATGAAG | 644 | m5IC*Aeom5CeoAeom5CeoTeoGeo*T*A*G*A*A*A*G*G*C*A*TeoGeoAeoAeo*IG | XOOOXXXXXXXXXXXXXOOOX |
| WV-7854 | CCACTGTAGAAAGGCATGAA | 645 | m5IC*m5CeoAeom5CeoAeom5CeoTeo*G*T*A*G*A*A*A*G*G*C*AeoTeoGeoAeo*IA | XOOOXXXXXXXXXXXXXOOOX |
| WV-7855 | GCCACTGTAGAAAGGCATGA | 646 | IG*m5CeoGeom5CeoAeom5CeoAeom5Ceo*T*G*T*A*G*A*A*A*G*G*m5CeoAeoTeoGeo*IA | XOOOXXXXXXXXXXXXXOOOX |
| WV-7856 | GGCCACTGTAGAAAGGCATG | 647 | IG*Geom5CeoGeom5CeoAeom5CeoAeom5Ceo*T*G*T*A*G*A*A*A*A*G*GeoGeoAeoTeo*IG | XOOOXXXXXXXXXXXXXOOOX |
| WV-7857 | AGGCCACTGTAGAAAGGCAT | 648 | IA*GeoGeom5Ceom5CeoAeom5CeoAeo*C*T*G*T*A*G*A*A*A*AeoGeom5CeoAeo*IT | XOOOXXXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-7858 | AAGGCCACTGTAGAAAGGCA | 649 | IA*AeoGeoGeom5Ceo*C*A*C*T*G*T*A*G*A*A*AeoGeoGeom5Ceo*IA | XOOOXXXXXXXXXXXOOOX |
| WV-7859 | TAAGGCCACTGTAGAAAGGC | 650 | IT*AeoAeoGeoGeo*C*C*A*C*T*G*T*A*G*A*AeoAeoGeoGeo*m5IC | XOOOXXXXXXXXXXXOOOX |
| WV-7860 | ATAAGGCCACTGTAGAAAGG | 651 | IA*TeoAeoAeoGeo*G*C*C*A*C*T*G*T*A*G*AeoAeoAeoGeo*IG | XOOOXXXXXXXXXXXOOOX |
| WV-7861 | GATAAGGCCACTGTAGAAAG | 652 | IG*AeoTeoAeoAeo*G*G*C*C*A*C*T*G*T*A*GeoAeoAeoAeo*IG | XOOOXXXXXXXXXXXOOOX |
| WV-7862 | GGATAAGGCCACTGTAGAAA | 653 | IG*GeoAeoTeoAeo*A*G*G*C*C*A*C*T*G*T*AeoGeoAeoAeo*IA | XOOOXXXXXXXXXXXOOOX |
| WV-8030 | GGACCTGAGGATGGACCGCG | 654 | Mod001L001mG*SmA*SmC*SmC*ST*SG*RA*SG*SG*RA*ST*SG*RG*SA*SmC*SmC*SmG*SmG | OSSSSSSRSRSSRSSSSSS |
| WV-8031 | GGACCTGAGGATGGACCGCG | 655 | Mod001L001mG*SmGmAm5CeomC*ST*SG*RA*SG*SG**RA*ST*SG*RG*SA*Sm5Ceom5CeomG*SmC*SmG | OSOOOSSRSRSSRSSOOSS |
| WV-8032 | TGCCACUGUAGAAGGCAUGATU | 656 | VPT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSOSSSSSSSSS |
| WV-8033 | GGACCTGAGGATGGACCGCG | 657 | Mod001L001mG*SmGmAm5CeomC*ST*SG*RA*SG*SG*RA*ST*SG*RG*SA*Sm5Ceom5CeomGmC*SmG | OSOOOSSRSRSSRSSOOOS |
| WV-8034 | GGACCTGAGGATGGACCGCG | 658 | Mod001L001Geo*SGeo*SGeo*SAeo*Sm5Ceo*Sm5Ceo*ST*SG*RA*SG*SG*RA*ST*SG*RG*SA*Sm5Ceo*Sm5Ceo*SGeo*Sm5Ceo*SGeo | OSSSSSSRSSRSSRSSSSSS |
| WV-8035 | GGACCTGAGGATGGACCGCG | 659 | Mod001L001Geo*RGeo*RGeo*RAeo*Rm5Ceo*Rm5Ceo*RT*SG*RA*SG*SG*RA*ST*SG*RG*SA*Sm5Ceo*Rm5Ceo*RGeo*Rm5Ceo*RGeo | ORRRRRSRSSRSSRSSRRRR |
| WV-8036 | GGACCTGAGGATGGACCGCG | 660 | Mod001L001Geo*SGeoAeom5Ceom5Ceo*ST*SG*RA*SG*SG*RA*ST*SG*RG*SA*Sm5Ceom5CeoGeom5Ceo*SGeo | OSOOOSSRSRSSRSSOOOS |
| WV-8037 | GGACCTGAGGATGGACCGCG | 661 | Mod001L001Geo*SGeoAeom5Ceom5Ceo*RT*SG*RA*SG*SG*RA*ST*SG*RG*SA*Sm5Ceom5CeoGeom5Ceo*SGeo | OSOOORSRSRSSRSSOOOS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8038 | GGACCTGAGGATGGACCGCG | 662 | Mod001L001Geo*RGeoAeom5Ceom5Ceo*ST*SG*RA*SG*SG*RA*ST*SG*RG*SA*Sm5Ceom5CeoGeom5Ceo*RGeo | OROOOSRSSRSSRSSRSOOOR |
| WV-8039 | GGACCTGAGGATGGACCGCG | 663 | Mod001L001Geo*RGeoAeom5Ceom5Ceo*RT*SG*RA*SG*SG*RA*ST*SG*RG*SA*Sm5Ceom5CeoGeom5Ceo*RGeo | OROOORSRSSRSSRSOOOR |
| WV-8040 | GGACCTGAGGATGGACCGCG | 664 | Mod001L001mG*RmA*RmC*RmC*RmC*RT*SG*RA*SG*SG*RA*ST*SG*RG*SA*SmC*RmC*RmG*RmC*RmG | ORRRRRSRSSRSSRSSRRRR |
| WV-8041 | GGACCTGAGGATGGACCGCG | 665 | Mod001L001mG*SmG*RmA*RmC*RmC*RmC*RT*SG*RA*SG*SG*RA*ST*SG*RG*SA*SmC*RmC*RmG*RmC*SmG | OSRRRRSRSSRSSRSSRRRS |
| WV-8042 | GGACCTGAGGATGGACCGCG | 666 | Mod001L001mG*SmGmAmCmC*ST*SG*RA*SG*SG*RA*ST*SG*RG*SA*SmCmCmGmC*SmG | OSOOOSRSSRSSRSSROOOS |
| WV-8043 | GGACCTGAGGATGGACCGCG | 667 | Mod001L001mG*SmG*SmA*SmC*SmC*ST*SG*RA*SG*SG*RA*ST*SG*RG*SA*Sm5Ceo*Sm5Ceo*SGeo*Sm5Ceo*SGeo | OSSSSSRSSRSSRSSSSSS |
| WV-8044 | GGACCTGAGGATGGACCGCG | 668 | Mod001L001mG*SmG*SmA*SmC*SmC*ST*SG*RA*SG*SG*RA*ST*SG*RG*SA*Sm5Ceo*Rm5Ceo*RGeo*Rm5Ceo*RGeo | OSSSSSRSSRSSRSSRRRR |
| WV-8045 | GGACCTGAGGATGGACCGCG | 669 | Mod001L001mG*SmG*SmA*SmC*SmC*ST*SG*RA*SG*SG*RA*ST*SG*RG*SA*Sm5Ceom5CeoGeom5Ceo*SGeo | OSSSSSRSSRSSRSOOOS |
| WV-8046 | GGACCTGAGGATGGACCGCG | 670 | Mod001L001mG*SmG*SmA*SmC*SmC*ST*SG*RA*SG*SG*RA*ST*SG*RG*SA*Sm5Ceom5CeoGeom5Ceo*SGeo | OSSSSSRSSRSSRSOOOS |
| WV-8047 | GGACCTGAGGATGGACCGCG | 671 | Mod001L001mG*SmG*SmA*SmC*SmC*ST*SG*RA*SG*SG*RA*ST*SG*RG*SA*Sm5Ceom5CeoGeom5Ceo*RGeo | OSSSSSRSSRSSRSOOOR |
| WV-8048 | GGACCTGAGGATGGACCGCG | 672 | Mod001L001mG*SmG*SmA*SmC*SmC*ST*SG*RA*SG*SG*RA*ST*SG*RG*SA*Sm5Ceom5CeoGeom5Ceo*RGeo | OSSSSSRSSRSSRSOOOR |
| WV-8049 | TGCCACUGUAGAAAGGCAUGATU | 673 | VPT*SfG*SmCfC*SmAfC*SmU*SfG*SmU*SfA*SmGfA*SmAfA*SmG*SfG*SmC*SfA*SmU*SfG*SmA*STGaNC6T*SmU | SSOSOSSSSSOSOSSSSSSSS |

TABLE 1A-continued oligonucleotides.
PNPLA3 oligonucleotides.

| WAVE ID | Naked sequence | SEQ ID NO: | Sequence | Stereochemistry |
|---|---|---|---|---|
| WV-8050 | TGCCACUGUAGAAAGGCATG ATU | 674 | VPT*SfG*SmCfC*SmAfC*SmUfG*SmUfA*SmGfA*SmAfA*SGeoGeom5CeoAeoTeoGeoAeoTGaNC6T*SmU | SSOSOSOSOSOSOSOOOOOOO OS |
| WV-8051 | TGCCACUGUAGAAAGGCATG ATU | 675 | VPT*SfG*SmCfC*SmAfC*SmUfG*SmUfA*SmGfA*SmAfA*SGeo*SGeo*Sm5Ceo*SAeo*STeo*SGeo*SAeo*STGaNC6T*SmU | SSOSOSOSOSOSOSOSSSSSSSS |
| WV-8052 | TGCCACUGUAGAAAGGCATG ATU | 676 | VPT*SfG*SmCfC*SmAfC*SmUfG*SmUfA*SmGfA*SmAfA*SGeo*RGeo*Rm5Ceo*RAeo*RTeo*RGeo*RAeo*RTGaNC6T*SmU | SSOSOSOSOSOSOSOSRRRRRRS |
| WV-8053 | TGCCACUGUAGAAAGGCATG ATU | 677 | VPT*SfG*SmCfC*SmAfC*SmUfG*SmUfA*SmGfA*SmAfA*SG*SG*SC*SA*ST*SG*SA*STGaNC6T*SmU | SSOSOSOSOSOSOSOSSSSSSSS |
| WV-8054 | TGCCACUGUAGAAAGGCATG ATU | 678 | VPT*SfG*SmCfC*SmAfC*SmUfG*SmUfA*SmGfA*SmAfA*SG*SG*SC*SmA*SmU*SG*SA*STGaNC6T*SmU | SSOSOSOSOSOSOSOSSSSSSSS |
| WV-8055 | TGCCACUGUAGAAAGGCATG ATU | 679 | T*SfG*SmCfC*SmAfC*SmU*SfG*SmU*SfA*SmGfA*SmAfA*SmG*SfG*SmC*SfG*SmU*SfG*SmA*STGaNC6T*SmU | SSOSOSSSSSOSOSOSSSSSSSS |
| WV-8056 | TGCCACUGUAGAAAGGCATG ATU | 680 | T*SfG*SmCfC*SmAfC*SmUfG*SmUfA*SmGfA*SmAfA*SGeoGeom5CeoAeoTeoGeoAeoTGaNC6T*SmU | SSOSOSOSOSOSOSOSOOOOOO OS |
| WV-8057 | TGCCACUGUAGAAAGGCATG ATU | 681 | T*SfG*SmCfC*SmAfC*SmUfG*SmUfA*SmGfA*SmAfA*SGeo*SGeo*Sm5Ceo*SAeo*STeo*SGeo*SAeo*STGaNC6T*SmU | SSOSOSOSOSOSOSOSSSSSSSS |
| WV-8058 | TGCCACUGUAGAAAGGCATG ATU | 682 | T*SfG*SmCfC*SmAfC*SmUfG*SmUfA*SmGfA*SmAfA*SGeo*RGeo*Rm5Ceo*RAeo*RTeo*RGeo*RAeo* | SSOSOSOSOSOSOSOSRRRRRRS |
| WV-8059 | TGCCACUGUAGAAAGGCATG ATU | 683 | RTGaNC6T*SmU*SG*SG*SC*SA*ST*SG*SA*STGaNC6T*SmU | SSOSOSOSOSOSOSOSSSSSSSS |
| WV-8060 | TGCCACUGUAGAAAGGCAUG ATU | 684 | T*SfG*SmCfC*SmAfC*SmUfG*SmUfA*SmGfA*SmAfA*SG*SG*SC*SmA*SmU*SG*SA*STGaNC6T*SmU | SSOSOSOSOSOSOSOSSSSSSSS |
| WV-8061 | TGCCACUGUAGAAAGGCAUG ATU | 685 | T*SfG*SmCfC*SmAfC*SfA*SmU*SfG*SmA*STGaNC6T*SmU | SSOSOSOSOSOSOSOSSSSSSSS |
| WV-8063 | TGCCACUGUAGAAAGGCAUT UTTTTTGGTAATCCACTTTCAG AGG | 686 | VPT*fG*mCfC*mAfC*mUfG*mUfA*mGfA*mAfA*mGfGmCfAmU*TGaNC6T*mUTTTTeo*Geo*Geo*Teo*Aeo*A*T*m5C*m5C*A*m5C*T*T*m5C*Aeo*Geo*Aeo*Geo | XXXOXOXOXOXOXOOOOXX OOOOXXXXXXXXXXXXXXX XXX |

TABLE 1A-continued oligonucleotides.
PNPLA3 oligonucleotides.

| WAVE ID | Naked sequence | SEQ ID NO: | Sequence | Stereochemistry |
|---|---|---|---|---|
| WV-8065 | TGCCACUGUAGAAAGGCAUT UTTTTTGGTAATCCACTTTCAG AGG | 687 | VPT*SfG*SmCfC*SmAfC*SmUfG*SmUfA*SmGfA* SmAfA*SmG*SfG*SmC*SfA*SmU*STGaNC6T* SmUTTTTTeo*Geo*Geo*Teo*Aeo*A*T*m5C*m5C* A*m5C*T*T*T*m5C*Aeo*Geo*Aeo*Geo*Geo | SSOSOSOSOSOSOSSSSSSOO OOOXXXXXXXXXXXXXXXXXX |
| WV-8067 | TGCCACUGUAGAAAGGCAUT UTTTTTGGTAATCCACTTTCAG AGG | 688 | VPT*SfG*SmCfC*SmAfC*SmUfG*SmUfA*SmGfA* SmAfA*SmG*SfG*SmC*SfA*SmU*ST*SmUTTTTTeo* Geo*Geo*Teo*Aeo*A*T*m5C*m5C*A*m5C*T*T *T*m5C*Aeo*Geo*Aeo*Geo*GeoL003Mod001 | SSOSOSOSOSOSOSSSSSSOO OOOXXXXXXXXXXXXXXXXXX O |
| WV-8069 | TGCCACUGUAGAAAGGCAUT UTTTTTGGTAATCCACTTTCAG AGG | 689 | T*SfG*SmCfC*SmAfC*SmUfG*SmUfA*SmGfA*SmAfA *SmG*SfG*SmC*SfA*SmU*STGaNC6T*SmUTTTTTeo* Geo*Geo*Teo*Aeo*A*T*m5C*m5C*A*m5C*T*T *T*m5C*Aeo*Geo*Aeo*Geo | SSOSOSOSOSOSOSSSSSSOO OOOXXXXXXXXXXXXXXXXXX |
| WV-8071 | TGCCACUGUAGAAAGGCAUT UTTTTTGGTAATCCACTTTCAG AGG | 690 | T*SfG*SmCfC*SmAfC*SmUfG*SmUfA*SmGfA*SmAfA *SmG*SfG*SmC*SfA*SmU*ST*SmUTTTTTeo*Geo* Geo*Teo*Aeo*A*T*m5C*m5C*A*m5C*T*T*T* m5C*Aeo*Geo*Aeo*Geo*GeoL003Mod001 | SSOSOSOSOSOSOSSSSSSOO OOOXXXXXXXXXXXXXXXXXX O |
| WV-8072 | GGACCTGAGGATGGACCGCG | 691 | Mod001L001Geo*Geo*Aeo*m5Ceo*m5Ceo*T*SG*RA *SG*SG*RA*ST*SG*RG*SA*m5Ceo*5m5Ceo*Geo *m5Ceo*Geo | OXXXXXSRSRSSSRSSXXXX |
| WV-8073 | GGACCTGAGGATGGACCGCG | 692 | Mod001L001Geo*Geo*Aeo*m5Ceo*m5Ceo*T*SG*RA *SG*SG*SA*ST*SG*RG*SA*m5Ceo*m5Ceo*Geo* m5Ceo*Geo | OXXXXXSRSSSSRSSXXXX |
| WV-8074 | GGACCTGAGGATGGACCGCG | 693 | Mod001L001Geo*Geo*Aeo*m5Ceo*m5Ceo*T*SG*RA *SG*SG*RA*ST*SG*RG*SA*m5Ceo*m5Ceo*Geo* m5Ceo*Geo | OXXXXXSRSRSSRSSXXXX |
| WV-8075 | TGCCACUGUAGAAAGGCATG ATU | 694 | VPT*SfG*SmCfC*SmAfC*SmUfG*SmUfA*SmGfA* SmAfA*SmG*SfG*SmC*SfA*SmU*SfG*SmA*ST* SmU | SSOSOSOSOSOSOSSSSSSSS |
| WV-8076 | TGCCACUGUAGAAAGGCATG ATU | 695 | T*SfG*SmCfC*SmAfC*SmU*SfG*SfA*SmGfA* SmAfA*SmG*SfG*SmC*SfA*SmU*SfG*SmA*ST* SmU | SSOSOSSSSOSOSSSSSSSS |
| WV-8077 | TGCCACUGUAGAAAGGCATG ATU | 696 | T*SfG*SmCfC*SmAfC*SmUfG*SmUfA*SmGfA*SmAfA *SGeoGeom5CeoAeoTeoGeoAeoT*SmU | SSOSOSOSOSOSOSOOOOOO OS |
| WV-8078 | TGCCACUGUAGAAAGGCATG ATU | 697 | T*SfG*SmCfC*SmAfC*SmUfG*SmUfA*SmGfA*SmAfA *SGeo*SGeo*Sm5Ceo*SAeo*STeo*SGeo*SAeo*ST* SmU | SSOSOSOSOSOSOSSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8079 | TGCCACUGUAGAAAGGCATG ATU | 698 | T*SfG*SmCfC*SmAfC*SmUfG*SmUfA*SmGfA*SmAfA*SGeo*RGeo*Rm5Ceo*RAeo*RTeo*RGeo*RAeo*RT*SmU | SSOSOSOSOSOSRRRRRRS |
| WV-8080 | TGCCACUGUAGAAGGCATG ATU | 699 | T*SfG*SmCfC*SmAfC*SmUfG*SmUfA*SmGfA*SmAfA*SG*SG*SC*SA*ST*SG*SA*ST*SmU | SSOSOSOSOSOSSSSSSSS |
| WV-8081 | TGCCACUGUAGAAGGCAUG ATU | 700 | T*SfG*SmCfC*SmAfC*SmUfG*SmUfA*SmGfA*SmAfA*SG*SG*SC*SmA*SmU*SG*SA*ST*SmU | SSOSOSOSOSOSSSSSSSS |
| WV-8082 | GGACCTGAGGATGGACCGCG | 701 | Geo*GeoAeom5Ceom5Ceo*T*G*A*G*G*A*T*G*G*A*m5CeoGeom5Ceo*Geo | XOOOXXXXXXXXXOOOX |
| WV-8083 | GGACCTGAGGATGGACCGCG | 702 | mG*SmGmAm5CeomC*ST*SG*RA*SG*SG*RA*ST*SG*RG*SA*Sm5CeomCeomGmC*SmG | SOOOSRSRSRSRSOOOS |
| WV-8084 | GGACCTGAGGATGGACCGCG | 703 | Geo*SGeo*SAeo*Sm5Ceo*Sm5Ceo*ST*SG*RA*SG*SG*RA*ST*SG*RG*SA*Sm5Ceo*Sm5Ceo*SGeo*Sm5Ceo*SGeo | SSSSSSRSRSRSRSSSSSS |
| WV-8085 | GGACCTGAGGATGGACCGCG | 704 | Geo*RGeo*RAeo*Rm5Ceo*Rm5Ceo*RT*SG*RA*SG*SG*RA*ST*SG*RG*SA*Rm5Ceo*Rm5Ceo*RGeo*Rm5Ceo*RGeo | RRRRRSRSRSRSRSRRRRR |
| WV-8086 | GGACCTGAGGATGGACCGCG | 705 | Geo*SGeoAeom5Ceo*ST*SG*RA*SG*SG*RA*ST*SG*RG*SA*Sm5CeomCeoGeomCeo*SGeo | SOOOSRSRSRSRSOOOS |
| WV-8087 | GGACCTGAGGATGGACCGCG | 706 | Geo*SGeoAeom5Ceom5Ceo*RT*SG*RA*SG*SG*RA*ST*SG*RG*SA*Sm5Ceom5CeoGeom5Ceo*SGeo | SOOORSRSRSRSRSOOOS |
| WV-8088 | GGACCTGAGGATGGACCGCG | 707 | Geo*RGeoAeom5Ceom5Ceo*ST*SG*RA*SG*SG*RA*ST*SG*RG*SA*Sm5Ceom5CeoGeom5Ceo*RGeo | ROOOSRSRSRSRSOOOR |
| WV-8089 | GGACCTGAGGATGGACCGCG | 708 | Geo*RGeoAeom5Ceom5Ceo*RT*SG*RA*SG*SG*RA*ST*SG*RG*SA*Sm5Ceom5CeoGeom5Ceo*RGeo | ROOORSRSRSRSRSOOOR |
| WV-8090 | GGACCTGAGGATGGACCGCG | 709 | mG*SmG*SmA*SmC*SmC*ST*SG*RA*SG*SG*RA*ST*SG*RG*SA*SmC*SmC*SmG*SmC*SmG | SSSSSSRSRSRSRSSSSSS |
| WV-8091 | GGACCTGAGGATGGACCGCG | 710 | mG*RmG*RmA*RmC*RmC*RT*SG*RA*SG*SG*RA*ST*SG*RG*SA*RmC*RmC*RmG*RmC*RmG | RRRRRSRSRSRSRSRRRRR |
| WV-8092 | GGACCTGAGGATGGACCGCG | 711 | mG*SmG*RmA*RmC*RmC*RT*SG*RA*SG*SG*RA*ST*SG*RG*SA*RmC*RmG*RmC*SmG | SRRRRSRSRSRSRSRRRS |
| WV-8093 | GGACCTGAGGATGGACCGCG | 712 | mG*SmGmAmCmC*ST*SG*RA*SG*SG*RA*ST*SG*RG*SA*SmCmCmGmC*SmG | SOOOSRSRSRSRSOOOS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8094 | TGCCACUGUAGAAAGGCAUGATU | 713 | VPT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSOSSSSSSSS |
| WV-8095 | TGCCACUGUAGAAAGGCAUGATU | 714 | T*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSOSSSSSSSS |
| WV-8096 | CUGUGACGUGAGGAUCCCAGCCUCUG | 715 | rCrUrGrUrGrArCrGrUrGrArGrGrArUrCrCrCrArGrCrCrUrCrUrG | OOOOOOOOOOOOOOOOOOOOOOOOOO |
| WV-8111 | GGACCUGAGGATGGACCGCG | 716 | Mod001L001mG*SmG*SmA*SmC*SmC*ST*SG*RA*SG*SG*SA*ST*SG*RG*SA*SmC*SmC*SmG*SmG | OSSSSSRSSSSSSRSSSSS |
| WV-8112 | GGACCUGAGGATGGACCGCG | 717 | Mod001L001mG*SmG*SmA*SmC*SmC*ST*SG*RA*SG*SG*SA*ST*SG*RG*SA*Sm5Ceo*Rm5Ceo*RGeo*Rm5Ceo*RGeo | OSSSSSRSSSSSSRSSSSS |
| WV-8132 | CTGTAGAAAGGCATGAAGCA | 718 | Mod001L001m5Ceo*TeoGeoTeoAeo*G*A*A*A*G*G*C*A*T*G*AeoAeoGeom5Ceo*Aeo | OXOOOXXXXXXXXXXXXOOOX |
| WV-8133 | CTGTAGAAAGGCATGAAGCA | 719 | Mod001L001m5Ceo*RTeoGeoTeoAeo*RG*SA*SA*SA*SG*RG*SC*SA*RT*SG*SAeoAeoGeom5Ceo*RAeo | OROOORSSSSRSSRSSOOOR |
| WV-8134 | CCACTGTAGAAAGGCATGAA | 720 | Mod001L001m5Ceo*m5CeoAeom5CeoCeo*G*T*A*G*A*A*A*G*C*AeoTeoGeoAeo*Aeo | OXOOOXXXXXXXXXXXXOOOX |
| WV-8135 | CCACTGTAGAAAGGCATGAA | 721 | Mod001L001m5Ceo*Rm5CeoAeom5CeoCeo*RG*ST*SA*SG*SA*SA*SA*SG*RG*SC*SAeoTeoGeoAeo*RAeo | OROOORSSSSSSRSSOOOR |
| WV-8136 | CTGTAGAAAGGCATGAAGCA | 722 | Mod001L001m5Ceo*Teo*Geo*Teo*Aeo*G*A*A*A*G*G*C*A*T*G*Aeo*Aeo*Geo*m5Ceo*Aeo | OXXXXXXXXXXXXXXXXXX |
| WV-8137 | CTGTAGAAAGGCATGAAGCA | 723 | Mod001L001m5Ceo*RTeo*RGeo*RTeo*RAeo*RG*SA*SA*SA*SG*RG*SC*SA*RT*SG*SAeo*RAeo*RGeo*Rm5Ceo*RAeo | ORRRRSSSSRSSRSSRRRR |
| WV-8138 | CAUGAAGCAGGAACAUACCA | 724 | mC*mA*mU*mG*mA*mA*G*C*A*G*G*A*A*C*A*mU*mA*mC*mC*mA | XXXXXXXXXXXXXXXXXX |
| WV-8139 | GCAUGAAGCAGGAACAUACC | 725 | mG*mC*mA*mU*mG*A*A*G*C*A*G*A*A*C*mA*mU*mA*mC*mC | XXXXXXXXXXXXXXXXXX |
| WV-8140 | GGCAUGAAGCAGGAACAUAC | 726 | mG*mG*mC*mA*mU*G*A*A*G*C*A*G*A*A*mC*mA*mU*mA*mC | XXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8141 | AGGCATGAAGCAGGAACAUA | 727 | mA*mG*mC*mA*T*G*A*A*G*C*A*G*G*A*mA*mC*mA*mU*mA | XXXXXXXXXXXXXXXXXXXX |
| WV-8142 | AAGGCATGAAGCAGGAACAU | 728 | mA*mA*mG*mG*mC*mC *A*T*G*A*A*G*C*A*G*G*mA*mA*mC*mA*mU | XXXXXXXXXXXXXXXXXXXX |
| WV-8143 | AAAGGCATGAAGCAGGAACA | 729 | mA*mA*mA*mG*mG*mC*A*T*G*A*A*G*C*A*G*mG*mA*mA*mC*mA | XXXXXXXXXXXXXXXXXXXX |
| WV-8144 | GAAAGGCATGAAGCAGGAAC | 730 | mG*mA*mA*mA*mG*G*C*A*T*G*A*A*G*C*A*mG*mG*mA*mA*mC | XXXXXXXXXXXXXXXXXXXX |
| WV-8145 | AGAAAGGCATGAAGCAGGAA | 731 | mA*mG*mA*mA*mA*G*G*C*A*T*G*A*A*G*C*mA*mG*mG*mA*mA | XXXXXXXXXXXXXXXXXXXX |
| WV-8146 | UAGAAAGGCATGAAGCAGGA | 732 | mU*mA*mG*mA*mA*A*G*G*C*A*T*G*A*A*G*mC*mA*mG*mG*mA | XXXXXXXXXXXXXXXXXXXX |
| WV-8147 | GUAGAAAGGCATGAAGCAGG | 733 | mG*mU*mA*mG*mA*A*A*G*G*C*A*T*G*A*A*G*mC*mA*mG*mG | XXXXXXXXXXXXXXXXXXXX |
| WV-8148 | UGUAGAAAGGCATGAAGCAG | 734 | mU*mG*mU*mA*mG*A*A*A*G*G*C*A*T*G*A*A*mG*mC*mA*mG | XXXXXXXXXXXXXXXXXXXX |
| WV-8149 | CUGUAGAAAGGCATGAAGCA | 735 | mC*mU*mG*mU*mA*G*A*A*A*G*G*C*A*T*G*A*mA*mG*mC*mA | XXXXXXXXXXXXXXXXXXXX |
| WV-8150 | ACUGUAGAAAGGCATGAAGC | 736 | mA*mC*mU*mG*mU*A*G*A*A*A*G*G*C*A*T*G*mA*mA*mG*mC | XXXXXXXXXXXXXXXXXXXX |
| WV-8151 | CACUGUAGAAAGGCATGAAG | 737 | mC*mA*mC*mU*mG*T*A*G*A*A*A*G*G*C*A*mU*mG*mA*mA*mG | XXXXXXXXXXXXXXXXXXXX |
| WV-8152 | CCACUGUAGAAAGGCAUGAA | 738 | mC*mC*mA*mC*mU*G*T*A*G*A*A*A*G*G*C*mA*mU*mG*mA*mA | XXXXXXXXXXXXXXXXXXXX |
| WV-8153 | GCCACUGUAGAAAGGCAUGA | 739 | mG*mC*mC*mA*mC*T*G*T*A*G*A*A*A*G*G*mC*mA*mU*mG*mA | XXXXXXXXXXXXXXXXXXXX |
| WV-8154 | GGCCACUGUAGAAAGGCAUG | 740 | mG*mG*mC*mC*mA*C*T*G*T*A*G*A*A*A*G*mC*mA*mU*mG | XXXXXXXXXXXXXXXXXXXX |
| WV-8155 | AGGCCACUGUAGAAAGGCAU | 741 | mA*mG*mG*mC*mC*A*C*T*G*T*A*G*A*A*A*mG*mC*mA*mU | XXXXXXXXXXXXXXXXXXXX |
| WV-8156 | AAGGCCACUGUAGAAAGGCA | 742 | mA*mA*mG*mG*mC*C*A*C*T*G*T*A*G*A*A*A*mG*mG*mC*mA | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8157 | UAAGGCCACTGTAGAAAGGC | 743 | mU*mA*mA*mG*mG*C*C*A*C*T*G*T*A*G*A*mA*mA*mG*mG*mC | XXXXXXXXXXXXXXXXXXXX |
| WV-8158 | AUAAGGCCACTGTAGAAAGG | 744 | mA*mU*mA*mA*mG*G*C*C*A*C*T*G*T*A*G*mA*mA*mA*mG*mG | XXXXXXXXXXXXXXXXXXXX |
| WV-8159 | GAUAAGGCCACTGTAGAAAG | 745 | mG*mA*mU*mA*mA*G*G*C*C*A*C*T*G*T*A*mG*mA*mA*mA*mG | XXXXXXXXXXXXXXXXXXXX |
| WV-8160 | GGAUAAGGCCACTGTAGAAA | 746 | mG*mG*mA*mU*mA*A*G*G*C*C*A*C*T*G*T*mA*mG*mA*mA*mA | XXXXXXXXXXXXXXXXXXXX |
| WV-8161 | CATGAAGCAGGAACATACCA | 747 | m5Ceo*Aeo*Teo*Geo*Aeo*A*G*C*A*G*G*A*A*C*A*Teo*Aeo*m5Ceo*m5Ceo*Aeo | XXXXXXXXXXXXXXXXXXXX |
| WV-8162 | GCATGAAGCAGGAACATACC | 748 | Geo*m5Ceo*Aeo*Teo*Geo*A*A*G*C*A*G*G*A*A*C*Aeo*Teo*Aeo*m5Ceo*m5Ceo | XXXXXXXXXXXXXXXXXXXX |
| WV-8163 | GGCATGAAGCAGGAACATAC | 749 | Geo*Geo*m5Ceo*Aeo*Teo*G*A*A*G*C*A*G*G*A*A*m5Ceo*Aeo*Teo*Aeo*m5Ceo | XXXXXXXXXXXXXXXXXXXX |
| WV-8164 | AGGCATGAAGCAGGAACATA | 750 | Aeo*Geo*Geo*m5Ceo*Aeo*T*G*A*A*G*C*A*G*G*A*A*m5Ceo*Aeo*Teo*Aeo | XXXXXXXXXXXXXXXXXXXX |
| WV-8165 | AAGGCATGAAGCAGGAACAT | 751 | Aeo*Aeo*Geo*Geo*m5Ceo*A*T*G*A*A*G*C*A*G*G*A*A*m5Ceo*Aeo*Teo | XXXXXXXXXXXXXXXXXXXX |
| WV-8166 | AAAGGCATGAAGCAGGAACA | 752 | Aeo*Aeo*Aeo*Geo*Geo*C*A*T*G*A*A*G*C*A*G*G*A*A*m5Ceo*Aeo | XXXXXXXXXXXXXXXXXXXX |
| WV-8167 | GAAAGGCATGAAGCAGGAAC | 753 | Geo*Aeo*Aeo*Aeo*Geo*G*C*A*T*G*A*A*G*C*A*G*G*A*A*m5Ceo | XXXXXXXXXXXXXXXXXXXX |
| WV-8168 | AGAAAGGCATGAAGCAGGAA | 754 | Aeo*Geo*Aeo*Aeo*Aeo*G*G*C*A*T*G*A*A*G*C*A*G*G*A*A | XXXXXXXXXXXXXXXXXXXX |
| WV-8169 | TAGAAAGGCATGAAGCAGGA | 755 | Teo*Aeo*Geo*Aeo*Aeo*A*G*G*C*A*T*G*A*A*G*C*A*G*G*A | XXXXXXXXXXXXXXXXXXXX |
| WV-8170 | GTAGAAAGGCATGAAGCAGG | 756 | Geo*Teo*Aeo*Geo*Aeo*A*A*G*G*C*A*T*G*A*A*G*C*A*G*G | XXXXXXXXXXXXXXXXXXXX |
| WV-8171 | TGTAGAAAGGCATGAAGCAG | 757 | Teo*Geo*Teo*Aeo*Geo*A*A*A*G*G*C*A*T*G*A*A*G*C*A*G | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8172 | CTGTAGAAAGGCATGAAGCA | 758 | m5Ceo*Teo*Geo*Teo*Aeo*G*A*A*A*G*C*A*T*G*Aeo*Teo*Aeo*Geo*m5Ceo*Aeo | XXXXXXXXXXXXXXXXXXXX |
| WV-8173 | ACTGTAGAAAGGCATGAAGC | 759 | Aeo*m5Ceo*Teo*Geo*Teo*A*G*A*A*A*G*G*C*A*T*Geo*Aeo*Aeo*Geo*m5Ceo | XXXXXXXXXXXXXXXXXXXX |
| WV-8174 | CACTGTAGAAAGGCATGAAG | 760 | m5Ceo*Aeo*m5Ceo*Teo*Geo*T*A*G*A*A*A*G*G*C*A*Teo*Geo*Aeo*Aeo*Geo | XXXXXXXXXXXXXXXXXXXX |
| WV-8175 | CCACTGTAGAAAGGCATGAA | 761 | m5Ceo*m5Ceo*Aeo*m5Ceo*Teo*G*T*A*G*A*A*A*G*G*C*Aeo*Teo*Geo*Aeo*Aeo | XXXXXXXXXXXXXXXXXXXX |
| WV-8176 | GCCACTGTAGAAAGGCATGA | 762 | Geo*m5Ceo*m5Ceo*Aeo*m5Ceo*T*G*T*A*G*A*A*A*G*G*m5Ceo*Aeo*Teo*Geo*Aeo | XXXXXXXXXXXXXXXXXXXX |
| WV-8177 | GGCCACTGTAGAAAGGCATG | 763 | Geo*Geo*m5Ceo*m5Ceo*Aeo*C*T*G*T*A*G*A*A*A*G*Geo*m5Ceo*Aeo*Teo*Geo | XXXXXXXXXXXXXXXXXXXX |
| WV-8178 | AGGCCACTGTAGAAAGGCAT | 764 | Aeo*Geo*Geo*m5Ceo*m5Ceo*A*C*T*G*T*A*G*A*A*A*Geo*Geo*m5Ceo*Aeo*Teo | XXXXXXXXXXXXXXXXXXXX |
| WV-8179 | AAGGCCACTGTAGAAAGGCA | 765 | Aeo*Aeo*Geo*Geo*m5Ceo*C*A*C*T*G*T*A*G*A*A*Aeo*Geo*Geo*m5Ceo*Aeo | XXXXXXXXXXXXXXXXXXXX |
| WV-8180 | TAAGGCCACTGTAGAAAGGC | 766 | Teo*Aeo*Aeo*Geo*Geo*C*C*A*C*T*G*T*A*G*A*Aeo*Aeo*Geo*Geo*m5Ceo | XXXXXXXXXXXXXXXXXXXX |
| WV-8181 | ATAAGGCCACTGTAGAAAGG | 767 | Aeo*Teo*Aeo*Aeo*Geo*G*C*C*A*C*T*G*T*A*G*Aeo*Aeo*Aeo*Geo*Geo | XXXXXXXXXXXXXXXXXXXX |
| WV-8182 | GATAAGGCCACTGTAGAAAG | 768 | Geo*Aeo*Teo*Aeo*Aeo*G*G*C*C*A*C*T*G*T*A*Geo*Aeo*Aeo*Aeo*Geo | XXXXXXXXXXXXXXXXXXXX |
| WV-8183 | GGATAAGGCCACTGTAGAAA | 769 | Geo*Geo*Aeo*Teo*Aeo*A*G*G*C*C*A*C*T*G*T*Aeo*Geo*Aeo*Aeo*Aeo | XXXXXXXXXXXXXXXXXXXX |
| WV-8184 | CAUGAAGCAGGAACAUACCA | 770 | m5IC*mA*mU*mG*mA*A*G*C*A*G*G*A*A*C*A*mU*mA*mC*mC*IA | XXXXXXXXXXXXXXXXXXXX |
| WV-8185 | GCAUGAAGCAGGAACAUACC | 771 | IG*mC*mA*mU*mG*A*A*G*C*A*G*G*A*A*C*mA*mU*mA*mC*m5IC | XXXXXXXXXXXXXXXXXXXX |
| WV-8186 | GGCAUGAAGCAGGAACAUAC | 772 | IG*IG*mC*mA*mU*G*A*A*G*C*A*G*G*A*A*mC*mA*mU*mA*m5IC | XXXXXXXXXXXXXXXXXXXX |
| WV-8187 | AGGCAUGAAGCAGGAACAUA | 773 | IA*mG*mG*mC*mA*T*G*A*A*G*C*A*G*G*A*mA*mC*mA*mU*IA | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8188 | AAGGCATGAAGCAGGAACAT | 774 | IA*mA*mG*mC*mA*T*G*A*A*G*C*A*G*G*mA*mA*mC*mA*IT | XXXXXXXXXXXXXXXXXXXX |
| WV-8189 | AAAGGCATGAAGCAGGAACA | 775 | IA*mA*mA*mG*mG*C*A*T*G*A*A*G*C*A*G*mG*mA*mA*mC*IA | XXXXXXXXXXXXXXXXXXXX |
| WV-8190 | GAAAGGCATGAAGCAGGAAC | 776 | IG*mA*mA*mA*mG*G*C*A*T*G*A*A*G*C*A*mG*mG*mA*mA*m5IC | XXXXXXXXXXXXXXXXXXXX |
| WV-8191 | AGAAAGGCATGAAGCAGGAA | 777 | IA*mG*mA*mA*mA*G*G*C*A*T*G*A*A*G*C*mA*mG*mG*mA*IA | XXXXXXXXXXXXXXXXXXXX |
| WV-8192 | TAGAAAGGCATGAAGCAGGA | 778 | IT*mA*mG*mA*mA*A*A*G*G*C*A*T*G*A*A*mG*mC*mA*mG*mG*IA | XXXXXXXXXXXXXXXXXXXX |
| WV-8193 | GTAGAAAGGCATGAAGCAGG | 779 | IG*mU*mA*mG*mA*A*A*A*G*G*C*A*T*G*A*mA*mG*mC*mA*mG*IG | XXXXXXXXXXXXXXXXXXXX |
| WV-8194 | TGTAGAAAGGCATGAAGCAG | 780 | IT*mG*mU*mA*mG*A*A*A*A*G*G*C*A*T*G*mA*mA*mG*mC*mA*IG | XXXXXXXXXXXXXXXXXXXX |
| WV-8195 | CTGTAGAAAGGCATGAAGCA | 781 | m5IC*mU*mG*mU*mA*G*A*A*A*A*G*G*C*A*T*mG*mA*mA*mG*mC*IA | XXXXXXXXXXXXXXXXXXXX |
| WV-8196 | ACTGTAGAAAGGCATGAAGC | 782 | IA*mC*mU*mG*mU*A*G*A*A*A*A*G*G*C*A*mT*mG*mA*mA*mG*m5IC | XXXXXXXXXXXXXXXXXXXX |
| WV-8197 | CACTGTAGAAAGGCATGAAG | 783 | m5IC*mA*mC*mU*mG*T*A*G*A*A*A*A*G*G*C*A*mT*mG*mA*mA*IG | XXXXXXXXXXXXXXXXXXXX |
| WV-8198 | CCACTGTAGAAAGGCATGAA | 784 | m5IC*mC*mA*mC*mU*G*T*A*G*A*A*A*A*G*G*C*mA*mT*mG*mA*IA | XXXXXXXXXXXXXXXXXXXX |
| WV-8199 | GCCACTGTAGAAAGGCATGA | 785 | IG*mC*mC*mA*mC*T*G*T*A*G*A*A*A*A*G*mG*mC*mA*mT*mG*IA | XXXXXXXXXXXXXXXXXXXX |
| WV-8200 | GGCCACTGTAGAAAGGCATG | 786 | IG*mG*mC*mC*mA*C*T*G*T*A*G*A*A*A*A*mG*mG*mC*mA*mT*IG | XXXXXXXXXXXXXXXXXXXX |
| WV-8201 | AGGCCACTGTAGAAAGGCAT | 787 | IA*mG*mG*mC*mC*A*C*T*G*T*A*G*A*A*A*mG*mG*mC*mA*IT | XXXXXXXXXXXXXXXXXXXX |
| WV-8202 | AAGGCCACTGTAGAAAGGCA | 788 | IA*mA*mG*mG*mC*C*A*C*T*G*T*A*G*A*A*mA*mG*mG*mC*IA | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8203 | TAAGGCCACTGTAGAAAGGC | 789 | IT*mA*mG*mC*C*A*C*T*G*T*A*G*A*mA*mA*mG*mG*m5IC | XXXXXXXXXXXXXXXXXXXX |
| WV-8204 | AUAAGGCCACTGTAGAAAGG | 790 | IA*mU*mA*mA*mG*C*C*A*C*T*G*T*A*G*mA*mA*mA*mG*IG | XXXXXXXXXXXXXXXXXXXX |
| WV-8205 | GAUAAGGCCACTGTAGAAAG | 791 | IG*mA*mU*mA*mA*G*C*C*A*C*T*G*T*A*mG*mA*mA*mA*IG | XXXXXXXXXXXXXXXXXXXX |
| WV-8206 | GGAUAAGGCCACTGTAGAAA | 792 | IG*mG*mA*mU*mA*A*G*C*C*A*C*T*G*T*mA*mG*mA*mA*IA | XXXXXXXXXXXXXXXXXXXX |
| WV-8207 | CATGAAGCAGGAACATACCA | 793 | m5IC*Aeo*Teo*Geo*Aeo*A*G*C*A*G*G*A*A*C*A*Teo*m5Ceo*m5Ceo*IA | XXXXXXXXXXXXXXXXXXXX |
| WV-8208 | GCATGAAGCAGGAACATACC | 794 | IG*m5Ceo*Aeo*Teo*Geo*A*A*G*C*A*G*G*A*A*C*Aeo*Teo*Aeo*m5Ceo*m5IC | XXXXXXXXXXXXXXXXXXXX |
| WV-8209 | GGCATGAAGCAGGAACATAC | 795 | IG*Geo*m5Ceo*Aeo*Teo*G*A*A*G*C*A*G*G*A*A*m5Ceo*Aeo*Teo*Aeo*m5IC | XXXXXXXXXXXXXXXXXXXX |
| WV-8210 | AGGCATGAAGCAGGAACATA | 796 | IA*Geo*Geo*m5Ceo*Aeo*T*G*A*A*G*C*A*G*G*A*A*Ceo*Aeo*Teo*IA | XXXXXXXXXXXXXXXXXXXX |
| WV-8211 | AAGGCATGAAGCAGGAACAT | 797 | IA*Aeo*Geo*Geo*m5Ceo*A*T*G*A*A*G*C*A*G*G*A*A*m5Ceo*Aeo*IT | XXXXXXXXXXXXXXXXXXXX |
| WV-8212 | AAAGGCATGAAGCAGGAACA | 798 | IA*Aeo*Aeo*Geo*Geo*C*A*T*G*A*A*G*C*A*G*G*A*A*m5Ceo*IA | XXXXXXXXXXXXXXXXXXXX |
| WV-8213 | GAAAGGCATGAAGCAGGAAC | 799 | IG*Aeo*Aeo*Aeo*Geo*G*C*A*T*G*A*A*G*C*A*G*G*Aeo*Aeo*m5IC | XXXXXXXXXXXXXXXXXXXX |
| WV-8214 | AGAAAGGCATGAAGCAGGAA | 800 | IA*Geo*Aeo*Aeo*Aeo*G*G*C*A*T*G*A*A*G*C*A*G*G*Aeo*IA | XXXXXXXXXXXXXXXXXXXX |
| WV-8215 | TAGAAAGGCATGAAGCAGGA | 801 | IT*Aeo*Geo*Aeo*Aeo*A*G*G*C*A*T*G*A*A*G*C*A*G*Geo*IA | XXXXXXXXXXXXXXXXXXXX |
| WV-8216 | GTAGAAAGGCATGAAGCAGG | 802 | IG*Teo*Aeo*Geo*Aeo*A*A*G*G*C*A*T*G*A*A*G*C*A*Geo*IG | XXXXXXXXXXXXXXXXXXXX |
| WV-8217 | TGTAGAAAGGCATGAAGCAG | 803 | IT*Geo*Teo*Aeo*Geo*A*A*A*G*G*C*A*T*G*A*A*G*C*Aeo*IG | XXXXXXXXXXXXXXXXXXXX |
| WV-8218 | CTGTAGAAAGGCATGAAGCA | 804 | m5IC*Teo*Geo*Teo*Aeo*G*A*A*A*G*G*C*A*T*G*A*A*G*m5Ceo*IA | XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8219 | ACTGTAGAAAGGCATGAAGC | 805 | IA*m5Ceo*Teo*Geo*Teo*A*G*A*A*A*G*C* A*T*Geo*Aeo*Aeo*m5IC | XXXXXXXXXXXXXXXXXXXX |
| WV-8220 | CACTGTAGAAAGGCATGAAG | 806 | m5IC*Aeo*m5Ceo*Teo*Geo*T*A*G*A*A*A*G* G*C*A*Teo*Geo*Aeo*Aeo*IG | XXXXXXXXXXXXXXXXXXXX |
| WV-8221 | CCACTGTAGAAAGGCATGAA | 807 | m5IC*m5Ceo*Aeo*m5Ceo*Teo*G*T*A*G*A*A*A *G*G*C*Aeo*Teo*Geo*Aeo*IA | XXXXXXXXXXXXXXXXXXXX |
| WV-8222 | GCCACTGTAGAAAGGCATGA | 808 | IG*m5Ceo*m5Ceo*Aeo*m5Ceo*T*G*T*A*G*A*A *A*G*m5Ceo*Aeo*Teo*Geo*IA | XXXXXXXXXXXXXXXXXXXX |
| WV-8223 | GGCCACTGTAGAAAGGCATG | 809 | IG*Geo*m5Ceo*m5Ceo*Aeo*C*T*G*T*A*G*A* A*A*G*Aeo*m5Ceo*Aeo*Teo*IG | XXXXXXXXXXXXXXXXXXXX |
| WV-8224 | AGGCCACTGTAGAAAGGCAT | 810 | IA*Geo*Geo*m5Ceo*m5Ceo*A*C*T*G*T*A*G* A*A*A*Geo*Geo*m5Ceo*Aeo*IT | XXXXXXXXXXXXXXXXXXXX |
| WV-8225 | AAGGCCACTGTAGAAAGGCA | 811 | IA*Aeo*Geo*Geo*m5Ceo*C*A*C*T*G*T*A*G* A*A*Aeo*Geo*Geo*m5Ceo*IA | XXXXXXXXXXXXXXXXXXXX |
| WV-8226 | TAAGGCCACTGTAGAAAGGC | 812 | IT*Aeo*Aeo*Geo*Geo*C*C*A*C*T*G*T*A*G* A*Aeo*Aeo*Geo*Geo*m5IC | XXXXXXXXXXXXXXXXXXXX |
| WV-8227 | ATAAGGCCACTGTAGAAAGG | 813 | IA*Teo*Aeo*Aeo*Geo*G*C*C*A*C*T*G*T*A* G*Aeo*Aeo*Aeo*Geo*IG | XXXXXXXXXXXXXXXXXXXX |
| WV-8228 | GATAAGGCCACTGTAGAAAG | 814 | IG*Aeo*Teo*Aeo*Aeo*G*C*C*A*C*T*G*T* A*Geo*Aeo*Aeo*Aeo*IG | XXXXXXXXXXXXXXXXXXXX |
| WV-8229 | GGATAAGGCCACTGTAGAAA | 815 | IG*Geo*Aeo*Teo*Aeo*A*G*C*C*A*C*T*G* T*Aeo*Geo*Aeo*Aeo*IA | XXXXXXXXXXXXXXXXXXXX |
| WV-8071 | TGCCACUGUAGAAAGG CAUTUTTTTTGG TAATCCACTTTCAGAGG | 816 | T*SfG*SmCfC*SmAfC*SmUfG*SmUfA*SmGfA* SmAfA*SmG*SfG*SmC*SfA*SmU*ST*SmUTTTTTeo *Geo*Geo*Teo*Aeo*A*T*m5C*m5C*A*m5C*T *T*T*m5C*Aeo*Geo*Aeo*Geo*GeoL003Mod001 | SSOSOSOSOSOSOSSSSSS OOOOO XXXXXXXXXXXXXXXXXXXO |
| WV-8069 | TGCCACUGUAGAAAGG CAUTUTTTTTGG TAATCCACTTTCAGAGG | 817 | T*SfG*SmCfC*SmAfC*SmUfG*SmUfA*SmGfA* SmAfA*SmG*SfG*SmC*SfA*SmU*STGaNC6T* SmUTTTTTeo*Geo*Teo*Aeo*A*T*m5C*m5C *A*m5C*T*T*m5C*Aeo*Geo*Aeo*Geo | SSOSOSOSOSOSOSSSSSS OOOOO XXXXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8067 | TGCCACUGUAGAAAGG CAUUUUUUGG TAATCCACTTTCAGAGG | 818 | VPT*SfG*SmCfC*SmAfC*SmUfG*SmUfA**SmGfA* SmAfA*SmG*SfG*SmC*SfA*SmU*ST*SmUTTTTeo *Geo*Geo*Teo*Aeo*A*T*m5C**m5C*A*m5C*T *T*T*m5C*Aeo*Geo*Aeo*Geo*GeoL003Mod001 | SSOSOSOSOSOSOSSSSSS OOOOO XXXXXXXXXXXXXXXXXXXXO |
| WV-8065 | TGCCACUGUAGAAAGG CAUUUUUUGG TAATCCACTTTCAGAGG | 819 | VPT*SfG*SmCfC*SmAfC*SmUfG*SmUfA**SmGfA* SmAfA*SmG*SfG*SmC*SfA*SmU*STGaNC6T* SmUTTTTeo*Geo*Geo*Teo*Aeo*A*T*m5C*m5C *A*m5C**T*T*m5C*Aeo*Geo*Aeo*Geo*Geo | SSOSOSOSOSOSOSSSSSS SOOOOO XXXXXXXXXXXXXXXXXXXXX |
| WV-8063 | TGCCACUGUAGAAAGG CAUUUUUUGG TAATCCACTTTCAGAGG | 820 | VPT*fG*mCfC*mAfC*mUfG*mUfA*mGfA*mAfA* mGfGmCfAmU*TGaNC6T*mUTTTTTeo*Geo*Geo*Teo *Aeo*A*T*m5C*m5C*A*m5C*T*T*m5C* Aeo*Geo*Geo*Geo | XXOXOXOXOXOXOXOOOO XXOOOOOXXXXXXXXXXXX XXXXXXXX |
| WV-8233 | UUGGUAUGUUCCUGCUUCAU GCCUUUCUACAGUGGCCCUUAUCCC | 821 | rUrUrGrGrUrArUrGrUrUrCrCrUrGrCrU rUrCrArUrGrCrCrUrUrCrUrArCrArG rUrGrGrCrCrUrUrArUrCrCrC | OOOOOOOOOOOOOOOOOOO OOOOOOOOOOOOOOOOOOO OOO |
| WV-8234 | UUGGUAUGUUCCUGCUUCAU CCCCUUCUACAGUGGCCCUUAUCCC | 822 | rUrUrGrGrUrArUrGrUrUrCrCrUrGrCrU rUrCrArUrCrCrCrCrUrUrCrUrArCrArG rUrGrGrCrCrUrUrArUrCrCrC | OOOOOOOOOOOOOOOOOOO OOOOOOOOOOOOOOOOOOO OOO |
| WV-8235 | CTGTAGAAAGGCATGAAGCA | 823 | L001m5Ceo*TeoGeoTeoAeo*G*A*A*A* G*G*C*A*T*G*AeoAeoGeom5Ceo* Aeo | OXOOOXXXXXXXXXXXOOOX |
| WV-8236 | CTGTAGAAAGGCATGAAGCA | 824 | L001m5Ceo*RTeoGeoGeoTeoAeo*RG*SA*SA *SA*SG*RG*SC*SA*RT*SG* SAeoAeoGeom5Ceo*RAeo | OROOORSSSRSRSSOOOR |
| WV-8237 | CCACTGTAGAAAGGCATGAAGCA | 825 | L001m5Ceo*m5CeoAeom5CeoTeo*G*T*A *G*A*A*A*G*C*AeoTeoGeoAeo* Aeo | OXOOOXXXXXXXXXXXOOOX |
| WV-8238 | CCACTGTAGAAAGGCATGAAGCA | 826 | L001m5Ceo*Rm5CeoAeom5CeoTeo*RG* ST*SA*SG*SA*SA*SA*SG*RG*SC* SAeoTeoGeoAeo*RAeo | OROOORSSSSSSRSSOOOR |
| WV-8239 | CTGTAGAAAGGCATGAAGCA | 827 | L001m5Ceo*Teo*Geo*Teo*Aeo*G*A* A*A*G*G*C*A*T*G*Aeo*Aeo*Geo *m5Ceo*Aeo | OXXXXXXXXXXXXXXXXXXX |
| WV-8240 | CTGTAGAAAGGCATGAAGCA | 828 | L001m5Ceo*RTeo*RGeo*RTeo*RAeo* RG*SA*SA*SG*RG*SC*SA*RT* SG*SAeo*RAeo*RGeo*Rm5Ceo*RAeo | ORRRRSSSRSSRSRSRRRR |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-2477 | CCUUCCCUGAAGGUUCCUCC | 829 | POmC*fC*mUfU*mCfC*mCfU*mGfA* mAfG*mGfU*mU*fC*mC*fU*mC*mC | XXOXOXOXOXOXXXXXXX |
| WV-8241 | TGCCACUGUAGAAAGGCAUGAUTU | 830 | PO5MRdT*SfG*SmCfC*SmAfC*SmUfG*SmUfA*SmGfA* SmAfA*SmG*sfG*SmC*sfA*SmU*sfG*SmA*STGaNC6T* SmU | SSOSOSOSOSO SSSSSSSSS |
| WV-8244 | CTGTAGAAAGGCATGAAGCA | 831 | mC*STeomGTeomA*SG*SA*SA*SA*SA*SG*RG*SC*SA*RT* SG*SmAmAmGmC*SmA | SOOOSSSSSRSSRSS OOOS |
| WV-8245 | CTGTAGAAAGGCATGAAGCA | 832 | m5Ceo*RTeoGeoTeoAeo*RG*SA*SA*SA*SG*RG*SC*SA* RT*SG*SAeoAeoGeom5Ceo*RAeo | ROOORSSSSRSSRSS OOOR |
| WV-8246 | CTGTAGAAAGGCATGAAGCA | 833 | m5IC*STeomGTeomA*SG*SA*SA*SA*SA*SG*RG*SC*SA*RT *SG*SmAmAmGmC*SIA | SOOOSSSSSRSSRSS OOOS |
| WV-8247 | CTGTAGAAAGGCATGAAGCA | 834 | m5IC*RTeoGeoTeoAeo*RG*SA*SA*SA*SG*RG*SC*SA*RT *SG*SAeoAeoGeom5Ceo*RIA | ROOORSSSSRSSRSS OOOR |
| WV-8248 | CCACUGTAGAAAGGCATGAA | 835 | mC*Sm5CeomAm5CeomU*SG*ST*SA*SG*SA*SA*SA*SG* RG*SC*SmATeomGmA*SmA | SOOOSSSSSSSSRSS OOOS |
| WV-8249 | CCACTGTAGAAAGGCATGAA | 836 | m5Ceo*Rm5CeoAeom5CeoTeo*RG*ST*SA*SG*SA*SA*SA* SG*RG*SC*SAeoTeoGeoAeo*RAeo | ROOORSSSSSSSSRSS OOOR |
| WV-8250 | CCACTGTAGAAAGGCATGAA | 837 | m5IC*Sm5CeomAm5CeomU*SG*ST*SA*SG*SA*SA*SA*SG *RG*SC*SmATeomGmA*SIA | SOOOSSSSSSSSRSS OOOS |
| WV-8251 | CCACTGTAGAAAGGCATGAA | 838 | m5IC*Rm5CeoAeom5CeoTeo*RG*ST*SA*SG*SA*SA*SA* SG*RG*SC*SAeoTeoGeoAeo*RIA | ROOORSSSSSSSSRSS OOOR |
| WV-8252 | CTGTAGAAAGGCATGAAGCA | 839 | m5Ceo*RTeo*RGeo*RTeo*RAeo*RG*SA*SA*SA*SG*RG *SC*SA*RT*SG*sAeo*RAeo*RGeo*Rm5Ceo*RAeo | RRRRRSSSSRSS RSSRRRR |
| WV-8253 | CCACTGTAGAAAGGCATGAA | 840 | m5Ceo*Rm5Ceo*RAeo*Rm5Ceo*RTeo*RG*ST*SA*SG*SA *SA*SA*SG*RG*SC*SAeo*RTeo*RGeo*RAeo*RAeo | RRRRRSSSSSSS RSSRRRR |
| WV-8255 | TGCCACUGUAGAAAGGCAUTU TTTTTGGTAATCCACTTTCAGAGG | 841 | VPT*fG*mCfC*mAfC*mUfG*mUfA*mGfA*mAfA* mGfGmCfAmU*AMC6T*mUTTTTTeo*Geo*Geo*Teo*Aeo*A *T*m5C*m5C*A*m5C*T*T*T*m5C*A*eo*Geo*Aeo* Geo*Geo | XXOXOXOXOXOX OOOXXOOOO XXXXXXXXX XXXXXXXX |
| WV-8256 | GGACCTGAGGATGGACCGCG | 842 | L001mG*SmG*SmA*SmC*SmC*ST*SG*RA*SG*SG*RA* ST*SG*RG*SA*SmC*SmC*SmG*SmC*SmG | OSSSSSSRSRSSR SSSSSS |
| WV-8257 | GGACCTGAGGATGGACCGCG | 843 | L001mG*SmG*SmA*SmC*SmC*ST*SG*RA*SG*SG*RA* ST*SG*RG*SA*Sm5Ceo*Rm5Ceo*RGeo*RGeo*Rm5Ceo*RGeo | OSSSSSSRSRSS RSSRRRR |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8258 | GGACCTGAGGATGGACCGCG | 844 | L001mG*SmG*SmA*SmC*SmC*ST*SG*RA*SG*SG*SA*ST*SG*RG*SA*SmC*SmC*SmG*SmC*SmG | OSSSSSSRSSSSSR SSSSSS |
| WV-8259 | GGACCTGAGGATGGACCGCG | 845 | L001mG*SmG*SmA*SmC*SmC*ST*SG*RA*SG*SG*SA*ST*SG*RG*SA*Sm5Ceo*Rm5Ceo*Rm5Ceo*RGeo | OSSSSSSRSSSSS RSSRRRR |
| WV-8260 | TGCCACUGUAGAAAGGCAUGATU | 846 | PO5MRdT*SfG*SmCfC*SmAfC*SmUfG*SmUfA*SmGfA*SmAfA*SmG*SmC*SfA*SmU*SfG*SmA*SAmC6T*SmU | SSOSOSOSOSO SSSSSSSS |
| WV-8263 | TGCCACUGUAGAAAGGCAUTU | 847 | 5MSdT*fG*mCfC*mAfC*mUfG*mUfA*mGfA*mAfA*mGfGmCfAmU*T*mU | XXOXOXOXOXOX OOOOXX |
| WV-8264 | TGCCACUGUAGAAAGGCAUTU | 848 | PO5MSdT*fG*mCfC*mAfC*mUfG*mUfA*mGfA*mAfA*mGfGmCfAmU*T*mU | XXOXOXOXOXOX OOOOXX |
| WV-8265 | TGCCACUGUAGAAAGGCAUTU | 849 | PS5MSdT*fG*mCfC*mAfC*mUfG*mUfA*mGfA*mAfA*mGfGmCfAmU*T*mU | XXOXOXOXOXOX OOOOXX |
| WV-8266 | TGCCACUGUAGAAAGGCAUTU | 850 | PH5MSdT*fG*mCfC*mAfC*mUfG*mUfA*mGfA*mAfA*mGfGmCfAmU*T*mU | XXOXOXOXOXOX OOOOXX |
| WV-8267 | TGCCACUGUAGAAAGGCAUTU | 851 | 5MRdT*fG*mCfC*mAfC*mUfG*mUfA*mGfA*mAfA*mGfGmCfAmU*T*mU | XXOXOXOXOXOX OOOOXX |
| WV-8268 | TGCCACUGUAGAAAGGCAUTU | 852 | PO5MRdT*fG*mCfC*mAfC*mUfG*mUfA*mGfA*mAfA*mGfGmCfAmU*T*mU | XXOXOXOXOXOX OOOOXX |
| WV-8269 | TGCCACUGUAGAAAGGCAUTU | 853 | PS5MRdT*fG*mCfC*mAfC*mUfG*mUfA*mGfA*mAfA*mGfGmCfAmU*T*mU | XXOXOXOXOXOX OOOOXX |
| WV-8270 | TGCCACUGUAGAAAGGCAUTU | 854 | PH5MRdT*fG*mCfC*mAfC*mUfG*mUfA*mGfA*mAfA*mGfGmCfAmU*T*mU | XXOXOXOXOXOX OOOOXX |
| WV-8271 | TGCCACUGUAGAAAGGCAUGATU | 855 | 5MSdT*fG*mCfC*mAfC*mUfG*mUfA*mGfA*mAfA*mGfGmCfAmUfGmA*T*mU | XXOXOXOXOXOX OOOOOOXX |
| WV-8272 | TGCCACUGUAGAAAGGCAUGATU | 856 | PO5MSdT*fG*mCfC*mAfC*mUfG*mUfA*mGfA*mAfA*mGfGmCfAmUfGmA*T*mU | XXOXOXOXOXOX OOOOOOXX |
| WV-8273 | TGCCACUGUAGAAAGGCAUGATU | 857 | PS5MSdT*fG*mCfC*mAfC*mUfG*mUfA*mGfA*mAfA*mGfGmCfAmUfGmA*T*mU | XXOXOXOXOXOX OOOOOOXX |
| WV-8274 | TGCCACUGUAGAAAGGCAUGATU | 858 | PH5MSdT*fG*mCfC*mAfC*mUfG*mUfA*mGfA*mAfA*mGfGmCfAmUfGmA*T*mU | XXOXOXOXOXOX OOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8275 | TGCCACUGUAGAAAGGCAUGAUU | 859 | 5MRdT*fG*mCfC*mAfC*mUfG*mUfA*mGfA*mAfA* mGfGmCfAmUfGmA*T*mU | XXOXOXOXOXOXOX OOOOOOXX |
| WV-8276 | TGCCACUGUAGAAAGGCAUGAUU | 860 | PO5MRdT*fG*mCfC*mAfC*mUfG*mUfA*mGfA*mAfA* mGfGmCfAmUfGmA*T*mU | XXXOXOXOXOXOXOX OOOOOOXX |
| WV-8277 | TGCCACUGUAGAAAGGCAUGAUU | 861 | PS5MRdT*fG*mCfC*mAfC*mUfG*mUfA*mGfA*mAfA* mGfGmCfAmUfGmA*T*mU | XXXOXOXOXOXOXOX OOOOOOXX |
| WV-8278 | TGCCACUGUAGAAAGGCAUGAUU | 862 | PH5MRdT*fG*mCfC*mAfC*mUfG*mUfA*mGfA*mAfA* mGfGmCfAmUfGmA*T*mU | XXXOXOXOXOXOXOX OOOOOOXX |
| WV-8279 | CCACTGTAGAAAGGCATGAA | 863 | Mod001L001m5Ceo*m5Ceo*Aeo*m5Ceo*Teo*G*T*A*G* A*A*A*G*C*Aeo*Teo*Geo*Aeo*Aeo | OXXXXXXXXXXX XXXXXXXXX |
| WV-8280 | CCACTGTAGAAAGGCATGAA | 864 | Mod001L001m5Ceo*Rm5Ceo*RAeo*Rm5Ceo*RTeo*RG*ST* SA*SG*SA*SA*SG*RG*SC*SAeo*RTeo*RGeo*RAeo *RAeo | ORRRRRSSSSSS RSSRRRR |
| WV-8323 | CCACTGTAGAAAGGCATGAA | 865 | L001m5Ceo*m5Ceo*Aeo*m5Ceo*Teo*G*T*A*G*A*A* A*G*C*Aeo*Teo*Geo*Aeo*Aeo | OXXXXXXXXXX XXXXXXXXX |
| WV-8324 | CCACTGTAGAAAGGCATGAA | 866 | L001m5Ceo*Rm5Ceo*RAeo*Rm5Ceo*RTeo*RG*ST*SA*SG *SA*SA*SG*RG*SC*SAeo*RTeo*RGeo*RAeo*RAeo | ORRRRRSSSSSS RSSRRRR |
| WV-8436 | TGCCACUGUAGAAAGGCAUUU | 867 | T*fG*mCnC*mAmC*mUmG*mUmA*mGmA*mAfA* mGmGmCmAmU*T*mU | XXXOXOXOXOXOXOX OOOOXX |
| WV-8437 | TGCCACUGUAGAAAGGCAUGAUU | 868 | T*fG*mCmC*mAmC*mUmG*mUmA*mGmA*mAfA* mGmGmCmAmUmG*mA*T*mU | XXXOXOXOXOXOXOX OOOOOOXX |
| WV-8438 | TGCCACUGUAGAAAGGCAUGAUU | 869 | T*fG*mCmC*mAmC*mUmG*mUmA*mGmA*mAfA*mG* mG*mC*mA*mU*T*mU | XXXOXOXOXOXOXO XXXXXXX |
| WV-8439 | TGCCACUGUAGAAAGGCAUGAUU | 870 | T*fG*mCmC*mAmC*mUmG*mUmA*mGmA*mAfA*mG* mG*mC*mA*mU*mG*mA*T*mU | XXXOXOXOXOXOXO XXXXXXXXX |
| WV-8440 | TGCCACUGUAGAAAGGCAUGAUU | 871 | T*mG*mCmC*mAmC*mUmG*mUmA*mGmA*mAmA* mGmGmCmAmU*T*mU | XXXOXOXOXOXOXOX OOOOXX |
| WV-8441 | TGCCACUGUAGAAAGGCAUGAUU | 872 | T*mG*mCmC*mAmC*mUmG*mUmA*mGmA*mAmA* mGmGmCmAmUmG*mA*T*mU | XXXOXOXOXOXOXOX OOOOOOXX |
| WV-8442 | TGCCACUGUAGAAAGGCAUUU | 873 | T*mG*mCmC*mAmC*mUmG*mUmA*mGmA*mAmA*mG *mG*mC*mA*mU*T*mU | XXXOXOXOXOXOXO XXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8443 | TGCCACUGUAGAAAGGCAUGAUU | 874 | T*mG*mCmC*mAmC*mUmG*mUmA*mGnA*mAmA*mG*mG*mC*mA*mU*mG*mA*T*mU | XXOXOXOXOXOXO XXXXXXXXX |
| WV-8558 | CTGTAGAAAGGCATGAAGCA | 875 | Mod001L001m5Ceo*RTeoGeoTeoAeo*RG*SA*SA*SA*SG*RG*SC*SA*RT*SG*SAeo*SAeo*SGeo*Sm5Ceo*SAeo | OROOORSSSSSRSSR SSSSSS |
| WV-8559 | CCACTGTAGAAAGGCATGAA | 876 | Mod001L001m5Ceo*Rm5CeoAeom5CeoTeo*RG*ST*SA*SG*SA*SA*SG*RG*SC*SA*SG*SC*SAeo*STeo*SGeo*SAeo | OROOORSSSSSSSSR SSSSSS |
| WV-8560 | CTGTAGAAAGGCATGAAGCA | 877 | Mod001L001m5Ceo*RTeoGeoTeoAeo*RG*SA*SA*SA*SG*RG*SC*SA*RT*SG*SmA*SmA*SmG*SmC*SmA | OROOORSSSSSRSSR SSSSSS |
| WV-8561 | CCACTGTAGAAAGGCATGAA | 878 | Mod001L001m5Ceo*Rm5CeoAeom5CeoTeo*RG*ST*SA*SG*SA*SA*SG*RG*SC*SA*SG*SC*SmA*SmU*SmG*SmA*SmA | OROOORSSSSSSSSR SSSSSS |
| WV-8562 | CTGTAGAAAGGCATGAAGCA | 879 | Mod001L001mC*STeoGeoTeomA*SG*SA*SA*SA*SG*RG*SC*SA*RT*SG*SAeo*SAeo*SGeo*Sm5Ceo*SAeo | OSOOOSSSSSRSSR SSSSSS |
| WV-8563 | CCACUGTAGAAAGGCATGAA | 880 | Mod001L001mC*Sm5CeoAeom5CeomU*SG*ST*SA*SA*SG*SA*SA*SG*RG*SC*SA*SG*SC*SAeo*STeo*SGeo*SAeo | OSOOOSSSSSSSSR SSSSSS |
| WV-8564 | CTGTAGAAAGGCATGAAGCA | 881 | Mod001L001mC*STeoGeoTeomA*SG*SA*SA*SA*SG*RG*SC*SA*RT*SG*SmA*SmA*SmG*SmC*SmA | OSOOOSSSSSRSSR SSSSSS |
| WV-8565 | CCACUGTAGAAAGGCATGAA | 882 | Mod001L001mC*Sm5CeoAeom5CeomU*SG*ST*SA*SG*SA*SA*SG*RG*SC*SA*SG*SC*SmA*SmU*SmG*SmA*SmA | OSOOOSSSSSSSSR SSSSSS |
| WV-8566 | CTGTAGAAAGGCATGAAGCA | 883 | Mod001L001m5Ceo*STeoGeoTeoAeo*SG*SA*SA*SA*SG*RG*SC*SA*RT*SG*SAeoAeoGeom5Ceo*SAeo | OSOOOSSSSSRSSRSS OOS |
| WV-8567 | CCACUGTAGAAAGGCATGAA | 884 | Mod001L001m5Ceo*Sm5CeoAeom5CeoTeo*SG*ST*SA*SG*SA*SA*SG*RG*SC*SAeoTeoGeoAeo*SAeo | OSOOOSSSSSSSRSS OOS |
| WV-8596 | CTGTAGAAAGGCATGAAGCA | 885 | Mod001L001m5Ceo*STeoGeoTeomA*SG*SA*SA*SA*SG*SC*SA*RT*SG*SmA*SmA*SmG*SmC*SmA | OSOOOSSSSSSSSR SSSS |
| WV-8597 | CTGTAGAAAGGCATGAAGCA | 886 | Mod001L001m5Ceo*STeoGeoTeomA*SG*SA*SA*SA*SG*RG*SC*SA*ST*SG*SmA*SmA*SmG*SmC*SmA | OSOOOSSSSSRSSR SSSS |
| WV-8598 | CTGTAGAAAGGCATGAAGCA | 887 | Mod001L001m5Ceo*STeoGeoTeoAeo*SG*SA*SA*SA*SG*SG*SC*SA*RT*SG*SAeoAeoGeom5Ceo*SAeo | OSOOOSSSSSSSSRSS OOS |
| WV-8599 | CTGTAGAAAGGCATGAAGCA | 888 | Mod001L001m5Ceo*STeoGeoTeoAeo*SG*SA*SA*SA*SG*RG*SC*SA*ST*SG*SAeoAeoGeom5Ceo*SAeo | OSOOOSSSSSRSSSSS OOS |
| WV-8600 | CTGTAGAAAGGCATGAAGCA | 889 | Mod001L001mC*TeoGeoTeomA*G*A*A*G*C*A*T*G*mA*mA*mG*mC*mA | OXOOOXXXXXXXXX XXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8601 | CTGTAGAAAGGCATGAAGCA | 890 | mC*STeoGeoTeomA*SG*SA*SA*SG*RG*SC*SA*RT*SG*SmA*SmA*SmG*SmC*SmA | SOOOSSSSSRSSRSSSSSS |
| WV-8602 | CCACUGTAGAAAGGCAUGAA | 891 | mC*Sm5CeoAeom5CeomU*SG*ST*SA*SG*SA*SA*SA*SG*RG*SC*SmA*SmU*SmG*SmA*SmA | SOOOSSSSSSSSRSSSSSS |
| WV-8603 | CTGTAGAAAGGCATGAAGCA | 892 | m5Ceo*STeoGeoTeoAeo*SG*SA*SA*SA*SG*RG*SC*SA*RT*SG*SAeoAeoGeom5Ceo*SAeo | SOOOSSSSSSSSSRSSOOOS |
| WV-8604 | CCACTGTAGAAAGGCATGAA | 893 | m5Ceo*Sm5CeoAeom5CeoTeo*SG*ST*SA*SG*SA*SA*SA*SG*RG*SC*SAeoTeoGeoAeo*SAeo | SOOOSSSSSSSSSRSSOOOS |
| WV-8605 | CTGTAGAAAGGCATGAAGCA | 894 | mC*STeoGeoTeomA*SG*SA*SA*SA*SG*SG*SC*SA*RT*SG*SmA*SmA*SmG*SmC*SmA | SOOOSSSSSSSSSRSSSSSS |
| WV-8606 | CTGTAGAAAGGCATGAAGCA | 895 | mC*STeoGeoTeomA*SG*SA*SA*SA*SA*SG*RG*SC*SA*ST*SG*SmA*SmA*SmG*SmC*SmA | SOOOSSSSSSSSRSSSSSSS |
| WV-8607 | CTGTAGAAAGGCATGAAGCA | 896 | m5Ceo*STeoGeoTeoAeo*SG*SA*SA*SA*SA*SG*SG*SC*SA*RT*SG*SAeoAeoGeom5Ceo*SAeo | SOOOSSSSSSSSSRSSOOOS |
| WV-8608 | CTGTAGAAAGGCATGAAGCA | 897 | m5Ceo*STeoGeoTeoAeo*SG*SA*SA*SA*SA*SG*RG*SC*SA*ST*SG*SAeoAeoGeom5Ceo*SAeo | SOOOSSSSSSSSRSSOOOS |
| WV-8609 | CTGTAGAAAGGCATGAAGCA | 898 | mC*TeoGeoTeomA*G*A*A*A*G*C*A*T*G*mA*mA*mG*mC*mA | XOOOXXXXXXXXXXXXXX |
| WV-8620 | CTGTAGAAAGGCATGAAGCA | 899 | L001mC*STeoGeoTeomA*SG*SA*SA*SA*SA*SG*RG*SC*SA*RT*SG*SmA*SmA*SmG*SmC*SmA | OSOOOOSSSSRSSSRSSSSSS |
| WV-8621 | CCACUGTAGAAAGGCAUGAA | 900 | L001mC*Sm5CeoAeom5CeomU*SG*ST*SA*SG*SA*SA*SA*SG*RG*SC*SmA*SmU*SmG*SmA*SmA | OSOOOSSSSSSSSSSR SSSSS |
| WV-8622 | CTGTAGAAAGGCATGAAGCA | 901 | L001m5Ceo*STeoGeoTeoAeo*SG*SA*SA*SA*SA*SG*RG*SC*SA*RT*SG*SAeoAeoGeom5Ceo*SAeo | OSOOOOSSSSRSSRSSSSOOOS |
| WV-8623 | CCACTGTAGAAAGGCATGAA | 902 | L001m5Ceo*Sm5CeoAeom5CeoTeo*SG*ST*SA*SG*SA*SA*SG*RG*SC*SAeoTeoGeoAeo*SAeo | OSOOOOSSSSSSSSRSSOOOS |
| WV-8624 | CTGTAGAAAGGCATGAAGCA | 903 | L001mC*STeoGeoTeomA*SG*SA*SA*SA*SA*SG*SG*SC*SA*RT*SG*SmA*SmA*SmG*SmC*SmA | OSOOOOSSSSSSSSSSRSSSSS |
| WV-8625 | CTGTAGAAAGGCATGAAGCA | 904 | L001mC*STeoGeoTeomA*SG*SA*SA*SA*SA*SG*RG*SC*SA*ST*SG*SmA*SmA*SmG*SmC*SmA | OSOOOOSSSSSSRSSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8626 | CTGTAGAAAGGCATGAAGCA | 905 | L001m5Ceo*STeoGeoTeoAeo*SG*SA*SA*SA*SG*SG*SC*SA*RT*SG*SAeoAeoGeomSCeo*SAeo | OSOOOOSSSSSSSRSSOOOS |
| WV-8627 | CTGTAGAAAGGCATGAAGCA | 906 | L001m5Ceo*STeoGeoTeoAeo*SG*SA*SA*SA*SA*SG*RG*SC*SA*ST*SG*SAeoAeoGeom5Ceo*SAeo | OSOOOOSSSSSRSSSSSOOOS |
| WV-8628 | CTGTAGAAAGGCATGAAGCA | 907 | L001mC*TeoGeoTeomA*G*A*A*A*G*C*A*T*G*mA*mA*mG*mC*mA | OXOOOXXXXXXXXXXXXXXXXX |
| WV-8689 | CCACTGTAGAAAGGCATGAA | 908 | Mod001L001mC*m5CeoAeom5CeomU*G*T*A*G*A*A*A*G*G*C*mA*mU*mG*mA*mA | OXOOOXXXXXXXXXXXXXXXXX |
| WV-8690 | CCACTGTAGAAAGGCATGAA | 909 | mC*m5CeoAeom5CeomU*G*T*A*G*A*A*A*G*G*C*mA*mU*mG*mA*mA | XOOOXXXXXXXXXXXXXXXXX |
| WV-8697 | CCACUGTAAAGGCATGAA | 910 | L001m5CeoAeom5CeomU*G*T*A*G*A*A*A*A*G*G*C*mA*mU*mG*mA*mA | OXOOOXXXXXXXXXXXXXXXXX |
| WV-8698 | TGCCACUGTAGAAAGGCAUGATU | 911 | PSSMRdT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSOSSSSSSSSS |
| WV-8699 | TGCCACUGTAGAAAGGCAUGATU | 912 | PSSMRdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSSSSSSSSS |
| WV-8700 | TGCCACUGTAGAAAGGCAUGATU | 913 | 5MRdT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSOSSSSSSSSS |
| WV-8701 | TGCCACUGTAGAAAGGCAUGATU | 914 | 5MRdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSSSSSSSSS |
| WV-8807 | CUGCUUCAUGCCUUUCUACAGUGG | 915 | rCrUrGrCrUrUrCrArUrGrCrCrUrUrUrCrUrArCrArGrUrG | OOOOOOOOOOOOOOOOO |
| WV-8808 | CUGCUUCAUCCCCUUCUACAGUGG | 916 | rCrUrGrCrUrUrCrArUrCrCrCrCrUrUrCrUrArCrArGrUrG | OOOOOOOOOOOOOOOOO |
| WV-8843 | UGTAGAAAGGCATGAAGCAG | 917 | mU*GeoTeoAeomG*A*A*A*G*G*C*A*T*G*A*mA*mG*mC*mA*mG | XOOOXXXXXXXXXXXXXXXXX |
| WV-8844 | UGUAGAAAGGCATGAAGCAG | 918 | mU*mG*mU*mA*mG*A*A*A*G*C*A*T*G*A*mAGeom5CeoAeo*mG | XXXXXXXXXXXXXXXOOOX |
| WV-8845 | TGTAGAAAGGCATGAAGCAG | 919 | Teo*GeoTeoAeGeo *A*A*A*G*G*C*A*T*G*A*mA*mG*mC*mA*mG | XOOOXXXXXXXXXXXXXXXXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-8846 | UGUAGAAAGGCAUGAAGCAG | 920 | mU*mG*mA*mG*mA*A*A*G*G*C*A*T*G*A*AeoGeom5CeoAeo*Geo | XXXXXXXXXXXXXXXXX OOOX |
| WV-8847 | CUGUAGAAGGCAUGAAGCA | 921 | mC*mU*mG*mU*mG*mA*G*A*A*A*G*G*C*A*T*G*mAAeoGeom5Ceo*mA | XXXXXXXXXXXXXXXXX OOOX |
| WV-8848 | CTGTAGAAAGGCAUGAAGCA | 922 | m5Ceo*TeoGeoTeoAeo*G*A*A*A*G*G*C*A*T*G*mA*mA*mG*mC*mA | XXXXXXXXXXXXXXXXX XXXXX |
| WV-8849 | CUGUAGAAAGGCAUGAAGCA | 923 | mC*mU*mG*mU*mG*mA*G*A*A*A*G*G*C*A*T*G*AeoAeoGeom5Ceo*Aeo | XXXXXXXXXXXXXXXXX OOOX |
| WV-8850 | ACUGUAGAAAGGCAUGAAGC | 924 | mA*m5CeoTeoGeomU*A*G*A*A*A*A*G*G*C*A*T*mG*mA*mA*mG*mC | XOOOXXXXXXXXXXXXX XXXXX |
| WV-8851 | ACUGUAGAAAGGCAUGAAGC | 925 | mA*mC*mU*mG*mU*mA*G*A*A*A*A*G*G*C*A*T*mGAeoAeoGeo*mC | XXXXXXXXXXXXXXXXX OOOX |
| WV-8852 | ACTGTAGAAAGGCAUGAAGC | 926 | Aeo*m5CeoGeoGeoTeo*A*G*A*A*A*A*G*G*C*A*T*mG*mA*mA*mG*mC | XOOOXXXXXXXXXXXXX XXXXX |
| WV-8853 | ACUGUAGAAAGGCAUGAAGC | 927 | mA*mC*mU*mG*mU*mA*G*A*A*A*A*G*G*C*A*T*GeoAeoAeoGeo*m5Ceo | XXXXXXXXXXXXXXXXX OOOX |
| WV-8854 | CACUGUAGAAAGGCAUGAAG | 928 | mC*Aeom5CeoTeomG*T*A*G*A*A*A*A*G*G*C*A*mU*mG*mA*mA*mG | XOOOXXXXXXXXXXXXX XXXXX |
| WV-8855 | CACUGUAGAAAGGCAUGAAG | 929 | mC*mA*mC*mU*mG*T*A*G*A*A*A*A*G*G*C*A*mUGeoAeoAeo*mG | XXXXXXXXXXXXXXXXX OOOX |
| WV-8856 | CACUGUAGAAAGGCAUGAAG | 930 | m5Ceo*Aeom5CeoTeoGeo*T*A*G*A*A*A*A*G*G*C*A*mU*mG*mA*mA*mG | XOOOXXXXXXXXXXXXX XXXXX |
| WV-8857 | CACUGUAGAAAGGCAUGAAG | 931 | mC*mA*mC*mU*mG*T*A*G*A*A*A*A*G*G*C*A*TeoGeoAeoAeo*Geo | XXXXXXXXXXXXXXXXX OOOX |
| WV-8858 | CCACUGUAGAAAGGCAUGAA | 932 | mC*mC*mA*mC*mU*G*T*A*G*A*A*A*A*G*G*C*mATeoGeoAeo*mA | XXXXXXXXXXXXXXXXX OOOX |
| WV-8859 | CCACUGUAGAAAGGCAUGAA | 933 | m5Ceo*m5CeoAeom5CeoTeo*G*T*A*G*A*A*A*A*G*G*C*mA*mU*mG*mA*mA | XOOOXXXXXXXXXXXXX XXXXX |
| WV-8860 | CCACUGUAGAAAGGCAUGAA | 934 | mC*mC*mA*mC*mU*G*T*A*G*A*A*A*A*G*G*C*AeoTeoGeoAeo*Aeo | XXXXXXXXXXXXXXXXX OOOX |
| WV-9400 | TGCCACUGUAGAAGGCAUGATU | 935 | T*SfG*SmCfC*SmAfC*SmUfG*SmUmA*SmGmA*SmAfA*SmG*SmG*SmC*SmA*SmU*SmG*SmA*STGaNC6T*SmU | SOSOSOSOSOSO SSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-9401 | TGCCACUGUAGAAAGGCAUGATU | 936 | 5MRdT*SfG*SmCfC*SmAfC*SmUfG*SmUmA*SmGmA*SmAfA*SmG*SmC*SmA*SmU*SmG*SmA*STGaNC6T*SmU | SSOSOSOSOSOSSSSSSSSS |
| WV-9402 | TGCCACUGUAGAAAGGCAUGATU | 937 | PO5MRdT*SfG*SmCfC*SmAfC*SmUfG*SmUmA*SmGmA*SmAfA*SmG*SmC*SmA*SmU*SmG*SmA*STGaNC6T*SmU | SSOSOSOSOSOSSSSSSSSS |
| WV-9403 | TGCCACUGUAGAAAGGCAUGATU | 938 | PS5MRdT*SfG*SmCfC*SmAfC*SmUfG*SmUmA*SmGmA*SmAfA*SmG*SmC*SmA*SmU*SmG*SmA*STGaNC6T*SmU | SSOSOSOSOSOSSSSSSSSS |
| WV-9404 | TGCCACUGUAGAAAGGCAUGATU | 939 | T*SfG*SmCmC*SmAmC*SmUmG*SmUmA*SmGmA*SmAfA*SmG*SmC*SmA*SmU*SmG*SmA*STGaNC6T*SmU | SSOSOSOSOSOSSSSSSSSS |
| WV-9405 | TGCCACUGUAGAAAGGCAUGATU | 940 | 5MRdT*SfG*SmCmC*SmAmC*SmUmG*SmUmA*SmGmA*SmAfA*SmG*SmC*SmA*SmU*SmG*SmA*STGaNC6T*SmU | SSOSOSOSOSOSSSSSSSSS |
| WV-9406 | TGCCACUGUAGAAAGGCAUGATU | 941 | PO5MRdT*SfG*SmCmC*SmAmC*SmUmG*SmUmA*SmGmA*SmAfA*SmG*SmC*SmA*SmU*SmG*SmA*STGaNC6T*SmU | SSOSOSOSOSOSSSSSSSSS |
| WV-9407 | TGCCACUGUAGAAAGGCAUGATU | 942 | PS5MRdT*SfG*SmCmC*SmAmC*SmUmG*SmUmA*SmGmA*SmAfA*SmG*SmC*SmA*SmU*SmG*SmA*STGaNC6T*SmU | SSOSOSOSOSOSSSSSSSSS |
| WV-9431 | TGTAGAAAGGGATGAAGCAG | 943 | Teo*Geo*Teo*Geo*Aeo*A*A*A*G*G*A*T*G*A*Aeo*Geo*m5Ceo*Aeo*Geo | XXXXXXXXXXXXXXXXXXXX |
| WV-9432 | CTGTAGAAAGGGATGAAGCA | 944 | m5Ceo*Teo*Geo*Teo*Aeo*G*A*A*A*G*G*A*T*G*Aeo*Geo*m5Ceo*Aeo | XXXXXXXXXXXXXXXXXXXX |
| WV-9433 | ACTGTAGAAAGGGATGAAGC | 945 | Aeo*m5Ceo*Teo*Geo*Teo*A*G*A*A*A*G*G*A*T*Geo*Aeo*Aeo*Geo*m5Ceo | XXXXXXXXXXXXXXXXXXXX |
| WV-9434 | CACTGTAGAAAGGGATGAAG | 946 | m5Ceo*Aeo*m5Ceo*Teo*Geo*T*A*G*A*A*A*G*G*A*Teo*Geo*Aeo*Aeo*Geo | XXXXXXXXXXXXXXXXXXXX |
| WV-9435 | CCACTGTAGAAAGGGATGAA | 947 | m5Ceo*m5Ceo*Aeo*m5Ceo*Teo*G*T*A*G*A*A*A*G*G*A*Teo*Geo*Aeo*Aeo | XXXXXXXXXXXXXXXXXXXX |
| WV-9436 | TGTAGAAAGGGATGAAGCAG | 948 | Teo*GeoTeoAeoGeo*A*A*A*G*G*A*T*G*A*AeoGeom5CeoAeo*Geo | XOOOXXXXXXXXXXXOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-9437 | CTGTAGAAAGGGATGAAGCA | 949 | m5Ceo*TeoGeoTeoAeo*G*A*A*G*G*A*T*G*AeoAeoGeom5Ceo*Aeo | XOOOXXXXXXXXXXXX OOOX |
| WV-9438 | ACTGTAGAAAGGGATGAAGC | 950 | Aeo*m5CeoTeoGeoTeo*A*G*A*A*A*G*G*A*T*GeoAeoGeo*m5Ceo | XOOOXXXXXXXXXXXX OOOX |
| WV-9439 | CACTGTAGAAAGGGATGAAG | 951 | m5Ceo*Aeom5CeoTeoGeo*T*A*G*A*A*A*G*G*G*A*TeoGeoAeo*Geo | XOOOXXXXXXXXXXXX OOOX |
| WV-9440 | CCACTGTAGAAAGGGATGAA | 952 | m5Ceo*m5CeoAeom5CeoTeo*G*T*A*G*A*A*A*G*G*G*AeoTeoGeoAeo*Aeo | XOOOXXXXXXXXXXXX OOOX |
| WV-9441 | UGTAGAAAGGGATGAAGCAG | 953 | mU*GeoTeoAeomG*A*A*A*G*G*A*T*G*A*mA*mG*mC*mA*mG | XOOOXXXXXXXXXXXX XXXXX |
| WV-9442 | CTGTAGAAAGGGATGAAGCA | 954 | mC*TeoGeoTeomA*G*A*A*A*G*G*G*A*T*G*mA*mA*mG*mC*mA | XOOOXXXXXXXXXXXX XXXXX |
| WV-9443 | ACTGTAGAAAGGGATGAAGC | 955 | mA*m5CeoTeoGeomU*A*G*A*A*A*G*G*G*A*T*mG*mA*mA*mG*mC | XOOOXXXXXXXXXXXX XXXXX |
| WV-9444 | CACTGTAGAAAGGGAUGAAG | 956 | mC*Aeom5CeoTeomG*T*A*G*A*A*A*G*G*G*A*mU*mG*mA*mA*mG | XOOOXXXXXXXXXXXX XXXXX |
| WV-9445 | CCACUGTAGAAAGGGAUGAA | 957 | mC*m5CeoAeom5CeomU*G*T*A*G*A*A*A*G*G*G*A*mA*mU*mG*mA*mA | XOOOXXXXXXXXXXXX XXXXX |
| WV-9495 | TGCCACUGUAGAAAGGCAUGAUU | 958 | T*SfG*SmCfC*SmAfC*SmUfG*SmUmA*SmGmA*SmAfA*SmG*SmG*SmC*SmA*SmU*SmG*SmA*SAMC6T*SmU | SSOSOSOSOSO SSSSSSSSS |
| WV-9496 | TGCCACUGUAGAAAGGCAUGAUU | 959 | 5MRdT*SfG*SmCfC*SmAfC*SmUfG*SmUmA*SmGmA*SmAfA*SmG*SmG*SmC*SmA*SmU*SmG*SmA*SAMC6T*SmU | SSOSOSOSOSO SSSSSSSSS |
| WV-9497 | TGCCACUGUAGAAAGGCAUGAUU | 960 | PO5M RdT*SfG*SmCfC*SmAfC*SmUfG*SmUmA*SmGmA*SmAfA*SmG*SmG*SmC*SmA*SmU*SmG*SmA*SAMC6T*SmU | SSOSOSOSOSO SSSSSSSSS |
| WV-9498 | TGCCACUGUAGAAAGGCAUGAUU | 961 | PS5M RdT*SfG*SmCfC*SmAfC*SmUfG*SmUmA*SmGmA*SmAfA*SmG*SmG*SmC*SmA*SmU*SmG*SmA*SAMC6T*SmU | SSOSOS OSOSOSO SSSSSSSSS |
| WV-9499 | TGCCACUGUAGAAAGGCAUGAUU | 962 | T*SfG*SmCmC*SmAmC*SmUmG*SmUmA*SmGmA*SmAfA*SmG*SmG*SmC*SmA*SmU*SmG*SmA*SAMC6T*SmU | SSOSOSOSOSO SSSSSSSSS |
| WV-9500 | TGCCACUGUAGAAAGGCAUGAUU | 963 | 5MRdT*SfG*SmCmC*SmAmC*SmUmG*SmUmA*SmGmA*SmAfA*SmG*SmG*SmC*SmA*SmU*SmG*SmA*SAMC6T*SmU | SSOSOSOSOSO SSSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| | | | SmU | |
| WV-9501 | TGCCACUGUAGAAAGGCAUGATU | 964 | PO5MRdT*sfG*SmCmC*SmAmC*SmGmG*SmUmA*SmGmA*SmAfA*SmG*SmG*SmC*SmA*SmU*SmG*SmA*SAMC6T*SmU | SSOSOSOSOSOSO SSSSSSSSS |
| WV-9502 | TGCCACUGUAGAAAGGCAUGATU | 965 | P5SMRdT*sfG*SmCmC*SmAmC*SmGmG*SmUmA*SmGmA*SmAfA*SmG*SmG*SmC*SmA*SmU*SmG*SmA*SAMC6T*SmU | SSOSOSOSOSOSO SSSSSSSSS |
| WV-9550 | TGCCACUGUAGAAAGGCAUGATU | 966 | Mod001L001T*sfG*SmCfC*SmAfC*SmUfG*SmUfA*SmGfA*SmAfA*SmG*sfG*SmC*sfA*SmU*sfG*SmA*ST*SmU | OSSOSOSOSOSOSO SSSSSSSSS |
| WV-9551 | TGCCACUGUAGAAAGGCAUGATU | 967 | Mod001L0015MRdT*sfG*SmCfC*SmAfC*SmUfG*SmUfA*SmGfA*SmAfA*SmG*sfG*SmC*sfA*SmU*sfG*SmA*ST*SmU | OSSOSOSOSOSOSO SSSSSSSSS |
| WV-9552 | TGCCACUGUAGAAAGGCAUGATU | 968 | Mod001L001T*sfG*SmCmC*SmAmC*SmUmG*SmUmA*SmGmA*SmAfA*SmG*SmG*SmC*SmA*SmU*SmG*SmA*ST*SmU | OSSOSOSOSOSOSO SSSSSSSSS |
| WV-9553 | TGCCACUGUAGAAAGGCAUGATU | 969 | Mod001L0015MRdT*sfG*SmCmC*SmAmC*SmUmG*SmUmA*SmGmA*SmAfA*SmG*SmG*SmC*SmA*SmU*SmG*SmA*ST*SmU | OSSOSOSOSOSOSO SSSSSSSSS |
| WV-9554 | TGCCACUGUAGAAAGGCAUGATU | 970 | 5MRdT*sfG*SmCfC*SmAfC*SmUfG*SmUfA*SmGfA*SmAfA*SmG*sfG*SmC*sfA*SmU*sfG*SmA*ST*SmU | SSOSOSOSOSOSO SSSSSSSSS |
| WV-9555 | TGCCACUGUAGAAAGGCAUGATU | 971 | T*sfG*SmCmC*SmAmC*SmUmG*SmUmA*SmGmA*SmAfA*SmG*SmG*SmC*SmA*SmU*SmG*SmA*ST*SmU | SSOSOSOSOSOSO SSSSSSSSS |
| WV-9556 | TGCCACUGUAGAAAGGCAUGATU | 972 | 5MRdT*sfG*SmCmC*SmAmC*SmUmG*SmUmA*SmGmA*SmAfA*SmG*SmG*SmC*SmA*SmU*SmG*SmA*ST*SmU | SSOSOSOSOSOSO SSSSSSSSS |
| WV-9670 | CTGTAGAAAGGCATGAAGCA | 973 | Mod001L001m5Ceo*STeoGeoTeoAeo*RG*SA*SA*SA*SG*RG*SC*SA*ST*SG*RAeoAeoGeom5Ceo*SAeo | OSOOORSSSSRSSSSR OOOS |
| WV-9671 | CTGTAGAAAGGCATGAAGCA | 974 | Mod001L001m5Ceo*STeoGeoTeoAeo*RG*SA*SA*SA*SG*RG*SC*SA*ST*SG*SAeoAeoGeom5Ceo*SAeo | OSOOORSSSSRSSSSS OOOS |
| WV-9672 | CTGTAGAAAGGCATGAAGCA | 975 | Mod001L001m5Ceo*STeoGeoTeoAeo*SG*SA*SA*SA*SG*RG*SC*SA*ST*SG*RAeoAeoGeom5Ceo*SAeo | OSOOOSSSSSRSSSSR OOOS |
| WV-9859 | CTGTAGAAAGGCATGAAGCA | 976 | Mod001L001m5Ceo*STeoGeoTeoAeo*RG*SA*SA*SA*SG*RG*SC*SA*RT*SG*RAeoAeoGeom5Ceo*SAeo | OSOOORSSSSRSSRSR OOOS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-9860 | CTGTAGAAAGGCATGAAGCA | 977 | Mod001L001mC*TeoGeoTeoAeo*G*A*A*A*G*C*A*T*G*Aeo*mA*mG*mC*mA | OXOOOXXXXXXXXXXXXXX |
| WV-9861 | CTGTAGAAAGGCATGAAGCA | 978 | Mod001L001mC*STeoGeoTeoAeo*RG*SA*SA*SA*SA*SG*RG*SC*SA*RT*SG*RAeo*SmA*SmG*SmC*SmA | OSOOORSSSSRSSRSR SSSS |
| WV-9862 | CTGTAGAAAGGCATGAAGCA | 979 | Mod001L001mC*STeoGeoTeoAeo*RG*SA*SA*SA*SA*SG*RG*SC*SA*ST*SG*RAeo*SmA*SmG*SmC*SmA | OSOOORSSSSRSSSSR SSSS |
| WV-9866 | TGCCACUGUAGAAAGGCAUGATU | 980 | VPT*SfG*SmCfC*SmAfC*SmUfG*SmUmA*SmGmA*SmAfA*SmG*SmG*SmC*SmA*SmU*SmG*SmA*STGaNC6T*SmU | SSOSOSOSOSOSO SSSSSSSSS |
| WV-9867 | TGCCACUGUAGAAAGGCAUGATU | 981 | VPT*SfG*SmCmC*SmAmC*SmUmG*SmUmA*SmGmA*SmAfA*SmG*SmG*SmC*SmA*SmU*SmG*SmA*STGaNC6T*SmU | SSOSOS OSOSOSO SSSSSSSSS |
| WV-9868 | CTGTAGAAAGGCATGAAGCA | 982 | Mod001L001mC*TeoGeoTeoAeo*G*A*A*A*G*C*A*T*G*mA*mG*mC*mA | OXOOOXXXXXXXXXXXXXX |
| WV-9869 | CTGTAGAAAGGCATGAAGCA | 983 | Mod001L001mC*STeoGeoTeoAeo*RG*SA*SA*SA*SA*SG*RG*SC*SA*RT*SG*SmA*SmA*SmG*SmC*SmA | OSOOORSSSSRSSRS SSSSS |
| WV-9870 | CTGTAGAAAGGCATGAAGCA | 984 | Mod001L001mC*STeoGeoTeoAeo*RG*SA*SA*SA*SA*SG*RG*SC*SA*ST*SG*SmA*SmA*SmG*SmC*SmA | OSOOORSSSSRSSSSS SSSS |
| WV-9883 | TGCCACUGUAGAAAGGCAUGATU | 985 | VPT*SfG*SmCfC*SmAfC*SmUfG*SmUmA*SmGmA*SmAfA*SmG*SmG*SmC*SmA*SmU*SmG*SmA*SAMC6T*SmU | SSOSOSOSOSOSO SSSSSSSSS |
| WV-9884 | TGCCACUGUAGAAAGGCAUGATU | 986 | VPT*SfG*SmCmC*SmAmC*SmUmG*SmUmA*SmGmA*SmAfA*SmG*SmG*SmC*SmA*SmU*SmG*SmA*SAMC6T*SmU | SSOSOSOSOSOSO SSSSSSSSS |
| WV-9889 | CTGTAGAAAGGCATGAAGCA | 987 | mSCeo*STeoGeoTeoAeo*RG*SA*SA*SA*SA*SG*RG*SC*SA*RT*SG*RAeoAeoGeom5Ceo*SAeo | SOOORSSSSRSSSRSR OOOS |
| WV-9890 | CTGTAGAAAGGCATGAAGCA | 988 | mSCeo*STeoGeoTeoAeo*RG*SA*SA*SA*SA*SG*RG*SC*SA*ST*SG*RAeoAeoGeom5Ceo*SAeo | SOOORSSSSRSSRSSSR OOOS |
| WV-9891 | CTGTAGAAAGGCATGAAGCA | 989 | mC*TeoGeoTeoAeo*G*A*A*A*G*C*A*T*G*mA*mG*mC*mA | XOOOXXXXXXXXXXXXX |
| WV-9892 | CTGTAGAAAGGCATGAAGCA | 990 | mC*STeoGeoTeoAeo*RG*SA*SA*SA*SA*SG*RG*SC*SA*RT*SG*SmA*SmA*SmG*SmC*SmA | SOOORSSSSRSSR SSSSSS |
| WV-9893 | CTGTAGAAAGGCATGAAGCA | 991 | mC*STeoGeoTeoAeo*RG*SA*SA*SA*SA*SG*RG*SC*SA*ST*SG*SmA*SmA*SmG*SmC*SmA | SOOORSSSSRSSSSS SSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-9894 | CTGTAGAAAGGCATGAAGCA | 992 | mC*TeoGeoTeoAeo*G*A*A*A*G*C*A*T*G*Aeo*mA*mG*mC*mA | XOOOOXXXXXXXXXXXXXX |
| WV-9895 | CTGTAGAAAGGCATGAAGCA | 993 | mC*STeoGeoTeoAeo*RG*SA*SA*SA*SG*RG*SC*SA*RT*SG*RAeo*SmA*SmG*SmC*SmA | SSSSRSSRSRSSSS |
| WV-9896 | CTGTAGAAAGGCATGAAGCA | 994 | mC*STeoGeoTeoAeo*RG*SA*SA*SA*SG*RG*SC*SA*ST*SG*RAeo*SmA*SmG*SmC*SmA | SOOORSSSSRSSSSRSSSS |
| WV-10247 | CTGTAGAAAGGCATGAAGCA | 995 | L001m5Ceo*STeoGeoTeoAeo*RG*SA*SA*SA*SG*RG*SC*SA*RT*SG*RAeoAeoGeom5Ceo*SAeo | SOOORSSSSRSSRSROOOS |
| WV-10248 | CTGTAGAAAGGCATGAAGCA | 996 | L001m5Ceo*STeoGeoTeoAeo*RG*SA*SA*SA*SG*RG*SC*SA*ST*SG*RAeoAeoGeom5Ceo*SAeo | OSOOORSSSSRSSSSSSOOOS |
| WV-10249 | CTGTAGAAAGGCATGAAGCA | 997 | L001mC*TeoGeoTeoAeo*G*A*A*A*G*C*A*T*G*Aeo*mA*mG*mC*mA | OXOOOXXXXXXXXXXXXXX |
| WV-10250 | CTGTAGAAAGGCATGAAGCA | 998 | L001mC*STeoGeoTeoAeo*RG*SA*SA*SA*SG*RG*SC*SA*RT*SG*SmA*SmA*SmG*SmC*SmA | OSOOORSSSSRSSRSSSSSS |
| WV-10251 | CTGTAGAAAGGCATGAAGCA | 999 | L001mC*STeoGeoTeoAeo*RG*SA*SA*SA*SG*RG*SC*SA*ST*SG*SmA*SmA*SmG*SmC*SmA | OSOOORSSSSRSSSSSSSS |
| WV-10252 | CTGTAGAAAGGCATGAAGCA | 1000 | L001mC*TeoGeoTeoAeo*G*A*A*A*G*C*A*T*G*Aeo*mA*mG*mC*mA | OXOOOXXXXXXXXXXXXXX |
| WV-10253 | CTGTAGAAAGGCATGAAGCA | 1001 | L001mC*STeoGeoTeoAeo*RG*SA*SA*SA*SG*RG*SC*SA*RT*SG*RAeo*SmA*SmG*SmC*SmA | SOOORSSSSRSSRSSSSRSSSS |
| WV-10254 | CTGTAGAAAGGCATGAAGCA | 1002 | L001mC*STeoGeoTeoAeo*RG*SA*SA*SA*SG*RG*SC*SA*ST*SG*RAeo*SmA*SmG*SmC*SmA | OSOOORSSSSRSSSSSSSS |
| WV-10320 | TCCUUCCCUGAAGGUUCCCUGU | 1003 | VPT*fC*mCfU*mUfC*mCfC*mUfG*mAfA*mGfG*mU*fU*mC*fC*mU*fC*mC*TGaNC6T*mU | XXXOXOXOXOXOXOXXXXXXXXXX |
| WV-10321 | TCCUUCCCUGAAGGUUCCCUGU | 1004 | VPT*fC*mCmU*mUmC*mCmC*mUmG*mAmA*mGfG*mU*mU*mC*mC*mU*mC*mC*TGaNC6T*mU | XXOXOXOXOXOXOXXXXXXXXXX |
| WV-10322 | TCCUUCCCUGAAGGUUCCCUGU | 1005 | P05MRdT*fC*mCmU*mUfC*mCfC*mUfG*mAfA*mGfG*mU*fU*mC*fC*mU*fC*mC*TGaNC6T*mU | XXOXOXOXOXOXOXXXXXXXXXX |
| WV-10323 | TCCUUCCCUGAAGGUUCCCUGU | 1006 | P05MRdT*fC*mCmU*mUmC*mCmC*mUmG*mAmA*mGfG*mU*mU*mC*mC*mU*mC*mC*TGaNC6T*mU | XXXOXOXOXOXOXOXXXXXXXXXX |
| WV-10324 | TCCUUCCCUGAAGGUUCCCUGU | 1007 | VPT*SfC*SmCfU*SmUfC*SmUfC*SmCfC*SmUfG*SmAfA*SmGfG*SmU*SfU*SmC*SfC*SmU*SfC*SmC*STGaNC6T*mU | SSOSOSOSOSOSOSSSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-10325 | TCCUUCCCUGAAGGUUCCUCCUU | 1008 | VPT*SfC*SmChU*SmCmC*SmUmG*SmAmA* SmGfG*SmU*SmU*SmC*SmC*SmU*SmC*SmC*STGaNC6T *SmU | SSOSOSOSOSO SSSSSSSS |
| WV-10326 | TCCUUCCCUGAAGGUUCCUCCUU | 1009 | PO5MRdT*SfC*SmCfU*SmUfC*SmCfC*SmUfG*SmAfA* SmGfG*SmU*SfU*SmC*SfC*SmU*SfC*SmC*STGaNC6T* SmU | SSOSOSOSOSO SSSSSSSSS |
| WV-10327 | TCCUUCCCUGAAGGUUCCUCCUU | 1010 | PO5MRdT*SfC*SmCmU*SmUmC*SmCmC*SmUmG*SmAmA* SmGfG*SmU*SmU*SmC*SmC*SmU*SmC*SmC*STGaNC6T *SmU | SSOSOSOSOSO SSSSSSSSS |
| WV-10432 | TGCCACUGUAGAAGGCAUGAUU | 1011 | 5tzdT*SfG*SmCfC*SmAfC*SmUfG*SmUfA*SmGfA*SmAfA* SmG*SfG*SmC*SfA*SmU*SfG*SmA*STGaNC6T*SmU | SSOSOSOSOSO SSSSSSSSS |
| WV-10433 | TGCCACUGUAGAAGGCAUGAUU | 1012 | 5tzdT*SfG*SmCmC*SmAmC*SmUmG*SmUmA*SmGmA* SmAfA*SmG*SmG*SmC*SmA*SmU*SmG*SmA*STGaNC6T *SmU | SSOSOSOSOSO SSSSSSSSS |
| WV-10434 | TGCCACUGUAGAAGGCAUGAUU | 1013 | 5tzdT*SfG*SmCfC*SmAfC*SmUfG*SmUfA*SmGfA*SmAfA* SmG*SfG*SmC*SfA*SmU*SfG*SmA*SAMC6T*SmU | SSOSOSOSOSO SSSSSSSSS |
| WV-10435 | TGCCACUGUAGAAGGCAUGAUU | 1014 | 5tzdT*SfG*SmCmC*SmAmC*SmUmG*SmUmA*SmGmA* SmAfA*SmG*SmG*SmC*SmA*SmU*SmG*SmA*SAMC6T* SmU | SSOSOSOSOSO SSSSSSSSS |
| WV-11957 | CTGTAGAAAGGCATGAAGCA | 1015 | Mod001L001m5IC*STeoGeoTeoAeo*RG*SA*SA*SA*SG*RG *SC*SA*ST*SG*RAeoAeoGeom5Ceo*SIA | OSOOORSSSSRSSSSSR OOOS |
| WV-11958 | CTGTAGAAAGGCATGAAGCA | 1016 | Mod001L001m5IC*STeoGeoTeoAeo*RG*SA*SA*SA*SG*RG *SC*SA*ST*SG*SA*SmA*SmA*SmG*SmC*SIA | OSOOORSSSSRSSSSSS SSSS |
| WV-11959 | CTGTAGAAAGGCATGAAGCA | 1017 | m5IC*STeoGeoTeoAeo*RG*SA*SA*SA*SG*RG*SC*SA*ST *SG*RAeoAeoGeom5Ceo*SIA | SOOORSSSSRSSSSR OOOS |
| WV-11960 | CTGTAGAAAGGCATGAAGCA | 1018 | m5IC*STeoGeoTeoAeo*RG*SA*SA*SA*SG*RG*SC*SA*ST *SG*SA*SmA*SmA*SmG*SmC*SIA | SOOORSSSSRSSSSSS SSSS |
| WV-11961 | CTGTAGAAAGGCATGAAGCA | 1019 | L001m5IC*STeoGeoTeoAeo*RG*SA*SA*SA*SG*RG*SC*SA *ST*SG*RAeoAeoGeom5Ceo*SIA | OSOOORSSSSRSSSSSR OOOS |
| WV-11962 | CTGTAGAAAGGCATGAAGCA | 1020 | L001m5IC*STeoGeoTeoAeo*RG*SA*SA*SA*SG*RG*SC*SA *ST*SG*SmA*SmA*SmG*SmC*SIA | OSOOORSSSSRSSSSSS SSSS |
| WV-12070 | TGCCACUGUAGAAGGCAUGAUU | 1021 | 5ptzdT*SfG*SmCfC*SmAfC*SmUfG*SmUfA*SmGfA*SmAfA* SmG*SfG*SmC*SfA*SmU*SfG*SmA*STGaNC6T*SmU | SSOSOSOSOSO SSSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-12071 | TGCCACUGUAGAAAGGCAUGAUU | 1022 | 5tzpodT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSO SSSSSSSSS |
| WV-12072 | TGCCACUGUAGAAAGGCAUGAUU | 1023 | 5mvpdT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSO SSSSSSSSS |
| WV-12073 | TGCCACUGUAGAAAGGCAUGAUU | 1024 | 5pacetdT*SfG*SmCfC*SmAfC*SmUfG*SmUfA*SmGfA*SmAfA*SmG*SfG*SmC*SfA*SmU*SfG*SmA*STGaNC6T*SmU | SSOSOSOSOSO SSSSSSSSS |
| WV-12098 | CACTGTAGAAAGGCATGAAGCAGG | 1025 | Mod001L001m5Ceo*SAeom5CeoTeoGeoTeoAeo*RG*SA*SA*SA*SG*RG*SC*SA*ST*SG*RAeoAeoGeom5CeoAeoGeo*SGeo | OSOOOORSSSSR SSSSROOOOS |
| WV-12099 | CACTGTAGAAAGGCATGAAGCAGG | 1026 | Mod001L001mC*SAeom5CeoTeoGeoTeoAeo*RG*SA*SA*SA*SG*RG*SC*SA*ST*SG*SmA*SmA*SmG*SmC*SmA*SmG*SmG | OSOOOORSSSSR SSSSSSSSSS |
| WV-12100 | CACTGTAGAAAGGCATGAAGCAGG | 1027 | m5Ceo*SAeom5CeoTeoGeoTeoAeo*RG*SA*SA*SA*SG*RG*SC*SA*ST*SG*RAeoAeoGeom5CeoAeoGeo*SGeo | SOOOORSSSSR SSSSROOOOS |
| WV-12101 | CACTGTAGAAAGGCATGAAGCAGG | 1028 | mC*SAeom5CeoTeoGeoTeoAeo*RG*SA*SA*SA*SG*RG*SC*SA*ST*SG*SmA*SmA*SmG*SmC*SmA*SmG*SmG | SOOOORSSSSR SSSSSSSSSS |
| WV-12102 | CACTGTAGAAAGGCATGAAGCAGG | 1029 | L001m5Ceo*SAeom5CeoTeoGeoTeoAeo*RG*SA*SA*SA*SG*RG*SC*SA*ST*SG*RAeoAeoGeom5CeoAeoGeo*SGeo | OSOOOORSSSSR SSSSROOOOS |
| WV-12103 | CACTGTAGAAAGGCATGAAGCAGG | 1030 | L001mC*SAeom5CeoTeoGeoTeoAeo*RG*SA*SA*SA*SG*RG*SC*SA*ST*SG*SmA*SmA*SmG*SmC*SmA*SmG*SmG | OSOOOORSSSSR SSSSSSSSSS |
| WV-12104 | CACTGTAGAAAGGCATGAAGCAGG | 1031 | Mod001L001m5Ceo*Aeom5CeoTeoGeoTeoAeo*G*A*A*A*G*C*A*T*G*AeoAeoGeom5CeoAeoGeo*Geo | OXOOOOOXXXXX XXXXXXOOOOOX |
| WV-12105 | CACTGTAGAAAGGCATGAAGCAGG | 1032 | Mod001L001mC*Aeom5CeoTeoGeoTeoAeo*G*A*A*A*G*G*C*A*T*G*mA*mA*mG*mC*mA*mG*mG | OXOOOOOXXXXX XXXXXXXXXXXX |
| WV-12106 | CACTGTAGAAAGGCATGAAGCAGG | 1033 | m5Ceo*Aeom5CeoTeoGeoTeoAeo*G*A*A*A*G*C*A*T*G*AeoAeoGeom5CeoAeoGeo*Geo | XOOOOOXXXXX XXXXXXOOOOOX |
| WV-12107 | CACTGTAGAAAGGCATGAAGCAGG | 1034 | mC*Aeom5CeoTeoGeoTeoAeo*G*A*A*A*G*G*C*A*T*G*mA*mA*mG*mC*mA*mG*mG | XOOOOOXXXXX XXXXXXXXXXXX |
| WV-12108 | CACTGTAGAAAGGCATGAAGCAGG | 1035 | L001m5Ceo*Aeom5CeoTeoGeoTeoAeo*G*A*A*A*G*C*A*T*G*AeoAeoGeom5CeoAeoGeo*Geo | OXOOOOOXXXXX XXXXXXOOOOOX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-12109 | CACTGTAGAAAGGCATGAAGCAGG | 1036 | L001mC*Aeom5CeoTeoGeoTeoAeo*G*A*A*A*G*G*C*A*T*G*mA*mG*mC*mA*mG*mG | OXOOOOOXXXXX XXXXXXXXXXXX |
| WV-12115 | TGCCACTGTAGAAAGGCATGATU | 1037 | T*SfG*SmCfC*SmAfC*SmUfG*SmUfA*SmGfA*SmAfA*SmG*SfG*SmC*SfA*SmU*SfG*SmA*SmU*SmU | SSOSOSOSOSOSO SSSSSSSSS |
| WV-12116 | TGCCACTGTAGAAAGGCATGATU | 1038 | T*SfG*SmCn001fC*SmAfC*SmUfG*SmUfA*SmGfA*SmAfA*SmG*SfG*SmC*SfA*SmU*SfG*SmA*SmU*SmU | SSnXSOSOSOSOSO SSSSSSSSS |
| WV-12117 | TGCCACTGTAGAAAGGCATGATU | 1039 | T*SfG*SmCfC*SmAn001fC*SmUfG*SmUfA*SmGfA*SmAfA*SmG*SfG*SmC*SfA*SmU*SfG*SmA*SmU*SmU | SSOSnXSOSOSOSO SSSSSSSSS |
| WV-12118 | TGCCACTGTAGAAAGGCATGATU | 1040 | T*SfG*SmCfC*SmAfC*SmUn001fG*SmUfA*SmGfA*SmAfA*SmG*SfG*SmC*SfA*SmU*SfG*SmA*SmU*SmU | SSOSOSnXSOSOSO SSSSSSSSS |
| WV-12119 | TGCCACTGTAGAAAGGCATGATU | 1041 | T*SfG*SmCfC*SmAfC*SmUfG*SmUn001fA*SmGfA*SmAfA*SmG*SfG*SmC*SfA*SmU*SfG*SmA*SmU*SmU | SSOSOSOSnXSOSO SSSSSSSSS |
| WV-12120 | TGCCACTGTAGAAAGGCATGATU | 1042 | T*SfG*SmCfC*SmAfC*SmUfG*SmUfA*SmGn001fA*SmAfA*SmG*SfG*SmC*SfA*SmU*SfG*SmA*SmU*SmU | SSOSOSOSOSnXSO SSSSSSSSS |
| WV-12121 | TGCCACTGTAGAAAGGCATGATU | 1043 | T*SfG*SmCfC*SmAfC*SmUfG*SmUfA*SmGfA*SmAn001fA*SmG*SfG*SmC*SfA*SmU*SfG*SmA*SmU*SmU | SSOSOSOSOSOSnX SSSSSSSSS |
| WV-12122 | TGCCACTGTAGAAAGGCATGATU | 1044 | T*SfG*SmCn001fC*SmAn001fC*SmUn001fG*SmUn001fA*SmGn001fA*SmAn001fA*SmG*SfG*SmC*SfA*SmU*SfG*SmA*SmU*SfG*SmA*SmU*SmU | SSnXSnXSnXSnXS nXsnX SSSSSSSSS |
| WV-12254 | TGCCACTGTAGAAAGGCATGATU | 1045 | 5ptzdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSO SSSSSSSSS |
| WV-12255 | TGCCACTGTAGAAAGGCATGATU | 1046 | 5tzpodT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSO SSSSSSSSS |
| WV-12256 | TGCCACTGTAGAAAGGCATGATU | 1047 | 5mvpdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSO SSSSSSSSS |
| WV-12257 | TGCCACTGTAGAAAGGCATGATU | 1048 | 5pacetdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOSOSO SSSSSSSSS |
| WV-12420 | CCUGCUUCAUGCCUUUCUCAGUG | 1049 | rCrCrUrGrCrUrUrCrArUrGrCrCrUrUrUrCrUrCrAr GrUrG | OOOOOOOOOOO OOOOOOOOOOOO |
| WV-12421 | CCUGCUUCAUCCCCUUCUCAGUG | 1050 | rCrCrUrGrCrUrUrCrArUrCrCrCrCrUrUrCrUrCrArG rUrG | OOOOOOOOOOO OOOOOOOOOOOO |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-12573 | TGCCACUGUAGAAAGGCAUGATU | 1051 | VPT*SfG*SmCfC*SmAfC*SmUfG*SmUfA*SmGfA*SmAfA*SmG*SfG*SmC*SfA*SmU*SfG*SmA*SfG*SmA*Stbclc6T*SmU | SOSOSOSOSOSOSOSSSSSSSSS |
| WV-12574 | TGCCACUGUAGAAAGGCAUGATU | 1052 | VPT*SfG*SmCfC*SmAfC*SmUfG*SmUfA*SmGfA*SmAfA*SmG*SfG*SmC*SfA*SmU*SfG*SmA*Sbbclc6T*SmU | SOSOSOSOSOSOSOSSSSSSSSS |
| WV-12874 | CUUCAUGCCUUUCUACAGUGGCCU | 1053 | rCrUrUrCrArUrGrCrCrUrUrUrCrUrArCrArGrUrGrGrCrCrU | OOOOOOOOOOOOOOOOOOOOOOO |
| WV-12875 | CUUCAUCCCCUUCUACAGUGGCCU | 1054 | rCrUrUrCrArUrCrCrCrCrUrUrCrUrArCrArGrUrGrGrCrCrU | OOOOOOOOOOOOOOOOOOOOOOO |
| WV-9261 | GCCACUGUAGAAAGGCAUGATU | 1055 | L009*fG*mCfC*mAfC*mUfG*mUfA*mGfA*mAfA*mGfGmCfAmUfGmA*T*mU | OOOOOOOOOOOOOOOOOOOOO |
| WV-9262 | TCCACUGUAGAAAGGCAUGATU | 1056 | T*L009*mCfC*mAfC*mUfG*mUfA*mGfA*mAfA*mGfGmCfAmUfGmA*T*mU | XXOXOXOXOXOXOXOOOOOXX |
| WV-9263 | TGCACUGUAGAAAGGCAUGATU | 1057 | T*fG*L009fC*mAfC*mUfG*mUfA*mGfA*mAfA*mGfGmCfAmUfGmA*T*mU | XXOXOXOXOXOXOXOOOOOXX |
| WV-9264 | TGCACUGUAGAAAGGCAUGATU | 1058 | T*fG*mCL009*mAfC*mUfG*mUfA*mGfA*mAfA*mGfGmCfAmUfGmA*T*mU | XXOXOXOXOXOXOXOOOOOXX |
| WV-9265 | TGCCCUGUAGAAAGGCAUGATU | 1059 | T*fG*mCfC*L009fC*mUfG*mUfA*mGfA*mAfA*mGfGmCfAmUfGmA*T*mU | XXOXOXOXOXOXOXOOOOOXX |
| WV-9266 | TGCCAUGUAGAAAGGCAUGATU | 1060 | T*fG*mCfC*mAL009*mUfG*mUfA*mGfA*mAfA*mGfGmCfAmUfGmA*T*mU | XXOXOXOXOXOXOXOOOOOXX |
| WV-9267 | TGCCACGUAGAAAGGCAUGATU | 1061 | T*fG*mCfC*mAfC*L009fG*mUfA*mGfA*mAfA*mGfGmCfAmUfGmA*T*mU | XXOXOXOXOXOXOXOOOOOXX |
| WV-9268 | TGCCACUGUAGAAAGGCAUGATU | 1062 | T*fG*mCfC*mAfC*mUL009*mUfA*mGfA*mAfA*mGfGmCfAmUfGmA*T*mU | XXOXOXOXOXOXOXOOOOOXX |
| WV-9269 | TGCCACUGUAGAAAGGCAUGATU | 1063 | T*fG*mCfC*mAfC*mUfG*L009fA*mGfA*mAfA*mGfGmCfAmUfGmA*T*mU | XXOXOXOXOXOXOXOOOOOXX |
| WV-9270 | TGCCACUGUAGAAAGGCAUGATU | 1064 | T*fG*mCfC*mAfC*mUfG*mUL009*mGfA*mAfA*mGfGmCfAmUfGmA*T*mU | XXOXOXOXOXOXOXOOOOOXX |
| WV-9271 | TGCCACUGUAAAAGGCAUGATU | 1065 | T*fG*mCfC*mAfC*mUfG*mUfA*L009fA*mAfA*mGfGmCfAmUfGmA*T*mU | XXOXOXOXOXOXOXOOOOOXX |
| WV-9272 | TGCCACUGUAGAAAGGCAUGATU | 1066 | T*fG*mCfC*mAfC*mUfG*mUfA*mGfA*mAL009*mGfGmCfAmUfGmA*T*mU | XXOXOXOXOXOXOXOOOOOXX |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-9273 | GCCACUGUAGAA AGGCAUGAUT | 1067 | Lo1o*fG*mCfC*mAfC*mUfG*mUfA*mGfA*mAfA*mGfGmCfAm UfGmA*T*mU | XXOXOXOXOXOX OXOOOOOOXX |
| WV-9274 | TCCACUGUAGAAA GGGCAUGAUT | 1068 | T*Lo1o*mCfC*mAfC*mUfG*mUfA*mGfA*mAfA*mGfGmCfAm UfGmA*T*mU | XXOXOXOXOXOX OXOOOOOOXX |
| WV-9275 | TGCACUGUAGAA AGGCAUGAUT | 1069 | T*fG*Lo1ofC*mAfC*mUfG*mUfA*mGfA*mAfA*mGfGmCfAm UfGmA*T*mU | XXOXOXOXOXOX OXOOOOOOXX |
| WV-9276 | TGCACUGUAGAA AGGCAUGAUT | 1070 | T*fG*mCLo1o*mAfC*mUfG*mUfA*mGfA*mAfA*mGfGmCfAm UfGmA*T*mU | XXOXOXOXOXOX OXOOOOOOXX |
| WV-9277 | TGCCCUGUAGAA AGGCAUGAUT | 1071 | T*fG*mCfC*Lo1ofC*mUfG*mUfA*mGfA*mAfA*mGfGmCfAm UfGmA*T*mU | XXOXOXOXOXOX OXOOOOOOXX |
| WV-9278 | TGCCAUGUAGAA AGGCAUGAUT | 1072 | T*fG*mCfC*mALo1o*mUfG*mUfA*mGfA*mAfA*mGfGmCfAm UfGmA*T*mU | XXOXOXOXOXOX OXOOOOOOXX |
| WV-9279 | TGCCACUGUAGAA AGGCAUGAUT | 1073 | T*fG*mCfC*mAfC*Lo1ofG*mUfA*mGfA*mAfA*mGfGmCfAm UfGmA*T*mU | XXOXOXOXOXOX OXOOOOOOXX |
| WV-9280 | TGCCACUUGUAGAA AGGCAUGAUT | 1074 | T*fG*mCfC*mAfC*mULo1o*mUfA*mGfA*mAfA*mGfGmCfAm UfGmA*T*mU | XXOXOXOXOXOX OXOOOOOOXX |
| WV-9281 | TGCCACUGUAGAA AGGCAUGAUT | 1075 | T*fG*mCfC*mAfC*mUfG*Lo1ofA*mGfA*mAfA*mGfGmCfAm UfGmA*T*mU | XXOXOXOXOXOX OXOOOOOOXX |
| WV-9282 | TGCCACUGUAGAA AGGCAUGAUT | 1076 | T*fG*mCfC*mAfC*mUfG*mUL o1o*mGfA*mAfA*mGfGmCfAm UfGmA*T*mU | XXOXOXOXOXOX OXOOOOOOXX |
| WV-9283 | TGCCACUGUAAAA GGCAUGAUT | 1077 | T*fG*mCfC*mAfC*mUfG*mUfA*Lo1ofA*mAfA*mGfGmCfAm UfGmA*T*mU | XXOXOXOXOXOX OXOOOOOOXX |
| WV-9284 | TGCCACUGUAGAA GGGCAUGAUT | 1078 | T*fG*mCfC*mAfC*mUfG*mUfA*mGfA*mAL o1o*mGfGmCfAm UfGmA*T*mU | XXOXOXOXOXOX OXOOOOOOXX |
| WV-13443 | CACTGTAGAAAGG AGGCATGAGCAGG | 1079 | VPf*SfG*SmCmC*SmAmC*SmUmG*SmUmA*SmGmA*SmAfA* SmG*SmG*SmC*SmA*SmU*SmG*SmA*Stbc1c6T*SmU | SSOSOSOSOSO SOSSSSSSSS |
| WV-13555 | CACTGTAGAAGG CATGAAGCAGG | 1080 | Mod001Lo01mC*SAeom5Ceo5TeoGeoTeoAeo*RG*SA*SA* SG*RG*SC*SA*ST*SG*RAeo*SmA*SmG*SmA*SmG*SmG | OSOOOOORSSS SRSSSSRSSSSSS |
| WV-13556 | CACTGTAGAAGG CATGAAGCAGG | 1081 | Mod001Lo01m5Ceo*SAeom5Ceo5TeoGeoTeoAeo*RG*SA*SA* SA*SG*RG*SC*SA*ST*SG*RAeo*SmA*SmG*SmC*SmA*SmG*SmG | OSOOOOORSSS SRSSSSRSSSSSS |

TABLE 1A-continued oligonucleotides.
PNPLA3 oligonucleotides.

| WAVE ID Naked Sequence | SEQ ID NO: | Sequence | Stereochemistry |
|---|---|---|---|
| WV-13557 CACTGTAGAAAGG CATGAAGCAGG | 1082 | Mod001L001m5Ceo*RAeom5CeoTeoGeoTeoAeo*RG*SA*SA* SA*SG*RG*SC*SA*ST*SG*RAeo*SmA*SmG*SmC*SmA*SmG*SmG | OROOOOORSSS SRSSSSRSRSSSSSS |
| WV-13558 CACTGTAGAAAGG CATGAAGCAGG | 1083 | Mod001L001m5Ceo*RAeom5CeoTeoGeoTeoAeo*RG*SA*SA* SA*SG*RG*SC*SA*ST*SG*SAeo*SmA*SmG*SmC*SmA*SmG*SmG | OROOOOORSSS SRSSSSSSSSSSSS |
| WV-13559 CACTGTAGAAAGG CATGAAGCAGG | 1084 | Mod001L001m5Ceo*SAeom5CeoTeoGeoTeoAeo*RG*SA*SA* SA*ST*SG*SC*SA*ST*SG*SAeo*SmA*SmG*SmC*SmA*SmG*SmG | OSOOOOORSSS SRSSSSSSSSSSSS |
| WV-13560 CACTGTAGAAAGG CATGAAGCAGG | 1085 | L001mC*SAeom5CeoTeoGeoTeoAeo*RG*SA*SA*SA*SG*RG* SC*SA*ST*SG*RAeo*SmA*SmG*SmC*SmA*SmG*SmG | OSOOOOORSSSS RSSSSSSSSSSS |
| WV-13561 CACTGTAGAAAGG CATGAAGCAGG | 1086 | L001m5Ceo*SAeom5CeoTeoGeoTeoAeo*RG*SA*SA*SA*SG* RG*SC*SA*ST*SG*RAeo*SmA*SmG*SmC*SmA*SmG*SmG | OSOOOOORSSS SRSSSSRSRSSSSSS |
| WV-13562 CACTGTAGAAAGG CATGAAGCAGG | 1087 | L001m5Ceo*RAeom5CeoTeoGeoTeoAeo*RG*SA*SA*SA*SG* RG*SC*SA*ST*SG*RAeo*SmA*SmG*SmC*SmA*SmG*SmG | OROOOOORSSSSR SSSSRSRSSSSSS |
| WV-13563 CACTGTAGAAAGG CATGAAGCAGG | 1088 | L001m5Ceo*RAeom5CeoTeoGeoTeoAeo*RG*SA*SA*SA*SG* RG*SC*SA*ST*SG*SAeo*SmA*SmG*SmC*SmA*SmG*SmG | OROOOOORSSS RSSSSSSSSSSSSS |
| WV-13564 CACTGTAGAAAGG CATGAAGCAGG | 1089 | L001m5Ceo*SAeom5CeoTeoGeoTeoAeo*RG*SA*SA*SA*SG* RG*SC*SA*ST*SG*SAeo*SmA*SmG*SmC*SmA*SmG*SmG | OSOOOOORSSS SRSSSSSSSSSSSSS |
| WV-13565 CACTGTAGAAAGG CATGAAGCAGG | 1090 | mC*SAeom5CeoTeoGeoTeoAeo*RG*SA*SA*SA*SA*SG*RG*SC* SA*ST*SG*RAeo*SmA*SmG*SmC*SmA*SmG*SmG | SOOOOORSSSS RSSSSSRSSSSSS |
| WV-13566 CACTGTAGAAAGG CATGAAGCAGG | 1091 | m5Ceo*SAeom5CeoTeoGeoTeoAeo*RG*SA*SA*SA*SG*RG* SC*SA*ST*SG*RAeo*SmA*SmG*SmC*SmA*SmG*SmG | SOOOOORSSSS RSSSSSRSSSSSSS |
| WV-13567 CACTGTAGAAAGG CATGAAGCAGG | 1092 | m5Ceo*RAeom5CeoTeoGeoTeoAeo*RG*SA*SA*SA*SG*RG* SC*SA*ST*SG*RAeo*SmA*SmG*SmC*SmA*SmG*SmG | ROOOOORSSSSR SSSSRSSSSSSS |
| WV-13568 CACTGTAGAAAGG CATGAAGCAGG | 1093 | m5Ceo*RAeom5CeoTeoGeoTeoAeo*RG*SA*SA*SA*SG*RG* SC*SA*ST*SG*SAeo*SmA*SmG*SmC*SmA*SmG*SmG | ROOOOORSSS SRSSSSSSSSSSSSS |
| WV-13569 CACTGTAGAAAGG CATGAAGCAGG | 1094 | m5Ceo*SAeom5CeoTeoGeoTeoAeo*RG*SA*SA*SA*SG*RG* SC*SA*ST*SG*SAeo*SmA*SmG*SmC*SmA*SmG*SmG | SOOOOORSSSSR SSSSSSSSSSSS |
| WV-13588 TGCCACTGTAGAAA GGGCAUGATU | 1095 | 5mpdT*SfG*SmCfC*SmAfC*SmUfG*SmUfA*SmGfA*SmAfA* SmG*SfG*SmC*SfA*SmU*SfG*SmA*STGaNC6T*SmU | SOSOSOSOSO SOSOSOSOSS |
| WV-13589 TGCCACTGTAGAAA GGGCAUGATU | 1096 | 5mrpdT*SfG*SmCfC*SmAfC*SmUfG*SmUfA*SmGfA*SmAfA* SmG*SfG*SmC*SfA*SmU*SfG*SmA*STGaNC6T*SmU | SSOSOSOSOSO SOSSSSSSSSSS |
| WV-13590 TGCCACTGTAGAAA GGGCAUGATU | 1097 | 5mspdT*SfG*SmCfC*SmAfC*SmUfG*SmUfA*SmGfA*SmAfA* SmG*SfG*SmC*SfA*SmU*SfG*SmA*STGaNC6T*SmU | SSOSOSOSOSO SOSOSOSOSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-13591 | TGCCACUGUAGAAAUGGCAUGATU | 1098 | 5mpdT*SfG*SmCfC*SmAfC*SmUfG*SmUfA*SmGfA*SmAfA*SmG*sfG*SmC*SfA*SmU*sfG*SmA*SAMC6T*SmU | SSOSOSOSOSOSOSSSSSSSS |
| WV-13592 | TGCCACUGUAGAAAUGGCAUGATU | 1099 | 5mrpdT*SfG*SmCfC*SmAfC*SmUfG*SmUfA*SmGfA*SmAfA*SmG*SfG*SmC*SfA*SmU*SfG*SmA*SAMC6T*SmU | SSOSOSOSOOSOSSSSSSSSS |
| WV-13593 | TGCCACUGUAGAAAUGGCAUGATU | 1100 | 5mspdT*SfG*SmCfC*SmAfC*SmUfG*SmUfA*SmGfA*SmAfA*SmC*sfG*SmC*SfA*SmU*sfG*SmA*SAMC6T*SmU | SSOSOSOSOSOSOSSSSSSSS |
| WV-13668 | ACTGTAGAAAGGCATGAAGCAG | 1101 | Mod001L001mA*Sm5CeoTeoGeoTeoAeo*RG*SA*SA*SA*SG*RG*SC*SA*ST*SG*RAeo*SmA*SmG*SmC*SmA*SmG | OSOOOORSSSSRSSSSRSSSSS |
| WV-13669 | ACTGTAGAAAGGCATGAAGCAG | 1102 | Mod001L001Aeo*Sm5CeoTeoGeoTeoAeo*RG*SA*SA*SA*SA*T SG*RG*SC*SA*S*SG*RAeo*SmA*SmG*SmC*SmA*SmG | OSOOOORSSSSRSSSSRSSSSS |
| WV-13670 | ACTGTAGAAAGGCATGAAGCAG | 1103 | Mod001L001Aeo*Rm5CeoTeoGeoTeoAeo*RG*SA*SA*SA*SA*SG*RG*SC*SA*ST*SG*RAeo*SmA*SmG*SmC*SmA*SmG | OROOOORSSSSRSSSSRSSSSS |
| WV-13671 | ACTGTAGAAAGGCATGAAGCAG | 1104 | Mod001L001Aeo*Rm5CeoTeoGeoTeoAeo*RG*SA*SA*SA*SA*SG*RG*SC*SA*ST*SG*SAeo*SmA*SmG*SmC*SmA*SmG | OROOOORSSSSRSSSSSSSSSS |
| WV-13672 | ACTGTAGAAAGGCATGAAGCAG | 1105 | Mod001L001Aeo*Sm5CeoTeoGeoTeoAeo*RG*SA*SA*SA*SA*SG*RG*SC*SA*ST*SG*SAeo*SmA*SmG*SmC*SmA*SmG | OSOOOORSSSSRSSSSSSSSSS |
| WV-13673 | ACTGTAGAAAGGCATGAAGCAG | 1106 | L001mA*Sm5CeoTeoGeoTeoAeo*RG*SA*SA*SA*SG*RG*SC*SA*ST*SG*RAeo*SmA*SmG*SmC*SmA*SmG | OSOOOORSSSSRSSSSRSSSSS |
| WV-13674 | ACTGTAGAAAGGCATGAAGCAG | 1107 | L001Aeo*Sm5CeoTeoGeoTeoAeo*RG*SA*SA*SA*SA*SG*RG*SC*SA*ST*SG*RAeo*SmA*SmG*SmC*SmA*SmG | OSOOOORSSSSRSSSSRSSSSS |
| WV-13675 | ACTGTAGAAAGGCATGAAGCAG | 1108 | L001Aeo*Rm5CeoTeoGeoTeoAeo*RG*SA*SA*SA*SA*SG*RG*SC*SA*ST*SG*RAeo*SmA*SmG*SmC*SmA*SmG | OROOOORSSSSRSSSSRSSSSS |
| WV-13676 | ACTGTAGAAAGGCATGAAGCAG | 1109 | L001Aeo*Rm5CeoTeoGeoTeoAeo*RG*SA*SA*SA*SA*SG*RG*SC*SA*ST*SG*SAeo*SmA*SmG*SmC*SmA*SmG | OROOOORSSSSRSSSSSSSSSS |
| WV-13677 | ACTGTAGAAAGGCATGAAGCAG | 1110 | L001Aeo*Sm5CeoTeoGeoTeoAeo*RG*SA*SA*SA*SA*SG*RG*SC*SA*ST*SG*SAeo*SmA*SmG*SmC*SmA*SmG | OSOOOORSSSSRSSSSSSSSSS |
| WV-13678 | ACTGTAGAAAGGCATGAAGCAG | 1111 | mA*Sm5CeoTeoGeoTeoAeo*RG*SA*SA*SA*SG*RG*SC*SA*ST*SG*RAeo*SmA*SmG*SmC*SmA*SmG | SOOOORSSSSRSSSSRSSSSS |
| WV-13679 | ACTGTAGAAAGGCATGAAGCAG | 1112 | Aeo*Sm5CeoTeoGeoTeoAeo*RG*SA*SA*SA*SG*RG*SC*SA*ST*SG*RAeo*SmA*SmG*SmC*SmA*SmG | SOOOORSSSSRSSSSRSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-13680 | ACTGTAGAAAGG CATGAAGCAG | 1113 | Aeo*Rm5CeoTeoGeoTeoAeo*RG*SA*SA*SG*RG*SC*SA* ST*SG*RAeo*SmA*SmG*SmC*SmA*SmG | ROOOORSSSS RSSSSRSSSSS |
| WV-13681 | ACTGTAGAAAGG CATGAAGCAG | 1114 | Aeo*Rm5CeoTeoGeoTeoAeo*RG*SA*SA*SG*RG*SC*SA* ST*SG*SAeo*SmA*SmG*SmC*SmA*SmG | ROOOORSSSS RSSSSSSSSSS |
| WV-13682 | ACTGTAGAAAGG CATGAAGCAG | 1115 | Aeo*SmSCeoTeoGeoTeoAeo*RG*SA*SA*SA*SG*RG*SC*SA* ST*SG*SAeo*SmA*SmG*SmC*SmA*SmG | SOOOORSSSS RSSSSSSSSSS |
| WV-13800 | CTGTAGAAAGGC ATGAAGCA | 1116 | Mod001L001m5Ceo*RTeoGeoTeoAeo*RG*SA*SA*SA*SG*RG* SC*SA*ST*SG*RAeo*SmA*SmG*SmC*SmA | OROOORSSSSR SSSSRSSSS |
| WV-13801 | CTGTAGAAAGGC ATGAAGCA | 1117 | L001m5Ceo*RTeoGeoTeoAeo*RG*SA*SA*SA*SG*RG*SC*SA* ST*SG*RAeo*SmA*SmG*SmC*SmA | OROOORSSSS RSSSSRSSSS |
| WV-13802 | CTGTAGAAAGGC ATGAAGCA | 1118 | mSCeo*RTeoGeoTeoAeo*RG*SA*SA*SA*SG*RG*SC*SA*ST* SG*RAeo*SmA*SmG*SmC*SmA | ROOORSSSS RSSSSRSSSS |
| WV-14090 | GCUUCAUGCCUU UCUACAGUGGCCU | 1119 | rGrCrUrUrCrArUrGrCrCrUrUrUrCrUrArCrArGrUrGrGrCr CrU | OOOOOOOOOO OOOOOOOOOO OOO |
| WV-14091 | GCUUCAUCCCUUC UACAGUGGCCU | 1120 | rGrCrUrUrCrArUrCrCrCrUrUrCrUrArCrArGrUrGrGrCr CrU | OOOOOOOOOO OOOOOOOOOO OOO |
| WV-14102 | TGCCACUGUAGAAA GGGCAUGATU | 1121 | VPT*SfG*SmC*SmAfC*SmUfG*SmUfA*SmGfA*SmAfA*SmG* sfG*SmC*sfA*SmU*sfG*SmA*SaamC6T*SmU | SSOSOSOSOSO SOSSSSSSSSS |
| WV-14103 | TGCCACUGUAGAAA GGGCAUGATU | 1122 | VPT*SfG*SmC*SmAfC*SmUfG*SmUfA*SmGfA*SmAfA*SmG* sfG*SmC*sfA*SmU*sfG*SmA*Spac6dT*SmU | SSOSOSOSOSO SOSSSSSSSSS |
| WV-14336 | TGCCACUGUAGAAA GGGCAUTU | 1123 | VPT*SfG*SmC*SmAfC*SmUfG*SmUfA*SmGfA*SmAfA*SmG* sfG*SmC*sfA*SmU*STGaNC6T*SmU | SSOSOSOSOSO SOSSSSSSS |

TABLE 1A-continued oligonucleotides.
PNPLA3 oligonucleotides.

| WAVE ID | Naked Sequence | SEQ ID NO: | Sequence | Stereochemistry |
|---|---|---|---|---|
| WV-14337 | TGCCACUGUAGAAA GGGCAUTU | 1124 | 5mrpdT*SfG*SmCfC*SmAfC*SmUfG*SmUfA*SmGfA*SmAfA* SmG*SfG*SmC*SfA*SmU*STGaNC6T*SmU | SSOSOSOSOSO SOSSSSSSS |
| WV-14338 | TGCCCACUGUAGAAA GGGCAUTU | 1125 | 5mspdT*SfG*SmCfC*SmAfC*SmUfG*SmUfA*SmGfA*SmAfA* SmG*SfG*SmC*SfA*SmU*STGaNC6T*SmU | SSOSOSOSOSO SOSSSSSSS |
| WV-14339 | TGCCACUGUAGAAA GGGCAUTU | 1126 | VPT*SfG*SmCfC*SmAfC*SmUfG*SmUfA*SmGfA*SmAfA* SmG*SfG*SmC*SfA*SmU*SAMC6T*SmU | SSOSOSOSOSO SOSSSSSSS |
| WV-14340 | TGCCCACUGUAGAAA GGGCAUTU | 1127 | 5mrpdT*SfG*SmCfC*SmAfC*SmUfG*SmUfA*SmGfA* SmAfA*SmG*SfG*SmC*SfA*SmU*SAMC6T*SmU | SSOSOSOSOSO SOSSSSSSS |
| WV-14341 | TGCCACUGUAGAAA LGGCAUTU | 1128 | 5mspdT*SfG*SmCfC*SmAfC*SmUfG*SmUfA*SmGfA* SmAfA*SmG*SfG*SmC*SfA*SmU*SAMC6T*SmU | SSOSOSOSOSO SOSSSSSSS |

The disclosure notes that some sequences, due to their length, are divided into multiple lines; however, these sequences, as are all oligonucleotides in Table 1A, are single-stranded (unless otherwise noted).

Moieties and modifications listed in the Tables (or compounds used to construct oligonucleotides comprising these moieties or modifications:
IT
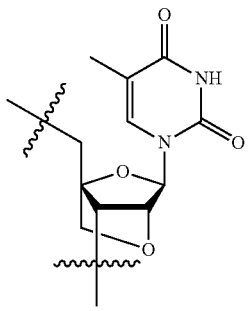 [SMILES: *C[C@]12CO[C@@H](C1*)[C@H](n1cc(C)c(=O)[nH]c1=O)O2]
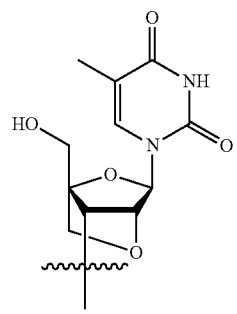 [SMILES: *C1[C@@H]2OC[C@]1(CO)O[C@H]2n1cc(C)c(=O)[nH]c1=O]
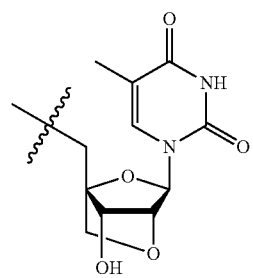 [SMILES: *C[C@]12CO[C@@H](C1O)[C@H](n1cc(C)c(=O)[nH]c1=O)O2]
IG
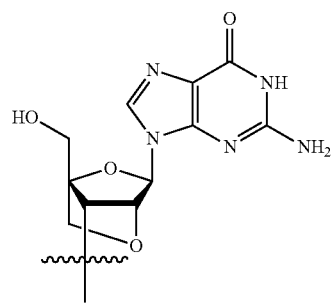 [SMILES: *C1[C@@H]2OC[C@]1(CO)O[C@H]2n1cnc2c(=O)[nH]c(N)nc21]

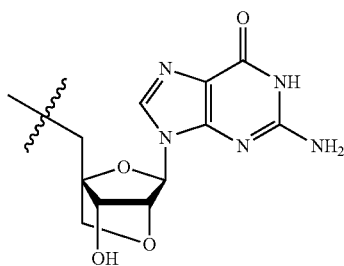 [SMILES: *C[C@]12CO[C@@H](C1O)[C@H](n1cnc3c(=O)[nH]c(N)nc31)O2]
IA
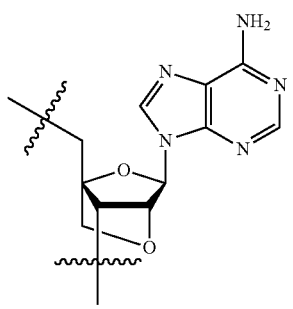 [SMILES: *C[C@]12CO[C@@H](C1*)[C@H](n1cnc3c(N)ncnc31)O2]
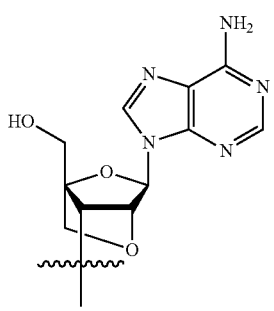 [SMILES: *C1[C@@H]2OC[C@]1(CO)O[C@H]2n1cnc2c(N)ncnc21]
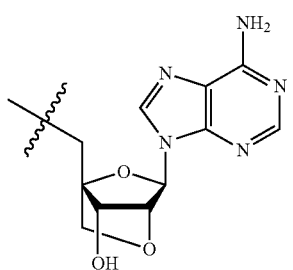 [SMILES: *C[C@]12CO[C@@H](C1O)[C@H](n1cnc3c(N)ncnc31)O2]
Im5C
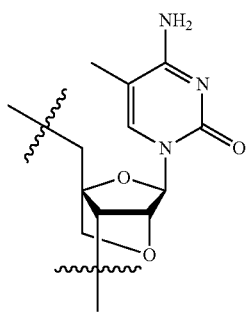 [SMILES: *C[C@]12CO[C@@H](C1*)[C@H](n1cc(C)c(N)nc1=O)O2]

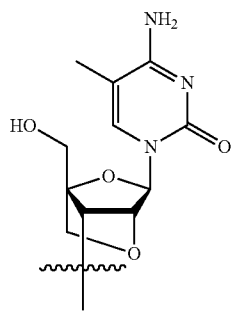
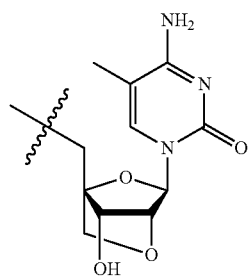 [SMILES: *C[C@]12CO[C@@H](C1O)[C@H](n1cc(C)c(N)nc1=O)O2]
MeOT 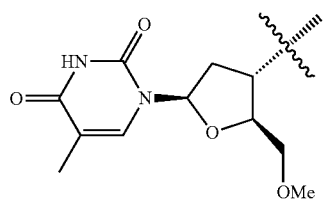
Mod001 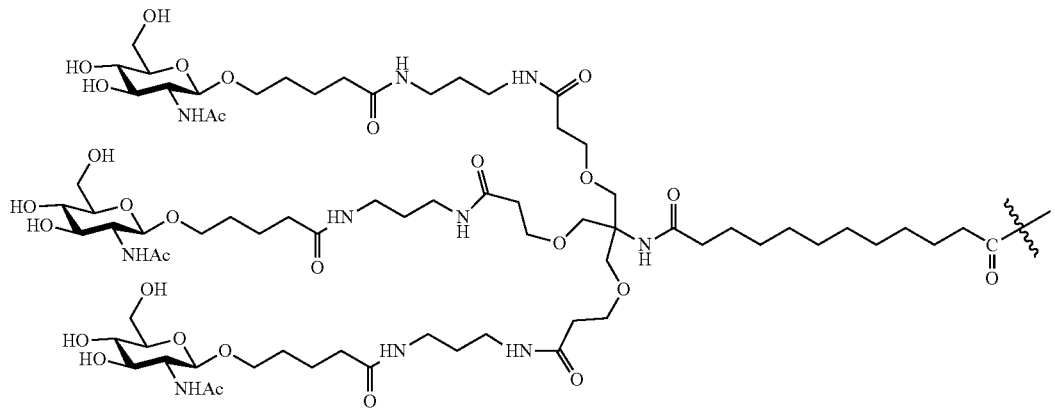
Mod022  CH₃CH₂CH₂—; connected to 5'-end of oligonucleotide chain through either a phosphate linkage (O or PO) or phosphorothioate linkage (* if the phosphorothioate not chirally controlled; can also be Sp if chirally controlled and has an Sp configuration, and Rp if chirally controlled and has an Rp configuration) as illustrated.
PH 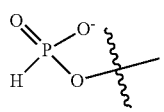
Mod023 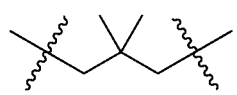 [SMILES: *CC(C)(C)C*]

-continued
VPT
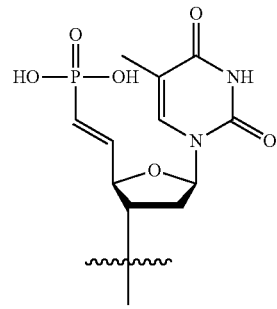
Mod034
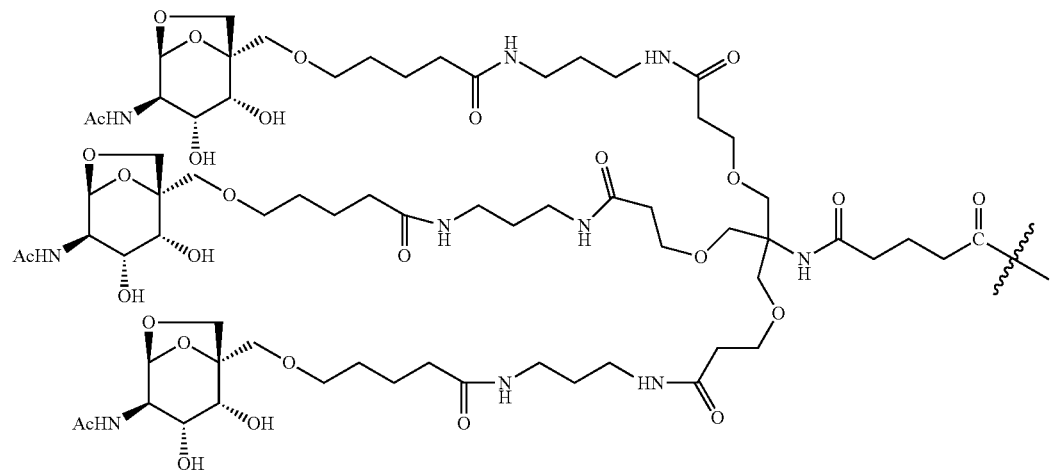 [SMILES: *C(=O)CCCC(=O)NC(COCCC(=O)NCCCNC(=O)CCCCOC[C@@]12CO[C@@H](O1)[C@H](NC(C)=O)[C@@H](O)[C@H]2O)(COCCC(=O)NCCCNC(=O)CCCCOC[C@@]12CO[C@@H](O1)[C@H](NC(C)=O)[C@@H](O)[C@H]2O)COCCC(=O)NCCCNC(=O)CCCCOC[C@@]12CO[C@@H](O1)[C@H](NC(C)=O)[C@@H](O)[C@H]2O]
Mod035
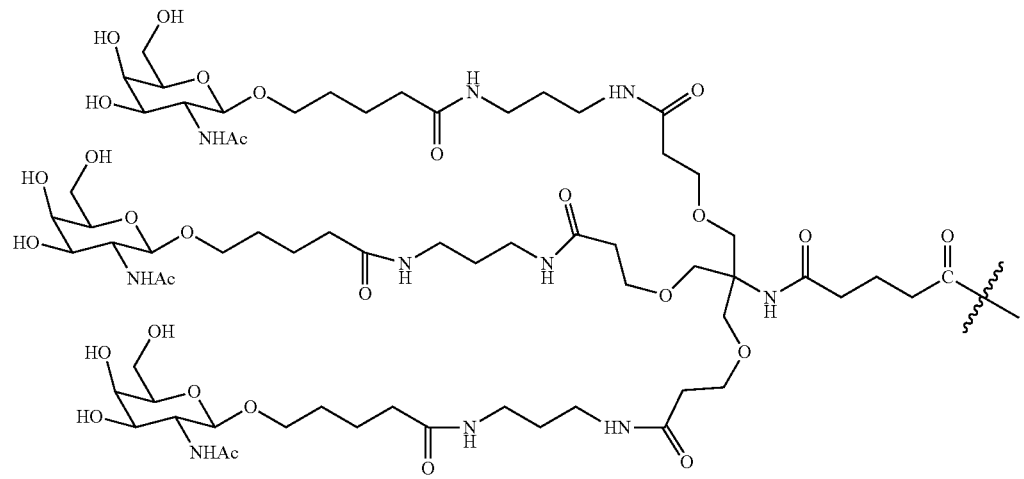 [SMILES: *C(=O)CCCC(=O)NC(COCCC(=O)NCCCNC(=O)CCCCOC1OC(CO)C(O)C(O)C1NC(C)=O)(COCCC(=O)NCCCNC(=O)CCCCOC1OC(CO)C(O)C(O)C1NC(C)=O)COCCC(=O)NCCCNC(=O)CCCCOC1OC(CO)C(O)C(O)C1NC(C)=O]
Mod036
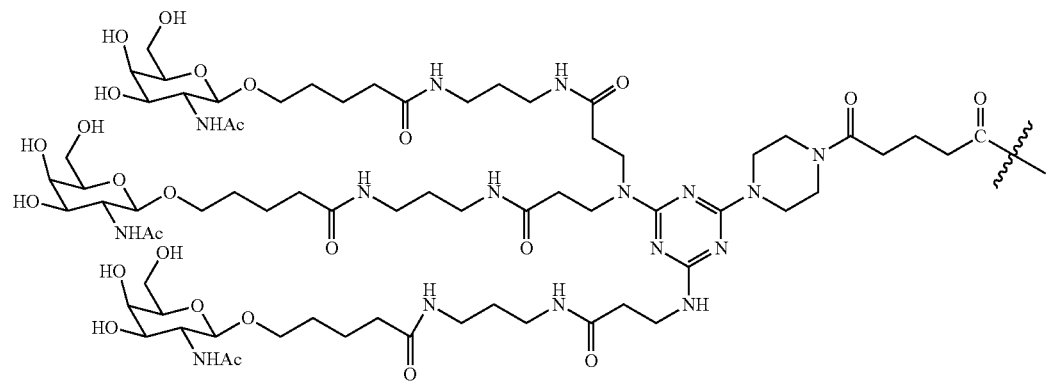 [SMILES: *C(=O)CCCC(=O)N1CCN(c2nc(NCCC(=O)NCCCNC(=O)CCCCOC3OC(CO)C(O)C(O)C3NC(C)=O)nc(N(CCC(=O)NCCCNC(=O)CCCCOC3OC(CO)C(O)C(O)C3NC(C)=O)CCC(=O)NCCCNC(=O)CCCCOC3OC(CO)C(O)C(O)C3NC(C)=O)n2)CC1]

Mod038 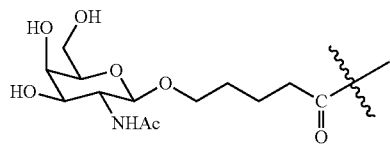 [SMILES: *C(=O)CCCCOC1OC(CO)C(O)C(O)C1NC(C)=O]
Mod039 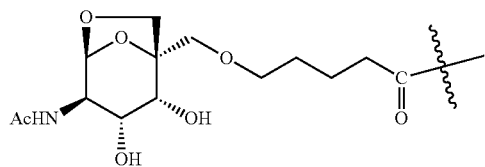 [SMILES: *C(=O)CCCCOC[C@@]12CO[C@@H](O1)[C@H](NC(C)=O)[C@@H](O)[C@H]2O]
Mod040 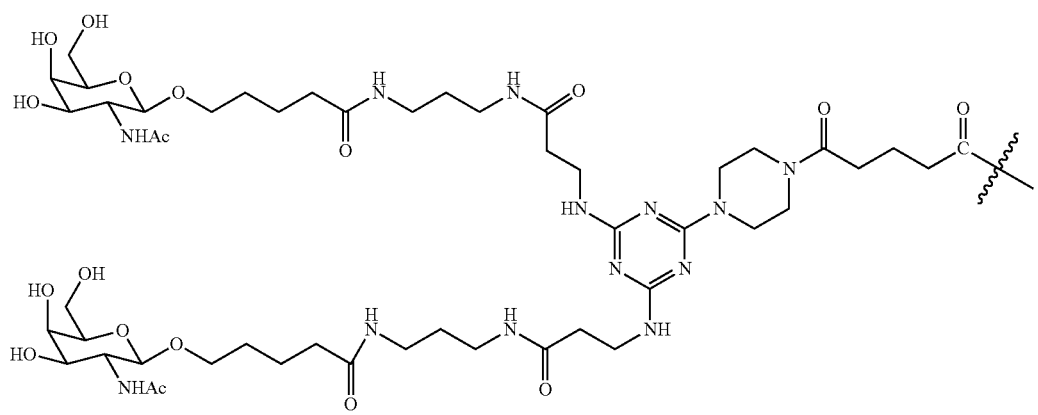 [SMILES: *C(=O)CCCC(=O)N1CCN(c2nc(NCCC(=O)NCCCNC(=O)CCCCOC3OC(CO)C(O)C(O)C3NC(C)=O)nc(NCCC(=O)NCCCNC(=O)CCCCOC3OC(CO)C(O)C(O)C3NC(C)=O)n2)CC1]
Mod041 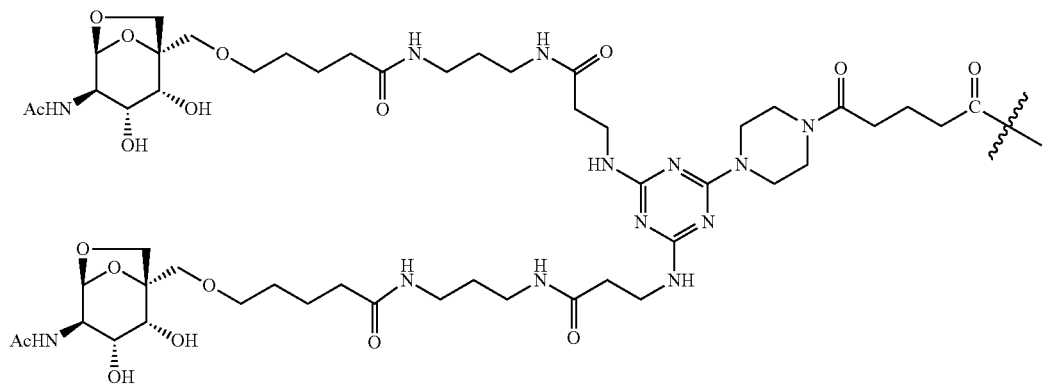 [SMILES: *C(=O)CCCC(=O)N1CCN(c2nc(NCCC(=O)NCCCNC(=O)CCCCOC[C@@]34CO[C@@H](O3)[C@H](NC(C)=O)[C@@H](O)[C@H]4O)nc(NCCC(=O)NCCCNC(=O)CCCCOC[C@@]34CO[C@@H](O3)[C@H](NC(C)=O)[C@@H](O)[C@H]4O)n2)CC1]
Mod079 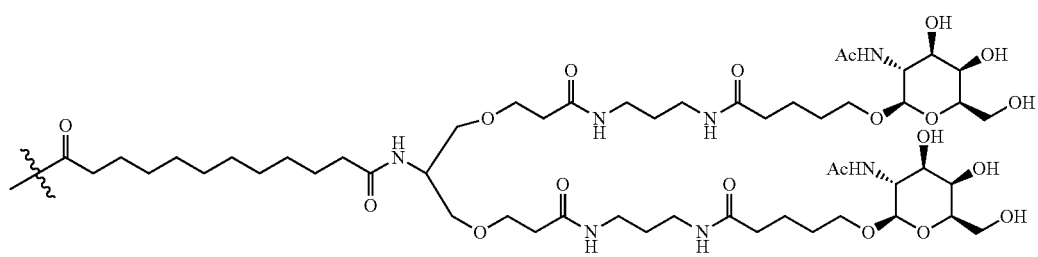 [SMILES: *C(=O)CCCCCCCCCCC(=O)NC(COCCC(=O)NCCCNC(=O)CCCCO[C@@H]1O[C@H](CO)[C@H](O)[C@H](O)[C@H]1NC(C)=O)COCCC(=O)NCCCNC(=O)CCCCO[C@@H]1O[C@H](CO)[C@H](O)[C@H](O)[C@H]1NC(C)=O]

-continued
Mod080
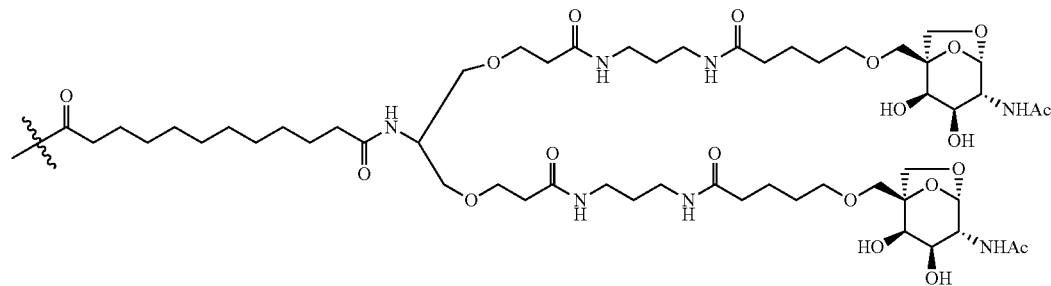 [SMILES: *C(=O)CCCCCCCCCCC(=O)NC(COCCC(=O)NCCCNC(=O)CCCCOC[C@@]12CO[C@@H](O1)[C@H](NC(C)=O)[C@@H](O)[C@H]2O)COCCC(=O)NCCCNC(=O)CCCCOC[C@@]12CO[C@@H](O1)[C@H](NC(C)=O)[C@@H](O)[C@H]2O]
Mod081
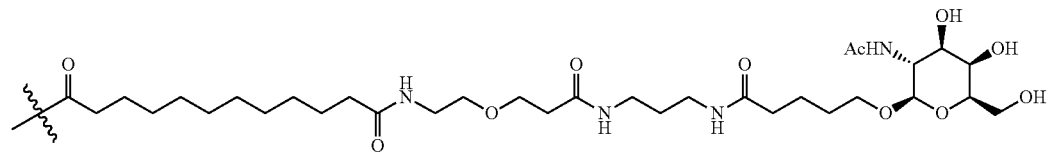 [SMILES: *C(=O)CCCCCCCCCCC(=O)NCCOCCC(=O)NCCCNC(=O)CCCCO[C@@H]1O[C@H](CO)[C@H](O)[C@H](O)[C@H]1NC(C)=O]
Mod082
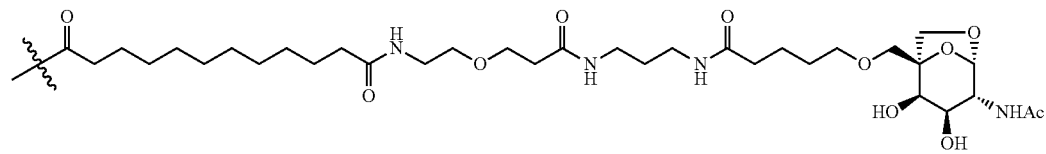 [SMILES: *C(=O)CCCCCCCCCCC(=O)NCCOCCC(=O)NCCCNC(=O)CCCCOC[C@@]12CO[C@@H](O1)[C@H](NC(C)=O)[C@@H](O)[C@H]2O]
Mod083
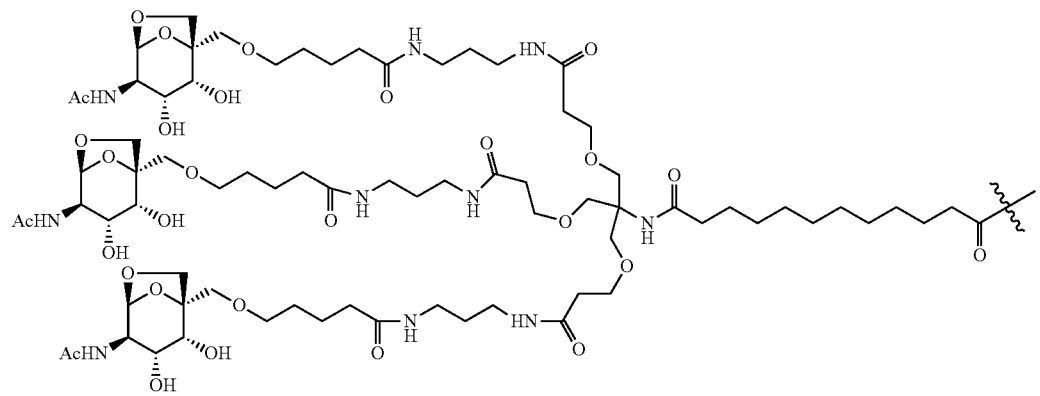 [SMILES: *C(=O)CCCCCCCCCCC(=O)NC(COCCC(=O)NCCCNC(=O)CCCCOC[C@@]12CO[C@@H](O1)[C@H](NC(C)=O)[C@@H](O)[C@H]2O)(COCCC(=O)NCCCNC(=O)CCCCOC[C@@]12CO[C@@H](O1)[C@H](NC(C)=O)[C@@H](O)[C@H]2O)COCCC(=O)NCCCNC(=O)CCCCOC[C@@]12CO[C@@H](O1)[C@H](NC(C)=O)[C@@H](O)[C@H]2O]
5mp
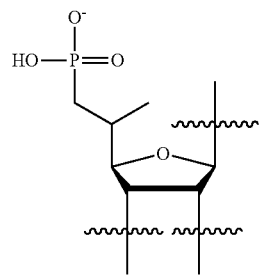
5MR
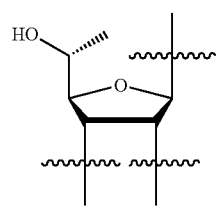

-continued
5mrp 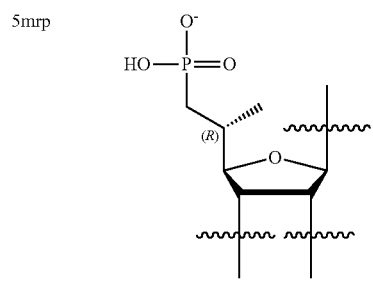
5MS 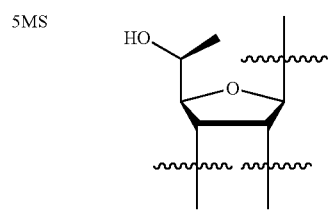
5msp 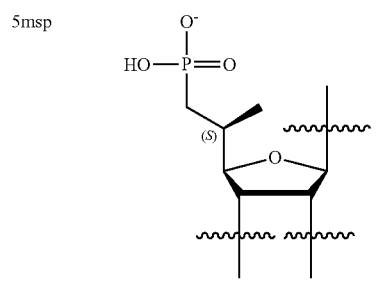
5mvp 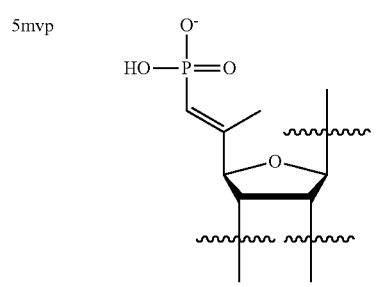
5pacet 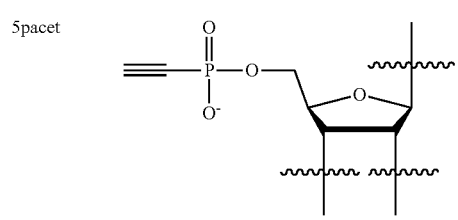
5ptz 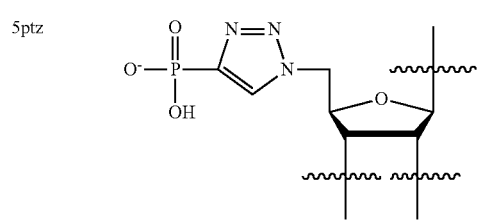

-continued
5tz 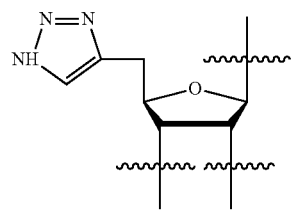
5tzpo 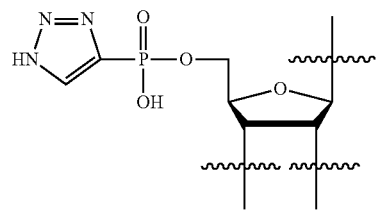
5mpdT 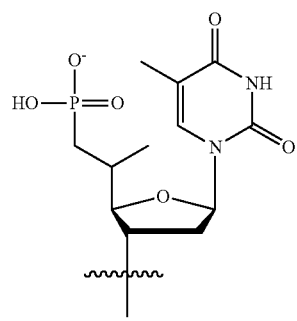
5MRdT 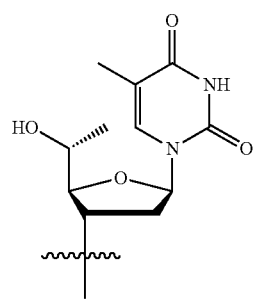
5mrpdT 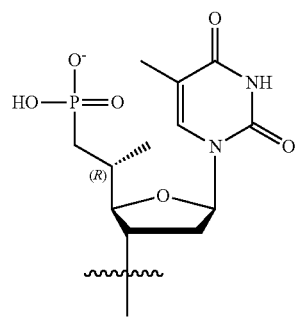

-continued
5MSdT
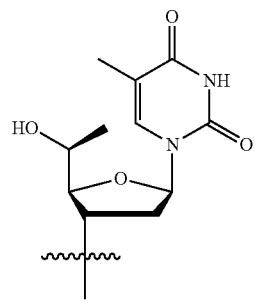
5mspdT
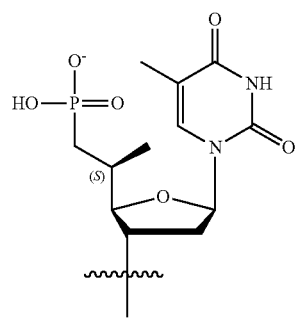
5mvpdT
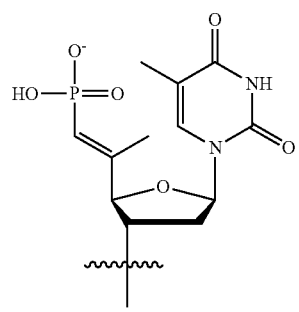
5pacetdT
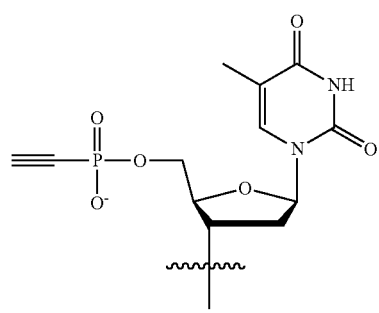
5ptzdT
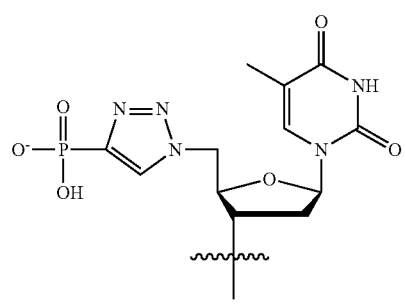

5tzdT
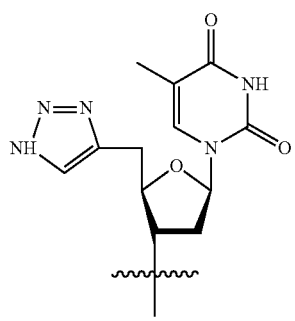 [SMILES: *[C@@H]1C[C@H](n2cc(C)c(=O)[nH]c2=O)O[C@@H]1Cc1c[nH]nn1]
5tzpodT
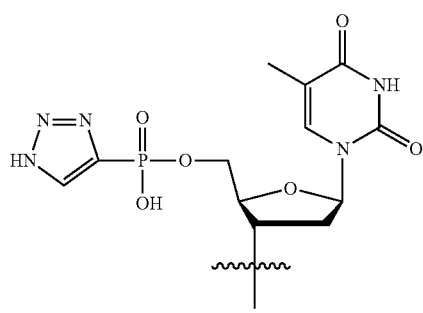
tbclc6T
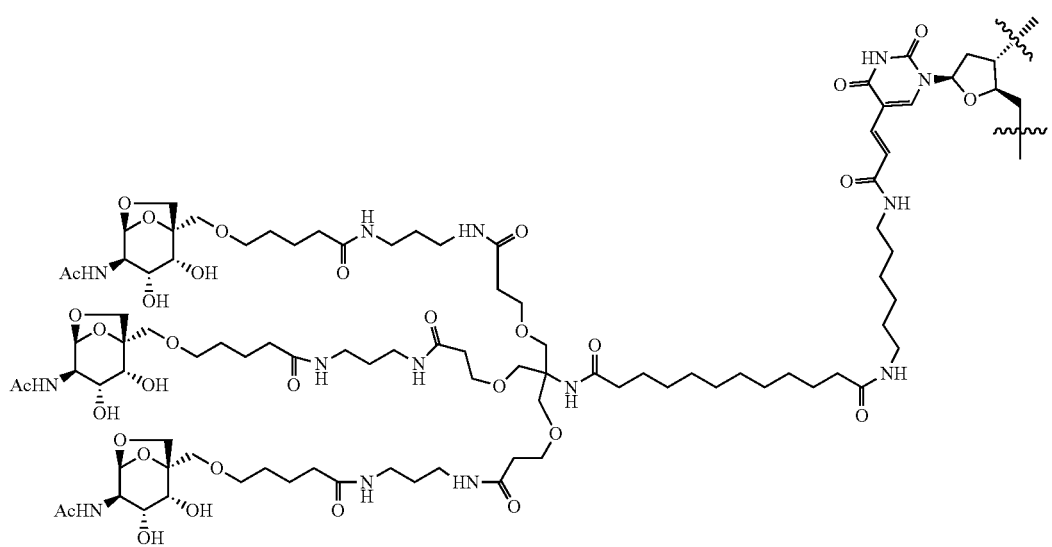

bbclc6T

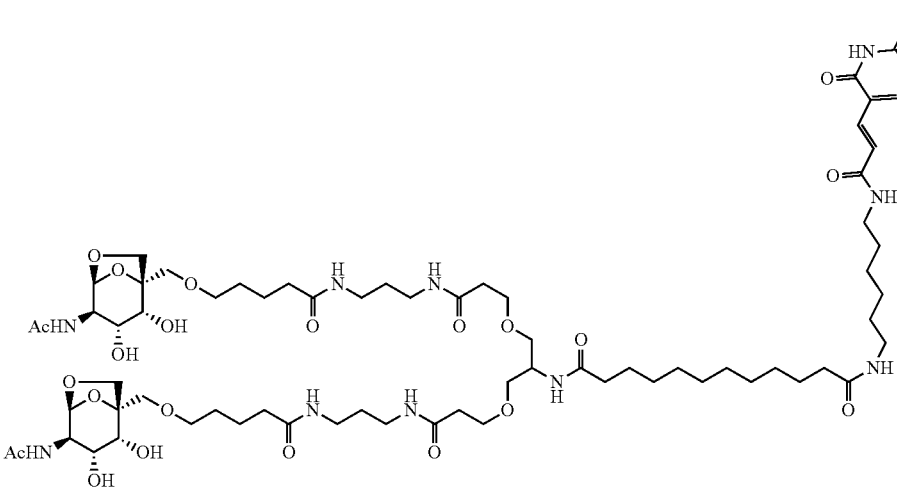

| | |
|---|---|
| L009 | —CH$_2$CH$_2$CH$_2$—. When L009 is present at the 5'-end of an oligonucleotide without a Mod, one end of L009 is connected to —OH and the other end connected to a 5'-carbon of the oligonucleotide chain via a linkage as indicated (e.g., in WV-9261, via a stereorandom phosphorothioate linkage ("*")). |

In some embodiments, a linker, e.g., L009, L010, etc., can replace a sugar, and is bonded on either end to an internucleotidic linkage. For example:

WV-9266 comprises . . . *mAL009*mUfG* . . . , which represents, from 5' to 3', a phosphorothioate (*), a sugar which is 2'-OMe (m) attached to a base (A), a phosphodiester linkage (not indicated), a L009 linker (L009), a phosphorothioate (*), a sugar which is 2'-OMe attached to a base which is U (mU), a phosphodiester linkage (not indicated), a sugar which is 2'-F (f) attached to a base (G) and a phosphorothioate.

WV-9267 comprises . . . *mAfC*L009fG* . . . , which represents, from 5' to 3', a phosphorothioate (*), a sugar which is 2'-OMe (m) attached to a base (A), a phosphodiester (not indicated), a sugar which is 2'-F (f) attached to a base (C), a phosphorothioate, a L009 linker (L009), a phosphodiester linkage (not indicated), a sugar which is 2'-F (f) attached to a base (G), and a phosphorothioate.

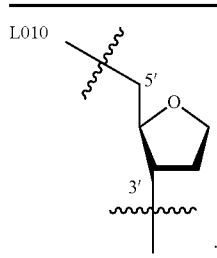

L010

L010 is connected in the same fashion as typically in DNA (the 5'-carbon of a first sugar is connected to a 3'-carbon of a second sugar via an internucleotidic linkage, and the 3'-carbon of the first sugar is connected to the 5'-carbon of a third sugar via an internucleotidic linkage). When L010 is present at the 5'-end of an oligonucleotide without a Mod, the 5'-carbon of L010 is connected to —OH and the 3'-carbon connected to a 5'-carbon of the oligonucleotide chain via a linkage as indicated (e.g., in WV-9250, via a stereorandom phosphorothioate linkage ("*")).

In some embodiments, L010 can replace a sugar, and L010 is bonded on either end to an internucleotidic linkage.
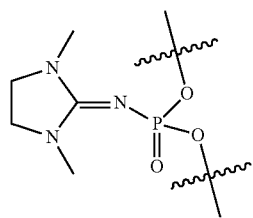
n001, nX
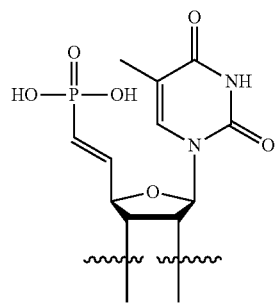
VPT
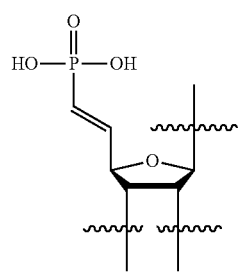
VP
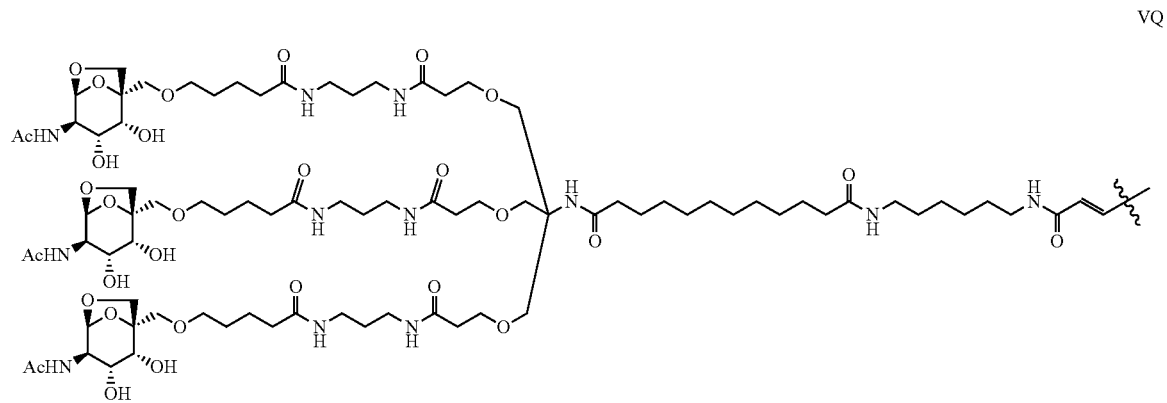
VQ
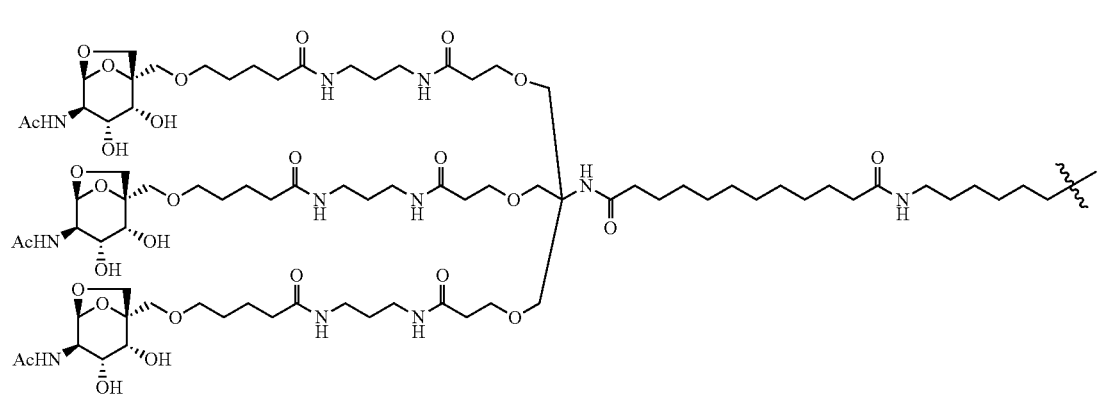
VR VS
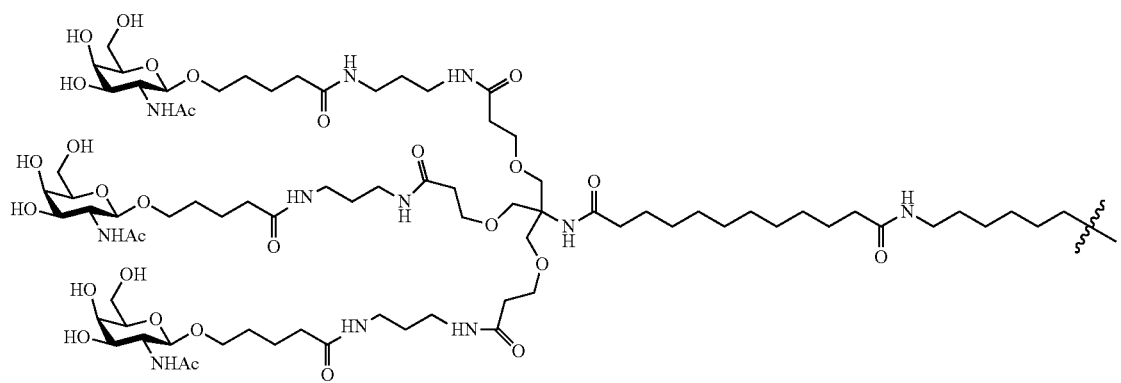
VT
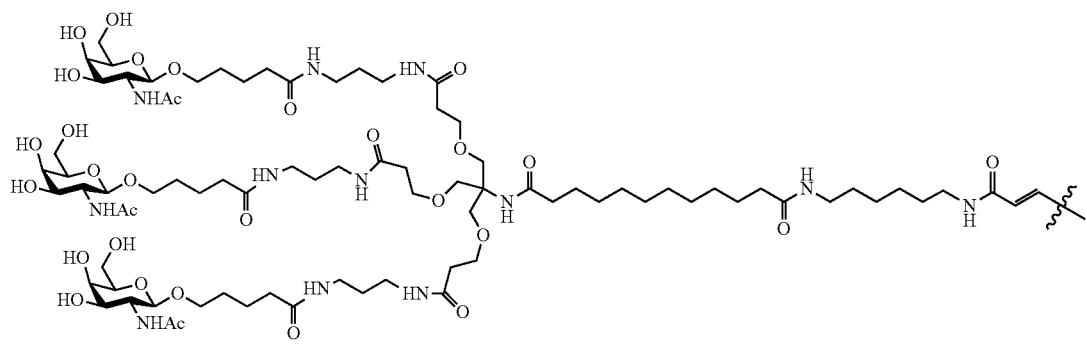
ADDITIONAL ABBREVIATIONS
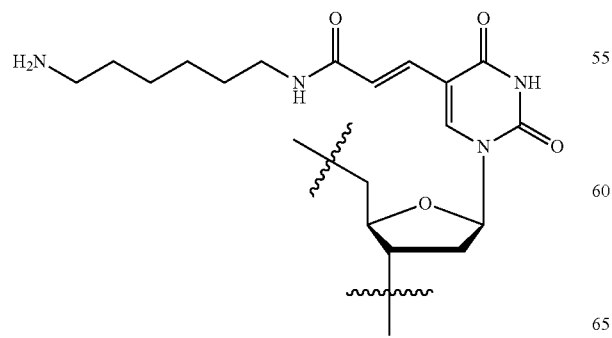

AMC6T:
eo: 2'-MOE
F, f: 2'-F
GaNC6T:

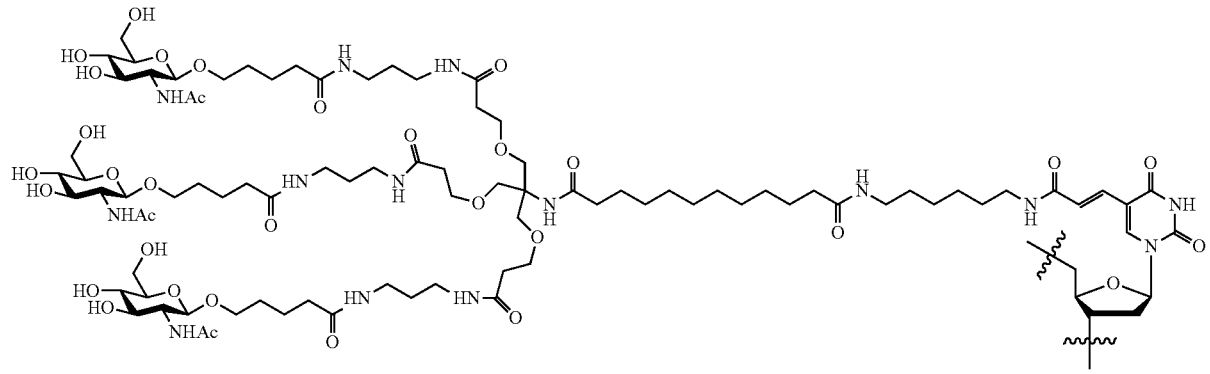

1: 2'-O—CH$_2$-4'

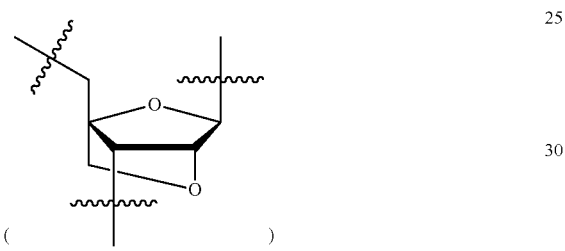

lmU:

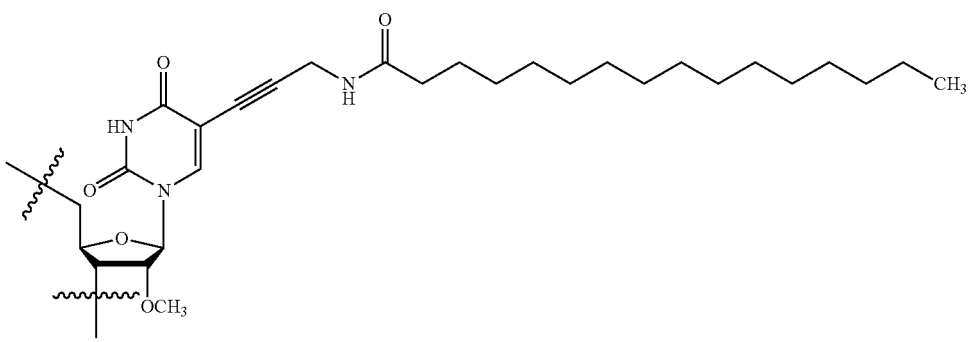

L001: —NH—(CH$_2$)$_6$— linker (C6 linker, C6 amine linker or C6 amino linker), connected to Mod, if any (if no Mod, —H, e.g., in WV-8240), through —NH—, and the 5'-end (e.g., in WV-2406) or 3'-end of oligonucleotide chain through either a phosphate linkage (O or PO) or phosphorothioate linkage (* if the phosphorothioate not chirally controlled; can also be Sp if chirally controlled and has an Sp configuration, and Rp if chirally controlled and has an Rp configuration) as illustrated. For example, in WV-2406, L001 is connected to Mod001 through —NH— (forming an amide group —C(O)—NH—), and is connected to the oligonucleotide chain through a phosphate linkage (OXXXXXXXXXXXXXXXXXXXX); in WV-2422, L001 is not connected to any Mod, but —H, through —NH—, and is connected to the oligonucleotide chain through a phosphate linkage (OXXXXXXXXXXXXXXXXXXXX)

L003:

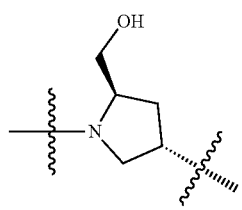

linker, connected to Mod, if any (if no Mod, —H, e.g., in WV-2426), through its amino group, and the 5'-end (e.g., in WV-2407) or 3'-end (e.g., in WV-8070) of oligonucleotide chain through either a phosphate linkage (O or PO) or phosphorothioate linkage (* if the phosphorothioate not chirally controlled; can also be Sp if chirally controlled and has an Sp configuration, and Rp if chirally controlled and has an Rp configuration) as illustrated. For example, in WV-2407, L003 is connected to Mod001 through its amino group (forming an amide group

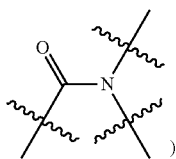 [SMILES: *C(=O)N(*)*]
)

and is connected to the 5'-end of oligonucleotide chain through a phosphate linkage (OXXXXXXXXX-XXXXXXXXXX); in WV-2426, L001 is not connected to any Mod, but —H, through —NH—, and is connected to the oligonucleotide chain through a phosphate linkage (OXXXXXXXXXXXXXXXXXXX); in WV-8070, L003 is connected to Mod001 through its amino group (forming an amide group

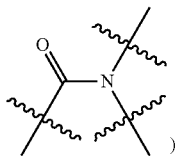 [SMILES: *C(=O)N(*)*]
)

and is connected to the 3'-end of oligonucleotide chain through a phosphate linkage ( . . . XXXXX-XXXXXXXXXXXXXXO)

m: 2'-OMe m5: methyl at 5-position of C (nucleobase is 5-methyl-cytosine)

m5Ceo: 5-methyl 2'-methoxyethyl C

OMe: 2'-OMe

O, PO: phosphodiester (phosphate); can be an end group (typically "PO"; for example in WV-4260: POT*fC* . . . ), or a linkage, e.g., a linkage between linker and oligonucleotide chain, an internucleotidic linkage, etc.

*, PS: Phosphorothioate; can be an end group (typically "PS", for example, in WV-2653: PST*fA* . . . ), or a linkage, e.g., a linkage between linker and oligonucleotide chain, an internucleotidic linkage, etc.

R, Rp: Phosphorothioate in Rp conformation

S, Sp: Phosphorothioate in Sp conformation

X: Stereorandom phosphorothioate

In some embodiments, a provided oligonucleotide composition is a single-stranded RNAi agent listed in Table 1A or otherwise described herein. In some embodiments, example properties of provided oligonucleotides were demonstrated.

In some embodiments, a provided oligonucleotide has a structure of any of formats illustrated in FIG. 1.

The present disclosure presents many non-limiting examples of oligonucleotides capable of mediating single-stranded RNA interference (e.g., single-stranded RNAi agents). Experimental data (not shown) demonstrated that various putative single-stranded RNAi agents were, in fact, capable of mediating RNA interference. In some experiments, an in vitro Ago-2 assay was used, including the use of a RNA test substrate WV-2372 (which targets a different gene, APOC3). The band representing the RNA test substrate is absent in the presence of oligonucleotides WV-1308 and WV-2420, indicating that these oligonucleotides are single-stranded RNAi agents capable of mediating RNA interference. The remaining lanes are controls: Substrate in the absence of negative control ASO WV-2134; substrate in the presence of negative control ASO WV-2134, which does not mediate RNA interference; substrate in the absence of test oligonucleotide WV-1308; substrate in the absence of test oligonucleotide WV-2420; substrate alone; no substrate, with added WV-2134; and no substrate, with added WV-1308. Also performed (data not shown) was an in vitro Ago-2 assay, using a APOC3 mRNA as a test substrate in a 3' RACE assay in Hep3B cells. A cleavage product of the APOC3 mRNA in the presence of test oligonucleotide WV-3021 was detected, the product corresponding to cleavage of the mRNA at a site corresponding to a cut between positions 10 and 11 of WV-3021. An artifactual cleavage product was also detected. Experimental data (not shown) demonstrated that dual mechanism oligonucleotide WV-2111 is capable of mediating knockdown by both RNase H and RNA interference. In an experiment, several oligonucleotides were capable of mediating RNA interference. The RNA test substrate was WV-2372. The experiment showed disappearance of the RNA test substrate in the presence of test oligonucleotides WV-1308; WV-2114; WV-2386; and WV-2387, indicating that all these oligonucleotides are capable of acting as single-stranded RNAi agents mediating RNA interference. The remaining lanes are controls. Thus, the experiment showed that oligonucleotides WV-1308, WV-2114, WV-2386, and WV-2387 were all able to mediate RNA interference. Thus, the experiments showed that several single-stranded RNAi agents (e.g., WV-1308, WV-2420, WV-3021, WV-2111, WV-2114, WV-2386, and WV-2387) are capable of mediating RNA interference. The present disclosure presents many non-limiting examples of oligonucleotides, having any of various sequences, formats, modifications, 5'-end regions, seed regions, post-seed regions, and 3'-end regions, and which are capable of mediating single-stranded RNA interference (e.g., single-stranded RNAi agents).

Formats of Oligonucleotides

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can have any format or portion thereof or structural element thereof described herein or known in the art.

In some embodiments, a PNPLA3 oligonucleotide can have any format or structural element thereof described herein or known in the art.

In some embodiments, a PNPLA3 oligonucleotide capable of directing a decrease in the expression and/or level of a target gene or its gene product can have any format or structural element thereof described herein or known in the art.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can have any format or structural element thereof described herein or known in the art.

Additional non-limiting examples of various ssRNAi formats are embodied by various single-stranded RNAi agents described herein.

In some embodiments, a provided single-stranded RNAi comprises a 5'-end represented by any 5'-end of any single-stranded RNAi format depicted in FIG. 1 or any single-stranded RNAi agent or single-stranded RNAi format described herein.

In some embodiments, a provided single-stranded RNAi comprises a 5'-end structure or 5'-end region represented by any 5'-end structure or 5'-end region of any single-stranded RNAi format depicted in FIG. 1 or any single-stranded RNAi agent or single-stranded RNAi format described herein.

In some embodiments, a provided single-stranded RNAi comprises a 5'-nucleotide represented by any 5'-nucleotide of any single-stranded RNAi format depicted in FIG. 1 or any single-stranded RNAi agent or single-stranded RNAi format described herein.

In some embodiments, a provided single-stranded RNAi comprises a 5'-nucleoside represented by any 5'-nucleoside of any single-stranded RNAi format depicted in FIG. 1 or any single-stranded RNAi agent or single-stranded RNAi format described herein.

In some embodiments, a provided single-stranded RNAi comprises a seed region represented by any seed region of any single-stranded RNAi format depicted in FIG. 1 or any single-stranded RNAi agent or single-stranded RNAi format described herein.

In some embodiments, a provided single-stranded RNAi comprises a post-seed region represented by any post-seed region of any single-stranded RNAi format depicted in FIG. 1 or any single-stranded RNAi agent or single-stranded RNAi format described herein.

In some embodiments, a provided single-stranded RNAi comprises a post-seed region or component thereof represented by any post-seed region or component thereof of any single-stranded RNAi format depicted in FIG. 1 or any single-stranded RNAi agent or single-stranded RNAi format described herein.

In some embodiments, a provided single-stranded RNAi comprises a 3'-terminal dinucleotide represented by any 3'-terminal dinucleotide of any single-stranded RNAi format depicted in FIG. 1 or any single-stranded RNAi agent or single-stranded RNAi format described herein.

In some embodiments, a provided single-stranded RNAi comprises a seed region having a pattern of internucleotidic linkages represented by the pattern of internucleotidic linkages of any seed region of any single-stranded RNAi format depicted in FIG. 1 or any single-stranded RNAi agent or single-stranded RNAi format described herein.

In some embodiments, a provided single-stranded RNAi comprises a post-seed region having a pattern of internucleotidic linkages represented by the pattern of internucleotidic linkages of any post-seed region of any single-stranded RNAi format depicted in FIG. 1 or any single-stranded RNAi agent or single-stranded RNAi format described herein.

In some embodiments, a provided single-stranded RNAi comprises a post-seed region or component thereof having a pattern of internucleotidic linkages represented by the pattern of internucleotidic linkages of any post-seed region or component thereof of any single-stranded RNAi format depicted in FIG. 1 or any single-stranded RNAi agent or single-stranded RNAi format described herein.

In some embodiments, a provided single-stranded RNAi comprises a 3'-terminal dinucleotide having a pattern of internucleotidic linkages represented by the pattern of internucleotidic linkages of any 3'-terminal dinucleotide of any single-stranded RNAi format depicted in FIG. 1 or any single-stranded RNAi agent or single-stranded RNAi format described herein.

In some embodiments, a provided single-stranded RNAi comprises a seed region having a pattern of chemical modifications represented by the pattern of chemical modifications of any seed region of any single-stranded RNAi format depicted in FIG. 1 or any single-stranded RNAi agent or single-stranded RNAi format described herein.

In some embodiments, a provided single-stranded RNAi comprises a post-seed region having a pattern of chemical modifications represented by the pattern of chemical modifications of any post-seed region of any single-stranded RNAi format depicted in FIG. 1 or any single-stranded RNAi agent or single-stranded RNAi format described herein.

In some embodiments, a provided single-stranded RNAi comprises a post-seed region or component thereof having a pattern of chemical modifications represented by the pattern of chemical modifications of any post-seed region or component thereof of any single-stranded RNAi format depicted in FIG. 1 or any single-stranded RNAi agent or single-stranded RNAi format described herein.

In some embodiments, a provided single-stranded RNAi comprises a 3'-terminal dinucleotide having a pattern of chemical modifications represented by the pattern of chemical modifications of any 3'-terminal dinucleotide of any single-stranded RNAi format depicted in FIG. 1 or any single-stranded RNAi agent or single-stranded RNAi format described herein.

In some embodiments, a provided single-stranded RNAi comprises a chemical modification represented by any chemical modification of any single-stranded RNAi format depicted in FIG. 1 or any single-stranded RNAi agent or single-stranded RNAi format described herein.

In some embodiments, a provided single-stranded RNAi comprises a chemical modification represented by any chemical modification of any single-stranded RNAi format depicted in FIG. 1 or described herein, wherein the chemical modification is conjugation of a moiety comprising a phosphate, linker, or a targeting moiety.

In some embodiments, a provided single-stranded RNAi comprises a chemical modification represented by any chemical modification of any single-stranded RNAi format depicted in FIG. 1 or described herein, wherein the chemical modification is conjugation of a moiety comprising a phosphate, linker, or a targeting moiety, wherein the targeting moiety comprises a GalNAc moiety. In some embodiments, a GalNAc is a protected or de-protected GalNAc.

In some embodiments, a PNPLA3 oligonucleotide is capable of decreasing the expression, activity and/or level of a target gene and/or a gene product thereof and has the format of any oligonucleotide described herein. In some embodiments, a PNPLA3 oligonucleotide is capable of decreasing the expression, activity and/or level of a target gene and/or a gene product thereof via a RNaseH-mediated mechanism or mechanism related to steric hindrance of translation and has the format of any oligonucleotide described herein. In some embodiments, a PNPLA3 oligonucleotide is capable of decreasing the expression, activity and/or level of a target gene and/or a gene product thereof via a RNaseH-mediated mechanism or mechanism related to steric hindrance of translation and has an asymmetric format. In some embodiments, a PNPLA3 oligonucleotide which has an asymmetric format comprises a first wing, a core and a second wing, wherein the core comprises a region of 5 or more contiguous 2'-deoxy nucleotides which can anneal to a target mRNA and form a structure recognized by RNaseH, and wherein the structure of the first and second wings are different. In some embodiments, the first and second wings differ in their 2'-modifications and/or internucleotidic linkages, or pattern of stereochemistry of the internucleotidic linkages.

In some embodiments, a PNPLA3 oligonucleotide is capable of decreasing the expression, activity and/or level of a target gene and/or a gene product thereof comprises a neutral internucleotidic linkage (e.g., a neutral backbone).

In some embodiments, a PNPLA3 oligonucleotide comprises a neutral backbone. In some embodiments, a PNPLA3 oligonucleotide comprises an internucleotidic linkage which is or comprises a triazole, neutral triazole, or alkyne. In some embodiments, a nucleic acid (including but not limited to a PNPLA3 oligonucleotide) which comprises an internucleotidic linkage which comprises a triazole, neutral triazole, or alkyne, wherein the internucleotidic linkage is stereocontrolled and in the Rp or Sp configuration. In some embodiments, an internucleotidic linkage comprising a triazole has a formula of:

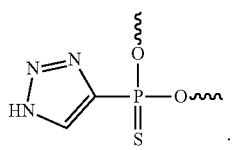

In some embodiments, an internucleotidic linkage comprising a neutral triazole has the formula of:

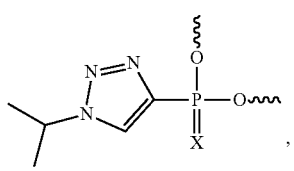

where X is O or S. In some embodiments, an internucleotidic linkage comprising an alkyne has the formula of:

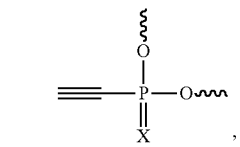

wherein X is O or S.

In some embodiments, an internucleotidic linkage comprises a cyclic guanidine. In some embodiments, an internucleotidic linkage comprises a cyclic guanidine and has the structure of:

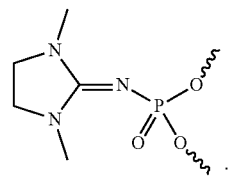

In some embodiments, a neutral internucleotidic linkage or internucleotidic linkage comprising a cyclic guanidine is stereochemically controlled. In some embodiments, a neutral internucleotidic linkage improves the activity, delivery and/or stability of a PNPLA3 oligonucleotide and/or the ability of a PNPLA3 oligonucleotide to perform endosomal escape.

As appreciated by those skilled in the art, in some instances, 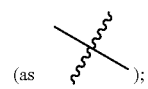 may be used to indicate a connection site (as );

in some instances, may be used to indicate a stereorandom connection.

Length of a PNPLA3 Oligonucleotide

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can have any length, wherein the length of a PNPLA3 oligonucleotide is such that the oligonucleotide is capable of directing a decrease in the expression and/or level of a target gene or its gene product.

In some embodiments, the length of a PNPLA3 oligonucleotide is such that the oligonucleotide is capable of directing a decrease in the expression and/or level of a target gene or its gene product.

In some embodiments, the length of a RNAi agent is such that the RNAi agent is capable of directing RNA interference of a specific target transcript in a sequence-specific manner. In some embodiments, the RNAi agent comprises a sufficient number of nucleobases of sufficient identity to recognize a target transcript. In some embodiments, the RNAi agent is also be of a length suitable for mediating RNAi interference.

The target portion of the sequence will be at least long enough to serve as a substrate for iRNA-directed cleavage at or near that portion. For example, the target sequence will generally be from about 9-36 nucleotides ("nt") in length, e.g., about 15-30 nucleotides in length, including all subranges therebetween. Examples of single-stranded RNAi agents of various lengths are shown in Table 1A.

FIG. 1 illustrates non-limiting examples of single-stranded RNAi agents having lengths from 19 to 25. Single-stranded RNAi agents having any of each of these lengths were constructed and found to be capable of knocking down a target gene. Thus, a provided single-stranded RNAi agent can be any of a variety of different lengths.

Non-limiting examples of formats of ssRNAi agents which are 19 bases long include: Formats 20-21 of FIG. 1.

Non-limiting examples of formats of ssRNAi agents which are 20 bases long include: Format 19 of FIG. 1.

5'-End of a PNPLA3 Oligonucleotide, Including a Single-Stranded RNAi Agent

In some embodiments, the structure of the 5'-end of a PNPLA3 oligonucleotide is such that the oligonucleotide is capable of directing a decrease in the expression and/or level of a target gene or its gene product.

In some embodiments, the structure of the 5'-end of a RNAi agent is such that the RNAi agent is capable of directing RNA interference of a specific target transcript in a sequence-specific manner.

In some embodiments, a provided oligonucleotide can comprise any 5'-end region, 5'-end structure, 5'-end group, 5'-end nucleoside, or 5'-end nucleotide described herein or known in the art. In some embodiments, a provided oligonucleotide capable of directing RNase H-mediated knockdown can comprise any 5'-end region, 5'-end structure, 5'-end group, 5'-end nucleoside, or 5'-end nucleotide described herein or known in the art. In some embodiments, a provided oligonucleotide capable of directing RNA interference can comprise any 5'-end region, 5'-end structure, 5'-end group, 5'-end nucleoside, or 5'-end nucleotide described herein or known in the art. In some embodiments, a provided oligonucleotide capable of directing RNA interference and RNase H-mediated knockdown can comprise any 5'-end region, 5'-end structure, 5'-end group, 5'-end nucleoside, or 5'-end nucleotide described herein or known in the art.

Among other things, the present disclosure recognizes that 5'-end structures of oligonucleotides, optionally in combination with additional features in accordance with the present disclosure, can provide unexpected advantages. In some embodiments, the present disclosures provides 5'-end groups (corresponding to 5'-HO—CH$_2$— of ribose found in natural RNA (or deoxyribose found in natural DNA)) that can surprisingly improve one or more properties and/or activities (e.g., stability, activity, manufacture cost, etc.) of oligonucleotides.

In some embodiments, 5'-OH groups of provided oligonucleotides are unmodified, i.e., they exist as free —OH. In some embodiments, a 5'-end group is 5'-HO—CH$_2$—. Among other things, the present disclosure demonstrates that a provided oligonucleotide with free 5'-OH groups can achieve properties and/or activities (e.g., stability, RNAi activity when used as ss-RNAi agent, etc.) comparable to an otherwise identical oligonucleotide comprising 5'-phosphate (or derivatives thereof) groups, despite reports in the literature that certain activities, e.g., RNAi activity, require presence of 5'-phosphate groups.

In some embodiments, a 5'-end group comprises no phosphorus atom. In some embodiments, a 5'-end group comprises no phosphate groups, or derivatives or bioisosteres thereof. In some embodiments, a 5'-end group comprises no acidic groups. In some embodiments, a 5'-end group comprises no carboxyl groups. In some embodiments, a 5'-end comprises no phosphorus atom or carboxyl groups. In some embodiments, a 5'-end group is 5'-HO—CH$_2$—. Among other things, the present disclosure demonstrates that provided oligonucleotides with no 5'-phosphates or derivatives or bioisosteres thereof can surprisingly achieve activities comparable to oligonucleotides that have 5'-phosphates but are otherwise identical, for example, in knockdown of mRNA levels of target genes, through RNAi pathways.

In some embodiments, a 5'-nucleoside unit of a provided oligonucleotide (which includes the sugar and nucleobase moieties but not the internucleotidic linkage between the 5'-nucleoside unit and the second nucleoside unit from the 5'-end) comprises no phosphate group, or derivatives or bioisosteres thereof. In some embodiments, a 5'-nucleoside unit comprises no phosphorus atom. In some embodiments, a 5'-nucleoside comprises no acidic groups. In some embodiments, a 5'-nucleoside unit comprises no —COOH groups or a salt form thereof.

In some embodiments, a 5'-end group is or comprises a phosphate group, or a derivative or a bioisostere thereof. In some embodiments, a 5'-nucleoside unit comprises a 5'-group which is a phosphate group, or a derivative or a bioisostere thereof. As appreciated by a person having ordinary skill in the art, a number of such groups are known in the art and can be utilized in accordance with the present disclosure.

In some embodiments, a 5'-end group is —CH$_2$—O—P(O)(OH)—(OH) or a salt form thereof. In some embodiments, a provided 5'-nucleoside unit has the structure of

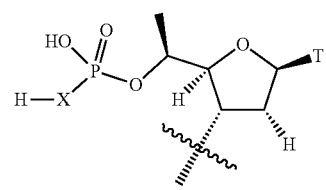

or a salt form thereof. In some embodiments, a provided 5'-nucleoside unit has the structure of

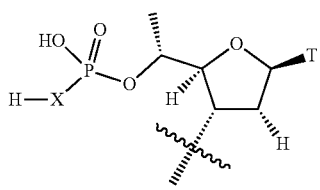

or a salt form thereof. In some embodiments, X is O. In some embodiments, X is S. In some embodiments, $R^E$ is —(R)—CH(CH$_3$)—O—P(O)(OH)—S—H or a salt form thereof. In some embodiments, $R^E$ is —(R)—CH(CH$_3$)—O—P(O)(OH)—O—H or a salt form thereof. In some embodiments, $R^E$ is —(S)—CH(CH$_3$)—O—P(O)(OH)—S—H or a salt form thereof. In some embodiments, $R^E$ is —(S)—CH(CH$_3$)—O—P(O)(OH)—O—H or a salt form thereof. In some embodiments, a provided 5'-nucleoside unit has the structure of

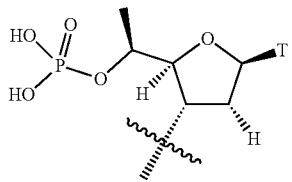

or a salt form thereof. In some embodiments, a provided 5'-nucleoside unit has the structure of

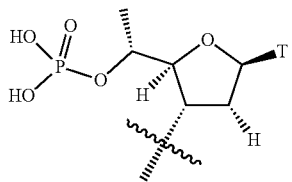

or a salt form thereof.

As readily appreciated by a person having ordinary skill in the art, provided compounds, e.g., oligonucleotides, or partial structures thereof, e.g., 5'-end structures, internucleotidic linkages, etc. of oligonucleotides, may partially, sometimes predominantly, exist as one or more salt forms thereof at certain pH, e.g., physiological pH, for example, due to one or more acidic and/or basic moieties therein. In some embodiments, a provided 5'-nucleoside unit may partially, sometimes predominately, exist as one or more its salt forms. For example, depending on pH,

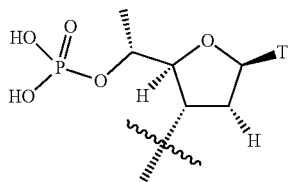

may exist as

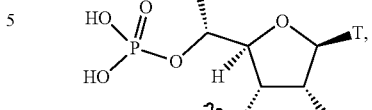

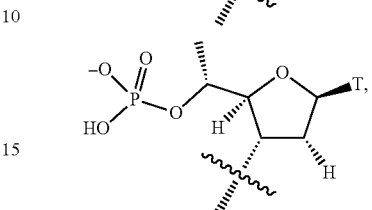

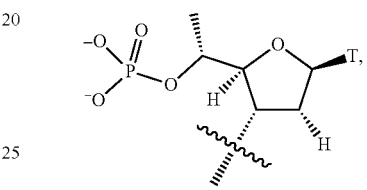

or any combinations thereof. Unless explicitly specified otherwise, all salt forms are included when provided compounds or structures are recited.

In some embodiments, $R^E$ is -L-P(O)(XR)$_2$ or a salt form thereof. In some embodiments, $R^E$ is -L-P(O)(XR)$_2$ or a salt form thereof, wherein each X is independently —O—, —S—, or a covalent bond. In some embodiments, $R^E$ is -L-P(O)(OR)$_2$ or a salt form thereof. In some embodiments, $R^E$ is -L-P(O)(OR)(SR) or a salt form thereof. In some embodiments, $R^E$ is -L-P(O)(OR)(R) or a salt form thereof. In some embodiments, L is a covalent bond, or a bivalent, optionally substituted, linear or branched C$_{1-6}$ aliphatic, wherein one or more methylene units are optionally and independently replaced with —O—, —S— or —N(R')—. In some embodiments, $R^E$ is -L-R$^{5s}$. In some embodiments, $R^E$ is —X-L-R. In some embodiments, $R^E$ is

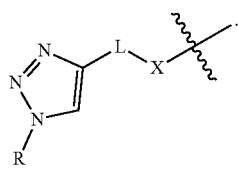

In some embodiments, X in $R^E$ is —C(R)$_2$—. In some embodiments, X is —O—. In some embodiments, X is —S—. In some embodiments, X is —N(R)—. In some embodiments, L comprises an optionally substituted, bivalent or multivalent

group. In some embodiments, L comprises an optionally substituted

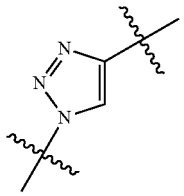 [SMILES: *c1cn(*)nn1]

group. In some embodiments, L comprises a

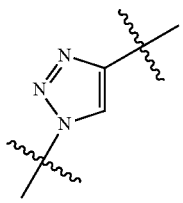 [SMILES: *c1cn(*)nn1]

group. In some embodiments, R is independently —H, or an optionally substituted group selected from $C_{1-10}$ alkyl, $C_{1-10}$ allyl, and $C_{6-14}$ aryl. In some embodiments, R is —H. In some embodiments, $R^E$ is optionally substituted

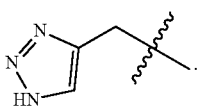

In some embodiments, $R^E$ is

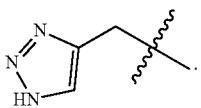

Many phosphate derivatives and/or bioisosteres, and 5'-nucleoside units are described in literature and can be utilized in accordance with the present disclosure, for example, some such structures are described in, e.g., US 2016-0194349; US 2016-0186175; US 20130323836, etc. In some embodiments, a 5' end group $R^E$, or a 5'-nucleoside unit, is described in, for example, Allerson et al. 2005 J. Med. Chem. 48: 901-04; Lima et al. 2012 Cell 150: 883-894; Prakash et al. 2015 Nucl. Acids Res. 43: 2993-3011; and/or Prakash et al. 2016 Bioorg. Med. Chem. Lett. 26: 26: 2817-2820, for example, T-VP, T-PO, etc.

Bridged Morpholinos and cyclohexenyl nucleotides and nucleosides are described in, for example, US patent application publication 2016-0186175, which can be utilized in accordance with the present disclosure.

Example embodiments of variables are extensively described in the present disclosure. For structures with two or more variables, unless otherwise specified, each variable can independently be any embodiment described herein.

In some embodiments, a PNPLA3 oligonucleotide capable of directing a decrease in the expression and/or level of a target gene or its gene product can comprise any 5'-end described herein or known in the art.

In some embodiments, a PNPLA3 oligonucleotide, a PNPLA3 oligonucleotide that directs RNA interference, a PNPLA3 oligonucleotide that directs RNase H-mediated knockdown can comprise any 5'-end described herein or known in the art.

In some embodiments, a PNPLA3 oligonucleotide, a PNPLA3 oligonucleotide that directs RNase H-mediated knockdown, or a PNPLA3 oligonucleotide that directs both RNA interference and RNase H-mediated knockdown can comprise any 5'-end described herein or known in the art.

In some embodiments, the 5'-end of a provided single-stranded RNAi agent comprises a phosphorus-comprising moiety (e.g., a 5'-end comprises a phosphorus). Non-limiting examples of ssRNAi formats wherein the 5'-end comprises a phosphorus-comprising moiety include Formats 1-15, 20-21, 23-31, 80-82, 92-95, 97-102, and 104-107 of FIG. 1.

In some embodiments, the 5'-end of a provided single-stranded RNAi agent does not comprise a phosphorus-comprising moiety (e.g., a 5'-end comprises a phosphorus). Non-limiting examples of ssRNAi formats wherein the 5'-end does not comprise a phosphorus-comprising moiety include Formats 16-19, 22, 32-79, 83-91, 96, and 103 of FIG. 1.

In some embodiments, the 5'-end of a provided single-stranded RNAi agent comprises a moiety comprising a phosphate, such as a phosphodiester, phosphorothioate, phosphorodithioate, H-phosphonate, or other moiety similar or identical to a phosphate-comprising internucleotidic linkage. In some embodiments, the 5'-end of a provided single-stranded RNAi agent comprises a moiety comprising a phosphate, but which is not a phosphodiester; such a moiety in some embodiments is referred to as a phosphate mimic, modified phosphate or phosphate analog.

In some embodiments, the 5'-end of a provided single-stranded RNAi agent does not comprise a moiety comprising a phosphate.

In some embodiments of a single-stranded RNAi agent, a 5' end structure has a structure selected from: 5'-(R)-Me OH T, 5'-(R)-Me PO T, 5'-(R)-Me PS T, 5'-(R)-Me PH T, 5'-(S)-Me OH T, 5'-(S)-Me PO T, 5'-(S)-Me PS T, and 5'-(S)-PH T.

In some embodiments of a provided single-stranded RNAi agent, which comprise a phosphorus-comprising moiety at the 5'-end structure which is represented by a structure selected from the Formula IV-a (Mod022 also known as C3 PO and n-propyl), IV-b (Mod022*), IV-c (POMod023*), IV-d (PSMod023*), and IV-e (PHMod023*):

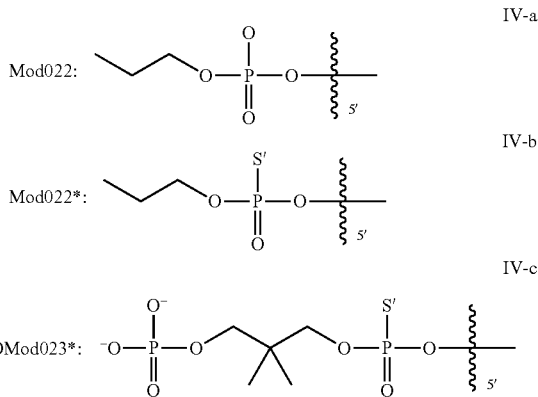

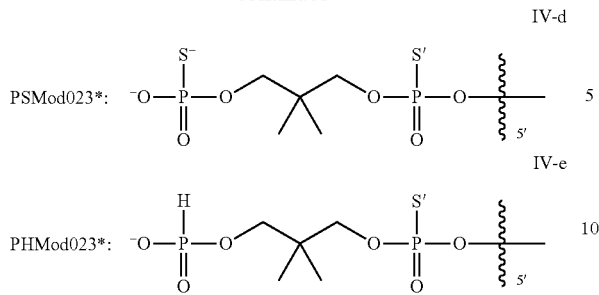

In some embodiments of a provided single-stranded RNAi agent, which comprise a phosphorus-comprising moiety at the 5'-end structure is represented by a structure selected of the structure of Formula IV-f (also known as n-propyl, C3 PO or Mod022):

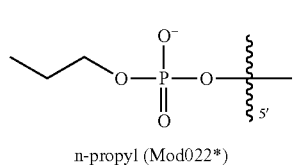

wherein 5' indicates the attachment point to the 5' carbon of a sugar.

In some embodiments of a provided single-stranded RNAi agent, which comprise a phosphorus-comprising moiety at the 5'-end structure is represented by a structure selected of the following structure (also known as C3 PS or Mod022*):

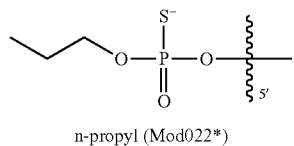 [SMILES: *OP(=O)([S-])OCCC]

wherein 5' indicates the attachment point to the 5' carbon of a sugar (e.g., of N1).

In some embodiments of a provided single-stranded RNAi agent, which comprise a phosphorus-comprising moiety at the 5'-end structure is represented by a structure selected of the structure of Formula IV-g (also known as DimethylC3 or C3dimethyl PS or Mod023*):

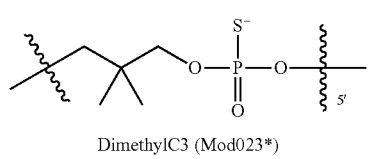

wherein 5' indicates the attachment point to the 5' carbon of a sugar (e.g., of N1).

In some embodiments, a single-stranded RNAi agent comprises a 5'-end structure which is selected from any of PO (phosphorodiester), Formula IV-h; PH (H-Phosphonate), Formula IV-i; and PS (Phosphorothioate), Formula IV j:

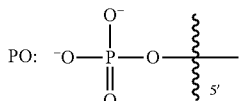
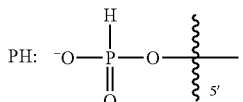
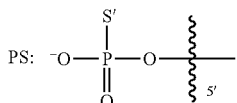

In some embodiments of a provided single-stranded RNAi agent, which comprise a phosphorus-comprising moiety at the 5'-end structure is represented by a structure selected from any of the following:

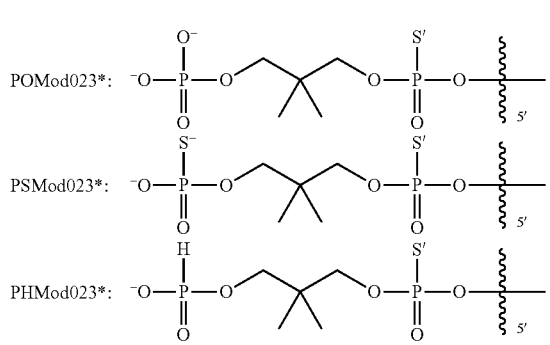

wherein 5' indicates the attachment point to the 5' carbon of a sugar (e.g., of N1).

In some embodiments, P in any of Formula IV-a to IV-j is stereorandom or stereodefined as in the Sp or Rp configuration.

In some embodiments, a 5'-end structure is selected from any of: a phosphate, a phosphate analogue, 5'-monophosphate ((HO)$_2$(O)P—O-5'), 5'-diphosphate ((HO)$_2$(O)P—O—P(HO)(O)—O-5'), 5'-triphosphate ((HO)$_2$(O)P—O—(HO)(O)P—O—P(HO)(O)—O-5'), 5'-guanosine cap (7-methylated or non-methylated) (7m-G-O-5'-(HO)(O)P—O—(HO)(O)P—O—P(HO)(O)—O-5'), 5'-adenosine cap (Appp), and any modified or unmodified nucleotide cap structure (N—O-5'-(HO)(O)P—O—(HO)(O)P—O—P (HO)(O)—O-5'), 5'-monothiophosphate (phosphorothioate; (HO)$_2$(S)P—O-5'), 5'-monodithiophosphate (phosphorodithioate; (HO)(HS)(S)P—O-5'), 5'-phosphorothiolate ((HO)$_2$(O)P—S-5'); any additional combination of oxygen/sulfur replaced monophosphate, diphosphate and triphosphates (e.g. 5'-alpha-thiotriphosphate, 5'-gamma-thiotriphosphate, etc.), 5'-phosphoramidates ((HO)$_2$(O)P—NH-5', (HO)(NH$_2$)(O)P—O-5'), 5'-alkylphosphonates (R=alkyl=methyl, ethyl, isopropyl, propyl, etc., e.g. RP(OH)(O)—O-5'-, (OH)$_2$(O)P-5'-CH$_2$—), 5'-alkyletherphosphonates (R=alkylether= methoxymethyl (MeOCH2-), ethoxymethyl, etc., e.g. RP(OH)(O)—O-5'-).

In some embodiments, a 5'-end comprising a phosphorus-comprising moiety can have particular advantages, in that the single-stranded RNAi agents comprising them may be more active in RNA interference.

In some embodiments, a 5' end structure has a structure of a 5'-nucleotide or a modified 5'-nucleotide, a 5'-nucleotide analog, a 5'-nucleoside or a modified 5'-nucleoside or a 5'-nucleoside analog.

In some embodiments, a 5' end structure, has a structure of any of: a 5'-guanosine cap, a 5'-adenosine cap, a 5'-monothiophosphate, a 5'-monodithiophosphate, a 5'-phosphorothiolate, a 5'-phosphoramidate, a 5'-alkylphosphonate, and a 5'-alkyletherphosphonate; a 5'-monophosphate, a 5'-diphosphate, and a 5'-triphosphate; 5'-triphosphate; a monophosphate, a diphosphate, or a triphosphate in which at least one oxygen atom of the monophosphate, diphosphate, or triphosphate is replaced with a sulfur atom; 5'-alpha-thiotriphosphate and 5'-gamma-thiotriphosphate; alkylphosphonate; alkylphosphonate has the formula: RP(OH)(O)—O-5' or (OH)$_2$(O)P-5'-CH$_2$—, wherein R is a C$_1$-C$_3$ alkyl; alkyletherphosphonate; or alkyletherphosphonate of the formula: RP(OH)(O)—O-5', wherein R is an alkylether.

Various 5'-nucleosides are described in, for example, U.S. patent application Ser. No. 14/959,714, published as US 2016-0194349 A1; U.S. patent application Ser. No. 14/983,907, published as US 2016-0186175 A1; or U.S. patent application Ser. No. 13/696,796, published as US 20130323836.

In some embodiments, a 5'-end structure is a vinylphosphonate.

In certain embodiments, oligomeric compounds are provided wherein said 5'-terminal compound has Formula VIII-c wherein G is F, OCH$_3$ or O(CH$_2$)$_2$—OCH$_3$.

In some embodiments, a 5' end structure has a structure selected from: 5'-(R)-Me OH T, 5'-(R)-Me PO T, 5'-(R)-Me PS T, 5'-(R)-Me PH T, 5'-(S)-Me OH T, 5'-(S)-Me PO T, 5'-(S)-Me PS T, and 5'-(S)-PH T.

In some embodiments, a 5' end structure has the structure of 5'-(R)-Me OH T.

In some embodiments, a 5' end structure has the structure of 5'-(R)-Me PO T.

In some embodiments, a 5' end structure has the structure of 5'-(R)-Me PS T.

In some embodiments, a 5' end structure has the structure of 5'-(R)-Me PH T.

In some embodiments, a 5' end structure has the structure of 5'-(S)-Me OH T.

In some embodiments, a 5' end structure has the structure of 5'-(S)-Me PO T.

In some embodiments, a 5' end structure has the structure of 5'-(S)-Me PS T.

In some embodiments of a single-stranded RNAi agent, a 5' end structure has the structure of 5'-(R)-Me PO T.

In some embodiments of a single-stranded RNAi agent, a 5' end structure has the structure of 5'-(R)-Me PS T.

In some embodiments of a single-stranded RNAi agent, a 5' end structure has the structure of 5'-(R)-Me PH T.

In some embodiments of a single-stranded RNAi agent, a 5' end structure has the structure of 5'-(S)-Me OH T.

In some embodiments of a single-stranded RNAi agent, a 5' end structure has the structure of 5'-(S)-Me PO T.

In some embodiments of a single-stranded RNAi agent, a 5' end structure has the structure of 5'-(S)-Me PS T.

In some embodiments of a single-stranded RNAi agent, a 5' end structure has the structure of 5'-(S)-Me PH T.

In some embodiments, a 5' end structure has the structure of 5'-(S)-Me PH T. In addition, some references such as EP 1520022 B1, paragraph 6, have reported that a 5' phosphate is required at the target-complementary strand (e.g., the antisense strand) of a siRNA duplex for RISC activity. U.S. Pat. No. 8,729,036, column 2, also noted that 5' phosphates are reported to be essential for RNA interference. U.S. Pat. No. 8,729,036, column 3, also reported that a 5' phosphate was required for single-stranded antisense siRNAs to trigger RNAi in HeLa S100 extract. However, the present disclosure has demonstrated that various single-stranded RNAi agents which do not comprise a 5' phosphate are capable of directing RNA interference.

In some embodiments, a 5'-end comprises a phosphate-comprising moiety such as T-VP or T-PO, or any other suitable RNAi agent 5'-end compound as described in, for example, Allerson et al. 2005 J. Med. Chem. 48: 901-04; Lima et al. 2012 Cell 150: 883-894; Prakash et al. 2015 Nucl. Acids Res. 43: 2993-3011; and/or Prakash et al. 2016 Bioorg. Med. Chem. Lett. 26: 26: 2817-2820.

In some embodiments, a 5'-end which does not comprise a phosphorus-comprising moiety can have particular advantages, in that the single-stranded RNAi agent can be easier to synthesize, and it may not be necessary to protect the phosphorus-comprising moiety from degradation. In some embodiments, a 5'-end of a provided single-stranded RNAi agent which does not comprise a phosphorus-comprising moiety comprises a moiety which can act as a substrate for a mammalian kinase which, inside a target cell, is able to attach a phosphorus-comprising moiety at the 5'-end of the single-stranded RNAi agent.

In some embodiments, a 5'-end does not comprise a phosphorus-comprising moiety.

In some embodiments of a single-stranded RNAi agent, the single-stranded RNAi agent comprises a 5' terminal OH, and the first nucleoside is 2'-deoxy.

In some embodiments of a single-stranded RNAi agent, the single-stranded RNAi agent comprises a 5' terminal OH, and the first nucleoside is 2'-deoxy T.

In some embodiments of a single-stranded RNAi agent, the single-stranded RNAi agent comprises a 5' terminal OH, and the first nucleoside is 2'-deoxy U.

In some embodiments of a single-stranded RNAi agent, the single-stranded RNAi agent comprises a 5' terminal OH, and the first nucleoside is 2'-deoxy A.

In some embodiments of a single-stranded RNAi agent, the single-stranded RNAi agent comprises a 5' terminal OH, and the first nucleoside is 2'-deoxy G.

In some embodiments of a single-stranded RNAi agent, the single-stranded RNAi agent comprises a 5' terminal OH, and the first nucleoside is 2'-deoxy C.

In some embodiments of a single-stranded RNAi agent, the single-stranded RNAi agent comprises a 5' terminal OH, and the first nucleoside is 2'-deoxy.

In some embodiments of a single-stranded RNAi agent, the single-stranded RNAi agent comprises a 5' terminal OH, and the first nucleoside is 2'-deoxy T. In some embodiments of a single-stranded RNAi agent, the single-stranded RNAi agent comprises a 5' terminal OH, and the first nucleoside is 2'-deoxy U.

In some embodiments of a single-stranded RNAi agent, the single-stranded RNAi agent comprises a 5' terminal OH, and the first nucleoside is 2'-deoxy A. In some embodiments of a single-stranded RNAi agent, the single-stranded RNAi agent comprises a 5' terminal OH, and the first nucleoside is 2'-deoxy G.

In some embodiments of a single-stranded RNAi agent, the single-stranded RNAi agent comprises a 5' terminal OH, and the first nucleoside is 2'-deoxy C.

In some embodiments of a single-stranded RNAi agent, the single-stranded RNAi agent comprises a 5' terminal OH, and the first nucleoside is 2'-OMe.

In some embodiments of a single-stranded RNAi agent, the single-stranded RNAi agent comprises a 5' terminal OH, and the first nucleoside is 2'-OMe T.

In some embodiments of a single-stranded RNAi agent, the single-stranded RNAi agent comprises a 5' terminal OH, and the first nucleoside is 2'-OMe U.

In some embodiments of a single-stranded RNAi agent, the single-stranded RNAi agent comprises a 5' terminal OH, and the first nucleoside is 2'-OMe A.

In some embodiments of a single-stranded RNAi agent, the single-stranded RNAi agent comprises a 5' terminal OH, and the first nucleoside is 2'-OMe G.

In some embodiments of a single-stranded RNAi agent, the single-stranded RNAi agent comprises a 5' terminal OH, and the first nucleoside is 2'-OMe C.

In some embodiments of a single-stranded RNAi agent, the single-stranded RNAi agent comprises a 5' terminal OH, and the first nucleoside is 2'-OMe.

In some embodiments of a single-stranded RNAi agent, the single-stranded RNAi agent comprises a 5' terminal OH, and the first nucleoside is 2'-OMe T.

In some embodiments of a single-stranded RNAi agent, the single-stranded RNAi agent comprises a 5' terminal OH, and the first nucleoside is 2'-OMe U. In some embodiments of a single-stranded RNAi agent, the single-stranded RNAi agent comprises a 5' terminal OH, and the first nucleoside is 2'-OMe A.

In some embodiments of a single-stranded RNAi agent, the single-stranded RNAi agent comprises a 5' terminal OH, and the first nucleoside is 2'-OMe G.

In some embodiments of a single-stranded RNAi agent, the single-stranded RNAi agent comprises a 5' terminal OH, and the first nucleoside is 2'-OMe C.

In some embodiments of a single-stranded RNAi agent, the single-stranded RNAi agent comprises a 5' terminal OH, and the first nucleoside is 2'-F.

In some embodiments of a single-stranded RNAi agent, the single-stranded RNAi agent comprises a 5' terminal OH, and the first nucleoside is 2'-F T.

In some embodiments of a single-stranded RNAi agent, the single-stranded RNAi agent comprises a 5' terminal OH, and the first nucleoside is 2'-F U.

In some embodiments of a single-stranded RNAi agent, the single-stranded RNAi agent comprises a 5' terminal OH, and the first nucleoside is 2'-F A.

In some embodiments of a single-stranded RNAi agent, the single-stranded RNAi agent comprises a 5' terminal OH, and the first nucleoside is 2'-F G.

In some embodiments of a single-stranded RNAi agent, the single-stranded RNAi agent comprises a 5' terminal OH, and the first nucleoside is 2'-F C.

In some embodiments of a single-stranded RNAi agent, the single-stranded RNAi agent comprises a 5' terminal OH, and the first nucleoside is 2'-F.

In some embodiments of a single-stranded RNAi agent, the single-stranded RNAi agent comprises a 5' terminal OH, and the first nucleoside is 2'-F T.

In some embodiments of a single-stranded RNAi agent, the single-stranded RNAi agent comprises a 5' terminal OH, and the first nucleoside is 2'-F U.

In some embodiments of a single-stranded RNAi agent, the single-stranded RNAi agent comprises a 5' terminal OH, and the first nucleoside is 2'-F A. In some embodiments of a single-stranded RNAi agent, the single-stranded RNAi agent comprises a 5' terminal OH, and the first nucleoside is 2'-F G. In some embodiments of a single-stranded RNAi agent, the single-stranded RNAi agent comprises a 5' terminal OH, and the first nucleoside is 2'-F C.

In some embodiments of a single-stranded RNAi agent, the single-stranded RNAi agent comprises a 5' terminal phosphate, and the first nucleoside is 2'-deoxy.

In some embodiments of a single-stranded RNAi agent, the single-stranded RNAi agent comprises a 5' terminal phosphate, and the first nucleoside is 2'-deoxy T.

In some embodiments of a single-stranded RNAi agent, the single-stranded RNAi agent comprises a 5' terminal phosphate, and the first nucleoside is 2'-deoxy U.

In some embodiments of a single-stranded RNAi agent, the single-stranded RNAi agent comprises a 5' terminal phosphate, and the first nucleoside is 2'-deoxy A.

In some embodiments of a single-stranded RNAi agent, the single-stranded RNAi agent comprises a 5' terminal phosphate, and the first nucleoside is 2'-deoxy G.

In some embodiments of a single-stranded RNAi agent, the single-stranded RNAi agent comprises a 5' terminal phosphate, and the first nucleoside is 2'-deoxy C.

In some embodiments of a single-stranded RNAi agent, the single-stranded RNAi agent comprises a 5' terminal phosphate, and the first nucleoside is 2'-deoxy.

In some embodiments of a single-stranded RNAi agent, the single-stranded RNAi agent comprises a 5' terminal phosphate, and the first nucleoside is 2'-deoxy T.

In some embodiments of a single-stranded RNAi agent, the single-stranded RNAi agent comprises a 5' terminal phosphate, and the first nucleoside is 2'-deoxy U.

In some embodiments of a single-stranded RNAi agent, the single-stranded RNAi agent comprises a 5' terminal phosphate, and the first nucleoside is 2'-deoxy A. In some embodiments of a single-stranded RNAi agent, the single-stranded RNAi agent comprises a 5' terminal phosphate, and the first nucleoside is 2'-deoxy G.

In some embodiments of a single-stranded RNAi agent, the single-stranded RNAi agent comprises a 5' terminal phosphate, and the first nucleoside is 2'-deoxy C.

In some embodiments of a single-stranded RNAi agent, the single-stranded RNAi agent comprises a 5' terminal phosphate, and the first nucleoside is 2'-F.

In some embodiments of a single-stranded RNAi agent, the single-stranded RNAi agent comprises a 5' terminal phosphate, and the first nucleoside is 2'-F T.

In some embodiments of a single-stranded RNAi agent, the single-stranded RNAi agent comprises a 5' terminal phosphate, and the first nucleoside is 2'-F U.

In some embodiments of a single-stranded RNAi agent, the single-stranded RNAi agent comprises a 5' terminal phosphate, and the first nucleoside is 2'-F A.

In some embodiments of a single-stranded RNAi agent, the single-stranded RNAi agent comprises a 5' terminal phosphate, and the first nucleoside is 2'-F G.

In some embodiments of a single-stranded RNAi agent, the single-stranded RNAi agent comprises a 5' terminal phosphate, and the first nucleoside is 2'-F C.

In some embodiments of a single-stranded RNAi agent, the single-stranded RNAi agent comprises a 5' terminal phosphate, and the first nucleoside is 2'-F.

In some embodiments of a single-stranded RNAi agent, the single-stranded RNAi agent comprises a 5' terminal phosphate, and the first nucleoside is 2'-F T.

In some embodiments of a single-stranded RNAi agent, the single-stranded RNAi agent comprises a 5' terminal phosphate, and the first nucleoside is 2'-F U. In some embodiments of a single-stranded RNAi agent, the single-stranded RNAi agent comprises a 5' terminal phosphate, and the first nucleoside is 2'-F A. In some embodiments of a single-stranded RNAi agent, the single-stranded RNAi agent comprises a 5' terminal phosphate, and the first nucleoside is 2'-F G.

In some embodiments of a single-stranded RNAi agent, the single-stranded RNAi agent comprises a 5' terminal phosphate, and the first nucleoside is 2'-F C.

In some embodiments of a single-stranded RNAi agent, the single-stranded RNAi agent comprises a 5' terminal phosphate, and the first nucleoside is 2'-OMe.

In some embodiments of a single-stranded RNAi agent, the single-stranded RNAi agent comprises a 5' terminal phosphate, and the first nucleoside is 2'-OMe T.

In some embodiments of a single-stranded RNAi agent, the single-stranded RNAi agent comprises a 5' terminal phosphate, and the first nucleoside is 2'-OMe U.

In some embodiments of a single-stranded RNAi agent, the single-stranded RNAi agent comprises a 5' terminal phosphate, and the first nucleoside is 2'-OMe A.

In some embodiments of a single-stranded RNAi agent, the single-stranded RNAi agent comprises a 5' terminal phosphate, and the first nucleoside is 2'-OMe G.

In some embodiments of a single-stranded RNAi agent, the single-stranded RNAi agent comprises a 5' terminal phosphate, and the first nucleoside is 2'-OMe C.

In some embodiments of a single-stranded RNAi agent, the single-stranded RNAi agent comprises a 5' terminal phosphate, and the first nucleoside is 2'-OMe. In some embodiments of a single-stranded RNAi agent, the single-stranded RNAi agent comprises a 5' terminal phosphate, and the first nucleoside is 2'-OMe T.

In some embodiments of a single-stranded RNAi agent, the single-stranded RNAi agent comprises a 5' terminal phosphate, and the first nucleoside is 2'-OMe U. In some embodiments of a single-stranded RNAi agent, the single-stranded RNAi agent comprises a 5' terminal phosphate, and the first nucleoside is 2'-OMe A. In some embodiments of a single-stranded RNAi agent, the single-stranded RNAi agent comprises a 5' terminal phosphate, and the first nucleoside is 2'-OMe G.

In some embodiments of a single-stranded RNAi agent, the single-stranded RNAi agent comprises a 5' terminal phosphate, and the first nucleoside is 2'-OMe C.

In some embodiments, a PNPLA3 oligonucleotide comprises an additional component which binds to ASPGR. In some embodiments, the additional component is on the 5' end of the oligonucleotide.

In some embodiments, a PNPLA3 oligonucleotide comprises an additional component which is or comprises a compound of Formula (K)

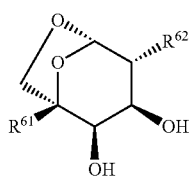

(K)

wherein R is —CN, —CH$_2$—CN, —C≡CH, —CH$_2$—N$_3$, —CH$_2$—NH$_2$, —CH$_2$—N(R)—S(O)$_2$—R, —CH$_2$—CO$_2$H, —CO$_2$H, —CH$_2$—OH, —CH$_2$—SH, —CH=CH—R, —CH$_2$—R, —CH$_2$—S—R, —CH$_2$—N(R)—R, —CH$_2$—N(R)—C(O)—R, —CH$_2$—N(R)—C(O)—O—R, —CH$_2$—N(R)—C(O)—N(R)—R, —CH$_2$—O—R, —CH$_2$—O—C(O)—R, —CH$_2$—O—C(O)—N(R)—R, —CH$_2$—O—C(O)—O—R, —CH$_2$—S(O)—R, —CH$_2$—S(O)$_2$—R, —CH$_2$—S(O)$_2$—N(R)—R, —C(O)—NH$_2$, —C(O)—O—R, —C(O)—N(R)—R, or aryl or heteroaryl, wherein the aryl or heteroaryl is optionally substituted with R, or R is —Z—X—Y wherein X is a linker or a drug delivery system, Y is absent or is a ligand selected from the group consisting of a small molecule, an amino acid sequence, a nucleic acid sequence, an antibody, an oligomer, a polymer, genetically derived material, a liposome, a nanoparticle, dye, fluorescent probe, or a combination thereof, and Z is absent or is —C≡C—, —CH=CH—, —CH$_2$—, —CH$_2$—O—, —C(O)—N(R)—, —CH$_2$—S—, —CH$_2$—S(O)—, —CH$_2$—S(O)$_2$—, —CH$_2$—S(O)$_2$—N(R)—, —C(O)—O—, —CH$_2$—N(R)—, —CH$_2$—N(R)—C(O)—, —CH$_2$—N(R)—S(O)$_2$—, —CH$_2$—N(R)—C(O)—O—, —CH$_2$—N(R)—C(O)—N(R)—, —CH$_2$—O—C(O)—, —CH$_2$—O—C(O)—N(R)—, —CH$_2$—O—C(O)—O—, or aryl or heteroaryl, wherein the aryl or heteroaryl is optionally substituted with R;

$R^{62}$ is —OH, —N$_3$, —N(R)$_2$, —N(R)—C(O)—R, —N(R)—C(O)—N(R)$_2$, —N(R)—C(O)—OR, tetrazole, or triazole, wherein the tetrazole and triazole are optionally substituted with R, and wherein when R is —CH$_2$—OH, R is —N$_3$, —N(R)$_2$, —N(R)—C(O)—R, —N(R)—C(O)—N(R)$_2$—N(R)—C(O)—OR, tetrazole, or triazole, wherein the tetrazole and triazole are optionally substituted with R; each R is independently —H, —(C$_1$-C$_5$)alkyl, halo-substituted (C$_1$-C$_5$) alkyl, or (C$_3$-C$_6$)cycloalkyl, wherein a —CH$_2$— group of the alkyl or cycloalkyl may be replaced with a heteroatom group selected from —O—, —S—, and —N(R)— and —CH$_3$ of the alkyl may be replaced with a heteroatom group selected from —N(R)$_2$, —OR, and —S(R) wherein the heteroatom groups are separated by at least 2 carbon atoms; each R is independently —H, —(C$_1$-C$_{20}$)alkyl, or (C$_3$-C$_6$) cycloalkyl wherein one to six —CH$_2$— groups of the alkyl or cycloalkyl separated by at least two carbon atoms may be replaced with —O—, —S—, or —N(R)—, and —CH$_3$ of the alkyl may be replaced with a heteroatom group selected from —N(R)$_2$, —OR, and —S(R) wherein the heteroatom groups are separated by at least 2 carbon atoms; and wherein the alkyl and cycloalkyl may be substituted with one to six halo atoms; and each R is independently —H, (C$_3$-C$_{20}$)cycloalkyl or (C$_1$-C$_{20}$)alkyl wherein one to six —CH$_2$— groups of the alkyl or cycloalkyl separated by at least two carbon atoms may be replaced with —O—, —S—, or —N(R)—, and —CH$_3$ of the alkyl may be replaced with a heteroatom group selected from —N(R)$_2$, —OR, and —S(R) wherein the heteroatom groups are separated by at least 2 carbon atoms; and wherein the alkyl and cycloalkyl may be substituted with one to six halo atoms.

In some embodiments, a PNPLA3 oligonucleotide comprises an additional component which is or comprises a compound of Formula (M)

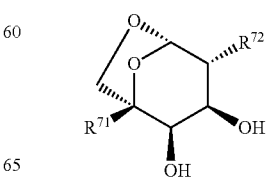

(M)

wherein R is —CN, —CH₂—CN, —C≡CH, —CH₂—N₃, —CH₂—NH₂, —CH₂—N(R)—S(O)₂—R, —CH₂—CO₂H, —CO₂H, —CH₂—OH, —CH₂—SH, —CH═CH—R, —CH₂—R, —CH₂—S—R, —CH₂—N(R)—R, —CH₂—N(R)—C(O)—R, —CH₂—N(R)—C(O)—O—R, —CH₂—N(R)—C(O)—N(R)—R, —CH₂—O—R, —CH₂—O—C(O)—R, —CH₂—O—C(O)—N(R)—R, —CH₂—O—C(O)—O—R, —CH₂—S(O)—R, —CH₂—S(O)₂—R, —CH₂—S(O)₂—N(R)—R, —C(O)—NH₂, —C(O)—O—R, —C(O)—N(R)—R, or aryl or heteroaryl, wherein the aryl or heteroaryl is optionally substituted with R, or R is —Z—X—Y, —Z—Y, —X—Y, —X, —Y, or —Z—X wherein X is a linker or a drug delivery system, Y is R or is a ligand selected from the group consisting of a small molecule, an amino acid sequence, a nucleic acid sequence, an antibody, an oligomer, a polymer, genetically derived material, a liposome, a nanoparticle, dye, fluorescent probe, or a combination thereof, and Z is —C≡C—, —CH═CH—, —CH₂—, —CH₂—O—, —C(O)—N(R)—, —CH₂—S—, —CH₂—S(O)—, —CH₂—S(O)₂—, —CH₂—S(O)₂—N(R)—, —C(O)—O—, —CH₂—N(R)—, —CH₂—N(R)—C(O)—, —CH₂—N(R)—S(O)₂—, —CH₂—N(R)—C(O)—O—, —CH₂—N(R)—C(O)—N(R)—, —CH₂—O—C(O)—, —CH₂—O—C(O)—N(R)—, —CH₂—O—C(O)—O—, or aryl or heteroaryl, wherein the aryl or heteroaryl is optionally substituted with R; R is —OH, —N₃, —N(R)₂, —N(R)—C(O)—R, —N(R)—C(O)—N(R)₂, —N(R)—C(O)—OR, —N(R)—S(O)₂—R¹ tetrazole, or triazole, wherein the tetrazole and triazole are optionally substituted with R and wherein when R is —CH₂—OH, R is —N₃, —N(R)₂, —N(R)—C(O)—R, —N(R)—C(O)—N(R)₂, —N(R)—C(O)—OR, N(R)—S(O)₂—R, tetrazole, or triazole, wherein the tetrazole and triazole are optionally substituted with R;

each R is independently —H, —(C₁-C₅)alkyl, halo-substituted (C₁-C₅)alkyl, or (C₃-C₆)cycloalkyl, wherein one or more —CH₂— groups of the alkyl or cycloalkyl may each be replaced with a heteroatom group independently selected from —O—, —S—, and —N(R)— and —CH₃ of the alkyl may be replaced with a heteroatom group selected from —N(R)₂, —OR, and —S(R) wherein the heteroatom groups are separated by at least 2 carbon atoms;

each R is independently —H, —(C₁-C₂₀)alkyl, or (C₃-C₆) cycloalkyl wherein one to six —CH₂— groups of the alkyl or cycloalkyl separated by at least two carbon atoms may each be replaced with a heteroatom independently selected from —O—, —S—, or —N(R)—, and —CH₃ of the alkyl may be replaced with a heteroatom group selected from —N(R)₂, —OR, and —S(R) wherein the heteroatom groups are separated by at least 2 carbon atoms; and wherein the alkyl and cycloalkyl may be substituted with halo atoms;

each R is independently —H, (C₃-C₂₀)cycloalkyl or (C₁-C₆₀)alkyl wherein one to six —CH₂— groups of the cycloalkyl or one to 20 —CH₂— groups of the alkyl may each be replaced with heteroatoms independently selected from —O—, —S—, and —N(R)— wherein the heteroatoms are separated by at least two carbon atoms, and —CH₃ of the alkyl may be replaced with a heteroatom group selected from —N(R)₂, —OR, and —S(R) wherein the heteroatom groups are separated by at least 2 carbon atoms; and wherein the alkyl and cycloalkyl may be substituted with halo atoms; and each R is independently H, —C≡CH, —C═CH₂, —CH₃, —N₃, —N(R)₂, —OH, —S(O)—(R), —S(O)₂—(R), —C(O)—OH, —S—S-aryl, —S—S-heteroaryl, heterocycyl, aryl or heteroaryl, wherein each aryl or heteroaryl is optionally substituted with R.

In some embodiments, $R^{61}$ or $R^{71}$ is —X—Y, and/or $R^{62}$ or $R^{72}$ is —NH—C(O)—CH₃.

In some embodiments, a PNPLA3 oligonucleotide comprises an additional component selected from the group consisting of:

benzyl (4-((2-((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)ethyl)amino)-4-oxobutyl)carbamate, benzyl (4-((1,3-bis((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)propan-2-yl)amino)-4-oxobutyl)carbamate, benzyl (4-((1,3-bis((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)-2-(((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)methyl)propan-2-yl)amino)-4-oxobutyl)carbamate, N-(2-((1-(1-(((1S,2R,3R,4R,5S)-4-acetamido-2,3-dihydroxy-6,8-dioxabicyclo[3.2.1]octan-1-yl)-2,5,8,11-tetraoxatridecan-13-yl)-1H-1,2,3-triazol-4-yl)methoxy)ethyl)-4-aminobutanamide, 4-amino-N-{1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]propan-2-yl}butanamide, 4-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)butanamide, 4-amino-N-[1,31-bis(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-2,6,10,14,18,22,26,30-octaoxahentriacontan-16-yl]butanamide, 4-amino-N-{1,31-bis(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-16-[15-(1-{[(1S,2R,3R,4R,5S)-4-(acetylamino)-2,3-dihydroxy-6,8-dioxabicyclo[3.2.1]oct-1-yl]methyl}-1H-1,2,3-triazol-4-yl)-2,6,10,14-tetraoxapentadec-1-yl]-2,6,10,14,18,22,26,30-octaoxahentriacontan-16-yl}butanamide, N-{(1S,2R,3R,4R,5S)-1-[(hexyloxy)methyl]-2,3-dihydroxy-6,8-dioxabicyclo[3.2.1]oct-4-yl}acetamide, N-[(1S,2R,3R,4R,5S)-2,3-dihydroxy-1-(2,5,8,11,14-pentaoxapentadec-1-yl)-6,8-dioxabicyclo[3.2.1]oct-4-yl]acetamide, N-((1S,2R,3R,4R,5S)-2,3-dihydroxy-1-(hydroxymethyl)-6,8-dioxabicyclo[3.2.1]octan-4-yl)-2,2,2-trifluoroacetamide, compound, N-[(1S,2R,3R,4R,5S)-2,3-dihydroxy-1-(hydroxymethyl)-6,8-dioxabicyclo[3.2.1]oct-4-yl]-2,2,2-trifluoroacetamide, N-[(1S,2R,3R,4R,5S)-2,3-dihydroxy-1-(hydroxymethyl)-6,8-dioxabicyclo[3.2.1]oct-4-yl]propanamide, N-[(1S,2R,3R,4R,5S)-2,3-dihydroxy-1-(hydroxymethyl)-6,8-dioxabicyclo[3.2.1]oct-4-yl]methanesulfonamide, N-[(1S,2R,3R,4R,5S)-2,3-dihydroxy-1-(hydroxymethyl)-6,8-dioxabicyclo[3.2.1]oct-4-yl]-2,2-difluoroacetamide, N-[(1S,2R,3R,4R,5S)-2,3-dihydroxy-1-(hydroxymethyl)-6,8-dioxabicyclo[3.2.1]oct-4-yl]-3,3,3-trifluoropropanamide, N-[(1S,2R,3R,4R,5S)-2,3-dihydroxy-1-(hydroxymethyl)-6,8-dioxabicyclo[3.2.1]oct-4-yl]-N-methylacetamide, N-[(1S,2R,3R,4R,5S)-2,3-dihydroxy-1-(hydroxymethyl)-6,8-dioxabicyclo[3.2.1]oct-4-yl]-N-methylmethanesulfonamide, tert-butyl [(1S,2R,3R,4R,5S)-2,3-dihydroxy-1-(hydroxymethyl)-6,8-dioxabicyclo[3.2.1]oct-4-yl]methylcarbamate, (1S,2R,3R,4R,5S)-1-(hydroxymethyl)-4-(methylamino)-6,8-dioxabicyclo[3.2.1]octane-2,3-diol hydrochloride, N-[(1S,2R,3R,4R,5S)-2,3-dihydroxy-1-(15-phenyl-2,5,8,11,14-pentaoxapentadec-1-yl)-6,8-dioxabicyclo[3.2.1]oct-4-yl]acetamide, N-[(1S,2R,3R,4R,5S)-1-(13-azido-2,5,8,11-tetraoxatridec-1-yl)-2,3-dihydroxy-6,8-dioxabicyclo[3.2.1]oct-4-yl]acetamide, N-[(1S,2R,3R,4R,5S)-2,3-dihydroxy-1-(2,5,8,11-tetraoxatetradec-13-en-1-yl)-6,8-dioxabicyclo[3.2.1]oct-4-yl]acetamide, N-[(1S,2R,3R,4R,5S)-2,3-dihydroxy-1-(2,5,8,11-tetraoxatetradec-13-yn-1-yl)-6,8-dioxabicyclo[3.2.1]oct-4-yl]acetamide, N-[(1S,2R,3R,4R,5S)-1-(13-amino-2,5,8,11-tetraoxatridec-1-yl)-2,3-dihydroxy-6,8-dioxabicyclo[3.2.1]oct-4-yl]acetamide, N-[(1S,2R,3R,4R,5S)-2,3-dihydroxy-1-(13-hydroxy-2,5,8,11-tetraoxatridec-1-yl)-6,8-dioxabicyclo[3.2.1]oct-4-yl]acetamide, 1-[(1S,2R,3R,4R,5S)-4-(acetylamino)-2,3-dihydroxy-6,8-dioxabicyclo[3.2.1]oct-1-yl]-2,5,8,11-tetraoxatridecan-13-oic acid, S-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}ethanethioate, N-{(1S,2R,3R,4R,5S)-2,3-dihydroxy-1-[13-(pyridin-2-yldisulfanyl)-2,5,8,11-tetraoxatridec-1-yl]-6,8-dioxabicyclo[3.2.1]oct-4-yl}acetamide, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-6-(pyridin-2-yldisulfanyl)hexanamide, N-[(1S,2R,3R,4R,5S)-1-(13-{4-[(3-[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}-2-aminopropoxy)methyl]-1H-1,2,3-triazol-1-yl}-2,5,8,11-tetraoxatridec-1-yl)-2,3-dihydroxy-6,8-dioxabicyclo[3.2.1]oct-4-yl]acetamide hydrochloric acid salt, 6-azido-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hept-6-enamide, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hept-6-ynamide, 7-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-7-oxoheptanoic acid (Sodium salt), benzyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate, 6-amino-N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)hexanamide acetate salt, N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-(2,5-dioxo-2,5-dihydro-1H-pyrrol-1-yl)hexanamide, N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-[(bromoacetyl)amino]hexanamide, 4-{[(2R)-5-(carbamoylamino)-2-{[(2R)-2-cyclopentyl-2-{[6-(2,5-dioxo-2,5-dihydro-1H-pyrrol-1-yl)hexanoyl]amino}acetyl]amino}pentanoyl]amino}benzyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,19-dioxo-1-(pyridin-2-yldisulfanyl)-7,10,13,16-tetraoxa-4,20-diazahexacosan-26-amide, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-3,31-dioxo-1-(pyridin-2-yldisulfanyl)-7,10,13,16,19,22,25,28-octaoxa-4,32-diazaoctatriacontan-38-amide, N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-(pyridin-2-yldisulfanyl)hexanamide, 2-(pyridin-2-yldisulfanyl)ethyl {6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}carbamate, N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-6-(4,4,5,5-tetramethyl-1,3,2-dioxaborolan-2-yl)hexanamide, N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}-N'-(1,3-dihydroxypropan-2-yl)heptanediamide, 6-azido-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide, 6-(benzyloxy)-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide, (1S,2R,3R,4R,5S)-4-(acetylamino)-1-{13-[4-({3-[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-bis(acetyloxy)-6,8-dioxabicyclo[3.2.1]oct-1-yl]-2,5,8,11-tetraoxatridecan-13-yl}-1H-1,2,3-triazol-4-yl)methoxy]methyl}-2-({6[(6hydroxyhexanoyl)amino]hexanoyl}amino)propoxy}methyl)-1H-1,2,3-triazol-1-yl]-2,5,8,11-tetraoxatridec-1-yl}-3-(acetyloxy)-6,8-dioxabicyclo[3.2.1]oct-2-yl acetate, benzyl [6-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-6-oxohexyl]carbamate, 6-amino-N-{6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}hexanamide acetate, 4-(benzyloxy)-N-(1,3-bis[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-amino-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)butanamide, N-(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)-4-hydroxybutanamide, and N-(2-{[6-({6-[(1,3-bis[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]-2-{[(1-{1-[(1S,2R,3R,4R,5S)-4-(acetylamino)-2,3-dihydroxy-6,8-dioxabicyclo[3.2.1]oct-1-yl]-2,5,8,11-tetraoxatridecan-13-yl}-1H-1,2,3-triazol-4-yl)methoxy]methyl}propan-2-yl)amino]-6-oxohexyl}amino)-6-oxohexyl]oxy}-1,3-dioxan-5-yl)-6-(pyridin-2-yldisulfanyl)hexanamide In some embodiments, a PNPLA3 oligonucleotide comprises an additional component of Formula (N)

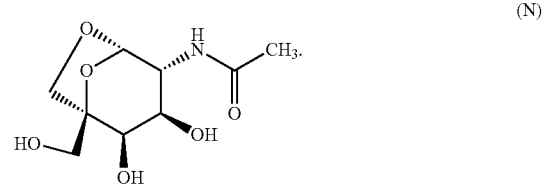 [SMILES: CC(=O)N[C@H]1[C@H]2OC[C@](CO)(O2)[C@H](O)[C@@H]1O]

(N)

In some embodiments, a PNPLA3 oligonucleotide comprises an additional component selected from:
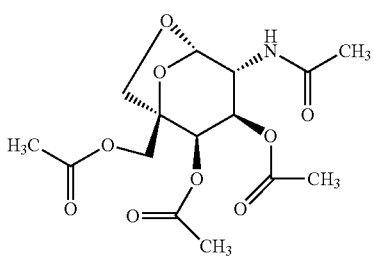 [SMILES: CC(=O)N[C@H]1[C@H]2OC[C@](COC(C)=O)(O2)[C@H](OC(C)=O)[C@@H]1OC(C)=O]
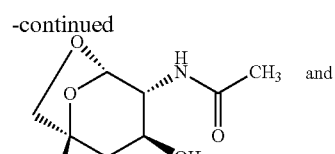
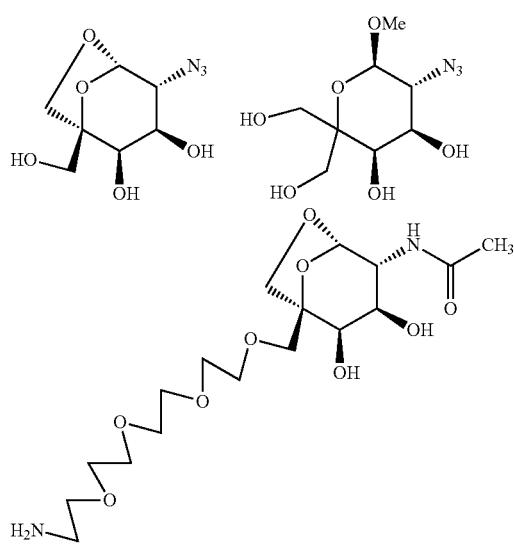
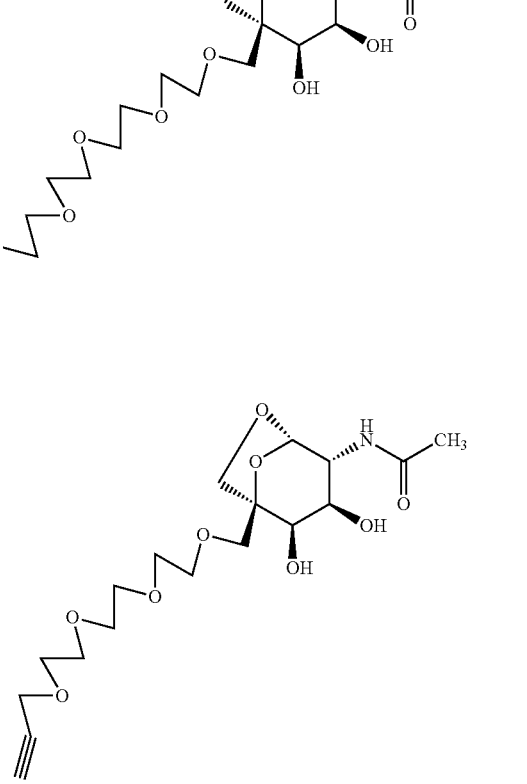
In some embodiments, a PNPLA3 oligonucleotide comprises an additional component selected from any of the following formulae:
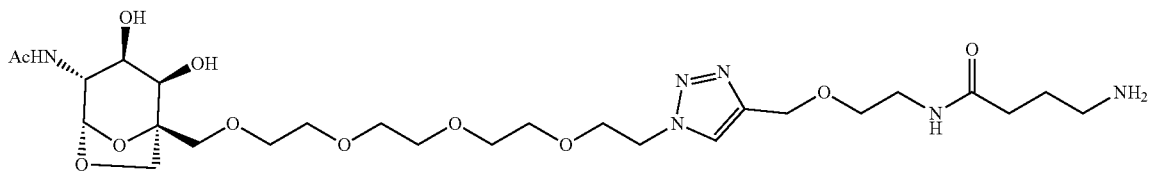
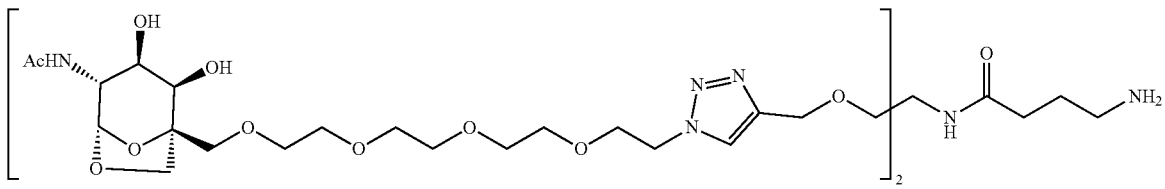
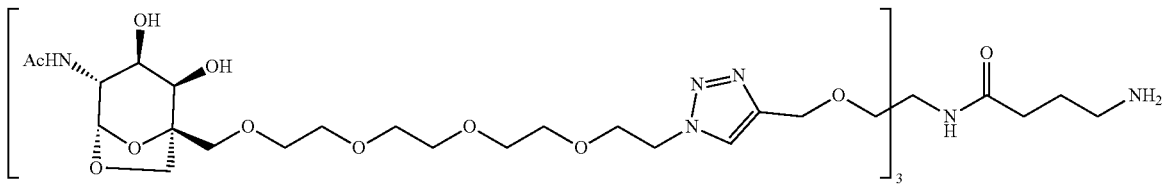

-continued
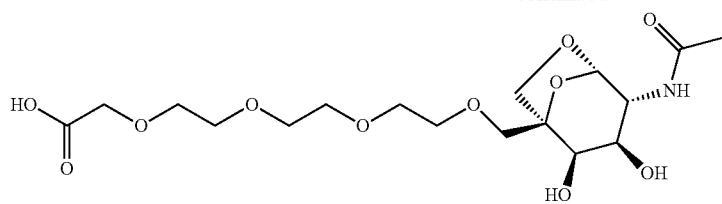
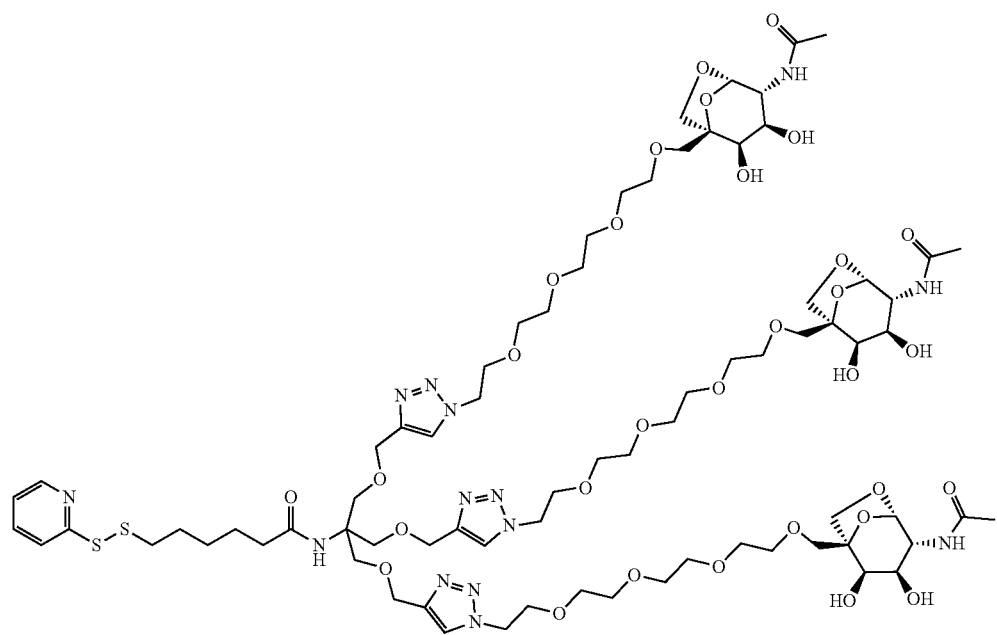
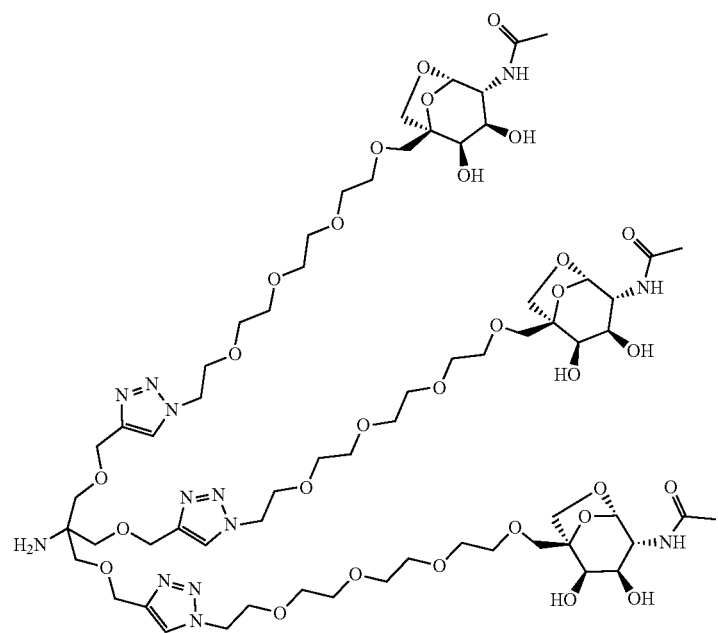

-continued
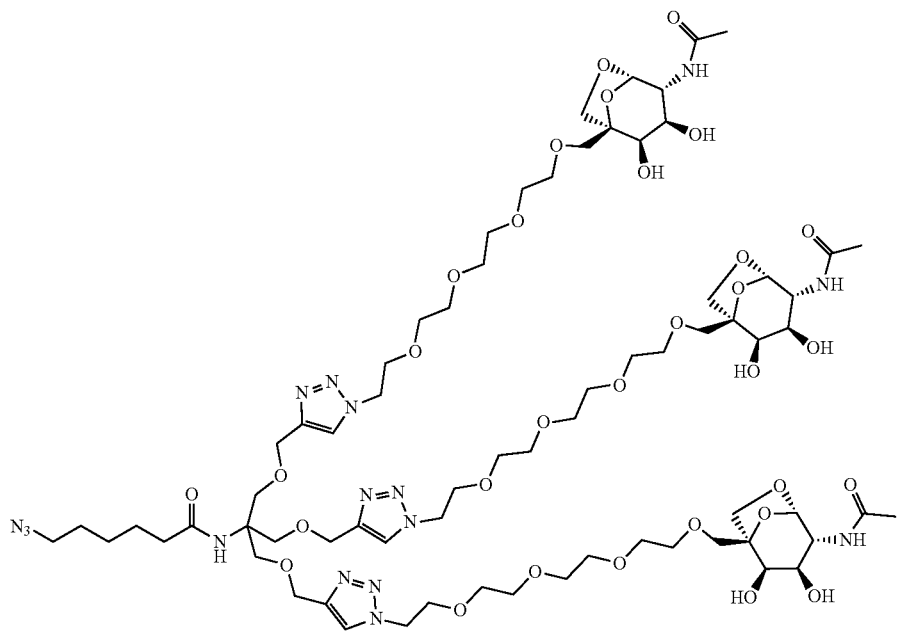
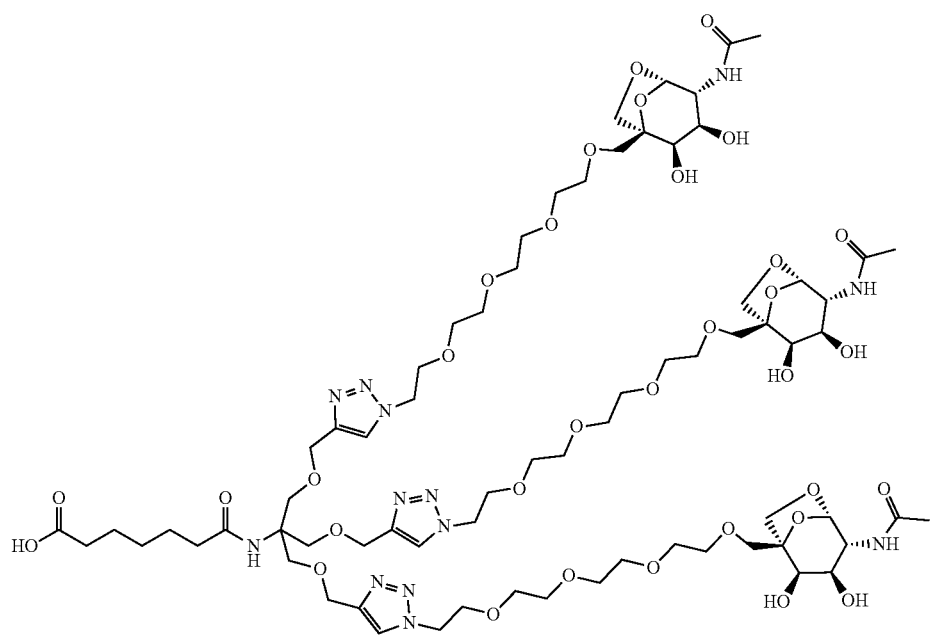

-continued
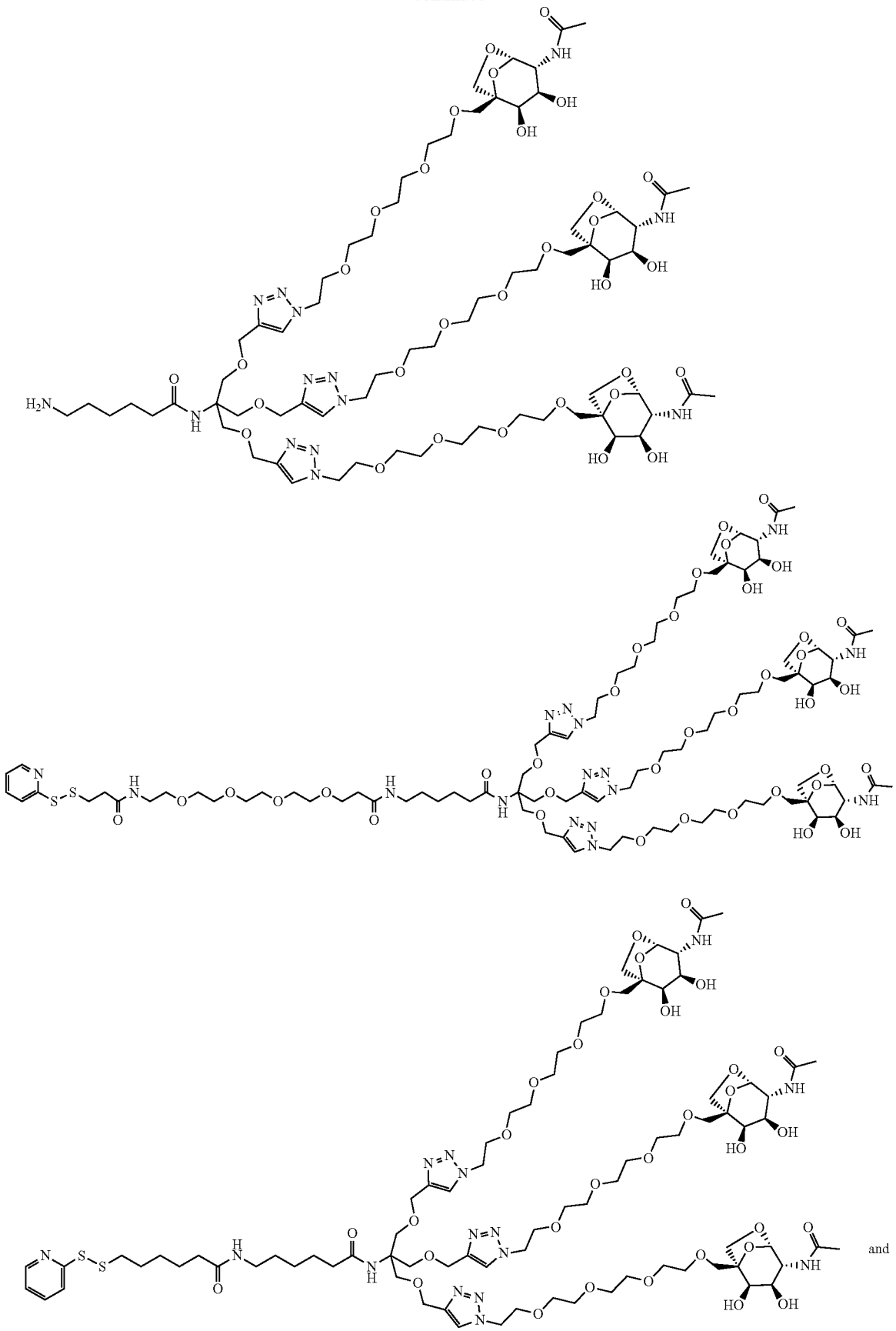
and

-continued

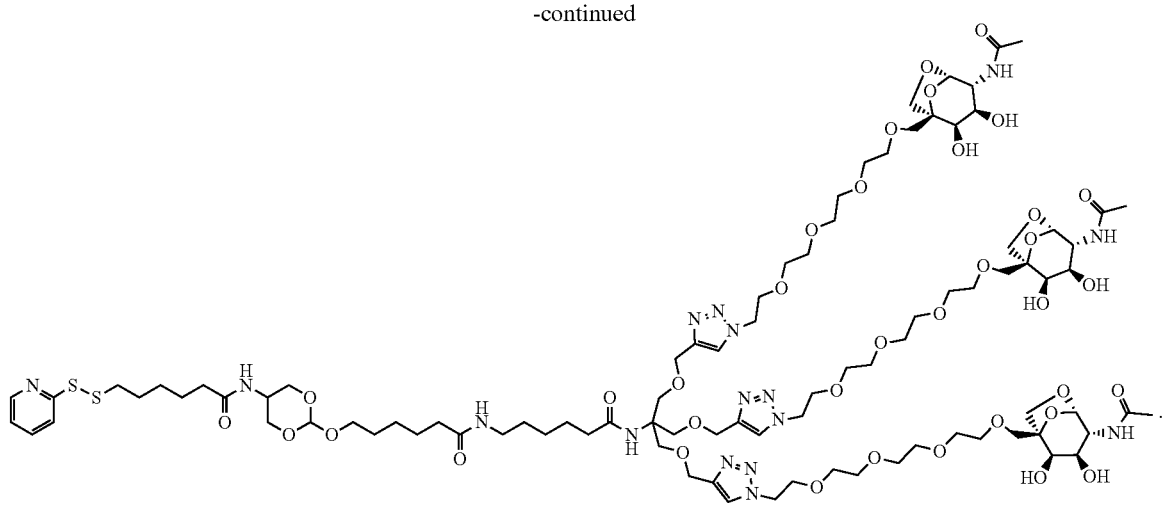

In some embodiments, the present disclosure pertains to:
a compound having the Formula O1:

$$Y^1\text{-}L^1\text{-}(Z^{10})_{za} \qquad \qquad \text{O1}$$

or a pharmaceutically acceptable salt of said compound
wherein $Y^1$ is an oligonucleotide targeting PNPLA3;
za is 1, 2, or 3; and
$L^1$ is a compound of Formula L11, L12, L13, L43, L44, L45, L46, L47, L48, L49, L50, L51, L52, L53 or L54 wherein the connection sites with $Y^1$ and $Z^{10}$ are indicated:

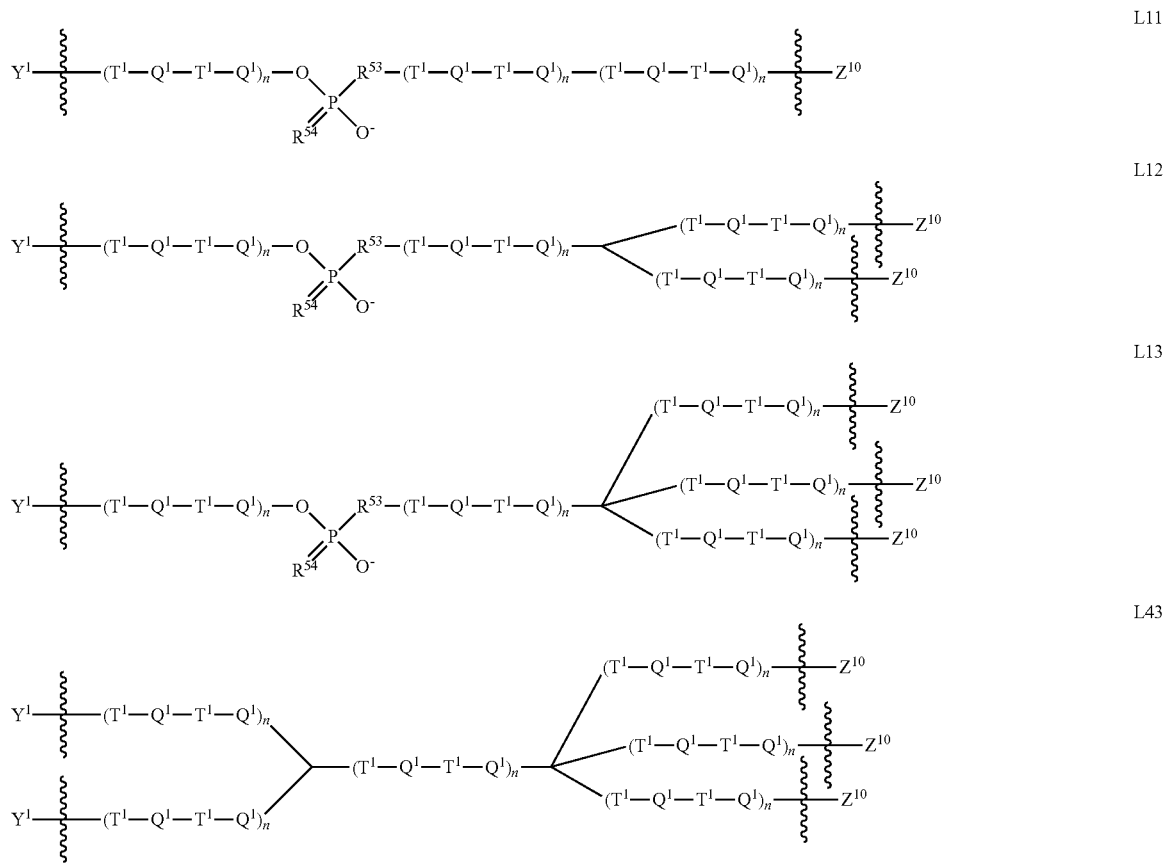

L44
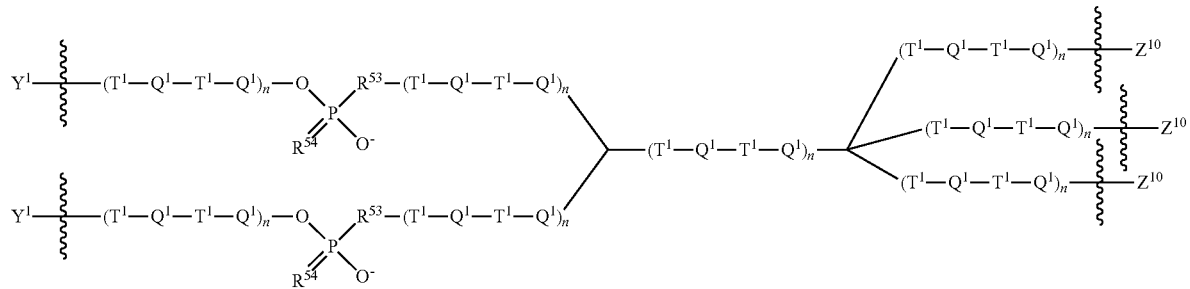
L45
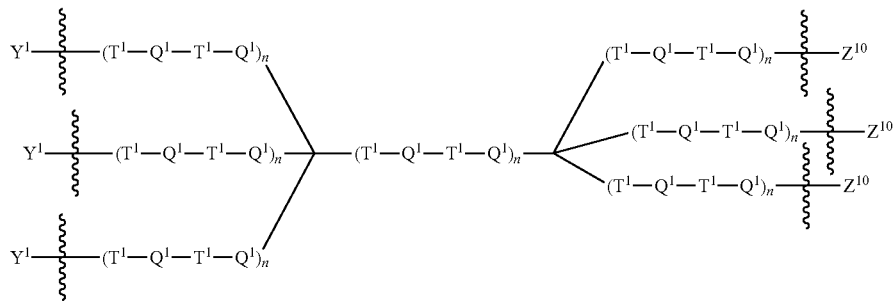
L46
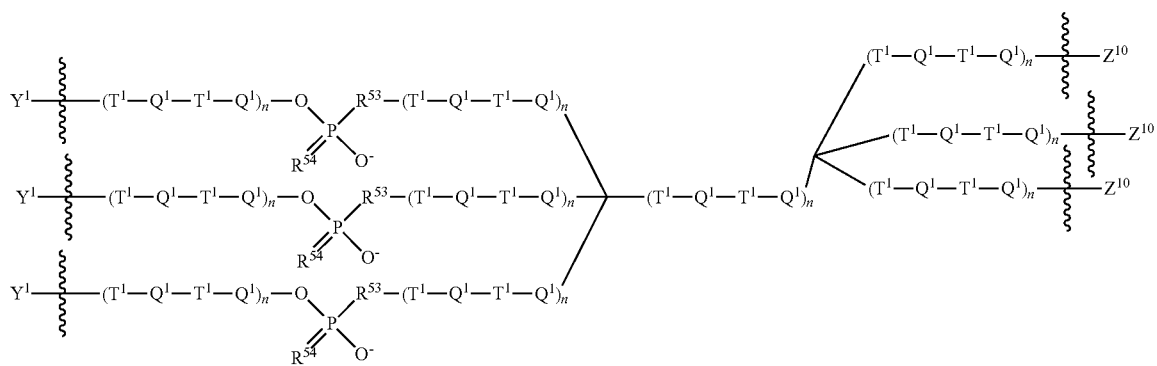
L47
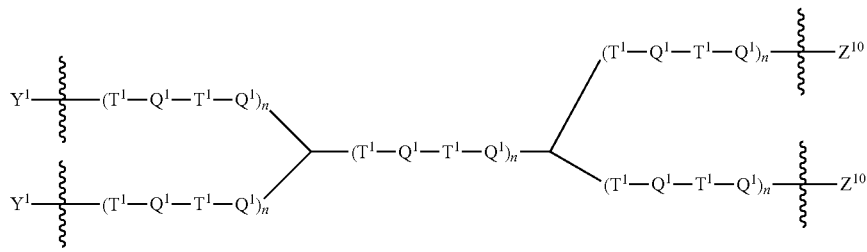
L48
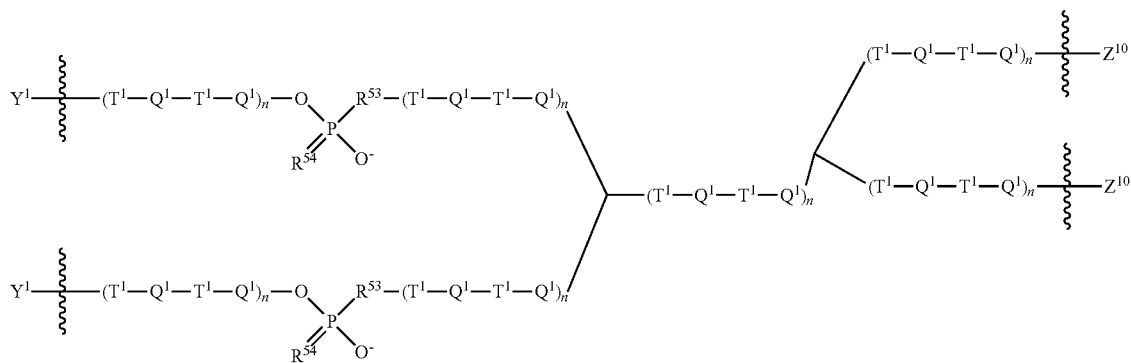

-continued
L49
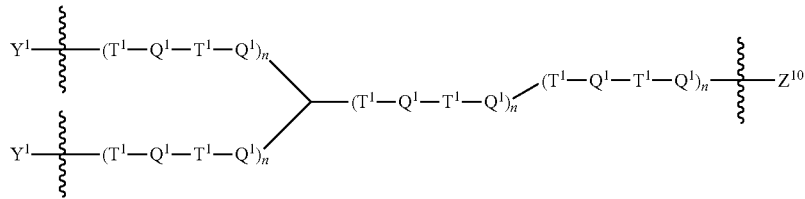
L50
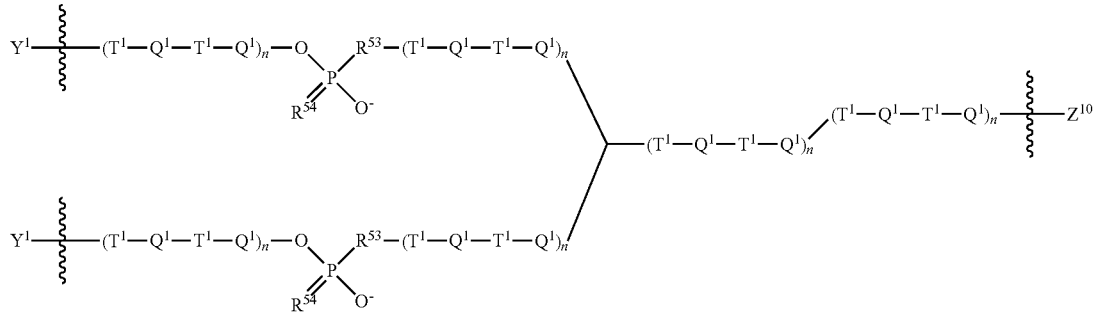
L51
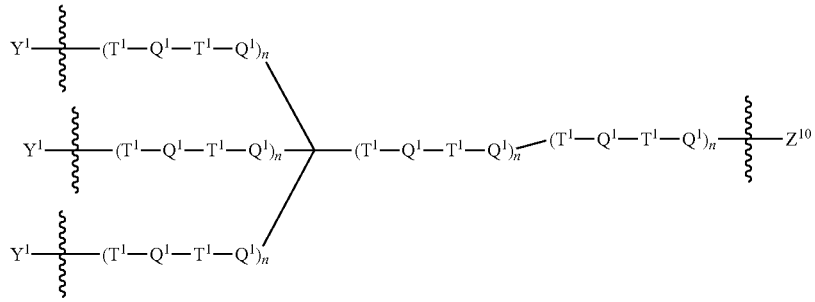
L52
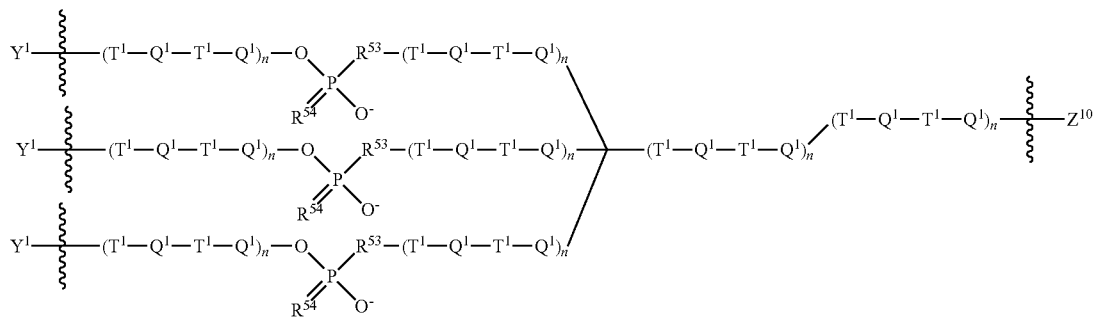
L53
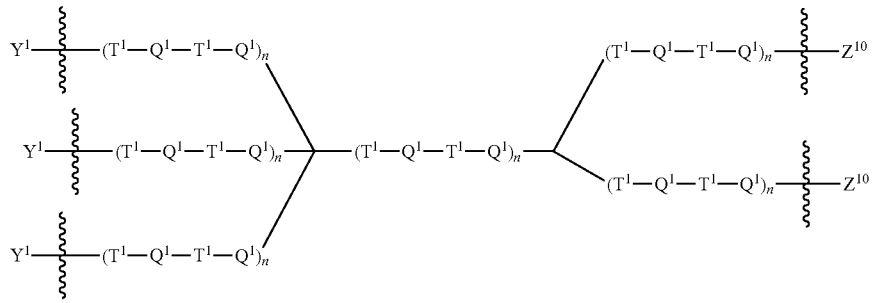

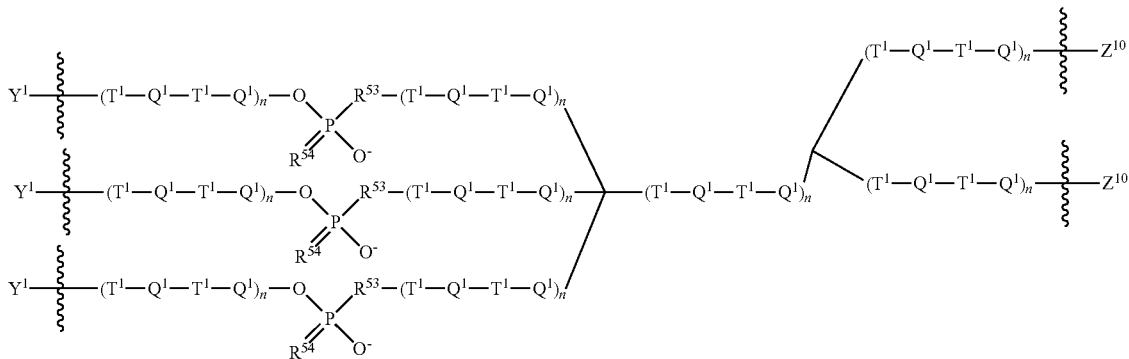

L54 wherein each $T^1$ is independently absent or is alkylene, alkenylene, or alkynylene, wherein one or more —$CH_2$— groups of the alkylene, alkenylene, or alkynylene may each independently be replaced with a heteroatom group independently selected from —O—, —S—, and —N($R^{49}$)— wherein the heteroatom groups are separated by at least 2 carbon atoms;

each $Q^1$ is independently absent or is —C(O)—, —C(O)—$NR^{49}$—, —$NR^{49}$—C(O)—, —O—C(O)—$NR^{49}$—, —$NR^{49}$—C(O)—O—, —$CH_2$—, —$NR^{49}$C(O)$NR^{49}$—, a bivalent heteroaryl group, or a heteroatom group selected from —O—, —S—, —S—S—, —S(O)—, —S(O)$_2$—, and —$NR^{49}$—, wherein at least two carbon atoms separate the heteroatom groups —O—, —S—, —S—S—, —S(O)—, —S(O)$_2$— and —$NR^{49}$— from any other heteroatom group, or a structure of the formula:

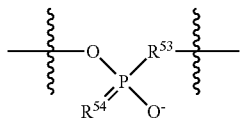

wherein $R^{53}$ is —O or —NH—, and $R^{54}$ is —O or —S;

each $R^{49}$ is independently —H, —($C_1$-$C_{20}$)alkyl, or —($C_3$-$C_6$)cycloalkyl wherein one to six —$CH_2$— groups of the alkyl or cycloalkyl separated by at least two carbon atoms may be replaced with —O—, —S—, or —N($R^{49a}$)—, and —$CH_3$ of the alkyl may be replaced with a heteroatom group selected from —N($R^{49a}$)$_2$, —$OR^{49a}$, and —S($R^{49a}$) wherein the heteroatom groups are separated by at least 2 carbon atoms; and wherein the alkyl and cycloalkyl may be substituted with halo atoms and wherein each $R^{49a}$ is independently —H, —($C_1$-$C_6$)alkyl, or —($C_3$-$C_6$)cycloalkyl;

$R^{53}$ is —O or —NH;

$R^{54}$ is —O or —S;

each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; wherein if n is greater than 0, each $T^1$ and each $Q^1$ of each ($T^1$-$Q^1$-$T^1$-$Q^1$) is independently selected; and each $Z^{10}$ is independently a compound of Formula Z12, Z13, Z14, Z15, Z16, Z17, Z18, Z19, Z20, or Z21, or a geometrical or position isomer thereof, wherein the connection site with Cis indicated:

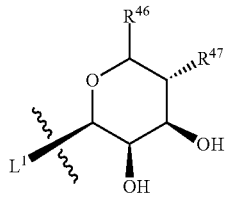

Z12

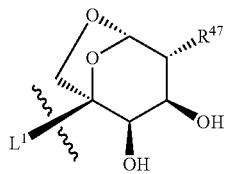

Z13

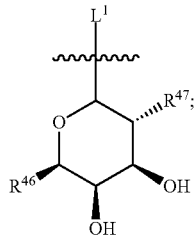

Z16 wherein each $R^{46}$ is independently —CN, —$CH_2$—CN, —C≡CH, —$CH_2$—$N_3$, —$CH_2$—$NH_2$, —$CH_2$—N($R^{52}$)—S(O)$_2$—$R^{51}$, —$CH_2$—$CO_2H$, —$CO_2H$, —$CH_2$—OH, —$CH_2$—SH, —CH=CH—$R^{51}$, —$CH_2$—$R^{51}$, —$CH_2$—S—$R^{51}$, —$CH_2$—N($R^{52}$)—$R^{51}$, —$CH_2$—N($R^{52}$)—C(O)—$R^{51}$, —$CH_2$—N($R^{52}$)—C(O)—O—$R^{51}$, —$CH_2$—N($R^{52}$)—C(O)—N($R^{52}$)—$R^{51}$, —$CH_2$—O—$R^{51}$, —$CH_2$—O—C(O)—$R^{51}$, —$CH_2$—O—C(O)—N($R^{52}$)—$R^{51}$, —$CH_2$—O—C(O)—O—$R^{51}$, —$CH_2$—S(O)—$R^{51}$, —$CH_2$—S(O)$_2$—$R^{51}$, —$CH_2$—S(O)$_2$—N($R^{52}$)—$R^{51}$, —C(O)—$NH_2$, —C(O)—O—$R^{51}$, —C(O)—N($R^{52}$)—$R^{51}$, or aryl or heteroaryl, wherein the aryl or heteroaryl is optionally substituted with $R^{5'}$ each $R^{47}$ is independently —OH, —$N_3$, —N($R^{48}$)$_2$, —N($R^{48}$)—C(O)—$R^{48}$, —N($R^{48}$)—C(O)—N($R^{48}$)$_2$, —N($R^{48}$)—C(O)—$OR^{48}$, —N($R^{48}$)—S(O)$_2$—$R^{48}$, tetrazole, or triazole, wherein the tetrazole and triazole are optionally substituted with $R^{48}$;

each $R^{48}$ is independently —H, —($C_1$-$C_5$)alkyl, halo-substituted ($C_1$-$C_5$)alkyl, halo substituted —($C_3$-$C_6$)cycloalkyl, —(C₁-C₅)alkenyl, —(C₁-C₅)alkynyl, halo substituted —(C₁-C₅)alkenyl, halo substituted —(C₁-C₅)alkynyl, or —(C₃-C₆)cycloalkyl, wherein a —CH$_2$— group of the alkyl or cycloalkyl may each be independently replaced with a heteroatom group selected from —O—, —S—, and —N(R$^{52}$)— and —CH$_3$ of the alkyl may each be independently replaced with a heteroatom group selected from —N(R$^{52}$)$_2$, —OR$^{52}$, and —S(R$^{52}$) wherein the heteroatom groups are separated by at least 2 carbon atoms;

each R$^{51}$ is independently —H, —(C$_3$-C$_{20}$)cycloalkyl, —(C$_1$-C$_{60}$)alkenyl, —(C$_1$-C$_{60}$)alkynyl, or —(C$_1$-C$_{60}$)alkyl wherein one to six —CH$_2$— groups of the cycloalkyl or one to 20 —CH$_2$— groups of the alkyl may each be independently replaced with heteroatoms independently selected from —O—, —S—, and —N(R$^{49}$)— wherein the heteroatoms are separated by at least two carbon atoms, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms, and wherein the alkyl, alkenyl, alkynyl, and cycloalkyl may be substituted with halo atoms; and each R$^{52}$ is independently —H, —(C$_1$-C$_{20}$)alkyl, —(C$_1$-C$_{20}$)alkenyl, —(C$_1$-C$_{20}$)alkynyl, or —(C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^{49}$)—, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms; and wherein the alkyl, alkenyl, alkynyl, and cycloalkyl may be substituted with halo atoms.

In some embodiments, Y$^1$ comprises at least 15 bases.

In some embodiments, the base sequence of Y$^1$ comprises or is the base sequence of any PNPLA3 oligonucleotide listed in Table 1A, or the base sequence of Y$^1$ comprises 15 contiguous bases of the sequence of any PNPLA3 oligonucleotide listed in Table 1A.

In some embodiments, Y$^1$ comprises at least 1 phosphodiester internucleotidic linkage.

In some embodiments, Y$^1$ comprises at least 1 chirally controlled modified internucleotidic linkage.

In some embodiments, Y$^1$ comprises at least 1 chirally controlled modified internucleotidic linkage which is a chirally controlled phosphorothioate.

In some embodiments, Y$^1$ comprises at least 1 chirally controlled modified internucleotidic linkage which is a chirally controlled phosphorothioate in the Sp configuration.

In some embodiments, Y$^1$ comprises at least 1 chirally controlled modified internucleotidic linkage which is a chirally controlled phosphorothioate in the Rp configuration.

In some embodiments, Y$^1$, wherein the chirally controlled modified internucleotidic linkage or chirally controlled phosphorothioate comprises a phosphorus chiral center which has a diastereopurity of at least 70% within the composition.

In some embodiments, Y$^1$, wherein the chirally controlled modified internucleotidic linkage or chirally controlled phosphorothioate comprises a phosphorus chiral center which has a diastereopurity of at least 70%, 75%, 80%, 85%, 90%, 91%, 92%, 93%, 94%, 95%, 96%, 97%, 98%, 99% or 99.5%.

In some embodiments, Y$^1$ comprises at least 1 sugar modification.

In some embodiments, Y$^1$ comprises at least 1 base modification.

In some embodiments, Y$^1$ further comprises a pattern of backbone linkages.

In some embodiments, Y$^1$ further comprises a pattern of backbone chiral centers.

In some embodiments, Y$^1$ further comprises a pattern of chemical modifications.

In some embodiments, Y$^1$ further comprises a pattern of backbone linkages, a pattern of backbone chiral centers, and a pattern of chemical modifications.

In some embodiments, the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of any oligonucleotide listed in Table 1A.

In some embodiments, the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of an oligonucleotide listed in Table 1A the base sequence of Y$^1$ comprises or is the base sequence of any PNPLA3 oligonucleotide listed in Table 1A, or the base sequence of Y$^1$ comprises 15 contiguous bases of the sequence of any PNPLA3 oligonucleotide listed in Table 1A.

In some embodiments, the oligonucleotide is capable of mediating a decrease in the expression, level and/or activity of a PNPLA3 target gene or a gene product thereof.

In some embodiments, the oligonucleotide is capable of mediating a decrease in the expression, level and/or activity of a PNPLA3 target gene or a gene product thereof via a mechanism mediated by RNaseH, steric hindrance and/or RNA interference.

In some embodiments:

each T$^1$ is independently absent or is alkylene, wherein one or more —CH$_2$— groups of the alkylene, may each independently be replaced with a heteroatom group independently selected from —O—, and —N(R$^{49}$)— wherein the heteroatom groups are separated by at least 2 carbon atoms;

each Q$^1$ is independently absent or is —C(O), —C(O)—NR$^{49}$, —NR$^{49}$—C(O), or a heteroatom group selected from —O—, and —NR$^{49}$, wherein at least two carbon atoms separate the heteroatom groups —O— and —NR$^{49}$ from any other heteroatom group;

each R$^{49}$ is independently —H, —(C$_1$-C$_6$)alkyl, or —(C$_3$-C$_6$)cycloalkyl wherein the alkyl and cycloalkyl may be substituted with halo atoms;

each n is independently 0, 1, 2, 3 or 4; wherein if n is greater than 0, each T$^1$ and each Q$^1$ of each (T$^1$-Q$^1$-T$^1$-Q$^1$) is independently selected;

each R$^{46}$ is —CH$_2$—OH;

each R$^{47}$ is —N(R$^{48}$)—C(O)—R$^{48}$; and each R$^{48}$ is independently —H, or —(C$_1$-C$_5$)alkyl.

In some embodiments, the present disclosure pertains to: a compound having the Formula O2:

or a pharmaceutically acceptable salt thereof wherein Y$^1$ is an oligonucleotide targets PNPLA3;

za is 1, 2, or 3;

L$^2$ is a linking group; and

Z$^{11}$ is a compound of Formula (B), wherein connection site with L$^2$ is indicated:

(B) 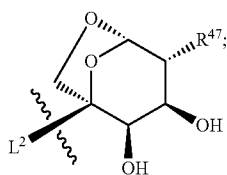

each $R^{47}$ is independently —OH, —N($R^{48}$)$_2$, —N($R^{48}$)—C(O)—$R^{48}$, —N($R^{48}$)—C(O)—N($R^{48}$)$_2$, —N($R^{48}$)—C(O)—O$R^{48}$, —N($R^{48}$)—S(O)$_2$—$R^{48}$, tetrazole, or triazole, wherein the tetrazole and triazole are optionally substituted with $R^{48}$;

each $R^{48}$ is independently —H, —(C$_1$-C$_5$)alkyl, halo-substituted —(C$_1$-C$_5$)alkyl, halo substituted —(C$_3$-C$_6$)cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or —(C$_3$-C$_6$)cycloalkyl, wherein a —CH$_2$— group of the alkyl or cycloalkyl may each be independently replaced with a heteroatom group selected from —O—, —S—, and —N($R^{52}$)— and —CH$_3$ of the alkyl may each be independently replaced with a heteroatom group selected from —N($R^{52}$)$_2$, —OR$^{52}$, and —S($R^{52}$) wherein the heteroatom groups are separated by at least 2 carbon atoms;

each $R^{49}$ is independently —H, —(C$_1$-C$_{20}$)alkyl, or —(C$_3$-C$_6$)cycloalkyl wherein one to six —CH$_2$— groups of the alkyl or cycloalkyl separated by at least two carbon atoms may be replaced with —O—, —S—, or —N($R^{49a}$)—, and —CH$_3$ of the alkyl may be replaced with a heteroatom group selected from —N($R^{49a}$)$_2$, —OR$^{49a}$, and —S($R^{49a}$) wherein the heteroatom groups are separated by at least 2 carbon atoms; and wherein the alkyl and cycloalkyl may be substituted with halo atoms and wherein each $R^{49a}$ is independently —H, —(C$_1$-C$_6$)alkyl, or —(C$_3$-C$_6$)cycloalkyl;

each $R^{52}$ is independently —H, —(C$_1$-C$_{20}$)alkyl, —(C$_1$-C$_{20}$)alkenyl, —(C$_1$-C$_{20}$)alkynyl, or —(C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N($R^{49}$)—, and —CH$_3$ of the alkyl may each be independently replaced with a heteroatom group selected from —N($R^{49}$)$_2$, —OR$^{49}$, and —S($R^{49}$) wherein the heteroatom groups are separated by at least 2 carbon atoms; and wherein the alkyl, alkenyl, alkynyl, and cycloalkyl may be substituted with halo atoms.

In some embodiments, $L^2$ is a compound of Formula L1, L2, L3, L4, L5, L6, L7, L8, L9, L10, L11, L12, L13 or L14, wherein connection sites with $Y^1$ and $Z^{11}$ are indicated:

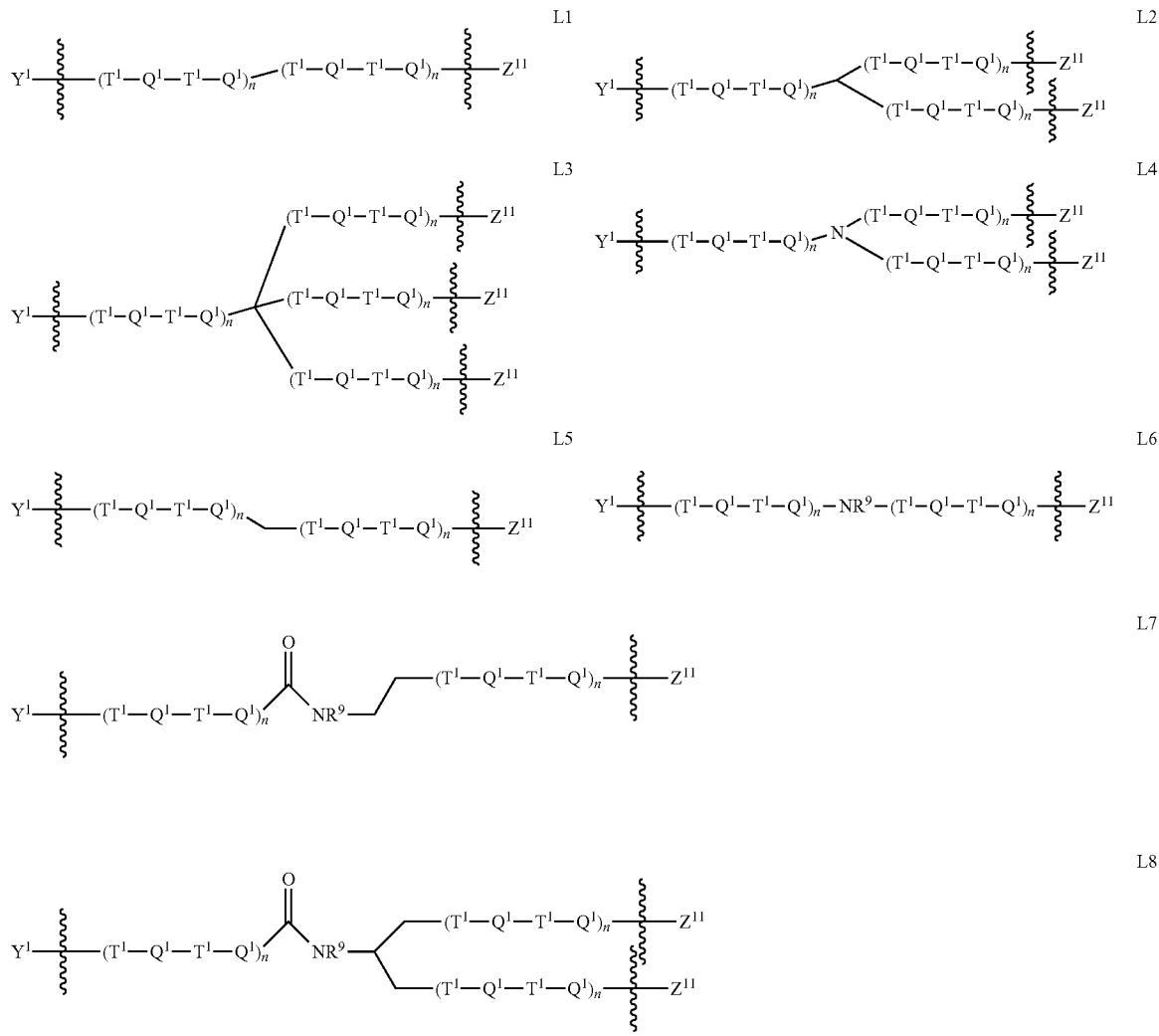

-continued

L9
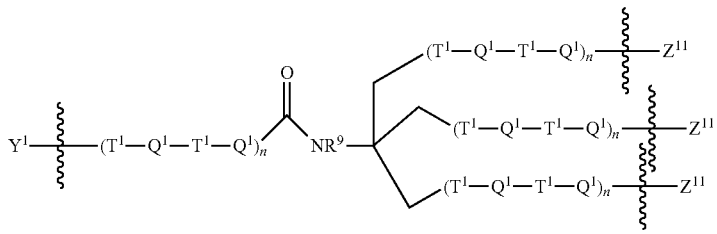

L10
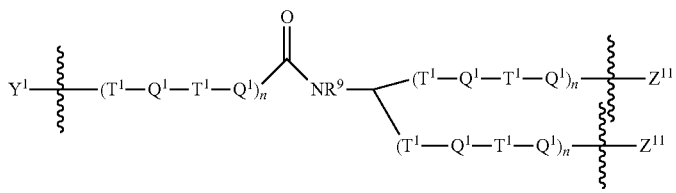

L11
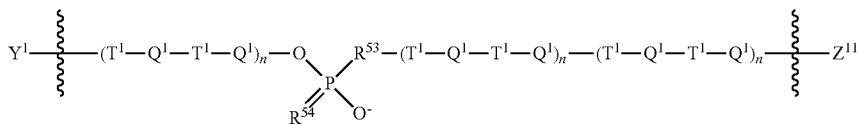

L12
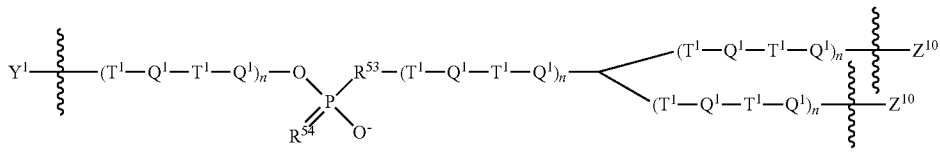

L13
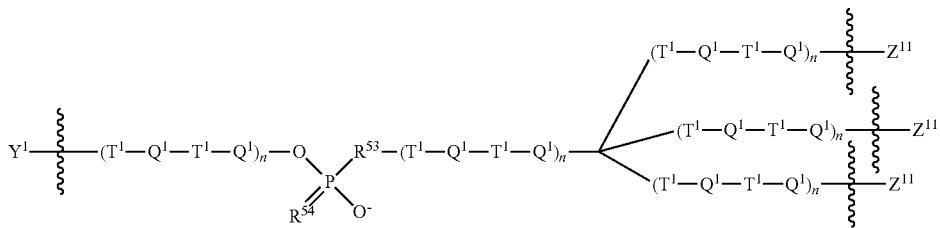

L14
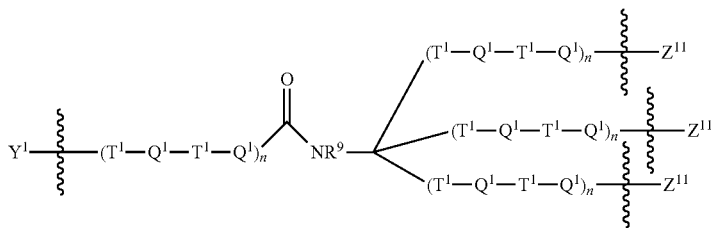

wherein each $T^1$ is independently absent or is alkylene, alkenylene, or alkynylene, wherein one or more —$CH_2$— groups of the alkylene, alkenylene, or alkynylene may each independently be replaced with a heteroatom group independently selected from —O—, —S—, and —N($R^{49}$)— wherein the heteroatom groups are separated by at least 2 carbon atoms;

each $Q^1$ is independently absent or is —C(O)—, —C(O)—$NR^{49}$—, —$NR^{49}$—C(O)—, —O—C(O)—$NR^{49}$—, —$NR^{49}$—C(O)—O—, —$CH_2$—, —$NR^{49}$C(O)$NR^{49}$—, a bivalent heteroaryl group, or a heteroatom group selected from —O—, —S—, —S—S—, —S(O)—, —S(O)$_2$—, and —$NR^{49}$—, wherein at least two carbon atoms separate the heteroatom groups —O—, —S—, —S—S—, —S(O)—, —S(O)$_2$— and —$NR^{49}$— from any other heteroatom group, or a structure of the formula:

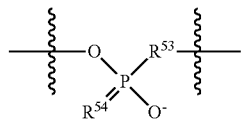

wherein $R^{53}$ is —O or —NH, and $R^{54}$ is —O or —S;

each $R^{49}$ is independently —H, —($C_1$-$C_{20}$)alkyl, or —($C_3$-$C_6$)cycloalkyl wherein one to six —$CH_2$— groups of the alkyl or cycloalkyl separated by at least two carbon atoms may be replaced with —O—, —S—, or —N($R^{49a}$)—, and —$CH_3$ of the alkyl may be replaced with a heteroatom group selected from —N($R^{49a}$)$_2$, —O$R^{49a}$, and —S($R^{49a}$) wherein the heteroatom groups are separated by at least 2 carbon atoms; and wherein the alkyl and cycloalkyl may be substituted with halo atoms; and wherein each $R^{49a}$ is independently —H, —($C_1$-$C_6$)alkyl, or —($C_3$-$C_6$)cycloalkyl;

$R^{53}$ is —O or —NH;

$R^{54}$ is —O or —S; and each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; wherein if n is greater than 0, each $T^1$ and each $Q^1$ of each ($T^1$-$Q^1$-$T^1$-$Q^1$) is independently selected.

In some embodiments, $Y^1$ comprises at least 15 bases.

In some embodiments, the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

In some embodiments, $Y^1$ comprises at least 1 phosphodiester internucleotidic linkage.

In some embodiments, $Y^1$ comprises at least 1 chirally controlled modified internucleotidic linkage.

In some embodiments, $Y^1$ comprises at least 1 chirally controlled modified internucleotidic linkage which is a chirally controlled phosphorothioate.

In some embodiments, $Y^1$ comprises at least 1 chirally controlled modified internucleotidic linkage which is a chirally controlled phosphorothioate in the Sp configuration.

In some embodiments, $Y^1$ comprises at least 1 chirally controlled modified internucleotidic linkage which is a chirally controlled phosphorothioate in the Rp configuration.

In some embodiments, $Y^1$, wherein the chirally controlled modified internucleotidic linkage or chirally controlled phosphorothioate comprises a phosphorus chiral center which has a diastereopurity of at least 70% within the composition.

In some embodiments, $Y^1$, wherein the chirally controlled modified internucleotidic linkage or chirally controlled phosphorothioate comprises a phosphorus chiral center which has a diastereopurity of at least 70%, 75%, 80%, 85%, 90%, 91%, 92%, 93%, 94%, 95%, 96%, 97%, 98%, 99% or 99.5%.

In some embodiments, $Y^1$ comprises at least 1 sugar modification.

In some embodiments, $Y^1$ comprises at least 1 base modification.

In some embodiments, the pattern of backbone linkages of the oligonucleotide is the pattern of backbone linkages of any oligonucleotide listed in Table 1A.

In some embodiments, the pattern of backbone chiral centers of the oligonucleotide is the pattern of backbone chiral centers of any oligonucleotide listed in Table 1A.

In some embodiments, the pattern of chemical modifications of the oligonucleotide is the pattern of chemical modifications of any oligonucleotide listed in Table 1A.

In some embodiments, the pattern of backbone linkages, the pattern of backbone chiral centers, and/or the pattern of chemical modifications of the oligonucleotide are the pattern of backbone linkages, the pattern of backbone chiral centers, and/or the pattern of chemical modifications of the oligonucleotide of any oligonucleotide listed in Table 1A.

In some embodiments, the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of any oligonucleotide listed in Table 1A.

In some embodiments, the pattern of backbone linkages, the pattern of backbone chiral centers, and the pattern of chemical modifications of the oligonucleotide are the pattern of backbone linkages, the pattern of backbone chiral centers, and/or the pattern of chemical modifications of $Y^1$ is that of an oligonucleotide listed in Table 1A and the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

In some embodiments, the oligonucleotide is capable of mediating a decrease in the expression, level and/or activity of a PNPLA3 target gene or a gene product thereof.

In some embodiments, the oligonucleotide is capable of mediating a decrease in the expression, level and/or activity of a PNPLA3 target gene or a gene product thereof via a mechanism mediated by RNaseH, steric hindrance and/or RNA interference.

In some embodiments: each $R^{47}$ is —N($R^{48}$)—C(O)—$R^{48}$; and each $R^{48}$ is independently —H, or —($C_1$-$C_5$)alkyl.

In some embodiments:

each $T^1$ is independently absent or is alkylene, wherein one or more —$CH_2$— groups of the alkylene, may each independently be replaced with a heteroatom group independently selected from —O—, and —N($R^{49}$)— wherein the heteroatom groups are separated by at least 2 carbon atoms;

each $Q^1$ is independently absent or is C(O), C(O)—$NR^{49}$, $NR^{49}$—C(O), or a heteroatom group selected from O, and $NR^{49}$, wherein at least two carbon atoms separate the heteroatom groups 0 and $NR^{49}$ from any other heteroatom group;

each $R^{49}$ is independently —H, —($C_1$-$C_6$)alkyl, or —($C_3$-$C_6$)cycloalkyl wherein the alkyl and cycloalkyl may be substituted with halo atoms;

each n is independently 0, 1, 2, 3 or 4; wherein if n is greater than 0, each $T^1$ and each $Q^1$ of each ($T^1$-$Q^1$-$T^1$-$Q^1$) is independently selected.

In some embodiments, the present disclosure pertains to: a comprising a compound comprising: (a) an oligonucleotide capable of targeting PNPLA3; (b) a linking group; and (c) 1, 2, or 3 moieties independently selected from $Z^{10}$ and $Z^{11}$; wherein the linking group links the oligonucleotide and the 1, 2 or 3 moieties, and wherein:

each $Z^{10}$ is independently a compound of Formula Z12, Z13, Z14, Z15, Z16, Z17, Z18, Z19, Z20, or Z21, or a geometrical or position isomer thereof, wherein the connection site with $L^1$ is indicated:

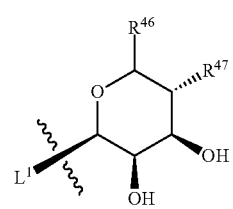

Z12

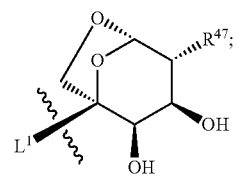

Z13

-continued

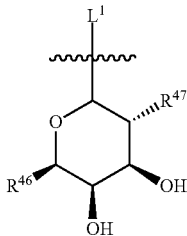

Z16 wherein each $R^{46}$ is independently —CN, —CH$_2$—CN, —C≡CH, —CH$_2$—N$_3$, —CH$_2$—NH$_2$, —CH$_2$—N(R$^{52}$)—S(O)$_2$—R$^{51}$, —CH$_2$—CO$_2$H, —CO$_2$H, —CH$_2$—OH, —CH$_2$—SH, —CH=CH—R$^{51}$, —CH$_2$—R$^{51}$, —CH$_2$—S—R$^{51}$, —CH$_2$—N(R$^{52}$)—R$^{51}$, —CH$_2$—N(R$^{52}$)—C(O)—R$^{51}$, —CH$_2$—N(R$^{52}$)—C(O)—O—R$^{51}$, —CH$_2$—N(R$^{52}$)—C(O)—N(R$^{52}$)—R$^{51}$, —CH$_2$—O—R$^{51}$, —CH$_2$—O—C(O)—R$^{51}$, —CH$_2$—O—C(O)—N(R$^{52}$)—R$^{51}$, —CH$_2$—S(O)$_2$—R$^{51}$, —CH$_2$—S(O)$_2$—R$^{51}$, —CH$_2$—S(O)$_2$—N(R$^{52}$)—R$^{51}$, —C(O)—NH$_2$, —C(O)—O—R$^{51}$, —C(O)—N(R$^{52}$)—R$^{51}$, or aryl or heteroaryl, wherein the aryl or heteroaryl is optionally substituted with R$^{51}$ each $R^{47}$ is independently —OH, —N$_3$, —N(R$^{48}$)$_2$, —N(R$^{48}$)—C(O)—R$^{48}$, —N(R$^{48}$)—C(O)—N(R$^{48}$)$_2$—N(R$^{48}$)—C(O)—OR$^{48}$, —N(R$^{48}$)—S(O)$_2$—R$^{48}$ tetrazole, or triazole, wherein the tetrazole and triazole are optionally substituted with R$^{48}$;

each $R^{48}$ is independently —H, halo-substituted (C$_1$-C$_5$) alkyl, halo substituted —(C$_3$-C$_6$)cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or —(C$_3$-C$_6$)cycloalkyl, wherein a —CH$_2$— group of the alkyl or cycloalkyl may each be independently replaced with a heteroatom group selected from —O—, —S—, and —N(R$^{52}$)— and —CH$_3$ of the alkyl may each be independently replaced with a heteroatom group selected from —N(R$^{52}$)$_2$, —OR$^{52}$, and —S(R$^{52}$) wherein the heteroatom groups are separated by at least 2 carbon atoms;

each $R^{51}$ is independently —H, —(C$_3$-C$_{20}$)cycloalkyl, —(C$_1$-C$_{60}$)alkenyl, —(C$_1$-C$_{60}$)alkynyl, or —(C$_1$-C$_{60}$)alkyl wherein one to six —CH$_2$— groups of the cycloalkyl or one to 20 —CH$_2$— groups of the alkyl may each be independently replaced with heteroatoms independently selected from —O—, —S—, and —N(R$^{49}$)— wherein the heteroatoms are separated by at least two carbon atoms, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms, and wherein the alkyl, alkenyl, alkynyl, and cycloalkyl may be substituted with halo atoms; and each $R^{52}$ is independently —H, —(C$_1$-C$_{20}$)alkyl, —(C$_1$-C$_{20}$)alkenyl, —(C$_1$-C$_{20}$)alkynyl, or —(C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^{49}$)—, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms; and wherein the alkyl, alkenyl, alkynyl, and cycloalkyl may be substituted with halo atoms;

each $R^{49}$ is independently —H, —(C$_1$-C$_{20}$)alkyl, or —(C$_3$-C$_6$)cycloalkyl wherein one to six —CH$_2$— groups of the alkyl or cycloalkyl separated by at least two carbon atoms may be replaced with —O—, —S—, or —N(R$^{49a}$)—, and —CH$_3$ of the alkyl may be replaced with a heteroatom group selected from —N(R$^{49a}$)$_2$, and —S(R$^{49a}$) wherein the heteroatom groups are separated by at least 2 carbon atoms; and wherein the alkyl and cycloalkyl may be substituted with halo atoms and wherein each $R^{49a}$ is independently —H, —(C$_1$-C$_6$)alkyl, or —(C$_3$-C$_6$)cycloalkyl;

each $R^{49a}$ is independently —H, —(C$_1$-C$_6$)alkyl, or —(C$_3$-C$_6$)cycloalkyl;

and $Z^{11}$ is a compound of Formula (B), wherein connection site with $L^2$ is indicated:

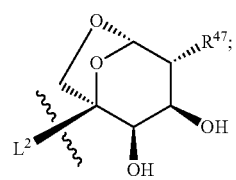

(B)

each $R^{47}$ is independently —OH, —N$_3$, —N(R$^{48}$)$_2$, —N(R$^{48}$)—C(O)—R$^{48}$, —N(R$^{48}$)—C(O)—N(R$^{48}$)$_2$, —N(R$^{48}$)—C(O)—OR$^{48}$, —N(R$^{48}$)—S(O)$_2$—R$^{48}$, tetrazole, or triazole, wherein the tetrazole and triazole are optionally substituted with R$^{48}$;

each $R^{48}$ is independently —H, —(C$_1$-C$_5$)alkyl, halo-substituted —(C$_1$-C$_5$)alkyl, halo substituted —(C$_3$-C$_6$)cycloalkyl, —(C$_1$-C$_5$)alkenyl, —(C$_1$-C$_5$)alkynyl, halo substituted —(C$_1$-C$_5$)alkenyl, halo substituted —(C$_1$-C$_5$)alkynyl, or —(C$_3$-C$_6$)cycloalkyl, wherein a —CH$_2$— group of the alkyl or cycloalkyl may each be independently replaced with a heteroatom group selected from —O—, —S—, and —N(R$^{52}$)— and —CH$_3$ of the alkyl may each be independently replaced with a heteroatom group selected from —N(R$^{52}$)$_2$, —OR$^{52}$, and —S(R$^{52}$) wherein the heteroatom groups are separated by at least 2 carbon atoms;

each $R^{49}$ is independently —H, —(C$_1$-C$_{20}$)alkyl, or —(C$_3$-C$_6$)cycloalkyl wherein one to six —CH$_2$— groups of the alkyl or cycloalkyl separated by at least two carbon atoms may be replaced with —O—, —S—, or —N(R$^{49a}$)—, and —CH$_3$ of the alkyl may be replaced with a heteroatom group selected from —N(R49a)$_2$, —OR', and —S(R$^{49a}$) wherein the heteroatom groups are separated by at least 2 carbon atoms; and wherein the alkyl and cycloalkyl may be substituted with halo atoms and wherein each $R^{49a}$ is independently —H, —(C$_1$-C$_6$)alkyl, or —(C$_3$-C$_6$)cycloalkyl;

46. each $R^{52}$ is independently —H, —(C$_1$-C$_{20}$)alkyl, —(C$_1$-C$_{20}$)alkenyl, —(C$_1$-C$_{20}$)alkynyl, or —(C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^{49}$)—, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms; and wherein the alkyl, alkenyl, alkynyl, and cycloalkyl may be substituted with halo atoms A chirally controlled PNPLA3 oligonucleotide composition comprising oligonucleotides of a particular oligonucleotide type characterized by:

a) a common base sequence and length, wherein the base sequence is complementary to a PNPLA3 target gene;

b) a common pattern of backbone linkages;

c) a common pattern of backbone chiral centers, wherein the common pattern of backbone chiral centers comprises at least one internucleotidic linkage comprising a chirally controlled chiral center;

which composition is chirally controlled in that it is enriched, relative to a substantially racemic preparation of oligonucleotides having the same common base sequence and length, for oligonucleotides of the particular oligonucleotide type; and wherein the oligonucleotide composition is capable of decreasing the expression, level and/or activity of a PNPLA3 target gene or a gene product thereof.

In some embodiments, the oligonucleotides are capable of capable of decreasing the expression, level and/or activity of a PNPLA3 target gene or a gene product thereof via a mechanism mediated by RNaseH, steric hindrance and/or RNA interference.

In some embodiments, the present disclosure pertains to: a composition comprising a compound of any one of the preceding claims.

In some embodiments, the present disclosure pertains to: a composition comprising an PNPLA3 oligonucleotide which is a single-stranded RNAi agent, wherein the single-stranded RNAi agent is complementary or substantially complementary to a PNPLA3 target RNA sequence, has a length of about 15 to about 49 nucleotides, and is capable of directing target-specific RNA interference, wherein the single-stranded RNAi agent comprises at least one non-natural base, sugar, and/or internucleotidic linkage, and wherein the composition is capable of decreasing the expression, level and/or activity of a PNPLA3 target gene or a gene product thereof.

In some embodiments, the oligonucleotide or oligonucleotides further comprise a bridged bicyclic ketal.

In some embodiments, $R^{CD}$ is

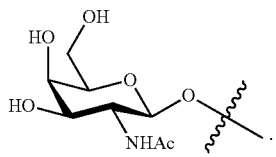

In some embodiments, $R^{CD}$ is

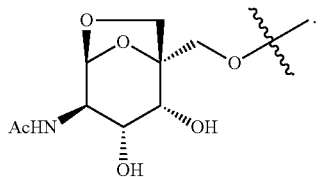

In some embodiments, $R^{CD}$ is of such a structure that $R^{CD}$—H is

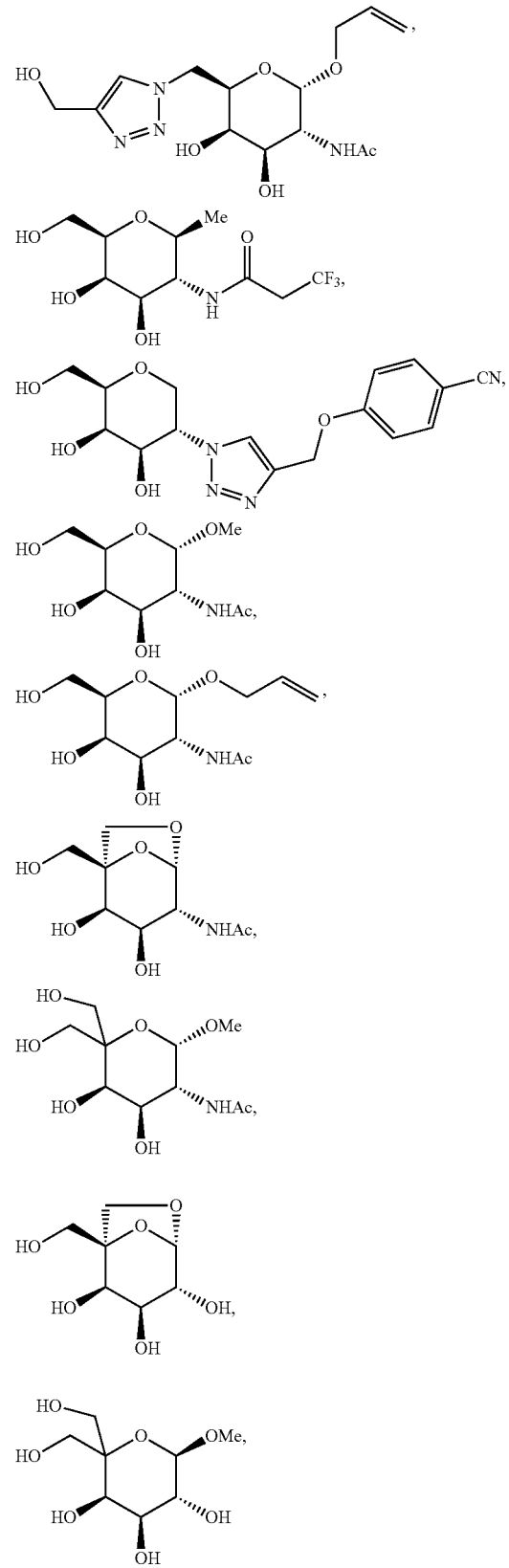

305
-continued
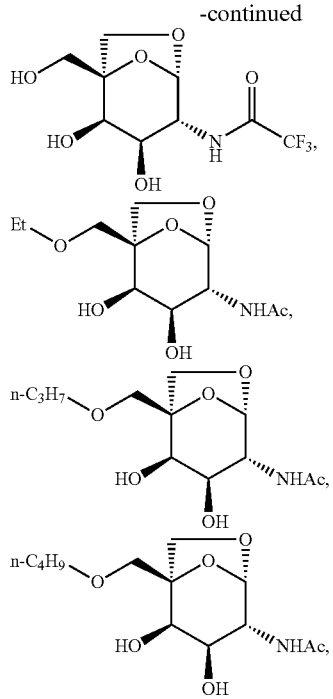
306
-continued
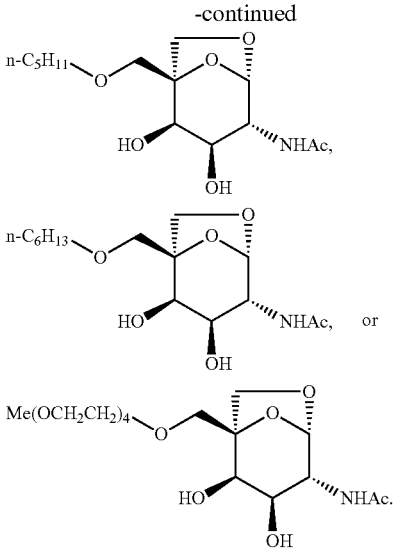
In some embodiments, $R^{CD}$ is connected to the oligonucleotide or oligonucleotides through a linker.
In some embodiments, the linker is $L^M$.
In some embodiments, the linker has the structure of
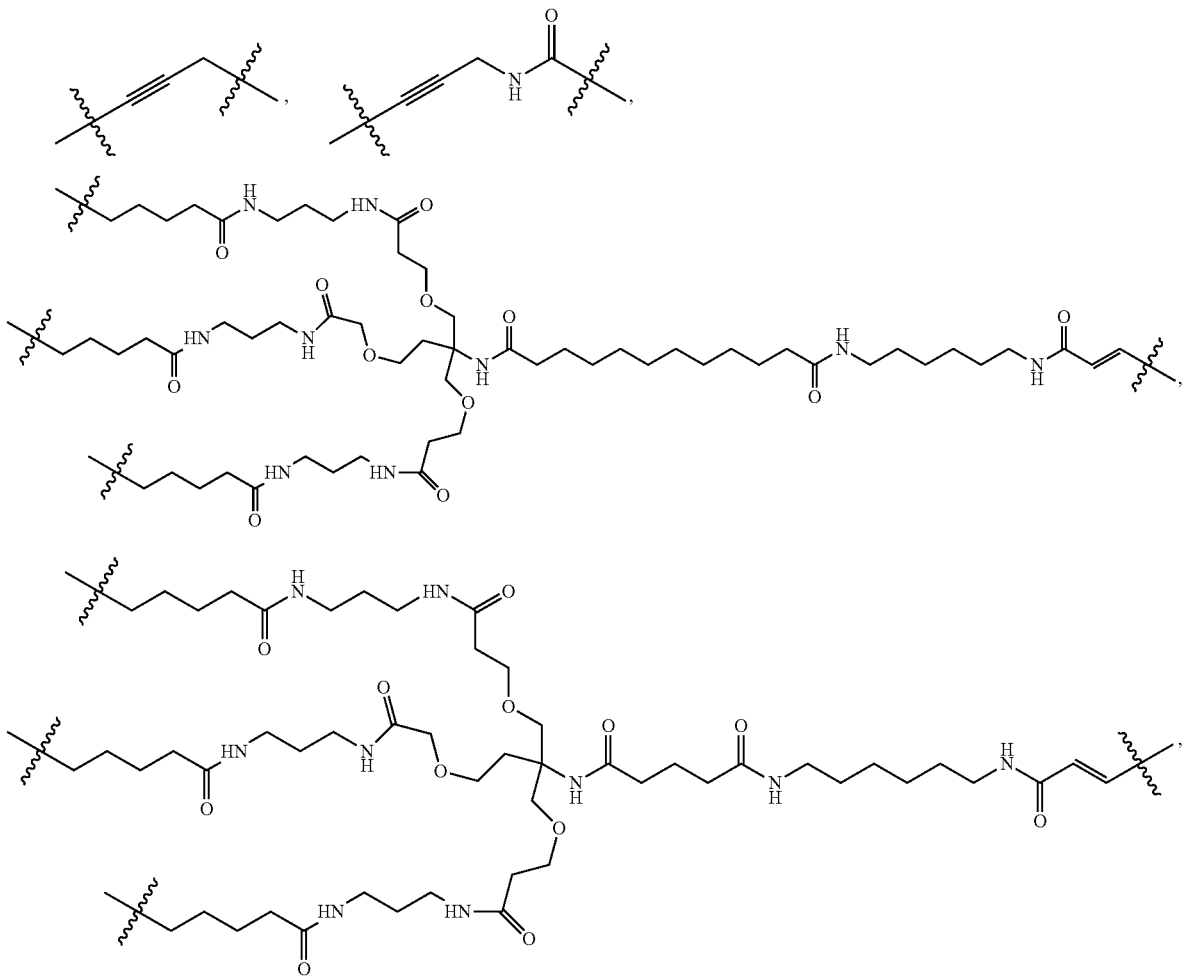

-continued
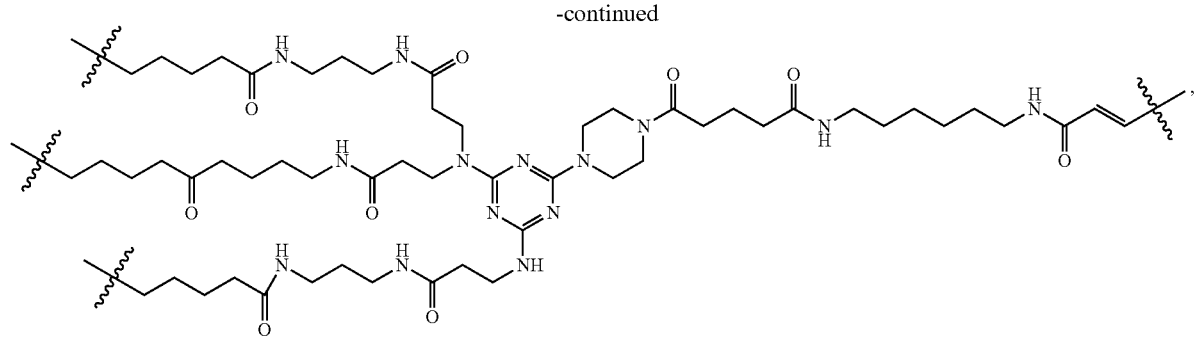
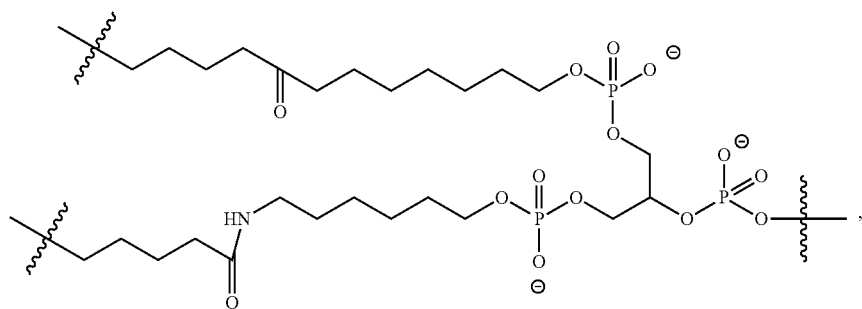
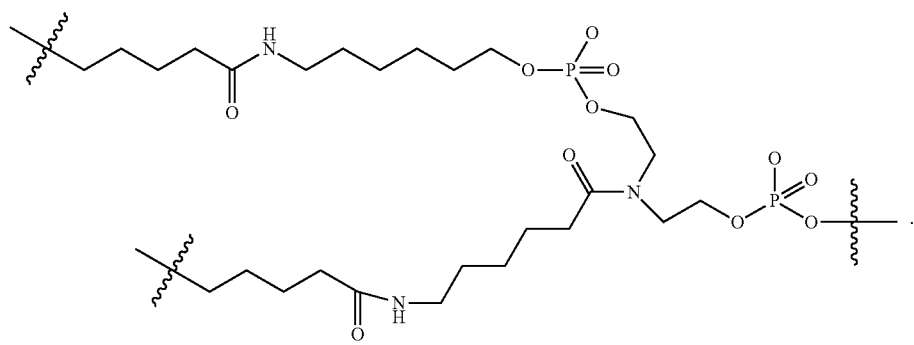 [SMILES: *CCCCC(=O)NCCCCCCOP(=O)(O)OCCN(CCOP(=O)(O)O*)C(=O)CCCCCNC(=O)CCCC*]
In some embodiments, $R^{CD}$ is selected from:
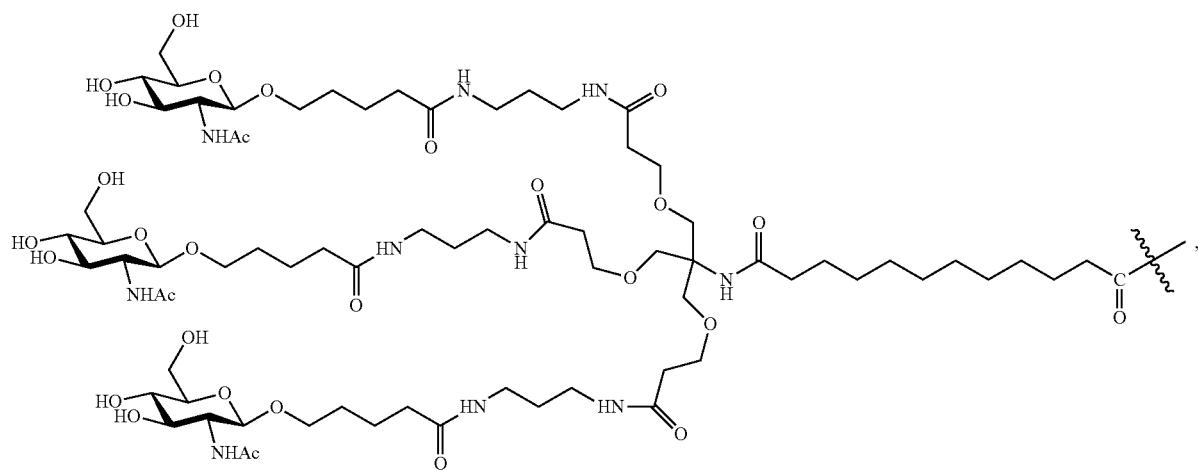

-continued
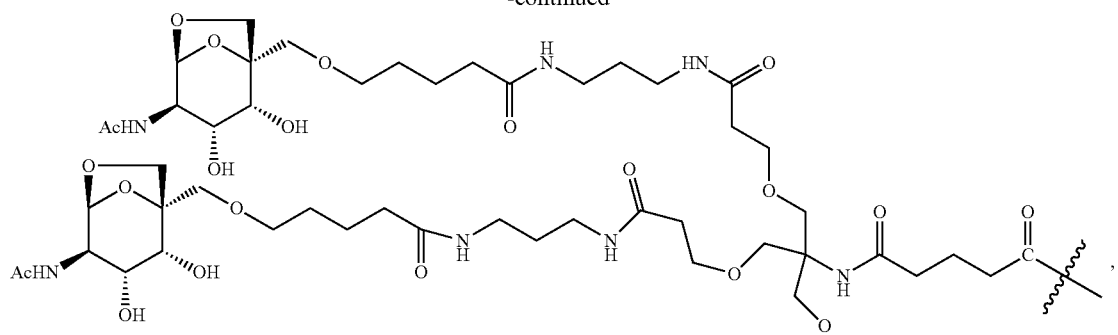
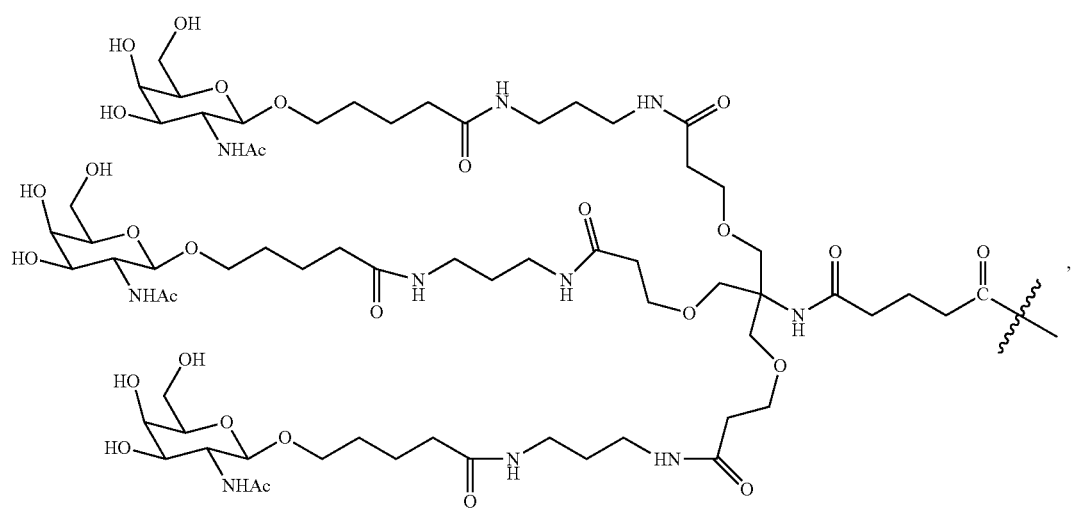
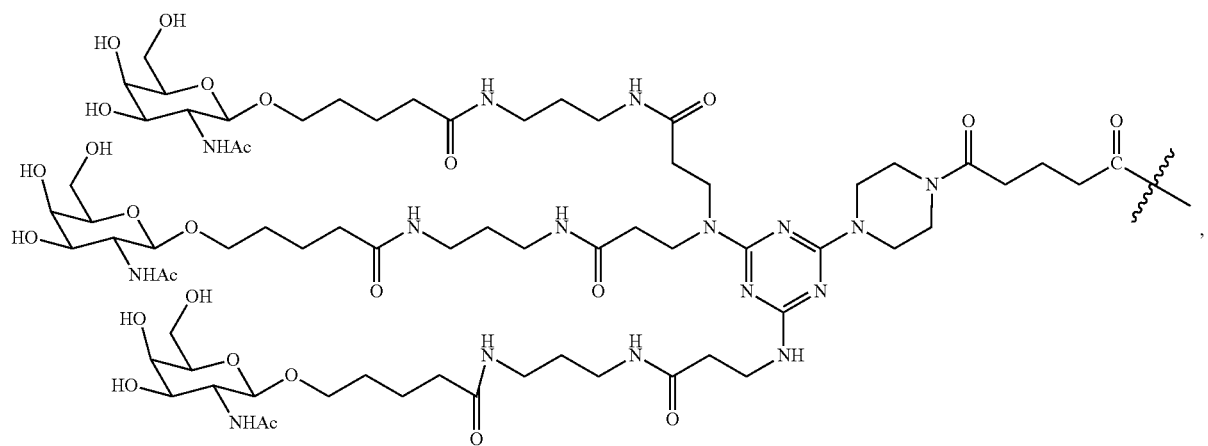

311
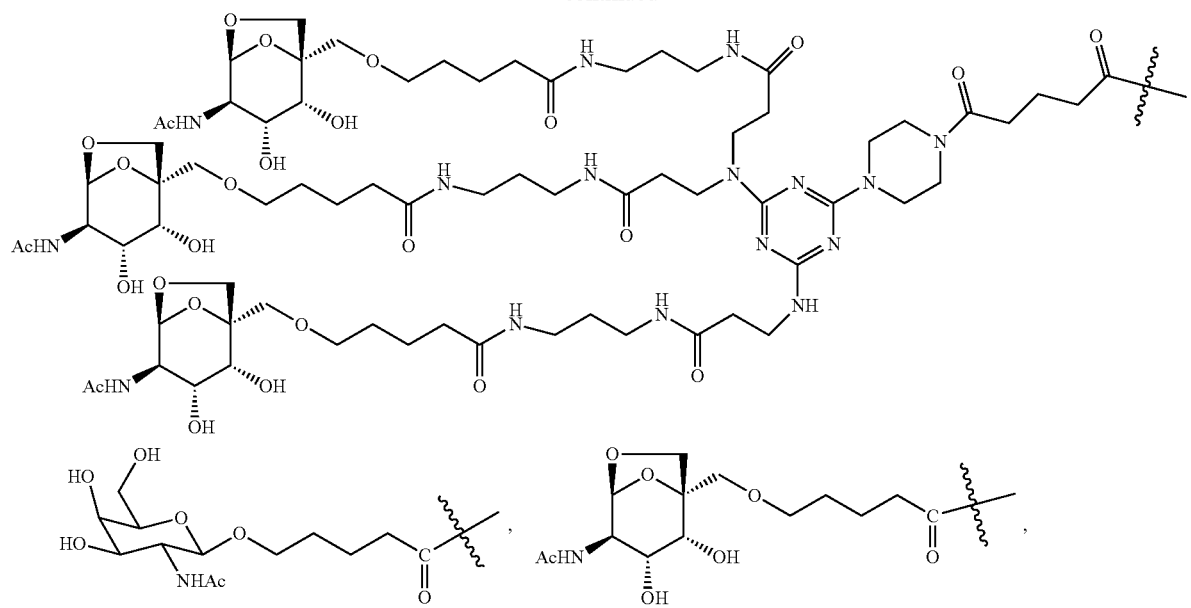
,
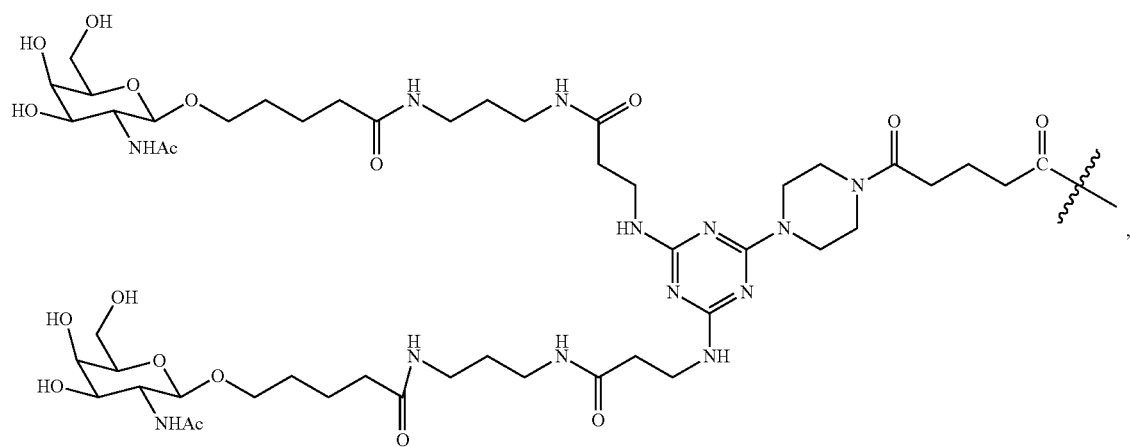
,
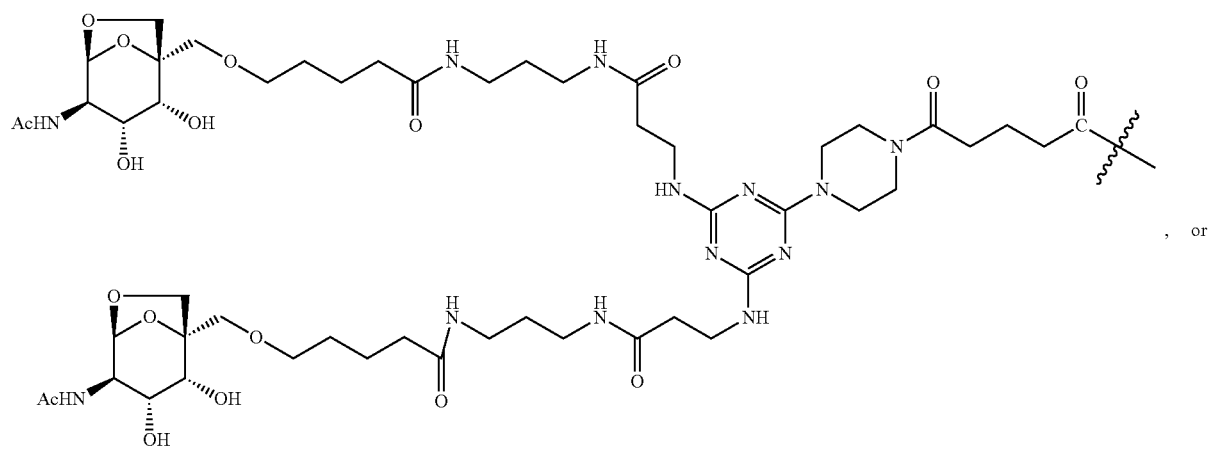
, or
312

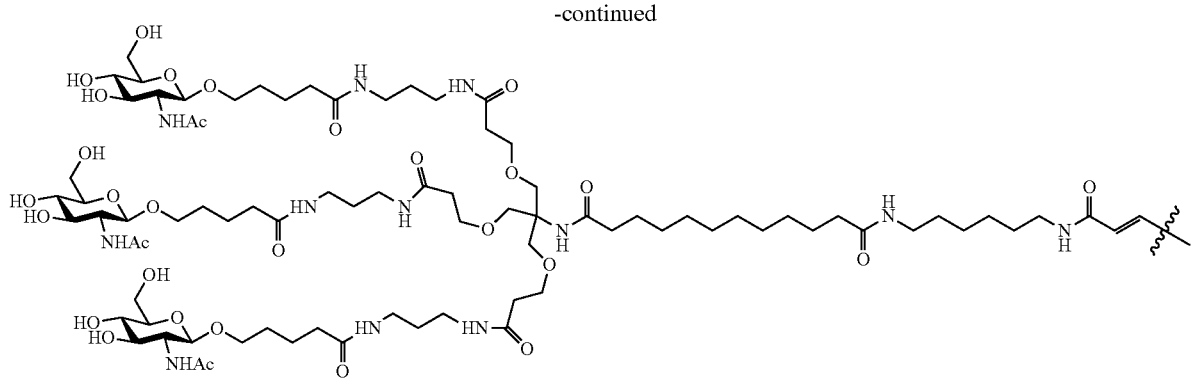

In some embodiments, the present disclosure pertains to: a pharmaceutical composition comprising a composition of any one of the preceding claims in a therapeutically effective amount, in admixture with at least one pharmaceutically acceptable excipient.

In some embodiments, the composition further comprises at least one additional pharmaceutical agent selected from the group consisting of an anti-inflammatory agent, an anti-diabetic agent, and a cholesterol/lipid modulating agent.

In some embodiments, said additional pharmaceutical agent is selected from the group consisting of an acetyl-CoA carboxylase-(ACC) inhibitor, a diacylglycerol O-acyltransferase 1 (DGAT-1) inhibitor, a diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family including IL1beta, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRalpha.

In some embodiments, the composition further comprises at least one additional pharmaceutical agent selected from the group consisting of cystamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

In some embodiments, the present disclosure pertains to: a method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a human in need of such reduction a therapeutically effective amount of a composition of any one of the preceding claims to a patient in need thereof.

In some embodiments, the present disclosure pertains to: a method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma in humans comprising the step of administering to a human in need of such treatment a therapeutically effective amount of a composition of any one of the preceding claims to a patient in need thereof.

In some embodiments, the present disclosure pertains to: a method for treating hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertriglyceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD), in humans comprising the step of administering to a human in need of such treatment a therapeutically effective amount of a composition of any one of the preceding claims to a patient in need thereof.

In some embodiments, the present disclosure pertains to: a method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma in humans comprising the step of administering to a human in need of such treatment a therapeutically effective amount of two separate pharmaceutical compositions comprising a. a first composition of any one of the preceding claims; and
b. a second composition comprising at least one additional pharmaceutical agent selected from the group consisting of an anti-inflammatory agent, an anti-diabetic agent, and a cholesterol/lipid modulating agent and at least one pharmaceutically acceptable excipient.

In some embodiments, said first composition and said second composition are administered simultaneously.

In some embodiments, said first composition and said second composition are administered sequentially and in any order.

In some embodiments, the present disclosure pertains to: a method for reducing portal hypertension, hepatic protein synthetic capability, hyperbilirubinemia, or encephalopathy in humans comprising the step of administering to a human in need of such treatment a therapeutically effective amount of a composition of any one of the preceding claims to a patient in need thereof.

In some embodiments, the present disclosure pertains to: a method of decreasing the expression, activity and/or level of a PNPLA3 target gene or a gene product thereof in a cell, comprising the step of contacting the cell with a compound or composition of any one of the preceding claims.

In some embodiments, the present disclosure pertains to: a method of decreasing the expression, activity and/or level of a PNPLA3 target gene or a gene product thereof in a patient, comprising the step of contacting the cell with a compound or composition of any one of the preceding claims.

In some embodiments, a GalNAc, as the term is used herein, refers to a chemical entity which is structurally similar to a GalNAc and/or which performs at least one function of a GalNAc (e.g., binding to ASPGR).

In some embodiments, a 5'-end of a single-stranded RNAi agent comprises a GalNAc or a variant or derivative thereof.

A non-limiting example of a GalNAc moiety at the 5'-end of a PNPLA3 oligonucleotide or single-stranded RNAi agent (e.g., 5' GalNAc moiety) is shown below, wherein the 5' end structure is represented by:

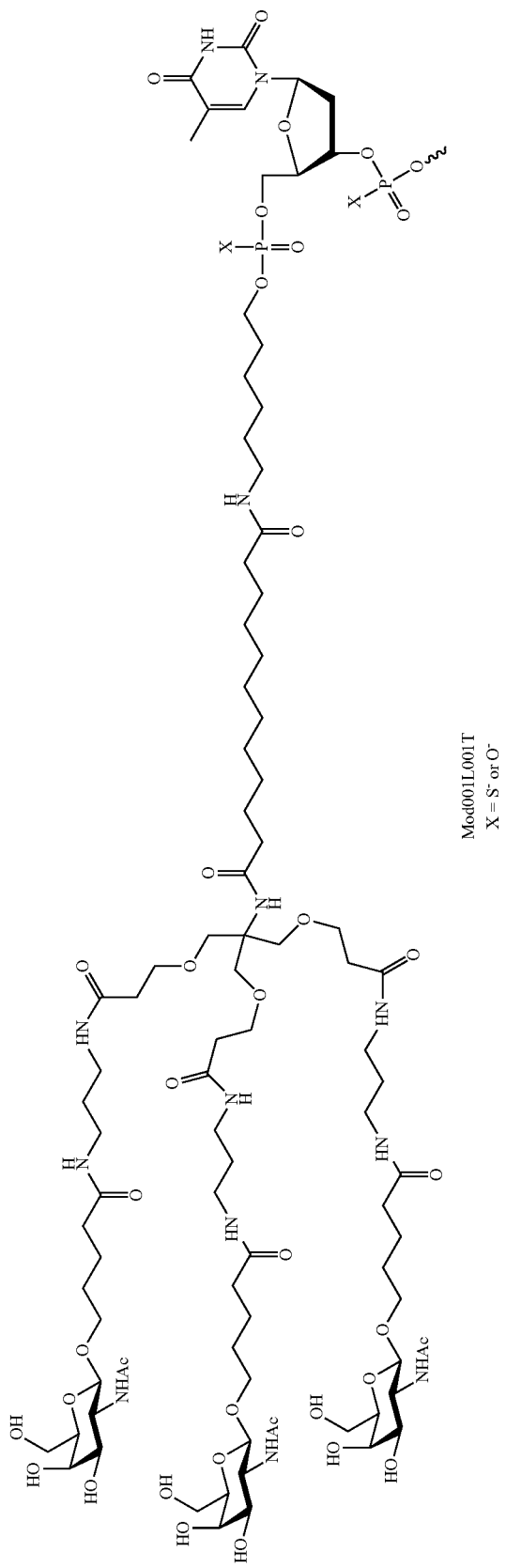

In some embodiments, a GalNAc moiety, e.g., a GalNAc or a variant or derivative thereof, is described in any of: Migawa et al. 2016 Bioorg. Med. Chem. Lett. 26: 2914-7; Ostergaard et al. 2015 Bioconjug. Chem. 26: 1451-1455; Prakash et al. 2014 Nucl. Acids Res. 42: 8796-8807; Prakash et al. 2016 J. Med. Chem. 59: 2718-33; Shemesh et al. 2016 Mol. Ther. Nucl. Acids 5: e319; St-Pierre et al. 2016 Bioorg. Med. Chem. 24: 2397-409; and/or Yu et al. 2016 Mol. Ther. Nucl. Acids 5: e317.

In some embodiments, a chemical moiety (e.g., additional component) conjugated to a PNPLA3 oligonucleotide binds to ASPGR.

In some embodiments, a chemical moiety (e.g., additional component) conjugated to a PNPLA3 oligonucleotide binds to ASPGR and comprises any of: Mod031, Mod034, Mod035, Mod036, Mod038, Mod039, Mod040, or Mod041.

In some embodiments, an additional component can be or comprise any of: Mod079, Mod080, Mod081, Mod082 or Mod083. In some embodiments, an additional component can be or comprise any of:

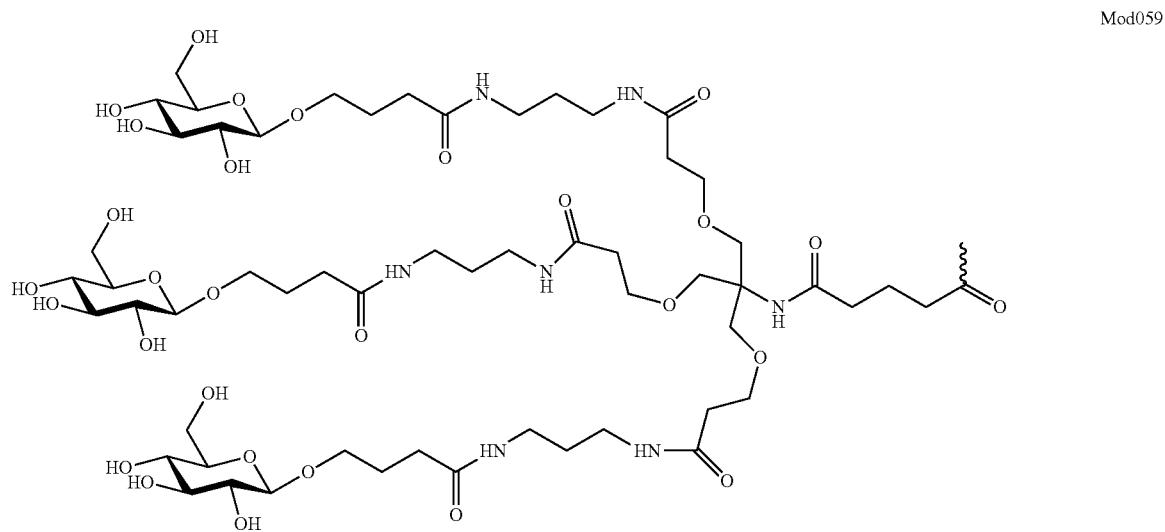

Mod059

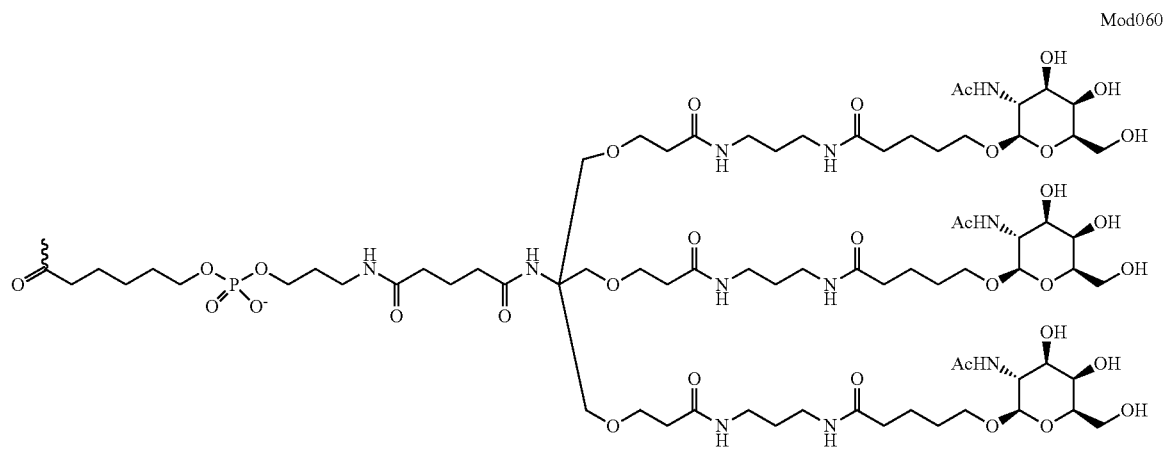

Mod060

-continued
Mod065
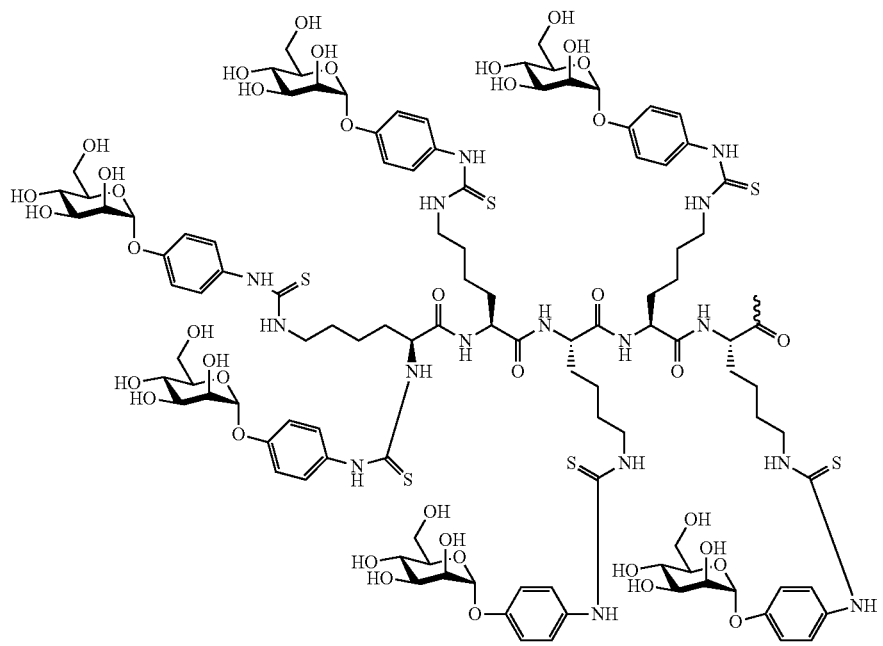
Mod070
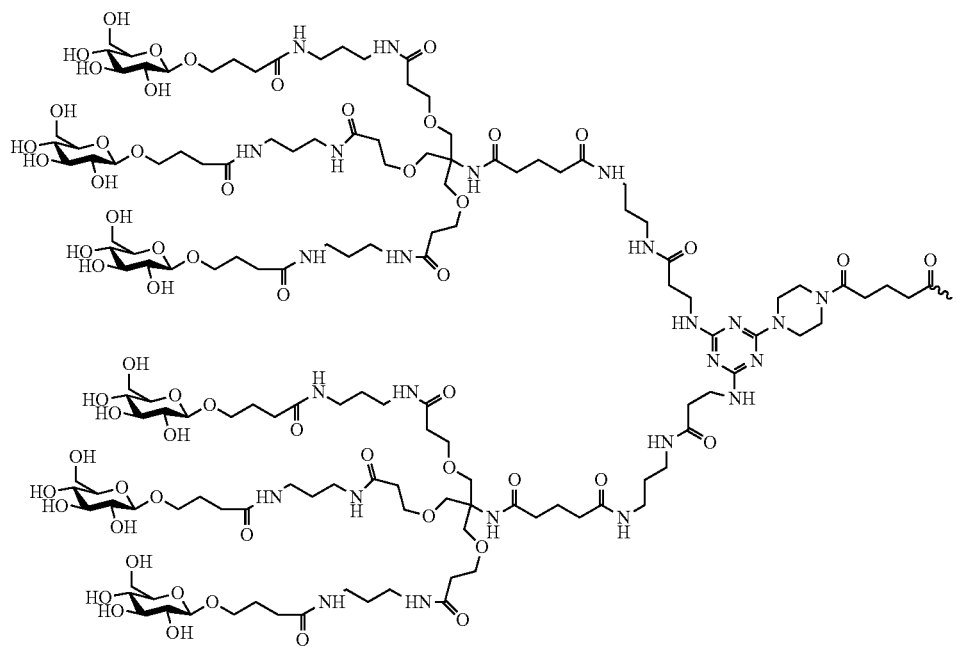

Mod071
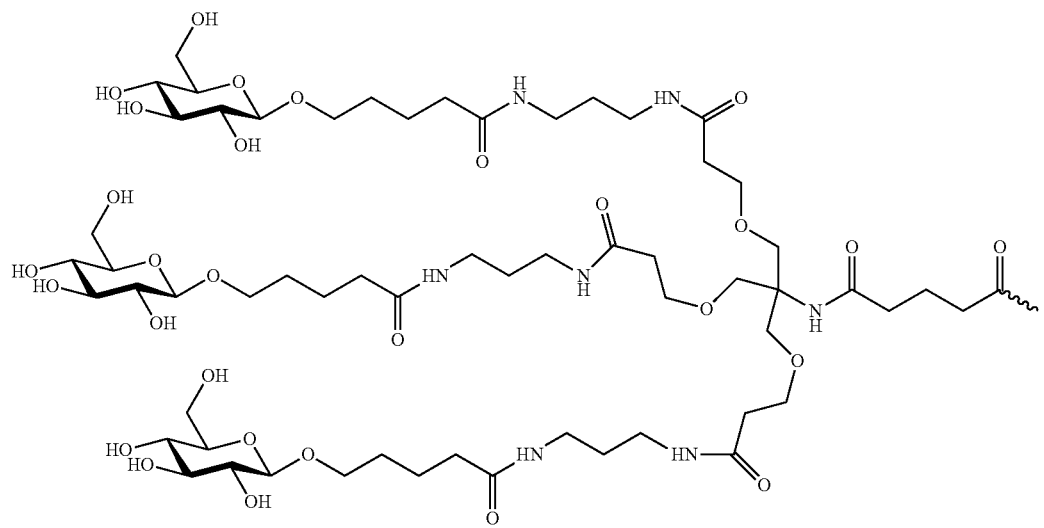
Mod072
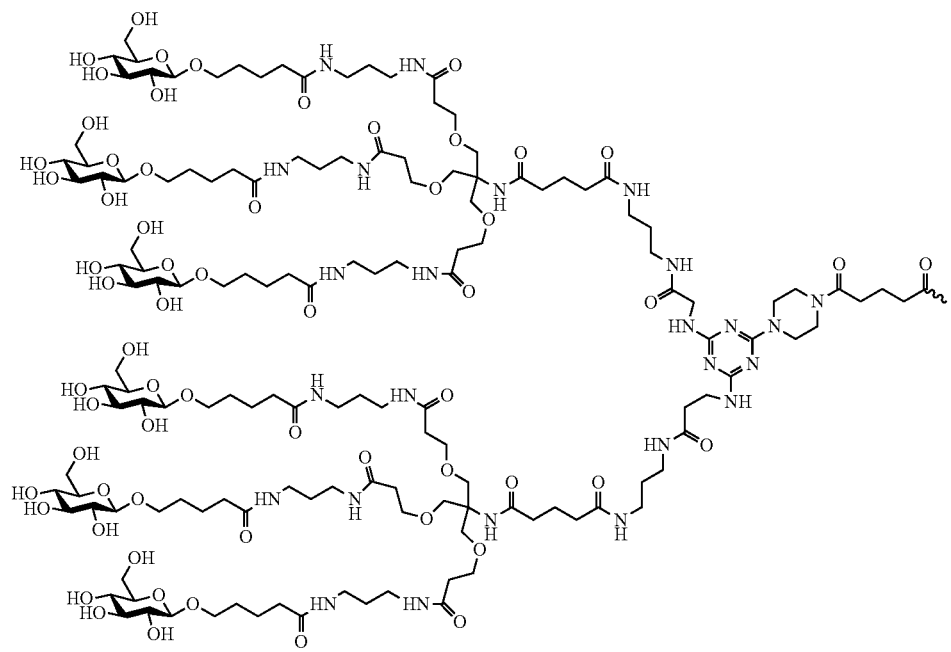

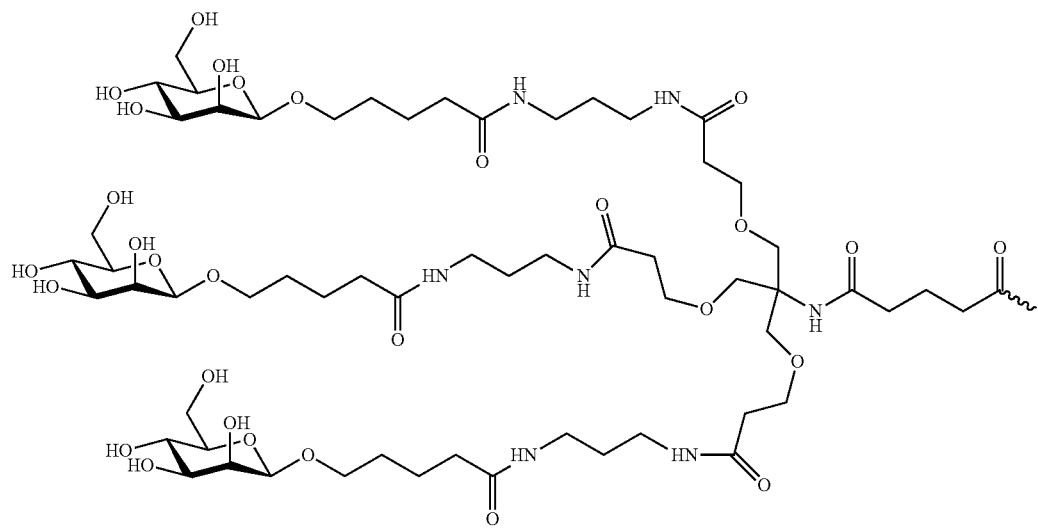
Mod073
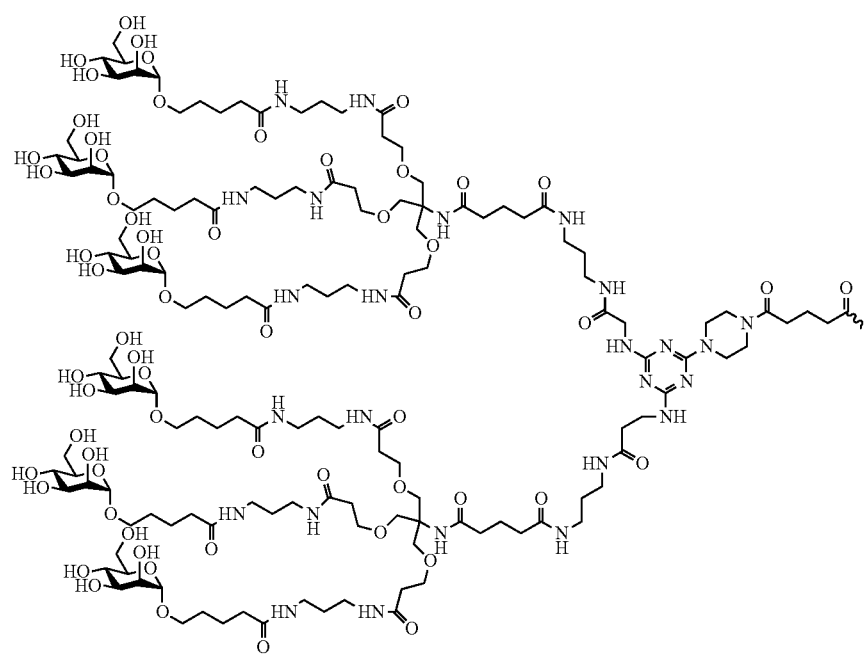
Mod074

Mod075
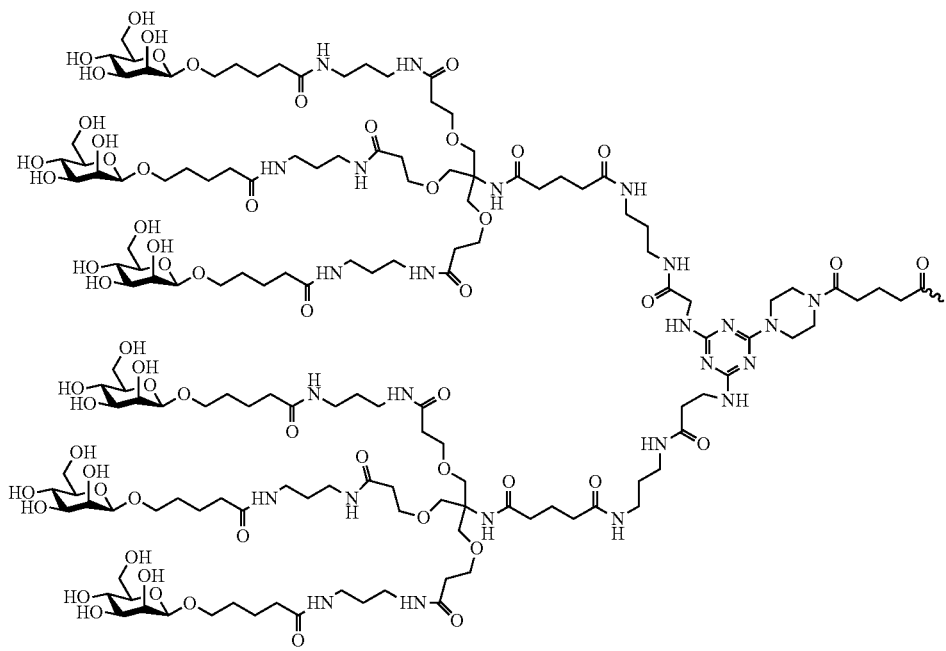
Mod076
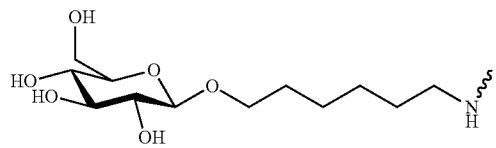
Mod077
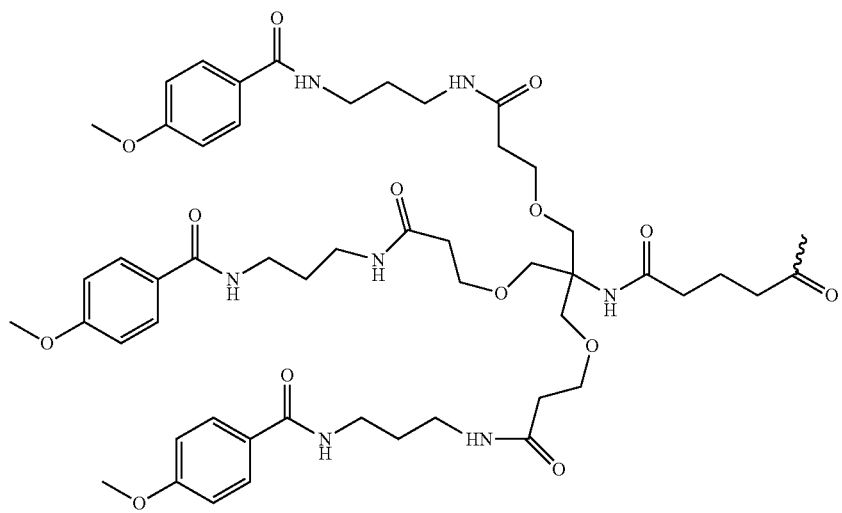

-continued
Mod084
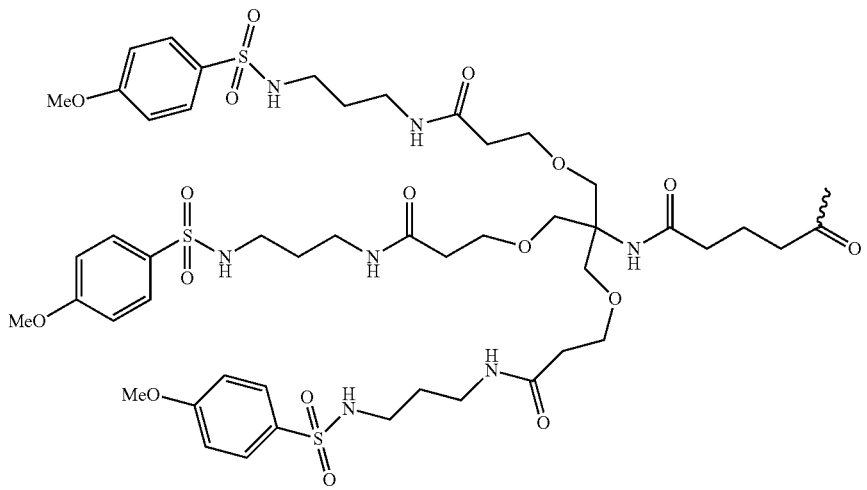
Mod085
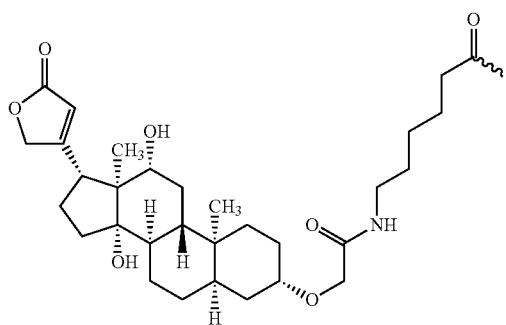
Mod087
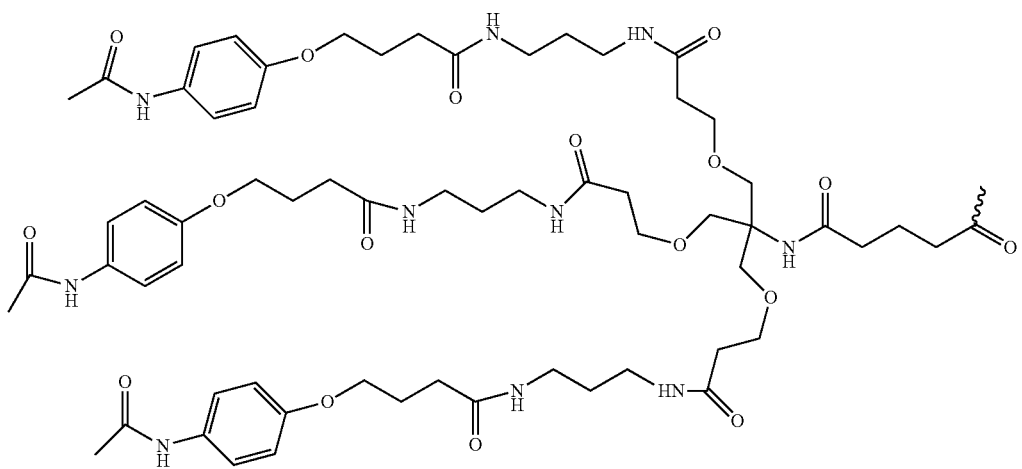

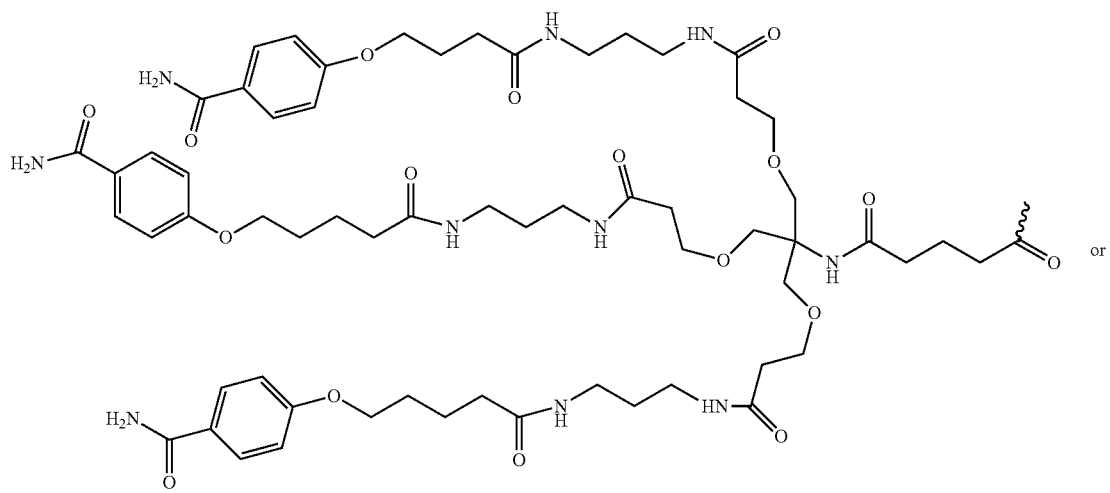

Mod088

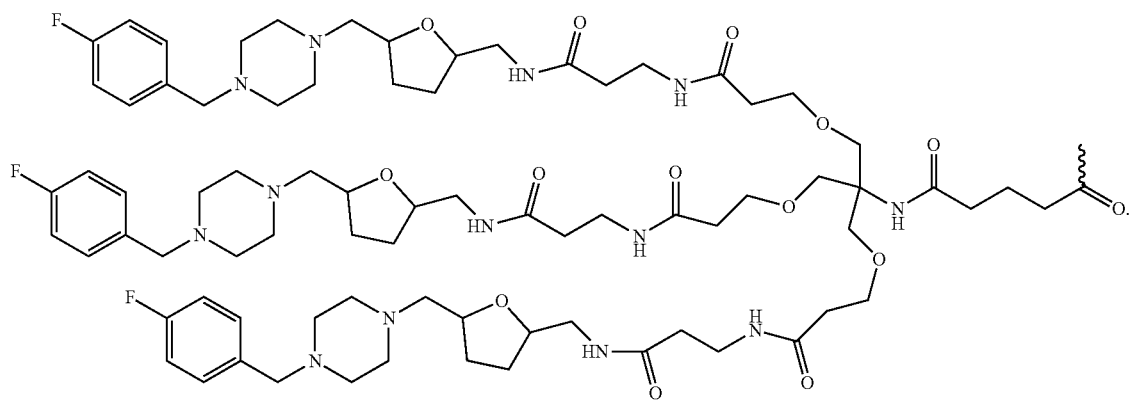

Mod089

In some embodiments, an additional component can be or comprise: Mod061:

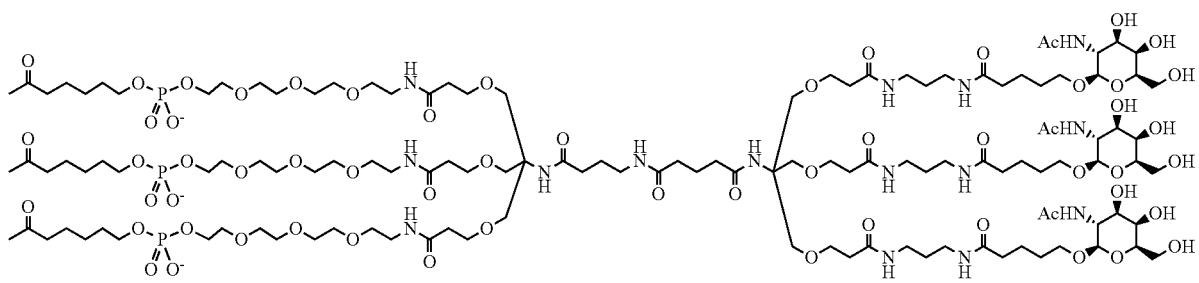

Mod061 wherein Mod061 is conjugated to three identical or nonidentical oligonucleotides.

5' Nucleoside or 5' Nucleotide of a PNPLA3 Oligonucleotide

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can comprise any 5'-nucleoside or 5'-nucleotide described herein or known in the art.

In some embodiments, the 5' nucleoside, e.g., the nucleoside at the 5'-end, of a single-stranded RNAi agent (e.g., in N1) can be any nucleoside, modified nucleoside or universal nucleoside known in the art.

In some embodiments, the 5' nucleotide, e.g., the nucleoside at the 5'-end, of a single-stranded RNAi agent (e.g., in N1) can comprise a 2' modification at the base.

In some embodiments, the nucleoside at the 5'-end of a single-stranded RNAi agent (e.g., in N1) can comprise a 2'-deoxy (DNA), 2'-F, 2'-OMe, or 2'-MOE, or an inverted nucleoside or nucleotide.

Non-limiting examples of ssRNAi agent formats in which the nucleoside at the 5'-end of the ssRNAi agent is a 2'-deoxy (DNA) include: Formats 1-5, 16-18, 22-29, 32-78, 84-93, 97, and 103-107 of FIG. 1.

Non-limiting examples of ssRNAi agent formats in which the nucleoside at the 5'-end of the ssRNAi agent is a 2'-F include: Formats 11-15, 19, 79-83, and 98-100 of FIG. 1.

Non-limiting examples of ssRNAi agent formats in which the nucleoside at the 5'-end of the ssRNAi agent is a 2'-OMe include: Formats 6-10, 20-21, 30-31, 94-96, and 101-102 of FIG. 1.

In some embodiments, the nucleobase at the 5'-end of a single-stranded RNAi agent (e.g., in N1) is T. In some embodiments, the nucleobase at the 5'-end of a single-stranded RNAi agent (e.g., in N1) is U. In some embodiments, the nucleobase at the 5'-end of a single-stranded RNAi agent (e.g., in N1) is A. In some embodiments, the nucleobase at the 5'-end of a single-stranded RNAi agent (e.g., in N1) is G. In some embodiments, the nucleobase at the 5'-end of a single-stranded RNAi agent (e.g., in N1) is C.

In some embodiments, a provided single-stranded RNAi agent has a 5' mismatch, wherein the nucleobase at the 5'-end of the single-stranded RNAi agent (position N1) has a mismatch from the corresponding position of the target transcript. As has been reported in the art, complementarity between the 5' nucleotide moiety and the corresponding position of the target transcript is not required for efficacious double-stranded siRNAs. Various example single-stranded RNAi agents described herein also have a 5' mismatch and are still capable of directing RNA interference. Efficacious ssRNAi agents have been constructed which have a mismatch with the sequence of the target mRNA at the 5' position (N1). Efficacious ssRNAi agents have been constructed which have a mismatch with the sequence of the target mRNA at the 5' position and the N1 position of the ssRNAi is T. In some embodiments, a provided single-stranded RNAi agent has a 5' mismatch at N1, wherein the nucleobase in N1 is T.

In some embodiments, the nucleoside at the 5' position is a LNA.

In some embodiments, the nucleoside at the 5' position is a 5'-H (deoxy). Efficacious ssRNAi agents have been constructed wherein the nucleoside at the 5' position is a 5'-H (deoxy). In some embodiments, the nucleoside at the 5' position is deoxy T, A, G, or C. In some embodiments, the nucleoside at the 5' position is deoxy T. In some embodiments, the nucleoside at the 5' position is deoxy A. In some embodiments, the nucleoside at the 5' position is a 2'-F. Efficacious ssRNAi agents have been constructed wherein the nucleoside at the 5' position is a 2'-F. In some embodiments, the nucleoside at the 5' position is a 2'-F A. In some embodiments, the nucleoside at the 5' position is a 2'-F G. In some embodiments, the nucleoside at the 5' position is a 2'-OMe. Efficacious ssRNAi agents have been constructed wherein the nucleoside at the 5' position is a 2'-OMe. In some embodiments, the nucleoside at the 5' position is a 2'-OMe U. In some embodiments, the nucleoside at the 5' position is a 2'-OMe A. In some embodiments, the nucleoside at the 5' position is a 2'-OMe C.

Seed Region of a PNPLA3 Oligonucleotide, Including a Single-Stranded RNAi Agent

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any seed region or portion or structural element thereof described herein or known in the art.

In some embodiments, a seed region of a provided single-stranded RNAi agent is a portion of the RNAi agent which is particularly important in binding of the RNAi agent to a transcript target. Lim et al. 2005 Nature 433: 769-773. In many cases, full complementarity between the seed region of the RNAi agent antisense strand and the mRNA target is reportedly required for high RNAi activity. For example, a single mismatch at position 6 in the seed region reportedly abolished double-stranded RNAi activity; Lim et al. 2005 Nature 433: 769-773. In contrast, dsRNAi antisense strands reportedly are more amenable to mismatches outside the seed region, e.g., at the 5' position, in the post-seed region, and in the 3'-terminal dinucleotide.

In some embodiments, each nucleotide in the seed region is 2'-OMe.

In some embodiments, each nucleotide in the seed region is 2'-OMe, and each nucleotide in the post-seed region is 2'-OMe.

In some embodiments, one nucleotide in the seed region is 2'-F and each other nucleotide in the seed region is 2'-OMe.

In some embodiments, one nucleotide in the seed region is 2'-F and each other nucleotide in the seed region is 2'-OMe, and one nucleotide in the post-seed region is 2'-F and each other nucleotide in the post-seed region is 2'-OMe.

In some embodiments, the nucleotide at position 2 (counting from the 5'-end) is 2'-F and each other nucleotide in the seed region is 2'-OMe, and one nucleotide in the post-seed region is 2'-F and each other nucleotide in the post-seed region is 2'-OMe.

In some embodiments, the nucleotide at position 2 (counting from the 5'-end) is 2'-F and each other nucleotide in the seed region is 2'-OMe, and the nucleotide at position 14 (counting from the 5'-end) is 2'-F and each other nucleotide in the post-seed region is 2'-OMe.

In some embodiments, a provided single-stranded RNAi agent comprises a seed region in which any number of N can be 2'-deoxy, 2'-F, 2'-OMe and/or 2'-OH, and/or have any other modification at the 2' position of the sugar.

Various non-limiting examples of seed regions of single-stranded RNAi agents are presented in Table 1A, the Figures, and elsewhere herein. In some embodiments, a provided single-stranded RNAi agent comprises a seed region, in which any one or more nucleotides in the seed region are independently 2'-F. In some embodiments, a provided single-stranded RNAi agent comprises a seed region, in which any 2 or more nucleotides in the seed region are independently 2'-F. In some embodiments, a provided single-stranded RNAi agent comprises a seed region, in which any 3 or more nucleotides in the seed region are independently 2'-F. In some embodiments, a provided single-stranded RNAi agent comprises a seed region, in which any 4 or more nucleotides in the seed region are independently 2'-F. In some embodiments, a provided single-stranded RNAi agent comprises a seed region, in which any 5 or more nucleotides in the seed region are independently 2'-F. In some embodiments, a provided single-stranded RNAi agent comprises a seed region, in which any 6 or more nucleotides in the seed region are independently 2'-F.

In some embodiments, a provided single-stranded RNAi agent comprises a seed region, in which any one or more nucleotides in the seed region are independently 2'-OMe. In some embodiments, a provided single-stranded RNAi agent comprises a seed region, in which any 2 or more nucleotides in the seed region are independently 2'-OMe. In some embodiments, a provided single-stranded RNAi agent comprises a seed region, in which any 3 or more nucleotides in the seed region are independently 2'-OMe. In some embodiments, a provided single-stranded RNAi agent comprises a seed region, in which any 4 or more nucleotides in the seed region are independently 2'-OMe. In some embodiments, a provided single-stranded RNAi agent comprises a seed region, in which any 5 or more nucleotides in the seed region are independently 2'-OMe. In some embodiments, a provided single-stranded RNAi agent comprises a seed region, in which any 6 or more nucleotides in the seed region are independently 2'-OMe. In some embodiments, a provided single-stranded RNAi agent comprises a seed region, in which 7 of N2 to N7 are independently 2'-OMe.

In some embodiments, a provided single-stranded RNAi agent comprises a seed region, in which any one or more nucleotides in the seed region are independently 2'-MOE. In some embodiments, a provided single-stranded RNAi agent comprises a seed region, in which any 2 or more nucleotides in the seed region are independently 2'-MOE. In some embodiments, a provided single-stranded RNAi agent comprises a seed region, in which any 3 or more nucleotides in the seed region are independently 2'-MOE. In some embodiments, a provided single-stranded RNAi agent comprises a seed region, in which any 4 or more nucleotides in the seed region are independently 2'-MOE. In some embodiments, a provided single-stranded RNAi agent comprises a seed region, in which any 5 or more nucleotides in the seed region are independently 2'-MOE. In some embodiments, a provided single-stranded RNAi agent comprises a seed region, in which any 6 or more nucleotides in the seed region are independently 2'-MOE. In some embodiments, a provided single-stranded RNAi agent comprises a seed region, in which 7 of N2 to N7 are independently 2'-MOE.

In some embodiments, a provided single-stranded RNAi agent comprises a seed region, in which any one or more nucleotides in the seed region are independently 2'-deoxy. In some embodiments, a provided single-stranded RNAi agent comprises a seed region, in which any 2 or more nucleotides in the seed region are independently 2'-deoxy. In some embodiments, a provided single-stranded RNAi agent comprises a seed region, in which any 3 or more nucleotides in the seed region are independently 2'-deoxy. In some embodiments, a provided single-stranded RNAi agent comprises a seed region, in which any 4 or more nucleotides in the seed region are independently 2'-deoxy. In some embodiments, a provided single-stranded RNAi agent comprises a seed region, in which any 5 or more nucleotides in the seed region are independently 2'-deoxy. In some embodiments, a provided single-stranded RNAi agent comprises a seed region, in which any 6 or more nucleotides in the seed region are independently 2'-deoxy. In some embodiments, a provided single-stranded RNAi agent comprises a seed region, in which 7 of N2 to N7 are independently 2'-deoxy.

In some embodiments, a provided single-stranded RNAi agent comprises a seed region, in which any one or more non-consecutive nucleotides in the seed region are independently 2'-F. In some embodiments, a provided single-stranded RNAi agent comprises a seed region, in which any 2 or more non-consecutive nucleotides in the seed region are independently 2'-F. In some embodiments, a provided single-stranded RNAi agent comprises a seed region, in which any 3 or more non-consecutive nucleotides in the seed region are independently 2'-F. In some embodiments, a provided single-stranded RNAi agent comprises a seed region, in which any 4 or more non-consecutive nucleotides in the seed region are independently 2'-F.

In some embodiments, a provided single-stranded RNAi agent comprises a seed region, in which any one or more non-consecutive nucleotides in the seed region are independently 2'-OMe. In some embodiments, a provided single-stranded RNAi agent comprises a seed region, in which any 2 or more non-consecutive nucleotides in the seed region are independently 2'-OMe. In some embodiments, a provided single-stranded RNAi agent comprises a seed region, in which any 3 or more non-consecutive nucleotides in the seed region are independently 2'-OMe. In some embodiments, a provided single-stranded RNAi agent comprises a seed region, in which any 4 or more non-consecutive nucleotides in the seed region are independently 2'-OMe.

In some embodiments, a provided single-stranded RNAi agent comprises a seed region, in which any one or more non-consecutive nucleotides in the seed region are independently 2'-MOE. In some embodiments, a provided single-stranded RNAi agent comprises a seed region, in which any 2 or more non-consecutive nucleotides in the seed region are independently 2'-MOE. In some embodiments, a provided single-stranded RNAi agent comprises a seed region, in which any 3 or more non-consecutive nucleotides in the seed region are independently 2'-MOE. In some embodiments, a provided single-stranded RNAi agent comprises a seed region, in which any 4 or more non-consecutive nucleotides in the seed region are independently 2'-MOE.

In some embodiments, a provided single-stranded RNAi agent comprises a seed region, in which any one or more non-consecutive nucleotides in the seed region are independently 2'-deoxy. In some embodiments, a provided single-stranded RNAi agent comprises a seed region, in which any 2 or more non-consecutive nucleotides in the seed region are independently 2'-deoxy. In some embodiments, a provided single-stranded RNAi agent comprises a seed region, in which any 3 or more non-consecutive nucleotides in the seed region are independently 2'-deoxy. In some embodiments, a provided single-stranded RNAi agent comprises a seed region, in which any 4 or more non-consecutive nucleotides in the seed region are independently 2'-deoxy.

In some embodiments, a provided single-stranded RNAi agent comprises a seed region, in which any 3 of the nucleotides in the seed region are independently 2'-deoxy.

In some embodiments, a provided single-stranded RNAi agent comprises a seed region, in which any one or more internucleotidic linkages in the seed region are independently PO (phosphodiester). In some embodiments, a provided single-stranded RNAi agent comprises a seed region, in which any 2 or more internucleotidic linkages in the seed region are independently PO. In some embodiments, a provided single-stranded RNAi agent comprises a seed region, in which any 3 or more internucleotidic linkages in the seed region are independently PO. In some embodiments, a provided single-stranded RNAi agent comprises a seed region, in which any 4 or more internucleotidic linkages in the seed region are independently PO. In some embodiments, a provided single-stranded RNAi agent comprises a seed region, in which any 5 or more internucleotidic linkages in the seed region are independently PO. In some embodiments, a provided single-stranded RNAi agent comprises a seed region, in which any 6 or more internucleotidic linkages in the seed region are independently PO. In some embodiments, a provided single-stranded RNAi agent comprises a seed region, in which 7 of N2 to N7 are independently PO.

In some embodiments, a provided single-stranded RNAi agent comprises a seed region, in which any one or more internucleotidic linkages in the seed region are independently PS (phosphorothioate). In some embodiments, a provided single-stranded RNAi agent comprises a seed region, in which any 2 or more internucleotidic linkages in the seed region are independently PS. In some embodiments, a provided single-stranded RNAi agent comprises a seed region, in which any 3 or more internucleotidic linkages in the seed region are independently PS. In some embodiments, a provided single-stranded RNAi agent comprises a seed region, in which any 4 or more internucleotidic linkages in the seed region are independently PS. In some embodiments, a provided single-stranded RNAi agent comprises a seed region, in which any 5 or more internucleotidic linkages in the seed region are independently PS. In some embodiments, a provided single-stranded RNAi agent comprises a seed region, in which any 6 or more internucleotidic linkages in the seed region are independently PS. In some embodiments, a provided single-stranded RNAi agent comprises a seed region, in which 7 of N2 to N7 are independently PS.

In some embodiments, a provided single-stranded RNAi agent comprises a seed region, in which any one or more internucleotidic linkages in the seed region are independently Sp (phosphorothioate in the Sp configuration). In some embodiments, a provided single-stranded RNAi agent comprises a seed region, in which any 2 or more internucleotidic linkages in the seed region are independently Sp. In some embodiments, a provided single-stranded RNAi agent comprises a seed region, in which any 3 or more internucleotidic linkages in the seed region are independently Sp. In some embodiments, a provided single-stranded RNAi agent comprises a seed region, in which any 4 or more internucleotidic linkages in the seed region are independently Sp. In some embodiments, a provided single-stranded RNAi agent comprises a seed region, in which any 5 or more internucleotidic linkages in the seed region are independently Sp. In some embodiments, a provided single-stranded RNAi agent comprises a seed region, in which any 6 or more internucleotidic linkages in the seed region are independently Sp. In some embodiments, a provided single-stranded RNAi agent comprises a seed region, in which 7 of N2 to N7 are independently Sp.

In some embodiments, a provided single-stranded RNAi agent comprises a seed region, in which any one or more internucleotidic linkages in the seed region are independently Rp (phosphorothioate in the Rp configuration). In some embodiments, a provided single-stranded RNAi agent comprises a seed region, in which any 2 or more internucleotidic linkages in the seed region are independently Rp. In some embodiments, a provided single-stranded RNAi agent comprises a seed region, in which any 3 or more internucleotidic linkages in the seed region are independently Rp. In some embodiments, a provided single-stranded RNAi agent comprises a seed region, in which any 4 or more internucleotidic linkages in the seed region are independently Rp. In some embodiments, a provided single-stranded RNAi agent comprises a seed region, in which any 5 or more internucleotidic linkages in the seed region are independently Rp. In some embodiments, a provided single-stranded RNAi agent comprises a seed region, in which any 6 or more internucleotidic linkages in the seed region are independently Rp. In some embodiments, a provided single-stranded RNAi agent comprises a seed region, in which 7 of N2 to N7 are independently Rp.

In some embodiments, a provided single-stranded RNAi agent comprises a seed region, in which any one or more non-consecutive internucleotidic linkages in the seed region are independently PO. In some embodiments, a provided single-stranded RNAi agent comprises a seed region, in which any 2 or more non-consecutive internucleotidic linkages in the seed region are independently PO. In some embodiments, a provided single-stranded RNAi agent comprises a seed region, in which any 3 or more non-consecutive internucleotidic linkages in the seed region are independently PO. In some embodiments, a provided single-stranded RNAi agent comprises a seed region, in which any 4 or more non-consecutive internucleotidic linkages in the seed region are independently PO.

In some embodiments, a provided single-stranded RNAi agent comprises a seed region, in which any one or more non-consecutive internucleotidic linkages in the seed region are independently Sp. In some embodiments, a provided single-stranded RNAi agent comprises a seed region, in which any 2 or more non-consecutive internucleotidic linkages in the seed region are independently Sp. In some embodiments, a provided single-stranded RNAi agent comprises a seed region, in which any 3 or more non-consecutive internucleotidic linkages in the seed region are independently Sp. In some embodiments, a provided single-stranded RNAi agent comprises a seed region, in which any 4 or more non-consecutive internucleotidic linkages in the seed region are independently Sp.

In some embodiments, a provided single-stranded RNAi agent comprises a seed region, in which any one or more non-consecutive internucleotidic linkages in the seed region are independently Rp. In some embodiments, a provided single-stranded RNAi agent comprises a seed region, in which any 2 or more non-consecutive internucleotidic linkages in the seed region are independently Rp. In some embodiments, a provided single-stranded RNAi agent comprises a seed region, in which any 3 or more non-consecutive internucleotidic linkages in the seed region are independently Rp. In some embodiments, a provided single-stranded RNAi agent comprises a seed region, in which any 4 or more non-consecutive internucleotidic linkages in the seed region are independently Rp.

In some embodiments, a provided single-stranded RNAi agent comprises a seed region, in which any one or more non-consecutive internucleotidic linkages in the seed region are independently PS. In some embodiments, a provided single-stranded RNAi agent comprises a seed region, in which any 2 or more non-consecutive internucleotidic linkages in the seed region are independently PS. In some embodiments, a provided single-stranded RNAi agent comprises a seed region, in which any 3 or more non-consecutive internucleotidic linkages in the seed region are independently PS. In some embodiments, a provided single-stranded RNAi agent comprises a seed region, in which any 4 or more non-consecutive internucleotidic linkages in the seed region are independently PS.

In some embodiments, a provided single-stranded RNAi agent comprises a seed region, in which the pattern of 2' modifications of the nucleotides comprises the pattern of 2' modifications of the nucleotides in the seed region of any single-stranded RNAi format shown in FIG. 1.

In some embodiments, a provided single-stranded RNAi agent comprises a seed region, in which the pattern of 2' modifications of the nucleotides comprises: fmfmfm, where f is 2'-F and m is 2'-OMe.

In some embodiments, a provided single-stranded RNAi agent comprises a seed region, in which the pattern of 2' modifications of the nucleotides comprises: fmfmfmf, where f is 2'-F and m is 2'-OMe.

In some embodiments, a provided single-stranded RNAi agent comprises a seed region, in which the pattern of 2' modifications of the nucleotides comprises: mfmfmf, where f is 2'-F and m is 2'-OMe.

In some embodiments, a provided single-stranded RNAi agent comprises a seed region, in which the pattern of 2' modifications of the nucleotides comprises: fmfmf, where f is 2'-F and m is 2'-OMe.

In some embodiments, a provided single-stranded RNAi agent comprises a seed region, in which the pattern of 2' modifications of the nucleotides comprises: mfmfmf, where f is 2'-F and m is 2'-OMe.

In some embodiments, a provided single-stranded RNAi agent comprises a seed region, in which the pattern of 2' modifications of the nucleotides comprises: mfmfm, where f is 2'-F and m is 2'-OMe.

In some embodiments, a provided single-stranded RNAi agent comprises a seed region, in which the pattern of 2' modifications of the nucleotides comprises: mfmfmfm, where f is 2'-F and m is 2'-OMe.

In some embodiments, a provided single-stranded RNAi agent comprises a seed region, in which the pattern of 2' modifications of the nucleotides comprises: fmfmf, where f is 2'-F and m is 2'-OMe.

In some embodiments, a provided single-stranded RNAi agent comprises a seed region, in which the pattern of 2' modifications of the nucleotides comprises: mfmfmfm, where f is 2'-F and m is 2'-OMe.

In some embodiments, a provided single-stranded RNAi agent comprises a seed region, in which the pattern of 2' modifications of the nucleotides comprises: mMfmf, where f is 2'-F, m is 2'-OMe, and M is 2'-MOE.

In some embodiments, a provided single-stranded RNAi agent comprises a seed region, in which the pattern of 2' modifications of the nucleotides comprises: mMfmfm, where f is 2'-F, m is 2'-OMe, and M is 2'-MOE.

In some embodiments, a provided single-stranded RNAi agent comprises a seed region, in which the pattern of 2' modifications of the nucleotides comprises: mMfm, where f is 2'-F, m is 2'-OMe, and M is 2'-MOE.

In some embodiments, a provided single-stranded RNAi agent comprises a seed region, in which the pattern of 2' modifications of the nucleotides comprises: mfMf, where f is 2'-F, m is 2'-OMe, and M is 2'-MOE.

In some embodiments, a provided single-stranded RNAi agent comprises a seed region, in which the pattern of 2' modifications of the nucleotides comprises: mfmfMf, where f is 2'-F, m is 2'-OMe, and M is 2'-MOE.

In some embodiments, a provided single-stranded RNAi agent comprises a seed region, in which the pattern of 2' modifications of the nucleotides comprises: mfmfMfm, where f is 2'-F, m is 2'-OMe, and M is 2'-MOE.

In some embodiments, a provided single-stranded RNAi agent comprises a seed region, in which the pattern of 2' modifications of the nucleotides comprises: mfmfM, where f is 2'-F, m is 2'-OMe, and M is 2'-MOE.

In some embodiments, a provided single-stranded RNAi agent comprises a seed region, in which the pattern of 2' modifications of the nucleotides comprises: mfMfMf, where f is 2'-F, m is 2'-OMe, and M is 2'-MOE.

In some embodiments, a provided single-stranded RNAi agent comprises a seed region, in which the pattern of 2' modifications of the nucleotides comprises: mfMfMfM, where f is 2'-F, m is 2'-OMe, and M is 2'-MOE.

In some embodiments, a provided single-stranded RNAi agent comprises a seed region, in which the pattern of 2' modifications of the nucleotides comprises: mfMfM, where f is 2'-F, m is 2'-OMe, and M is 2'-MOE.

In some embodiments, a provided single-stranded RNAi agent comprises a seed region, in which the pattern of 2' modifications of the nucleotides comprises: fdfdfd, where d is 2'-deoxy and m is 2'-OMe.

In some embodiments, a provided single-stranded RNAi agent comprises a seed region, in which the pattern of 2' modifications of the nucleotides comprises: fdfdfdf, where d is 2'-deoxy and m is 2'-OMe.

In some embodiments, a provided single-stranded RNAi agent comprises a seed region, in which the pattern of 2' modifications of the nucleotides comprises: dfdfdf, where d is 2'-deoxy and m is 2'-OMe.

In some embodiments, a provided single-stranded RNAi agent comprises a seed region, in which the pattern of 2' modifications of the nucleotides comprises: fdfdf, where d is 2'-deoxy and m is 2'-OMe.

In some embodiments, a provided single-stranded RNAi agent comprises a seed region, in which the pattern of 2' modifications of the nucleotides comprises: ffmmmm, where f is 2'-F and m is 2'-OMe.

In some embodiments, a provided single-stranded RNAi agent comprises a seed region, in which the pattern of 2' modifications of the nucleotides comprises: fmmmm, where f is 2'-F and m is 2'-OMe.

In some embodiments, a provided single-stranded RNAi agent comprises a seed region, in which the pattern of 2' modifications of the nucleotides comprises: ffmmm, where f is 2'-F and m is 2'-OMe.

In some embodiments, a provided single-stranded RNAi agent comprises a seed region, in which the pattern of 2' modifications of the nucleotides comprises: ffmm, where f is 2'-F and m is 2'-OMe.

In some embodiments, a provided single-stranded RNAi agent comprises a seed region, in which the pattern of 2' modifications of the nucleotides comprises: ffmmmmmm, where f is 2'-F and m is 2'-OMe.

In some embodiments, a provided single-stranded RNAi agent comprises a seed region, in which the pattern of 2' modifications of the nucleotides comprises: ffmmmmm, where f is 2'-F and m is 2'-OMe.

In some embodiments, a provided single-stranded RNAi agent comprises a seed region, in which the pattern of 2' modifications of the nucleotides comprises: mmmm, where m is 2'-OMe.

In some embodiments, a provided single-stranded RNAi agent comprises a seed region, in which the pattern of 2' modifications of the nucleotides comprises: mmmmm, where m is 2'-OMe.

In some embodiments, a provided single-stranded RNAi agent comprises a seed region, in which the pattern of 2' modifications of the nucleotides comprises: mmmmmm, where m is 2'-OMe.

In some embodiments, a provided single-stranded RNAi agent comprises a seed region, in which the pattern of 2' modifications of the nucleotides comprises: mfmfm, where f is 2'-F and m is 2'-OMe.

In some embodiments, a provided single-stranded RNAi agent comprises a seed region, in which the pattern of internucleotidic linkages comprises the pattern of internucleotidic linkages in the seed region of any single-stranded RNAi format shown in FIG. 1.

In some embodiments, a provided single-stranded RNAi agent comprises a seed region, in which the pattern of internucleotidic linkages comprises: XOXOXO, where X is phosphorothioate and O is phosphodiester.

In some embodiments, a provided single-stranded RNAi agent comprises a seed region, in which the pattern of internucleotidic linkages comprises: XOXOXOX, where X is phosphorothioate and O is phosphodiester.

In some embodiments, a provided single-stranded RNAi agent comprises a seed region, in which the pattern of internucleotidic linkages comprises: OXOXOX, where X is phosphorothioate and O is phosphodiester.

In some embodiments, a provided single-stranded RNAi agent comprises a seed region, in which the pattern of internucleotidic linkages comprises: XOXOX, where X is phosphorothioate and O is phosphodiester.

In some embodiments, a provided single-stranded RNAi agent comprises a seed region, in which the pattern of internucleotidic linkages comprises: OXOXOX, where X is phosphorothioate and O is phosphodiester.

In some embodiments, a provided single-stranded RNAi agent comprises a seed region, in which the pattern of internucleotidic linkages comprises: OXOXOXO, where X is phosphorothioate and O is phosphodiester.

In some embodiments, a provided single-stranded RNAi agent comprises a seed region, in which the pattern of internucleotidic linkages comprises: OXOXO, where X is phosphorothioate and O is phosphodiester.

In some embodiments, a provided single-stranded RNAi agent comprises a seed region, in which the pattern of internucleotidic linkages comprises: OXOX, where X is phosphorothioate and O is phosphodiester.

In some embodiments, a provided single-stranded RNAi agent comprises a seed region, in which the pattern of internucleotidic linkages comprises: XXOXOX, where X is phosphorothioate and O is phosphodiester.

In some embodiments, a provided single-stranded RNAi agent comprises a seed region, in which the pattern of internucleotidic linkages comprises: XXOXOXO, where X is phosphorothioate and O is phosphodiester.

In some embodiments, a provided single-stranded RNAi agent comprises a seed region, in which the pattern of internucleotidic linkages comprises: XXOXO, where X is phosphorothioate and O is phosphodiester.

In some embodiments, a provided single-stranded RNAi agent comprises a seed region, in which the pattern of internucleotidic linkages comprises: XXOX, where X is phosphorothioate and O is phosphodiester.

In some embodiments, a provided single-stranded RNAi agent comprises a seed region, in which the pattern of internucleotidic linkages comprises: OOOOOO, where O is phosphodiester.

In some embodiments, a provided single-stranded RNAi agent comprises a seed region, in which the pattern of internucleotidic linkages comprises: OOOOO, where O is phosphodiester.

In some embodiments, a provided single-stranded RNAi agent comprises a seed region, in which the pattern of internucleotidic linkages comprises: OOOO, where O is phosphodiester.

In some embodiments, a provided single-stranded RNAi agent comprises a seed region, in which the pattern of internucleotidic linkages comprises: SOSOSO, where S is a phosphorothioate in the Sp configuration and O is phosphodiester.

In some embodiments, a provided single-stranded RNAi agent comprises a seed region, in which the pattern of internucleotidic linkages comprises: SOSOSOS, where S is a phosphorothioate in the Sp configuration and O is phosphodiester.

In some embodiments, a provided single-stranded RNAi agent comprises a seed region, in which the pattern of internucleotidic linkages comprises: OSOSOS, where S is a phosphorothioate in the Sp configuration and O is phosphodiester.

In some embodiments, a provided single-stranded RNAi agent comprises a seed region, wherein the seed region comprises a phosphorothioate in the Sp configuration.

In some embodiments, a provided single-stranded RNAi agent comprises a seed region, wherein the seed region comprises a phosphorothioate in the Sp configuration and a phosphodiester.

In some embodiments, a provided single-stranded RNAi agent comprises a seed region, in which the pattern of internucleotidic linkages comprises: SOSOS, where S is a phosphorothioate in the Sp configuration and O is phosphodiester.

In some embodiments, a provided single-stranded RNAi agent comprises a seed region, in which the pattern of internucleotidic linkages comprises: SOSSSS, where S is a phosphorothioate in the Sp configuration and O is phosphodiester.

In some embodiments, a provided single-stranded RNAi agent comprises a seed region, in which the pattern of internucleotidic linkages comprises: SOSSS, where S is a phosphorothioate in the Sp configuration and O is phosphodiester.

In some embodiments, a provided single-stranded RNAi agent comprises a seed region, in which the pattern of internucleotidic linkages comprises: SOSS, where S is a phosphorothioate in the Sp configuration and O is phosphodiester.

In some embodiments, a provided single-stranded RNAi agent comprises a seed region, in which the pattern of internucleotidic linkages comprises the pattern of internucleotidic linkages in the seed region of a first single-stranded RNAi format shown in FIG. 1; and the pattern of 2' modifications of the nucleotides comprises the pattern of 2' modifications of the nucleotides in the seed region of a second single-stranded RNAi format shown in FIG. 1.

In some embodiments, a provided single-stranded RNAi agent comprises a seed region, in which the pattern of internucleotidic linkages comprises the pattern of internucleotidic linkages in the seed region of a first single-stranded RNAi format shown in FIG. 1; and the pattern of 2' modifications of the nucleotides comprises the pattern of 2' modifications of the nucleotides in the seed region of the first single-stranded RNAi format shown in FIG. 1.

Post-Seed Region of a PNPLA3 Oligonucleotide, Including a Single-Stranded RNAi Agent In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any post-seed region or portion or structural element thereof described herein or known in the art.

In some embodiments of a single-stranded RNAi agent, a post-seed region comprises: a sequence of nucleotides comprising at least 1 2'-F modifications. In some embodiments of a single-stranded RNAi agent, a post-seed region comprises: a sequence of nucleotides comprising at least 2 to 20 2'-F modifications.

In some embodiments of a single-stranded RNAi agent, a post-seed region comprises: a sequence of nucleotides comprising at least 1 2'-OMe modifications. In some embodiments of a single-stranded RNAi agent, a post-seed region comprises: a sequence of nucleotides comprising at least 2 to 20 2'-OMe modifications.

In some embodiments of a single-stranded RNAi agent, a post-seed region comprises: a sequence of nucleotides comprising at least 1 total 2'-OMe and/or 2'-F modifications. In some embodiments of a single-stranded RNAi agent, a post-seed region comprises: a sequence of nucleotides comprising at least 2 to 20 total 2'-OMe and/or 2'-F modifications.

In some embodiments of a single-stranded RNAi agent, a post-seed region comprises: at least 2 to 10 consecutive pairs of nucleotides having 2'-F and 2'-OMe or 2'-OMe and 2'-F modifications.

In some embodiments of a single-stranded RNAi agent, a post-seed region comprises a pattern of alternating 2'-modifications, wherein the pattern comprises 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe, 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe, 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises 2'-F, 2'-OMe, 2'-F, 2'-OMe, 2'-F, 2'-OMe, 2'-F, 2'-OMe, 2'-F, 2'-OMe, 2'-F, 2'-OMe, 2'-F, 2'-OMe. In some embodiments of a single-stranded RNAi agent, a post-seed region comprises a pattern of alternating 2'-modifications, wherein the pattern comprises fmfmfmfmfm.

In some embodiments of a single-stranded RNAi agent, a post-seed region comprises a pattern of alternating 2'-modifications, wherein the pattern comprises mfmf, mfmfmf, mfmfmfmf, mfmfmfmfmf, mfmfmfmfmfmf, mfmfmfmfmfmfmf, mfmfmfmfmfmfmfmf, mfmfmfmfmfmfmfmfmf, mfmfmfmfmfmfmfmfmfmf, where m is 2'-OMe and f is 2'-F.

In some embodiments, each nucleotide in the seed region is 2'-OMe.

In some embodiments, each nucleotide in the seed region is 2'-OMe, and each nucleotide in the post-seed region is 2'-OMe.

In some embodiments, one nucleotide in the seed region is 2'-F and each other nucleotide in the seed region is 2'-OMe.

In some embodiments, one nucleotide in the seed region is 2'-F and each other nucleotide in the seed region is 2'-OMe, and one nucleotide in the post-seed region is 2'-F and each other nucleotide in the post-seed region is 2'-OMe.

In some embodiments, the nucleotide at position 2 (counting from the 5'-end) is 2'-F and each other nucleotide in the seed region is 2'-OMe, and one nucleotide in the post-seed region is 2'-F and each other nucleotide in the post-seed region is 2'-OMe.

In some embodiments, the nucleotide at position 2 (counting from the 5'-end) is 2'-F and each other nucleotide in the seed region is 2'-OMe, and the nucleotide at position 14 (counting from the 5'-end) is 2'-F and each other nucleotide in the post-seed region is 2'-OMe.

Without wishing to be bound by any particular theory, the present disclosure suggests that, in at least some cases, reducing the number of 2'-F nucleotides (e.g., replacing them with 2'-OMe, 2'-deoxy or any other nucleotide which is not 2'-F) can allow in vitro potency, and allow or increase stability, while reducing potential toxicity related to 2'-F.

In some embodiments, a post-seed region comprises at least 1, 2, 3, 4, 5 6, 7, 8 or 9 phosphorothioates and/or at least 1, 2, 3, 4, 5 6, 7, 8 or 9 phosphodiester internucleotidic linkages.

In some embodiments of a single-stranded RNAi agent, a post-seed region comprises one or more sets of consecutive phosphorothioates and/or one or more sets of consecutive phosphodiesters.

In some embodiments, a single-stranded RNAi agent comprises a post-seed region which comprises a span of sugars having a pattern of modifications of any of: mfmfmfmfmfmfm, mfmfmfmfmfm, mfmfmfmfm, mfmfmfm, mfmfm, mfm, fmfmfmfmfmfm, fmfmfmfmfm, fmfmfmfm, fmfmfm, and fmfm, wherein m is 2'-OMe and f is 2'-F.

In some embodiments, a single-stranded RNAi agent comprises a post-seed region which comprises a span of sugars having a pattern of modifications of any of: dddfdfdfdfdfd, dddfdfdfdfd, dddfdfdfd, dddfdfd, and dddfd, wherein d is 2'-deoxy and f is 2'-F.

In some embodiments, a single-stranded RNAi agent comprises a post-seed region which comprises a span of sugars having a pattern of modifications of any of: dfdfdfdfdfdfd, fdfdfdfdfdfd, and fdfdfdfdfd.

In some embodiments, a single-stranded RNAi agent comprises a post-seed region which comprises a span of sugars having a pattern of modifications of any of: fdfdfdfd, fdfdfd, and fdfd.

In some embodiments, a single-stranded RNAi agent comprises a post-seed region which comprises a span of internucleotidic linkages having a pattern of any of: XOXOXOXOOOO, OXOXOXOOOO, XOXOXOXOOO, XOXOXOXOO, XOXOXOOOO, OXOXOXOO, XOXOXOOO, OXOXOOOO, OXOXOXOO, XOXOOO, OXOXOOO, OXOXOO, and XOXOOO, wherein O is phosphodiester and X is a stereorandom phosphorothioate.

In some embodiments, a single-stranded RNAi agent comprises a post-seed region which comprises a span of internucleotidic linkages having a pattern of OOOOOOO.

In some embodiments, a single-stranded RNAi agent comprises a post-seed region which comprises a span of internucleotidic linkages having a pattern of any of: OOOOOO, OOOOO, OOOO, and OOO.

In some embodiments, a single-stranded RNAi agent comprises a post-seed region which comprises a span of internucleotidic linkages having a pattern of any of: OOOOOOOOXXXXXX, OOOOOOOOXXXXX, OOOOOOOOXXXX, OOOOOOOOXXX, OOOOOOOOXX, OOOOOOOOX, OOOOOOOXXXXXX, OOOOOOXXXXXX, OOOOOXXXXXX, OOOOXXXXXX, OOOXXXXXX, OOXXXXXX, OXXXXXX, OOOOOOX, OOOOOX, OOOOX, and OOOX.

In some embodiments, a single-stranded RNAi agent comprises a post-seed region which comprises a span of internucleotidic linkages having a pattern of any of: OOOOOOOXXXXX, OOOOOOOXXXX, OOOOOOOXXX, OOOOOOXXXXX, OOOOOOXXXX, OOOOOXXXXX, OOOOOXXXX, OOOOXXXX, OOOOXXX, OOOXXXXX, OOOXXXX, and OOOXXX.

In some embodiments, a single-stranded RNAi agent comprises a post-seed region which comprises at least one chiral internucleotidic linkage. In some embodiments, a single-stranded RNAi agent comprises a post-seed region which comprises at least one chirally controlled internucleotidic linkage. In some embodiments, a single-stranded RNAi agent comprises a post-seed region which comprises at least one chirally controlled internucleotidic linkage which is a phosphorothioate. In some embodiments, a single-stranded RNAi agent comprises a post-seed region which comprises at least one chirally controlled internucleotidic linkage which is a phosphorothioate in the Sp configuration. In some embodiments, a single-stranded RNAi agent comprises a post-seed region which comprises at least one chirally controlled internucleotidic linkage which is a phosphorothioate in the Rp configuration.

In some embodiments, a single-stranded RNAi agent comprises a post-seed region which comprises a span of internucleotidic linkages having a pattern of any of: OSSSOSSSSSSSS, OSSSOSSSSSSS, OSSSOSSSSSS, OSSSOSSSSSS, OSSSOSSSSS, OSSSOSSSS, OSSSOSSS, OSSSOSS, OSSSOS, OSSSOSSSS, OSSSOSSS, OSSSOS, OSSSOS, and OSSSO, wherein O is phosphodiester and S is a phosphorothioate in the Sp configuration.

In some embodiments, a single-stranded RNAi agent comprises a post-seed region which comprises a span of internucleotidic linkages having a pattern of any of: OSOSOSOSSSSSSS, OSOSOSOSSSSSSS, OSOSOSOSSSSSS, OSOSOSOSSSS, OSOSOSOSSSS, OSOSOSOSSSS, OSOSOSOSSS, and OSOSOSOSS.

In some embodiments, a single-stranded RNAi agent comprises a post-seed region which comprises a span of internucleotidic linkages having a pattern of any of: SOSOSOSSSSSSSS, OSOSOSSSSSSS, SOSOSSSSSSS, OSOSSSSSSS, SOSSSSSSS, and OSSSSSSS.

In some embodiments, a single-stranded RNAi agent comprises a post-seed region which comprises a span of internucleotidic linkages having a pattern of any of: SOSOSOSSSSSSSS, SOSOSOSSSSSS, SOSOSO SSSSSS, SOSOSOSSSSS, SOSOSOSSSS, SOSOSOSSS, SSSSSSSSS, SSSSSSS, SSSSSS, SSSSS, SSSS, SSS, and SS.

In some embodiments, a single-stranded RNAi agent comprises a post-seed region which comprises a span of internucleotidic linkages having a pattern of any of: OSSSSSO, OSSSSS, OSSSS, SSSSSO, SSSSO, and SSSO.

In some embodiments, a single-stranded RNAi agent comprises a post-seed region which comprises a span of internucleotidic linkages having a pattern of any of: SOSOSOSOSOOOOOS, SOSOSOSOSOOOOO, SOSOSOSOOOOO, SOSOSOSOOOO, SOSOSOSO-SOOO, and SOSOSOSOSOO.

In some embodiments, a single-stranded RNAi agent comprises a post-seed region which comprises a span of internucleotidic linkages having a pattern of any of: OSOSOSOSOOOOOS, SOSOSOSOOOOOS, OSOSO-SOOOOOS, SOSOSOOOOOS, OSOSOOOOOS, SOSOOOOOOS, and OSOOOOOOS.

In some embodiments, a single-stranded RNAi agent comprises a post-seed region which comprises a span of internucleotidic linkages having a pattern of any of: XOOOXOOXXXXX, XOOOXOOXXXX, XOOOXOO XXX, XOOOXOOXX, XOOOXOOX, XOOOXOO, OOOXOOXXXXX, OOXOOXXXXX, OXOOXXXXX, XOOXXXXX, and OOXXXXXX.

In some embodiments, a single-stranded RNAi agent comprises a post-seed region which comprises a span of internucleotidic linkages having a pattern of any of: XOXOXOXXXXXX, XOXOXOXXXXX, XOXOXO XXXX, XOXOXOXXX, XOXOXOXX, XOXOXOX, OXOXOXXXXXX, XOXOXXXXXX, OXOXXXXXX, XOXXXXXX, and OXXXXXX.

In some embodiments, a single-stranded RNAi agent comprises a post-seed region which comprises a span of internucleotidic linkages having a pattern of any of: XXXOOOXOXOXXX, XXXOOOXOXOXX, XXXOOO XOXOX, XXXOOOXOXO, XXXOOOXOX, XXXOOOXO, XXOOOXOXOXXX, XOOOXOXOXXX, OOOXOXOXXX, OOXOXOXXX, OXOXOXXX, XOXOXXX, XXOOOXOXOXX, XXOOOXOXOX, XOOOXOXOXX, and XOOOXOXOX.

In some embodiments, a single-stranded RNAi agent comprises a post-seed region which comprises a span of internucleotidic linkages having a pattern of any of: XOOOXOXO, XOOOXOX, XOOOXO, OOOXOXO, OOOXOX, and OOOXO.

In some embodiments, a single-stranded RNAi agent comprises a post-seed region which comprises a span of internucleotidic linkages having a pattern of any of: XOXOOOXOXOXXX, XOXOOOXOXOXX, XOXOOO XOXOX, XOXOOOXOXO, XOXOOOXOX, XOXOOO XO, XOXOOOX, OXOOOXOXOXXX, XOOOXO XOXXX, OOXOXOXXX, OOXOXOXXX, OXOXOXXX, OXOOOXOXOXX, OXOOOXOXOX, XOOOXOXOXX, and XOOOXOXOX.

In some embodiments, a single-stranded RNAi agent comprises a post-seed region which comprises a span of internucleotidic linkages having a pattern of any of: OOOOOOS, OOOOOSO, OOOOSOO, OOOSOOO, OOSOOOO, OSOOOOO, and SOOOOOO.

In some embodiments, a hybrid oligonucleotide comprises a (a) seed region capable of annealing to a first complementary target mRNA region; and (b) a post-seed region comprising a 2'-deoxy region, wherein the hybrid oligonucleotide is capable of directing both RNA interference and RNase H-mediated knockdown, wherein the 2'-deoxy region comprises at least 5 consecutive 2'-deoxy. In some embodiments, the 2'-deoxy can be DNA, or a modified nucleotide, e.g., a modified nucleotide with a 2'-deoxy, wherein the DNA or modified nucleotide comprise a natural sugar and/or a natural base, and/or a modified base, and/or any internucleotidic linkage. In some embodiments, the 2'-deoxy region comprises a stretch of consecutive nucleotides, wherein each nucleotide is 2'-deoxy and each internucleotidic linkage is a phosphorothioate. In some embodiments, the 2'-deoxy region comprises a stretch of consecutive nucleotides of at least 5, 6, 7, 8, 9, 10, 11, 12, 13, 14, 15, 16, 17, 18, 19, 20 or 21 nucleotides, wherein each nucleotide is 2'-deoxy and each internucleotidic linkage is a phosphorothioate.

As non-limiting examples of a post-seed region in a single-stranded RNAi agent: Formats 2, 7, 8, 9, 12 and 13 (which each comprise a set of 6 consecutive phosphodiesters; and a set of 6 consecutive phosphodithioates), Format 3 (6 consecutive phosphorodithioates), Formats 4, 5 and 6, Formats 10 and 11; and various other single-stranded RNAi agents disclosed herein.

In some embodiments of a single-stranded RNAi agent, a post-seed region comprises a mismatch at the most 3' position.

In some embodiments, a provided single-stranded RNAi agent can comprise a mismatch at any one or more of: the 5' position, either or both of the 3'-terminal dinucleotide, and the most 3' position of the region between the seed region and the 3'-end region.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any post-seed region or portion or structural element thereof described herein or known in the art.

3'-End Region of a PNPLA3 Oligonucleotide, Including a Single-Stranded RNAi Agent In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can comprise any 3'-end region described herein or known in the art.

In some embodiments, the 3'-end region of a PNPLA3 oligonucleotide is such that the oligonucleotide is capable of directing a decrease in the expression and/or level of a target gene or its gene product.

In some embodiments, the 3'-end region of a RNAi agent is such that the RNAi agent is capable of directing RNA interference of a specific target transcript in a sequence-specific manner.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any 3'-end region and/or 3'-terminal dinucleotide and/or 3'-end cap described herein or known in the art. In some embodiments, a 3'-end region can comprise a GalNAc moiety. In some embodiments, a GalNAc moiety is any GalNAc, or variant, derivative or modification thereof, as described herein or known in the art.

In some embodiments, a 3'-end region and/or 3'-terminal dinucleotide and/or 3'-end cap performs two functions: (a) decreasing the sensitivity of the oligonucleotide to exo- and/or endonucleases; and (b) allowing the function of the oligonucleotide, wherein the function is directing RNA interference, directing RNase H-mediated knockdown, or directing both RNA interference and RNase H-mediated knockdown.

Thus, the 3'-end region of the single-stranded RNAi agent can comprise a 3'-terminal dinucleotide and/or a 3'-end cap.

In a mammalian cell, Dicer reportedly processes double-stranded RNA (dsRNA) into 19-23 base pair siRNAs, which comprise a double-stranded region, with each strand terminating in a single-stranded 3' overhang, which can be 1 to 4 nt long, but is typically a 3'-terminal dinucleotide. Bernstein et al. 2001 Nature 409: 363; Elbashir et al. 2001 Nature 411: 494-498; Elbashir et al. 2001 EMBO J. 20: 6877. The two dinucleotide overhangs reportedly do not contribute to target specificity. They do, however, reportedly help protect the ends of the siRNA from nuclease degradation and sometimes improve activity. Elbashir et al. 2001 Nature 411: 494-498; Elbashir et al. 2001 EMBO J. 20: 6877-6888; and Kraynack et al. 2006 RNA 12:163-176. Thus, it is reportedly not necessary for a functional double-stranded RNAi agent for a 3'-terminal dinucleotide to comprise a sequence complementary to the target gene sequence.

In artificial double-stranded RNAi agents, the 3' single-stranded dinucleotide overhangs have reportedly been experimentally replaced with various moieties, including other single-stranded dinucleotides, nucleotides, and 3'-end caps. The 3'-terminal dinucleotides of a 21-mer are reportedly often replaced by an artificial dinucleotide, such as UU, TT, dTdT, sdT, dTsdT, sdTsdT, or sdTdT. Replacing up to four nucleotides on each end of the siRNA with deoxyribonucleotides has reportedly been well tolerated, whereas complete substitution with deoxyribonucleotides results in no RNAi activity. International PCT Publication No. WO 00/44914, and Beach et al. International PCT Publication No. WO 01/68836 preliminarily reported that siRNA may include modifications to either the phosphate-sugar backbone or the nucleoside to include at least one of a nitrogen or sulfur heteroatom. Kreutzer et al. Canadian Patent Application No. 2,359,180, also report certain chemical modifications for use in dsRNA constructs in order to counteract activation of double-stranded RNA-dependent protein kinase PKR, specifically 2'-amino or 2-O-methyl nucleotides, and nucleotides containing a 2'-0 or 4'-C methylene bridge. Additional 3'-terminal nucleotide overhangs include dT (deoxythimidine), 2'-0,4'-C-ethylene thymidine (eT), and 2-hydroxyethyl phosphate (hp). Other artificial 3' overhangs (3'-terminal dinucleotides) include dinucleotides of sequences AA, CC, GG, and UG. Elbashir et al. 2001

EMBO J. 20: 6877-6888. In some embodiments, a 3'-terminal dinucleotide reportedly is AA.

Alternatively, in a double-stranded RNAi agent, one or both of the 3'-terminal dinucleotides can reportedly be deleted (and not replaced), leaving a functional siRNA comprising two 19-nt strands forming a 19-bp blunt-ended duplex. Deleting and not replacing the 3'-terminal dinucleotide in a double-stranded RNAi agent reportedly leaves the ends of the strands vulnerable to nucleases; to compensate for this, an artificial 3'-end cap can be added. The 3'-end caps are reportedly non-nucleotidic; they are not nucleotides as they do not comprise all components of a nucleotide (phosphate, sugar and base). The dinucleotide overhangs in a double-stranded RNAi agent can reportedly sometimes functionally be replaced by a 3'-end cap, leaving a blunt-ended 19-bp duplex with one or two 3'-end caps, which can protect the molecule from nucleases. In general, a 3'-end cap reportedly must not prevent RNA interference mediated by the RNAi agent; many 3'-end caps also impart an added advantage, such as increased RNAi activity and/or stability against nucleases.

Without wishing to be bound by any particular theory, the present application notes that in at least some cases, previously-described 3'-end caps reportedly are theorized to interact with a PAZ domain. In some embodiments, a 3'-end cap is reportedly a PAZ ligand. WO 2015/051366. Reportedly, Dicer is an RNase III enzyme and is composed of six recognizable domains. Reportedly, at or near the N-terminus is an approx. 550 aa DExH-box RNA helicase domain, which is immediately followed by a conserved approx. 100 aa domain called DUF283; just C-terminal to DUF283 domain is the PAZ (for Piwi/Argonaute/Zwille) domain, which recognizes single stranded dinucleotide overhangs. Myers et al. 2005. in RNA interference Technology, ed. Appasani, Cambridge University Press, Cambridge UK, p. 29-54; Bernstein et al. 2001 Nature 409: 363-366; and Schauer et al. 2002 Trends Plant Sci. 7: 487-491; Lingel et al. 2003 Nature 426: 465-469; Song et al. 2003 Nature Struct. Biol. 10: 1026-1032; Yan et al. 2003 Nature 426: 468-474; Lingel et al. 2004 Nature Struct. Mol. Biol. 1 1: 576-577; Ma et al. 2004 Nature 429: 318-322. Reportedly, the PAZ domain in Dicer could also bind RNA to position the catalytic domains for cleavage. Zhang et al. 2004 Cell 1 18: 57-68. In some embodiments, a 3'-end cap is a PAZ ligand which interacts with a PAZ domain.

In some embodiments, a 3'-end cap can allow two functions: (1) allowing RNA interference; and (2) increasing duration of activity and/or biological half-life, which may be accomplished, for example, by increased binding to the PAZ domain of Dicer and/or reducing or preventing degradation of the RNAi agent (e.g., by nucleases such as those in the serum or intestinal fluid).

Various 3'-terminal dinucleotides are described in the oligonucleotides listed in Table 1A.

In some embodiments, a provided single-stranded RNAi agent comprises a pair of 3'-terminal nucleotides. The penultimate nucleotide is 2'-OMe and the 5' nucleotide is 2'-OMe.

In some embodiments, a provided single-stranded RNAi agent comprises a pair of 3'-terminal nucleotides and the penultimate nucleotide is 2'-deoxy and the 5' nucleotide is 2'-OMe. Non-limiting examples of single-stranded RNAi agents disclosed herein of this structure include: Formats 10, 11, 13 and 14, FIG. 1; and various other single-stranded RNAi agents disclosed herein.

In some embodiments, a provided single-stranded RNAi agent comprises a pair of 3'-terminal nucleotides and the penultimate nucleotide is 2'-deoxy and the 5' nucleotide is 2'-OMe, and wherein the penultimate nucleotide comprises a linker.

In some embodiments, a provided single-stranded RNAi agent comprises a pair of 3'-terminal nucleotides and wherein the penultimate nucleotide comprises a linker.

In some embodiments, a provided single-stranded RNAi agent comprises a pair of 3'-terminal nucleotides and the penultimate nucleotide is 2'-deoxy and the 5' nucleotide is 2'-OMe, and wherein the penultimate nucleotide comprises a linker conjugated to an additional chemical moiety.

In some embodiments, a provided single-stranded RNAi agent comprises a pair of 3'-terminal nucleotides and the penultimate nucleotide is 2'-deoxy T and the 5' nucleotide is 2'-OMe U, and wherein the penultimate nucleotide comprises a linker conjugated to an additional chemical moiety.

In some embodiments, a provided single-stranded RNAi agent comprises a pair of 3'-terminal nucleotides and wherein the penultimate nucleotide comprises a linker conjugated to an additional chemical moiety selected from: a targeting moiety, a lipid moiety, a carbohydrate moiety, a bicyclic ketal, and a GalNAc moiety.

In some embodiments, a provided single-stranded RNAi agent comprises a pair of 3'-terminal nucleotides and the penultimate nucleotide is 2'-deoxy and the 5' nucleotide is 2'-OMe, and wherein the penultimate nucleotide comprises a linker conjugated to an additional chemical moiety selected from: a targeting moiety, a lipid moiety, a carbohydrate moiety, a bicyclic ketal, and a GalNAc moiety.

In some embodiments, a provided single-stranded RNAi agent comprises a pair of 3'-terminal nucleotides and the penultimate nucleotide is 2'-deoxy T and the 5' nucleotide is 2'-OMe U, and wherein the penultimate nucleotide comprises a linker conjugated to an additional chemical moiety selected from: a targeting moiety, a lipid moiety, a carbohydrate moiety, a bicyclic ketal, and a GalNAc moiety.

In some embodiments, a 3'-end region or 3'-end cap comprises a GN3, or any other suitable RNAi agent 3'-end region compound as described in, for example, Allerson et al. 2005 J. Med. Chem. 48: 901-04; Lima et al. 2012 Cell 150: 883-894; Prakash et al. 2015 Nucl. Acids Res. 43: 2993-3011; and/or Prakash et al. 2016 Bioorg. Med. Chem. Lett. 26: 26: 2817-2820.

Various 3'-end caps have been described in the literature.

Generally, a 3'-end cap is joined to the 3'-terminal internucleotidic linkage. The 3'-terminal internucleotidic linkage can be selected from: a phosphodiester, a phosphorothioate, a phosphodithionate, and any internucleotidic linkage described herein.

A 3'-end cap for a provided single-stranded RNAi agent can be selected from, for example, any 3'-end cap described herein.

In some embodiments, a 3'-end cap is selected from: 2',3'-cyclic phosphate, C3 (or C6, C7, C12) aminolinker, thiol linker, carboxyl linker, non-nucleotidic spacers (C3, C6, C9, C12, abasic, triethylene glycol, hexaethylene glycol), biotin, and fluorescein.

In some embodiments, a 3'-end cap is selected from any 3'-end cap described in WO 2015/051366, including but not limited to C3, amino C3, C6, C8, C10, and C12. In some embodiments, a 3'-end cap is selected from: Triethylene glycol, Cyclohexyl (or Cyclohex), Phenyl, BP (Biphenyl), Adamantane and Lithocholic acid (or Lithochol), as described in U.S. Pat. Nos. 8,097,716; 8,084,600; 8,344, 128; 8,404,831; and 8,404,832.

Various functional 3'-end caps suitable for a provided RNAi agent are described in, for example, EP 1520022 B1;

U.S. Pat. Nos. 8,097,716, 8,084,600; 8,404,831; 8,404,832, and 8,344,128; and WO 2015/051366.

In addition, the present disclosure notes that disclosed herein are various 5'-end structures and 3'-end regions, and combinations thereof, which function in single-stranded RNAi agents. However, it is noted, in contrast, many 5'-end structures and 3'-end caps, and combinations thereof, have previously been reported to reduce or eliminate the RNA interference ability of various double-stranded RNAi agents. See, for example, Czauderna et al. 2003 Nucl. Acids Res. 31:2705-2716; Hadwiger et al. 2005, pages 194-206, in RNA interference Technology, ed. K. Appasani, Cambridge University Press, Cambridge, UK; Deleavey et al. 2009 Curr. Prot. Nucl. Acid Chem. 16.3.1-16.3.22; Terrazas et al. 2009 Nucleic Acids Res. 37: 346-353; Harboth et al. 2003 Antisense Nucl. Acid Drug Dev 13: 83-105; Song et al. 2003 Nature Med. 9: 347-351; U.S. Pat. No. 5,998,203; Lipardi et al. 2001 Cell 107: 299-307; Schwarz et al. 2002 Mol. Cell 10: 537-548; and WO 2015/051366.

A Bicyclic Ketal, Additional Optional Structural Elements of a PNPLA3 Oligonucleotide In some embodiments, a PNPLA3 oligonucleotide, a PNPLA3 oligonucleotide capable of directing a decrease in the expression and/or level of a target gene or its gene product can comprise any structural element or pattern thereof described herein or known in the art.

A Bicyclic Ketal, Optional Additional Chemical Moiety Conjugated to a PNPLA3 Oligonucleotide In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides can comprise any optional additional chemical moiety, including but not limited to, a targeting moiety, a lipid moiety, a carbohydrate moiety, a bicyclic ketal, a GalNAc moiety, etc., described herein or known in the art.

In some embodiments, a PNPLA3 oligonucleotide, a PNPLA3 oligonucleotide that is capable of directing a decrease in the expression and/or level of a target gene or its gene product can comprise any optional additional chemical moiety, including but not limited to, a targeting moiety, a lipid moiety, a carbohydrate moiety, a bicyclic ketal, a GalNAc moiety, etc., described herein or known in the art.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any optional additional chemical moiety, including but not limited to, a targeting moiety, a lipid moiety, a carbohydrate moiety, a bicyclic ketal, a GalNAc moiety, etc., described herein or known in the art.

In some embodiments, an additional chemical moiety is conjugated to single-stranded RNAi agent.

Optional Additional Chemical Moiety Conjugated to a PNPLA3 Oligonucleotide: A Targeting Moiety In some embodiments, a provided oligonucleotide composition further comprises a targeting moiety (e.g., a targeting compound, agent, ligand, or component). A targeting moiety can be either conjugated or not conjugated to a lipid or a PNPLA3 oligonucleotide or single-stranded RNAi agent. In some embodiments, a targeting moiety is conjugated to a PNPLA3 oligonucleotide or single-stranded RNAi agent. In some embodiments, a PNPLA3 oligonucleotide or single-stranded RNAi agent is conjugated to both a lipid and a targeting moiety. As described in here, in some embodiments, a PNPLA3 oligonucleotide or single-stranded RNAi agent is a provided oligonucleotide. Thus, in some embodiments, a provided oligonucleotide composition further comprises, besides a lipid and oligonucleotides, a target elements. Various targeting moieties can be used in accordance with the present disclosure, e.g., lipids, antibodies, peptides, carbohydrates, etc.

Targeting moieties can be incorporated into provided technologies through many types of methods in accordance with the present disclosure. In some embodiments, targeting moieties are physically mixed with provided oligonucleotides to form provided compositions. In some embodiments, targeting moieties are chemically conjugated with oligonucleotides.

In some embodiments, provided compositions comprise two or more targeting moieties. In some embodiments, provided oligonucleotides comprise two or more conjugated targeting moieties. In some embodiments, the two or more conjugated targeting moieties are the same. In some embodiments, the two or more conjugated targeting moieties are different. In some embodiments, provided oligonucleotides comprise no more than one target component. In some embodiments, oligonucleotides of a provided composition comprise different types of conjugated targeting moieties. In some embodiments, oligonucleotides of a provided composition comprise the same type of targeting moieties.

In some embodiments, provided compositions comprise two or more targeting moieties. In some embodiments, provided oligonucleotides capable of directing single-stranded RNA interference comprise two or more conjugated targeting moieties. In some embodiments, the two or more conjugated targeting moieties are the same. In some embodiments, the two or more conjugated targeting moieties are different. In some embodiments, provided oligonucleotides capable of directing single-stranded RNA interference comprise no more than one target component. In some embodiments, oligonucleotides of a provided composition comprise different types of conjugated targeting moieties. In some embodiments, oligonucleotides of a provided composition comprise the same type of targeting moieties.

Targeting moieties can be conjugated to oligonucleotides optionally through linkers. Various types of linkers in the art can be utilized in accordance of the present disclosure. In some embodiments, a linker comprise a phosphate group, which can, for example, be used for conjugating targeting moieties through chemistry similar to those employed in oligonucleotide synthesis. In some embodiments, a linker comprises an amide, ester, or ether group. In some embodiments, a linker has the structure of -L-. Targeting moieties can be conjugated through either the same or different linkers compared to lipids.

Targeting moieties, optionally through linkers, can be conjugated to oligonucleotides at various suitable locations. In some embodiments, targeting moieties are conjugated through the 5'-OH group. In some embodiments, targeting moieties are conjugated through the 3'-OH group. In some embodiments, targeting moieties are conjugated through one or more sugar moieties. In some embodiments, targeting moieties are conjugated through one or more bases. In some embodiments, targeting moieties are incorporated through one or more internucleotidic linkages. In some embodiments, a PNPLA3 oligonucleotide may contain multiple conjugated targeting moieties which are independently conjugated through its 5'-OH, 3'-OH, sugar moieties, base moieties and/or internucleotidic linkages. Targeting moieties and lipids can be conjugated either at the same, neighboring and/or separated locations. In some embodiments, a target component is conjugated at one end of a PNPLA3 oligonucleotide, and a lipid is conjugated at the other end.

In some embodiments, a provided composition further comprises a targeting component or moiety. A targeting component can be either incorporated into (targeting moiety) or not incorporated into a PNPLA3 oligonucleotide. In some embodiments, a targeting component is a lipid. In some embodiments, a targeting component is a carbohydrate or a bicyclic ketal. In some embodiments, a targeting component is —$R^{LD}$ as described in the present disclosure. In some embodiments, a targeting component is —$R^{CD}$ as described in the present disclosure.

Targeting components can be incorporated into provided technologies through many types of methods in accordance with the present disclosure, for example, those described for lipids and carbohydrates. In some embodiments, targeting components are physically mixed with provided oligonucleotides to form provided compositions. In some embodiments, targeting components are chemically conjugated with oligonucleotide moieties.

In some embodiments, provided compositions comprise two or more targeting components. In some embodiments, provided oligonucleotides comprise two or more conjugated targeting components. In some embodiments, the two or more conjugated targeting components are the same. In some embodiments, the two or more conjugated targeting components are different. In some embodiments, provided oligonucleotides comprise no more than one targeting component. In some embodiments, oligonucleotides of a provided composition comprise different types of conjugated targeting components. In some embodiments, oligonucleotides of a provided composition comprise the same type of targeting components.

Targeting components can be conjugated to oligonucleotides optionally through linkers, for example, as described for lipids and carbohydrates. Various types of linkers in the art can be utilized in accordance of the present disclosure. In some embodiments, a linker comprise a phosphate group, which can, for example, be used for conjugating targeting components through chemistry similar to those employed in oligonucleotide synthesis. In some embodiments, a linker comprises an amide, ester, or ether group. In some embodiments, a linker has the structure of -L-. Targeting components can be conjugated through either the same or different linkers compared to lipids.

Targeting components, optionally through linkers, can be conjugated to oligonucleotides at various suitable locations. In some embodiments, targeting components are conjugated through the 5'-OH group. In some embodiments, targeting components are conjugated through the 3'-OH group. In some embodiments, targeting components are conjugated through one or more sugar moieties. In some embodiments, targeting components are conjugated through one or more bases. In some embodiments, targeting components are incorporated through one or more internucleotidic linkages. In some embodiments, a PNPLA3 oligonucleotide may contain multiple conjugated targeting components which are independently conjugated through its 5'-OH, 3'-OH, sugar moieties, base moieties and/or internucleotidic linkages. Targeting components and lipids can be conjugated either at the same, neighboring and/or separated locations. In some embodiments, a targeting component is conjugated at one end of a PNPLA3 oligonucleotide, and a lipid is conjugated at the other end.

In some embodiments, a targeting component interacts with a protein on the surface of targeted cells. In some embodiments, such interaction facilitates internalization into targeted cells. In some embodiments, a targeting component comprises a sugar moiety. In some embodiments, a targeting component comprises a polypeptide moiety. In some embodiments, a targeting component comprises an antibody. In some embodiments, a targeting component is an antibody. In some embodiments, a targeting component comprises an inhibitor. In some embodiments, a targeting component is a moiety from a small molecule inhibitor. In some embodiments, an inhibitor is an inhibitor of a protein on the surface of targeted cells. In some embodiments, an inhibitor is a carbonic anhydrase inhibitor. In some embodiments, an inhibitor is a carbonic anhydrase inhibitor expressed on the surface of target cells. In some embodiments, a carbonic anhydrase is I, II, III, IV, V, VI, VII, VIII, IX, X, XI, XII, XIII, XIV, XV or XVI. In some embodiments, a carbonic anhydrase is membrane bound. In some embodiments, a carbonic anhydrase is IV, IX, XII or XIV. In some embodiments, an inhibitor is for IV, IX, XII and/or XIV. In some embodiments, an inhibitor is a carbonic anhydrase III inhibitor. In some embodiments, an inhibitor is a carbonic anhydrase IV inhibitor. In some embodiments, an inhibitor is a carbonic anhydrase IX inhibitor. In some embodiments, an inhibitor is a carbonic anhydrase XII inhibitor. In some embodiments, an inhibitor is a carbonic anhydrase XIV inhibitor. In some embodiments, an inhibitor comprises or is a sulfonamide (e.g., those described in Supuran, C T. *Nature Rev Drug Discover* 2008, 7, 168-181, which sulfonamides are incorporated herein by reference). In some embodiments, an inhibitor is a sulfonamide. In some embodiments, targeted cells are muscle cells.

In some embodiments, a targeting component is $R^{TD}$, wherein $R^{TD}$ is $R^{LD}$ or $R^{CD}$ as described in the present disclosure.

In some embodiments, a targeting component is $R^{LD}$ as defined and described in the present disclosure. In some embodiments, the present disclosure provides oligonucleotides comprising $R^{LD}$. In some embodiments, the present disclosure provides oligonucleotide compositions comprising oligonucleotides comprising $R^{LD}$. In some embodiments, the present disclosure provides oligonucleotide compositions comprising a first plurality of oligonucleotides comprising $R^{LD}$. In some embodiments, the present disclosure provides chirally controlled oligonucleotide compositions of oligonucleotides comprising $R^{LD}$.

In some embodiments, a targeting component is $R^{CD}$ as defined and described in the present disclosure. In some embodiments, the present disclosure provides oligonucleotides comprising $R^{CD}$. In some embodiments, the present disclosure provides oligonucleotide compositions comprising oligonucleotides comprising $R^{CD}$. In some embodiments, the present disclosure provides oligonucleotide compositions comprising a first plurality of oligonucleotides comprising $R^{CD}$. In some embodiments, the present disclosure provides chirally controlled oligonucleotide compositions of oligonucleotides comprising $R^{CD}$.

In some embodiments, $R^{TD}$ comprises or is
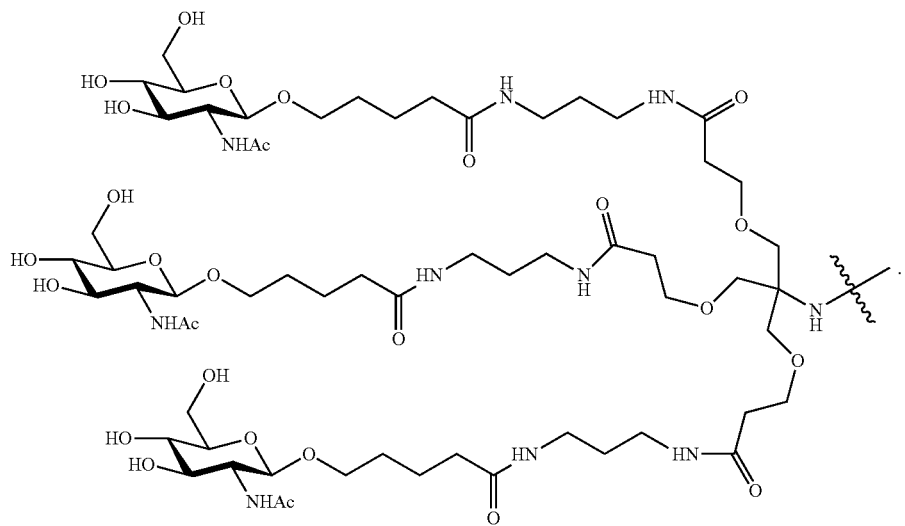
In some embodiments, $R^{TD}$ comprises or is
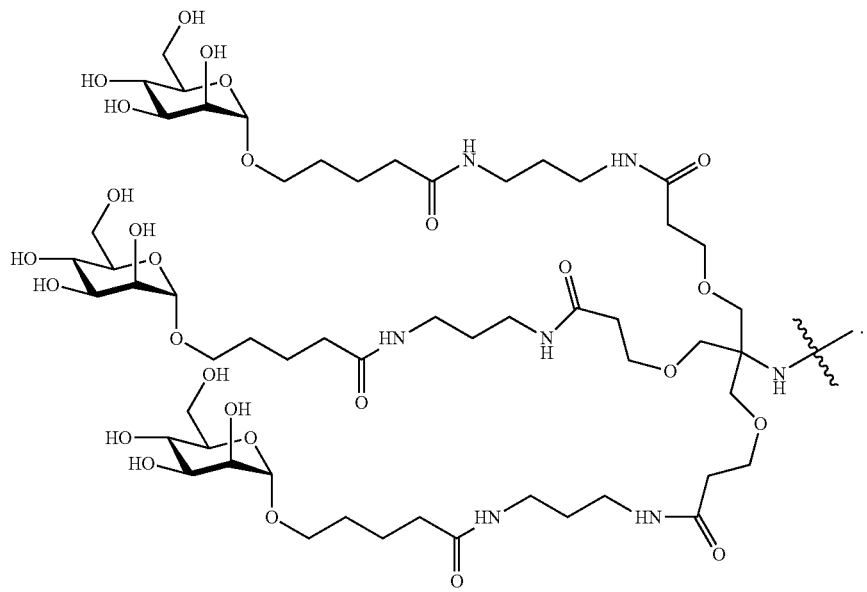
In some embodiments, $R^{TD}$ comprises or is
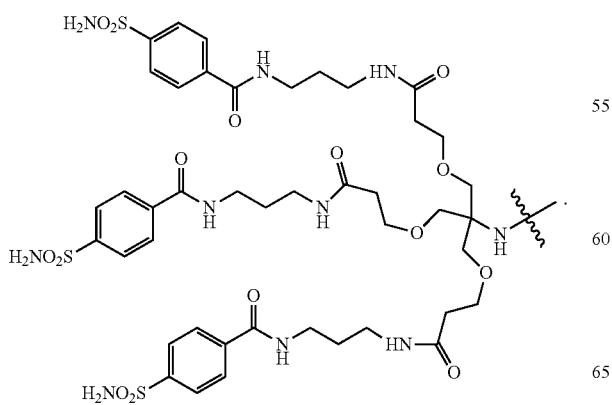

In some embodiments, $R^{TD}$ comprises or is
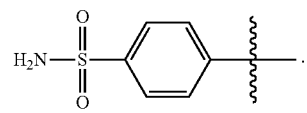
In some embodiments, $R^{TD}$ comprises or is
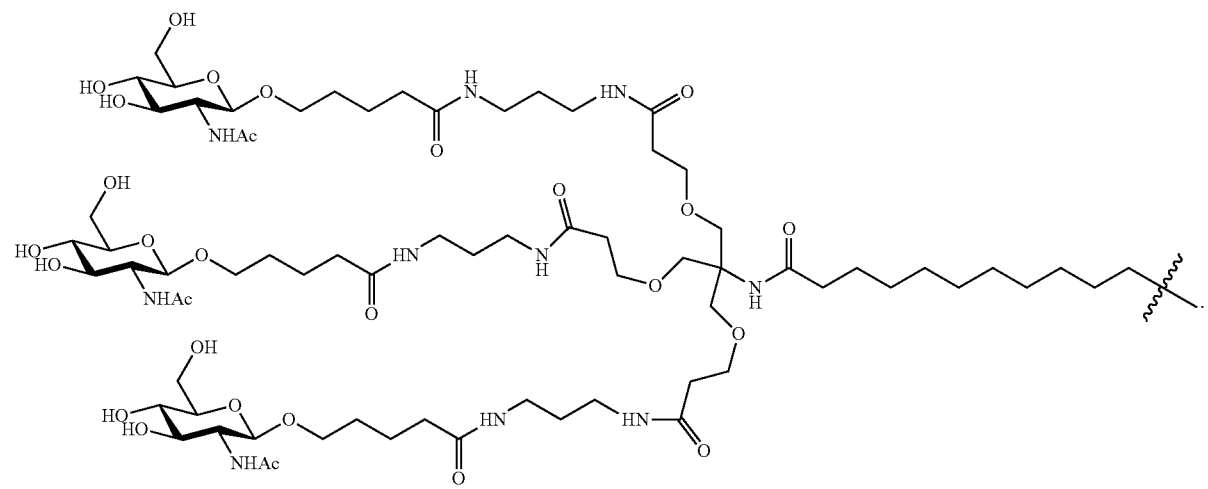
In some embodiments, $R^{TD}$ comprises or is
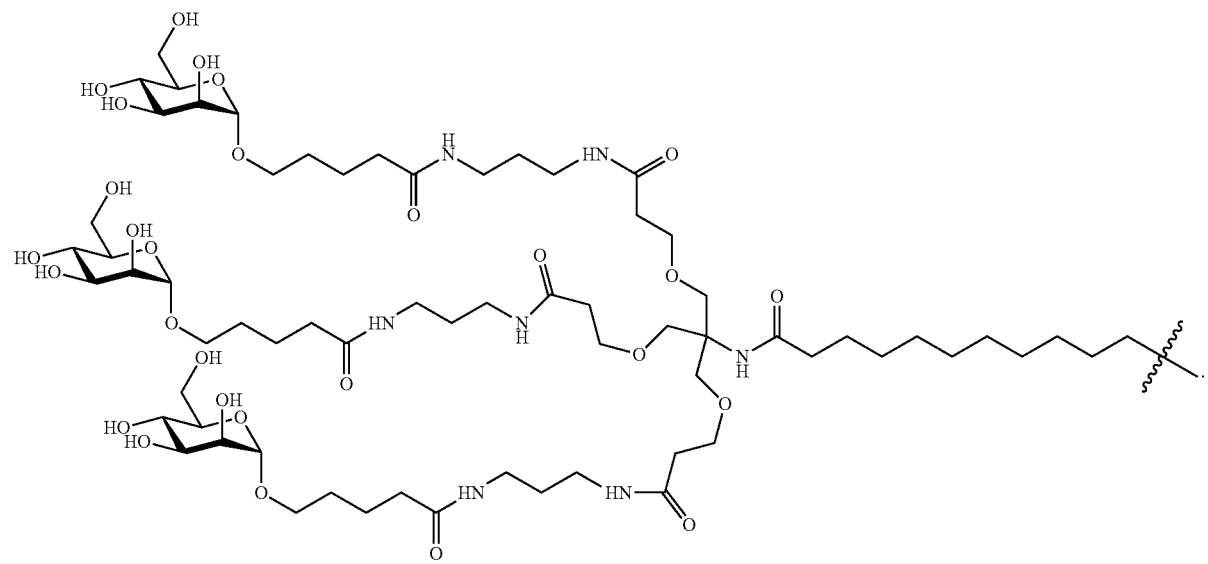

In some embodiments, $R^{1D}$ comprises or is
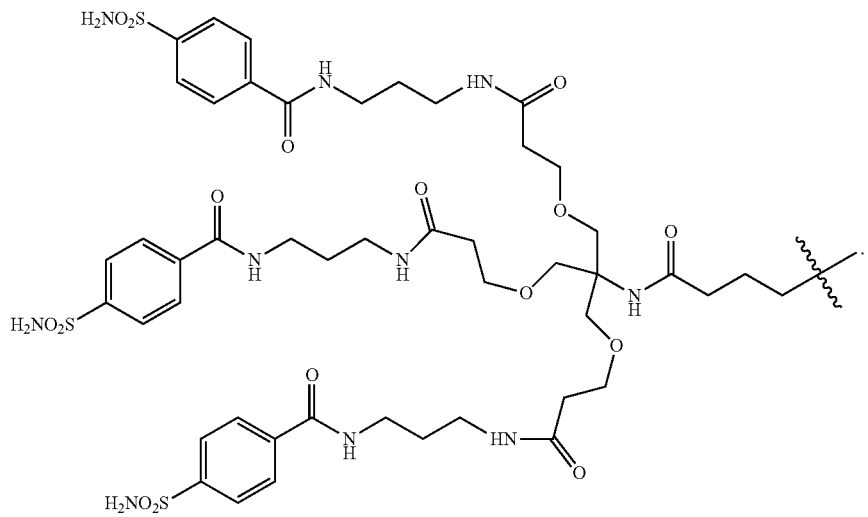 [SMILES: *CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, comprises or is
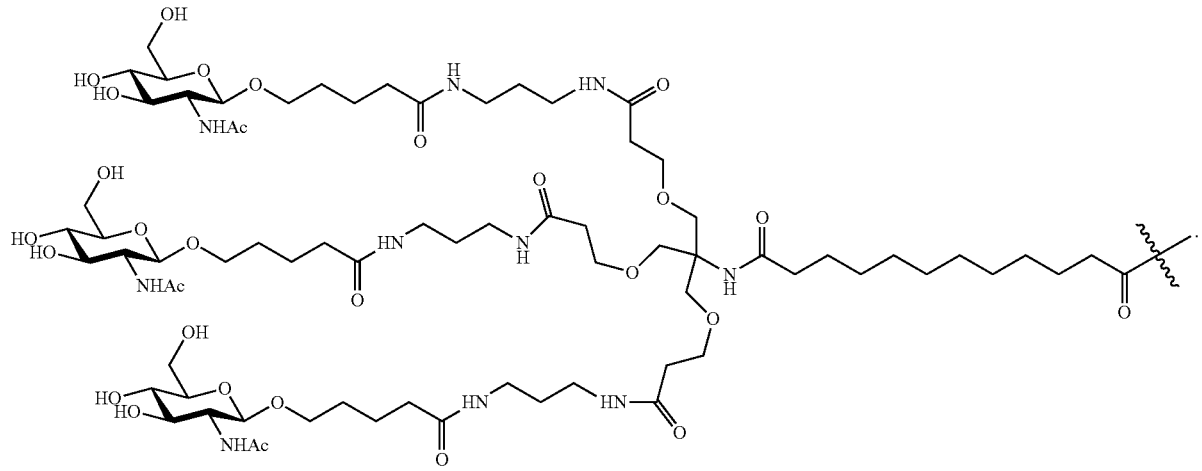
In some embodiments, $R^{TD}$ comprises or is
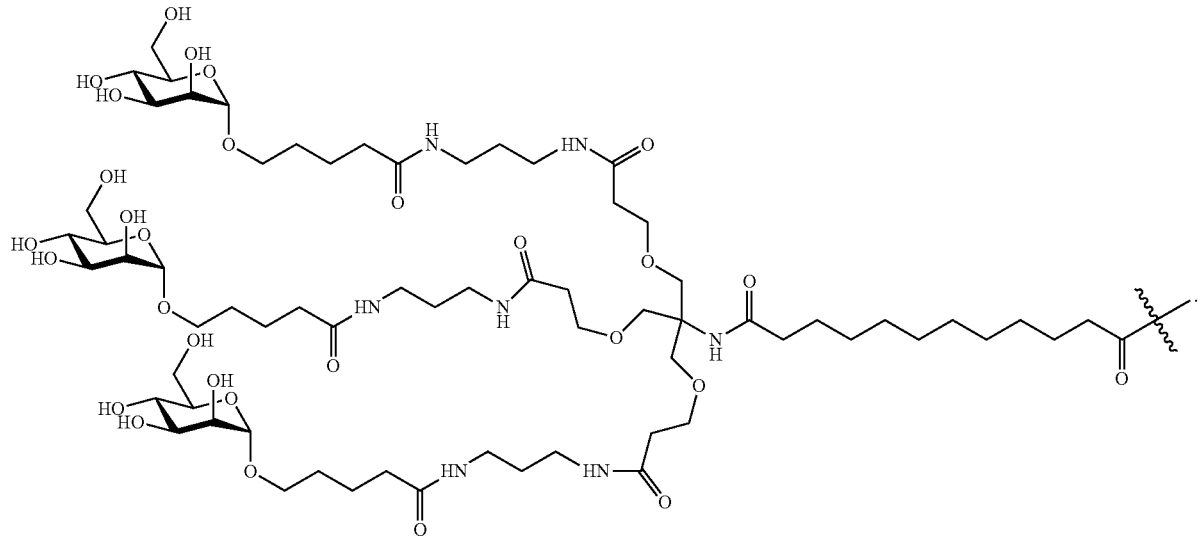

In some embodiments, $R^{TD}$ comprises or is
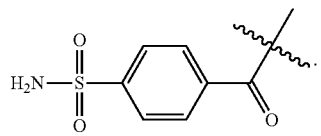 [SMILES: *C(=O)c1ccc(S(N)(=O)=O)cc1]
In some embodiments, $R^{TD}$ comprises or is
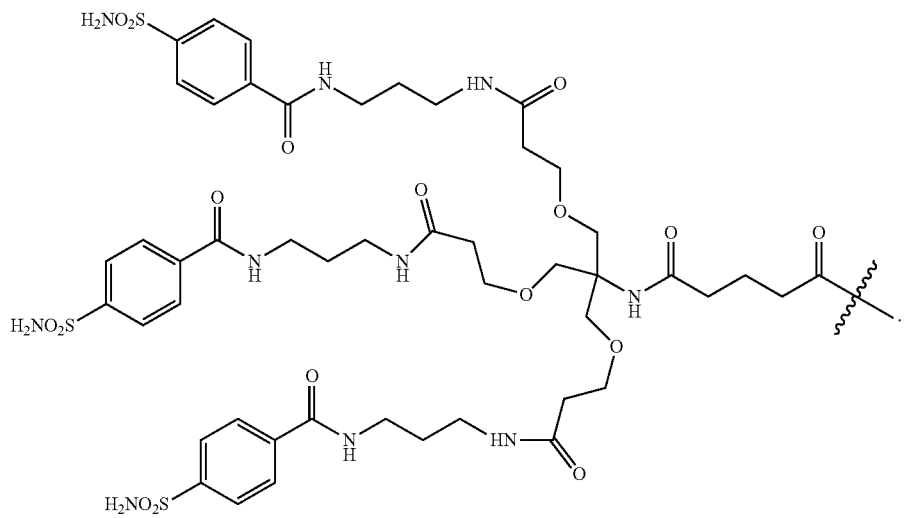 [SMILES: *C(=O)CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, $R^{TD}$ comprises or is
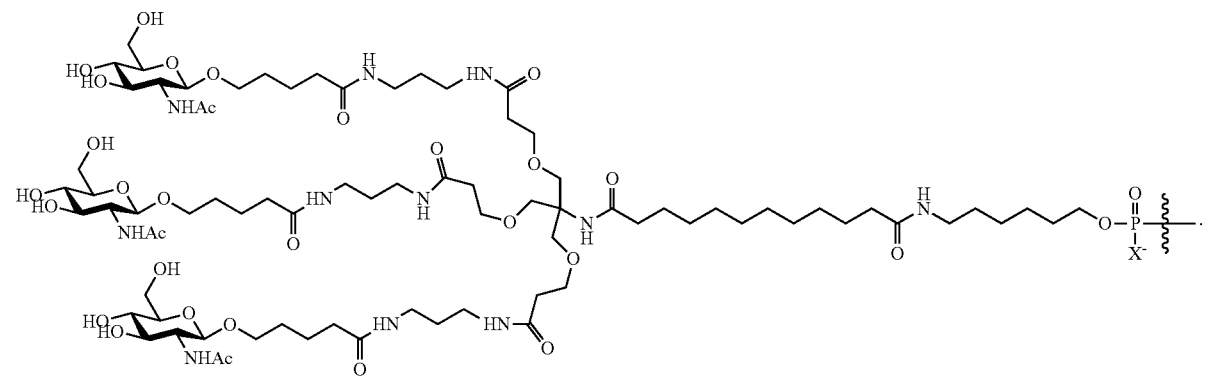
X = O or S In some embodiments, comprises or is

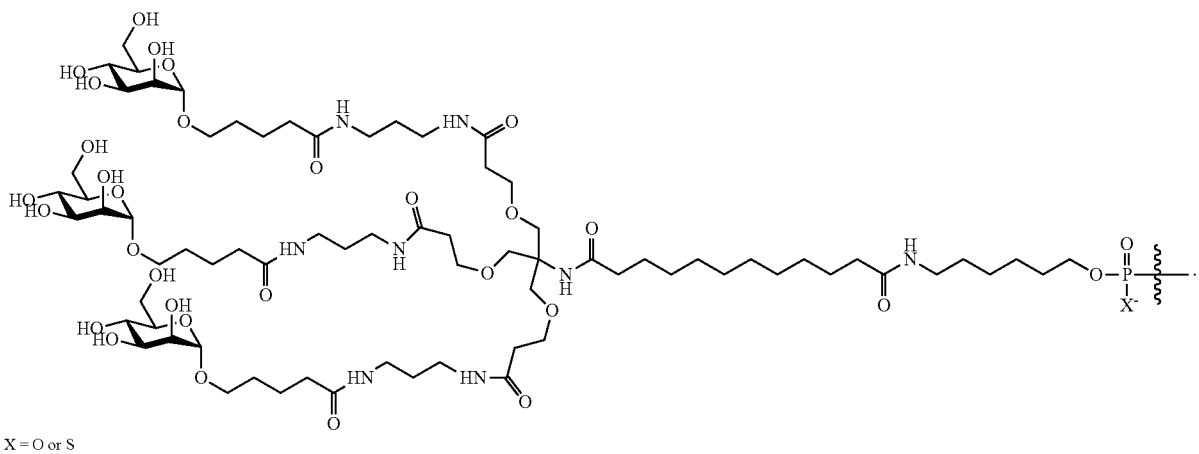

X = O or S

In some embodiments, $R^{TD}$ comprises or is

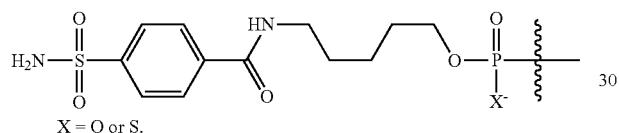

X = O or S.

In some embodiments, $R^{TD}$ comprises or is

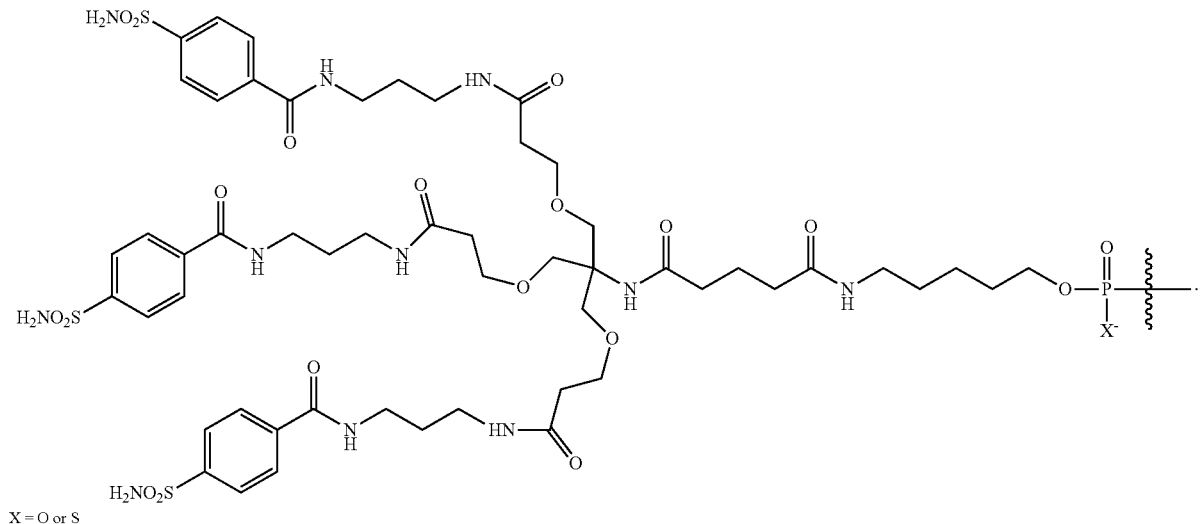

X = O or S

In some embodiments, $R^{TD}$ is a targeting component that comprises or is a lipid moiety. In some embodiments, X is O. In some embodiments, X is S.

In some embodiments, the present disclosure provides technologies (e.g., reagents, methods, etc.) for conjugating various moieties to oligonucleotide moieties. In some embodiments, the present disclosure provides technologies for conjugating targeting component to oligonucleotide moieties. In some embodiments, the present disclosure provides acids comprising targeting components for conjugation, e.g., $R^{LD}$—COOH. In some embodiments, the present disclosure provides linkers for conjugation, e.g., $L^M$. A person having ordinary skill in the art understands that many known and widely practiced technologies can be utilized for conjugation with oligonucleotide moieties in accordance with the present disclosure. In some embodiments, a provided acid is

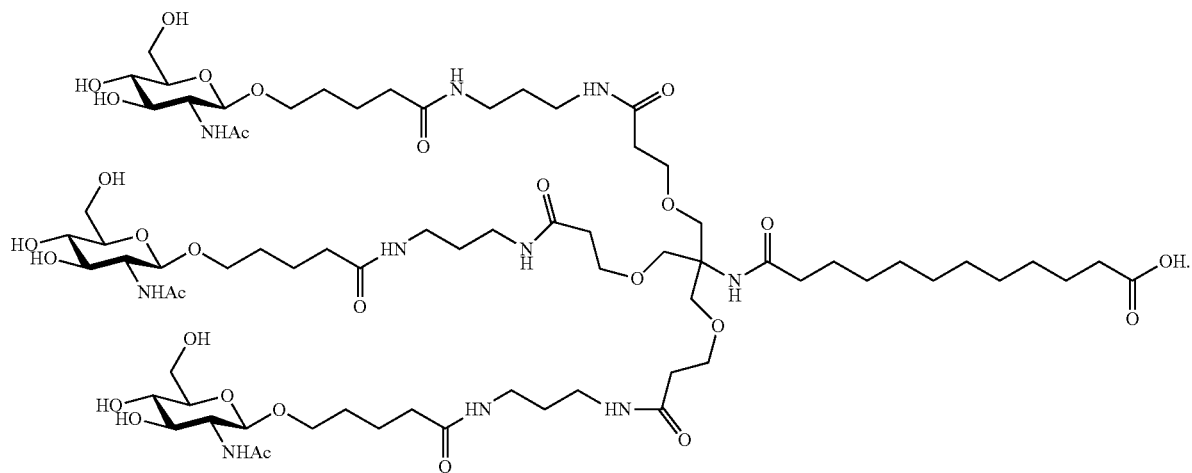
In some embodiments, a provided acid is
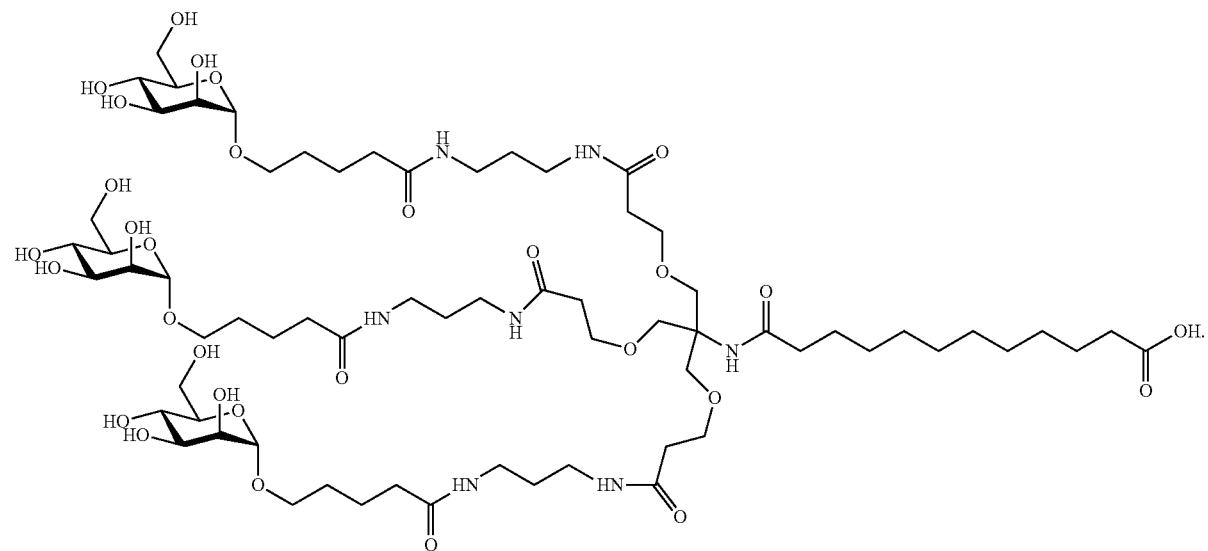
In some embodiments, a provided acid is
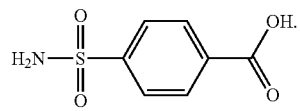 [SMILES: NS(=O)(=O)c1ccc(C(=O)O)cc1]

In some embodiments, a provided acid is

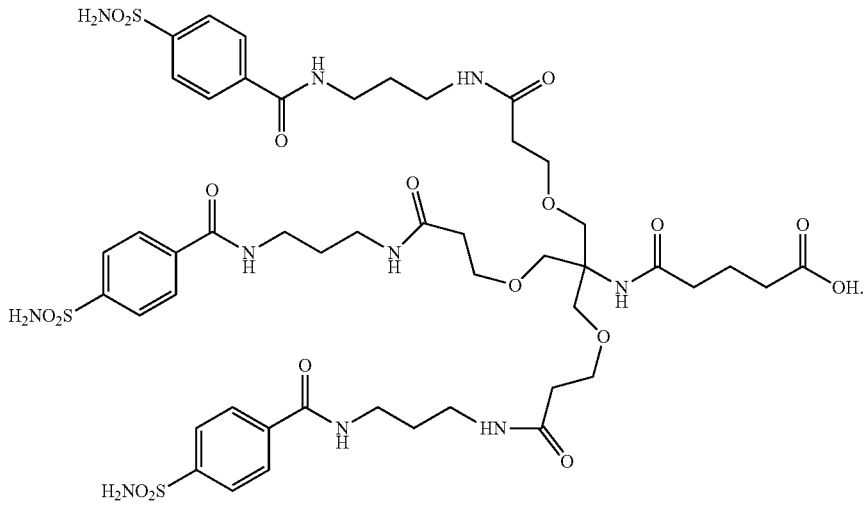 [SMILES: NS(=O)(=O)c1ccc(C(=O)NCCCNC(=O)CCOCC(COCCC(=O)NCCCNC(=O)c2ccc(S(N)(=O)=O)cc2)(COCCC(=O)NCCCNC(=O)c2ccc(S(N)(=O)=O)cc2)NC(=O)CCCC(=O)O)cc1]

In some embodiments, a provided acid is a fatty acid, which can provide a lipid moiety as a targeting component. In some embodiments, the present disclosure provides methods and reagents for preparing such acids.

In some embodiments, a targeting moiety is a lipid moiety, e.g., moiety of cholesterol or derivatives thereof ($R^{TD}$—H is an optionally substituted cholesterol or derivatives thereof).

In some embodiments, a targeting moiety is a peptide. In some embodiments, a targeting moiety is protein or a domain thereof. In some embodiments, a targeting moiety is antibody or a portion thereof.

Optional Additional Chemical Moieties Conjugated to a PNPLA3 Oligonucleotide: A Lipid Moiety In some embodiments, provided oligonucleotides or oligonucleotide compositions further comprise one or more lipids or lipid moieties. In some embodiments, a lipid is a lipid moiety. In some embodiments, a lipid moiety is or comprises a lipid which is conjugated directly or indirectly to a PNPLA3 oligonucleotide. In some embodiments, lipid conjugation can achieve one or more unexpected, greatly improved properties (e.g., activities, toxicities, distribution, pharmacokinetics, etc.). As appreciated by a person having ordinary skill in the art, various carbohydrate moieties are described in the literature and can be utilized in accordance with the present disclosure.

Lipid moieties can be incorporated into oligonucleotides at various locations, for example, sugar units, internucleotidic linkage units, nucleobase units, etc., optionally through one or more bivalent or multivalent linkers (which can be used to connect two or more carbohydrate moieties to oligonucleotides). In some embodiments, the present disclosure provides technologies for lipid incorporation into oligonucleotides. In some embodiments, the present disclosure provides technologies for incorporating lipid moieties, optionally through one or more linkers, at nucleobase units, as an alternative and/or addition to incorporation at internucleotidic linkages and/or sugar units, thereby providing enormous flexibility and/or improved properties and/or activities. In some embodiments, a provided oligonucleotide comprises at least one lipid moiety, optionally through a linker, incorporated into the oligonucleotide at a nucleobase unit.

In some embodiments, provided oligonucleotides have the structure of:

$$A^c\text{-}[\text{-}L^M\text{-}(R^D)_a]_b, \text{ or } [(A^c)_a\text{-}L^M]_b\text{-}R^D,$$

wherein:
$A^c$ is a PNPLA3 oligonucleotide chain ($[H]_b$-$A^c$ is a PNPLA3 oligonucleotide);
a is 1-1000;
b is 1-1000;
each $L^M$ is independently a linker; and
each $R^D$ is independently $R^{LD}$ or $R^{CD}$,
$R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy;
$R^{LD}$ is an optionally substituted, linear or branched group selected from a $C_{1-100}$ aliphatic group wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP (NR')O—, —OP(R')O—, or —OP(OR')[B(R')$_3$]O—; and one or more carbon atoms are optionally and independently replaced with Cy;

$L^M$ is a covalent bond, or a bivalent or multivalent, optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$;

$Cy^L$ is an optionally substituted tetravalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon;

each $R^1$ is independently —R, —C(O)R, —C(O)OR, or —S(O)$_2$R; and each R is independently —H, or an optionally substituted group selected from $C_{1-30}$ aliphatic, $C_{1-30}$ heteroaliphatic having 1-10 heteroatoms independently selected from oxygen, nitrogen, sulfur, phosphorus and silicon, $C_{6-30}$ aryl, $C_{6-30}$ arylaliphatic, $C_{6-30}$ arylheteroaliphatic having 1-10 heteroatoms independently selected from oxygen, nitrogen, sulfur, phosphorus and silicon, 5-30 membered heteroaryl having 1-10 heteroatoms independently selected from oxygen, nitrogen, sulfur, phosphorus and silicon, and 3-30 membered heterocyclyl having 1-10 heteroatoms independently selected from oxygen, nitrogen, sulfur, phosphorus and silicon, or two R groups are optionally and independently taken together to form a covalent bond, or:

two or more R groups on the same atom are optionally and independently taken together with the atom to form an optionally substituted, 3-30 membered monocyclic, bicyclic or polycyclic ring having, in addition to the atom, 0-10 heteroatoms independently selected from oxygen, nitrogen, sulfur, phosphorus and silicon; or two or more R groups on two or more atoms are optionally and independently taken together with their intervening atoms to form an optionally substituted, 3-30 membered monocyclic, bicyclic or polycyclic ring having, in addition to the intervening atoms, 0-10 heteroatoms independently selected from oxygen, nitrogen, sulfur, phosphorus and silicon.

In some embodiments, $R^{CD}$ is a carbohydrate moiety or a bicyclic ketal. In some embodiments, $R^{CD}$ comprises at least one monosaccharide, disaccharide, or polysaccharide units. In some embodiments, $R^{CD}$ comprises at least one GalNAc moiety or a derivative thereof.

In some embodiments, $R^{LD}$ is a lipid moiety. In some embodiments, $R^{LD}$ comprises one or more optionally substituted $C_{6-20}$ aliphatic chain. In some embodiments, $R^{LD}$ comprises one or more unsubstituted $C_{6-20}$ aliphatic chain.

In some embodiments, at least one $L^M$ is directly bound to a sugar unit of a provided oligonucleotide. In some embodiments, a $L^M$ directly binds to a sugar unit incorporates a lipid moiety into a PNPLA3 oligonucleotide. In some embodiments, a $L^M$ directly binds to a sugar unit incorporates a carbohydrate moiety into a PNPLA3 oligonucleotide. In some embodiments, a $L^M$ directly binds to a sugar unit incorporates a $R^{LD}$ group into a PNPLA3 oligonucleotide. In some embodiments, a $L^M$ directly binds to a sugar unit incorporates a $R^{CD}$ group into a PNPLA3 oligonucleotide.

In some embodiments, at least one $L^M$ is directly bound to an internucleotidic linkage unit of a provided oligonucleotide. In some embodiments, a $L^M$ directly binds to an internucleotidic linkage unit incorporates a lipid moiety into a PNPLA3 oligonucleotide. In some embodiments, a $L^M$ directly binds to an internucleotidic linkage unit incorporates a carbohydrate moiety into a PNPLA3 oligonucleotide. In some embodiments, a $L^M$ directly binds to an internucleotidic linkage unit incorporates a $R^{LD}$ group into a PNPLA3 oligonucleotide. In some embodiments, a $L^M$ directly binds to an internucleotidic linkage unit incorporates a $R^{CD}$ group into a PNPLA3 oligonucleotide.

In some embodiments, at least one $L^M$ is directly bound to a nucleobase unit of a provided oligonucleotide. In some embodiments, a $L^M$ directly binds to a nucleobase unit incorporates a lipid moiety into a PNPLA3 oligonucleotide. In some embodiments, a $L^M$ directly binds to a nucleobase unit incorporates a carbohydrate moiety into a PNPLA3 oligonucleotide. In some embodiments, a $L^M$ directly binds to a nucleobase unit incorporates a $R^{LD}$ group into a PNPLA3 oligonucleotide. In some embodiments, a $L^M$ directly binds to a nucleobase unit incorporates a $R^{CD}$ group into a PNPLA3 oligonucleotide.

In some embodiments, [H]$_b$-A$^c$ is a PNPLA3 oligonucleotide described in the present disclosure.

In some embodiments, incorporation of a lipid into a provided oligonucleotide improves distribution and/or pharmacokinetics. In some embodiments, incorporation of a lipid into a provided oligonucleotide improves one or more measurement of pharmacokinetics selected from: $C_{max}$, peak plasma concentration of a drug after administration; $t_{max}$, time to reach $C_{max}$; $C_{min}$, lowest (trough) concentration that a drug reaches before the next dose is administered; elimination half-life, the time required for the concentration of the drug to reach half of its original value; elimination rate constant, rate at which a drug is removed from the body; area under the curve, integral of the concentration-time curve (after a single dose or in steady state); and clearance, volume of plasma cleared of the drug per unit time. Without being bound to any particular theory, this disclosure notes that optimization of a pharmacokinetic characteristic such as half-life can be distinguished from maximization. In some embodiments, in general, it may be desirable for a particular drug to have a half-life sufficient to allow performance of its desired function, but short enough to minimize off-target effects and other toxicity. In some embodiments, an optimized half-life is long enough to allow activity while minimizing toxicity; a prolonged or maximized half-life may be undesirable.

In some embodiments, provided oligonucleotide compositions further comprise one or more lipids. In some embodiments, provided oligonucleotide compositions further comprise one or more fatty acids. In some embodiments, the lipids can be incorporated into provided oligonucleotides in the compositions. In some embodiments, two or more same or different lipids can be incorporated into one oligonucleotide, through either the same or differently chemistry and/or locations.

Many lipids can be utilized in provided technologies in accordance with the present disclosure. In some embodiments, a lipid comprises an $R^{LD}$ group. In some embodiments, $R^{LD}$ is an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting of carbon and hydrogen atoms. In some embodiments, -Cy- is an optionally substituted bivalent group selected from a $C_{3-20}$ cycloaliphatic ring, a $C_{6-20}$ aryl ring, a 5-20 membered heteroaryl ring having 1-10 heteroatoms independently selected from oxygen, nitrogen, sulfur, phosphorus and silicon, and a 3-20 membered heterocyclyl ring having 1-10 heteroatoms independently selected from oxygen, nitrogen, sulfur, phosphorus, boron and silicon.

In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

In some embodiments, $R^{LD}$ is an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, and -Cy-. In some embodiments, $R^{LD}$ is a hydrocarbon group consisting carbon and hydrogen atoms.

The aliphatic group of $R^{LD}$ can be a variety of suitable length. In some embodiments, it is $C_{10}$-$C_{80}$. In some embodiments, it is $C_{10}$-$C_{75}$. In some embodiments, it is $C_{10}$-$C_{70}$. In some embodiments, it is $C_{10}$-$C_{65}$. In some embodiments, it is $C_{10}$-$C_{60}$. In some embodiments, it is $C_{10\text{-}050}$. In some embodiments, it is $C_{10}$-$C_{40}$. In some embodiments, it is $C_{10}$-$C_{35}$. In some embodiments, it is $C_{10}$-$C_{30}$. In some embodiments, it is $C_{10}$-$C_{25}$. In some embodiments, it is $C_{10}$-$C_{24}$. In some embodiments, it is $C_{10}$-$C_{23}$. In some embodiments, it is $C_{10}$-$C_{22}$. In some embodiments, it is $C_{10}$-$C_{21}$. In some embodiments, it is $C_{12}$-$C_{22}$. In some embodiments, it is $C_{13}$-$C_{22}$. In some embodiments, it is $C_{14}$-$C_{22}$. In some embodiments, it is $C_{15}$-$C_{22}$. In some embodiments, it is $C_{16}$-$C_{22}$. In some embodiments, it is $C_{17}$-$C_{22}$. In some embodiments, it is $C_{18}$-$C_{22}$. In some embodiments, it is $C_{10}$-$C_{20}$. In some embodiments, the lower end of the range is C10, $C_{11}$, $C_{12}$, $C_{13}$, $C_{14}$, $C_{15}$, $C_{16}$, $C_{17}$, or $C_{18}$. In some embodiments, the higher end of the range is $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{35}$, $C_{40}$, $C_{45}$, $C_{50}$, $C_{55}$, or $C_{60}$. In some embodiments, it is $C_{10}$. In some embodiments, it is $C_{11}$. In some embodiments, it is $C_{12}$. In some embodiments, it is $C_{13}$. In some embodiments, it is $C_{14}$. In some embodiments, it is $C_{15}$. In some embodiments, it is $C_{16}$. In some embodiments, it is $C_{17}$. In some embodiments, it is $C_{18}$. In some embodiments, it is $C_{19}$. In some embodiments, it is $C_{20}$. In some embodiments, it is $C_{21}$. In some embodiments, it is $C_{22}$. In some embodiments, it is $C_{23}$. In some embodiments, it is $C_{24}$. In some embodiments, it is $C_{25}$. In some embodiments, it is $C_{30}$. In some embodiments, it is $C_{35}$. In some embodiments, it is $C_{40}$. In some embodiments, it is $C_{45}$. In some embodiments, it is $C_{50}$. In some embodiments, it is $C_{55}$. In some embodiments, it is $C_{60}$.

In some embodiments, a lipid comprises no more than one $R^{LD}$ group. In some embodiments, a lipid comprises two or more $R^{LD}$ groups.

In some embodiments, a lipid is conjugated to a biologically active agent, optionally through a linker, as a moiety comprising an $R^{LD}$ group. In some embodiments, a lipid is conjugated to a biologically active agent, optionally through a linker, as a moiety comprising no more than one $R^{LD}$ group. In some embodiments, a lipid is conjugated to a biologically active agent, optionally through a linker, as an $R^{LD}$ group. In some embodiments, a lipid is conjugated to a biologically active agent, optionally through a linker, as a moiety comprising two or more $R^{LD}$ groups.

In some embodiments, $R^{LD}$ is an optionally substituted, $C_{10}$-$C_{40}$ saturated or partially unsaturated, aliphatic chain. In some embodiments, a lipid comprises an optionally substituted $C_{10}$-$C_{40}$ saturated or partially unsaturated, aliphatic chain.

In some embodiments, $R^{LD}$ is an optionally substituted $C_{10}$-$C_{40}$ linear, saturated or partially unsaturated, aliphatic chain. In some embodiments, a lipid comprises an optionally substituted $C_{10}$-$C_{40}$ linear, saturated or partially unsaturated, aliphatic chain.

In some embodiments, $R^{LD}$ is a $C_{10}$-$C_{40}$ linear, saturated or partially unsaturated, aliphatic chain, optionally substituted with one or more $C_{1-4}$ aliphatic groups. In some embodiments, a lipid comprises a $C_{10}$-$C_{40}$ linear, saturated or partially unsaturated, aliphatic chain, optionally substituted with one or more $C_{1-4}$ aliphatic groups. In some embodiments, $R^{LD}$ is a $C_{10}$-$C_{40}$ linear, saturated or partially unsaturated, aliphatic chain, optionally substituted with one or more $C_{1-2}$ aliphatic groups. In some embodiments, a lipid comprises a $C_{10}$-$C_{40}$ linear, saturated or partially unsaturated, aliphatic chain, optionally substituted with one or more $C_{1-2}$ aliphatic groups. In some embodiments, $R^{LD}$ is a $C_{10}$-$C_{40}$ linear, saturated or partially unsaturated, aliphatic chain, optionally substituted with one or more methyl groups. In some embodiments, a lipid comprises a $C_{10}$-$C_{40}$ linear, saturated or partially unsaturated, aliphatic chain, optionally substituted with one or more methyl groups.

In some embodiments, $R^{LD}$ is an unsubstituted $C_{10}$-$C_{40}$ linear, saturated or partially unsaturated, aliphatic chain. In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{40}$ linear, saturated or partially unsaturated, aliphatic chain. In some embodiments, a lipid comprises two or more optionally substituted $C_{10}$-$C_{40}$ linear, saturated or partially unsaturated, aliphatic chain.

In some embodiments, $R^{LD}$ is an optionally substituted, $C_{10}$-$C_{60}$ saturated or partially unsaturated, aliphatic chain. In some embodiments, a lipid comprises an optionally substituted $C_{10}$-$C_{60}$ saturated or partially unsaturated, aliphatic chain.

In some embodiments, $R^{LD}$ is an optionally substituted $C_{10}$-$C_{60}$ linear, saturated or partially unsaturated, aliphatic chain. In some embodiments, a lipid comprises an optionally substituted $C_{10}$-$C_{60}$ linear, saturated or partially unsaturated, aliphatic chain.

In some embodiments, $R^{LD}$ is a $C_{10}$-$C_{60}$ linear, saturated or partially unsaturated, aliphatic chain, optionally substituted with one or more $C_{1-4}$ aliphatic groups. In some embodiments, a lipid comprises a $C_{10}$-$C_{60}$ linear, saturated or partially unsaturated, aliphatic chain, optionally substituted with one or more $C_{1-4}$ aliphatic groups. In some embodiments, $R^{LD}$ is a $C_{10}$-$C_{60}$ linear, saturated or partially unsaturated, aliphatic chain, optionally substituted with one or more $C_{1-2}$ aliphatic groups. In some embodiments, a lipid comprises a $C_{10}$-$C_{60}$ linear, saturated or partially unsaturated, aliphatic chain, optionally substituted with one or more $C_{1-2}$ aliphatic groups. In some embodiments, $R^{LD}$ is a $C_{10}$-$C_{60}$ linear, saturated or partially unsaturated, aliphatic chain, optionally substituted with one or more methyl groups. In some embodiments, a lipid comprises a $C_{10}$-$C_{60}$ linear, saturated or partially unsaturated, aliphatic chain, optionally substituted with one or more methyl groups.

In some embodiments, $R^{LD}$ is an unsubstituted $C_{10}$-$C_{60}$ linear, saturated or partially unsaturated, aliphatic chain. In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain. In some embodiments, a lipid comprises two or more optionally substituted $C_{10}$-$C_{60}$ linear, saturated or partially unsaturated, aliphatic chain.

In some embodiments, $R^{LD}$ is an optionally substituted, $C_{10}$-$C_{80}$ saturated or partially unsaturated, aliphatic chain. In some embodiments, a lipid comprises an optionally substituted $C_{10}$-$C_{80}$ saturated or partially unsaturated, aliphatic chain.

In some embodiments, $R^{LD}$ is an optionally substituted $C_{10}$-$C_{80}$ linear, saturated or partially unsaturated, aliphatic chain. In some embodiments, a lipid comprises an optionally substituted $C_{10}$-$C_{80}$ linear, saturated or partially unsaturated, aliphatic chain.

In some embodiments, $R^{LD}$ is a $C_{10}$-$C_{80}$ linear, saturated or partially unsaturated, aliphatic chain, optionally substituted with one or more $C_{1-4}$ aliphatic groups. In some embodiments, a lipid comprises a $C_{10}$-$C_{80}$ linear, saturated or partially unsaturated, aliphatic chain, optionally substituted with one or more $C_{1-4}$ aliphatic groups. In some embodiments, $R^{LD}$ is a $C_{10}$-$C_{80}$ linear, saturated or partially unsaturated, aliphatic chain, optionally substituted with one or more $C_{1-2}$ aliphatic groups. In some embodiments, a lipid comprises a $C_{10}$-$C_{80}$ linear, saturated or partially unsaturated, aliphatic chain, optionally substituted with one or more $C_{1-2}$ aliphatic groups. In some embodiments, $R^{LD}$ is a $C_{10}$-$C_{80}$ linear, saturated or partially unsaturated, aliphatic chain, optionally substituted with one or more methyl groups. In some embodiments, a lipid comprises a $C_{10}$-$C_{80}$ linear, saturated or partially unsaturated, aliphatic chain, optionally substituted with one or more methyl groups.

In some embodiments, $R^{LD}$ is an unsubstituted $C_{10}$-$C_{80}$ linear, saturated or partially unsaturated, aliphatic chain. In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{80}$ linear, saturated or partially unsaturated, aliphatic chain. In some embodiments, a lipid comprises two or more optionally substituted $C_{10}$-$C_{80}$ linear, saturated or partially unsaturated, aliphatic chain.

In some embodiments, $R^{LD}$ is or comprises a $C_{10}$ saturated linear aliphatic chain. In some embodiments, $R^{LD}$ is or comprises a C10 partially unsaturated linear aliphatic chain. In some embodiments, $R^{LD}$ is or comprises a $C_{11}$ saturated linear aliphatic chain. In some embodiments, $R^{LD}$ is or comprises a $C_{11}$ partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a $C_{12}$ saturated linear aliphatic chain. In some embodiments, $R^{LD}$ is or comprises a $C_{12}$ partially unsaturated linear aliphatic chain. In some embodiments, $R^{LD}$ is or comprises a C14 saturated linear aliphatic chain. In some embodiments, $R^{LD}$ is or comprises a C14 partially unsaturated linear aliphatic chain. In some embodiments, $R^{LD}$ is or comprises a C15 saturated linear aliphatic chain. In some embodiments, $R^{LD}$ is or comprises a C15 partially unsaturated linear aliphatic chain. In some embodiments, $R^{LD}$ is or comprises a $C_{16}$ saturated linear aliphatic chain. In some embodiments, $R^{LD}$ is or comprises a $C_{16}$ partially unsaturated linear aliphatic chain. In some embodiments, $R^{LD}$ is or comprises a C17 saturated linear aliphatic chain. In some embodiments, $R^{LD}$ is or comprises a $C_{17}$ partially unsaturated linear aliphatic chain. In some embodiments, $R^{LD}$ is or comprises a $C_{18}$ saturated linear aliphatic chain. In some embodiments, $R^{LD}$ is or comprises a $C_{18}$ partially unsaturated linear aliphatic chain. In some embodiments, $R^{LD}$ is or comprises a $C_{19}$ saturated linear aliphatic chain. In some embodiments, $R^{LD}$ is or comprises a $C_{19}$ partially unsaturated linear aliphatic chain. In some embodiments, $R^{LD}$ is or comprises a $C_{20}$ saturated linear aliphatic chain. In some embodiments, $R^{LD}$ is or comprises a $C_{20}$ partially unsaturated linear aliphatic chain. In some embodiments, $R^{LD}$ is or comprises a $C_{21}$ saturated linear aliphatic chain. In some embodiments, $R^{LD}$ is or comprises a $C_{21}$ partially unsaturated linear aliphatic chain. In some embodiments, $R^{LD}$ is or comprises a $C_{22}$ saturated linear aliphatic chain. In some embodiments, $R^{LD}$ is or comprises a $C_{22}$ partially unsaturated linear aliphatic chain. In some embodiments, $R^{LD}$ is or comprises a $C_{23}$ saturated linear aliphatic chain. In some embodiments, $R^{LD}$ is or comprises a $C_{23}$ partially unsaturated linear aliphatic chain. In some embodiments, $R^{LD}$ is or comprises a $C_{24}$ saturated linear aliphatic chain. In some embodiments, $R^{LD}$ is or comprises a $C_{24}$ partially unsaturated linear aliphatic chain. In some embodiments, $R^{LD}$ is or comprises a $C_{25}$ saturated linear aliphatic chain. In some embodiments, $R^{LD}$ is or comprises a $C_{25}$ partially unsaturated linear aliphatic chain. In some embodiments, $R^{LD}$ is or comprises a $C_{26}$ saturated linear aliphatic chain. In some embodiments, $R^{LD}$ is or comprises a $C_{26}$ partially unsaturated linear aliphatic chain. In some embodiments, $R^{LD}$ is or comprises a $C_{27}$ saturated linear aliphatic chain. In some embodiments, $R^{LD}$ is or comprises a $C_{27}$ partially unsaturated linear aliphatic chain. In some embodiments, $R^{LD}$ is or comprises a $C_{28}$ saturated linear aliphatic chain. In some embodiments, $R^{LD}$ is or comprises a $C_{28}$ partially unsaturated linear aliphatic chain. In some embodiments, $R^{LD}$ is or comprises a $C_{29}$ saturated linear aliphatic chain. In some embodiments, $R^{LD}$ is or comprises a $C_{29}$ partially unsaturated linear aliphatic chain. In some embodiments, $R^{LD}$ is or comprises a $C_{30}$ saturated linear aliphatic chain. In some embodiments, $R^{LD}$ is or comprises a $C_{30}$ partially unsaturated linear aliphatic chain.

In some embodiments, $R^{LD}$ is derived from cholesterol or a derivatives thereof, e.g., $R^{LD}$—H is optionally substituted cholesterol or a derivative thereof.

In some embodiments, a lipid has the structure of $R^{LD}$—OH. In some embodiments, a lipid has the structure of $R^{LD}$—C(O)OH. In some embodiments, $R^{LD}$ is

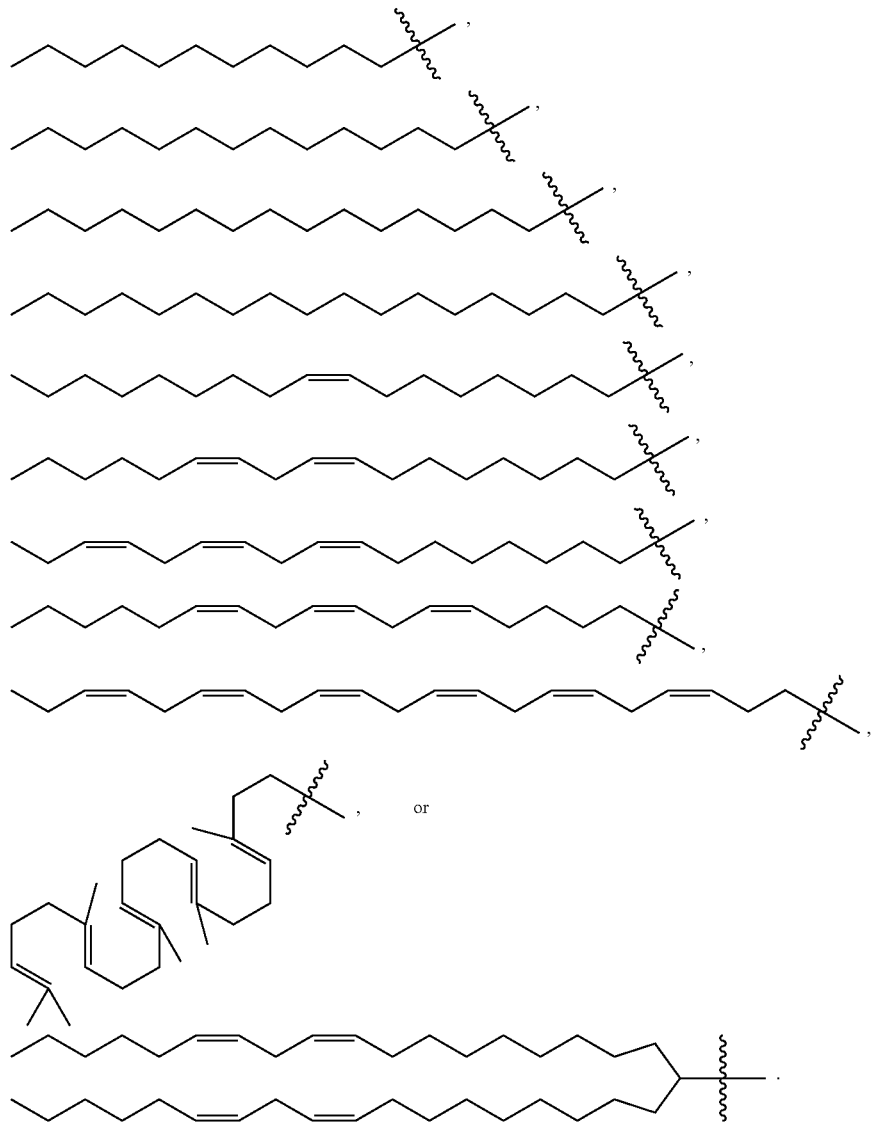

In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid, arachidonic acid, and dilinoleyl. In some embodiments, a lipid is lauric acid, myristic acid, palmitic acid, stearic acid, oleic acid, linoleic acid, alpha-linolenic acid, gamma-linolenic acid, docosahexaenoic acid (DHA or cis-DHA), turbinaric acid and dilinoleyl. In some embodiments, a lipid has a structure of:

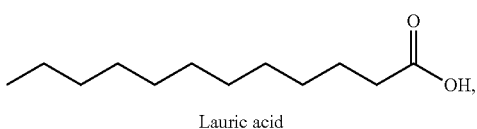

Lauric acid

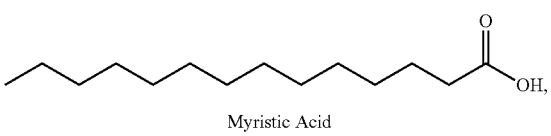

Myristic Acid

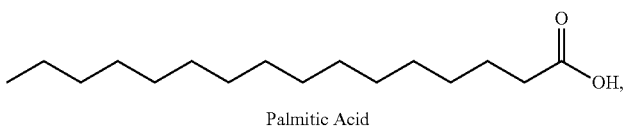

Palmitic Acid

-continued

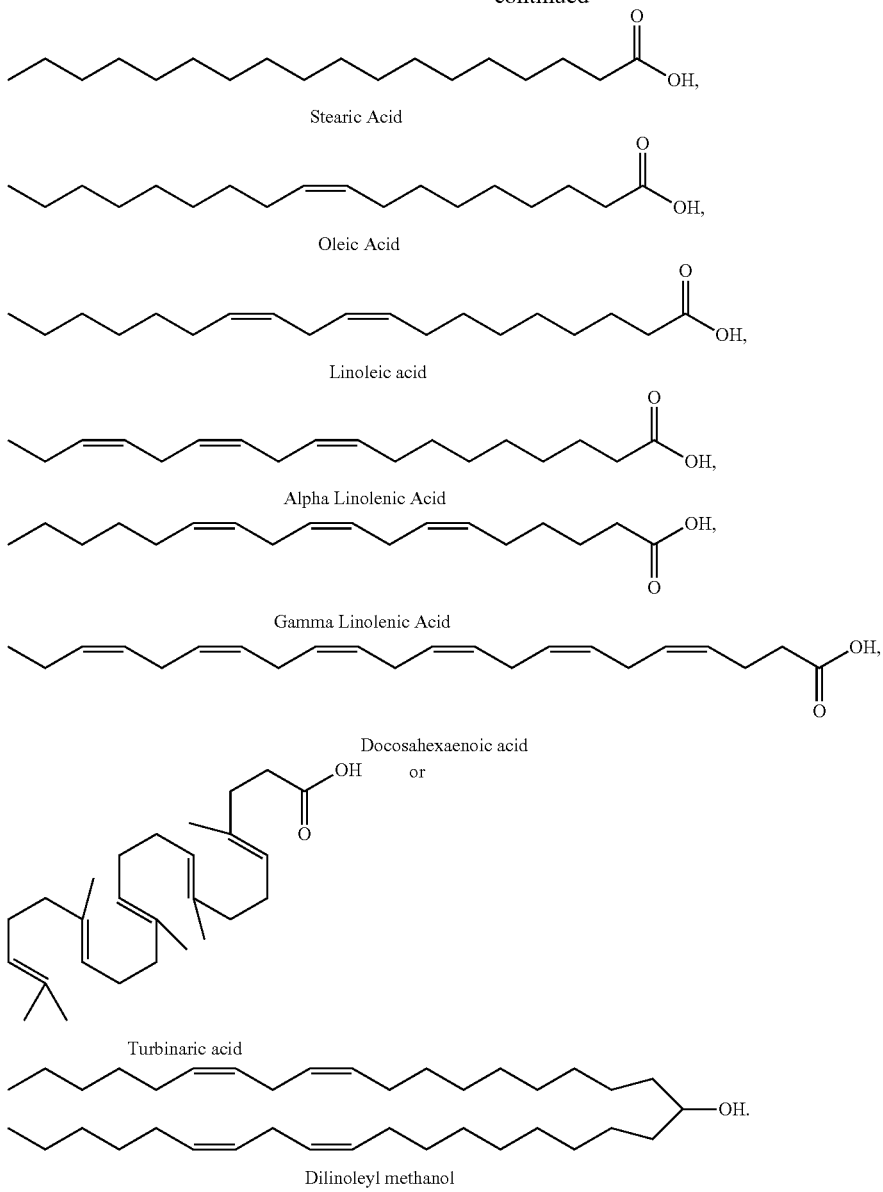

In some embodiments, a lipid is, comprises or consists of any of: an at least partially hydrophobic or amphiphilic molecule, a phospholipid, a triglyceride, a diglyceride, a monoglyceride, a fat-soluble vitamin, a sterol, a fat and a wax. In some embodiments, a lipid is any of: a fatty acid, glycerolipid, glycerophospholipid, sphingolipid, sterol lipid, prenol lipid, saccharolipid, polyketide, and other molecule.

Lipids can be incorporated into provided technologies through many types of methods in accordance with the present disclosure. In some embodiments, lipids are physically mixed with provided oligonucleotides to form provided compositions. In some embodiments, lipids are chemically conjugated with oligonucleotide moieties.

In some embodiments, provided compositions comprise two or more lipids. In some embodiments, provided oligonucleotides comprise two or more conjugated lipids. In some embodiments, the two or more conjugated lipids are the same. In some embodiments, the two or more conjugated lipids are different. In some embodiments, provided oligonucleotides comprise no more than one lipid. In some embodiments, oligonucleotides of a provided composition comprise different types of conjugated lipids. In some embodiments, oligonucleotides of a provided composition comprise the same type of lipids.

Lipids can be conjugated to oligonucleotides optionally through linkers. Various types of linkers in the art can be utilized in accordance of the present disclosure. In some embodiments, a linker is $L^M$ as described in the present disclosure. In some embodiments, a linker comprise a phosphate group, which can, for example, be used for conjugating lipids through chemistry similar to those employed in oligonucleotide synthesis. In some embodiments, a linker comprises an amide, ester, or ether group.

In some embodiments, a linker has the structure of -$L^M$-. In some embodiments, $L^M$ is $L^D$. In some embodiments, $L^D$ is $T^D$ having the structure of

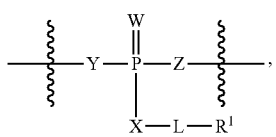

wherein each variable is independently as defined and described. In some embodiments, $T^D$ has the structure of formula I. In some embodiments, $T^D$ with the 5'-O— of a PNPLA3 oligonucleotide moiety form a phosphorothioate linkage (—OP(O)(S⁻)O—). In some embodiments, $T^D$ with the 5'-O— of a PNPLA3 oligonucleotide moiety form an Sp phosphorothioate linkage. In some embodiments, $T^D$ with the 5'-O— of a PNPLA3 oligonucleotide moiety form an Rp phosphorothioate linkage. In some embodiments, $T^D$ with the 5'-O— of a PNPLA3 oligonucleotide moiety form a phosphate linkage (—OP(O)(O⁻)O—). In some embodiments, $T^D$ with the 5'-O— of a PNPLA3 oligonucleotide moiety form a phosphorodithioate linkage. In some embodiments, $L^D$ is -L-$T^D$-. In some embodiments, Y connects to -L- and —Z— is a covalent bond, so that P directly connects to a hydroxyl group of the oligonucleotide moiety. In some embodiments, P connects to the 5'-end hydroxyl (5'-O—) to form a phosphate group (natural phosphate linkage) or phosphorothioate group (phosphorothioate linkage). In some embodiments, the phosphorothioate linkage is chirally controlled and can be either Rp or Sp. Unless otherwise specified, chiral centers in the linkers (e.g., P in $T^D$) can be either stereorandom or chirally controlled, and they are not considered as part of the backbone chiral centers, e.g., for determining whether a composition is chirally controlled. In some embodiments, $L^D$ is —NH—(CH$_2$)$_6$-$T^D$-. In some embodiments, $L^D$ is —C(O)—NH—(CH$_2$)$_6$-$T^D$-.

In some embodiments, a linker has the structure of -L-. In some embodiments, after conjugation to oligonucleotides, a lipid forms a moiety having the structure of -L-$R^{LD}$, wherein each of L and $R^{LD}$ is independently as defined and described herein.

In some embodiments, -L- comprises a bivalent aliphatic chain. In some embodiments, -L- comprises a phosphate group. In some embodiments, -L- comprises a phosphorothioate group. In some embodiments, -L- has the structure of —C(O)NH—(CH$_2$)$_6$—OP(=O)(S⁻)—. In some embodiments, -L- has the structure of —C(O)NH—(CH$_2$)$_6$—OP(=O)(O⁻)—.

Lipids, optionally through linkers, can be incorporated into oligonucleotides at various suitable locations. In some embodiments, lipids are conjugated through the 5'-OH group. In some embodiments, lipids are conjugated through the 3'-OH group. In some embodiments, lipids are conjugated through one or more sugar moieties. In some embodiments, lipids are conjugated through one or more bases. In some embodiments, lipids are incorporated through one or more internucleotidic linkages. In some embodiments, a PNPLA3 oligonucleotide may contain multiple conjugated lipids which are independently conjugated through its 5'-OH, 3'-OH, sugar moieties, base moieties and/or internucleotidic linkages.

In some embodiments, a linker is a moiety that connects two parts of a composition; as a non-limiting example, a linker physically connects a PNPLA3 oligonucleotide moiety to a lipid. Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group.

In some embodiments, a lipid is conjugated to an active compound optionally through a linker moiety. A person having ordinary skill in the art appreciates that various technologies can be utilized to conjugate lipids to active compound in accordance with the present disclosure. For example, for lipids comprising carboxyl groups, such lipids can be conjugated through the carboxyl groups. In some embodiments, a lipid is conjugated through a linker having the structure of -L-, wherein L is as defined and described in formula I. In some embodiments, L comprises a phosphate diester or modified phosphate diester moiety. In some embodiments, a compound formed by lipid conjugation has the structure of ($R^{LD}$-L-)$_a$-(active compound), wherein a is 1 or an integer greater than 1, and each of $R^{LD}$ and L is independently as defined and described herein. In some embodiments, a is 1. In some embodiments, a is greater than 1. In some embodiments, a is 1-50. In some embodiments, an active compound is a PNPLA3 oligonucleotide. For example, in some embodiments, a conjugate has any of the following structures:

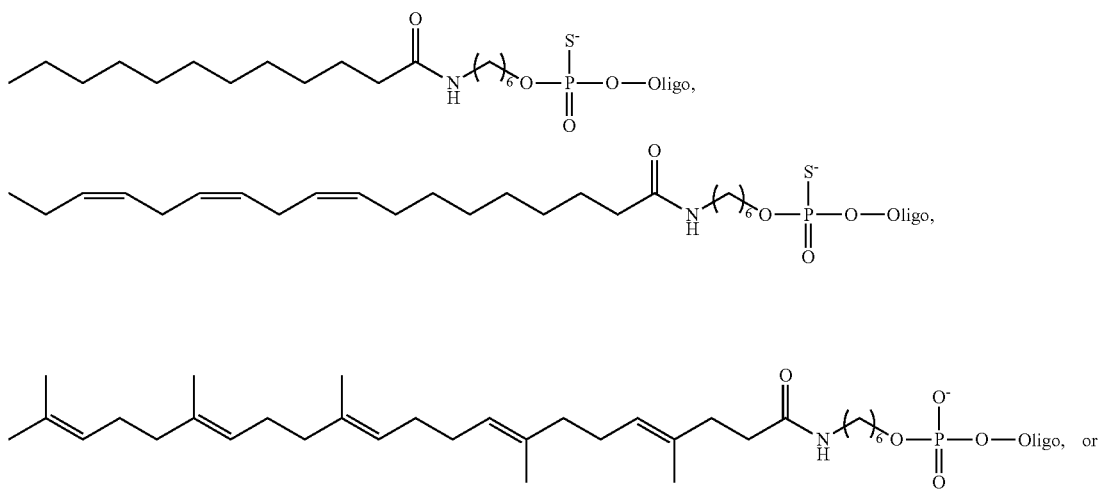

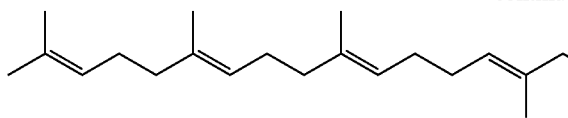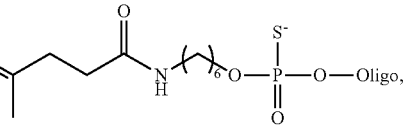

wherein Oligo indicates an oligonucleotide.

In some embodiments, a linker is selected from: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; and a linker comprising at least one peptide-based cleavage group. In some embodiments, a linker, e.g., $L^M$, has the structure of -$L^{LD}$-. In some embodiments, a linker, e.g., $L^M$, has the structure of -L-. In some embodiments, a linker comprises a linkage of formula I. In some embodiments, a linker is —C(O)NH—$(CH_2)_6$-$L^1$-, wherein $L^1$ has the structure of formula I as described herein. In some embodiments, a linker is —C(O)NH—$(CH_2)_6$—O—P(=O)(SR$^1$)—O—. In some embodiments, $R^1$ is —H, and a linker is —C(O)NH—$(CH_2)_6$—O—P(=O)(SH)—O—, in some conditions, e.g., certain pH, —C(O)NH—$(CH_2)_6$—O—P(=O)(S$^-$)—O—. In some embodiments, a linker is —C(O)NH—$(CH_2)_6$—O—P(=S)(SR$^1$)—O—. In some embodiments, $R^1$ is —H, and a linker is —C(O)NH—$(CH_2)_6$—O—P(=S)(SH)—O—, in some conditions, e.g., certain pH, —C(O)NH—$(CH_2)_6$—O—P(=S)(S$^-$)—O—. In some embodiments, a linker is —C(O)NH—$(CH_2)_6$—O—P(=S)(OR$^1$)—O—, wherein $R^1$ is —$CH_2CH_2CN$. In some embodiments, a linker is —C(O)NH—$(CH_2)_6$—O—P(=S)(SR$^1$)—O—, wherein $R^1$ is —$CH_2CH_2CN$. In some embodiments, a provided oligonucleotide is coupled with a linker and forms a structure of H-linker-oligonucleotide. In some embodiments, a provided oligonucleotide is conjugated to a lipid and forms the structure of lipid-linker-oligonucleotide, e.g., $R^{LD}$-$L^{LD}$-oligonucleotide. In some embodiments, the —O— end of a linker is connected to a PNPLA3 oligonucleotide. In some embodiments, the —O— end of a linker is connected to the 5'-end oligonucleotide (—O— being the oxygen in the 5'-OH).

In some embodiments, a linker, e.g., $L^M$, comprises a PO (phosphodiester linkage), a PS (phosphorothioate linkage) or PS2 (phosphorodithioate linkage). A non-limiting example including a PS linker is shown below. In some embodiments, a linker is —O—P(O)(OH)—O— [phosphodiester], —O—P(O)(SH)—O— [phosphorothioate] or —O—P(S)(SH)—O— [phosphorodithioate]. In some embodiments, a linker comprises a C6 amino moiety (—NH—$(CH_2)_6$—), which is illustrated below. In some embodiments, a linker comprises a C6 amino bound to a PO, a PS, or PS2. In some embodiments, a linker is a C6 amino bound to a PO, a PS, or PS2. In some embodiments, a linker, e.g., $L^{LD}$ or L, is —C(O)—NH—$(CH_2)_6$—P(O)(OH)—. In some embodiments, a linker, e.g., $L^{LD}$ or L, is —C(O)—NH—$(CH_2)_6$—P(O)(OH)—, wherein —C(O)— is connected to a lipid moiety and —P(O)(OH)— is connected to a PNPLA3 oligonucleotide moiety. In some embodiments, a linker, e.g., $L^{LD}$ or L, is —C(O)—NH—$(CH_2)_6$—P(O)(OH)—, wherein —C(O)— is connected to a lipid moiety and —P(O)(OH)— is connected to the 5'-O— of a PNPLA3 oligonucleotide moiety. In some embodiments, a linker, e.g., $L^{LD}$ or L, is —C(O)—NH—$(CH_2)_6$—P(O)(OH)—, wherein —C(O)— is connected to a lipid moiety and —P(O)(OH)— is connected to the 3'-O— of a PNPLA3 oligonucleotide moiety. In some embodiments, a linker, e.g., $L^{LD}$ or L, is —C(O)—NH—$(CH_2)_6$—P(O)(SH)—. In some embodiments, a linker, e.g., $L^{LD}$ or L, is —C(O)—NH—$(CH_2)_6$—P(O)(SH)—, wherein —C(O)— is connected to a lipid moiety and —P(O)(SH)— is connected to a PNPLA3 oligonucleotide moiety. In some embodiments, a linker, e.g., $L^{LD}$ or L, is —C(O)—NH—$(CH_2)_6$—P(O)(SH)—, wherein —C(O)— is connected to a lipid moiety and —P(O)(SH)— is connected to the 5'-O— of a PNPLA3 oligonucleotide moiety. In some embodiments, a linker, e.g., $L^{LD}$ or L, is —C(O)—NH—$(CH_2)_6$—P(O)(SH)—, wherein —C(O)— is connected to a lipid moiety and —P(O)(SH)— is connected to the 3'-O— of a PNPLA3 oligonucleotide moiety. In some embodiments, a linker, e.g., $L^{LD}$ or L, is —C(O)—NH—$(CH_2)_6$—P(S)(SH)—. In some embodiments, a linker, e.g., $L^{LD}$ or L, is —C(O)—NH—$(CH_2)_6$—P(S)(SH)—, wherein —C(O)— is connected to a lipid moiety and —P(S)(SH)— is connected to a PNPLA3 oligonucleotide moiety. In some embodiments, a linker, e.g., $L^{LD}$ or L, is —C(O)—NH—$(CH_2)_6$—P(S)(SH)—, wherein —C(O)— is connected to a lipid moiety and —P(S)(SH)— is connected to the 5'-O— of a PNPLA3 oligonucleotide moiety. In some embodiments, a linker, e.g., $L^{LD}$ or L, is —C(O)—NH—$(CH_2)_6$—P(S)(SH)—, wherein —C(O)— is connected to a lipid moiety and —P(S)(SH)— is connected to the 3'-O— of a PNPLA3 oligonucleotide moiety. As appreciated by a person having ordinary skill in the art, at certain pH —P(O)(OH)—, —P(O)(SH)—, —P(S)(SH)— may exist as —P(O)(O$^-$)—, —P(O)(S$^-$)—, —P(S)(S$^-$)—, respectively. In some embodiments, a lipid moiety is $R^{LD}$.

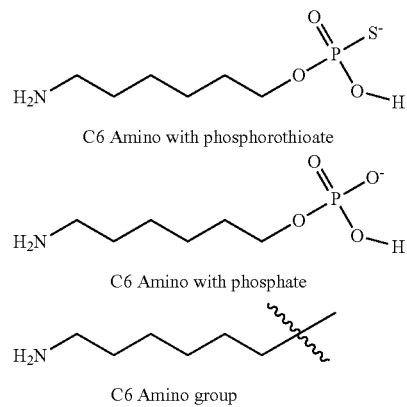

C6 Amino with phosphorothioate

C6 Amino with phosphate

C6 Amino group

Various chemistry and linkers can be used for conjugation in accordance with the present disclosure. For example, in some embodiment, a lipid is incorporated using chemistry described below, or similar processes:

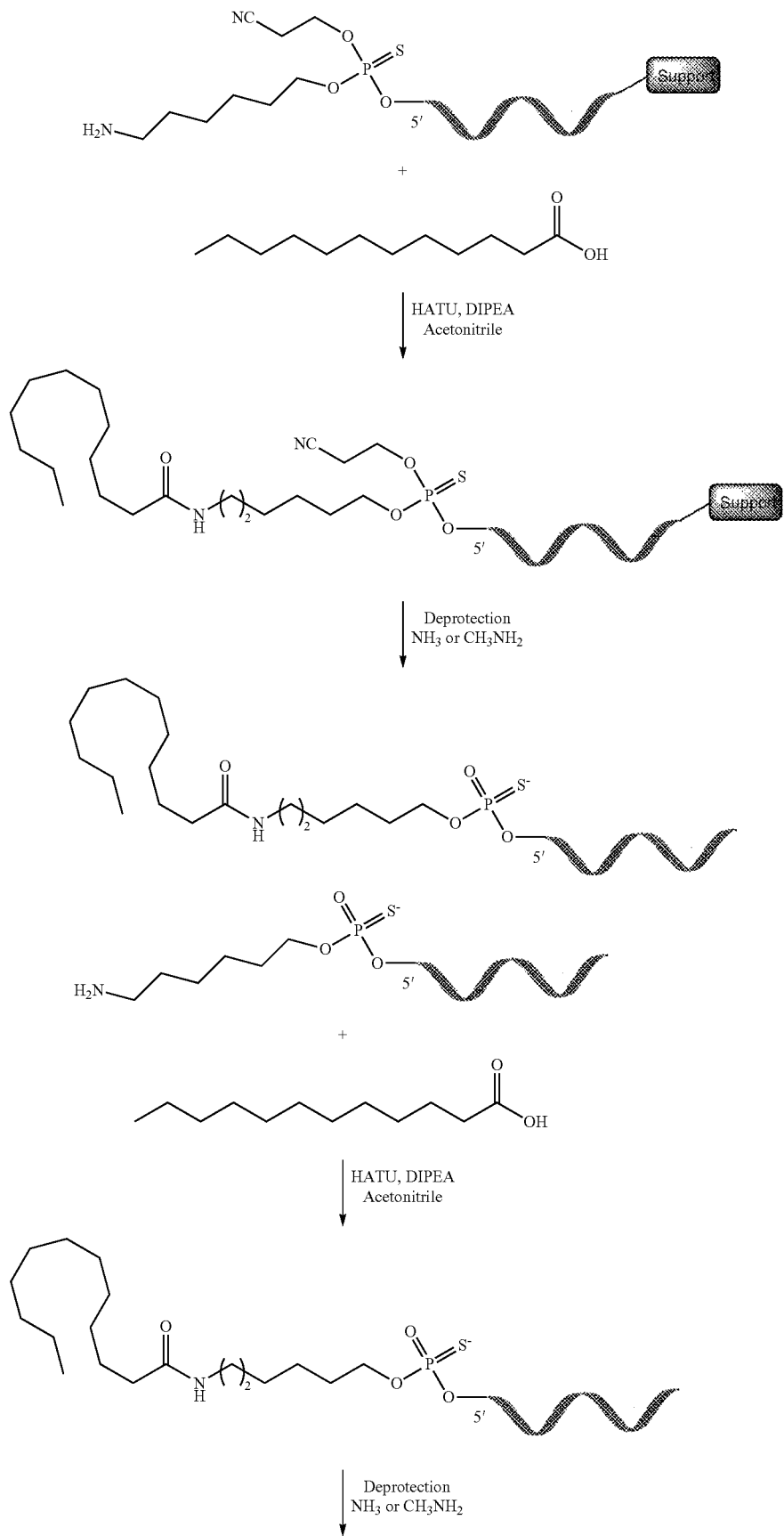

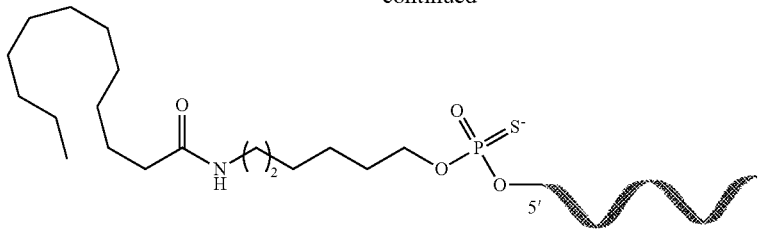

In some embodiments, a lipid is incorporated into a PNPLA3 oligonucleotide directly through a nucleobase, for example:

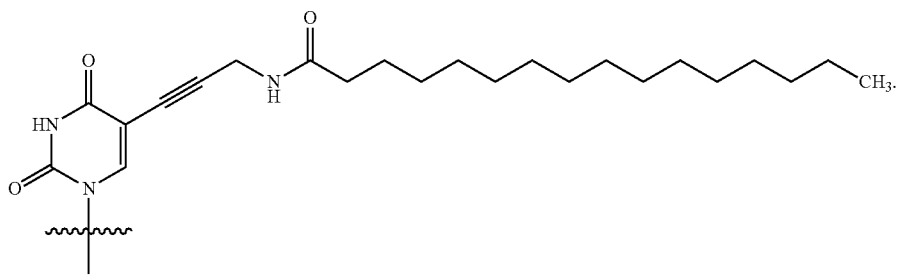 [SMILES: *n1cc(C#CCNC(=O)CCCCCCCCCCCCCCC)c(=O)[nH]c1=O]

In some embodiments, a provided oligonucleotide comprises -$L^M$-$R^{LD}$ directly bonded to a nucleobase. In some embodiments, a provided oligonucleotide comprises

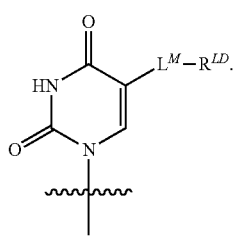

In some embodiments, a linker ($L^M$) is

In some embodiments, a linker ($L^M$) is

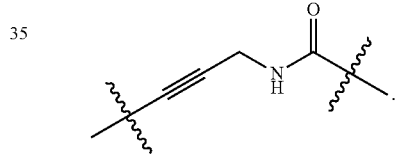

In some embodiments, a lipid moiety, $R^{LD}$, is

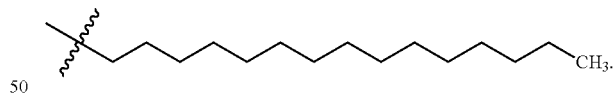

In some embodiments, a provided oligonucleotide comprises

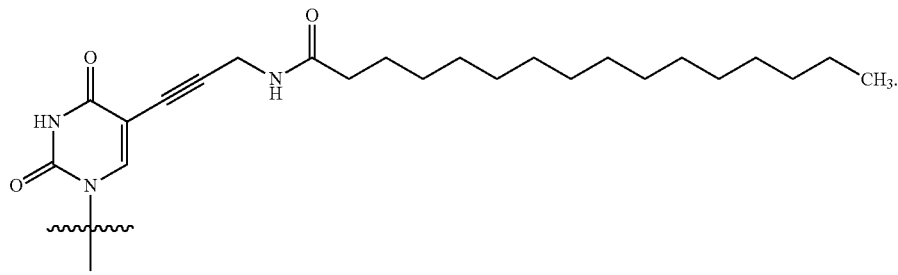 [SMILES: *n1cc(C#CCNC(=O)CCCCCCCCCCCCCCC)c(=O)[nH]c1=O]

In some embodiments, a provided oligonucleotide comprises a carbohydrate moiety connected to the oligonucleotide moiety, option through a linker, at a nucleobase. In some embodiments, the nucleobase is T. In some embodiments, the nucleobase is protected T. In some embodiments, the nucleobase is optionally substituted T. In some embodiments, the connection is at the 5-carbon of a T or an optionally substituted T. In some embodiments, a provided oligonucleotide comprises one or more -$L^M$-($R^{LD}$)a, wherein each variable is independently as described in the present disclosure. In some embodiments, a provided oligonucleotide comprises one or more -$L^M$-($R^{LD}$)a, which is bonded to a nucleobase, wherein each variable is independently as described in the present disclosure. In some embodiments, a provided oligonucleotide comprises one or more

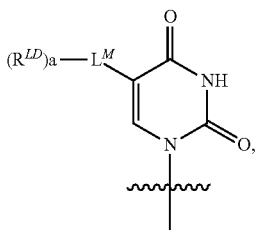

wherein each variable is independently as described in the present disclosure. In some embodiments, a provided oligonucleotide comprises one or more

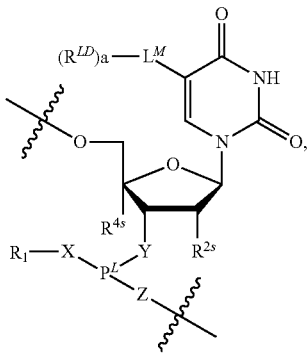

wherein each variable is independently as described in the present disclosure. In some embodiments, a provided oligonucleotide comprises one or more

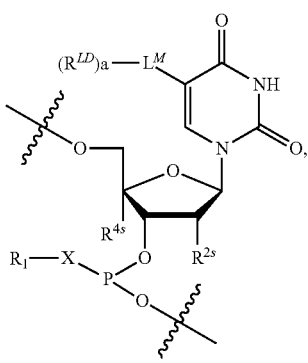

wherein each variable is independently as described in the present disclosure. In some embodiments, a provided oligonucleotide comprises one or more

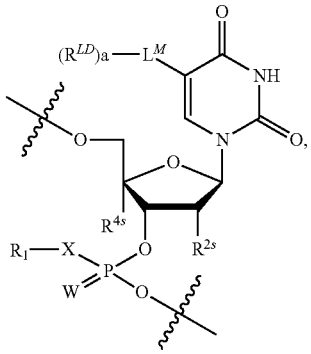

wherein each variable is independently as described in the present disclosure. In some embodiments, a provided oligonucleotide comprises one or more

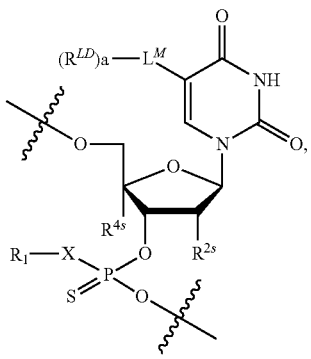

wherein each variable is independently as described in the present disclosure. In some embodiments, a provided oligonucleotide comprises one or more

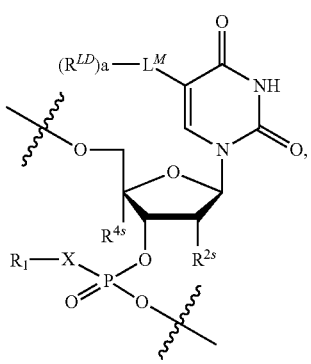

wherein each variable is independently as described in the present disclosure. In some embodiments, a provided oligonucleotide comprises one or more

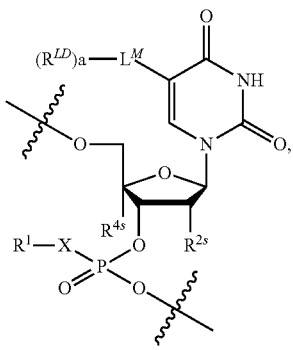

wherein X is O or S, R¹ is H, and each other variable is independently as described in the present disclosure. In some embodiments, $R^{2s}$ and $R^{4s}$ are hydrogen. In some embodiments, a provided oligonucleotide comprises one or more

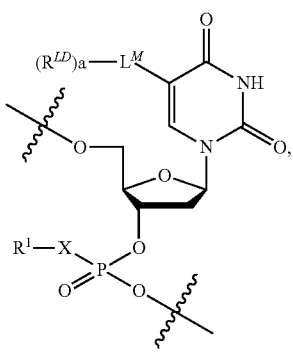

wherein X is O or S, R¹ is H, and each other variable is independently as described in the present disclosure.

In some embodiments, a is 1. In some embodiments, a provided oligonucleotide comprises one or more $-L^M-R^{CD}$, which is bonded to a nucleobase, wherein each variable is independently as described in the present disclosure. In some embodiments, the nucleobase is T. In some embodiments, the nucleobase is protected T. In some embodiments, the nucleobase is optionally substituted T. In some embodiments, the connection is at the 5-carbon of a T or an optionally substituted T. In some embodiments, a provided oligonucleotide comprises one or more

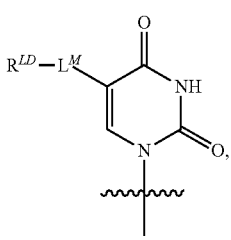

wherein each variable is independently as described in the present disclosure. In some embodiments, a provided oligonucleotide comprises one or more

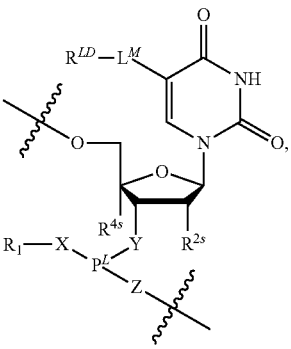

wherein each variable is independently as described in the present disclosure. In some embodiments, a provided oligonucleotide comprises one or more

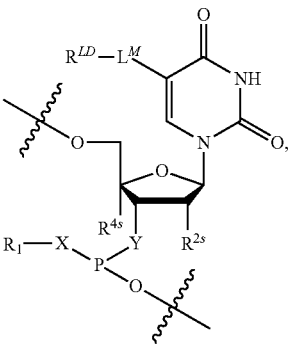

wherein each variable is independently as described in the present disclosure. In some embodiments, a provided oligonucleotide comprises one or more

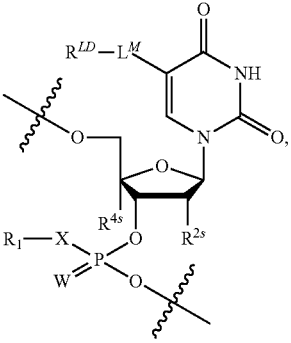

wherein each variable is independently as described in the present disclosure. In some embodiments, a provided oligonucleotide comprises one or more

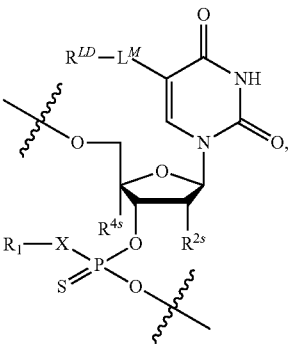

wherein each variable is independently as described in the present disclosure. In some embodiments, a provided oligonucleotide comprises one or more

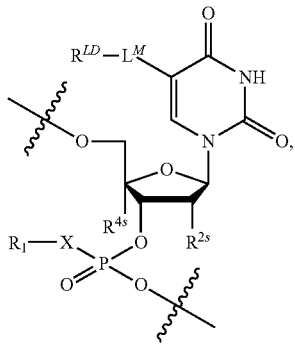

wherein each variable is independently as described in the present disclosure. In some embodiments, a provided oligonucleotide comprises one or more

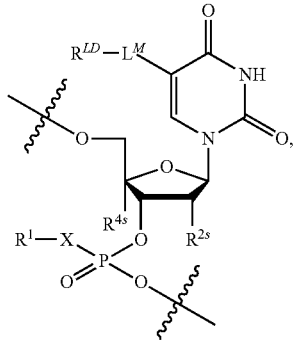

wherein X is O or S, $R^1$ is H, and each other variable is independently as described in the present disclosure. In some embodiments, $R^{2s}$ and $R^{4s}$ are hydrogen. In some embodiments, a provided oligonucleotide comprises one or more

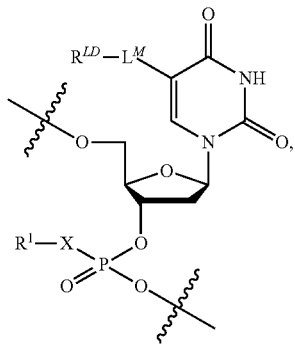

wherein X is O or S, $R^1$ is H, and each other variable is independently as described in the present disclosure.

In some embodiments, the present disclosure provides a composition comprising a PNPLA3 oligonucleotide comprising a lipid moiety comprising or being a $C_{10}$-$C_{40}$ linear, saturated or partially unsaturated, aliphatic chain. In some embodiments, the present disclosure provides a composition comprising a PNPLA3 oligonucleotide comprising a lipid moiety comprising or being a $C_{10}$-$C_{40}$ linear, saturated or partially unsaturated, aliphatic chain, optionally substituted with one or more $C_{1-4}$ aliphatic group.

In some embodiments, a composition comprises a PNPLA3 oligonucleotide comprising a lipid moiety formed through conjugation of a compound selected from: lauric acid, myristic acid, palmitic acid, stearic acid, oleic acid, linoleic acid, alpha-linolenic acid, gamma-linolenic acid, docosahexaenoic acid (cis-DHA), turbinaric acid, arachidonic acid, and dilinoleyl alcohol In some embodiments, a linker is a moiety that connects two parts of a composition; as a non-limiting example, a linker physically connects a PNPLA3 oligonucleotide to a lipid. Non-limiting examples of suitable linkers include: an uncharged linker; a charged linker; a linker comprising an alkyl; a linker comprising a phosphate; a branched linker; an unbranched linker; a linker comprising at least one cleavage group; a linker comprising at least one redox cleavage group; a linker comprising at least one phosphate-based cleavage group; a linker comprising at least one acid-cleavage group; a linker comprising at least one ester-based cleavage group; a linker comprising at least one peptide-based cleavage group. In some embodiments, a linker is an uncharged linker or a charged linker. In some embodiments, a linker comprises an alkyl.

In some embodiments, a linker comprises a phosphate. In various embodiments, a phosphate can also be modified by replacement of a bridging oxygen, (i.e. oxygen that links the phosphate to the nucleoside), with nitrogen (bridged phosphoramidates), sulfur (bridged phosphorothioates) and carbon (bridged methylenephosphonates). The replacement can occur at the either linking oxygen or at both the linking oxygens. In some embodiments, the bridging oxygen is the 3'-oxygen of a nucleoside, replacement with carbon is done. In some embodiments, the bridging oxygen is the 5'-oxygen of a nucleoside, replacement with nitrogen is done. In various embodiments, the linker comprising a phosphate comprises any one or more of: a phosphorodithioate, phosphoramidate, boranophosphonate, or a compound of formula (I):

where $R^3$ is selected from OH, SH, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In some embodiments, a linker comprises a direct bond or an atom such as oxygen or sulfur, a unit such as NR', C(O), C(O)NH, SO, $SO_2$, $SO_2$NH or a chain of atoms, such as substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, where one or more methylenes can be interrupted or terminated by O, S, S(O), SO$_2$, N(R$_1$)$_2$, C(O), cleavable linking group, substituted or unsubstituted aryl, substituted or unsubstituted heteroaryl, substituted or unsubstituted heterocyclic; where R$^1$ is hydrogen, acyl, aliphatic or substituted aliphatic.

In some embodiments, a linker is a branched linker. In some embodiments, a branchpoint of the branched linker may be at least trivalent, but may be a tetravalent, pentavalent or hexavalent atom, or a group presenting such multiple valencies. In some embodiments, a branchpoint is —N, —N(Q)-C, —O—C, —S—C, —SS—C, —C(O)N(Q)-C, —OC(O)N(Q)-C, —N(Q)C(O)—C, or —N(Q)C(O)O—C; wherein Q is independently for each occurrence H or optionally substituted alkyl. In other embodiment, the branchpoint is glycerol or glycerol derivative.

In one embodiment, a linker comprises at least one cleavable linking group. As a non-limiting example, a cleavable linking group can be sufficiently stable outside the cell, but which upon entry into a target cell is cleaved to release the two parts the linker is holding together. As a non-limiting example, a cleavable linkage group, such as a disulfide bond can be susceptible to pH. As a non-limiting example, a linker can include a cleavable linking group that is capable of being cleaved by an enzyme. As a non-limiting example, a linker can contain a peptide bond, which can be used when targeting cell types rich in peptidases, such as liver cells and synoviocytes. As a non-limiting example, suitability of a candidate cleavable linking group can be evaluated by testing the ability of a degradative agent (or condition) to cleave the candidate linking group. In some embodiments, a linker comprises a redox cleavable linking group, a phosphate-based cleavable linking groups, which are cleavable by agents that degrade or hydrolyze the phosphate group, a linker comprises an acid cleavable linking group, an ester-based linking group, and/or a peptide-based cleaving group.

Any linker reported in the art can be used, including, as non-limiting examples, those described in: U.S. Pat. App. No. 20150265708.

In some embodiments, a lipid is conjugated to a PNPLA3 oligonucleotide using any method known in the art in accordance with the present disclosure.

Targeting Moieties

In some embodiments, a provided oligonucleotide or oligonucleotide composition further comprises a targeting component or moiety. A targeting moiety can be either conjugated or not conjugated to a PNPLA3 oligonucleotide moiety. In some embodiments, a targeting moiety is a lipid. In some embodiments, a targeting moiety is a carbohydrate or a bicyclic ketal. In some embodiments, a targeting moiety is —R$^{LD}$ as described in the present disclosure. In some embodiments, a targeting moiety is —R$^{CD}$ as described in the present disclosure.

Targeting moieties can be incorporated into provided technologies through many types of methods in accordance with the present disclosure, for example, those described for lipids and carbohydrates. In some embodiments, targeting moieties are physically mixed with provided oligonucleotides to form provided compositions. In some embodiments, a targeting moiety is conjugated to a PNPLA3 oligonucleotide. In some embodiments, a targeting moiety is not conjugated to a PNPLA3 oligonucleotide.

In some embodiments, provided compositions comprise two or more targeting moieties. In some embodiments, provided oligonucleotides comprise two or more conjugated targeting moieties. In some embodiments, the two or more conjugated targeting moieties are the same. In some embodiments, the two or more conjugated targeting moieties are different. In some embodiments, provided oligonucleotides comprise no more than one targeting moiety. In some embodiments, oligonucleotides of a provided composition comprise different types of conjugated targeting moieties. In some embodiments, oligonucleotides of a provided composition comprise the same type of targeting moieties.

Targeting moieties can be conjugated to oligonucleotides optionally through linkers, for example, as described for lipids and carbohydrates. Various types of linkers in the art can be utilized in accordance of the present disclosure. In some embodiments, a linker comprises a phosphate group, which can, for example, be used for conjugating targeting moieties through chemistry similar to those employed in oligonucleotide synthesis. In some embodiments, a linker comprises an amide, ester, or ether group. In some embodiments, a linker has the structure of -L-. Targeting moieties can be conjugated through either the same or different linkers compared to lipids.

Targeting moieties, optionally through linkers, can be conjugated to oligonucleotides at various suitable locations. In some embodiments, targeting moieties are conjugated through the 5'-OH group. In some embodiments, targeting moieties are conjugated through the 3'-OH group. In some embodiments, targeting moieties are conjugated through one or more sugar moieties. In some embodiments, targeting moieties are conjugated through one or more bases. In some embodiments, targeting moieties are incorporated through one or more internucleotidic linkages. In some embodiments, a PNPLA3 oligonucleotide may contain multiple conjugated targeting moieties which are independently conjugated through its 5'-OH, 3'-OH, sugar moieties, base moieties and/or internucleotidic linkages. Targeting moieties and lipids can be conjugated either at the same, neighboring and/or separated locations. In some embodiments, a targeting moiety is conjugated at one end of a PNPLA3 oligonucleotide, and a lipid is conjugated at the other end.

In some embodiments, a targeting moiety interacts with a protein on the surface of targeted cells. In some embodiments, such interaction facilitates internalization into targeted cells. In some embodiments, a targeting moiety comprises a sugar moiety. In some embodiments, a targeting moiety comprises a polypeptide moiety. In some embodiments, a targeting moiety comprises an antibody. In some embodiments, a targeting moiety is an antibody. In some embodiments, a targeting moiety comprises an inhibitor. In some embodiments, a targeting moiety is a moiety from a small molecule inhibitor. In some embodiments, an inhibitor is an inhibitor of a protein on the surface of targeted cells. In some embodiments, an inhibitor is a carbonic anhydrase inhibitor. In some embodiments, an inhibitor is a carbonic anhydrase inhibitor expressed on the surface of target cells. In some embodiments, a carbonic anhydrase is I, II, III, IV, V, VI, VII, VIII, IX, X, XI, XII, XIII, XIV, XV or XVI. In some embodiments, a carbonic anhydrase is membrane bound. In some embodiments, a carbonic anhydrase is IV, IX, XII or XIV. In some embodiments, an inhibitor is for IV, IX, XII and/or XIV. In some embodiments, an inhibitor is a carbonic anhydrase III inhibitor. In some embodiments, an inhibitor is a carbonic anhydrase IV inhibitor. In some embodiments, an inhibitor is a carbonic anhydrase IX inhibitor. In some embodiments, an inhibitor is a carbonic anhydrase XII inhibitor. In some embodiments, an inhibitor is a carbonic anhydrase XIV inhibitor. In some embodiments, an inhibitor comprises or is a sulfonamide (e.g., those described in Supuran, C T. *Nature Rev Drug Discover* 2008, 7, 168-181, which sulfonamides are incorporated herein by reference). In some embodiments, an inhibitor is a sulfonamide. In some embodiments, targeted cells are muscle cells.

In some embodiments, a targeting moiety is $R^{TD}$, wherein $R^{TD}$ is $R^{LD}$ or $R^{CD}$ as described in the present disclosure.

In some embodiments, a targeting moiety is $R^{LD}$ as defined and described in the present disclosure. In some embodiments, the present disclosure provides oligonucleotides comprising $R^{LD}$. In some embodiments, the present disclosure provides oligonucleotide compositions comprising oligonucleotides comprising $R^{LD}$. In some embodiments, the present disclosure provides oligonucleotide compositions comprising a first plurality of oligonucleotides comprising $R^{LD}$. In some embodiments, the present disclosure provides chirally controlled oligonucleotide compositions of oligonucleotides comprising $R^{LD}$.

In some embodiments, a targeting moiety is $R^{CD}$ as defined and described in the present disclosure. In some embodiments, the present disclosure provides oligonucleotides comprising $R^{CD}$. In some embodiments, the present disclosure provides oligonucleotide compositions comprising oligonucleotides comprising $R^{CD}$. In some embodiments, the present disclosure provides oligonucleotide compositions comprising a first plurality of oligonucleotides comprising $R^{CD}$. In some embodiments, the present disclosure provides chirally controlled oligonucleotide compositions of oligonucleotides comprising $R^{CD}$.

In some embodiments, $R^{TD}$ comprises or is

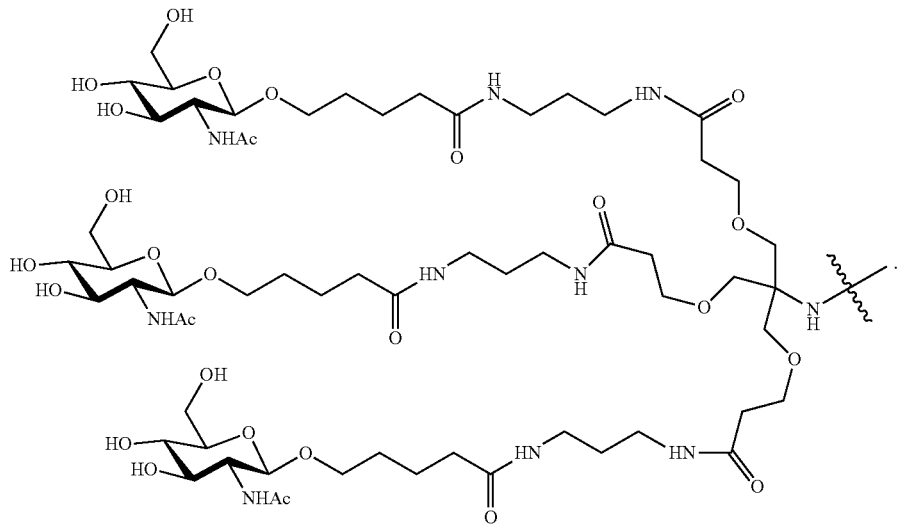

In some embodiments, $R^{TD}$ comprises or is

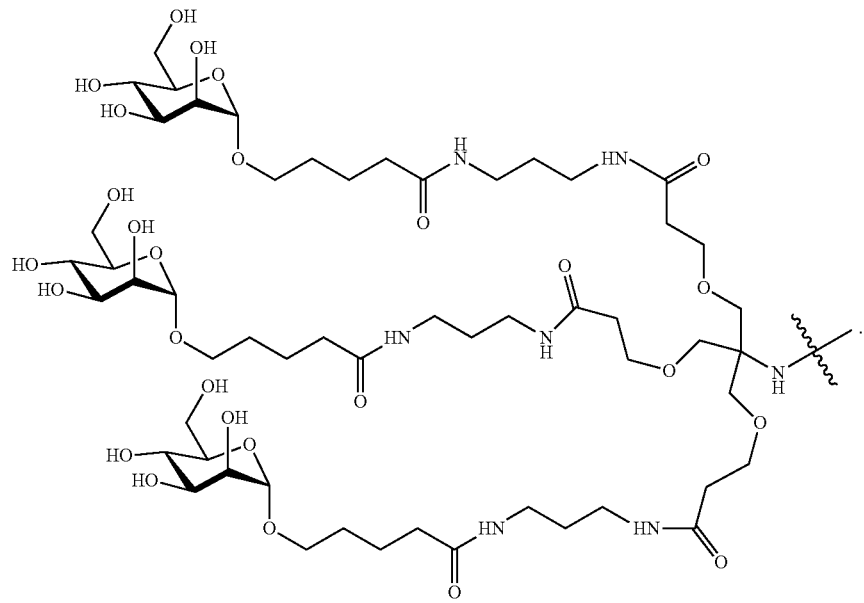

In some embodiments, $R^{TD}$ comprises or is
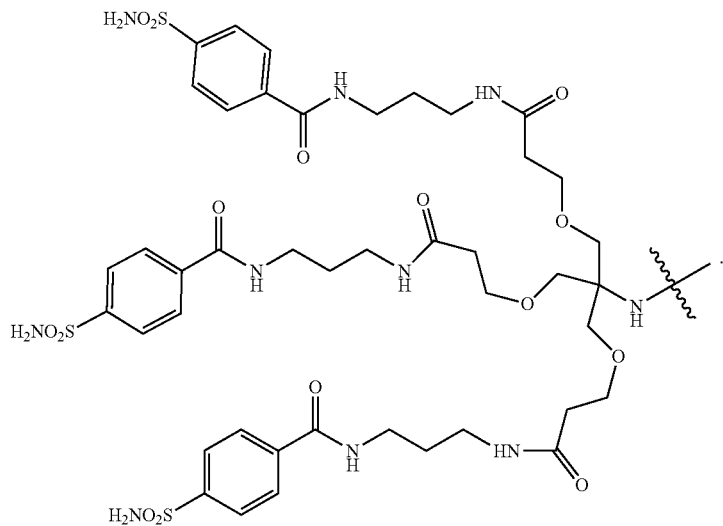 [SMILES: *NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]
In some embodiments, $R^{TD}$ comprises or is
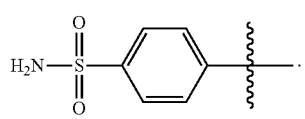
In some embodiments, $R^{TD}$ comprises or is
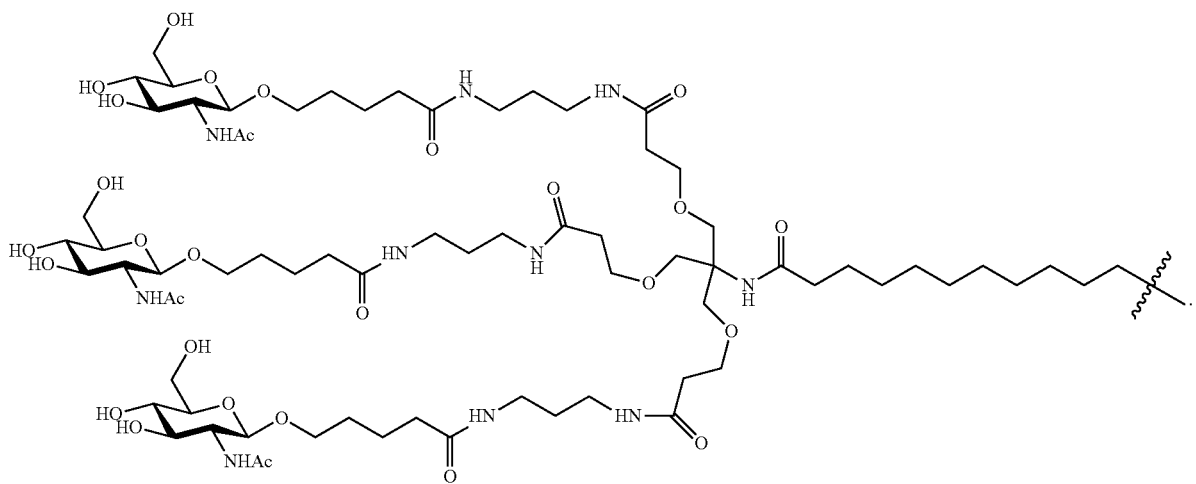

In some embodiments, $R^{TD}$ comprises or is
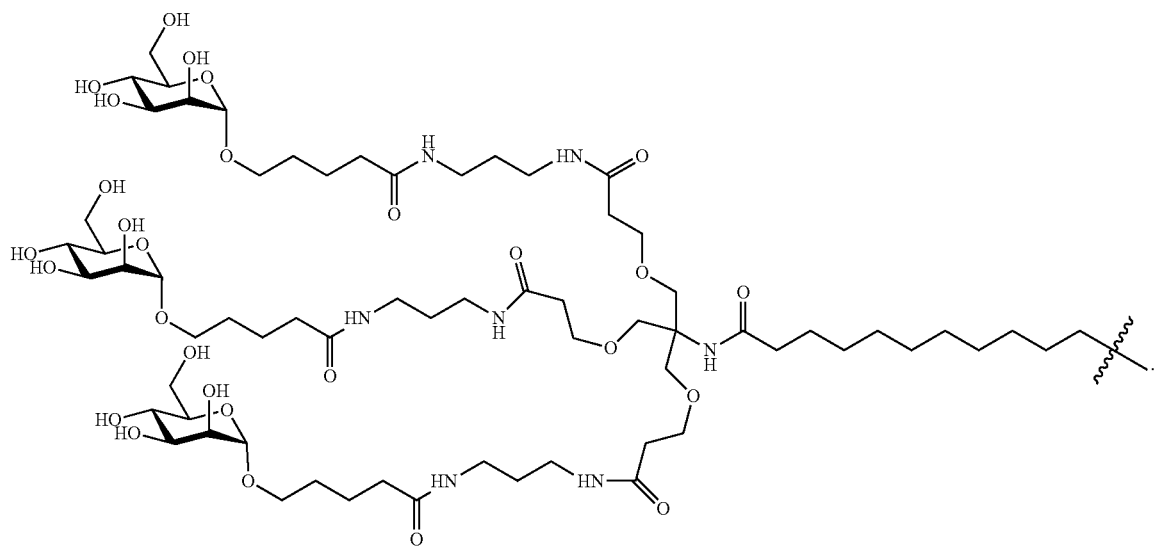
In some embodiments, $R^{TD}$ comprises or is
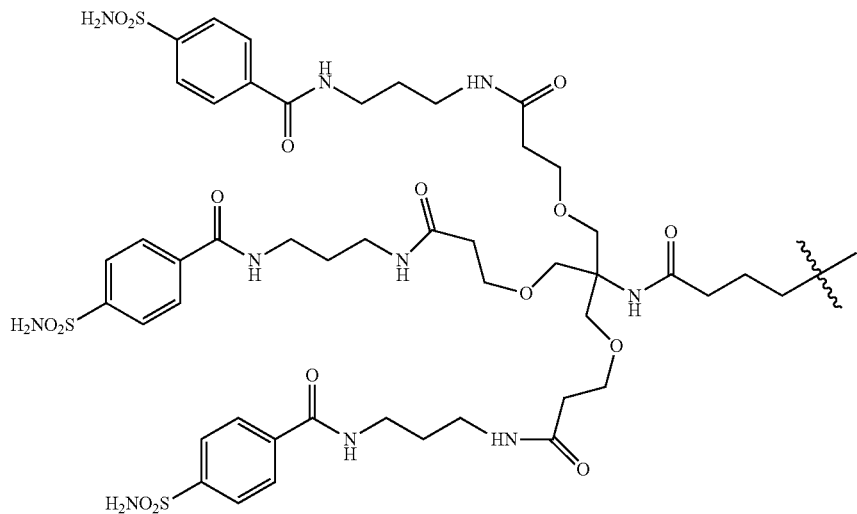
In some embodiments, comprises or is
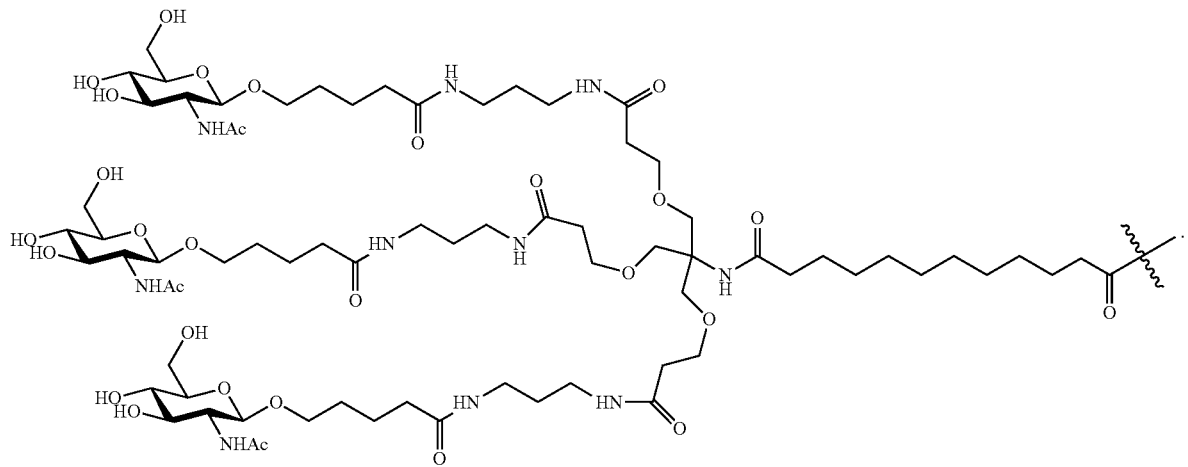

In some embodiments, $R^{TD}$ comprises or is
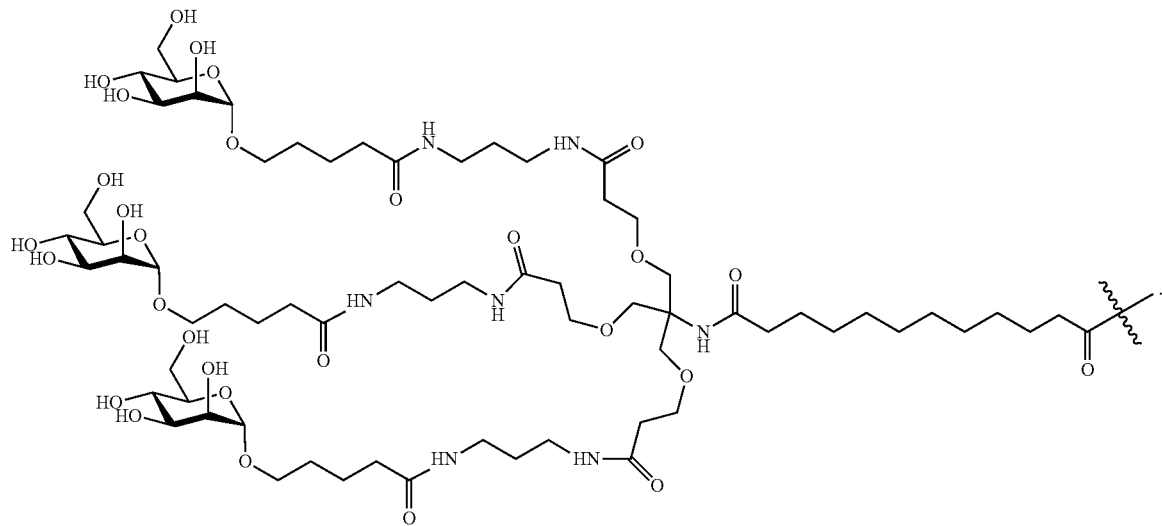
In some embodiments, $R^{1D}$ comprises or is
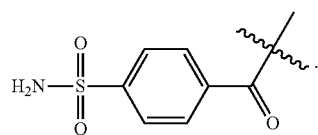 [SMILES: *C(=O)c1ccc(S(N)(=O)=O)cc1]
In some embodiments, $R^{TD}$ comprises or is
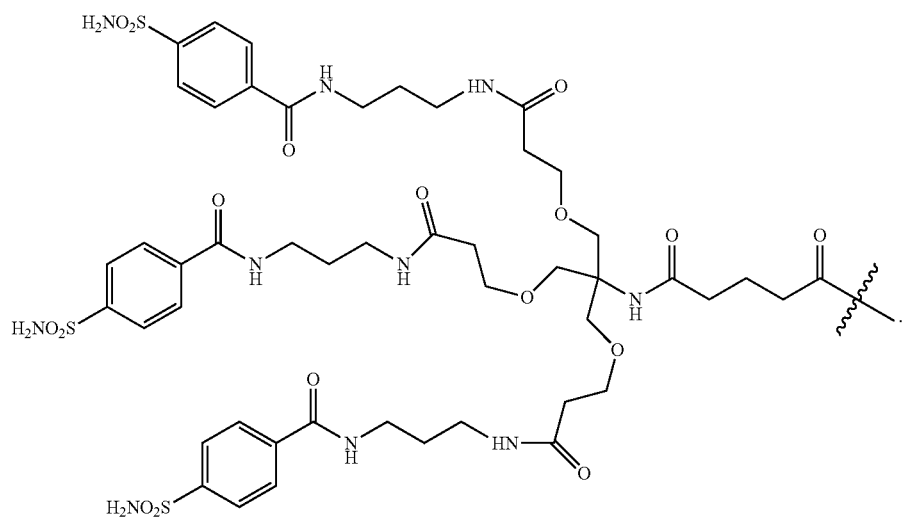 [SMILES: *C(=O)CCCC(=O)NC(COCCC(=O)NCCCNC(=O)c1ccc(S(N)(=O)=O)cc1)(COCCC(=O)NCCCNC(=O)c1ccc(S(N)(=O)=O)cc1)COCCC(=O)NCCCNC(=O)c1ccc(S(N)(=O)=O)cc1]

In some embodiments, $R^{TD}$ comprises or is
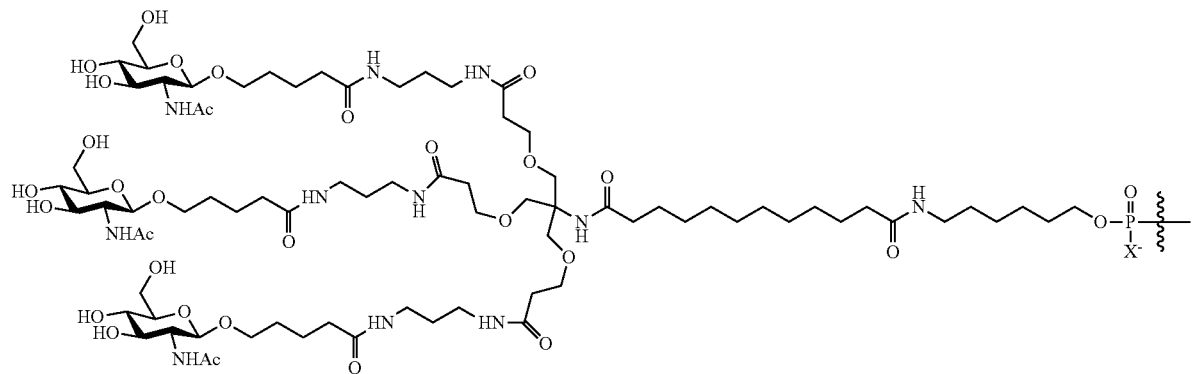
X = O or S
In some embodiments, $R^{TD}$ comprises or is
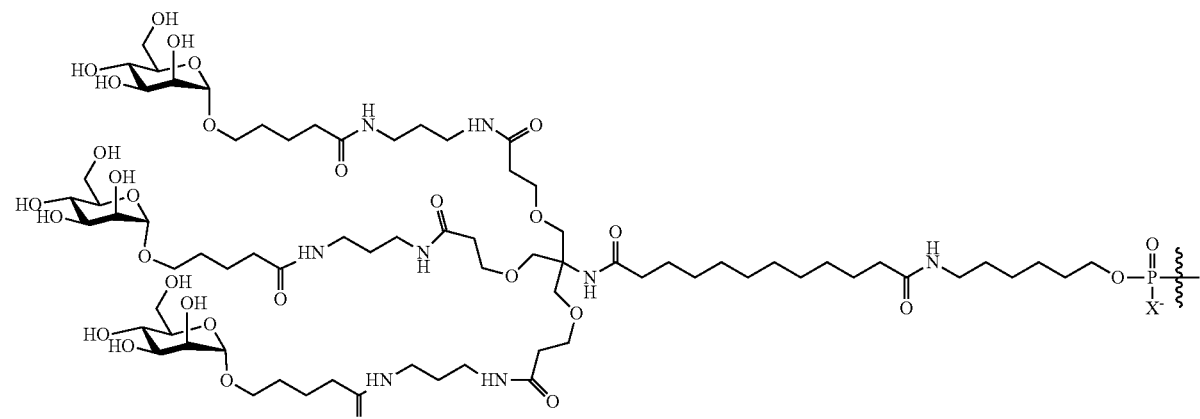
X = O or S
In some embodiments, $R^{TD}$ comprises or is
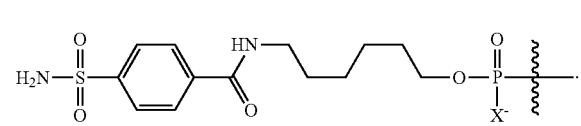
X = O or S In some embodiments, $R^{TD}$ comprises or is

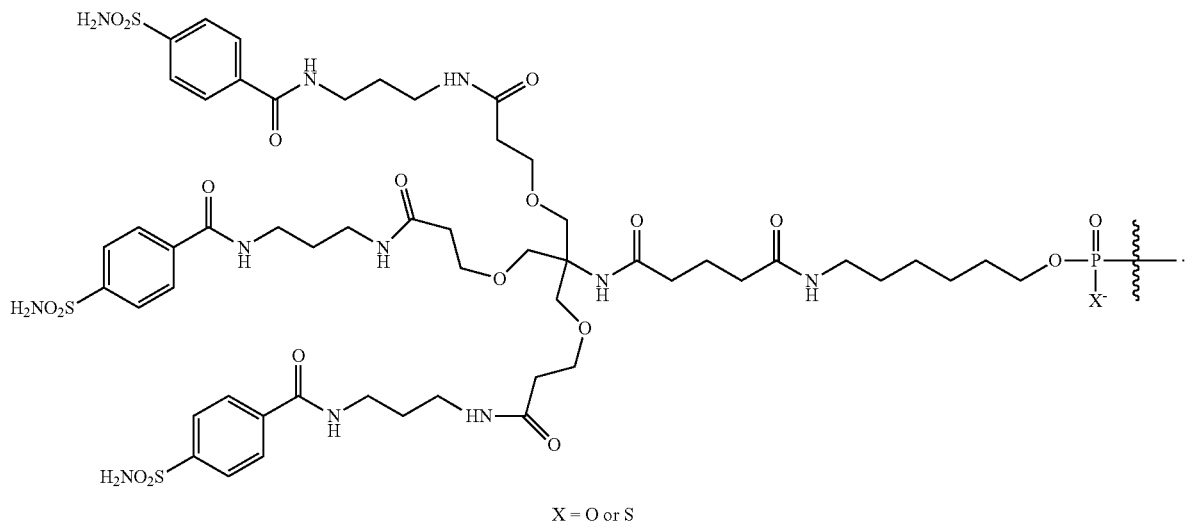

X = O or S

In some embodiments, $R^{TD}$ is a targeting moiety that comprises or is a lipid moiety. In some embodiments, X is O. In some embodiments, X is S.

In some embodiments, the present disclosure provides technologies (e.g., reagents, methods, etc.) for conjugating various moieties to oligonucleotide moieties. In some embodiments, the present disclosure provides technologies for conjugating targeting moiety to oligonucleotide moieties. In some embodiments, the present disclosure provides acids comprising targeting moieties for conjugation, e.g., $R^{LD}$—COOH. In some embodiments, the present disclosure provides linkers for conjugation, e.g., $L^M$. A person having ordinary skill in the art understands that many known and widely practiced technologies can be utilized for conjugation with oligonucleotide moieties in accordance with the present disclosure. In some embodiments, a provided acid is

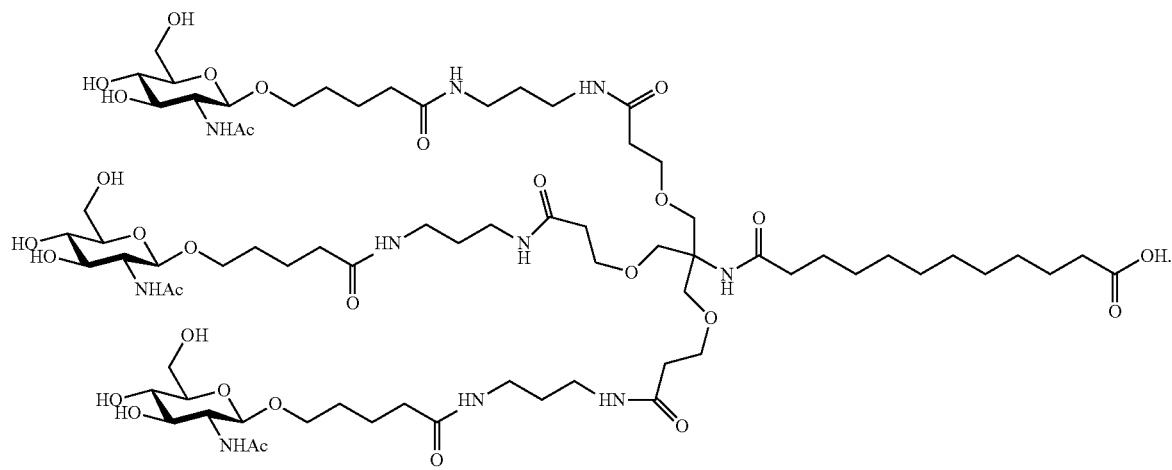

In some embodiments, a provided acid is
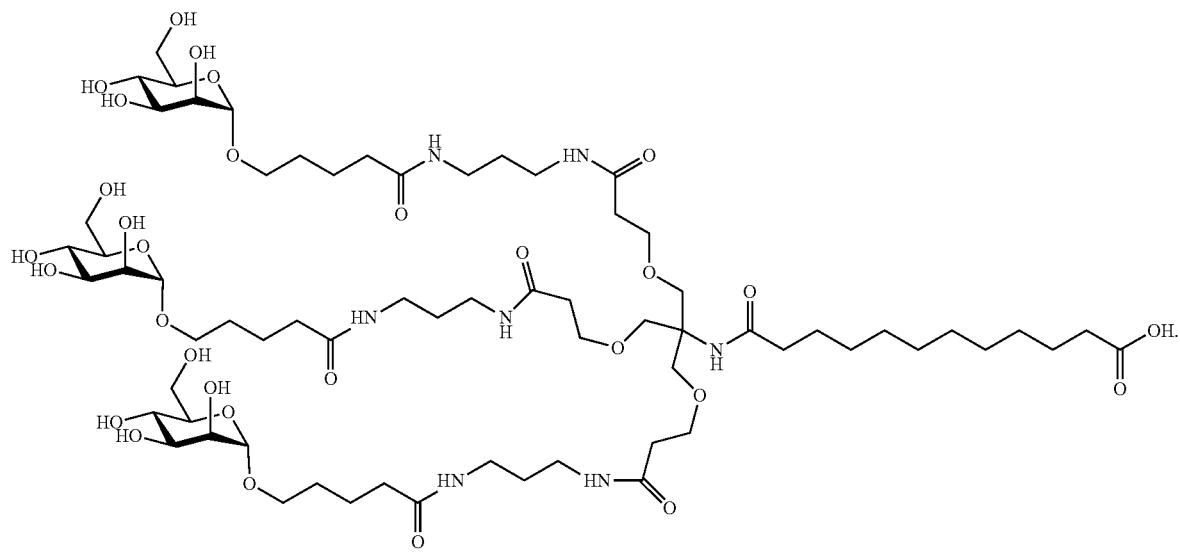
In some embodiments, a provided acid is
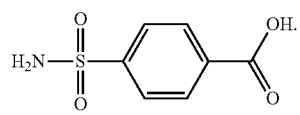 [SMILES: NS(=O)(=O)c1ccc(C(=O)O)cc1]
In some embodiments, a provided acid is
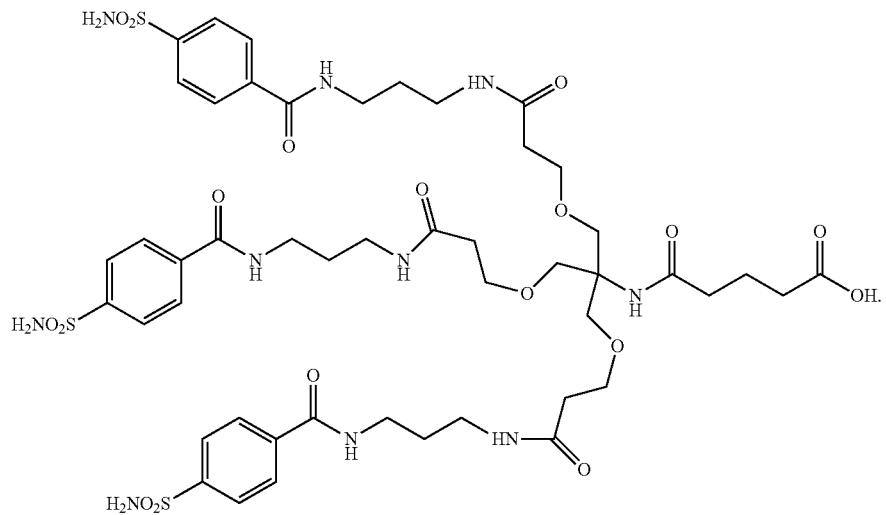 [SMILES: NS(=O)(=O)c1ccc(C(=O)NCCCNC(=O)CCOCC(COCCC(=O)NCCCNC(=O)c2ccc(S(N)(=O)=O)cc2)(COCCC(=O)NCCCNC(=O)c2ccc(S(N)(=O)=O)cc2)NC(=O)CCCC(=O)O)cc1]

In some embodiments, a provided acid is a fatty acid, which can provide a lipid moiety as a targeting moiety. In some embodiments, the present disclosure provides methods and reagents for preparing such acids.

In some embodiments, a PNPLA3 oligonucleotide, a PNPLA3 oligonucleotide capable of directing a decrease in the expression and/or level of a target gene or its gene product can comprise any lipid described herein or known in the art.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any lipid described herein or known in the art.

In some embodiments, a provided oligonucleotide comprises a lipid moiety. In some embodiments, a lipid moiety is incorporated by conjugation with a lipid. In some embodiments, a lipid is a fatty acid. In some embodiments, a PNPLA3 oligonucleotide is conjugated to a fatty acid. In some embodiments, a provided single-stranded RNAi agent comprises a lipid. In some embodiments, a provided single-stranded RNAi agent comprises a lipid conjugated to a nucleotide in the seed region. In some embodiments, a provided single-stranded RNAi agent comprises a lipid conjugated to a nucleotide in the post-seed region. In some embodiments, a provided single-stranded RNAi agent comprises a lipid conjugated at the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$, $16^{th}$, $17^{th}$, $18^{th}$, $19^{th}$, $20^{th}$, $21^{st}$, $22^{nd}$, $23^{rd}$, $24^{th}$ or $25^{th}$ nucleotide (counting from the 5'-end). In some embodiments, a provided single-stranded RNAi agent comprises a lipid conjugated at the $9^{th}$ or $11^{th}$ nucleotide (counting from the 5'-end). In some embodiments, a PNPLA3 oligonucleotide is conjugated at the base to a fatty acid. In some embodiments, a provided single-stranded RNAi agent comprises a lipid. In some embodiments, a provided single-stranded RNAi agent comprises a lipid conjugated at the base at the $9^{th}$ or $11^{th}$ nucleotide (counting from the 5'-end).

In some embodiments, a fatty acid comprises 10, 11, 12, 13, 14, 15, 16, 17, 18, 19, 20, 21, 22, 23, 24, 25, 26, 27, 28, 29, 30 or more carbon atoms. In some embodiments, a fatty acid comprises 10 or more carbon atoms. In some embodiments, a fatty acid comprises 11 or more carbon atoms. In some embodiments, a fatty acid comprises 12 or more carbon atoms. In some embodiments, a fatty acid comprises 13 or more carbon atoms. In some embodiments, a fatty acid comprises 14 or more carbon atoms. In some embodiments, a fatty acid comprises 15 or more carbon atoms. In some embodiments, a fatty acid comprises 16 or more carbon atoms. In some embodiments, a fatty acid comprises 17 or more carbon atoms. In some embodiments, a fatty acid comprises 18 or more carbon atoms. In some embodiments, a fatty acid comprises 19 or more carbon atoms. In some embodiments, a fatty acid comprises 20 or more carbon atoms. In some embodiments, a fatty acid comprises 30 or more carbon atoms.

In some embodiments, a lipid is palmitic acid. In some embodiments, a lipid is stearic acid or turbinaric acid. In some embodiments, a lipid is stearic acid. In some embodiments, a lipid is turbinaric acid.

In some embodiments, a lipid comprises an optionally substituted, $C_{10}$-$C_{80}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{60}$ saturated or partially unsaturated, aliphatic chain.

In some embodiments, a lipid comprises an optionally substituted $C_{10}$-$C_{60}$ linear, saturated or partially unsaturated, aliphatic chain.

In some embodiments, a lipid comprises a $C_{10}$-$C_{60}$ linear, saturated or partially unsaturated, aliphatic chain, optionally substituted with one or more $C_{1-4}$ aliphatic group.

In some embodiments, a lipid comprises an optionally substituted, $C_{10}$-$C_{60}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{60}$ saturated or partially unsaturated, aliphatic chain.

In some embodiments, a lipid comprises an optionally substituted $C_{10}$-$C_{60}$ linear, saturated or partially unsaturated, aliphatic chain.

In some embodiments, a lipid comprises a $C_{10}$-$C_{60}$ linear, saturated or partially unsaturated, aliphatic chain, optionally substituted with one or more $C_{1-4}$ aliphatic group.

In some embodiments, a lipid comprises an optionally substituted, $C_{10}$-$C_{40}$ saturated or partially unsaturated aliphatic group, wherein one or more methylene units are optionally and independently replaced by an optionally substituted group selected from $C_1$-$C_6$ alkylene, $C_1$-$C_6$ alkenylene, —C≡C—, a $C_1$-$C_6$ heteroaliphatic moiety, —C(R')$_2$—, -Cy-, —O—, —S—, —S—S—, —N(R')—, —C(O)—, —C(S)—, —C(NR')—, —C(O)N(R')—, —N(R')C(O)N(R')—, —N(R')C(O)—, —N(R')C(O)O—, —OC(O)N(R')—, —S(O)—, —S(O)$_2$—, —S(O)$_2$N(R')—, —N(R')S(O)$_2$—, —SC(O)—, —C(O)S—, —OC(O)—, and —C(O)O—, wherein each variable is independently as defined and described herein.

In some embodiments, a lipid comprises an optionally substituted $C_{10}$-$C_{60}$ saturated or partially unsaturated, aliphatic chain.

In some embodiments, a lipid comprises an optionally substituted $C_{10}$-$C_{60}$ linear, saturated or partially unsaturated, aliphatic chain.

In some embodiments, a lipid comprises a $C_{10}$-$C_{60}$ linear, saturated or partially unsaturated, aliphatic chain, optionally substituted with one or more $C_{1-4}$ aliphatic group.

In some embodiments, a lipid comprises an unsubstituted $C_{10}$-$C_{80}$ linear, saturated or partially unsaturated, aliphatic chain.

In some embodiments, a lipid comprises no more than one optionally substituted $C_{10}$-$C_{60}$ linear, saturated or partially unsaturated, aliphatic chain.

In some embodiments, a lipid comprises two or more optionally substituted $C_{10}$-$C_{60}$ linear, saturated or partially unsaturated, aliphatic chain.

In some embodiments, a lipid comprises an unsubstituted $C_{10}$-$C_{60}$ linear, saturated or partially unsaturated, aliphatic chain.

In some embodiments, a lipid comprises no more than one optionally substituted $C_{10}$-$C_{60}$ linear, saturated or partially unsaturated, aliphatic chain.

In some embodiments, a lipid comprises two or more optionally substituted $C_{10}$-$C_{60}$ linear, saturated or partially unsaturated, aliphatic chain.

In some embodiments, a lipid comprises an unsubstituted $C_{10}$-$C_{40}$ linear, saturated or partially unsaturated, aliphatic chain.

In some embodiments, a lipid comprises no more than one optionally substituted $C_{10}$-$C_{60}$ linear, saturated or partially unsaturated, aliphatic chain.

In some embodiments, a lipid comprises two or more optionally substituted $C_{10}$-$C_{60}$ linear, saturated or partially unsaturated, aliphatic chain.

In some embodiments, a lipid comprises a $C_{10}$-$C_{40}$ linear, saturated or partially unsaturated, aliphatic chain.

In some embodiments, a lipid comprises a $C_{10}$-$C_{30}$ linear, saturated or partially unsaturated, aliphatic chain.

In some embodiments, a lipid comprises a $C_{10}$-$C_{20}$ linear, saturated or partially unsaturated, aliphatic chain.

In some embodiments, a lipid comprises a $C_{10}$-$C_{16}$ linear, saturated or partially unsaturated, aliphatic chain.

In some embodiments, a lipid comprises a $C_{12}$-$C_{16}$ linear, saturated or partially unsaturated, aliphatic chain.

In some embodiments, a lipid comprises a $C_{14}$-$C_{16}$ linear, saturated or partially unsaturated, aliphatic chain.

In some embodiments, a lipid comprises a $C_{10}$-$C_{40}$ linear, saturated or partially unsaturated, aliphatic chain, optionally substituted with one or more $C_{1-4}$ aliphatic group.

In some embodiments, a lipid is selected from the group consisting of: lauric acid, myristic acid, palmitic acid, stearic acid, oleic acid, linoleic acid, alpha-linolenic acid, gamma-linolenic acid, docosahexaenoic acid (DHA or cis-DHA), turbinaric acid and dilinoleyl.

In some embodiments, a lipid is not conjugated to the oligonucleotide.

In some embodiments, a lipid is conjugated to the oligonucleotide.

In some embodiments, a lipid is conjugated to the oligonucleotide with a linker. In some embodiments, a linker has the structure of -L-.

In some embodiments, a targeting moiety is conjugated to a PNPLA3 oligonucleotide. In some embodiments, a provided oligonucleotide comprises one or more targeting moieties. In some embodiments, a targeting moiety is conjugated via a linker.

In some embodiments, a provided oligonucleotide comprises one or more lipid moieties, and one or more targeting moieties.

In some embodiments, a provided single-stranded RNAi agent comprises a lipid. In some embodiments, a provided single-stranded RNAi agent comprises a lipid moiety, wherein the lipid is C16 linear. In some embodiments, a provided single-stranded RNAi agent comprises a lipid, wherein the lipid is palmitic acid.

In some embodiments, a provided single-stranded RNAi agent comprises a lipid conjugated to a base. In some embodiments, a provided single-stranded RNAi agent comprises a lipid, wherein the lipid is $C_{16}$ linear conjugated to a base. In some embodiments, a provided single-stranded RNAi agent comprises a lipid, wherein the lipid is palmitic acid conjugated to a base.

In some embodiments, the present disclosure pertains to a chirally controlled oligonucleotide composition, wherein the composition further comprises a lipid. In some embodiments, a lipid is stearic acid or turbinaric acid. In some embodiments, a lipid is conjugated to the oligonucleotide.

In some embodiments, conjugation of a lipid to a PNPLA3 oligonucleotide improves at least one property of the oligonucleotide. In some embodiments, the property is increased activity (e.g., increased ability to mediate single-stranded RNA interference), or improved distribution to a tissue. In some embodiments, lipid conjugation improves activity. In some embodiments, lipid conjugation improves deliveries to one or more target tissues. In some embodiments, the tissue is muscle tissue. In some embodiments, the tissue is skeletal muscle, gastrocnemius, triceps, heart or diaphragm.

In some embodiments, a lipid comprises an optionally substituted, C10-C80 saturated or partially unsaturated aliphatic group, wherein one or more methylene units are optionally and independently replaced by an optionally substituted group selected from C1-C6 alkylene, C1-C6 alkenylene, a C1-C6 heteroaliphatic moiety, —C(R)$_2$—, -Cy-, —O—, —S—, —S—S—, —N(R)—, —C(O)—, —C(S)—, —C(NR)—, —C(O)N(R)—, —N(R)C(O)N(R), —N(R)C(O)—, —N(R)C(O)O—, —OC(O)N(R)—, —S(O)—, —S(O)$_2$—, —S(O)$_2$N(R)—, —N(R)S(O)$_2$—, —SC(O)—, —C(O)S—, —OC(O)—, and —C(O)O—, wherein each variable is independently as defined and described herein. In some embodiments, a lipid comprises an optionally substituted C10-C60 saturated or partially unsaturated, aliphatic chain. In some embodiments, a lipid comprises an optionally substituted C10-C60 linear, saturated or partially unsaturated, aliphatic chain. In some embodiments, a lipid comprises a C10-C60 linear, saturated or partially unsaturated, aliphatic chain, optionally substituted with one or more C1-4 aliphatic group. In some embodiments, a lipid comprises an optionally substituted, C10-C60 saturated or partially unsaturated aliphatic group, wherein one or more methylene units are optionally and independently replaced by an optionally substituted group selected from C1-C6 alkylene, C1-C6 alkenylene, a C1-C6 heteroaliphatic moiety, —C(R)$_2$—, -Cy-, —O—, —S—, —S—S—, —N(R)—, —C(O)—, —C(S)—, —C(NR)—, —C(O)N(R)—, —N(R)C(O)N(R), —N(R)C(O)—, —N(R)C(O)O—, —OC(O)N(R)—, —S(O)—, —S(O)$_2$—, —S(O)$_2$N(R)—, —N(R)S(O)$_2$—, —SC(O)—, —C(O)S—, —OC(O)—, and —C(O)O—, wherein each variable is independently as defined and described herein. In some embodiments, a lipid comprises an optionally substituted C10-C60 saturated or partially unsaturated, aliphatic chain. In some embodiments, a lipid comprises an optionally substituted C10-C60 linear, saturated or partially unsaturated, aliphatic chain. In some embodiments, a lipid comprises a C10-C60 linear, saturated or partially unsaturated, aliphatic chain, optionally substituted with one or more C1-4 aliphatic group. In some embodiments, a lipid comprises an optionally substituted, C10-C40 saturated or partially unsaturated aliphatic group, wherein one or more methylene units are optionally and independently replaced by an optionally substituted group selected from C1-C6 alkylene, C1-C6 alkenylene, a C1-C6 heteroaliphatic moiety, —C(R)$_2$—, -Cy-, —O—, —S—, —S—S—, —N(R)—, —C(O)—, —C(S)—, —C(NR)—, —C(O)N(R)—, —N(R)C(O)N(R), —N(R)C(O)—, —N(R)C(O)O—, —OC(O)N(R)—, —S(O)—, —S(O)$_2$—, —S(O)$_2$N(R)—, —N(R)S(O)$_2$—, —SC(O)—, —C(O)S—, —OC(O)—, and —C(O)O—, wherein each variable is independently as defined and described herein. In some embodiments, a lipid comprises an optionally substituted C10-C60 saturated or partially unsaturated, aliphatic chain. In some embodiments, a lipid comprises an optionally substituted C10-C60 linear, saturated or partially unsaturated, aliphatic chain. In some embodiments, a lipid comprises a C10-C60 linear, saturated or partially unsaturated, aliphatic chain, optionally substituted with one or more C1-4 aliphatic group. In some embodiments, a lipid comprises an unsubstituted C10-C80 linear, saturated or partially unsaturated, aliphatic chain. In some embodiments, a lipid comprises no more than one optionally substituted C10-C60 linear, saturated or partially unsaturated, aliphatic chain. In some embodiments, a lipid comprises two or more optionally substituted C10-C60 linear, saturated or partially unsaturated, aliphatic chain. In some embodiments, a lipid comprises an unsubstituted C10-C60 linear, saturated or partially unsaturated, aliphatic chain. In some embodiments, a lipid comprises no more than one optionally substituted C10-C60 linear, saturated or partially unsaturated, aliphatic chain. In some embodiments, a lipid comprises two or more optionally substituted C10-C60 linear, saturated or partially unsaturated, aliphatic chain. In some embodiments, a lipid comprises an unsubstituted C10-C40 linear, saturated or partially unsaturated, aliphatic chain. In some embodiments, a lipid comprises no more than one optionally substituted C10-C60 linear, saturated or partially unsaturated, aliphatic chain. In some embodiments, a lipid comprises two or more optionally substituted C10-C60 linear, saturated or partially unsaturated, aliphatic chain. In some embodiments, a lipid comprises a C10-C40 linear, saturated or partially unsaturated, aliphatic chain. In some embodiments, a lipid comprises a C10-C40 linear, saturated or partially unsaturated, aliphatic chain, optionally substituted with one or more C1-4 aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, the lipid is not conjugated to the oligonucleotide. In some embodiments, the lipid is conjugated to the oligonucleotide.

In some embodiments, conjugation of a lipid to a PNPLA3 oligonucleotide surprisingly improves at least one property of the oligonucleotide. In some embodiments, the property is increased activity (e.g., increased ability to mediate single-stranded RNA interference), or improved distribution to a tissue. In some embodiments, the tissue is muscle tissue. In some embodiments, the tissue is skeletal muscle, gastrocnemius, triceps, heart or diaphragm. In some embodiments, oligonucleotides comprising lipid moieties form, for example, micelles. In some embodiments, example improved properties are demonstrated, e.g., in one or more of the Figures.

In some embodiments, when assaying example oligonucleotides in mice, tested oligonucleotides are intravenous injected via tail vein in male C57BL/10ScSnDMDmdx mice (4-5 weeks old), at tested amounts, e.g., 10 mg/kg, 30 mg/kg, etc. In some embodiments, tissues are harvested at tested times, e.g., on Day, e.g., 2, 7 and/or 14, etc., after injection, in some embodiments, fresh-frozen in liquid nitrogen and stored in −80° C. until analysis.

Various assays can be used to assess oligonucleotide levels in accordance with the present disclosure. In some embodiments, hybrid-ELISA is used to quantify oligonucleotide levels in tissues using test article serial dilution as standard curve: for example, in an example procedure, maleic anhydride activated 96 well plate (Pierce 15110) was coated with 50 l of capture probe at 500 nM in 2.5% NaHCO$_3$ (Gibco, 25080-094) for 2 hours at 37° C. The plate was then washed 3 times with PBST (PBS+0.1% Tween-20), and blocked with 5% fat free milk-PBST at 37° C. for 1 hour. Test article oligonucleotide was serial diluted into matrix. This standard together with original samples were diluted with lysis buffer (4 M Guanidine; 0.33% N-Lauryl Sarcosine; 25 mM Sodium Citrate; 10 mM DTT) so that oligonucleotide amount in all samples is less than 100 ng/ml. 20 l of diluted samples were mixed with 180 l of 333 nM detection probe diluted in PBST, then denatured in PCR machine (65° C., 10 min, 95° C., 15 min, 4° C.). 50 l of denatured samples were distributed in blocked ELISA plate in triplicates, and incubated overnight at 4° C. After 3 washes of PBST, 1:2000 streptavidin-AP in PBST was added, 50 l per well and incubated at room temperature for 1 hour. After extensive wash with PBST, 100 l of AttoPhos (Promega S1000) was added, incubated at room temperature in dark for 10 min and read on plate reader (Molecular Device, M5) fluorescence channel. Ex435 nm, Em555 nm. Oligonucleotides in samples were calculated according to standard curve by 4-parameter regression.

As described and demonstrated in the present disclosure, in some embodiments, lipid conjugation improves delivery to a tissue. In some embodiments, lipid conjugation improves delivery to muscle. In some embodiments, lipid conjugation comprises conjugation with a fatty acid. In some embodiments, oligonucleotides are conjugated with turbinaric acid. In some embodiments, conjugation with turbinaric acid is particularly effective in improving oligonucleotide delivery to muscle.

In some embodiments, provided oligonucleotides are stable in both plasma and tissue homogenates.

In some embodiments, a provided single-stranded RNAi agent comprises a lipid conjugated at position 9 or 11 (counting from the 5'-end). In some embodiments, a provided single-stranded RNAi agent comprises a lipid, wherein the lipid is C16 linear conjugated at position 9 or 11 (counting from the 5'-end). In some embodiments, a provided single-stranded RNAi agent comprises a lipid, wherein the lipid is palmitic acid conjugated at position 9 or 11 (counting from the 5'-end).

In some embodiments, a provided single-stranded RNAi agent comprises a lipid conjugated to a base at position 9 or 11 (counting from the 5'-end). In some embodiments, a provided single-stranded RNAi agent comprises a lipid, wherein the lipid is C16 linear conjugated to a base at position 9 or 11 (counting from the 5'-end). In some embodiments, a provided single-stranded RNAi agent comprises a lipid, wherein the lipid is palmitic acid conjugated to a base at position 9 or 11 (counting from the 5'-end).

In some embodiments, a provided single-stranded RNAi agent comprises a lipid conjugated to a U base at position 9 or 11 (counting from the 5'-end). In some embodiments, a provided single-stranded RNAi agent comprises a lipid, wherein the lipid is C16 linear conjugated to a U base at position 9 or 11 (counting from the 5'-end). In some embodiments, a provided single-stranded RNAi agent comprises a lipid, wherein the lipid is palmitic acid conjugated to a U base at position 9 or 11 (counting from the 5'-end).

In some embodiments, a provided single-stranded RNAi comprises a structure of ImU, or 5'-lipid-2' OMeU.

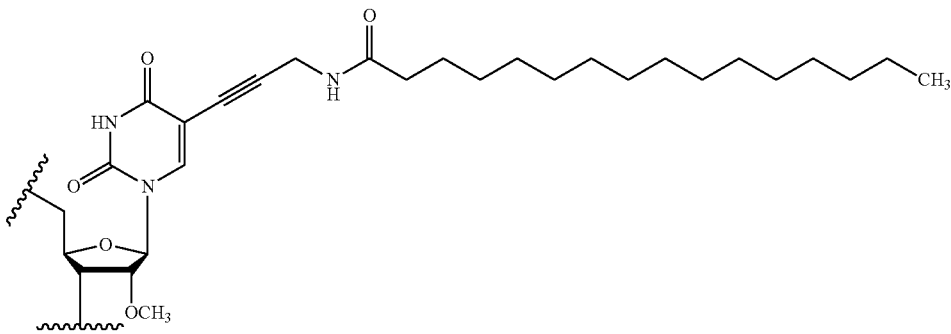

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any additional chemical moiety, including but not limited to, a lipid, described in any of U.S. Pat. Nos. 5,614,503; 5,780,009; 6,074,863; 6,258,581; 6,489,117; 6,677,445; 6,828,435; 6,846,921; 7,416,849; 7,494,982; 7,981,871; 8,106,022; 8,148,344; 8,318,508; 8,389,707; 8,450,467; 8,507,455; 8,703,731; 8,828,956; 8,901,046; 9,107,904; 9,352,048; 9,370,581; 9,370,582; 9,387,257; 9,388,415; 9,388,416; 9,393,316; and 9,404,112.

Optional Additional Chemical Moieties Conjugated to a PNPLA3 Oligonucleotide: A Carbohydrate Moiety or a Bicyclic Ketal, Including but not Limited to, a GalNAc Moiety In some embodiments, provided oligonucleotides or oligonucleotide compositions comprise one or more carbohydrates or carbohydrate moieties or bicyclic ketal moieties. In some embodiments, a carbohydrate moiety is a carbohydrate. In some embodiments, a carbohydrate moiety is or comprises a carbohydrate which is conjugated directly or indirectly to a PNPLA3 oligonucleotide. In some embodiments, carbohydrate moieties facilitate targeted delivery of oligonucleotides to desired locations, e.g., cells, tissues, organs, etc. In some embodiments, provided carbohydrate moieties facilitate delivery to liver. As appreciated by a personal having ordinary skill in the art, various carbohydrate moieties are described in the literature and can be utilized in accordance with the present disclosure.

Carbohydrate moieties can be incorporated into oligonucleotides at various locations, for example, sugar units, internucleotidic linkage units, nucleobase units, etc., optionally through one or more bivalent or multivalent (which can be used to connect two or more carbohydrate moieties to oligonucleotides) linkers. In some embodiments, the present disclosure provides technologies for carbohydrate incorporation into oligonucleotides. In some embodiments, the present disclosure provides technologies for incorporating carbohydrate moieties, optionally through one or more linkers, at nucleobase units, as alternative and/or addition to incorporation at internucleotidic linkages and/or sugar units, thereby providing enormous flexibility and/or improved properties and/or activities. In some embodiments, a provided oligonucleotide comprises at least one carbohydrate moiety, optionally through a linker, incorporated into the oligonucleotide at a nucleobase unit.

In some embodiments, a linker is $L^M$, wherein $L^M$ is a covalent bond, or a bivalent or multivalent, optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with Cy. In some embodiments, $L^M$ is bivalent. In some embodiments, $L^M$ is multivalent. In some embodiments, $L^M$ is

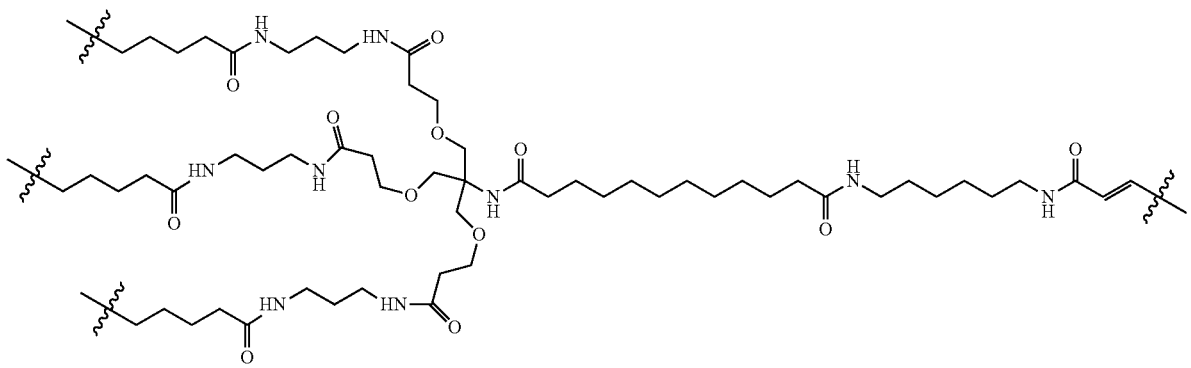

wherein $L^M$ is directly bond to a nucleobase, for example, as in:
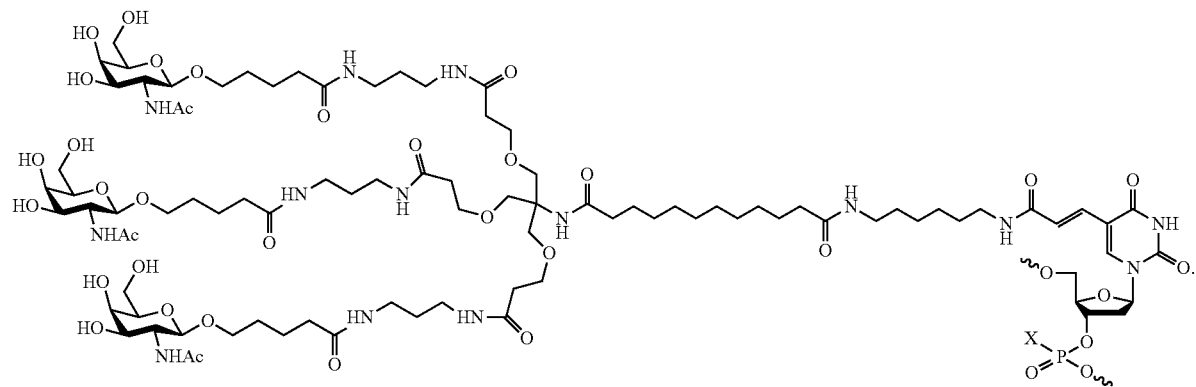
X = S⁻ or O⁻
In some embodiments, $L^M$ is
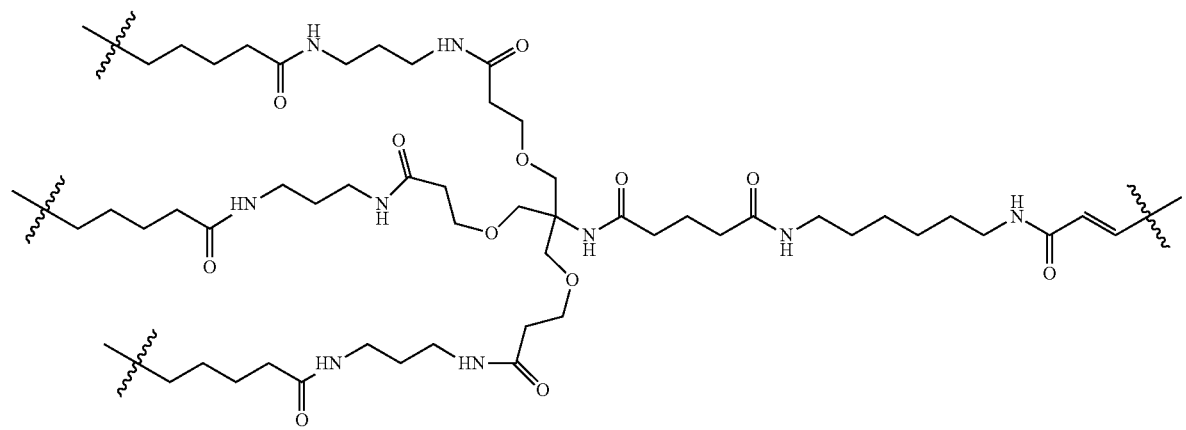 [SMILES: */C=C/C(=O)NCCCCCCNC(=O)CCCC(=O)NC(COCCC(=O)NCCCNC(=O)CCCC*)(COCCC(=O)NCCCNC(=O)CCCC*)COCCC(=O)NCCCNC(=O)CCCC*]
In some embodiments, $L^M$ is
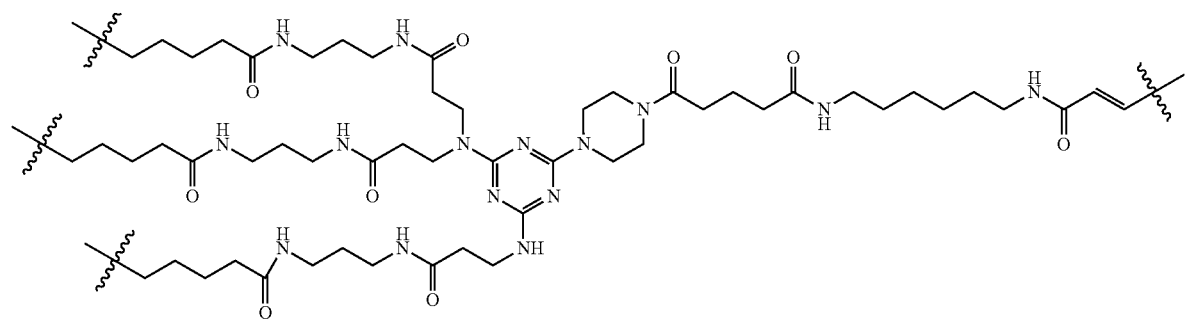 [SMILES: */C=C/C(=O)NCCCCCCNC(=O)CCCC(=O)N1CCN(c2nc(NCCC(=O)NCCCNC(=O)CCCC*)nc(N(CCC(=O)NCCCNC(=O)CCCC*)CCC(=O)NCCCNC(=O)CCCC*)n2)CC1]

In some embodiments, $L^M$ is

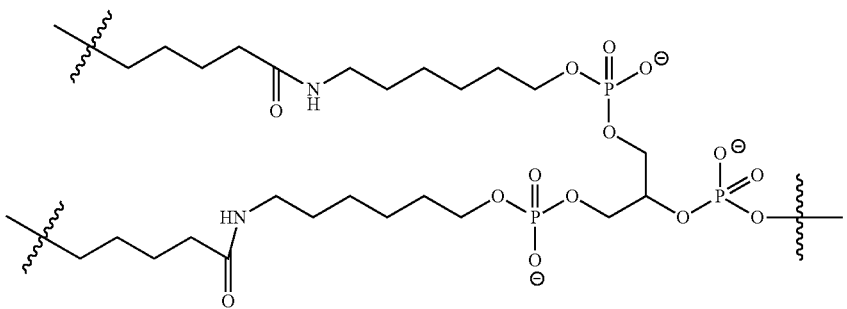 [SMILES: *CCCCC(=O)NCCCCCCOP(=O)([O-])OCC(COP(=O)([O-])OCCCCCCNC(=O)CCCC*)OP(=O)([O-])O*]

In some embodiments, $L^M$ is

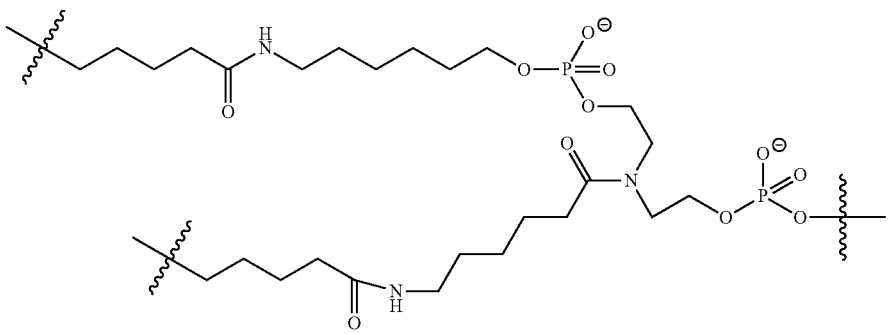 [SMILES: *CCCCC(=O)NCCCCCCOP(=O)([O-])OCCN(CCOP(=O)([O-])O*)C(=O)CCCCCNC(=O)CCCC*]

In some embodiments, a carbohydrate moiety or bicyclic ketal or bicyclic ketal moiety is $R^{CD}$, wherein $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are optionally and independently replaced with $Cy^L$. In some embodiments, $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)$_S$—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are independently replaced with a tetravalent monosaccharide, disaccharide or polysaccharide moiety. In some embodiments, $R^{CD}$ is an optionally substituted, linear or branched group selected from a $C_{1-100}$ aliphatic group and a $C_{1-100}$ heteroaliphatic group having 1-30 heteroatoms independently selected from oxygen, nitrogen, sulfur, phosphorus, boron and silicon, wherein one or more methylene units are optionally and independently replaced with $C_{1-6}$ alkylene, $C_{1-6}$ alkenylene, —C≡C—, —C(R')$_2$—, —O—, —S—, —S—S—, —N(R')—, —C(O)—, —C(S)—, —C(NR')—, —C(O)N(R')—, —N(R')C(O)N(R')—, —N(R')C(O)O—, —S(O)—, —S(O)$_2$—, —S(O)$_2$N(R')—, —C(O)S—, —C(O)O—, —P(O)(OR')—, —P(O)(SR')—, —P(O)(R')—, —P(O)(NR')—, —P(S)(OR')—, —P(S)(SR')—, —P(S)(R')—, —P(S)(NR')—, —P(R')—, —P(OR')—, —P(SR')—, —P(NR')—, —P(OR')[B(R')$_3$]—, —OP(O)(OR')O—, —OP(O)(SR')O—, —OP(O)(R')O—, —OP(O)(NR')O—, —OP(OR')O—, —OP(SR')O—, —OP(NR')O—, —OP(R')O—, or —OP(OR')[B(R')$_3$]O—; and one or more carbon atoms are independently replaced with a tetravalent GalNac moiety, or a tetravalent moiety of a GalNac derivative.

In some embodiments, $R^{CD}$ is optionally substituted

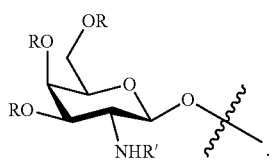

In some embodiments, $R^1$ is —C(O)R. In some embodiments, $R^{CD}$ is a monosaccharide moiety. In some embodiments, $R^{CD}$ is a monovalent GalNac moiety. In some embodiments, $R^{CD}$ is

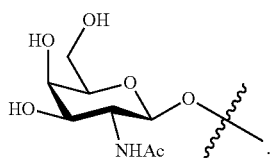

In some embodiments, $R^{CD}$ is optionally substituted

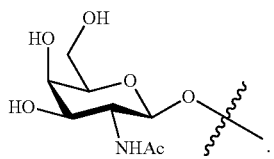

In some embodiments, $R^{CD}$ is optionally substituted

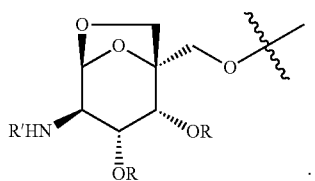

In some embodiments, $R^1$ is —C(O)R. In some embodiments, $R^{CD}$ is optionally substituted

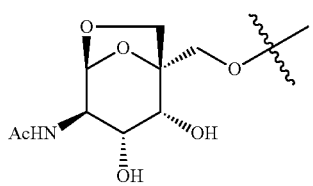

In some embodiments, $R^{CD}$ is a disaccharide moiety. In some embodiments, $R^{CD}$ is a polysaccharide moiety.

In some embodiments, $R^{CD}$ has the structure of $R^G$-L-, wherein $R^G$ is —H, or an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon. In some embodiments, $R^{CD}$ has the structure of $R^G$-L-, wherein $R^G$ is an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon. In some embodiments, $R^{CD}$ has the structure of $R^G$-L-, wherein $R^G$ is an optionally substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein at least one heteroatom is oxygen. In some embodiments, $R^G$ is substituted, and at least one substitute of each $R^G$ is bonded to $R^G$ through an oxygen atom. In some embodiments, $R^G$ is substituted, and at least one substitute of each $R^G$ is bonded to $R^G$ through a nitrogen atom. In some embodiments, $R^G$ is independently substituted, and each carbon atom of each $R^G$ is independently bonded to a substituent through an oxygen or nitrogen atom. In some embodiments, $R^G$ is independently substituted, and each carbon atom of each $R^G$ is independently bonded to a substituent through an oxygen or nitrogen atom. In some embodiments, $R^G$ is optionally substituted 3-20 membered heterocyclyl having 1-10 oxygen atoms. In some embodiments, $R^G$ is optionally substituted 3-6 membered heterocyclyl having one oxygen atom. In some embodiments, each $R^G$ is independently optionally substituted 3-20 membered heterocyclyl having 1-10 oxygen atoms. In some embodiments, $R^G$ is independently optionally substituted 3-6 membered heterocyclyl having one oxygen atom. In some embodiments, each carbon of the heterocyclyl ring of $R^G$ is independently boned to an oxygen or nitrogen atom. In some embodiments, two or more carbon atoms of the heterocyclyl ring of $R^G$ are independently boned to an oxygen or nitrogen atom. In some embodiments, two or more carbon atoms of the heterocyclyl ring of $R^G$ are independently boned to an oxygen or nitrogen atom. In some embodiments, three or more carbon atoms of the heterocyclyl ring of $R^G$ are independently boned to an oxygen or nitrogen atom. In some embodiments, four or more carbon atoms of the heterocyclyl ring of $R^G$ are independently boned to an oxygen or nitrogen atom. In some embodiments, five or more carbon atoms of the heterocyclyl ring of $R^G$ are independently boned to an oxygen or nitrogen atom. In some embodiments, two or more carbon atoms of the heterocyclyl ring of $R^G$ are independently boned to an oxygen atom. In some embodiments, three or more carbon atoms of the heterocyclyl ring of $R^G$ are independently boned to an oxygen atom. In some embodiments, four or more carbon atoms of the heterocyclyl ring of $R^G$ are independently boned to an oxygen atom. In some embodiments, five or more carbon atoms of the heterocyclyl ring of $R^G$ are independently boned to an oxygen atom. In some embodiments, $R^G$—H is $C_{3-20}$ polyol comprising a —CHO or —C(O)— group.

In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are R groups. In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OR or —N(R)$_2$ groups. In some embodiments, $R^{CD}$ has the structure of $R^G$-L-, wherein $R^G$ is —H, or a substituted group selected from $C_3$-$C_{20}$ cycloaliphatic, and 3-20 membered heterocyclyl having 1-10 heteroatoms independently selected from oxygen, nitrogen, sulfur, phosphorus, boron and silicon, wherein 1-20 of the substituents are —OH and —N(R)₂. In some embodiments, $R^{CD}$ has the structure of $R^G$-L-, wherein $R^G$ is —H, or a substituted group selected from C₃-C₂₀ cycloaliphatic, and 3-20 membered heterocyclyl having 1-10 heteroatoms independently selected from oxygen, nitrogen, sulfur, phosphorus, boron and silicon, wherein 1-20 of the substituents are —OH and —NHR. In some embodiments, $R^{CD}$ has the structure of $R^G$-L-, wherein $R^G$ is —H, or a substituted group selected from C3-C20 cycloaliphatic, and 3-20 membered heterocyclyl having 1-10 heteroatoms independently selected from oxygen, nitrogen, sulfur, phosphorus, boron and silicon, wherein 1-20 of the substituents are —OH and —NHC(O)R.

In some embodiments, $R^G$ is substituted 3-20 membered heterocyclyl having 1-10 heteroatoms independently selected from oxygen, nitrogen, sulfur, phosphorus, boron and silicon. In some embodiments, $R^G$ is substituted 3-20 membered heterocyclyl having 1-10 heteroatoms independently selected from oxygen and nitrogen. In some embodiments, $R^G$ is substituted 3-20 membered heterocyclyl having 1-10 oxygen. In some embodiments, $R^G$ is substituted

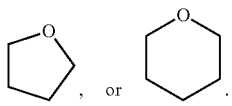

In some embodiments, $R^G$ is substituted

In some embodiments, $R^G$ is substituted

In some embodiments, $R^G$ is

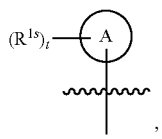

wherein each variable is independently as described in the present disclosure. In some embodiments, t is 1, 2, 3, 4, 5, 6, 7, 8, 9, or 10. In some embodiments, t is at least 1, 2, 3, 4, 5, 6, 7, 8, 9, or 10. In some embodiments, t is at least 1. In some embodiments, t is at least 2. In some embodiments, t is at least 3. In some embodiments, t is at least 4. In some embodiments, t is at least 5. In some embodiments, t is at least 6. In some embodiments, each $R^{1s}$ is independently —OR¹ or —N(R')₂. In some embodiments, each R¹ is independently —C(O)R. In some embodiments, each $R^{1s}$ is independently —OR' or —NHR'. In some embodiments, each $R^{1s}$ is independently —OH or —NHR'. In some embodiments, each $R^{1s}$ is independently —OH or —NHC(O)R. In some embodiments, Ring A is optionally substituted

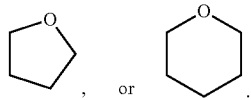 [SMILES: C1CCOC1 ; "," ; C1CCOCC1 ; "."]

In some embodiments, Ring A is optionally substituted

In some embodiments, Ring A is optionally substituted

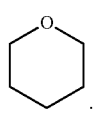

In some embodiments, $R^G$ is

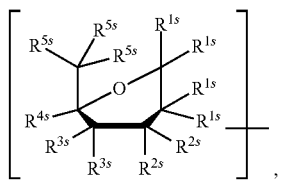

wherein each variable is independently as described in the present disclosure (i.e., $R^G$—H is

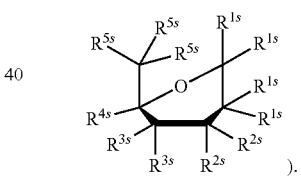

).

In some embodiments, at least 1, 2, 3, 4, 5, or 6 of $R^{1s}$, $R^{2s}$, $R^{3s}$, $R^{4s}$ and $R^{5s}$ are independently —OR' or —N(R')₂. In some embodiments, at least 1, 2, 3, 4, 5, or 6 of $R^{1s}$, $R^{2s}$, $R^{3s}$, $R^{4s}$ and $R^{5s}$ are independently —OR' or —NHR'. In some embodiments, at least 1, 2, 3, 4, 5, or 6 of $R^{1s}$, $R^{2s}$, $R^{3s}$, $R^{4s}$ and $R^{5s}$ are independently —OH or —NHR'. In some embodiments, at least 1, 2, 3, 4, 5, or 6 of $R^{1s}$, $R^{2s}$, $R^{3s}$, $R^{4s}$ and $R^{5s}$ are independently —OH or —NHC(O)R. In some embodiments, at least 1, 2, 3, 4, 5, or 6 of $R^{1s}$, $R^{2s}$, $R^{3s}$, $R^{4s}$ and $R^{5s}$ are —OH.

In some embodiments, each ring carbon atom of the cycloaliphatic or heterocyclic ring of $R^G$ is independently substituted. In some embodiments, no more than 1, 2, 3, 4, 5, 6, 7, 8, 9, or 10 ring carbon atoms of the cycloaliphatic or heterocyclic ring of $R^G$ are not substituted. In some embodiments, no more than 1 ring carbon atom is not substituted. In some embodiments, no more than 2 ring carbon atoms are not substituted. In some embodiments, no more than 3 ring carbon atoms are not substituted. In some embodiments, no more than 4 ring carbon atoms are not substituted. In some embodiments, no more than 5 ring carbon atoms are not substituted. In some embodiments, no more than 6 ring carbon atoms are not substituted. In some embodiments, no more than 7 ring carbon atoms are not substituted. In some embodiments, no more than 8 ring carbon atoms are not substituted. In some embodiments, no more than 9 ring carbon atoms are not substituted. In some embodiments, no more than 10 ring carbon atoms are not substituted. In some embodiments, no more than 1, 2, 3, 4, 5, 6, 7, 8, 9, or 10 ring carbon atoms of the cycloaliphatic or heterocyclic ring of $R^G$ are not substituted with —OH or —N(R')$_2$. In some embodiments, no more than 1 ring carbon atom is not substituted with —OH or —N(R')$_2$. In some embodiments, no more than 2 ring carbon atoms are not substituted with —OH or —N(R')$_2$. In some embodiments, no more than 3 ring carbon atoms are not substituted with —OH or —N(R')$_2$. In some embodiments, no more than 4 ring carbon atoms are not substituted with —OH or —N(R')$_2$. In some embodiments, no more than 5 ring carbon atoms are not substituted with —OH or —N(R')$_2$. In some embodiments, no more than 6 ring carbon atoms are not substituted with —OH or —N(R')$_2$. In some embodiments, no more than 7 ring carbon atoms are not substituted with —OH or —N(R')$_2$. In some embodiments, no more than 8 ring carbon atoms are not substituted with —OH or —N(R')$_2$. In some embodiments, no more than 9 ring carbon atoms are not substituted with —OH or —N(R')$_2$. In some embodiments, no more than 10 ring carbon atoms are not substituted with —OH or —N(R')$_2$. In some embodiments, no more than 1, 2, 3, 4, 5, 6, 7, 8, 9, or 10 ring carbon atoms of the cycloaliphatic or heterocyclic ring of $R^G$ are not substituted with —OH. In some embodiments, no more than 1 ring carbon atom is not substituted with —OH. In some embodiments, no more than 2 ring carbon atoms are not substituted with —OH. In some embodiments, no more than 3 ring carbon atoms are not substituted with —OH. In some embodiments, no more than 4 ring carbon atoms are not substituted with —OH. In some embodiments, no more than 5 ring carbon atoms are not substituted with —OH. In some embodiments, no more than 6 ring carbon atoms are not substituted with —OH. In some embodiments, no more than 7 ring carbon atoms are not substituted with —OH. In some embodiments, no more than 8 ring carbon atoms are not substituted with —OH. In some embodiments, no more than 9 ring carbon atoms are not substituted with —OH. In some embodiments, no more than 10 ring carbon atoms are not substituted with —OH. In some embodiments, at least 10%, 20%, 30%, 40%, 50%, 60%, 70%, 80%, 90%, or 95% percent of the ring carbon atoms of the cycloaliphatic or heterocyclic ring of $R^G$ are substituted with —OH or —N(R')$_2$. In some embodiments, no more than 10%, 20%, 30%, 40%, 50%, 60%, 70%, 80%, 90%, or 95% of the ring carbon atoms of the cycloaliphatic or heterocyclic ring of $R^G$ are not substituted with —OH. In some embodiments, no more than 10% of the ring carbon atoms are not substituted with —OH. In some embodiments, no more than 20% of the ring carbon atoms are not substituted with —OH. In some embodiments, each ring carbon atom of the cycloaliphatic or heterocyclic ring of $R^G$ is independently substituted. In some embodiments, at least 1, 2, 3, 4, 5, 6, 7, 8, 9, or 10 ring carbon atoms of the cycloaliphatic or heterocyclic ring of $R^G$ are substituted. In some embodiments, at least 1 ring carbon atom is substituted. In some embodiments, at least 2 ring carbon atoms are substituted. In some embodiments, at least 3 ring carbon atoms are substituted. In some embodiments, at least 4 ring carbon atoms are substituted. In some embodiments, at least 5 ring carbon atoms are substituted. In some embodiments, at least 6 ring carbon atoms are substituted. In some embodiments, at least 7 ring carbon atoms are substituted. In some embodiments, at least 8 ring carbon atoms are substituted. In some embodiments, at least 9 ring carbon atoms are substituted. In some embodiments, at least 10 ring carbon atoms are substituted. In some embodiments, at least 1, 2, 3, 4, 5, 6, 7, 8, 9, or 10 ring carbon atoms of the cycloaliphatic or heterocyclic ring of $R^G$ are substituted with —OH or —N(R')$_2$. In some embodiments, at least 1 ring carbon atom is substituted with —OH or —N(R')$_2$. In some embodiments, at least 2 ring carbon atoms are substituted with —OH or —N(R')$_2$. In some embodiments, at least 3 ring carbon atoms are substituted with —OH or —N(R')$_2$. In some embodiments, at least 4 ring carbon atoms are substituted with —OH or —N(R')$_2$. In some embodiments, at least 5 ring carbon atoms are substituted with —OH or —N(R')$_2$. In some embodiments, at least 6 ring carbon atoms are substituted with —OH or —N(R')$_2$. In some embodiments, at least 7 ring carbon atoms are substituted with —OH or —N(R')$_2$. In some embodiments, at least 8 ring carbon atoms are substituted with —OH or —N(R')$_2$. In some embodiments, at least 9 ring carbon atoms are substituted with —OH or —N(R')$_2$. In some embodiments, at least 10 ring carbon atoms are substituted with —OH or —N(R')$_2$. In some embodiments, at least 1, 2, 3, 4, 5, 6, 7, 8, 9, or 10 ring carbon atoms of the cycloaliphatic or heterocyclic ring of $R^G$ are substituted with —OH. In some embodiments, at least 1 ring carbon atom is substituted with —OH. In some embodiments, at least 2 ring carbon atoms are substituted with —OH. In some embodiments, at least 3 ring carbon atoms are substituted with —OH. In some embodiments, at least 4 ring carbon atoms are substituted with —OH. In some embodiments, at least 5 ring carbon atoms are substituted with —OH. In some embodiments, at least 6 ring carbon atoms are substituted with —OH. In some embodiments, at least 7 ring carbon atoms are substituted with —OH. In some embodiments, at least 8 ring carbon atoms are substituted with —OH. In some embodiments, at least 9 ring carbon atoms are substituted with —OH. In some embodiments, at least 10 ring carbon atoms are substituted with —OH. In some embodiments, at least 10%, 20%, 30%, 40%, 50%, 60%, 70%, 80%, 90%, or 95% percent of the ring carbon atoms of the cycloaliphatic or heterocyclic ring of $R^G$ are substituted with —OH or —N(R')$_2$. In some embodiments, at least 10% the ring carbon atoms are substituted with —OH or —N(R')$_2$. In some embodiments, at least 20% the ring carbon atoms are substituted with —OH or —N(R')$_2$. In some embodiments, at least 30% of the ring carbon atoms are substituted with —OH or —N(R')$_2$. In some embodiments, at least 40% of the ring carbon atoms are substituted with —OH or —N(R')$_2$. In some embodiments, at least 50% of the ring carbon atoms are substituted with —OH or —N(R')$_2$. In some embodiments, at least 60% of the ring carbon atoms are substituted with —OH or —N(R')$_2$. In some embodiments, at least 70% of the ring carbon atoms are substituted with —OH or —N(R')$_2$. In some embodiments, at least 80% of the ring carbon atoms are substituted with —OH or —N(R')$_2$. In some embodiments, at least 90% of the ring carbon atoms are substituted with —OH or —N(R')$_2$. In some embodiments, at least 95% of the ring carbon atoms are substituted with —OH or —N(R')$_2$. In some embodiments, at least 10%, 20%, 30%, 40%, 50%, 60%, 70%, 80%, 90%, or 95% of the ring carbon atoms of the cycloaliphatic or heterocyclic ring of $R^G$ are substituted with —OH. In some embodiments, at least 10% of the ring carbon atoms are substituted with —OH. In some embodiments, at least 20% of the ring carbon atoms are substituted with —OH. In some embodiments, at least 30% of the ring carbon atoms are substituted with —OH. In some embodiments, at least 40% of the ring carbon atoms are substituted with —OH. In some embodiments, at least 50% of the ring carbon atoms are substituted with —OH. In some embodiments, at least 60% of the ring carbon atoms are substituted with —OH. In some embodiments, at least 70% of the ring carbon atoms are substituted with —OH. In some embodiments, at least 80% of the ring carbon atoms are substituted with —OH. In some embodiments, at least 90% of the ring carbon atoms are substituted with —OH. In some embodiments, at least 95% of the ring carbon atoms are substituted with —OH. In some embodiments, at least one ring carbon atom is substituted with —N(R')$_2$. In some embodiments, at least one ring carbon atom is substituted with —NHC(O)R. In some embodiments, at least one ring carbon atom is substituted with —NHC(O)R, wherein R is optionally substituted C$_{1-6}$ aliphatic. In some embodiments, at least one ring carbon atom is substituted with —NHAc.

In some embodiments, R$^G$ is optionally substituted

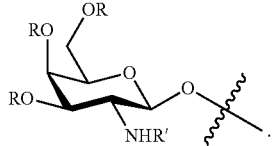

In some embodiments, R$^1$ is —C(O)R. In some embodiments, R$^G$ is

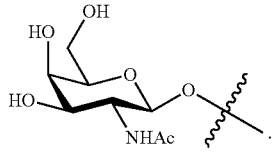

In some embodiments, R$^G$ is optionally substituted

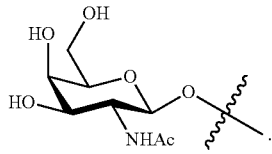

In some embodiments, R$^G$ is optionally substituted

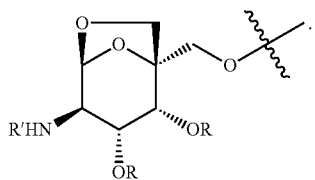

In some embodiments, R$^1$ is —C(O)R. In some embodiments, R$^G$ is optionally substituted

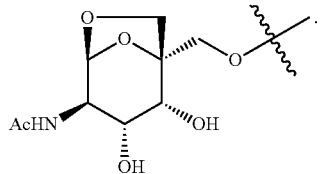

In some embodiments, R$^{CD}$, or R$^G$, is of such a structure that R$^{CD}$—H, or R$^G$—H, is

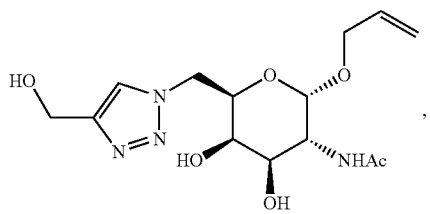

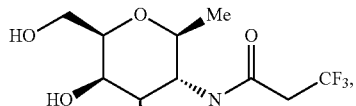

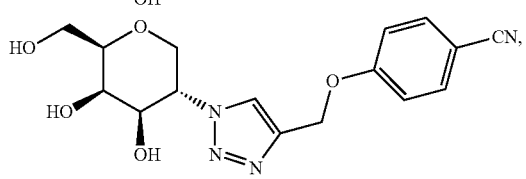

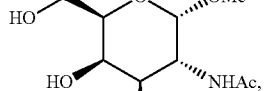

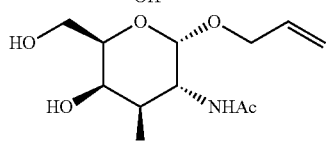

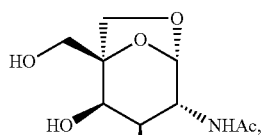
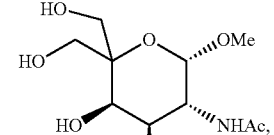

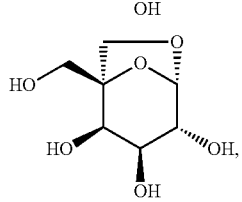
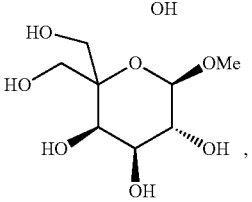

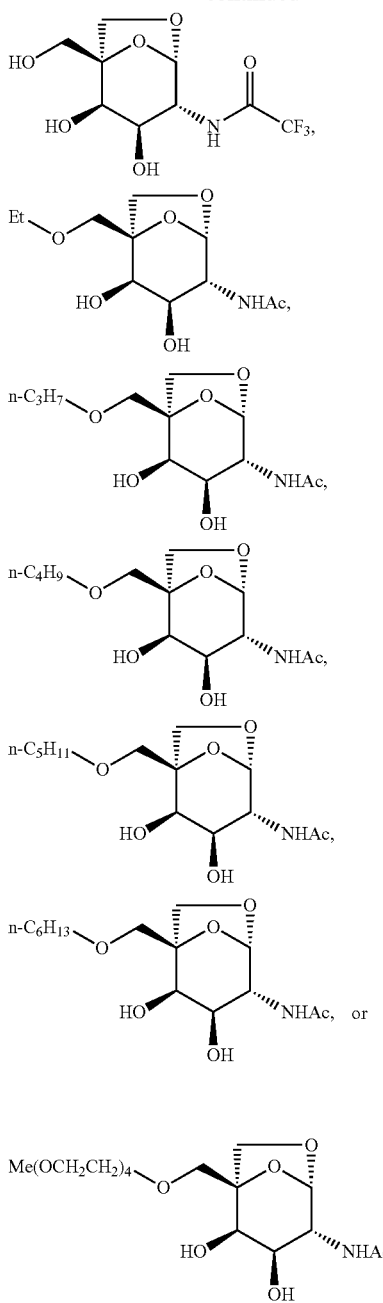

In some embodiments, $R^{CD}$, or $R^G$, is of such a structure that $R^{CD}$—H, or $R^G$—H, is a ligand for the asialoglycoprotein receptor (ASGPR). Various other ASGPR ligands are known in the art and can be utilized in accordance with the present disclose. In some embodiments, carbohydrate moieties described in are useful for targeted delivery of provided oligonucleotides to liver.

In some embodiments, L is a covalent bond. In some embodiments, L is bivalent optionally substituted $C_{1-6}$ aliphatic wherein one or more methylene units are independently and optionally replaced with —O—. In some embodiments, L is —O—CH$_2$—.

In some embodiments, $R^{CD}$ is an oligomeric or polymeric moiety of $R^G$—H, wherein each $R^G$ is independently as described in the present disclosure.

In some embodiments, a PNPLA3 oligonucleotide or single-stranded RNAi agent comprises any targeting moiety described herein or known in the art. In some embodiments, a PNPLA3 oligonucleotide is a single-stranded RNAi agent.

In some embodiments, a targeting moiety is a ligand for the asialoglycoprotein receptor (ASGPR).

In some embodiments, a targeting moiety is a ligand for the asialoglycoprotein receptor (ASGPR) disclosed in: Sanhueza et al. J. Am. Chem. Soc., 2017, 139 (9), pp 3528-3536.

In some embodiments, a targeting moiety is a ligand for the asialoglycoprotein receptor (ASGPR) disclosed in Liras et al. US 20160207953.

In some embodiments, a targeting moiety is a substituted-6,8-dioxabicyclo[3.2.1]octane-2,3-diol derivative disclosed in Liras et al. US 20160207953.

In some embodiments, a targeting moiety is a ligand for the asialoglycoprotein receptor (ASGPR) disclosed in Liras et al. US 20150329555.

In some embodiments, a targeting moiety is a substituted-6,8-dioxabicyclo[3.2.1]octane-2,3-diol derivative disclosed in Liras et al. US 20150329555.

In some embodiments, an additional chemical moiety conjugated to a PNPLA3 oligonucleotide or single-stranded RNAi agent is a GalNAc moiety. In some embodiments, an additional chemical moiety conjugated to a PNPLA3 oligonucleotide or single-stranded RNAi agent is a GalNAc moiety which is conjugated at any position.

In some embodiments, an additional chemical moiety conjugated to a PNPLA3 oligonucleotide or single-stranded RNAi agent is a GalNAc moiety, conjugated via a linker to a 5'-H T. In some embodiments, an additional chemical moiety conjugated to a PNPLA3 oligonucleotide or single-stranded RNAi agent is a GalNAc moiety, conjugated via a linker to a 5'-H T which is conjugated at any position.

In some embodiments, an additional chemical moiety is GaNC6T (also known as TGaNC6T, or conjugation of a GalNAc moiety to 5'H T via amino C6 linker) at any position.

In some embodiments, an additional chemical moiety is GaNC6T, e.g., conjugation of a GalNAc moiety to 5'H T via amino C6 linker (e.g., at the penultimate or antepenultimate nucleotide [counting 5' to 3']; for example, the 5' nucleotide of the 3'-terminal dinucleotide (e.g., the 5' nucleotide of the 3'-terminal dinucleotide is, of the two nucleotides of the 3'-terminal dinucleotide, the nucleotide closer to the 5'-end of the oligonucleotide) or the nucleotide immediately 5' to the 5' nucleotide of the 3'-terminal dinucleotide:

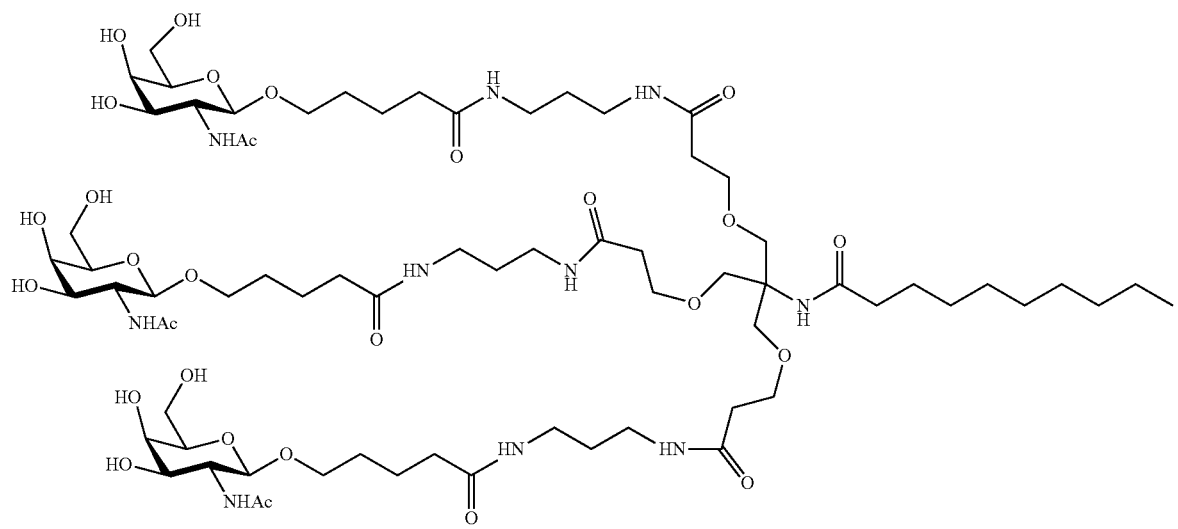

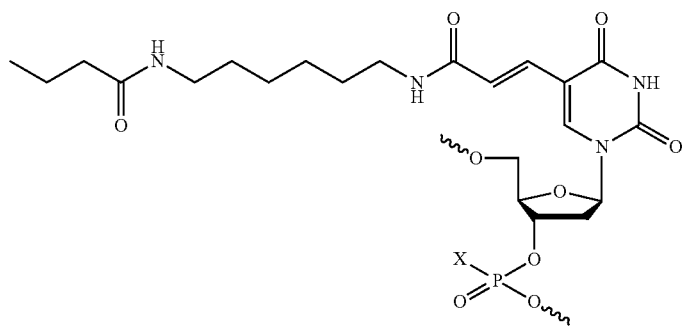

X = S⁻ or O⁻

In some embodiments or single-stranded RNAi agent, the oligonucleotide or single-stranded RNAi agent comprises a linker conjugating a GalNAc moiety to the oligonucleotide or single-stranded RNAi agent. In some embodiments or single-stranded RNAi agent, the oligonucleotide or single-stranded RNAi agent comprises a linker conjugating a GalNAc moiety to the oligonucleotide or single-stranded RNAi agent, wherein the linker is attached at the 2' position of a sugar. In some embodiments or single-stranded RNAi agent, the oligonucleotide or single-stranded RNAi agent comprises a linker conjugating a GalNAc moiety to the oligonucleotide or single-stranded RNAi agent, wherein the linker is attached to a base. In some embodiments or single-stranded RNAi agent, the oligonucleotide or single-stranded RNAi agent comprises a linker conjugating a GalNAc moiety to the oligonucleotide or single-stranded RNAi agent, wherein the linker is attached to a T base. In some embodiments or single-stranded RNAi agent, the oligonucleotide or single-stranded RNAi agent comprises a linker conjugating a GalNAc moiety to the oligonucleotide or single-stranded RNAi agent.

In some embodiments, a linker attaching a GalNAc moiety is a biocleavable linker. Such a linker allows the intracellular removal of the GalNAc moiety, so that the GalNAc moiety will not interfere with Ago-2 activity or RNA interference.

In some embodiments, a GalNAc moiety is conjugated to a PNPLA3 oligonucleotide or single-stranded RNAi agent at the penultimate or antepenultimate nucleotide.

In some embodiments, a GalNAc moiety can be conjugated at the penultimate nucleotide of a single-stranded RNAi agent (the more 5' position of a 3'-terminal dinucleotide), or at the antepenultimate nucleotide of a single-stranded RNAi agent (the nucleotide immediate 5' to the 3'-terminal dinucleotide). Without wishing to be bound by any particular theory, this disclosure suggests that the penultimate or antepenultimate nucleotide of a single-stranded RNAi agent (e.g., the more 5' position of a 3'-terminal dinucleotide) can be adjacent to a pocket in Ago-2, and a GalNAc moiety may be capable of insertion into said pocket, such that the GalNAc moiety does not interfere with Ago-2 activity. Without wishing to be bound by any particular theory, this disclosure suggests that if a GalNAc moiety is attached at the penultimate or antepenultimate nucleotide, it may thus not be necessary to cleave the GalNAc moiety to allow RNAi activity, and it may thus be acceptable to use a more robust, non-biocleavable linker to attach a GalNAc moiety to the oligonucleotide or single-stranded RNAi agent. The more robust linker thus is less susceptible to cleavage, increasing the probability that a GalNAc moiety will increase delivery of the oligonucleotide or single-stranded RNAi agent.

In some embodiments, the GalNAc moiety is attached via a AMC6 linker.

In some embodiments, the GalNAc moiety is attached via a AMC6 linker attached at a T base (AMC6T).

In some embodiments, AMC6T has a structure of:

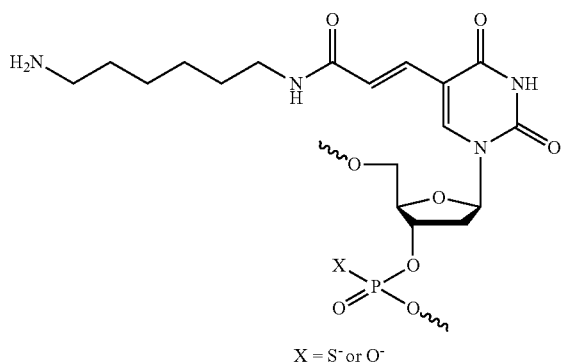

X = S⁻ or O⁻

In some non-limiting examples, AMC6T is either the penultimate or antepenultimate nucleotide [counting 5' to 3']; for example, the 5' nucleotide of the 3'-terminal dinucleotide, or the nucleotide immediately 5' to the 5' nucleotide of the 3'-terminal dinucleotide.

In some embodiments of a single-stranded RNAi agent, the single-stranded RNAi agent comprises a AMC6T at the penultimate or antepenultimate nucleotide.

As disclosed herein, GaNC6T is a component in an efficacious single-stranded RNAi agent. In some non-limiting examples, GaNC6T is either at the penultimate or antepenultimate nucleotide [counting 5' to 3']; for example, the 5' nucleotide of the 3'-terminal dinucleotide, or the nucleotide immediately 5' to the 5' nucleotide of the 3'-terminal dinucleotide. In some non-limiting examples disclosed herein, GaNC6T is at nucleotide position 20 out of 21 (counting from the 5'-end), or 24 out of 25 (counting from the 5'-end).

In some embodiments, a PNPLA3 oligonucleotide or single-stranded RNAi agent is conjugated to Tri-antennary GalNAc Acid (e.g., via a C10, C3 or triazine linker):

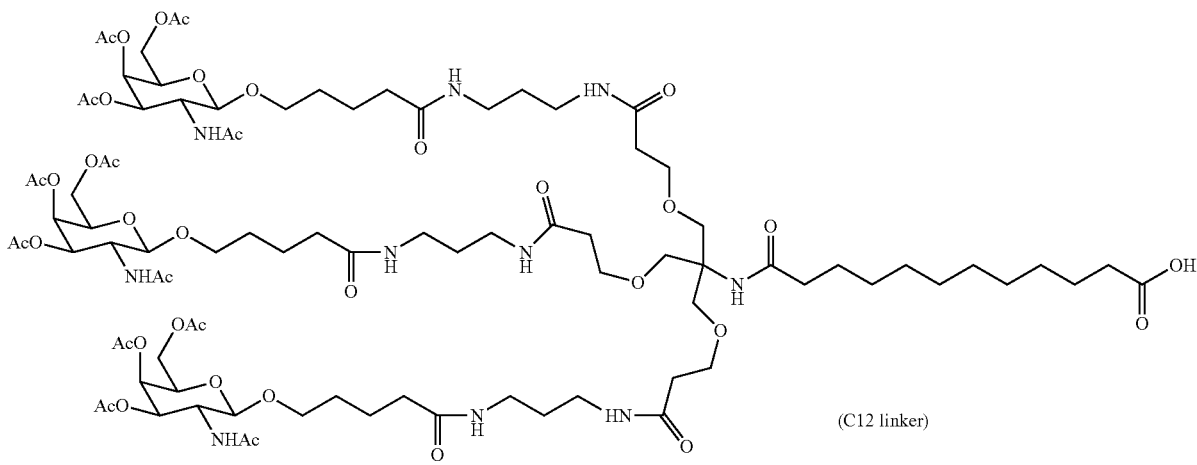

(C12 linker)

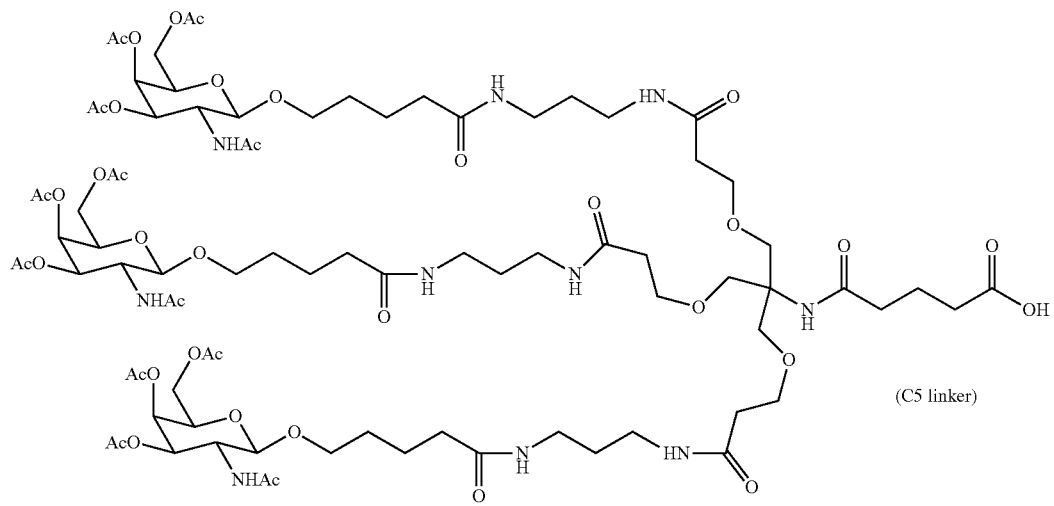

(C5 linker)

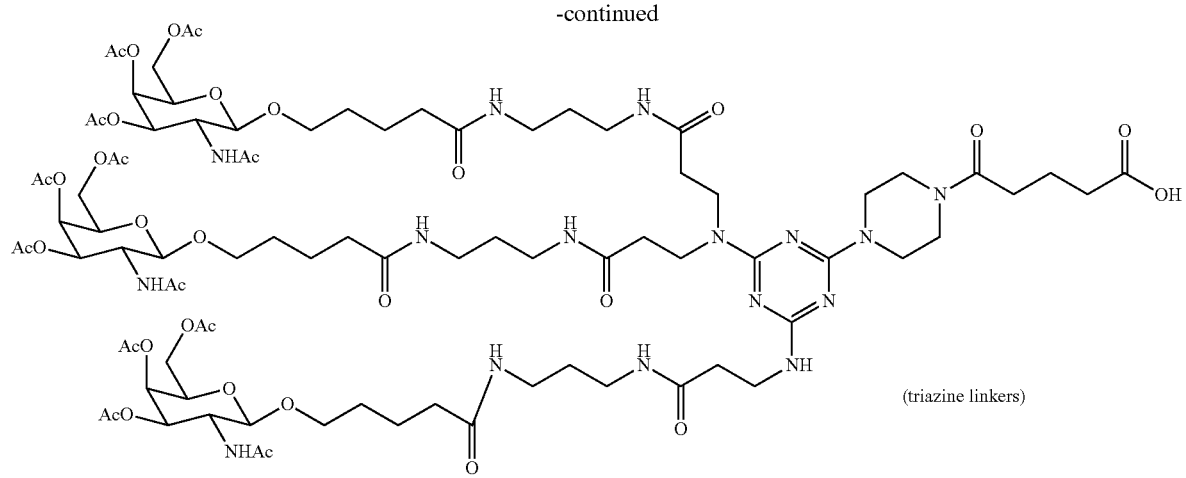

(triazine linkers)

These structures represent the protected versions, as they comprise —OAc (—O-acetate groups). In some embodiments, the Ac groups are removed during de-protection following conjugation of the compound to the oligonucleotide. In some embodiments, de-protection is performed with concentrated ammonium hydroxide, e.g., as described in Example 37B. In the de-protected versions of these structures, —OAc is replaced by —OH.

In some embodiments, a GalNAc moiety is conjugated at the 5'-end. Each of these additional chemical moieties (Tri-antennary GalNAc Acid, with each of the C12, C5 or triazine linkers) was conjugated to a PNPLA3 oligonucleotide targeting Factor XI (FXI), which operates via a RNase H mechanism.

Several oligonucleotides were constructed; each comprises a PNPLA3 oligonucleotide targeting Factor XI (FXI), which operates via a RNase H mechanism, with each conjugated to a different Tri-antennary GalNAc Acid, with each of the C12, C5 or triazine linkers. The Tri-antennary GalNAc Acid has been revealed experimentally (data not shown) to improve the delivery of the oligonucleotides to the liver.

In some embodiments, the present disclosure pertains to any oligonucleotide conjugated to Tri-antennary GalNAc Acid. In some embodiments, the present disclosure pertains to any oligonucleotide conjugated to Tri-antennary GalNAc Acid via a C10, C3 or triazine linker. In some embodiments, the present disclosure pertains to any oligonucleotide conjugated to Tri-antennary GalNAc Acid, wherein the oligonucleotide directs knockdown of a target transcript mediated by a RNase H or RNA interference mechanism. In some embodiments, the present disclosure pertains to any oligonucleotide conjugated to Tri-antennary GalNAc Acid via a C10, C3 or triazine linker, wherein the oligonucleotide directs knockdown of a target transcript mediated by a RNase H or RNA interference mechanism.

In some embodiments, the present disclosure pertains to any oligonucleotide conjugated to Tri-antennary GalNAc Acid, wherein the oligonucleotide directs knockdown of a target transcript mediated by a RNase H or RNA interference mechanism, wherein the RNA interference mechanism is directed by a RNAi agent comprising 1, 2 or more strands. In some embodiments, the present disclosure pertains to any oligonucleotide conjugated to Tri-antennary GalNAc Acid via a C10, C3 or triazine linker, wherein the oligonucleotide directs knockdown of a target transcript mediated by a RNase H or RNA interference mechanism, wherein the RNA interference mechanism is directed by a RNAi agent comprising 1, 2 or more strands.

In addition, the present disclosure shows that in provided oligonucleotides capable of directing single-stranded RNA interference it is not necessary for the first nucleotide on the 5'-end of a single-stranded RNAi agent to match the corresponding portion of the sequence of the target transcript.

Oligonucleotides capable of directing single-stranded RNA interference were prepared and characterized using a variety of methods in accordance of the present disclosure. In some embodiments, a provided oligonucleotide composition is a single-stranded RNAi agent of a PNPLA3 oligonucleotide type listed in Table 1A. In some embodiments, a provided oligonucleotide composition is a single-stranded RNAi agent of a PNPLA3 oligonucleotide type listed as any of Formats illustrated in FIG. 1.

In some embodiments, a PNPLA3 oligonucleotide is capable of directing knockdown of a target transcript by both RNase H-mediated knockdown and RNA interference. Such a PNPLA3 oligonucleotide is described herein a dual mechanism or hybrid oligonucleotide.

In some embodiments, a PNPLA3 oligonucleotide, a PNPLA3 oligonucleotide that directs RNA interference, a PNPLA3 oligonucleotide that directs RNase H-mediated knockdown, or a PNPLA3 oligonucleotide that directs both RNA interference and RNase H-mediated knockdown can comprise any additional chemical moiety, including but not limited to, any GalNAc moiety described or referenced in any of: U.S. Pat. Nos. 5,382,524; 5,491,075; 5,545,553; 5,705,367; 5,733,765; 5,786,184; 5,798,233; 5,854,042; 5,871,990; 5,945,322; 6,165,469; 6,187,310; 6,342,382; 6,465,220; 6,503,744; 6,699,705; 6,723,545; 6,780,624; 6,825,019; 6,905,867; 6,911,337; 7,026,147; 7,078,207; 7,138,258; 7,166,717; 7,169,593; 7,169,914; 7,189,836; 7,192,756; 7,202,353; 7,208,304; 7,211,657; 7,217,549; 7,220,848; 7,238,509; 7,338,932; 7,371,838; 7,384,771; 7,462,474; 7,598,068; 7,608,442; 7,682,787; 7,723,092; 8,039,218; 8,137,941; 8,268,596; 8,871,723; or 9,222,080.

Dual Mechanism or Hybrid Oligonucleotide

In some embodiments, a PNPLA3 oligonucleotide or a PNPLA3 oligonucleotide that directs both RNA interference and RNase H-mediated knockdown can comprise structural element of any oligonucleotide described herein or known in the art.

As disclosed herein, some oligonucleotides are capable of directing knockdown of a transcript target by both RNase H-mediated knockdown and RNA interference.

As disclosed herein, some oligonucleotides (including but not limited to those described herein as dual mechanism or hybrid oligonucleotides or hybrid RNAi agents) are capable of directing knockdown of a transcript target by both RNase H-mediated knockdown and RNA interference.

Wishing to be bound by any particular theory, the present disclosure suggests that a hybrid oligonucleotide can have particular advantages to either a PNPLA3 oligonucleotide capable of directing knockdown solely by RNase H-mediated knockdown, or a PNPLA3 oligonucleotide capable of directing knockdown solely by RNA interference. For example, if several hybrid oligonucleotides are introduced into the same cell, some but not all hybrid oligonucleotide may participate in the RISC pathway; those which do not are available to participate in the RNase H-mediated pathway. For example, if several hybrid oligonucleotides are introduced into the same cell, some but not all hybrid oligonucleotide may participate in the RNase H-mediated pathway; those which do not are available to participate in the RISC pathway. Without wishing to be bound by any particular theory, the present disclosure suggests that a hybrid oligonucleotide may be able to mediate more efficacious knockdown than a PNPLA3 oligonucleotide capable of directing knockdown solely by RNase H-mediated knockdown, or a PNPLA3 oligonucleotide capable of directing knockdown solely by RNA interference, as the hybrid oligonucleotide is capable of directing knockdown via both pathways. In at least some cells, levels of RNase H activity and RNA interference may differ from cell compartment to cell compartment. In some embodiments, a hybrid oligonucleotide can direct knockdown in various cell compartments via RNase H-mediated knockdown or RNA interference. In some embodiments, if RNase H is saturated with oligonucleotides, the excess oligonucleotides can be available for RNA interference-mediated knockdown. In some embodiments, if Ago-2 is saturated with oligonucleotides, the excess oligonucleotides can be available for RNase H-mediated knockdown.

In some embodiments, a hybrid oligonucleotide comprises a structure which allows both knockdown via RNase H-mediated knockdown and knockdown via RNA interference.

Reportedly, RNase H and RNAi both involve knockdown of a target mRNA, but they involve different mechanisms. Reportedly, RNase H naturally involves a single-stranded DNA molecule which binds to a mRNA target and decreases expression by either sterically hindering translation, or by the RNA/DNA duplex acting as a substrate for RNase H, which cleaves the mRNA target.

In contrast, reportedly, RNAi naturally involves a double-stranded RNA molecule, naturally produced by Dicer with two 3' overhangs, including an antisense and a sense strand. The strands are separated as the duplex is unwound and the antisense incorporated into the RISC (RNA interference silencing complex), including Argonaute-2. The antisense strand acts as a guide for RISC to identify the complementary mRNA target and cleave it. As shown herein, certain formats of single-stranded RNAi agents are also efficacious, although single-stranded RNAi agents are not naturally produced by Dicer.

Reportedly, RNase H and RISC naturally prefer two structurally distinct types of molecules. RNase H naturally uses a single-stranded DNA molecule to target the mRNA target, forming a DNA/RNA duplex. Reportedly, RISC reportedly naturally uses a single-stranded RNA antisense strand to target the mRNA target, forming a RNA/RNA duplex. Crooke et al. 1995 Biochem. J. 312: 599-608; and Elbashir et al. Nature 2001 411: 494.

Crooke et al. 1995 Biochem. J. 312: 599-608 also reported that *E. coli* RNase H1 had been crystallized and studied, and that the preferred substrate was reportedly a RNA/DNA duplex. In the DNA strand, 2'-modifications such as 2'-OMe and 2'-F reportedly reduced or eliminated RNase H activity. In addition, for RNA interference, full replacement of RNA by DNA reportedly abolishes RNA interference activity of double-stranded RNAi agents. Elbashir et al. 2001 EMBO J. 20: 6877-6888. Thus, reportedly, RNase H-mediated knockdown reportedly requires a span of DNA (2'-deoxy), while RNA interference can be abolished by replacement of a span of nucleotides with DNA (2'-deoxy).

In contrast, as shown herein, 2'-OMe and 2'-F modifications are highly suitable for single-stranded RNAi agents. The Applicants thus designed and constructed several oligonucleotides which comprise (a) a seed region comprising 2'-modified nucleotides; and (b) a post-seed region comprising a stretch of 2'-deoxy (2'-deoxy) nucleotides. These are shown herein to function via both the RNAi and RNase H-mediated knockdown mechanisms.

In some embodiments, a hybrid oligonucleotide comprises a (a) seed region capable of annealing to a first complementary target mRNA region and mediating RNA interference; and (b) a post-seed region comprising a 2'-deoxy (2'-deoxy) region capable of annealing a second complementary target mRNA region and directing RNase H-mediated knockdown. The seed region can optionally comprise RNA or a modified nucleotide, e.g., with a 2' modification (including but not limited to 2'-F, 2'-OMe and 2'-MOE), wherein the RNA or modified nucleotide comprise a natural sugar and/or a natural base, and/or a modified base, and/or an internucleotidic linkage.

A minimum length for a DNA (2'-deoxy) region efficacious for RNase H-mediated knockdown, in at least some cases, is reported to be about 5 consecutive DNA (2'-deoxy); this minimum deoxy length reportedly correlated with the minimum length required for efficient RNase H activation in vitro using partially purified mammalian RNase H enzyme. Monia et al. 1993 JBC 268: 14514-14522.

In some embodiments, a hybrid oligonucleotide comprises a (a) seed region capable of annealing to a first complementary target mRNA region; and (b) a post-seed region comprising a 2'-deoxy region, wherein the hybrid oligonucleotide is capable of directing both RNA interference and RNase H-mediated knockdown, wherein the 2'-deoxy region comprises at least 5 consecutive 2'-deoxy. In some embodiments, the 2'-deoxy can be DNA, or a modified nucleotide, e.g., a modified nucleotide with a 2'-deoxy, wherein the DNA or modified nucleotide comprise a natural sugar and/or a natural base, and/or a modified base, and/or any internucleotidic linkage. In some embodiments, the 2'-deoxy region comprises a stretch of consecutive nucleotides, wherein each nucleotide is 2'-deoxy and each internucleotidic linkage is a phosphorothioate. In some embodiments, the 2'-deoxy region comprises a stretch of consecutive nucleotides of at least 5, 6, 7, 8, 9, 10, 11, 12, 13, 14, 15, 16, 17, 18, 19, 20 or 21 nucleotides, wherein each nucleotide is 2'-deoxy and each internucleotidic linkage is a phosphorothioate.

In some embodiments, a hybrid oligonucleotide comprises a (a) seed region capable of annealing to a first complementary target mRNA region; and (b) a post-seed region comprising a 2'-deoxy region, wherein the hybrid oligonucleotide is capable of directing both RNA interference and RNase H-mediated knockdown, wherein the 2'-deoxy region comprises at least 5 consecutive 2'-deoxy. In some embodiments, the 2'-deoxy can be DNA, or a modified nucleotide, e.g., a modified nucleotide with a 2'-deoxy, wherein the DNA or modified nucleotide comprise a natural sugar and/or a natural base, and/or a modified base, and/or any internucleotidic linkage. In some embodiments, the 2'-deoxy region comprises or is a span of consecutive nucleotides, wherein each nucleotide is 2'-deoxy and each internucleotidic linkage is a phosphorothioate. In some embodiments, the 2'-deoxy region comprises or is a stretch of consecutive nucleotides, wherein each nucleotide is 2'-deoxy and each internucleotidic linkage is a phosphorothioate. In some embodiments, the 2'-deoxy region comprises a stretch of consecutive nucleotides of at least 5, 6, 7, 8, 9, 10, 11, 12, 13, 14, 15, 16, 17, 18, 19, 20 or 21 nucleotides, wherein each nucleotide is 2'-deoxy and each internucleotidic linkage is a phosphorothioate.

Without wishing to be bound by any particular theory, the present disclosure notes that WO 2015/107 425 has reported that cleavage mediated by RNase H can be modulated by the arrangement of chiral centers in phosphorothioates in an antisense oligonucleotide directing RNase H cleavage. For example, the placement of a single Rp flanked by at least 2 or 3 Sp can alter the cleavage pattern, such that the number of cleavage sites is reduced and the site of RNase H-mediated cleavage is controlled.

In some embodiments, a hybrid oligonucleotide comprises a (a) seed region capable of annealing to a first complementary target mRNA region; and (b) a post-seed region comprising a 2'-deoxy region, wherein the hybrid oligonucleotide is capable of directing both RNA interference and RNase H-mediated knockdown, wherein the 2'-deoxy region comprises a stretch of consecutive nucleotides of at least 5, 6, 7, 8, 9, 10, 11, 12, 13, 14, 15, 16, 17, 18, 19, 20 or 21 nucleotides, wherein each nucleotide is 2'-deoxy and each internucleotidic linkage is a phosphorothioate.

In some embodiments, a hybrid oligonucleotide comprises a (a) seed region capable of annealing to a first complementary target mRNA region; and (b) a post-seed region comprising a 2'-deoxy region, wherein the hybrid oligonucleotide is capable of directing both RNA interference and RNase H-mediated knockdown, wherein the 2'-deoxy region comprises a stretch of consecutive nucleotides of at least 9 nucleotides, wherein each nucleotide is 2'-deoxy and each internucleotidic linkage is a phosphorothioate.

In some embodiments, the first and second complementary target mRNA regions are regions of the same target mRNA.

In some embodiments, the first and second complementary target mRNA regions are regions of different target mRNAs.

In some embodiments of a hybrid oligonucleotide, a seed region comprises a DNA region capable of annealing to a complementary target mRNA region and directing RNase H-mediated knockdown.

Without wishing to be bound by any particular theory, the present disclosure notes that, in many cases, RNase H cleaves a single-stranded RNA target which is bound to a single-stranded DNA. In some embodiments, a hybrid oligonucleotide comprises a single-stranded 2'-deoxy portion, which is capable of binding to a target RNA transcript, forming a substrate for RNase H. In some embodiments, a hybrid oligonucleotide comprises a single-stranded 2'-deoxy portion (which comprises internucleotidic linkages which can be any internucleotidic linkage described herein or known in the art), which is capable of binding to a target RNA transcript, forming a substrate for RNase H.

In some embodiments of a single-stranded RNAi agent, a post-seed region comprises: a sequence of nucleotides comprising at least 4 consecutive 2'-deoxy. In some embodiments of a single-stranded RNAi agent, a post-seed region comprises: a sequence of nucleotides comprising at least 5 consecutive 2'-deoxy. In some embodiments of a single-stranded RNAi agent, a post-seed region comprises: a sequence of nucleotides comprising at least 6 consecutive 2'-deoxy. In some embodiments of a single-stranded RNAi agent, a post-seed region comprises: a sequence of nucleotides comprising at least 7 consecutive 2'-deoxy. In some embodiments of a single-stranded RNAi agent, a post-seed region comprises: a sequence of nucleotides comprising at least 8 consecutive 2'-deoxy. In some embodiments of a single-stranded RNAi agent, a post-seed region comprises: a sequence of nucleotides comprising at least 9 consecutive 2'-deoxy. In some embodiments of a single-stranded RNAi agent, a post-seed region comprises: a sequence of nucleotides comprising at least 10 to 20 consecutive 2'-deoxy.

In some embodiments of a hybrid oligonucleotide, a post-seed region comprises: at least 9 consecutive 2'-deoxy. In some embodiments of a single-stranded RNAi agent, a post-seed region comprises: at least 10 consecutive 2'-deoxy. The ability of various single-stranded RNAi agents and antisense oligonucleotides to mediate RNA interference or RNase H knockdown is described herein and shown, as non-limiting examples, in the Figures and Tables.

Experimental data (not shown) and described in detail elsewhere herein demonstrated that putative dual mechanism oligonucleotides are capable of mediating both RNA interference and RNase H knockdown. RNA interference was tested in either of two different in vitro Ago-2 assays, and RNase H knockdown was tested in an in vitro RNase H assay.

The experiments used an RNase H assay, with WV-1868 (ASO, mediating a RNase H knockdown mechanism) as a positive control, and WV-2110 (a single-stranded RNAi agent) as a negative control. RNA molecule WV-2372 is used as a test substrate. In the RNase H assay, dual mechanism oligonucleotide WV-2111 mediated RNase H knockdown.

Allele Specific Suppression

In some embodiments, provided oligonucleotides are capable of directing a decrease in the expression and/or level of a target gene or its gene product. In some embodiments, provided oligonucleotides are capable of mediating allele-specific suppression (or allele-specific knockdown).

In some embodiments, in some disease states, a patient (e.g., a human patient) can comprise two copies of the same gene, wherein one copy is wild-type (which is not disease-related), whereas the other copy on another chromosome has a mutation (which is disease-related). In some embodiments, the wild-type and mutant alleles can be differentiated by a particular sequence at the mutation, or else can be differentiated by a sequence outside the deleterious mutation (e.g., at a SNP). Knocking down both the mutant and wild-type alleles can sometimes be undesirable, because expression of the wild-type gene may be necessary or beneficial, while expression of the mutant gene may be deleterious or disease-related.

In some embodiments, a target sequence can be designed which recognizes the mutant transcript (e.g., one comprising the deleterious mutation or a targeted SNP) preferentially over the wild-type transcript.

In some embodiments, an allele-specific oligonucleotide maximizes knock-down of the mutant allele while minimizing knock-down of the wild-type allele, in a process referenced as allele-specific suppression or allele-specific knockdown. In some embodiments, a PNPLA3 oligonucleotide is capable of selectively targeting the mutant allele of a gene. In some embodiments, a PNPLA3 oligonucleotide is capable of knocking down the mutant allele compared to the wild-type allele with a specificity of at least 2-, 3-, 4-, 5-, 6-, 7-, 8-, 9-, 10-, 15-, 20-, 25-, 30-, 35-, 40-, 45- or 50-fold. In some embodiments, a PNPLA3 oligonucleotide is capable of selectively targeting the mutant allele of a gene, wherein the mutant allele is represented by one allele and the wild-type allele is represented by a different allele. In some embodiments, a mutation can be a double mutation (e.g., two mutations in close proximity that often occur together in the same genome). In some embodiments, a mutation is in PNPLA3. In some embodiments, a mutation is a double mutation in PNPLA3. In some embodiments, the I148M mutation is in PNPLA3. In some embodiments, an allele-specific oligonucleotide is an antisense oligonucleotide. In some embodiments, an allele-specific oligonucleotide is a PNPLA3 oligonucleotide or single-stranded RNAi agent. In some embodiments, an allele-specific oligonucleotide is a PNPLA3 oligonucleotide or single-stranded RNAi agent which has or comprises any format or structure described herein.

In some embodiments, an allele-specific RNAi agent maximizes knock-down of the mutant allele while minimizing knock-down of the wild-type allele, in a process referenced as allele-specific suppression. In some embodiments, a PNPLA3 oligonucleotide or single-stranded RNAi agent is capable of selectively targeting the mutant allele of a gene. In some embodiments, a PNPLA3 oligonucleotide or single-stranded RNAi agent is capable of knocking down the mutant allele compared to the wild-type allele with a specificity of at least 2-, 3-, 4-, 5-, 6-, 7-, 8-, 9-, 10-, 15-, 20-, 25-, 30-, 35-, 40-, 45- or 50-fold. In some embodiments, a PNPLA3 oligonucleotide or single-stranded RNAi agent is capable of selectively targeting the mutant allele of a gene, wherein the mutant allele is represented by one allele and the wild-type allele is represented by a different allele. In some embodiments, a mutation can be a double mutation (e.g., two mutations in close proximity that often occur together in the same genome). In some embodiments, a mutation is in PNPLA3. In some embodiments, a mutation is a double mutation in PNPLA3. In some embodiments, the I148M mutation is in PNPLA3.

In some embodiments, a non-limiting example of a method of designing an allele-specific RNAi agent is to incorporate into the base sequence a SNP or single-nucleotide polymorphism, wherein the mutant allele is represented by one allele of a SNP and the wild-type allele is represented by a different allele of the SNP. In some embodiments, a SNP can be at a location which is not the site of the disease-related mutation, but nonetheless serves to differentiate the two alleles.

In some embodiments, a non-limiting example of a method of designing an allele-specific RNAi agent is to incorporate into the base sequence a mutation, wherein the mutant allele is represented by one allele and the wild-type allele is represented by a different allele. In some embodiments, a mutation can be a double mutation (e.g., two mutations in close proximity that often occur together in the same genome). In some embodiments, a mutation is in PNPLA3. In some embodiments, a mutation is a double mutation in PNPLA3. In some embodiments, the I148M mutation is in PNPLA3.

In some embodiments, a PNPLA3 oligonucleotide or single-stranded RNAi agent comprises a SNP or other sequence which differentiates between a mutant and a wild-type allele of a gene, and is capable of selectively knocking down the mutant allele relative to the wild-type allele.

In some embodiments, the target sequence of a PNPLA3 oligonucleotide or single-stranded RNAi agent represents one allele of a target transcript.

As shown in the present disclosure, a provided single-stranded RNAi agent is capable of directing allele-specific RNA interference, wherein the ssRNAi is capable of knocking down a target mRNA having one sequence (e.g., a mutant sequence), but does not or does not significantly knock down a target mRNA having a related by different sequence (e.g., a wild-type version of the mutant sequence). In some embodiments, the mutant and wild-type sequences differ at one base position. In some embodiments, the mutant and wild-type sequences differ at two base positions. In some embodiments, the mutant and wild-type sequences differ at three base positions.

In some embodiments, a PNPLA3 oligonucleotide or single-stranded RNAi agent is capable of directing RNA interference against an allele of a target gene while not mediating RNA interference against a different allele of a target gene at the same concentration.

In some embodiments, a PNPLA3 oligonucleotide or single-stranded RNAi agent capable of directing allele-specific suppression comprises in its base sequence one or more SNPs at specific positions. These specific positions can be positions known or suspected to be sensitive to mismatches; e.g., a mismatch at one or more of these positions can alter the level of RNAi activity. See, for example, Miller et al. 2003 Proc. Natl. Acad. Sci. USA 100: 7195-7200; Brummelkamp et al. 2002 Cancer Cell 2: 243; and Naito et al. 2004 Nucl. Acids Res. 32: W124-W129. In many cases, full complementarity of the seed region to a mRNA target is necessary or beneficial for high RNAi activity; in contrast, complementary is not required in many cases at the 5' nucleotide moiety or at the 3'-terminal dinucleotide. In some embodiments, an allele-specific single-stranded RNAi agent has a SNP in the seed region.

In some embodiments, a PNPLA3 oligonucleotide or single-stranded RNAi agent is capable of mediating allele-specific suppression.

In some embodiments, a PNPLA3 oligonucleotide is capable of mediating allele-specific suppression.

In some embodiments, a single-stranded RNAi agent is capable of mediating allele-specific suppression.

In some embodiments, a PNPLA3 oligonucleotide or single-stranded RNAi agent is capable of mediating allele-specific suppression of PNPLA3.

In some embodiments, a PNPLA3 oligonucleotide is capable of mediating allele-specific suppression of PNPLA3.

In some embodiments, a single-stranded RNAi agent is capable of mediating allele-specific suppression of PNPLA3.

In some embodiments, In some embodiments, an allele-specific single-stranded RNAi agent has a SNP in the seed region, which lies between the seed and the 3'-terminal dinucleotide.

In some embodiments, a PNPLA3 oligonucleotide or single-stranded RNAi agent has a base sequence comprising one or more SNPs at any position.

In some embodiments, a PNPLA3 oligonucleotide or single-stranded RNAi agent has a base sequence comprising one or more SNPs at any position selected from 3, 4, 5, 6, 7, 8, 9, 10, 11, 12, 13, 14, 15, 16, 17, 18, or 19.

In some embodiments, a PNPLA3 oligonucleotide or single-stranded RNAi agent has a base sequence comprising one or more SNPs at any position inside the seed region.

In some embodiments, a PNPLA3 oligonucleotide or single-stranded RNAi agent has a base sequence comprising one or more SNPs at any position outside the seed region.

In some embodiments, a PNPLA3 oligonucleotide or single-stranded RNAi agent has a base sequence comprising one or more SNPs at any position in the post-seed region.

In some embodiments, a PNPLA3 oligonucleotide or single-stranded RNAi agent has a base sequence comprising one or more SNPs at any of positions: 8, 9, 10, 11, 12, 13, 14, 15, 16, 17, or 18.

In some embodiments, a PNPLA3 oligonucleotide or single-stranded RNAi agent has a base sequence comprising one or more SNPs at any of positions: 14 or 17.

In some embodiments, a PNPLA3 oligonucleotide or single-stranded RNAi agent has a base sequence comprising one or more SNPs at any of positions: 9 or 10.

In some embodiments, a PNPLA3 oligonucleotide or single-stranded RNAi agent has a base sequence comprising two or more SNPs.

In some embodiments, a PNPLA3 oligonucleotide or single-stranded RNAi agent has a base sequence comprising two SNPs.

In some embodiments, a PNPLA3 oligonucleotide or single-stranded RNAi agent has a base sequence comprising two SNPs, one each at positions 14 and 17.

In some embodiments, a PNPLA3 oligonucleotide or single-stranded RNAi agent is capable of directing allele-specific suppression against a mutant allele of a gene relative to a wild-type allele of the same gene.

In some embodiments, a PNPLA3 oligonucleotide or single-stranded RNAi agent is capable of directing allele-specific suppression against a mutant allele of PNPLA3 relative to a wild-type allele of PNPLA3.

Table 70A shows the in vitro potency and allelic specific suppression directed by different PNPLA3 single-stranded RNAi agents. Tested oligonucleotide is: WV-3387 in Huh7 and Hep3B cells. Table 70B and Table 70C shows the in vitro potency and IC50 for different single-stranded RNAi agents, which target PNPLA3. Tested oligonucleotides are: WV-4054 and WV-4098. WV-4054 has a sequence complementary to a pair of SNPs, rs738408 T and rs738409 G, at positions 14 and 17, and is able to mediate allele-specific RNA interference against cells (Huh7) which comprise these two SNPs. This oligonucleotide does not mediate significant RNAi interference at the tested concentrations in different cells (Hep3B) which do not comprise these SNPs, but rather have rs738408C and rs738409 C. In addition, single-stranded RNAi agent WV-4098 is also able to knock-down a complementary sequence (with SNPs rs738408 T and rs738409 Gin Huh7 cells), but not a non-complementary sequence (with SNPs rs738408C and rs738409 C in Hep3B cells) at the tested concentrations.

Table 71 shows the in vitro potency and allele-specific knock-down directed by single-stranded RNAi agents to PNPLA3. Tested oligonucleotides are: Table 71A, WV-2477, WV-3387, and WV-4054; Table 71B, non-allele specific control ASO WV-3387; and Table 71C, allele specific ssRNAi WV-4054.

Table 90A to 90F shows in vitro allele-specific suppression of different oligonucleotides, which target PNPLA3. The double mutation in I148M in tested oligonucleotides is shown in Table 90A, as are cartoons of the oligonucleotide formats tested. Oligonucleotides with the I148M double mutation were tested against: Hep3B cells (wild-type) and Huh7 cells (with double mutation). Oligonucleotides were delivered with lipofectamine and cells were tested at 48 hours. Oligonucleotides tested are: Table 90B, WV-7778 to WV-7793; and WV-3858 to WV-3864; Table 90C, WV-7794 to WV-7816; Table 90D, WV-7817 to WV-7839; Table 90E, WV-7840 to WV-7862; and Table 90F, WV-993, WV-3390, and WV-4054, wherein WV-4054 is a single-stranded RNAi agent. In these data, oligonucleotides used were antisense oligonucleotides which have a wing-core-wing format, wherein the core was 2'-deoxy phosphorothioate (random in stereochemistry), and the wings were fully 2'-OMe, fully 2'-MOE, or all 2'-OMe with 5' and 3'-terminal LNA, or all 2'-MOE with 5' and 3'-terminal LNA. The wings are also phosphodiester and 5' and 3'-terminal stereorandom phosphorothioate.

The data demonstrate that many oligonucleotides were capable of directing allele-specific suppression (e.g., allele-specific knock-down). Oligonucleotides shown in Table 90B to 90E showed significant knock-down of the mutant allele in Huh7 cells and comparatively less knockdown of the wild-type allele in Hep3B cells. A single mismatch, even in the wings, was sufficient to mediate allele-specific suppression; however, in at least some cases, allele-specific suppression was increased when the two mismatches were both present in the DNA core.

Without wishing to be bound by any particular theory, the present disclosure notes that, in many cases, introduction of a stereocontrolled chiral internucleotidic linkage (in place of a stereorandom chiral internucleotidic linkage) can increase the allele-specific suppression, stability, efficacy, specificity, delivery, and/or albumin binding of a PNPLA3 oligonucleotide.

In some embodiments, a PNPLA3 oligonucleotide capable of mediating allele-specific suppression comprises one or more stereopure chiral internucleotidic linkages.

In some embodiments, a PNPLA3 oligonucleotide capable of mediating allele-specific suppression comprises one or more stereopure chiral internucleotidic linkages in the Sp configuration.

In some embodiments, a PNPLA3 oligonucleotide capable of mediating allele-specific suppression comprises one or more stereopure chiral internucleotidic linkages in the Sp configuration and one or more stereopure chiral internucleotidic linkages in the Rp configuration.

In some embodiments, a PNPLA3 oligonucleotide capable of mediating allele-specific suppression comprises one or more stereopure phosphorothioates.

In some embodiments, a PNPLA3 oligonucleotide capable of mediating allele-specific suppression comprises one or more stereopure phosphorothioates in the Sp configuration.

In some embodiments, a PNPLA3 oligonucleotide capable of mediating allele-specific suppression comprises one or more stereopure phosphorothioates in the Rp configuration.

In some embodiments, a PNPLA3 oligonucleotide capable of mediating allele-specific suppression comprises one or more stereopure phosphorothioates in the Sp configuration and one or more stereopure phosphorothioates in the Rp configuration.

In some embodiments, a PNPLA3 oligonucleotide capable of allele-specific suppression of a target gene or its gene product can comprise any structure or format described herein.

Multimers of Oligonucleotides

In some embodiments, a multimer comprises two or more of: a PNPLA3 oligonucleotide, a PNPLA3 oligonucleotide that directs RNA interference, a PNPLA3 oligonucleotide that directs RNase H-mediated knockdown and/or or a PNPLA3 oligonucleotide that directs both RNA interference and RNase H-mediated knockdown can have any format or structural element thereof described herein or known in the art.

In some embodiments, a provided composition comprises a combination of one or more provided oligonucleotide types. One of skill in the chemical and medicinal arts will recognize that the selection and amount of each of the one or more types of provided oligonucleotides in a provided composition will depend on the intended use of that composition. That is to say, one of skill in the relevant arts would design a provided chirally controlled oligonucleotide composition such that the amounts and types of provided oligonucleotides contained therein cause the composition as a whole to have certain desirable characteristics (e.g., biologically desirable, therapeutically desirable, etc.).

In some embodiments, a provided oligonucleotide type is selected from those described in WO/2014/012081 and WO/2015/107425, the oligonucleotides, oligonucleotide types, oligonucleotide compositions, and methods thereof of each of which are incorporated herein by reference. In some embodiments, a provided chirally controlled oligonucleotide composition comprises oligonucleotides of a PNPLA3 oligonucleotide type selected from those described in WO/2014/012081 and WO/2015/107425.

In some embodiments, the present disclosure pertains to a composition comprising a chirally controlled oligonucleotide composition, wherein the sequence of the oligonucleotide comprises or consists of the sequence of any chirally controlled oligonucleotide composition disclosed herein.

In some embodiments, the present disclosure pertains to a composition comprising a chirally controlled oligonucleotide composition, wherein the sequence of the oligonucleotide comprises or consists of the sequence of any single-stranded RNAi agent composition listed in Table 1A or otherwise described herein.

In some embodiments, the present disclosure pertains to compositions comprising a multimer of oligonucleotides, e.g., single-stranded RNAi agents, antisense oligonucleotides and/or other oligonucleotides, at least one of which has a structure, sequence or other characteristic as described herein.

In some embodiments, the present disclosure pertains to compositions comprising a multimer of single-stranded RNAi agents, antisense oligonucleotides and/or other oligonucleotides, wherein the multimer is at least about 16 kD in size.

In some embodiments, the present disclosure pertains to compositions comprising a multimer of single-stranded RNAi agents, antisense oligonucleotides and/or other oligonucleotides, and further comprises a carbohydrate moiety, lipid moiety, targeting moiety, or other compound.

In some embodiments, the present disclosure pertains to compositions comprising a multimer of single-stranded RNAi agents, antisense oligonucleotides and/or other oligonucleotides, and further comprises a carbohydrate moiety, lipid moiety, targeting moiety, or other compound, the total weight of which is at least about 16 kD in size.

In some embodiments, the multimer can comprise at least 2 single-stranded RNAi agents, antisense oligonucleotides and/or other oligonucleotides. In some embodiments, the multimer can comprise at least 3 single-stranded RNAi agents, antisense oligonucleotides and/or other oligonucleotides. In some embodiments, the multimer can comprise at least 4 single-stranded RNAi agents, antisense oligonucleotides and/or other oligonucleotides. In some embodiments, the multimer can comprise at least 5 single-stranded RNAi agents, antisense oligonucleotides and/or other oligonucleotides. In some embodiments, the multimer can comprise at least 6 single-stranded RNAi agents, antisense oligonucleotides and/or other oligonucleotides. In some embodiments, the multimer can comprise at least 7 single-stranded RNAi agents, antisense oligonucleotides and/or other oligonucleotides. In some embodiments, the multimer can comprise at least 8 single-stranded RNAi agents, antisense oligonucleotides and/or other oligonucleotides. In some embodiments, the multimer can comprise at least 9 single-stranded RNAi agents, antisense oligonucleotides and/or other oligonucleotides. In some embodiments, the multimer can comprise at least 10 single-stranded RNAi agents, antisense oligonucleotides and/or other oligonucleotides.

Without wishing to be bound by any particular theory, the present disclosure suggests that multimerization of oligonucleotides can provide a multimer which has a total molecular weight sufficient for transport via the lymphatic system. Supersaxo et al. reported that there is a linear relationship between the molecular weight of a drug and the proportion of a dose absorbed lymphatically, and that molecules with a molecular weight greater than 16 kD are absorbed mainly by the lymphatics, which drain a subcutaneous injection site. Supersaxo et al. 1990 Pharm. Res. 7: 167-9. In some embodiments, a PNPLA3 oligonucleotide has a molecular weight of around 8 kD. In some embodiments, a multimer comprising multiple oligonucleotides has a molecular weight of at least around 16 kD.

Without wishing to be bound by any particular theory, the present disclosure notes that subcutaneous injections are reportedly widely utilized for delivery of drugs, including, but not limited to, those with limited oral availability, or as a means to modify or extend the release profile. McLennan et al. 2005 Drug Disc. Today: Technologies 2: 89-96. Subcutaneous injection reportedly results in delivery to the interstitial area underlying the dermis of the skin, from where drugs enter the circulatory system, or the lymphatic system; transport is reportedly affected by molecular weight, particle size, charge, hydrophilicity, and interaction with components in the interstitium. Drug formulation characteristics, such as drug concentration, injection volume, ionic strength, viscosity, and pH can also all reportedly play roles in diffusion from the subcutaneous injection site. McLennan et al. 2005; Paniagua et al. 2012 Lymphology 45: 144-153; and Bagby et al. 2012 Pharmaceutics 4: 276-295.

In some embodiments, one or more characteristic of molecular weight, particle size, charge, hydrophilicity, and interaction with components in the interstitium, drug concentration, injection volume, ionic strength, viscosity, and/or pH are modulated to improve or maximize the efficacy, bioavailability or delivery of a composition comprising a PNPLA3 oligonucleotide.

As noted above, molecules with a molecular weight greater than 16 kD are reportedly absorbed mainly by the lymphatics. Supersaxo et al. 1990 Pharm. Res. 7: 167-9. In some embodiments, the present disclosure pertains to a composition comprising a multimer of oligonucleotides, wherein the multimer has a total molecular weight of at least about 16 kD. In some embodiments, the present disclosure pertains to a composition comprising two or more different types or sizes of multimers of oligonucleotides, wherein the one or more of the different types of multimer has a total molecular weight of at least about 16 kD.

In some embodiments, each oligonucleotide in a multimer can target the same or different targets. In some embodiments, wherein the each oligonucleotide in a multimer can target the same or different targets, administration of the multimer can be used to treat a disease involving overexpression or multiple target genes. In some embodiments, wherein the each oligonucleotide in a multimer can target the same or different targets, administration of the multimer can be used to treat different diseases involving overexpression of different target genes.

In some embodiments, each oligonucleotide in a multimer can target the same sequence in the same target. In some embodiments, each oligonucleotide in a multimer can target different sequences in the same target.

Non-limiting examples of multimers are shown in Table 89A.

In some embodiments, a multimer comprises two or more oligonucleotides directly connected to each other (e.g., via a bond or direct bond, such as a covalent bond), or via a linker.

Any linker described herein or known in the art can be used to link the oligonucleotides in a multimer. Various approaches for construction of multimers and use of various linkers is illustrated in Table 89B and 89C.

Without wishing to be bound by any particular theory, the present disclosure notes that, in at least some cases, a phosphorothioate in the Rp configuration is particularly susceptible to nuclease cleavage. In some embodiments of Multimer Type 2, a multimer is essentially a single long oligonucleotide, wherein the oligonucleotide comprises multiple shorter oligonucleotides, which are connected by short linker oligonucleotides. In some embodiments of Multimer Type 2, a multimer is essentially a single long oligonucleotide, wherein the oligonucleotide comprises multiple shorter oligonucleotides, which are connected by short linker oligonucleotides, wherein the short linker oligonucleotides comprise one or more internucleotidic linkages in the Rp configuration. In some embodiments of Multimer Type 2, a multimer is essentially a single long oligonucleotide, wherein the oligonucleotide comprises multiple shorter oligonucleotides, which are connected by short linker oligonucleotides, wherein the short linker oligonucleotides comprise one or more phosphorothioates in the Rp configuration.

Non-limiting examples of linkers include: a cleavable linker or a biodegradable linker; a non-cleavable or non-biodegradable linker; a linker comprising one or more internucleotidic linkages comprising a chiral center in the Rp configuration; a linker comprising one or more internucleotidic linkages comprising a chiral phosphorus in the Rp configuration; a linker comprising one or more phosphorothioate in the Rp configuration; a linker comprising two or more phosphorothioate in the Rp configuration; a linker comprising three or more phosphorothioate in the Rp configuration; a photocleavable linker; 1-(5-(N-maleimidomethyl)-2-nitrophenyl)ethanol N-hydroxysuccinimide ester; a linker comprising a maleimido moiety; a linker comprising a N-hydroxysuccinimide ester moiety; a linker conjugated to a PNPLA3 oligonucleotide at a base; a linker conjugated to a PNPLA3 oligonucleotide at an internucleotidic linkage; a linker conjugated at a sugar; a phosphodiester; a phosphotriester; a methylphosphonate; a P3'→N5' phosphoramidate; a N3'→P5' phosphoramidate; a N3'→P5' thio-phosphoramidate; a phosphorothioate linkage; a thiourea linker; a C5 or C6 linker, as described in U.S. Pat. No. 9,572,891; a linker comprising a alkyl, cycloalkyl, aryl, heterocyclyl, and heteroaryl; a linker comprising a substituted alkyl, cycloalkyl, aryl, heterocyclyl, and heteroaryl; a linker of the structure of formula (A) of U.S. Pat. No. 9,512,163; a linker comprising a C1-C12 hydrocarbyl chain; a polyethylene glycol linker; a hexaethylene glycol linker; a hydrocarbyl chain; a substituted hydrocarbyl chain; a linker comprising one or more of: alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, or alkynylhereroaryl; a linker comprising a peptide having an amino acid sequence selected from: ALAL, APISFFELG, FL, GFN, R/KXX, GRWHTVGLRWE, YL, GF, and FF, in which X is any amino acid; a linker comprising the formula —(CH$_2$)wS—S(CH$_2$)m-, wherein n and m are independently integers from 0 to 10; a linker comprising a low pH-labile bond; a linker comprising a low pH-labile bond comprising an amine, an imine, an ester, a benzoic imine, an amino ester, a diortho ester, a polyphosphoester, a polyphosphazene, an acetal, a vinyl ether, a hydrazone, an azidomethyl-methylmaleic anhydride, a thiopropionate, a masked endosomolytic agent or a citraconyl group; a branched linker; a cleavable linker susceptible to cleavage agents, e.g., pH, redox potential or the presence of degradative molecules; a redox cleavable linker; a phosphate-based cleavable linker; a phosphate-based cleavable linker comprising: —O—P(O)(OH)—O—, —O—P(S)(OH)—O—, —O—P(S)(SH)—O—, —O—P(O)(OH)—S—, P(O)(OH)—S—, —O—P(S)(OH)—S—, —S—P(S)(OH)—O—, —O—P(O)(H)—O—, —O—P(S)(H)—O—, —S—P(O)(OH)—O—, —S—P(O)(H)—O—, —S—P(S)(H)—O—, —S—P(O)(H)—S—, or —O—P(S)(H)—S—; an acid cleavable linker; an ester-based linker; a peptide-based cleavable linker; and moieties comprising any of these linkers.

In some embodiments, a linker comprises a polypeptide that is more susceptible to cleavage by an endopeptidase in the mammalian extract than the targeting oligonucleotides. In some embodiments, the endopeptidase is trypsin, chymotrypsin, elastase, thermolysin, pepsin, or endopeptidase V8. In some embodiments, the endopeptidase is cathepsin B, cathepsin D, cathepsin L, cathepsin C, papain, cathepsin S or endosomal acidic insulinase.

Various linkers and methods of multimerization of oligonucleotides are described in, as non-limiting examples: U.S. Pat. Nos. 9,370,582; 9,371,348; 9,512,163; 9,572,891; and 6,031,091; and international published patent applications WO1998000435; WO2014043544; and WO2013040429.

The disclosure also notes that any linker described herein, or known in the art, can be used to link one or more oligonucleotides to each other, or to link one or more moiety (as non-limiting examples, a targeting moiety, a carbohydrate moiety, a GalNAc moiety, a lipid moiety, etc.) to one or more oligonucleotides (as non-limiting examples, a single-stranded RNAi agent, an antisense oligonucleotide, a double-stranded RNAi agent, a PNPLA3 oligonucleotide capable of directing or inhibiting exon skipping, etc.).

Example Methods for Preparing Oligonucleotides and Compositions

Methods for preparing provided oligonucleotides and oligonucleotide compositions are widely known in the art, including but not limited to those described in WO/2010/064146, WO/2011/005761, WO/2013/012758, WO/2014/010250, US2013/0178612, WO/2014/012081, WO/2015/107425, PCT/US2016/043542, and PCT/US2016/043598, the methods and reagents of each of which is incorporated herein by reference.

Chirally Controlled Oligonucleotides.

In some embodiments, provided oligonucleotides are capable of directing a decrease in the expression and/or level of a target gene or its gene product. In some embodiments, provided oligonucleotides are chirally controlled.

In some embodiments, the present disclosure provides chirally controlled oligonucleotide compositions that, when compared to a reference condition [e.g., absence of the composition, presence of a reference composition (e.g., a stereorandom composition of oligonucleotides having the same base sequence, the same chemical modifications, etc., a PNPLA3 oligonucleotide or single-stranded RNAi agent of another stereoisomer, etc.), and combinations thereof], are capable of directing a decrease in the expression and/or level of a target gene or its gene product.

In some embodiments, the present disclosure provides chirally controlled oligonucleotide compositions that, when compared to a reference condition [e.g., absence of the composition, presence of a reference composition (e.g., a stereorandom composition of oligonucleotides having the same base sequence, the same chemical modifications, etc., a PNPLA3 oligonucleotide or single-stranded RNAi agent of another stereoisomer, etc.), and combinations thereof], mediate improved knockdown of transcripts via single-stranded RNA interference or RNase H.

Among other things, the present disclosure provides chirally controlled ssRNAi agents and chirally controlled compositions comprising one or more specific nucleotide types. In some embodiments, the phrase "oligonucleotide type," as used herein, defines a PNPLA3 oligonucleotide that has a particular base sequence, pattern of backbone linkages, pattern of backbone chiral centers, and pattern of backbone phosphorus modifications (e.g., "—XLR$^1$" groups). Oligonucleotides of a common designated "type" are structurally identical to one another with respect to base sequence, pattern of backbone linkages, pattern of backbone chiral centers, and pattern of backbone phosphorus modifications. In some embodiments, oligonucleotides of a PNPLA3 oligonucleotide type are identical.

In some embodiments, a provided chirally controlled oligonucleotide or single-stranded RNAi agent in the disclosure has properties different from those of the corresponding stereorandom oligonucleotide or single-stranded RNAi agent mixture. In some embodiments, a chirally controlled oligonucleotide or single-stranded RNAi agent has lipophilicity different from that of the stereorandom oligonucleotide or single-stranded RNAi agent mixture. In some embodiments, a chirally controlled oligonucleotide or single-stranded RNAi agent has different retention time on HPLC. In some embodiments, a chirally controlled oligonucleotide or single-stranded RNAi agent may have a peak retention time significantly different from that of the corresponding stereorandom oligonucleotide or single-stranded RNAi agent mixture. During oligonucleotide or single-stranded RNAi agent purification using HPLC as generally practiced in the art, certain chirally controlled oligonucleotide or single-stranded RNAi agents will be largely if not totally lost. During oligonucleotide or single-stranded RNAi agent purification using HPLC as generally practiced in the art, certain chirally controlled oligonucleotide or single-stranded RNAi agents will be largely if not totally lost. One of the consequences is that certain diastereomers of a stereorandom oligonucleotide or single-stranded RNAi agent mixture (certain chirally controlled oligonucleotide or single-stranded RNAi agents) are not tested in assays. Another consequence is that from batches to batches, due to the inevitable instrumental and human errors, the supposedly "pure" stereorandom oligonucleotide or single-stranded RNAi agent will have inconsistent compositions in that diastereomers in the composition, and their relative and absolute amounts, are different from batches to batches. The chirally controlled oligonucleotide or single-stranded RNAi agent and chirally controlled oligonucleotide or single-stranded RNAi agent compositions provided in this disclosure overcome such problems, as a chirally controlled oligonucleotide or single-stranded RNAi agent is synthesized in a chirally controlled fashion as a single diastereomer (diastereoisomer), and a oligonucleotide or single-stranded RNAi agent comprises predetermined levels of one or more individual oligonucleotide or single-stranded RNAi agent types.

One of skill in the chemical and synthetic arts will appreciate that synthetic methods of the present disclosure provide for a degree of control during each step of the synthesis of a provided single-stranded RNAi agent such that each nucleotide unit of the single-stranded RNAi agent can be designed and/or selected in advance to have a particular stereochemistry at the linkage phosphorus and/or a particular modification at the linkage phosphorus, and/or a particular base, and/or a particular sugar. In some embodiments, a provided single-stranded RNAi agent is designed and/or selected in advance to have a particular combination of stereocenters at the linkage phosphorus of the internucleotidic linkage.

In some embodiments, a provided single-stranded RNAi agent made using methods of the present disclosure is designed and/or determined to have a particular combination of linkage phosphorus modifications. In some embodiments, a provided single-stranded RNAi agent made using methods of the present disclosure is designed and/or determined to have a particular combination of bases. In some embodiments, a provided single-stranded RNAi agent made using methods of the present disclosure is designed and/or determined to have a particular combination of sugars. In some embodiments, a provided single-stranded RNAi agent made using methods of the present disclosure is designed and/or determined to have a particular combination of one or more of the above structural characteristics.

Methods of the present disclosure exhibit a high degree of chiral control. For instance, methods of the present disclosure facilitate control of the stereochemical configuration of every single linkage phosphorus within a provided single-stranded RNAi agent. In some embodiments, methods of the present disclosure provide an single-stranded RNAi agent comprising one or more modified internucleotidic linkages independently having the structure of Formula I.

In some embodiments, methods of the present disclosure provide an single-stranded RNAi agent which is a unimer. In some embodiments, methods of the present disclosure provide an single-stranded RNAi agent which is a unimer of configuration Rp. In some embodiments, methods of the present disclosure provide an single-stranded RNAi agent which is a unimer of configuration Sp.

In some embodiments, methods of the present disclosure provide a chirally controlled single-stranded RNAi agent composition, i.e., an single-stranded RNAi agent composition that contains predetermined levels of individual single-stranded RNAi agent types. In some embodiments a PNPLA3 oligonucleotide or a single-stranded RNAi agent comprises one single-stranded RNAi agent type. In some embodiments, a single-stranded RNAi agent comprises more than one single-stranded RNAi agent type. In some embodiments, a PNPLA3 oligonucleotide or single-stranded RNAi agent composition comprises a plurality of oligonucleotide and/or single-stranded RNAi agent types. Example chirally controlled oligonucleotide and single-stranded RNAi agent compositions made in accordance with the present disclosure are described herein.

In some embodiments, a PNPLA3 oligonucleotide comprises a chiral internucleotidic linkage (e.g., is stereocontrolled). In some embodiments, a PNPLA3 oligonucleotide comprises a chiral internucleotidic linkage which is stereocontrolled and a chiral internucleotidic linkage which is not stereocontrolled. In some embodiments, a PNPLA3 oligonucleotide comprises a chiral internucleotidic linkage which is stereocontrolled and an internucleotidic linkage which is not chiral. Various non-limiting examples of formats of stereocontrolled (chirally controlled) oligonucleotides are shown in Tables 71A to 71C. In some embodiments, a PNPLA3 oligonucleotide has a structure of Format S1. In some embodiments, a PNPLA3 oligonucleotide has a structure of Format S2. In some embodiments, a PNPLA3 oligonucleotide has a structure of Format S3. In some embodiments, a PNPLA3 oligonucleotide has a structure of Format S4. In some embodiments, a PNPLA3 oligonucleotide has a structure of Format S5. In some embodiments, a PNPLA3 oligonucleotide has a structure of Format S6. In some embodiments, a PNPLA3 oligonucleotide has a structure of Format S7. In some embodiments, a PNPLA3 oligonucleotide has a structure of Format S8. In some embodiments, a PNPLA3 oligonucleotide has a structure of Format S9. In some embodiments, a PNPLA3 oligonucleotide has a structure of Format S10. In some embodiments, a PNPLA3 oligonucleotide has a structure of Format S11. In some embodiments, a PNPLA3 oligonucleotide has a structure of Format S12. In some embodiments, a PNPLA3 oligonucleotide has a structure of Format S13. In some embodiments, a PNPLA3 oligonucleotide has a structure of Format S14. In some embodiments, a PNPLA3 oligonucleotide has a structure of Format S15. In some embodiments, a PNPLA3 oligonucleotide has a structure of Format S16. In some embodiments, a PNPLA3 oligonucleotide has a structure of Format S17. In some embodiments, a PNPLA3 oligonucleotide has a structure of Format S18. In some embodiments, a PNPLA3 oligonucleotide has a structure of Format S19. In some embodiments, a PNPLA3 oligonucleotide has a structure of Format S20. In some embodiments, a PNPLA3 oligonucleotide has a structure of Format S21. In some embodiments, a PNPLA3 oligonucleotide has a structure of Format S22. In some embodiments, a PNPLA3 oligonucleotide has a structure of Format S23. In some embodiments, a PNPLA3 oligonucleotide has a structure of Format S24. In some embodiments, a PNPLA3 oligonucleotide has a structure of Format S25. In some embodiments, a PNPLA3 oligonucleotide has a structure of Format S26. In some embodiments, a PNPLA3 oligonucleotide has a structure of Format S27. In some embodiments, a PNPLA3 oligonucleotide has a structure of Format S28. In some embodiments, a PNPLA3 oligonucleotide has a structure of Format S29. In some embodiments, a PNPLA3 oligonucleotide has a structure of Format S30. In some embodiments, a PNPLA3 oligonucleotide has a structure of Format S31. In some embodiments, a PNPLA3 oligonucleotide has a structure of Format S32. In some embodiments, a PNPLA3 oligonucleotide has a structure of Format S33. In some embodiments, a PNPLA3 oligonucleotide has a structure of Format S34. In some embodiments, a PNPLA3 oligonucleotide has a structure of Format S35. In some embodiments, a PNPLA3 oligonucleotide has a structure of Format S36. In some embodiments, a PNPLA3 oligonucleotide has a structure of Format S37. In some embodiments, a PNPLA3 oligonucleotide has a structure of Format S38. In some embodiments, a PNPLA3 oligonucleotide has a structure of Format S39. In some embodiments, a PNPLA3 oligonucleotide has a structure of Format S40. In some embodiments, a PNPLA3 oligonucleotide has a structure of Format S41. In some embodiments, a PNPLA3 oligonucleotide has a structure of Format S42. In some embodiments, a PNPLA3 oligonucleotide has a structure of Format S43. In some embodiments, a PNPLA3 oligonucleotide has a structure of Format S44.

In some embodiments, methods of the present disclosure provide chirally pure compositions with respect to the configuration of the linkage phosphorus. That is to say, in some embodiments, methods of the present disclosure provide compositions of wherein the oligonucleotide exists in the composition in the form of a single diastereomer with respect to the configuration of the linkage phosphorus.

In some embodiments, methods of the present disclosure provide chirally uniform compositions with respect to the configuration of the linkage phosphorus. That is to say, in some embodiments, methods of the present disclosure provide compositions of in which all nucleotide units therein have the same stereochemistry with respect to the configuration of the linkage phosphorus, e.g., all nucleotide units are of the Rp configuration at the linkage phosphorus or all nucleotide units are of the Sp configuration at the linkage phosphorus.

In some embodiments, a PNPLA3 oligonucleotide or a single-stranded RNAi agent comprises at least one Sp (e.g., a phosphorothioate or other internucleotidic linkage having a chiral center, in the Sp configuration). In some embodiments, a PNPLA3 oligonucleotide or a single-stranded RNAi agent comprises at least 5 Sp. In some embodiments, a PNPLA3 oligonucleotide or a single-stranded RNAi agent comprises at least 10 Sp. In some embodiments, a PNPLA3 oligonucleotide or a single-stranded RNAi agent comprises at least 15 to 25 Sp.

As shown herein, the incorporation of one or more Sp internucleotidic linkage or one or more Sp PS (phosphorothioate) performs two functions for a single-stranded RNAi agent: (a) it increases stability against nucleases; and (b) does not interfere with RNA interference activity. While single-stranded RNAi agents and double-stranded RNAi agents differ in many aspects, this disclosure notes that, reportedly, many chemical modifications have been attempted for double-stranded RNAi agents, wherein the modifications did not both (a) stabilize the molecule against nucleases; and (b) allow RNA interference activity. Many chemical modifications reportedly perform one function but not the other. Some chemical modifications of double-stranded RNAi agents reportedly stabilized the molecule against nucleases, but interfered with or abolished RNAi activity. Other chemical modifications of double-stranded RNAi agents reportedly did not interfere with RNAi activity, but also did not stabilize the molecules against nucleases. See, for example, Czauderna et al. 2003 Nucl. Acids Res. 31: 2705-2716; Hadwiger et al. 2005, pages 194-206, in RNA interference Technology, ed. K. Appasani, Cambridge University Press, Cambridge, UK; Deleavey et al. 2009 Curr. Prot. Nucl. Acid Chem. 16.3.1-16.3.22; Terrazas et al. 2009 Nucl. Acids Res. 37: 346-353; Schwarz et al. 2002 Mol. Cell 10: 537-548; and Lipardi et al. 2001 Cell 107: 299-307. Only a minority of chemical modifications of double-stranded RNAi agents were capable of performing both functions. Furthermore, Matranga et al. 2005 Cell 123: 607-620 showed that introduction of a single Sp internucleotidic linkage (e.g., a single Sp PS) into the sense strand of a double-stranded RNAi agent greatly decreased RISC assembly and RNA interference activity. Thus, the chemical modification of a double-stranded RNAi agent with a single Sp internucleotidic linkage (e.g., a single Sp PS) did not (b) allow RNA interference activity. Thus, this disclosure endeavored to test the effect(s) of incorporation of Sp internucleotidic linkages or Sp PS into a single-stranded RNAi agent. The data shown herein show that, surprisingly, the incorporation of a Sp internucleotidic linkage or Sp PS performs two functions for a single-stranded RNAi agent: (a) it increases stability against nucleases; and (b) does not interfere with RNA interference activity.

As shown in the data shown in Table 45, the stability of a single-stranded RNAi agent against nucleases was increased by converting a stereorandom phosphorothioate at the 5'-end and/or 3'-end to a phosphorothioate in the Sp configuration. Additional increases in stability were obtained by converting stereorandom phosphorothioates at nuclease cleavage sites identified herein to phosphorothioates in the Sp configuration.

Without wishing to be bound by any particular theory, the disclosure suggests that incorporation of phosphorothioates or other chiral internucleotidic linkages in a Sp configuration may protect single-stranded RNAi agents from nucleases. Experiments revealed nuclease cleavage sites identified in a stereorandom single-stranded RNAi agent, WV-2817, which targets a different gene, APOC3. These major cleavage sites are between two pyrimidines (5'-U'U-3', 5'-U'U-3' or 5'-T'U-3', where indicates the cleavage site). Additional major nuclease cleavage sites were identified for stereorandom single-stranded RNAi agent WV-3242: 5'-U'U-3', 5'-C'U-3', and 5'-T'U-3'. Of the six major nuclease cleavage sites, five were between two adjacent pyrimidines and one was adjacent to a pyrimidine. Experimental data shown in Table 45 indicates that replacing one or more of the nuclease cleavage sites with a Sp internucleotidic linkage (or chiral internucleotidic linkage in a Sp configuration, e.g., a Sp PS or a phosphorothioate in the Sp configuration) greatly increased the stability of the single-stranded RNAi agents.

Single-stranded RNAi agents comprising multiple Sp internucleotidic linkages (e.g., Sp PS) were also tested to determine if the Sp abolished RNAi activity. The present disclosure notes that previous work has shown that many stereorandom oligonucleotides can decrease or completely lose their enzymatic or biological activity if converted into stereocontrolled versions. For many previously described oligonucleotides, introduction of Sp internucleotidic linkages can decrease or abolish activity.

Table 44 shows that, surprisingly, in addition to increasing stability, replacing multiple internucleotidic linkages (whether stereorandom or phosphodiester) with Sp internucleotidic linkages (e.g., Sp PS) did not decrease or eliminate RNA interference activity of a single-stranded RNAi agent. These results are also surprising because, reportedly, the introduction of a Sp PS into a stereorandom oligonucleotide in many cases is known to reduce biological activity. Thus, the introduction of one or more Sp internucleotidic linkages or Sp PS both increased stability of a single-stranded RNAi agent, and did not decrease or abolish RNAi activity.

Table 69A to C also shows that, surprisingly, in addition to increasing stability, replacing multiple internucleotidic linkages (whether stereorandom or phosphodiester) with Sp internucleotidic linkages (e.g., Sp PS) increased stability in and simultaneously did not decrease or eliminate RNA interference activity of a single-stranded RNAi agent. In some cases, activity was increased. These results are also surprising because, reportedly, the introduction of a Sp PS into a stereorandom oligonucleotide in many cases is known to reduce biological activity. Thus, the introduction of one or more Sp internucleotidic linkages or Sp PS both increased stability of a single-stranded RNAi agent, and did not decrease or abolish RNAi activity.

In some embodiments or a single-stranded RNAi agent, the oligonucleotide or single-stranded RNAi comprises 1 or more Sp internucleotidic linkages. In some embodiments or a single-stranded RNAi agent, the oligonucleotide or single-stranded RNAi comprises 1 or more Sp internucleotidic linkages at the 5' and/or 3'-end of the oligonucleotide or single-stranded RNAi agent. In some embodiments or a single-stranded RNAi agent, the oligonucleotide or single-stranded RNAi comprises 1 or more Sp internucleotidic linkages at sites susceptible to nuclease cleavage.

In some embodiments or a single-stranded RNAi agent, the oligonucleotide or single-stranded RNAi comprises 1 or more Sp PS. In some embodiments or a single-stranded RNAi agent, the oligonucleotide or single-stranded RNAi comprises 1 or more Sp PS at the 5' and/or 3'-end of the oligonucleotide or single-stranded RNAi agent. In some embodiments or a single-stranded RNAi agent, the oligonucleotide or single-stranded RNAi comprises 1 or more Sp PS at sites susceptible to nuclease cleavage.

Among other things, the present disclosure recognizes the challenge of stereoselective (rather than stereorandom or racemic) preparation of single-stranded RNAi agents. Among other things, the present disclosure provides methods and reagents for stereoselective preparation of single-stranded RNAi agents comprising multiple (e.g., more than 5, 6, 7, 8, 9, or 10) internucleotidic linkages, and particularly for single-stranded RNAi agents comprising multiple (e.g., more than 5, 6, 7, 8, 9, or 10) chiral internucleotidic linkages. In some embodiments, in a stereorandom or racemic preparation of single-stranded RNAi agents, at least one chiral internucleotidic linkage is formed with less than 90:10, 95:5, 96:4, 97:3, or 98:2 diastereoselectivity. In some embodiments, for a stereoselective or chirally controlled preparation of single-stranded RNAi agents, each chiral internucleotidic linkage is formed with greater than 90:10, 95:5, 96:4, 97:3, or 98:2 diastereoselectivity. In some embodiments, for a stereoselective or chirally controlled preparation of single-stranded RNAi agents, each chiral internucleotidic linkage is formed with greater than 95:5 diastereoselectivity. In some embodiments, for a stereoselective or chirally controlled preparation of single-stranded RNAi agents, each chiral internucleotidic linkage is formed with greater than 96:4 diastereoselectivity. In some embodiments, for a stereoselective or chirally controlled preparation of single-stranded RNAi agents, each chiral internucleotidic linkage is formed with greater than 97:3 diastereoselectivity. In some embodiments, for a stereoselective or chirally controlled preparation of single-stranded RNAi agents, each chiral internucleotidic linkage is formed with greater than 98:2 diastereoselectivity. In some embodiments, for a stereoselective or chirally controlled preparation of single-stranded RNAi agents, each chiral internucleotidic linkage is formed with greater than 99:1 diastereoselectivity. In some embodiments, diastereoselectivity of a chiral internucleotidic linkage in an single-stranded RNAi agent may be measured through a model reaction, e.g. formation of a dimer under essentially the same or comparable conditions wherein the dimer has the same internucleotidic linkage as the chiral internucleotidic linkage, the 5'-nucleoside of the dimer is the same as the nucleoside to the 5'-end of the chiral internucleotidic linkage, and the 3'-nucleoside of the dimer is the same as the nucleoside to the 3'-end of the chiral internucleotidic linkage.

In some embodiments, a PNPLA3 oligonucleotide or a single-stranded RNAi agent is a composition designed to comprise multiple oligonucleotide or single-stranded RNAi agent types. In some embodiments, methods of the present disclosure allow for the generation of a library of chirally controlled single-stranded RNAi agents such that a preselected amount of any one or more chirally controlled single-stranded RNAi agent types can be mixed with any one or more other chirally controlled single-stranded RNAi agent types to create a chirally controlled single-stranded RNAi agent composition. In some embodiments, the preselected amount of an single-stranded RNAi agent type is a composition having any one of the above-described diastereomeric purities.

In some embodiments, the present disclosure provides methods for making a chirally controlled single-stranded RNAi agent comprising steps of:

(1) coupling;
(2) capping;
(3) modifying;
(4) deblocking; and
(5) repeating steps (1)-(4) until a desired length is achieved.

When describing the provided methods, the word "cycle" has its ordinary meaning as understood by a person of ordinary skill in the art. In some embodiments, one round of steps (1)-(4) is referred to as a cycle.

In some embodiments, the present disclosure provides methods for making chirally controlled single-stranded RNAi agent compositions, comprising steps of:

(a) providing an amount of a first chirally controlled single-stranded RNAi agent; and
(b) optionally providing an amount of one or more additional chirally controlled single-stranded RNAi agents.

In some embodiments, a first chirally controlled single-stranded RNAi agent is an single-stranded RNAi agent type, as described herein. In some embodiments, a one or more additional chirally controlled single-stranded RNAi agent is a one or more single-stranded RNAi agent type, as described herein.

One of skill in the relevant chemical and synthetic arts will recognize the degree of versatility and control over structural variation and stereochemical configuration of a provided single-stranded RNAi agent when synthesized using methods of the present disclosure. For instance, after a first cycle is complete, a subsequent cycle can be performed using a nucleotide unit individually selected for that subsequent cycle which, in some embodiments, comprises a nucleobase and/or a sugar that is different from the first cycle nucleobase and/or sugar. Likewise, the chiral auxiliary used in the coupling step of the subsequent cycle can be different from the chiral auxiliary used in the first cycle, such that the second cycle generates a phosphorus linkage of a different stereochemical configuration. In some embodiments, the stereochemistry of the linkage phosphorus in the newly formed internucleotidic linkage is controlled by using stereochemically pure phosphoramidites. Additionally, the modification reagent used in the modifying step of a subsequent cycle can be different from the modification reagent used in the first or former cycle. The cumulative effect of this iterative assembly approach is such that each component of a provided single-stranded RNAi agent can be structurally and configurationally tailored to a high degree. An additional advantage to this approach is that the step of capping minimizes the formation of "n−1" impurities that would otherwise make isolation of a provided single-stranded RNAi agent extremely challenging, and especially single-stranded RNAi agents of longer lengths.

In some embodiments, an example cycle of the method for making chirally controlled single-stranded RNAi agents is illustrated in example schemes described in the present disclosure. In some embodiments, an example cycle of the method for making chirally controlled single-stranded RNAi agents is illustrated in Scheme I. In some embodiments, ● represents the solid support, and optionally a portion of the growing chirally controlled single-stranded RNAi agent attached to the solid support. The chiral auxiliary exemplified has the structure of formula 3-I:

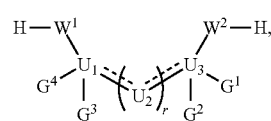

Formula 3-I which is further described below. "Cap" is any chemical moiety introduced to the nitrogen atom by the capping step, and in some embodiments, is an amino protecting group. One of ordinary skill in the art understands that in the first cycle, there may be only one nucleoside attached to the solid support when started, and cycle exit can be performed optionally before deblocking. As understood by a person of skill in the art, $B^{PRO}$ is a protected base used in single-stranded RNAi agent synthesis. Each step of the above-depicted cycle of Scheme I is described further below.

Scheme I. Syntesis of chirally controlled single-stranded RNAi agent.

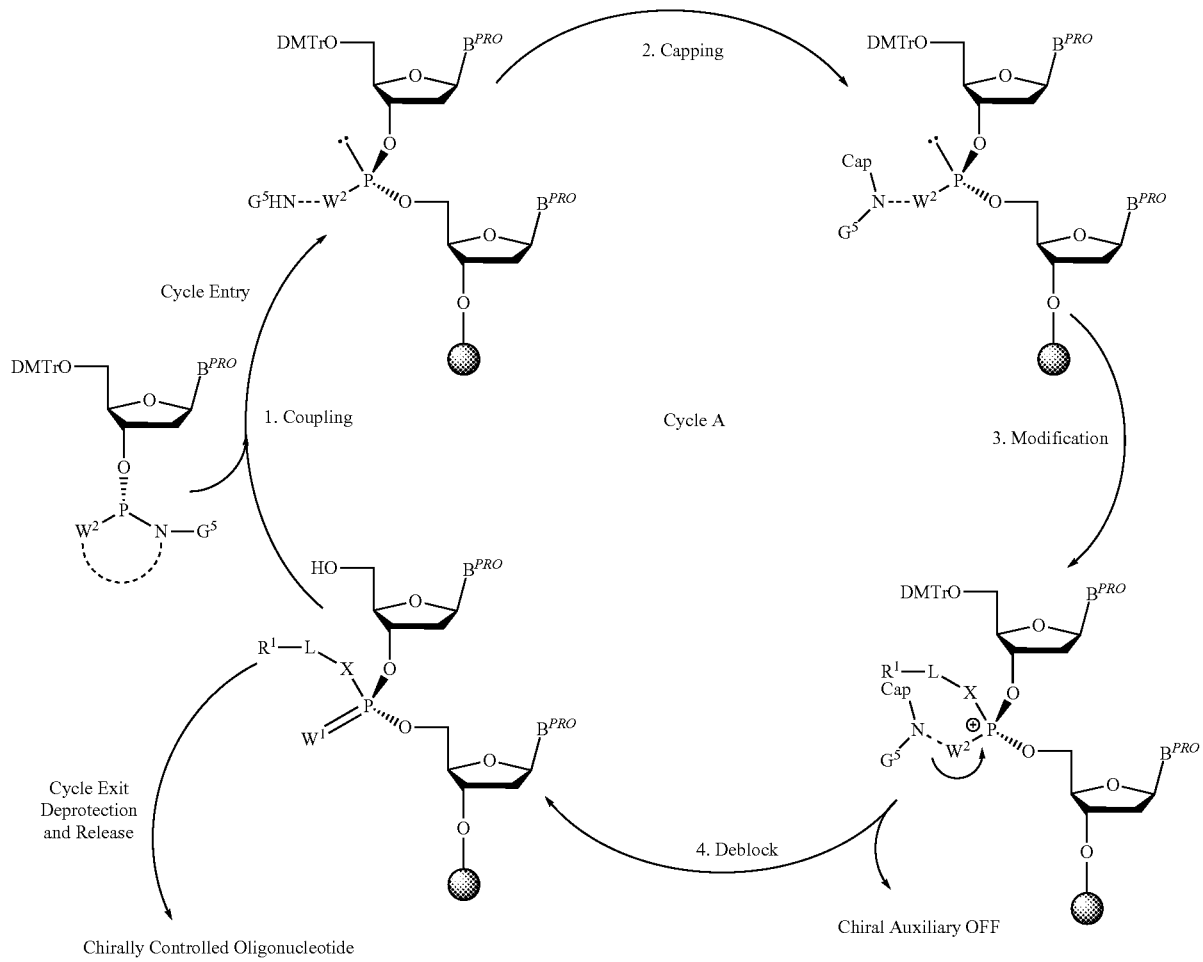

Synthesis on Solid Support

In some embodiments, the synthesis of a provided single-stranded RNAi agent is performed on solid phase. In some embodiments, reactive groups present on a solid support are protected. In some embodiments, reactive groups present on a solid support are unprotected. During single-stranded RNAi agent synthesis a solid support is treated with various reagents in several synthesis cycles to achieve the stepwise elongation of a growing single-stranded RNAi agent chain with individual nucleotide units. The nucleoside unit at the end of the chain which is directly linked to the solid support is termed "the first nucleoside" as used herein. A first nucleoside is bound to a solid support via a linker moiety, i.e. a diradical with covalent bonds between either of a CPG, a polymer or other solid support and a nucleoside. The linker stays intact during the synthesis cycles performed to assemble the oligonucleotide chain and is cleaved after the chain assembly to liberate the oligonucleotide from the support.

Solid supports for solid-phase nucleic acid synthesis include the supports described in, e.g., U.S. Pat. Nos. 4,659,774, 5,141,813, 4,458,066; Caruthers U.S. Pat. Nos. 4,415,732, 4,458,066, 4,500,707, 4,668,777, 4,973,679, and 5,132,418; Andrus et al. U.S. Pat. Nos. 5,047,524, 5,262, 530; and Koster U.S. Pat. No. 4,725,677 (reissued as RE34, 069). In some embodiments, a solid phase is an organic polymer support. In some embodiments, a solid phase is an inorganic polymer support. In some embodiments, an organic polymer support is polystyrene, aminomethyl polystyrene, a polyethylene glycol-polystyrene graft copolymer, polyacrylamide, polymethacrylate, polyvinylalcohol, highly cross-linked polymer (HCP), or other synthetic polymers, carbohydrates such as cellulose and starch or other polymeric carbohydrates, or other organic polymers and any copolymers, composite materials or combination of the above inorganic or organic materials. In some embodiments, an inorganic polymer support is silica, alumina, controlled polyglass (CPG), which is a silica-gel support, or aminopropyl CPG. Other useful solid supports include fluorous solid supports (see e.g., WO/2005/070859), long chain alkylamine (LCAA) controlled pore glass (CPG) solid supports (see e.g., S. P. Adams, K. S. Kavka, E. J. Wykes, S. B. Holder and G. R. Galluppi, *J. Am. Chem. Soc.*, 1983, 105, 661-663; G. R. Gough, M. J. Bruden and P. T. Gilham, *Tetrahedron Lett.,* 1981, 22, 4177-4180). Membrane supports and polymeric membranes (see e.g. Innovation and Perspectives in Solid Phase Synthesis, Peptides, Proteins and Nucleic Acids, ch 21 pp 157-162, 1994, Ed. Roger Epton and U.S. Pat. No. 4,923,901) are also useful for the synthesis of nucleic acids. Once formed, a membrane can be chemically functionalized for use in nucleic acid synthesis. In addition to the attachment of a functional group to the membrane, the use of a linker or spacer group attached to the membrane is also used in some embodiments to minimize steric hindrance between the membrane and the synthesized chain.

Other suitable solid supports include those generally known in the art to be suitable for use in solid phase methodologies, including, for example, glass sold as Primer™ 200 support, controlled pore glass (CPG), oxalyl-controlled pore glass (see, e.g., Alul, et al., *Nucleic Acids Research,* 1991, 19, 1527), TentaGel Support—an aminopolyethyleneglycol derivatized support (see, e.g., Wright, et al., Tetrahedron Lett., 1993, 34, 3373), and Poros-a copolymer of polystyrene/divinylbenzene.

Surface activated polymers have been demonstrated for use in synthesis of natural and modified nucleic acids and proteins on several solid supports mediums. A solid support material can be any polymer suitably uniform in porosity, having sufficient amine content, and sufficient flexibility to undergo any attendant manipulations without losing integrity. Examples of suitable selected materials include nylon, polypropylene, polyester, polytetrafluoroethylene, polystyrene, polycarbonate, and nitrocellulose. Other materials can serve as a solid support, depending on the design of the investigator. In consideration of some designs, for example, a coated metal, in particular gold or platinum can be selected (see e.g., US publication No. 20010055761). In one embodiment of single-stranded RNAi agent synthesis, for example, a nucleoside is anchored to a solid support which is functionalized with hydroxyl or amino residues. Alternatively, a solid support is derivatized to provide an acid labile trialkoxytrityl group, such as a trimethoxytrityl group (TMT). Without being bound by theory, it is expected that the presence of a trialkoxytrityl protecting group will permit initial detritylation under conditions commonly used on DNA synthesizers. For a faster release of single-stranded RNAi agent material in solution with aqueous ammonia, a diglycoate linker is optionally introduced onto the support.

In some embodiments, a provided single-stranded RNAi agent alternatively is synthesized from the 5' to 3' direction. In some embodiments, a nucleic acid is attached to a solid support through its 5' end of the growing nucleic acid, thereby presenting its 3' group for reaction, i.e. using 5'-nucleoside phosphoramidites or in enzymatic reaction (e.g. ligation and polymerization using nucleoside 5'-triphosphates). When considering the 5' to 3' synthesis the iterative steps of the present disclosure remain unchanged (i.e. capping and modification on the chiral phosphorus).

Linking Moiety

A linking moiety or linker is optionally used to connect a solid support to a compound comprising a free nucleophilic moiety. Suitable linkers are known such as short molecules which serve to connect a solid support to functional groups (e.g., hydroxyl groups) of initial nucleosides molecules in solid phase synthetic techniques. In some embodiments, the linking moiety is a succinamic acid linker, or a succinate linker (—CO—CH$_2$—CH$_2$—CO—), or an oxalyl linker (—CO—CO—). In some embodiments, the linking moiety and the nucleoside are bonded together through an ester bond. In some embodiments, a linking moiety and a nucleoside are bonded together through an amide bond. In some embodiments, a linking moiety connects a nucleoside to another nucleotide or nucleic acid. Suitable linkers are disclosed in, for example, *Oligonucleotides And Analogues A Practical Approach,* Ekstein, F. Ed., IRL Press, N.Y., 1991, Chapter 1 and Solid-Phase Supports for Oligonucleotide Synthesis, Pon, R. T., *Curr. Prot. Nucleic Acid Chem.,* 2000, 3.1.1-3.1.28.

A linker moiety is used to connect a compound comprising a free nucleophilic moiety to another nucleoside, nucleotide, or nucleic acid. In some embodiments, a linking moiety is a phosphodiester linkage. In some embodiments, a linking moiety is an H-phosphonate moiety. In some embodiments, a linking moiety is a modified phosphorus linkage as described herein. In some embodiments, a universal linker (UnyLinker) is used to attached the oligonucleotide to the solid support (Ravikumar et al., *Org. Process Res. Dev.,* 2008, 12 (3), 399-410). In some embodiments, other universal linkers are used (Pon, R. T., *Curr. Prot. Nucleic Acid Chem.,* 2000, 3.1.1-3.1.28). In some embodiments, various orthogonal linkers (such as disulfide linkers) are used (Pon, R. T., *Curr. Prot. Nucleic Acid Chem.,* 2000, 3.1.1-3.1.28).

Among other things, the present disclosure recognizes that a linker can be chosen or designed to be compatible with a set of reaction conditions employed in single-stranded RNAi agent synthesis. In some embodiments, to avoid degradation of single-stranded RNAi agents and to avoid desulfurization, auxiliary groups are selectively removed before de-protection. In some embodiments, DPSE group can selectively be removed by F$^-$ ions. In some embodiments, the present disclosure provides linkers that are stable under a DPSE de-protection condition, e.g., 0.1M TBAF in MeCN, 0.5M HF-Et$_3$N in THF or MeCN, etc. In some embodiments, a provided linker is the SP linker. In some embodiments, the present disclosure demonstrates that the SP linker is stable under a DPSE de-protection condition, e.g., 0.1M TBAF in MeCN, 0.5M HF-Et$_3$N in THF or MeCN, etc.; they are also stable, e.g., under anhydrous basic conditions, such as om1M DBU in MeCN.

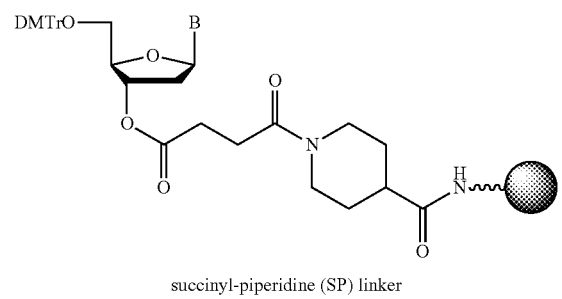

succinyl-piperidine (SP) linker

In some embodiments, an example linker is:

DMTrO—[structure with B, O, and succinyl linker to solid support]

succinyl linker

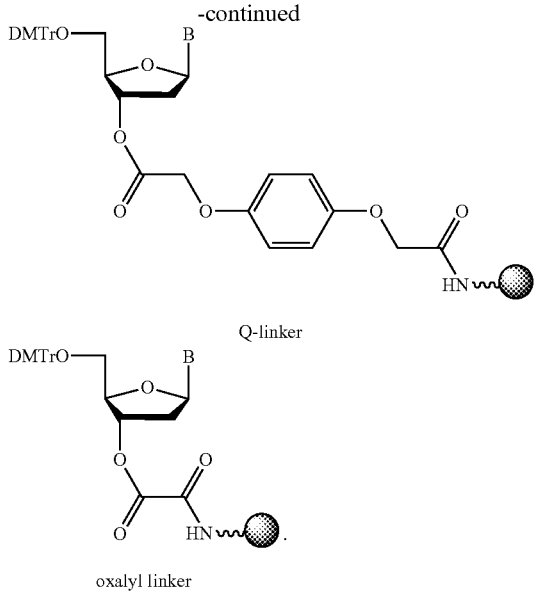

Q-linker oxalyl linker

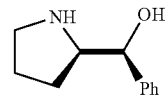

Formula O

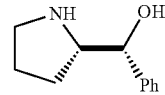

Formula P

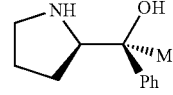

Formula Q

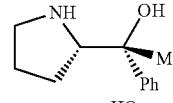

Formula R

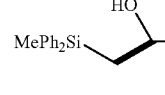

DPSE

In some embodiments, the succinyl linker, Q-linker or oxalyl linker is not stable to one or more DPSE-deprotection conditions using $F^-$.

General Conditions—Solvents for Synthesis

Syntheses of provided oligonucleotides are generally performed in aprotic organic solvents. In some embodiments, a solvent is a nitrile solvent such as, e.g., acetonitrile. In some embodiments, a solvent is a basic amine solvent such as, e.g., pyridine. In some embodiments, a solvent is an ethereal solvent such as, e.g., tetrahydrofuran. In some embodiments, a solvent is a halogenated hydrocarbon such as, e.g., dichloromethane. In some embodiments, a mixture of solvents is used. In certain embodiments a solvent is a mixture of any one or more of the above-described classes of solvents.

In some embodiments, when an aprotic organic solvent is not basic, a base is present in the reacting step. In some embodiments where a base is present, the base is an amine base such as, e.g., pyridine, quinoline, or N,N-dimethylaniline. Example other amine bases include pyrrolidine, piperidine, N-methyl pyrrolidine, pyridine, quinoline, N,N-dimethylaminopyridine (DMAP), or N,N-dimethylaniline.

In some embodiments, a base is other than an amine base.

In some embodiments, an aprotic organic solvent is anhydrous. In some embodiments, an anhydrous aprotic organic solvent is freshly distilled. In some embodiments, a freshly distilled anhydrous aprotic organic solvent is a basic amine solvent such as, e.g., pyridine. In some embodiments, a freshly distilled anhydrous aprotic organic solvent is an ethereal solvent such as, e.g., tetrahydrofuran. In some embodiments, a freshly distilled anhydrous aprotic organic solvent is a nitrile solvent such as, e.g., acetonitrile.

Chiral Reagent/Chiral Auxiliary

In some embodiments, chiral reagents are used to confer stereoselectivity in the production of chirally controlled oligonucleotides. Many different chiral reagents, also referred to by those of skill in the art and herein as chiral auxiliaries, may be used in accordance with methods of the present disclosure. Examples of such chiral reagents are described herein and in Wada I, II and III, referenced above. In some embodiments of the disclosure, a chiral reagent is a compound of one of the following formulae:

As demonstrated herein, when used for preparing a chiral internucleotidic linkage, to obtain stereoselectivity generally stereochemically pure chiral reagents are utilized.

Additional chiral auxiliaries and their use can be found in e.g., Wada I (JP4348077; WO2005/014609; WO2005/092909), Wada II (WO2010/064146), Wada III (WO2012/039448), Chiral Control (WO2010/064146), etc.

Activation

An achiral H-phosphonate moiety is treated with the first activating reagent to form the first intermediate. In one embodiment, the first activating reagent is added to the reaction mixture during the condensation step. Use of the first activating reagent is dependent on reaction conditions such as solvents that are used for the reaction. Examples of the first activating reagent are phosgene, trichloromethyl chloroformate, bis(trichloromethyl)carbonate (BTC), oxalyl chloride, $Ph_3PCl_2$, $(PhO)_3PCl_2$, N,N'-bis(2-oxo-3-oxazolidinyl)phosphinic chloride (BopCl), 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP).

The example of achiral H-phosphonate moiety is a compound shown in the above Scheme. DBU represents 1,8-diazabicyclo[5.4.0]undec-7-ene. $H^+DBU$ may be, for example, ammonium ion, alkylammonium ion, heteroaromatic iminium ion, or heterocyclic iminium ion, any of which is primary, secondary, tertiary or quaternary, or a monovalent metal ion.

Reacting with Chiral Reagent

After the first activation step, the activated achiral H-phosphonate moiety reacts with a chiral reagent.

Stereospecific Condensation Step

A chiral intermediate is treated with the second activating reagent and a nucleoside to form a condensed intermediate. The nucleoside may be on solid support. Examples of the second activating reagent are 4,5-dicyanoimidazole (DCI), 4,5-dichloroimidazole, 1-phenylimidazolium triflate (PhIMT), benzimidazolium triflate (BIT), benztriazole, 3-nitro-1,2,4-triazole (NT), tetrazole, 5-ethylthiotetrazole (ETT), 5-benzylthiotetrazole (BTT), 5-(4-nitrophenyl)tetrazole, N-cyanomethylpyrrolidinium triflate (CMPT), N-cyanomethylpiperidinium triflate, N-cyanomethyldimethylammonium triflate. A chiral intermediate of Formula Z-Va ((Z-Vb), (Z-Va'), or (Z-Vb')) may be isolated as a monomer. Usually, the chiral intermediate of Z-Va ((Z-Vb), (Z-Va'), or (Z-Vb')) is not isolated and undergoes a reaction in the same pot with a nucleoside or modified nucleoside to provide a chiral phosphite compound, a condensed intermediate. In other embodiments, when the method is performed via solid phase synthesis, the solid support comprising the compound is filtered away from side products, impurities, and/or reagents.

Capping Step

If the final nucleic acid is larger than a dimer, the unreacted —OH moiety is capped with a blocking group and the chiral auxiliary in the compound may also be capped with a blocking group to form a capped condensed intermediate. If the final nucleic acid is a dimer, then the capping step is not necessary.

Modifying Step

The compound is modified by reaction with an electrophile. The capped condensed intermediate may be executed modifying step. In some embodiments, the modifying step is performed using a sulfur electrophile, a selenium electrophile or a boronating agent. Examples of modifying steps are step of oxidation and sulfurization.

In some embodiments of the method, the sulfur electrophile is a compound having one of the following formulas:
$S_8$ (Formula Z-B), $Z^{z1}$—S—S—$Z^{z2}$, or $Z^{z1}$—S-$_{Vz}$-$Z^{z2}$; wherein $Z^{z1}$ and $Z^{z2}$ are independently alkyl, aminoalkyl, cycloalkyl, heterocyclic, cycloalkylalkyl, heterocycloalkyl, aryl, heteroaryl, alkyloxy, aryloxy, heteroaryloxy, acyl, amide, imide, or thiocarbonyl, or $Z^{z1}$ and $Z^{z2}$ are taken together to form a 3 to 8 membered alicyclic or heterocyclic ring, which may be substituted or unsubstituted; $_{Vz}$ is $SO_2$, O, or $NR^f$, and $R^f$ is hydrogen, alkyl, alkenyl, alkynyl, or aryl.

Additional sulfur electrophiles are known in the art.

In some embodiments, after the modifying step, a chiral auxiliary group falls off from the growing oligonucleotide chain. In some embodiments, after the modifying step, a chiral auxiliary group remains connected to the internucleotidic phosphorus atom.

In some embodiments of the method, the modifying step is an oxidation step. In some embodiments of the method, the modifying step is an oxidation step using similar conditions as described above in this application. In some embodiments, an oxidation step is as disclosed in, e.g., JP 2010-265304 A and WO2010/064146.

Chain Elongation Cycle and De-Protection Step

The capped condensed intermediate is deblocked to remove the blocking group at the 5'-end of the growing nucleic acid chain to provide a compound. The compound is optionally allowed to re-enter the chain elongation cycle to form a condensed intermediate, a capped condensed intermediate, a modified capped condensed intermediate, and a 5'-deprotected modified capped intermediate. Following at least one round of chain elongation cycle, the 5'-deprotected modified capped intermediate is further deblocked by removal of the chiral auxiliary ligand and other protecting groups for, e.g., nucleobase, modified nucleobase, sugar and modified sugar protecting groups, to provide a nucleic acid. In other embodiments, the nucleoside comprising a 5'-OH moiety is an intermediate from a previous chain elongation cycle as described herein. In yet other embodiments, the nucleoside comprising a 5'-OH moiety is an intermediate obtained from another known nucleic acid synthetic method. In embodiments where a solid support is used, the phosphorus-atom modified nucleic acid is then cleaved from the solid support. In certain embodiments, the nucleic acids is left attached on the solid support for purification purposes and then cleaved from the solid support following purification.

In yet other embodiments, the nucleoside comprising a 5'-OH moiety is an intermediate obtained from another known nucleic acid synthetic method. In yet other embodiments, the nucleoside comprising a 5'-OH moiety is an intermediate obtained from another known nucleic acid synthetic method as described in this application. In yet other embodiments, the nucleoside comprising a 5'-OH moiety is an intermediate obtained from another known nucleic acid synthetic method comprising one or more cycles illustrated in Scheme I. In some embodiments, the present disclosure provides oligonucleotide synthesis methods that use stable and commercially available materials as starting materials. In some embodiments, the present disclosure provides oligonucleotide synthesis methods to produce stereocontrolled phosphorus atom-modified oligonucleotide derivatives using an achiral starting material.

In some embodiments, the method of the present disclosure does not cause degradations under the de-protection steps. Further the method does not require special capping agents to produce phosphorus atom-modified oligonucleotide derivatives.

Condensing Reagent

Condensing reagents (CR) useful in accordance with methods of the present disclosure are of any one of the following general formulae:

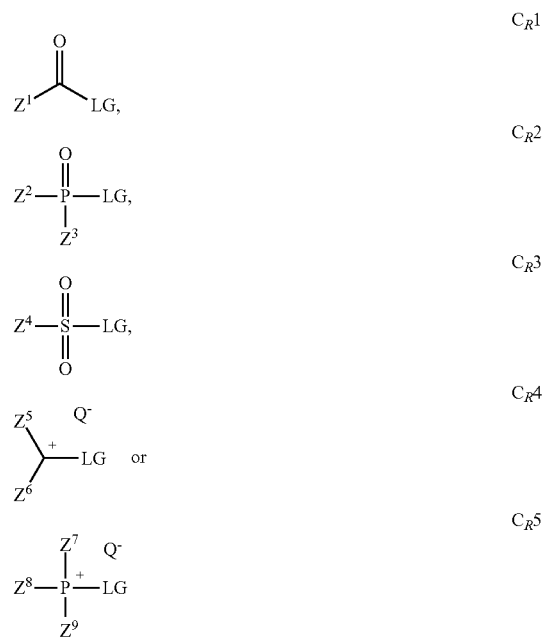

wherein $Z^1$, $Z^2$, $Z^3$, $Z^4$, $Z^5$, $Z^6$, $Z^7$, $Z^8$, and $Z^9$ are independently optionally substituted group selected from alkyl, aminoalkyl, cycloalkyl, heterocyclic, cycloalkylalkyl, heterocycloalkyl, aryl, heteroaryl, alkyloxy, aryloxy, or heteroaryloxy, or wherein any of $Z^2$ and $Z^3$, $Z^5$ and $Z^6$, $Z^7$ and $Z^8$, $Z^8$ and $Z^9$, $Z^9$ and $Z^7$, or $Z^7$ and $Z^8$ and $Z^9$ are taken together to form a 3 to 20 membered alicyclic or heterocyclic ring; $Q^-$ is a counter anion; and LG is a leaving group.

In some embodiments, a counter ion of a condensing reagent CR is Cl⁻, Br⁻, BF₄⁻, PF₆⁻, TfO⁻, Tf₂N⁻, AsF₆⁻, ClO₄⁻, or SbF₆⁻, wherein Tf is CF₃SO₂. In some embodiments, a leaving group of a condensing reagent CR is F, Cl, Br, I, 3-nitro-1,2,4-triazole, imidazole, alkyltriazole, tetrazole, pentafluorobenzene, or 1-hydroxybenzotriazole.

In some embodiments, a condensing reagent is selected from those described in WO/2006/066260.

In some embodiments, a condensing reagent is 1,3-dimethyl-2-(3-nitro-1,2,4-triazol-1-yl)-2-pyrrolidin-1-yl-1,3,2-diazaphospholidinium hexafluorophosphate (MNTP), or 3-nitro-1,2,4-triazol-1-yl-tris(pyrrolidin-1-yl)phosphonium hexafluorophosphate (PyNTP):

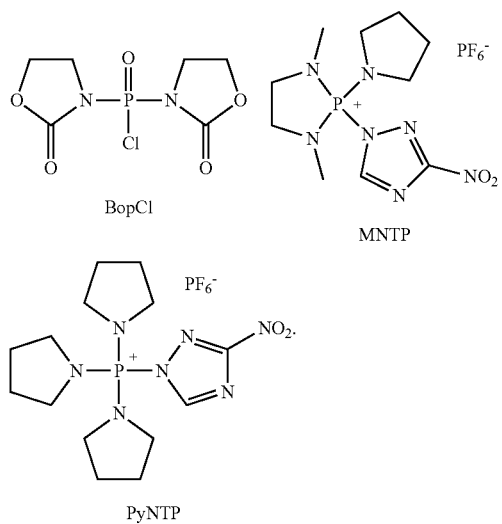

Selection of Base and Sugar of Nucleoside Coupling Partner

As described herein, nucleoside coupling partners for use in accordance with methods of the present disclosure can be the same as one another or can be different from one another. In some embodiments, nucleoside coupling partners for use in the synthesis of a provided oligonucleotide are of the same structure and/or stereochemical configuration as one another. In some embodiments, each nucleoside coupling partner for use in the synthesis of a provided oligonucleotide is not of the same structure and/or stereochemical configuration as certain other nucleoside coupling partners of the oligonucleotide. Example nucleobases and sugars for use in accordance with methods of the present disclosure are described herein. One of skill in the relevant chemical and synthetic arts will recognize that any combination of nucleobases and sugars described herein are contemplated for use in accordance with methods of the present disclosure.

Coupling Step

Example coupling procedures and chiral reagents and condensing reagents for use in accordance with the present disclosure are outlined in, inter alia, Wada I (JP4348077; WO2005/014609; WO2005/092909), Wada II (WO2010/064146), Wada III (WO2012/039448), and Chiral Control (WO2010/064146). Chiral nucleoside coupling partners for use in accordance with the present disclosure are also referred to herein as "Wada amidites." In some embodiments, a coupling partner has the structure of

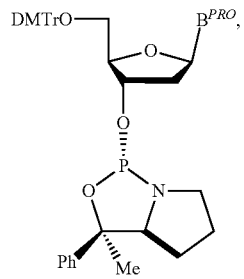

wherein $B^{PRO}$ is a protected nucleobase. In some embodiments, a coupling partner has the structure of

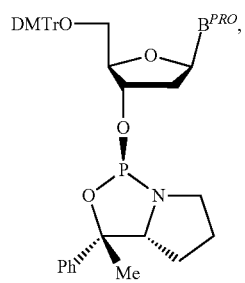

wherein $B^{PRO}$ is a protected nucleobase. In some embodiments, a coupling partner has the structure of

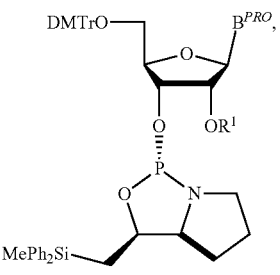

wherein $B^{PRO}$ is a protected nucleobase, and $R^1$ is as defined and described herein. In some embodiments, a coupling partner has the structure of

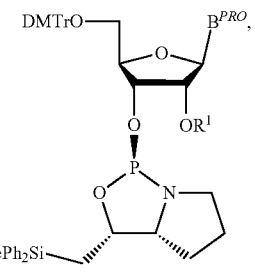

wherein $B^{PRO}$ is a protected nucleobase, and $R^1$ is as defined and described herein. In some embodiments, $R^1$ is optionally substituted $C_{1-6}$ alkyl. In some embodiments, $R^1$ is Me.

Additional examples are described in WO/2010/064146, WO/2011/005761, WO/2013/012758, WO/2014/010250, US2013/0178612, WO/2014/012081, WO/2015/107425, WO/2017/015555, and WO/2017/062862, the phosphoramidites of each of which is incorporated herein by reference.

In some embodiments, the step of coupling comprises reacting a free hydroxyl group of a nucleotide unit of a PNPLA3 oligonucleotide with a nucleoside coupling partner under suitable conditions to effect the coupling. In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

Once the appropriate hydroxyl group of the growing oligonucleotide has been deblocked, the support is washed and dried in preparation for delivery of a solution comprising a chiral reagent and a solution comprising an activator. In some embodiments, a chiral reagent and an activator are delivered simultaneously. In some embodiments, co-delivery comprises delivering an amount of a chiral reagent in solution (e.g., a phosphoramidite solution) and an amount of activator in a solution (e.g., a CMPT solution) in a polar aprotic solvent such as a nitrile solvent (e.g., acetonitrile).

In some embodiments, the step of coupling provides a crude product composition in which the chiral phosphite product is present in a diastereomeric excess of >95%. In some embodiments, the chiral phosphite product is present in a diastereomeric excess of >96%. In some embodiments, the chiral phosphite product is present in a diastereomeric excess of >97%. In some embodiments, the chiral phosphite product is present in a diastereomeric excess of >98%. In some embodiments, the chiral phosphite product is present in a diastereomeric excess of >99%.

Capping Step:

Provided methods for making chirally controlled oligonucleotides comprise a step of capping. In some embodiments, a step of capping is a single step. In some embodiments, a step of capping is two steps. In some embodiments, a step of capping is more than two steps. In some embodiments, a step of capping comprises steps of capping the free amine of the chiral auxiliary and capping any residual unreacted 5' hydroxyl groups. In some embodiments, the free amine of the chiral auxiliary and the unreacted 5' hydroxyl groups are capped with the same capping group. In some embodiments, the free amine of the chiral auxiliary and the unreacted 5' hydroxyl groups are capped with different capping groups. In certain embodiments, capping with different capping groups allows for selective removal of one capping group over the other during synthesis of the oligonucleotide. In some embodiments, the capping of both groups occurs simultaneously. In some embodiments, the capping of both groups occurs iteratively. In certain embodiments, capping occurs iteratively and comprises a first step of capping the free amine followed by a second step of capping the free 5' hydroxyl group, wherein both the free amine and the 5' hydroxyl group are capped with the same capping group. For instance, in some embodiments, the free amine of the chiral auxiliary is capped using an anhydride (e.g., phenoxyacetic anhydride, i.e., Pac$_2$O) prior to capping of the 5' hydroxyl group with the same anhydride. In certain embodiments, the capping of the 5' hydroxyl group with the same anhydride occurs under different conditions (e.g., in the presence of one or more additional reagents). In some embodiments, capping of the 5' hydroxyl group occurs in the presence of an amine base in an ethereal solvent (e.g., NMI (N-methylimidazole) in THF). The phrase "capping group" is used interchangeably herein with the phrases "protecting group" and "blocking group". In some embodiments, an amine capping group is characterized in that it effectively caps the amine such that it prevents rearrangement and/or decomposition of the intermediate phosphite species. In some embodiments, a capping group is selected for its ability to protect the amine of the chiral auxiliary in order to prevent intramolecular cleavage of the internucleotide linkage phosphorus. In some embodiments, a 5' hydroxyl group capping group is characterized in that it effectively caps the hydroxyl group such that it prevents the occurrence of "shortmers," e.g., "n-m" (m and n are integers and m<n; n is the number of bases in the targeted oligonucleotide) impurities that occur from the reaction of a PNPLA3 oligonucleotide chain that fails to react in a first cycle but then reacts in one or more subsequent cycles. The presence of such shortmers, especially "n−1", has a deleterious effect upon the purity of the crude oligonucleotide and makes final purification of the oligonucleotide tedious and generally low-yielding. In some embodiments, a particular cap is selected based on its tendency to facilitate a particular type of reaction under particular conditions. For instance, in some embodiments, a capping group is selected for its ability to facilitate an E1 elimination reaction, which reaction cleaves the cap and/or auxiliary from the growing oligonucleotide. In some embodiments, a capping group is selected for its ability to facilitate an E2 elimination reaction, which reaction cleaves the cap and/or auxiliary from the growing oligonucleotide. In some embodiments, a capping group is selected for its ability to facilitate a (3-elimination reaction, which reaction cleaves the cap and/or auxiliary from the growing oligonucleotide.

Modifying Step:

As used herein, the phrase "modifying step", "modification step" and "P-modification step" are used interchangeably and refer generally to any one or more steps used to install a modified internucleotidic linkage. In some embodiments, the modified internucleotidic linkage having the structure of Formula I. A P-modification step of the present disclosure occurs during assembly of a provided oligonucleotide rather than after assembly of a provided oligonucleotide is complete. Thus, each nucleotide unit of a provided oligonucleotide can be individually modified at the linkage phosphorus during the cycle within which the nucleotide unit is installed. In some embodiments, a suitable P-modification reagent is a sulfur electrophile, selenium electrophile, oxygen electrophile, boronating reagent, or an azide reagent.

For instance, in some embodiments, a selenium reagent is elemental selenium, a selenium salt, or a substituted diselenide. In some embodiments, an oxygen electrophile is elemental oxygen, peroxide, or a substituted peroxide. In some embodiments, a boronating reagent is a borane-amine (e.g., N,N-diisopropylethylamine (BH$_3$.DIPEA), borane-pyridine (BH$_3$.Py), borane-2-chloropyridine (BH$_3$.CPy), borane-aniline (BH$_3$.An)), a borane-ether reagent (e.g., borane-tetrahydrofuran (BH$_3$.THF)), a borane-dialkylsulfide reagent (e.g., BH$_3$.Me$_2$S), aniline-cyanoborane, or a triphenylphosphine-carboalkoxyborane. In some embodiments, an azide reagent is comprises an azide group capable of undergoing subsequent reduction to provide an amine group.

In some embodiments, a P-modification reagent is a sulfurization reagent as described herein. In some embodiments, a step of modifying comprises sulfurization of phosphorus to provide a phosphorothioate linkage or phosphorothioate triester linkage. In some embodiments, a step of modifying provides a PNPLA3 oligonucleotide having an internucleotidic linkage of Formula I.

In some embodiments, the present disclosure provides sulfurizing reagents, and methods of making, and use of the same.

In some embodiments, such sulfurizing reagents are thiosulfonate reagents.

Various sulfurizing reagents and thiosulfonate reagents are known in the art.

In some embodiments, a sulfurization reagent for use in accordance with the present disclosure is characterized in that the moiety transferred to phosphorus during sulfurization is a substituted sulfur (e.g., —SR) as opposed to a single sulfur atom (e.g., —S⁻ or =S).

In some embodiments, a sulfurization reagent for use in accordance with the present disclosure is characterized in that the activity of the reagent is tunable by modifying the reagent with a certain electron withdrawing or donating group.

In some embodiments, a sulfurization reagent for use in accordance with the present disclosure is characterized in that it is crystalline. In some embodiments, a sulfurization reagent for use in accordance with the present disclosure is characterized in that it has a high degree of crystallinity. In certain embodiments, a sulfurization reagent for use in accordance with the present disclosure is characterized by ease of purification of the reagent via, e.g., recrystallization. In certain embodiments, a sulfurization reagent for use in accordance with the present disclosure is characterized in that it is substantially free from sulfur-containing impurities. In some embodiments, sulfurization reagents which are substantially free from sulfur-containing impurities show increased efficiency.

In some embodiments, the provided chirally controlled oligonucleotide comprises one or more phosphate diester linkages. To synthesize such chirally controlled oligonucleotides, one or more modifying steps are optionally replaced with an oxidation step to install the corresponding phosphate diester linkages. In some embodiments, the oxidation step is performed in a fashion similar to ordinary oligonucleotide synthesis. In some embodiments, an oxidation step comprises the use of I$_2$. In some embodiments, an oxidation step comprises the use of I$_2$ and pyridine. In some embodiments, an oxidation step comprises the use of 0.02 M I$_2$ in a THF/pyridine/water (70:20:10—v/v/v) co-solvent system. An example cycle is depicted in Scheme I-c.

In some embodiments, a phosphorothioate is directly formed through sulfurization by a sulfurization reagents, e.g., 3-phenyl-1,2,4-dithiazolin-5-one. In some embodiments, after a direct installation of a phosphorothioate, a chiral auxiliary group remains attached to the internucleotidic phosphorus atom. In some embodiments, an additional de-protecting step is required to remove the chiral auxiliary (e.g., for DPSE-type chiral auxiliary, using TBAF, HF-Et$_3$N, etc.).

In some embodiments, a phosphorothioate precursor is used to synthesize chirally controlled oligonucleotides comprising phosphorothioate linkages.

In some embodiments, the provided chirally controlled oligonucleotide comprises one or more phosphate diester linkages and one or more phosphorothioate diester linkages. In some embodiments, the provided chirally controlled oligonucleotide comprises one or more phosphate diester linkages and one or more phosphorothioate diester linkages, wherein at least one phosphate diester linkage is installed after all the phosphorothioate diester linkages when synthesized from 3' to 5'. To synthesize such chirally controlled oligonucleotides, in some embodiments, one or more modifying steps are optionally replaced with an oxidation step to install the corresponding phosphate diester linkages, and a phosphorothioate precursor is installed for each of the phosphorothioate diester linkages. In some embodiments, a phosphorothioate precursor is converted to a phosphorothioate diester linkage after the desired oligonucleotide length is achieved. In some embodiments, the deprotection/release step during or after cycle exit converts the phosphorothioate precursors into phosphorothioate diester linkages.

In some embodiments, a phosphorothioate precursor is a phosphorus protecting group as described herein, e.g., 2-cyanoethyl (CE or Cne), 2-trimethylsilylethyl, 2-nitroethyl, 2-sulfonylethyl, methyl, benzyl, o-nitrobenzyl, 2-(p-nitrophenyl)ethyl (NPE or Npe), 2-phenylethyl, 3-(N-tert-butylcarboxamido)-1-propyl, 4-oxopentyl, 4-methylthio-1-butyl, 2-cyano-1,1-dimethylethyl, 4-N-methylaminobutyl, 3-(2-pyridyl)-1-propyl, 2-[N-methyl-N-(2-pyridyl)]aminoethyl, 2-(N-formyl,N-methyl)aminoethyl, 4-[N-methyl-N-(2,2,2-trifluoroacetyl)amino]butyl. Examples are further depicted below.

As noted above, in some embodiments, sulfurization occurs under conditions which cleave the chiral reagent from the growing oligonucleotide. In some embodiments, sulfurization occurs under conditions which do not cleave the chiral reagent from the growing oligonucleotide.

In some embodiments, a sulfurization reagent is dissolved in a suitable solvent and delivered to the column. In certain embodiments, the solvent is a polar aprotic solvent such as a nitrile solvent. In some embodiments, the solvent is acetonitrile. In some embodiments, a solution of sulfurization reagent is prepared by mixing a sulfurization reagent (e.g., a thiosulfonate derivative as described herein) with BSTFA (N,O-bis-trimethylsilyl-trifluoroacetamide) in a nitrile solvent (e.g., acetonitrile). In some embodiments, BSTFA is not included. For example, the present inventors have found that relatively more reactive sulfurization reagents of general formula $R^{s2}$—S—S(O)$_2$—$R^{s3}$ can often successfully participate in sulfurization reactions in the absence of BSTFA. To give but one example, the inventors have demonstrated that where $R^{s2}$ is p-nitrophenyl and $R^{s3}$ is methyl then no BSTFA is required. In light of this disclosure, those skilled in the art will readily be able to determine other situations and/or sulfurization reagents that do not require BSTFA.

In some embodiments, the sulfurization step is performed at room temperature. In some embodiments, the sulfurization step is performed at lower temperatures such as about 0° C., about 5° C., about 10° C., or about 15° C. In some embodiments, the sulfurization step is performed at elevated temperatures of greater than about 20° C.

In some embodiments, a sulfurization reaction is run for about 1 minute to about 120 minutes. In some embodiments, a sulfurization reaction is run for about 1 minute to about 90 minutes. In some embodiments, a sulfurization reaction is run for about 1 minute to about 60 minutes. In some embodiments, a sulfurization reaction is run for about 1 minute to about 30 minutes. In some embodiments, a sulfurization reaction is run for about 1 minute to about 25 minutes. In some embodiments, a sulfurization reaction is run for about 1 minute to about 20 minutes. In some embodiments, a sulfurization reaction is run for about 1 minute to about 15 minutes. In some embodiments, a sulfurization reaction is run for about 1 minute to about 10 minutes. In some embodiments, a sulfurization reaction is run for about 5 minute to about 60 minutes.

In some embodiments, a sulfurization reaction is run for about 5 minutes. In some embodiments, a sulfurization reaction is run for about 10 minutes. In some embodiments, a sulfurization reaction is run for about 15 minutes. In some embodiments, a sulfurization reaction is run for about 20 minutes. In some embodiments, a sulfurization reaction is run for about 25 minutes. In some embodiments, a sulfurization reaction is run for about 30 minutes. In some embodiments, a sulfurization reaction is run for about 35 minutes. In some embodiments, a sulfurization reaction is run for about 40 minutes. In some embodiments, a sulfurization reaction is run for about 45 minutes. In some embodiments, a sulfurization reaction is run for about 50 minutes. In some embodiments, a sulfurization reaction is run for about 55 minutes. In some embodiments, a sulfurization reaction is run for about 60 minutes.

It was unexpectedly found that certain of the sulfurization modification products made in accordance with methods of the present disclosure are unexpectedly stable. In some embodiments, it the unexpectedly stable products are phosphorothioate triesters. In some embodiments, the unexpectedly stable products are chirally controlled oligonucleotides comprising one or more internucleotidic linkages having the structure of Formula I-c.

One of skill in the relevant arts will recognize that sulfurization methods described herein and sulfurization reagents described herein are also useful in the context of modifying H-phosphonate oligonucleotides such as those described in Wada II (WO2010/064146).

In some embodiments, the sulfurization reaction has a stepwise sulfurization efficiency that is at least about 80%, 85%, 90%, 95%, 96%, 97%, or 98%. In some embodiments, the sulfurization reaction provides a crude dinucleotide product composition that is at least 98% pure. In some embodiments, the sulfurization reaction provides a crude tetranucleotide product composition that is at least 90% pure. In some embodiments, the sulfurization reaction provides a crude dodecanucleotide product composition that is at least 70% pure. In some embodiments, the sulfurization reaction provides a crude icosanucleotide product composition that is at least 50% pure.

Once the step of modifying the linkage phosphorus is complete, the oligonucleotide undergoes another deblock step in preparation for re-entering the cycle. In some embodiments, a chiral auxiliary remains intact after sulfurization and is deblocked during the subsequent deblock step, which necessarily occurs prior to re-entering the cycle. The process of deblocking, coupling, capping, and modifying, are repeated until the growing oligonucleotide reaches a desired length, at which point the oligonucleotide can either be immediately cleaved from the solid support or left attached to the support for purification purposes and later cleaved. In some embodiments, one or more protecting groups are present on one or more of the nucleotide bases, and cleavage of the oligonucleotide from the support and deprotection of the bases occurs in a single step. In some embodiments, one or more protecting groups are present on one or more of the nucleotide bases, and cleavage of the oligonucleotide from the support and deprotection of the bases occurs in more than one step. In some embodiments, deprotection and cleavage from the support occurs under basic conditions using, e.g., one or more amine bases. In certain embodiments, the one or more amine bases comprise propyl amine. In certain embodiments, the one or more amine bases comprise pyridine.

In some embodiments, cleavage from the support and/or deprotection occurs at elevated temperatures of about 30° C. to about 90° C. In some embodiments, cleavage from the support and/or deprotection occurs at elevated temperatures of about 40° C. to about 80° C. In some embodiments, cleavage from the support and/or deprotection occurs at elevated temperatures of about 50° C. to about 70° C. In some embodiments, cleavage from the support and/or deprotection occurs at elevated temperatures of about 60° C. In some embodiments, cleavage from the support and/or deprotection occurs at ambient temperatures.

Example purification procedures are described herein and/or are known generally in the relevant arts.

Noteworthy is that the removal of the chiral auxiliary from the growing oligonucleotide during each cycle is beneficial for at least the reasons that (1) the auxiliary will not have to be removed in a separate step at the end of the oligonucleotide synthesis when potentially sensitive functional groups are installed on phosphorus; and (2) unstable phosphorus-auxiliary intermediates prone to undergoing side reactions and/or interfering with subsequent chemistry are avoided. Thus, removal of the chiral auxiliary during each cycle makes the overall synthesis more efficient.

While the step of deblocking in the context of the cycle is described above, additional general methods are included below.

Deblocking Step

In some embodiments, the step of coupling is preceded by a step of deblocking. For instance, in some embodiments, the 5' hydroxyl group of the growing oligonucleotide is blocked (i.e., protected) and must be deblocked in order to subsequently react with a nucleoside coupling partner.

In some embodiments, acidification is used to remove a blocking group. In some embodiments, the acid is a Brønsted acid or Lewis acid. Useful Brønsted acids are carboxylic acids, alkylsulfonic acids, arylsulfonic acids, phosphoric acid and its derivatives, phosphonic acid and its derivatives, alkylphosphonic acids and their derivatives, arylphosphonic acids and their derivatives, phosphinic acid, dialkylphosphinic acids, and diarylphosphinic acids which have a pKa (25° C. in water) value of −0.6 (trifluoroacetic acid) to 4.76 (acetic acid) in an organic solvent or water (in the case of 80% acetic acid). The concentration of the acid (1 to 80%) used in the acidification step depends on the acidity of the acid. Consideration to the acid strength must be taken into account as strong acid conditions will result in depurination/depyrimidination, wherein purinyl or pyrimidinyl bases are cleaved from ribose ring and or other sugar ring. In some embodiments, an acid is selected from $R^{a1}COOH$, $R^{a1}SO_3H$, $R^{a3}SO_3H$,

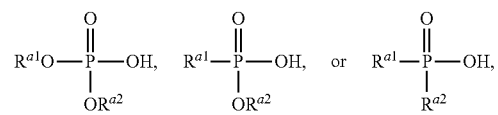

wherein each of $R^{a1}$ and $R^{a2}$ is independently hydrogen or an optionally substituted alkyl or aryl, and $W^3$ is an optionally substituted alkyl or aryl.

In some embodiments, acidification is accomplished by a Lewis acid in an organic solvent. Examples of such useful Lewis acids are $Zn(X^a)_2$ wherein $X^a$ is Cl, Br, I, or $CF_3SO_3$.

In some embodiments, the step of acidifying comprises adding an amount of a Brønsted or Lewis acid effective to remove a blocking group without removing purine moieties from the condensed intermediate.

Acids that are useful in the acidifying step also include, but are not limited to 10% phosphoric acid in an organic solvent, 10% hydrochloric acid in an organic solvent, 1% trifluoroacetic acid in an organic solvent, 3% dichloroacetic acid or trichloroacetic acid in an organic solvent or 80% acetic acid in water. The concentration of any Brønsted or Lewis acid used in this step is selected such that the concentration of the acid does not exceed a concentration that causes cleavage of a nucleobase from a sugar moiety.

In some embodiments, acidification comprises adding 1% trifluoroacetic acid in an organic solvent. In some embodiments, acidification comprises adding about 0.1% to about 8% trifluoroacetic acid in an organic solvent. In some embodiments, acidification comprises adding 3% dichloroacetic acid or trichloroacetic acid in an organic solvent. In some embodiments, acidification comprises adding about 0.1% to about 10% dichloroacetic acid or trichloroacetic acid in an organic solvent. In some embodiments, acidification comprises adding 3% trichloroacetic acid in an organic solvent. In some embodiments, acidification comprises adding about 0.1% to about 10% trichloroacetic acid in an organic solvent. In some embodiments, acidification comprises adding 80% acetic acid in water. In some embodiments, acidification comprises adding about 50% to about 90%, or about 50% to about 80%, about 50% to about 70%, about 50% to about 60%, about 70% to about 90% acetic acid in water. In some embodiments, the acidification comprises the further addition of cation scavengers to an acidic solvent. In certain embodiments, the cation scavengers can be triethylsilane or triisopropylsilane. In some embodiments, a blocking group is deblocked by acidification, which comprises adding 1% trifluoroacetic acid in an organic solvent. In some embodiments, a blocking group is deblocked by acidification, which comprises adding 3% dichloroacetic acid in an organic solvent. In some embodiments, a blocking group is deblocked by acidification, which comprises adding 3% trichloroacetic acid in an organic solvent. In some embodiments, a blocking group is deblocked by acidification, which comprises adding 3% trichloroacetic acid in dichloromethane.

In certain embodiments, methods of the present disclosure are completed on a synthesizer and the step of deblocking the hydroxyl group of the growing oligonucleotide comprises delivering an amount solvent to the synthesizer column, which column contains a solid support to which the oligonucleotide is attached. In some embodiments, the solvent is a halogenated solvent (e.g., dichloromethane). In certain embodiments, the solvent comprises an amount of an acid. In some embodiments, the solvent comprises an amount of an organic acid such as, for instance, trichloroacetic acid. In certain embodiments, the acid is present in an amount of about 1% to about 20% w/v. In certain embodiments, the acid is present in an amount of about 1% to about 10% w/v. In certain embodiments, the acid is present in an amount of about 1% to about 5% w/v. In certain embodiments, the acid is present in an amount of about 1 to about 3% w/v. In certain embodiments, the acid is present in an amount of about 3% w/v. Methods for deblocking a hydroxyl group are described further herein. In some embodiments, the acid is present in 3% w/v is dichloromethane.

In some embodiments, the chiral auxiliary is removed before the deblocking step. In some embodiments, the chiral auxiliary is removed during the deblocking step.

In some embodiments, cycle exit is performed before the deblocking step. In some embodiments, cycle exit is preformed after the deblocking step.

General Conditions for Blocking Group/Protecting Group Removal

Functional groups such as hydroxyl or amino moieties which are located on nucleobases or sugar moieties are routinely blocked with blocking (protecting) groups (moieties) during synthesis and subsequently deblocked. In general, a blocking group renders a chemical functionality of a molecule inert to specific reaction conditions and can later be removed from such functionality in a molecule without substantially damaging the remainder of the molecule (see e.g., Green and Wuts, Protective Groups in Organic Synthesis, 2nd Ed., John Wiley & Sons, New York, 1991). For example, amino groups can be blocked with nitrogen blocking groups. Chemical functional groups can also be blocked by including them in a precursor form. Thus an azido group can be considered a blocked form of an amine as the azido group is easily converted to the amine. Further representative protecting groups utilized in nucleic acid synthesis are known (see e.g. Agrawal et al., Protocols for Oligonucleotide Conjugates, Eds., Humana Press, New Jersey, 1994, Vol. 26, pp. 1-72).

Various methods are known and used for removal of blocking groups from nucleic acids. In some embodiments, all blocking groups are removed. In some embodiments, a portion of blocking groups are removed. In some embodiments, reaction conditions can be adjusted to selectively remove certain blocking groups.

In some embodiments, nucleobase blocking groups, if present, are cleavable with an acidic reagent after the assembly of a provided oligonucleotide. In some embodiment, nucleobase blocking groups, if present, are cleavable under neither acidic nor basic conditions, e.g. cleavable with fluoride salts or hydrofluoric acid complexes. In some embodiments, nucleobase blocking groups, if present, are cleavable in the presence of base or a basic solvent after the assembly of a provided oligonucleotide. In certain embodiments, one or more of the nucleobase blocking groups are characterized in that they are cleavable in the presence of base or a basic solvent after the assembly of a provided oligonucleotide but are stable to the particular conditions of one or more earlier deprotection steps occurring during the assembly of the provided oligonucleotide.

In some embodiments, blocking groups for nucleobases are not required. In some embodiments, blocking groups for nucleobases are required. In some embodiments, certain nucleobases require one or more blocking groups while other nucleobases do not require one or more blocking groups.

In some embodiments, the oligonucleotide is cleaved from the solid support after synthesis. In some embodiments, cleavage from the solid support comprises the use of propylamine. In some embodiments, cleavage from the solid support comprises the use of propylamine in pyridine. In some embodiments, cleavage from the solid support comprises the use of 20% propylamine in pyridine. In some embodiments, cleavage from the solid support comprises the use of propylamine in anhydrous pyridine. In some embodiments, cleavage from the solid support comprises the use of 20% propylamine in anhydrous pyridine. In some embodiments, cleavage from the solid support comprises use of a polar aprotic solvent such as acetonitrile, NMP, DMSO, sulfone, and/or lutidine. In some embodiments, cleavage from the solid support comprises use of solvent, e.g., a polar aprotic solvent, and one or more primary amines (e.g., a $C_{1-10}$ amine), and/or one or more of methoxylamine, hydrazine, and pure anhydrous ammonia.

In some embodiments, deprotection of oligonucleotide comprises the use of propylamine. In some embodiments, deprotection of oligonucleotide comprises the use of propylamine in pyridine. In some embodiments, deprotection of oligonucleotide comprises the use of 20% propylamine in pyridine. In some embodiments deprotection of oligonucleotide comprises the use of propylamine in anhydrous pyridine. In some embodiments, deprotection of oligonucleotide comprises the use of 20% propylamine in anhydrous pyridine.

In some embodiments, the oligonucleotide is deprotected during cleavage.

In some embodiments, cleavage of oligonucleotide from solid support, or deprotection of oligonucleotide, is performed at about room temperature. In some embodiments, cleavage of oligonucleotide from solid support, or deprotection of oligonucleotide, is performed at elevated temperature. In some embodiments, cleavage of oligonucleotide from solid support, or deprotection of oligonucleotide, is performed at above about 30° C., 40° C., 50° C., 60° C., 70° C., 80° C. 90° C. or 100° C. In some embodiments, cleavage of oligonucleotide from solid support, or deprotection of oligonucleotide, is performed at about 30° C., 40° C., 50° C., 60° C., 70° C., 80° C. 90° C. or 100° C. In some embodiments, cleavage of oligonucleotide from solid support, or deprotection of oligonucleotide, is performed at about 40-80° C. In some embodiments, cleavage of oligonucleotide from solid support, or deprotection of oligonucleotide, is performed at about 50-70° C. In some embodiments, cleavage of oligonucleotide from solid support, or deprotection of oligonucleotide, is performed at about 60° C.

In some embodiments, cleavage of oligonucleotide from solid support, or deprotection of oligonucleotide, is performed for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed for about 0.1-5 hrs. In some embodiments, cleavage of oligonucleotide from solid support, or deprotection of oligonucleotide, is performed for about 3-10 hrs. In some embodiments, cleavage of oligonucleotide from solid support, or deprotection of oligonucleotide, is performed for about 5-15 hrs. In some embodiments, cleavage of oligonucleotide from solid support, or deprotection of oligonucleotide, is performed for about 10-20 hrs. In some embodiments, cleavage of oligonucleotide from solid support, or deprotection of oligonucleotide, is performed for about 15-25 hrs. In some embodiments, cleavage of oligonucleotide from solid support, or deprotection of oligonucleotide, is performed for about 20-40 hrs. In some embodiments, cleavage of oligonucleotide from solid support, or deprotection of oligonucleotide, is performed for about 2 hrs. In some embodiments, cleavage of oligonucleotide from solid support, or deprotection of oligonucleotide, is performed for about 5 hrs. In some embodiments, cleavage of oligonucleotide from solid support, or deprotection of oligonucleotide, is performed for about 10 hrs. In some embodiments, cleavage of oligonucleotide from solid support, or deprotection of oligonucleotide, is performed for about 15 hrs. In some embodiments, cleavage of oligonucleotide from solid support, or deprotection of oligonucleotide, is performed for about 18 hrs. In some embodiments, cleavage of oligonucleotide from solid support, or deprotection of oligonucleotide, is performed for about 24 hrs.

In some embodiments, cleavage of oligonucleotide from solid support, or deprotection of oligonucleotide, is performed at room temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at room temperature for about 5-48 hrs. In some embodiments, cleavage of oligonucleotide from solid support, or deprotection of oligonucleotide, is performed at room temperature for about 10-24 hrs. In some embodiments, cleavage of oligonucleotide from solid support, or deprotection of oligonucleotide, is performed at room temperature for about 18 hrs. In some embodiments, cleavage of oligonucleotide from solid support, or deprotection of oligonucleotide, is performed at elevated temperature for more than 0.1 hr, 1 hr, 2 hrs, 5 hrs, 10 hrs, 15 hrs, 20 hrs, 24 hrs, 30 hrs, or 40 hrs. In some embodiments, cleavage of oligonucleotide from solid support, or deprotection of oligonucleotide, is performed at elevated temperature for about 0.5-5 hrs. In some embodiments, cleavage of oligonucleotide from solid support, or deprotection of oligonucleotide, is performed at about 60° C. for about 0.5-5 hrs. In some embodiments, cleavage of oligonucleotide from solid support, or deprotection of oligonucleotide, is performed at about 60° C. for about 2 hrs.

In some embodiments, cleavage of oligonucleotide from solid support, or deprotection of oligonucleotide comprises the use of propylamine and is performed at room temperature or elevated temperature for more than 0.1 hr, 1 hr, 2 hrs, 5 hrs, 10 hrs, 15 hrs, 20 hrs, 24 hrs, 30 hrs, or 40 hrs. Example conditions are 20% propylamine in pyridine at room temperature for about 18 hrs, and 20% propylamine in pyridine at 60° C. for about 18 hrs.

In some embodiments, prior to cleavage from solid support, a step is performed to remove a chiral auxiliary group, if one is still attached to an internucleotidic phosphorus atom. In some embodiments, for example, one or more DPSE type chiral auxiliary groups remain attached to internucleotidic phosphorus atoms during the oligonucleotide synthesis cycle. Suitable conditions for removing remaining chiral auxiliary groups are widely known in the art, e.g., those described in Wada I, Wada II, Wada III, Chiral Control, etc. In some embodiments, a condition for removing DPSE type chiral auxiliary is TBAF or HF-Et$_3$N, e.g., 0.1M TBAF in MeCN, 0.5M HF-Et$_3$N in THF or MeCN, etc. In some embodiments, the present disclosure recognizes that a linker may be cleaved during the process of removing a chiral auxiliary group. In some embodiments, the present disclosure provides linkers, such as the SP linker, that provides better stability during chiral auxiliary group removal. Among other things, certain linkers provided by the present disclosure provided improved yield and/or purity.

In some embodiments, an example cycle is depicted in Scheme I.

Scheme I. Example cycle using DPSE chiral auxiliary.

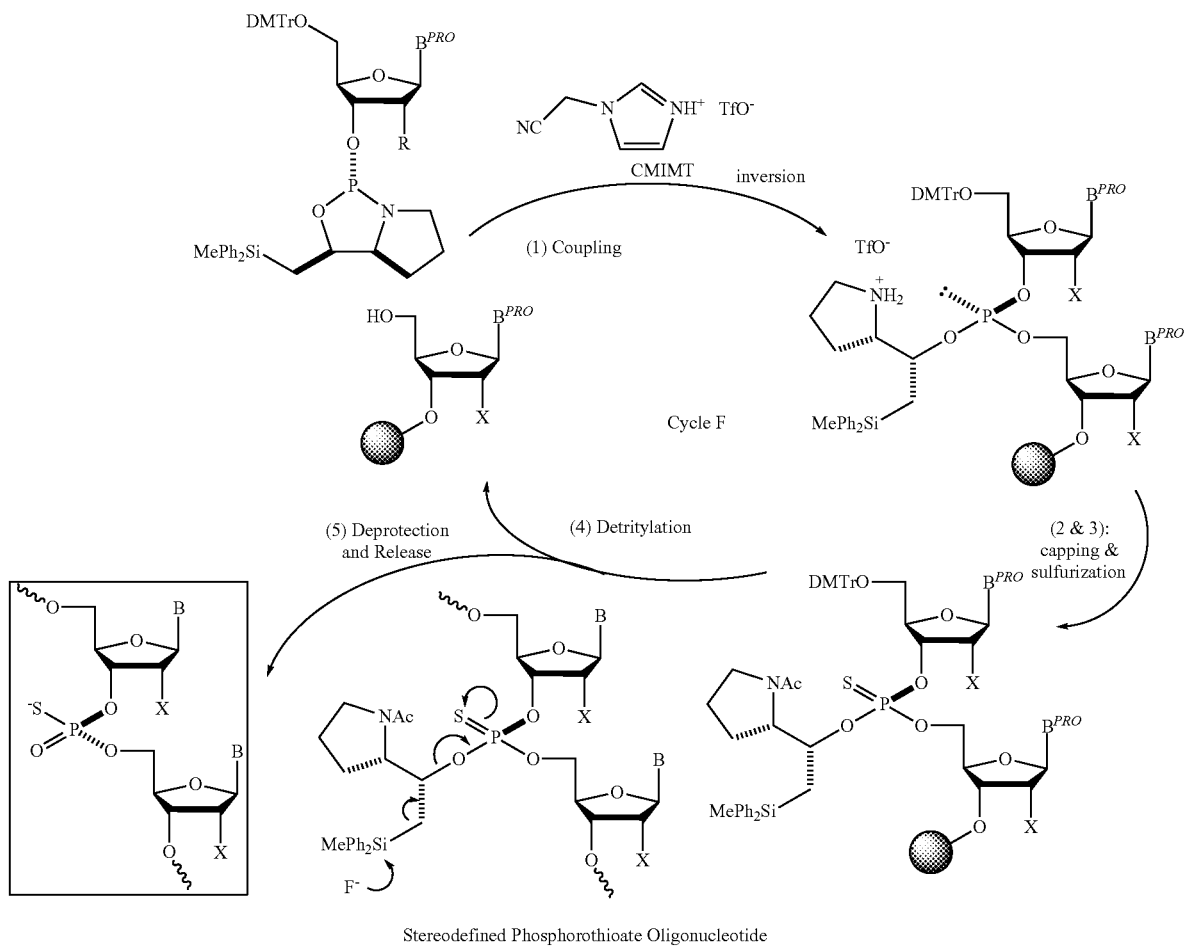

In some embodiments, X is H or a 2'-modification. In some embodiments, X is H or —OR', wherein $R^1$ is not hydrogen. In some embodiments, X is H or —OR', wherein $R^1$ is optionally substituted $C_{1-6}$ alkyl. In some embodiments, X is H. In some embodiments, X is —OMe. In some embodiments, X is —OCH$_2$CH$_2$OCH$_3$. In some embodiments, X is —F.

It is understood by a person having ordinary skill in the art that different types of cycles may be combined to provide complete control of the chemical modifications and stereochemistry of oligonucleotides. In some embodiments, for example, a PNPLA3 oligonucleotide synthesis process may contain one or more Cycles. In some embodiments, a provided method comprises at least one cycle using a DPSE-type chiral auxiliary.

In some embodiments, the present disclosure provides methods for preparing provided oligonucleotide and oligonucleotide compositions. In some embodiments, a provided method comprises the step of providing a provided chiral reagent having the structure of

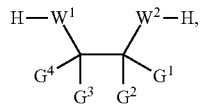

wherein $W^1$ is —NG$^5$, $W^2$ is O, each of $G^1$ and $G^3$ is independently hydrogen or an optionally substituted group selected from $C_{1-10}$ aliphatic, heterocyclyl, heteroaryl and aryl, $G^2$ is —C(R)$_2$Si(R)$_3$, and $G^4$ and $G^5$ are taken together to form an optionally substituted saturated, partially unsaturated or unsaturated heteroatom-containing ring of up to about 20 ring atoms which is monocyclic or polycyclic, fused or unfused, wherein each R is independently hydrogen, or an optionally substituted group selected from $C_1$-$C_6$ aliphatic, carbocyclyl, aryl, heteroaryl, and heterocyclyl. In some embodiments, a provided chiral reagent has the structure of

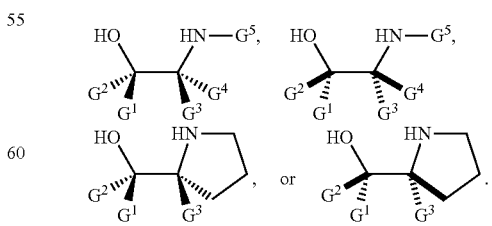

In some embodiments, a provided methods comprises providing a phosphoramidite comprising a moiety from a chiral reagent having the structure of

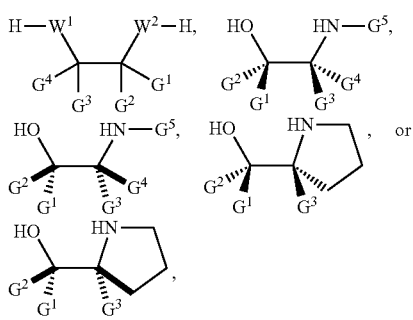
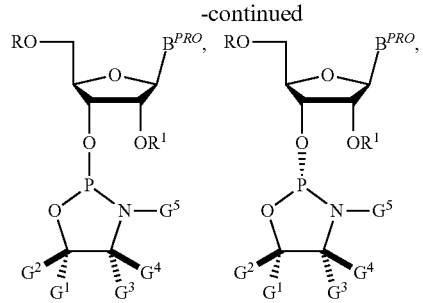
wherein —W¹H and —W²H, or the hydroxyl and amino groups, form bonds with the phosphorus atom of the phosphoramidite. In some embodiments, —W¹H and —W²H, or the hydroxyl and amino groups, form bonds with the phosphorus atom of the phosphoramidite, e.g., in
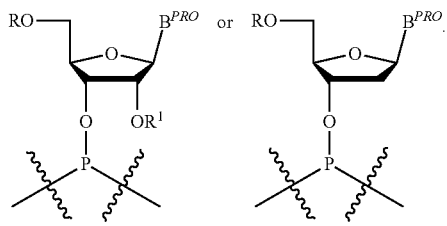
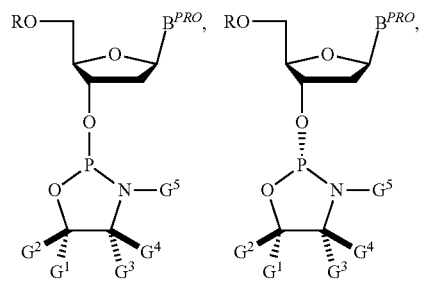
In some embodiments, a phosphoramidite has the structure of
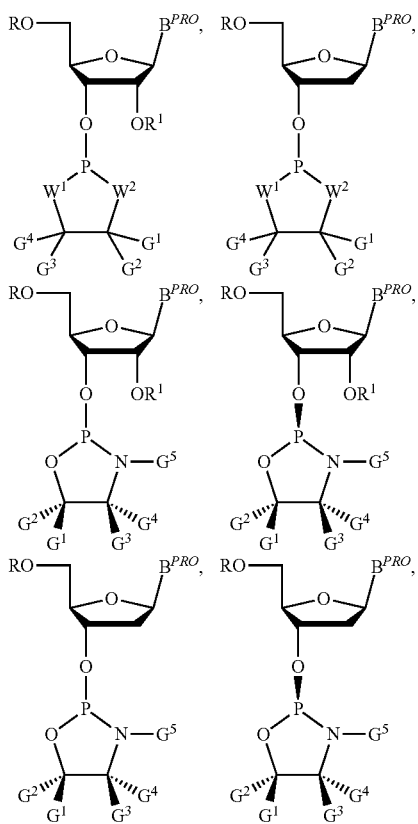
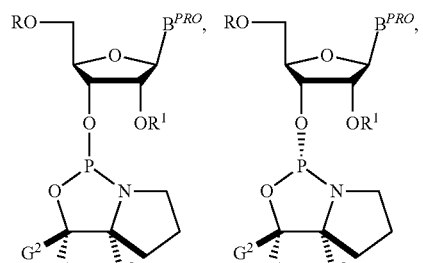
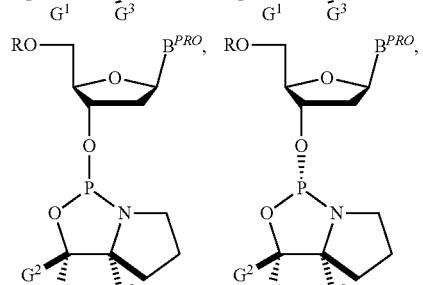
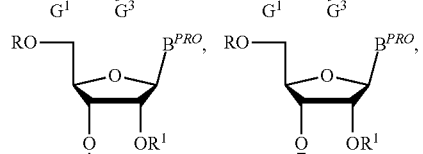
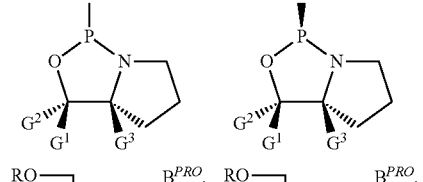
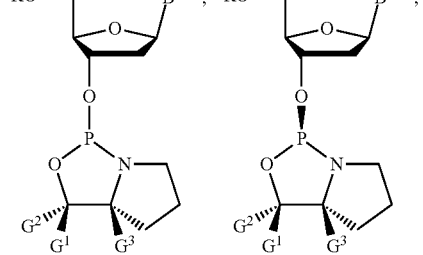

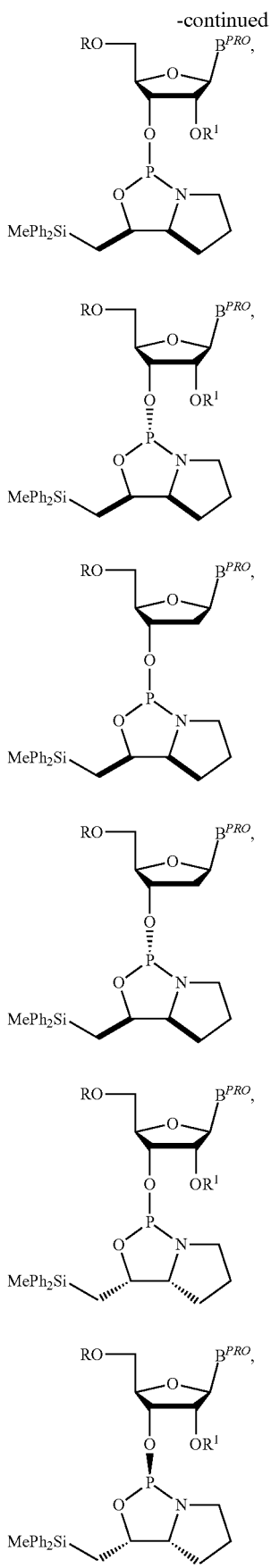

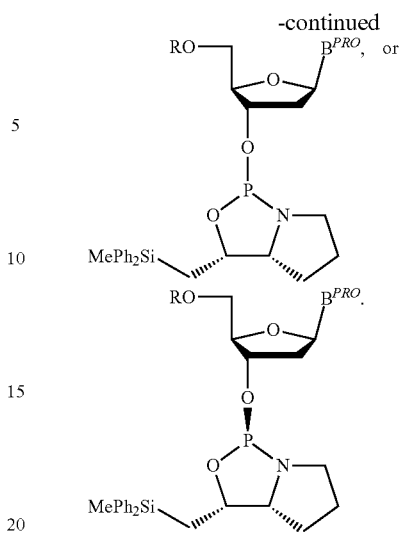

In some embodiments, R is a protection group. In some embodiments, R is DMTr. In some embodiments, $G^2$ is —C(R)$_2$Si(R)$_3$, wherein —C(R)$_2$— is optionally substituted —CH$_2$—, and each R of —Si(R)$_3$ is independently an optionally substituted group selected from C$_{1-10}$ aliphatic, heterocyclyl, heteroaryl and aryl. In some embodiments, at least one R of —Si(R)$_3$ is independently optionally substituted C$_{1-10}$ alkyl. In some embodiments, at least one R of —Si(R)$_3$ is independently optionally substituted phenyl. In some embodiments, one R of —Si(R)$_3$ is independently optionally substituted phenyl, and each of the other two R is independently optionally substituted C$_{1-10}$ alkyl. In some embodiments, one R of —Si(R)$_3$ is independently optionally substituted C$_{1-10}$ alkyl, and each of the other two R is independently optionally substituted phenyl. In some embodiments, $G^2$ is optionally substituted —CH$_2$Si(Ph)(Me)$_2$. In some embodiments, $G^2$ is optionally substituted —CH$_2$Si(Me)(Ph)$_2$. In some embodiments, $G^2$ is —CH$_2$Si(Me)(Ph)$_2$. In some embodiments, $G^4$ and $G^5$ are taken together to form an optionally substituted saturated 5-6 membered ring containing one nitrogen atom (to which $G^5$ is attached). In some embodiments, $G^4$ and $G^5$ are taken together to form an optionally substituted saturated 5-membered ring containing one nitrogen atom. In some embodiments, $G^1$ is hydrogen. In some embodiments, $G^3$ is hydrogen. In some embodiments, both $G^1$ and $G^3$ are hydrogen. In some embodiments, both $G^1$ and $G^3$ are hydrogen, $G^2$ is —C(R)$_2$Si(R)$_3$, wherein —C(R)$_2$— is optionally substituted —CH$_2$—, and each R of —Si(R)$_3$ is independently an optionally substituted group selected from C$_{1-10}$ aliphatic, heterocyclyl, heteroaryl and aryl, and $G^4$ and $G^5$ are taken together to form an optionally substituted saturated 5-membered ring containing one nitrogen atom. In some embodiments, a provided method further comprises providing a fluoro-containing reagent. In some embodiments, a provided fluoro-containing reagent removes a chiral reagent, or a product formed from a chiral reagent, from oligonucleotides after synthesis. Various known fluoro-containing reagents, including those F$^-$ sources for removing —SiR$_3$ groups, can be utilized in accordance with the present disclosure, for example, TBAF, HF$_3$-Et$_3$N etc. In some embodiments, a fluoro-containing reagent provides better results, for example, shorter treatment time, lower temperature, less de-sulfurization, etc, compared to traditional methods, such as concentrated ammonia. In some embodiments, for certain fluoro-containing reagent, the present disclosure provides linkers for improved results, for example, less cleavage of oligonucleotides from support during removal of chiral reagent (or product formed therefrom during oligonucleotide synthesis). In some embodiments, a provided linker is an SP linker. In some embodiments, the present disclosure demonstrated that a HF-base complex can be utilized, such as HF—NR$_3$, to control cleavage during removal of chiral reagent (or product formed therefrom during oligonucleotide synthesis). In some embodiments, HF—NR$_3$ is HF-NEt$_3$. In some embodiments, HF—NR$_3$ enables use of traditional linkers, e.g., succinyl linker.

In some embodiments, a method for production of a PNPLA3 oligonucleotide comprises at least one cycle using a DPSE-type chiral auxiliary, such as that shown in the following non-limiting example:

Coupling:

For the coupling step, all amidites were dissolved either in acetonitrile (ACN) or in 20% isobutyronitrile (IBN)/ACN at a concentration of 0.2M; the solutions were dried over molecular sieves (3 Å) NLT 4h before use (10%, v/v). Dual activators (CMIMT and ETT) coupling approach were utilized for the manufacture of an oligonucleotide. Both activators were dissolved in ACN at a concentration of 0.6M. CMIMT has been used for the efficient coupling of stereo defined nucleotides and ETT is an activator used for the coupling of random/standard amidites/nucleotides. 2.5 equivalent of amidites used for coupling of stereo defined nucleotide over 10 min recycle time (linear recycle mode, 212 cm/hr). The molar ratio of CMIMT activator to stereo defined amidite was maintained at 6.1:1 (CMIMT/Amidite=6.1/1) in the coupling step. All random amidites

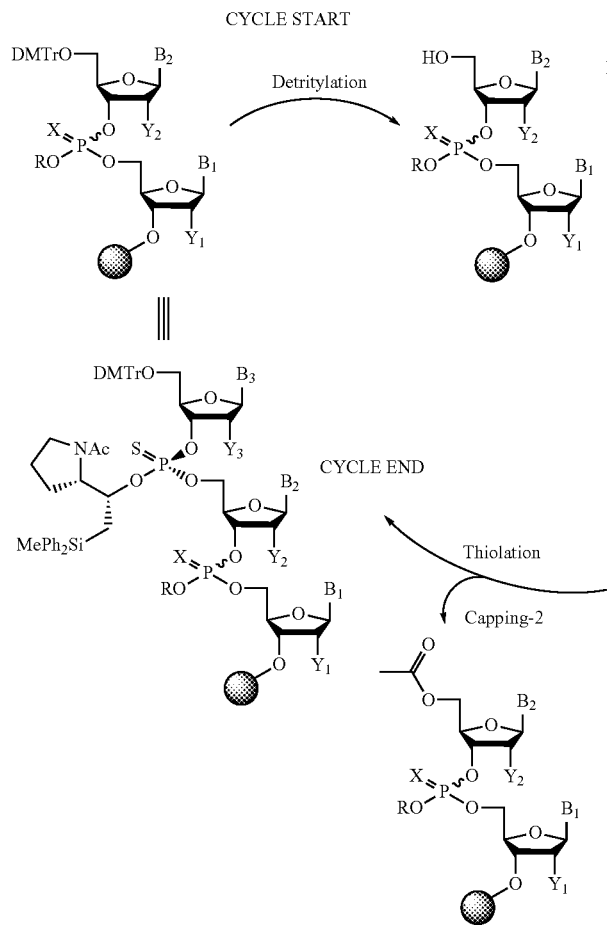
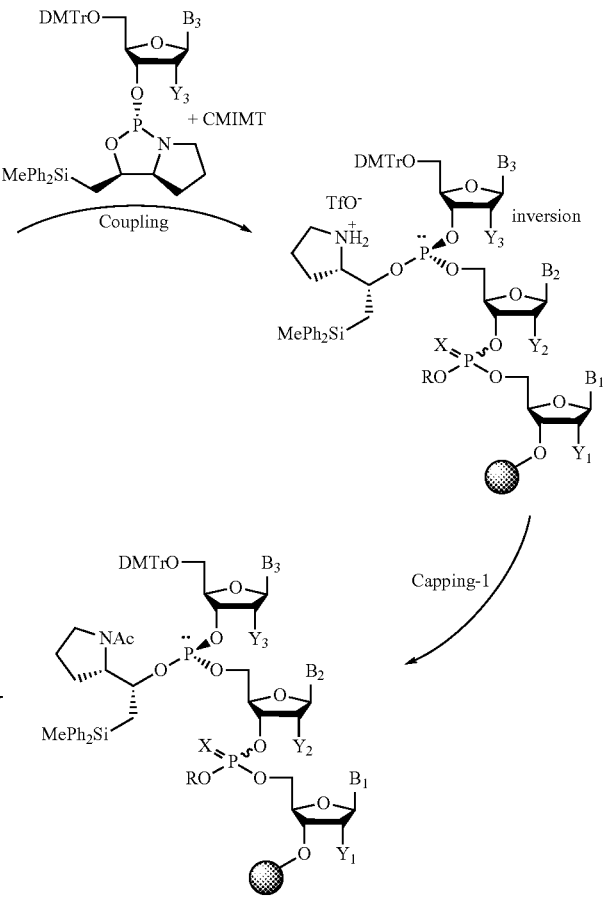

Detritylation:

The synthesis of an oligonucleotide started with 2'-F-U-DMTr loaded CPG solid support (3% dichloroacetic acid (DCA) in toluene was used for the removal of dimethoxy trityl group (DMTr) from the initial nucleobase attached on the solid support followed by an UV watch command mode at the wavelength of 436 nm. Linear flowrate, 424 cm/hr, used for detritylation.

were coupled for 8 min with ETT activator. The molar ratio of ETT to random/standard amidites was 4.5:1.

Cap 1:

Cap 1 is a step that is performed before thiolation. 1-1.5 CV Cap B solution is used over 4 min contact time for capping of the auxiliary amine on DPSE. Capping of DPSE chiral auxiliary with Cap B solution helps to reduce the content of early failure and post FLP impurities.

Thiolation:

Following the Cap 1 step, the phosphorous triester linkages, P(III), were stabilized with thiolating reagent, 0.2M xanthane hydride (XH) in pyridine, (0.6 CV) over 6 min contact time to form a stable P(V) bond.

Oxidation:

It is noted here that the Cap 1 step is not necessary for standard nucleotide cycle. So, after coupling of standard nucleotides onto the solid support, the phosphorous triester linkages, P(III), were oxidized with 0.05M of iodine/water/pyridine solution (3.5 eq.) over 2 min contact time to form a stable P(V) bond.

Cap 2 (Post-Thio/Ox-Capping):

In general, 97-100% coupling efficiency was observed in the coupling step based on DMTr release cation. Residual uncoupled hydroxyl groups, typically 1-3% by detrit monitor, on the solid support were blocked with Cap A and Cap B solution using 0.4 CV over 0.8 min to prevent formation of deletion sequences. In case, any auxiliary amine remained un-capped in the pre-capping step will also be capped in this step.

Cycle Repeated

The synthetic cycle (DPSE cycle=Detritylation→ Coupling→Cap 1→Thiolation→Cap2 and Standard cycle= Detritylation→Coupling→Oxidation→Cap2) was repeated until the desired length of oligonucleotide synthesized on the solid support.

In some embodiments, the present disclosure comprises a method for manufacturing a PNPLA3 oligonucleotide composition directed to a selected target sequence, the method comprising manufacturing a provided oligonucleotide composition capable of directing single-stranded RNA interference and comprising a first plurality of oligonucleotides, each of which has a base sequence complementary to the target sequence. In some embodiments, a provided method further comprises providing a pharmaceutically acceptable carrier.

As appreciated by a person having ordinary skill in the art, provided oligonucleotides can also be prepared through known solution phase synthesis using provided reagents and methods in accordance with the present disclosure.

As non-limiting examples, provided oligonucleotides can also be prepared through any process known in the art, including but not limited to, those described in: JP 4348044; WO2005092909; U.S. Pat. No. 9,394,333; WO2011005761; U.S. Pat. Nos. 8,470,987; 8,859,755; 8,822,671; WO2013012758; EP 13817386; WO2014012081; WO2015107425; WO2017015555; and WO2017062862.

Double-Stranded Oligonucleotides Comprising a Single-Stranded Oligonucleotide Disclosed Herein In some embodiments, a PNPLA3 oligonucleotide is a single-stranded or double-stranded oligonucleotide. In some embodiments, the disclosure encompasses a double-stranded oligonucleotide or molecule comprising a single-stranded oligonucleotide as disclosed herein, and another oligonucleotide which is at least partially complementary to it. In some embodiments, the present disclosure pertains to compositions comprising such a double-stranded oligonucleotide.

In some embodiments, the disclosure encompasses a double-stranded molecule comprising a single-stranded oligonucleotide as disclosed herein, and another oligonucleotide which is at least partially complementary to it, e.g., one or both ends of the molecule has a 3' or 5' overhang.

In some embodiments, the disclosure encompasses a double-stranded molecule comprising a single-stranded oligonucleotide as disclosed herein, and another oligonucleotide which is fully complementary to it.

In some embodiments, the disclosure encompasses a double-stranded molecule capable of directing RNA interference comprising a single-stranded oligonucleotide as disclosed herein, and another oligonucleotide which is at least partially complementary to it.

In some embodiments, the disclosure encompasses a double-stranded molecule capable of directing RNA interference comprising a single-stranded oligonucleotide as disclosed herein, and another oligonucleotide which is at least partially complementary to it, e.g., one or both ends of the molecule capable of directing RNA interference has a 3' or 5' overhang.

In some embodiments, the disclosure encompasses a double-stranded molecule capable of directing RNA interference comprising a single-stranded oligonucleotide as disclosed herein, and another oligonucleotide which is fully complementary to it.

In some embodiments, the disclosure encompasses a double-stranded molecule capable of directing RNA interference and RNase H-mediated knockdown comprising a single-stranded oligonucleotide as disclosed herein, and another oligonucleotide which is at least partially complementary to it.

In some embodiments, the disclosure encompasses a double-stranded molecule capable of directing RNA interference and RNase H-mediated knockdown comprising a single-stranded oligonucleotide as disclosed herein, and another oligonucleotide which is at least partially complementary to it, e.g., one or both ends of the molecule capable of directing RNA interference and RNase H-mediated knockdown has a 3' or 5' overhang.

In some embodiments, the disclosure encompasses a double-stranded molecule capable of directing RNA interference and RNase H-mediated knockdown comprising a single-stranded oligonucleotide as disclosed herein, and another oligonucleotide which is fully complementary to it.

Provided first oligonucleotides and oligonucleotide compositions can have any format, structural element or base sequence of any oligonucleotide disclosed herein, and further comprise a second oligonucleotide or oligonucleotide strand at least partially complementary to the first oligonucleotide. In some embodiments, the first and/or second oligonucleotide can comprise any format, structural element or base sequence of (or a base sequence at least partially complementary to a base sequence of) any oligonucleotide disclosed herein. In some embodiments, a structural element is a 5'-end structure, 5'-end region, 5'-nucleotide, seed region, post-seed region, 3'-end region, 3'-terminal dinucleotide, 3'-end cap, or any portion of any of these structures, GC content, long GC stretch, and/or any modification, chemistry, stereochemistry, pattern of modification, chemistry or stereochemistry, or additional chemical moiety (e.g., including but not limited to, a targeting moiety, a lipid moiety, a GalNAc moiety, a carbohydrate moiety, etc.), any component, or any combination of any of the above.

Biological Applications

As described herein, provided compositions and methods are capable of improving knockdown, including, single-stranded RNA interference of transcripts. In some embodiments, provided compositions and methods provide improved single-stranded RNA interference of transcripts compared to a reference pattern, which is a pattern from a reference condition selected from the group consisting of absence of the composition, presence of a reference composition, and combinations thereof. An improvement can be an improvement of any desired biological functions.

In some embodiments, the present disclosure provides a method for improving single-stranded RNA interference of a target transcript, comprising administering a composition comprising a first plurality of oligonucleotides, wherein the single-stranded RNA interference of the target transcript is improved relative to reference conditions selected from the group consisting of absence of the composition, presence of a reference composition, and combinations thereof.

In some embodiments, the present disclosure provides a method of mediating single-stranded RNA interference of a target, the method comprising steps of:

contacting a single-stranded RNA interference system containing the target transcript with a PNPLA3 oligonucleotide composition comprising a first plurality of oligonucleotides, in an amount, for a time, and under conditions sufficient for a set of single-stranded RNA interference products to be generated that is different from a set generated under reference conditions selected from the group consisting of absence of the composition, presence of a reference composition, and combinations thereof.

In some embodiments, the present disclosure provides compositions and methods for treating or preventing diseases, including but not limited to those described in references cited in this disclosure.

In some embodiments, the present disclosure provides a method for treating or preventing a disease, comprising administering to a subject a PNPLA3 oligonucleotide composition described herein.

In some embodiments, the present disclosure provides a method for treating or preventing a disease, comprising administering to a subject a PNPLA3 oligonucleotide composition comprising a first plurality of oligonucleotides, which:

1) have a common base sequence complementary to a target sequence in a transcript; and 2) comprise one or more modified sugar moieties and modified internucleotidic linkages, the oligonucleotide composition being characterized in that, when it is contacted with the transcript in a single-stranded RNA interference system, RNAi-mediated knockdown of the transcript is improved relative to that observed under reference conditions selected from the group consisting of absence of the composition, presence of a reference composition, and combinations thereof.

In some embodiments, the present disclosure provides a method for treating or preventing a disease, comprising administering to a subject a PNPLA3 oligonucleotide composition comprising a first plurality of oligonucleotides capable of directing single-stranded RNA interference, wherein oligonucleotides are of a particular oligonucleotide type defined by:

1) base sequence;
2) pattern of backbone linkages;
3) pattern of backbone chiral centers; and
4) pattern of backbone phosphorus modifications, which composition is chirally controlled in that it is enriched, relative to a substantially racemic preparation of oligonucleotides having the same base sequence, for oligonucleotides of the particular oligonucleotide type, wherein:

the oligonucleotide composition being characterized in that, when it is contacted with the transcript in a single-stranded RNA interference system, RNAi-mediated knockdown of the transcript is improved relative to that observed under reference conditions selected from the group consisting of absence of the composition, presence of a reference composition, and combinations thereof.

In some embodiments, a disease is one in which administering a provided composition capable of directing single-stranded RNA interference can repair, restore or introduce a new beneficial function.

In some embodiments, a disease is one in which, after administering a provided composition, a gene is effectively knocked down by improving single-stranded RNA interference system of the gene transcript.

In some embodiments, a disease is cancer.

In some embodiments, the present disclosure provides a method of treating a disease by administering a composition comprising a first plurality of oligonucleotides sharing a common base sequence comprising a common base sequence, which nucleotide sequence is complementary to a target sequence in the target transcript, the improvement that comprises using as the oligonucleotide composition a stereocontrolled oligonucleotide composition characterized in that, when it is contacted with the transcript in a PNPLA3 oligonucleotide or a single-stranded RNA interference system, RNAi-mediated knockdown of the transcript is improved relative to that observed under reference conditions selected from the group consisting of absence of the composition, presence of a reference composition, and combinations thereof.

In some embodiments, a disease is cancer.

In some embodiments, a disease treatment comprises knockdown of a gene function by improving single-stranded RNA interference system.

In some embodiments, a PNPLA3 oligonucleotide or a single-stranded RNAi agent targets a target mRNA transcript.

In some embodiments, the common base sequence is capable of hybridizing with a transcript in a cell. In some embodiments, a common base sequence hybridizes with a transcript of any gene described herein or known in the art.

Treatment of Disorders

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion.

In some embodiments, provided oligonucleotides target PNPLA3.

In some embodiments, PNPLA3 is a gene, or a gene product thereof (including, but not limited to, a transcript or protein), also known as: PNPLA3, adiponutrin, ADPN, C22orf20, acylglycerol O-acyltransferase or calcium-independent phospholipase A2-epsilon, iPLA(2)epsilon, patatin-like phospholipase domain-containing 3; External IDs:

MGI: 2151796; HomoloGene: 11883; GeneCards: PNPLA3; Species; Human: Entrez; 80339; Ensembl; ENSG00000100344; UniProt; Q9NST1; RefSeq (mRNA); NM_025225; RefSeq (protein); NP_079501; Location (UCSC); Chr 22: 43.92-43.96 Mb; Species; Mouse: Entrez; 116939; Ensembl; ENSMUSG00000041653; UniProt; Q91WW7; RefSeq (mRNA); NM_054088; RefSeq (protein); NP_473429.2 NP_473429; Location (UCSC); Chr 15: 84.17-84.19 Mb. Patatin-like phospholipase domain-containing protein 3 (PNPLA3) also known as adiponutrin (ADPN), acylglycerol O-acyltransferase or calcium-independent phospholipase A2-epsilon (iPLA2-epsilon) is reportedly an enzyme that in humans is encoded by the PNPLA3 gene. PNPLA3 encodes a 481 amino acid protein that belongs to the patatin-like phospholipase family. The progenitor of this family, patatin, is reportedly a major protein of potato tubers and has nonspecific lipid acyl hydrolase activity. A variant (I148M) in PNPLA3 (Patatin-like phospholipase domain containing 3) was reportedly strongly associated with increased hepatic fat levels and with hepatic inflammation. A marker of PNPLA3-I148M is reportedly SNP rs738409. The association between PNPLA3-I148M and hepatic fat content reportedly remained highly significant after adjusting for BMI, diabetes status, ethanol use, as well as global and local ancestry, and was associated with a significant increase in liver TG content in all three ethnic groups. The frequencies of the PNPLA3-I148M allele reportedly mirrored the relative prevalence of NAFLD in the three ethnic groups; the highest frequency was in Hispanics (0.49), with lower frequencies observed in European Americans (0.23) and African-Americans (0.17). Collins et al. 2003 Genome Res. 13 (1): 27-36; Collins et al. 2005 Genome Biol. 5 (10): R84; Dunham et al. 1999 Nature. 402 (6761): 489-95; Gerhard et al. 2004 Genome Res. 14 (10B): 2121-7; Jenkins et al. 2005 J. Biol. Chem. 279 (47): 48968-75; Kienesberger et al. 2009 J. Lipid Res. 50 Suppl.: S63-8; Lake et al. 2006 J. Lipid Res. 46 (11): 2477-87; Liu et al. 2004 J. Clin. Endocrinol. Metab. 89 (6): 2684-9; Strausberg et al. 2003 Proc. Natl. Acad. Sci. U.S.A. 99 (26): 16899-903; Wilson et al. 2006 J Lipid Res. 47 (9): 1940-9.

In some embodiments, a PNPLA3-related disorder is a disorder related to, caused and/or associated with abnormal or excessive activity, level and/or expression or abnormal tissue or inter- or intracellular distribution of an PNPLA3 gene or a gene product thereof. Non-limiting examples of an PNPLA3-related disorder include: liver disease, fatty liver (e.g., accumulation of fat in the liver, or an increase in or supra-normal hepatic fat), hepatic steatosis (e.g., simple fatty liver), steatohepatitis, hepatitis, nonalcoholic fatty liver disease (e.g., NAFLD), and/or one or more disease and/or one or more symptom or condition associated with or secondary to a liver disease, including but not limited to: inflammation, destruction of liver cells (e.g., hepatocellular necrosis), scarring of the liver (e.g., fibrosis), irreversible, advanced scarring of the liver (e.g., cirrhosis), insulin resistance, diabetes, dyslipidemia, increased protein activity in the hedgehog (Hh) signaling pathway, fatigue, weakness, nausea, abdominal pain, spider-like blood vessels, jaundice, itching, edema, ascites, mental confusion, obesity, hepatocellular carcinoma.

In some embodiments, non-limiting examples of a PNPLA3-related disorder include: hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertrygliceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD).

In some embodiments, non-limiting examples of a PNPLA3-related disorder include: fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma.

The present disclosure pertains to methods of using oligonucleotides disclosed herein which are capable of targeting PNPLA3 and useful for treating and/or manufacturing a treatment for a PNPLA3-related disorder. In some embodiments, a base sequence of a PNPLA3 oligonucleotide or a single-stranded RNAi agent can comprise or consist of a base sequence which has a specified maximum number of mismatches from a specified base sequence.

Treatment of a PNPLA3-Related Disorder

In some embodiments, the present disclosure pertains to a PNPLA3 oligonucleotide which targets PNPLA3 (e.g., a PNPLA3 oligonucleotide comprising a PNPLA3 target sequence or a sequence complementary to a PNPLA3 target sequence). In some embodiments, the present disclosure pertains to a PNPLA3 oligonucleotide which directs target-specific knockdown of PNPLA3. In some embodiments, the present disclosure pertains to a PNPLA3 oligonucleotide which directs target-specific knockdown of PNPLA3 mediated by RNaseH and/or RNA interference. Various such oligonucleotides capable of targeting PNPLA3 are disclosed herein.

In some embodiments, non-limiting examples of an PNPLA3-related disorder include: liver disease, fatty liver (e.g., accumulation of fat in the liver, or an increase in or supra-normal hepatic fat), hepatic steatosis (e.g., simple fatty liver), steatohepatitis, hepatitis, nonalcoholic fatty liver disease (e.g., NAFLD), and/or one or more disease and/or one or more symptom or condition associated with or secondary to a liver disease, including but not limited to: inflammation, destruction of liver cells (e.g., hepatocellular necrosis), scarring of the liver (e.g., fibrosis), irreversible, advanced scarring of the liver (e.g., cirrhosis), insulin resistance, diabetes, dyslipidemia, increased protein activity in the hedgehog (Hh) signaling pathway, fatigue, weakness, nausea, abdominal pain, spider-like blood vessels, jaundice, itching, edema, ascites, mental confusion, obesity, hepatocellular carcinoma.

In some embodiments, the present disclosure pertains to a method of treating or ameliorating an PNPLA3-related disorder in a patient thereof, the method comprising the step of administering to the patient a therapeutically effective amount of a PNPLA3 oligonucleotide which targets PNPLA3.

In some embodiments, the present disclosure pertains to a method of treating or ameliorating an PNPLA3-related disorder in a patient thereof, the method comprising the step of administering to the patient a therapeutically effective amount of a PNPLA3 oligonucleotide which targets PNPLA3, wherein the PNPLA3-related disorder is selected from: liver disease, fatty liver, steatosis, steatohepatitis, hepatitis, and nonalcoholic fatty liver disease.

In some embodiments, the present disclosure pertains to a method for introducing a PNPLA3 oligonucleotide that decreases PNPLA3 gene expression into a cell, the method comprising: contacting the cell with a PNPLA3 oligonucleotide. In some embodiments, the oligonucleotide is an antisense oligonucleotide or single-stranded RNAi agent.

In some embodiments, the present disclosure pertains to a method for decreasing PNPLA3 gene expression in a mammal in need thereof, the method comprising: administering to the mammal a nucleic acid-lipid particle comprising a PNPLA3 oligonucleotide which targets PNPLA3. In some embodiments, the oligonucleotide is an antisense oligonucleotide or single-stranded RNAi agent.

In some embodiments, the present disclosure pertains to a method for the in vivo delivery of a PNPLA3 oligonucleotide that targets PNPLA3 gene expression, the method comprising: administering to a mammal a PNPLA3 oligonucleotide which targets PNPLA3. In some embodiments, the oligonucleotide is an antisense oligonucleotide or single-stranded RNAi agent. In some embodiments, the mammal is a human. In some embodiments, the mammal is afflicted with and/or suffering from a PNPLA3-related disorder. In some embodiments, the mammal is afflicted with and/or suffering from a PNPLA3-related disorder selected from: liver disease, fatty liver, steatosis, steatohepatitis, hepatitis, and nonalcoholic fatty liver disease.

In some embodiments, the method of the present disclosure is for the treatment of hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertryglicemia, elevated low density lipoprotein (LDL) cholesterol levels (hypercholesterolemia), insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD), in humans wherein the method comprises administering to a subject a therapeutically effective amount of a PNPLA3 oligonucleotide of the present disclosure.

In some embodiments, the method reduces portal hypertension, hepatic protein synthetic capability, hyperbilirubinemia, or encephalopathy wherein the method comprise administering to a subject a therapeutically effective amount of a PNPLA3 oligonucleotide of the present disclosure.

The present disclosure is also directed at a method for the treatment of reduction of at least one point in severity of nonalcoholic fatty liver disease or non-alcoholic steatohepatitis grading scoring systems, reduction of the level of serum markers of non-alcoholic steatohepatitis activity, reduction of non-alcoholic steatohepatitis disease activity or reduction in the medical consequences of non-alcoholic steatohepatitis in humans administering to a subject a therapeutically effective amount of a PNPLA3 oligonucleotide of the present disclosure.

In some embodiments, the present disclosure pertains to a method for treating and/or ameliorating one or more symptoms associated with a PNPLA3-related disorder in a mammal in need thereof, the method comprising: administering to the mammal a therapeutically effective amount of a PNPLA3 oligonucleotide which targets PNPLA3. In some embodiments, the present disclosure pertains to a method for reducing susceptibility to a PNPLA3-related disorder in a mammal in need thereof, the method comprising: administering to the mammal a therapeutically effective amount of a PNPLA3 oligonucleotide which targets PNPLA3. In some embodiments, the present disclosure pertains to a method for preventing or delaying the onset of a PNPLA3-related disorder in a mammal in need thereof, the method comprising: administering to the mammal a therapeutically effective amount of a PNPLA3 oligonucleotide which targets PNPLA3. In some embodiments, the present disclosure pertains to a method for treating and/or ameliorating one or more symptoms associated with a PNPLA3-related disorder in a mammal in need thereof, the method comprising: administering to the mammal a therapeutically effective amount of a nucleic acid-lipid particle comprising a PNPLA3 oligonucleotide which targets PNPLA3. In some embodiments, the present disclosure pertains to a method for reducing susceptibility to a PNPLA3-related disorder in a mammal in need thereof, the method comprising: administering to the mammal a therapeutically effective amount of a nucleic acid-lipid particle comprising a PNPLA3 oligonucleotide which targets PNPLA3. In some embodiments, the present disclosure pertains to a method for preventing or delaying the onset of a PNPLA3-related disorder in a mammal in need thereof, the method comprising: administering to the mammal a therapeutically effective amount of a nucleic acid-lipid particle comprising a PNPLA3 oligonucleotide which targets PNPLA3. In some embodiments, the oligonucleotide is an antisense oligonucleotide or single-stranded RNAi agent. In some embodiments, the mammal is a human. In some embodiments, the mammal is afflicted with and/or suffering from a PNPLA3-related disorder. In some embodiments, the mammal is afflicted with and/or suffering from a PNPLA3-related disorder selected from: liver disease, fatty liver, steatosis, steatohepatitis, hepatitis, and nonalcoholic fatty liver disease.

In some embodiments, the present disclosure pertains to a method of inhibiting PNPLA3 expression in a cell, the method comprising: (a) contacting the cell with a PNPLA3 oligonucleotide which targets PNPLA3; and (b) maintaining the cell produced in step (a) for a time sufficient to obtain degradation of the mRNA transcript of an PNPLA3 gene, thereby inhibiting expression of the PNPLA3 gene in the cell. In some embodiments, PNPLA3 expression is inhibited by at least 30%. In some embodiments, the oligonucleotide is an antisense oligonucleotide or single-stranded RNAi agent.

In some embodiments, the present disclosure pertains to a method of treating a disorder mediated by PNPLA3 expression comprising administering to a human in need of such treatment a therapeutically effective amount of a PNPLA3 oligonucleotide which targets PNPLA3. In some embodiments, the oligonucleotide is an antisense oligonucleotide or single-stranded RNAi agent.

In some embodiments, the present disclosure pertains to a compound comprising a PNPLA3 oligonucleotide which targets PNPLA3 for use in a subject to treat a PNPLA3-related disorder. In some embodiments, the oligonucleotide is an antisense oligonucleotide or single-stranded RNAi agent. In some embodiments, a PNPLA3-related disorder is selected from: liver disease, fatty liver, steatosis, steatohepatitis, hepatitis, or nonalcoholic fatty liver disease.

In some embodiments, a subject is administered a second agent (e.g., an additional therapeutic agent). In some embodiments, the second agent is a PNPLA3 oligonucleotide. In some embodiments, the oligonucleotide targets PNPLA3. In some embodiments, the oligonucleotide is an antisense oligonucleotide or single-stranded RNAi agent.

The oligonucleotides of the present disclosure can be administered alone or in combination with one or more additional therapeutic agents. By "administered in combination" or "combination therapy" it is meant that the oligonucleotide of the present disclosure and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Thus, the compositions and methods of prevention and treatment described herein include use of combination agents.

The combination agents are administered to a mammal in a therapeutically effective amount. By "therapeutically effective amount" it is meant an amount of a PNPLA3 oligonucleotide of the present disclosure that, when administered alone or in combination with an additional therapeutic agent to a mammal, is effective to treat the desired disease/condition (e.g., obesity, diabetes, and cardiovascular conditions).

Accordingly, oligonucleotides of the present disclosure may be co-administered with agents for the treatment of non-alcoholic steatohepatitis (NASH) and/or non-alcoholic fatty liver disease (NAFLD) (i.e., anti-NASH and anti-NAFLD agents), such as Orlistat, TZDs and other insulin sensitizing agents, FGF21 analogs, Metformin, Omega-3-acid ethyl esters (e.g. Lovaza), Fibrates, HMG CoA-reductase Inhibitors, Ezitimbe, Probucol, Ursodeoxycholic acid, TGR5 agonists, FXR agonists, Vitamin E, Betaine, Pentoxifylline, CB1 antagonists, Carnitine, N-acetylcysteine, Reduced glutathione, lorcaserin, the combination of naltrexone with buproprion, SGLT2 Inhibitors, Phentermine, Topiramate, Incretin (GLP and GIP) analogs and Angiotensin-receptor blockers. Preferred agents for the treatment of non-alcoholic steatohepatitis (NASH) and/or non-alcoholic fatty liver disease (NAFLD) (i.e., anti-NASH and anti-NAFLD agents) are an acetyl-CoA carboxylase (ACC) inhibitor, a ketohexokinase (KHK) inhibitor, a GLP-1 receptor agonist, an FXR agonist, a CB1 antagonist, an ASK1 inhibitor, an inhibitor of CCR2 and/or CCR5, a PNPLA3 inhibitor, a DGAT1 inhibitor, a DGAT2 inhibitor, an FGF21 analog, an FGF19 analog, an SGLT2 inhibitor, a PPAR agonist, an AMPK activator, an SCD1 inhibitor or an MPO inhibitor. A commonly assigned patent application PCT/IB2017/057577 filed Dec. 1, 2017. is directed to GLP-1 receptor agonists. Most preferred are a FXR agonist, an apoptosis signal-regulating kinase 1 (ASK1) inhibitor, a PPAR agonist, a GLP-1 receptor agonist, a SGLT inhibitor, a an ACC inhibitor and a KHK inhibitor.

Further, oligonucleotides of the present disclosure may be co-administered with anti-diabetic agents include (e.g. insulins, metfomin, DPPIV inhibitors (e.g., sitagliptin), GLP-1 receptor agonists, analogues and mimetics, SGLT1 and SGLT2 inhibitors (e.g., ertuglifozin)). Preferred agents are metaformin, sitagliptin and ertuglifozin. Suitable anti-diabetic agents include an acetyl-CoA carboxylase-(ACC) inhibitor such as those described in WO2009144554, WO2003072197, WO2009144555 and WO2008065508, a diacylglycerol O-acyltransferase 1 (DGAT-1) inhibitor, such as those described in WO09016462 or WO2010086820, AZD7687 or LCQ908, a diacylglycerol O-acyltransferase 2 (DGAT-2) inhibitor, such as those described in WO2015/140658, monoacylglycerol O-acyltransferase inhibitors, a phosphodiesterase (PDE)-10 inhibitor, an AMPK activator, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone and rosiglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) receptor agonist (e.g., exendin-3 and exendin-4), liraglutide, albiglutide, exenatide (Byetta®), albiglutide, lixisenatide, dulaglutide, semaglutide, NN-9924, TTP-054. TTP-273, a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 activator (e.g., resveratrol, GSK2245840 or GSK184072), a dipeptidyl peptidease IV (DPP-IV) inhibitor (e.g., those in WO2005116014, sitagliptin, vildagliptin, alogliptin, dutogliptin, linagliptin and saxagliptin), an insulin secreatagogue, a fatty acid oxidation inhibitor, an A2 antagonist, a c-jun amino-terminal kinase (JNK) inhibitor, glucokinase activators (GKa) such as those described in WO2010103437, WO2010103438, WO2010013161, WO2007122482, TTP-399, TTP-355, TTP-547, AZD1656, ARRY403, MK-0599, TAK-329, AZD5658 or GKM-001, insulin, an insulin mimetic, a glycogen phosphorylase inhibitor (e.g. GSK1362885), a VPAC2 receptor agonist, SGLT2 inhibitors, such as those described in E. C. Chao et al. Nature Reviews Drug Discovery 9, 551-559 (July 2010) including dapagliflozin, canagliflozin, empagliflozin, tofogliflozin (CSG452), Ertugliflozin, ASP-1941, THR1474, TS-071, ISIS388626 and LX4211 as well as those in WO2010023594, a glucagon receptor modulator such as those described in Demong, D. E. et al. Annual Reports in Medicinal Chemistry 2008, 43, 119-137, GPR119 modulators, particularly agonists, such as those described in WO2010140092, WO2010128425, WO2010128414, WO2010106457, Jones, R. M. et al. in Medicinal Chemistry 2009, 44, 149-170 (e.g. MBX-2982, GSK1292263, APD597 and PSN821), FGF21 derivatives or analogs such as those described in Kharitonenkov, A. et al. et al., Current Opinion in Investigational Drugs 2009, 10(4) 359-364, TGR5 (also termed GPBAR1) receptor modulators, particularly agonists, such as those described in Zhong, M., Current Topics in Medicinal Chemistry, 2010, 10(4), 386-396 and INT777, GPR40 agonists, such as those described in Medina, J. C., Annual Reports in Medicinal Chemistry, 2008, 43, 75-85, including but not limited to TAK-875, GPR120 modulators, particularly agonists, high affinity nicotinic acid receptor (HM74A) activators, and SGLT1 inhibitors, such as GSK1614235. A further representative listing of anti-diabetic agents that can be combined with the oligonucleotides of the present disclosure can be found, for example, at page 28, line 35 through page 30, line 19 of WO2011005611. Preferred anti-diabetic agents are metformin and DPP-IV inhibitors (e.g., sitagliptin, vildagliptin, alogliptin, dutogliptin, linagliptin and saxagliptin). Other antidiabetic agents could include inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKC□, PKC□, PKC□), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostain receptors (e.g. SSTR1, SSTR2, SSTR3 and SSTRS), inhibitors or modulators of PDHK2 or PDHK4, inhibitors of MAP4K4, modulators of IL1 family including IL1beta, modulators of RXRalpha. In addition suitable anti-diabetic agents include mechanisms listed by Carpino, P. A., Goodwin, B. Expert Opin. Ther. Pat, 2010, 20(12), 1627-51.

Suitable anti-obesity agents include 11□-hydroxy steroid dehydrogenase-1 (11□-HSD type 1) inhibitors, stearoyl-CoA desaturase-1 (SCD-1) inhibitor, MCR-4 agonists, cholecystokinin-A (CCK-A) agonists, monoamine reuptake inhibitors (such as sibutramine), sympathomimetic agents, □3 adrenergic agonists, dopamine agonists (such as bromocriptine), melanocyte-stimulating hormone analogs, 5HT2c agonists, melanin concentrating hormone antagonists, leptin (the OB protein), leptin analogs, leptin agonists, galanin antagonists, lipase inhibitors (such as tetrahydrolipstatin, i.e. orlistat), anorectic agents (such as a bombesin agonist), neuropeptide-Y antagonists (e.g., NPY Y5 antagonists), PYY3-36 (including analogs thereof), thyromimetic agents, dehydroepiandrosterone or an analog thereof, glucocorticoid agonists or antagonists, orexin antagonists, glucagon-like peptide-1 agonists, ciliary neurotrophic factors (such as Axokine™ available from Regeneron Pharmaceuticals, Inc., Tarrytown, N.Y. and Procter & Gamble Company, Cincinnati, Ohio), human agouti-related protein (AGRP) inhibitors, ghrelin antagonists, histamine 3 antagonists or inverse agonists, neuromedin U agonists, MTP/ApoB inhibitors (e.g., gut-selective MTP inhibitors, such as dirlotapide), opioid antagonist, orexin antagonist, the combination of naltrexone with buprorion and the like.

Preferred anti-obesity agents for use in the combination aspects of the present disclosure include gut-selective MTP inhibitors (e.g., dirlotapide, mitratapide and implitapide, R56918 (CAS No. 403987) and CAS No. 913541-47-6), CCKa agonists (e.g., N-benzyl-2-[4-(1H-indol-3-ylmethyl)-5-oxo-1-phenyl-4,5-dihydro-2,3,6,10b-tetraaza-benzo[e]azulen-6-yl]-N-isopropyl-acetamide described in PCT Publication No. WO 2005/116034 or US Publication No. 2005-0267100 A1), 5HT2c agonists (e.g., lorcaserin), MCR4 agonist (e.g., compounds described in U.S. Pat. No. 6,818, 658), lipase inhibitor (e.g., Cetilistat), PYY3-36 (as used herein "PYY3-36" includes analogs, such as peglated PYY3-36 e.g., those described in US Publication 2006/0178501), opioid antagonists (e.g., naltrexone), the combination of naltrexone with buprorion, oleoyl-estrone (CAS No. 180003-17-2), obinepitide (TM30338), pramlintide (Symlin®), tesofensine (N52330), leptin, liraglutide, bromocriptine, orlistat, exenatide (Byetta®), AOD-9604 (CAS No. 221231-10-3), phentermine and topiramate (trade name: Qsymia), and sibutramine. Preferably, oligonucleotides of the present disclosure and combination therapies are administered in conjunction with exercise and a sensible diet.

Those skilled in the art will recognize that oligonucleotides of the present disclosure may also be used in conjunction with cardiovascular or cerebrovascular treatments as described in the paragraphs below. Oligonucleotides of the present disclosure may also be used with cardiovascular therapies including PCI, stenting, drug eluting stents, stem cell therapy and medical devices such as implanted pacemakers, defibrillators, or cardiac resynchronization therapy.

The oligonucleotides of the present disclosure may be used in combination with cholesterol modulating agents (including cholesterol lowering agents) such as a lipase inhibitor, an HMG-CoA reductase inhibitor, an HMG-CoA synthase inhibitor, an HMG-CoA reductase gene expression inhibitor, an HMG-CoA synthase gene expression inhibitor, an MTP/Apo B secretion inhibitor, a CETP inhibitor, a bile acid absorption inhibitor, a cholesterol absorption inhibitor, a cholesterol synthesis inhibitor, a squalene synthetase inhibitor, a squalene epoxidase inhibitor, a squalene cyclase inhibitor, a combined squalene epoxidase/squalene cyclase inhibitor, a fibrate, niacin, an ion-exchange resin, an antioxidant, an ACAT inhibitor or a bile acid sequestrant or an agent such as mipomersen.

Examples of suitable cholesterol/lipid lowering agents and lipid profile therapies include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants (such as questran); ACAT inhibitors; MTP inhibitors; lipooxygenase inhibitors; choesterol absorption inhibitors; and cholesteryl ester transfer protein inhibitors. Other atherosclerotic agents include PCSK9 modulators.

Administration of a PNPLA3 Oligonucleotide or a Single-Stranded RNAi Agent

In some embodiments, provided oligonucleotides are capable of directing a decrease in the expression and/or level of a target gene or its gene product. In some embodiments, provided oligonucleotides are capable of directing a decrease in the expression and/or level of a target gene or its gene product via RNA interference. In some embodiments, provided oligonucleotides are capable of directing a decrease in the expression and/or level of a target gene or its gene product via a biochemical mechanism which does not involve RNA interference or RISC (including, but not limited to, RNaseH-mediated knockdown or steric hindrance of gene expression). In some embodiments, provided oligonucleotides are capable of directing a decrease in the expression and/or level of a target gene or its gene product via RNA interference and/or RNase H-mediated knockdown. In some embodiments, provided oligonucleotides are capable of directing a decrease in the expression and/or level of a target gene or its gene product by sterically blocking translation after annealing to a target gene mRNA, and/or by altering or interfering with mRNA splicing and/or exon inclusion or exclusion. In some embodiments, provided oligonucleotides are administered with any vehicle, in any dosing regiment, and in any manner described herein or known in the art.

In some embodiments, a provided oligonucleotide composition is administered at a dose and/or frequency lower than that of an otherwise comparable reference oligonucleotide composition with comparable effect in improving the knockdown of a target transcript. In some embodiments, a stereocontrolled oligonucleotide composition is administered at a dose and/or frequency lower than that of an otherwise comparable stereorandom reference oligonucleotide composition with comparable effect in improving the knockdown of the target transcript.

In some embodiments, the present disclosure recognizes that properties, e.g., improved single-stranded RNA interference activity, etc. of oligonucleotides and compositions thereof can be optimized by chemical modifications and/or stereochemistry. In some embodiments, the present disclosure provides methods for optimizing oligonucleotide properties through chemical modifications and stereochemistry.

By controlling of chemical modifications and/or stereochemistry, the present disclosure provides improved oligonucleotide compositions and methods. In some embodiments, provided oligonucleotides capable of directing single-stranded RNA interference comprise chemical modifications. In some embodiments, provided oligonucleotides capable of directing single-stranded RNA interference comprise base modifications, sugar modifications, internucleotidic linkage modifications, or any combinations thereof. In some embodiments, provided oligonucleotides capable of directing single-stranded RNA interference comprise base modifications. In some embodiments, provided oligonucleotides capable of directing single-stranded RNA interference comprise sugar modifications. In some embodiments, provided oligonucleotides comprises 2'-modifications on the sugar moieties. In some embodiments, provided oligonucleotides comprises one or more modified internucleotidic linkages and one or more natural phosphate linkages. A natural phosphate linkage can be incorporated into various locations of a PNPLA3 oligonucleotide. In some embodiments, a natural phosphate linkage is incorporated into the 5'-end region. In some embodiments, a natural phosphate linkage is incorporated into the middle of a PNPLA3 oligonucleotide. In some embodiments, the present disclosure provides a method comprising administering a composition comprising a first plurality of oligonucleotides, which composition displays improved delivery as compared with a reference composition comprising a plurality of oligonucleotides, each of which also has the common base sequence but which differs structurally from the oligonucleotides of the first plurality in that:

individual oligonucleotides within the reference plurality differ from one another in stereochemical structure; and/or at least some oligonucleotides within the reference plurality have a structure different from a structure represented by the plurality of oligonucleotides of the composition.

In some embodiments, the present disclosure provides a method of administering a PNPLA3 oligonucleotide composition comprising a first plurality of oligonucleotides capable of directing single-stranded RNA interference and having a common nucleotide sequence, the improvement that comprises:

administering a PNPLA3 oligonucleotide comprising a first plurality of oligonucleotides that is characterized by improved delivery relative to a reference oligonucleotide composition of the same common nucleotide sequence.

In some embodiments, provided oligonucleotides, compositions and methods provide improved systemic delivery. In some embodiments, provided oligonucleotides, compositions and methods provide improved cytoplasmatic delivery. In some embodiments, improved delivery is to a population of cells. In some embodiments, improved delivery is to a tissue. In some embodiments, improved delivery is to an organ. In some embodiments, improved delivery is to an organism. Example structural elements (e.g., chemical modifications, stereochemistry, combinations thereof, etc.), oligonucleotides, compositions and methods that provide improved delivery are extensively described in this disclosure.

In some embodiments, the present disclosure provides a method of identifying and/or characterizing a PNPLA3 oligonucleotide composition, the method comprising steps of:

providing at least one composition comprising a first plurality of oligonucleotides; and assessing delivery relative to a reference composition.

In some embodiments, the present disclosure provides a method of identifying and/or characterizing a PNPLA3 oligonucleotide composition, the method comprising steps of:

providing at least one composition comprising a first plurality of oligonucleotides; and assessing cellular uptake relative to a reference composition.

In some embodiments, properties of a provided oligonucleotide compositions are compared to a reference oligonucleotide composition. In some embodiments, a reference oligonucleotide composition comprises a reference plurality of oligonucleotides.

In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages.

In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications.

In some embodiments, a reference composition is a composition of oligonucleotides having the same base sequence but different chemical modifications. In some embodiments, a reference composition is a composition of oligonucleotides having the same base sequence, base modifications, internucleotidic linkage modifications but different sugar modifications. In some embodiments, a reference composition has fewer 2'-modified sugar modifications. In some embodiments, a reference composition is a composition of oligonucleotides having the same base sequence, base modifications, sugar modifications but different internucleotidic linkage modifications. In some embodiments, a reference composition has more internucleotidic linkage modifications. In some embodiments, a reference composition has fewer natural phosphate linkages. In some embodiments, a reference composition comprising oligonucleotides having no natural phosphate linkages.

In some embodiments, a reference composition is a composition comprising a reference plurality of oligonucleotides wherein individual oligonucleotides within the reference plurality differ from one another in stereochemical structure. In some embodiments, a reference composition is a composition comprising a reference plurality of oligonucleotides, wherein at least some oligonucleotides within the reference plurality have a structure different from a structure represented by a plurality of oligonucleotides of a composition compared to the reference composition.

In some embodiments, a reference oligonucleotide composition comprises a reference plurality of oligonucleotides capable of directing single-stranded RNA interference and having the same common nucleotide sequence but lacking at least one of the one or more modified sugar moieties in oligonucleotides of the oligonucleotide composition compared to the reference composition. In some embodiments, a reference oligonucleotide composition comprises a reference plurality of oligonucleotides capable of directing single-stranded RNA interference and having the same common nucleotide sequence but have no modified sugar moieties. In some embodiments, a reference oligonucleotide composition comprises a reference plurality of oligonucleotides capable of directing single-stranded RNA interference and having the same common nucleotide sequence but do not comprise natural phosphate linkages. In some embodiments, a reference composition is a PNPLA3 oligonucleotide or a single-stranded RNAi agent of oligonucleotides having the same chemical modification patterns. In some embodiments, a reference composition is a PNPLA3 oligonucleotide or a single-stranded RNAi agent of another stereoisomer.

In some embodiments, a reference oligonucleotide composition of a provided oligonucleotide composition is a comparable composition absence of the lipids in the provided composition. In some embodiments, a reference oligonucleotide composition is a stereorandom oligonucleotide composition. In some embodiments, a reference oligonucleotide composition is a stereorandom composition of oligonucleotides of which all internucleotidic linkages are phosphorothioate. In some embodiments, a reference oligonucleotide composition is a DNA oligonucleotide composition with all phosphate linkages. In some embodiments, a reference composition is a composition of oligonucleotides having the same base sequence and the same chemical modifications. In some embodiments, a reference composition is a composition of oligonucleotides having the same base sequence and the same pattern of chemical modifications. In some embodiments, a reference composition is a chirally un-controlled (or stereorandom) composition of oligonucleotides having the same base sequence and chemical modifications. In some embodiments, a reference composition is a composition of oligonucleotides having the same base sequence but different chemical modifications. In some embodiments, a reference composition is a composition of oligonucleotides having the same base sequence, base modifications, internucleotidic linkage modifications but different sugar modifications. In some embodiments, a reference composition has fewer 2'-modified sugar modifications. In some embodiments, a reference composition is a composition of oligonucleotides having the same base sequence, base modifications, sugar modifications but different internucleotidic linkage modifications. In some embodiments, a reference composition has more internucleotidic linkage modifications. In some embodiments, a reference composition has fewer natural phosphate linkages. In some embodiments, a reference composition comprising oligonucleotides having no natural phosphate linkages. In some embodiments, a reference composition is a composition comprising a reference plurality of oligonucleotides wherein individual oligonucleotides within the reference plurality differ from one another in stereochemical structure. In some embodiments, a reference composition is a composition comprising a reference plurality of oligonucleotides, wherein at least some oligonucleotides within the reference plurality have a structure different from a structure represented by a plurality of oligonucleotides of a composition compared to the reference composition. In some embodiments, a reference oligonucleotide composition comprises a reference plurality of oligonucleotides capable of directing single-stranded RNA interference and having the same common nucleotide sequence but lacking at least one of the one or more modified sugar moieties in oligonucleotides of the oligonucleotide composition compared to the reference composition. In some embodiments, a reference oligonucleotide composition comprises a reference plurality of oligonucleotides capable of directing single-stranded RNA interference and having the same common nucleotide sequence but have no modified sugar moieties. In some embodiments, a reference oligonucleotide composition comprises a reference plurality of oligonucleotides capable of directing single-stranded RNA interference and having the same common nucleotide sequence but do not comprise natural phosphate linkages. In some embodiments, a reference composition is a PNPLA3 oligonucleotide or a single-stranded RNAi agent of oligonucleotides having the same chemical modification patterns. In some embodiments, a reference composition is a PNPLA3 oligonucleotide or a single-stranded RNAi agent of another stereoisomer.

In some embodiments, oligonucleotides of the first plurality comprise one or more structural elements (e.g., modifications, stereochemistry, patterns, etc.) that oligonucleotides of the reference plurality do not all have. Such structural elements can be any one described in this disclosure.

In some embodiments, oligonucleotides of the first plurality comprise more phosphorothioate linkages the PNPLA3 oligonucleotides of the reference composition. In some embodiments, oligonucleotides of the first plurality comprise more phosphorothioate linkages the PNPLA3 oligonucleotides of the reference composition at the 5'-end region. In some embodiments, oligonucleotides of the first plurality comprise more phosphorothioate linkages the PNPLA3 oligonucleotides of the reference composition at the 3'-end region. In some embodiments, oligonucleotides of the first plurality comprise more Sp chiral internucleotidic linkages the PNPLA3 oligonucleotides of the reference composition. In some embodiments, oligonucleotides of the first plurality comprise more Sp phosphorothioate linkages the PNPLA3 oligonucleotides of the reference composition. In some embodiments, oligonucleotides of the first plurality comprise more Sp phosphorothioate linkages the PNPLA3 oligonucleotides of the reference composition at the 5'-end region. In some embodiments, oligonucleotides of the first plurality comprise more Sp phosphorothioate linkages the PNPLA3 oligonucleotides of the reference composition at the 3'-end region. In some embodiments, oligonucleotides of the first plurality comprise more modified bases the PNPLA3 oligonucleotides of the reference composition. In some embodiments, oligonucleotides of the first plurality comprise more methylated bases the PNPLA3 oligonucleotides of the reference composition. In some embodiments, oligonucleotides of the first plurality comprise more methylated bases the PNPLA3 oligonucleotides of the reference composition at the 5'-end region. In some embodiments, oligonucleotides of the first plurality comprise more methylated bases the PNPLA3 oligonucleotides of the reference composition at the 3'-end region. In some embodiments, oligonucleotides of the first plurality comprise fewer 2'-MOE modifications the PNPLA3 oligonucleotides of the reference composition. In some embodiments, oligonucleotides of the first plurality comprise fewer 2'-MOE modifications the PNPLA3 oligonucleotides of the reference composition. In some embodiments, oligonucleotides of the first plurality comprise fewer 2'-MOE modifications the PNPLA3 oligonucleotides of the reference composition at the 5'-end region. In some embodiments, oligonucleotides of the first plurality comprise fewer 2'-MOE modifications the PNPLA3 oligonucleotides of the reference composition at the 3'-end region. In some embodiments, individual oligonucleotides within the reference plurality differ from one another in stereochemical structure. In some embodiments, at least some oligonucleotides within the reference plurality have a structure different from a structure represented by the plurality of oligonucleotides of the composition. In some embodiments, the reference composition is a substantially racemic preparation of oligonucleotides that share the base sequence. In some embodiments, the reference composition is a PNPLA3 oligonucleotide or a single-stranded RNAi agent of another oligonucleotide type. In some embodiments, oligonucleotides of the reference composition comprise more phosphorothioate linkages. In some embodiments, oligonucleotides of the reference composition comprise only phosphorothioate linkages. In some embodiments, oligonucleotides of the reference composition comprise fewer modified sugar moieties. In some embodiments, oligonucleotides of the reference composition comprise fewer modified sugar moieties, wherein the modification is 2'-OR$^1$. In some embodiments, oligonucleotides of the reference composition comprise more modified sugar moieties. In some embodiments, oligonucleotides of the reference composition comprise more modified sugar moieties, the modification is 2'-OR$^1$. In some embodiments, oligonucleotides of the reference composition comprise fewer phosphorothioate linkages. In some embodiments, oligonucleotides of the reference composition comprise fewer methylated bases. In some embodiments, oligonucleotides of the reference composition comprise more 2'-MOE modifications. In some embodiments, oligonucleotides of the reference composition comprise fewer natural phosphate linkages. In some embodiments, oligonucleotides of the reference composition comprise fewer natural phosphate linkages at the 5'- and/or 3'-end region. In some embodiments, oligonucleotides of a provided composition comprise fewer 2'-MOE modifications the PNPLA3 oligonucleotides of the reference composition. In some embodiments, oligonucleotides of a provided composition comprise fewer 2'-MOE modifications the PNPLA3 oligonucleotides of the reference composition. In some embodiments, oligonucleotides of a provided composition comprise fewer 2'-MOE modifications the PNPLA3 oligonucleotides of the reference composition at the 5'-end region. In some embodiments, oligonucleotides of a provided composition comprise fewer 2'-MOE modifications the PNPLA3 oligonucleotides of the reference composition at the 3'-end region. In some embodiments, individual oligonucleotides within the reference plurality differ from one another in stereochemical structure. In some embodiments, at least some oligonucleotides within the reference plurality have a structure different from a structure represented by the plurality of oligonucleotides of the composition. In some embodiments, the reference composition is a substantially racemic preparation of oligonucleotides that share the base sequence. In some embodiments, the reference composition is a PNPLA3 oligonucleotide or a single-stranded RNAi agent of another oligonucleotide type. In some embodiments, oligonucleotides of the reference composition comprise more phosphorothioate linkages. In some embodiments, oligonucleotides of the reference composition comprise only phosphorothioate linkages. In some embodiments, oligonucleotides of the reference composition comprise fewer modified sugar moieties. In some embodiments, oligonucleotides of the reference composition comprise fewer modified sugar moieties, wherein the modification is 2'-OR$^1$. In some embodiments, oligonucleotides of the reference composition comprise more modified sugar moieties. In some embodiments, oligonucleotides of the reference composition comprise more modified sugar moieties, the modification is 2'-OR'. In some embodiments, oligonucleotides of the reference composition comprise fewer phosphorothioate linkages. In some embodiments, oligonucleotides of the reference composition comprise fewer methylated bases. In some embodiments, oligonucleotides of the reference composition comprise more 2'-MOE modifications. In some embodiments, oligonucleotides of the reference composition comprise fewer natural phosphate linkages. In some embodiments, oligonucleotides of the reference composition comprise fewer natural phosphate linkages at the 5'- and/or 3'-end region. In some embodiments, oligonucleotides of a reference plurality comprise fewer nucleotidic units comprising —F. In some embodiments, oligonucleotides of a reference plurality comprise fewer 2'-F modified sugar moieties. In some embodiments, oligonucleotides of a reference plurality comprise fewer chirally controlled modified internucleotidic linkages.

In some embodiments, provided chirally controlled oligonucleotide compositions comprises oligonucleotides of one oligonucleotide type. In some embodiments, provided chirally controlled oligonucleotide compositions comprises oligonucleotides of only one oligonucleotide type. In some embodiments, provided chirally controlled oligonucleotide compositions has oligonucleotides of only one oligonucleotide type. In some embodiments, provided chirally controlled oligonucleotide compositions comprises oligonucleotides of two or more oligonucleotide types. In some embodiments, using such compositions, provided methods can target more than one target. In some embodiments, a PNPLA3 oligonucleotide or a single-stranded RNAi agent comprising two or more oligonucleotide types targets two or more targets. In some embodiments, a PNPLA3 oligonucleotide or a single-stranded RNAi agent comprising two or more oligonucleotide types targets two or more mismatches. In some embodiments, a single oligonucleotide type targets two or more targets, e.g., mutations. In some embodiments, a target region of oligonucleotides of one oligonucleotide type comprises two or more "target sites" such as two mutations or SNPs.

In some embodiments, oligonucleotides in a provided chirally controlled oligonucleotide composition optionally comprise modified bases or sugars. In some embodiments, a provided chirally controlled oligonucleotide composition does not have any modified bases or sugars. In some embodiments, a provided chirally controlled oligonucleotide composition does not have any modified bases. In some embodiments, oligonucleotides in a provided chirally controlled oligonucleotide composition comprise modified bases and sugars. In some embodiments, oligonucleotides in a provided chirally controlled oligonucleotide composition comprise a modified base. In some embodiments, oligonucleotides in a provided chirally controlled oligonucleotide composition comprise a modified sugar. Modified bases and sugars for oligonucleotides are widely known in the art, including but not limited in those described in the present disclosure. In some embodiments, a modified base is 5-mC. In some embodiments, a modified sugar is a 2'-modified sugar. Suitable 2'-modification of oligonucleotide sugars are widely known by a person having ordinary skill in the art. In some embodiments, 2'-modifications include but are not limited to 2'-OR$^1$, wherein R$^1$ is not hydrogen. In some embodiments, a 2'-modification is 2'-OR$^1$, wherein R$^1$ is optionally substituted C$_{1-6}$ aliphatic. In some embodiments, a 2'-modification is 2'-MOE. In some embodiments, a modification is 2'-halogen. In some embodiments, a modification is 2'-F. In some embodiments, modified bases or sugars may further enhance activity, stability and/or selectivity of a chirally controlled oligonucleotide composition, whose common pattern of backbone chiral centers provides unexpected activity, stability and/or selectivity.

In some embodiments, a provided chirally controlled oligonucleotide composition does not have any modified sugars. In some embodiments, a provided chirally controlled oligonucleotide composition does not have any 2'-modified sugars. In some embodiments, the present disclosure surprising found that by using chirally controlled oligonucleotide compositions, modified sugars are not needed for stability, activity, and/or control of cleavage patterns. Furthermore, in some embodiments, the present disclosure surprisingly found that chirally controlled oligonucleotide compositions of oligonucleotides without modified sugars deliver better properties in terms of stability, activity, turnover and/or control of cleavage patterns. For example, in some embodiments, it is surprising found that chirally controlled oligonucleotide compositions of oligonucleotides having no modified sugars dissociates much faster from cleavage products and provide significantly increased turnover than compositions of oligonucleotides with modified sugars.

As discussed in detail herein, the present disclosure provides, among other things, a chirally controlled oligonucleotide composition, meaning that the composition contains a plurality of oligonucleotides of at least one type. Each oligonucleotide molecule of a particular "type" is comprised of preselected (e.g., predetermined) structural elements with respect to: (1) base sequence; (2) pattern of backbone linkages; (3) pattern of backbone chiral centers; and (4) pattern of backbone P-modification moieties. In some embodiments, provided oligonucleotide compositions contain oligonucleotides that are prepared in a single synthesis process. In some embodiments, provided compositions contain oligonucleotides having more than one chiral configuration within a single oligonucleotide molecule (e.g., where different residues along the oligonucleotide have different stereochemistry); in some such embodiments, such oligonucleotides may be obtained in a single synthesis process, without the need for secondary conjugation steps to generate individual oligonucleotide molecules with more than one chiral configuration.

Oligonucleotide compositions as provided herein can be used as single-stranded RNAi agents. In addition, oligonucleotide compositions as provided herein can be used as reagents for research and/or diagnostic purposes. One of ordinary skill in the art will readily recognize that the present disclosure disclosure herein is not limited to particular use but is applicable to any situations where the use of synthetic oligonucleotides is desirable. Among other things, provided compositions are useful in a variety of therapeutic, diagnostic, agricultural, and/or research applications.

In some embodiments, provided oligonucleotide compositions comprise oligonucleotides and/or residues thereof that include one or more structural modifications as described in detail herein. In some embodiments, provided oligonucleotide compositions comprise oligonucleotides that contain one or more modified nucleotides. In some embodiments, provided oligonucleotide compositions comprise oligonucleotides that contain one or more artificial nucleic acids or residues, including but not limited to: peptide nucleic acids (PNA), Morpholino and locked nucleic acids (LNA), glycon nucleic acids (GNA), threose nucleic acids (TNA), Xeno nucleic acids (XNA), manitol nucleic acid (MNA), anitol nucleic acid (ANA), and F-HNA, and any combination thereof. In some embodiments, a provided oligonucleotide comprises a Morpholino as described in Braasch et al. 2002 Biochem. 41: 4503-4510, or U.S. Pat. Nos. 5,698,685; 5,166,315; 5,185,444; or 5,034,506. In some embodiments, a provided oligonucleotide comprises a F-HNA as described in U.S. Pat. Nos. 8,088,904; 8,440,803; or 8,796,437; or in WO 2017/011276. Various modified nucleotides, including modified sugars are described in, for example, WO 2016/154096 and WO 2016/141236.

In any of the embodiments, the disclosure is useful for oligonucleotide-based modulation of gene expression, immune response, etc. Accordingly, stereo-defined, oligonucleotide compositions of the disclosure, which contain oligonucleotides of predetermined type (i.e., which are chirally controlled, and optionally chirally pure), can be used in lieu of conventional stereo-random or chirally impure counterparts. In some embodiments, provided compositions show enhanced intended effects and/or reduced unwanted side effects. Certain embodiments of biological and clinical/therapeutic applications of the disclosure are discussed explicitly below.

Various dosing regimens can be utilized to administer provided chirally controlled oligonucleotide compositions. In some embodiments, multiple unit doses are administered, separated by periods of time. In some embodiments, a given composition has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, all doses within a dosing regimen are of the same unit dose amount. In some embodiments, different doses within a dosing regimen are of different amounts. In some embodiments, a dosing regimen comprises a first dose in a first dose amount, followed by one or more additional doses in a second dose amount different from the first dose amount. In some embodiments, a dosing regimen comprises a first dose in a first dose amount, followed by one or more additional doses in a second (or subsequent) dose amount that is same as or different from the first dose (or another prior dose) amount. In some embodiments, a dosing regimen comprises administering at least one unit dose for at least one day. In some embodiments, a dosing regimen comprises administering more than one dose over a time period of at least one day, and sometimes more than one day. In some embodiments, a dosing regimen comprises administering multiple doses over a time period of at least week. In some embodiments, the time period is at least 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per week for more than one week. In some embodiments, a dosing regimen comprises administering one dose per week for 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose every two weeks for more than two week period. In some embodiments, a dosing regimen comprises administering one dose every two weeks over a time period of 2, 3, 4, 5, 6, 7, 8, 9, 10, 11, 12, 13, 14, 15, 16, 17, 18, 19, 20, 21, 22, 23 24, 25, 26, 27, 28, 29, 30, 31, 32, 33, 34, 35, 36, 37, 38, 39, 40 or more (e.g., about 45, 50, 55, 60, 65, 70, 75, 80, 85, 90, 95, 100 or more) weeks. In some embodiments, a dosing regimen comprises administering one dose per month for one month. In some embodiments, a dosing regimen comprises administering one dose per month for more than one month. In some embodiments, a dosing regimen comprises administering one dose per month for 2, 3, 4, 5, 6, 7, 8, 9, 10, 11, 12, or more months. In some embodiments, a dosing regimen comprises administering one dose per week for about 10 weeks. In some embodiments, a dosing regimen comprises administering one dose per week for about 20 weeks. In some embodiments, a dosing regimen comprises administering one dose per week for about 30 weeks. In some embodiments, a dosing regimen comprises administering one dose per week for 26 weeks. In some embodiments, a PNPLA3 oligonucleotide or a single-stranded RNAi agent is administered according to a dosing regimen that differs from that utilized for a chirally uncontrolled (e.g., stereorandom) oligonucleotide composition of the same sequence, and/or of a different chirally controlled oligonucleotide composition of the same sequence. In some embodiments, a PNPLA3 oligonucleotide or a single-stranded RNAi agent is administered according to a dosing regimen that is reduced as compared with that of a chirally uncontrolled (e.g., stereorandom) oligonucleotide composition of the same sequence in that it achieves a lower level of total exposure over a given unit of time, involves one or more lower unit doses, and/or includes a smaller number of doses over a given unit of time. In some embodiments, a PNPLA3 oligonucleotide or a single-stranded RNAi agent is administered according to a dosing regimen that extends for a longer period of time than does that of a chirally uncontrolled (e.g., stereorandom) oligonucleotide composition of the same sequence Without wishing to be limited by theory, Applicant notes that in some embodiments, the shorter dosing regimen, and/or longer time periods between doses, may be due to the improved stability, bioavailability, and/or efficacy of a chirally controlled oligonucleotide composition. In some embodiments, a PNPLA3 oligonucleotide or a single-stranded RNAi agent has a longer dosing regimen compared to the corresponding chirally uncontrolled oligonucleotide composition. In some embodiments, a PNPLA3 oligonucleotide or a single-stranded RNAi agent has a shorter time period between at least two doses compared to the corresponding chirally uncontrolled oligonucleotide composition. Without wishing to be limited by theory, Applicant notes that in some embodiments longer dosing regimen, and/or shorter time periods between doses, may be due to the improved safety of a chirally controlled oligonucleotide composition.

In some embodiments, with their improved delivery (and other properties), provided compositions can be administered in lower dosages and/or with lower frequency to achieve biological effects, for example, clinical efficacy.

A single dose can contain various amounts of oligonucleotides. In some embodiments, a single dose can contain various amounts of a type of chirally controlled oligonucleotide, as desired suitable by the application. In some embodiments, a single dose contains about 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300 or more (e.g., about 350, 400, 450, 500, 550, 600, 650, 700, 750, 800, 850, 900, 950, 1000 or more) mg of a type of chirally controlled oligonucleotide. In some embodiments, a single dose contains about 1 mg of a type of chirally controlled oligonucleotide. In some embodiments, a single dose contains about 5 mg of a type of chirally controlled oligonucleotide. In some embodiments, a single dose contains about 10 mg of a type of chirally controlled oligonucleotide. In some embodiments, a single dose contains about 15 mg of a type of chirally controlled oligonucleotide. In some embodiments, a single dose contains about 20 mg of a type of chirally controlled oligonucleotide. In some embodiments, a single dose contains about 50 mg of a type of chirally controlled oligonucleotide. In some embodiments, a single dose contains about 100 mg of a type of chirally controlled oligonucleotide. In some embodiments, a single dose contains about 150 mg of a type of chirally controlled oligonucleotide. In some embodiments, a single dose contains about 200 mg of a type of chirally controlled oligonucleotide. In some embodiments, a single dose contains about 250 mg of a type of chirally controlled oligonucleotide. In some embodiments, a single dose contains about 300 mg of a type of chirally controlled oligonucleotide. In some embodiments, a chirally controlled oligonucleotide is administered at a lower amount in a single dose, and/or in total dose, than a chirally uncontrolled oligonucleotide. In some embodiments, a chirally controlled oligonucleotide is administered at a lower amount in a single dose, and/or in total dose, than a chirally uncontrolled oligonucleotide due to improved efficacy. In some embodiments, a chirally controlled oligonucleotide is administered at a higher amount in a single dose, and/or in total dose, than a chirally uncontrolled oligonucleotide. In some embodiments, a chirally controlled oligonucleotide is administered at a higher amount in a single dose, and/or in total dose, than a chirally uncontrolled oligonucleotide due to improved safety.

Biologically Active Oligonucleotides

In some embodiments, the present disclosure encompasses oligonucleotides which capable of acting as single-stranded RNAi agents.

In some embodiments, provided compositions include one or more oligonucleotides fully or partially complementary to strand of: structural genes, genes control and/or termination regions, and/or self-replicating systems such as viral or plasmid DNA. In some embodiments, provided compositions include one or more oligonucleotides that are or act as RNAi agents or other RNA interference reagents (RNAi agents or iRNA agents), shRNA, antisense oligonucleotides, self-cleaving RNAs, ribozymes, fragment thereof and/or variants thereof (such as Peptidyl transferase 23S rRNA, RNase P, Group I and Group II introns, GIR1 branching ribozymes, Leadzyme, Hairpin ribozymes, Hammerhead ribozymes, HDV ribozymes, Mammalian CPEB3 ribozyme, VS ribozymes, glmS ribozymes, CoTC ribozyme, etc.), microRNAs, microRNA mimics, supermirs, aptamers, antimirs, antagomirs, U1 adaptors, triplex-forming oligonucleotides, RNA activators, long non-coding RNAs, short non-coding RNAs (e.g., piRNAs), immunomodulatory oligonucleotides (such as immunostimulatory oligonucleotides, immunoinhibitory oligonucleotides), GNA, LNA, ENA, PNA, TNA, morpholinos, G-quadruplex (RNA and DNA), antiviral oligonucleotides, and decoy oligonucleotides.

In some embodiments, provided compositions include one or more hybrid (e.g., chimeric) oligonucleotides. In the context of the present disclosure, the term "hybrid" broadly refers to mixed structural elements of oligonucleotides. Hybrid oligonucleotides may refer to, for example, (1) a PNPLA3 oligonucleotide molecule having mixed classes of nucleotides, e.g., part DNA and part RNA within the single molecule (e.g., DNA-RNA); (2) complementary pairs of nucleic acids of different classes, such that DNA:RNA base pairing occurs either intramolecularly or intermolecularly; or both; (3) a PNPLA3 oligonucleotide with two or more kinds of the backbone or internucleotide linkages.

In some embodiments, provided compositions include one or more oligonucleotide that comprises more than one classes of nucleic acid residues within a single molecule. For example, in any of the embodiments described herein, a PNPLA3 oligonucleotide may comprise a DNA portion and an RNA portion. In some embodiments, a PNPLA3 oligonucleotide may comprise a unmodified portion and modified portion.

Provided oligonucleotide compositions can include oligonucleotides containing any of a variety of modifications, for example as described herein. In some embodiments, particular modifications are selected, for example, in light of intended use. In some embodiments, it is desirable to modify one or both strands of a double-stranded oligonucleotide (or a double-stranded portion of a single-stranded oligonucleotide). In some embodiments, the two strands (or portions) include different modifications. In some embodiments, the two strands include the same modifications. One of skill in the art will appreciate that the degree and type of modifications enabled by methods of the present disclosure allow for numerous permutations of modifications to be made. Examples of such modifications are described herein and are not meant to be limiting.

The phrase "antisense strand" as used herein, refers to a PNPLA3 oligonucleotide that is substantially or 100% complementary to a target sequence of interest. The phrase "antisense strand" includes the antisense region of both oligonucleotides that are formed from two separate strands, as well as unimolecular oligonucleotides that are capable of forming hairpin or dumbbell type structures. In reference to a double-stranded RNAi agent such as a siRNA, the antisense strand is the strand preferentially incorporated into RISC, and which targets RISC-mediated knockdown of a RNA target. In reference to a double-stranded RNAi agent, the terms "antisense strand" and "guide strand" are used interchangeably herein; and the terms "sense strand" or "passenger strand" are used interchangeably herein in reference to the strand which is not the antisense strand.

The phrase "sense strand" refers to a PNPLA3 oligonucleotide that has the same nucleoside sequence, in whole or in part, as a target sequence such as a messenger RNA or a sequence of DNA.

By "target sequence" is meant any nucleic acid sequence whose expression or activity is to be modulated. The target nucleic acid can be DNA or RNA, such as endogenous DNA or RNA, viral DNA or viral RNA, or other RNA encoded by a gene, virus, bacteria, fungus, mammal, or plant. In some embodiments, a target sequence is associated with a disease or disorder. In reference to RNA interference and RNase H-mediated knockdown, a target sequence is generally a RNA target sequence.

By "specifically hybridizable" and "complementary" is meant that a nucleic acid can form hydrogen bond(s) with another nucleic acid sequence by either traditional Watson-Crick or other non-traditional types. In reference to the nucleic molecules of the present disclosure, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al, 1987, CSH Symp. Quant. Biol. LIT pp. 123-133; Frier et al., 1986, Proc. Nat. Acad. Sci. USA 83:9373-9377; Turner et al., 1987, J. Am. Chem. Soc. 109:3783-3785)

A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9,10 out of 10 being 50%, 60%, 70%, 80%, 90%, and 100% complementary). "Perfectly complementary" or 100% complementarity means that all the contiguous residues of a nucleic acid sequence will hydrogen bond with the same number of contiguous residues in a second nucleic acid sequence. Less than perfect complementarity refers to the situation in which some, but not all, nucleoside units of two strands can hydrogen bond with each other. "Substantial complementarity" refers to polynucleotide strands exhibiting 90% or greater complementarity, excluding regions of the polynucleotide strands, such as overhangs, that are selected so as to be noncomplementary. Specific binding requires a sufficient degree of complementarity to avoid non-specific binding of the oligomeric compound to non-target sequences under conditions in which specific binding is desired, e.g., under physiological conditions in the case of in vivo assays or therapeutic treatment, or in the case of in vitro assays, under conditions in which the assays are performed. In some embodiments, non-target sequences differ from corresponding target sequences by at least 5 nucleotides.

When used as therapeutics, a provided oligonucleotide is administered as a pharmaceutical composition. In some embodiments, the pharmaceutical composition comprises a therapeutically effective amount of a provided oligonucleotide comprising, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or otic administration. In further embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

Pharmaceutical Compositions

When used as therapeutics, a provided oligonucleotide or oligonucleotide composition described herein is administered as a pharmaceutical composition. In some embodiments, the pharmaceutical composition comprises a therapeutically effective amount of a provided oligonucleotides, or a pharmaceutically acceptable salt thereof, and at least one pharmaceutically acceptable inactive ingredient selected from pharmaceutically acceptable diluents, pharmaceutically acceptable excipients, and pharmaceutically acceptable carriers. In some embodiments, the pharmaceutical composition is formulated for intravenous injection, oral administration, buccal administration, inhalation, nasal administration, topical administration, ophthalmic administration or otic administration. In some embodiments, the pharmaceutical composition is a tablet, a pill, a capsule, a liquid, an inhalant, a nasal spray solution, a suppository, a suspension, a gel, a colloid, a dispersion, a suspension, a solution, an emulsion, an ointment, a lotion, an eye drop or an ear drop.

In some embodiments, the present disclosure provides a pharmaceutical composition comprising chirally controlled oligonucleotide, or composition thereof, in admixture with a pharmaceutically acceptable excipient. One of skill in the art will recognize that the pharmaceutical compositions include the pharmaceutically acceptable salts of the chirally controlled oligonucleotide, or composition thereof, described above.

A variety of supramolecular nanocarriers can be used to deliver nucleic acids. Example nanocarriers include, but are not limited to liposomes, cationic polymer complexes and various polymeric. Complexation of nucleic acids with various polycations is another approach for intracellular delivery; this includes use of PEGlyated polycations, polyethyleneamine (PEI) complexes, cationic block co-polymers, and dendrimers. Several cationic nanocarriers, including PEI and polyamidoamine dendrimers help to release contents from endosomes. Other approaches include use of polymeric nanoparticles, microspheres, liposomes, dendrimers, biodegradable polymers, conjugates, prodrugs, inorganic colloids such as sulfur or iron, antibodies, implants, biodegradable implants, biodegradable microspheres, osmotically controlled implants, lipid nanoparticles, emulsions, oily solutions, aqueous solutions, biodegradable polymers, poly(lactide-coglycolic acid), poly(lactic acid), liquid depot, polymer micelles, quantum dots and lipoplexes. In some embodiments, a PNPLA3 oligonucleotide is conjugated to another molecular.

Additional nucleic acid delivery strategies are known in addition to the example delivery strategies described herein.

In therapeutic and/or diagnostic applications, the compounds of the disclosure can be formulated for a variety of modes of administration, including systemic and topical or localized administration. Techniques and formulations generally may be found in Remington, The Science and Practice of Pharmacy, (20th ed. 2000).

Provided oligonucleotides, and compositions thereof, are effective over a wide dosage range. For example, in the treatment of adult humans, dosages from about 0.01 to about 1000 mg, from about 0.5 to about 100 mg, from about 1 to about 50 mg per day, and from about 5 to about 100 mg per day are examples of dosages that may be used. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, The Science and Practice of Pharmacy (20th ed. 2000). Preferred pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, a provided single-stranded RNAi agent is formulated in a pharmaceutical composition described in U.S. Applications Nos. 61/774,759; 61/918,175, filed Dec. 19, 2013; 61/918,927; 61/918,182; 61/918,941; 62/025,224; 62/046,487; or International Applications No. PCT/US04/042911; PCT/EP2010/070412; or PCT/IB2014/059503.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, The Science and Practice of Pharmacy (20th ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intraarticular, intra-sternal, intra-synovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection.

The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

In certain embodiments, oligonucleotides and compositions are delivered to the CNS. In certain embodiments, oligonucleotides and compositions are delivered to the cerebrospinal fluid. In certain embodiments, oligonucleotides and compositions are administered to the brain parenchyma. In certain embodiments, oligonucleotides and compositions are delivered to an animal/subject by intrathecal administration, or intracerebroventricular administration. Broad distribution of oligonucleotides and compositions, described herein, within the central nervous system may be achieved with intraparenchymal administration, intrathecal administration, or intracerebroventricular administration.

In certain embodiments, parenteral administration is by injection, by, e.g., a syringe, a pump, etc. In certain embodiments, the injection is a bolus injection. In certain embodiments, the injection is administered directly to a tissue, such as striatum, caudate, cortex, hippocampus and cerebellum.

In certain embodiments, methods of specifically localizing a pharmaceutical agent, such as by bolus injection, decreases median effective concentration (EC50) by a factor of 20, 25, 30, 35, 40, 45 or 50. In certain embodiments, the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

In certain embodiments, an antisense oligonucleotide is delivered by injection or infusion once every month, every two months, every 90 days, every 3 months, every 6 months, twice a year or once a year.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of an active compound into preparations which can be used pharmaceutically. The preparations formulated for oral administration may be in the form of tablets, dragees, capsules, or solutions.

Pharmaceutical preparations for oral use can be obtained by combining an active compound with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, an active compound may be dissolved or suspended in suitable liquids, such as fatty oils, liquid paraffin, or liquid polyethylene glycols (PEGs). In addition, stabilizers may be added.

A composition can be obtained by combining an active compound with a lipid. In some embodiments, the lipid is conjugated to an active compound. In some embodiments, the lipid is not conjugated to an active compound. In some embodiments, a lipid comprises a $C_{10}$-$C_{40}$ linear, saturated or partially unsaturated, aliphatic chain. In some embodiments, a lipid comprises a $C_{10}$-$C_{40}$ linear, saturated or partially unsaturated, aliphatic chain, optionally substituted with one or more $C_{1-4}$ aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. In some embodiments, a lipid has a structure of any of:

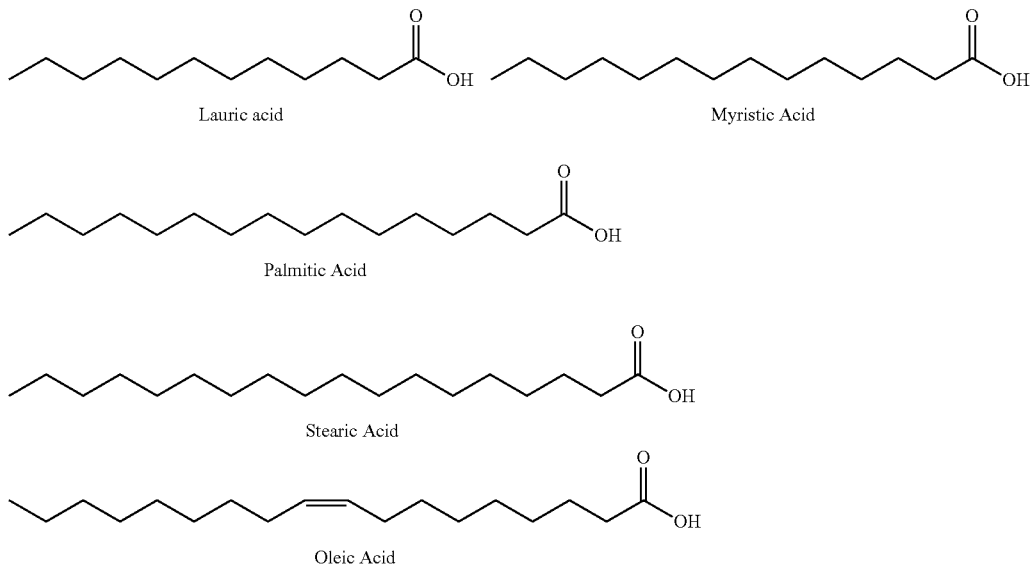

Lauric acid

Myristic Acid

Palmitic Acid

Stearic Acid

Oleic Acid

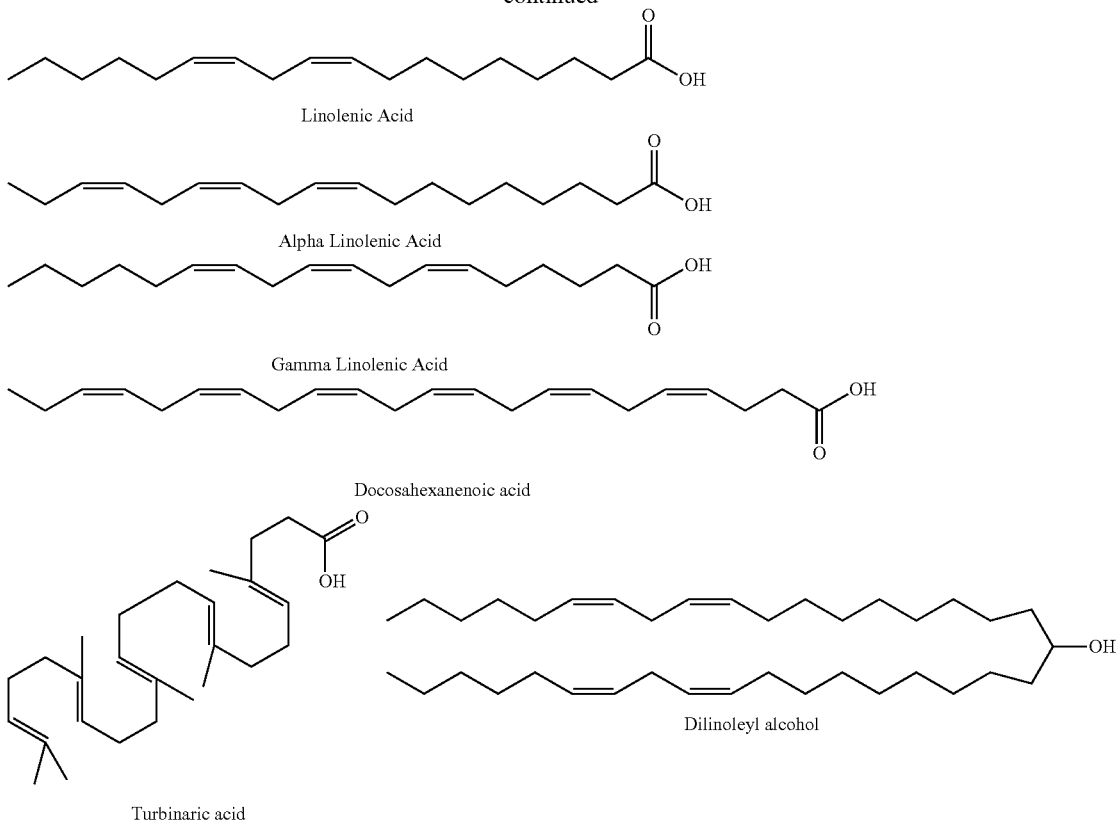

In some embodiments, an active compound is any oligonucleotide or other nucleic acid described herein. In some embodiments, an active compound is a nucleic acid of a sequence comprising or consisting of any sequence of any nucleic acid listed in Table 1A. In some embodiments, a composition comprises a lipid and an active compound, and further comprises another component selected from: another lipid, and a targeting compound or moiety. In some embodiments, a lipid includes, without limitation: an amino lipid; an amphipathic lipid; an anionic lipid; an apolipoprotein; a cationic lipid; a low molecular weight cationic lipid; a cationic lipid such as CLinDMA and DLinDMA; an ionizable cationic lipid; a cloaking component; a helper lipid; a lipopeptide; a neutral lipid; a neutral zwitterionic lipid; a hydrophobic small molecule; a hydrophobic vitamin; a PEG-lipid; an uncharged lipid modified with one or more hydrophilic polymers; phospholipid; a phospholipid such as 1,2-dioleoyl-sn-glycero-3-phosphoethanolamine; a stealth lipid; a sterol; a cholesterol; and a targeting lipid; and any other lipid described herein or reported in the art. In some embodiments, a composition comprises a lipid and a portion of another lipid capable of mediating at least one function of another lipid. In some embodiments, a targeting compound or moiety is capable of targeting a compound (e.g., a composition comprising a lipid and a active compound) to a particular cell or tissue or subset of cells or tissues. In some embodiments, a targeting moiety is designed to take advantage of cell- or tissue-specific expression of particular targets, receptors, proteins, or other subcellular components; In some embodiments, a targeting moiety is a ligand (e.g., a small molecule, antibody, peptide, protein, carbohydrate, aptamer, etc.) that targets a composition to a cell or tissue, and/or binds to a target, receptor, protein, or other subcellular component.

Certain example lipids for use in preparation of a composition for delivery of an active compound allow (e.g., do not prevent or interfere with) the function of an active compound. Non-limiting example lipids include: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

As described in the present disclosure, lipid conjugation, such as conjugation with fatty acids, may improve one or more properties of oligonucleotides.

In some embodiments, a composition for delivery of an active compound is capable of targeting an active compound to particular cells or tissues, as desired. In some embodiments, a composition for delivery of an active compound is capable of targeting an active compound to a muscle cell or tissue. In some embodiments, the present disclosure pertains to compositions and methods related to delivery of active compounds, wherein the compositions comprise an active compound a lipid. In various embodiments to a muscle cell or tissue, the lipid is selected from: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl. The example lipids used include stearic acid, oleic acid, alpha-linolenic acid, gamma-linolenic acids, cis-DHA, turbinaric acid and dilinoleyl acid. In these Tables, "TBD" indicates that the particular composition was effective for delivery, but the numerical results were outside the standard range, and thus the final results remain to be determined; however, the compositions indicated as "TBD" in the Tables were efficacious at delivery of an active compound.

A composition comprising an active compound and any of: stearic acid, oleic acid, alpha-linolenic acid, gamma-linolenic acid, cis-DHA or turbinaric acid, was able to deliver an active compound to gastrocnemius muscle tissue. A composition comprising an active compound and any of: stearic acid, alpha-linolenic, gamma-linolenic, cis-DHA, or turbinaric acid, was able to deliver an active compound to heart muscle tissue. A composition comprising an active compound and any of: stearic acid, oleic acid, alpha-linolenic acid, gamma-linolenic acid, cis-DHA or turbinaric acid, was able to deliver an active compound to quadriceps muscle tissue. A composition comprising an active compound and any of: stearic, oleic, alpha-linolenic, gamma-linolenic, cis-DHA, or turbinaric acid was able to deliver an active compound to the gastrocnemius muscle tissue. A composition comprising an active compound and any of: stearic acid, alpha-linolenic, gamma-linolenic, cis-DHA, or turbinaric acid was able to deliver an active compound to heart muscle tissue. A composition comprising an active compound and any of: dilinoleyl, stearic acid, oleic acid, alpha-linolenic, gamma-linolenic, cis-DHA or turbinaric acid was able to delivery an active compound to the diaphragm muscle tissue.

Thus: A composition comprising a lipid, selected from: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl, and an active compound is capable of delivering an active compound to extra-hepatic cells and tissues, e.g., muscle cells and tissues.

Depending upon the particular condition, or disease state, to be treated or prevented, additional therapeutic agents, which are normally administered to treat or prevent that condition, may be administered together with oligonucleotides of this disclosure. For example, chemotherapeutic agents or other anti-proliferative agents may be combined with the oligonucleotides of this disclosure to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Example Uses

In some embodiments, the present disclosure encompasses the use of a composition comprising a lipid and a PNPLA3 oligonucleotide or a single-stranded RNAi agent. In some embodiments, the present disclosure provides methods for delivering a PNPLA3 oligonucleotide or a single-stranded RNAi agent to a target location comprising administering a provided composition. In some embodiments, a provided method delivers a PNPLA3 oligonucleotide or a single-stranded RNAi agent into a cell. In some embodiments, a provided method delivers a PNPLA3 oligonucleotide or a single-stranded RNAi agent into a muscle cell. In some embodiments, a provided method delivers a PNPLA3 oligonucleotide or a single-stranded RNAi agent into a cell within a tissue. In some embodiments, a provided method delivers a PNPLA3 oligonucleotide or a single-stranded RNAi agent into a cell within an organ. In some embodiments, a provided method delivers a PNPLA3 oligonucleotide or a single-stranded RNAi agent into a cell within a subject, comprising administering to the subject a provided composition. In some embodiments, a provided method delivers a PNPLA3 oligonucleotide or a single-stranded RNAi agent into cytoplasm. In some embodiments, a provided method delivers a PNPLA3 oligonucleotide or a single-stranded RNAi agent into nucleus.

In some embodiments, the present disclosure pertains to methods related to the delivery of a PNPLA3 oligonucleotide or a single-stranded RNAi agent to a cell or tissue, or a cell or tissue in a mammal (e.g., a human subject), which method pertains to a use of a composition comprising a biological agent and a lipid. any one or more additional components selected from: a polynucleotide, a dye, an intercalating agent (e.g. an acridine), a cross-linker (e.g. psoralene, or mitomycin C), a porphyrin (e.g., TPPC4, texaphyrin, or Sapphyrin), a polycyclic aromatic hydrocarbon (e.g., phenazine, or dihydrophenazine), an artificial endonuclease, a chelating agent, EDTA, an alkylating agent, a phosphate, an amino, a mercapto, a PEG (e.g., PEG-40K), MPEG, [MPEG]2, a polyamino, an alkyl, a substituted alkyl, a radiolabeled marker, an enzyme, a hapten (e.g. biotin), a transport/absorption facilitator (e.g., aspirin, vitamin E, or folic acid), a synthetic ribonuclease, a protein, e.g., a glycoprotein, or peptide, e.g., a molecule having a specific affinity for a co-ligand, or antibody e.g., an antibody, a hormone, a hormone receptor, a non-peptidic species, a lipid, a lectin, a carbohydrate, a vitamin, a cofactor, or a drug. In some embodiments, the present disclosure pertains to compositions or methods related to a composition comprising a PNPLA3 oligonucleotide or a single-stranded RNAi agent and a lipid comprising a $C_{10}$-$C_{60}$ linear, saturated or partially unsaturated, aliphatic chain. In some embodiments, the present disclosure pertains to compositions or methods related to a composition comprising a PNPLA3 oligonucleotide or a single-stranded RNAi agent and a lipid comprising a $C_{10}$-$C_{60}$ linear, saturated or partially unsaturated, aliphatic chain, optionally substituted with one or more $C_{1-4}$ aliphatic group. In some embodiments, the present disclosure provides chirally controlled oligonucleotide compositions and a lipid selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl, wherein the composition is suitable for delivery of the oligonucleotide to a muscle cell or tissue, or a muscle cell or tissue in a mammal (e.g., a human subject). In some embodiments, a PNPLA3 oligonucleotide or a single-stranded RNAi agent is a PNPLA3 oligonucleotide comprising one or more chiral internucleotidic linkages, and a provided composition is a PNPLA3 oligonucleotide or a single-stranded RNAi agent. In some embodiments, a PNPLA3 oligonucleotide or a single-stranded RNAi agent is a PNPLA3 oligonucleotide comprising one or more chiral internucleotidic linkages, and a provided composition is a non-chirally controlled oligonucleotide composition of the oligonucleotide.

In some embodiments, the present disclosure pertains to a method of delivering a PNPLA3 oligonucleotide or a single-stranded RNAi agent to a cell or tissue, wherein the method comprises steps of: providing a composition comprising a PNPLA3 oligonucleotide or a single-stranded RNAi agent and a lipid; and contacting the cell or tissue with the composition; in some embodiments, the present disclosure pertains to a method of administering a PNPLA3 oligonucleotide or a single-stranded RNAi agent to a subject, wherein the method comprises steps of: providing a composition comprising a PNPLA3 oligonucleotide or a single-stranded RNAi agent and a lipid; and administering the composition to the subject. In some embodiments, a lipid comprises a $C_{10}$-$C_{60}$ linear, saturated or partially unsaturated, aliphatic chain. In some embodiments, a lipid comprises a $C_{10}$-$C_{60}$ linear, saturated or partially unsaturated, aliphatic chain, optionally substituted with one or more $C_{1-4}$ aliphatic group. In some embodiments, the lipid is selected from the group consisting of: lauric acid, myristic acid, palmitic acid, stearic acid, oleic acid, linoleic acid, alpha-linolenic acid, gamma-linolenic acid, docosahexaenoic acid (cis-DHA), turbinaric acid and dilinoleyl.

In some embodiments, a PNPLA3 oligonucleotide or a single-stranded RNAi agent is a PNPLA3 oligonucleotide, whose sequence is or comprises an element that is substantially complementary to a targeted element in a cellular nucleic acid. In some embodiments, a targeted element is or comprises a sequence element that is associated with a muscle disease, disorder or condition. In some embodiments, a muscle disease, disorder or condition is DMD. In some embodiments, a cellular nucleic acid is or comprises a transcript. In some embodiments, a cellular nucleic acid is or comprises a primary transcript. In some embodiments, a cellular nucleic acid is or comprises a genomic nucleic acid.

The present disclosure encompasses the recognition that certain lipids and other compounds are useful for delivery of single-stranded RNAi agents to cells and tissues, e.g., in a mammal or human subject. Many technologies for delivering such agents can suffer from an inability to target desired cells or tissues.

Delivery of single-stranded RNAi agents to tissues outside the liver remains difficult. Juliano reported that, despite advances at the clinical level, effective delivery of oligonucleotides in vivo remains a major challenge, especially at extra-hepatic sites. Juliano 2016 Nucl. Acids Res. Doi: 10.1093/nar/gkw236. Lou also reported that delivery of RNAi agent to organs beyond the liver remains the biggest hurdle to using the technology for a host of diseases. Lou 2014 SciBX 7(48); doi:10.1038/scibx.2014.1394.

The present disclosure encompasses certain surprising findings, including that certain lipids and other compounds are particularly effective at delivering single-stranded RNAi agents, including oligonucleotides, to particular cells and tissues, including cells and tissues outside the liver, including, as non-limiting examples, muscle cells and tissues.

In some embodiments, provided compositions alter single-stranded RNA interference system so that an undesired target and/or biological function are suppressed. In some embodiments, in such cases provided composition can also induce cleavage of the transcript after hybridization.

In some embodiments, provided compositions alter single-stranded RNA interference system so a desired target and/or biological function is enhanced. In some embodiments, provided compositions, by incorporating chemical modifications, stereochemistry and/or combinations thereof, effectively suppress or prevent cleavage of a target transcript after contact.

In some embodiments, each oligonucleotide of a plurality comprises one or more modified sugar moieties and modified internucleotidic linkages. In some embodiments, each oligonucleotide of a plurality comprises two or more modified sugar moieties. In some embodiments, each oligonucleotide of a plurality comprises three or more modified sugar moieties. In some embodiments, each oligonucleotide of a plurality comprises four or more modified sugar moieties. In some embodiments, each oligonucleotide of a plurality comprises five or more modified sugar moieties. In some embodiments, each oligonucleotide of a plurality comprises ten or more modified sugar moieties. In some embodiments, each oligonucleotide of a plurality comprises about 15 or more modified sugar moieties. In some embodiments, each oligonucleotide of a plurality comprises about 20 or more modified sugar moieties. In some embodiments, each oligonucleotide of a plurality comprises about 25 or more modified sugar moieties.

EXEMPLIFICATION

The foregoing has been a description of certain non-limiting embodiments of the disclosure. Accordingly, it is to be understood that the embodiments of the disclosure herein described are merely illustrative of the application of the principles of the disclosure. Reference herein to details of the illustrated embodiments is not intended to limit the scope of the claims.

Certain methods for preparing oligonucleotides and oligonucleotide compositions are widely known in the art and can be utilized in accordance with the present disclosure, including but not limited to those described in WO/2010/064146, WO/2011/005761, WO/2013/012758, WO/2014/010250, US2013/0178612, WO/2014/012081, WO/2015/107425, WO/2017/015555, and WO/2017/062862, the methods and reagents of each of which are incorporated herein by reference.

Applicant describes herein certain examples of provided oligonucleotide and compositions thereof, and methods for preparing, assessing, assaying, and using, etc., certain provided oligonucleotides and compositions thereof.

Example 1. Example Protocols for Assessing Oligonucleotides

As a personal having ordinary skill in the art appreciates, many technologies (e.g., reagents, methods, etc.) can be utilized to assess activities and properties of provided oligonucleotides. Below is one example protocol describing reverse transfection of oligonucleotides (using certain oligonucleotides that can function as ssRNAi as examples) in 96 Well Plate format using Lipofectamine® 2000 (Invitrogen) for assessing oligonucleotide activities in cells:

1. Prepare each ssRNAi, preferably in multiple (e.g., 8) doses, e.g., in a final volume of 25 uL. Example initial concentration could be 150 nM; serial dilution, for example in Opti-MEM® medium without serum, typically by a factor of 4.
2. Lipofectamine® 2000 is desirably mixed gently before use, then diluted 0.25 µl Lipofectamine® 2000 in 25 µl Opti-MEM® medium without serum in a separate vessel. Further gentle mixing can be followed by incubation, e.g., for 5 minutes at room temperature.
3. After incubation, diluted Lipofectamine® 2000 (e.g., 25 uL) can be added to the (diluted) ssRNAi molecules (typically comparable volume, e.g., 25 uL). The combination is desirably mixed gently and may be incubated, e.g., for 15 minutes at room temperature, to allow complex formation to occur.
4. Complexes are then contacted with cells, for example by adding 100 µl complete growth medium without antibiotics with 15,000 Hep3B cells to each ssRNAi molecule-Lipofectamine® 2000 complex. This gives a final volume of 150 µl, and final oligo concentrations are 25, 6.25, 1.56, 0.39, 0.097, 0.024, 0.0061, and 0.0015 nM. Mix gently by rocking the plate back and forth.
5. Cells are incubated, e.g., at 37° C. in a $CO_2$ incubator for 48 hours.
6. Cells are harvested and mRNA is isolated, e.g., using TurboCapture mRNA kit (Qiagen), as per vendor provided protocol.
7. cDNA is prepared, e.g., using Roche cDNA synthesis Kit (Roche), as per vendor provided protocol.
8. Target knockdown is quantified, e.g., by Taqman assays using gene-specific Taqman probes multiplexed with HPRT1 probes, in LightCycler® 480 Probes Master mix (Roche), as per vendor provided protocol. Typically, data are normalized, for example relative to a housekeeping gene such as HPRT1 (Hypoxanthine Phosphoribosyltransferase 1).
9. If multiple dose strengths/concentrations were utilized, dose-response curves can be prepared for each ssRNAi agent, e.g., using Prism Software. $IC_{50}$ can be determined if desired.

Similar protocols can be used for different oligonucleotides targeting other genes and can use different cells.

Alternatively or additionally, one or more activities and properties of oligonucleotides can be assessed using other technologies (e.g., reagents, kits, methods, etc.) in accordance with the present disclosure. Certain data generated from various types of assays are provided in the Tables, demonstrating, for example, unexpectedly high activities, stability, selectivity, etc., of presently provided technologies.

Various models are available for assessing provided technologies in subjects. In some embodiments, provided technologies show high activities, stability, and/or selectivity when administered to animals. Those skilled in the art are aware of animal systems that are considered to be relevant to and/or predictive for certain relevant human diseases, disorders and/or conditions that might benefit from oligonucleotide therapy as described herein.

Example 2. Example IC50 of Certain Provided Oligonucleotides

IC50 of certain oligonucleotides (which may function as antisense oligonucleotides to PNPLA3) measured using a protocol such as that presented in Example 1 are provided in the following Table.

| Wave ID | IC 50 (nM) | Position | Oligonucleotide Start Position |
|---|---|---|---|
| WV-3380 | 1.5 | CDS | 1508 |
| WV-3393 | 1.1 | CDS | 1510 |
| WV-3402 | 1.7 | CDS | 1511 |
| WV-3421 | 1.4 | 3'UTR | 1721 |
| WV-3399 | 0.77 | 3'UTR | 1853 |
| WV-3404 | 1.6 | 3'UTR | 1862 |
| WV-3443 | 1.6 | 3'UTR | 1863 |
| WV-3391 | 0.65 | 3'UTR | 2129 |
| WV-3394 | 1.4 | 3'UTR | 2130 |
| WV-3408 | 0.92 | 3'UTR | 2135 |
| WV-3387 | 1.2 | 3'UTR | 2136 |
| WV-3381 | 1.4 | 3'UTR | 2656 |

Example 3. Example Compounds for Incorporating Moieties—Synthesis of Tri-Antennary GalNAc (with C12, C5, or Triazine Linkers)

In some embodiments, the present disclosure provides technologies (e.g., reagents, methods, conjugates, etc.) for incorporating various moieties (e.g., carbohydrate moieties, lipid moieties, targeting moieties, etc.) into provided oligonucleotide. Described herein are certain examples for incorporating carbohydrate moieties. In some embodiments, a carbohydrate moiety may function as a targeting moiety.

Example 3-1. Synthesis of 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic acid

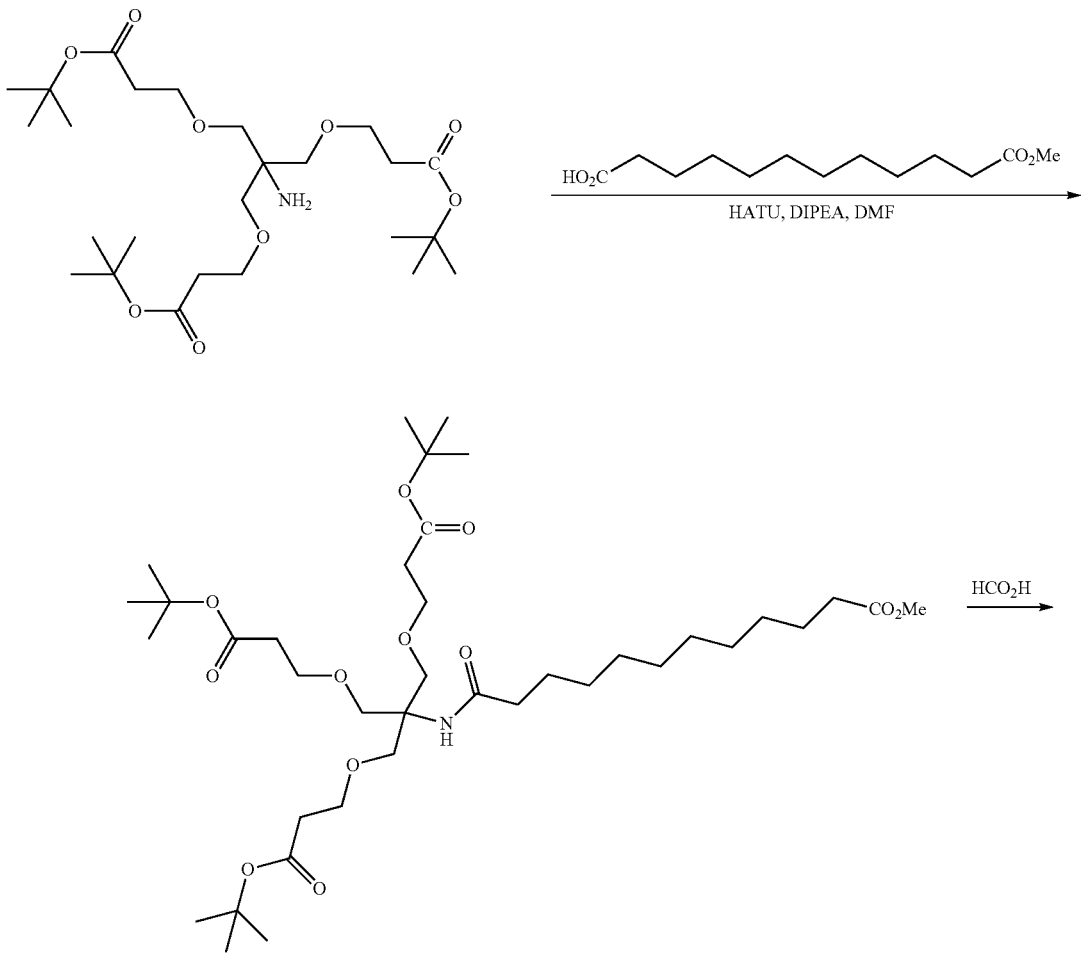

71%

523   524
-continued
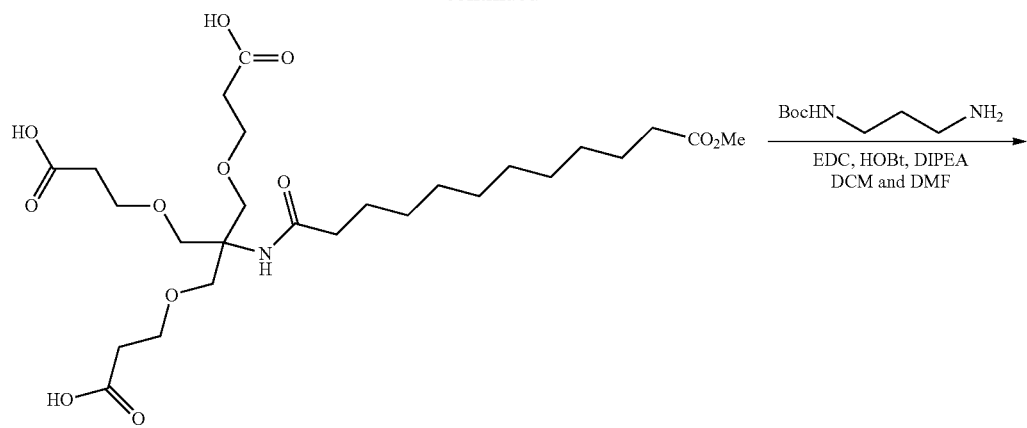
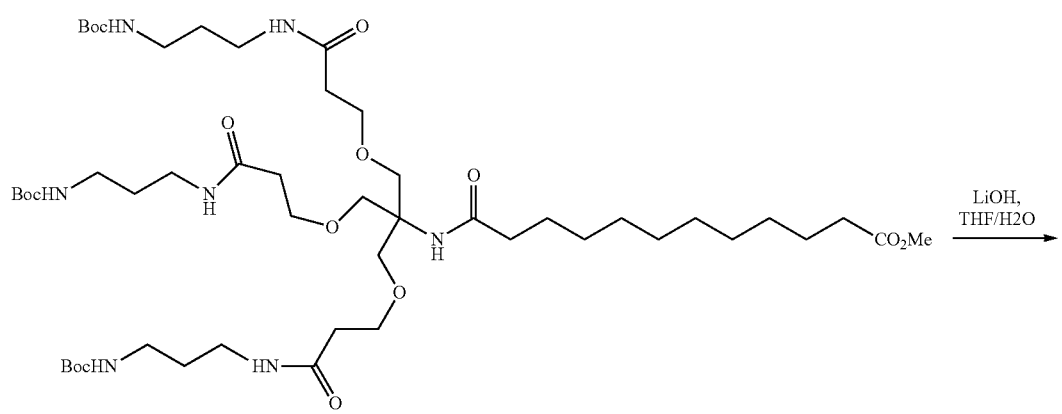
94% over 2 steps
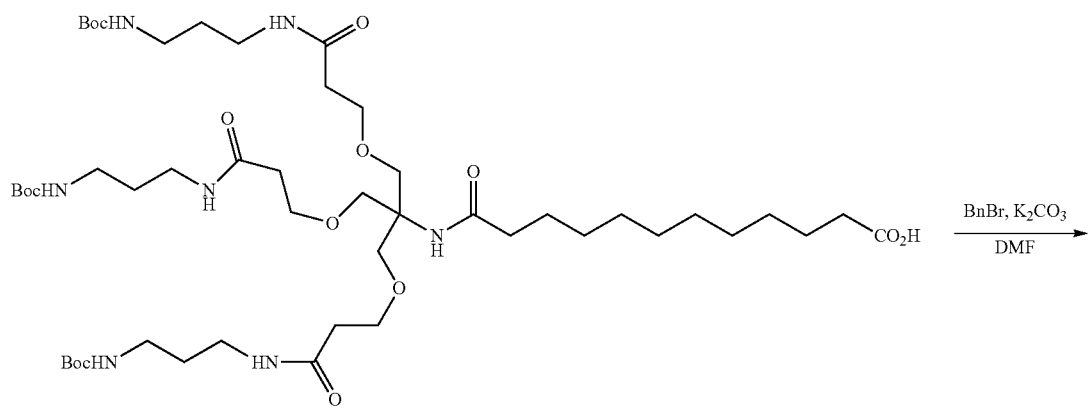
98%

525
526
-continued
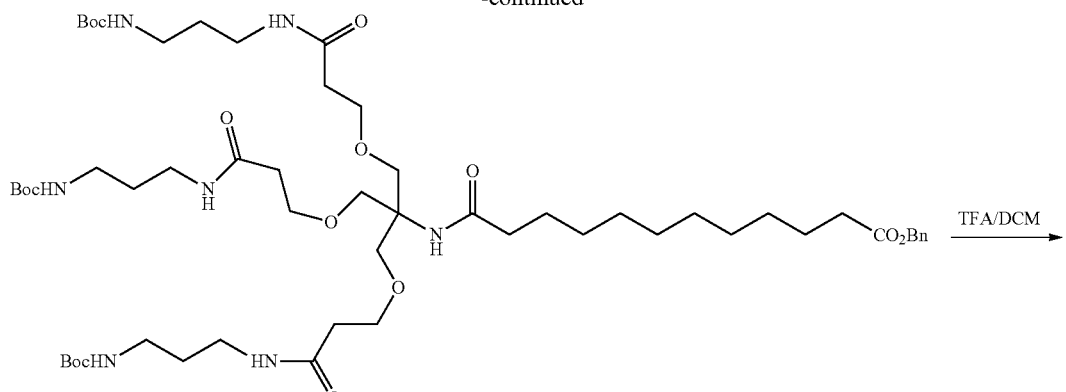
94%
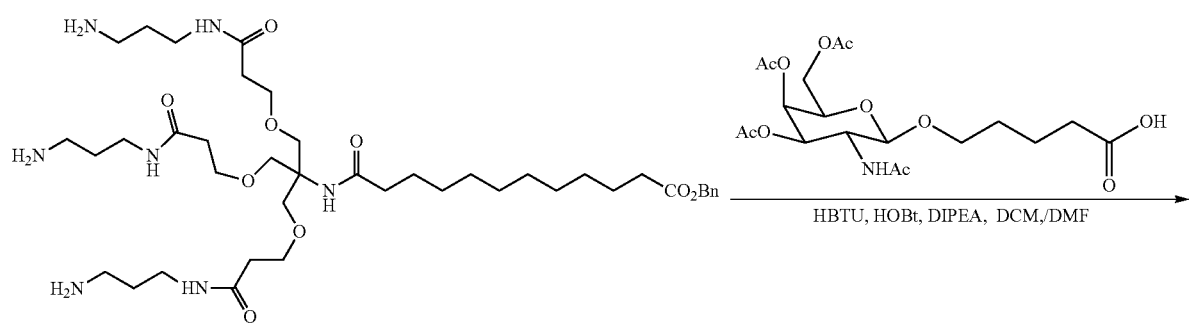
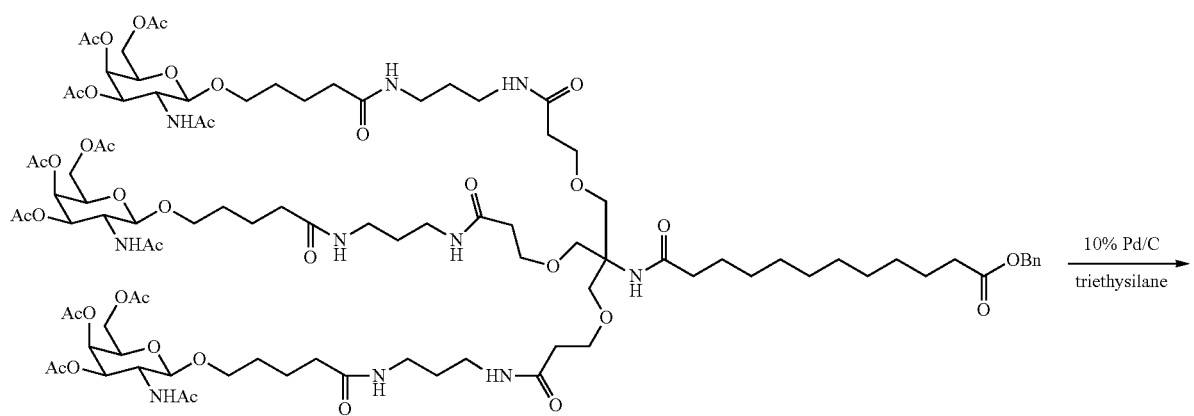
87% over 2 steps

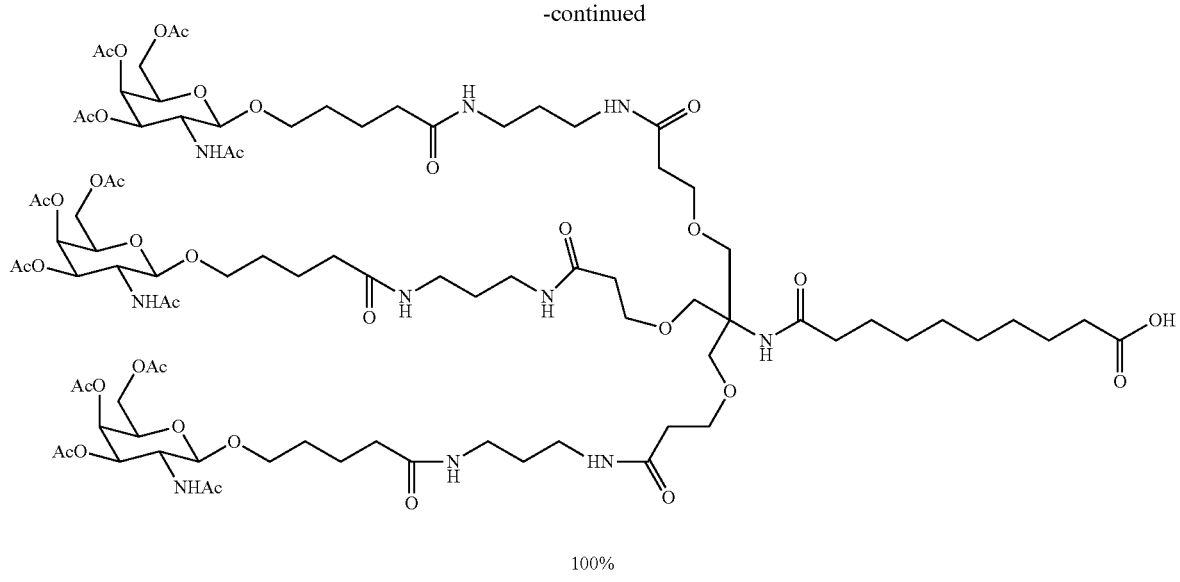

Step 1: To a solution of di-tert-butyl 3,3'-((2-amino-2-((3-(tert-butoxy)-3-oxopropoxy)methyl)propane-1,3-diyl)bis(oxy))dipropanoate (5.0 g, 9.89 mmol) and 12-methoxy-12-oxododecanoic acid (2.416 g, 9.89 mmol) in DMF (45 mL) was added HATU (3.76 g, 9.89 mmol) and DIPEA (2.58 ml, 14.83 mmol). The reaction mixture was stirred at room temperature for 5 hrs. Solvent was concentrated under reduced pressure, and diluted with brine, extracted with EtOAc, dried over anhydrous sodium sulfate, and concentrated to give a residue, which was purified by ISCO (120 g gold silica gel cartridge) eluting with 10% EtOAc in hexane to 40% EtOAc in hexane to give di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.13 g, 7.01 mmol, 70.9% yield) as a colorless oil. $^1$H NMR (400 MHz, Chloroform-d) δ 6.03 (s, 1H), 3.74-3.61 (m, 15H), 2.45 (t, J=6.3 Hz, 6H), 2.31 (td, J=7.5, 3.9 Hz, 2H), 2.19-2.10 (m, 2H), 1.64-1.59 (m, 4H), 1.46 (s, 27H), 1.32-1.24 (m, 12H); MS (ESI), 732.6 (M+H)+.

Step 2: A solution of di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.0 g, 6.83 mmol) in formic acid (50 mL) was stirred at room temperature for 48 hrs. Solvent was evaporated under reduced pressure, co-evaporated with toluene (3x) to give a white solid, which was dried under high vacuum for 2 days. LC-MS and H NMR showed the reaction is not complete. The crude product was redissolved in formic acid (50 mL). The reaction mixture was stirred at room temperature for 24 hrs. LC-MS showed the reaction was complete. Solvent was evaporated under reduced pressure, co-evaporated with toluene (3x), dried over high vacuum to give 3,3'-((2-((2-carboxyethoxy)methyl)-2-(12-methoxy-12-oxododecanamido)propane-1,3-diyl)bis(oxy))dipropanoic acid (4.00 g) as a white solid. MS (ESI): 562.4 (M−H)$^-$.

Step 3: A solution of 3,3'-((2-((2-carboxyethoxy)methyl)-2-(12-methoxy-12-oxododecanamido)propane-1,3-diyl)bis(oxy))dipropanoic acid (3.85 g, 6.83 mmol) and HOBt (3.88 g, 28.7 mmol) in DCM (60 mL) and DMF (15 mL) at 0° C. was added tert-butyl (3-aminopropyl)carbamate (4.76 g, 27.3 mmol), EDAC HCl salt (5.24 g, 27.3 mmol) and DIPEA (8.33 ml, 47.8 mmol). The reaction mixture was stirred at 0° C. for 15 minutes and at room temperature for 20 hrs. LC-MS showed the reaction was not complete. t-Butyl (3-aminopropyl) carbamate (1.59 g, 9.12 mmol) and EDC HCl salt (1.75 g, 9.13 mol) was added into the reaction mixture. The reaction mixture was continually stirred at room temperature for 4 hrs. Solvent was evaporated to give a residue, which was dissolved in EtOAc (300 mL), washed with water (1x), saturated sodium bicarbonate (2x), 10% citric acid (2x) and water, dried over sodium sulfate, and concentrated to give a residue which was purified by ISCO (80 g gold cartridge) eluting with DCM to 30% MeOH in DCM to give methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.61 g, 6.40 mmol, 94% yield over 2 steps) as a white solid. MS (ESI): 1033.5 (M+H)+.

Step 4: To a solution of methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.56 g, 6.35 mmol) in THF (75 mL) was added aq. LiOH (0.457 g, 19.06 mmol) in water (25 mL). The mixture was stirred at room temperature for overnight. LC-MS showed the reaction was completed. Solvent was evaporated, acidified using 1 N HCl (45 mL), extracted with DCM (3x), dried over anhydrous sodium sulfate, concentrated to give 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol, 98% yield) as a white solid. MS (ESI): 1019.6 (M+H)$^+$.

Step 5: To a solution of 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol) and (bromomethyl)benzene (1.272 g, 7.44 mmol) in DMF (40 mL) was added K$_2$CO$_3$ (2.57 g, 18.59 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO (80 g cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.41 g, 5.78 mmol, 93% yield) as a colorless oil. $^1$H NMR (400 MHz, DMSO-$d_6$) δ 7.80 (t, J=5.7 Hz, 3H), 7.39-7.30 (m, 5H), 6.95 (s, 1H), 6.74 (t, J=5.8 Hz, 3H), 5.07 (s, 2H), 3.53 (J, J=7.3 Hz, 6H), 3.51 (s, 6H), 3.02 (q, J=6.7 Hz, 6H), 2.94-2.85 (m, 6H), 2.29 (dt, J=26.1, 6.9 Hz, 8H), 2.02 (q, J=9.7, 8.6 Hz, 2H), 1.56-1.39 (m, 10H), 1.35 (s, 27H), 1.20 (brs, 14H); MS (ESI): 1019.6 (M+H)$^+$.

Step 6: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (2.42 g, 2.183 mmol) in DCM (40 mL) was added 2,2,2-trifluoroacetic acid (8 ml, 105 mmol). The reaction mixture was stirred at room temperature for overnight. Solvent was evaporated under reduced pressure, co-evaporated with toluene (2×), triturated with ether, dried under high vacuum for overnight. Directly use TFA salt for next step.

Step 7: To a solution of 5-(((2R,3R,4R,5R,6R)-3-acetamido-4,5-diacetoxy-6-(acetoxymethyl)tetrahydro-2H-pyran-2-yl)oxy)pentanoic acid (3.91 g, 8.73 mmol), HBTU (3.48 g, 9.17 mmol) and HOBT (1.239 g, 9.17 mmol) in DCM (25 mL) was added DIPEA (6.08 ml, 34.9 mmol) followed by benzyl 12-((1,19-diamino-10-((3-aminopropyl)amino)-3-oxopropoxy)methyl)-5,15-dioxo-8,12-dioxa-4,16-diazanonadecan-10-yl)amino)-12-oxododecanoate (1.764 g, 2.183 mmol) in DMF (4.0 mL). The mixture was stirred at room temperature for 5 hrs. Solvent was evaporated under reduced pressure to give a residue, which was purified by ISCO (40 g gold column) eluting with 5% MeOH in DCM for 5 column value to remove HOBt followed by 5% to 30% MeOH in DCM to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic benzyl ester (3.98 g, 87% yield) as a white solid. $^1$H NMR (400 MHz, DMSO-$d_6$) δ 7.82-7.74 (m, 6H), 7.69 (t, J=5.6 Hz, 3H), 7.33-7.27 (m, 5H), 6.94 (s, 1H), 5.16 (d, J=3.4 Hz, 3H), 5.03 (s, 2H), 4.92 (dd, J=11.2, 3.4 Hz, 3H), 4.43 (d, J=8.4 Hz, 3H), 4.02-3.95 (m, 9H), 3.82 (dt, J=11.2, 8.8 Hz, 3H), 3.65 (dt, J=10.5, 5.6 Hz, 3H), 3.51-3.44 (m, 12H), 3.36 (dt, J=9.6, 6.0 Hz, 3H), 3.01-2.95 (m, 12H), 2.29 (t, J=7.4 Hz, 2H), 2.23 (t, J=6.3 Hz, 6H), 2.05 (s, 9H), 1.99 (t, J=7.0 Hz, 8H), 1.94 (s, 9H), 1.84 (s, 9H), 1.72 (s, 9H), 1.50-1.14 (m, 34H); MS (ESI): 1049.0 (M/2+H)$^+$.

Step 8: To a round bottom flask flushed with Ar was added 10% Pd/C (165 mg, 0.835 mmol) and EtOAc (15 mL). A solution of Benzyl protected tris-GalNAc (1.75 g, 0.835 mmol) in methanol (15 mL) was added followed by triethylsilane (2.67 ml, 16.70 mmol) dropwise. The mixture was stirred at room temperature for 3 hrs. LC-MS showed the reaction was complete, diluted with EtOAc, and filtered through celite, washed with 20% MeOH in EtOAc, concentrated under reduced pressure to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic acid (1.67 g, 0.832 mmol, 100% yield) as a white solid. $^1$H NMR (400 MHz, DMSO-$d_6$) δ 11.95 (s, 1H), 7.83-7.74 (m, 6H), 7.69 (t, J=5.7 Hz, 3H), 6.93 (s, 1H), 5.16 (d, J=3.4 Hz, 3H), 4.92 (dd, J=11.2, 3.4 Hz, 3H), 4.43 (d, J=8.4 Hz, 3H), 4.01-3.94 (m, 9H), 3.82 (dt, J=11.3, 8.8 Hz, 3H), 3.66 (dt, J=10.7, 5.6 Hz, 3H), 3.54-3.43 (m, 12H), 3.41-3.33 (m, 3H), 3.03-2.94 (m, 12H), 2.24 (t, J=7.4 Hz, 10H), 2.14 (t, J=7.4 Hz, 2H), 2.06 (s, 9H), 2.00 (t, J=7.2 Hz, 8H), 1.95 (s, 9H), 1.84 (s, 9H), 1.73 (s, 9H), 1.51-1.14 (m, 34H). MS (ESI): 1003.8 (M/2+H)$^+$.

Example 3-2. Synthesis of 22-(((2R,3R,4R,5R,6R)-3-acetamido-4,5-diacetoxy-6-(acetoxymethyl)tetrahydro-2H-pyran-2-yl)oxy)-7,7-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,12,18-trioxo-9-oxa-6,13,17-triazadocosanoic acid

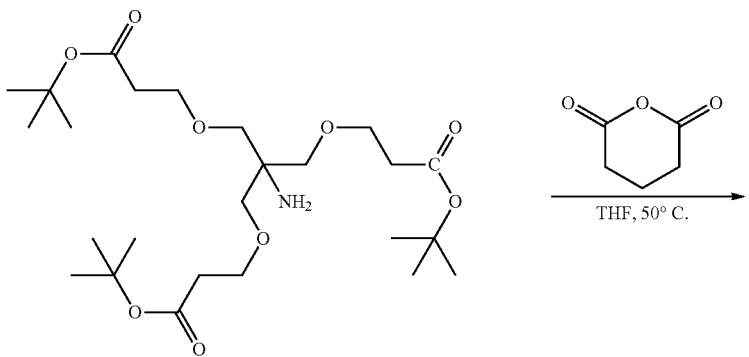

531
532
-continued
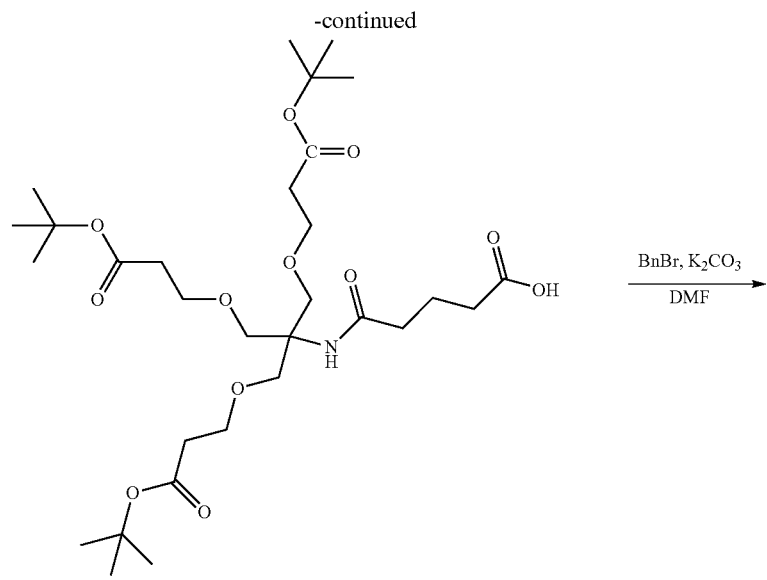
BnBr, K$_2$CO$_3$
DMF
without purification,
use directly for next step
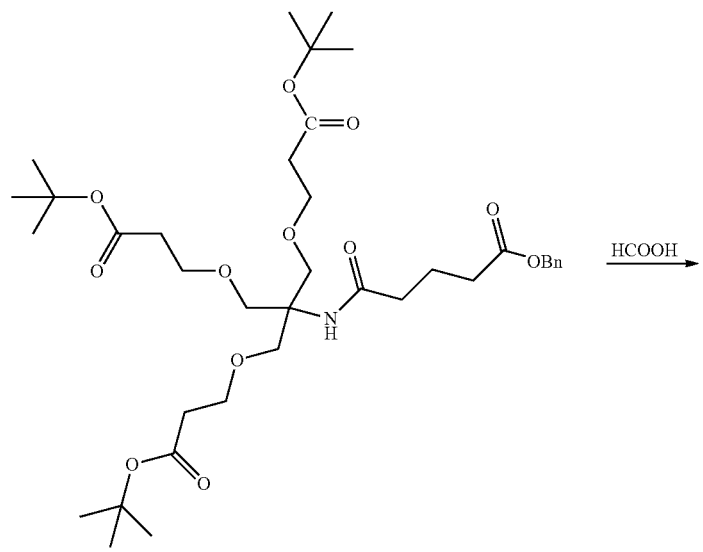
HCOOH
97% over 2 steps
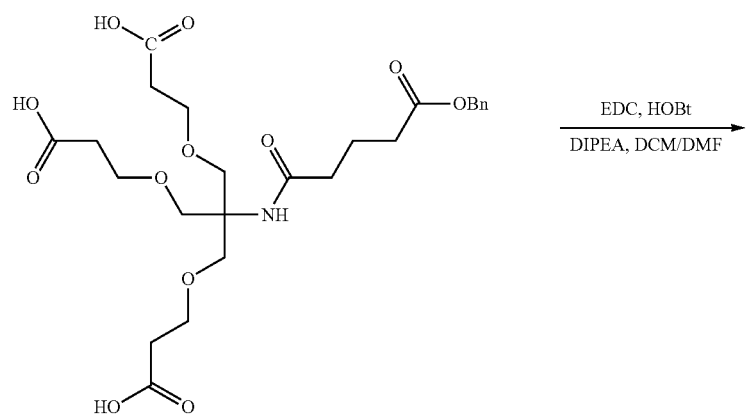
EDC, HOBt
DIPEA, DCM/DMF 533
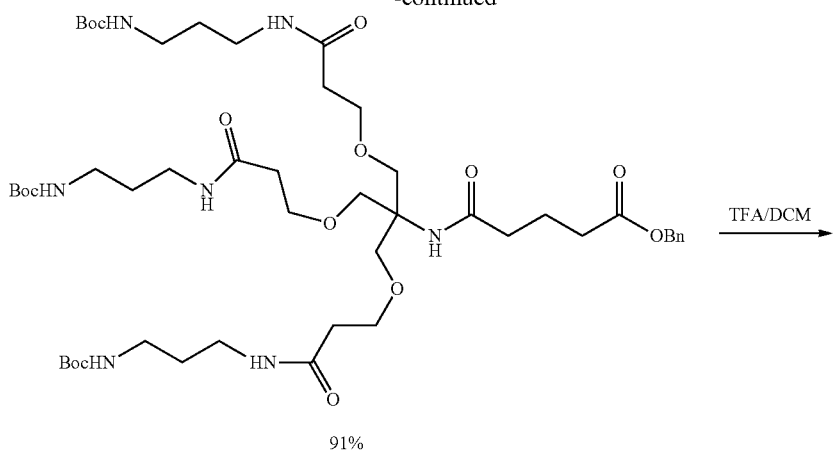
91%
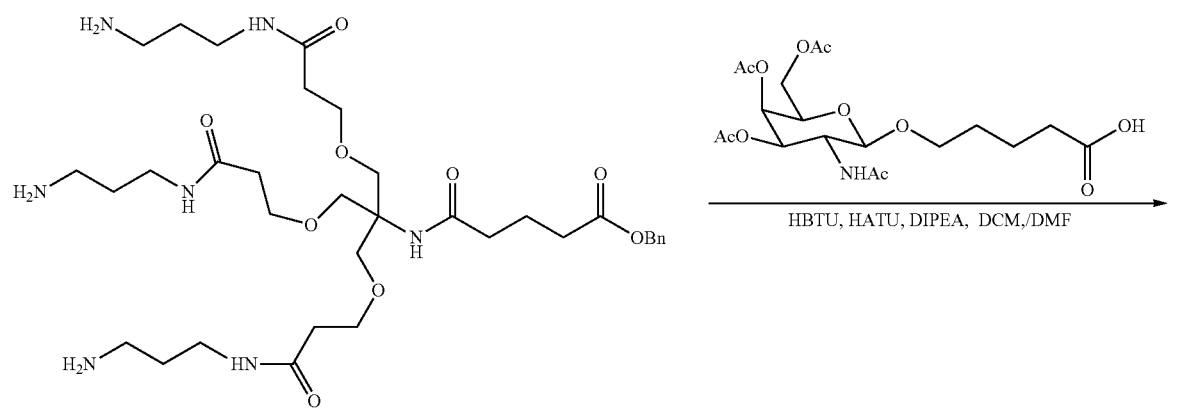
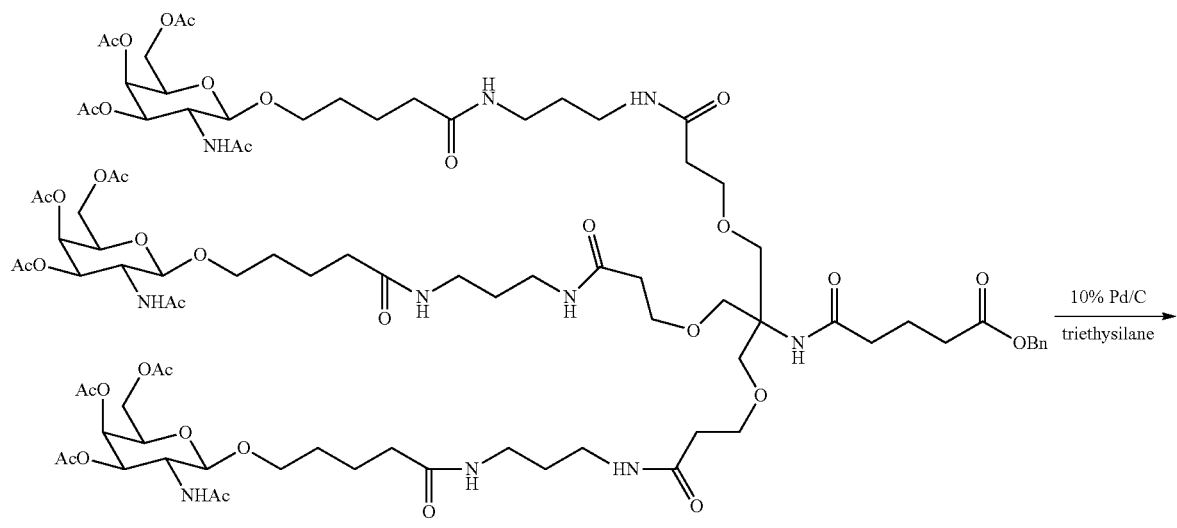
59% over 2 steps
534

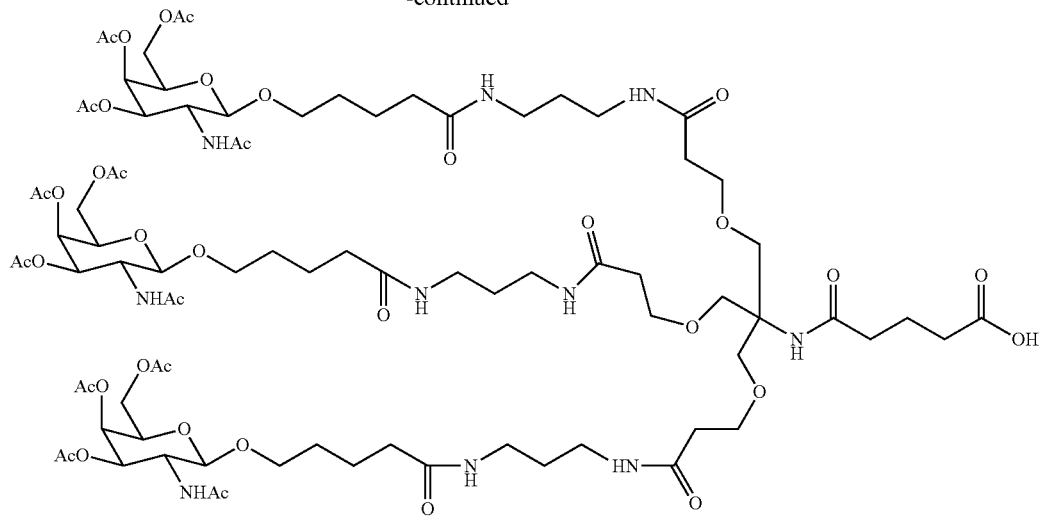

99%

Step 1: A solution of di-tert-butyl 3,3'-((2-amino-2-((3-(tert-butoxy)-3-oxopropoxy)methyl)propane-1,3-diyl)bis(oxy))dipropanoate (4.0 g, 7.91 mmol) and dihydro-2H-pyran-2,6(3H)-dione (0.903 g, 7.91 mmol) in THF (40 mL) was stirred at 50° C. for 3 hrs and at rt for 3 hrs. LC-MS showed desired product. Solvent was evaporated to give the acid, which was directly used for next step without purification.

Step 2: To a solution of 5-((9-((3-(tert-butoxy)-3-oxopropoxy)methyl)-2,2,16,16-tetramethyl-4,14-dioxo-3,7,11,15-tetraoxaheptadecan-9-yl)amino)-5-oxopentanoic acid (4.90 g, 7.91 mmol) and (bromomethyl)benzene (1.623 g, 9.49 mmol) in DMF was added anhydrous $K_2CO_3$ (3.27 g, 23.73 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO eluting with 10% EtOAc in hexane to 50% EtOAc in hexane to give di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate (5.43 g, 7.65 mmol, 97% yield) as a colorless oil. $^1$H NMR (400 MHz, Chloroform-d) δ 7.36-7.28 (m, 5H), 6.10 (s, 1H), 5.12 (s, 2H), 3.70 (s, 6H), 3.64 (t, J=8.0 Hz, 6H), 2.50-2.38 (m, 8H), 2.22 (t, J=7.3 Hz, 2H), 1.95 (p, J=7.4 Hz, 2H), 1.45 (s, 27H); MS, 710.5 (M+H)$^+$.

Step 3: A solution of di-tert-butyl 3,3'-((2-(5-(benzyloxy)-5-oxopentanamido)-2-((3-(tert-butoxy)-3-oxopropoxy)methyl)propane-1,3-diyl)bis(oxy))dipropanoate (5.43 g, 7.65 mmol) in formic acid (50 mL) was stirred at room temperature for 48 hrs. LC-MS showed the reaction was not complete. Solvent was evaporated under reduced pressure. The crude product was re-dissolved in formic acid (50 mL) and was stirred at room temperature for 6 hrs. LC-MS showed the reaction was complete. Solvent was evaporated under reduced pressure, co-evaporated with toluene (3x) under reduced pressure, and dried under vacuum to give 3,3'-((2-(5-(benzyloxy)-5-oxopentanamido)-2-((2-carboxyethoxy)methyl)propane-1,3-diyl)bis(oxy))dipropanoic acid (4.22 g, 7.79 mmol, 102% yield) as a white solid. $^1$H NMR (500 MHz, DMSO-d$_6$) δ 12.11 (s, 3H), 7.41-7.27 (m, 5H), 6.97 (s, 1H), 5.07 (s, 2H), 3.55 (t, J=6.4 Hz, 6H), 3.53 (s, 6H), 2.40 (t, J=6.3 Hz, 6H), 2.37-2.26 (m, 2H), 2.08 (t, J=7.3 Hz, 2H), 1.70 (p, J=7.4 Hz, 2H); MS, 542.3 (M+H)$^+$.

Step 4: A solution of 3,3'-((2-(5-(benzyloxy)-5-oxopentanamido)-2-((2-carboxyethoxy)methyl)propane-1,3-diyl)bis(oxy))dipropanoic acid (4.10 g, 7.57 mmol) and HOBt (4.60 g, 34.1 mmol) in DCM (60 mL) and DMF (15 mL) at 0° C. was added tert-butyl (3-aminopropyl)carbamate (5.94 g, 34.1 mmol), EDAC HCl salt (6.53 g, 34.1 mmol) and DIPEA (10.55 ml, 60.6 mmol). The reaction mixture was stirred at 0° C. for 15 minutes and at room temperature for 20 hrs. LC-MS showed the reaction was not complete. EDAC HCl salt (2.0 g) and tert-butyl (3-aminopropyl)carbamate (1.0 g) was added into the reaction mixture. The reaction mixture was stirred at room temperature for 4 hrs. Solvent was evaporated to give a residue, which was dissolved in EtOAc (300 mL), washed with water (1x), saturated sodium bicarbonate (2x), 10% citric acid (2x) and water, dried over sodium sulfate, and concentrated to give a residue which was purified by ISCO (80 g gold cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (6.99 g, 6.92 mmol, 91% yield) as a white solid. $^1$H NMR (500 MHz, Chloroform-d) δ 7.38-7.33 (m, 5H), 6.89 (brs, 3H), 6.44 (s, 1H), 5.23 (brs, 3H), 5.12 (s, 2H), 3.71-3.62 (m, 12H), 3.29 (q, J=6.2 Hz, 6H), 3.14 (q, J=6.5 Hz, 6H), 2.43 (dt, J=27.0, 6.7 Hz, 8H), 2.24 (t, J=7.2 Hz, 2H), 1.96 (p, J=7.5 Hz, 2H), 1.64-1.59 (m, 6H), 1.43 (d, J=5.8 Hz, 27H); MS (ESI): 1011.5 (M+H)$^+$.

Step 5: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (0.95 g, 0.940 mmol) in DCM (5 mL) was added TFA (5 mL). The reaction mixture was stirred at room temperature for 4 hrs. LC-MS showed the reaction was completed. Solvent was evaporated under reduced pressure to give benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. Directly use for next step without purification.

Step 6: To a solution of 5-(((2R,3R,4R,5R,6R)-3-acetamido-4,5-diacetoxy-6-(acetoxymethyl)tetrahydro-2H-pyran-2-yl)oxy)pentanoic acid (1.684 g, 3.76 mmol), HBTU (1.246 g, 3.29 mmol) and HOBT (0.052 g, 0.376 mmol) in DCM (40 mL) followed by 10-(5-(benzyloxy)-5-oxopentanamido)-N1,N19-dichloro-10-((3-(chloroammonio)propyl)amino)-3-oxopropoxy)methyl)-5,15-dioxo-8,12-dioxa-4,16-diazanonadecane-1,19-diaminium (0.767 g, 0.940 mmol) in DMF (2.0 mL). The mixture was stirred at room temperature for 5 hrs. Solvent was evaporated under reduced pressure to give a residue, which was purified by ISCO (40 g gold column) eluting with DCM to 30% MeOH in DCM to give 22-(((2R,3R,4R,5R,6R)-3-acetamido-4,5-diacetoxy-6-(acetoxymethyl)tetrahydro-2H-pyran-2-yl)oxy)-7,7-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,12,18-trioxo-9-oxa-6,13,17-triazadocosanoic benzyl ester (1.11 g, 0.556 mmol, 59% yield) as a white solid. MS (ESI): 1000.0 (M/2+H)+.

Step 7: To a round bottom flask flushed with Ar was added 10% Pd/C (100 mg, 0.500 mmol) and EtOAc (10 mL). A solution of 22-(((2R,3R,4R,5R,6R)-3-acetamido-4,5-diacetoxy-6-(acetoxymethyl)tetrahydro-2H-pyran-2-yl)oxy)-7,7-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,12,18-trioxo-9-oxa-6,13,17-triazadocosanoic benzyl ester (1.00 g, 0.500 mmol) in methanol (10 mL) was added followed by triethylsilane (1.599 ml, 10.01 mmol) dropwise. The mixture was stirred at room temperature for 3 hrs. LC-MS showed the reaction was complete, diluted with EtOAc, and filtered through celite, washed with 20% MeOH in EtOAc, concentrated under reduced pressure to give 22-(((2R,3R,4R,5R,6R)-3-acetamido-4,5-diacetoxy-6-(acetoxymethyl)tetrahydro-2H-pyran-2-yl)oxy)-7,7-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,12,18-trioxo-9-oxa-6,13,17-triazadocosan-1-oic acid (0.9433 g, 0.494 mmol, 99% yield) as a white solid. $^1$H NMR (500 MHz, DMSO-$d_6$) δ 7.85-7.78 (m, 6H), 7.72 (t, J=5.7 Hz, 3H), 7.03 (s, 1H), 5.20 (d, J=3.4 Hz, 3H), 4.95 (dd, J=11.2, 3.5 Hz, 3H), 4.47 (d, J=8.3 Hz, 3H), 4.05-3.99 (m, 9H), 3.85 (dt, J=11.0, 8.8 Hz, 3H), 3.69 (dt, J=10.6, 5.8 Hz, 3H), 3.52 (dd, J=12.3, 5.6 Hz, 12H), 3.39 (dt, J=11.2, 6.3 Hz, 3H), 3.02 (p, J=6.3 Hz, 12H), 2.26 (t, J=6.4 Hz, 6H), 2.17 (t, J=7.5 Hz, 2H), 2.11-2.07 (m, 11H), 2.03 (t, J=7.1 Hz, 6H), 1.98 (s, 9H), 1.87 (s, 9H), 1.76 (s, 9H), 1.53-1.18 (m, 20H); MS (ESI): 1909.4 (M+H)+.

Example 3-3. Synthesis of 5-(4-(4-((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-6-(bis(3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-1,3,5-triazin-2-yl)piperazin-1-yl)-5-oxopentanoic acid

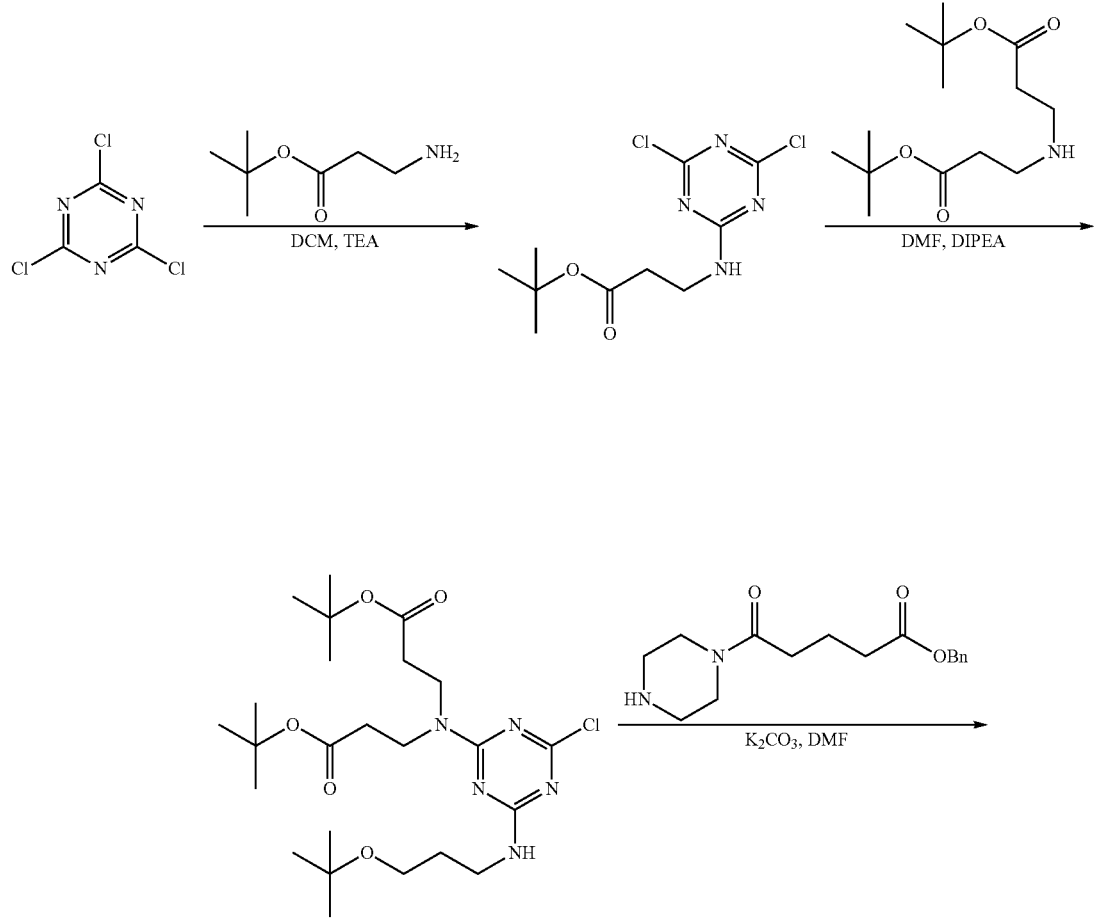

-continued
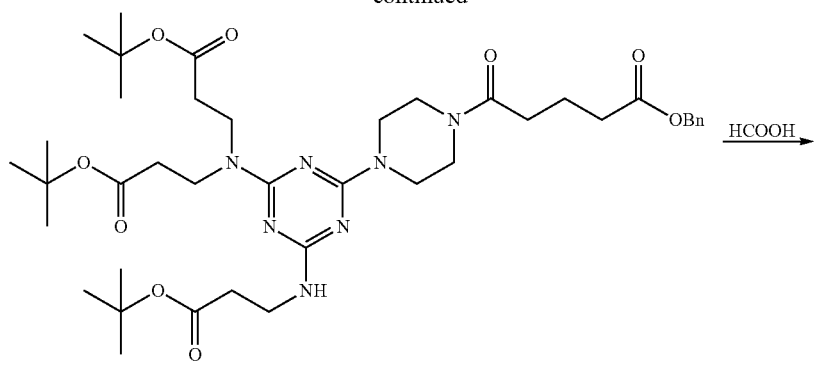
30% over 3 steps
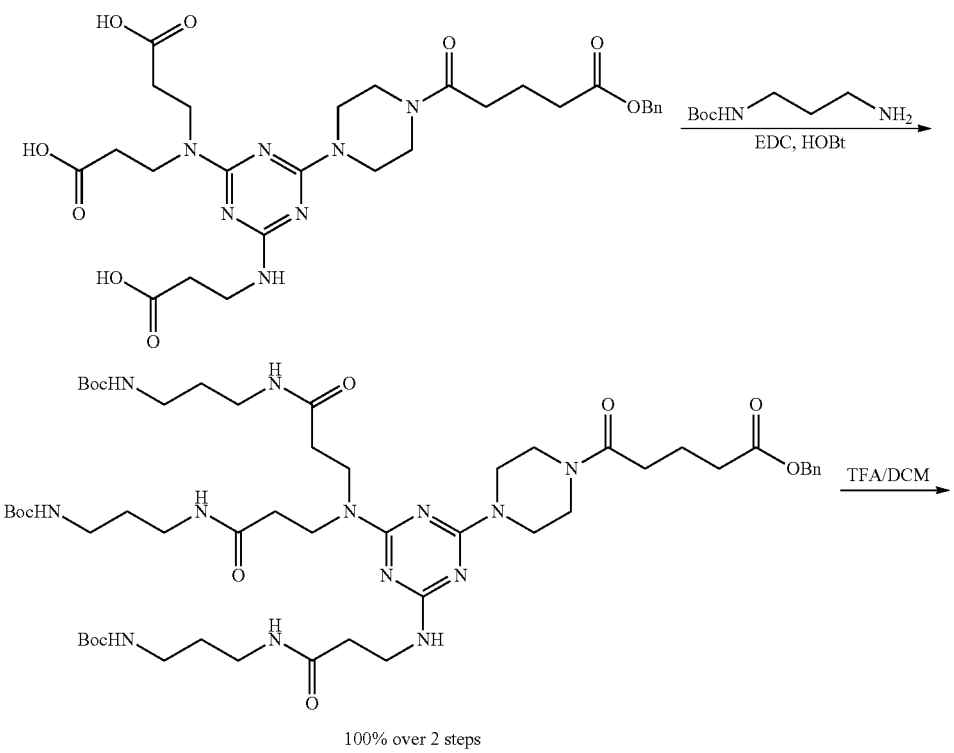
100% over 2 steps
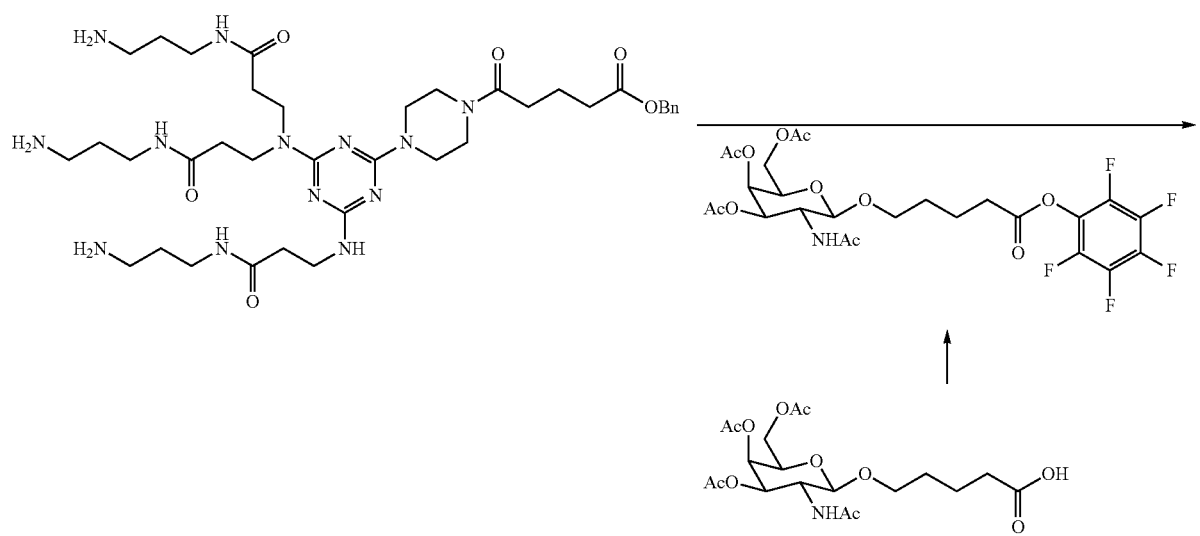

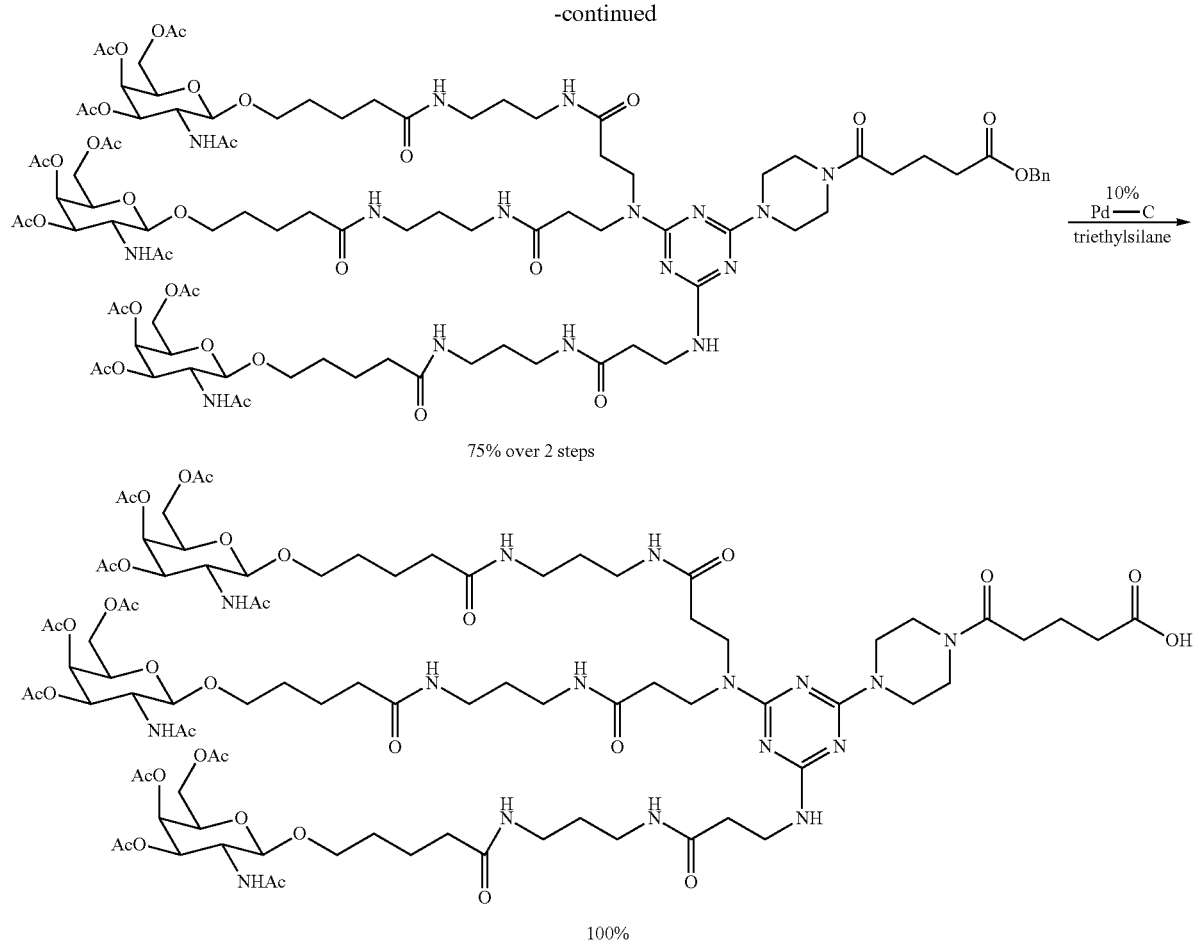

75% over 2 steps

100%

Steps 1 to 3: To a solid reagent 2,4,6-trichloro-1,3,5-triazine (0.700 g, 3.80 mmol) in DCM (25 mL) at 0° C. was added tert-butyl 3-aminopropanoate HCl salt (0.690 g, 3.80 mmol) and TEA (0.635 ml, 4.56 mmol). The reaction mixture was stirred at 0° C. for 1 hrs. LC-MS showed the desired product. Solvent was evaporated under reduced pressure to give a residue, which was directly used for next step. To a solution of tert-butyl 3-((4,6-dichloro-1,3,5-triazin-2-yl)amino)propanoate (1.114 g, 3.80 mmol) in DMF (15 mL) was added di-tert-butyl 3,3'-azanediyldipropanoate (1.039 g, 3.80 mmol) and DIPEA (1.324 ml, 7.60 mmol). The reaction mixture was stirred at room temperature for 2 hrs. LC-MS showed desired product. To the above reaction mixture was added benzyl 5-oxo-5-(piperazin-1-yl)pentanoate (1.103 g, 3.80 mmol) and K$_2$CO$_3$ (1.576 g, 11.40 mmol). The reaction mixture was stirred at room temperature for overnight. Diluted with EtOAc, filtered and concentrated under reduced pressure to give a residue, which was purified by ISCO (40 g gold) eluting with 10% EtOAc in hexane to 50% EtOAc in hexane to give di-tert-butyl 3,3'-((44445-(benzyloxy)-5-oxopentanoyl)piperazin-1-yl)-6-((3-(tert-butoxy)-3-oxopropyl)amino)-1,3,5-triazin-2-yl)azanediyl)dipropionate (0.90 g, 30%) as a colorless oil. $^1$H NMR (500 MHz, Chloroform-d) δ 7.43-7.31 (m, 5H), 5.12 (s, 2H), 3.81-3.66 (m, 8H), 3.60 (dd, J=7.6, 4.8 Hz, 4H), 3.40 (t, J=5.1 Hz, 2H), 2.57-2.44 (m, 8H), 2.39 (t, J=7.4 Hz, 2H), 2.06-1.95 (m, 2H), 1.45 (s, 9H), 1.43 (s, 18H); MS (ESI): 784.7 (M+H)$^+$.

Step 4: A solution of di-tert-butyl 3,3'-((4-(4-(5-(benzyloxy)-5-oxopentanoyl)piperazin-1-yl)-6-((3-(tert-butoxy)-3-oxopropyl)amino)-1,3,5-triazin-2-yl)azanediyl)dipropanoate (0.90 g, 1.148 mmol) in formic acid (20 mL) was stirred at room temperature for overnight. LC-MS showed the reaction was not completed and solvent was evaporated. Formic acid (20 mL) was added to the reaction mixture and the reaction mixture was stirred at room temperature for overnight. LC-MS showed the reaction was complete. Solvent was concentrated, co-evaporated with toluene (2×) and dried under vacuum for overnight to give 3,3'-((4-(4-(5-(benzyloxy)-5-oxopentanoyl)piperazin-1-yl)-6-((2-carboxyethyl)amino)-1,3,5-triazin-2-yl)azanediyl)dipropanoic acid (0.75 g, 1.218 mmol, 106% yield) as a white solid. MS (ESI), 616.5 (M+H)$^+$.

Step 5: A solution of 3,3'-((4-(4-(5-(benzyloxy)-5-oxopentanoyl)piperazin-1-yl)-6-((2-carboxyethyl)amino)-1,3,5-triazin-2-yl)azanediyl)dipropanoic acid (0.707 g, 1.148 mmol) and HOBt (0.651 g, 4.82 mmol) in DCM (60 mL) and DMF (15 mL) at 0° C. was added tert-butyl (3-aminopropyl) carbamate (0.840 g, 4.82 mmol), EDAC HCl salt (0.924 g, 4.82 mmol) and DIPEA (1.400 ml, 8.04 mmol). The reaction mixture was stirred at 0° C. for 15 minutes and at room temperature for 20 hrs. LC-MS showed the reaction was not complete. t-Butyl (3-aminopropyl) carbamate (0.28 g) and EDC HCl salt (0.46 g) was added into the reaction mixture. The reaction mixture was continually stirred at room temperature for 4 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give benzyl 5-(4-(4-(bis(3-((3-((tert-butoxycarbonyl)amino)propyl)amino)-3-oxopropyl)amino)-6-((3-((tertbutoxycarbonyl) amino)propyl)amino)-3-oxopropyl)amino)-1,3,5-triazin-2-yl)piperazin-1-yl)-5-oxopentanoate (1.24 g, 1.144 mmol, 100% yield) as a white solid. MS (ESI): 1084.8 (M+H)$^+$.

Step 6: A solution of benzyl 5-(4-(4-(bis(3-((3-((tert-butoxycarbonyl)amino)propyl)amino)-3-oxopropyl)amino)-6-((3-((tertbutoxycarbonyl) amino)propyl)amino)-3-oxopropyl)amino)-1,3,5-triazin-2-yl)piperazin-1-yl)-5-oxopentanoate (328.3 mg, 0.303 mmol) in DCM (5.0 mL) was added TFA (3.0 mL). The reaction mixture was stirred at room temperature for 3 hrs. Solvent was evaporated under reduced pressure, use directly for next step without purification. MS (ESI): 784.6 (M+H)$^+$.

Step 7: To a solution of 5-(((2R,3R,4R,5R,6R)-3-acetamido-4,5-diacetoxy-6-(acetoxymethyl)tetrahydro-2H-pyran-2-yl)oxy)pentanoic acid (0.570 g, 1.273 mmol) in DCM (6 mL) was added DIPEA (0.40 mL, 2.296 mmol) and perfluorophenyl 2,2,2-trifluoroacetate (0.535 g, 1.910 mmol). The reaction mixture was stirred at room temperature for 2 hrs. Solvent was evaporated under reduced pressure to give a residue, directly use for next step. MS (ESI): 614.3 (M+H)$^+$. A solution of benzyl 5-(4-(4-((3-((3-aminopropyl)amino)-3-oxopropyl)amino)-6-(bis(3-((3-aminopropyl)amino)-3-oxopropyl)amino)-1,3,5-triazin-2-yl)piperazin-1-yl)-5-oxopentanoate (0.238 g, 0.303 mmol) in DCM (15 mL) and DMF (3 mL) was added DIPEA (0.633 ml, 3.64 mmol), and a solution of (2R,3R,4R,5R,6R)-5-acetamido-2-(acetoxymethyl)-6-((5-oxo-5-(perfluorophenoxy)pentyl)oxy)tetrahydro-2H-pyran-3,4-diyl diacetate (0.781 g, 1.273 mmol) in DCM (6 mL). The reaction mixture was stirred at room temperature for 4 hrs. Solvent was evaporated under reduced pressure to give a residue, which was purified by ISCO (40 g gold) eluting with DCM to 40% MeOH in DCM to give 5-(4-(4-((3-((3-(5-(((2R,3R,4R,5R,6R)-3-acetamido-4,5-diacetoxy-6-(acetoxymethyl)tetrahydro-2H-pyran-2-yl)oxy)pentanamido) propyl)amino)-3-oxopropyl)amino)-6-(bis(3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-1,3,5-triazin-2-yl)piperazin-1-yl)-5-oxopentanoic benzyl ester (0.47 g, 0.227 mmol, 74.9% yield) as a white solid. $^1$H NMR (500 MHz, DMSO-d$_6$) δ 7.82-7.78 (m, 6H), 7.70 (t, J=5.7 Hz, 3H), 7.35-7.28 (m, 5H), 6.63 (brs, 1H), 5.20 (d, J=3.3 Hz, 3H), 5.08 (s, 2H), 4.95 (dd, J=11.2, 3.4 Hz, 3H), 4.47 (d, J=8.4 Hz, 3H), 4.05-3.96 (m, 9H), 3.85 (dt, J=11.1, 8.8 Hz, 3H), 3.72-3.53 (m, 12H), 3.43-3.36 (m, 6H), 3.05-2.97 (m, 12H), 2.41-2.27 (m, 10H), 2.08 (s, 9H), 2.03 (d, J=7.0 Hz, 6H), 1.98 (s, 9H), 1.87 (s, 9H), 1.75 (s, 9H), 1.47 (s, 9H), 1.53-1.19 (m, 13H); MS (ESI): 1037.0 (M+H)/2$^+$.

Step 8: To a solution of 5-(4-(4-((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-6-(bis(3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-1,3,5-triazin-2-yl)piperazin-1-yl)-5-oxopentanoic benzyl ester (0.39 g, 0.188 mmol) in EtOAc (10 mL) was added 10% Pd—C (50 mg) followed by 10 mL MeOH under Ar. triethylsilane (0.601 ml, 3.76 mmol) was added to the reaction mixture slowly. The reaction mixture was stirred at room temperature for 2 hrs. filtered through celite, washed with 50% MeOH in EtOAc, solvents were evaporated under reduced pressure to give 5-(4-(4-((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-6-(bis(3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropyl)amino)-1,3,5-triazin-2-yl)piperazin-1-yl)-5-oxopentanoic acid (0.373 g, 100% yield) a white solid. $^1$H NMR (500 MHz, DMSO-d$_6$) δ 7.82-7.78 (m, 6H), 7.71 (t, J=5.7 Hz, 3H), 6.64 (s, 1H), 5.20 (d, J=3.3 Hz, 3H), 4.95 (dd, J=11.2, 3.4 Hz, 3H), 4.47 (d, J=8.5 Hz, 3H), 4.06-3.96 (m, 9H), 3.85 (dt, J=11.1, 8.8 Hz, 3H), 3.73-3.56 (m, 11H), 3.45-3.35 (m, 5H), 3.09-2.98 (m, 13H), 2.37-2.28 (m, 10H), 2.25 (t, J=7.3 Hz, 2H), 2.09 (s, 9H), 2.03 (t, J=7.0 Hz, 6H), 1.98 (s, 9H), 1.88 (s, 9H), 1.76 (s, 9H), 1.74-1.67 (m, 2H), 1.55-1.40 (m, 15H); MS (ESI): 1983.4 (M+H)$^+$.

Example 4A. Example Compounds for Incorporating Moieties

Synthesis of 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid.

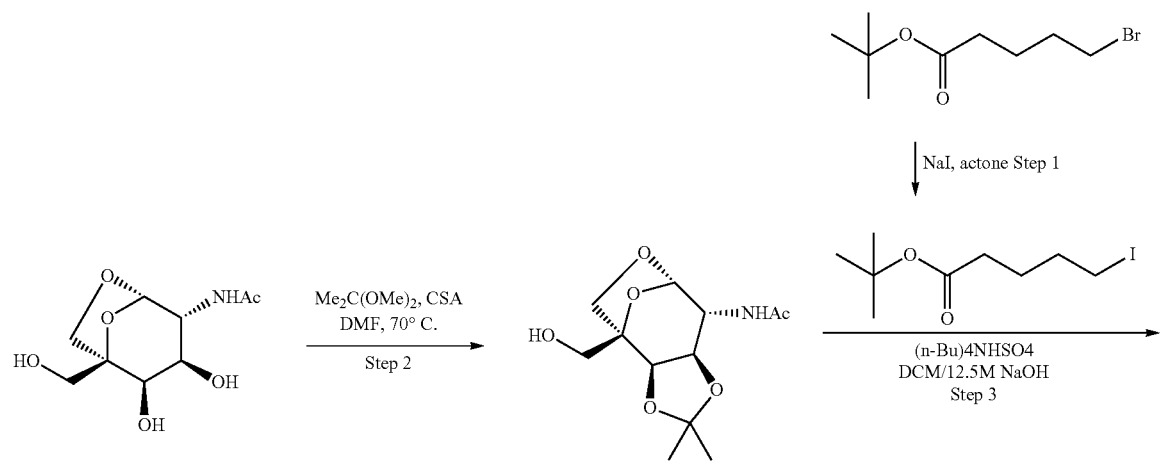

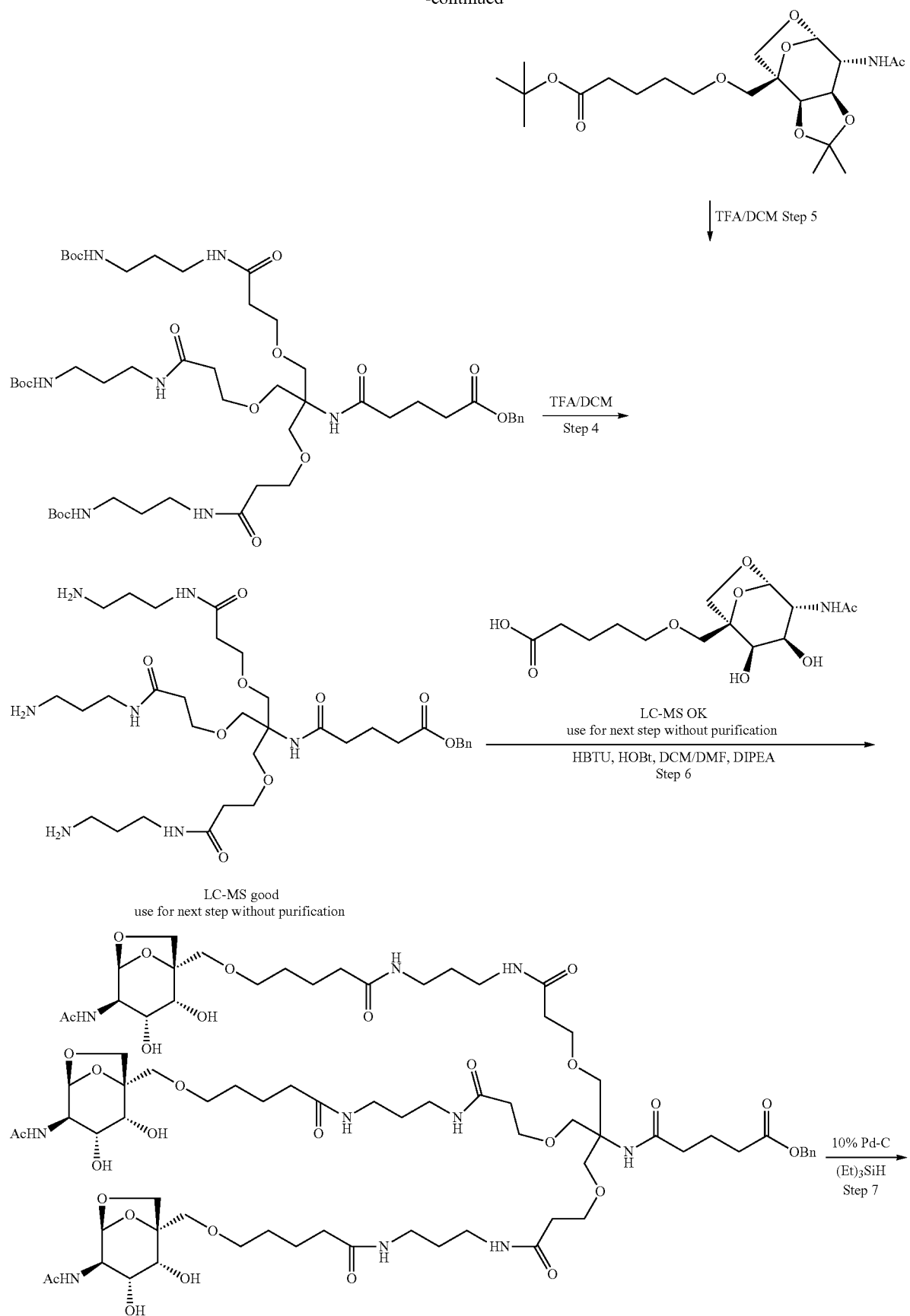

-continued

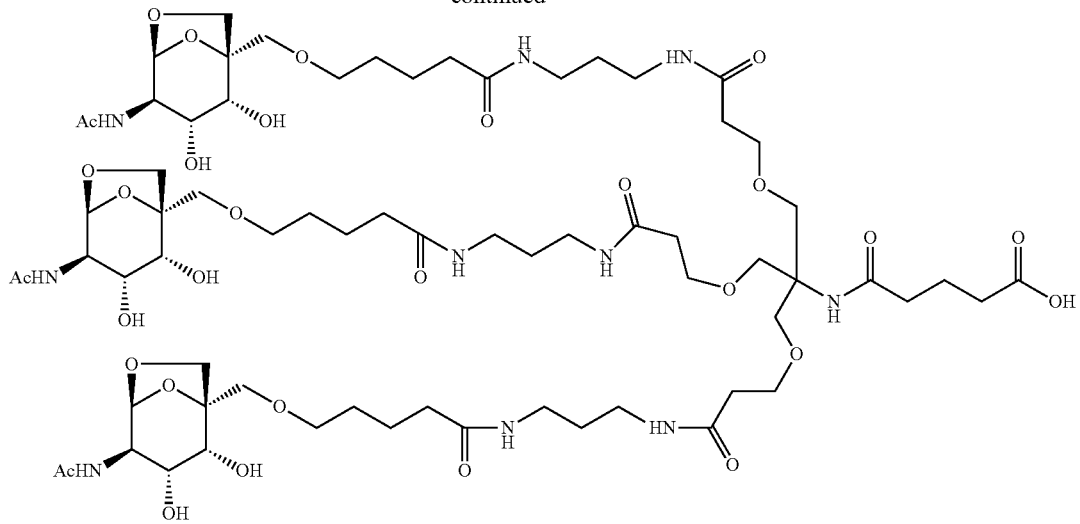

Step 1: To a solution of tert-butyl 5-bromopentanoate (4.0 g, 16.87 mmol) in acetone (80 mL) was added NaI (7.59 g, 50.6 mmol). The reaction mixture was stirred at 57° C. for 2 hrs, filtered, and washed with EtOAc. Solvent was evaporated under reduced pressure to give a residue, which was dissolved in EtOAc, washed with water, brine, dried over $Na_2SO_4$, concentrated to give a residue, which was purified by ISCO (40 g column) eluting with 20% EtOAc in hexane to 50% EtOAc in hexane to give tert-butyl 5-iodopentanoate (4.54 g, 15.98 mmol, 95% yield) as a yellow oil. $^1$H NMR (500 MHz, Chloroform-d) δ 3.19 (t, J=6.9 Hz, 2H), 2.24 (t, J=7.3 Hz, 2H), 1.86 (p, J=7.1 Hz, 2H), 1.70 (p, J=7.4 Hz, 2H), 1.45 (s, 9H).

Step 2: To a solution of N-((1S,2R,3R,4R,5S)-2,3-dihydroxy-1-(hydroxymethyl)-6,8-dioxabicyclo[3.2.1]octan-4-yl)acetamide (600 mg, 2.57 mmol) in DMF (15 mL) was added 2,2-dimethoxypropane (2087 µl, 17.03 mmol) followed by (+/−)-camphor-10-sulphonic acid (264 mg, 1.135 mmol). The reaction mixture was stirred at 70° C. for 24 hrs. The reaction mixture was cooled down to room temperature, and then methanol (2.5 mL) was added. The reaction mixture was stirred at room temperature for 30 minutes and neutralized with TEA (0.10 mL). The solvent was evaporated and the residue was coevaporated with toluene. The residue was purified by ISCO (24 g gold) eluting with EtOAc to 10% MeOH in EtOAc to give N-((3aR,4S,7S,8R,8aR)-4-(hydroxymethyl)-2,2-dimethylhexahydro-4,7-epoxy[1,3]dioxolo[4,5-d]oxepin-8-yl)acetamide (666 mg, 2.437 mmol, 95% yield). $^1$H NMR (500 MHz, DMSO-$d_6$) δ 8.09 (d, J=8.1 Hz, 1H), 5.15-5.05 (m, 2H), 4.26 (d, J=5.8 Hz, 1H), 4.09 (dd, J=7.3, 5.8 Hz, 1H), 3.80-3.60 (m, 5H), 1.83 (s, 3H), 1.37 (s, 3H), 1.26 (s, 3H); MS, 274.3 (M+H)$^+$.

Step 3: To a solution of tert-butyl 5-iodopentanoate (1310 mg, 4.61 mmol) and N-((3aR,4S,7S,8R,8aR)-4-(hydroxymethyl)-2,2-dimethylhexahydro-4,7-epoxy[1,3]dioxolo[4,5-d]oxepin-8-yl)acetamide 7 (420 mg, 1.537 mmol) in DCM (10.5 mL) was added tetrabutylammonium hydrogensulfate (783 mg, 2.305 mmol) followed by 12.5 M sodium hydroxide solution (7 mL). The reaction mixture was stirred at room temperature for 24 hrs. The reaction mixture was diluted with DCM and water, extracted with DCM (2×). The organic layer was washed with 1 N HCl solution, and dried over sodium sulfate. Solvent was concentrated under reduce pressure to give a residue. The resulting crude material was added ethyl acetate (30 mL) and sonicated for 5 minutes. The result precipitate was filtered, washed with ethyl acetate (10 mL×2). LC-MS showed the filter does not contain desired product and was tetrabutylammonium salt. The filtrate was concentrated under reduced pressure to give a residue, which was purified by ISCO (40 g silica gel gold cartridge) eluting with 50% EtOAc in hexane to EtOAc to give tert-butyl 5-(((3aR,4S,7S,8R,8aR)-8-acetamido-2,2-dimethylhexahydro-4,7-epoxy[1,3]dioxolo[4,5-d]oxepin-4-yl)methoxy)pentanoate (0.470 g, 1.094 mmol, 71.2% yield) as a yellowish oil. $^1$H NMR (500 MHz, Chloroform-d) δ 5.56 (d, J=9.1 Hz, 1H), 4.21 (d, J=5.9 Hz, 1H), 4.12 (dtd, J=7.7, 3.8, 1.7 Hz, 1H), 3.99 (t, J=6.3 Hz, 1H), 3.90 (d, J=9.5 Hz, 1H), 3.77 (d, J=2.0 Hz, 2H), 3.67 (d, J=9.5 Hz, 1H), 3.52 (ddt, J=30.5, 9.2, 5.8 Hz, 2H), 2.23 (t, J=7.1 Hz, 2H), 2.03 (d, J=14.5 Hz, 3H), 1.65-1.55 (m, 7H), 1.44 (s, 9H), 1.35 (s, 3H); MS, 452.4 (M+Na)$^+$.

Step 4: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (0.168 g, 0.166 mmol) in DCM (3 mL) was added TFA (3 mL). The reaction mixture was stirred at room temperature for 3 hrs. LC-MS showed the reaction was completed. Solvent was evaporated under reduced pressure to give benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. MS, 710.5 (M+H)+. Directly use for next step without purification.

Step 5: To a solution of tert-butyl 5-(((3aR,4S,7S,8R,8aR)-8-acetamido-2,2-dimethylhexahydro-4,7-epoxy[1,3]dioxolo[4,5-d]oxepin-4-yl)methoxy)pentanoate (285 mg, 0.664 mmol) in DCM (5 mL) was added TFA (5 mL) was stirred at room temperature for 4 hrs. LC-MS showed the reaction was complete. Solvent was evaporated to give 5-(((1S,2R,3R,4R,5S)-4-acetamido-2,3-dihydroxy-6,8-dioxabicyclo[3.2.1]octan-1-yl)methoxy)pentanoic acid. MS (ESI): 334.3 (M+H)+. Directly use for next step without purification.

Step 6: To a solution of 5-(((1S,2R,3R,4R,5S)-4-acetamido-2,3-dihydroxy-6,8-dioxabicyclo[3.2.1]octan-1-yl)methoxy)pentanoic acid (221 mg, 0.664 mmol) in DCM (10 mL) was added DIPEA (2313 µl, 13.28 mmol), HBTU (208 mg, 0.548 mmol), HOBT (67.3 mg, 0.498 mmol), a solution of benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate (118 mg, 0.166 mmol) (GL08-02) in DMF (3.0 mL) and DCM (5.0 mL). The reaction mixture was stirred at room temperature for overnight. LC-MS showed the desired product. Solvent was evaporated under reduced pressure to give a residue, which was purified by ISCO (24 g gold cartridge) eluting with DCM to 80% MeOH in DCM to give benzyl 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oate (272 mg, 0.164 mmol, 99% yield) (product @ tube 30 to 42 (40% MeOH in DCM to 60% MeOH in DCM)). $^1$H NMR (500 MHz, DMSO-d$_6$) δ 7.89 (d, J=7.8 Hz, 3H), 7.81 (t, J=5.7 Hz, 3H), 7.75 (s, 3H), 7.34 (q, J=7.5, 6.9 Hz, 5H), 7.05 (s, 1H), 5.07 (s, 5H), 4.83 (d, J=5.3 Hz, 3H), 4.56 (d, J=7.1 Hz, 3H), 3.73 (dd, J=23.3, 9.2 Hz, 6H), 3.64 (d, J=7.0 Hz, 6H), 3.58-3.35 (m, 27H), 3.02 (p, J=6.2 Hz, 12H), 2.33 (t, J=7.6 Hz, 2H), 2.26 (t, J=6.4 Hz, 6H), 2.10 (t, J=7.6 Hz, 2H), 2.04 (t, J=7.4 Hz, 6H), 1.82 (s, 9H), 1.72 (q, J=7.6 Hz, 2H), 1.52-1.39 (m, 18H); MS (ESI), 1656.3 (M+H)$^+$.

Step 7: To a solution of benzyl 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oate (270 mg, 0.163 mmol) in EtOAc (10 mL) was added 10% Pd—C (50 mg), and MeOH (5.0 mL), and triethylsilane (1042 µl, 6.52 mmol). The reaction mixture was stirred at room temperature for 1 hr, filtered, and concentrated to give 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid (246 mg, 0.157 mmol, 96% yield) as a white solid. $^1$H NMR (500 MHz, DMSO-d$_6$) δ 11.99 (brs, 1H), 7.89 (d, J=7.9 Hz, 3H), 7.82 (t, J=5.4 Hz, 3H), 7.75 (t, J=5.7 Hz, 3H), 7.03 (s, 1H), 5.07 (d, J=1.6 Hz, 3H), 4.83 (brs, 3H), 4.56 (brs, 3H), 3.79-3.68 (m, 6H), 3.64 (d, J=7.2 Hz, 6H), 3.58-3.34 (m, 27H), 3.02 (p, J=6.3 Hz, 12H), 2.27 (t, J=6.4 Hz, 6H), 2.17 (t, J=7.5 Hz, 2H), 2.08 (t, J=7.5 Hz, 2H), 2.04 (t, J=7.3 Hz, 6H), 1.82 (s, 9H), 1.65 (p, J=7.5 Hz, 2H), 1.54-1.40 (m, 18H); MS(ESI), 1566.3 (M+H)+.

Example 4B

Synthesis of 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid

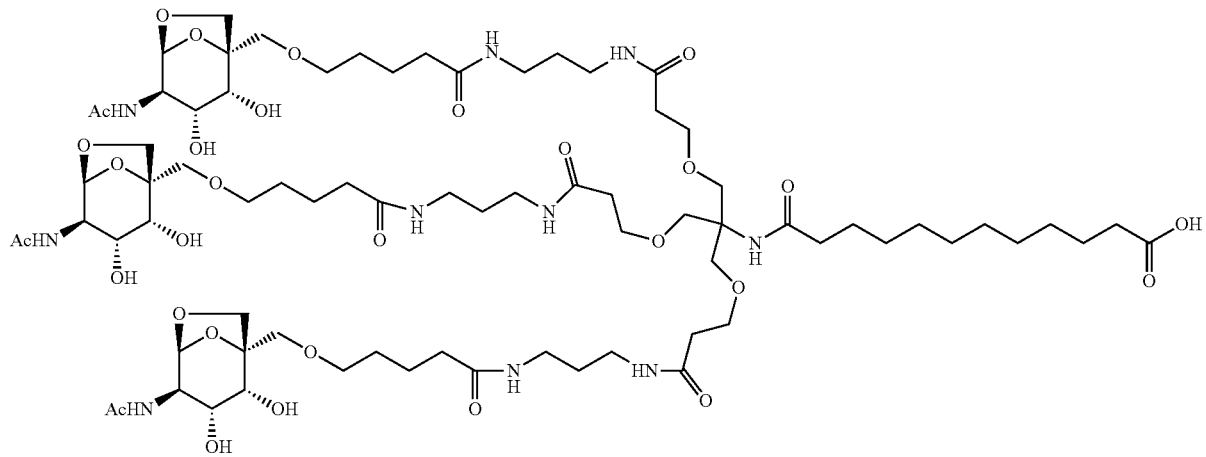 [SMILES: CC(=O)N[C@H]1[C@H]2OC[C@](COCCCCC(=O)NCCCNC(=O)CCOCC(COCCC(=O)NCCCNC(=O)CCCCOC[C@@]34CO[C@@H](O3)[C@H](NC(C)=O)[C@@H](O)[C@H]4O)(COCCC(=O)NCCCNC(=O)CCCCOC[C@@]34CO[C@@H](O3)[C@H](NC(C)=O)[C@@H](O)[C@H]4O)NC(=O)CCCCCCCCCCC(=O)O)(O2)[C@H](O)[C@@H]1O]

18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid was synthesized using the same procedure as 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid. $^1$H NMR (400 MHz, DMSO-d$_6$) δ 7.90 (d, J=7.8 Hz, 3H), 7.83 (t, J=5.7 Hz, 3H), 7.76 (t, J=5.7 Hz, 3H), 6.98 (d, J=6.2 Hz, 1H), 5.09 (s, 3H), 3.81-3.69 (m, 6H), 3.69-3.62 (m, 6H), 3.62-3.40 (m, 24H), 3.04 (p, J=6.1 Hz, 9H), 2.28 (t, J=6.4 Hz, 4H), 2.18 (t, J=7.3 Hz, 2H), 2.06 (t, J=7.7 Hz, 6H), 1.84 (s, 6H), 1.48 (tq, J=14.9, 7.4 Hz, 16H), 1.23 (s, 8H). MS(ESI), 1664.0 (M+H)$^+$.

Example 5. Example Compounds for Incorporating Moieties
Synthesis of 5-(4-(4,6-bis((3-((3-(5-((((2R,3R,4R,5R, 6R)-3-acetamido-4,5-diacetoxy-6-(acetoxymethyl) tetrahydro-2H-pyran-2-yl)oxy)pentanamido)propyl) amino)-3-oxopropyl)amino)-1,3,5-triazin-2-yl) piperazin-1-yl)-5-oxopentanoic acid
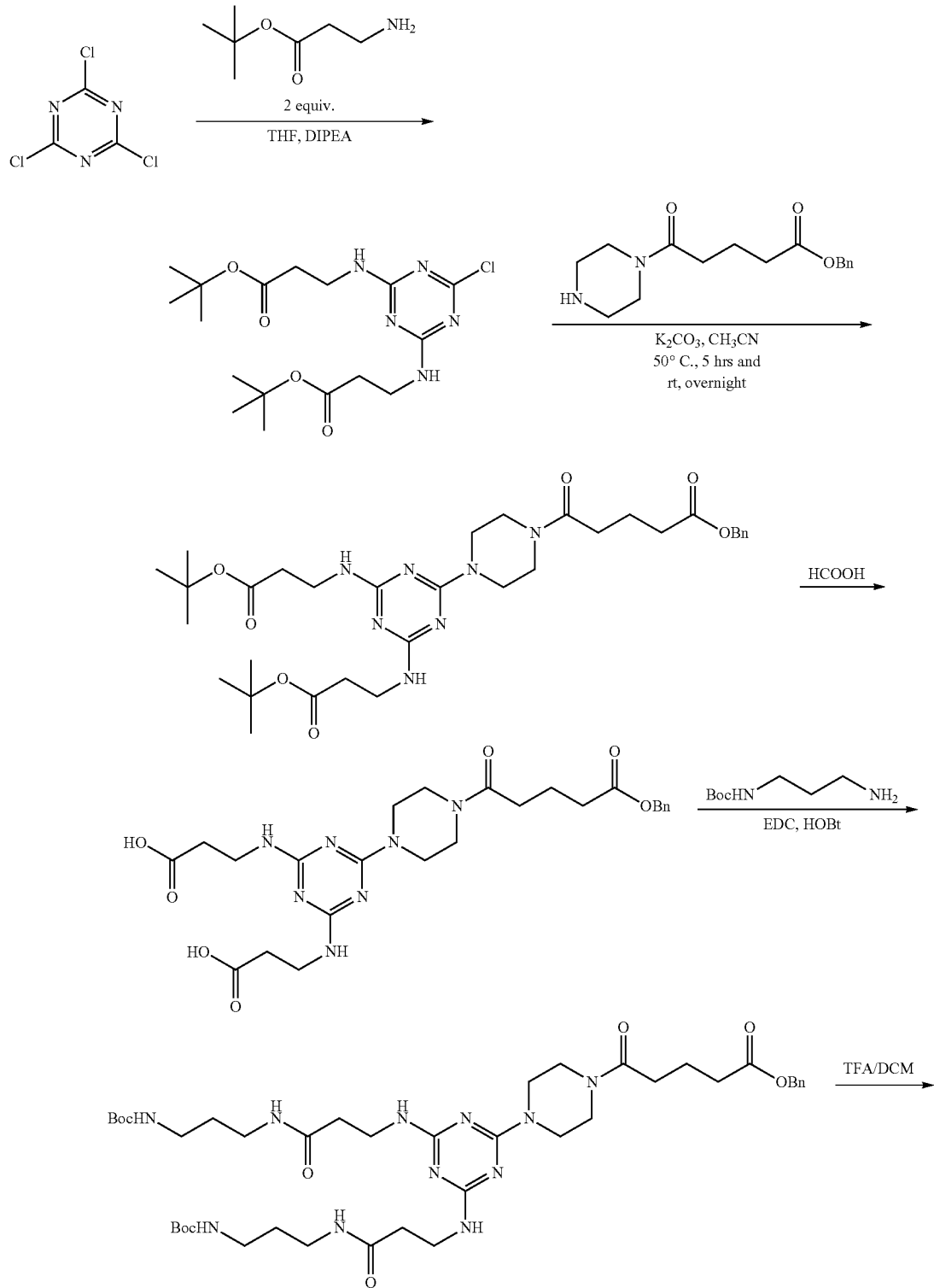

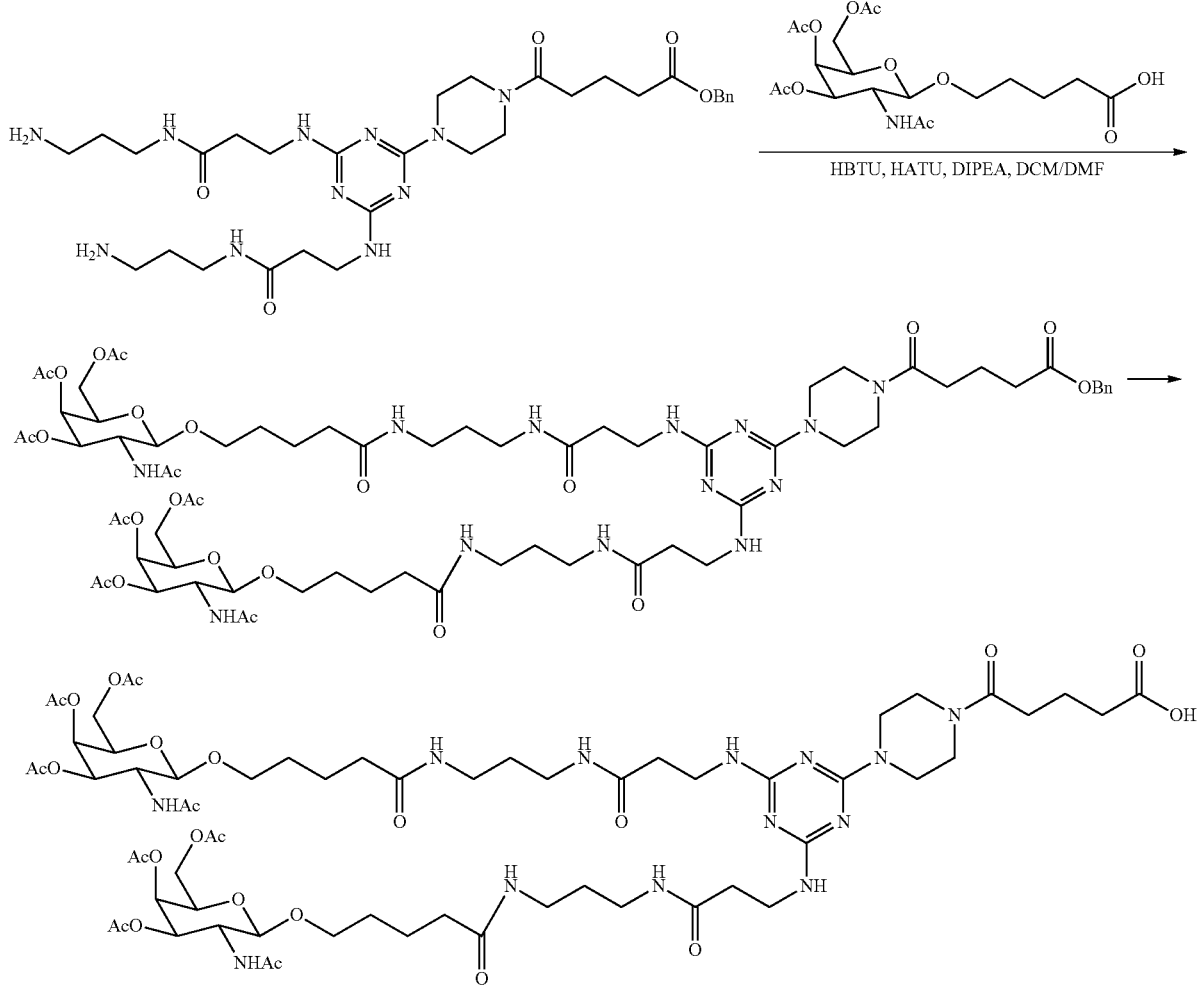

Steps 1 to 2: To a solid reagent 2,4,6-trichloro-1,3,5-triazine (0.500 g, 2.71 mmol) in THF (30 mL) was added tert-butyl 3-aminopropanoate HCl salt (0.985 g, 5.42 mmol) and DIPEA (2.36 ml, 13.56 mmol). The reaction mixture was stirred at room temperature for 5 hrs. LC-MS showed the desired product; MS(ESI): 402.4 (M+H)$^+$. Solvent was evaporated under reduced pressure to give a residue, which was directly used for next step. To a solution of di-tert-butyl 3,3'-[(6-chloro-1,3,5-triazine-2,4-diyl)bis(azanediyl))dipropionate (1.052 g, 2.71 mmol) in acetonitrile (50 mL) was added benzyl 5-oxo-5-(piperazin-1-yl)pentanoate (1.103 g, 3.80 mmol) and K$_2$CO$_3$ (2.248 g, 16.27 mmol). The reaction mixture was stirred at room temperature for overnight and at 50° C. Diluted with EtOAc, filtered and concentrated under reduced pressure to give a residue, which was purified by ISCO (40 g gold) eluting with 20% EtOAc in hexane to 50% EtOAc in hexane to give di-tert-butyl 3,3'-((6-(4-(5-(benzyloxy)-5-oxopentanoyl)piperazin-1-yl)-1,3,5-triazine-2,4-diyl)bis(azanediyl))dipropionate (1.13 g, 64%) as a white solid. $^1$H NMR (400 MHz, Chloroform-d) δ 7.43-7.30 (m, 5H), 5.15 (s, 2H), 3.75 (brs, 4H), 3.63 (brs, 6H), 3.43 (brs, 2H), 2.51 (q, J=7.0, 6.5 Hz, 6H), 2.42 (t, J=7.4 Hz, 2H), 2.09-1.96 (m, 2H), 1.48 (s, 18H); MS (ESI): 656.6 (M+H)$^+$.

Step 3: A solution of di-tert-butyl 3,3'-((6-(4-(5-(benzyloxy)-5-oxopentanoyl)piperazin-1-yl)-1,3,5-triazine-2,4-diyl)bis(azanediyl))dipropionate (1.10 g, 1.68 mmol) in formic acid (20 mL) was stirred at room temperature for overnight. LC-MS showed the reaction was not completed and solvent was evaporated. Formic acid (20 mL) was added to the reaction mixture and the reaction mixture was stirred at room temperature for 5 hrs. LC-MS showed the reaction was complete. Solvent was concentrated, co-evaporated with toluene (2×) and dried under vacuum for overnight to give 3,3'-((6-(4-(5-(benzyloxy)-5-oxopentanoyl)piperazin-1-yl)-1,3,5-triazine-2,4-diyl)bis(azanediyl))dipropionic acid (0.91 g, 100% yield) as a white solid. MS (ESI), 544.2 (M+H)$^+$.

Step 4: A solution of 3,3'-((6-(4-(5-(benzyloxy)-5-oxopentanoyl)piperazin-1-yl)-1,3,5-triazine-2,4-diyl)bis(azanediyl))dipropionic acid (0.91 g, 1.68 mmol) and HOBt (0.76 g, 4.36 mmol) in DCM (30 mL) and DMF (3 mL) at 0° C. was added tert-butyl (3-aminopropyl)carbamate (0.840 g, 4.36 mmol), EDC HCl salt (0.836 g, 4.36 mmol) and DIPEA (1.460 ml, 8.39 mmol). The reaction mixture was stirred at 0° C. for 15 minutes and at room temperature for 20 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give benzyl 5-(4-(4,6-bis((3-43-((tert-butoxycarbonyl)amino)propyl)

amino)-3-oxopropyl)amino)-1,3,5-triazin-2-yl)piperazin-1-yl)-5-oxopentanoate (1.11 g, 77% yield) as a white solid. MS (ESI): 857.5 (M+H)⁺.

Step 5: A solution of benzyl 5-(4-(4,6-bis((3-((3-((tert-butoxycarbonyl)amino)propyl)amino)-3-oxopropyl)amino)-1,3,5-triazin-2-yl)piperazin-1-yl)-5-oxopentanoate (212.3 mg, 0.250 mmol) in DCM (5.0 mL) was added TFA (3.0 mL). The reaction mixture was stirred at room temperature for 3 hrs. Solvent was evaporated under reduced pressure, use directly for next step without purification. MS (ESI): 656.3 (M+H)⁺.

Step 6: To a solution of 5-(((2R,3R,4R,5R,6R)-3-acetamido-4,5-diacetoxy-6-(acetoxymethyl)tetrahydro-2H-pyran-2-yl)oxy)pentanoic acid (333 mg, 0.740 mmol) in DCM (5 mL) was added DIPEA (2.16 ml, 12.4 mmol), HBTU (235 mg, 0.620 mmol), HOBT (67 mg, 0.50 mmol), a solution of benzyl 5-(4-(4,6-bis((3-((3-aminopropyl)amino)-3-oxopropyl)amino)-1,3,5-triazin-2-yl)piperazin-1-yl)-5-oxopentanoate (163 mg, 0.250 mmol) in DCM (3.0 mL). The reaction mixture was stirred at room temperature for 3 hrs. LC-MS showed the desired product. Solvent was evaporated under reduced pressure to give a residue, which was purified by ISCO (24 g gold cartridge) eluting with DCM to 50% MeOH in DCM to give (2R,2'R,3R,3'R,4R,4'R,5R,5'R,6R,6'R)-((((((3,3'-((6-(4-(5-(benzyloxy)-5-oxopentanoyl) piperazin-1-yl)-1,3,5-triazine-2,4-diyl)bis (azanediyl))bis(propanoyl))bis(azanediyl))bis(propane-3,1-diyl))bis(azanediyl))bis(5-oxopentane-5,1-diyl))bis(oxy)) bis(5-acetamido-2-(acetoxymethyl) tetrahydro-2H-pyran-6,3,4-triyl) tetraacetate (460 mg) containing some HOBt. MS (ESI), 1515.7 (M+H)⁺.

Step 7: To a solution of (2R,2'R,3R,3'R,4R,4'R,5R,5'R,6R,6'R)-((((((3,3'-((6-(4-(5-(benzyloxy)-5-oxopentanoyl) piperazin-1-yl)-1,3,5-triazine-2,4-diyl)bis(azanediyl))bis (propanoyl))bis(azanediyl))bis(propane-3,1-diyl))bis (azanediyl))bis(5-oxopentane-5,1-diyl))bis(oxy))bis(5-acetamido-2-(acetoxymethyl)tetrahydro-2H-pyran-6,3,4-triyl) tetraacetate (0.44 g, 0.290 mmol) in EtOAc (20 mL) was added 10% Pd—C (40 mg) followed by 2.0 mL MeOH under Ar. Triethylsilane (2.784 ml, 17.43 mmol) was added to the reaction mixture slowly. The reaction mixture was stirred at room temperature for 2 hrs, filtered through celite, washed with 50% MeOH in EtOAc. Solvents were evaporated under reduced pressure to give 5-(4-(4,6-bis((3-((3-(5-(((2R,3R,4R,5R,6R)-3-acetamido-4,5-diacetoxy-6-(acetoxymethyl)tetrahydro-2H-pyran-2-yl)oxy)pentanamido) propyl)amino)-3-oxopropyl)amino)-1,3,5-triazin-2-yl) piperazin-1-yl)-5-oxopentanoic acid (0.43 g, 100% yield) a white solid. MS (ESI): 1425.0 (M+H)⁺.

Example 6. Example Compounds for Incorporating Moieties

Synthesis of 5-(4-(4,6-bis((3-((3-(5-(((1S,2R,3R,4R,5S)-4-acetamido-2,3-dihydroxy-6,8-dioxabicyclo [3.2.1]octan-1-yl)methoxy)pentanamido)propyl) amino)-3-oxopropyl)amino)-1,3,5-triazin-2-yl) piperazin-1-yl)-5-oxopentanoic acid

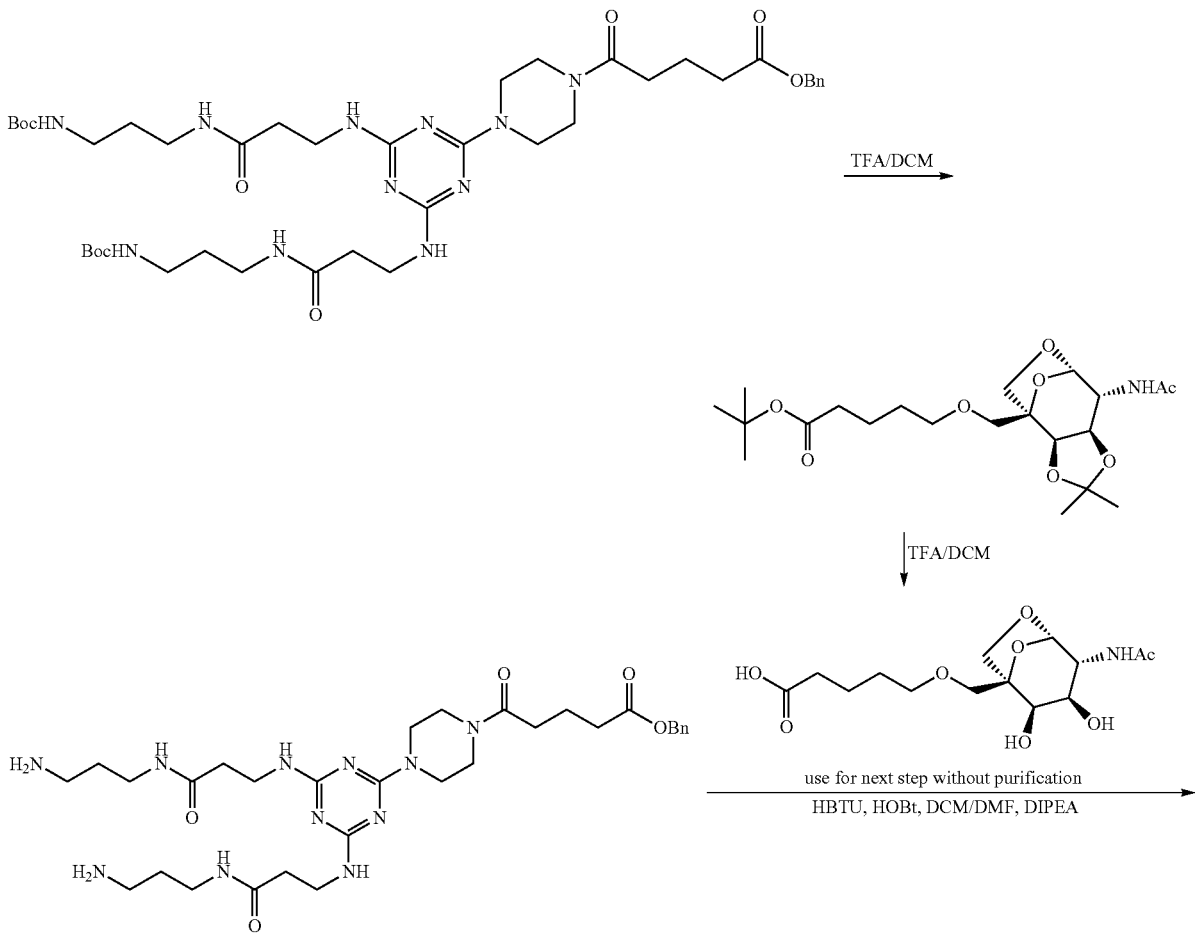

-continued

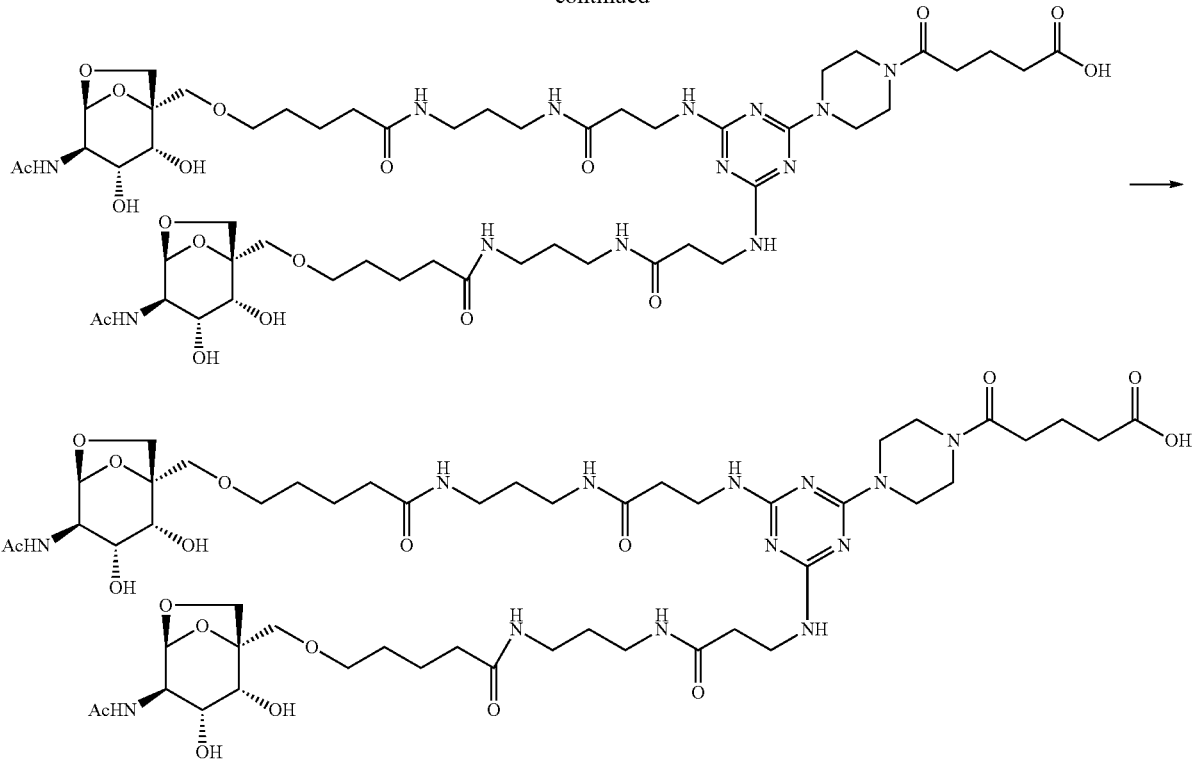

Step 1: A solution of benzyl 5-(4-(4,6-bis((3-((3-((tert-butoxycarbonyl)amino)propyl)amino)-3-oxopropyl)amino)-1,3,5-triazin-2-yl)piperazin-1-yl)-5-oxopentanoate (212.3 mg, 0.250 mmol) in DCM (5.0 mL) was added TFA (3.0 mL). The reaction mixture was stirred at room temperature for 3 hrs. Solvent was evaporated under reduced pressure, use directly for next step without purification. MS (ESI): 656.3 (M+H)+.

Step 2: To a solution of tert-butyl 5-(((3aR,4S,7S,8R,8aR)-8-acetamido-2,2-dimethylhexahydro-4,7-epoxy[1,3]dioxolo[4,5-d]oxepin-4-yl)methoxy)pentanoate (373 mg, 0.870 mmol) in DCM (5 mL) was added TFA (5 mL) was stirred at room temperature for 4 hrs. LC-MS showed the reaction was complete. Solvent was evaporated to give 5-(((1S,2R,3R,4R,5S)-4-acetamido-2,3-dihydroxy-6,8-dioxabicyclo[3.2.1]octan-1-yl)methoxy)pentanoic acid. MS (ESI): 334.3 (M+H)+. Directly use for next step without purification.

Step 3: To a solution of 55-(((1S,2R,3R,4R,5S)-4-acetamido-2,3-dihydroxy-6,8-dioxabicyclo[3.2.1]octan-1-yl)methoxy)pentanoic acid (289 mg, 0.870 mmol) in DCM (5 mL) was added DIPEA (2.16 ml, 12.4 mmol), HBTU (330 mg, 0.870 mmol), HOBT (67 mg, 0.50 mmol), a solution of benzyl 5-(4-(4,6-bis((3-((3-aminopropyl)amino)-3-oxopropyl)amino)-1,3,5-triazin-2-yl)piperazin-1-yl)-5-oxopentanoate (163 mg, 0.250 mmol) in DCM (3.0 mL). The reaction mixture was stirred at room temperature for 3 hrs. LC-MS showed the desired product. Solvent was evaporated under reduced pressure to give a residue, which was purified by ISCO (24 g gold cartridge) eluting with DCM to 50% MeOH in DCM to give benzyl 5-(4-(4,6-bis((3-((3-(5-(((1S,2R,3R,4R,5S)-4-acetamido-2,3-dihydroxy-6,8-dioxabicyclo[3.2.1]octan-1-yl)methoxy)pentanamido)propyl)amino)-3-oxopropyl)amino)-1,3,5-triazin-2-yl)piperazin-1-yl)-5-oxopentanoate (227 mg, 71%). MS (ESI), 1287.0 (M+H)+.

Step 4: To a solution of benzyl 5-(4-(4,6-bis((3-((3-(5-(((1S,2R,3R,4R,5S)-4-acetamido-2,3-dihydroxy-6,8-dioxabicyclo[3.2.1]octan-1-yl)methoxy)pentanamido)propyl)amino)-3-oxopropyl)amino)-1,3,5-triazin-2-yl)piperazin-1-yl)-5-oxopentanoate (0.167 g, 0.130 mmol) in EtOAc (10 mL) was added 10% Pd—C (50 mg) followed by 2.0 mL MeOH under Ar. Triethylsilane (1.66 ml, 10.39 mmol) was added to the reaction mixture slowly. The reaction mixture was stirred at room temperature for 2 hrs, filtered through celite, washed with 50% MeOH in EtOAc. Solvents were evaporated under reduced pressure to give 5-(4-(4,6-bis((3-((3-(5-(((1S,2R,3R,4R,5S)-4-acetamido-2,3-dihydroxy-6,8-dioxabicyclo[3.2.1]octan-1-yl)methoxy)pentanamido)propyl)amino)-3-oxopropyl)amino)-1,3,5-triazin-2-yl)piperazin-1-yl)-5-oxopentanoic acid (32 mg, 21% yield) a white solid. MS (ESI): 1196.7 (M+H)+.

Example 7. Example Preparation of Certain Phosphoramidites

In some embodiments, the present disclosure provides monomers (phosphoramidites) and methods thereof for oligonucleotide preparation. In some embodiments, provided phosphoramidites comprise 5′-end structures that provides special and/or greatly improved activities and/or properties. In some embodiments, provided phosphoramidites comprise desired chemical moieties, e.g., carbohydrate moieties, lipid moieties, etc., for incorporation into oligonucleotides. In some embodiments, provided phosphoramidites comprise linkers/handles for incorporation of desired chemical moieties, e.g., carbohydrate moieties, lipid moieties, etc. Many technologies can be utilized to prepare phosphoramidites in accordance with the present disclosure, including but not limited to those described in WO/2010/064146, WO/2011/005761, WO/2013/012758, WO/2014/010250, US2013/

0178612, WO/2014/012081, WO/2015/107425, WO/2017/015555, and WO/2017/062862, the methods and reagents of each of which are incorporated herein by reference. Provided below as examples are preparation of certain phosphoramidites.

Example 7-1. Preparation of Thymidine-5′-dimethylvinylphosphonate-2′-deoxy-3′-CNE Phosphoramidite

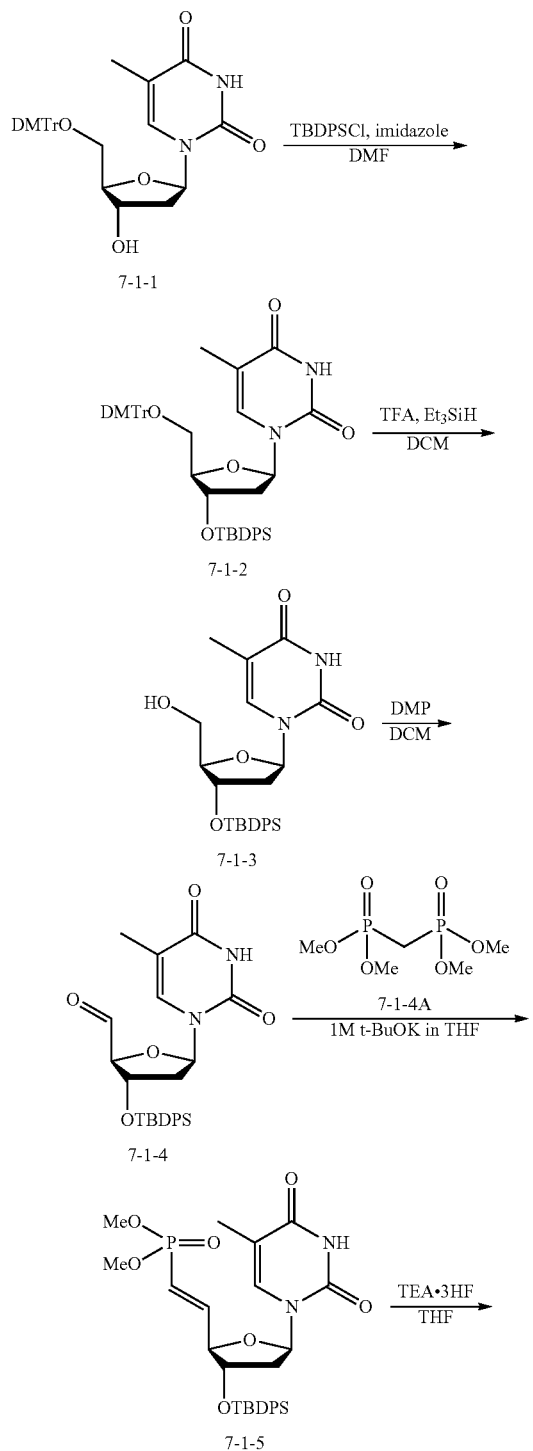

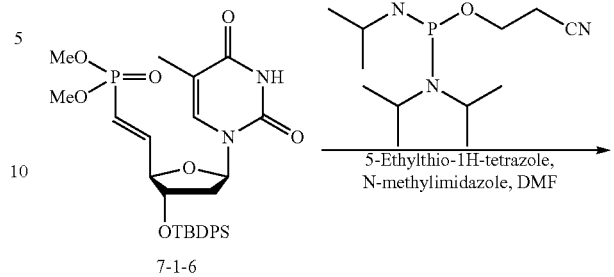

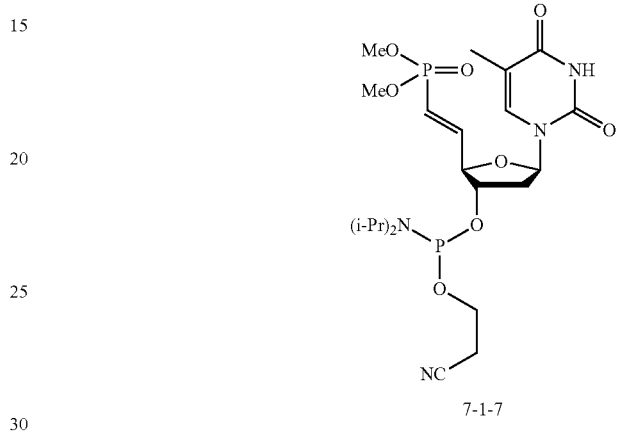

Preparation of Compound 7-1-2

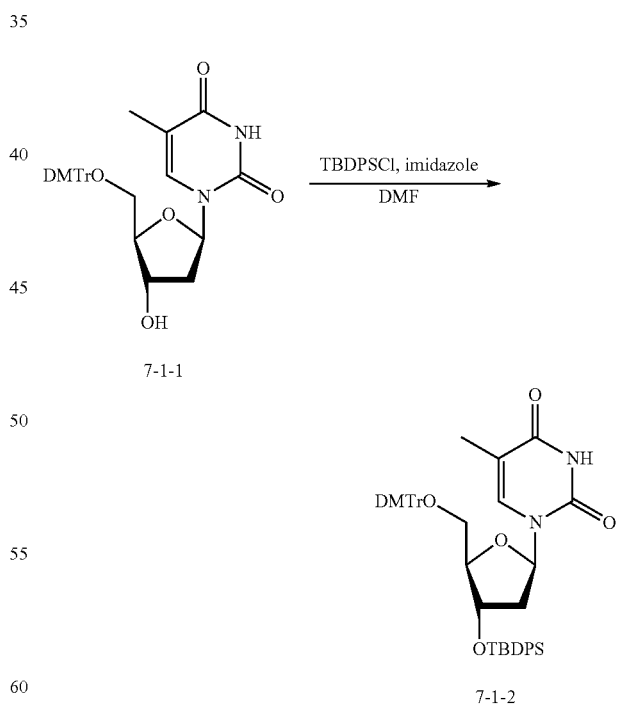

To a solution of compound 7-1-1 (20.00 g, 36.72 mmol, 1.00 eq.) in DMF (100.00 mL) was added imidazole (25.00 g, 367.20 mmol, 10.00 eq.) followed by TBDPSCl (50.47 g, 183.60 mmol, 47.17 mL, 5.00 eq.). The reaction mixture was stirred at 25° C. for 16 h. TLC (Dichloromethane:Methanol=1:1) showed compound 7-1-1 was consumed completely. EtOAc (300 mL) was added and the mixture was washed with water (60 mL*3). The organic phase was dried over Na$_2$SO$_4$, filtered and concentrated. The residue was purified by column chromatography on silica gel (Petroleum ether: Ethyl acetate=20:1, 1:1, 1:4). Compound 7-1-2 (30.00 g) was obtained as white foamy solid. $^1$H NMR: (CDCl$_3$, 400 MHz) δ=8.165 (s, 1H), 7.575-7.080 (m, 21H), 6.718-6.741 (m, 4H), 6.473 (d, J=2.8 Hz, 1H), 4.520-4.534 (m, 1H), 4.037-4.043 (d, J=2.4 Hz, 1H), 3.758 (s, 6H), 3.184-3.217 (m, 1H), 2.841-2.874 (m, 1H), 2.319-2.338 (m, 1H), 2.025-2.078 (m, 1H), 1.321 (s, 3H), 1.021 (s, 9H).

Preparation of Compound 7-1-3

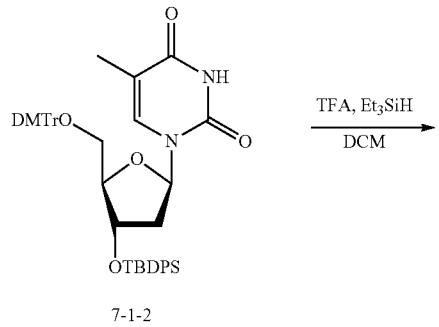

7-1-2

Preparation of Compound 7-1-4

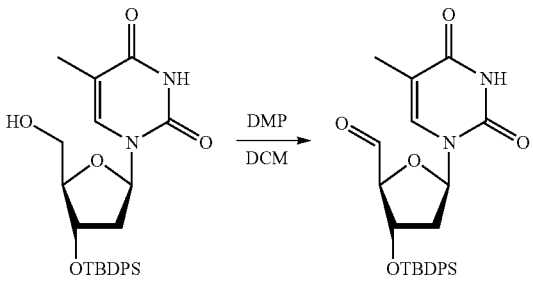

7-1-3      7-1-4

To a solution of compound 7-1-3 (18.00 g, 37.45 mmol, 1.00 eq.) in DCM (500 mL) was added DMP (17.47 g, 41.20 mmol, 12.75 mL, 1.10 eq.) at 0° C. The reaction mixture was stirred at 25° C. for 3 h. TLC (Petroleum ether: Ethyl acetate=1:1) showed the reaction was complete. Na$_2$SO$_3$ (sat., 100 mL) and NaHCO$_3$(sat. 100 mL) was added successively. The mixture was extracted with DCM (100 mL*3). The organic phase was dried over Na$_2$SO$_4$ and concentrated. Compound 7-1-4 (17.92 g, crude) was obtained as yellow oil.

Preparation of Compound 7-1-5

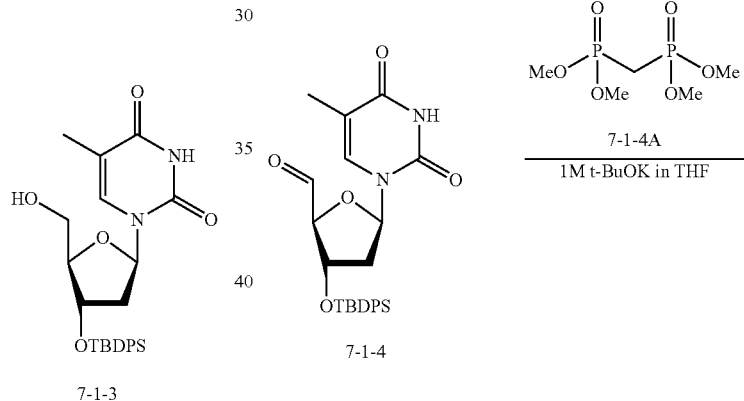

7-1-4

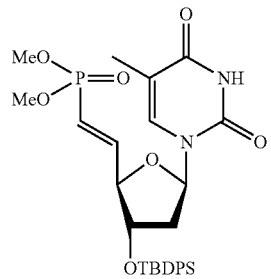

7-1-5

To a solution of compound 7-1-2 (25.00 g, 31.93 mmol, 1.00 eq.) in DCM (250 mL) was added TFA (8.37 g, 73.44 mmol, 5.44 mL, 2.30 eq.). The color of the solution turned to red. Et$_3$SiH (8.17 g, 70.24 mmol, 11.19 mL, 2.20 eq.) was added at 25° C. The reaction mixture was stirred at 25° C. for 2 h and the red solution became colorless. TLC (Petroleum ether: Ethyl acetate=1:1) showed compound 7-1-2 was consumed completely. The solvent was removed under reduced pressure, and the residue was dissolved in EtOAc (100 mL). The organic phase was washed with NaHCO$_3$(40 mL), brine, dried over Na$_2$SO$_4$, filtered and concentrated. The residue was purified by column chromatography on silica gel (Petroleum ether: Ethyl acetate=20:1, 1:1). Compound 7-1-3 (9.80 g, 56.20% yield, 88% purity) was obtained as white solid. $^1$H NMR: (CDCl$_3$, 400 MHz) δ=8.108 (s, 1H), 7.643 (s, 1H), 7.403-7.412 (m, 6H), 7.269 (d, J=4.8 Hz, 2H), 6.217 (d, J=5.6 Hz, 1H), 4.451 (s, 1H), 3.975 (s, 1H), 3.631 (d, J=12 Hz, 1H), 3.255 (s, 1H), 2.264-2.296 (m, 1H), 2.136-2.184 (m, 1H), 1.957 (s, 1H), 1.859 (s, 3H), 1.090 (s, 9H).

To a solution of compound 7-1-4A (16.08 g, 69.26 mmol, 1.85 eq.) in THF (29 mL) was added t-BuOK (1 M, 69.26 mL, 1.85 eq.) at 0° C. The mixture was stirred at 0° C. for 10 min, then warmed up to 25° C. for 30 min. The above mixture was added to a solution of compound 7-1-4 (17.92 g, 37.44 mmol, 1.00 eq.) in THF (36 mL) at 0° C. The reaction mixture was stirred at 0° C. for 1 h and then allowed to warm up to 25° C. in 80 min. TLC (Dichloromethane: Methanol=20:1) showed the reaction was complete. To the reaction mixture water (200 mL) was added and extracted with EtOAc (300 mL*4). The organic phase was dried (Na$_2$SO$_4$), filtered and concentrated. The residue was purified by column chromatography on silica gel (PE (10% DCM): EA=10:1, 1:8). Compound 7-1-5 (15.00 g,) was obtained as yellow solid.

Preparation of Compound 7-1-6

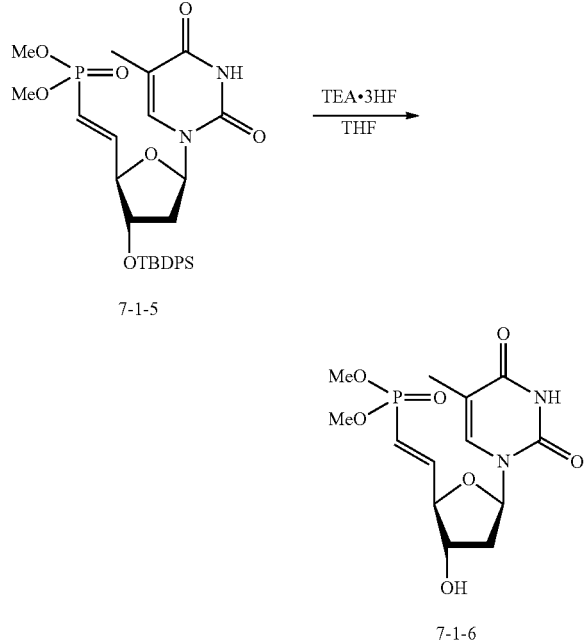

7-1-5

7-1-6

To a solution of compound 7-1-5 (21.00 g, 35.92 mmol, 1.00 eq.) in THF (60 mL) was added N, N-diethylethanamine; trihydrofluoride (28.95 g, 179.59 mmol, 29.24 mL, 5.00 eq.) at 25° C. The reaction mixture was stirred at 25° C. for 20 h. TLC (Dichloromethane:Methanol=10:1) showed the reaction was complete. The reaction mixture was concentrated under reduced pressure and the mixture was neutralized with Na$_2$CO$_3$ (aq., sat) until pH=7. The water phase was freeze-dried. The freeze-drying solid was washed with DCM:MeOH=10:1(300 mL*2). The organic phase was concentrated. The residue obtained was purified by column chromatography on silica gel (Dichloromethane:Methanol=100:1,100:8). Compound 7-1-6 (5.20 g, 15.02 mmol, 41.81% yield) was obtained as white solid. $^1$H NMR: (CDCl$_3$, 400 MHz) δ=9.521 (s, 1H), 7.120 (s, 1H), 6.974-7.074 (m, 1H), 6.372-6.405 (m, 1H), 5.961-6.050 (m, 1H), 4.684 (s, 1H), 4.504-4.518 (m, 1H), 4.393-4.409 (m, 1H), 3.726-3.775 (m, 6H), 3.151-3.180 (m, 2H), 2.411-2.427 (m, 1H), 1.930-2.218 (m, 1H), 1.927 (s, 3H).

Preparation of Compound 7-1-7

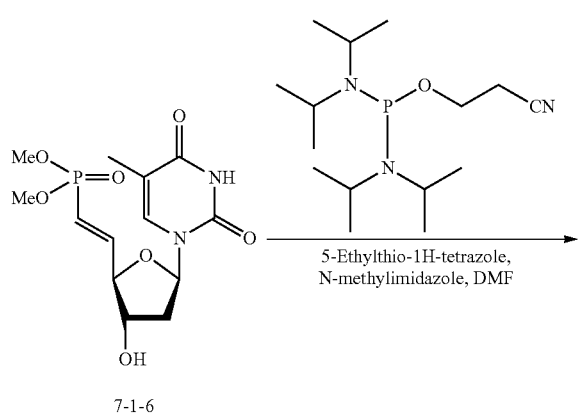

7-1-6

7-1-7

To a solution of compound 7-1-6 (3.80 g, 10.97 mmol, 1.00 eq.) in DMF (23 mL) was added 5-ethylsulfanyl-2H-tetrazole (1.43 g, 10.97 mmol, 1.00 eq.), 1-methylimidazole (1.80 g, 21.94 mmol, 1.75 mL, 2.00 eq.) and 3-bis(diisopropylamino)phosphanyloxypropanenitrile (4.96 g, 16.46 mmol, 5.22 mL, 1.50 eq.). The reaction mixture was stirred at 25° C. under N$_2$ for 3 h. TLC (Dichloromethane:Methanol=10:1) showed the reaction was complete. The reaction mixture was diluted with EtOAc (200 mL). The reaction mixture was washed with aq. saturated. NaHCO$_3$ solution (20 mL*4), dried over Na$_2$SO$_4$, filtered and concentrated under reduced pressure. The column was eluted with MeOH (20 min), EA (20 min), Petroleum ether (20 min), and Petroleum ether/Ethyl acetate (20 min). The residue thus obtained was purified by silica gel column chromatography (elution with Petroleum ether:EtOAc=10:1, 1:1 and then EtOAc/Acetonitrile=1000:1,100:2,100:4). Compound 7-1-7 (4.80 g, 8.78 mmol, 80.04% yield) was obtained as yellow solid. MS: LCMS, Calculated C22H36N4O8P2, 546.2008; Observed in +Ve mode 568.95; 569.43[M+Na]. $^1$H NMR: (CDCl$_3$, 400 MHz) δ=9.489 (s, 1H), 7.233 (s, 1H), 6.835-7.035 (m, 1H), 6.303-6.337 (m, 1H), 5.931-5.983 (m, 1H), 4.388-4.504 (m, 1H), 3.703-3.846 (m, 1H), 3.666-3.694 (m, 6H), 3.533-3.559 (m, 2H), 2.594-2.702 (m, 2H), 2.162-2.578 (m, 2H), 1.863 (s, 3H), 1.111-1.189 (m, 12H). $^{13}$C NMR (101 MHz, CDCl$_3$) δ 163.66, 162.54, 150.47, 150.40, 148.68, 148.61, 148.41, 148.35, 135.10, 135.01, 118.73, 118.25, 117.76, 117.61, 116.91, 116.85, 116.38, 111.74, 84.83, 84.79, 84.75, 84.72, 84.62, 84.56, 84.53, 84.50, 84.40, 84.33, 77.40, 77.29, 77.09, 76.77, 76.03, 75.87, 75.49, 75.48, 75.34, 75.32, 58.21, 58.19, 58.16, 58.12, 58.00, 57.92, 52.59, 52.55, 52.54, 52.52, 52.49, 52.46, 45.33, 45.27, 43.43, 43.40, 43.30, 43.27, 38.45, 38.40, 38.37, 36.45, 24.62, 24.57, 24.54, 24.49, 24.46, 22.96, 22.94, 22.88, 22.85, 20.47, 20.39, 20.37, 20.30, 20.11, 20.04, 12.50, 12.48. $^{31}$P NMR (162 MHz, CDCl$_3$) δ 149.40, 149.38, 19.99, 19.64, 14.10.

Example 7-2. Stereopure L-DPSE-5'-DMT-5'VP-dT Amidite, 7-2-8

Preparation of L-DPSE-NOPCl

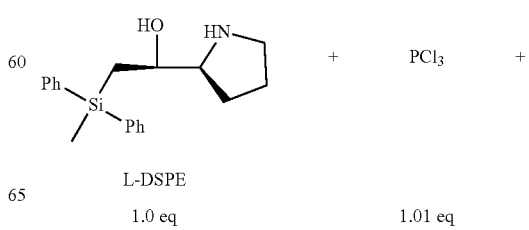

L-DSPE 1.0 eq

PCl$_3$ 1.01 eq

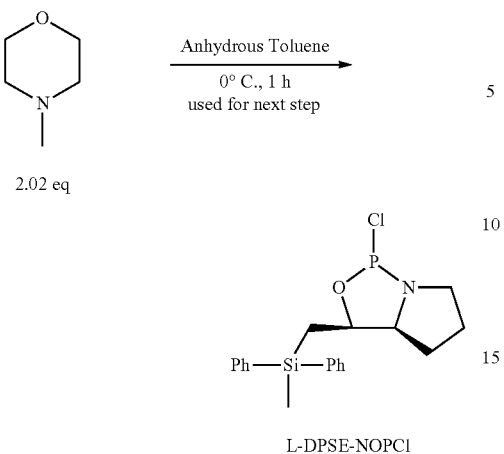

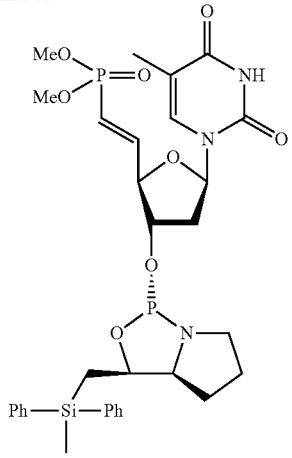

L-DPSE (8.82 g, 28.5 mmol) was dried by azeotropic evaporation with anhydrous toluene (60 ml) at 35° C. in a rotary evaporator and further dried in high vacuum for overnight. A solution of this dried L-DPSE and 4-methylmorpholine (5.82 g, 6.33 mL, 57.5 mmol) which was dissolved in anhydrous toluene (50 ml) was added to a solution of PCl$_3$ (4.0 g, 2.5 mL, 29.0 mmol) in anhydrous toluene (25 ml) placed in 250 mL three neck round bottomed flask which was cooled at −5° C. under argon (start Temp: −2° C., Max: 5° C. temp, 10 min addition) and the reaction mixture was stirred at 0° C. for another 40 min. After that the precipitated white solid was filtered by vacuum under argon using special filter tube (Chemglass: Medium Frit, Airfree, Schlenk). The solvent was removed by rotary evaporator under argon at bath temperature (25° C.) and the crude oily mixture was obtained and dried under vacuum overnight (~15 h) and used for next step.

Preparation of L-DPSE-5'-DMT-5'VP-dT Amidite

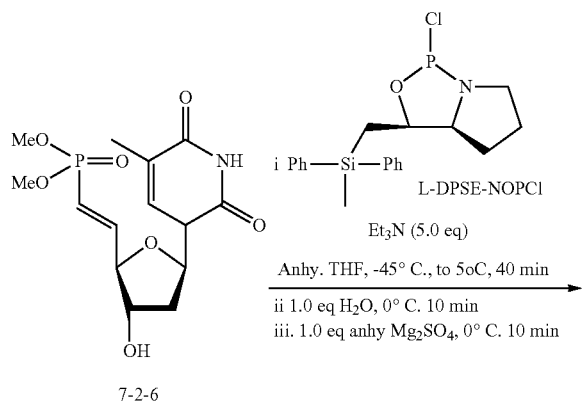

Compound 7-2-6 (7.0 g, 20.2 mmol) was dried two times by co-evaporation with 75 mL of anhydrous toluene at 45° C. and kept at high vacuum for overnight. Then the dried Compound 7-2-6, was dissolved in dry THF (70 mL) in a 250 mL three neck flasks under argon, followed by the addition of triethylamine (14 mL, 101 mmol) and the mixture was cooled to −45° C. To this cooled reaction mixture was added a solution of the crude L-DPSE-NOPCl (28.5 mmol, 1.4 eq, in THF 50 mL) from the previous step via syringe dropwise (~10 min, maintaining the internal temperature −40 to −35° C.). The reaction mixture was then gradually warmed to 5° C. After 30 min at 5° C., TLC and LC-MS analysis indicated the complete conversion of SM to product (total reaction time 2 h). The reaction mixture was cooled in an ice bath, and was quenched by addition of water (0.36 mL, 20.2 mmol) and stirred for 10 min followed by added anhydrous Mg$_2$SO$_4$ (3.0 g, 20.2 mmol). The reaction was filtered through Airfree, Schlenk filter tube, washed with dry THF (50 mL) and evaporated under rotary evaporation at 28° C. to afford the pale-yellow solid of the crude product, which was dried under high vacuum for overnight. The dried crude product was purified by 120 silica column (which was pre-deactivated with 3 column volume of ethyl acetate with 5% TEA) using ethyl acetate/hexane mixture with 5% TEA as a solvent. After column purification, fractions were analyzed by TLC and LC-MS and pooled together. Solvent was evaporated in a rotary evaporator at 28° C. and the residue was dried under high vacuum to afford the product as a white solid. Yield: 11.8 g (87%). $^1$H NMR (400 MHz, Chloroform-d) δ 7.46 (ddt, J=16.5, 7.6, 2.7 Hz, 4H), 7.33-7.17 (m, 6H), 6.93-6.88 (m, 1H), 6.75 (ddd, J=22.6, 17.2, 4.4 Hz, 1H), 6.16 (dd, J=7.5, 6.3 Hz, 1H), 5.85 (ddd, J=19.2, 17.1, 1.8 Hz, 1H), 4.71 (dt, J=8.7, 5.7 Hz, 1H), 4.38 (dp, J=10.7, 3.6 Hz, 1H), 4.15 (tt, J=5.6, 2.7 Hz, 1H), 3.68 (dd, J=11.1, 3.7 Hz, 6H), 3.55-3.29 (m, 2H), 3.09 (tdd, J=10.8, 8.8, 4.3 Hz, 1H), 2.11 (ddd, J=13.9, 6.3, 3.3 Hz, 1H), 1.96 (s, 1H), 1.87 (d, J=1.2 Hz, 3H), 1.85-1.73 (m, 2H), 1.70-1.49 (m, 2H), 1.38 (ddd, J=15.9, 10.4, 6.3 Hz, 2H), 1.26-1.11 (m, 2H), 0.60 (s, 3H). $^{31}$P NMR (162 MHz, CDCl$_3$) δ 152.41, 19.95. $^{13}$C NMR (101 MHz, CDCl$_3$) δ 171.07, 163.62, 163.59, 150.21, 150.19, 148.49, 148.43, 136.61, 135.84, 135.15, 134.57, 134.33, 129.48, 129.42, 127.97, 127.93, 127.81, 118.38, 116.50, 111.52, 85.02, 84.72, 84.70, 84.51, 84.48, 79.25, 79.16, 77.40, 77.28, 77.08, 76.76, 74.93, 74.91, 74.83, 74.81, 68.01, 67.98, 60.35, 52.60, 52.55, 52.47, 52.42, 47.03, 46.67, 38.12, 38.08, 27.18, 25.85, 25.82, 21.01, 17.58, 17.54, 14.19, 12.58, −3.00, −3.27. MS: LCMS, Calculated C32H41N3O8P2Si, 685.7255: Observed in +Ve mode: 686.21 [M+H], 708.14 [M+Na].
Example 7-3. Synthesis of 5′-DMT-2′OMe-5-Lipid-3′-CNE Phosphoramidite—Incorporation of Desired Moieties Through Nucleobases
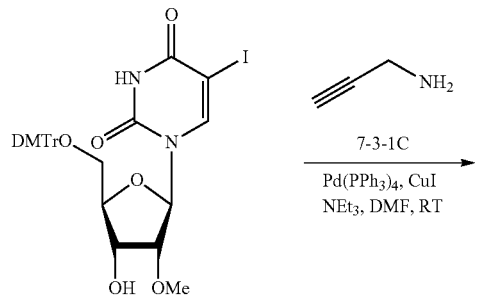
7-3-1
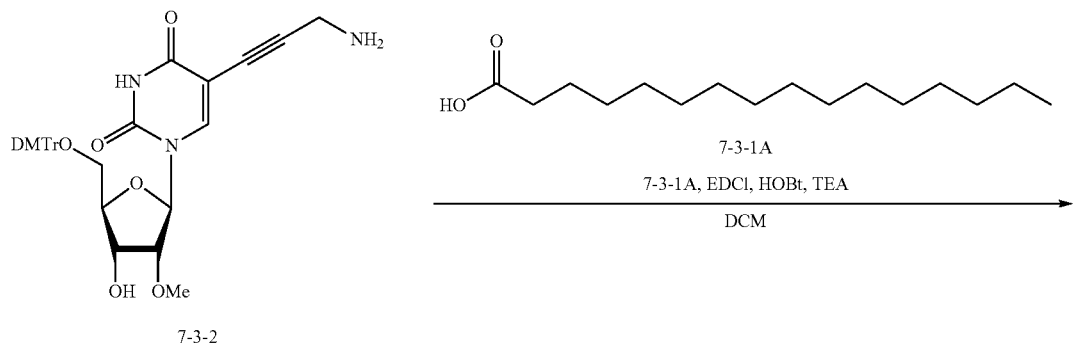
7-3-2
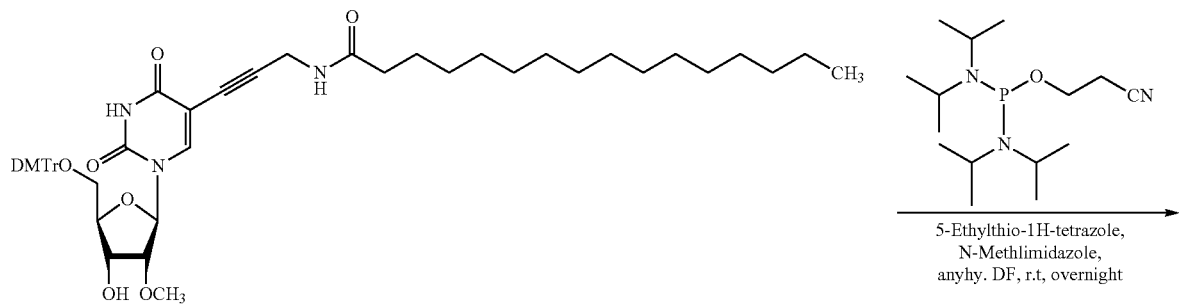
7-3-3

-continued

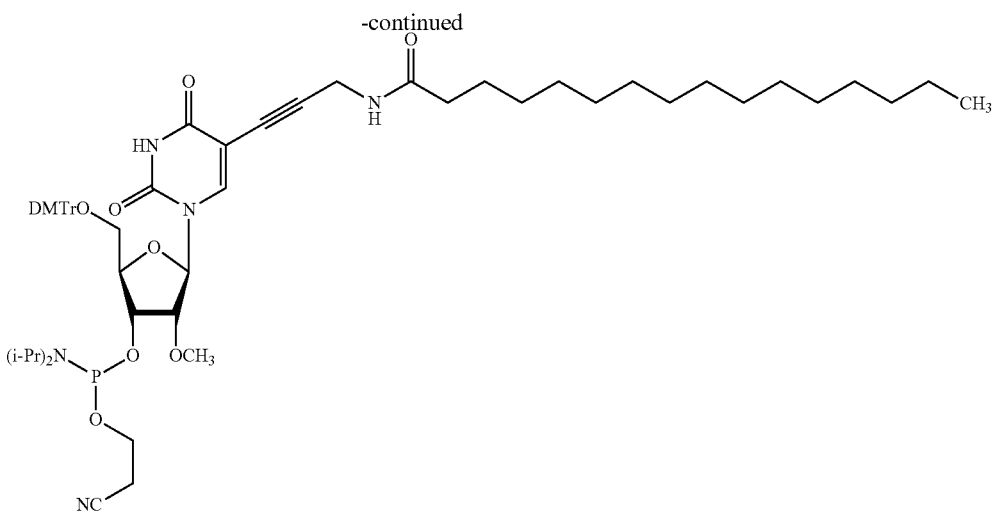

5'-DMT-2'OMe-5-Lipid-3'-CNE phosphoramidite

Preparation of Compound 7-3-2

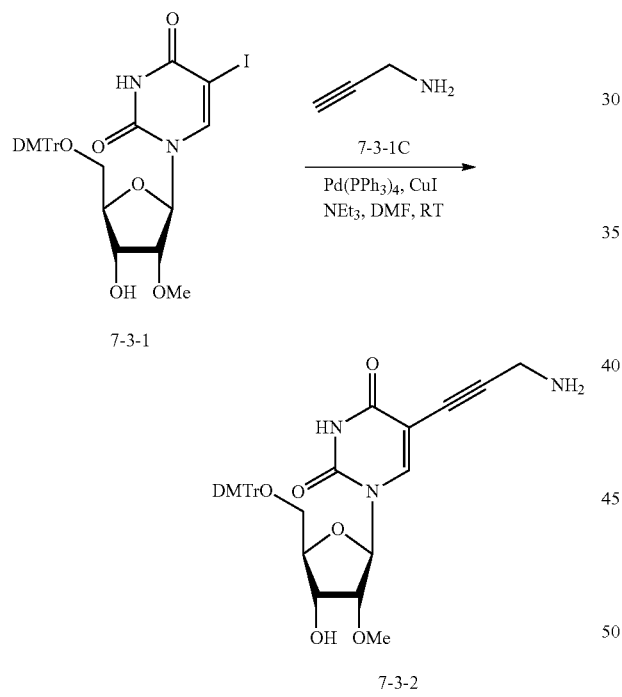

A mixture of compound 7-3-1 (13.00 g, 18.94 mmol), prop-2-yn-1-amine (2.09 g, 37.87 mmol, 2.43 mL), CuI (901.63 mg, 4.73 mmol), Pd(PPh$_3$)$_4$ (2.19 g, 1.89 mmol) and TEA (3.83 g, 37.87 mmol, 5.25 mL) in DMF (130 mL) was degassed and purged with N$_2$ for 3 times, and then the mixture was stirred at 25° C. for 12 hour under N$_2$ atmosphere and dark. LC-MS showed Compound 7-3-1 was consumed completely and one main peak with desired MS was detected. The mixture was concentrated in vacuo. The residue was purified by column chromatography (SiO$_2$, Dichloromethane/Methanol=100/1 to 0:1). Compound 7-3-2 (11.00 g, crude) was obtained as a yellow solid. $^1$H NMR (400 MHz, CDCl$_3$): δ=8.23 (s, 1H), 7.48-7.14 (m, 13H), 6.83 (br d, J=7.3 Hz, 5H), 5.94 (br s, 1H), 4.48 (br t, J=5.8 Hz, 2H), 4.05 (br d, J=6.4 Hz, 2H), 3.93 (br d, J=2.9 Hz, 1H), 3.81-3.70 (m, 8H), 3.62 (s, 4H), 3.52 (br d, J=11.0 Hz, 2H), 3.35 (br d, J=9.0 Hz, 1H). LCMS: (M+H⁺): 614.2. TLC (Dichloromethane/Methanol=10:1) Rf=0.19.

Preparation of Compound 7-3-3

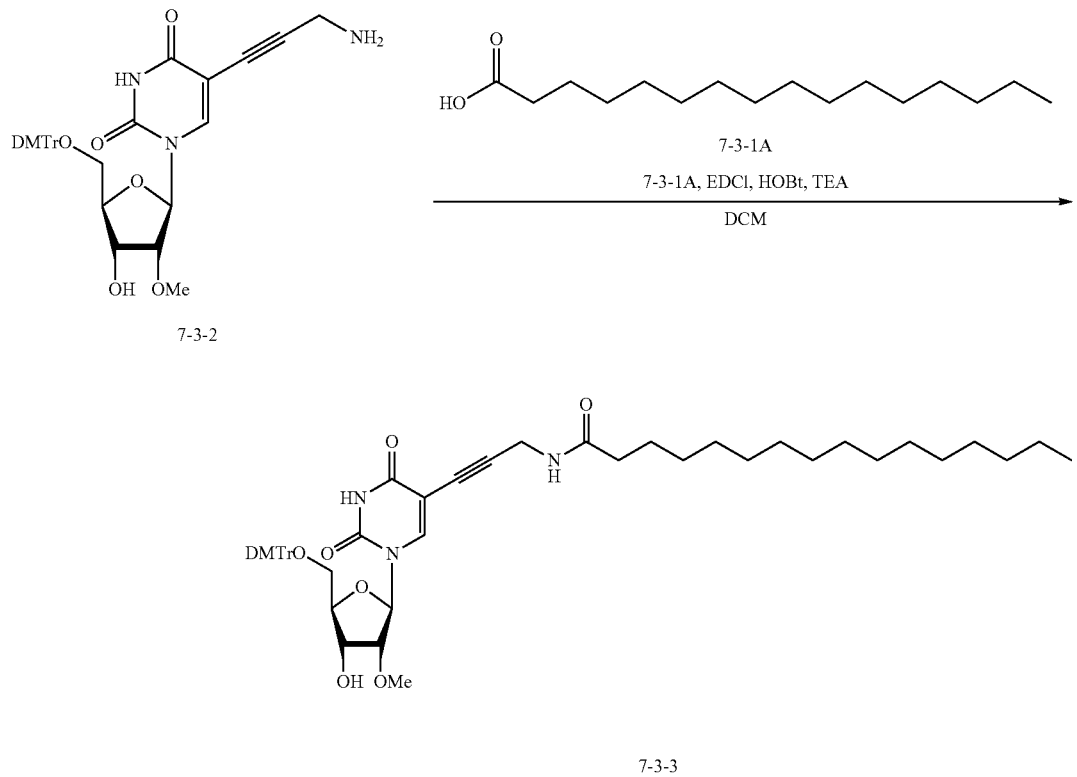

To a solution of palmitic acid (5.06 g, 19.72 mmol) in DCM (130 mL) was added TEA (3.63 g, 35.85 mmol, 4.97 mL), EDCl (5.15 g, 26.89 mmol), HOBt (3.63 g, 26.89 mmol), and Compound 7-3-3 (11.00 g, 17.93 mmol). The mixture was stirred at 25° C. for 1 hour. LC-MS showed Compound 7-3-3 was consumed completely and one main peak with desired MS was detected. The mixture was concentrated in vacuo. The residue was purified by column chromatography (SiO₂, Dichloromethane: Ethyl acetate=10/1 to 0:1 Dichloromethane: Ethyl acetate=100/1 to 0:1). Compound 7-3-3 (6.20 g, 40.58% yield) was obtained as a yellow solid. $^1$H NMR (400 MHz, CDCl₃): δ=8.25 (s, 1H), 7.50-7.14 (m, 10H), 6.90-6.77 (m, 4H), 5.93 (d, J=2.0 Hz, 1H), 5.01 (br s, 1H), 4.53-4.44 (m, 1H), 4.06 (br d, J=6.8 Hz, 1H), 3.94 (dd, J=2.0, 5.1 Hz, 1H), 3.83-3.73 (m, 9H), 3.63 (s, 3H), 3.55-3.48 (m, 1H), 3.39 (dd, J=2.5, 11.1 Hz, 1H), 2.79 (q, J=7.1 Hz, 1H), 1.85-1.76 (m, 2H), 1.50-1.41 (m, 2H), 1.24 (br s, 22H), 0.87 (t, J=6.7 Hz, 3H). $^{13}$CNMR (100 MHz, CDCl₃): δ=172.37, 162.32, 158.66, 158.58, 158.55, 149.58, 144.63, 142.49, 135.55, 135.44, 130.14, 130.00, 129.94, 128.08, 127.86, 126.91, 113.51, 113.35, 99.62, 89.56, 87.56, 86.85, 83.77, 83.68, 74.14, 68.49, 61.77, 58.82, 55.24, 45.30, 36.10, 31.89, 29.84, 29.67, 29.63, 29.49, 29.37, 29.33, 25.42, 22.66, 14.79, 14.11, 9.74. LCMS: (M+H⁺): 850.4.

Preparation of 5'-DMT-2'OMe-5-Lipid-3'-CNE Phosphoramidite

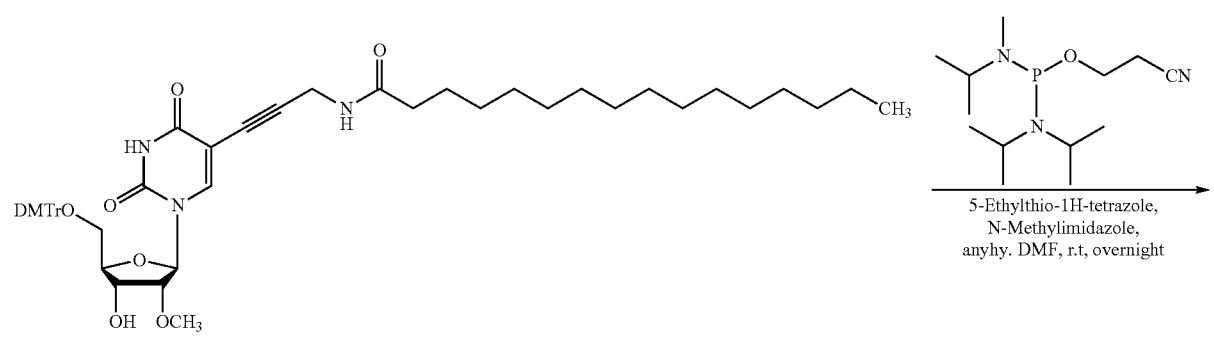

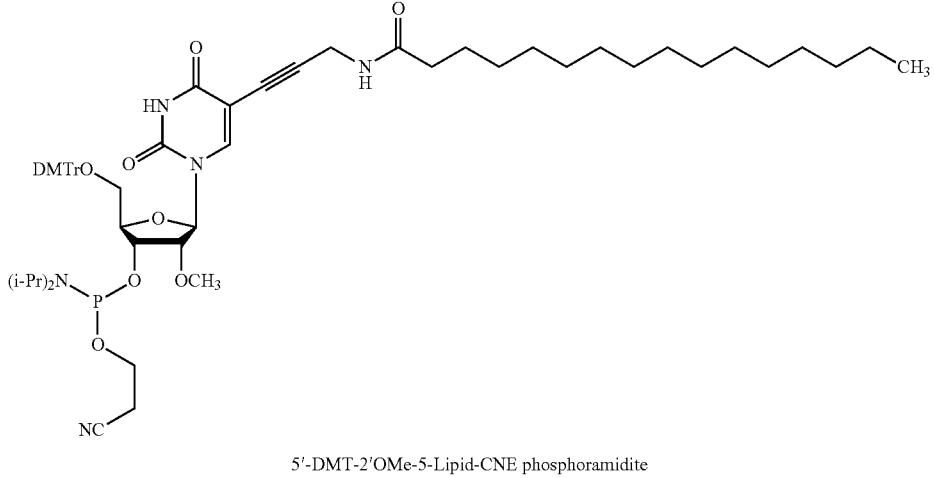

5'-DMT-2'OMe-5-Lipid-CNE phosphoramidite

Compound 7-3-3 (2.8 g, 3.29 mmol) was co-evaporated with anhydrous toluene two times (25 mL×2) and dried under high vacuum overnight. The dried foamy solid was dissolved in anhydrous DMF (5 ml) and was added 5-ethylthio-1H-tetrazole (0.43 g, 3.29 mmol), N-methylimidazole (0.052 mL, 0.66 mmol) followed by 2-cyanoethyl-N,N,N',N'-tetraisopropylphosphordiamidite (1.49 g, 4.93 mmol). The reaction mixture was stirred at room temperature under argon atmosphere for overnight. After TLC indicated completion, the reaction was diluted with EtOAc (70 mL) and washed with aq. saturated. NaHCO$_3$ solution (10 mL), and dried over Mg$_2$SO$_4$. The solvent was evaporated under reduced pressure and dried in high vacuum for night. The dried crude product was purified by Combi-Flash Rf (Teledyne ISCO) using 80 g silica column (which was pre-deactivated with 3 column volume of ethyl acetate with 5% TEA) with Hexane/Ethyl acetate/Acetonitrile which contains 5% TEA as an eluent to afford 5'-DMT-2'OMe-5-Lipid-3'CNE phosphoramidite as a foamy solid. Yield 3.1 g (90%). $^{31}$P NMR (162 MHz, CDCl$_3$) δ 150.58 (s) 150.26 (s). $^{13}$C NMR (101 MHz, CDCl$_3$) δ 172.20, 172.18, 161.78, 161.66, 158.70, 158.68, 149.45, 149.35, 144.71, 144.57, 142.69, 142.62, 137.91, 135.63, 135.53, 135.49, 135.40, 130.16, 130.11, 128.08, 128.06, 128.01, 127.00, 126.97, 117.71, 117.51, 113.39, 113.36, 113.32, 99.75, 99.46, 89.30, 89.26, 88.49, 88.00, 87.05, 86.84, 83.86, 83.04, 82.98, 82.93, 82.66, 77.39, 77.27, 77.07, 76.75, 74.45, 74.30, 69.88, 69.77, 69.64, 62.10, 61.24, 58.94, 58.92, 58.65, 58.47, 58.44, 57.97, 57.76, 55.30, 55.27, 43.35, 43.32, 43.23, 43.19, 36.11, 36.09, 33.26, 31.90, 29.88, 29.67, 29.65, 29.63, 29.58, 29.50, 29.37, 29.33, 25.41, 24.70, 24.64, 24.61, 24.57, 24.54, 24.50, 22.66, 20.47, 20.40, 20.34, 20.27, 14.82, 14.09. $^1$H NMR (400 MHz, Chloroform-d) δ 7.40 (dd, J=10.5, 7.6 Hz, 2H), 7.35-7.12 (m, 7H), 6.78 (ddd, J=9.0, 4.2, 2.7 Hz, 4H), 4.82 (dt, J=22.1, 4.9 Hz, 1H), 4.57-4.38 (m, 1H), 4.24-4.10 (m, 1H), 4.06-3.96 (m, 1H), 3.86-3.67 (m, 7H), 3.67-3.58 (m, 2H), 3.57-3.39 (m, 6H), 3.25 (ddd, J=13.5, 11.3, 2.8 Hz, 1H), 2.55 (t, J=6.1 Hz, 1H), 2.30 (t, J=6.2 Hz, 1H), 1.71 (qd, J=7.4, 7.0, 1.4 Hz, 2H), 1.38 (dtt, J=10.5, 7.7, 2.8 Hz, 2H), 1.09 (dd, J=6.7, 5.1 Hz, 17H), 0.97 (d, J=6.8 Hz, 3H), 0.80 (t, J=6.6 Hz, 3H). MS: LCMS: Calculated, C59H82N5O10P; 1051.5730; Observed +Ve mode: m/z: 1153.69 [M+Et$_3$N].

Example 7-4. Synthesis of 5'-(R)—C-Me-5'-DMT-dT-CNE Amidite

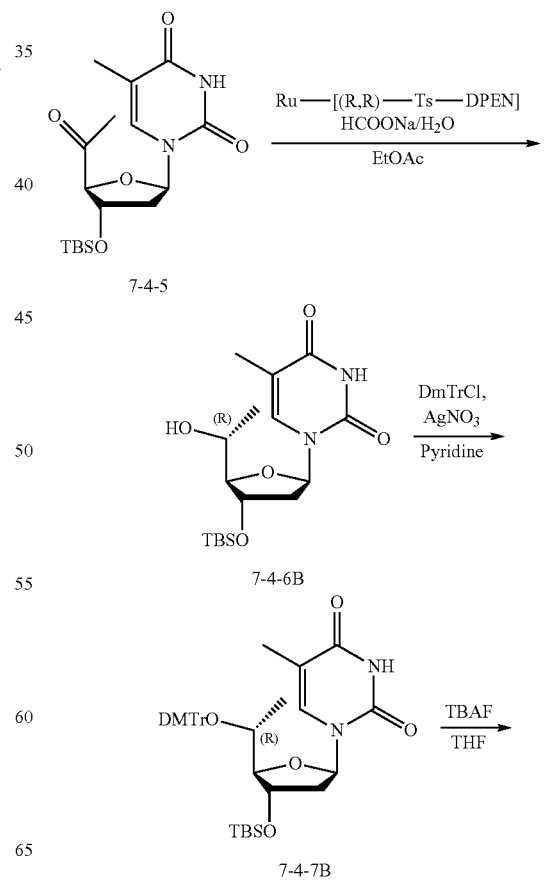

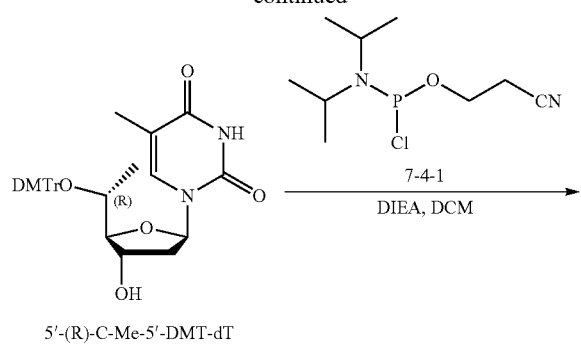

5'-(R)-C-Me-5'-DMT-dT

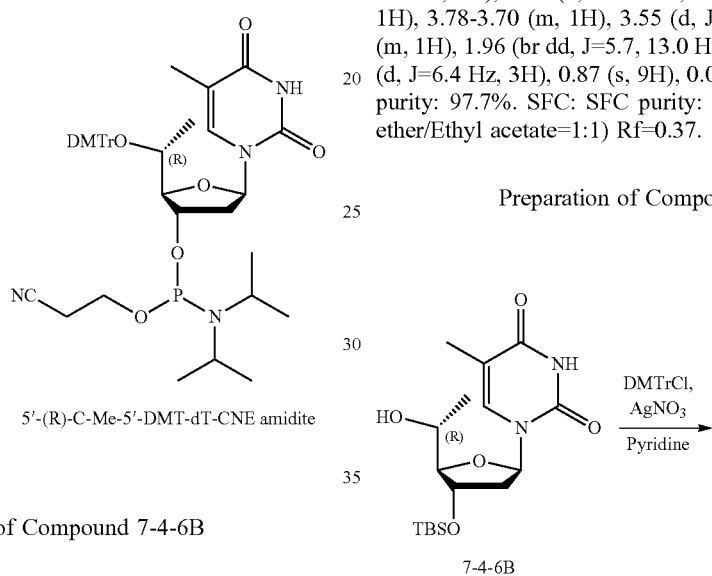

5'-(R)-C-Me-5'-DMT-dT-CNE amidite

Preparation of Compound 7-4-6B

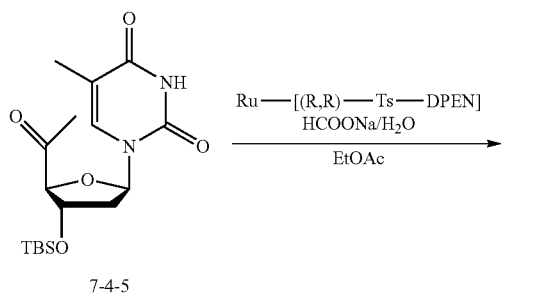

To a solution of compound 7-4-5 (46.00 g, 124.83 mmol) in a mixture of EtOAc (460.00 mL) and sodium formate (353.17 g, 5.19 mol) dissolved in Water (1.84 L), and then [[(1R,2R)-2-amino-1,2-diphenyl-ethyl]-(p-tolylsulfonyl)amino]-chloro-ruthenium; 1-isopropyl-4-methyl-benzene (1.59 g, 2.50 mmol) was added. The resulting two-phase mixture was stirred for 12 h at 25° C. under $N_2$. TLC showed the starting material was consumed. The mixture was extracted with EtOAc (50 mL*3). The combined organic was washed with brine (30 mL), dried over $Na_2SO_4$, filtered and concentrated to get the crude. The residue was purified by re-crystallization from Petroleum ether/Ethyl acetate=5:1 to give the compound 7-4-6B as a white solid (36.00 g, 77.83% yield) as a white solid. $^1$H NMR (400 MHz, DMSO-d6): δ=11.31 (s, 1H), 7.67 (s, 1H), 6.16 (dd, J=5.5, 8.8 Hz, 1H), 5.05 (d, J=5.1 Hz, 1H), 4.49 (br d, J=5.1 Hz, 1H), 3.78-3.70 (m, 1H), 3.55 (d, J=3.7 Hz, 1H), 2.20-2.09 (m, 1H), 1.96 (br dd, J=5.7, 13.0 Hz, 1H), 1.77 (s, 3H), 1.11 (d, J=6.4 Hz, 3H), 0.87 (s, 9H), 0.09 (s, 6H). HPLC: HPLC purity: 97.7%. SFC: SFC purity: 99.1%. TLC (Petroleum ether/Ethyl acetate=1:1) Rf=0.37.

Preparation of Compound 7-4-7B

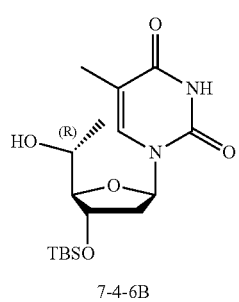

Compound 7-4-6B (18.00 g, 48.58 mmol) was dried by azeotropic distillation on a rotary evaporator with pyridine (100 mL) and toluene (100 mL*2). A solution of compound 7-4-6B (18.00 g, 48.58 mmol) and DMTCl (1.89 g, 5.59 mmol) in the mixture of pyridine (180.00 mL) and THF (720.00 mL) was degassed and purged with $N_2$ for 3 times and then $AgNO_3$ (14.19 g, 83.56 mmol) was added. The mixture was stirred at 25° C. for 15 hr. TLC showed the starting material was consumed. MeOH (5 mL) was added and stirred for 15 min and then the mixture was filtered and the cake was washed with toluene (300 mL*3). The filtrate was concentrated to obtain the compound 7-4-7B as a yellow oil (65.38 g, crude). The mixture was used directly to next step without any purification. TLC (Petroleum ether/Ethyl acetate) Rf=0.63.

577
Preparation of 5'-(R)—C-Me-5'-DMTr-dT

578
Preparation of 5'-(R)—C-Me-5'-DMT-dT-CNE-amidite

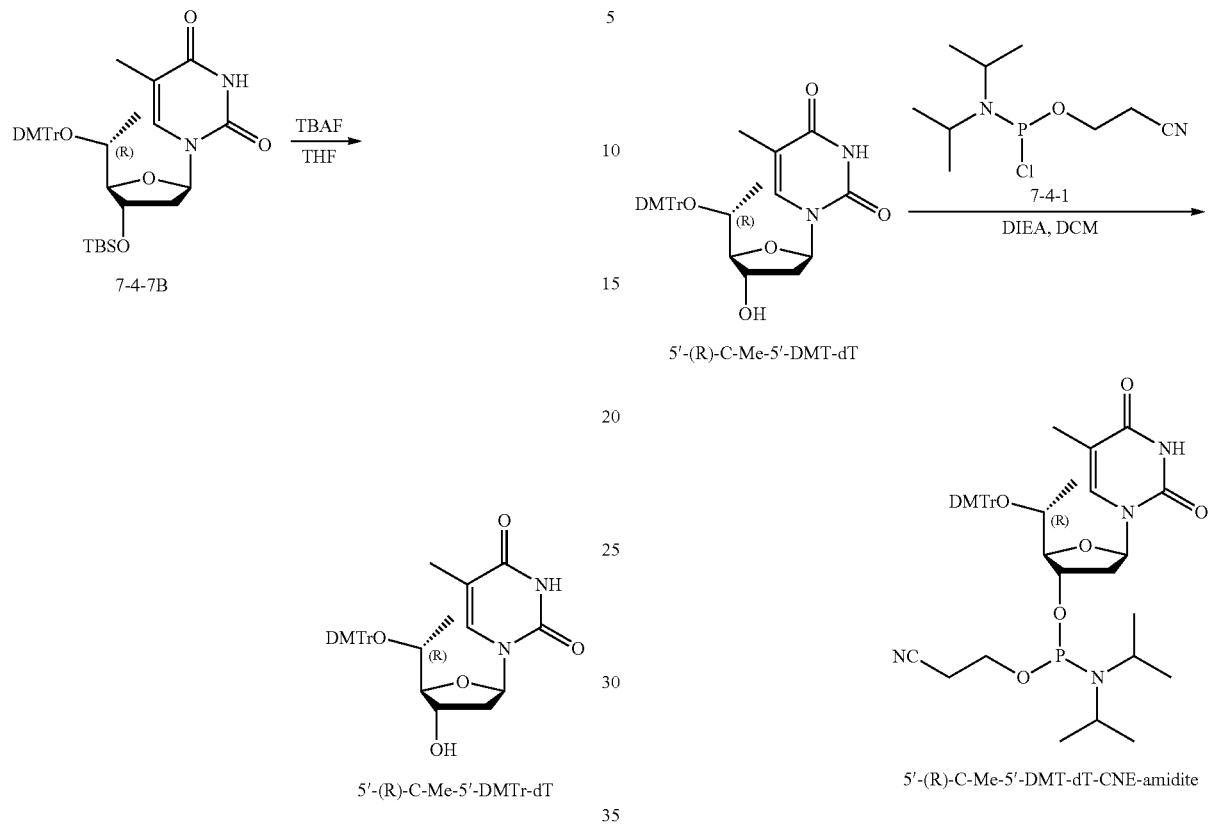

To a solution of compound 7-4-7B (65.38 g, 97.16 mmol) in THF (650.00 mL) was added TBAF (1 M, 184.60 mL). The mixture was stirred at 25° C. for 12 hours. TLC showed the starting material was consumed. The mixture was concentrated to provide the crude and then sat. NaCl (5% aq., 200 mL*2) was added and the mixture was extracted with EtOAc (200 mL*3). The combined organic phase was dried over $Na_2SO_4$, filtered and concentrated to provide the crude product, which was purified by MPLC (Petroleum ether: Ethyl acetate 5:1,1:1,1:4,5% TEA) to provide 5'-(R)—C-Me-5'-DMTr-dT as a white solid (47.50 g, 85.03 mmol, 87.52% yield). $^1$H NMR (400 MHz, DMSO-d6): δ=11.32 (s, 1H), 7.46 (br d, J=7.8 Hz, 2H), 7.37-7.25 (m, 6H), 7.23-7.16 (m, 1H), 7.07 (s, 1H), 6.89 (dd, J=4.6, 8.5 Hz, 4H), 6.12 (t, J=7.2 Hz, 1H), 5.27 (d, J=4.6 Hz, 1H), 4.54-4.46 (m, 1H), 3.73 (d, J=1.8 Hz, 6H), 3.62 (t, J=2.9 Hz, 1H), 3.40-3.34 (m, 1H), 2.09-2.02 (m, 2H), 1.40 (s, 3H), 0.77 (d, J=6.2 Hz, 3H). $^{13}$C NMR (101 MHz, DMSO-d6): δ=163.98, 158.58, 150.81, 146.95, 137.11, 136.79, 135.76, 130.49, 130.41, 128.20, 128.15, 127.04, 113.54, 113.52, 110.16, 89.87, 86.24, 83.35, 70.28, 70.05, 60.20, 55.47, 55.35, 21.20, 17.82, 14.52, 12.08. HPLC: HPLC purity: 98.7%. LC-MS: (M−H$^+$)=557.2. LCMS purity: 98.9%. SFC: SFC purity: 100.0%. TLC (Petroleum ether/Ethyl acetate=1:1, 5% TEA) Rf=0.02.

5'-(R)—C-Me-5'-OMT-dT (5 g, 8.95 mmol) was dried with toluene (50 mL). To a solution of DIEA (1.39 g, 10.74 mmol, 1.87 mL) and 5'-(R)—C-Me-5'-DMT-dT (5 g, 8.95 mmol) in anhydrous DCM (50 mL) was added compound 7-4-1 (2.76 g, 9.40 mmol) under $N_2$ at 0° C. The mixture was stirred at 15° C. for 2 h. TLC showed the starting material was consumed and two new spots were found. The mixture was quenched by addition of saturated aq. $NaHCO_3$ (20 mL) and extracted with DCM (30 mL*3). The combined organic phase was dried over $Na_2SO_4$, filtered and concentrated to provide the crude product, which was purified on a Combiflash instrument from Teledyne. A 40 g silica gel cartridge column was first pre-treated by eluting with 10% EtOAc/Petroleum ether containing 5% $Et_3N$ (300 mL). The crude product was dissolved in a 2:1 volume: volume mixture of methylene chloride: petroleum ether containing 5% $Et_3N$ and loaded onto the column. After loading, the purification process was run using the following gradient: 10 to 50% EtOAc/Petroleum ether containing 5% $Et_3N$. Fractions were collected. After evaporation of the solvent, 5'-(R)—C-Me-5'-DMT-dT-CNE-amidite was obtained as a white solid (3.6 g, 53% yield). $^1$H NMR (400 MHz, CHLOROFORM-d) δ=8.11 (br s, 1H), 7.53 (br d, J=7.7 Hz, 3H), 7.42 (br t, J=8.2 Hz, 4H), 7.32-7.17 (m, 4H), 7.07-6.99 (m, 1H), 6.84 (br d, J=8.2 Hz, 4H), 6.31 (br dd, J=5.5, 8.7 Hz, 1H), 4.94 (br s, 1H), 3.96-3.73 (m, 10H), 3.72-3.41 (m, 4H), 2.65 (td, J=6.1, 18.0 Hz, 2H), 2.53-2.37 (m, 1H), 2.10 (br d, J=8.2 Hz, 1H), 1.47 (br s, 4H), 1.33-1.16 (m, 15H), 1.00-0.90 (m, 3H). $^{31}$P NMR (162 MHz, CHLOROFORM-d) δ=148.81 (s, 1P), 148.35 (s, 1P).

Example 7-5. Synthesis of 5'-(S)—C-Me-5'-DMT-dT-CNE Amidite
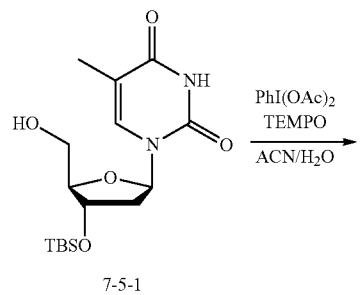
7-5-1
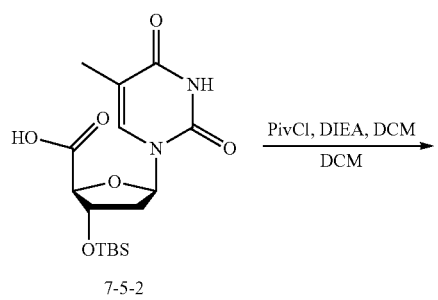
7-5-2
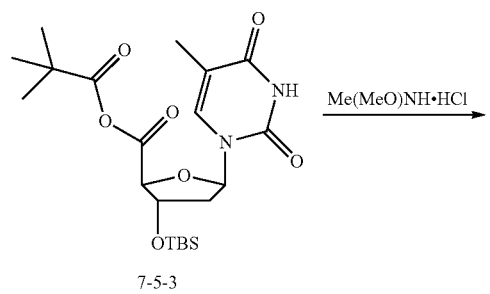
7-5-3
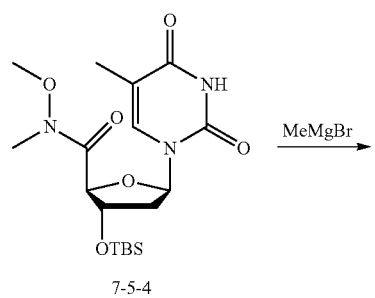
7-5-4
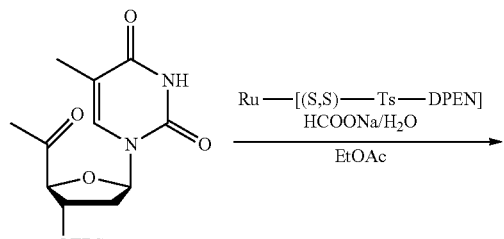
7-5-5
-continued
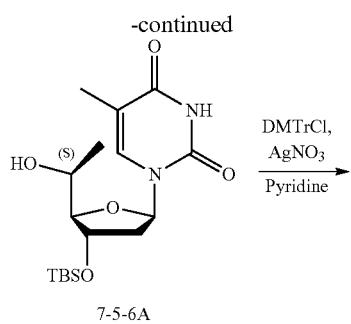
7-5-6A
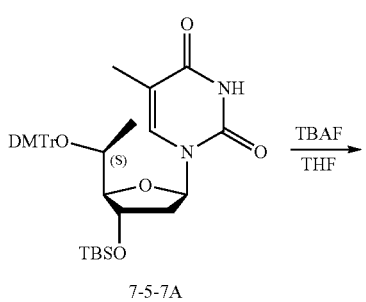
7-5-7A
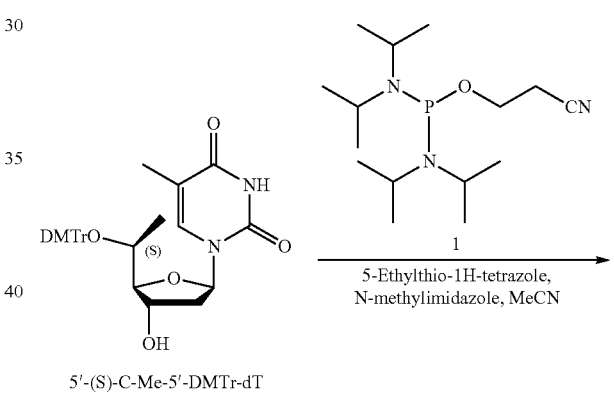
5'-(S)-C-Me-5'-DMTr-dT
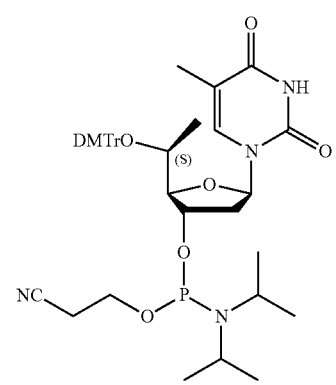
5'-(S)-C-Me-5'-DMT-dT-CNE-phosphoramidite

Preparation of Compound 7-5-2

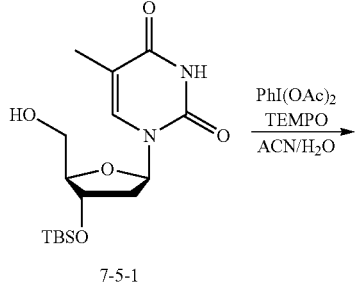

7-5-1

To a solution of compound 7-5-1 (63.00 g, 176.72 mmol) in the mixture of H₂O (250.00 mL) and MeCN (250.00 mL) was added PhI(OAc)₂ (125.23 g, 388.79 mmol) and TEMPO (5.56 g, 35.34 mmol) at 10° C. The mixture was stirred at 25° C. for 2 hours. TLC (Petroleum ether/Ethyl acetate=1:1, Rf=0) showed the starting material was consumed. The mixture was concentrated, and MTBE (1 L) was added. The mixture was stirred for 0.5 h and then filtered. The cake was washed with MTBE (1 L*2), and dried to provide compound 7-5-2 as a white solid (126 g, 96.23% yield). ¹H NMR (400 MHz, DMSO): δ=11.21 (s, 1H), 7.89 (d, J=1.0 Hz, 1H), 6.18 (dd, J=5.9, 8.6 Hz, 1H), 4.61-4.41 (m, 1H), 4.17 (d, J=0.9 Hz, 1H), 2.51-2.26 (m, 3H), 2.09-1.85 (m, 2H), 1.74-1.58 (m, 3H), 0.90-0.58 (m, 10H), 0.00 (d, J=2.0 Hz, 6H). LC-MS: (M+H⁺): 371.1. TLC (Petroleum ether/Ethyl acetate=1:1) Rf=0.

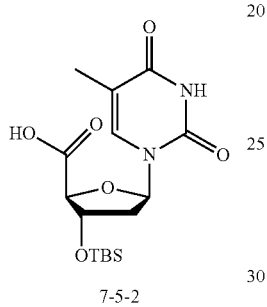

7-5-2

Preparation of Compound 7-5-3

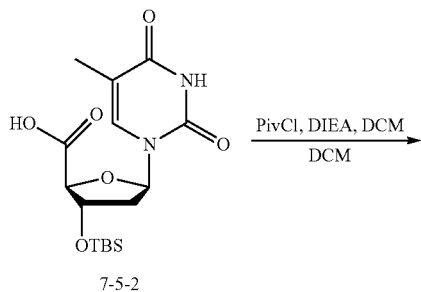

7-5-2

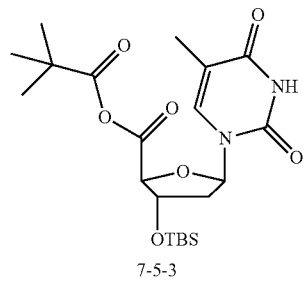

7-5-3

To a solution of compound 7-5-2 (50.00 g, 134.96 mmol) in DCM (500.00 mL) was added DIEA (34.89 g, 269.92 mmol, 47.15 mL) and 2,2-dimethylpropanoyl chloride (21.16 g, 175.45 mmol). The mixture was stirred at −10-0° C. for 1.5 hours. TLC showed the starting material was consumed. The mixture in DCM was used directly for next step. TLC (Petroleum ether/Ethyl acetate=1:1) Rf=0.15.

Preparation of Compound 7-5-4

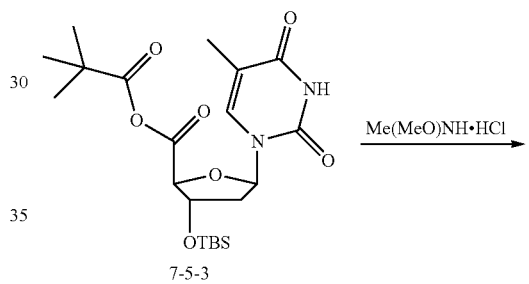

7-5-3

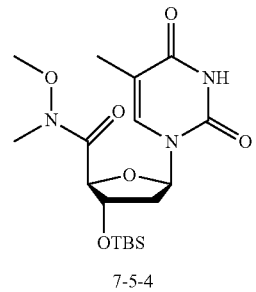

7-5-4

To compound 7-5-3 in DCM was added TEA (40.94 g, 404.55 mmol, 56.08 mL) and N-methoxymethanamine hydrochloride (19.73 g, 202.27 mmol). The mixture was stirred at 0° C. for 1 h. TLC showed the starting material was consumed. The mixture was washed with HCl (1N, 100 mL) and then aqueous NaHCO₃ (100 mL). The organic layer was dried over Na₂SO₄, filtered and concentrated to provide the crude product, which was purified by silica gel chromatography (Petroleum ether/Ethyl acetate=30/1, 0/1) to afford compound 7-5-4 as a white solid (95.5 g, 85.63% yield). ¹H NMR (400 MHz, CDCl₃): δ=8.29 (s, 1H), 8.19 (br s, 1H), 6.46 (dd, J=5.1, 9.3 Hz, 1H), 4.71 (s, 1H), 4.38 (d, J=4.2 Hz, 1H), 3.65 (s, 3H), 3.15 (s, 3H), 2.18-2.08 (m, 1H), 2.00-1.90 (m, 1H), 1.87 (d, J=1.1 Hz, 3H), 0.88-0.74 (m, 10H), 0.00 (d, J=3.7 Hz, 6H). TLC (Petroleum ether/Ethyl acetate=1:1) Rf=0.43.

Preparation of Compound 7-5-5

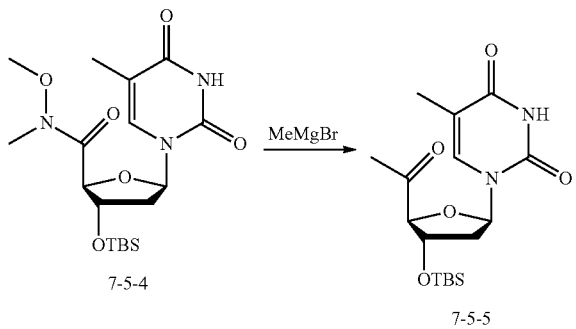

To a solution of compound 7-5-4 (115.00 g, 278.09 mmol) in THF (1.20 L) was added MeMgBr (3 M, 185.39 mL) at 0° C. The mixture was stirred at 0° C. for 2 h. TLC showed the starting material was consumed. To the mixture was added water (1 L) at 0° C. and the mixture was extracted with EtOAc (300 mL*2). The combined organic phase was dried over $Na_2SO_4$, filtered and concentrated to provide the compound 7-5-5 as a white solid (100.00 g, 97.58% yield). The mixture was used directly without further purification. $^1$H NMR (400 MHz, $CDCl_3$): δ=8.81 (br s, 1H), 7.95 (s, 1H), 6.41 (dd, J=5.6, 8.1 Hz, 1H), 4.60-4.40 (m, 2H), 2.40-2.16 (m, 4H), 1.98 (s, 3H), 1.02-0.83 (m, 10H), 0.14 (d, J=3.3 Hz, 6H), 0.20-0.00 (m, 1H). TLC (Petroleum ether/Ethyl acetate=1:1) Rf=0.68.

Preparation of Compound 7-5-6A

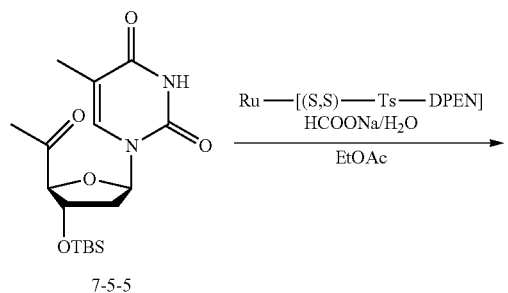

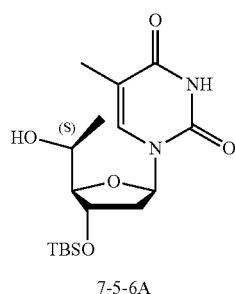

To a solution of compound 7-5-5 (46.00 g, 124.83 mmol) in the mixture of EtOAc (460.00 mL) and sodium formate (353.17 g, 5.19 mol) dissolved in water (1.84 L), and N-[(1S,2S)-2-amino-1,2-diphenyl-ethyl]-4-methyl-benzenesulfonamide chlororuthenium; 1-isopropyl-4-methyl-benzene (1.59 g, 2.50 mmol) was added. The resulting two-phase mixture was stirred for 12 h at 25° C. under $N_2$. TLC showed the starting material was consumed. The mixture was extracted with EtOAc (500 mL*3). The combined organic was washed with brine (300 mL), dried over $Na_2SO_4$, filtered and concentrated to provide the crude product. The mixture was purified by MPLC (Petroleum ether/MTBE=10:1 to 1:1) seven times to provide compound 7-5-6A as a yellow oil (25.6 g, 57.53% yield). $^1$H NMR (400 MHz, DMSO-d6): δ=11.28 (s, 1H), 7.85 (s, 1H), 6.16 (t, J=6.8 Hz, 1H), 5.04 (d, J=4.6 Hz, 1H), 4.46-4.29 (m, 1H), 3.79 (br t, J=6.8 Hz, 1H), 3.59 (br s, 1H), 3.32 (s, 1H), 2.21-2.09 (m, 1H), 2.06-1.97 (m, 1H), 1.76 (s, 3H), 1.17-1.08 (m, 4H), 0.91-0.81 (m, 10H), 0.08 (s, 6H). SFC: SFC purity: 98.6%. TLC (Petroleum ether/Ethyl acetate=1:1) Rf=0.38.

Preparation of Compound 7-5-7A

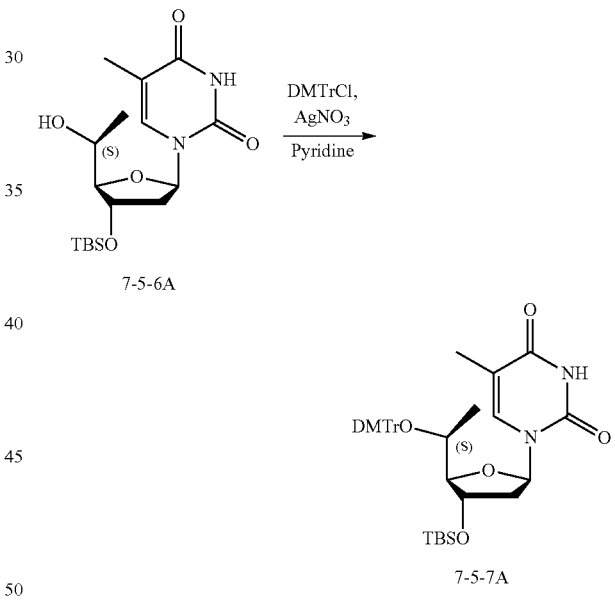

Compound 7-5-6A (12.80 g, 34.55 mmol) was dried by azeotropic distillation on a rotary evaporator with pyridine (100 mL) and toluene (100 mL*2). To a solution of compound 7-5-6A (12.80 g, 34.55 mmol) and DMTCl (1.89 g, 5.59 mmol) in the mixture of pyridine (120.00 mL) and THF (400.00 mL) was degassed and purged with $N_2$ for 3 times and then $AgNO_3$ (10.09 g, 59.43 mmol) was added. The mixture was stirred at 25° C. for 15 hr. TLC showed the starting material was consumed. MeOH (5 mL) was added and stirred for 15 min and then the mixture was filtered and the cake was washed with toluene (300 mL*3). The filtrate was concentrated to get the compound 7-7-7A as a yellow oil (46.50 g, crude). The mixture was used directly to next step without any purification. TLC (Petroleum ether/Ethyl acetate) Rf=0.63.

Preparation of 5'-(S)—C-Me-5'-DMT-dT

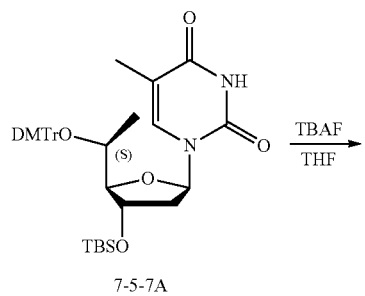

7-5-7A

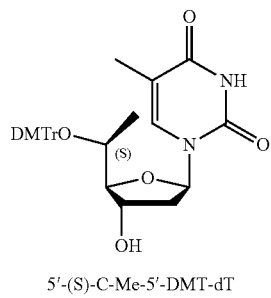

5'-(S)-C-Me-5'-DMT-dT

To a solution of compound 7-5-7A (46.50 g, 69.11 mmol) in THF (460.00 mL) was added TBAF (1 M, 131.31 mL). The mixture was stirred at 25° C. for 5 hrs. TLC showed the starting material was consumed. The mixture was concentrated and then sat. NaCl (5% aq., 200 mL) was added and the aqueous phase was extracted with EtOAc (200 mL*3). The combined organic layer was dried over $Na_2SO_4$, filtered and concentrated to provide the crude product, which was purified by MPLC (Petroleum ether/Ethyl acetate 5:1, 1:1, 1:4, 5% TEA) to provide 5'-(S)—C-Me-5'-DMT-dT as a white solid (29.0 g, 75.12% yield). $^1$H NMR (400 MHz, DMSO-d6): δ=11.35 (s, 1H), 7.56 (s, 1H), 7.58-7.53 (m, 1H), 7.44 (d, J=7.8 Hz, 2H), 7.37-7.24 (m, 6H), 7.23-7.17 (m, 1H), 6.87 (t, J=8.3 Hz, 4H), 6.13 (t, J=6.9 Hz, 1H), 5.21 (d, J=4.9 Hz, 1H), 4.23 (br s, 1H), 3.73 (d, J=2.9 Hz, 6H), 3.67 (t, J=3.7 Hz, 1H), 3.57-3.46 (m, 1H), 2.23-2.04 (m, 2H), 1.67 (s, 3H), 1.70-1.65 (m, 1H), 0.71 (d, J=6.2 Hz, 3H). $^{13}$CNMR (101 MHz, DMSO-d6): δ=170.78, 164.16, 158.64, 158.59, 150.86, 146.71, 137.00, 136.75, 135.97, 130.65, 130.52, 128.38, 128.07, 127.11, 113.48, 110.11, 89.78, 86.41, 83.87, 70.58, 70.22, 60.21, 55.48, 21.20, 18.08, 14.53, 12.54. HPLC: HPLC purity: 98.4%. LCMS: (M−H+) =557.2; LCMS purity: 99.0%. SFC: SFC purity: 99.4%. TLC (Petroleum ether/Ethyl acetate=1:1, 5% TEA) Rf=0.01.

Preparation of 5'-(S)—C-Me-5'-DMT-dT-CNE-amidite

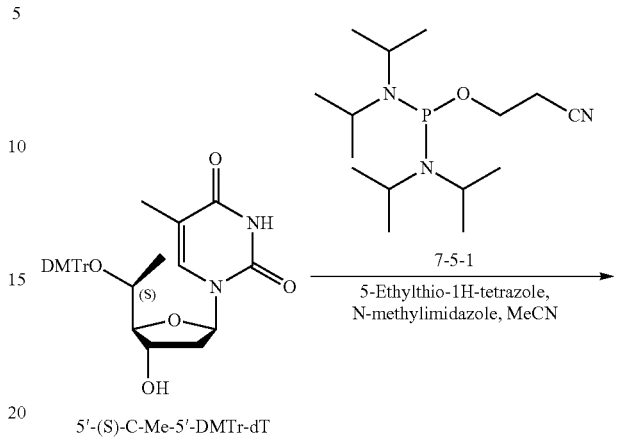

5'-(S)-C-Me-5'-DMTr-dT

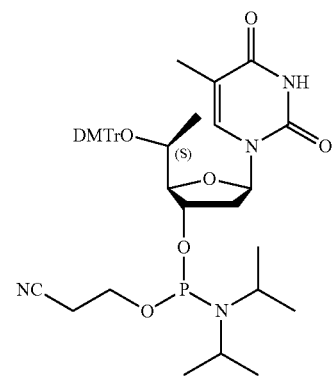

5'-(S)-C-Me-5'-DMT-dT-CNE-amidite

To a solution of 5'-(S)—C-Me-5'-DMT-dT (5.00 g, 8.95 mmol) in MeCN (50.00 mL) was added 5-ethylsulfanyl-2H-tetrazole (1.17 g, 8.95 mmol), 1-methylimidazole (1.47 g, 17.90 mmol, 1.43 mL) and compound 7-5-1 (4.05 g, 13.43 mmol, 4.26 mL). The reaction mixture was stirred at 20° C. under $N_2$ for 2 hrs. TLC and LC-MS showed some starting material was consumed and the desired substance was formed. The reaction mixture was concentrated under reduced pressure, and the residue was diluted with EtOAc (20 mL). The reaction mixture was washed with aq. saturated $NaHCO_3$ solution (20 mL), dried over $Na_2SO_4$, filtered and concentrated to provide the crude product, which was purified by MPLC (Petroleum ether 5% TEA: Ethyl acetate from 10:1 to 1:1) to provide 5'-(S)—C-Me-5'-DMT-dT-CNE-amidite as a white solid (4.3 g, 63.31% yield). $^1$H NMR (400 MHz, CHLOROFORM-d) δ=8.19 (br s, 1H), 7.69-7.60 (m, 1H), 7.54 (s, 1H), 7.43-7.33 (m, 2H), 7.32-7.07 (m, 8H), 6.73 (ddd, J=3.7, 5.8, 9.0 Hz, 4H), 6.27-6.15 (m, 1H), 4.49-4.37 (m, 1H), 3.82-3.65 (m, 8H), 3.63-3.55 (m, 2H), 3.53-3.39 (m, 3H), 2.50 (t, J=6.3 Hz, 1H), 2.46-2.31 (m, 1H), 2.29-2.19 (m, 1H), 2.16-2.04 (m, 1H), 1.68 (s, 3H), 1.20-1.00 (m, 13H), 0.95 (d, J=6.8 Hz, 3H), 0.92-0.74 (m, 4H). $^{31}$P NMR (162 MHz, CHLOROFORM-d) δ=149.11 (s, 1P), 148.99 (s, 1P).

Example 7-6. Synthesis of L-DPSE-5'-(R)—C-Me-5'-DMT-dT Amidite

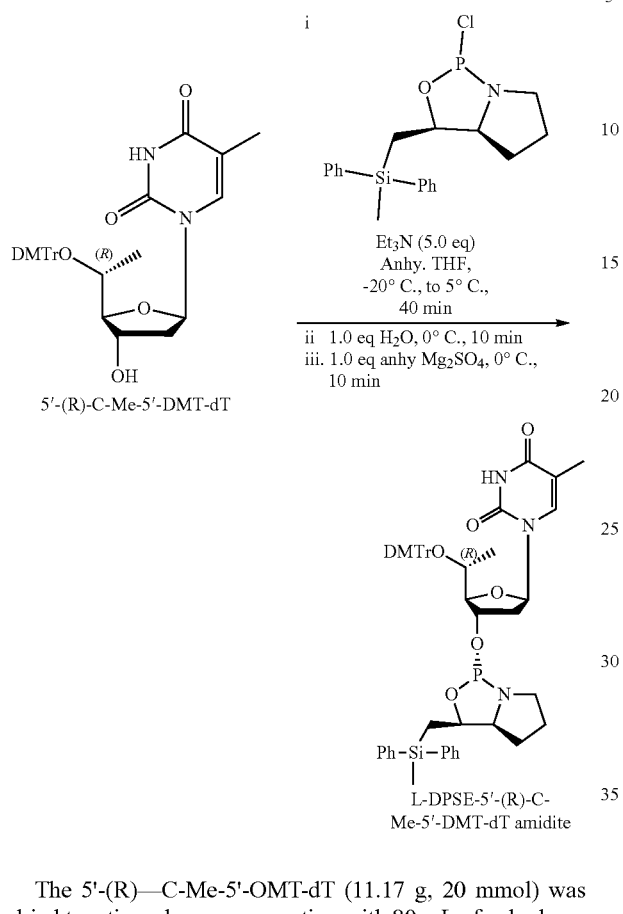

The 5'-(R)—C-Me-5'-OMT-dT (11.17 g, 20 mmol) was dried two times by co-evaporation with 80 mL of anhydrous toluene at 45° C. and kept at high vacuum for overnight. Then the dried 5'-(R)—C-Me-5'-OMT-dT was dissolved in dry THF (80 mL) in 500 mL three neck flasks under argon, followed by the addition of triethylamine (13.93 mL, 100 mmol) and the mixture was cooled to −40° C. To this cooled reaction mixture was added the solution of the crude L-DPSE-NOPCl (30 mmol, 1.4 eq, in THF 40 mL), from a stock through syringe dropwise (~15 min, maintaining the internal temperature −40- to −35° C.). The mixture was then gradually warmed to 5° C. After 30 min at 5° C., TLC and LC-MS analysis indicated the complete conversion of SM to product (total reaction time 2 h). The reaction mixture was cooled in an ice bath and the reaction quenched by addition of water (0.36 mL, 20 mmol). The mixture was stirred for 10 min followed by addition of anhydrous $Mg_2SO_4$ (3.0 g, 20 mmol). The reaction was filtered through Airfree, Schlenk filter tube, washed with dry THF (60 mL) and the solvent was evaporated under rotary evaporation at 28° C. to afford the crude product as a off-white solid which was dried under high vacuum for overnight. The dried crude product was purified by Combi-Flash Rf (Teledyne ISCO) using a 220 silica column (which was pre-deactivated with 3 column volume of ethyl acetate with 5% TEA) with ethyl acetate/hexane mixture contains 5% TEA as a solvent. Fractions were analyzed by TLC and LC-MS and pooled together. Solvent was evaporated in a rotary evaporator at 28° C. and the residue was dried under high vacuum to afford the product as a white solid. Yield: 16.3 g (91%). $^1H$ NMR (400 MHz, Chloroform-d) δ 7.50-7.36 (m, 6H), 7.35-7.06 (m, 13H), 6.85 (d, J=1.4 Hz, 1H), 6.73 (dq, J=8.7, 3.2 Hz, 4H), 6.13 (dd, J=9.3, 5.3 Hz, 1H), 5.10 (td, J=7.8, 7.1, 3.4 Hz, 1H), 4.80 (dt, J=8.6, 5.8 Hz, 1H), 4.04 (q, J=7.1 Hz, 1H), 3.69 (d, J=2.3 Hz, 6H), 3.57-3.36 (m, 3H), 3.29-3.05 (m, 2H), 2.05 (dd, J=13.6, 5.5 Hz, 1H), 1.96 (s, 2H), 1.73-1.50 (m, 3H), 1.47-1.32 (m, 2H), 1.30 (d, J=1.2 Hz, 3H), 1.17 (t, J=7.2 Hz, 2H), 0.75 (d, J=6.5 Hz, 3H), 0.60 (s, 3H). $^{31}P$ NMR (162 MHz, $CDCl_3$) δ 151.34 (s). MS: LCMS: Calculated, C51H56N3O8PSi, 897.3574; Observed +Ve mode: m/z: 898.52 [M+H]; 999.95 [M+Et3N]. $^{13}C$ NMR (101 MHz, $CDCl_3$) δ 171.12, 163.83, 158.65, 158.61, 150.21, 146.50, 136.96, 136.71, 136.59, 135.94, 135.54, 134.60, 134.34, 130.24, 130.15, 129.45, 129.39, 128.02, 127.96, 127.94, 127.88, 127.79, 126.86, 113.17, 113.11, 110.93, 89.27, 89.25, 86.48, 83.68, 79.09, 78.99, 77.42, 77.30, 77.10, 76.78, 71.78, 71.70, 70.26, 68.39, 68.36, 60.39, 55.24, 47.19, 46.83, 46.09, 39.48, 39.44, 27.35, 25.97, 25.93, 21.05, 18.33, 17.85, 17.81, 14.23, 11.73, 11.45.

Example 7-7. Synthesis of L-DPSE-5'-(S)—C-Me-5'-DMT-dT Amidite

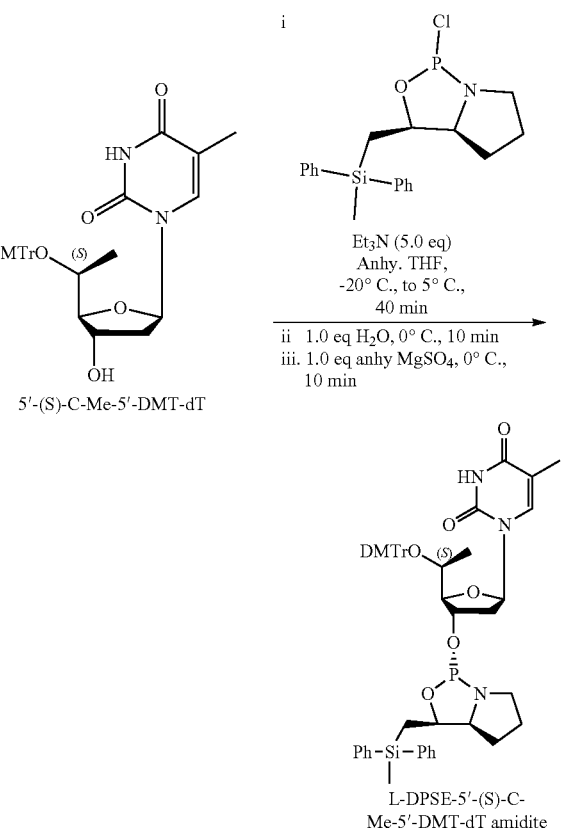

5'-(S)—C-Me-5'-OMT-dT (1.20 g, 2 mmol) was dried two times by co-evaporation with 20 mL of anhydrous toluene at 45° C. and kept at high vacuum for overnight. Then the dried 5'-(S)—C-Me-5'-OMT-dT was dissolved in dry THF (20 mL) in a 100 mL three neck flasks under argon, followed by the addition of triethylamine (1.4 mL, 10 mmol) and the mixture was cooled to −40° C. To this cooled reaction mixture was added the solution of the crude L-DPSE- NOPCl (3 mmol, 1.5 eq, in THF 3.0 mL) from a stock was through syringe dropwise ~5 min (maintaining the internal temperature −40° C., then gradually warmed to 5° C.). After 30 min at 5° C., TLC and LC-MS analysis indicated complete conversion of SM to product (total reaction time 1.5 h). The reaction mixture was cooled in an ice bath and the reaction was quenched by addition of water (0.036 mL, 2 mmol). The mixture was stirred for 10 min, followed by addition of anhydrous MgSO$_4$ (0.3 g, 2 mmol). The reaction was filtered through Airfree, Schlenk filter tube and washed with dry THF (20 mL). The solvent was evaporated under rotary evaporation at 28° C. to provide the off-white solid which was dried under high vacuum for overnight. The dried crude product was purified by Combi-Flash Rf (Teledyne ISCO) using 40 g silica column (which was pre-deactivated with 3 column volume of ethyl acetate with 5% TEA) with ethyl acetate/hexane mixture containing 5% TEA as a solvent. After column purification, fractions were analyzed by TLC and LC-MS and were pooled together and evaporated in a rotary evaporator at 28° C. The residue was dried under high vacuum to afford L-DPSE-5'-(S)—C-Me-5'-DMT-dT amidite as a white solid. Yield: 1.27 g (70%). $^{31}$P NMR (162 MHz, CDCl$_3$) δ 149.73 (s). MS: LC-MS; Calculated: C51H56N3O8PSi, 897.3574; Observed +Ve mode: m/z: 898.56 [M+H].

Example 7-8. Synthesis of L-DPSE-5'-DMT-5-C6-aminolinker Amidite—Incorporation of Desired Moieties Through Nucleobases The 5'-DMT-5-C6 amino TFA-dT (25 g, 31.5 mmol, from Berry& Associates Inc) was dried two times by co-evaporation with 100 mL of anhydrous toluene at 45° C. and kept at high vacuum for overnight. Then the dried material was dissolved in dry THF (100 mL) in 500 mL three neck flasks under argon, followed by the addition of triethylamine (21.92 mL, 157 mmol) and then was cooled to −70° C. To this cooled reaction mixture was added a solution of the crude L-DPSE-NOPCl (44 mmol, 1.4 eq, in THF 44 mL), from a stock via syringe dropwise (~15 min, maintaining the internal temperature −60- to 50° C.). The mixture was gradually warmed to 5° C. After 30 min at 5° C., TLC and LC-MS analysis indicated complete conversion of SM to product (total reaction time 2 h). The reaction mixture was cooled in an ice bath and quenched by addition of water (0.56 mL, 31.5 mmol), and stirred for 10 min followed by added anhydrous Mg$_2$SO$_4$ (3.8 g, 31.5 mmol). The reaction was filtered through Airfree, Schlenk filter tube, washed with dry THF (80 mL), and evaporated under rotary evaporation at 28° C. to afford the crude product as off-white solid, which was dried under high vacuum for overnight. The dried crude product was purified by Combi-Flash Rf (Teledyne ISCO) using 220 silica column (which was pre-deactivated with 3 column volume of ethyl acetate with 5% TEA) with ethyl acetate/hexane mixture contains 5% TEA as a solvent. After column purification fractions were analyzed by TLC and LC-MS, and pooled together. Solvent was evaporated in a rotary evaporator at 28° C. and the residue was dried under high vacuum to afford the product as a white solid. Yield: 30 g (88%). MS: LC-MS; Calculated: C60H67F3N5O10PSi,

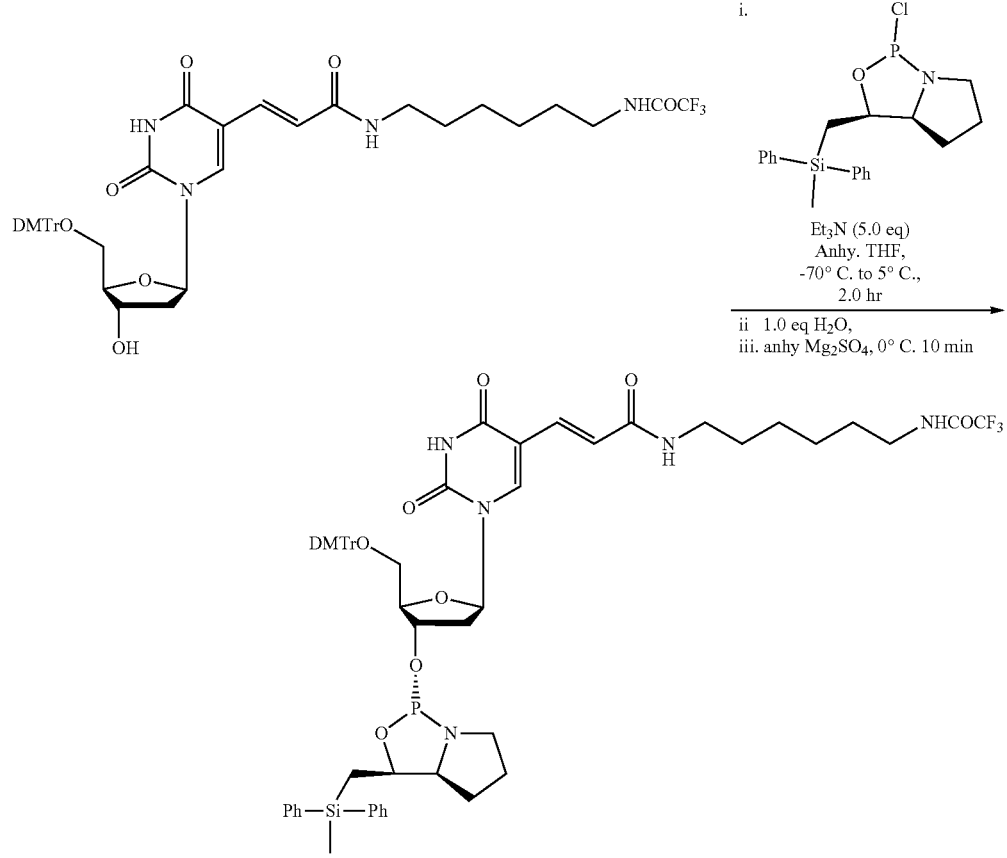

1133.4347; Observed in +Ve mode: 1235.55 (M+Et3N). $^1$H NMR (400 MHz, Chloroform-d) δ 7.78 (s, 1H), 7.40 (ddd, J=9.8, 6.5, 2.2 Hz, 5H), 7.32 (d, J=7.3 Hz, 2H), 7.30-7.09 (m, 15H), 6.99 (d, J=15.5 Hz, 1H), 6.76 (dd, J=8.9, 2.7 Hz, 4H), 6.54 (d, J=15.5 Hz, 1H), 5.12 (t, J=6.1 Hz, 1H), 4.66-4.49 (m, 2H), 4.04 (q, J=7.1 Hz, 1H), 3.81 (q, J=3.0 Hz, 1H), 3.67 (s, 6H), 3.41 (ddt, J=14.8, 10.2, 7.7 Hz, 1H), 3.30-3.13 (m, 4H), 3.12-2.91 (m, 4H), 1.96 (s, 2H), 1.92-1.69 (m, 2H), 1.58 (ddt, J=15.1, 11.6, 8.0 Hz, 1H), 1.50-1.29 (m, 5H), 1.18 (tq, J=15.8, 8.8, 8.0 Hz, 9H), 0.52 (s, 3H). $^{31}$P NMR (162 MHz, CDCl$_3$) δ 150.88 (s). $^{13}$C NMR (101 MHz, CDCl$_3$) δ 171.18, 165.77, 161.89, 158.76, 158.74, 157.85, 157.49, 157.12, 156.76, 149.17, 144.52, 139.69, 136.68, 135.86, 135.53, 135.44, 134.54, 134.30, 131.15, 129.97, 129.89, 129.44, 129.38, 128.09, 127.93, 127.91, 127.18, 122.36, 120.31, 117.44, 114.58, 113.42, 113.39, 111.72, 110.53, 86.65, 86.04, 86.02, 85.67, 79.28, 79.19, 77.42, 77.31, 77.11, 76.79, 73.20, 73.12, 68.05, 68.02, 63.09, 60.41, 55.27, 46.96, 46.60, 45.81, 40.48, 39.56, 38.88, 29.33, 28.52, 27.23, 25.83, 21.04, 17.55, 17.52, 14.20.

Example 7-9. Synthesis of 5-Alkynyl Thioacetate-5'-DMT-3'CNE-2'OMe-U Amidite was dissolved in anhydrous THF (14 ml, ~0.5 mmol/mL) under argon and to the solution was added 5-ethylthio-1H-tetrazole (1.05 g, 8.07 mmol), N-methylimidazole (0.045 g, 0.044 mL, 0.67 mmol) followed by 2-cyanoethyl-N,N,N',N'-tetraisopropylphosphordiamidite (2.23 g, 2.34 mL, 7.39 mmol). The reaction mixture was stirred at room temperature under argon for 5 h. TLC (solvent system: 40% CH$_3$CN/EtOAC/5% TEA) which was pre-equilibrated with the above solvent system indicated the completion of reaction at 5 h, which was also confirmed with LC-MS. The reaction mixture was diluted with EtOAc (100 mL) and the solution was transferred to separating funnel, washed with aq. saturated. NaHCO$_3$ solution (40 mL) and dried over anhydrous Mg$_2$SO$_4$. The dried solution was evaporated under rotary evaporation at bath temperature 28° C. to afford the crude product as off-yellow solid which was further dried under high vacuum for overnight. The dried crude product was purified in Combi-Flash Rf (Teledyne ISCO) using 80 g flash silica column, which was pre-deactivated with 2 column volume (CV 125 mL, 60 mL/min), of ethyl acetate with 5% TEA, followed by equilibration with 20% EtOAc/Hexane for 2 column volume. The compound was purified

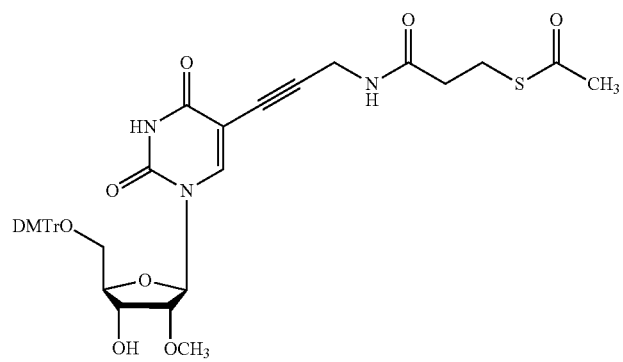

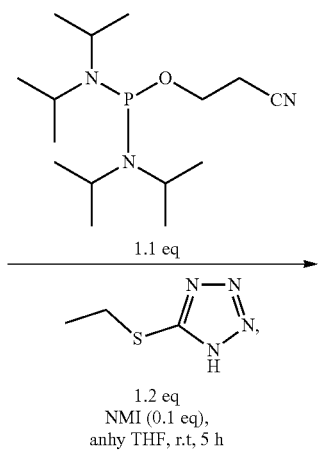

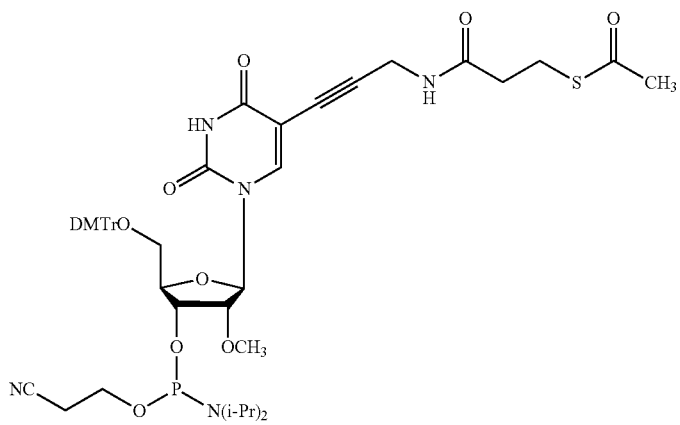

Compound 7-9-1 (5.0 g, 6.72 mmol) was co-evaporated with anhydrous toluene two times (40 mL×2) and dried under high vacuum for overnight. The dried yellow solid using Hexane/EtOAc/CH$_3$CN mixture containing 5% TEA as a solvent system. After purification column fractions were analyzed by TLC and LC-MS. Desired fractions were pooled together and evaporated in a rotary evaporator at 28° C. and was dried under high vacuum afforded 7-9-2-CNE amidite as white solid. Yield: 4.8 g (76%). MS: LC-MS; Calculated: C48H58N5O11PS, 943.35; Observed in +Ve mode: m/z 1045.92 (M+Et3N). $^1$H NMR (400 MHz, Chloroform-d) δ 8.36-8.07 (m, 1H), 7.47-7.09 (m, 10H), 6.78 (dt, J=9.1, 3.8 Hz, 4H), 5.87 (dd, J=26.6, 3.1 Hz, 1H), 4.73 (d, J=14.9 Hz, 1H), 4.57-4.30 (m, 1H), 4.21-4.00 (m, 2H), 3.86-3.32 (m, 17H), 3.23 (ddd, J=13.0, 11.2, 2.5 Hz, 1H), 2.91 (td, J=7.0, 2.4 Hz, 2H), 2.54 (q, J=6.1 Hz, 1H), 2.27 (d, J=24.2 Hz, 4H), 1.96 (d, J=7.1 Hz, 3H), 1.21-0.82 (m, 14H). $^{31}$P NMR (162 MHz, CDCl$_3$) δ 150.60 (s), 150.24 (s). $^{13}$C NMR (101 MHz, CDCl$_3$) δ 195.80, 169.61, 161.45, 158.70, 158.68, 149.06, 144.75, 144.61, 142.82, 135.67, 135.58, 135.48, 135.38, 130.18, 130.16, 130.12, 128.14, 128.11, 128.09, 128.02, 127.01, 117.69, 117.53, 113.42, 113.38, 113.34, 99.60, 99.33, 88.98, 88.95, 88.50, 88.06, 87.06, 86.85, 83.89, 82.99, 82.62, 77.34, 77.22, 77.02, 76.70, 74.55, 74.40, 69.74, 69.62, 62.04, 61.26, 60.38, 58.97, 58.59, 58.47, 58.45, 57.89, 57.68, 55.34, 55.31, 43.33, 43.21, 35.44, 35.41, 30.54, 29.95, 24.71, 24.65, 24.63, 24.58, 24.56, 24.49, 21.04, 20.50, 20.43, 20.38, 20.31, 14.20.

As readily appreciated by those skilled in the art, compound 7-9-2 can be utilized in oligonucleotide synthesis as a phosphoramidite in accordance with the present disclosure, thereby incorporating a protected thiol group into oligonucleotides. After deprotection, free thiol groups can be utilized to link oligonucleotide monomers to form multimers, by forming one or more disulfide bonds, in accordance with the present disclosure.

As appreciated by a person having ordinary skill in the art, many technologies (e.g., chemistry, reagents, linkers, methods, etc.) can be utilized to prepare oligonucleotides (including those with various 5'-end structures) and to incorporate various chemical moieties, e.g., carbohydrate moieties, lipid moieties, targeting moieties, etc., into oligonucleotides in accordance with the present disclosure, for example but not limited to those described in WO/2010/064146, WO/2011/005761, WO/2013/012758, WO/2014/010250, US2013/0178612, WO/2014/012081, WO/2015/107425, WO/2017/015555, and WO/2017/062862. Described herein are example technologies for preparing oligonucleotides, including those comprising various moieties.

As shown in Tables 61 to 73, various oligonucleotides were constructed and tested for their ability to mediate knockdown of PNPLA3, including in vitro. Without wishing to be bound by any theory, the present disclosure suggests that at least some of the oligonucleotides in Tables 61 to 73 may be capable of mediating knockdown via a RISC-mediated ssRNAi mechanism. In addition, some of the oligonucleotides in these tables have a hybrid format. In addition, at least some of the oligonucleotides described herein are capable of mediating knockdown of PNPLA3 in an allele-specific manner.

Table 61. Table 61 shows in vitro efficacy of different single-stranded RNAi agents, which target PNPLA3. Oligonucleotides tested are: WV-4054 and WV-4098. Oligonucleotides were tested in Hep3B (I/I) cells, with is homozygous wild-type (I/I aa in PNPLA3); and in Huh7 cells, which is homozygous mutant (M/M aa in PNPLA3). IC50 of WV-4054 in Huh7 cells was 0.239 nM; and IC50 of WV-4098 in Huh7 cells was 0.158 nM. Oligonucleotides WV-4054 and WV-4098 differ in length but are both capable of mediating allele-specific knockdown of PNPLA3. The ability of WV-4098 to mediate knockdown via a RNA interference mechanism is supported by the finding that a CRISPR knockout of AGO-2 (which is required for RNA interference) prevented the ability of WV-4098 to knockdown gene expression, while knockouts of AGO-1, AGO-3 and AGO-4 (which are not required for RNA interference) did not (data not shown).

TABLE 61A

Activity of oligonucleotides.

| Conc. (exp 10) (nM) | WV-4054-Hep3b | | WV-4054-Huh7 | |
|---|---|---|---|---|
| 0.796 | 1.226 | 1.121 | 0.280 | 0.449 |
| 0.495 | 0.910 | 1.010 | 0.478 | 0.402 |
| 0.194 | 1.068 | 1.024 | 0.419 | 0.367 |
| −0.107 | 0.843 | 1.160 | 0.405 | 0.449 |
| −0.408 | 0.976 | 0.942 | 0.422 | 0.584 |
| −0.709 | 0.798 | 0.917 | 0.750 | 0.601 |
| −1.010 | 0.832 | 1.038 | 0.798 | 0.755 |
| −1.612 | 1.053 | 0.923 | 0.969 | 0.792 |
| −2.214 | 0.956 | 0.929 | 0.809 | 0.798 |

Table 62. Table 62 shows the in vitro potency and IC$_{50}$ for different single-stranded RNAi agents, which target PNPLA3. Tested oligonucleotides are: WV-2477 (positive control), WV-3380 (positive control), WV-4018, WV-4019, WV-4020, WV-4021, WV-4022, WV-4023, WV-4024, and WV-4025, each tested in Hep3B (Hep) and Huh7 (Huh) cells. Oligonucleotides for PNPLA3 assays were delivered using Lipofectamine® 2000 transfection reagent (ThermoFisher, Grand Island, N.Y.). In this and other tables, oligonucleotides were tested at concentrations of 2, 8.25 and 33 nM.

TABLE 62

Activity of oligonucleotides.

| | 2 nM | | 8.25 nM | | 33 nM |
|---|---|---|---|---|---|
| Control | | 94.6 | 103.5 | 102.8 | 102.1 | 108.7 |
| WV-2477-Hep | | 91.4 | 110.2 | 103.5 | 101.4 | 102.1 |
| WV-2477_Huh | | 86.2 | 90.5 | 96.4 | 84.5 | 98.4 |
| WV-3380-Hep | 51.1 | 46.3 | 30.8 | 26.4 | 4.9 | 8.8 |
| WV-3380-Huh | | 59.7 | 53.5 | 58.9 | 10.3 | |
| WV-4018-Hep | 61.1 | 47.0 | | 94.0 | 72.7 | 65.5 |
| WV-4018-Huh | 43.4 | 46.9 | 61.8 | 51.6 | 63.6 | 66.7 |
| WV-4019-Hep | 75.3 | 88.3 | 117.3 | 119.7 | 84.7 | 79.6 |
| WV-4019-Huh | 67.7 | 68.1 | 77.7 | 77.2 | 67.7 | 74.0 |
| WV-4020-Hep | 74.7 | 68.8 | 87.1 | 92.7 | 52.1 | 59.5 |
| WV-4020-Huh | 70.0 | 81.6 | 71.0 | 91.2 | 54.6 | 77.2 |
| WV-4021-Hep | 64.6 | 81.2 | 76.8 | 85.9 | 45.4 | 56.6 |
| WV-4021-Huh | 68.6 | 64.0 | 69.1 | 69.6 | 64.0 | 68.1 |
| WV-4022-Hep | 66.0 | 75.3 | | 97.3 | 56.3 | 62.9 |
| WV-4022-Huh | 49.5 | 62.7 | 63.6 | 58.9 | 58.1 | 77.2 |
| WV-4023-Hep | 62.9 | 90.8 | 76.3 | 79.6 | 46.7 | 47.6 |
| WV-4023-Huh | 70.5 | 66.7 | 71.5 | 75.1 | 64.0 | 67.7 |
| WV-4024-Hep | 74.7 | 77.4 | 99.3 | 100.7 | 54.7 | 75.8 |
| WV-4024-Huh | 70.0 | 63.1 | 104.0 | 91.2 | 79.9 | 88.7 |
| WV-4025-Hep | 61.1 | 65.5 | 65.5 | | 83.5 | 55.1 |
| WV-4025-Huh | 58.9 | 71.5 | 69.1 | 66.3 | 79.9 | 63.6 |

Table 63. Table 63 shows the in vitro potency and IC$_{50}$ for different single-stranded RNAi agents, which target PNPLA3. Tested oligonucleotides are: WV-2477 (positive control), WV-3380 (positive control), WV-4026, WV-4027, WV-4028, WV-4029, WV-4030, WV-4031, WV-4032, and WV-4033, each tested in Hep3B (Hep) and Huh7 (Huh) cells.

TABLE 63

Activity of oligonucleotides.

| | 2 nM | | 8.25 nM | | 33 nM | |
|---|---|---|---|---|---|---|
| Control | | 94.6 | 103.5 | 102.8 | 102.1 | 108.7 |
| WV-2477-Hep | | 91.4 | 110.2 | 103.5 | 101.4 | 102.1 |
| WV-2477_Huh | | 86.2 | 90.5 | 96.4 | 84.5 | 98.4 |
| WV-3380-Hep | 51.1 | 46.3 | 30.8 | 26.4 | 4.9 | 8.8 |
| WV-3380-Huh | | 59.7 | 53.5 | 58.9 | 10.3 | |
| WV-4026-Hep | | 104.2 | 115.7 | 105.7 | 103.5 | 86.5 |
| WV-4026-Huh | 74.0 | 76.1 | 84.5 | 70.5 | 71.5 | 68.1 |
| WV-4027-Hep | 64.6 | 76.3 | 71.2 | 77.4 | 39.0 | 51.1 |
| WV-4027-Huh | 69.1 | 75.1 | 55.7 | 69.1 | 60.1 | 61.4 |
| WV-4028-Hep | 79.0 | 71.2 | 102.8 | 107.2 | 70.2 | 53.6 |
| WV-4028-Huh | 74.0 | 70.0 | 64.5 | 65.4 | 83.9 | 76.7 |
| WV-4029-Hep | 79.6 | 87.7 | 81.8 | 100.0 | 57.8 | 79.6 |
| WV-4029-Huh | | 74.0 | 74.6 | 79.4 | 116.2 | 102.6 |
| WV-4030-Hep | | 85.9 | 93.3 | 105.0 | 68.8 | 80.1 |
| WV-4030-Huh | 51.6 | 67.7 | 75.1 | 69.1 | 71.5 | |
| WV-4031-Hep | 85.9 | 101.4 | 104.2 | 122.3 | 51.1 | 56.3 |
| WV-4031-Huh | 73.5 | 72.0 | 100.4 | 91.2 | 95.7 | 95.0 |
| WV-4032-Hep | 78.5 | 73.7 | | 121.4 | 51.8 | 62.0 |
| WV-4032-Huh | 81.0 | 82.2 | 100.4 | 105.4 | 107.7 | 124.5 |
| WV-4033-Hep | 84.1 | 85.3 | 100.0 | | 83.5 | 83.5 |
| WV-4033-Huh | 52.4 | 38.9 | 57.3 | 59.7 | 107.7 | 81.0 |

Table 64. Table 64 shows the in vitro potency and IC$_{50}$ for different single-stranded RNAi agents, which target PNPLA3. Tested oligonucleotides are: WV-2477 (positive control), WV-3380 (positive control), WV-4034, WV-4035, WV-4036, WV-4037, WV-4038, WV-4039, WV-4040, WV-4041, each tested in Hep3B (Hep) and Huh7 (Huh) cells.

TABLE 64

Activity of oligonucleotides.

| | 2 nM | | 8.25 nM | | 33 nM | |
|---|---|---|---|---|---|---|
| Control | | 94.6 | 103.5 | 102.8 | 102.1 | 108.7 |
| WV-2477-Hep | | 91.4 | 110.2 | 103.5 | 101.4 | 102.1 |
| WV-2477_Huh | | 86.2 | 90.5 | 96.4 | 84.5 | 98.4 |
| WV-3380-Hep | 51.1 | 46.3 | 30.8 | 26.4 | 4.9 | 8.8 |
| WV-3380-Huh | | 59.7 | 53.5 | 58.9 | 10.3 | |
| WV-4034-Hep | 100.0 | 100.0 | 100.0 | 100.0 | 100.0 | 100.0 |
| WV-4034-Huh | 73.0 | 76.7 | 91.2 | 78.8 | 101.1 | 119.4 |
| WV-4035-Hep | 81.8 | 77.4 | 92.7 | 104.2 | 57.8 | 84.7 |
| WV-4035-Huh | 75.1 | 81.6 | 82.2 | 63.1 | 101.1 | 115.4 |
| WV-4036-Hep | 76.3 | 77.4 | 82.9 | 77.4 | 49.7 | 54.0 |
| WV-4036-Huh | 74.6 | 75.1 | 72.5 | 67.2 | 75.6 | 87.4 |
| WV-4037-Hep | 79.6 | 68.3 | 75.8 | 97.3 | 80.7 | 72.7 |
| WV-4037-Huh | 69.6 | 82.7 | 76.7 | 87.4 | 94.4 | 81.0 |
| WV-4038-Hep | 64.2 | 71.2 | 74.2 | 97.9 | 83.5 | 83.5 |
| WV-4038-Huh | 69.1 | 85.1 | 78.3 | 67.2 | 86.8 | 69.6 |
| WV-4039-Hep | 69.3 | 70.2 | 46.0 | 77.9 | 48.6 | 45.7 |
| WV-4039-Huh | 63.1 | 79.9 | 64.0 | 58.9 | 61.0 | 50.6 |
| WV-4040-Hep | 74.2 | 67.8 | 92.7 | 75.8 | 50.0 | 59.9 |
| WV-4040-Huh | 88.0 | 70.0 | 73.5 | 78.3 | 71.0 | 66.3 |
| WV-4041-Hep | 77.4 | 75.8 | 82.9 | 95.9 | 61.1 | 60.7 |
| WV-4041-Huh | 99.1 | 93.7 | 83.9 | 82.7 | 67.2 | 61.0 |

Table 65. Table 65 shows the in vitro potency and IC$_{50}$ for different single-stranded RNAi agents, which target PNPLA3. Tested oligonucleotides are: WV-3380 (positive control), WV-2477 (positive control), WV-4042, WV-4043, WV-4044, WV-4045, WV-4046, WV-4047, WV-4048, and WV-4049, each tested in Hep3B (Hep) and Huh7 (Huh) cells.

TABLE 65

Activity of oligonucleotides.

| | 2 nM | | 8.25 nM | | 33 nM | |
|---|---|---|---|---|---|---|
| Control | 111.9 | 113.4 | 113.4 | 119.1 | 100.1 | 111.9 |
| WV-2477-Hep | 99.4 | 100.1 | 115.8 | 107.3 | 103.7 | 119.1 |
| WV-2477-Huh | 96.9 | 91.6 | 89.7 | 109.7 | 96.9 | 91.0 |
| WV-3380-Hep | 39.8 | 52.6 | 35.7 | 26.3 | 5.9 | |
| WV-3380-Huh | 54.5 | 60.5 | | 46.8 | 22.7 | |
| WV-4042-Hep | 63.8 | 67.5 | 86.6 | 72.8 | 49.0 | 49.4 |
| WV-4042-Huh | | 66.2 | | 48.4 | 25.4 | 28.2 |
| WV-4043-Hep | 64.3 | 60.8 | 83.6 | 68.4 | 52.9 | 41.8 |
| WV-4043-Huh | 48.4 | 64.8 | 48.4 | 56.8 | 47.1 | 52.6 |
| WV-4044-Hep | 70.8 | 66.5 | 83.0 | 73.3 | 20.6 | 33.7 |
| WV-4044-Huh | 86.7 | 109.0 | 72.9 | 81.4 | 38.5 | 33.3 |
| WV-4045-Hep | 86.0 | 80.2 | 100.8 | 103.0 | 44.8 | 42.1 |
| WV-4045-Huh | 81.4 | 79.2 | 80.9 | 76.5 | 45.2 | 62.6 |
| WV-4046-Hep | 117.4 | 96.7 | 92.1 | 82.5 | 24.9 | 22.9 |
| WV-4046-Huh | 83.7 | 73.9 | 71.9 | 56.4 | 44.6 | 41.9 |
| WV-4047-Hep | 86.0 | 76.4 | 98.8 | 111.1 | 53.3 | 51.8 |
| WV-4047-Huh | 63.5 | 94.2 | 78.7 | 71.9 | 56.0 | 38.0 |
| WV-4048-Hep | 79.1 | 70.3 | 95.4 | 98.8 | 37.4 | 27.2 |
| WV-4048-Huh | 93.6 | 76.5 | 81.4 | 81.4 | 46.5 | 44.9 |
| WV-4049-Hep | | 107.3 | 107.3 | 111.9 | 36.1 | 55.9 |
| WV-4049-Huh | 87.3 | 98.2 | 88.5 | 89.7 | 62.6 | 62.2 |

Table 66. Table 66 shows the in vitro potency and IC$_{50}$ for different single-stranded RNAi agents, which target PNPLA3. Tested oligonucleotides are: WV-2477 (positive control), WV-3380 (positive control), WV-4050, WV-4051, WV-4052, WV-4053, WV-4054, WV-4055, WV-4056, WV-4057, each tested in Hep3B (Hep) and Huh7 (Huh) cells.

TABLE 66

Activity of oligonucleotides.

| | 2 nM | | 8.25 nM | | 33 nM | |
|---|---|---|---|---|---|---|
| Control | 111.9 | 113.4 | 113.4 | 119.1 | 100.1 | 111.9 |
| WV-2477-Hep | 99.4 | 100.1 | 115.8 | 107.3 | 103.7 | 119.1 |
| WV-2477-Huh | 96.9 | 91.6 | 89.7 | 109.7 | 96.9 | 91.0 |
| WV-3380-Hep | 39.8 | 52.6 | 35.7 | 26.3 | 5.9 | |
| WV-3380-Huh | 54.5 | 60.5 | | 46.8 | 22.7 | |
| WV-4050-Hep | 71.8 | 75.9 | 98.8 | 75.9 | 54.8 | 55.2 |
| WV-4050-Huh | 69.0 | 80.9 | 63.0 | 57.6 | 46.8 | 57.6 |
| WV-4051-Hep | 73.8 | 80.8 | 92.8 | 69.4 | 40.4 | 59.1 |
| WV-4051-Huh | 67.1 | 74.9 | 54.9 | 58.8 | 47.4 | 37.5 |
| WV-4052-Hep | 79.1 | 77.0 | 113.4 | 97.4 | 51.5 | 44.8 |
| WV-4052-Huh | 67.1 | 67.1 | 84.9 | 80.3 | 75.5 | 52.6 |
| WV-4053-Hep | 89.0 | 69.8 | 100.0 | | 63.4 | 57.1 |
| WV-4053-Huh | 56.0 | 64.3 | 76.0 | 68.0 | 84.3 | 59.2 |
| WV-4054-Hep | 100.0 | 100.0 | 100.0 | 100.0 | 106.6 | 111.9 |
| WV-4054-Huh | 30.6 | 31.7 | | 38.8 | 53.0 | 47.8 |
| WV-4055-Hep | 92.1 | 105.8 | 100.0 | | 58.7 | 72.3 |
| WV-4055-Huh | 69.9 | 80.9 | 95.5 | 81.4 | 77.6 | 71.9 |
| WV-4056-Hep | 86.6 | 81.3 | | 116.6 | 54.0 | 65.6 |
| WV-4056-Huh | 84.9 | | 78.7 | 101.0 | 62.2 | 76.5 |
| WV-4057-Hep | 105.8 | 95.4 | 110.3 | 105.1 | 46.1 | 50.8 |
| WV-4057-Huh | 87.9 | 79.8 | 107.5 | 92.3 | 72.9 | 50.5 |

Table 67. Table 67 shows the in vitro potency and IC$_{50}$ for different single-stranded RNAi agents, which target PNPLA3. Tested oligonucleotides are: WV-2477 (positive control), WV-3380 (positive control), WV-4058, WV-4059, WV-4060, WV-4061, WV-4062, WV-4063, WV-4064, and WV-4065. Oligonucleotides were tested in Hep3B (Hep) and Huh7 (Huh-7 or Huh or P-Huh7 or P-Huh-7) cells.

TABLE 67

Activity of oligonucleotides.

| | 2 nM | | 8.25 nM | | 33 nM | |
|---|---|---|---|---|---|---|
| Control | 111.9 | 113.4 | 113.4 | 119.1 | 100.1 | 111.9 |
| WV-2477-Hep | 99.4 | 100.1 | 115.8 | 107.3 | 103.7 | 119.1 |
| WV-2477-Huh | 96.9 | 91.6 | 89.7 | 109.7 | 96.9 | 91.0 |
| WV-3380-Hep | 39.8 | 52.6 | 35.7 | 26.3 | 5.9 | |
| WV-3380-Huh | 54.5 | 60.5 | | 46.8 | 22.7 | |
| WV-4058-Hep | 67.0 | 78.0 | 73.3 | 62.5 | 67.0 | 56.3 |
| WV-4058-Huh | 73.9 | 79.8 | 86.7 | 70.9 | 55.6 | 59.6 |
| WV-4059-Hep | 64.7 | 70.3 | 74.8 | 53.7 | 74.3 | 63.4 |
| WV-4059-Huh | 74.4 | 63.0 | 65.7 | 74.4 | 44.3 | 43.9 |
| WV-4060-Hep | 80.8 | 68.9 | | 107.3 | 43.0 | 63.4 |
| WV-4060-Huh | 77.6 | 39.9 | 72.9 | 66.2 | 66.6 | 79.2 |
| WV-4061-Hep | 115.8 | 93.4 | | 108.8 | 57.5 | 66.1 |
| WV-4061-Huh | 70.9 | 60.0 | 87.9 | 68.0 | 61.7 | 70.4 |
| WV-4062-Hep | 97.4 | 91.5 | 111.9 | | 78.0 | 59.5 |
| WV-4062-Huh | | 81.4 | 94.2 | 83.2 | 101.7 | 82.6 |
| WV-4063-Hep | 86.6 | 82.5 | 98.1 | 119.9 | 47.0 | 54.0 |
| WV-4063-Huh | | 79.2 | 76.5 | 77.6 | 58.8 | 75.5 |
| WV-4064-Hep | 72.8 | 83.6 | 111.1 | 91.5 | 61.2 | 56.3 |
| WV-4064-Huh | 71.4 | 59.2 | 53.4 | 52.6 | 50.1 | 66.2 |
| WV-4065-Hep | 109.6 | 107.3 | 87.2 | 101.5 | 33.7 | 68.4 |
| WV-4065-Huh | 92.3 | 86.1 | 89.1 | 97.5 | 67.1 | 76.0 |

Table 68. Table 68 shows the in vitro potency for different single-stranded RNAi agents, which target PNPLA3. Tested oligonucleotides are: WV-4098, WV-7462, WV-7464, WV-7467, and WV-7469.

TABLE 68

Activity of oligonucleotides.

Part 1. Activity in Hep3B cells.

| Conc. | WV-4098 | | WV-7462 | | WV-7464 | |
|---|---|---|---|---|---|---|
| 0.006 | 97.9 | 94.5 | 112.3 | 100.9 | 106.4 | 107.3 |
| 0.025 | 134.1 | 100.9 | 96.2 | 87.9 | 155.5 | 99.2 |
| 0.01 | 99.5 | 97.9 | 92.5 | 95.0 | 108.9 | 109.4 |
| 0.4 | 84.4 | 94.2 | 74.2 | 90.5 | 96.5 | 105.6 |
| 1.6 | 88.3 | 84.4 | 99.6 | 82.4 | 80.8 | 97.0 |
| 6.25 | 131.4 | 137.0 | 120.3 | 142.1 | 81.2 | 121.1 |

| Conc. | WV-7467 | | WV-7469 | |
|---|---|---|---|---|
| 0.006 | 103.9 | 105.9 | 93.9 | 100.7 |
| 0.025 | 99.9 | 108.8 | 97.4 | 84.9 |
| 0.01 | 91.0 | 106.0 | 90.8 | 107.1 |
| 0.4 | 100.5 | 100.1 | 75.8 | 81.1 |
| 1.6 | 83.8 | 82.0 | 76.0 | 72.5 |
| 6.25 | 100.0 | 100.3 | 77.0 | 82.8 |

Part 2. Activity in Huh7 (P-Huh7) cells.

| Conc. | WV-4098 | | WV-7462 | | WV-7464 | |
|---|---|---|---|---|---|---|
| 0.006 | 105.8 | 115.7 | 129.8 | 116.1 | 110.5 | 131.0 |
| 0.025 | 102.1 | 105.0 | 110.0 | 94.3 | 116.6 | 127.3 |
| 0.01 | 77.2 | 95.8 | 93.3 | 72.8 | 79.1 | 104.5 |
| 0.4 | 83.8 | 65.4 | 66.2 | 66.4 | 93.8 | 54.2 |
| 1.6 | 40.8 | 54.7 | 50.9 | 46.1 | 58.1 | 45.0 |
| 6.25 | 43.0 | 34.2 | 49.8 | 32.9 | 48.9 | 34.3 |

| Conc. | WV-7467 | | WV-7469 | |
|---|---|---|---|---|
| 0.006 | 109.2 | 129.2 | 86.0 | 87.3 |
| 0.025 | 99.9 | 107.2 | 90.5 | 102.1 |
| 0.01 | 73.3 | 63.7 | 72.0 | 65.6 |
| 0.4 | 88.0 | 66.7 | 54.0 | 46.2 |
| 1.6 | 49.1 | 33.4 | 41.2 | 28.6 |
| 6.25 | 48.5 | 38.8 | 32.0 | 28.5 |

Concentration (Conc.) of oligonucleotides is provided. Cells used and oligonucleotide used are also provided. Numbers represent PNPLA3 mRNA level (PNPLA3/HPRT1), wherein 100 would represent 100% mRNA level (no knockdown) and 0 would represent 0% mRNA level (or 100% knockdown). Data from replicates are shown.

Table 69. Tables 69A and B show the in vitro potency and $IC_{50}$ for different single-stranded RNAi agents, which target PNPLA3. Tested oligonucleotides are: Table 69A, WV-4098, WV-4075, WV-7465, WV-7466, and WV-7468; and Table 69B, WV-3380, WV-4098, and WV-7469.

TABLE 69A

Activity of oligonucleotides.

Part 1. Activity in Hep3B cells.

| Conc. | WV-4098 | | WV-4075 | | WV-7463 | |
|---|---|---|---|---|---|---|
| 0.006 | 97.9 | 94.5 | 77.4 | 80.1 | 90.8 | 106.9 |
| 0.025 | 134.1 | 100.9 | 91.1 | 109.1 | 119.9 | 97.2 |
| 0.01 | 99.5 | 97.9 | 85.3 | 86.6 | 106.7 | 90.9 |
| 0.4 | 84.4 | 94.2 | 83.1 | 95.8 | 79.4 | 86.3 |
| 1.6 | 88.3 | 84.4 | 110.5 | 112.5 | 127.0 | 112.5 |
| 6.25 | 131.4 | 137.0 | 115.8 | 135.8 | 148.7 | 164.1 |

| Conc. | WV-7465 | | WV-7466 | | WV-7468 | |
|---|---|---|---|---|---|---|
| 0.006 | 101.1 | 102.2 | 124.3 | 98.9 | 97.9 | 97.0 |
| 0.025 | 118.5 | 116.3 | 140.4 | 121.2 | 118.1 | 112.1 |
| 0.01 | 102.0 | 110.0 | 126.4 | 113.2 | 100.2 | 88.8 |
| 0.4 | 131.3 | 132.4 | 112.0 | 139.2 | 92.7 | 96.6 |
| 1.6 | 108.2 | 95.5 | 102.5 | 98.1 | 83.9 | 97.7 |
| 6.25 | 98.1 | 107.2 | 126.6 | 128.5 | 120.7 | 134.7 |

Part 2. Activity in Huh7 cells.

| Conc. | WV-4098 | | WV-4075 | | WV-7463 | |
|---|---|---|---|---|---|---|
| 0.006 | 105.8 | 115.7 | 111.3 | 119.4 | 116.9 | 131.9 |
| 0.025 | 102.1 | 105.0 | 101.8 | 95.8 | 116.9 | 119.4 |
| 0.01 | 77.2 | 95.8 | 96.5 | 94.1 | 95.3 | 77.9 |
| 0.4 | 83.8 | 65.4 | 85.9 | 81.0 | 62.6 | 50.7 |
| 1.6 | 40.8 | 54.7 | 58.6 | 67.8 | 50.1 | 45.6 |
| 6.25 | 43.0 | 34.2 | 70.8 | 57.7 | 60.0 | 67.1 |

| Conc. | WV-7465 | | WV-7466 | | WV-7468 | |
|---|---|---|---|---|---|---|
| 0.006 | 119.6 | 126.5 | 100.1 | 124.8 | 69.3 | 95.2 |
| 0.025 | 114.8 | 111.8 | 95.0 | 106.6 | 69.8 | 84.9 |
| 0.01 | 104.9 | 101.4 | 50.1 | 61.3 | 54.2 | 48.5 |
| 0.4 | 84.5 | 64.3 | 64.1 | 43.3 | 55.5 | 38.1 |
| 1.6 | 55.3 | 55.2 | 40.2 | 35.3 | 37.4 | 33.5 |
| 6.25 | 79.4 | 57.3 | 50.2 | 46.5 | 60.3 | 41.4 |

Concentration (Conc.) of oligonucleotides is provided. Cells used and oligonucleotide used are also provided. Numbers represent PNPLA3 mRNA level (PNPLA3/HPRT1), wherein 100 would represent 100% mRNA level (no knockdown) and 0 would represent 0% mRNA level (or 100% knockdown). Data from replicates are shown.

TABLE 69B

Activity of oligonucleotides.

| Conc. | Hep3B-WV3380 | | Huh7-WV-3380 | |
|---|---|---|---|---|
| 0.006 | 83.9 | 88.2 | 87.5 | 101.8 |
| 0.025 | 92.3 | 88.7 | 90.1 | 105.4 |
| 0.01 | 75.3 | 70.6 | 75.5 | |
| 0.4 | 40.2 | 49.4 | 79.1 | 69.3 |
| 1.6 | 22.6 | 20.8 | 52.2 | 52.2 |
| 6.25 | 5.3 | 4.4 | 18.6 | 15.5 |

| Conc. | Hep3B-WV-4098 | | Huh7-WV-4098 | |
|---|---|---|---|---|
| 0.006 | 97.9 | 94.5 | 105.8 | 115.7 |
| 0.025 | 134.1 | 100.9 | 102.1 | 105.0 |

TABLE 69B-continued

Activity of oligonucleotides.

| | | | | |
|---|---|---|---|---|
| 0.01 | 99.5 | 97.9 | 77.2 | 95.8 |
| 0.4 | 84.4 | 94.2 | 83.8 | 65.4 |
| 1.6 | 88.3 | 84.4 | 40.8 | 54.7 |
| 6.25 | 131.4 | 137.0 | 43.0 | 34.2 |
| Conc. | Hep3B-WV-7469 | | Huh-WV-7469 | |
| 0.006 | 93.9 | 100.7 | 86.0 | 87.3 |
| 0.025 | 97.4 | 84.9 | 90.5 | 102.1 |
| 0.01 | 90.8 | 107.1 | 72.0 | 65.6 |
| 0.4 | 75.8 | 81.1 | 54.0 | 46.2 |
| 1.6 | 76.0 | 72.5 | 41.2 | 28.6 |
| 6.25 | 77.0 | 82.8 | 32.0 | 28.5 |

Concentration (Conc.) of oligonucleotides is provided. Cells used and oligonucleotide used are also provided. Numbers represent PNPLA3 mRNA level (PNPLA3/HPRT1), wherein 100 would represent 100% mRNA level (no knockdown) and 0 would represent 0% mRNA level (or 100% knockdown). Data from replicates are shown.

Table 69C shows a rat liver homogenate stability assay (24 hours). Tested oligonucleotides were: WV-4098, WV-7463, WV-7462, WV-7316, WV-4075, WV-7469, WV-7464, WV-7468, WV-7467, WV-7466, WV-7465.

TABLE 69C

Stability of oligonucleotides.

| WV-4075 | | | WV-4098 | | | WV-7316 | | |
|---|---|---|---|---|---|---|---|---|
| 23.5 | 23.5 | 24.3 | 19.2 | 18.3 | 17.4 | 16.8 | 18.7 | 18.3 |
| WV-7462 | | | WV-7463 | | | WV-7464 | | |
| 21.1 | 20.7 | 21.4 | 15.0 | 16.2 | 15.4 | 45.7 | 43.6 | 45.8 |
| WV-7465 | | | WV-7466 | | | WV-7467 | | |
| 85.6 | 86.1 | 87.6 | 65.2 | 69.6 | 69.8 | 54.7 | 57.1 | 56.0 |
| WV-7468 | | | WV-7469 | | | | | |
| 55.7 | 55.6 | | 50.0 | 43.0 | 45.0 | 41.8 | | |

Numbers indicate percentage of full-length oligonucleotide remaining after 24 hr treatment with rat liver homogenate. 100 would represent 100% of full length oligonucleotide remaining; 0 would represent 0% of full length oligonucleotide remaining. Different oligonucleotides have different numbers of stereocontrolled phosphorothioate internucleotidic linkages. Data from replicates are shown.

Table 70. Table 70 shows the IC50 for different single-stranded RNAi agents. Tested oligonucleotides are: WV-2477, WV-4054, and WV-3387 in Huh7 and Hep3B cells. WV-2477 did not significantly knock down PNPLA3 in either cells. WV-4054 has a sequence complementary to a pair of SNPs, rs738408 T and rs738409 G, and is able to mediate allele-specific RNA interference against cells (Huh7) which comprise these two SNPs. This oligonucleotide does not mediate significant RNAi interference at the tested concentrations in different cells (Hep3B) which do not comprise these SNPs, but rather have rs738408C and rs738409 C. In addition, single-stranded RNAi agent WV-4098 is also able to knock-down a complementary sequence (with SNPs rs738408 T and rs738409 G in Huh7 cells), but not a non-complementary sequence (with SNPs rs738408C and rs738409 C in Hep3B cells) at the tested concentrations.

TABLE 70

IC50 of oligonucleotides.

| Oligonucleotide-cell tested | IC50 (nM) | 95% CI |
|---|---|---|
| WV-4054-Hep3b | NA | — |
| WV-4054-Huh7 | 0.239 | 0.15 to 0.38 |
| WV-4098-Hep3b | NA | — |
| WV-4098-Huh7 | 0.158 | 0.10 to 0.22 |

Table 71. Tables 71A to 71D show non-limiting examples of formats of stereocontrolled (e.g., chirally controlled) oligonucleotides (e.g., single-stranded RNAi agents).

Table 72. Table 72 shows the in vitro potency in primary cynomolgus hepatic cells of ssRNAi WV-4054.

Table 74. Table 74 shows the efficacy of antisense oligonucleotides in knockdown of PNPLA3 mediated by RNase H, in a Hep3B 24 hour assay. Tested oligonucleotides are: WV-1868 (negative control), WV-3367, WV-3368, WV-3369, WV-3370, WV-3371, WV-3372, WV-3373, WV-3374, WV-3375, WV-3376, WV-3377, WV-3378, WV-3379, and WV-3380. WV-1868 is an antisense oligonucleotide (operating through RNase H-mediated knockdown), while other tested oligonucleotides are RNAi agents. Cell used were PCH cells.

Table 73. Table 73 shows the structure of PNPLA3 ssRNAi agents WV-7467, WV-7469, WV-7466, and WV-7468; and ASO WV-6825.

As shown in Tables 74 to 90, various oligonucleotides were constructed and tested for their ability to mediate knockdown of PNPLA3, including in vitro. Without wishing to be bound by any theory, the present disclosure suggests that at least some of the oligonucleotides in Tables 74 to 90 may be capable of mediating knockdown via a RNaseH-mediated mechanism. In addition, some of the oligonucleotides in these tables have a hybrid format.

Table 74. Table 74 shows the in vitro potency of ASOs to PNPLA3. Tested oligonucleotides are: WV-1868, and WV-3367 to WV-3380. Cells used were Hep3B cells.

TABLE 74

Activity of oligonucleotides.

| Wave ID | 2.0 nM | 8.2 nM | 33 nM |
|---|---|---|---|
| Control | .96 | 1.08 | 1.13 |
| WV-1868 | 1.18 | 1.06 | .85 |
| WV-3367 | 1.07 | 1.04 | .77 |
| WV-3368 | 1.17 | .96 | .58 |
| WV-3369 | 1.12 | .98 | 1.03 |
| WV-3370 | 1.23 | .88 | .67 |
| WV-3371 | 1.24 | 1.19 | .65 |
| WV-3372 | 1.08 | 1.17 | 1.05 |
| WV-3373 | 1.22 | 1.14 | 1.15 |
| WV-3374 | 1.19 | .99 | .76 |
| WV-3375 | 1.14 | 1.0 | .63 |
| WV-3376 | 1.14 | .72 | .39 |
| WV-3377 | .92 | .52 | .12 |
| WV-3378 | 1.07 | .48 | .15 |
| WV-3379 | 1.18 | .45 | .16 |
| WV-3380 | .31 | .12 | .06 |

Table 75. Table 75 shows the in vitro potency of ASOs to PNPLA3. Tested oligonucleotides are: WV-1868, and WV-3381 to WV-3394.

TABLE 75

Activity of oligonucleotides.

| Wave ID | 2.0 nM | 8.2 nM | 33 nM |
|---|---|---|---|
| Control | .95 | 1.07 | 1.12 |
| WV-1868 | 1.18 | 1.07 | .85 |
| WV-3381 | .48 | .11 | .18 |
| WV-3382 | .99 | .33 | .18 |
| WV-3383 | 1.02 | .55 | .31 |
| WV-3384 | 1.16 | .42 | .13 |
| WV-3385 | 1.03 | .42 | .18 |
| WV-3386 | .57 | .22 | .23 |
| WV-3387 | .23 | .08 | .11 |
| WV-3388 | 1.08 | .95 | 1.03 |
| WV-3389 | 1.07 | 1.15 | .79 |
| WV-3390 | .63 | .25 | .05 |
| WV-3391 | .46 | .18 | .14 |
| WV-3392 | .42 | .13 | .08 |
| WV-3393 | .33 | .11 | .05 |
| WV-3394 | .46 | .20 | .10 |

Table 76. Tables 76A and B show the in vitro potency of ASOs to PNPLA3. Tested oligonucleotides are: Table 76A, WV-1868, and WV-3395 to WV-3408; Table 76B, WV-1868, and WV-3409 to WV-3422.

TABLE 76A

Activity of oligonucleotides.

| Wave ID | 2.0 nM | 8.2 nM | 33 nM |
|---|---|---|---|
| Control | .96 | 1.07 | 1.12 |
| WV-1868 | 1.18 | 1.06 | .85 |
| WV-3395 | .33 | .28 | .33 |
| WV-3396 | 1.02 | .51 | .23 |
| WV-3397 | .83 | .37 | .14 |
| WV-3398 | 1.07 | .22 | .06 |
| WV-3399 | .4 | .22 | .26 |
| WV-3400 | .87 | .52 | .18 |
| WV-3401 | 1.09 | .43 | .12 |
| WV-3402 | .37 | .12 | .06 |
| WV-3403 | 1.2 | 1.08 | .92 |
| WV-3404 | .29 | .15 | .25 |
| WV-3405 | .86 | .33 | .21 |
| WV-3406 | 1.18 | 1.26 | 1.14 |
| WV-3407 | .95 | .56 | .23 |
| WV-3408 | .31 | .15 | .21 |

TABLE 76B

Activity of oligonucleotides.

| Wave ID | 2.0 nM | 8.2 nM | 33 nM |
|---|---|---|---|
| Control | .96 | 1.07 | 1.12 |
| WV-1868 | 1.17 | 1.06 | .85 |
| WV-3409 | .6 | .31 | .45 |
| WV-3410 | .89 | .23 | .19 |
| WV-3411 | .63 | .12 | .07 |
| WV-3412 | .87 | .34 | .08 |
| WV-3413 | .85 | .31 | .05 |
| WV-3414 | 1.07 | .75 | .32 |
| WV-3415 | 1.02 | .25 | .44 |
| WV-3416 | .55 | .28 | .25 |
| WV-3417 | .68 | .23 | .31 |
| WV-3418 | .55 | .15 | .28 |
| WV-3419 | .81 | .63 | .38 |
| WV-3420 | 1.12 | .87 | .27 |
| WV-3421 | .48 | .17 | .23 |
| WV-3422 | 1.01 | .6 | .38 |

Table 77. Table 77 shows the in vitro potency of ASOs to PNPLA3. Tested oligonucleotides are: WV-1868, and WV-3423 to WV-3436.

TABLE 77

Activity of oligonucleotides.

| Wave ID | 2.0 nM | 8.2 nM | 33 nM |
|---|---|---|---|
| Control | 1.05 | 1.15 | 1.03 |
| WV-1868 | 1.07 | 1.07 | 1.03 |
| WV-3423 | .62 | .42 | .3 |
| WV-3424 | .69 | .4 | .2 |
| WV-3425 | 1.02 | .68 | .35 |
| WV-3426 | .92 | .46 | .37 |
| WV-3427 | .87 | .74 | .6 |
| WV-3428 | 1.08 | .88 | .97 |
| WV-3429 | 1.02 | .6 | .37 |
| WV-3430 | 1.13 | .94 | .48 |
| WV-3431 | .63 | .38 | .23 |
| WV-3432 | .97 | .63 | .31 |
| WV-3433 | .63 | .26 | .18 |
| WV-3434 | .81 | .31 | .2 |
| WV-3435 | .58 | .33 | .28 |
| WV-3436 | .93 | .71 | .5 |

Table 78. Table 78 shows the in vitro potency of ASOs to PNPLA3. Tested oligonucleotides are: WV-1868, and WV-3437 to WV-3450.

TABLE 78

Activity of oligonucleotides.

| Wave ID | 2.0 nM | 8.2 nM | 33 nM |
|---|---|---|---|
| Control | 1.05 | 1.15 | 1.03 |
| WV-1868 | 1.06 | 1.06 | 1.03 |
| WV-3437 | 1.06 | .54 | .22 |
| WV-3438 | .93 | .85 | 1 |
| WV-3439 | 1.01 | .75 | .56 |
| WV-3440 | 1.04 | 1.03 | .67 |
| WV-3441 | 1.16 | .8 | .38 |
| WV-3442 | 1.03 | .57 | .29 |
| WV-3443 | .45 | .25 | .2 |
| WV-3444 | .65 | .38 | .23 |
| WV-3445 | 1.18 | .78 | .42 |
| WV-3446 | .8 | .45 | .25 |
| WV-3447 | .86 | .59 | .25 |
| WV-3448 | .81 | .52 | .22 |
| WV-3449 | .74 | .43 | .2 |
| WV-3450 | .96 | .95 | .92 |

Table 79. Table 79 shows the efficacy of antisense oligonucleotides in knockdown of PNPLA3 mediated by RNase H, in a Hep3B 24 hour assay. Tested oligonucleotides are: WV-1868 (control), WV-3451, WV-3452, WV-3453, WV-3454, WV-3455, WV-3456, WV-3457, WV-3458, WV-3459, WV-3460, WV-3461, and WV-3462. WV-1868 is an antisense oligonucleotide (operating through RNase H-mediated knockdown), while other tested oligonucleotides are RNAi agents.

TABLE 79

Activity of oligonucleotides.

| Wave ID | 2.0 nM | 8.2 nM | 33 nM |
|---|---|---|---|
| Control | 1.05 | 1.15 | 1.04 |
| WV-1868 | 1.06 | 1.06 | 1.02 |
| WV-3451 | .97 | .55 | .24 |
| WV-3452 | 1.01 | .52 | .18 |
| WV-3453 | .43 | .19 | .19 |
| WV-3454 | .51 | .22 | .1 |
| WV-3455 | .62 | .35 | .18 |
| WV-3456 | .78 | .52 | .22 |
| WV-3457 | .74 | .37 | .11 |
| WV-3458 | .64 | .28 | .22 |

TABLE 79-continued

Activity of oligonucleotides.

| Wave ID | 2.0 nM | 8.2 nM | 33 nM |
|---|---|---|---|
| WV-3459 | 1.15 | 1.09 | .9 |
| WV-3460 | .77 | .4 | .43 |
| WV-3461 | 1.13 | .54 | .23 |
| WV-3462 | .93 | .42 | .2 |

Table 81. Table 81 shows the in vitro potency and $IC_{50}$ for different oligonucleotides which target PNPLA3. Tested oligonucleotides are: WV-2477 (which knocks down the target via a RNA interference-mediated mechanism) and WV-3387 (which knocks down the target via RNase H-mediated knockdown).

TABLE 81

Activity of oligonucleotides.

| Conc. (nM) (exp 10) | WV-2477-Hep3b | | WV-2447-Huh7 | | WV-3387-Hep3b | | WV-3387-Huh7 | |
|---|---|---|---|---|---|---|---|---|
| 0.796 | 1.031 | | | 1.029 | 0.928 | 0.148 | 0.095 | 0.154 | 0.186 |
| 0.495 | | 0.982 | | 0.884 | 0.143 | 0.092 | 0.163 | 0.218 |
| 0.194 | 1.144 | 0.989 | 1.103 | 0.994 | 0.221 | 0.162 | 0.183 | |
| −0.107 | 1.068 | 1.201 | 1.259 | 1.008 | 0.273 | 0.254 | 0.321 | 0.361 |
| −0.408 | 1.193 | 1.075 | 0.947 | 1.111 | 0.350 | 0.385 | 0.515 | 0.490 |
| −0.709 | 1.113 | 1.003 | | 0.974 | 0.560 | 0.534 | 0.537 | 0.708 |
| −1.010 | 1.193 | 1.010 | 0.866 | 0.902 | 0.644 | 0.704 | 0.652 | 0.974 |
| −1.612 | | 0.989 | 1.044 | 1.051 | 0.861 | 0.820 | 1.029 | 0.825 |
| −2.214 | 1.185 | 0.976 | 0.954 | 1.051 | 0.929 | 0.956 | 0.947 | 0.866 |

| | IC50 (nM) | 95% CI |
|---|---|---|
| WV-2477-Hep3b | NA | — |
| WV-2477-Huh7 | NA | — |
| WV-3387-Hep3b | 0.205 | 0.16 to 0.254 |
| WV-3387-Huh7 | 0.311 | 0.186 to 0.602 |

Table 82. Table 82 shows the efficacy of antisense oligonucleotides in knockdown of PNPLA3 mediated by RNase H, in a Hep3B assay. Tested oligonucleotides are: WV-3380 (positive control), WV-3387, WV-3391, WV-3393, WV-3402, WV-3411, WV-3416, WV-3443, and WV-3454.

TABLE 82

Activity of oligonucleotides.

| Wave ID | IC50 (nM) |
|---|---|
| WV-3380 | 4.28 |
| WV-3387 | 1.29 |
| WV-3391 | 2.31 |
| WV-3393 | 2.21 |
| WV-3402 | 1.55 |
| WV-3411 | 5.32 |
| WV-3416 | 4.68 |
| WV-3443 | 1.22 |
| WV-3454 | 3.39 |

Table 83. Table 83 shows the IC50 of ASOs to PNPLA3 in Huh7 cells. Tested oligonucleotides are: WV-3380, WV-3387, WV-3391, WV-3393, WV-3402, WV-3411, WV-3416, WV-3443, and WV-3454.

TABLE 83

Activity of oligonucleotides.

| Wave ID | HEP3B IC50 (nM) | Huh7 IC50 (nM) |
|---|---|---|
| WV-3380 | 4.28 | 3.86 |
| WV-3387 | 1.29 | 1.91 |
| WV-3391 | 2.31 | 2.96 |
| WV-3393 | 2.21 | 5.5 |
| WV-3402 | 1.55 | 2.85 |
| WV-3411 | 5.32 | 8.27 |
| WV-3416 | 4.68 | 9.0 |
| WV-3443 | 1.22 | 2.55 |
| WV-3454 | 3.39 | 4.30 |

Table 84. Table 84 shows the in vitro potency of ASOs to PNPLA3. Tested oligonucleotides are: WV-3380, WV-3393, WV-3402, WV-3421, WV-3390, WV-3399, WV-3404, WV-3443, WV-3391, WV-3394, WV-3408, WV-3387, and WV-3381.

TABLE 84

IC50 of oligonucleotides.

| Wave ID | IC 50 nM |
|---|---|
| WV-3380 | 1.5 |
| WV-3393 | 1.1 |
| WV-3402 | 1.7 |
| WV-3421 | 1.4 |
| WV-3399 | 0.77 |
| WV-3404 | 1.6 |
| WV-3443 | 1.6 |
| WV-3391 | 0.65 |
| WV-3394 | 1.4 |
| WV-3408 | 0.92 |
| WV-3387 | 1.2 |
| WV-3381 | 1.4 |

Table 85. Table 85 shows the IC50 of ASOs to PNPLA3. Tested oligonucleotides are: WV-3380, WV-3381, WV-3387, WV-3391, WV-3393, WV-3394, WV-3399, WV-3402, WV-3404, WV-3408, WV-3421, and WV-3443.

TABLE 85

IC50 of oligonucleotides.
Oligonucleotides had various sequences, and were
in the coding segment (CDS) or 3' untranslated
region (3'UTR) of PNPLA3.

| Wave ID | IC 50 nM | Position |
|---|---|---|
| WV-3380 | 1.5 | CDS |
| WV-3393 | 1.1 | CDS |
| WV-3402 | 1.7 | CDS |
| WV-3421 | 1.4 | 3'UTR |
| WV-3399 | 0.77 | 3'UTR |
| WV-3404 | 1.6 | 3'UTR |
| WV-3443 | 1.6 | 3'UTR |
| WV-3391 | 0.65 | 3'UTR |
| WV-3394 | 1.4 | 3'UTR |
| WV-3408 | 0.92 | 3'UTR |
| WV-3387 | 1.2 | 3'UTR |
| WV-3381 | 1.4 | 3'UTR |

Oligonucleotides had various sequences, and were in the coding segment (CDS) or 3' untranslated region (3'UTR) of PNPLA3.

Table 86. Table 86 shows the in vitro potency of ASOs to PNPLA3. Tested oligonucleotides are: WV-3421, WV-3393, WV-3380, and WV-3402. In the data shown in Tables 86 and 87, oligonucleotides with human sequences were tested in cyno cells. Ovals indicate a mismatch, wherein the oligo sequence matches the human sequence, but has a mismatch with the cyno sequence.

TABLE 86

Activity of oligonucleotides.

| Oligonucleotide | 0 nM | 0.01 nM | 1 nM | 8 nM | 25 nM |
|---|---|---|---|---|---|
| WV-3421 | .99 | .78 | .52 | .18 | .12 |
| WV-3380 | 1.01 | 1.12 | .99 | .55 | .29 |
| WV-3393 | .99 | 1.02 | .94 | .48 | .37 |
| WV-3402 | .96 | 1.01 | .82 | .56 | .39 |

Numbers represent relative PNPLA3 mRNA levels (PNPLA3/GAPDH). 1.0 would represent 100% mRNA level or 0% knockdown, and 0.0 would represent 0.0% mRNA level or 100% knockdown. Numbers are approximate, and error bars are not included. Cynomolgus monkey cells were treated in vitro.

Table 87. Table 87 shows the in vitro potency of ASOs to PNPLA3. Tested oligonucleotides are: WV-3404, WV-3399, WV-3443, and WV-3421.

TABLE 87

Activity of oligonucleotides.

| Oligonucleotide | 0 nM | 0.01 nM | 1 nM | 8 nM | 25 nM |
|---|---|---|---|---|---|
| WV-3404 | 1.01 | .95 | .81 | .33 | .36 |
| WV-3443 | 1.01 | 1.07 | 1.14 | .52 | .39 |
| WV-3399 | 1.04 | .97 | .83 | .84 | .80 |

Numbers represent relative PNPLA3 mRNA levels (PNPLA3/GAPDH). 1.0 would represent 100% mRNA level or 0% knockdown, and 0.0 would represent 0.0% mRNA level or 100% knockdown. Numbers are approximate, and error bars are not included. Cynomolgus monkey cells were treated in vitro.

While not wishing to be bound by any particular theory, the present disclosure notes that further experiments also provided additional data supporting the conclusions that various putative single-stranded RNAi agents were, in fact, capable of mediating RNA interference; and that various oligonucleotides designed to be capable of mediating knockdown via a RNaseH-mediated mechanism in fact mediated knockdown via a RNaseH-mediated mechanism. The finding that a PNPLA3 oligonucleotide to a different target directed knockdown via a RNaseH-mediated mechanism supports the idea that another oligonucleotide of the same or a similar format but which has a PNPLA3 and is capable of knocking down PNPLA3 may likely do so also via a RNaseH-mediated mechanism.

In one experiment, an in vitro RNase H assay was performed, with APOC3 oligonucleotide WV-1868 (ASO, mediating a RNase H knockdown mechanism of a non-PNPLA3 gene, APOC3) as a positive control, and APOC3 oligonucleotide WV-2110 (a single-stranded RNAi agent) as a negative control. RNA molecule WV-2372 is used as a test substrate. In the RNase H assay, dual mechanism APOC3 oligonucleotide WV-2111 mediated RNase H knockdown (data not shown).

In another experiment, an in vitro Ago-2 assay (for single-stranded RNA interference) was performed. This assay was performed with single-stranded RNAi agents to another gene, APOC3, but which have formats which are similar or identical to various formats described for PNPLA3 oligonucleotides. The finding that a PNPLA3 oligonucleotide to a different target directed RNA interference supports the idea that another oligonucleotide of the same or a similar format but which has a PNPLA3 and is capable of knocking down PNPLA3 may likely do so also via directed RNA interference.

A RNA test substrate was WV-2372 (APOC3). In the results, the band representing the RNA test substrate is absent in the presence of APOC3 oligonucleotides WV-1308 and WV-2420, indicating that these oligonucleotides are single-stranded RNAi agents capable of mediating RNA interference. Various controls were used: Substrate in the absence of negative control ASO WV-2134; substrate in the presence of negative control ASO WV-2134, which does not mediate RNA interference; substrate in the absence of test oligonucleotide WV-1308; substrate in the absence of test oligonucleotide WV-2420; substrate alone; no substrate, with added WV-2134; and no substrate, with added WV-1308 (data not shown).

In another experiment, in vitro Ago-2 assay was (for single-stranded RNA interference) performed, using a APOC3 mRNA as a test substrate in a 3' RACE assay in Hep3B cells. A cleavage product of the APOC3 mRNA in the presence of test oligonucleotide WV-3021 was detected, corresponding to cleavage of the mRNA at a site corresponding to a cut between positions 10 and 11 of WV-3021 (data not shown), which result is consistent with RNA interference. An artifactual cleavage product was also detected.

In other experiments, dual mechanism (hybrid format) APOC3 oligonucleotide WV-2111 was shown to be capable of mediating knockdown by both RNase H and RNA interference. A RNA substrate for WV-2111, which comprises the sequence of GCUGGCCUCC-CAAUAAAGCUGGACA (SEQ ID NO: 1129), which is complementary to the sequence of APOC3 oligonucleotide WV-2111, was found to be cleaved in the presence of WV-2111 at the following positions: GC/UGGC/C/U/CC/CAAUA//AAGCUGGACA (SEQ ID NO: 1130), wherein / indicates a cleavage site in a position typical of RNaseH activity, and // indicates a cleavage site in a position typical of Ago-2 (RNA interference) activity. These data support the idea that WV-2111 mediates knockdown via both RNaseH and RNA interference mechanisms.

Several oligonucleotides were also found to be capable of mediating RNA interference in an Ago-2 in vitro assay. A RNA test substrate was APOC3 oligonucleotide WV-2372; this substrate disappeared in the presence of APOC3 oligonucleotides WV-1308, WV-2114, WV-2386, or WV-2387 (each tested separately), indicating that each of these oligonucleotides is capable of acting as single-stranded RNAi agents mediating RNA interference.

While not wishing to be bound by any particular theory, the present disclosure suggests that at least some of the oligonucleotides designated herein as single-stranded RNAi agents mediate knockdown via a RISC (RNA interference silencing complex); however, in at least some experiments, oligonucleotides designated herein as single-stranded RNAi agents were capable of mediating an observed knockdown of the protein level of a target greater than the observed knockdown of the corresponding mRNA level, and, while not wishing to be bound by any particular theory, the present disclosure suggests that this observation is consistent with the conjecture that some oligonucleotides designated herein as single-stranded RNAi agents which are capable of knocking down of a target gene or protein may be able to do so via a RISC-mediated mechanism and/or steric hindrance.

The present disclosure presents many non-limiting examples of oligonucleotides, having any of various sequences, formats, modifications, 5'-end regions, seed regions, post-seed regions, and 3'-end regions, and which are capable of mediating single-stranded RNA interference (e.g., single-stranded RNAi agents).

Figure 3A:
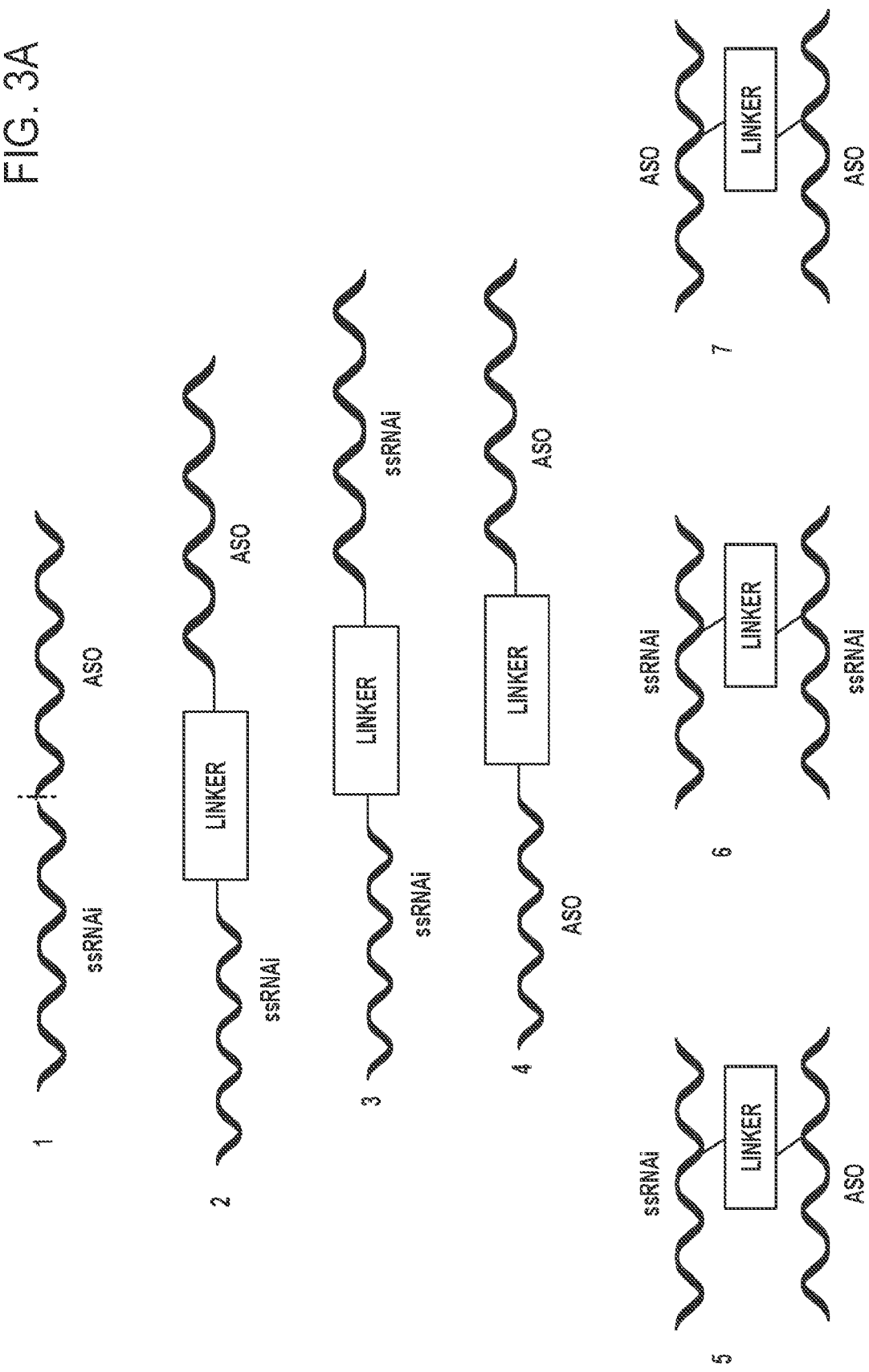
Figure 3B:
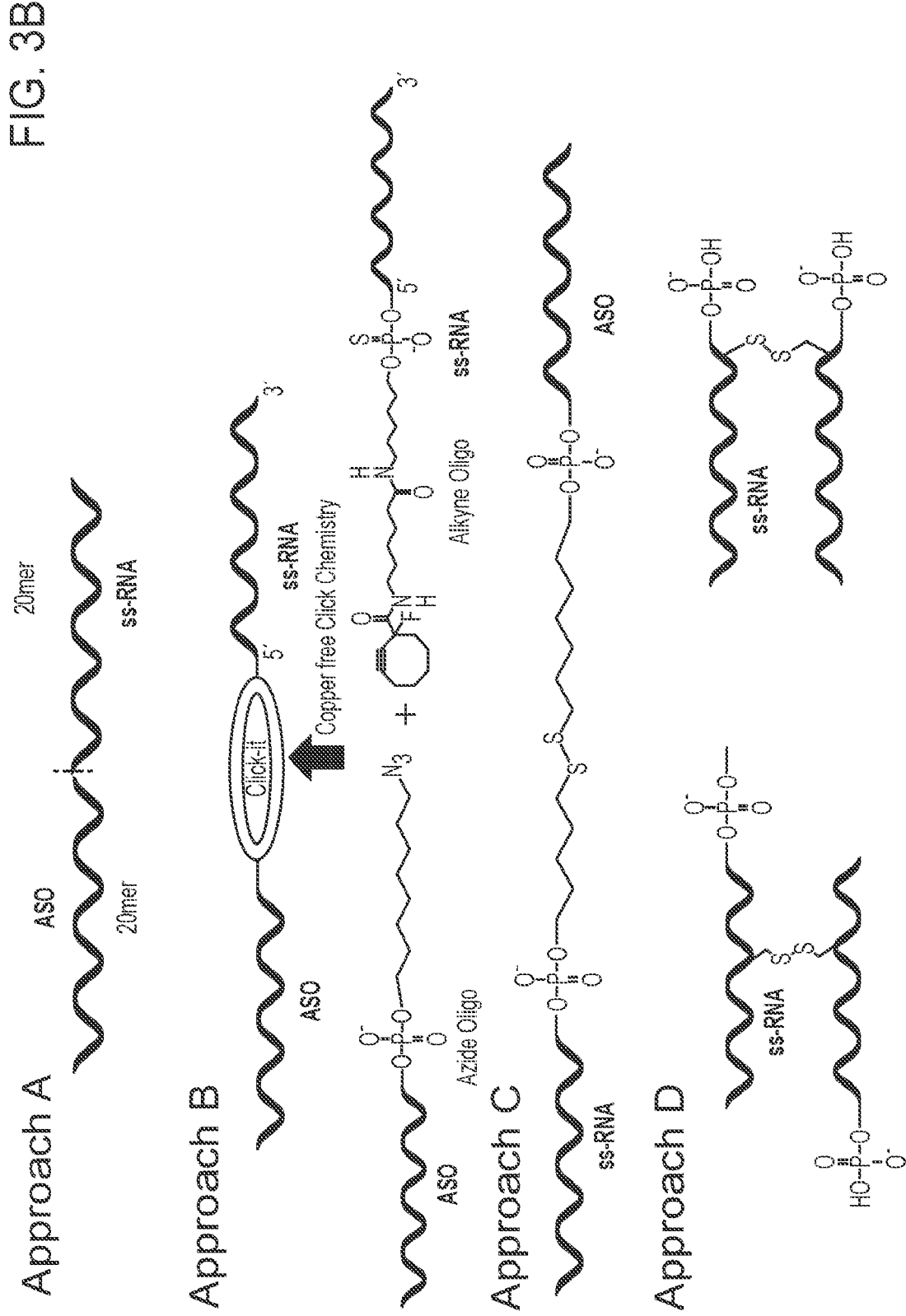
FIG. 3B shows example chemistry approaches for joining monomers, which monomers may perform their functions through various pathways, to form multimers.

FIG. 3. FIGS. 3A and 3B show example multimer formats. Oligonucleotides can be joined directly and/or through linkers. As illustrated, a multimer can comprise oligonucleotide monomers of the same or different structures/types. In some embodiments, a monomer of a multimer is an ssRNAi agent. In some embodiments, a monomer of a multimer is a RNase H-dependent antisense oligonucleotide (ASO). Monomers can be joined through various positions, for example, the 5'-end, the 3'-end, or positions in between.

Shown directly below is a phosphoramidite useful for linking oligonucleotide monomers through formation of disulfide linkers. After incorporation into oligonucleotide monomers, a thioester can be hydrolyzed to release a free thiol, which can react with a thiol of another oligonucleotide monomer to form a disulfide bond, thereby linking oligonucleotide monomers together. Multiple thiol groups may be incorporated into oligonucleotides so that multimers of various numbers of monomers may be formed.

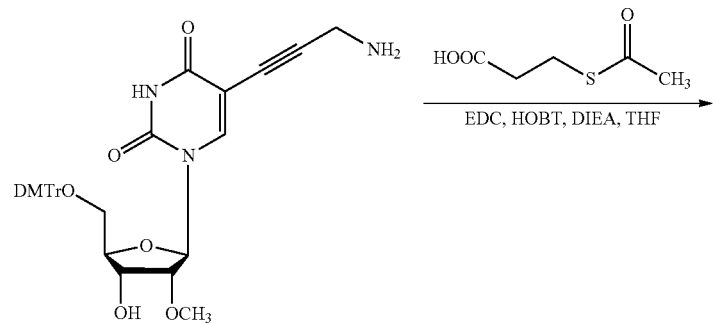

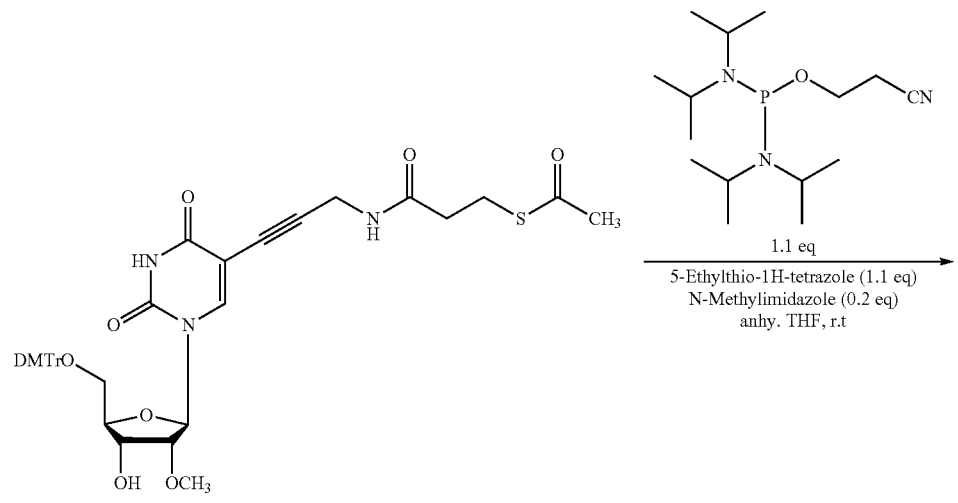

WV-NU-016

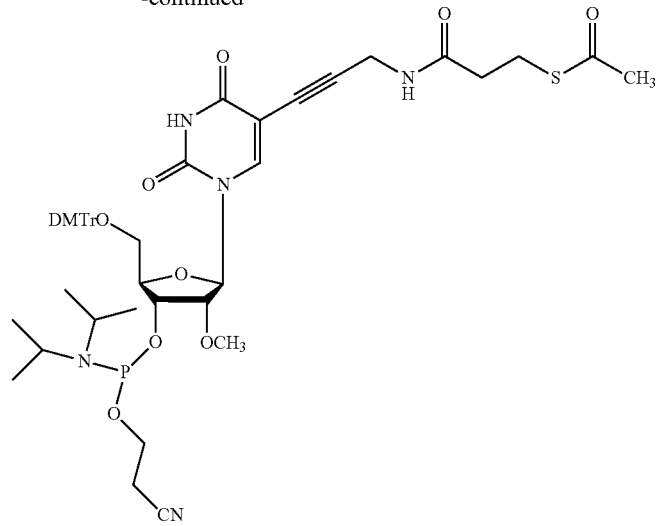

WV-NU-016-CNE

Table 90 shows in vitro allele-specific suppression of different oligonucleotides which target PNPLA3. Example oligonucleotides are completely complementary to target sequences of one allele, which target sequences comprise one or two SNP sites. One SNP site is associated with I148M change in protein sequence. Oligonucleotides comprising target-binding sequences that are completely complementary to target sequences comprising both SNPs were assessed in Hep3B cells (wild-type, C and C, I148) and Huh7 cells (with double mutation, T and G, M148). The double mutation was tested at various positions (8 and 11; 9 and 12; 10 and 13; etc.) and with various modifications to identify oligonucleotides capable of allele-specific knockdown of PNPLA3.

As shown in Table 90B, WV-7778 to WV-7793 and WV-3858 to WV-3864 were tested. In these oligonucleotides, the first and the last internucleotidic linkages in the wings are stereorandom PS and the others are PO; the 5' wing and the 3' wing comprise 2'-OMe. Several oligonucleotides demonstrated allele-specific knockdown of PNPLA3.

TABLE 90B

Activity of oligonucleotides.

|  | Hep3B |  | Huh7 |  |
| --- | --- | --- | --- | --- |
| mock | 100 | 100 | 100 | 100 |
| WV-7778 | 92.8 | 86.9 | 63.6 | 52.7 |
| WV-7779 | 92.6 | 85.8 | 59.2 | 48.0 |
| WV-7780 | 102.3 | 97.1 | 36.4 | 34.8 |
| WV-7781 | 111.8 | 102.4 | 46.1 | 38.9 |
| WV-7782 | 108.5 | 94.7 | 43.3 | 35.0 |
| WV-7783 | 110.2 | 97.5 | 36.6 | 33.7 |
| WV-7784 | 105.0 | 95.9 | 41.2 | 41.9 |
| WV-7785 | 108.7 | 107.4 | 73.8 | 57.5 |
| WV-3858 | 103.3 | 103.6 | 55.1 | 52.3 |
| WV-3859 | 94.7 | 96.1 | 41.8 | 41.2 |
| WV-3860 | 104.2 | 94.1 | 46.7 | 45.6 |
| WV-3861 | 101.8 | 99.2 | 47.1 | 45.2 |
| WV-3862 | 97.1 | 96.5 | 44.0 | 42.3 |
| WV-3863 | 99.7 | 86.0 | 42.0 | 51.5 |
| WV-3864 | 97.8 | 96.8 | 53.5 | 38.9 |
| WV-7786 | 99.1 | 104.3 | 37.0 | 38.0 |
| WV-7787 | 84.2 | 87.5 | 23.0 | 25.1 |
| WV-7788 | 80.4 | 88.0 | 35.5 | 28.5 |

TABLE 90B-continued

Activity of oligonucleotides.

|  | Hep3B |  | Huh7 |  |
| --- | --- | --- | --- | --- |
| WV-7789 | 82.7 | 85.7 | 25.4 | 25.5 |
| WV-7790 | 80.8 | 85.1 | 27.4 | 29.8 |
| WV-7791 | 87.1 | 80.1 | 40.8 | 42.1 |
| WV-7792 | 78.1 | 73.1 | 42.5 | 46.5 |
| WV-7793 | 68.3 | 65.1 | 49.9 | 44.9 |

As shown in Table 90C, WV-7794 to WV-7816 were tested. In these oligonucleotides, the first and the last internucleotidic linkages in the wings are stereorandom PS and the others are PO; the 5' wing and the 3' wing comprise 2'-MOE. Several oligonucleotides demonstrated allele-specific knockdown of PNPLA3.

TABLE 90C

Activity of oligonucleotides.

|  | Hep3B |  | Huh7 |  |
| --- | --- | --- | --- | --- |
| mock | 100 | 100 | 100 | 100 |
| WV-7794 | 47.6 | 44.5 | 25.0 | 20.6 |
| WV-7795 | 58.5 | 52.8 | 14.3 | 14.8 |
| WV-7796 | 54.6 | 56.4 | 16.3 | 15.5 |
| WV-7797 | 75.1 | 74.2 | 13.5 | 12.8 |
| WV-7798 | 78.4 | 79.8 | 11.9 | 13.7 |
| WV-7799 | 89.9 | 92.4 | 23.5 | 25.7 |
| WV-7800 | 93.6 | 92.2 | 34.1 | 29.9 |
| WV-7801 | 90.3 | 90.3 | 38.4 | 29.3 |
| WV-7802 | 101.1 | 101.3 | 25.1 | 29.6 |
| WV-7803 | 102.0 | 103.2 | 24.8 | 25.8 |
| WV-7804 | 95.9 | 97.2 | 27.8 | 32.7 |
| WV-7805 | 100.5 | 95.5 | 21.9 | 22.0 |
| WV-7806 | 110.6 | 105.4 | 22.0 | 21.2 |
| WV-7807 | 96.2 | 101.5 | 21.1 | 23.8 |
| WV-7808 | 95.5 | 101.0 | 21.5 | 18.8 |
| WV-7809 | 85.3 | 84.2 | 17.1 | 15.7 |
| WV-7810 | 92.0 | 95.9 | 25.2 | 21.6 |
| WV-7811 | 100.1 | 100.0 | 26.6 | 27.1 |
| WV-7812 | 79.5 | 82.1 | 22.3 | 21.1 |
| WV-7813 | 83.7 | 76.2 | 23.7 | 18.2 |
| WV-7814 | 87.8 | 82.8 | 44.3 | 39.2 |
| WV-7815 | 78.1 | 74.8 | 45.3 | 37.1 |
| WV-7816 | 59.5 | 52.4 | 24.5 | 20.5 |

As shown in Table 90D, WV-7817 to WV-7839 were tested. In these oligonucleotides, the first and the last nucleotide are LNA; the 5' wing has a LNA at the 5' end of the oligonucleotide followed by several 2'-OMe; and the 3' wing has several 2'-OMe followed by a LNA at the 3' end of the oligonucleotide. Several oligonucleotides demonstrated allele-specific knockdown of PNPLA3.

TABLE 90D

Activity of oligonucleotides.

|  | Hep3B |  | Huh7 |  |
|---|---|---|---|---|
| mock | 100 | 100 | 100 | 100 |
| WV-7817 | 71.4 | 60.1 | 34.0 | 30.2 |
| WV-7818 | 68.1 | 75.8 | 44.0 | 30.0 |
| WV-7819 | 68.5 | 76.6 | 20.7 | 20.7 |
| WV-7820 | 87.7 | 86.0 | 24.0 | 22.4 |
| WV-7821 | 90.1 | 89.3 | 17.7 | 15.3 |
| WV-7822 | 101.2 | 87.2 | 19.6 | 11.7 |
| WV-7823 | 83.3 | 87.7 | 22.9 | 17.8 |
| WV-7824 | 99.0 | 101.9 | 31.1 | 31.6 |
| WV-7825 | 94.0 | 89.5 | 28.7 | 22.6 |
| WV-7826 | 95.6 | 87.5 | 21.2 | 17.6 |
| WV-7827 | 113.3 | 104.4 | 22.1 | 19.3 |
| WV-7828 | 108.1 | 102.8 | 25.7 | 23.6 |
| WV-7829 | 99.8 | 97.9 | 20.5 | 21.7 |
| WV-7830 | 95.9 | 87.8 | 18.5 | 19.2 |
| WV-7831 | 89.8 | 89.2 | 21.3 | 23.4 |
| WV-7832 | 76.2 | 71.7 | 9.4 | 11.8 |
| WV-7833 | 68.2 | 76.8 | 14.1 | 10.4 |
| WV-7834 | 69.5 | 71.2 | 17.4 | 16.5 |
| WV-7835 | 69.6 | 68.7 | 11.0 | 9.4 |
| WV-7836 | 59.8 | 67.8 | 18.3 | 21.0 |
| WV-7837 | 60.8 | 63.7 | 25.6 | 28.4 |
| WV-7838 | 48.2 | 50.5 | 16.8 | 13.5 |
| WV-7839 | 35.0 | 39.1 | 10.5 | 11.8 |

As shown in Table 90E, WV-7840 to WV-7862 were tested. In these oligonucleotides, the first and the last nucleotide are LNA; the 5' wing has a LNA at the 5' end of the oligonucleotide followed by several 2'-MOE; and the 3' wing has several 2'-MOE (or 5-methyl 2'-MOE) followed by a LNA at the 3' end of the oligonucleotide. Several oligonucleotides demonstrated allele-specific knockdown of PNPLA3.

TABLE 90E

Activity of oligonucleotides.

|  | Hep3B |  | Huh7 |  |
|---|---|---|---|---|
| mock | 100 | 100 | 100 | 100 |
| WV-7840 | 32.7 | 37.7 | 12.8 | 14.8 |
| WV-7841 | 45.9 | 49.8 | 8.1 | 10.6 |

TABLE 90E-continued

Activity of oligonucleotides.

|  | Hep3B |  | Huh7 |  |
|---|---|---|---|---|
| WV-7842 | 43.2 | 50.4 | 7.6 | 7.0 |
| WV-7843 | 53.7 | 61.0 | 8.7 | 10.6 |
| WV-7844 | 69.2 | 69.0 | 14.3 | 14.9 |
| WV-7845 | 80.8 | 83.7 | 15.0 | 13.7 |
| WV-7846 | 77.1 | 86.3 | 16.5 | 15.7 |
| WV-7847 | 85.2 | 96.4 | 18.5 | 15.6 |
| WV-7848 | 87.2 | 89.4 | 21.7 | 18.0 |
| WV-7849 | 65.0 | 74.2 | 17.2 | 16.7 |
| WV-7850 | 98.8 | 107.4 | 15.3 | 18.7 |
| WV-7851 | 105.0 | 95.8 | 11.4 | 15.9 |
| WV-7852 | 113.7 | 86.9 | 14.2 | 14.2 |
| WV-7853 | 108.5 | 90.7 | 10.1 | 14.3 |
| WV-7854 | 109.6 | 94.9 | 11.3 | 12.4 |
| WV-7855 | 81.9 | 82.8 | 7.4 | 5.4 |
| WV-7856 | 86.3 | 82.0 | 11.5 | 11.2 |
| WV-7857 | 95.3 | 78.1 | 14.6 | 15.6 |
| WV-7858 | 63.0 | 66.3 | 8.6 | 9.8 |
| WV-7859 | 65.4 | 61.5 | 12.9 | 15.9 |
| WV-7860 | 69.4 | 70.0 | 30.4 | 34.2 |
| WV-7861 | 51.9 | 49.0 | 14.8 | 26.8 |
| WV-7862 | 37.4 | 41.3 | 10.4 | 11.2 |

As shown in Table 90F, WV-993, WV-3390, and WV-4054 were tested.

TABLE 90F

Activity of oligonucleotides.

|  | Hep3B |  | Huh7 |  |
|---|---|---|---|---|
| mock | 100.0 | 100.0 | 100.0 | 100.0 |
| UT (untreated) | 92.4 | 98.7 | 93.1 | 107.0 |
| WV-993 10 nM | 108.0 | 117.8 | 115.8 | 137.6 |
| WV-3390 2 nM | 84.5 | 84.1 | 46.5 | 57.6 |
| WV-3390 10 nM | 50.0 | 53.9 | 15.7 | 24.4 |
| WV-4054 2 nM | 95.8 | 95.1 | 30.0 | 35.7 |
| WV-4054 10 nM | 85.5 | 91.8 | 30.2 | 37.5 |

As shown in Table 90G, WV-3860 to WV-3864 were tested. Oligonucleotides had mismatches (between wildtype and mutant alleles) at positions 8 and 11 (WV-3860); 9 and 12 (WV-3861); 10 and 13 (WV-3862); 11 and 14 (WV-3863); and 12 and 15 (WV-3864). Several oligonucleotides demonstrated allele-specific knockdown of PNPLA3, particularly at a concentration of 8 nM.

TABLE 90G

Activity of oligonucleotides.

| nM | WV-3860 Hep3B | | WV-3861 Hep3B | | WV-3862 Hep3B | | WV-3863 Hep3B | |
|---|---|---|---|---|---|---|---|---|
| 50 | 37.7 | 44.4 | 44.3 | 47.7 | 21.9 | 32.3 | 32.0 | 32.8 |
| 20 | 83.9 | 89.7 | 87.7 | 93.9 | 64.7 | 72.1 | 81.7 | 87.3 |
| 8 | 95.8 | 95.4 | 101.9 | 103.4 | 90.8 | 92.0 | 84.3 | 93.9 |
| 3.2 | 105.9 | 93.0 | 94.3 | 90.7 | 98.1 | 98.3 | 88.3 | 86.8 |
| 1.28 | 100.9 | 93.4 | 81.0 | 95.4 | 91.0 | 92.7 | 90.9 | 87.4 |
| 0.512 | 90.5 | 96.6 | 94.9 | 88.3 | 92.5 | 93.3 | 87.1 | 88.7 |
| 0.205 | 110.1 | 99.0 | 93.2 | 95.4 | 95.7 | 89.5 | 89.7 | 92.5 |
| 0.082 | 96.6 | 95.6 | 94.8 | 96.2 | 95.3 | 97.8 | 86.7 | 93.9 |
| 0.033 | 98.5 | 88.1 | 98.0 | 95.3 | 103.7 | 93.2 | 93.3 | 87.8 |
| 0.013 | 97.1 | 95.6 | 91.1 | 92.4 | 100.9 | 90.9 | 91.7 | 90.9 |

TABLE 90G-continued

Activity of oligonucleotides.

| nM | WV-3864 Hep3B | | WV-3860 Huh7 | | WV-3861 Huh7 | | WV-3862 Huh7 | |
|---|---|---|---|---|---|---|---|---|
| 50 | 31.8 | 43.9 | 11.4 | 9.3 | 12.4 | 8.4 | 6.8 | 8.4 |
| 20 | 98.4 | 99.4 | 23.7 | 25.9 | 25.9 | 24.4 | 16.8 | 14.0 |
| 8 | 100.7 | 107.4 | 47.9 | 51.3 | 46.0 | 44.0 | 40.7 | 42.6 |
| 3.2 | 94.9 | 102.7 | 84.1 | 67.6 | 63.7 | 68.7 | 56.9 | 77.6 |
| 1.28 | 96.3 | 95.6 | 100.5 | 83.9 | 80.4 | 83.7 | 77.3 | 81.0 |
| 0.512 | 89.7 | 102.4 | 100.5 | 97.3 | 85.9 | 87.5 | 78.0 | 85.6 |
| 0.205 | 96.3 | 93.8 | 101.6 | 99.9 | 83.7 | 76.6 | 73.4 | 85.7 |
| 0.082 | 89.5 | 92.1 | 81.4 | 87.3 | 85.3 | 84.1 | 78.9 | 89.3 |
| 0.033 | 92.7 | 94.2 | 114.4 | 90.6 | 100.4 | 87.6 | 87.5 | 84.6 |
| 0.013 | 91.7 | 106.0 | 107.0 | 93.7 | 82.3 | 88.1 | 78.3 | 91.6 |

| nM | WV-3863 Huh7 | | WV-3864 Huh7 | |
|---|---|---|---|---|
| 50 | 5.6 | 10.6 | 8.4 | 8.3 |
| 20 | 20.0 | 13.4 | 16.5 | 13.9 |
| 8 | 37.4 | 40.8 | 47.9 | 43.3 |
| 3.2 | 67.5 | 60.5 | 75.6 | 65.5 |
| 1.28 | 84.9 | 82.5 | 86.2 | 87.0 |
| 0.512 | 79.4 | 81.1 | 95.6 | 91.0 |
| 0.205 | 83.0 | 86.3 | 89.1 | 96.1 |
| 0.082 | 79.5 | 92.5 | 89.4 | 77.9 |
| 0.033 | 79.7 | 102.1 | 104.6 | 86.4 |
| 0.013 | 94.6 | 96.8 | 93.0 | 104.9 |

As shown in Table 90H, WV-7804 to WV-7808 were tested. Oligonucleotides had mismatches at positions 8 and 11 (WV-7804); 9 and 12 (WV-7805); 10 and 13 (WV-7806); 11 and 14 (WV-7807); and 12 and 15 (WV-7808). Some oligonucleotides demonstrated allele-specific knockdown of PNPLA3, particularly at concentrations of 3.2 and 8 nM.

TABLE 90H

Activity of oligonucleotides.

| nM | WV-7804 Hep3B | | WV-7805 Hep3B | | WV-7806 Hep3B | | WV-7807 Hep3B | |
|---|---|---|---|---|---|---|---|---|
| 50 | 63.3 | 69.5 | 60.3 | 62.7 | 69.6 | 65.1 | 75.0 | 75.5 |
| 20 | 84.6 | 98.4 | 81.8 | 86.1 | 90.1 | 89.4 | 95.3 | 95.4 |
| 8 | 101.1 | 102.9 | 96.9 | 98.5 | 100.8 | 94.7 | 101.2 | 95.5 |
| 3.2 | 92.9 | 95.1 | 90.7 | 98.1 | 98.9 | 92.1 | | 88.8 |
| 1.28 | 95.5 | 98.6 | 91.3 | 97.0 | 95.9 | 90.9 | 97.3 | 103.6 |
| 0.512 | 96.2 | 110.4 | 95.5 | 97.9 | 95.9 | 94.8 | 100.9 | 92.7 |
| 0.205 | 92.0 | 99.5 | 90.5 | 100.7 | 99.3 | 94.7 | 96.4 | 99.8 |
| 0.082 | 97.6 | 93.6 | 92.2 | 107.6 | 92.3 | 93.8 | 93.4 | 103.7 |
| 0.033 | 98.4 | 101.4 | 98.5 | 104.0 | 99.6 | 90.1 | 89.2 | 93.3 |
| 0.013 | 96.7 | 100.4 | 95.0 | 105.8 | 90.1 | 97.5 | 90.6 | 87.5 |

| nM | WV-7808 Hep3B | | WV-7804 Huh7 | | WV-7805 Huh7 | | WV-7806 Huh7 | |
|---|---|---|---|---|---|---|---|---|
| 50 | 72.2 | | 4.4 | 7.5 | 1.7 | 8.4 | 9.8 | 3.8 |
| 20 | 98.9 | | 3.5 | 11.1 | 7.1 | 11.9 | 2.8 | 7.2 |
| 8 | 117.8 | | 25.1 | 23.3 | 19.6 | 11.6 | 13.8 | 12.5 |
| 3.2 | 109.5 | | 45.3 | 48.0 | 36.1 | 38.4 | 28.8 | 39.7 |
| 1.28 | 116.3 | | 68.9 | 77.1 | 59.2 | 76.2 | 68.7 | 68.5 |
| 0.512 | 110.9 | | 74.6 | 76.0 | 75.3 | 78.4 | 66.6 | 82.4 |
| 0.205 | 109.3 | | 73.6 | 86.5 | 69.8 | 81.1 | 69.7 | 80.3 |
| 0.082 | 116.8 | | 82.9 | 89.4 | 75.0 | 86.9 | 78.6 | 79.7 |
| 0.033 | 111.1 | | 81.8 | 96.1 | 78.0 | 95.8 | 89.4 | 87.3 |
| 0.013 | 104.6 | | 86.7 | 90.4 | 79.6 | 95.0 | 88.6 | 98.0 |

| nM | WV-7807 Huh7 | | WV-7808 Huh7 | |
|---|---|---|---|---|
| 50 | 3.0 | 3.9 | 1.8 | 1.4 |
| 20 | 12.6 | 9.1 | 1.9 | 5.2 |
| 8 | 25.1 | 14.9 | 14.2 | 9.1 |
| 3.2 | 46.9 | 41.5 | 37.1 | 33.2 |
| 1.28 | 78.0 | 70.4 | 63.6 | 65.2 |
| 0.512 | 85.3 | 73.7 | 71.0 | 77.4 |
| 0.205 | 98.8 | 68.5 | 79.2 | 92.3 |
| 0.082 | 92.6 | 75.3 | 88.0 | 71.2 |
| 0.033 | 85.6 | 81.9 | 84.1 | 83.5 |
| 0.013 | 85.5 | 94.7 | 95.3 | 78.1 |

As shown in Table 90I, WV-7827 to WV-7831 were tested. Oligonucleotides had mismatches at positions 8 and 11 (WV-7827); 9 and 12 (WV-7828); 10 and 13 (WV-7829); 11 and 14 (WV-7830); and 12 and 15 (WV-7831). Several oligonucleotides demonstrated allele-specific knockdown of PNPLA3, particularly at concentrations of 3.2 and 8 nM.

TABLE 90I

Activity of oligonucleotides.

| nM | WV-7827 Hep3B | | WV-7828 Hep3B | | WV-7829 Hep3B | | WV-7830 Hep3B | |
|---|---|---|---|---|---|---|---|---|
| 50    | 37.01  | 34.29  | 36.95 | 32.75 | 25.05  | 33.48  | 36.76  | 54.22  |
| 20    | 79.06  | 85.05  | 85.88 | 77.16 | 82.21  | 79.79  | 79.33  | 87.62  |
| 8     | 97.28  | 89.87  | 93.46 | 91.76 | 99.65  | 98.83  | 97.94  | 97.83  |
| 3.2   | 94.15  | 89.12  | 97.63 | 90.63 | 92.57  | 92.37  |        | 104.59 |
| 1.28  | 97.02  | 95.4   | 94.2  | 88.81 | 93.55  | 94.13  | 100.19 | 113.12 |
| 0.512 | 105.31 | 93.06  | 97.26 | 96.7  | 95.81  | 104.04 | 107.33 | 109.89 |
| 0.205 | 107.16 | 97.39  | 92    | 91.65 | 103.76 | 102.33 | 104.56 | 100.78 |
| 0.082 | 100.92 | 101.71 | 94.43 | 88.97 | 93.95  | 105.59 | 94.95  | 110.09 |
| 0.033 | 98.82  | 95.76  | 92.83 | 92.84 | 91.46  | 103.11 | 97.7   | 93.54  |
| 0.013 | 96.78  | 93.38  | 92.91 | 90.28 | 86.25  | 104.33 | 96.73  | 98.6   |

| nM | WV-7831 Hep3B | | WV-7827 Huh7 | | WV-7828 Huh7 | | WV-7829 Huh7 | |
|---|---|---|---|---|---|---|---|---|
| 50    | 53.44  | 62.49  | 3.75  | 3.01  | 2.29  | 1.48  | 5.61   | 7.19  |
| 20    | 97.35  | 92.9   | 6.33  | 5.79  | 16.31 | 9.08  | 16.41  | 9.26  |
| 8     | 103.88 | 103.69 | 13.45 | 13.44 | 9.77  | 24.96 | 31.07  | 18.62 |
| 3.2   | 104.8  | 99.48  | 34.11 | 44.07 | 31.43 | 31.51 | 54.15  | 31.49 |
| 1.28  | 99.77  | 102.88 | 57.91 | 67.23 | 63.32 | 69.34 | 78.28  | 65.69 |
| 0.512 | 102.56 | 99.81  | 80.58 | 87.32 | 83.18 | 75.78 | 94.09  | 75.96 |
| 0.205 | 111.83 | 98.89  | 71.87 | 84.73 | 74.94 | 76.52 | 87.05  | 90.6  |
| 0.082 | 102.02 | 93.55  | 74.43 | 76.07 | 82.31 | 87.03 | 97.43  | 87.48 |
| 0.033 | 93.54  | 101.84 | 77.64 | 80.62 | 89.1  | 89.96 | 108.41 | 81.93 |
| 0.013 | 101.47 | 100.78 | 77.47 | 74.02 | 83.14 | 79.83 | 100.58 | 88.97 |

| nM | WV-7830 Huh7 | | WV-7831 Huh7 | |
|---|---|---|---|---|
| 50    | 4.11  | 5.5   | 3.5   | 5.45   |
| 20    | 6.32  | 5.86  | 5.62  | 10.22  |
| 8     | 12.5  | 16.99 | 15.15 | 23.97  |
| 3.2   | 35.34 | 40.2  | 35    | 40.3   |
| 1.28  | 56.82 | 76.27 | 73.64 | 73.96  |
| 0.512 | 86.38 | 77.53 | 83.87 | 88.08  |
| 0.205 | 80.08 | 79.81 | 85.02 | 86.98  |
| 0.082 | 95.69 | 98.61 | 82.31 | 111.77 |
| 0.033 | 86.65 | 93.2  | 85.86 | 85.82  |
| 0.013 | 94.2  | 85.75 | 81.84 | 93.28  |

As shown in Table 90J, WV-993 (negative control), WV-3390 (positive control), WV-4054, WV-7850 to WV-7854 were tested. The oligonucleotides had mismatches at positions 8 and 11 (WV-7850); 9 and 12 (WV-7851); 10 and 13 (WV-7852); 11 and 14 (WV-7853); and 12 and 15 (WV-7854). Several oligonucleotides demonstrated high allele-specific knockdown of PNPLA3, particularly at concentrations of 3.2 and 8 nM.

TABLE 90J

Activity of oligonucleotides.

| nM | WV-7850 Hep3B | | WV-7851 Hep3B | | WV-7852 Hep3B | | WV-7853 Hep3B | |
|---|---|---|---|---|---|---|---|---|
| 50    | 38.95  | 43.11 | 38.2   | 54.32  | 34.89 | 44.6   | 28.33  | 29.79  |
| 20    | 65.77  | 72.48 | 80.99  | 84.09  | 69.74 | 74.87  | 66.38  | 50.49  |
| 8     | 92.95  | 82.91 | 93.58  | 96.06  | 89.54 | 101.29 | 85.15  | 81.31  |
| 3.2   | 91.26  | 86.61 | 90.46  | 94.37  | 97.29 | 91.77  |        | 96.08  |
| 1.28  | 111.06 | 94.39 | 98.64  | 92.99  | 89.98 | 111.31 | 96.26  | 97.11  |
| 0.512 | 106.14 | 87.28 | 94.61  | 94.09  | 96.79 | 95.82  | 109.19 | 105.33 |
| 0.205 | 84.62  | 87.72 | 100.09 | 99.5   | 111.54 | 99.81 | 95.06  | 94.02  |
| 0.082 | 97.3   | 89.13 | 90.19  | 87.13  | 92.11 | 100.64 | 95.93  | 104.77 |
| 0.033 | 88.83  | 89.09 | 96.09  | 101.92 | 96.1  | 95.83  | 95.56  | 95.83  |
| 0.013 | 91.98  | 92.51 | 100.59 | 92.81  | 98.94 | 109.53 | 99.05  | 97.36  |

| nM | WV-7854 Hep3B | | WV-7850 Huh7 | | WV-7851 Huh7 | | WV-7852 Huh7 | |
|---|---|---|---|---|---|---|---|---|
| 50  | 16.7  | 18.84 | 2.74  | 4.3   | 2.13  | 1.26  | 8.39  | 7.43  |
| 20  | 63.04 | 59.9  | 5.33  | 5.88  | 6.09  | 4.64  | 7.76  | 5.84  |
| 8   | 82.27 | 80.67 | 11.67 | 9.74  | 1.12  | 14.86 | 9.96  | 10.6  |
| 3.2 | 92.77 | 89.43 | 25.14 | 13.84 | 31.45 | 25.89 | 28.6  | 25.4  |

TABLE 90J-continued

Activity of oligonucleotides.

| 1.28 | 90.63 | 83.96 | 57.25 | 62.49 | 55.19 | 52.3 | 49.96 | 56.13 |
| 0.512 | 88.27 | 86.56 | 75.21 | 73.3 | 81.73 | 81.67 | 72.77 | 87.64 |
| 0.205 | 89.69 | 88.92 | 71.16 | 74.28 | 91.84 | 94.95 | 82.61 | 85.11 |
| 0.082 | 95.16 | 89.43 | 84.71 | 75.77 | 91 | 79.62 | 96.22 | 83.67 |
| 0.033 | 99.41 | 94.3 | 80.67 | 93.66 | 84.27 | 79.5 | 72.16 | 70.12 |
| 0.013 | 88 | 96.49 | 96.84 | 104.2 | 86.94 | 81.37 | 94.13 | 88.49 |

| nM | WV-7853 Huh7 | | WV-7854 Huh7 | |
|---|---|---|---|---|
| 50 | 2.91 | 3.83 | 0.56 | 5.35 |
| 20 | 5.38 | 4.3 | 2.43 | 7.48 |
| 8 | 6.36 | 8.51 | 9.91 | 10.31 |
| 3.2 | 27.05 | 23.79 | 23.52 | 22.24 |
| 1.28 | 47.78 | 62.17 | 47.66 | 45.94 |
| 0.512 | 70.13 | 93.78 | 76.63 | 66.5 |
| 0.205 | 96.01 | 74.6 | 84.06 | 72.69 |
| 0.082 | 82.68 | 90.37 | 79.33 | 82.72 |
| 0.033 | 89.38 | 93.35 | 89.39 | 83.68 |
| 0.013 | 86.29 | 95.77 | 98.79 | 96.55 |

As shown in Table 90K and 90L, WV-3860 to WV-3864, WV-7804 to WV-7808, WV-7827 to WV-7831, and WV-7850 to WV-7854 were tested. WV-4054 demonstrated high allele-specific activity.

TABLE 90K

Activity of oligonucleotides.

| nM | WV-3390 Hep3B | | WV-3390 Huh7 | |
|---|---|---|---|---|
| 50 | 8.21 | 7.25 | 8.29 | 8.93 |
| 20 | 6.38 | 7.65 | 8.38 | 6.55 |
| 8 | 12.25 | 18.67 | 14.29 | 10.45 |
| 3.2 | 45.11 | 53.94 | 44.3 | 57.9 |
| 1.28 | 77.33 | 87.7 | 75.75 | 79.58 |
| 0.512 | 89.66 | 91.59 | 75.55 | 114.48 |
| 0.205 | 88.47 | 99.01 | 77.44 | 93.14 |
| 0.082 | 90.52 | 101.67 | 81.19 | 91 |
| 0.033 | 100.47 | 102.34 | 78.08 | 106.05 |
| 0.013 | 111.98 | 101.98 | 93.49 | 92.23 |

| nM | WV-4054 Hep3B | | WV-4054 Huh7 | |
|---|---|---|---|---|
| 8 | 77.1 | 75.46 | 25.4 | 28.99 |
| 3.2 | 64.83 | 77.36 | 19.76 | 30.45 |
| 1.28 | 75.7 | 80.58 | 20.26 | 28 |
| 0.512 | 83.19 | 91.18 | 27.99 | 30.12 |
| 0.205 | 96.79 | 100.8 | 48.79 | 51.24 |
| 0.082 | 96.97 | 105.15 | 51.71 | 65.92 |
| 0.033 | 98.21 | 96.76 | 82.73 | 90.69 |
| 0.013 | 100.71 | 110.73 | 89.25 | 101.52 |

| nM | WV-993 Hep3B | | WV-993 Huh7 | |
|---|---|---|---|---|
| 50 | 46.96 | 63.05 | 64.33 | 84.69 |
| 20 | 85.99 | 93.33 | 85.91 | 92.58 |

TABLE 90K-continued

Activity of oligonucleotides.

| 8 | 94.55 | 112.34 | 108.31 | 90.19 |
| 3.2 | 94.42 | 101.21 | 98.4 | 102.07 |
| 1.28 | 90.96 | 98.52 | 104.92 | 108.34 |
| 0.512 | 87.71 | 95.84 | 96.98 | 87.06 |
| 0.205 | 91.78 | 93.62 | 114.92 | 90.64 |
| 0.082 | 86.49 | 96.33 | 109.17 | 101.77 |
| 0.033 | 87.45 | 104.34 | 102.65 | 92.43 |
| 0.013 | 90.55 | 100.97 | 114.84 | 108.07 |

TABLE 90L

IC50 of various oligonucleotides in Huh7 cells (mutant allele).

| Mismatch Positions | Oligonucleotides 2'OMe | IC$_{50}$ (nM) | Oligonucleotides 2'MOE | IC$_{50}$ (nM) |
|---|---|---|---|---|
| 8, 11 | WV-3860 | 10.6 | WV-7804 | 4.0 |
| 9, 12 | WV-3861 | 10.4 | WV-7805 | 3.0 |
| 10, 13 | WV-3862 | 10.6 | WV-7806 | 2.6 |
| 11, 14 | WV-3863 | 7.8 | WV-7807 | 4.0 |
| 12, 15 | WV-3864 | 9.5 | WV-7808 | 2.9 |

| Mismatch Positions | Oligonucleotides 2'MOE LNA | IC$_{50}$ (nM) | Oligonucleotides 2'OMe LNA | IC$_{50}$ (nM) |
|---|---|---|---|---|
| 8, 11 | WV-7850 | 1.6 | WV-7827 | 3.8 |
| 9, 12 | WV-7851 | 2.2 | WV-7828 | 2.8 |
| 10, 13 | WV-7852 | 1.9 | WV-7829 | 3.0 |
| 11, 14 | WV-7853 | 1.8 | WV-7830 | 2.6 |
| 12, 15 | WV-7854 | 1.3 | WV-7831 | 3.3 |

TABLE 91

Activity of oligonucleotides.
PNPLA3 mRNA level
(PNPLA3/HPRT1)

| Conc (nM) exp 10 | 1.477 | 1.079 | 0.681 | 0.283 | −0.114 | −0.512 | −0.910 | −1.308 |
|---|---|---|---|---|---|---|---|---|
| WV-7808 | 0.200 | 0.366 | 0.424 | 0.576 | 0.803 | 0.910 | 1.217 | 1.131 |
| | 0.081 | 0.221 | 0.374 | 0.613 | 0.987 | 1.050 | 1.314 | 1.080 |
| WV-8690 | 0.199 | 0.388 | 0.503 | 0.808 | 0.897 | 1.000 | 1.148 | 1.068 |
| | 0.208 | 0.313 | 0.754 | 0.932 | 1.058 | 1.236 | 1.286 | 1.138 |
| WV-8858 | 0.233 | 0.446 | 0.595 | 0.838 | 0.911 | 0.916 | 0.965 | 1.213 |
| | 0.240 | 0.340 | 0.727 | 1.036 | 1.039 | 1.403 | 0.874 | |

TABLE 91-continued

Activity of oligonucleotides.
PNPLA3 mRNA level
(PNPLA3/HPRT1)

| Conc (nM) exp 10 | 1.477 | 1.079 | 0.681 | 0.283 | −0.114 | −0.512 | −0.910 | −1.308 |
|---|---|---|---|---|---|---|---|---|
| WV-8859 | 0.086 | 0.292 | 0.279 | 0.710 | 0.850 | 1.071 | 0.956 | 1.091 |
|  | 0.083 | 0.217 | 0.505 | 0.754 | 0.981 | 1.258 | 1.131 | 1.454 |
| WV-8860 | 0.234 | 0.386 | 0.385 | 0.751 | 0.867 | 0.947 | 1.358 | 1.057 |
|  | 0.162 | 0.321 | 0.503 | 1.002 | 1.100 | 1.075 | 1.250 | 1.241 |

TABLE 92

Activity of oligonucleotides.

|  | 1.477 | 1.079 | 0.681 | 0.283 | −0.115 | −0.513 | −0.911 | −1.308 |
|---|---|---|---|---|---|---|---|---|
| WV-7807 | 0.102 | 0.331 | 0.588 | 0.790 | 1.037 | 0.989 | 1.271 | 1.147 |
|  | 0.137 | 0.397 | 0.453 | 0.814 | 1.160 | 1.099 | 1.257 | 1.027 |
| WV-8854 | 0.117 | 0.375 | 0.678 | 0.831 | 0.962 | 1.021 | 1.258 | 1.277 |
|  | 0.112 | 0.363 | 0.559 | 0.793 | 1.134 | 1.237 | 1.226 | 1.186 |
| WV-8855 | 0.174 | 0.553 | 0.745 | 0.873 | 0.890 | 0.968 | 0.954 | 1.088 |
|  | 0.181 | 0.462 | 0.690 | 0.737 | 1.102 | 1.168 | 0.930 | 1.006 |
| WV-8856 | 0.055 | 0.239 | 0.496 | 0.779 | 0.815 | 0.937 | 1.029 | 1.027 |
|  | 0.069 | 0.288 | 0.654 | 0.884 | 1.172 | 1.146 | 0.937 | 1.222 |
| WV-8857 | 0.237 | 0.445 | 0.967 | 0.928 | 0.976 | 0.790 | 0.992 | 1.119 |
|  | 0.188 | 0.504 | 0.783 | 0.932 | 1.031 | 1.046 | 1.086 | 1.067 |

TABLE 93

Activity of oligonucleotides.

|  | 1.477 | 1.079 | 0.681 | 0.283 | −0.114 | −0.512 | −0.910 | −1.308 |
|---|---|---|---|---|---|---|---|---|
| WV-7806 | 0.15 | 0.24 | 0.29 | 0.71 | 0.92 | 1.03 | 1.02 | 1.10 |
|  | 0.14 | 0.16 | 0.30 | 0.56 | 0.67 | 0.84 | 1.02 | 0.89 |
| WV-8850 | 0.57 | 0.61 | 0.59 | 1.09 | 1.08 | 1.04 | 1.11 | 1.29 |
|  | 0.44 | 0.52 | 0.60 | 0.65 | 0.81 | 0.76 | 0.96 | 0.93 |
| WV-8851 | 0.18 | 0.41 | 0.43 | 0.95 | 0.93 | 1.00 | 1.08 | 1.05 |
|  | 0.17 | 0.27 | 0.63 | 0.71 | 0.70 | 1.01 | 0.90 | 0.85 |
| WV-8852 | 0.55 | 0.29 | 0.32 | 0.83 | 1.04 | 1.23 | 0.90 | 1.28 |
|  | 0.14 | 0.18 | 0.26 | 0.49 | 0.77 | 0.83 | 1.09 | 0.92 |
| WV-8853 | 0.21 | 0.38 | 0.41 | 0.76 | 1.24 | 0.92 | 1.08 | 0.93 |
|  | 0.13 | 0.20 | 0.44 | 0.61 | 0.94 | 0.64 | 0.87 | 0.95 |

TABLE 94

Activity of oligonucleotides.

|  | 1.477 | 1.079 | 0.681 | 0.283 | −0.114 | −0.512 | −0.910 | −1.308 |
|---|---|---|---|---|---|---|---|---|
| WV-7805 | 0.29 | 0.33 | 0.44 | 0.72 | 0.95 | 0.96 | 0.93 | 0.99 |
|  | 0.15 | 0.27 | 0.41 | 0.73 | 1.12 | 1.19 | 0.78 | 0.87 |
| WV-8609 | 0.33 | 0.37 | 0.48 | 0.90 | 0.84 | 0.81 | 1.02 | 1.04 |
|  | 0.13 | 0.29 | 0.56 | 0.76 | 0.89 | 1.15 | 1.07 | 0.91 |
| WV-8847 | 0.24 | 0.37 | 0.58 | 0.78 | 0.89 | 1.20 | 0.91 | 0.97 |
|  | 0.14 | 0.23 | 0.64 | 0.79 | 0.90 | 1.16 | 0.94 | 1.19 |
| WV-8848 | 0.19 | 0.32 | 0.47 | 0.69 | 0.93 | 0.88 | 0.92 | 0.92 |
|  | 0.19 | 0.16 | 0.46 | 0.74 | 0.88 | 0.79 | 1.03 | 1.09 |
| WV-8849 | 0.24 | 0.39 | 0.55 | 0.79 | 1.17 | 0.97 | 1.16 | 0.95 |
|  | 0.28 | 0.29 | 0.54 | 0.82 | 1.05 | 1.13 | 1.17 | 1.05 |

TABLE 95

|  | 1.477 | 1.079 | 0.681 | 0.283 | −0.114 | −0.512 | −0.910 | −1.308 |
|---|---|---|---|---|---|---|---|---|
| WV-7804 | 0.29 | 0.37 | 0.51 | 0.81 | 0.85 | 1.16 | 0.87 | 0.89 |
|  | 0.19 | 0.22 | 0.47 | 0.82 | 0.85 | 0.94 | 1.05 | 1.06 |
| WV-8843 | 0.53 | 0.72 | 0.62 | 1.00 | 0.98 | 0.85 | 0.92 | 0.98 |
|  | 0.45 | 0.51 | 0.61 | 0.93 | 0.93 | 1.01 | 0.90 | 1.01 |
| WV-8844 | 0.25 | 0.44 | 0.58 | 0.78 | 0.71 | 0.86 | 0.86 | 1.00 |
|  | 0.22 | 0.21 | 0.48 | 0.76 | 1.02 | 1.06 | 0.74 | 1.16 |
| WV-8845 | 0.23 | 0.42 | 0.52 | 0.82 | 0.99 | 0.87 | 0.77 | 1.11 |
|  | 0.17 | 0.25 | 0.44 | 0.76 | 0.90 | 0.97 | 0.99 | 0.88 |
| WV-8846 | 0.20 | 0.38 | 0.55 | 0.60 | 0.90 | 0.76 | 0.88 | 0.98 |
|  | 0.17 | 0.25 | 0.39 | 0.71 | 1.11 | 0.92 | 0.83 | 1.04 |

TABLE 98

Activity of oligonucleotides.
10 nM.

|  | Hep3B | | Huh7 | |
|---|---|---|---|---|
| mock | 100 | 100 | 100 | 100 |
| WV-7794 | 47.6 | 44.5 | 25.0 | 20.6 |
| WV-7795 | 58.5 | 52.8 | 14.3 | 14.8 |
| WV-7796 | 54.6 | 56.4 | 16.3 | 15.5 |
| WV-7797 | 75.1 | 74.2 | 13.5 | 12.8 |
| WV-7798 | 78.4 | 79.8 | 11.9 | 13.7 |
| WV-7799 | 89.9 | 92.4 | 23.5 | 25.7 |
| WV-7800 | 93.6 | 92.2 | 34.1 | 29.9 |
| WV-7801 | 90.3 | 90.3 | 38.4 | 29.3 |
| WV-7802 | 101.1 | 101.3 | 25.1 | 29.6 |
| WV-7803 | 102.0 | 103.2 | 24.8 | 25.8 |
| WV-7804 | 95.9 | 97.2 | 27.8 | 32.7 |
| WV-7805 | 100.5 | 95.5 | 21.9 | 22.0 |
| WV-7806 | 110.6 | 105.4 | 22.0 | 21.2 |
| WV-7807 | 96.2 | 101.5 | 21.1 | 23.8 |
| WV-7808 | 95.5 | 101.0 | 21.5 | 18.8 |
| WV-7809 | 85.3 | 84.2 | 17.1 | 15.7 |
| WV-7810 | 92.0 | 95.9 | 25.2 | 21.6 |
| WV-7811 | 100.1 | 100.0 | 26.6 | 27.1 |
| WV-7812 | 79.5 | 82.1 | 22.3 | 21.1 |
| WV-7813 | 83.7 | 76.2 | 23.7 | 18.2 |
| WV-7814 | 87.8 | 82.8 | 44.3 | 39.2 |
| WV-7815 | 78.1 | 74.8 | 45.3 | 37.1 |
| WV-7816 | 59.5 | 52.4 | 24.5 | 20.5 |

TABLE 99

Activity of oligonucleotides.
10 nM.

|  | Hep3B | | Huh7 | |
|---|---|---|---|---|
| mock | 100 | 100 | 100 | 100 |
| WV-7778 | 92.8 | 86.9 | 63.6 | 52.7 |
| WV-7779 | 92.6 | 85.8 | 59.2 | 48.0 |
| WV-7780 | 102.3 | 97.1 | 36.4 | 34.8 |
| WV-7781 | 111.8 | 102.4 | 46.1 | 38.9 |
| WV-7782 | 108.5 | 94.7 | 43.3 | 35.0 |
| WV-7783 | 110.2 | 97.5 | 36.6 | 33.7 |
| WV-7784 | 105.0 | 95.9 | 41.2 | 41.9 |
| WV-7785 | 108.7 | 107.4 | 73.8 | 57.5 |
| WV-3858 | 103.3 | 103.6 | 55.1 | 52.3 |
| WV-3859 | 94.7 | 96.1 | 41.8 | 41.2 |
| WV-3860 | 104.2 | 94.1 | 46.7 | 45.6 |
| WV-3861 | 101.8 | 99.2 | 47.1 | 45.2 |
| WV-3862 | 97.1 | 96.5 | 44.0 | 42.3 |
| WV-3863 | 99.7 | 86.0 | 42.0 | 51.5 |
| WV-3864 | 97.8 | 96.8 | 53.5 | 38.9 |
| WV-7786 | 99.1 | 104.3 | 37.0 | 38.0 |
| WV-7787 | 84.2 | 87.5 | 23.0 | 25.1 |
| WV-7788 | 80.4 | 88.0 | 35.5 | 28.5 |
| WV-7789 | 82.7 | 85.7 | 25.4 | 25.5 |
| WV-7790 | 80.8 | 85.1 | 27.4 | 29.8 |
| WV-7791 | 87.1 | 80.1 | 40.8 | 42.1 |
| WV-7792 | 78.1 | 73.1 | 42.5 | 46.5 |

TABLE 99-continued

Activity of oligonucleotides.
10 nM.

|  | Hep3B | | Huh7 | |
|---|---|---|---|---|
| WV-7793 | 68.3 | 65.1 | 49.9 | 44.9 |

TABLE 100

Activity of oligonucleotides.
% mRNA remaining
(RhPNPLA3/hSFRS9)
Monkey hepatocytes at 48 hrs.

|  | 10 nM | | 3 nM | | 1 nM | |
|---|---|---|---|---|---|---|
| Mock | 100 | 100 | 100 | 100 | 100 | 100 |
| WV-3421 | 28.7 | 35.4 | 44.6 | 31.8 | 61.3 | 53.8 |
| WV-7794 | 64.1 | 74.4 | 104.3 | 96.2 | 115.5 | 121.3 |
| WV-7795 | 80.8 | 88.4 | 130.2 | 115.9 | 109.0 | 130.0 |
| WV-7796 | 51.3 | 53.4 | 83.8 | 95.5 | 106.9 | 103.3 |
| WV-7797 | 51.4 | 48.5 | 97.3 | 81.4 | 115.1 | 126.7 |
| WV-7798 | 65.2 | 56.8 | 84.8 | 86.8 | 106.8 | 104.0 |
| WV-7799 | 96.5 | 102.5 | 104.7 | 117.6 | 108.9 | 129.6 |
| WV-7800 | 66.1 | 78.8 | 113.3 | 111.3 | 114.9 | 128.1 |
| WV-7801 | 113.1 | 117.7 | 116.0 | 112.7 | 113.3 | 118.5 |
| WV-7802 | 101.6 | 110.7 | 105.8 | 120.3 | 113.3 | 123.9 |
| WV-7803 | 52.5 | 59.6 | 73.6 | 79.4 | 106.5 | 129.4 |
| WV-7804 | 95.5 | 91.3 | 111.3 | 137.4 | 116.5 | 122.1 |
| WV-7805 | 84.7 | 97.8 | 111.7 | 111.1 | 114.3 | 118.7 |
| WV-7806 | 91.2 | 87.2 | 129.7 | 121.3 | 124.8 | 121.8 |
| WV-7807 | 64.5 | 89.2 | 108.5 | 119.7 | 108.6 | 123.7 |
| WV-7808 | 39.4 | 48.1 | 94.7 | 105.8 | 105.1 | 125.5 |
| WV-7809 | 46.5 | 36.8 | 77.0 | 64.9 | 85.1 | 101.2 |
| WV-7810 | 46.7 | 46.5 | 62.1 | 78.5 | 75.8 | 94.7 |
| WV-7811 | 70.4 | 78.7 | 88.2 | 84.0 | 101.1 | 96.6 |
| WV-7812 | 47.2 | 53.3 | 74.5 | 80.7 | 97.7 | 77.8 |
| WV-7813 | 43.0 | 38.3 | 76.5 | 71.2 | 97.0 | 89.7 |
| WV-7814 | 49.8 | 51.2 | 102.8 | 96.1 | 105.9 | 131.8 |
| WV-7815 | 56.0 | 52.5 | 88.3 | 83.8 | 83.4 | 94.9 |
| WV-7816 | 29.3 | 19.7 | 51.5 | 57.5 | 84.4 | 68.4 |

TABLE 101

Activity of oligonucleotides.
PNPLA3 mRNA Level
(PNPLA3/GAPDH)

|  | 0.12 nM | 0.4 nM | 1.1. nM |
|---|---|---|---|
| WV-993 | 99.8 | 77.9 | 74.5 |
| WV-3421 | 74.9 | 44.6 | 24.0 |
| WV-7805 | 105.4 | 99.2 | 83.8 |
| WV-9890 | 108.6 | 78.4 | 78.3 |
| WV-12100 | 104.6 | 102.7 | 93.2 |

TABLE 101-continued

Activity of oligonucleotides.
PNPLA3 mRNA Level
(PNPLA3/GAPDH)

|  | 0.12 nM | 0.4 nM | 1.1. nM |
|---|---|---|---|
| WV-9893 | 93.7 | 103.8 | 79.8 |
| WV-12101 | 124.1 | 67.6 | 36.6 |

TABLE 102A

Activity of oligonucleotides.
Primary cyno hepatocytes.

| Conc. (nM) | WV-9893 | | WV-3421 | | WV-2101 | |
|---|---|---|---|---|---|---|
| 1.079181 | 116.7 | 90.2 | 13.6 | 6.5 | 20.1 | 27.6 |
| 0.681241 | 135.5 | 98.9 | 13.9 | 5.4 | 20.1 | |
| 0.283301 | 86.5 | 126.1 | 32.9 | 23.7 | 11.0 | 37.7 |
| −0.11464 | 105.3 | 108.9 | 70.7 | 46.7 | 40.7 | |
| −0.51258 | 121.9 | 114.1 | 89.3 | 81.5 | 70.0 | 97.1 |
| −0.91052 | 112.7 | 137.8 | 124.2 | 113.7 | 81.7 | 114.1 |
| −1.30846 | 116.0 | 110.1 | 134.7 | 80.5 | 81.0 | 72.6 |
| −1.7064 | 120.5 | 106.7 | 105.7 | 140.0 | 82.5 | 77.1 |
| −2.10434 | 120.5 | 108.0 | 131.0 | 95.2 | 98.4 | 88.2 |
| −2.50228 | 94.8 | 99.6 | 89.2 | 85.4 | 106.7 | 89.7 |

TABLE 102B

Tm of oligonucleotides.

| ASO | Length | Duplex Tm(° C.) WV-12420 Full match | Duplex Tm(° C.) WV-12421 Two mismatches | Δ difference Full match vs two mismatches |
|---|---|---|---|---|
| WV-7805 | 20-mer | 63.52 | 47.62 | 15.9 |
| WV-9891 | 20-mer | 61.62 | 44.77 | 16.9 |
| WV-9890 | 20-mer | 61.57 | 46.67 | 14.9 |
| WV-9893 | 20-mer | 58.67 | 43.52 | 15.2 |
| WV-12106 | 24-mer | 71.52 | 59.72 | 11.8 |
| WV-12107 | 24-mer | 69.57 | 57.77 | 11.8 |
| WV-12100 | 24-mer | 70.77 | 59.57 | 11.2 |
| WV-12101 | 24-mer | 67.52 | 56.62 | 10.9 |

The Tm of various oligonucleotides was measured while in duplex with a RNA which was completely complementary, or which was completely complementary except for two mismatches (representing the mutant allele). Conditions used were: 1 μM Duplex in 1×PBS (pH 7.2); Temperature Range: 15° C.-90° C.; Temperature Rate: 0.5° C./min; Measurement Interval: 0.5° C.

TABLE 103

Activity of oligonucleotides.
Huh7 cells.

| Conc. (nM) | 1 | 0.52288 | 0.04576 | −0.4314 | −0.9085 | −1.3856 | −1.8627 |
|---|---|---|---|---|---|---|---|
| WV-7805 | 7.0 | 23.5 | 64.7 | 80.4 | 88.2 | 92.5 | 99.5 |
| | 5.1 | 24.7 | 78.9 | 74.1 | 86.7 | | |
| WV-9890 | 1.6 | 35.0 | | 90.4 | 90.3 | 92.6 | 104.6 |
| | 13.1 | 29.2 | 73.7 | 88.5 | 87.1 | 95.8 | 105.5 |
| WV-12100 | 12.4 | 33.8 | 63.6 | 90.6 | | 102.3 | 101.5 |
| | 10.2 | 27.6 | 76.6 | 80.0 | 83.6 | 80.7 | 85.0 |
| WV-9893 | 10.4 | 28.7 | 74.3 | 86.3 | 87.7 | 116.1 | 93.8 |
| | 4.3 | 36.4 | 80.4 | 91.5 | 110.3 | 108.6 | 106.5 |
| WV-12101 | | 4.6 | 19.8 | 60.3 | 85.8 | 92.0 | 108.3 |
| | | 6.8 | 19.2 | 60.0 | 81.1 | 81.0 | 85.6 |

TABLE 104

Activity of oligonucleotides.
nM

| Conc. (nM) | 50 | 20 | 8 | 3.2 | 1.28 | 0.51 | 0.20 | 0.081 | 0.032 | 0.013 |
|---|---|---|---|---|---|---|---|---|---|---|
| WV-7850 | 39.0 | 65.8 | 93.0 | 91.3 | 111.1 | 106.1 | 84.6 | 97.3 | 88.8 | 92.0 |
| Hep3B | 43.1 | 72.5 | 82.9 | 86.6 | 94.4 | 87.3 | 87.7 | 89.1 | 89.1 | 92.5 |
| WV-7851 | 38.2 | 81.0 | 93.6 | 90.5 | 98.6 | 94.6 | 100.1 | 90.2 | 96.1 | 100.6 |
| Hep3B | 54.3 | 84.1 | 96.1 | 94.4 | 93.0 | 94.1 | 99.5 | 87.1 | 101.9 | 92.8 |
| WV-7852 | 34.9 | 69.7 | 89.5 | 97.3 | 90.0 | 96.8 | 111.5 | 92.1 | 96.1 | 98.9 |
| Hep3B | 44.6 | 74.9 | 101.3 | 91.8 | 111.3 | 95.8 | 99.8 | 100.6 | 95.8 | 109.5 |
| WV-7853 | 28.3 | 66.4 | 85.2 | | 96.3 | 109.2 | 95.1 | 95.9 | 95.6 | 99.1 |
| Hep3B | 29.8 | 50.5 | 81.3 | 96.1 | 97.1 | 105.3 | 94.0 | 104.8 | 95.8 | 97.4 |
| WV-7854 | 16.7 | 63.0 | 82.3 | 92.8 | 90.6 | 88.3 | 89.7 | 95.2 | 99.4 | 88.0 |
| Hep3B | 18.8 | 59.9 | 80.7 | 89.4 | 84.0 | 86.6 | 88.9 | 89.4 | 94.3 | 96.5 |
| WV-7850 | 2.7 | 5.3 | 11.7 | 25.1 | 57.3 | 75.2 | 71.2 | 84.7 | 80.7 | 96.8 |
| Huh7 | 4.3 | 5.9 | 9.7 | 13.8 | 62.5 | 73.3 | 74.3 | 75.8 | 93.7 | 104.2 |
| WV-7851 | 2.1 | 6.1 | 1.1 | 31.5 | 55.2 | 81.7 | 91.8 | 91.0 | 84.3 | 86.9 |
| Huh7 | 1.3 | 4.6 | 14.9 | 25.9 | 52.3 | 81.7 | 95.0 | 79.6 | 79.5 | 81.4 |
| WV-7852 | 8.4 | 7.8 | 10.0 | 28.6 | 50.0 | 72.8 | 82.6 | 96.2 | 72.2 | 94.1 |
| Huh7 | 7.4 | 5.8 | 10.6 | 25.4 | 56.1 | 87.6 | 85.1 | 83.7 | 70.1 | 88.5 |
| WV-7853 | 2.9 | 5.4 | 6.4 | 27.1 | 47.8 | 70.1 | 96.0 | 82.7 | 89.4 | 86.3 |
| Huh7 | 3.8 | 4.3 | 8.5 | 23.8 | 62.2 | 93.8 | 74.6 | 90.4 | 93.4 | 95.8 |
| WV-7854 | 0.6 | 2.4 | 9.9 | 23.5 | 47.7 | 76.6 | 84.1 | 79.3 | 89.4 | 98.8 |
| Huh7 | 5.4 | 7.5 | 10.3 | 22.2 | 45.9 | 66.5 | 72.7 | 82.7 | 83.7 | 96.6 |

TABLE 105

Activity of oligonucleotides.

| nM | 50 | 20 | 8 | 3.2 | 1.28 | 0.51 | 0.204 | 0.081 | 0.032 | 0.013 |
|---|---|---|---|---|---|---|---|---|---|---|
| WV-7827 | 37.0 | 79.1 | 97.3 | 94.2 | 97.0 | 105.3 | 107.2 | 100.9 | 98.8 | 96.8 |
| Hep3B | 34.3 | 85.1 | 89.9 | 89.1 | 95.4 | 93.1 | 97.4 | 101.7 | 95.8 | 93.4 |
| WV-7828 | 37.0 | 85.9 | 93.5 | 97.6 | 94.2 | 97.3 | 92.0 | 94.4 | 92.8 | 92.9 |
| Hep3B | 32.8 | 77.2 | 91.8 | 90.6 | 88.8 | 96.7 | 91.7 | 89.0 | 92.8 | 90.3 |
| WV-7829 | 25.1 | 82.2 | 99.7 | 92.6 | 93.6 | 95.8 | 103.8 | 94.0 | 91.5 | 86.3 |
| Hep3B | 33.5 | 79.8 | 98.8 | 92.4 | 94.1 | 104.0 | 102.3 | 105.6 | 103.1 | 104.3 |
| WV-7830 | 36.8 | 79.3 | 97.9 |  | 100.2 | 107.3 | 104.6 | 95.0 | 97.7 | 96.7 |
| Hep3B | 54.2 | 87.6 | 97.8 | 104.6 | 113.1 | 109.9 | 100.8 | 110.1 | 93.5 | 98.6 |
| WV-7831 | 53.4 | 97.4 | 103.9 | 104.8 | 99.8 | 102.6 | 111.8 | 102.0 | 93.5 | 101.5 |
| Hep3B | 62.5 | 92.9 | 103.7 | 99.5 | 102.9 | 99.8 | 98.9 | 93.6 | 101.8 | 100.8 |
| WV-7827 | 3.8 | 6.3 | 13.5 | 34.1 | 57.9 | 80.6 | 71.9 | 74.4 | 77.6 | 77.5 |
| Huh7 | 3.0 | 5.8 | 13.4 | 44.1 | 67.2 | 87.3 | 84.7 | 76.1 | 80.6 | 74.0 |
| WV-7828 | 2.3 | 16.3 | 9.8 | 31.4 | 63.3 | 83.2 | 74.9 | 82.3 | 89.1 | 83.1 |
| Huh7 | 1.5 | 9.1 | 25.0 | 31.5 | 69.3 | 75.8 | 76.5 | 87.0 | 90.0 | 79.8 |
| WV-7829 | 5.6 | 16.4 | 31.1 | 54.2 | 78.3 | 94.1 | 87.1 | 97.4 | 108.4 | 100.6 |
| Huh7 | 7.2 | 9.3 | 18.6 | 31.5 | 65.7 | 76.0 | 90.6 | 87.5 | 81.9 | 89.0 |
| WV-7830 | 4.1 | 6.3 | 12.5 | 35.3 | 56.8 | 86.4 | 80.1 | 95.7 | 86.7 | 94.2 |
| Huh7 | 5.5 | 5.9 | 17.0 | 40.2 | 76.3 | 77.5 | 79.8 | 98.6 | 93.2 | 85.8 |
| WV-7831 | 3.5 | 5.6 | 15.2 | 35.0 | 73.6 | 83.9 | 85.0 | 82.3 | 85.9 | 81.8 |
| Huh7 | 5.5 | 10.2 | 24.0 | 40.3 | 74.0 | 88.1 | 87.0 | 111.8 | 85.8 | 93.3 |

TABLE 106

Activity of oligonucleotides.

| nM | 50 | 20 | 8 | 3.2 | 1.28 | 0.51 | 0.204 | 0.081 | 0.032 | 0.013 |
|---|---|---|---|---|---|---|---|---|---|---|
| WV-7804 | 63.3 | 84.6 | 101.1 | 92.9 | 95.5 | 96.2 | 92.0 | 97.6 | 98.4 | 96.7 |
| Hep3B | 69.5 | 98.4 | 102.9 | 95.1 | 98.6 | 110.4 | 99.5 | 93.6 | 101.4 | 100.4 |
| WV-7805 | 60.3 | 81.8 | 96.9 | 90.7 | 91.3 | 95.5 | 90.5 | 92.2 | 98.5 | 95.0 |
| Hep3B | 62.7 | 86.1 | 98.5 | 98.1 | 97.0 | 97.9 | 100.7 | 107.6 | 104.0 | 105.8 |
| WV-7806 | 69.6 | 90.1 | 100.8 | 98.9 | 95.9 | 95.9 | 99.3 | 92.3 | 99.6 | 90.1 |
| Hep3B | 65.1 | 89.4 | 94.7 | 92.1 | 90.9 | 94.8 | 94.7 | 93.8 | 90.1 | 97.5 |
| WV-7807 | 75.0 | 95.3 | 101.2 |  | 97.3 | 100.9 | 96.4 | 93.4 | 89.2 | 90.6 |
| Hep3B | 75.5 | 95.4 | 95.5 | 88.8 | 103.6 | 92.7 | 99.8 | 103.7 | 93.3 | 87.5 |
| WV-7808 Hep3B | 72.2 | 98.9 | 117.8 | 109.5 | 116.3 | 110.9 | 109.3 | 116.8 | 111.1 | 104.6 |
| WV-7804 | 4.4 | 3.5 | 25.1 | 45.3 | 68.9 | 74.6 | 73.6 | 82.9 | 81.8 | 86.7 |
| Huh7 | 7.5 | 11.1 | 23.3 | 48.0 | 77.1 | 76.0 | 86.5 | 89.4 | 96.1 | 90.4 |
| WV-7805 | 1.7 | 7.1 | 19.6 | 36.1 | 59.2 | 75.3 | 69.8 | 75.0 | 78.0 | 79.6 |
| Huh7 | 8.4 | 11.9 | 11.6 | 38.4 | 76.2 | 78.4 | 81.1 | 86.9 | 95.8 | 95.0 |
| WV-7806 | 9.8 | 2.8 | 13.8 | 28.8 | 68.7 | 66.6 | 69.7 | 78.6 | 89.4 | 88.6 |
| Huh7 | 3.8 | 7.2 | 12.5 | 39.7 | 68.5 | 82.4 | 80.3 | 79.7 | 87.3 | 98.0 |
| WV-7807 | 3.0 | 12.6 | 25.1 | 46.9 | 78.0 | 85.3 | 98.8 | 92.6 | 85.6 | 85.5 |
| Huh7 | 3.9 | 9.1 | 14.9 | 41.5 | 70.4 | 73.7 | 68.5 | 75.3 | 81.9 | 94.7 |
| WV-7808 | 1.8 | 1.9 | 14.2 | 37.1 | 63.6 | 71.0 | 79.2 | 88.0 | 84.1 | 95.3 |
| Huh7 | 1.4 | 5.2 | 9.1 | 33.2 | 65.2 | 77.4 | 92.3 | 71.2 | 83.5 | 78.1 |

TABLE 107

Activity of oligonucleotides.

| nM | WV-7805 Hep3B | | WV-7805 Huh7 | |
|---|---|---|---|---|
| 20 | 81.8 | 86.1 | 7.1 | 11.9 |
| 8 | 96.9 | 98.5 | 19.6 | 11.6 |
| 3.2 | 90.7 | 98.1 | 36.1 | 38.4 |
| 1.28 | 91.3 | 97.0 | 59.2 | 76.2 |
| 0.512 | 95.5 | 97.9 | 75.3 | 78.4 |
| 0.2048 | 90.5 | 100.7 | 69.8 | 81.1 |
| 0.08192 | 92.2 | 107.6 | 75.0 | 86.9 |
| 0.032768 | 98.5 | 104.0 | 78.0 | 95.8 |
| 0.013107 | 95.0 | 105.8 | 79.6 | 95.0 |

In some tests of PNPLA3 oligonucleotides, APOC3 oligonucleotide WV-1868 (which targets APOC3, a gene different than PNPLA2) is used as a negative control.

TABLE 108

Activity of oligonucleotides.

| nM | 2 | | 8.25 | | 33 | |
|---|---|---|---|---|---|---|
| Control | 1.002 | 1.082 | 1.192 | 1.105 | 1.031 | 1.038 |
| WV-1868 | 1.105 | 1.016 | 1.120 | 0.995 | 1.023 | 1.023 |
| WV-3451 | 0.962 | 0.975 | 0.484 | 0.617 | 0.218 | 0.256 |
| WV-3452 | 1.060 | 0.948 | 0.526 | 0.505 | 0.189 | 0.172 |
| WV-3453 | 0.388 | 0.487 | 0.181 | 0.197 | 0.217 | 0.156 |
| WV-3454 | 0.509 | 0.502 | 0.260 | 0.186 | 0.138 | 0.064 |
| WV-3455 | 0.613 | 0.617 | 0.342 | 0.347 | 0.197 | 0.155 |
| WV-3456 | 0.724 | 0.843 | 0.468 | 0.545 | 0.218 | 0.223 |
| WV-3457 | 0.714 | 0.776 | 0.367 | 0.362 | 0.132 | 0.096 |
| WV-3458 | 0.672 | 0.618 | 0.251 | 0.309 | 0.256 | 0.180 |
| WV-3459 | 1.184 | 1.105 | 1.097 | 1.067 | 0.820 | 0.975 |
| WV-3460 | 0.849 | 0.689 | 0.436 | 0.367 | 0.461 | 0.382 |
| WV-3461 | 0.989 | 1.243 | 0.471 | 0.600 | 0.261 | 0.198 |
| WV-3462 | 0.833 | 1.040 | 0.417 | 0.446 | 0.286 | 0.120 |

TABLE 108-continued

|  | 2 |  | 8.25 |  | 33 |  |
|---|---|---|---|---|---|---|
| Control | 1.002 | 1.082 | 1.192 | 1.105 | 1.031 | 1.038 |
| WV-1868 | 1.105 | 1.016 | 1.120 | 0.995 | 1.023 | 1.023 |
| WV-3437 | 1.045 | 1.067 | 0.564 | 0.501 | 0.256 | 0.181 |
| WV-3438 | 0.861 | 0.989 | 0.935 | 0.760 | 1.009 | 0.982 |
| WV-3439 | 1.009 | 1.016 | 0.770 | 0.734 | 0.576 | 0.530 |
| WV-3440 |  | 1.038 | 1.060 | 0.982 | 0.729 | 0.613 |
| WV-3441 | 1.082 | 1.234 | 0.680 | 0.903 | 0.313 | 0.433 |
| WV-3442 | 1.120 | 0.935 | 0.477 | 0.643 | 0.223 | 0.347 |
| WV-3443 | 0.477 | 0.410 | 0.278 | 0.204 | 0.229 | 0.171 |
| WV-3444 | 0.714 | 0.592 | 0.350 | 0.396 | 0.234 | 0.209 |
| WV-3445 | 1.304 | 1.060 | 0.776 | 0.760 | 0.439 | 0.388 |
| WV-3446 | 0.849 | 0.729 | 0.455 | 0.430 | 0.247 | 0.235 |
| WV-3447 | 0.786 | 0.929 | 0.568 | 0.604 | 0.201 | 0.292 |
| WV-3448 | 0.776 | 0.837 | 0.458 | 0.568 | 0.218 | 0.226 |
| WV-3449 | 0.776 | 0.704 | 0.404 | 0.449 | 0.252 | 0.130 |
| WV-3450 | 1.084 | 0.851 | 1.077 | 0.839 | 0.924 | 0.905 |

|  | 2 |  | 8.25 |  | 33 |  |
|---|---|---|---|---|---|---|
| Control | 1.002 | 1.082 | 1.192 | 1.105 | 1.031 | 1.038 |
| WV-1868 | 1.105 | 1.016 | 1.120 | 0.995 | 1.023 | 1.023 |
| WV-3423 | 0.634 | 0.600 | 0.407 | 0.419 | 0.315 | 0.280 |
| WV-3424 | 0.634 | 0.754 | 0.350 | 0.445 | 0.124 | 0.286 |
| WV-3425 | 1.002 | 1.023 | 0.729 | 0.643 | 0.347 | 0.345 |
| WV-3426 | 1.023 | 0.797 | 0.487 | 0.427 | 0.364 | 0.367 |
| WV-3427 | 0.849 | 0.897 | 0.709 | 0.781 | 0.621 | 0.572 |
| WV-3428 | 1.052 | 1.089 | 0.831 | 0.922 | 0.942 | 1.002 |
| WV-3429 | 1.060 | 0.982 | 0.588 | 0.604 | 0.401 | 0.340 |
| WV-3430 | 1.074 | 1.184 | 0.935 | 0.942 | 0.505 | 0.449 |
| WV-3431 | 0.600 | 0.675 | 0.391 | 0.364 | 0.208 | 0.237 |
| WV-3432 | 0.975 | 0.955 | 0.630 | 0.639 | 0.276 | 0.326 |
| WV-3433 | 0.596 | 0.685 | 0.240 | 0.270 | 0.215 | 0.146 |
| WV-3434 | 0.885 | 0.714 | 0.261 | 0.342 | 0.206 | 0.193 |
| WV-3435 | 0.584 | 0.584 | 0.350 | 0.311 | 0.288 | 0.261 |
| WV-3436 | 1.074 | 0.797 | 0.760 | 0.661 | 0.515 | 0.477 |

|  | 2 |  | 8.25 |  | 33 |  |
|---|---|---|---|---|---|---|
| Control | 0.910 | 1.000 | 0.996 | 1.136 | 1.105 | 1.136 |
| WV-1868 | 1.278 | 1.075 | 0.936 | 1.176 | 0.809 | 0.879 |
| WV-3409 | 0.690 | 0.498 | 0.329 | 0.274 | 0.488 | 0.405 |
| WV-3410 | 0.832 | 0.936 | 0.217 | 0.231 | 0.241 | 0.134 |
| WV-3411 | 0.685 | 0.588 | 0.114 | 0.116 | 0.037 | 0.108 |
| WV-3412 |  | 0.873 | 0.383 | 0.286 | 0.089 | 0.070 |
| WV-3413 | 0.855 | 0.838 | 0.336 | 0.263 | 0.030 | 0.071 |
| WV-3414 | 1.105 | 1.024 | 0.798 | 0.709 | 0.290 | 0.333 |

| WV-3415 | 1.024 |  | 0.298 | 0.185 | 0.484 | 0.393 |
|---|---|---|---|---|---|---|
| WV-3416 | 0.541 | 0.568 | 0.273 | 0.260 | 0.246 | 0.241 |
| WV-3417 | 0.734 | 0.622 | 0.331 | 0.137 | 0.298 | 0.300 |
| WV-3418 | 0.530 | 0.568 | 0.185 | 0.114 | 0.258 | 0.298 |
| WV-3419 | 0.962 | 0.639 | 0.680 | 0.588 | 0.377 | 0.362 |
| WV-3420 |  | 1.113 | 0.956 | 0.771 | 0.375 | 0.159 |
| WV-3421 | 0.502 | 0.443 | 0.169 | 0.148 | 0.218 | 0.228 |
| WV-3422 | 0.923 | 1.083 | 0.680 | 0.516 | 0.365 | 0.372 |

|  | 2 |  | 8.25 |  | 33 |  |
|---|---|---|---|---|---|---|
| Control | 0.910 | 1.000 | 0.996 | 1.136 | 1.105 | 1.136 |
| WV-1868 | 1.278 | 1.075 | 0.936 | 1.176 | 0.809 | 0.879 |
| WV-3395 | 0.419 | 0.247 | 0.336 | 0.198 | 0.338 | 0.331 |
| WV-3396 | 1.024 | 0.982 | 0.452 | 0.553 | 0.249 | 0.195 |
| WV-3397 | 0.685 | 0.976 | 0.365 |  | 0.182 | 0.096 |
| WV-3398 | 1.053 |  | 0.159 | 0.273 | 0.061 | 0.052 |
| WV-3399 | 0.357 | 0.440 | 0.284 | 0.141 | 0.221 | 0.282 |
| WV-3400 | 0.867 | 0.861 | 0.553 | 0.458 | 0.184 | 0.160 |
| WV-3401 | 1.252 | 0.904 | 0.481 | 0.383 | 0.133 | 0.093 |
| WV-3402 | 0.437 | 0.302 | 0.122 | 0.096 | 0.070 | 0.046 |
| WV-3403 | 1.176 | 1.218 | 1.003 | 1.144 | 0.879 | 0.929 |
| WV-3404 | 0.195 | 0.367 | 0.155 | 0.135 | 0.269 | 0.215 |
| WV-3405 | 1.024 | 0.695 | 0.377 | 0.258 | 0.194 | 0.208 |
| WV-3406 | 1.287 | 1.075 | 1.314 | 1.201 | 1.314 | 0.969 |
| WV-3407 | 0.949 | 0.917 | 0.609 | 0.498 | 0.326 | 0.125 |
| WV-3408 | 0.239 | 0.360 | 0.107 | 0.187 | 0.265 | 0.161 |

|  | 2 |  | 8.25 |  | 33 |  |
|---|---|---|---|---|---|---|
| Control | 0.910 | 1.000 | 0.996 | 1.136 | 1.105 | 1.136 |
| WV-1868 | 1.278 | 1.075 | 0.936 | 1.176 | 0.809 | 0.879 |
| WV-3381 | 0.560 | 0.391 | 0.103 | 0.108 | 0.146 | 0.199 |
| WV-3382 | 0.949 | 1.024 | 0.393 | 0.271 | 0.132 | 0.211 |
| WV-3383 | 1.031 | 0.996 | 0.617 | 0.458 | 0.455 | 0.133 |
| WV-3384 | 1.252 | 1.060 | 0.402 | 0.416 | 0.136 | 0.133 |
| WV-3385 | 0.962 | 1.098 | 0.407 | 0.410 | 0.221 | 0.123 |
| WV-3386 | 0.680 | 0.440 | 0.186 | 0.246 | 0.265 | 0.176 |
| WV-3387 | 0.269 | 0.191 | 0.100 | 0.067 | 0.081 | 0.141 |
| WV-3388 | 1.168 | 0.982 | 0.849 | 1.053 | 1.168 | 0.892 |
| WV-3389 | 1.083 | 1.031 | 1.399 | 0.879 | 0.771 | 0.804 |
| WV-3390 | 0.676 | 0.580 | 0.226 | 0.265 | 0.035 | 0.051 |
| WV-3391 | 0.505 | 0.396 | 0.187 | 0.153 | 0.107 | 0.176 |
| WV-3392 | 0.462 | 0.362 | 0.139 | 0.116 | 0.093 | 0.070 |
| WV-3393 | 0.273 | 0.391 | 0.102 | 0.111 | 0.060 | 0.044 |
| WV-3394 | 0.509 | 0.405 | 0.263 | 0.133 | 0.109 | 0.097 |

TABLE 109A

Activity of oligonucleotides.

| Conc (nM) | 20 | 8 | 3.2 | 1.28 | 0.512 | 0.205 | 0.0819 | 0.0328 | 0.0131 | 0.0052 |
|---|---|---|---|---|---|---|---|---|---|---|
| WV-8148 | 111.7 | 111.5 | 102.6 | 105.8 | 102.9 | 103.1 | 92 | 96.5 | 99.6 | 118.7 |
| Hep3B | 97.3 | 114.3 | 107.8 | 106.6 | 105.8 | 106.6 | 90.9 | 100.8 | 95.3 | 105.5 |
| WV-8149 | 128.4 | 118 | 104.2 | 99.8 | 104.8 | 103.2 | 97.1 | 102.1 | 104.6 | 96.5 |
| Hep3B | 135.8 | 131.3 | 108.8 | 108.5 | 94.5 | 106.1 | 107.8 | 99.3 | 103.3 | 102.4 |
| WV-8150 | 120.7 | 123.7 | 115 | 99.8 | 98.6 | 100.9 | 88.5 | 92.3 | 103.1 | 102 |
| Hep3B | 113 | 111.8 | 98.4 | 102.1 | 102.3 | 100 | 103 | 100.8 | 104 | 107.9 |
| WV-8151 | 112.3 | 147 | 108.4 | 103.4 | 104.6 | 104.6 | 111.1 | 100.1 | 102.4 | 100 |
| Hep3B | 119.6 | 124.3 | 106.6 | 101.6 | 110.1 | 104.1 | 113.7 | 100.3 | 100.3 | 104.7 |
| WV-8152 | 119.1 | 139.2 | 113 | 107 | 112.7 | 121 | 112.4 | 111.7 | 88.5 | 114.7 |
| Hep3B | 133.7 | 149 | 118.1 | 103.2 | 101.7 | 101.8 | 102.5 | 94.6 | 98.3 | 104.2 |
| WV-8148 | 26.6 | 41.6 | 64.4 | 90.6 | 91.8 | 86.5 | 98.2 | 90.5 | 99.6 | 94.1 |
| Huh7 | 35.5 | 54 | 65.7 | 87.4 | 85.8 | 87.5 | 86.8 | 100.9 | 99.3 | 90.2 |
| WV-8149 | 23.2 | 33.1 | 64.6 | 83.6 | 87.2 | 94.4 | 82.9 | 94.8 | 79.1 | 92.5 |
| Huh7 | 27.5 | 44.3 | 65.7 | 89.5 | 84.5 | 87.9 | 92 | 94.6 | 85.1 |  |
| WV-8150 | 26.3 | 26.6 | 55 | 80.4 | 86.7 | 91.5 | 86.9 | 90.1 | 88.4 | 84.7 |
| Huh7 | 20 | 29.6 | 52.7 | 92.1 | 83.4 | 91.9 | 97 | 84 | 86.9 | 93.5 |
| WV-8151 | 13.4 | 28.7 | 59.7 | 82 | 90.6 | 92.4 | 90.2 | 84.4 | 78.1 | 85.7 |
| Huh7 | 23.6 | 32.8 | 63.6 | 77.7 | 101.1 | 92.6 | 91.6 | 100.9 | 83.4 | 90.2 |
| WV-8152 | 13.2 | 36.7 | 58.3 | 90.9 | 94.4 | 95.7 | 76.1 | 84.3 | 90.3 | 85.2 |
| Huh7 | 18.1 | 47.5 | 61 | 84.7 | 93.9 | 86.2 | 96 | 92.6 | 84 | 90.1 |

TABLE 109A-continued

Activity of oligonucleotides.

| nM | 20 | 8 | 3.2 | 1.28 | 0.512 | 0.205 | 0.0819 | 0.0328 | 0.0131 | 0.0052 |
|---|---|---|---|---|---|---|---|---|---|---|
| WV-8194 | 102.9 | 103.8 | 85.5 | 90.8 | 90.8 | 102.3 | 96.8 | 101.1 | 95.8 | 95.5 |
| Hep3B | 93.3 | 95.7 | 87.8 | 90 | 78.5 | 77.4 | 86.4 | 78.1 | 81 | 88.2 |
| WV-8195 | 107.9 | 103.7 | 96.6 | 91.5 | 91.7 | 92.1 | 94.1 | 105.6 | 107.4 | 95.7 |
| Hep3B | 123 | 101.5 | 92.9 | 89.4 | 92 | 86 | 88.3 | 101.9 | 104.3 | 99.3 |
| WV-8196 | 86.5 | 108.1 | 106 | 90.1 | 96.1 | 87.3 | 93.3 | 87.9 | 100.1 | 103.5 |
| Hep3B | 112.8 | 126.8 | 98.2 | 86.9 | 83.2 | 82.4 | 88.8 | 95.5 | 92.8 | 101.9 |
| WV-8197 | 140.8 | 123.5 | 108.9 | 87 | 91.5 | 92.8 | 106.1 | 98.1 | 107.7 | 94.5 |
| Hep3B | 143.8 | 132.1 | 98.1 | 85.6 | 85.3 | 80.7 | 84.6 | 88 | 95.2 | 93.5 |
| WV-8198 | 99.5 | 101 | 89.4 | 85.4 | 88.6 | 94.9 | 88.4 | 95.8 | 95 | 97.2 |
| Hep3B | 119.8 | 90.9 | 85.3 | 95.8 | 93.3 | 80.1 | 82.9 | 82.4 | 86.9 | 88 |
| WV-8194 | 8.1 | 13.3 | 32.2 | 69.5 | 91.6 | 100.4 | 89.2 | 91.8 | 90.4 | 81.5 |
| Huh7 | 7.4 | 31.2 | 38 | 76 | 86.9 | 93.6 | 92.5 | 92 | 87.5 | 104.3 |
| WV-8195 | 7.3 | 27 | 41.1 | 64.1 | 83.2 | 96.5 | 95.1 | 84.7 | 89.8 | 87.3 |
| Huh7 | 14 | 20 | 37.1 | 57.8 | 95 | 94.3 | 85.4 | 90.7 | 97.6 | 85.8 |
| WV-8196 | 8.9 | 19.5 | 26.7 | 64.4 | 78.5 | 88.3 | 83.2 | 88.1 | 81.1 | 81.1 |
| Huh7 | 14.3 | 19.9 | 37.1 | 57.3 | 91.7 | 91.8 | 88.5 | 84.5 | 84 | 91.9 |
| WV-8197 | 4.1 | 27.3 | 40.8 | 65.6 | 88.8 | 91.7 | 95.6 | 96 | 90.6 | 93.3 |
| Huh7 | 14.8 | 26.8 | 44 | 62.4 | 83.9 | 96.5 | 89.1 | 97.9 | 92.9 | 81.8 |
| WV-8198 | 7.9 | 19.9 | 36.5 | 68.6 | 94.6 | 90.6 | 90 | 94 | 90.9 | 89.9 |
| Huh7 | 6.9 | 26.7 | 47.9 | 63.8 | 83.1 | 99.5 | 97.2 | 97.1 | 88.1 | 97.8 |

| Conc (nM) | 20 | 8 | 3.2 | 1.28 | 0.512 | 0.205 | 0.0819 | 0.0328 | 0.0131 | 0.0052 |
|---|---|---|---|---|---|---|---|---|---|---|
| WV-8171 | 102.4 | 98.1 | 108.8 | 104.7 | 111.4 | 107.4 | 102.2 | 112 | 95.9 | 92.4 |
| Hep3B | 94.9 | 94.6 | 89.8 | 102.6 | 97.2 | 101.8 | 96.4 | 98.9 | 97.7 | 90.6 |
| WV-8172 | 105 | 105.3 | 116.3 | 108.9 | 120 | 105.5 | 101.4 | 100.9 | 94.3 | 99.9 |
| Hep3B | 92.8 | 90.5 | 92.7 | 90.1 | 96.8 | 90.6 | 97.9 | 92.5 | 96.7 | 84.7 |
| WV-8173 | 96.9 | 90.2 | 99.1 | 108.6 | 107.1 | 103.6 | 105.9 | 100.6 | 95.6 | 100.2 |
| Hep3B | 104.3 | 96.4 | 99 | 98.2 | 99.9 | 103.3 | 95.7 | 96.4 | 97.7 | 95.1 |
| WV-8174 | 98 | 85.2 | 93.3 | 96.1 | 83.8 | 84.7 | 83 | 86.3 | 93.7 | 105.9 |
| Hep3B | 115.5 | 112.5 | 95.7 | 98.7 | 86.6 | 97.4 | 93.6 | 82.7 | 90.4 | 99.2 |
| WV-8175 | 98.2 | 91 | 90.6 | 88 | 95.9 | 94.2 | 86.7 | 96 | 106.2 | 91.3 |
| Hep3B | 102.6 | 91.1 | 89.4 | 87.1 | 93.7 | 98.8 | 102.7 | 83.9 | 95.7 | 88.1 |
| WV-8171 | 22.1 | 39.4 | 56.7 | 76.8 | 76 | 87.5 | 75.8 | 95.2 | 83.1 | 77.8 |
| Huh7 | 19.2 | 58.8 | 66.5 | 77.9 | 89.6 | 88.9 | 93.8 | 91 | 90.8 | 97.2 |
| WV-8172 | 13.9 | 30 | 54.5 | 80.4 | 88.1 | 87.6 | 79.8 | 85.4 | 82 | 98.4 |
| Huh7 | 20.6 | 43.1 | 54.6 | 78.4 | 89.4 | 92.4 | 93.6 | 99.8 | 109.4 | 105.5 |
| WV-8173 | 37.2 | 44.1 | 78.6 | 106.3 | 113.7 | 106.6 | 105.3 | 103.7 | 97.6 | 93.3 |
| Huh7 | 41 | 75.8 | 85.6 | 100.6 | 111.3 | 103.2 | 114.4 | 117.5 | 107.3 | 107.7 |
| WV-8174 | 30.2 | 47.6 | 66.3 | 69.3 | 92.1 | 85.6 | 85.6 | 76.1 | 87.3 | 89.8 |
| Huh7 | 19 | 40.9 | 52.4 | 77.2 | 92.2 | 96.6 | 88.8 | 92 | 92.1 | 91.8 |
| WV-8175 | 11.5 | 26.5 | 45.9 | 69.1 | 86.1 | 85.6 | 82.6 | 92.9 | 97 | 83.7 |
| Huh7 | 12.5 | 26.7 | 45.2 | 77.6 | 86.4 | 94.5 | 102.9 | 91.7 | 92 | 85.9 |

| nM | 20 | 8 | 3.2 | 1.28 | 0.512 | 0.205 | 0.0819 | 0.0328 | 0.0131 | 0.0052 |
|---|---|---|---|---|---|---|---|---|---|---|
| WV-8217 | 88.4 | 85.5 | 87.5 | 86.9 | 89.2 | 90 | 98.6 | 98.5 | 97.1 | 86.5 |
| Hep3B | 93.3 | 83.5 | 76.7 | 80.1 | 78 | 77.9 | 77.6 | 74.8 | 79.8 | 86.6 |
| WV-8218 | 100.6 | 94.9 | 92 | 93.1 | 99.6 | 96 | 98.2 | 95.5 | 92.9 | 87.4 |
| Hep3B | 99.3 | 96.4 | 99.2 | 96.3 | 95.5 | 100.8 | 100.5 | 93.6 | 96.7 | 96.3 |
| WV-8219 | 147.3 | 128.9 | 107.6 | 106.1 | 104.8 | 106.8 | 98.6 | 101.5 | 96.5 | 110.7 |
| Hep3B | 126.8 | 103.2 | 94.8 | 93.5 | 94.2 | 96 | 100.6 | 103.5 | 96.7 | 102.9 |
| WV-8220 | 104.2 | 115.4 | 103.9 | 97 | 106.9 | 102.2 | 99.4 | 105.1 | 99.1 | 95.3 |
| Hep3B | 100 | 89.8 | 96.8 | 95.5 | 107.4 | 106.4 | 104.3 | 95.9 | 117 | 101 |
| WV-8221Hep3B | 110.2 | 104.7 | 97.7 | 102.6 | 104.1 | 106.4 | 102.6 | 100.3 | 102 | 98.4 |
|  | 94.5 | 98.5 | 101.6 | 99.7 | 99.4 | 108.4 | 103 | 107.1 | 100.3 | 103.3 |
| WV-8217 | 26.8 | 37.9 | 58.2 | 81.9 | 94 | 101.3 | 112 | 105.2 | 97.8 | 28.2 |
| Huh7 | 27.7 | 41 | 57.6 | 90.7 | 109.2 | 102.4 | 110.5 | 109.9 | 105.5 | 105.2 |
| WV-8218 | 21.6 | 45.8 | 56.1 | 77.7 | 86.9 | 97.3 | 82.6 | 88.5 | 86.1 | 73.9 |
| Huh7 | 20.9 | 28.8 | 55.3 | 78.1 | 106.9 | 107.3 | 107.6 | 95.6 | 104.1 | 82.8 |
| WV-8219 | 31.5 | 31 | 42.7 | 62.7 | 92 | 91.7 | 85.7 | 75.7 | 77.2 | 85.7 |
| Huh7 | 26 | 31.8 | 47.9 | 75 | 85.5 | 92.1 | 83.6 | 89.7 | 93.1 | 91.3 |
| WV-8220 | 4.8 | 16.3 | 31.8 | 66.1 | 78.6 | 77.8 | 79.7 | 71.7 | 81.1 | 80.3 |
| Huh7 | 11.8 | 30.1 | 54.4 | 77.4 | 105.6 | 98.6 | 90.5 | 85.7 | 93.9 | 85.5 |
| WV-8221 | 6.2 | 21.4 | 31.8 | 48.6 | 78.3 | 85.8 | 75.5 | 83.8 | 85.3 | 93 |
| Huh7 | 4.6 | 19.1 | 35.2 | 59.6 | 104.8 | 105.8 | 99.2 | 100.1 | 93.2 | 88.7 |

TABLE 109B

Activity of oligonucleotides.
IC50 in Huh7 cells (mutant allele):

| Oligonucleotide | IC50 (nM) | Oligonucleotide | IC50 (nM) |
|---|---|---|---|
| WV-8148 | 7.3 | WV-8197 | 3.2 |
| WV-8149 | 9.2 | WV-8198 | 3.5 |
| WV-8150 | 5.5 | WV-8217 | 5.4 |
| WV-8151 | 7.9 | WV-8218 | 5.9 |
| WV-8152 | 12.6 | WV-8219 | 3.1 |
| WV-8171 | 11.2 | WV-8220 | 5.5 |
| WV-8172 | 5.2 | WV-8221 | 2.6 |
| WV-8173 | 12 | WV-8194 | 3.5 |
| WV-8174 | 6.6 | WV-8195 | 3 |
| WV-8175 | 4.2 | WV-8196 | 2.8 |

TABLE 110

Activity of oligonucleotides.
Huh7 cells:

|  | 50 | 20 | 8 | 3.2 | 1.28 | 0.512 | 0.204 | 0.081 | 0.032 | 0.013 |
|---|---|---|---|---|---|---|---|---|---|---|
| WV-3861 | 23.1 | 43.8 | 72.8 | 101.4 | 102.4 | 103.3 | 85.5 | 91.9 | 93.7 | 92.0 |
|  | 30.1 | 52.2 | 89.3 | 103.4 | 95.9 | 93.4 | 99.4 | 104.5 | 89.7 | 104.8 |
| WV-7805 | 8.0 | 13.3 | 32.7 | 65.4 | 87.0 | 83.1 | 91.2 | 84.1 | 76.1 | 85.3 |
|  | 10.1 | 22.7 | 49.1 | 82.1 | 87.8 | 81.8 | 82.5 | 77.8 | 87.9 | 79.1 |
| WV-7828 | 5.3 | 15.3 | 26.8 | 60.5 | 88.1 | 85.0 | 92.1 | 85.8 | 84.2 | 90.3 |
|  | 4.3 | 10.0 | 41.1 | 54.4 | 79.6 | 90.2 | 89.0 | 90.2 | 99.3 | 83.6 |
| WV-7851 | 4.1 | 4.4 | 20.0 | 42.9 | 63.8 | 85.3 | 77.7 | 79.3 | 84.6 | 93.4 |
|  | 6.7 | 6.6 | 20.3 | 47.5 | 86.7 | 79.7 | 97.4 | 97.4 | 85.0 | 89.4 |
| WV-8149 | 18.4 | 29.4 | 35.5 | 71.2 | 88.8 | 91.2 | 75.3 | 84.9 | 86.5 | 90.6 |
|  | 46.2 | 21.9 | 47.2 | 80.7 | 86.5 | 93.9 | 83.9 | 90.5 | 101.4 | 95.3 |
| WV-8172 | 20.5 | 13.7 | 30.4 | 53.8 | 73.3 | 85.2 | 74.8 | 80.7 | 87.0 | 84.4 |
|  | 20.3 | 21.9 | 41.3 | 59.0 | 78.7 | 83.5 | 91.1 | 92.5 | 91.8 | 104.3 |
| WV-8195 | 23.2 | 11.4 | 15.4 | 64.8 | 71.9 | 74.1 | 82.8 | 87.0 | 88.5 | 76.4 |
|  | 22.7 | 14.6 | 23.5 | 62.1 | 80.2 | 85.0 | 99.0 | 99.6 | 104.0 | 100.4 |
| WV-8218 | 6.6 | 13.1 | 13.4 | 53.7 | 73.0 | 93.6 | 94.6 | 93.8 | 88.0 | 92.3 |
|  | 20.2 | 14.0 | 30.6 | 57.7 | 97.4 | 117.6 | 99.8 | 101.2 | 114.2 | 109.0 |
| WV-3864 | 3.7 | 22.4 | 60.6 | 94.6 | 92.3 | 99.2 | 88.2 | 97.2 | 92.0 | 104.1 |
|  | 18.9 | 27.5 | 68.5 | 114.8 | 95.1 | 113.1 | 100.1 | 117.6 | 110.2 | 118.9 |
| WV-7808 | 6.6 | 12.6 | 34.8 | 66.1 | 73.0 | 88.8 | 93.9 | 90.6 | 91.2 | 94.2 |
|  | 6.4 | 14.2 | 32.3 | 80.2 | 106.0 | 106.7 | 107.6 | 89.2 | 103.4 | 97.6 |
| WV-7831 | 4.8 | 7.9 | 27.1 | 62.1 | 80.6 | 82.5 | 91.4 | 92.8 | 93.6 | 93.7 |
|  | 8.0 | 13.1 | 29.4 | 62.2 | 90.7 | 122.5 | 105.5 | 120.7 | 115.5 | 97.9 |
| WV-7854 | 2.0 | 7.1 | 21.5 | 49.2 | 74.1 | 83.3 | 116.8 | 75.8 | 83.4 | 95.0 |
|  | 5.0 | 5.3 | 17.0 | 50.4 | 100.7 | 99.7 | 103.2 | 99.8 | 101.7 | 90.1 |
| WV-8152 |  | 14.4 | 33.7 | 80.7 | 82.8 | 80.8 | 84.3 | 86.5 | 89.7 | 88.2 |
|  | 23.4 | 40.1 | 77.3 | 106.3 | 96.3 | 97.7 | 99.9 | 97.1 | 79.5 |  |
| WV-8175 | 17.6 | 13.5 | 18.2 | 48.5 | 69.7 | 87.0 | 72.8 | 91.4 | 86.5 | 81.6 |
|  | 22.4 | 16.5 | 19.2 | 51.1 | 108.5 | 89.7 | 87.4 | 102.0 | 91.2 | 95.4 |
| WV-8198 | 16.6 | 8.3 | 15.1 | 43.7 | 78.0 | 81.9 | 82.7 | 75.3 | 91.5 | 88.2 |
|  | 7.1 | 5.1 | 23.9 | 46.3 | 93.6 | 103.2 | 103.6 | 93.8 | 125.9 | 96.0 |
| WV-8221 | 16.0 | 9.6 | 12.4 | 31.8 | 73.1 | 101.6 | 96.7 | 77.9 | 86.7 | 94.3 |
|  | 13.0 | 10.9 | 16.2 | 44.1 | 85.5 | 102.0 | 110.9 | 123.8 | 101.9 | 102.9 |

TABLE 111

Activity of oligonucleotides.

| Oligonucleotide | 2 nM | Oligonucleotide | 2 nM |
|---|---|---|---|
| VVV-4098 | 30 | VVV-9277 | 44 |
| VVV-9273 | 72 | VVV-9278 | 55 |
| VVV-9274 | 73 | VVV-9279 | 39 |
| VVV-9275 | 74 | VVV-9280 | 82 |
| VVV-9276 | 52 | VVV-9281 | 68 |

Several PNPLA3 ssRNAi agents were also prepared and tested which have an abasic site, specifically a (phosphaneyl)oxy)propan-1-ol (PS) or 3'-(phosphaneyl)oxy)tetrahydrofuran. Results for oligonucleotide administration at 2 nM is shown, and oligonucleotides were also tested at 0, 0.05, 0.128, 0.32, and 0.8 nM (data not shown). Numbers are approximate and represent residual PNPLA3 mRNA level (PNPLA3/HPRT1), wherein 100 would represent 100% residual mRNA level (0% knockdown) and 0 would represent 0% residual mRNA level (100% knockdown). In the various tables herein, the level of mRNA is measured, unless otherwise noted.

TABLE 112

Activity of oligonucleotides.

| Oligonucleotide | 2 nM | Oligonucleotide | 2 nM |
|---|---|---|---|
| VVV-4098 | 31 | VVV-4098 | 31 |
| VVV-9261 | 62 | VVV-9272 | 81 |
| VVV-9262 | 69 | VVV-9284 | 75 |
| VVV-9263 | 72 |  |  |
| VVV-9264 | 62 |  |  |

TABLE 112-continued

Activity of oligonucleotides.

| Oligonucleotide | 2 nM | Oligonucleotide | 2 nM |
|---|---|---|---|
| VVV-9265 | 56 | | |
| VVV-9266 | 64 | | |
| VVV-9267 | 43 | | |
| VVV-9268 | 69 | | |
| VVV-9269 | 71 | | |

Several APOC3 ssRNAi agents were also prepared and tested which have C3 modification. Results for oligonucleotide administration at 2 nM is shown, and oligonucleotides were also tested at 0, 0.05, 0.128, 0.32, and 0.8 nM (data not shown). Numbers are approximate and represent residual PNPLA3 mRNA level (PNPLA3/HPRT1), wherein 100 would represent 100% residual mRNA level (0% knockdown) and 0 would represent 0% residual mRNA level (100% knockdown). In the various tables herein, the level of mRNA is measured, unless otherwise noted.

TABLE 113

Activity of oligonucleotides.

| Oligonucleotide | 25 nM |
|---|---|
| VVV-3421 | 13 |
| VVV-9434 | 63 |
| VVV-9439 | 55 |
| VVV-9444 | 37 |
| VVV-3421 | 12 |
| VVV-9435 | 62 |
| VVV-9440 | 37 |
| VVV-9445 | 34 |
| VVV-3421 | 17 |
| VVV-9431 | 92 |
| VVV-9436 | 70 |
| VVV-9441 | 73 |
| VVV-9432 | 53 |
| VVV-9437 | 36 |
| VVV-9442 | 54 |
| VVV-9433 | 77 |
| VVV-9438 | 44 |
| VVV-9443 | 69 |

Data is shown for 25 nM; oligonucleotides were also tested at 0, 1.6, and 6.2 nM (data not shown). Oligonucleotides were tested in vitro in primary cynomolgus hepatocytes.

TABLE 114

Activity of oligonucleotides.

| | Hep3b (wt) | Huh7 (mutant) |
|---|---|---|
| VVV-9890 | 88 | 37 |
| VVV-12100 | 103 | 27 |
| VVV-9893 | 67 | 10 |
| VVV-12101 | 69 | 8 |

Primary cynomolgus hepatocytes. Data is shown for 4 nM. Oligonucleotides were also tested at 0, 0.1, 0.25, 0.66, 1.6, and 10 nM (data not shown). Numbers represent residual PNPLA3 mRNA level (PNPLA3/HPRT1) and numbers are approximate.

WV-9893 and WV-12101 have an asymmetrical format.

Additional oligonucleotides which have an asymmetrical format, but which are stereorandom, were tested, which have the double mutation at P9/P12 (positions 9 and 12). WV-8609, WV-8847, WV-8848, WV-8849 all had an IC50 of around 4 to 5 nM.

TABLE 115A

Activity of oligonucleotides.

| VVV-7805 | 58 |
|---|---|
| VVV-8603 | 46 |
| VVV-8608 | 73 |
| VVV-9889 | 69 |
| VVV-9890 | 76 |
| VVV-8609 | 26 |
| VVV-8601 | 61 |
| VVV-8605 | 65 |
| VVV-8606 | 105 |
| VVV-9891 | 43 |
| VVV-9892 | 52 |
| VVV-9893 | 115 |

Several PNPLA3 oligonucleotides, some of which have an asymmetrical structure, were tested for stability in rat liver homogenate at 2 days. Numbers represent % of full-length oligonucleotide remaining; numbers are approximate.

TABLE 115B

Activity of oligonucleotides.

| Oligonucleotide | Ligand | mFX1/mHPRT1 |
|---|---|---|
| VVV-3969 | Tri-GalNAc | 23 |
| VVV-5287 | Tri-PFE ligand | 22 |
| VVV-7299 | Bi-GalNAc | 22 |
| VVV-7300 | Bi-PFE ligand | 20 |
| VVV-7297 | Mono-GalNAc | 74 |
| VVV-7298 | Mono-PFE ligand | 43 |

Several oligonucleotides were also prepared which target a mouse homolog of different gene, Factor XI (FXI or F11), and which comprised an additional component, which was a tri-, bi- or mono-antennary ligand which was either a GalNAc or a PFE ligand. These were administered to mice at 0.3, 1 or 3 mpK QDx3. Numbers below represent the mFXI/mHPRT1 mRNA level relative to control at 3 mpk. Mice were also administered oligonucleotides at 0.3 and 1 mpk (data not shown).

TABLE 115C

Oligonucleotides.

| Oligo-nucleotide | Sequence | SEQ ID NO | Naked Sequence | Stereo-chemistry |
|---|---|---|---|---|
| WV-7297 | Mod038L001Teo * Geo * Geo * Teo * Aeo * A * T * m5C * m5C * A * m5C * T * T * T * m5C * Aeo * Geo * Aeo * Geo * Geo | 1131 | TGGTAA TCCACTT TCAGAGG | OXXXXXXXXXX XXXXXXXXX |

TABLE 115C-continued

Oligonucleotides.

| Oligo-nucleotide | Sequence | SEQ ID NO | Naked Sequence | Stereo-chemistry |
|---|---|---|---|---|
| WV-7298 | Mod039L001Teo * Geo * Geo * Teo * Aeo * A * T * m5C * m5C * A * m5C * T * T * T * m5C * Aeo * Geo * Aeo * Geo * Geo | 1132 | TGGTAA TCCACTT TCAGAGG | OXXXXXXXXXX XXXXXXXXX |
| WV-7299 | Mod040L001Teo * Geo * Geo * Teo * Aeo * A * T * m5C * m5C * A * m5C * T * T * T * m5C * Aeo * Geo * Aeo * Geo * Geo | 1133 | TGGTAA TCCACTT TCAGAGG | OXXXXXXXXXX XXXXXXXXX |
| WV-7300 | Mod041L001Teo * Geo * Geo * Teo * Aeo * A * T * m5C * m5C * A * m5C * T * T * T * m5C * Aeo * Geo * Aeo * Geo * Geo | 1134 | TGGTAA TCCACTT TCAGAGG | OXXXXXXXXXX XXXXXXXXX |
| WV-5287 | Mod034L001Teo * Geo * Geo * Teo * Aeo * A * T * m5C * m5C * A * m5C * T * T * T * m5C * Aeo * Geo * Aeo * Geo * Geo | 1135 | TGGTAA TCCACTT TCAGAGG | OXXXXXXXXXX XXXXXXXXX |

The various components (e.g., *, Mod038, etc.) in this table are the same as those in Table 1A. All of these oligonucleotides are single-stranded, though the sequences are split into multiple lines for formatting.

Various oligonucleotides were constructed which comprise a tri-, bis- or mono-antennary ligand which is either the PFE ligand or GalNAc.

In some experiments, compounds were constructed which comprise an oligonucleotide conjugated to a mono-, bis- or tri-antennary GalNAc (also designated Ref. GalNAc or Reference GalNAc) or PFE ligand (also described as PFE ASPGR ligand, PFE GalNAc, bridged bicyclic ketal or bicyclic ligand).

In some embodiments, oligonucleotides are PNPLA3 oligonucleotides. In some embodiments, oligonucleotides target a different gene, APOC3.

Such APOC3 oligonucleotides include:

TABLE 115D

Oligonucleotides.

| Oligo-nucleotide | Ligand | Alternative designation of ligand and linker (L001 is a linker) | Example describing example synthesis of ligand | Example describing example synthesis of oligonucleotide with ligand |
|---|---|---|---|---|
| WV-8877 | None | — | — | — |
| WV-7107 | None | — | — | 37A |
| WV-6558 | Ref. GalNAc Tri-antennary | Mod001L001 | 38 (protected version) | 37A, 37B |
| WV-9542 | PFE ligand Tri-antennary | Mod083L001 | 31, 40 | 37C |
| WV-9543 | Ref GalNAc Bis-antennary | Mod079L001 | 35 (protected version) | 37D |
| WV-9544 | PFE ligand Bis-antennary | Mod080L001 | 32, 33 | 37E |
| WV-9545 | Ref GalNAc Mono-antennary | Mod081L001 | 36 (protected version) | 37F |
| WV-9546 | PFE ligand Mono-antennary | Mod082L001 | 34 | 37G |

Ref GalNAc Tri-antennary is also designated Tri-GalNAc; PFE ligand Tri-antennary is also designated Tri-PFE ligand; Ref. GalNAc Bis-antennary is also designated Bis-GalNAc; PFE ligand Bis-antennary is also designated Bis-PFE ligand; Ref. GalNAc Mono-antennary is also designated Mono-GalNAc; and PFE ligand Mono-antennary is also designated Mono-PFE ligand. The structures of Mod001, Mod079, Mod080, Mod081, Mod082, Mod083 and L001 are provided in the legend to Table 1A and in other texts herein. Ligands are also described in Example 27. Mod083 is also described in Example 4A and 4B.

The GalNAc structures in Examples 29, 35, and 36 represent the protected versions, as they comprise —OAc (—O-acetate groups). In construction of the listed oligonucleotides, the Ac groups are removed during de-protection following conjugation of the compound to the oligonucleotide. De-protection is performed, for example, with concentrated ammonium hydroxide, e.g., as described in Example 37B. In the de-protected versions of these structures, —OAc is replaced by —OH. WV-8877 (negative control) targets a different gene, which is not APOC3 or PNPLA3.

The APOC3 oligonucleotide WV-7107, conjugated with GalNAc or PFE ligand at different valencies (mono, bis or triantennary) and the negative control were separately administered to Tg (transgenic) mice harboring the human APOC3 transgene (B6.Cg-Tg(APOC3)2Bres/J) on day 1, and APOC3 knockdown was monitored by serum hAPOC3 protein reduction.

| WAVE ID | Sequence | SEQ ID NO | Naked Sequence | Stereo-chemistry |
|---|---|---|---|---|
| WV-6558 | Mod001L001Aeo * SGeom5CeoTeoTeo * RC * ST * ST * SG * RT * SC * SC * RA * SG* SC * RTeoTeoTeoAeo * STeo | 1136 | AGCTTCTTGTC CAGCTTTAT | OSOOORSSSRS SRSSROOOS |
| WV-9542 | Mod083L001Aeo * SGeom5CeoTeoTeo * RC * ST * ST * SG * RT * SC * SC * RA * SG* SC * RTeoTeoTeoAeo * STeo | 1137 | AGCTTCTTGTC CAGCTTTAT | OSOOORSSSRS SRSSROOOS |
| WV-9543 | Mod079L001Aeo * SGeom5CeoTeoTeo * RC * ST * ST * SG * RT * SC * SC * RA * SG* SC * RTeoTeoTeoAeo * STeo | 1138 | AGCTTCTTGTC CAGCTTTAT | OSOOORSSSRS SRSSROOOS |
| WV-9544 | Mod080L001Aeo * SGeom5CeoTeoTeo * RC * ST * ST * SG * RT * SC * SC * RA * SG* SC * RTeoTeoTeoAeo * STeo | 1139 | AGCTTCTTGTC CAGCTTTAT | OSOOORSSSRS SRSSROOOS |
| WV-9545 | Mod081L001Aeo * SGeom5CeoTeoTeo * RC * ST * ST * SG * RT * SC * SC * RA * SG* SC * RTeoTeoTeoAeo * STeo | 1140 | AGCTTCTTGTC CAGCTTTAT | OSOOORSSSRS SRSSROOOS |
| WV-9546 | Mod082L001Aeo * SGeom5CeoTeoTeo * RC * ST * ST * SG * RT * SC * SC * RA * SG* SC * RTeoTeoTeoAeo * STeo | 1141 | AGCTTCTTGTC CAGCTTTAT | OSOOORSSSRS SRSSROOOS |

The various components (e.g., *, Mod083, etc.) in this table are the same as those in Table 1A. All of these oligonucleotides are single-stranded, though the sequences are split into multiple lines for formatting.

PNPLA3 oligonucleotides comprising various ligands (including but not limited to Ref. GalNAc Tri-antennary, PFE ligand Tri-antennary, Ref. GalNAc Bis-antennary, PFE ligand Bis-antennary, Ref. GalNAc Mono-antennary, PFE ligand Mono-antennary) were constructed via methods akin to those described for corresponding APOC3 oligonucleotides.

TABLE 115E

Activity of oligonucleotides

| Day | 0 | 8 | 15 | 22 | 29 | 36 | 43 | 50 |
|---|---|---|---|---|---|---|---|---|
| PBS | 1.52 | 0.95 | 1.50 | 0.56 | 0.96 | 1.07 | 1.57 | 1.74 |
|  | 0.59 | 0.73 | 0.74 | 0.87 | 0.90 | 0.90 | 0.73 | 0.71 |
|  | 1.21 | 0.99 | 1.10 | 1.34 | 0.89 | 0.82 | 0.62 | 0.78 |
|  | 0.67 | 1.14 | 0.89 | 0.99 | 0.89 | 0.86 | 0.95 | 0.86 |
|  | 1.01 | 1.20 | 0.76 | 1.24 | 1.35 | 1.36 | 1.13 | 0.91 |
| WV-8877 | 1.56 | 1.24 | 1.67 | 1.59 | 2.37 | 1.56 | 1.47 | 2.27 |
|  | 0.78 | 0.73 | 0.85 | 0.80 | 1.15 | 0.61 | 0.75 | 1.19 |
|  | 1.08 | 0.81 | 1.42 |  | 1.84 | 1.21 | 1.73 | 3.05 |
|  | 0.71 | 1.21 | 0.74 | 0.62 | 1.02 | 1.07 | 0.95 | 1.48 |
|  | 1.28 | 1.21 | 0.60 | 0.80 | 1.13 | 1.50 | 0.86 |  |
| WV-6558 | 2.74 | 0.06 | 0.05 | 0.06 | 0.11 | 0.38 | 0.69 | 1.43 |
|  | 1.15 | 0.17 | 0.05 | 0.04 | 0.09 | 0.27 | 0.01 | 0.81 |
|  | 0.38 | 0.04 | 0.05 | 0.10 | 0.18 | 0.45 | 0.53 | 1.07 |
|  | 0.44 |  |  |  |  |  |  |  |
|  | 0.41 | 0.04 | 0.04 | 0.08 | 0.09 | 0.11 | 0.13 | 0.22 |
| WV-9542 | 1.10 | 0.23 | 0.05 | 0.07 | 0.13 | 0.23 | 0.32 | 0.78 |
|  | 0.71 | 0.03 | 0.02 | 0.04 | 0.06 | 0.09 | 0.20 | 0.28 |
|  | 0.59 | 0.05 | 0.04 | 0.08 | 0.16 | 0.72 | 0.90 | 0.80 |
|  | 0.32 | 0.03 | 0.02 | 0.04 | 0.09 | 0.37 | 0.54 | 0.55 |
|  | 0.40 | 0.03 | 0.03 | 0.06 | 0.21 | 0.39 | 0.49 | 0.58 |
| WV-9543 | 0.48 | 0.03 | 0.05 | 0.09 | 0.08 | 0.21 | 0.27 | 0.49 |
|  | 1.19 | 0.06 | 0.06 | 0.09 | 0.06 | 0.09 | 0.57 | 0.96 |
|  | 0.79 | 0.05 | 0.04 | 0.17 | 0.06 | 0.15 | 0.42 | 0.80 |
|  | 0.79 | 0.09 | 0.03 | 0.28 | 0.20 | 0.17 | 0.28 | 0.59 |
|  | 0.48 | 0.04 | 0.02 | 0.08 | 0.06 | 0.12 | 0.17 | 0.32 |
| WV-9544 | 0.91 |  | 0.04 | 0.06 | 0.06 | 0.19 | 0.26 | 0.67 |
|  | 0.94 | 0.10 | 0.03 | 0.08 | 0.09 | 0.15 | 0.34 | 0.76 |
|  | 1.72 | 0.19 | 0.04 | 0.07 | 0.09 | 0.25 | 0.60 | 0.83 |
|  | 1.92 | 0.28 | 0.07 | 0.10 | 0.11 | 0.13 | 0.26 | 0.56 |
|  | 0.81 | 0.04 | 0.05 | 0.11 | 0.12 | 0.20 | 0.32 | 0.73 |

TABLE 115E-continued

Activity of oligonucleotides

| Day | 0 | 8 | 15 | 22 | 29 | 36 | 43 | 50 |
|---|---|---|---|---|---|---|---|---|
| WV-9545 | 0.49 | 0.03 | 0.07 | 0.16 | 0.21 | 0.32 | 0.66 | 0.60 |
|  | 1.14 | 0.22 | 0.04 | 0.10 | 0.15 | 0.58 | 0.76 | 0.97 |
|  | 0.58 | 0.03 | 0.04 | 0.15 | 0.27 | 0.67 | 1.16 | 0.97 |
|  | 0.64 | 0.03 | 0.04 | 0.19 | 0.42 | 0.98 | 1.38 | 0.96 |
|  | 0.60 | 0.05 | 0.03 | 0.08 |  |  |  |  |
| WV-9546 | 3.33 | 0.20 | 0.06 | 0.27 | 0.24 | 0.49 | 1.13 | 1.31 |
|  | 1.03 | 0.11 | 0.04 | 0.09 | 0.14 | 0.46 | 0.55 | 0.68 |
|  | 1.20 | 0.28 | 0.12 | 0.20 | 0.31 | 0.95 | 1.75 | 1.39 |
|  | 0.71 | 0.15 | 0.04 | 0.19 | 0.39 | 0.26 | 0.75 | 0.36 |
|  | 0.18 | 0.04 | 0.02 | 0.20 | 0.28 | 0.21 | 0.56 | 0.56 |

All oligonucleotides were administered to animals at a 3 mg/kg single dose (s.c.) at day 1. In addition, WV-6558 and WV-9542 were also administered to animals at a 1 mg/kg single dose (s.c.) at day 1. Serum was collected at days 0, 8, 15, 22, 29, 36, 43, and 50. Each group contained 5 animals. PBS and WV-8877 (which targets a gene which is not APOC3) were negative controls.

Numbers indicate relative APOC3 protein level, wherein 1.00 represents 100% relative to PBS. In various in vivo studies, including this one, tested animals were transgenic mice expressing the human APOC3 gene.

TABLE 115F

Part I. Oligonucleotide accumulation in the liver

| PBS | WV-6558 | WV-9542 | WV-9543 | WV-9544 | WV-9545 | WV-9546 |
|---|---|---|---|---|---|---|
| 0 | 2.95 | 1.73 | 3.52 | 3.82 | 2.02 | 4.27 |
| 0 | 2.46 | 1.69 | 2.49 | 4.19 | 1.99 | 1.37 |
| 0 | 2.48 | 0.45 | 1.14 | 2.74 | 1.30 | 1.29 |
| 0 | 1.85 | 1.09 | 2.12 | 2.26 | 1.14 | 1.25 |
| 0 | 1.79 | 1.43 | 4.26 | 1.88 | 1.07 | 0.82 |

Oligonucleotide accumulation in the liver was also analyzed after a single 3 mg/kg dose, 30 min. Numbers indicate µg of oligonucleotide/g of tissue. Tested animals were transgenic mice expressing the human APOC3 gene.

In the same experiment: Oligonucleotide accumulation in the liver was also analyzed for WV-6558 and WV-9542 after a single 1 mg/kg dose, 30 min. Numbers indicate μg of oligonucleotide/g of tissue.

| PBS | VVV-6558 1 mpk | VVV-9542 1 mpk |
|---|---|---|
| 0 | 1.92 | 0.46 |
| 0 | 1.77 | 1.08 |
| 0 | 1.43 | 0.56 |
| 0 | 0.68 | 0.30 |
| 0 | 0.18 | 0.67 |

TABLE 115F

| | | Part II. Oligonucleotide accumulation in the liver | | | |
|---|---|---|---|---|---|
| PBS | WV-6558 | WV-9542 | WV-9543 | WV-9544 | WV-9545 | WV-9546 |
| 0 | 3.30 | 2.93 | 6.83 | 4.56 | 3.55 | 3.83 |
| 0 | 3.49 | 2.20 | 6.56 | 4.45 | 2.23 | 4.05 |
| 0 | 3.18 | 1.34 | 4.58 | 2.72 | 1.94 | 2.28 |
| 0 | 2.41 | 1.61 | 3.87 | 2.31 | 3.03 | 2.12 |
| 0 | 1.43 | 2.90 | 4.10 | 2.36 | 1.85 | 3.50 |

Oligonucleotide accumulation in the liver was also analyzed after a single 3 mg/kg dose, 8 days. Numbers indicate μg of oligonucleotide/g of tissue. Tested animals were transgenic mice expressing the human APOC3 gene.

In the same experiment: Oligonucleotide accumulation in the liver was also analyzed for WV-6558 and WV-9542 after a single 1 mg/kg (1 mpk) dose, 8 days. Numbers indicate μg of oligonucleotide/g of tissue.

TABLE 116

| | Activity of oligonucleotides. | |
|---|---|---|
| PBS | VVV-6558 1 mpk | VVV-9542 1 mpk |
| 0 | 0.72 | 1.08 |
| 0 | 0.74 | 1.20 |
| 0 | 0.60 | 0.75 |
| 0 | 0.55 | 0.57 |
| 0 | 0.63 | 0.63 |

The data show the efficacy of various ligands conjugated to APOC3 oligonucleotides; these same ligands can also be conjugated onto PNPLA3 oligonucleotides.

Various PNPLA3 RNAi agents were tested for stability in rat liver homogenate. Numbers represent percent of full-length oligonucleotide remaining at 5 days; oligonucleotides were also tested at 2 days (data not shown); and numbers are approximate. Some oligonucleotides comprise a 5'-DNA-T and some oligonucleotides comprise a 5'-Rc-Me-T.

TABLE 117

| Activity of oligonucleotides. | |
|---|---|
| VVV-8095 | 62 |
| VVV-9495 | 61 |
| VVV-9499 | 86 |
| VVV-8701 | 49 |
| VVV-9496 | 71 |
| VVV-9500 | 99 |

Various PNPLA3 oligonucleotides were also tested for efficacy with an additional component which is a tri-antennary GalNAc conjugate (including, but not limited to WV-7805, WV-8132, WV-8566, WV-8599, WV-9859, and WV-9670). Oligonucleotides were tested in vitro on Huh7-148 OE cells (which comprise the mutant allele of PNPLA3) at 10 nM. Numbers represent PNPLA3 mRNA levels (PN-PLA3/HPRT1), and numbers are approximate. In many cases, the oligonucleotides did not demonstrate significant knockdown of wild-type PNPLA3 in cynomolgus (non-human primate or NHP) hepatocytes. For example, WV-8132, WV-8600, WV-9868 and WV-9860 did not demonstrate significant knockdown of wild-type PNPLA3 in cynomolgus (non-human primate or NHP) hepatocytes when tested at up to 10 nM (data not shown).

TABLE 118

| Activity of oligonucleotides. | | | |
|---|---|---|---|
| Negative control | 100 | Negative control | 100 |
| VVV-993 | 117 | VVV-993 | 117 |
| VVV-7805 | 20 | VVV-8600 | 47 |
| VVV-8132 | 54 | VVV-8564 | 47 |
| VVV-8566 | 67 | VVV-8596 | 62 |
| VVV-8599 | 82 | VVV-8597 | 38 |
| VVV-9859 | 56 | | |
| VVV-9670 | 57 | | |
| VVV-993 | 117 | VVV-993 | 117 |
| VVV-9868 | 48 | VVV-9860 | 65 |
| VVV-9869 | 50 | VVV-9861 | 58 |
| VVV-9870 | 53 | VVV-9862 | 62 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 119

| | Activity of oligonucleotides. | | | | | | | |
|---|---|---|---|---|---|---|---|---|
| Time (mins) | 0 | 5 | 10 | 15 | 20 | 30 | 45 | 60 |
| WV-7805 + WV-8807 | 100.0 | 94.1 | 93.4 | 88.6 | 90.6 | 82.8 | 74.5 | 73.4 |
| WV-8603 + WV-8807 | 100.0 | 93.1 | 89.7 | 84.4 | 91.0 | 82.4 | 73.0 | 66.4 |
| WV-8608 + WV-8807 | 100.0 | 95.4 | 92.2 | 89.8 | 87.4 | 81.4 | 79.7 | 72.1 |
| WV-9889 + WV-8807 | 100.0 | 90.9 | 87.7 | 81.9 | 85.7 | 74.4 | 72.9 | 66.4 |
| WV-9890 + WV-8807 | 100.0 | 92.7 | 89.6 | 85.4 | 88.7 | 77.0 | 75.8 | 66.8 |
| WV-7805 + WV-8808 | 100.0 | 99.5 | 97.7 | 98.1 | 96.9 | 96.2 | 95.6 | 93.4 |
| WV-8603 + WV-8808 | 100.0 | 102.2 | 99.4 | 100.3 | 99.1 | 98.5 | 99.2 | 95.6 |
| WV-8608 + WV-8808 | 100.0 | 98.8 | 97.5 | 96.9 | 95.9 | 96.9 | 95.5 | 94.1 |
| WV-9889 + WV-8808 | 100.0 | 99.9 | 99.2 | 99.5 | 98.6 | 97.8 | 97.2 | 96.3 |
| WV-9890 + WV-8808 | 100.0 | 107.5 | 100.7 | 100.8 | 99.1 | 104.2 | 98.3 | 97.5 |
| WV-8601 + WV-8807 | 100.0 | 93.1 | 90.9 | 90.4 | 91.4 | 88.2 | 85.6 | 80.1 |
| WV-8605 + WV-8807 | 100.0 | 98.3 | 96.0 | 96.4 | 96.0 | 96.0 | 87.1 | 86.7 |

TABLE 119-continued

Activity of oligonucleotides.

| Time (mins) | 0 | 5 | 10 | 15 | 20 | 30 | 45 | 60 |
|---|---|---|---|---|---|---|---|---|
| WV-8606 + WV-8807 | 100.0 | 90.1 | 91.6 | 90.7 | 90.9 | 86.6 | 82.4 | 79.1 |
| WV-8609 + WV-8807 | 100.0 | 92.1 | 89.0 | 83.8 | 85.5 | 75.6 | 75.7 | 69.0 |
| WV-8601 + WV-8808 | 100.0 | 99.0 | 100.2 | 100.2 | 97.8 | 97.6 | 97.2 | 94.1 |
| WV-8605 + WV-8808 | 100.0 | 100.7 | 99.7 | 100.9 | 98.4 | 99.1 | 98.5 | 94.6 |
| WV-8606 + WV-8808 | 100.0 | 101.2 | 97.6 | 98.1 | 96.3 | 97.0 | 96.5 | 93.9 |
| WV-8609 + WV-8808 | 100.0 | 96.7 | 93.7 | 98.6 | 96.8 | 95.6 | 96.2 | 94.5 |
| WV-9891 + WV-8807 | 100.0 | 91.6 | 88.3 | 86.1 | 87.9 | 79.8 | 75.6 | 75.2 |
| WV-9892 + WV-8807 | 100.0 | 93.2 | 86.9 | 83.5 | 84.3 | 74.2 | 64.2 | 58.6 |
| WV-9893 + WV-8807 | 100.0 | 94.6 | 88.6 | 86.6 | 88.6 | 77.4 | 69.0 | 65.6 |
| WV-9891 + WV-8808 | 100.0 | 98.3 | 98.6 | 96.9 | 95.0 | 94.2 | 92.8 | 89.8 |
| WV-9892 + WV-8808 | 100.0 | 100.7 | 101.8 | 100.7 | 99.3 | 97.9 | 97.4 | 95.7 |
| WV-9893 + WV-8808 | 100.0 | 100.1 | 100.3 | 100.2 | 99.3 | 96.3 | 96.1 | 93.5 |
| WV-9894 + WV-8807 | 100.0 | 96.2 | 90.1 | 85.1 | 84.7 | 79.5 | 76.8 | 74.9 |
| WV-9895 + WV-8807 | 100.0 | 97.0 | 92.5 | 87.1 | 84.3 | 77.0 | 71.8 | 70.7 |
| WV-9896 + WV-8807 | 100.0 | 98.2 | 93.2 | 86.0 | 81.8 | 74.8 | 69.2 | 70.0 |
| WV-9894 + WV-8808 | 100.0 | 98.8 | 97.1 | 97.4 | 96.1 | 94.0 | 95.4 | 91.4 |
| WV-9895 + WV-8808 | 100.0 | 99.9 | 97.1 | 98.5 | 99.3 | 96.1 | 96.4 | 93.6 |
| WV-9896 + WV-8808 | 100.0 | 99.2 | 99.0 | 98.3 | 96.4 | 95.6 | 93.8 | 90.6 |

Various PNPLA3 oligonucleotides were tested in vitro in an RNaseH assay. PNPLA3 oligonucleotides were incubated in the presence of target RNA which was the wt allele (WV-8808) or the 148 allele (WV-8807). Numbers represent the percentage of target RNA (WV-8808 or WV-8807) remaining. In this table, 100.00 would represent 100% PNPLA3 mRNA level and 0.00 would represent 0% PNPLA3 mRNA after treatment with oligonucleotides.

The PNPLA3 oligonucleotides WV-980, WV-9893, WV-8606 and WV-7805 also significantly reduced PNPLA3 148 mutant mRNA levels in Huh7 cells with PNLA3 148 mutation (to between about 25 to 55% residual mutant PNPLA3, relative to HPRT1, at 12.5 nM), but these oligonucleotides did not significantly reduce wt PNPLA3 levels in Huh7 cells with wt PNPLA3 (about 90% or more residual wt PNPLA3 level at 12.5 nM).

TABLE 120

Activity of oligonucleotides.

| Conc. (nM) (exp10) | 1.398 | 0.796 | 0.194 | −0.408 | −1.010 | −1.612 | −2.214 | −2.816 |
|---|---|---|---|---|---|---|---|---|
| WV-3380 | 0.059 | 0.193 | 0.568 | 0.809 | 0.809 | 0.917 | 1.032 | 0.983 |
|  | 0.092 | 0.365 | 0.720 | 0.862 |  | 1.004 | 1.121 |  |
| WV-3986 | 0.379 | 0.444 | 0.673 | 0.790 | 0.870 | 0.870 | 0.993 | 0.933 |
|  | 0.486 | 0.551 | 0.752 | 0.901 | 1.007 | 0.939 | 0.876 | 1.140 |
| WV-3987 | 0.400 | 0.521 | 0.742 | 0.870 | 0.959 | 0.889 | 0.986 | 0.952 |
|  | 0.451 | 0.594 | 0.914 | 0.966 | 1.086 | 0.972 | 1.021 | 1.072 |
| WV-3988 | 0.496 | 0.521 | 0.742 | 1.021 | 0.946 | 1.079 | 0.907 | 0.959 |
|  | 0.328 | 0.615 | 0.920 | 1.057 | 1.064 | 0.979 | 0.901 | 1.133 |
| WV-3393 | 0.115 | 0.165 | 0.438 | 0.795 | 0.882 | 1.028 | 1.086 | 0.986 |
|  | 0.080 | 0.218 | 0.555 | 0.835 | 0.952 | 1.064 | 0.933 | 1.057 |
| WV-3989 | 0.316 | 0.279 | 0.547 | 0.790 | 0.852 | 0.993 | 0.966 | 1.000 |
|  | 0.295 | 0.412 | 0.651 | 0.889 | 1.049 | 1.140 | 0.986 | 1.173 |
| WV-3990 | 0.259 | 0.444 | 0.624 | 0.979 | 1.109 | 1.021 | 1.007 | 0.993 |
|  | 0.274 | 0.559 | 0.779 | 0.959 | 1.079 | 1.042 | 1.049 | 1.164 |

Various PNPLA3 oligonucleotides were tested in vitro in Hep3B cells at 48 hours after treatment with oligonucleotide. In this table, 1.00 would represent 100% PNPLA3 mRNA level and 0.00 would represent 0% PNPLA3 mRNA after treatment with oligonucleotides.

TABLE 121

Activity of oligonucleotides.

| Conc. (nM) (exp10) | 1.398 | 0.796 | 0.194 | −0.408 | −1.010 | −1.612 | −2.214 | −2.816 |
|---|---|---|---|---|---|---|---|---|
| WV-3402 | 0.146 | 0.207 | 0.457 | 0.907 | 0.933 | 0.959 | 0.939 | 0.952 |
|  | 0.104 | 0.319 | 0.697 | 0.914 | 0.926 | 1.028 | 1.094 | 1.102 |
| WV-3991 | 0.216 | 0.423 | 0.582 | 0.858 | 0.907 | 0.966 | 0.870 | 0.966 |
|  | 0.303 | 0.500 | 0.722 | 1.049 | 0.895 | 0.979 | 1.042 | 1.035 |

TABLE 121-continued

Activity of oligonucleotides.

| Conc. (nM) (exp10) | 1.398 | 0.796 | 0.194 | −0.408 | −1.010 | −1.612 | −2.214 | −2.816 |
|---|---|---|---|---|---|---|---|---|
| WV-3992 | 0.303 | 0.384 | 0.594 | 0.823 | 0.818 | 0.907 | 0.847 | 0.852 |
|  | 0.321 | 0.423 | 0.673 | 0.914 | 0.933 | 0.907 | 0.959 | 1.057 |

Various PNPLA3 oligonucleotides were tested in vitro in Hep3B cells at 48 hours after treatment with oligonucleotide. In this table, 1.00 would represent 100% PNPLA3 mRNA level and 0.00 would represent 0% PNPLA3 mRNA after treatment with oligonucleotides.

TABLE 122

Activity of oligonucleotides.

| Conc. (nM) (exp 10) | 1.398 | 0.796 | 0.194 | −0.408 | −1.010 | −1.612 | −2.214 | −2.816 |
|---|---|---|---|---|---|---|---|---|
| WV-3387 | 0.091 | 0.205 | 0.527 | 0.811 | 1.070 | 0.881 | 0.977 | 0.971 |
|  | 0.081 | 0.135 | 0.391 | 0.851 | 1.033 | 0.964 | 0.944 | 1.070 |
| WV-3993 | 0.998 | 0.912 | 1.026 | 1.062 | 1.308 | 1.019 | 1.019 | 0.957 |
|  | 0.869 | 0.912 | 1.123 | 1.077 | 1.084 | 1.048 | 1.055 | 1.100 |
| WV-3994 | 0.944 | 0.991 | 1.195 | 1.040 | 1.107 | 1.012 | 1.123 | 0.971 |
|  | 0.857 | 0.991 | 1.146 | 1.077 | 1.092 | 1.138 | 1.033 | 1.154 |

Various PNPLA3 oligonucleotides were tested in vitro in Hep3B cells at 48 hours after treatment with oligonucleotide. In this table, 1.00 would represent 100% PNPLA3 mRNA level and 0.00 would represent 0% PNPLA3 mRNA after treatment with oligonucleotides.

TABLE 123

Activity of oligonucleotides.

| Conc. (nM) (exp10) | 1.398 | 0.796 | 0.194 | −0.408 | −1.010 | −1.612 | −2.214 | −2.816 |
|---|---|---|---|---|---|---|---|---|
| WV-3391 | 0.176 | 0.264 | 0.502 | 0.912 | 0.944 | 1.170 | 1.077 | 0.887 |
|  | 0.141 | 0.230 | 0.531 | 0.788 | 1.040 | 1.146 | 1.005 | 1.005 |
| WV-3995 | 0.925 | 1.026 | 0.977 | 1.131 | 1.162 | 0.984 | 1.123 | 0.811 |
|  | 0.751 | 0.957 |  | 1.123 |  | 1.162 | 1.062 | 0.971 |
| WV-3996 | 0.893 | 0.899 | 0.833 | 0.991 | 1.203 | 1.146 | 1.138 | 0.964 |
|  | 0.875 | 0.899 | 0.851 | 1.187 |  | 1.123 | 1.040 | 1.131 |

Various PNPLA3 oligonucleotides were tested in vitro in Hep3B cells at 48 hours after treatment with oligonucleotide. In this table, 1.00 would represent 100% PNPLA3 mRNA level and 0.00 would represent 0% PNPLA3 mRNA after treatment with oligonucleotides.

TABLE 124

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-3380 | 86.7 | 79.0 | 58.4 | 60.3 | 27.2 | 28.6 |
| wv-4054 | 60.3 | 49.1 | 67.6 | 53.4 | 65.5 | 45.5 |
| wv-4098 | 62.0 | 43.3 | 57.7 | 50.9 | 38.5 | 52.8 |
| WV-6585 | 58.8 | 56.9 | 71.3 | 90.8 | 89.4 | 79.0 |
| WV-6586 | 82.1 | 53.7 | 82.5 | 79.5 | 89.0 | 66.2 |
| WV-6587 | 49.9 | 45.3 | 103.1 | 56.0 | 74.7 | 77.9 |
| WV-6588 | 58.6 | 60.9 | 82.1 | 84.9 | 86.5 | 85.3 |
| WV-6589 | 61.8 | 51.3 | 92.2 | 94.4 | 77.8 | 83.5 |
| WV-6590 | 63.7 | 64.3 | 62.9 | 83.9 | 85.5 | 60.8 |
| WV-6591 | 83.3 | 71.4 | 74.7 | 75.2 | 76.3 | 94.2 |
| WV-6592 | 49.7 | 39.8 | 51.4 | 40.4 | 54.3 | 39.4 |
| WV-6593 | 68.1 | 77.7 | 58.3 | 89.3 | 64.6 | 70.7 |
| WV-6594 | 82.1 | 53.7 | 58.7 | 59.1 | 61.6 | 62.2 |
| WV-4054 | 58.7 | 35.6 | 55.3 | 49.8 | 66.0 | 60.3 |
| WV-6595 | 40.9 | 52.4 | 58.0 | 54.5 | 60.5 | 56.2 |
| WV-6596 | 48.6 | 40.2 | 57.2 | 49.4 | 46.9 | 49.2 |
| WV-6597 | 27.7 | 31.4 | 41.8 | 52.7 | 61.3 | 45.0 |

TABLE 124-continued

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-6598 | 40.1 | 35.4 | 59.1 | 53.6 | 44.5 | 42.3 |
| WV-6599 | 37.3 | 54.3 | 73.0 | 61.8 | 76.6 | 69.6 |
| WV-6600 | 64.7 | 67.5 | 88.7 | 105.6 | 95.3 | 115.7 |
| WV-6601 | 74.2 | 48.0 | 64.4 | 51.4 | 97.0 | 81.9 |
| WV-6602 | 64.7 | 51.6 | 64.0 | 63.3 | 95.8 | 64.1 |
| WV-6603 | 57.8 | 40.4 | 85.7 | 73.9 | 67.1 | 71.1 |
| WV-6604 | 50.7 | 50.5 | 57.8 | 47.0 | 72.0 | 47.1 |
| WV-6605 | 52.1 | 52.5 | 58.2 | 57.8 | 58.9 | 57.8 |
| WV-6606 | 27.1 | 56.6 | 52.4 | 51.1 | 77.7 | 53.9 |
| WV-6607 | 35.7 | 41.6 | 44.0 | 37.0 | 76.2 | 53.7 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 125

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-3380 | 86.7 | 79.0 | 58.4 | 60.3 | 27.2 | 28.6 |
| wv-4054 | 60.3 | 49.1 | 67.6 | 53.4 | 65.5 | 45.5 |
| wv-4098 | 62.0 | 43.3 | 57.7 | 50.9 | 38.5 | 52.8 |
| WV-6608 | 74.0 | 71.3 | 64.3 | 80.2 | 90.8 | 81.4 |
| WV-6609 | 88.6 | 51.9 | 71.6 | 57.7 | 66.3 | 61.2 |
| WV-6610 | 51.1 | 59.5 | 65.1 | 51.7 | 61.2 | 60.6 |
| WV-6611 | 40.9 | 47.5 | 61.7 | 57.3 | 63.2 | 75.1 |
| WV-6612 | 50.9 | 59.8 | 50.6 | 53.3 | 75.4 | 54.3 |
| WV-6613 | 39.0 | 49.1 | 49.5 | 35.6 | 53.8 | 43.5 |
| WV-6614 | 51.6 | 65.2 | 43.6 | 59.6 | 47.8 | 67.1 |
| WV-6615 | 45.7 | 70.0 | 40.0 | 41.6 | 44.1 | 53.2 |
| WV-5305 | 61.4 | 82.3 | 73.1 | 100.3 | 83.3 | 101.0 |
| WV-6616 | 63.6 | 49.3 | 67.0 | 74.3 | 62.0 | 70.1 |
| WV-6617 | 67.5 | 45.2 | 44.0 | 54.6 | 54.9 | 59.2 |
| WV-6618 | 53.4 | 44.2 | 45.4 | 46.4 | 66.5 | 32.9 |
| WV-6619 | 56.7 | 28.9 | 64.4 | 50.3 | 49.7 | 42.9 |
| WV-6620 | 61.8 | 55.6 | 57.8 | 90.1 | 37.8 | 52.5 |
| WV-6621 | 63.3 | 51.1 | 55.0 | 73.3 | 31.4 | 54.7 |
| WV-6622 | 67.5 | 34.7 | 55.2 | 48.0 | 27.4 | 61.7 |
| WV-6623 | 57.1 | 56.5 | 73.3 | 88.7 | 78.4 | 95.9 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 126

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-3380 | 86.7 | 79.0 | 58.4 | 60.3 | 27.2 | 28.6 |
| wv-4054 | 60.3 | 49.1 | 67.6 | 53.4 | 65.5 | 45.5 |
| wv-4098 | 62.0 | 43.3 | 57.7 | 50.9 | 38.5 | 52.8 |
| WV-6624 | 59.2 | 71.5 | 52.2 | 78.3 | 64.7 | 59.0 |
| WV-6625 | 53.7 | 50.7 | 49.4 | 41.9 | 53.1 | 51.1 |
| WV-6626 | 62.3 | 58.2 | 65.0 | 70.4 | 39.7 | 53.9 |
| WV-6627 | 57.5 | 51.1 | 66.9 | 59.1 | 49.2 | 52.9 |
| WV-6628 | 44.8 | 48.6 | 61.5 | 59.8 | 50.4 | 63.3 |
| WV-6629 | 61.4 | 54.4 | 59.5 | 86.7 | 52.5 | 58.3 |

TABLE 126-continued

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-6630 | 40.8 | 54.1 | 44.5 | 46.3 | 56.3 | 54.3 |
| WV-6631 | 61.0 | 61.4 | 47.6 | 111.2 | 75.1 | 70.1 |
| WV-6632 | 67.5 | 96.3 | 93.1 | 79.0 | 84.8 | 86.5 |
| WV-6633 | 61.1 | 56.4 | 51.8 | 37.1 | 40.6 | 46.0 |
| WV-6634 | 66.7 | 65.7 | 52.8 | 51.9 | 39.1 | 39.0 |
| WV-6635 | 90.3 | 63.6 | 72.6 | 68.6 | 66.7 | 70.6 |
| WV-6636 | 68.0 | 40.3 | 57.7 | 55.9 | 45.1 | 50.6 |
| WV-6637 | 68.0 | 46.2 | 46.9 | 60.4 | 40.2 | 69.4 |
| WV-6638 | 46.2 | 38.0 | 64.8 | 41.3 | 40.3 | 32.9 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 127

Activity of oligonucleotides.

|  | 0.312 nM | | 1.25 nM | | 5 nM | |
|---|---|---|---|---|---|---|
| Control | 76.5 | 84.9 | 111.7 | 106.6 | 113.9 | 99.1 |
| WV-3380 | 86.7 | 79.0 | 58.4 | 60.3 | 27.2 | 28.6 |
| wv-4054 | 60.3 | 49.1 | 67.6 | 53.4 | 65.5 | 45.5 |
| wv-4098 | 62.0 | 43.3 | 57.7 | 50.9 | 38.5 | 52.8 |
| WV-6639 | 94.8 | 81.0 | 113.1 | 90.2 | 68.5 | 69.4 |
| WV-6640 | 91.3 | 78.0 | 60.4 | 87.5 | 87.7 | 61.7 |
| WV-6641 | 76.4 | 113.6 | 83.1 | 87.6 | 59.6 | 65.0 |
| WV-6642 | 95.0 | 104.3 | 90.6 | 98.5 | 74.8 | 73.5 |
| WV-6643 | 126.6 | 90.1 | 96.8 | 77.1 | 60.0 | 75.3 |
| WV-6644 | 125.8 | 94.5 | 89.9 | 85.1 | 81.4 | 63.5 |
| WV-6645 | 93.1 | 74.3 | 97.7 | 66.4 | 68.9 | 40.8 |
| WV-6646 | 83.5 | 80.4 | 85.1 | 60.9 | 56.7 | 33.7 |
| WV-6647 | 92.9 | 77.7 | 91.8 | 79.8 | 125.9 | 62.3 |
| WV-6648 | 104.4 | 88.7 | 92.0 | 111.5 | 67.3 | 73.3 |
| WV-6649 | 106.9 | 85.8 | 79.7 | 85.5 | 78.4 | 74.5 |
| WV-6650 | 94.6 | 79.2 | 87.4 | 91.5 | 66.5 | 97.9 |
| WV-6651 | 116.4 | 74.8 | 92.2 | 96.8 | 58.0 | 57.3 |
| WV-6652 | 114.1 | 70.2 | 110.9 | 94.0 | 88.6 | 66.4 |
| WV-6653 | 116.1 | 89.1 | 90.0 | 100.0 | 77.3 | 72.9 |
| WV-6654 | 84.9 | 99.0 | 101.1 | 128.1 | 67.4 | 70.9 |
| WV-6655 | 102.0 | 99.5 | 116.9 | 83.8 | 114.7 | 85.6 |
| WV-6656 | 115.3 | 119.9 | 114.7 | 85.2 | 101.0 | 108.4 |
| WV-6657 | 88.6 | 94.1 | 114.1 | 109.7 | 94.6 | 100.4 |
| WV-6658 | 114.4 | 92.2 | 131.2 | 134.7 | 133.3 | 90.6 |
| WV-6659 | 116.9 | 104.2 | 122.1 | 96.6 | 99.8 | 122.3 |
| WV-6660 | 104.7 | 79.5 | 124.1 | 100.2 | 79.7 | 88.5 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 129

Activity of oligonucleotides.

|  | 0 | 0.1 nM | 0.4 nM | 3.0 nM | 12.5 nM |
|---|---|---|---|---|---|
| WV-4098 | 96.1 | 76.8 | 61.7 | 58.2 | 53.6 |
| | 105.7 | 73.2 | 58.3 | 47.9 | 57.9 |
| WV-7776 | 107.4 | 92.5 | 117.0 | 85.0 | 74.7 |
| | 85.4 | 93.1 | 102.7 | 73.4 | 62.5 |
| WV-7777 | 107.4 | 107.4 | 88.2 | 63.2 | 71.7 |
| | 90.9 | 90.9 | 73.4 | 73.1 | 59.8 |

Various PNPLA3 oligonucleotides were tested in vitro in cells after treatment with oligonucleotide. In this table, 100.00 would represent 100% PNPLA3 mRNA level and 0.00 would represent 0% PNPLA3 mRNA after treatment with oligonucleotides.

TABLE 130

Activity of oligonucleotides.

|  | WV-4098 | WV-7465 | WV-8076 |
|---|---|---|---|
| 0 | 103.4 | 112.5 | 101.0 |
|  | 86.2 | 95.5 | 109.7 |
| 0.02 nM | 82.5 | 62.8 | 67.2 |
|  | 91.2 | 61.6 | 79.1 |
| 0.1 nM | 54.4 | 39.5 | 46.5 |
|  | 56.3 | 48.4 | 72.2 |
| 0.4 nM | 49.6 | 31.2 | 46.6 |
|  | 48.1 | 42.7 | 43.9 |
| 3.125 nM | 21.9 | 39.2 | 82.0 |
|  | 33.7 | 37.1 | 79.7 |

Various PNPLA3 oligonucleotides were tested in vitro in Huh7 cells. Residual levels of PNPLA3 mRNA are shown, wherein PNPLA3 is relative to HPRT1. In this table, 100.00 would represent 100% PNPLA3 mRNA level and 0.00 would represent 0% PNPLA3 mRNA after treatment with oligonucleotides.

TABLE 131

Activity of oligonucleotides.

|  | WV-4098 | WV-8080 | WV-8081 |
|---|---|---|---|
| 0 | 103.4 | 83.3 | 79.2 |
|  | 86.2 | 109.8 | 89.9 |
| 0.02 nM | 82.5 | 58.1 | 97.2 |
|  | 91.2 | 89.1 | 92.4 |
| 0.1 nM | 54.4 | 71.2 | 91.7 |
|  | 56.3 | 72.1 | 95.5 |
| 0.4 nM | 49.6 | 79.8 | 94.4 |
|  | 48.1 | 97.9 | 108.2 |
| 3.125 nM | 21.9 | 59.3 | 115.6 |
|  | 33.7 | 62.0 | 122.4 |

Various PNPLA3 oligonucleotides were tested in vitro in Huh7 cells. Residual levels of PNPLA3 mRNA are shown, wherein PNPLA3 is relative to HPRT1. In this table, 100.00 would represent 100% PNPLA3 mRNA level and 0.00 would represent 0% PNPLA3 mRNA after treatment with oligonucleotides.

TABLE 132

Activity of oligonucleotides.

|  | WV-4098 | WV-8077 | WV-8078 | WV-8079 |
|---|---|---|---|---|
| 0 | 103.4 | 108.4 | 94.0 | 80.9 |
|  | 86.2 | 107.6 | 98.3 | 87.7 |
| 0.02 nM | 82.5 | 102.1 | 96.4 | 71.1 |
|  | 91.2 |  | 99.8 | 69.3 |
| 0.1 nM | 54.4 | 87.6 | 93.9 | 75.6 |
|  | 56.3 | 87.9 | 118.3 | 97.5 |
| 0.4 nM | 49.6 | 83.4 | 91.0 | 88.6 |
|  | 48.1 | 97.1 | 116.6 | 120.6 |
| 3.125 nM | 21.9 | 79.8 | 73.7 | 105.4 |
|  | 33.7 | 74.8 | 87.7 |  |

Various PNPLA3 oligonucleotides were tested in vitro in Huh7 cells. Residual levels of PNPLA3 mRNA are shown, wherein PNPLA3 is relative to HPRT1. In this table, 100.00 would represent 100% PNPLA3 mRNA level and 0.00 would represent 0% PNPLA3 mRNA after treatment with oligonucleotides.

TABLE 133

Activity of oligonucleotides.

|  | WV-4098 | WV-7465 |
|---|---|---|
| 0 | 103.4 | 112.5 |
|  | 86.2 | 95.5 |
| 0.02 nM | 82.5 | 62.8 |
|  | 91.2 | 61.6 |
| 0.1 nM | 54.4 | 39.5 |
|  | 56.3 | 48.4 |
| 0.4 nM | 49.6 | 31.2 |
|  | 48.1 | 42.7 |
| 3.125 nM | 21.9 | 39.2 |
|  | 33.7 | 37.1 |

Various PNPLA3 oligonucleotides were tested in Huh7 cells. Residual levels of PNPLA3 mRNA are shown, wherein PNPLA3 is relative to HPRT1. In this table, 100.00 would represent 100% PNPLA3 mRNA level and 0.00 would represent 0% PNPLA3 mRNA after treatment with oligonucleotides.

Several PNPLA3 oligonucleotides were also tested in vitro for cytokine release, including WV-8061, WV-8291, WV-8698, and WV-8700. None of the 4 PNPLA3 ssRNAi agents induced cytokine release (IL-1β, IL-6, MCP-1, IL-12p40, IL-12p70, IL-1a, MIP-1 a, MIP-1 (3, TNFα) in any of the donor samples. In contrast, positive control induced cytokine activation even at low concentrations (0.78 ug/ml).

Example 27. Example Additional Components of Oligonucleotides

Various oligonucleotides were designed and constructed which comprise various additional components. Various additional PNPLA3 oligonucleotides described herein can also be conjugated to these additional components.

These additional components include those listed herein:
Tri-antennary ligand is also known as Tri-PFE ASPGR ligand or Tri-PFE ligand or Tri-PFE:

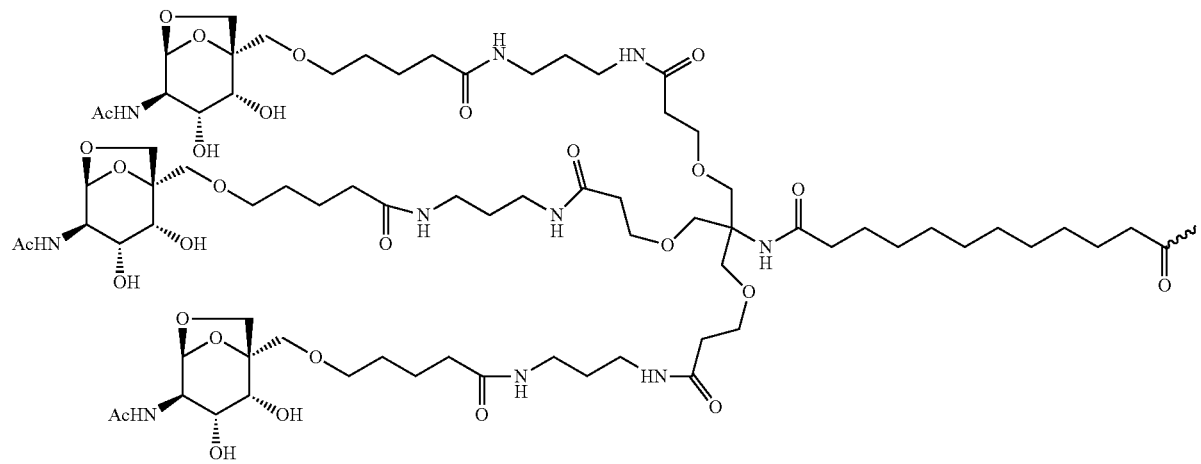

Bis-antennary (or bi-antennary) ligand, also known as bis-(or bi-) antennary PFE ligand or bis-(or bi-) antennary PFE ASPGR ligand or bis-PFE:

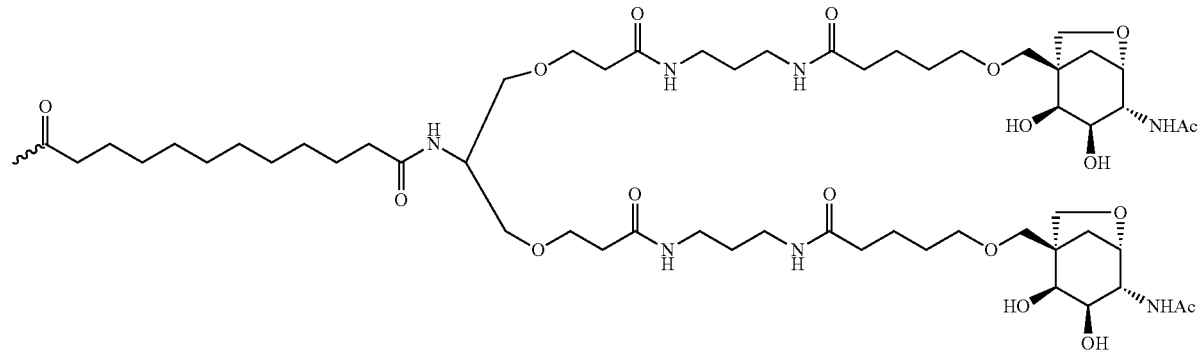

Mono-antennary ligand, also known as mono-antennary PFE ligand or mono-antennary PFE ASPGR ligand or mono-PFE:

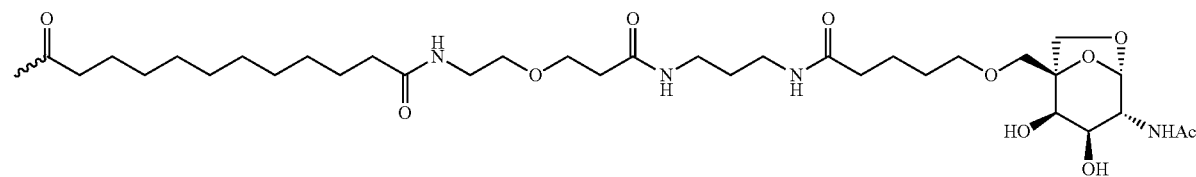

Tri-antennary GalNAc or Tri-GalNAc:

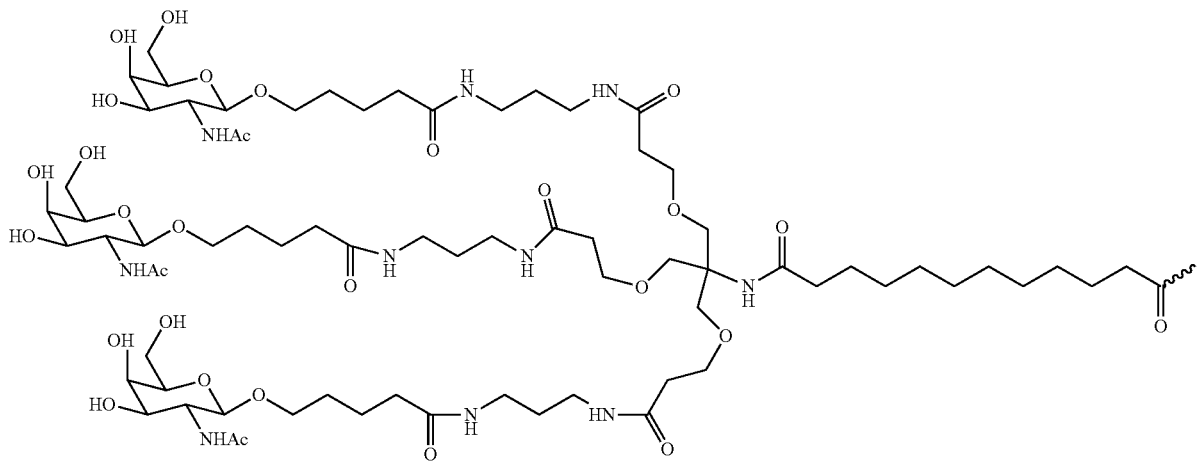

Protected versions of:
Bis-antennary (bi-antennary) GalNAc or bis-GalNAc:

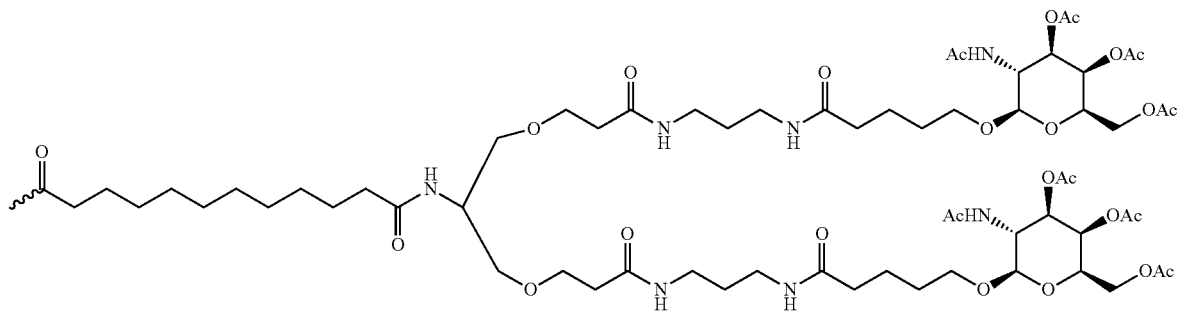

Mono-antennary GalNAc or Mono-GalNAc:

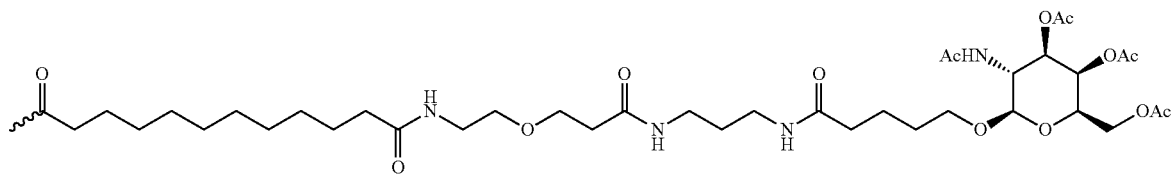

These structures represent the protected versions, as they comprise —OAc (—O-acetate groups). In some embodiments, the Ac groups are removed during de-protection following conjugation of the compound to the oligonucleotide. In some embodiments, de-protection is performed with concentrated ammonium hydroxide, e.g., as described in Example 37B. In the de-protected versions of these structures, —OAc is replaced by —OH.

Some non-limiting examples of processes for production of various additional components are described below:

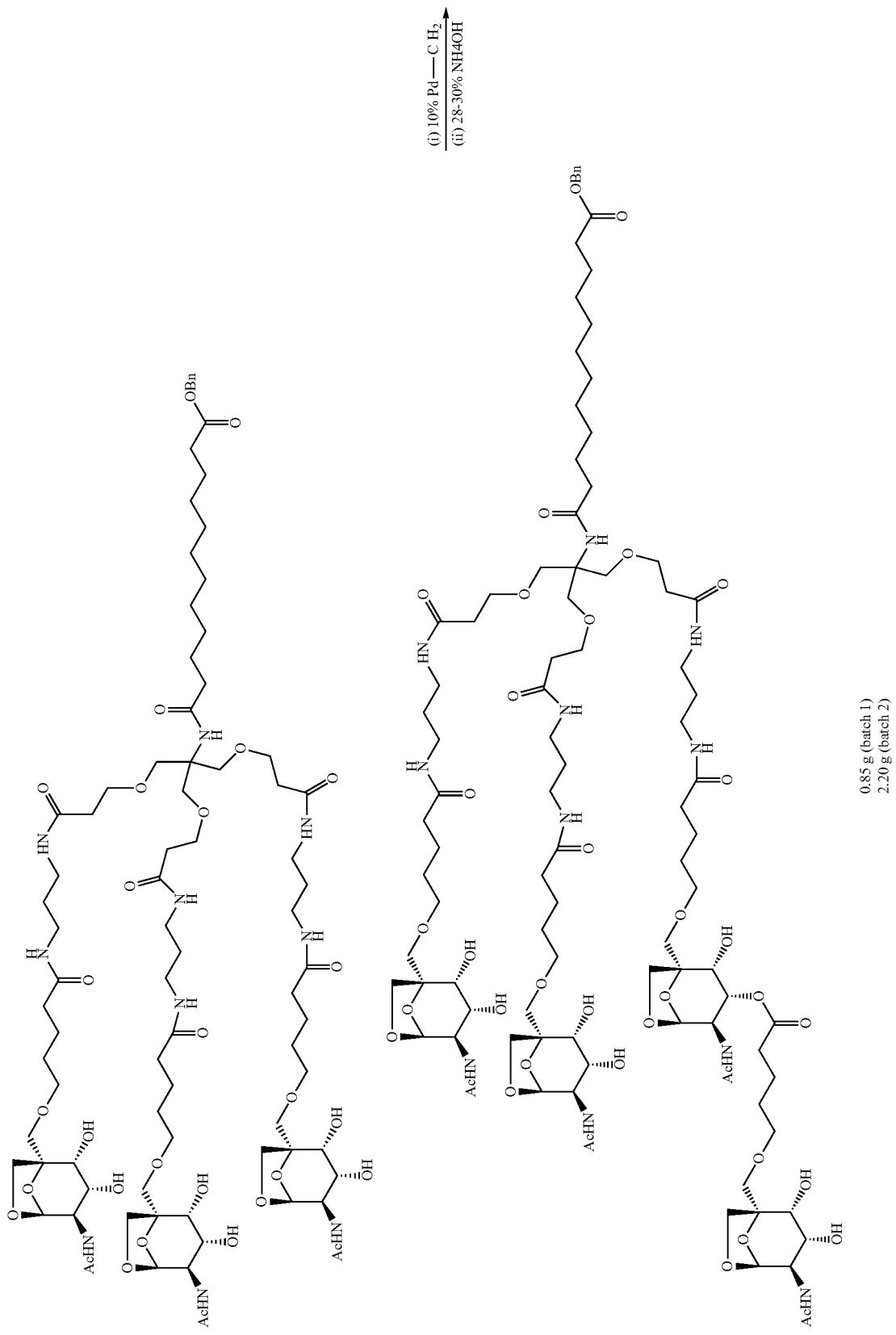

-continued
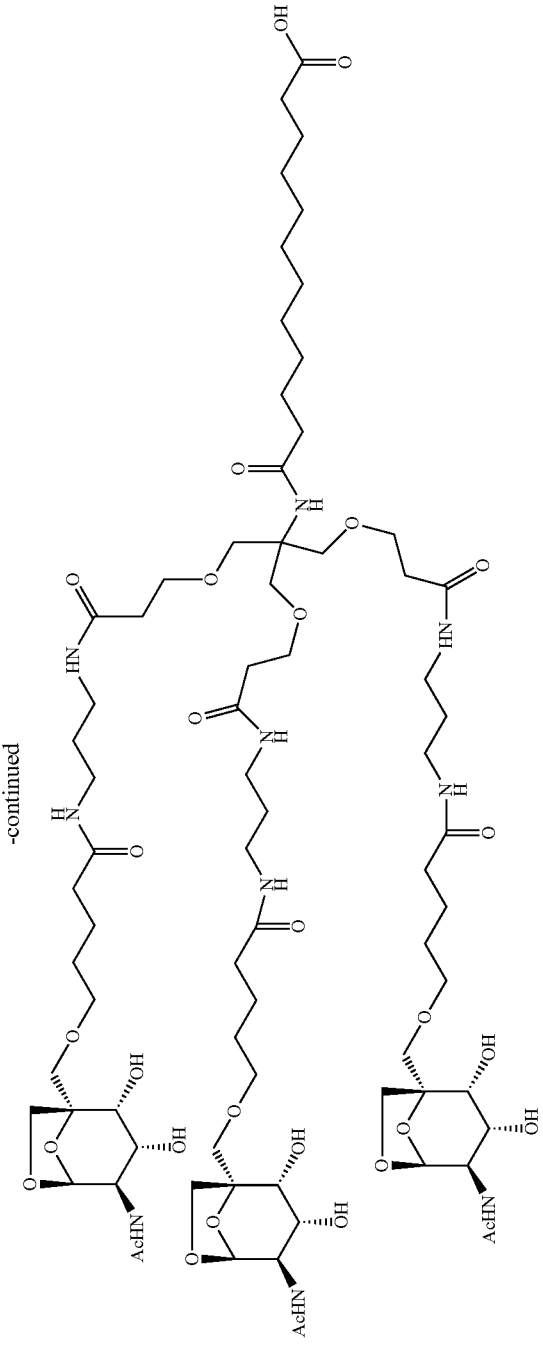
purified by C18 cartridge eluting with 0.1% TFA in water and acetonitrile
0.566 g (GL-N12-55) (containng 4 TFA)
2.14 g (GL-N12-58) (containing 3.7 TFA)
$\xrightarrow{\text{TFA (30 eq)}}_{\text{DCM}}$
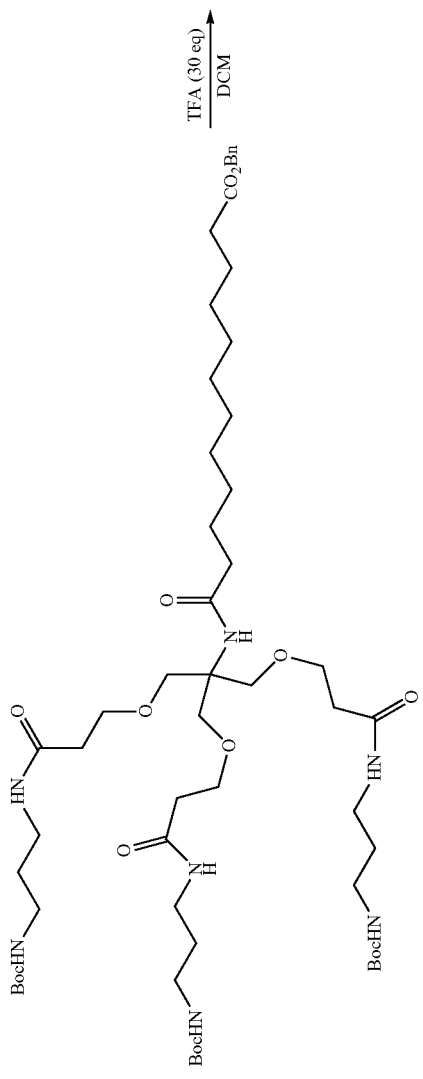
34.4 g

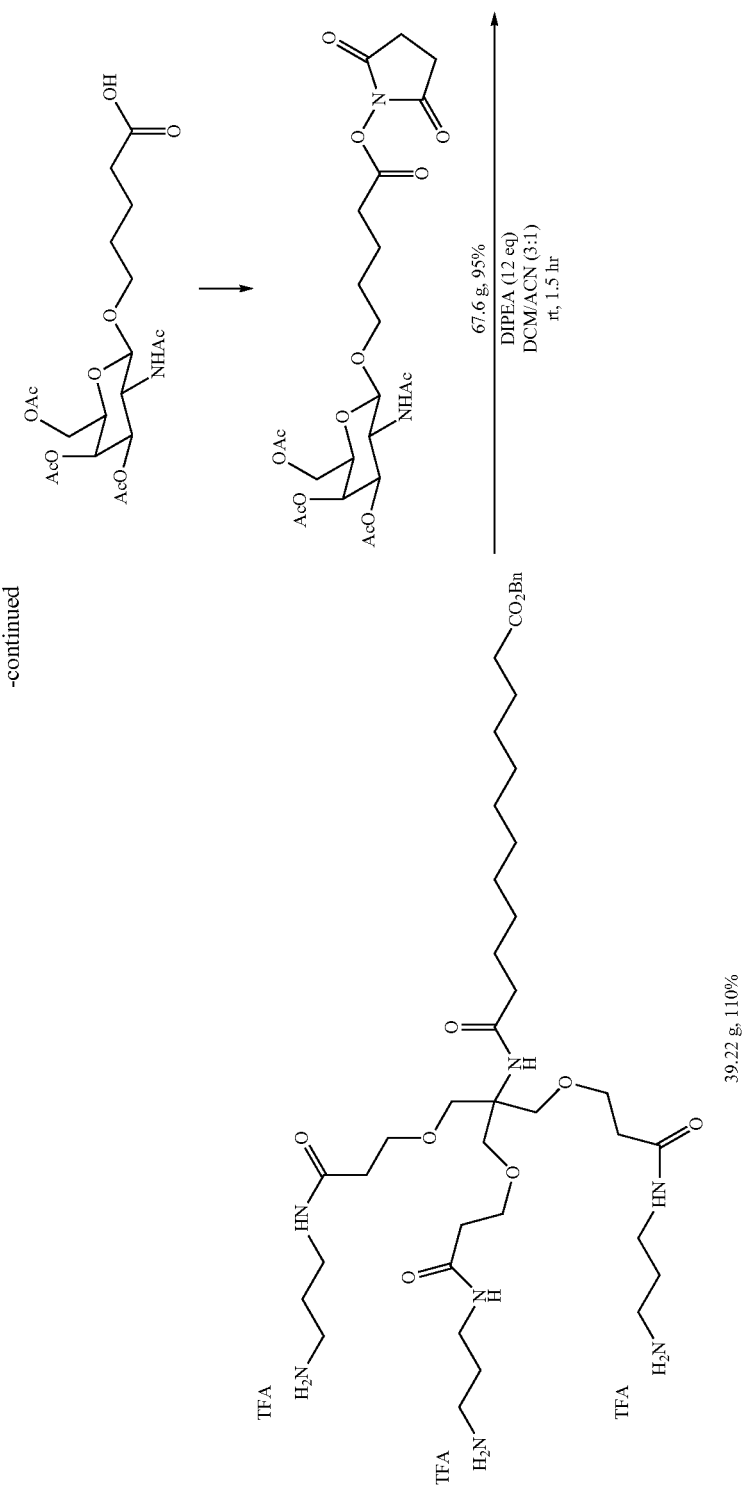

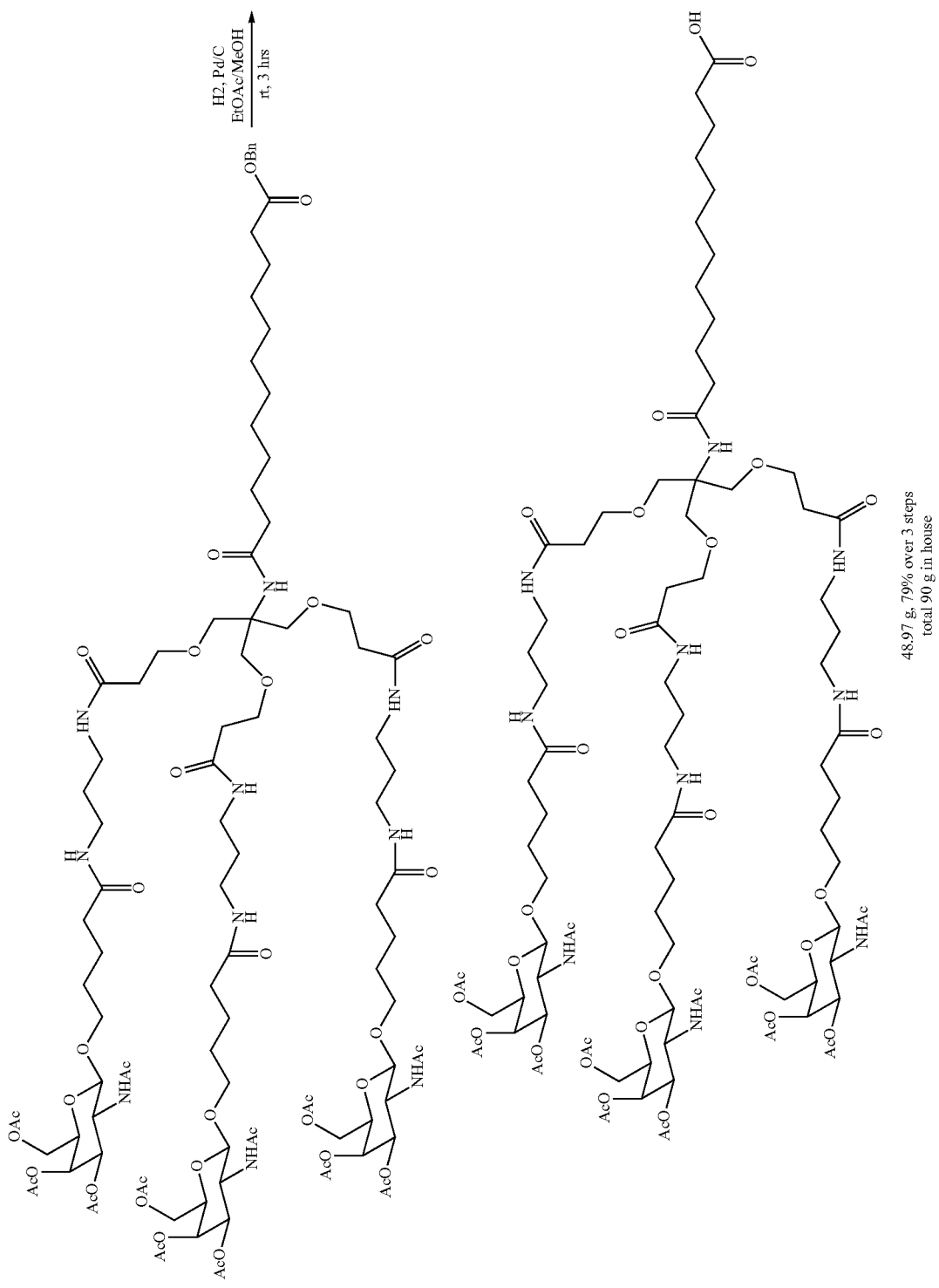

-continued
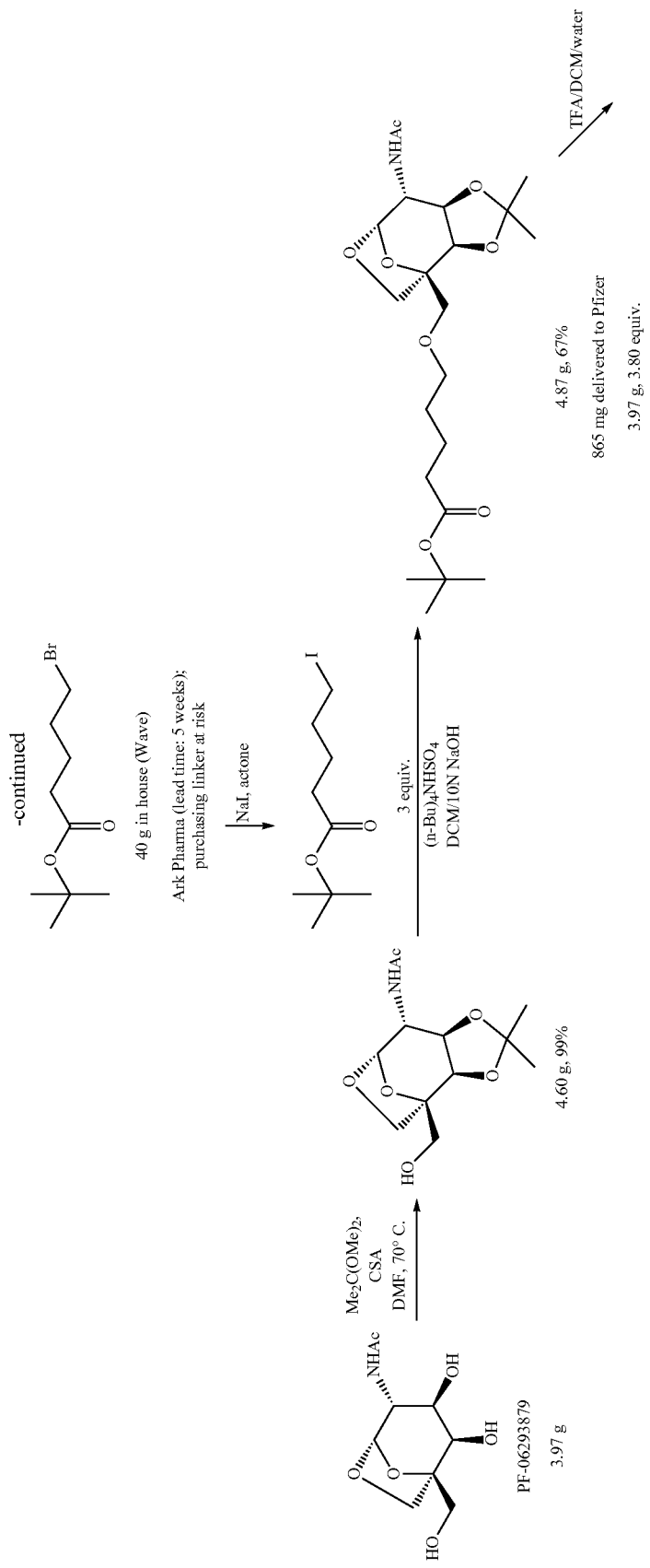

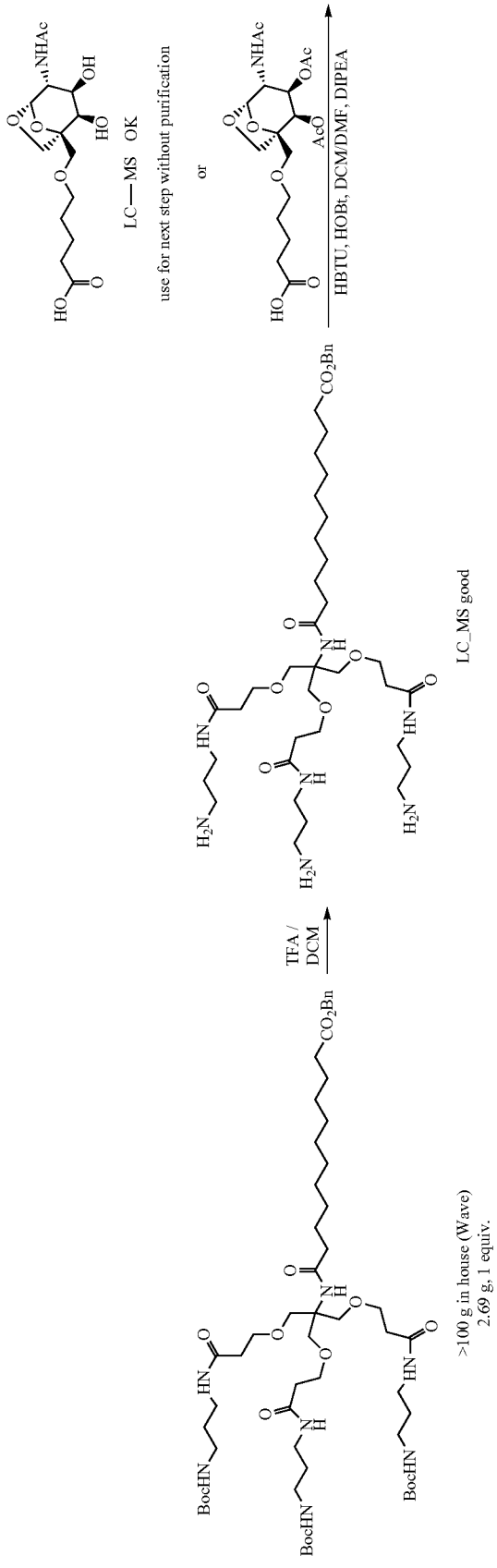

-continued
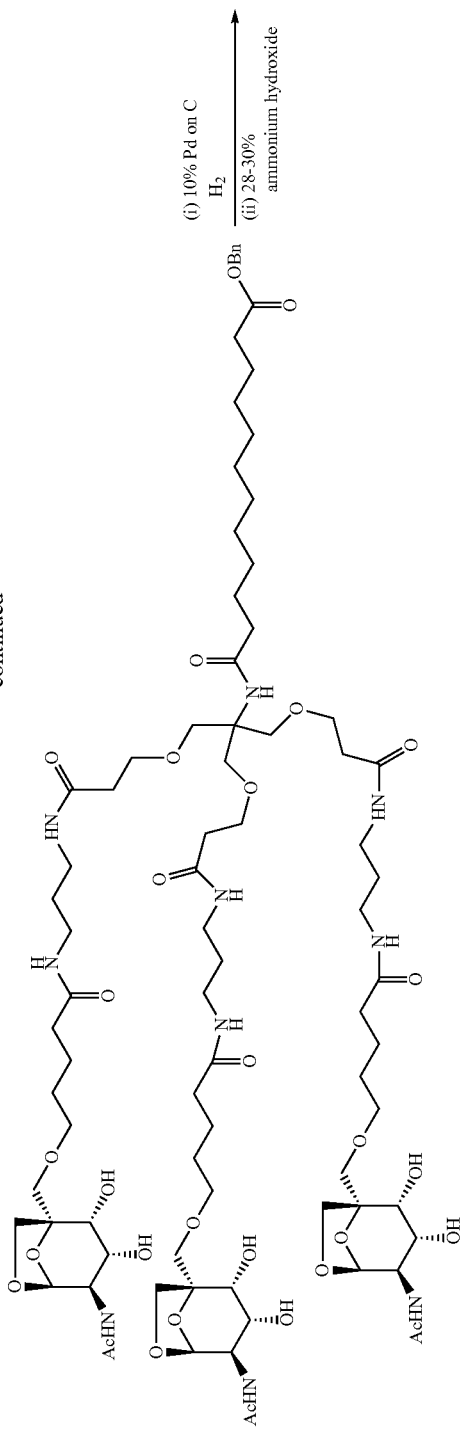
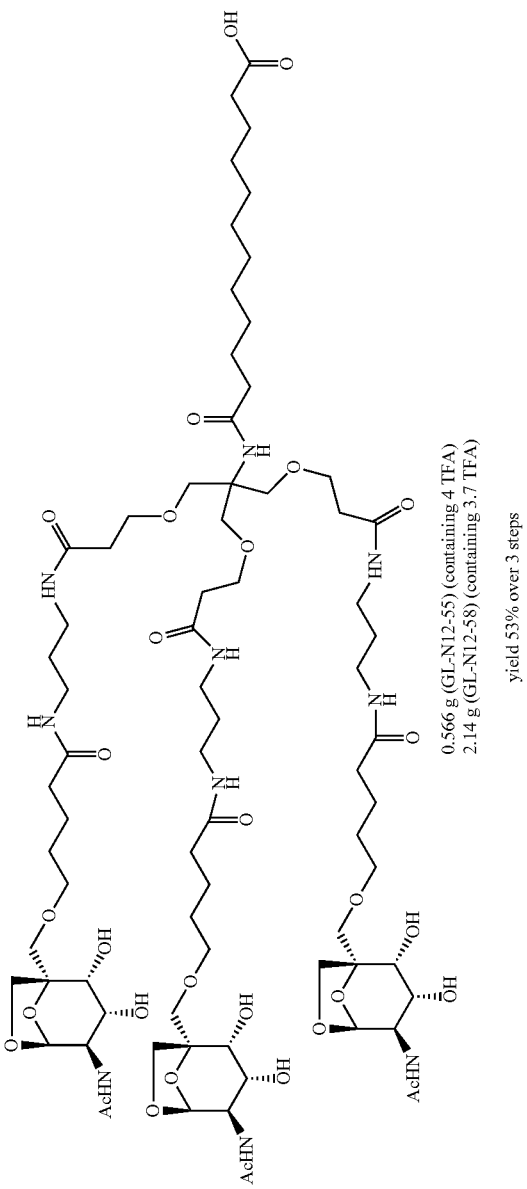
(i) 10% Pd on C H₂
(ii) 28-30% ammonium hydroxide
3.10 g (containing some product related impurity)
0.566 g (GL-N12-55) (containing 4 TFA)
2.14 g (GL-N12-58) (containing 3.7 TFA)
yield 53% over 3 steps

667 668
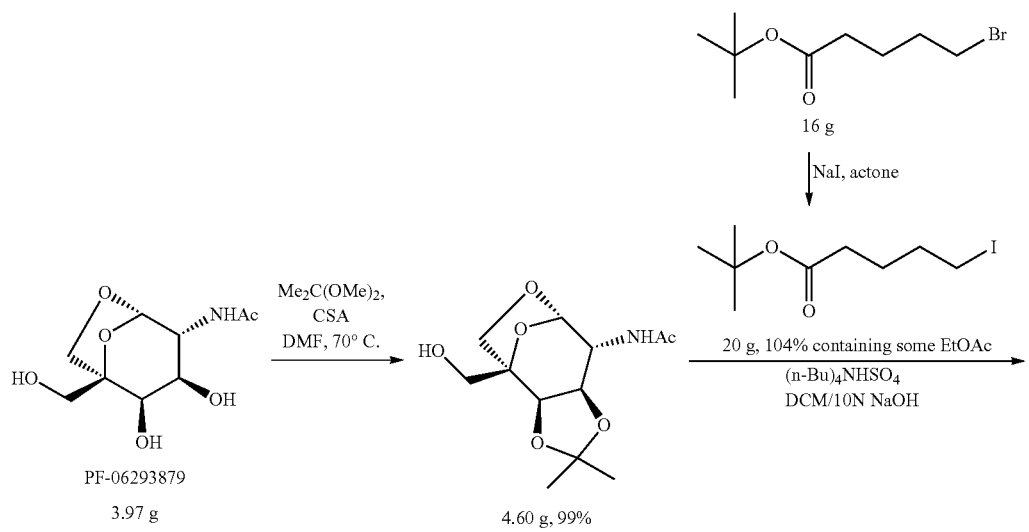
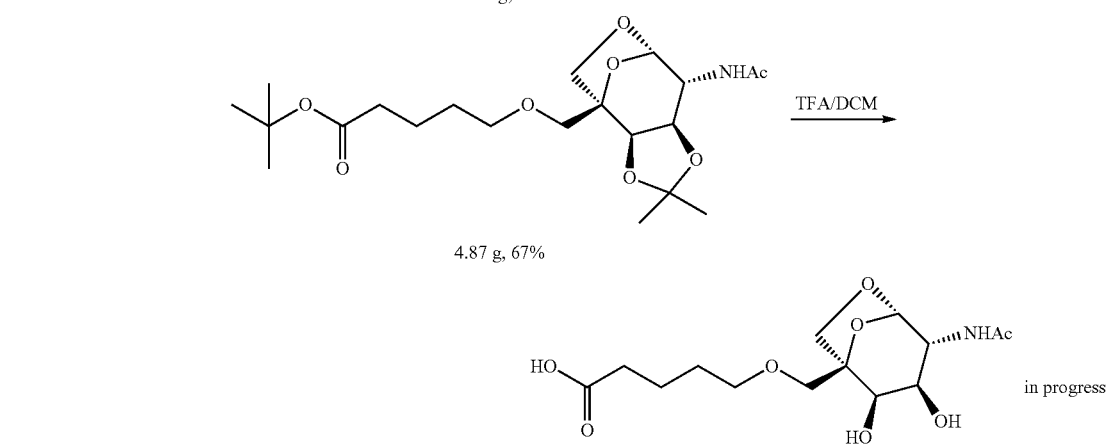
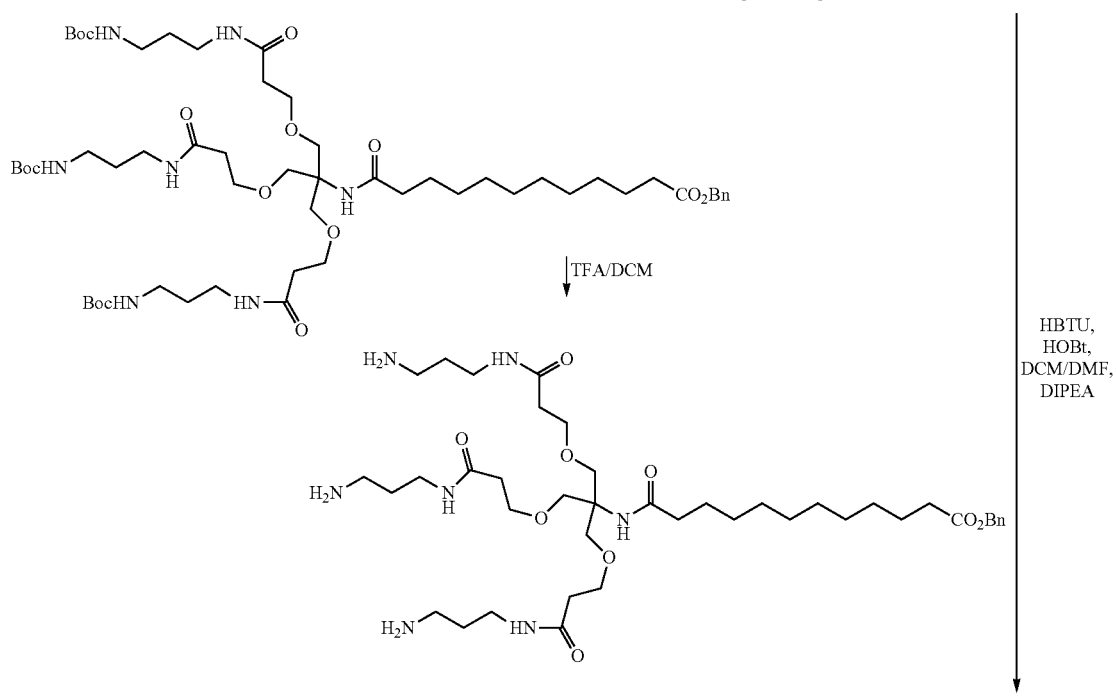

-continued

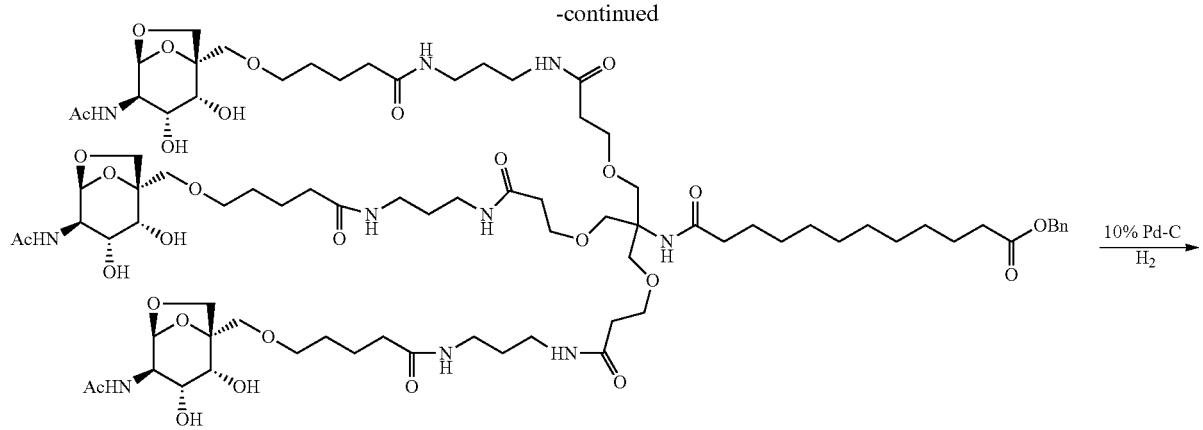

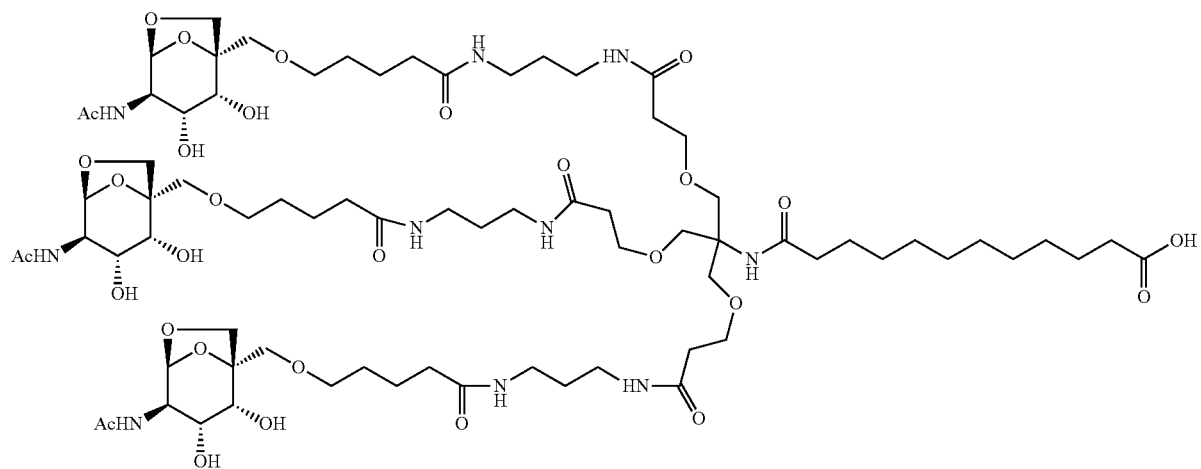

target: 2 g

Various additional components described herein can be conjugated to various oligonucleotides described herein.

Example 28. Example Analytical Methods 1.5 minute run LRMS (low resolution mass spectroscopy): Waters Acqity HSS T3, 2.1 mm×50 mm, C18, 1.7 µm; Mobile Phase: A: 0.1% formic acid in water (v/v); Mobile phase B: 0.1% formic acid in acetonitrile (v/v); Flow-1.25 ml/minute; Initial conditions: A-95%:B-5%; hold at initial from 0.0-0.1 minute; Linear Ramp to A-5%:B-95% over 0.1-1.0 minute; hold at A-5%:B-95% from 1.0-1.1 minute; return to initial conditions 1.1-1.5 minute.

3.0 minute run LRMS (low resolution mass spectroscopy): Waters Acqity HSS T3, 2.1 mm×50 mm, C18, 1.7 µm; Mobile Phase: A: 0.1% formic acid in water (v/v); Mobile phase B: 0.1% formic acid in acetonitrile (v/v); Flow-1.25 ml/minute; Initial conditions: A-95%:B-5%; hold at initial from 0.0-0.1 minute; Linear Ramp to A-5%:B-95% over 0.1-2.6 minute; hold at A-5%:B-95% from 2.6-2.95 minute; return to initial conditions 2.95-3.0 minute.

5-carboxypentyl 5,9,16,22-tetraoxo-11,11-bis{[3-oxo-3-({3-{[(5-[3,4,6-tri-O-acetyl-2-(acetylamino)-2-deoxy-β-D-galactopyranosyl]oxy}pentanoyl)amino]propyl}amino)propoxy]methyl}-26-{[3,4,6-tri-O-acetyl-2-(acetylamino)-2-deoxy-β-D-galactopyranosyl]oxy}-13-oxa-4,10,17,21-tetraazahexacos-1-yl phosphate
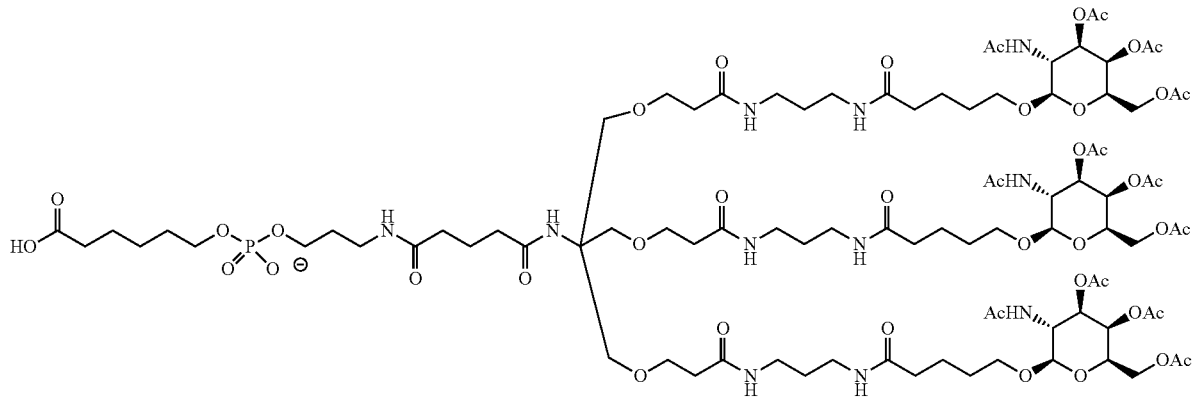
Reaction Scheme
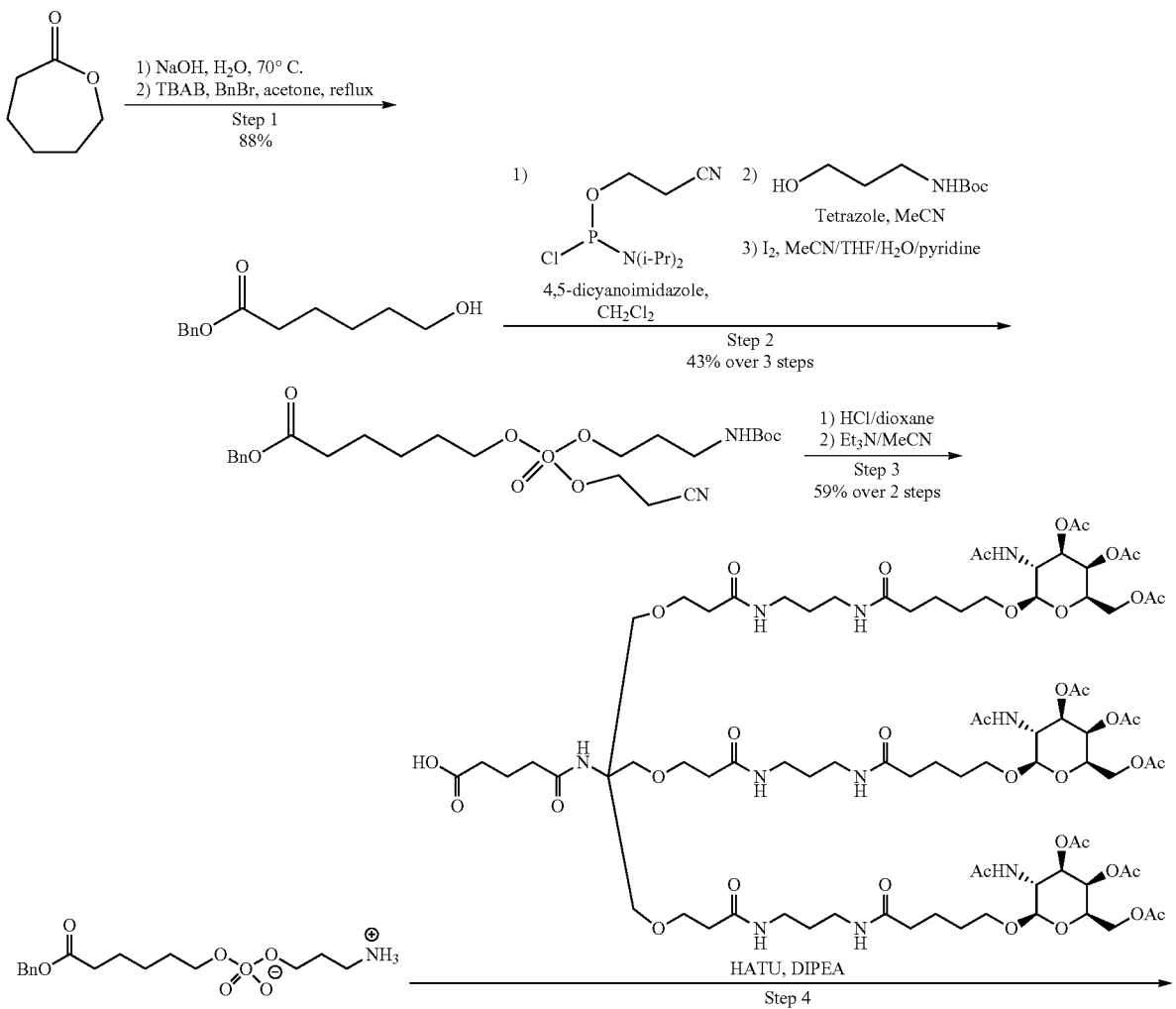

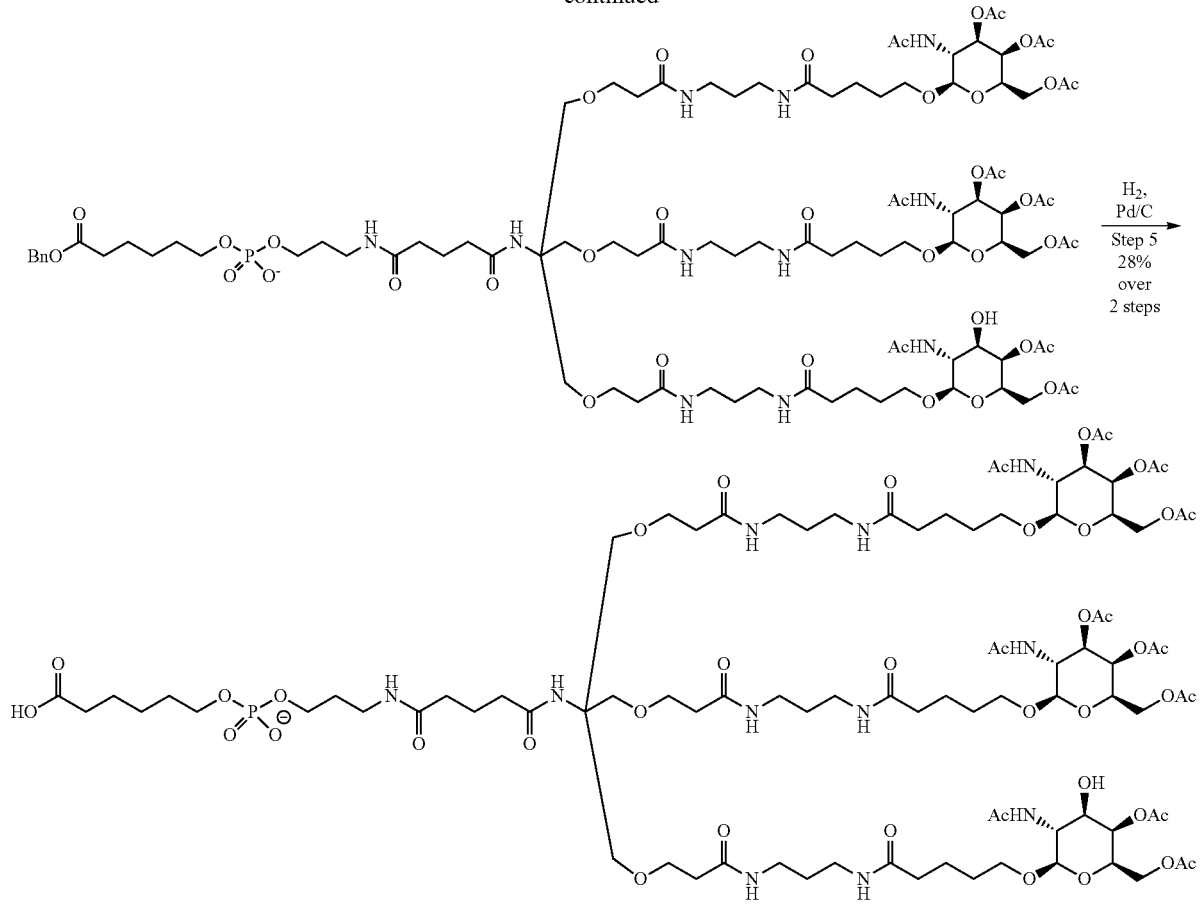

Step 1: 6-Hydroxyhexanoate. A mixture of sodium hydroxide (9.02 g, 226 mmol) and 6-hexanolactone (25 mL, 0.23 mmol) in water (401 mL) was heated at 70° C. overnight. TLC showed complete consumption of the starting material. The water was removed carefully at 50° C. with a rotary evaporator and the resulting white solid was azeotroped with toluene. After drying under high vacuum overnight, the solid was suspended in acetone (100 mL) and tetrabutylammonium bromide (3.64 g, 11.3 mmol) and benzyl bromide (32.2 mL, 271 mmol) were added. The reaction mixture was heated at reflux until TLC analysis showed complete consumption of intermediate carboxylic acid (96 h). The solvent was removed in vacuo and the residue was partitioned between aqueous hydrochloric acid and ethyl acetate. The aqueous layer was extracted with ethyl acetate (×2). The combined organic extracts were washed with saturated sodium bicarbonate (×2), brine, dried over magnesium sulfate, filtered and concentrated in vacuo. The crude residue was purified by a silica gel plug (20-70% ethyl acetate in heptane) to afford the title compound as a colorless oil (43.9 g, 88%). $^1$H NMR (600 MHz, CDCl$_3$) δ ppm 7.40-7.30 (m, 5H), 5.12 (s, 2H), 3.63 (t, 2H), 2.38 (t, 2H), 1.73-1.65 (m, 2H), 1.62-1.53 (m, 2H), 1.44-1.35 (m, 2H), 1.28 (br.s., 1H).

Step 2: Benzyl 6-(((3-((tert-butoxycarbonyl)amino) propoxy) (2-cyanoethoxy)phosphoryl)oxy)hexanoate. To a solution of 2-cyanoethyl-N,N-diisopropylchlorophosphoramidite (20.3 g, 67.5 mmol) in anhydrous dichloromethane (150 mL) at 0° C. was slowly added 4,5-dicyanoimidazole (1 M in acetonitrile, 31.5 mL, 31.5 mmol) at 0° C. 6-hydroxyhexanoate (10.0 g, 45.0 mmol) was then added dropwise to the mixture at 0° C. under an inert atmosphere. The mixture was stirred at 0° C. until TLC analysis showed consumption of starting material (1 h). The reaction was quenched with saturated sodium bicarbonate (80 mL). The biphasic mixture was then separated and the aqueous layer was extracted with dichloromethane (2×60 mL). The combined organic phase was washed with brine, dried over anhydrous sodium sulfate, filtered and concentrated to dryness to give the crude product (23.0 g, >100%) as a light yellow oil, which was used in the next step directly. This crude material was dissolved in acetonitrile (50 mL) and added dropwise over 10 min to a solution of 3-(Boc-amino)-1-propanol (10.0 g, 57.2 mmol) and tetrazole (19.1 g, 272 mmol) in anhydrous acetonitrile (300 mL). The resulting colorless solution was stirred at ambient temperature for 1.5 h. TLC showed the starting material was consumed completely. Then a solution of 12 (0.4 M in THF/H$_2$O/pyridine (78:20:2), 90 mL, 54.4 mmol) was added slowly to the above reaction mixture and at the end of the addition the brown color didn't dissipate. The mixture was stirred at ambient temperature until TLC analysis showed the reaction was complete (1 h). The mixture was quenched with saturated sodium sulfite and concentrated in vacuo to remove the organic solvents. The remaining mixture was diluted with water and extracted with ethyl acetate (×2). The combined organic phase was washed with saturated ammonium chloride and brine, dried over anhydrous sodium sulfate, filtered and concentrated in vacuo. The crude material was purified by silica gel flash chromatography (20-75 ethyl acetate in petroleum ether) to afford the title compound as colorless oil (10.0 g, 43% over three steps). $^1$H NMR (400 MHz, CDCl$_3$) δ ppm 7.41-7.28 (m, 5H), 5.11 (s, 2H), 4.23 (ddd, 2H), 4.18-4.04 (m, 4H), 3.24 (q, 2H), 2.75 (ddd, 2H), 2.38 (t, 2H), 1.87 (dq, 2H), 1.76-1.64 (m, 4H), 1.43 (s, 9H), 1.31-1.20 (m, 2H).

Step 3: 3-Ammoniopropyl (6-(benzyloxy)-6-oxohexyl) phosphate. To a solution of benzyl 6-(43-((tert-butoxycarbonyl)amino)propoxy)(2-cyanoethoxy)phosphoryl)oxy)hexanoate (9.00 g, 17.6 mmol) in anhydrous 1,4-dioxane (36 mL) was added hydrochloric acid (100 mL, 400 mmol, 4 M in dioxane) dropwise at 0° C. The resulting colorless solution was stirred at ambient temperature for 1.5 h. The mixture was concentrated to dryness to give the crude product (7.90 g) as a colorless gum, which was used in the next step directly. To a solution of this crude material acetonitrile (72 mL) was added triethylamine (36 mL, 0.26 mmol). The resulting white suspension was stirred at 25° C. for 16 h. The mixture was then concentrated and the crude material was purified by silica gel flash chromatography (5-50% methanol in dichloromethane, 1% ammonium hydroxide) to afford the title compound as a white solid (3.70 g, 59% over two steps). $^1$H NMR (400 MHz, CD$_3$OD) δ ppm 7.41-7.27 (m, 5H), 5.11 (s, 2H), 3.95 (dt, 2H), 3.85 (q, 2H), 3.08 (t, 2H), 2.39 (t, 2H), 1.94 (dq, 2H), 1.78-1.56 (m, 4H), 1.51-1.34 (m, 2H). LCMS (m/z) for $C_{16}H_{27}NO_6P^+$ (M+H)$^+$ 360.1; retention time=0.677 min (UPLC 1.5 min method).

Step 4: 6-(Benzyloxy)-6-oxohexyl 26-{[4,6-di-O-acetyl-2-(acetylamino)-2-deoxy-β-D-galactopyranosyl]oxy}-5,9,16,22-tetraoxo-11,11-bis{[3-oxo-3-({3-[(5-{[3,4,6-tri-O-acetyl-2-(acetylamino)-2-deoxy-β-D-galactopyranosyl]oxy}pentanoyl)amino]propyl}amino)propoxy]methyl}-13-oxa-4,10,17,21-tetraazahexacos-1-yl phosphate. A solution of N,N-diisopropylethylamine (305 mg, 2.36 mmol, 0.41 mL) and 3-ammoniopropyl 6-(benzyloxy)-6-oxohexyl phosphate (297 mg, 0.825 mmol) in N,N-dimethylformamide (5 mL) was added to a solution of 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid (1.50 g, 0.790 mmol) in DMF (10 mL). 1-[Bis(dimethylamino)methylene]-1H-1,2,3-triazolo[4,5-b]pyridinium 3-oxid hexafluorophosphate (328 mg, 0.065 mmol) was then added to the reaction mixture at room temperature. After 1 h, the reaction was quenched with saturated ammonium chloride (30 mL) and extracted with dichloromethane (4×30 mL). The combined organic layers were washed with brine, dried over sodium sulfate, filtered and concentrated. The crude product was taken forward without further purification. LCMS (m/z) for $C_{98}H_{155}N_{11}O_{43}PNa_2^{2+}$ (M+2Na)$^{2+}$ 1125.5; retention time=0.71 min (UPLC 1.5 min method).

Step 5: Example 29. The crude tris-benzyl ester 6-(benzyloxy)-6-oxohexyl 26-{[4,6-di-O-acetyl-2-(acetylamino)-2-deoxy-beta-D-galactopyranosyl]oxy}-5,9,16,22-tetraoxo-11,11-bis{[3-oxo-3-({3-[(5-{[3,4,6-tri-O-acetyl-2-(acetylamino)-2-deoxy-β-D-galactopyranosyl]oxy}pentanoyl)amino]propyl}amino)propoxy]methyl}-13-oxa 4,10,17,21-tetraazahexacos-1-yl phosphate (1.77 g, 0.790 mmol) was dissolved in methanol (0.05 M) and hydrogenated using an H-cube (10% Pd/C with a flow rate of 1.0 mL/min under full H2 at 60° C.). Product obtained cleanly and the bulk material was purified by preparatory HPLC [Column: Phenomenex Gemini XB C18 150 mm×3.0 mm 5 µm. Gradient conditions: mobile phase A=0.1% 10 mM triethylammonium acetate pH7 in water, mobile phase B=0.1% 10 mM triethylammonium acetate pH7 in acetonitrile (22-100-22% B/A, 27.0 mL/min)]. The bulk material was obtained as a white solid containing triethylammonium acetate (14 equiv. by $^1$H NMR integration) (475 mg). The purity of the product was calculated to be 49 wt % and the yield was determined to be 233 mg (14%)$^1$H NMR (600 MHz, CD$_3$OD) δ 5.34 (d, 3H), 5.07 (dd, 3H), 4.57 (d, 3H), 4.22-4.05 (m, 9H), 4.02 (t, 3H), 3.94-3.81 (m, 7H), 3.72-3.63 (m, 12H), 3.54 (dt, 3H), 3.35 (s, 6H), 3.26-3.20 (m, 17H), 3.19 (q, 84H, triethylammonium acetate), 2.43 (t, 6H), 2.30-2.17 (m, 13H), 2.14 (s, 9H), 2.03 (s, 9H), 1.95 (s, 9H), 1.93 (s, 9H), 1.93 (s, 42H, triethylammonium acetate), 1.90-1.78 (m, 4H), 1.74-1.57 (m, 22H), 1.49-1.38 (m, 2H), 1.30 (t, 126H). LCMS (m/z) for $C_{93}H_{154}N_{11}O_{44}P^{2+}$ (M+2H)$^{2+}$ 1080.5; retention time: 0.65 min (UPLC 1.5 min method).

18-{[27-({(2R,3R,4R,5R,6R)-3-(acetylamino)-4,5-bis(acetyloxy)-6-[(acetyloxy)methyl]tetrahydro-2H-pyran-2-yl}oxy)-12,12-bis({3-[(3-{[5-({(2R,3R,4R,5R,6R)-3-(acetylamino)-4,5-bis(acetyloxy)-6-[(acetyloxy)methyl]tetrahydro-2H-pyran-2-yl}oxy)pentanoyl]amino}propyl)amino]-3-oxopropoxy}methyl)-6,10,17,23-tetraoxo-14-oxa-5,11,18,22-tetraazaheptacosan-1-oyl]amino}-43-carboxy-18-(25-carboxy-19,19-dioxido-5-oxo-2,9,12,15,18,20-hexaoxa-6-aza-19-λ~5~-phosphapentacos-1-yl)-37,37-dioxido-13,23-dioxo-3,6,9,16,20,27,30,33,36,38-decaoxa-12,24-diaza-37-λ~5~-phosphatritetracont-1-yl 5-carboxypentyl phosphate

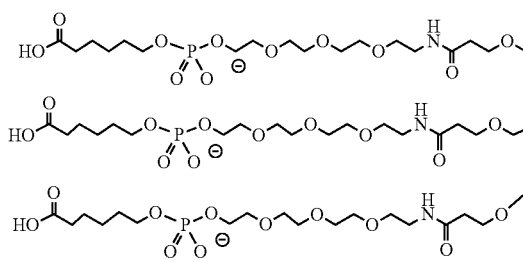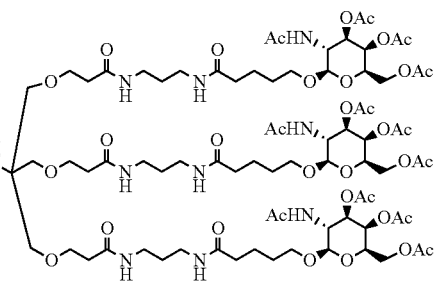

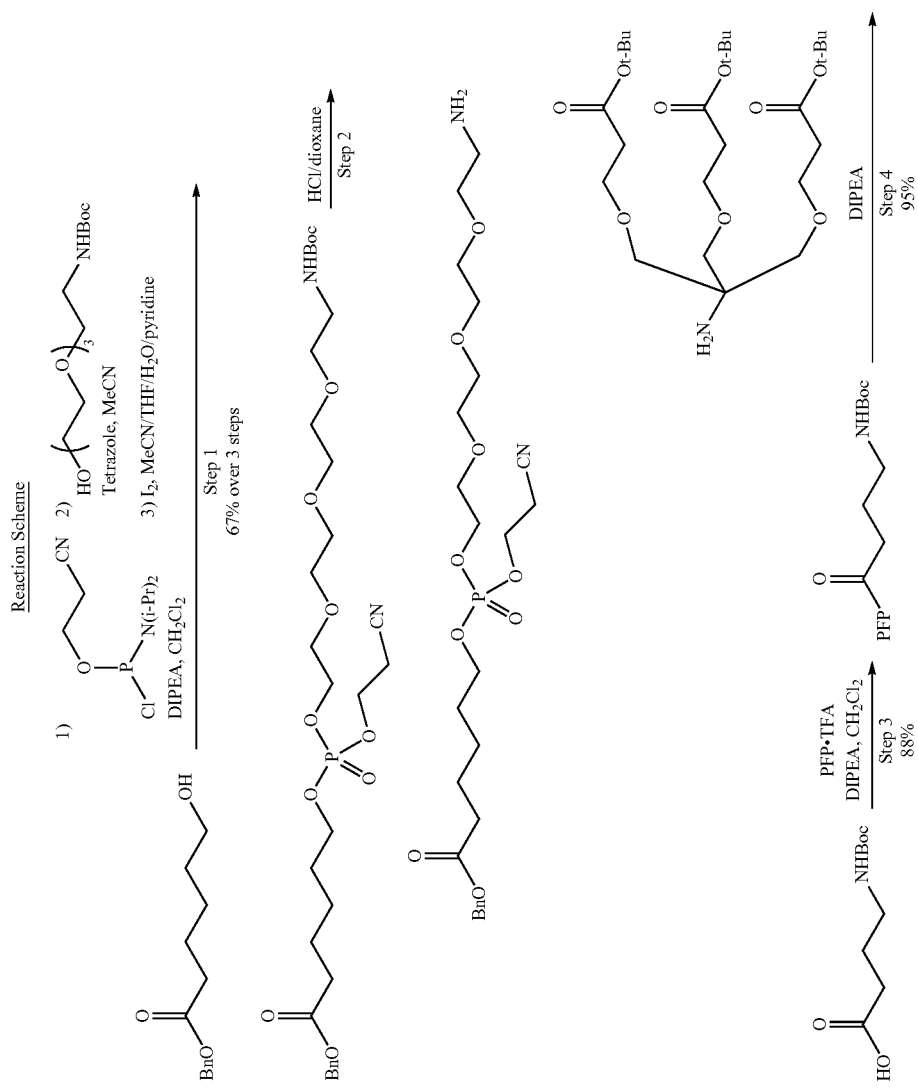

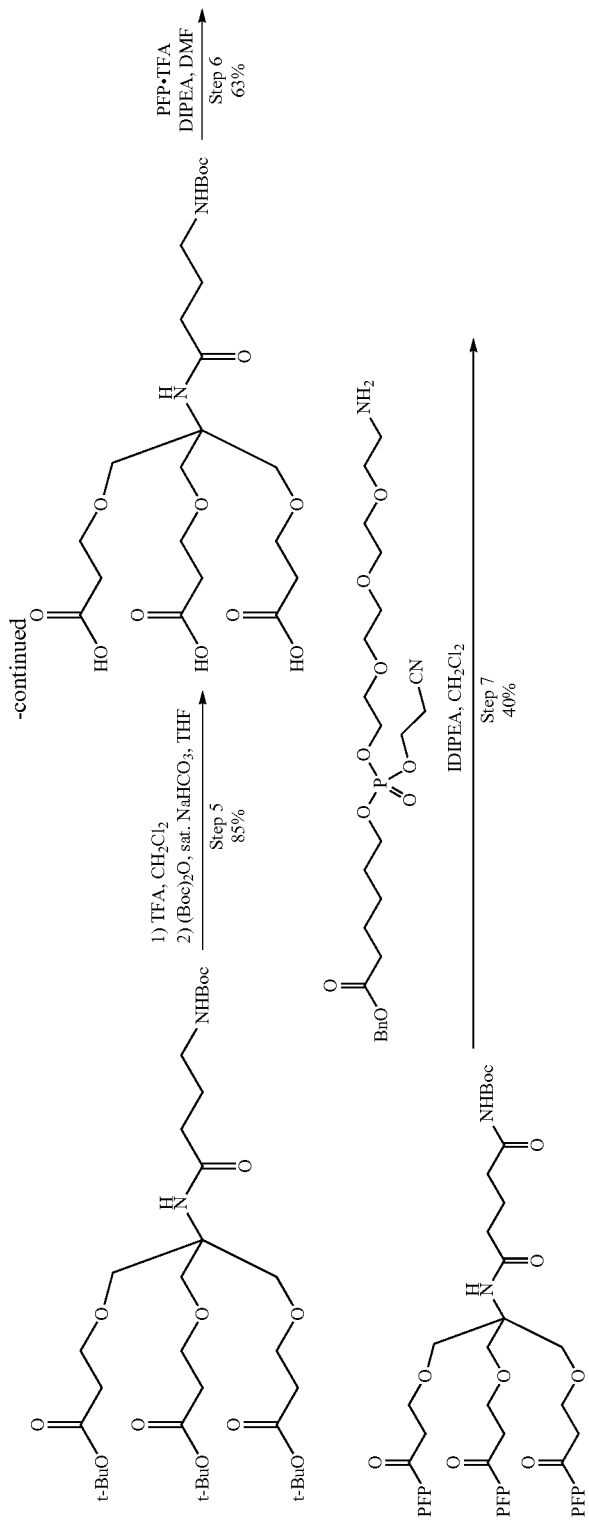

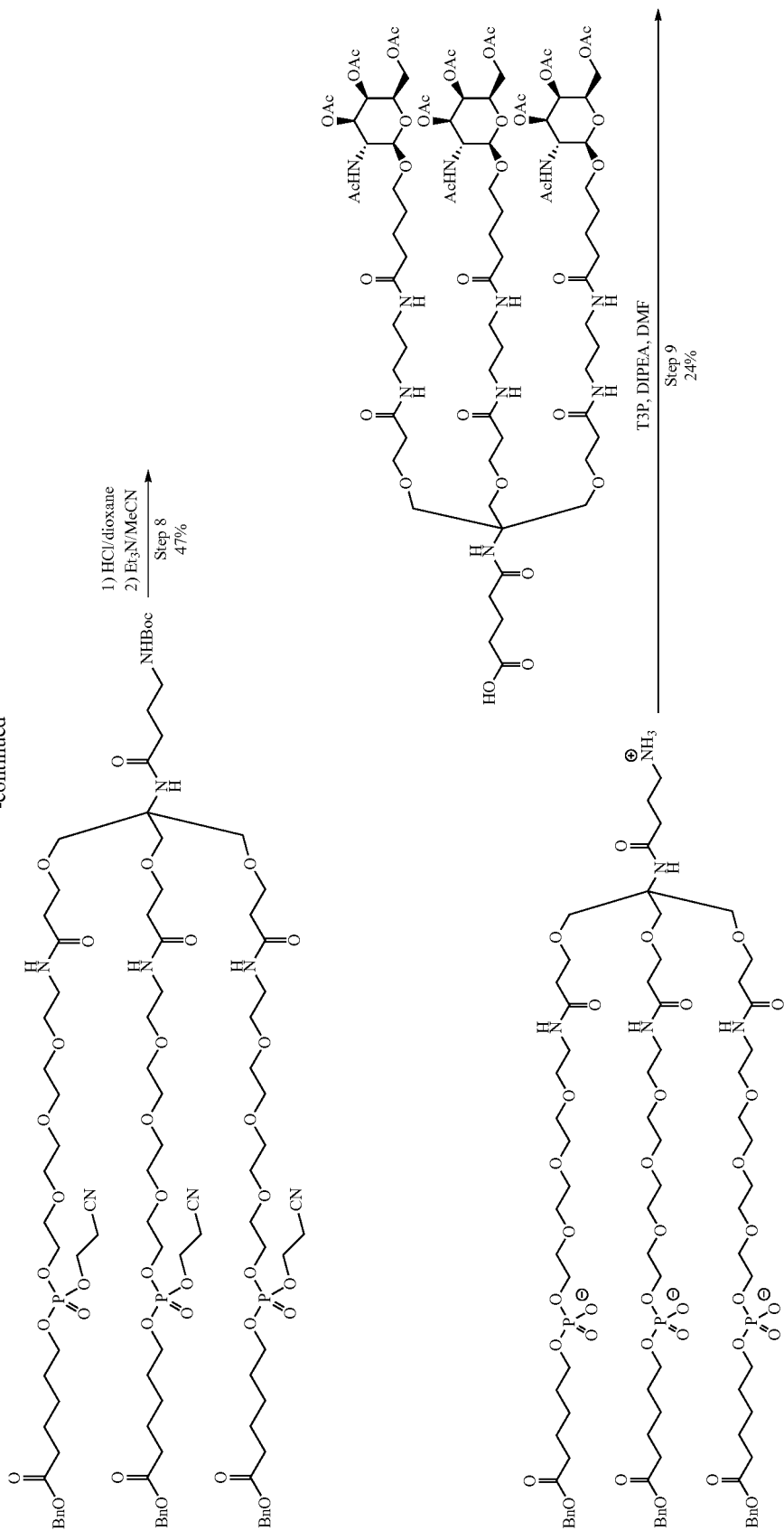

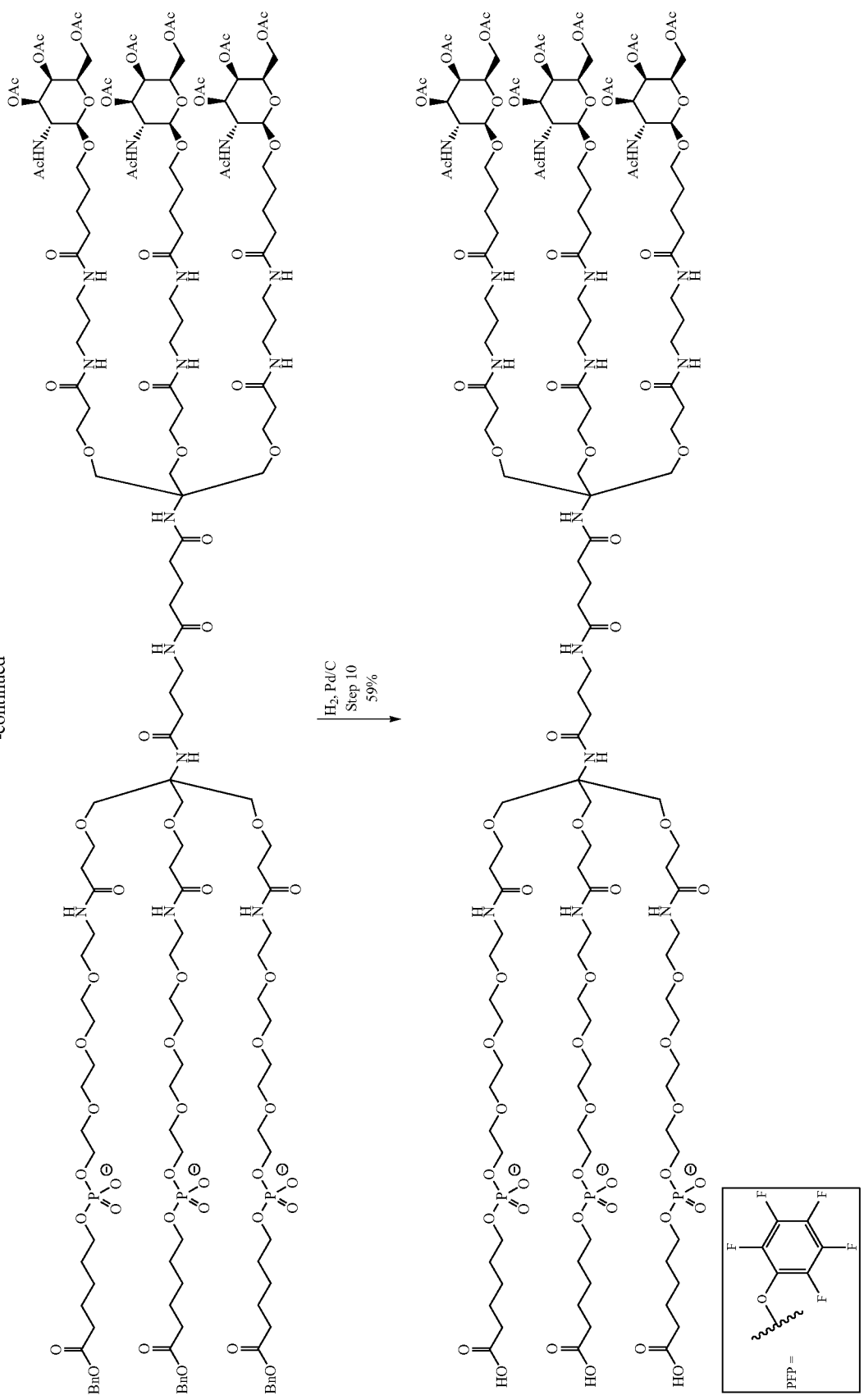

Step 1: Benzyl 6-(42-(2-(2-(2-aminoethoxy)ethoxy)ethoxy)ethoxy)(2-cyanoethoxy)phosphoryl)oxy)hexanoate. This compound was prepared from tert-butyl (2-(2-(2-(2-hydroxyethoxy)ethoxy)ethoxy)ethyl)carbamate (6.03 g, 20.5 mmol) and 2-cyanoethyl-N,N-diisopropylchlorophosphoramidite (6.87 mL, 30.8 mmol) and 6-Hydroxyhexanoate (6.85 g, 30.8 mmol) in an analogous manner to Example 29, Step 2. The title compound was obtained after purification by silica gel flash chromatography (50-100% ethyl acetate in heptane then 5% methanol in ethyl acetate) as a yellow oil (8.64 g, 67% over three steps). $^1$H NMR (400 MHz, CDCl$_3$) δ ppm 7.40-7.31 (m, 5H), 5.11 (s, 2H), 5.04 (s, 1H), 4.31-4.15 (m, 4H), 4.08 (q, 2H), 3.71 (ddd, 2H), 3.69-3.58 (m, 8H), 3.53 (t, 2H), 3.31 (q, 2H), 2.77 (t, 2H), 2.37 (t, 2H), 1.76-1.63 (m, 4H), 1.44 (s, 9H), 1.48-1.36 (m, 2H). LCMS (m/z) for $C_{29}H_{47}N_2NaO_{11}P^+$ (M+Na)$^+$ 653.5; retention time=0.93 min (UPLC 1.5 min method).

Step 2: 2-(2-(2-(2-((((6-(Benzyloxy)-6-oxohexyl)oxy)(2-cyanoethoxy)phosphoryl)oxy)ethoxy)ethoxy)ethoxy)ethan-1-aminium chloride. To a solution of benzyl 6-(((2-(2-(2-(2-aminoethoxy)ethoxy)ethoxy)ethoxy)(2-cyanoethoxy)phosphoryl)oxy) hexanoate (8.64 g, 14.1 mmol) in 1,4-dioxane (33 mL) at 0° C. was added a solution of hydrochloric acid (4 M in 1,4-dioxane, 87 mL, 348 mmol). The resulting mixture was stirred at ambient temperature for 1 h. The solvent was removed in vacuo to yield 8.76 g (>100%) title compound as a yellow oil. The crude product was used without further purification. $^1$H NMR (400 MHz, CD$_3$OD) δ ppm 7.45-7.26 (m, 5H), 5.12 (s, 2H), 4.29-4.19 (m, 4H), 4.12 (q, 2H), 3.79-3.69 (m, 4H), 3.67 (m, 8H), 3.13 (t, 2H), 2.88 (ddd, 2H), 2.41 (t, 2H), 1.81-1.59 (m, 4H), 1.51-1.37 (m, 2H). LCMS (m/z) for $C_{24}H_{40}N_2O_9P^+$ (M+H)$^+$ 531.5; retention time=0.70 min (UPLC 1.5 min method).

Step 3: Pentafluorophenyl 4-[(tert-butoxycarbonyl)amino]butanoate. To a solution of 4-(tert-butoxycarbonylamino)butyric acid (12.0 g, 59.0 mmol) in dichloromethane was added N,N-diisopropylethylamine (20.6 mL, 118 mmol) at ambient temperature followed by pentafluorophenyl trifluoroacetate (12.2 mL, 70.9 mmol) at 0° C. The reaction mixture was warmed to ambient temperature and stirred for 17 h. The reaction mixture was then concentrated. Purification of the crude material by silica gel flash chromatography (10-60% ethyl acetate in heptane) afforded the title compound as a white solid (19.1 g, 88%). $^1$H NMR (400 MHz, CDCl$_3$) δ ppm 4.65 (s, 1H), 3.25 (q, 2H), 2.72 (t, 2H), 1.96 (p, 2H), 1.45 (s, 9H). LCMS (m/z) for $C_{15}H_{16}F_5NNaO_4^+$ (M+Na)$^+$ 392.3; retention time=1.01 min (UPLC 1.5 min method).

Step 4: tert-Butyl 11,11-bis[(3-tert-butoxy-3-oxopropoxy)methyl]-2,2-dimethyl-4,9-dioxo-3,13-dioxa-5,10-diazahexadecan-16-oate. N,N-diisopropylethylamine (13.0 g, 101 mmol, 17.6 mL) was added to a solution of pentafluorophenyl 4-[(tert-butoxycarbonyl)amino]butanoate (9.68 g, 26.2 mmol) in THF (25 mL). tert-Butyl 3-{2-amino-3-(3-tert-butoxy-3-oxopropoxy)-2-[(3-tert-butoxy-3-oxopropoxy)methyl]propoxy}propanoate$^1$ (10.2 g, 20.2 mmol) was then added to the reaction in a slow stream as a solution in THF (50 mL) and the reaction was stirred at 50° C. for 78 h. The reaction was concentrated and purified twice by silica gel chromatography (0-20% methanol in dichloromethane and again 0-100% ethyl acetate in heptane) to afford the title compound as a colorless oil (13.3 g, 95%). $^1$H NMR (400 MHz, CDCl$_3$) δ ppm 6.27-6.13 (m, 1H), 5.02-4.84 (m, 1H), 3.70 (s, 6H), 3.64 (t, 6H), 3.16 (q, 2H), 2.45 (t, 6H), 2.20 (t, 2H), 1.78 (quin, 2H), 1.45 (s, 36H).

$^1$ This compound was prepared according to a reported literature procedure: Cardonna, C. M.; Gawley, R. E. *J. Org. Chem.* 2002, 67, 1411.

Step 5: 11,11-bis[(2-carboxyethoxy)methyl]-2,2-dimethyl-4,9-dioxo-3,13-dioxa-5,10-diazahexadecan-16-oic acid. Trifluoroacetic acid (46 g, 0.40 mol, 30 mL) was added to a solution of tert-butyl 11,11-bis[(3- tert-butoxy-3-oxopropoxy)methyl]-2,2-dimethyl-4,9-dioxo-3,13-dioxa-5,10-diazahexadecan-16-oate (13.3 g, 19.2 mmol) dichloromethane (100 mL) and the resulting solution was stirred at room temperature. After 20 h, the reaction mixture was concentrated. The resultant residue was then suspended in a mixture of tetrahydrofuran (30 mL) and saturated aqueous sodium bicarbonate (160 mL) to which was added di-tert-butyl dicarbonate (12.6 g, 57.7 mmol). The resultant suspension was heated to 40° C. Two additional aliquots of di-tert-butyl dicarbonate (3.70 g, 17.0 mmol each), were added to the reaction mixture, one at 30 min and then second at 90 min and the reaction was allowed to stir at 40° C. After 20 h, the reaction mixture was washed once with ethyl acetate and the wash was discarded. The pH of the aqueous layer was adjusted to pH=3 with 1 N hydrochloric acid. The aqueous layer was then extracted with ethyl acetate (×2) and the combined extracts were dried over magnesium sulfate, filtered, and concentrated to afford the title compound as a colorless oil which was used in the subsequent step without purification. $^1$H NMR (400 MHz, CD$_3$OD) δ ppm 4.45-4.30 (m, 12H), 3.70 (q, 2H), 3.23 (t, 6H), 2.84 (t, 2H), 2.34 (quin, 2H), 2.18 (s, 9H).

Step 6: Pentafluorophenyl 3-(2-[(4-aminobutanoyl)amino]-3-[3-oxo-3-(pentafluorophenoxy)propoxy]-2-{[3-oxo-3-(pentafluorophenoxy)propoxy]methyl}propoxy)propanoate. N,N-diisopropylethylamine (17.0 g, 132 mmol, 23.0 mL) was added to a solution of 11,11-bis[(2-carboxyethoxy)methyl]-2,2-dimethyl-4,9-dioxo-3,13-dioxa-5,10-diazahexadecan-16-oic acid (7.49 g, 13.0 mmol) in N,N-dimethylformamide (100 mL). Pentafluorophenyl trifluoroacetate (20.4 g, 72.7 mmol, 12.5 mL) was then added to the reaction mixture dropwise over 15 min resulting in a light pink solution that turned yellow over time. After 1 h, the reaction was quenched with saturated sodium bicarbonate. The resultant mixture was extracted with ethyl acetate (×2). The combined organic extracts were washed with brine, dried over sodium sulfate, filtered, and concentrated. The resultant residue was purified by silica gel chromatography (0-80% ethyl acetate in heptane) to afford the title compound as a colorless oil (8.76 g, 63% over 2 steps). $^1$H NMR (400 MHz, (CD$_3$)$_2$SO) δ ppm 7.10 (s, 1H), 6.73 (t, 1H), 3.70 (t, 6H), 3.64 (s, 6H), 2.98 (t, 6H), 2.87 (q, 2H), 2.03 (t, 2H), 1.53 (quin, 2H), 1.36 (s, 9H).

Step 7: Dibenzyl 27-({4-[(tert-butoxycarbonyl)amino]butanoyl}amino)-8,46-bis(2-cyanoethoxy)-27-[19-(2-cyanoethoxy)-19-oxido-5,26-dioxo-28-phenyl-2,9,12,15,18,20,27-heptaoxa-6-aza-19-λ~5~-phosphaoctacos-1-yl]-22,32-dioxo-7,9,12,15,18,25,29,36,39,42,45,47-dodecaoxa-21,33-diaza-8,46-diphosphatripentacontane-1,53-dioate 8,46-dioxide. Both of the starting materials were azeotroped with toluene twice and placed under high vacuum overnight prior to use. To a solution of pentafluorophenyl 3-(2-[(4-aminobutanoyl)amino]-3-[3-oxo-3-(pentafluorophenoxy)propoxy]-2-{[3-oxo-3-(pentafluorophenoxy) propoxy]methyl}propoxy)propanoate (3.97 g, 3.89 mmol) in dichloromethane (15 mL) was added N,N-diisopropylethylamine (6.8 mL, 39 mmol). Then a solution of 2-(2-(2-(2-((((6-(Benzyloxy)-6-oxohexyl)oxy)(2-cyanoethoxy)phosphoryl)oxy)ethoxy)ethoxy)ethoxy)ethan-1-aminium chloride (8.76 g crude, 14.0 mmol) in dichloromethane (25 mL) was added at 0° C. The reaction mixture was warmed to ambient temperature and stirred until TLC analysis showed consumption of starting material (15 h). The solvent was removed in vacuo, and the residue was redissolved in ethyl acetate. The solution was washed with water, saturated sodium bicarbonate and then water again, and the combined aqueous layers were extracted with ethyl acetate once. The combined organic extracts were dried with magnesium sulfate, filtered and concentrated in vacuo. The crude material was purified by silica gel flash chromatography (0-22% methanol in dichloromethane) to afford the title compound as a colorless gum (3.23 g, 40%). $^1$H NMR (400 MHz, CDCl$_3$) δ ppm 7.38-7.30 (m, 15H), 6.71 (s, 3H), 6.52 (s, 1H), 5.19 (t, 1H), 5.11 (s, 6H), 4.32-4.14 (m, 12H), 4.08 (q, 6H), 3.76-3.60 (m, 42H), 3.55 (t, 6H), 3.43 (q, 6H), 3.14 (dd, 2H), 2.77 (t, 6H), 2.42 (t, 6H), 2.38 (t, 6H), 2.23 (t, 2H), 1.79-1.64 (m, 14H), 1.46-1.38 (m, 15H). LCMS (m/z) for $C_{94}H_{151}F_5N_8O_{36}P_3^{2+}$ (M+2H)$^{2+}$ 1031.0; retention time=1.00 min (UPLC 1.5 min method).

Step 8: 29-[(4-Ammoniobutanoyl)amino]-29-(19,19-dioxido-5,26-dioxo-28-phenyl-2,9,12,15,18,20,27-heptaoxa-6-aza-19-λ~5~-phosphaoctacos-1-yl)-10,10-dioxido-3,24,34-trioxo-1-phenyl-2,9,11,14,17,20,27,31,38,41,44-undecaoxa-23,35-diaza-10-λ~5~-phosphahexatetracontan-46-yl 6-(benzyloxy)-6-oxohexyl phosphate. To a solution of dibenzyl 27-({4-[(tert-butoxycarbonyl)amino]butanoyl}amino)-8,46-bis(2-cyanoethoxy)-27-[19-(2-cyanoethoxy)-19-oxido-5,26-dioxo-28-phenyl-2,9,12,15,18,20,27-heptaoxa-6-aza-19-λ~5~-phosphaoctacos-1-yl]-22,32-dioxo-7,9,12,15,18,25,29,36,39,42,45,47-dodecaoxa-21,33-diaza-8,46-diphosphatripentacontane-1,53-dioate 8,46-dioxide (3.22 g, 1.56 mmol) in 1,4-dioxane (18 mL) at 0° C. was added a solution of hydrochloric acid (4 M in 1,4-dioxane, 16 mL, 63 mmol). The resulting mixture was stirred at ambient temperature for 1 h. The solvent was then removed to provide an oily residue. This crude was suspended in acetonitrile (18 mL) and triethylamine (12 mL, 86 mmol) was added. The reaction mixture was stirred at ambient temperature for 40 h and subsequently concentrated in vacuo. The crude material was purified by reverse phase HPLC with a Phenomenex NX-C18 column (5-100% acetonitrile in water, containing 0.1% sodium hydroxide) and lyophilized to provide the title compound as a colorless oil (1.33 g, 47% over two steps). $^1$H NMR (400 MHz, CD$_3$OD) δ ppm 7.41-7.27 (m, 15H), 5.11 (s, 6H), 4.03-3.92 (m, 6H), 3.85 (q, 6H), 3.71-3.58 (m, 42H), 3.55 (t, 6H), 3.38 (t, 6H), 2.99 (t, 2H), 2.44 (t, 6H), 2.42-2.29 (m, 8H), 1.92 (p, 2H), 1.72-1.57 (m, 12H), 1.48-1.37 (m, 6H). LCMS (m/z) for $C_{80}H_{134}N_5O_{34}P_3^{2+}$ (M+2H)$^{2+}$ 901.5; retention time=0.77 min (UPLC 1.5 min method).

Step 9: 29-{[27-({(2R,3R,4R,5R,6R)-3-(acetylamino)-4,5-bis(acetyloxy)-6-[(acetyloxy)methyl]tetrahydro-2H-pyran-2-yl}oxy)-12,12-bis({3-[(3-{[5-({(2R,3R,4R,5R,6R)-3-(acetylamino)-4,5-bis(acetyloxy)-6-[(acetyloxy)methyl]tetrahydro-2H-pyran-2-yl}oxy)pentanoyl]amino}propyl)amino]-3-oxopropoxy}methyl)-6,10,17,23-tetraoxo-14-oxa-5,11,18,22-tetraazaheptacosan-1-oyl]amino}-29-(19,19-dioxido-5,26-dioxo-28-phenyl-2,9,12,15,18,20,27-heptaoxa-6-aza-19-λ~5~-phosphaoctacos-1-yl)-10,10-dioxido-3,24,34-trioxo-1-phenyl-2,9,11,14,17,20,27,31,38,41,44-undecaoxa-23,35-diaza-10-λ~5~-phosphahexatetracontan-46-yl 6-(benzyloxy)-6-oxohexyl phosphate. Both of the starting materials were azeotroped with toluene three times and placed under high vacuum overnight before use. To a solution of the amine 29-[(4-ammoniobutanoyl)amino]-29-(19,19-dioxido-5,26-dioxo-28-phenyl-2,9,12,15,18,20,27-heptaoxa-6-aza-19-λ~5~-phosphaoctacos-1-yl)-10,10-dioxido-3,24,34-trioxo-1-phenyl-2,9,11,14,17,20,27,31,38,41,44-undecaoxa-23,35-diaza-10-λ~5~-phosphahexatetracontan-46-yl 6-(benzyloxy)-6-oxohexyl phosphate (270 mg, 0.147 mmol) in anhydrous dimethylformamide (0.5 mL) was added 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid (337 mg, 0.177 mmol) in dimethylformamide (1.5 mL), N,N-diisopropylethylamine (0.21 mL, 1.18 mmol) and then Propylphosphonic anhydride solution (50 wt. % in ethyl acetate, 0.26 mL, 0.44 mmol). The reaction mixture was stirred at 50° C. for 17 h. Upon cooling to ambient temperature, water was added and the mixture was extracted with 85:15 CH$_2$Cl$_2$:i-PrOH (100 mL×3). The organic extracts were dried over sodium sulfate, filtered and concentrated in vacuo. The crude material was purified by reverse phase HPLC with a Phenomenex NX-C18 column (35-100 acetonitrile in water, containing 10 mM triethylammonium acetate) and freeze dried to provide 202 mg of the desired product containing triethylammonium acetate (12.3 equiv. based on $^1$H NMR integration). The purity of this product was calculated to be 66 wt % and the yield was determined to be 133 mg (24%). This material was used in the next step without further purification. $^1$H NMR (400 MHz, CD$_3$OD) δ ppm 7.43-7.24 (m, 15H), 5.33 (d, 3H), 5.11 (s, 6H), 5.07 (dd, 3H), 4.57 (d, 3H), 4.22-3.80 (m, 25H), 3.75-3.57 (m, 59H), 3.57-3.47 (m, 12H), 3.41-3.34 (m, 12H), 3.20 (q, 74H, triethylammonium acetate), 2.48-2.35 (m, 18H), 2.27-2.17 (m, 12H), 2.14 (s, 9H), 2.02 (s, 9H), 1.96, (s, 111H, triethylammonium acetate) 1.95 (s, 9H), 1.93 (s, 9H), 1.77-1.54 (m, 33H), 1.44 (m 9H), 1.31 (t, 111H, triethylammonium acetate). LCMS (m/z) for $C_{164}H_{266}N_{15}O_{72}P_3^{2+}$ (M+2H)$^{2+}$ 1845.8; retention time=1.07 min (UPLC 3 min method).

Step 10: Example 30. A mixture of 29-{[27-({(2R,3R,4R,5R,6R)-3-(acetylamino)-4,5-bis(acetyloxy)-6-[(acetyloxy)methyl]tetrahydro-2H-pyran-2-yl}oxy)-12,12-bis({3-[(3-{[5-({(2R,3R,4R,5R,6R)-3-(acetylamino)-4,5-bis(acetyloxy)-6-[(acetyloxy)methyl]tetrahydro-2H-pyran-2-yl}oxy)pentanoyl]amino}propyl)amino]-3-oxopropoxy}methyl)-6,10,17,23-tetraoxo-14-oxa-5,11,18,22-tetraazaheptacosan-1-oyl]amino}-29-(19,19-dioxido-5,26-dioxo-28-phenyl-2,9,12,15,18,20,27-heptaoxa-6-aza-19-λ~5~-phosphaoctacos-1-yl)-10,10-dioxido-3,24,34-trioxo-1-phenyl-2,9,11,14,17,20,27,31,38,41,44-undecaoxa-23,35-diaza-10-λ~5~-phosphahexatetracontan-46-yl 6-(benzyloxy)-6-oxohexyl phosphate (200 mg, 0.0330 mmol, 66 wt %) and 10% palladium on carbon (7.0 mg, 0.0066 mmol) in methanol (2 mL) was stirred under hydrogen pressure (50 psi) at 25° C. for 20 h. The catalyst was filtered through 0.45 um nylon acrodisc, and washed with methanol (40 mL). The filtrate was then concentrated and the resulting oil was dissolved in 1:1 mixture of acetonitrile and water (22 mL), adjusted to pH 5.70 by hydrochloric acid (1 N). The solution was lyophilized overnight to afford the title compound as a hygroscopic white solid (13 equiv triethylamine hydrochloride salt) (110 mg, 59%). $^1$H NMR (600 MHz, CD$_3$OD) δ ppm 5.34 (d, 3H), 5.07 (dd, 3H), 4.57 (d, 3H), 4.20-3.91 (m, 14H), 3.93-3.84 (m, 9H), 3.75-3.62 (m, 63H), 3.60-3.50 (m, 10H), 3.43-3.35 (m, 8H), 3.27-3.14 (m, 80H, triethylamine hydrochloride), 3.12-2.90 (m, 2H), 2.57-2.38 (m, 12H), 2.30-2.20 (m, 18H), 2.14 (s, 9H), 2.03 (s, 9H), 1.95-1.94 (m, 18H), 1.89-1.83 (m, 1H), 1.73-1.55 (m, 34H), 1.46-1.40 (m, 9H), 1.31 (t, 120H, triethylamine hydrochloride). LCMS (m/z) for $C_{143}H_{249}N_{15}O_{72}P_3^{3+}$ (M+3H)$^{3+}$ 1141.2; retention time=1.06 min (UPLC 3 min method).

1-[(1S,2R,3R,4R,5S)-4-(acetylamino)-2,3-bis(acetyloxy)-6,8-dioxabicyclo[3.2.1]oct-1-yl]-18,18-bis{17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oic acid
5
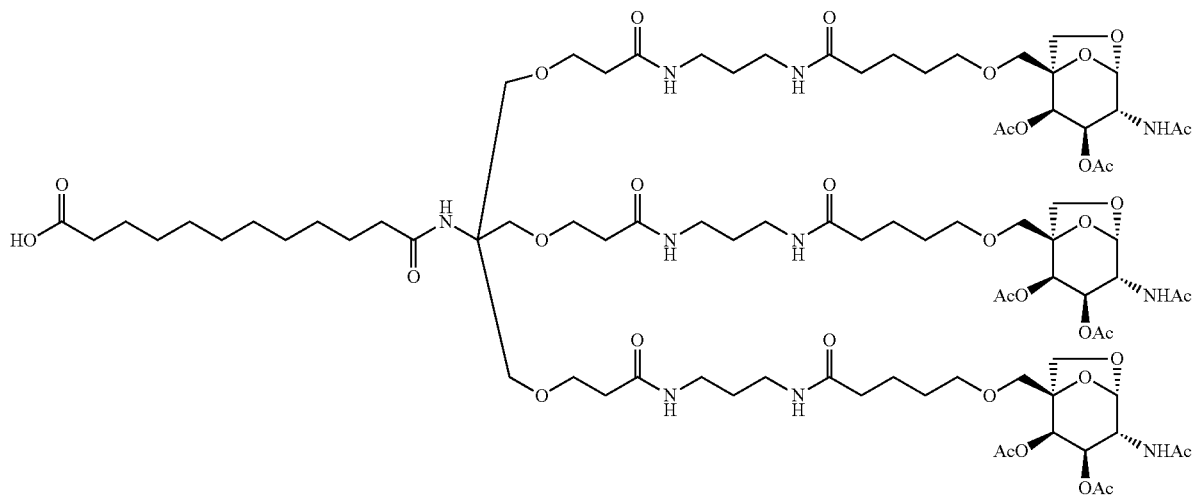 [SMILES: CC(=O)N[C@H]1[C@H]2OC[C@](COCCCCC(=O)NCCCNC(=O)CCOCC(COCCC(=O)NCCCNC(=O)CCCCOC[C@@]34CO[C@@H](O3)[C@H](NC(C)=O)[C@@H](OC(C)=O)[C@H]4OC(C)=O)(COCCC(=O)NCCCNC(=O)CCCCOC[C@@]34CO[C@@H](O3)[C@H](NC(C)=O)[C@@H](OC(C)=O)[C@H]4OC(C)=O)NC(=O)CCCCCCCCCCC(=O)O)(O2)[C@H](OC(C)=O)[C@@H]1OC(C)=O]
Synthetic Scheme
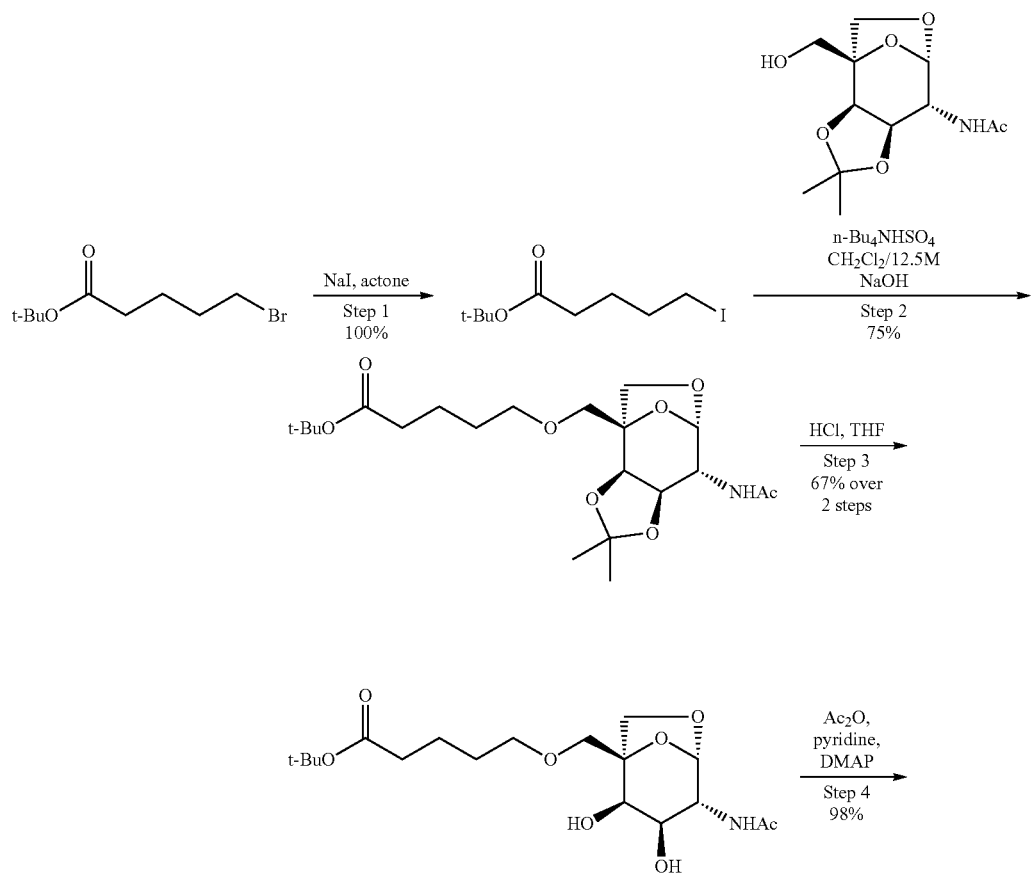

691  692
-continued
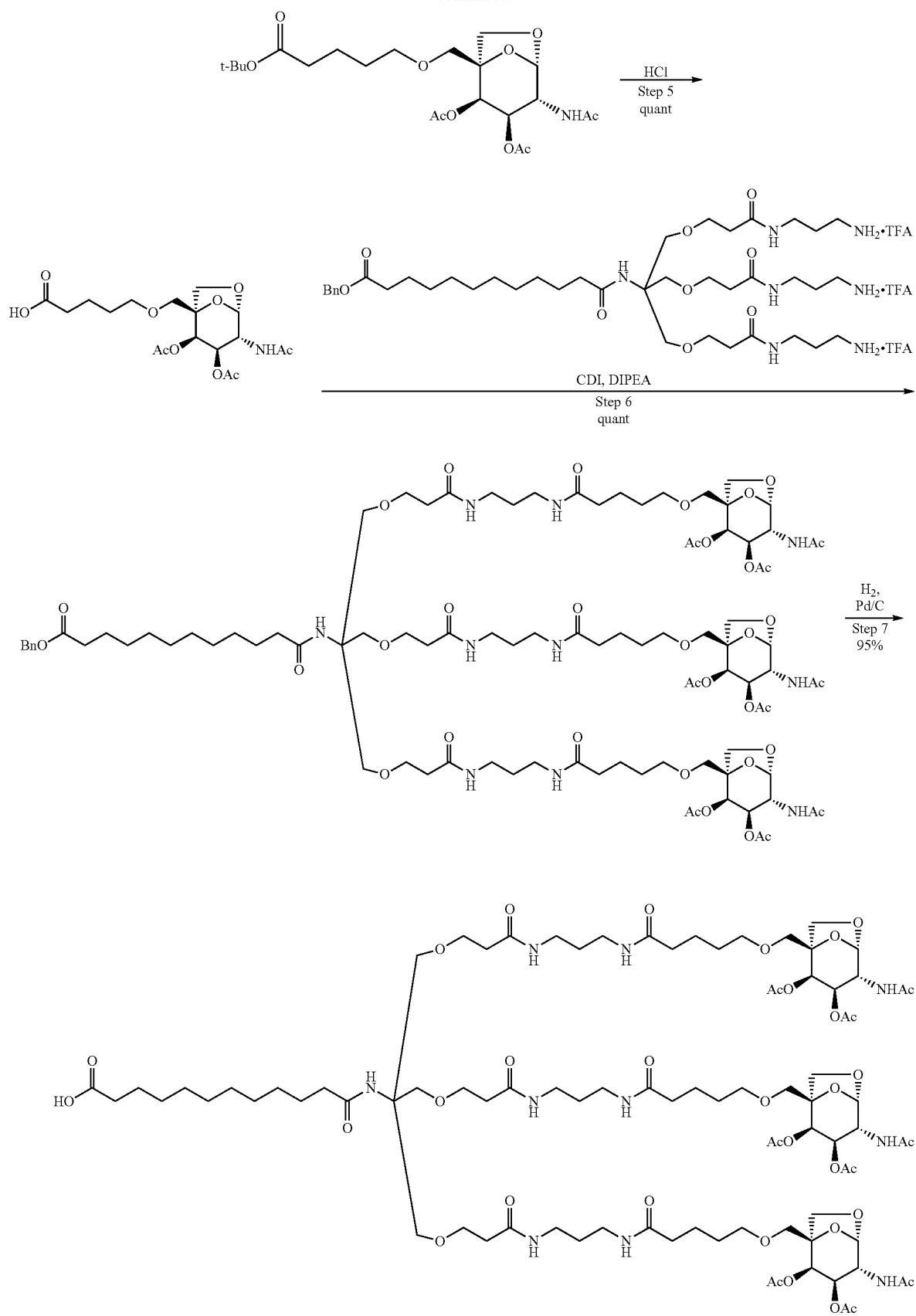

Step 1: tert-Butyl 5-iodopentanoate. To a solution of tert-butyl 5-bromopentanoate (60.0 g, 250 mmol) in acetone (400 mL) was added sodium iodide (94.8 g, 633 mmol). The reaction mixture was stirred at 57° C. for 4 h, cooled to room temperature, filtered and washed with dichloromethane. The solvent was evaporated under reduced pressure to give a residue which was dissolved dichloromethane, washed with saturated sodium bicarbonate (200 mL) and brine (100 mL). The separated organic phase was dried over sodium sulfate, filtered, and concentrated to afford the title compound as a yellow oil (69.3 g, 100%). $^1$H NMR (600 MHz, CDCl$_3$) δ ppm 3.20 (t, 2H), 2.25 (t, 2H), 1.86 (p, 2H), 1.70 (p, 2H), 1.45 (s, 9H).

Step 2: tert-Butyl 5-{[(1S,2R,6R,7R,8S)-7-(acetylamino)-4,4-dimethyl-3,5,9,11-tetraoxatricyclo[6.2.1.0~2,6~]undec-1-yl]methoxy}pentanoate. To a solution of tert-butyl 5-iodopentanoate (59 g, 0.21 mol) and N-((3aR,4S,7S,8R,8aR)-4-(hydroxymethyl)-2,2-dimethylhexahydro-4,7-epoxy[1,3]dioxolo[4,5-d]oxepin-8-yl)acetamide (20 g, 69 mmol) in dichloromethane (210 mL) was added tetrabutylammonium hydrogensulfate (35.3 g, 104 mmol) followed by 12.5 M sodium hydroxide solution (160 mL) in an ice bath. The reaction mixture was stirred at room temperature for 24 h. The reaction mixture was partitioned between dichloromethane (200 mL) and water (200 mL). The separated organic phase was washed by 1 N hydrochloric acid (300 mL), dried over sodium sulfate, filtered, and concentrated. The crude was triturated in diethyl ether (500 mL) at ambient temperature for 30 min. The resultant solid was removed by filtration and the filter cake was rinsed by diethyl ether (100 mL). The filtrate was concentrated, and dried in vacuo overnight to afford the crude of the title compound as a yellow oil (50.9 g, 45.5 wt % pure determined by qNMR with 1,3,5-trimethoxyben as the internal standard) which was used in next step without purification. LCMS (m/z) for $C_{21}H_{36}NO_8^+$ (M+H)$^+$ 430.3; retention time=0.88 min (UPLC 1.5 min method).

Step 3: tert-Butyl 5-{[(1S,2R,3R,4R,5S)-4-(acetylamino)-2,3-dihydroxy-6,8-dioxabicyclo[3.2.1]oct-1-yl]methoxy}pentanoate. To an ice cold solution of the crude of tert-butyl 5-{[(1S,2R,6R,7R,8S)-7-(acetylamino)-4,4-dimethyl-3,5,9,11-tetraoxatricyclo[6.2.1.0~2,6~]undec-1-yl]methoxy}pentanoate (50.9 g, 45.5 wt %, 53.9 mmol) in tetrahydrofuran (105 mL) was added a solution of concentrated hydrochloric acid (16 mL) in water (49 mL) via addition funnel over 5 min. The reaction solution was stirred at room temperature under nitrogen for 6 h. The reaction mixture was diluted with 2-methyl-tetrahydrofuran (300 mL) and washed with brine (100 mL). The aqueous phase was extracted with dichloromethane (300 mL). Each separated organic phase was washed by a mixture of saturated sodium bicarbonate (75 mL) and brine (75 mL), then brine (120 mL). The organic phases were combined, dried over sodium sulfate, filtered, concentrated, and azeotroped by heptane (100 mL) followed by methyl-t-butyl-ether (100 mL). The resulting crude was triturated in methyl-t-butyl-ether (200 mL) at room temperature for 15 min. The resulting precipitate was collected by filtration, rinsed with methyl-t-butyl-ether (200 mL), and dried in vacuo to afford the title compound as white solid (17.9 g, 66% over 2 steps). $^1$H NMR (400 MHz, CDCl$_3$) δ ppm 5.79 (d, 1H), 5.36 (d, 1H), 4.07-3.88 (m, 4H), 3.79-3.62 (m, 4H), 3.60-3.46 (m, 2H), 3.37 (d, 1H), 2.30-2.19 (m, 2H), 2.07 (s, 3H), 1.75-1.51 (m, 4H), 1.45 (s, 9H). LCMS (m/z) for $C_{18}H_{32}NO_8^+$ (M+H)$^+$ 390.5; retention time=0.70 min (UPLC 1.5 min method).

Step 4: tert-Butyl 5-{[(1S,2R,3R,4R,5S)-4-(acetylamino)-2,3-bis(acetyloxy)-6,8-dioxabicyclo[3.2.1]oct-1-yl]methoxy}pentanoate. Acetic anhydride (18.7 g, 183 mmol) was added dropwise to an ice cold solution of tert-butyl 5-{[(1S,2R,3R,4R,5S)-4-(acetylamino)-2,3-dihydroxy-6,8-dioxabicyclo[3.2.1]oct-1-yl]methoxy}pentanoate (18.6 g, 49.7 mmol) and pyridine (14.0 g, 183 mmol), and dimethylaminopyridine (1.12 g, 9.16 mmol) in dichloromethane (150 mL). The mixture was stirred at room temperature for 2.5 h. The reaction mixture was quenched by hydrochloric acid (1 N, 150 mL) and extracted with dichloromethane (200 mL). The organic phase was washed with hydrochloric acid (1 N, 150 mL), saturated sodium bicarbonate (150 mL) dried over sodium sulfate, concentrated, and azeotroped with heptane (4×100 mL) to the crude which was purified by a silica gel plug (210 g silica gel, 100% heptane (1 L), then 25% ethyl acetate in heptane (2 L), followed by 100% ethyl acetate (2 L)) to afford the title compound as white solid (21.2 g, 98%). $^1$H NMR (400 MHz, CDCl$_3$) δ ppm 5.65 (d, 1H), 5.41-5.39 (m, 2H), 5.09 (dd, 1H), 4.34 (t, 1H), 3.93 (d, 1H), 3.75 (d, 1H), 3.65 (d, 1H), 3.50 (d, 1H), 3.45 (td, 1H), 3.38 (td, 1H), 2.21 (t, 2H), 2.17 (s, 3H), 2.00 (s, 3H), 1.98 (s, 3H), 1.64-1.52 (m, 4H), 1.44 (s, 9H). LCMS (m/z) for $C_{22}H_{35}NNaO_{10}^+$ (M+Na)$^+$ 496.1; retention time=0.85 min (UPLC 1.5 min method).

Step 5: 5-{[(1S,2R,3R,4R,5S)-4-(acetylamino)-2,3-bis(acetyloxy)-6,8-dioxabicyclo[3.2.1]oct-1-yl]methoxy}pentanoic acid. To a solution of tert-butyl 5-{[(1S,2R,3R,4R,5S)-4-(acetylamino)-2,3-bis(acetyloxy)-6,8-dioxabicyclo[3.2.1]oct-1-yl]methoxy}pentanoate (21.1 g, 44.6 mmol) in dichloromethane (110 mL) placed in an ice bath was added hydrochloric acid (11 g, 0.31 mol, 78 mL, 4.0 M in 1,4-dioxane). The cooling bath was removed and the reaction was stirred at ambient temperature under nitrogen for 4 h. The reaction mixture was concentrated, and azeotroped with diethyl ether (200 mL), ethyl acetate (200 mL), and heptane (3×200 mL), and finally dried by vacuum overnight to afford the title compound as a white solid (18.6 g, quantitative). $^1$H NMR (400 MHz, CD$_3$CN) δ ppm 8.84 (br.s., 1H), 6.50 (d, 1H), 5.35 (d, 1H), 5.30 (d, 1H), 5.00 (dd, 1H), 4.17-4.07 (m, 1H), 3.93 (d, 1H), 3.78-3.56 (m, 2H), 3.52 (d, 1H), 3.49-3.34 (m, 2H), 2.26 (t, 2H), 2.12 (s, 3H), 1.92 (s, 3H), 1.85 (s, 3H), 1.60-1.47 (m, 4H). LCMS (m/z) for $C_{18}H_{28}NO_{10}^+$ (M+H)$^+$ 418.0; retention time=0.60 min (UPLC 1.5 min method).

Step 6: Benzyl 1-[(1S,2R,3R,4R,5S)-4-(acetylamino)-2,3-bis(acetyloxy)-6,8-dioxabicyclo[3.2.1]oct-1-yl]-18,18-bis{17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oate. To a solution of 5-{[(1S,2R,3R,4R,5S)-4-(acetylamino)-2,3-bis(acetyloxy)-6,8-dioxabicyclo[3.2.1]oct-1-yl]methoxy}pentanoic acid (1.53 g, 3.63 mmol) in acetonitrile (6 mL) was added 1,1'-carbonyldiimidazole (0.580 g, 3.56 mmol) and the reaction mixture was stirred at room temperature. After 3 h, benzyl 12-((1,19-diamino-10-((3-((3-aminopropyl)amino)-3-oxopropoxy)methyl)-5,15-dioxo-8,12-dioxa-4,16-diazanonadecan-10-yl)amino)-12-oxododecanoate tris-trifluoroacetate salt (1.58 g, 1.03 mmol, 75.4 wt %) was added to the reaction mixture as a solution in acetonitrile (6 mL) followed by N,N-diisopropylethylamine (0.540 g, 4.14 mmol). The reaction mixture was stirred at room temperature overnight. The reaction mixture was concentrated, diluted by dichloromethane (70 mL), washed by hydrochloric acid (1 N, 30 mL), brine (30 mL), and saturated sodium bicarbonate (30 mL). The organic phase was dried over sodium sulfate, filtered, and concentrated. The resultant residue was purified by a silica gel plug (20 g silica gel, eluted with dichloromethane (100 mL), 10% methanol in dichloromethane (200 mL), followed by 25% methanol in dichloromethane (200 mL)) to afford the title compound as a white glass (2.25 g, quantitative yield). $^1$H NMR (600 MHz, CD$_3$OD) δ ppm δ 7.73-7.30 (m, 5H), 5.44 (d, 3H), 5.32 (s, 3H), 5.12-5.09 (m, 5H), 4.18 (d, 3H), 4.00 (d, 3H), 3.71 (dd, 6H), 3.68-3.67 (m, 12H), 3.51-3.45 (m, 6H), 3.41-3.38 (m, 3H), 3.21 (q, 12H), 2.42 (t, 6H), 2.35 (t, 2H), 2.22-2.17 (m, 6H), 2.16 (s, 9H), 1.94 (s, 18H), 1.72-1.58 (m, 16H), 1.58-1.42 (m, 8H), 1.38-1.29 (m, 12H). LCMS (m/z) for $C_{95}H_{150}N_{10}O_{36}^{2+}$ $(M+2H)^{2+}$ 1004.7; retention time=0.86 min (UPLC 3 min method)

Step 7: Example 31. A mixture of benzyl 1-[(1S,2R,3R,4R,5S)-4-(acetylamino)-2,3-bis(acetyloxy)-6,8-dioxabicyclo[3.2.1]oct-1-yl]-18,18-bis {17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oate (2.36 g, 1.18 mmol) and 10% palladium on carbon (0.376 mg) in methanol (14 mL) was stirred under hydrogen pressure (50 psi) at 25° C. in a stirred Parr reactor for 4.5 h. The reaction mixture was filtered through celite to remove the catalyst. The celite was washed with methanol (20 mL) and the combined filtrates were concentrated and azeotroped with methyl tert-butyl ether (3×20 mL). The crude was triturated in methyl tert-butyl ether (20 mL) overnight. The resulting white solid was collected by filtration, dried in vacuo to afford the title compound as a white solid (2.14 g, 95%). $^1$H NMR (600 MHz, CD$_3$OD) δ ppm 5.45 (d, 3H), 5.32 (s, 3H), 5.11 (dd, 3H), 4.18 (d, 3H), 4.01 (d, 3H), 3.72 (dd, 6H), 3.70-3.64 (m, 12H), 3.52-3.47 (m, 6H), 3.42-3.39 (m, 3H), 3.22 (q, 12H), 2.42 (t, 6H), 2.28 (t, 2H), 2.19 (t, 6H) 2.16 (s, 9H) 1.95 (s, 18H) 1.73-1.50 (m, 24H) 1.38-1.29 (m, 12H). LCMS (m/z) for $C_{88}H_{143}N_{10}O_{36}^+$ 1916.2 (M+H)$^+$; retention time=1.35 min (UPLC 3 min method).

1-[(1S,2R,3R,4R,5S)-4-(acetylamino)-2,3-bis(acetyloxy)-6,8-dioxabicyclo[3.2.1]oct-1-yl]-18-{17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oic acid

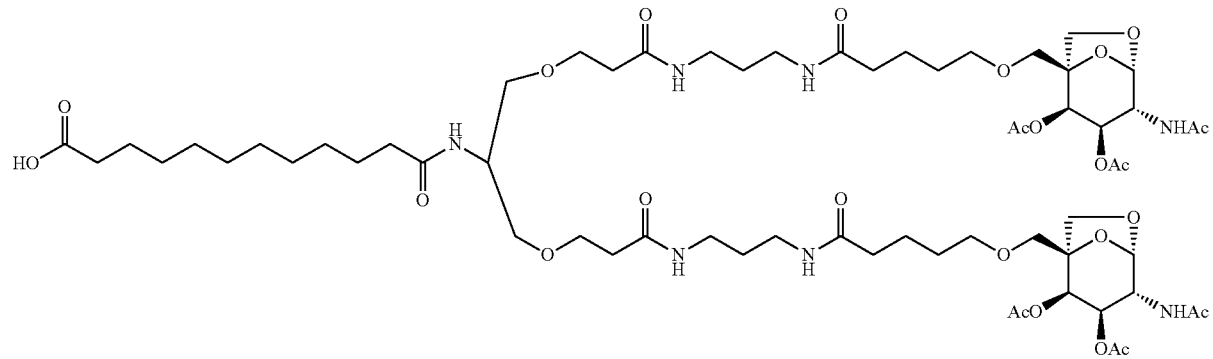 [SMILES: CC(=O)N[C@H]1[C@H]2OC[C@](COCCCCC(=O)NCCCNC(=O)CCOCC(COCCC(=O)NCCCNC(=O)CCCCOC[C@@]34CO[C@@H](O3)[C@H](NC(C)=O)[C@@H](OC(C)=O)[C@H]4OC(C)=O)NC(=O)CCCCCCCCCCC(=O)O)(O2)[C@H](OC(C)=O)[C@@H]1OC(C)=O]

Reaction Scheme

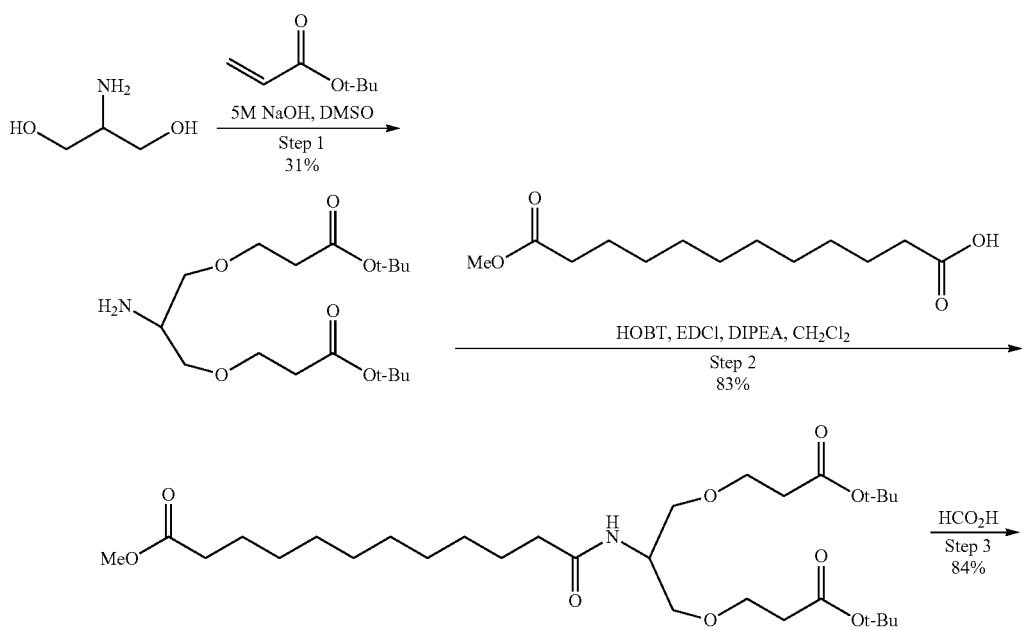

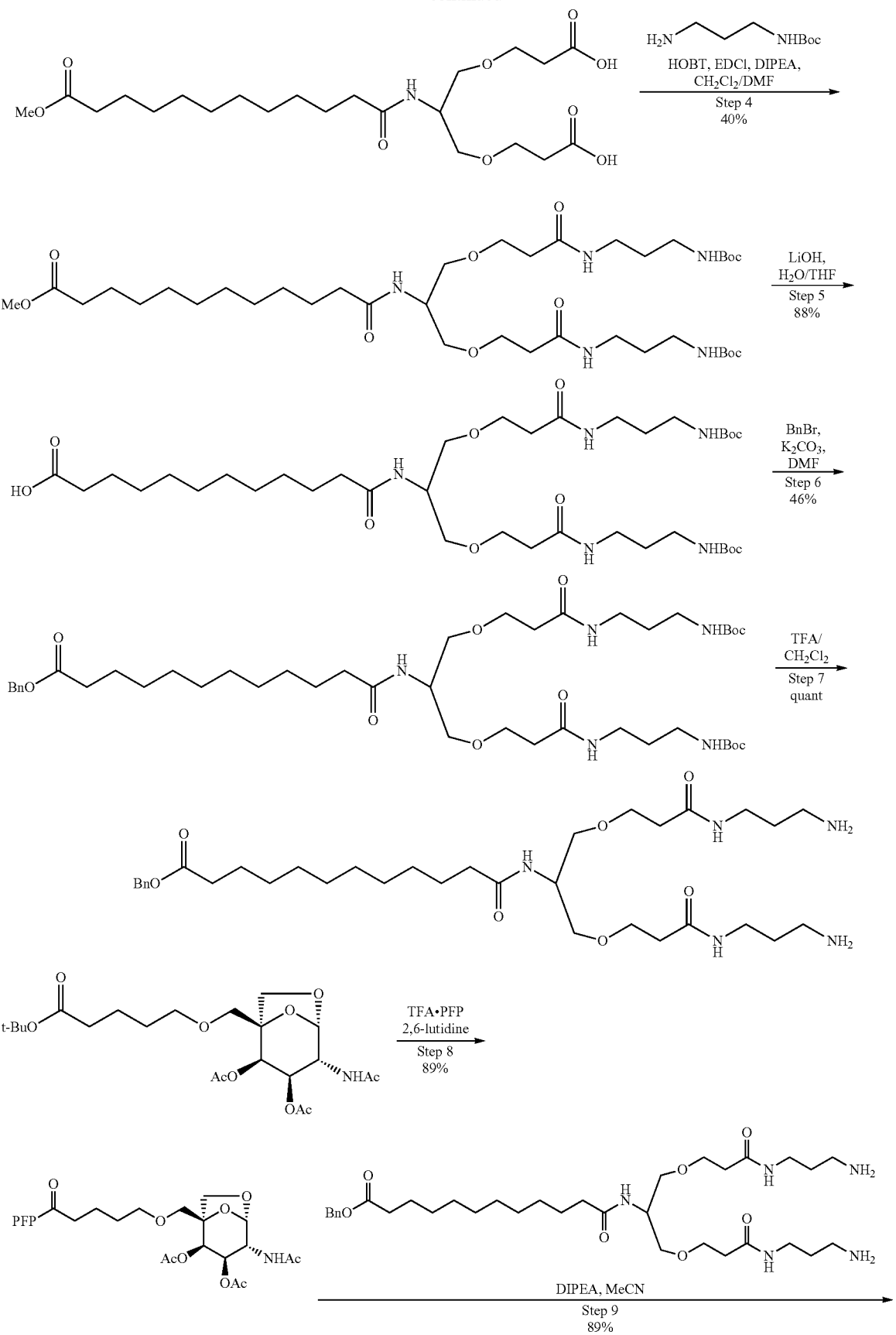

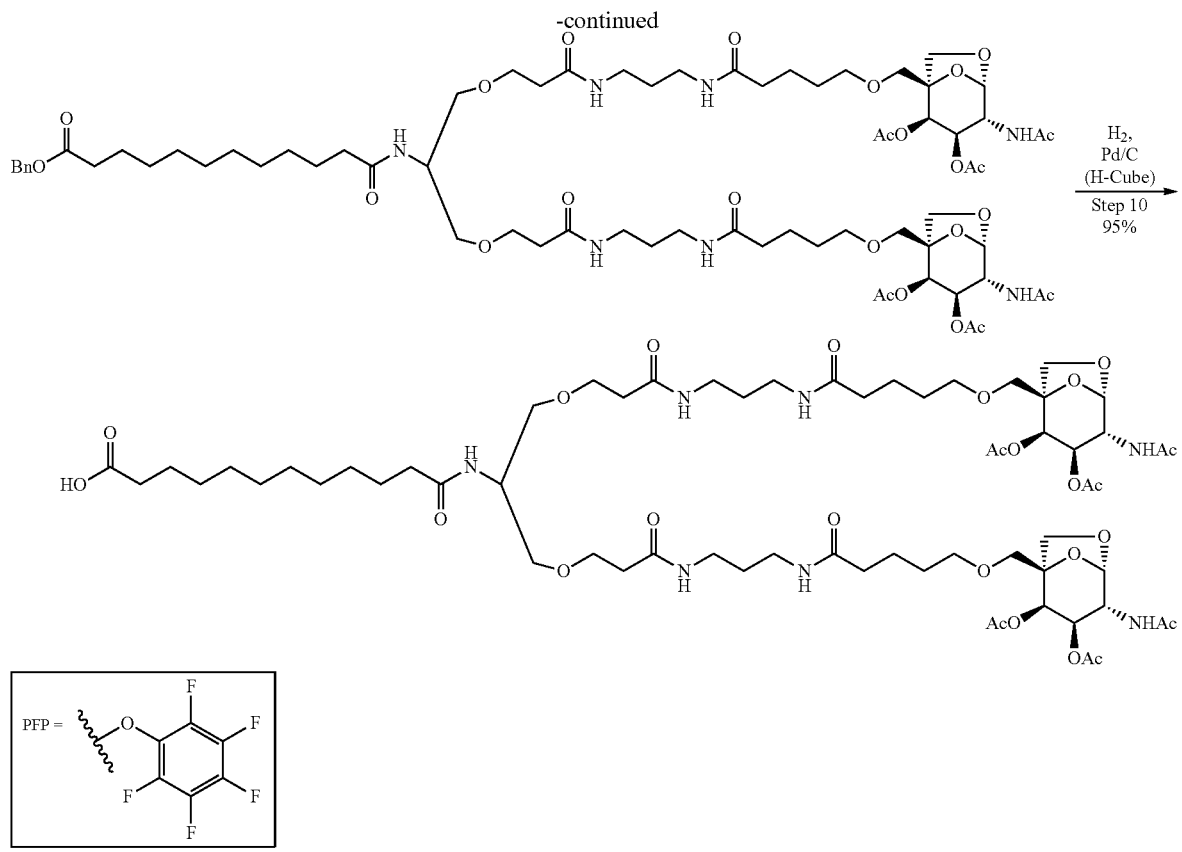

Step 1: di-tert-Butyl 3,3'-[(2-aminopropane-1,3-diyl)bis(oxy)]dipropanoate. 1,1-Dimethylethyl 2-propenoate (1.44 kg, 11.3 mol) was added to a stirred suspension of 2-amino-1,3-propanediol (500 g, 5.49 mol) in dimethylsulfoxide (1.5 L) dropwise over 1 hour at −5° C. The reaction mixture was then allowed to warm to 25° C. and stirring at that temperature continued until TLC analysis showed consumption of the starting material (16 h). The reaction mixture was diluted with water (3 L) and the mixture was extracted with ethyl acetate (5 L×1, 2.5 L×2). The combined organic layers were dried over sodium sulfate, filtered and concentrated in vacuo to afford a residue (1.30 kg). The crude was purified by column chromatography (5% ethyl acetate in petroleum ether then 10% methanol in dichloromethane) to afford the title compound as yellow oil (600 g, 31%). $^1$H NMR (400 MHz, CDCl$_3$) δ ppm 3.69-3.60 (m, 4H), 3.45-3.37 (m, 2H), 3.29 (dd, 2H), 3.18-3.00 (m, 1H), 2.44 (t, 4H), 1.42 (s, 18H).

Step 2: Methyl 12-oxo-12-[(2,2,16,16-tetramethyl-4,14-dioxo-3,7,11,15-tetraoxaheptadecan-9-yl)amino]dodecanoate. This reaction was carried out 2 batches in parallel. 1,12-Dodecanedioic acid monomethyl ester (128 g, 0.524 mmol), hydroxybenzotriazole (70.7 g, 0.524 mmol), diisopropylethylamine (271 g, 2.10 mol) and 1-(3-dimethylaminopropyl)-3-ethylcarbodiimide hydrochloride (201 g, 1.05 mol) were added in to a stirred solution of di-tert-Butyl 3,3'-[(2-aminopropane-1,3-diyl)bis(oxy)]dipropanoate (182 g, 0.524 mol) in dichloromethane (1.6 L) at 20° C. and the reaction was stirred at room temperature until TLC analysis showed consumption of starting material (12 h). The two batches of this reaction mixture were combined, diluted with water (2 L) and stirred at room temperature for 10 minutes. The organic layer was separated and dried over sodium sulfate, filtered and concentrated. The resultant crude residue was purified by silica gel chromatography (20-50% ethyl acetate in petroleum ether) to afford the title compound as a light yellow oil (500 g, 83%). $^1$H NMR (400 MHz, CDCl$_3$) δ ppm 6.21 (d, 1H), 4.14-4.03 (m, 1H), 3.68-3.54 (m, 7H), 3.49 (dd, 2H), 3.32 (dd, 2H), 2.49-2.30 (m, 4H), 2.21 (t, 2H), 2.10 (t, 2H), 1.53 (br.s., 4H), 1.37 (s, 18H), 1.09-1.27 (m, 12H)

Step 3: 3,3'-[{2-[(12-Methoxy-12-oxododecanoyl)amino]propane-1,3-diyl}bis(oxy)]dipropanoic acid. A solution of methyl 12-oxo-12-[(2,2,16,16-tetramethyl-4,14-dioxo-3,7,11,15-tetraoxaheptadecan-9-yl)amino]dodecanoate (546 g, 0.950 mol) in formic acid (2.5 L) was stirred at 30-35° C. until TLC analysis showed consumption of starting material (18 h). The mixture was concentrated to afford a crude residue which was triturated in petroleum ether/ethyl acetate (10:1, 1.5 L) at 20° C. for 12 h. The resultant slurry was filtrated and the filter cake was dried in vacuo to afford the title compound as a white solid (370 g, 84%). $^1$H NMR (400 MHz, CDCl$_3$) δ ppm 10.02 (br.s., 2H), 6.33 (d, 1H), 4.27-4.16 (m, 1H), 3.73 (t, 4H), 3.66 (s, 3H), 3.59 (dd, 2H), 3.45 (dd, 2H), 2.59 (t, 4H), 2.30 (t, 2H), 2.20 (t, 2H), 1.66-1.53 (m, 4H), 1.26 (br.s., 12H).

Step 4: Methyl 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oate. 1-(3-Dimethylaminopropyl)-3-ethylcarbodiimide hydrochloride (348 g, 1.82 mol), hydroxybenzotriazole (205 g, 1.52 mol), and diisopropylethylamine (470 g, 3.64 mol) were added to a stirred solution of 3,3'-[{2-[(12-methoxy-12-oxododecanoyl)amino]propane-1,3-diyl}bis(oxy)]dipropanoic acid (280 g, 0.606 mmol) in DCM/DMF (2 L/250 mL) at 0-5° C.

tert-Butyl (3-aminopropyl)carbamate (243 g, 1.39 mol) was then added to the reaction mixture at 0-5° C. in 4 portions over 20 min. The reaction was then allowed to warm to 25° C. and stirring was continued at that temperature until TLC analysis showed consumption of the starting material (12 h). The reaction mixture was concentrated and the resultant residue diluted with water (2 L). Then the mixture was extracted with ethyl acetate (2 L×1, 700 mL×2) and the combined organic layers were dried over sodium sulfate, filtered and concentrated. The resultant residue was purified by silica gel chromatography (100% ethyl acetate followed by 10% methanol in dichloromethane) to afford a white solid which was triturated in petroleum ether/ethyl acetate (1:2, 1 L) at 15° C. After 16 h the slurry was filtered and the filter cake was washed with ethyl acetate (200 mL) and subsequently dried in vacuo. The resultant solid was once again was triturated in petroleum ether/ethyl acetate (1:3, 600 mL) at 15° C. for 24 h. The slurry was filtered and the filter cake was washed with ethyl acetate (200 mL). The cake was dried in vacuo to obtain the title compound as a white solid (190 g, 40%). $^1$H NMR (400 MHz, $(CD_3)_2SO$) δ ppm 7.81 (t, 2H), 7.63 (d, 1H), 6.76 (t, 2H), 4.01-3.85 (m, 1H), 3.64-3.48 (m, 7H), 3.41-3.22 (m, 4H), 3.02 (q, 4H), 2.90 (q, 4H), 2.28 (t, 6H), 2.05 (t, 2H), 1.57-1.43 (m, 8H), 1.37 (s, 18H), 1.22 (br.s., 12H).

Step 5: 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oic acid. A solution of lithium hydroxide monohydrate (35.7 g, 853 mmol) in water (400 mL) was added to a stirred solution of methyl 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oate (220 g, 284 mmol) in tetrahydrofuran (1.2 L) at 20° C. The reaction mixture was then heated to 28° C. until TLC analysis showed consumption of starting material (18 h). The reaction mixture was concentrated and the resultant residue was diluted with water (2 L). The mixture was then washed with dichloromethane (1 L×2) and was acidified with aqueous hydrochloric acid (1 N, 900 mL) to pH <4. The mixture was extracted with dichloromethane (1 L×2) and the combined organic layers were dried over sodium sulfate, filtered and concentrated to afford the title compound as a light yellow gum (190 g, 88%). $^1$H NMR (400 MHz, $(CD_3)_2SO$) δ ppm 11.97 (br.s., 1H), 7.81 (t, 2H), 7.62 (d, 1H), 6.75 (t, 2H), 3.98-3.87 (m, 1H), 3.56 (t, 4H), 3.38-3.24 (m, 4H), 3.02 (q, 4H), 2.90 (q, 4H), 2.28 (t, 4H), 2.18 (t, 2H), 2.05 (t, 2H), 1.57-1.41 (m, 8H), 1.37 (s, 18H), 1.23 (br.s., 12H).

Step 6: Benzyl 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oate. Potassium carbonate (107 g, 773 mmol) and benzyl bromide (52.9 g, 309 mmol) were added to a stirred solution of 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oic acid (196 g, 258 mmol) in N,N-dimethylformamide (800 mL) at 20° C. The reaction mixture was then heated to 35° C. until TLC analysis showed consumption of starting material (12 h). The mixture was diluted with water (1.5 L) and extracted with methyl tert-butyl ether (1 L×1, 500 mL×2). The combined organic layers were washed with 5% aqueous lithium chloride (800 mL×2), dried over sodium sulfate, filtered and concentrated. The resultant residue was first purified by silica gel chromatography (10% methanol in dichloromethane) and subsequently by preparative HPLC (prepL-LD, Phenomenex Luna C18 250*80 mm*10 um, 30-100% acetonitrile in water modified with 10 mM ammonium bicarbonate, 250 mL/min) to afford the title compound as a white solid (100 g, 46%). $^1$H NMR (400 MHz, $CDCl_3$) δ ppm 7.41-7.28 (m, 5H), 6.86 (t, 2H), 6.61 (d, 1H), 5.21 (t, 2H), 5.11 (s, 2H), 4.26-4.14 (m, 1H), 3.81-3.72 (m, 2H), 3.72-3.63 (m, 2H), 3.58 (dd, 2H), 3.41 (dd, 2H), 3.36-3.24 (m, 4H), 3.16 (q, 4H), 2.52-2.38 (m, 4H), 2.35 (t, 2H), 2.19 (t, 2H), 1.68-1.55 (m, 8H), 1.43 (s, 18H), 1.34-1.20 (m, 12H).

Step 7: Benzyl 12-[(1,3-bis{3-[(3-aminopropyl)amino]-3-oxopropoxy}propan-2-yl)amino]-12-oxododecanoate. A stirred solution of benzyl 15-(13,13-dimethyl-5,11-dioxo-2,12-dioxa-6,10-diazatetradec-1-yl)-2,2-dimethyl-4,10,17-trioxo-3,13-dioxa-5,9,16-triazaoctacosan-28-oate (5.0 g, 5.9 mmol) in dichloromethane (35 mL), was cooled in an ice bath. Trifluoroacetic acid (8.8 mL, 0.12 mol) was added drop-wise over 15 minutes. After an additional 15 minutes, the ice bath was removed and the reaction stirred at ambient temperature for 2 hours. The reaction was concentrated and acetonitrile (20 mL) was added. The solution was concentrated and dried on high vacuum pump overnight. The resulting oil was dissolved in dichloromethane (125 mL) and MP-Carbonate resin (Biotage) (18 g, 3.1 mmol/g) was added to free base the material. The mixture was stirred for 2.5 hours at ambient temperature under nitrogen. The resin was then filtered off and washed with dichloromethane (25 mL) followed by methanol (25 mL). The combined filtrates were concentrated and dried in vacuo overnight to afford the title compound as a white solid (4.1 g, quantitative). $^1$H NMR (400 MHz, $CD_3OD$) δ ppm 7.40-7.28 (m, 5H), 5.11 (s, 2H), 4.17-4.06 (m, 1H), 3.70 (t, 4H), 3.46 (d, 4H), 3.30-3.28 (m, 4H, overlapping with methanol shift), 2.95 (t, 4H), 2.46 (t, 4H), 2.36 (t, 2H), 2.20 (t, 2H), 1.85 (m, 4H), 1.61 (d, 4H), 1.30 (br.s., 12H).

Step 8: Pentafluorophenyl 5-{[(1S,2R,3R,4R,5S)-4-(acetylamino)-2,3-bis(acetyloxy)-6,8-dioxabicyclo[3.2.1]oct-1-yl]methoxy}pentanoate. To a solution of tert-butyl 5-{[(1S,2R,3R,4R,5S)-4-(acetylamino)-2,3-bis(acetyloxy)-6,8-dioxabicyclo[3.2.1]oct-1-yl]methoxy}pentanoate (0.990 g, 2.04 mmol) in dichloromethane (8 mL) placed in an ice bath was added trifluoroacetic acid (1.90 g, 170 mmol) and the reaction was stirred at ambient temperature under nitrogen overnight. Deprotection of ester was complete as confirmed by LCMS [(m/z) for $C_{18}H_{28}NO_{10}^+$ (M+H)$^+$ 418.0]. The reaction mixture was cooled to 0° C. and 2,6-lutidine (2.18 g, 20.5 mmol) followed by pentafluorophenyl trifluoroacetate (0.86 g, 3.06 mmol mL) were added sequentially via addition funnel and the reaction mixture was stirred at ambient temperature. After 3 h, the reaction was quenched by addition of hydrochloric acid (1 N, 150 mL) and extracted with dichloromethane (200 mL). The organic phase was washed with hydrochloric acid (1 N, 3×150 mL) and saturated sodium bicarbonate (150 mL), then subsequently dried over sodium sulfate, filtered, and concentrated. The crude residue was purified by silica gel chromatography (25-75% ethyl acetate in heptane) to afford the title compound as white solid (1.03 g, 87%). $^1$H NMR (600 MHz, $CD_3CN$) δ ppm 6.49 (d, 1H), 5.36 (d, 1H), 5.30 (s, 1H), 5.01 (dd, 1H), 4.10 (t, 1H), 3.94 (d, 1H), 3.69 (dd, 2H), 3.55-3.46 (m, 2H), 3.46-3.36 (m, 1H), 2.72 (t, 2H), 2.12 (s, 3H), 1.91 (s, 3H), 1.85 (s, 3H), 1.80-1.68 (m, 2H), 1.66-1.53 (m, 2H). LCMS (m/z) for $C_{24}H_{27}F_5NO_{10}^+$ (M+H)$^+$ 584.8; Retention time=0.94 min (UPLC 1.5 min method).

Step 9: Benzyl 1-[(1S,2R,3R,4R,5S)-4-(acetylamino)-2,3-bis(acetyloxy)-6,8-dioxabicyclo[3.2.1]oct-1-yl]-18-{17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10- diazaheptadec-1-yl}-7,13,20-trioxo-2,16-dioxa-8,12,19-triazahentriacontan-31-oate. To a suspension of benzyl 12-[(1,3-bis {3-[(3-aminopropyl)amino]-3-oxopropoxy}propan-2-yl)amino]-12-oxododecanoate (1.05 g, 1.31 mmol) in a mixture of acetonitrile (18 mL) and dimethylformamide (8 mL) was added N,N-diisopropylethylamine (1.83 ml, 10.5 mmol). The resultant mixture was then added to a solution of pentafluorophenyl 5-{[(1S,2R,3R,4R,5S)-4-(acetylamino)-2,3-bis(acetyloxy)-6,8-dioxabicyclo[3.2.1]oct-1-yl]methoxy}pentanoate (1.75 g, 3.00 mmol) in acetonitrile (5 mL) and the reaction was stirred under nitrogen at ambient temperature for 2 hours. The reaction was then diluted with 1 N hydrochloric acid (50 ml) and extracted with dichloromethane (2×125 mL). The combined dichloromethane extracts were dried over sodium sulfate, filtered and concentrated. The resultant residue was purified by column chromatography (20-100% ethyl acetate in heptane and then 0-30% methanol in dichloromethane) to afford the title compound as a white solid (1.71 g, 89%). $^1$H NMR (600 MHz, CD$_3$OD) δ ppm 7.37-7.28 (m, 5H), 5.46 (d, 2H), 5.34 (s, 2H), 5.17-5.07 (m, 4H), 4.20 (d, 2H), 4.15-4.09 (m, 1H), 4.02 (d, 2H), 3.67-3.79 (m, 8H), 3.57-3.18 (m, 18H, overlapping with methanol peak), 2.45 (t, 4H), 2.38 (t, 2H), 2.25-2.12 (m, 12H), 1.96 (s, 12H), 1.76-1.48 (m, 14H), 1.43-1.25 (m, 14H).

Step 10: Example 32. A solution of benzyl 1-[(1S,2R,3R,4R,5S)-4-(acetylamino)-2,3-bis(acetyloxy)-6,8-dioxabicyclo[3.2.1]oct-1-yl]-18-{17-[(1S,2R,3R,4R,5S)-4-(acetylamino)-2,3-bis(acetyloxy)-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oate (1.71 g, 1.18 mmol) in methanol (24 mL) was passed through a small 10% Pd/C Catcart on the H-cube under full H2 (20 bar) at 25° C. and 1 mL/min flow rate. The Catcart was rinsed with additional methanol (10 mL) and the flow-through was concentrated to an oil. The residue was dissolved in dichloromethane and concentrated (2×25 mL) to afford a sticky white foam. The material was dried on vacuum pump overnight and subsequently dissolved in acetonitrile/water (3.8 mL, 1:1) and lyophilized to a white solid (1.52 g, 95%). $^1$H NMR (400 MHz, CD$_3$OD) δ ppm 5.44 (d, 2H), 5.32 (s, 2H), 5.12-5.09 (m, 2H), 4.18 (d, 2H), 4.13-4.10 (m, 1H) 4.01 (d, 2H) 3.79-3.67 (m, 8H), 3.56-3.35 (m, 10H), 3.26-3.14 (m, 8H), 2.43 (t, 4H), 2.28 (t, 2H), 2.23-2.14 (m, 12H) 1.97-1.92 (m, 12H), 1.74-1.50 (m, 14H), 1.41-1.28 (m, 14H). LCMS (m/z) for $C_{63}H_{104}N_7O_{25}^+$ (M+H)$^+$ 1359.1; retention time=0.80 min (UPLC 1.5 min run).

1-[(1S,2R,3R,4R,5S)-4-(acetylamino)-2,3-dihydroxy-6,8-dioxabicyclo[3.2.1]oct-1-yl]-18-{17-[(1S,2R,3R,4R,5S)-4-(acetylamino)-2,3-dihydroxy-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oic acid

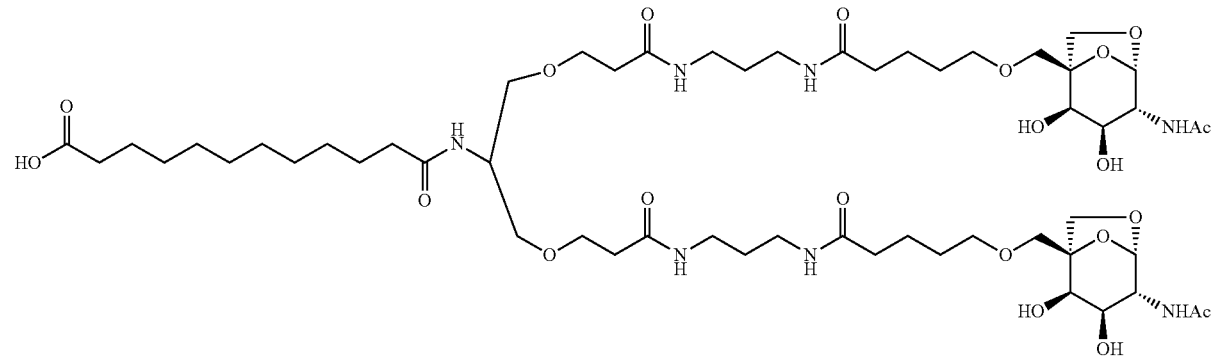 [SMILES: CC(=O)N[C@H]1[C@H]2OC[C@](COCCCCC(=O)NCCCNC(=O)CCOCC(COCCC(=O)NCCCNC(=O)CCCCOC[C@@]34CO[C@@H](O3)[C@H](NC(C)=O)[C@@H](O)[C@H]4O)NC(=O)CCCCCCCCCCC(=O)O)(O2)[C@H](O)[C@@H]1O]

Reaction Scheme

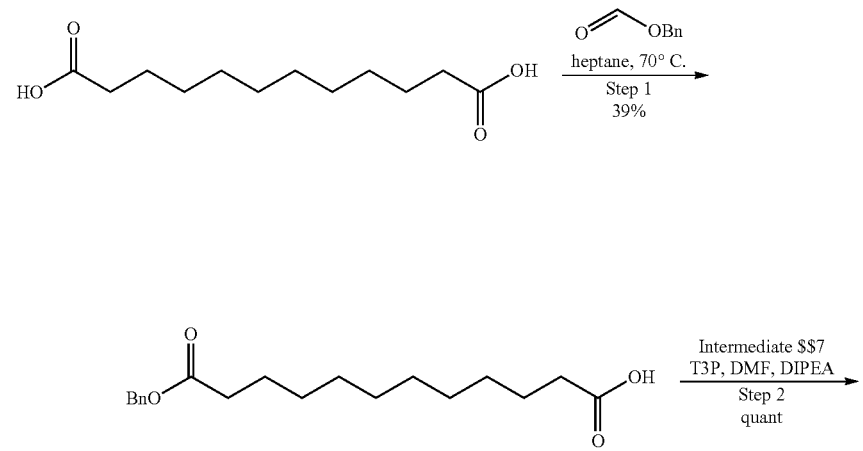

-continued
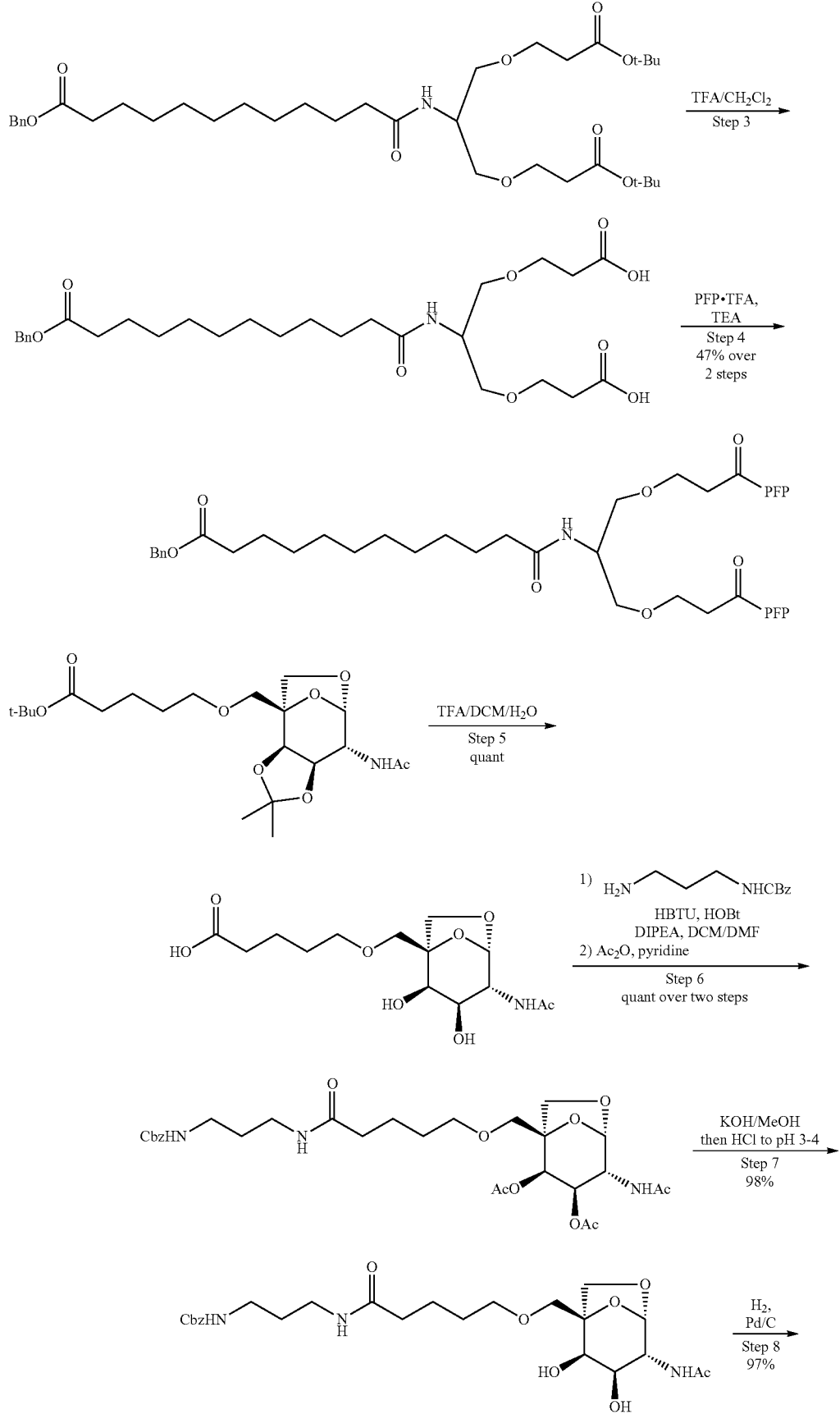

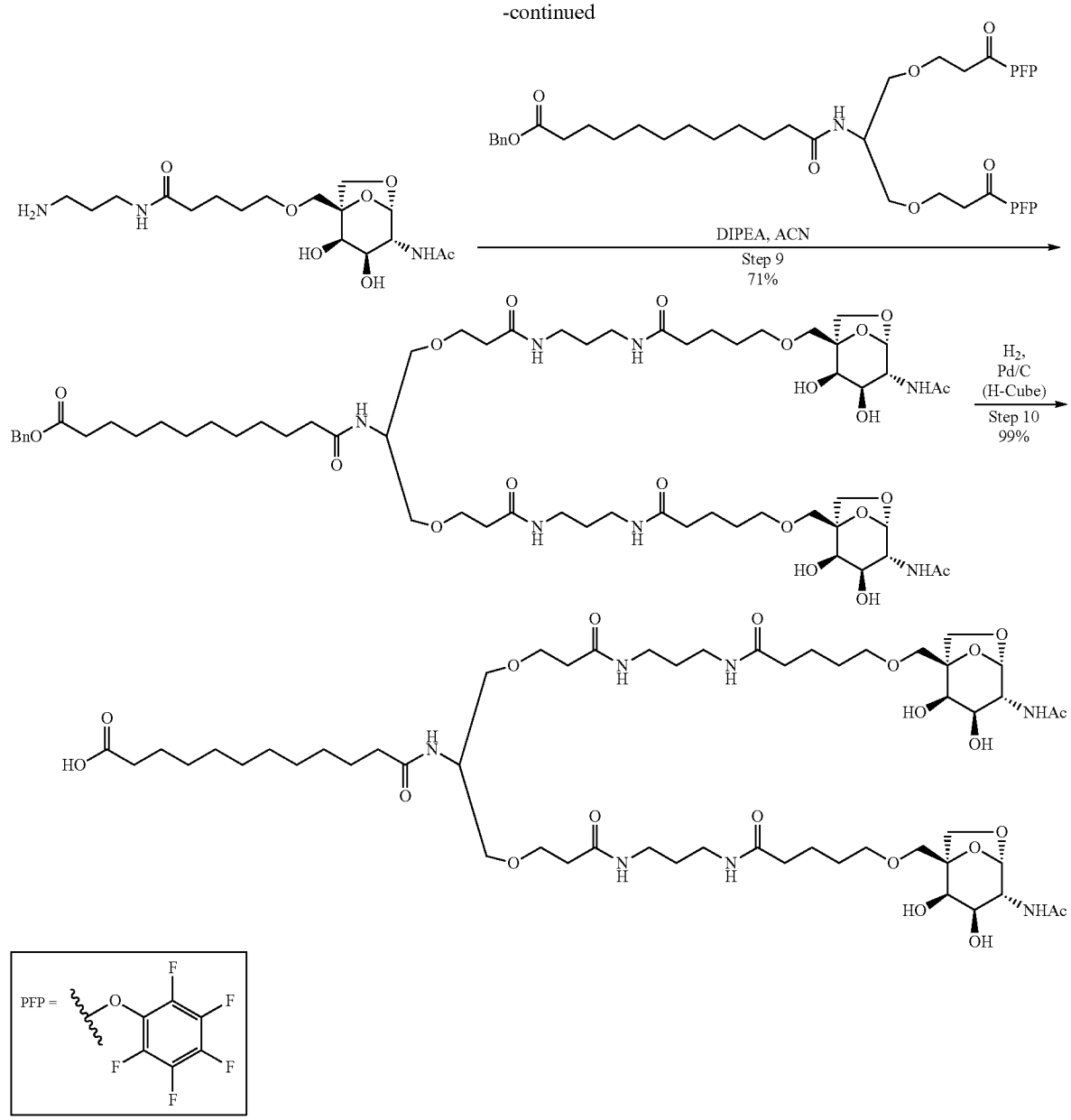

Step 1: 12-(Benzyloxy)-12-oxododecanoic acid. Dodecanedioic acid (15.0 g, 65.0 mmol) and Dowex-H-form (65 g) were added to a mixture of heptane (0.52 L), and benzyl formate (142 g, 1.04 mol, 130 mL) and the reaction was heated to reflux for 24 h. The reaction was then cooled and the resin filtered off. The filtrate was concentrated in vacuo and the resultant residue was purified by silica gel chromatography (0-20% ethyl acetate in heptane) to afford a slushy residue. The isolate was slurried overnight (5% ethyl acetate in heptane, 20 mL). The mixture was filtered by vacuum filtration and the resultant solid washed with heptane to afford the title compound as a white solid (6.66 g, 39%). $^1$H NMR (400 MHz, CDCl$_3$) δ ppm 7.36 (s, 5H), 5.12 (s, 2H), 2.42-2.30 (m, 4H), 1.75-1.54 (m, 4H), 1.45-1.16 (m, 12H).

Step 2: Benzyl 12-oxo-12-[(2,2,16,16-tetramethyl-4,14-dioxo-3,7,11,15-tetraoxaheptadecan-9-yl)amino]dodecanoate. n-Propylphosphonic acid anhydride, cyclic trimer (2.3 g, 3.6 mmol, 2.0 mL, 50% in ethyl acetate) was added to a suspension of 12-(benzyloxy)-12-oxododecanoic acid (0.95 g, 2.98 mmol), di-tert-butyl 3, 3'-[(2-aminopropane-1,3-diyl)bis(oxy)]dipropanoate (1.03 g, 2.98 mmol) and N,N-diisopropylethylamine (1.2 g, 8.9 mmol, 1.6 mL) in dimethylformamide (8 mL) and the reaction mixture was stirred at room temperature overnight. The reaction mixture was diluted with ethyl acetate (100 mL) and washed with hydrochloric acid (1 N, 30 mL), saturated sodium bicarbonate (30 mL), and brine (30 mL). The organic phase was dried over sodium sulfate, filtered, and concentrated to afford a residue which was then azeotroped with heptane (3×40 mL) to afford the title compound as a solid (2.0 g, 100%). $^1$H NMR (600 MHz, CD$_3$CN) δ ppm 7.41-7.31 (m, 5H), 6.34 (d, 1H), 5.08 (s, 2H), 4.01 (td, 1H), 3.67-3.58 (m, 4H), 3.44 (dd, 2H), 3.36 (dd, 2H), 2.40 (t, 4H), 2.33 (t, 2H), 2.09 (t, 2H), 1.61-1.49 (m, 4H), 1.43 (s, 18H), 1.30-1.25 (m, 12H).

LCMS (m/z) for $C_{36}H_{60}NO_9^+$ (M+H)$^+$ 650.5; retention time=1.23 min (UPLC 1.5 min method)

Step 3: 3,3'-[(2-{[12-(benzyloxy)-12-oxododecanoyl]amino}propane-1,3-diyl)bis(oxy)]dipropanoic acid. A solution of 12-oxo-12-[(2,2,16,16-tetramethyl-4,14-dioxo-3,7,11,15-tetraoxaheptadecan-9-yl)amino]dodecanoate (1.60 g, 2.47 mmol) in trifluoracetic acid (15 g, 130 mmol, 10.0 mL) was stirred at ambient temperature overnight. The reaction mixture was concentrated and the resultant residue was azeotroped with diethyl ether (4×70 mL) at 20° C. and subsequently dried in vacuo overnight to afford the title compound as a gum (4.03 g, 99%, 2.11 equiv TFA). $^1$H NMR (600 MHz, CD$_3$CN) δ ppm 7.52-7.24 (m, 5H), 6.89 (d, 1H), 5.14-5.04 (m, 2H), 4.15-4.01 (m, 1H), 3.65 (t, 4H), 3.49-3.46 (m, 2H), 3.44-3.41 (m, 2H), 2.50 (t, 4H), 2.33 (t, 2H), 2.21 (t, 2H), 1.57 (td, 4H), 1.23-1.32 (m, 12H). LCMS (m/z) for $C_{28}H_{44}NO_9^+$ (M+H)$^+$ 538.6; retention time=0.92 min (UPLC 1.5 min method).

Step 4: Benzyl 12-({1,3-bis[3-oxo-3-(pentafluorophenoxy)propoxy]propan-2-yl}amino)-12-oxododecanoate. To a suspension of 3,3'-[(2-{[12-(benzyloxy)-12-oxododecanoyl]amino}propane-1,3-diyl)bis(oxy)]dipropanoic acid (1.57 g, 2.41 mmol, 1 equiv TFA) di-isopropylethylamine (3.11 g, 24.1 mmol, 4.20 mL) in dimethylformamide (10 mL) pentafluorophenyl trifluoroacetate (5.40 g, 19.3 mmol, 3.31 mL) was added dropwise in an ice-bath. The resulting solution was stirred at ambient temperature. The reaction mixture was concentrated and azeotroped with heptane (2×20 mL). The resulting residue was diluted with ethyl acetate (80 mL), washed with 10% citric acid (30 mL), saturated sodium bicarbonate (30 mL), and brine (30 mL), dried over Na$_2$SO$_4$, and concentrated. The crude was purified by silica gel chromatography (0-60% ethyl acetate in heptane) to afford the title compound as a solid (983 mg, 47%). $^1$H NMR (600 MHz, CD$_3$CN-d$_3$) δ ppm 7.44-7.24 (m, 5H), 6.23 (d, 1H), 5.08 (s, 2H), 4.08 (td, 1H), 3.81-3.76 (m, 4H), 3.53-3.42 (m, 4H), 2.92 (t, 4H), 2.32 (t, 2H), 2.07 (t, 2H), 1.62-1.46 (m, 4H), 1.32-1.19 (m, 12H). LCMS (m/z) for $C_{40}H_{42}NO_9^+$ (M+H)$^+$ 870.6; retention time=1.23 min (UPLC 1.5 min method).

Step 5: 5-{[(1S,2R,3R,4R,5S)-4-(Acetylamino)-2,3-dihydroxy-6,8-dioxabicyclo[3.2.1]oct-1-yl]methoxy}pentanoic acid. To a solution of tert-butyl 5-{[(1S,2R,6R,7R,8S)-7-(acetylamino)-4,4-dimethyl-3,5,9,11-tetraoxatricyclo[6.2.1.0~2,6~]undec-1-yl]methoxy}pentanoate (2.09 g, 4.87 mmol) in dichloromethane (15 mL) and water (2 mL) was added trifluoroacetic acid (22 g, 200 mmol, 15 mL) and the reaction mixture was stirred at ambient temperature overnight. The crude was concentrated, azeotroped with toluene (3×50 mL), then heptane (3×50 ml), and dried in vacuo to afford the title compound as a gum (2.08 g, quantitative, 0.83 equiv TFA). LCMS (m/z) for $C_{14}H_{24}NO_8^+$ (M+H)$^+$ 334.2; retention time=0.45 min (UPLC 1.5 min method)

Step 6: (1S,2R,3R,4R,5S)-4-(Acetylamino)-1-(3,9-dioxo-1-phenyl-2,14-dioxa-4,8-diazapentadecan-15-yl)-6,8-dioxabicyclo[3.2.1]octane-2,3-diyl diacetate. To solution of 5-{[(1S,2R,3R,4R,5S)-4-(acetylamino)-2,3-dihydroxy-6,8-dioxabicyclo[3.2.1]oct-1-yl]methoxy}pentanoic acid containing about 1 equiv TFA (1.0 g, 2.05 mmol) in dichloromethane (12 mL) and dimethylformamide (5 mL) was added di-isopropylethylamine (1.59 g, 12.3 mmol), o-(benzotriazol-1-yl)-N,N,N',N'-tetramethyluronium hexafluorophosphate (0.93 g, 2.46 mmol) and 1H-benzotriazol-1-ol (277 mg, 2.05 mmol). The cloudy mixture was stirred at room temperature for 20 min. Benzyl n-(3-aminopropyl)carbamate hydrochloride (502 mg, 2 mmol) was then added. The resulting mixture was stirred at ambient temperature overnight. Formation of amide product was confirmed by LCMS [$C_{25}H_{38}N_3O_9^+$, (M+H)$^+$ 524.5]. The reaction mixture was concentrated to 5 mL and diluted with pyridine (6 mL). To this solution was added acetic anhydride (6.0 g, 60 mmol) and the reaction mixture was stirred at 50° C. overnight. The reaction mixture was cooled to room temperature, diluted with ethyl acetate (70 mL), washed with hydrochloric acid (1 N, 30 mL), saturated sodium bicarbonate (30 mL), and brine (30 mL). The separated organic phase was dried over sodium sulfate, filtered, and concentrated. The crude was purified by silica gel chromatography (0-15% methanol in dichloromethane) to afford the title compound as a glass (1.28 g, 100%). LCMS (m/z) for $C_{29}H_{42}N_3O_{11}^+$, (M+H)$^+$ 608.5; retention time=0.70 min (UPLC 1.5 min method)

Step 7: Benzyl {3-[(5-{[(1S,2R,3R,4R,5S)-4-(acetylamino)-2,3-dihydroxy-6,8-dioxabicyclo[3.2.1]oct-1-yl]methoxy}pentanoyl)amino]propyl}carbamate. To a suspension (1S,2R,3R,4R,5S)-4-(acetylamino)-1-(3,9-dioxo-1-phenyl-2,14-dioxa-4,8-diazapentadecan-15-yl)-6,8-dioxabicyclo[3.2.1]octane-2,3-diyl diacetate (1.5 g, 2.47 mmol) in methanol (8 mL) was added potassium hydroxide (1 M in methanol, 5.3 mL, 5.3 mmol). The reaction mixture was stirred at room temperature for 1 h. The reaction mixture was then treated with hydrochloric acid (4.0 M in dioxane, 1.5 mL) dropwise. The resulting slurry was concentrated and triturated in ethanol (15 mL) for 10 min. The resulting potassium chloride precipitate was removed by filtration, rinsed by ethanol (5 mL). The filtrate was concentrated, dried by vacuum to afford the entitled compound as a gum (1.28 g, 98%). $^1$H NMR (600 MHz, METHANOL-d$_4$) δ ppm 7.41-7.25 (m, 5H), 5.21 (s, 1H), 5.07 (s, 2H), 3.93 (dd, 2H), 3.86 (d, 1H), 3.77 (d, 1H), 3.71 (dd, 1H), 3.65 (d, 1H), 3.58 (d, 1H), 3.53-3.46 (m, 2H), 3.20 (t, 2H), 3.15 (t, 2H), 2.20 (t, 2H), 1.99 (s, 3H), 1.70-1.62 (m, 4H), 1.61-1.53 (m, 2H). LCMS (m/z) for $C_{25}H_{38}N_3O_9^+$, (M+H)$^+$ 524.5; retention time=0.64 min (UPLC 1.5 min method)

Step 8: 5-{[(1S,2R,3R,4R,5S)-4-(Acetylamino)-2,3-dihydroxy-6,8-dioxabicyclo[3.2.1]oct-1-yl]methoxy-N-(3-aminopropyl)pentanamide. A mixture of benzyl {3-[(5-{[(1S,2R,3R,4R,5S)-4-(acetylamino)-2,3-dihydroxy-6,8-dioxabicyclo[3.2.1]oct-1-yl]methoxy}pentanoyl)amino}propyl}carbamate (1.60 g, 2.4 mmol) and 10% palladium on carbon (200 mg) in methanol (20 mL) was stirred under hydrogen pressure (50 psi) at ambient temperature in a Parr reactor overnight. The reaction mixture was filtered through celite. The celite was washed with methanol (50 mL) and the combined filtrates were concentrated, and dried in vacuo to afford the title compound as a solid (925 mg, 97%). $^1$H NMR (600 MHz, METHANOL-d$_4$) δ ppm 5.21 (s, 1H), 3.94 (d, 1H), 3.90 (d, 1H), 3.86 (d, 1H), 3.77 (d, 1H), 3.71 (dd, 1H), 3.65 (d, 1H), 3.61 (d, 1H), 3.58-3.46 (m, 2H), 3.26 (t, 2H), 2.82 (t, 2H), 2.22 (t, 2H), 1.99 (s, 3H), 1.76 (quin, 2H), 1.68 (quin, 2H), 1.63-1.56 (m, 2H). LCMS (m/z) for $C_{17}H_{32}N_3O_7^+$, (M+H)$^+$ 390.5; retention time=0.47 min (UPLC 1.5 min method)

Step 9: Benzyl 1-[(1S,2R,3R,4R,5S)-4-(acetylamino)-2,3-dihydroxy-6,8-dioxabicyclo[3.2.1]oct-1-yl]-18-{17-[(1S,2R,3R,4R,5S)-4-(acetylamino)-2,3-dihydroxy-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oate. A mixture of 5-{[(1S,2R,3R,4R,5S)-4-(acetylamino)-2,3-dihydroxy-6,8-dioxabicyclo[3.2.1]oct-1-yl]methoxy}-N-(3-aminopropyl)pentanamide (607 mg, 1.40 mmol) and benzyl 12-({1,3-bis[3-oxo-3-(pentafluorophenoxy)propoxy]propan-2-yl}amino)-12-oxododecanoate (500 mg, 0.58 mmol), and N,N-diisopropylethylamine (200 mg, 2.0 mmol) in a mixture of dichloromethane (8 mL) and dimethylformamide (3 mL) was stirred at room temperature overnight. The reaction mixture was concentrated, azeotroped with heptane (3×10 mL), and concentrated. The crude residue was purified by silica gel chromatography (0-40% methanol in dichloromethane) to afford the title compound as a glass (520 mg, 71%). $^1$H NMR (600 MHz, METHANOL-$d_4$) δ ppm 7.37-7.29 (m, 5H), 5.21 (s, 2H), 5.11 (s, 2H), 4.11 (t, 1H), 3.94 (dd, 4H), 3.87 (d, 2H), 3.77 (d, 2H), 3.75-3.67 (m, 6H), 3.64 (d, 2H), 3.57 (d, 2H), 3.55-3.42 (m, 8H), 3.23-3.19 (m, 8H), 2.43 (t, 4H), 2.36 (t, 2H), 2.20 (q, 6H), 1.98 (s, 6H), 1.72-1.54 (m, 16H), 1.35-1.28 (m, 12H). LCMS $C_{62}H_{102}N_7O_{21}^+$, (M+H)$^+$ 1280.3; retention time=1.45 min (UPLC 3 min method)

Step 10: Example 33. 1-[(1S,2R,3R,4R,5S)-4-(acetylamino)-2,3-dihydroxy-6,8-dioxabicyclo[3.2.1]oct-1-yl]-18,18-bis {17-[(1S,2R,3R,4R,5S)-4-(acetylamino)-2,3-dihydroxy-6,8-dioxabicyclo[3.2.1]oct-1-yl]-5,11-dioxo-2,16-dioxa-6,10-diazaheptadec-1-yl}-7,13,20-trioxo-2,16-dioxa-8,12,19-triazahentriacontan-31-oic acid. A solution of benzyl 1-[(1S,2R,3R,4R,5S)-4-(acetylamino)-2,3-dihydroxy-6,8-dioxabicyclo[3.2.1]oct-1-yl]-18-{17-[(1S,2R,3R,4R,5S)-4-(acetylamino)-2,3-dihydroxy-6,8-dioxabicyclo[3.2.1]oct-1-yl]-5,11-dioxo-2,16-dioxa-6,10-diazaheptadec-1-yl}-7,13,20-trioxo-2,16-dioxa-6,10-diazaheptadec-1-yl}-7,13,20-trioxo-2,16-dioxa-8,12,19-triazahentriacontan-31-oate (520 mg, 0.41 mmol) in methanol (16 mL) was passed through 10% Pd/C 30×4 CatCart® on ThalesNano H-Cube Pro™ with a flow rate of 1 mL/min at 25° C. under full H2. The system was rinsed by methanol (20 mL). The filtrate was concentrated, azeotroped with methylene chloride (20 mL), then heptane (20 mL). The resulting residue was dissolved in acetonitrile/water (1:1, 20 mL) and freeze dried to afford the title compound as a white solid (477 mg, 99%). $^1$H NMR (600 MHz, METHANOL-$d_4$) δ ppm 5.21 (s, 2H), 4.11 (t, 1H), 3.98-3.87 (m, 4H), 3.87 (d, 2H), 3.78 (d, 2H), 3.74-3.67 (m, 6H), 3.65 (d, 2H), 3.58 (d, 2H), 3.55-3.45 (m, 8H), 3.21 (q, 8H), 2.43 (t, 4H), 2.27 (t, 2H), 2.23-2.16 (m, 6H), 1.99 (s, 6H), 1.72-1.62 (m, 8H), 1.63-1.54 (m, 8H), 1.35-1.28 (m, 12H). LCMS (m/z) for $C_{55}H_{96}N_7O_{21}^+$, (M+H)$^+$ 1190.7; retention time=1.07 min (UPLC 3 min method).

1-[(1S,2R,3R,4R,5S)-4-(acetylamino)-2,3-dihydroxy-6,8-dioxabicyclo[3.2.1]oct-1-yl]-7,13,20-trioxo-2,16-dioxa-8,12,19-triazahentriacontan-31-oic acid

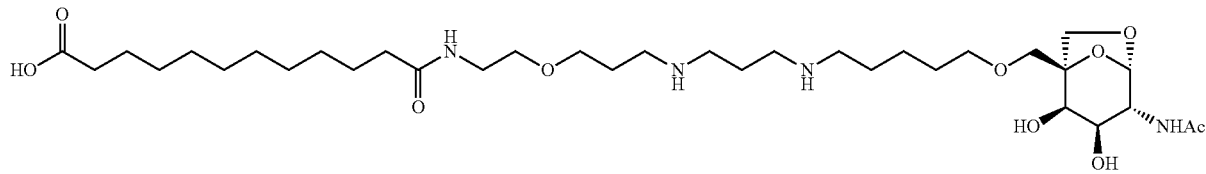 [SMILES: CC(=O)N[C@H]1[C@H]2OC[C@](COCCCCCNCCCNCCCOCCNC(=O)CCCCCCCCCCC(=O)O)(O2)[C@H](O)[C@@H]1O]

Reaction Scheme

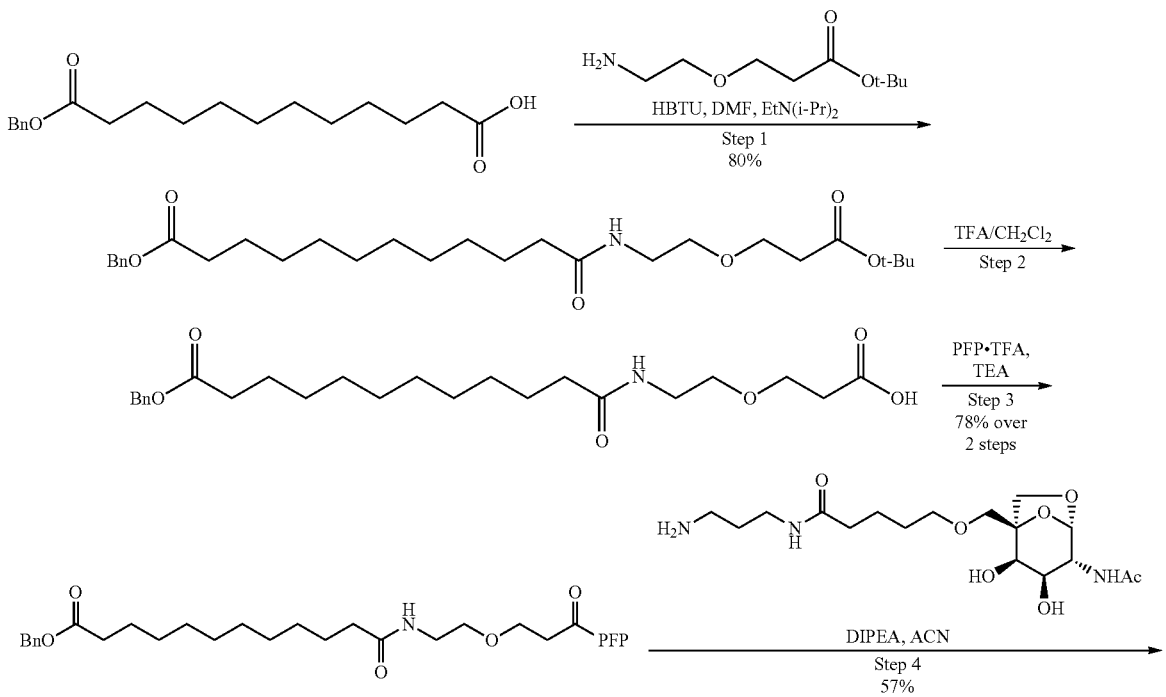

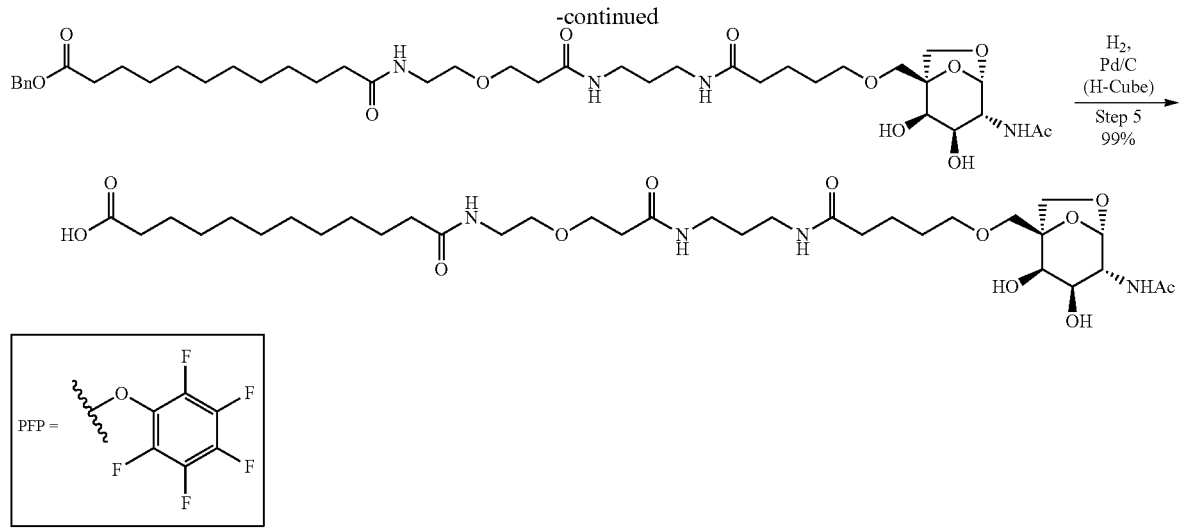

Step 1: Benzyl 12-{[2-(3-tert-butoxy-3-oxopropoxy)ethyl]amino}-12-oxododecanoate 12-benzyloxy-12-oxodecanoic acid (2.33 g, 7.26 mmol), tert-butyl 3-(2-aminoethoxy)propanoate (1.25 g, 6.60 mmol) and N,N-diisopropylethylamine (2.3 ml, 13 mmol) were dissolved in N,N-dimethylformamide (35 mL). To this solution was added N,N,N',N'-tetramethyl-O-(1H-benzotriazol-1-yl)uronium hexafluorophosphate, O-(Benzotriazol-1-yl)-N,N,N',N'-tetramethyluronium hexafluorophosphate (2.75 g, 7.26 mmol) and the reaction stirred at ambient temperature for 16 h. The reaction was concentrated and the residue was dissolved in ethyl acetate (100 mL) and washed sequentially with saturated sodium bicarbonate, water, and brine (25 mL each). The organic layer was then dried over sodium sulfate, filtered and concentrated to a colorless oil. The residue was purified by silica gel chromatography (0-100% ethyl acetate in heptane) to afford the desired product as a white solid (2.58 g, 80%). $^1$H NMR (400 MHz, CDCl$_3$) δ ppm 7.41-7.30 (m, 5H), 6.18 (br.s., 1H), 5.12 (s, 2H), 3.69 (t, 2H), 3.57-3.51 (m, 2H), 3.49-3.42 (m, 2H), 2.49 (t, 2H), 2.36 (t, 2H), 2.23-2.14 (m, 2H), 1.63 (d, 4H), 1.47 (s, 9H), 1.36-1.22 (m, 12H).

Step 2: 3-(2-{[12-(Benzyloxy)-12-oxododecanoyl]amino}ethoxy)propanoic acid. Benzyl 12-{[2-(3-tert-butoxy-3-oxopropoxy)ethyl]amino}-12-oxododecanoate (2.58 g, 5.25 mmol) was dissolved in dichloromethane (12 mL). To this was added trifluoroacetic acid (20 ml, 0.27 mol). After 2 h stirring at ambient temperature, the reaction was concentrated. The resultant residue was dissolved in toluene and concentrated (2×20 mL) and subsequently dried on vacuum pump to afford a solid (2.21 g). $^1$H NMR (400 MHz, CDCl$_3$) δ ppm 7.41-7.30 (m, 5H) 6.08 (br.s., 1H) 5.12 (s, 2H) 3.74 (t, 2H) 3.61-3.51 (m, 2H) 3.50-3.40 (m, 2H) 2.64 (t, 2H) 2.36 (t, 2H) 2.25-2.11 (m, 2H) 1.72-1.54 (m, 4H) 1.27 (m, 12H).

Step 3: Benzyl 12-oxo-12-({2-[3-oxo-3-(pentafluorophenoxy)propoxy]ethyl}amino)dodecanoate. N,N-diisopropylethylamine (3.52 ml, 20.2 mmol) was added to a solution of 3-(2-{[12-(benzyloxy)-12-oxododecanoyl]amino}ethoxy)propanoic acid (2.20 g, 5.05 mmol) in dimethylformamide (24 mL). To this was then added pentafluorophenol-2,2,2-trifluoroacetate (1.74 mL, 10.1 mmol) in a slow stream. The reaction turned purple in color and was stirred at ambient temperature for 18 h. The reaction mixture was concentrated to ⅓ volume on a rotary evaporator (50° C., high vacuum pump) and the resultant concentrate was diluted with ethyl acetate (300 mL), washed with 10% citric acid (100 mL), saturated sodium bicarbonate (100 mL) and brine (100 mL). The organic layer was dried over sodium sulfate, filtered, and concentrated. The residue was purified by silica gel chromatography (0-100% ethyl acetate in heptane) to afford the desired product as a yellow solid (2.46 g, 78% over 2 steps). $^1$H NMR (400 MHz, CDCl$_3$) δ ppm 7.41-7.30 (m, 5H), 5.85 (br.s., 1H) 5.12 (s, 2H), 3.85 (t, 2H), 3.64-3.54 (m, 2H), 3.52-3.43 (m, 2H), 2.94 (t, 2H), 2.36 (t, 2H), 2.16 (t, 2H), 1.70-1.60 (m, 4H), 1.26 (m, 12H).

Step 4: Benzyl 1-[(1S,2R,3R,4R,5S)-4-(acetylamino)-2,3-dihydroxy-6,8-dioxabicyclo[3.2.1]oct-1-yl]-20-oxo-2,16-dioxa-8,12,19-triazahentriacontan-31-oate. A mixture of 5-{[(1S,2R,3R,4R,5S)-4-(acetylamino)-2,3-dihydroxy-6,8-dioxabicyclo[3.2.1]oct-1-yl]methoxy}-N-(3-aminopropyl)pentanamide (172 mg, 0.440 mmol) and benzyl 12-oxo-12-({2-[3-oxo-3-(pentafluorophenoxy)propoxy]ethyl}amino)dodecanoate (220 mg, 0.402 mmol), N,N-diisopropylethylamine (95 mg, 0.73 mmol) in a mixture of dichloromethane (3.3 mL) and dimethylformamide (0.7 mL) was stirred at room temperature overnight. The reaction mixture was concentrated, azeotroped with heptane (3×10 mL), and concentrated. The crude was purified by silica gel chromatography (0-25% methanol in dichloromethane to afford the title compound as an oil (185 mg, 57%). $^1$H NMR (600 MHz, METHANOL-d$_4$) δ ppm 7.39-7.28 (m, 5H), 5.21 (s, 1H), 5.11 (s, 2H), 3.99-3.89 (m, 2H), 3.87 (d, 1H), 3.77 (d, 1H), 3.75-3.67 (m, 3H), 3.64 (d, 1H), 3.57 (d, 1H), 3.55-3.44 (m, 4H), 3.38-3.32 (m, 2H), 3.26-3.16 (m, 4H), 2.44 (t, 2H), 2.36 (t, 2H), 2.19 (td, 4H), 1.99 (s, 3H), 1.70-1.55 (m, 10H), 1.33-1.25 (m, 12H). LCMS (m/z) for $C_{41}H_{67}N_4O_{12}^+$, $(M+H)^+$ 807.8; retention time=1.60 min (UPLC 3 min method).

Step 5: Example 34. A solution of benzyl 1-[(1S,2R,3R,4R,5S)-4-(acetylamino)-2,3-dihydroxy-6,8-dioxabicyclo[3.2.1]oct-1-yl]-20-oxo-2,16-dioxa-8,12,19-triazahentriacontan-31-oate (0.22 g, 0.25 mmol) in methanol (22 mL) was passed through 10% Pd/C 30×4 CatCart® on ThalesNano H-cube Pro™ with a flow rate of 1 mL/min at 25° C. under full H$_2$. The system was rinsed by methanol (40 mL). The filtrate was concentrated, azeotroped with methylene chloride (20 mL), then heptane (20 mL). The resulting residue was dissolved in acetonitrile/water (1:1, 20 mL) and freeze dried to afford the title compound as a white solid (177 mg, 99%). ¹H NMR (600 MHz, METHANOL-d₄) δ ppm 5.20 (s, 1H), 4.01-3.89 (m, 2H), 3.87 (d, 1H), 3.77 (d, 1H), 3.75-3.68 (m, 3H), 3.65 (d, 1H), 3.57 (d, 1H), 3.55-3.45 (m, 4H), 3.34 (t, 2H), 3.27-3.14 (m, 4H), 2.44 (t, 2H), 2.28 (t, 2H), 2.20 (td, 4H), 1.98 (s, 3H), 1.67 (t, 4H), 1.63-1.54 (m, 6H), 1.35-1.28 (m, 12H). $C_{34}H_{61}N_4O_{12}^+$, (M+H)⁺ 717.7; retention time=1.12 min (UPCL 3 min method).

5,11,18-trioxo-16-{[3-oxo-3-({3-[(5-{[3,4,6-tri-O-acetyl-2-(acetylamino)-2-deoxy-β-D-galactopyranosyl]oxy}pentanoyl)amino]propyl}amino)propoxy]methyl}-1-{[3,4,6-tri-O-acetyl-2-(acetylamino)-2-deoxy-β-D-galactopyranosyl]oxy}-14-oxa-6,10,17-triazanonacosan-29-oic acid

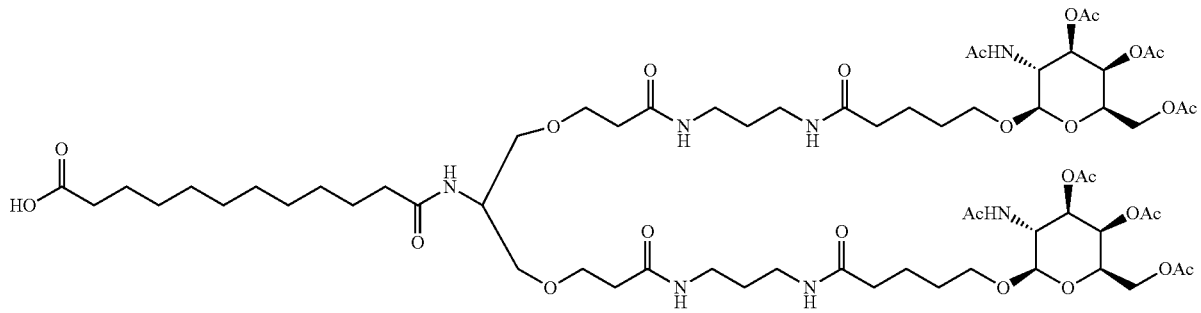 [SMILES: CC(=O)N[C@H]1[C@H](OCCCCC(=O)NCCCNC(=O)CCOCC(COCCC(=O)NCCCNC(=O)CCCCO[C@@H]2O[C@H](COC(C)=O)[C@H](OC(C)=O)[C@H](OC(C)=O)[C@H]2NC(C)=O)NC(=O)CCCCCCCCCCC(=O)O)O[C@H](COC(C)=O)[C@H](OC(C)=O)[C@@H]1OC(C)=O]

Reaction Scheme

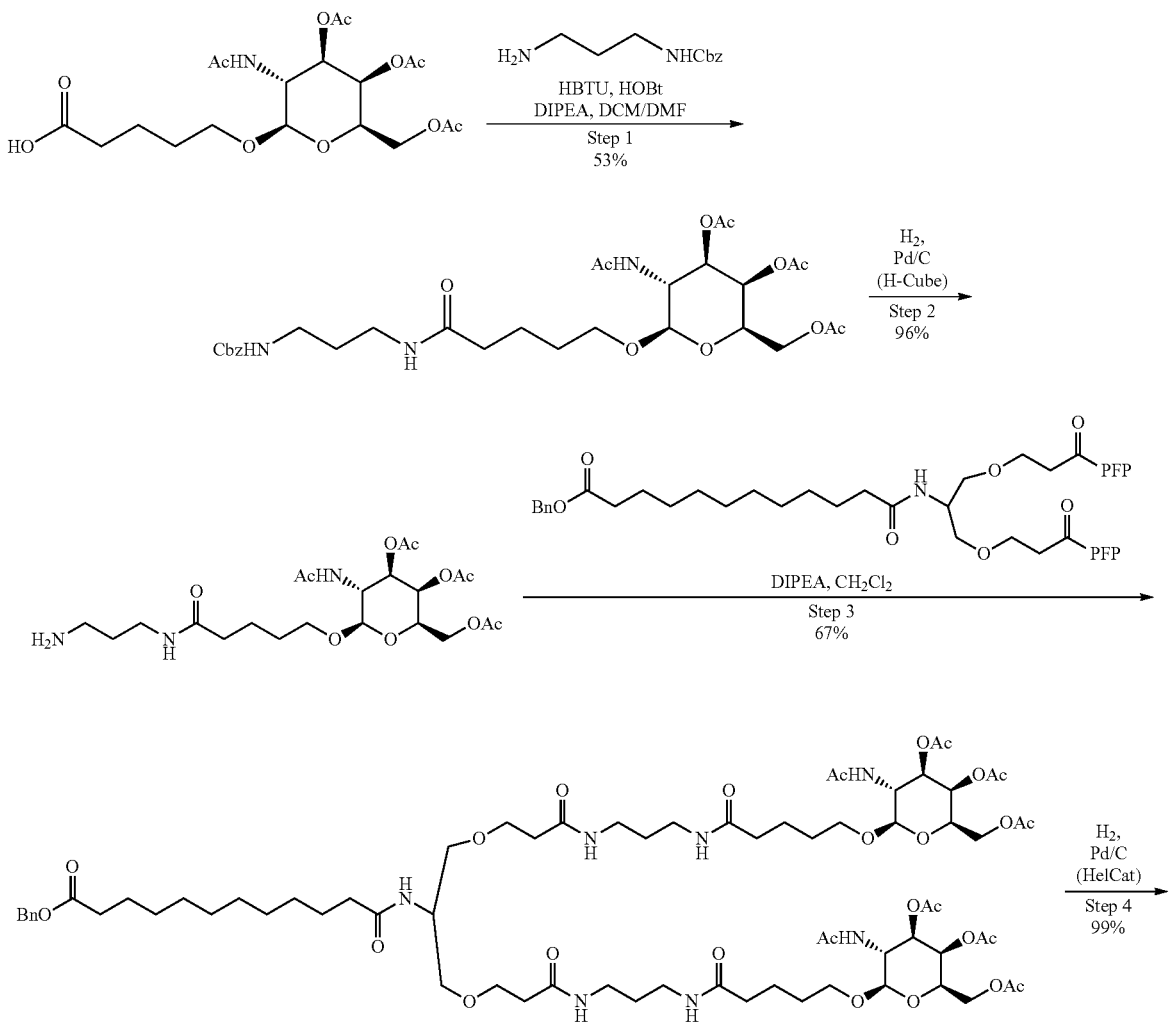

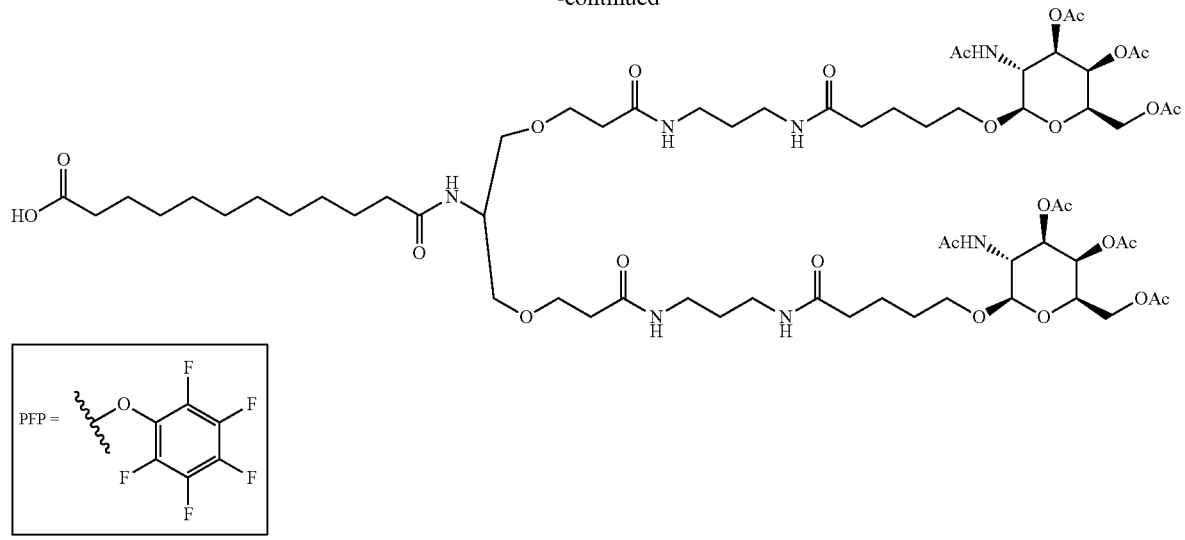

Step 1: Benzyl {3-[(5-{[3,4,6-tri-O-acetyl-2-(acetylamino)-2-deoxy-β-D-galactopyranosyl]oxy}pentanoyl)amino]propyl}carbamate. N,N-diisopropylethylamine (1.38 mL, 7.95 mmol) was added to a solution of benzyl (3-aminopropyl)carbamate hydrochloride salt (0.713 g, 2.01 mmol) in N,N-dimethylformamide (3.5 mL). The resultant mixture was then added to a solution of 5-(((2R,3R,4R,5R,6R)-3-acetamido-4,5-diacetoxy-6-(acetoxymethyl)tetrahydro-2H-pyran-2-yl)oxy)pentanoic acid (1.19 g, 2.65 mmol) in dimethylformamide (10 mL). 1-[Bis(dimethylamino)methylene]-1H-1,2,3-triazolo[4,5-b]pyridinium 3-oxid hexafluorophosphate (1.11 g, 2.91 mmol) was then added and the reaction mixture was stirred at ambient temperature under an atmosphere of nitrogen (2.5 h). The reaction was quenched with saturated ammonium chloride (50 mL) and extracted with dichloromethane (4×75 mL). The combined organic layers were washed with brine (50 mL), dried over sodium sulfate, filtered and concentrated. The resultant oil was purified by silica gel chromatography (2-6% methanol in dichloromethane) to afford the desired product as a white foam (0.904 g, 53%). $^1$H NMR (400 MHz, CD$_3$OD) δ ppm 7.41-7.25 (m, 5H), 5.33 (d, 1H), 5.12-5.02 (m, 3H), 4.54 (d, 1H), 4.19-4.03 (m, 3H), 4.03-3.97 (m, 1H), 3.91-3.82 (m, 1H), 3.60-3.46 (m, 2H), 3.11-3.25 (m, 4H), 2.16-2.23 (m, 2H), 2.13 (s, 3H), 2.02 (s, 3H), 1.95 (s, 3H), 1.92 (s, 3H), 1.73-1.53 (m, 6H), 1.40-1.34 (m, 2H).

Step 2: N-(3-aminopropyl)-5-{[3,4,6-tri-O-acetyl-2-(acetylamino)-2-deoxy galactopyranosyl]oxy}pentanamide acetate salt. Benzyl {3-[(5-{[3,4,6-tri-O-acetyl-2-(acetylamino)-2-deoxy-β-D-galactopyranosyl]oxy}pentanoyl)amino]propyl}carbamate 5-{[3,4,6-tri-O-acetyl-2-(acetylamino)-2-deoxy-β-D-galactopyranosyl]oxy}pentanoic acid (1.01 g, 1.59 mmol) was dissolved in a mixture of methanol (30 mL) and glacial acetic acid (91 uL, 1.6 mmol). To this was added 10% Pd/C (0.2 g, wet) under nitrogen and the reaction mixture was placed in a sealed, stirred Parr reactor under 50 psi hydrogen. After 16 h the head space was purged with nitrogen (×4) and filtered through a 0.45 um nylon syringe filter. The filter was washed with methanol and the combined filtrates were concentrated to afford the title compound as a white foam (0.86 g mg, 96%). $^1$H NMR (400 MHz, CD$_3$OD) δ ppm 5.34 (d, 1H), 5.06-5.02 (m, 1H), 4.52 (d, 1H), 4.19-4.05 (m, 3H), 4.04-3.98 (m, 1H), 3.92-3.84 (m, 1H), 3.56-3.47 (m, 1H), 2.98-2.89 (m, 2H), 2.23 (t, 2H), 2.14 (s, 3H), 2.06 (d, 1H), 2.03 (s, 3H), 1.94 (d, 5H), 1.91 (s, 3H), 1.83 (m, 2H), 1.74-1.54 (m, 4H), 1.39-1.31 (m, 1H).

Step 3: Benzyl 5,11,18-trioxo-16-{[3-oxo-3-({3-[(5-{[3,4,6-tri-O-acetyl-2-(acetylamino)-2-deoxy-β-D-galactopyranosyl]oxy}pentanoyl)amino]propyl}amino)propoxy]methyl}-1-{[3,4,6-tri-O-acetyl-2-(acetylamino)-2-deoxy-β-D-galactopyranosyl]oxy}-14-oxa-6,10,17-triazanonacosan-29-oate Benzyl 12-({1,3-bis[3-oxo-3-(pentafluorophenoxy)propoxy]propan-2-yl}amino)-12-oxododecanoate (150 mg, 0.172 mmol), N-(3-aminopropyl)-5-{[3,4,6-tri-O-acetyl-2-(acetylamino)-2-deoxy-β-D-galactopyranosyl]oxy}pentanamide acetate salt (233 mg, 0.414 mmol) and N,N-diisopropylethylamine (0.15 ml, 0.862 mmol) were dissolved in dichloromethane (3.5 mL) and stirred at ambient temperature for 64 h. The reaction mixture was concentrated and heptane was added and the residue concentrated once again (×3). The resultant residue was purified by silica gel chromatography (4-14% methanol in dichloromethane) to afford the desired product as a colorless glass (175 mg, 67%). The compound was then dissolved in a mixture of acetonitrile and water (1:1, 30 mL) and freeze dried to afford a white solid. $^1$H NMR (400 MHz, CDCl$_3$) δ ppm 7.42-7.37 (m, 5H), 7.15 (br.s., 2H) 6.94-6.84 (m, 3H), 6.51-6.45 (m, 2H), 5.38 (d, 2H), 5.20 (d, 2H), 5.14 (s, 2H), 4.65-4.57 (m, 2H), 4.27-4.06 (m, 8H), 4.02-3.90 (m, 4H), 3.73 (br.s., 6H), 3.63-3.42 (m, 8H), 3.37-3.26 (m, 8H), 2.47 (br.s., 5H), 2.38 (t, 3H), 2.34-2.15 (m, 15H), 2.12 (s, 6H), 2.03 (s, 6H), 1.98 (s, 6H), 1.78 (br.s., 4H) 1.28 (d, 14H).

Step 4: Example 35. 10% Pd/C (30 mg, wet) was added to a solution of Benzyl-5,11,18-trioxo-16-{[3-oxo-3-({3-[(5-{[3,4,6-tri-O-acetyl-2-(acetylamino)-2-deoxy-β-D-galactopyranosyl]oxy}pentanoyl)amino]propyl}amino)propoxy]methyl}-1-{[3,4,6-tri-O-acetyl-2-(acetylamino)-2-deoxy-β-D-galactopyranosyl]oxy}-14-oxa-6,10,17-triazanonacosan-29-oate (282 mg, 0.187 mmol) in methanol (5 mL). The mixture was placed in the HelCat under 50 psi hydrogen and stirred at ambient temperature for 16 h. The head space was then purged with nitrogen (×3) and the solution was filtered through a 0.2 um nylon syringe filter. The filter was washed with methanol and the combined filtrates were concentrated to afford the title compound as a white foam which was then dissolved in a mixture of acetonitrile and water (1:1, 20 mL) and freeze dried to a white solid (262 mg, 99%). $^1$H NMR (400 MHz, CD$_3$OD) δ ppm 5.33 (d, 2H), 5.08-5.04 (m, 2H), 4.55 (d, 2H) 4.21-3.98 (m, 10H), 3.91-3.83 (m, 2H), 3.69 (t, 4H) 3.60-3.44 (m, 8H), 3.24-3.19 (m, 8H), 2.43 (t, 4H), 2.31-2.16 (m, 8H), 2.14 (s, 6H), 2.06-2.00 (m, 6H), 1.94 (d, 10H), 1.73-

1.55 (m, 15H), 1.40-1.28 (m, 12H). LCMS (m/z) for $C_{65}H_{108}N_7O_{27}^+$ (M+H)$^+$ 1419.7; retention time=1.34 min (UPLC 3.0 min run)

5,11,18-trioxo-1-{[3,4,6-tri-O-acetyl-2-(acetylamino)-2-deoxy-β-D-galactopyranosyl]oxy}-14-oxa-6,10,17-triazanonacosan-29-oic acid

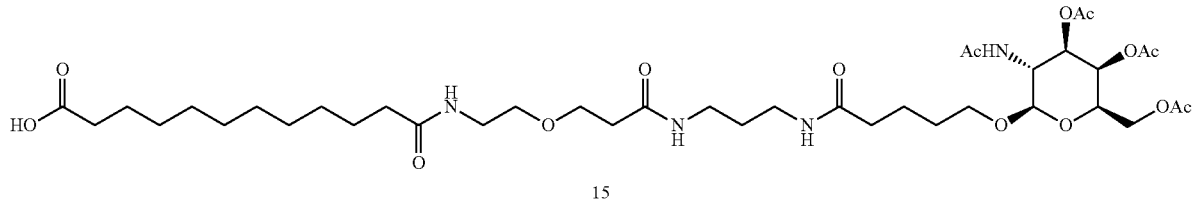

15

Reaction Scheme

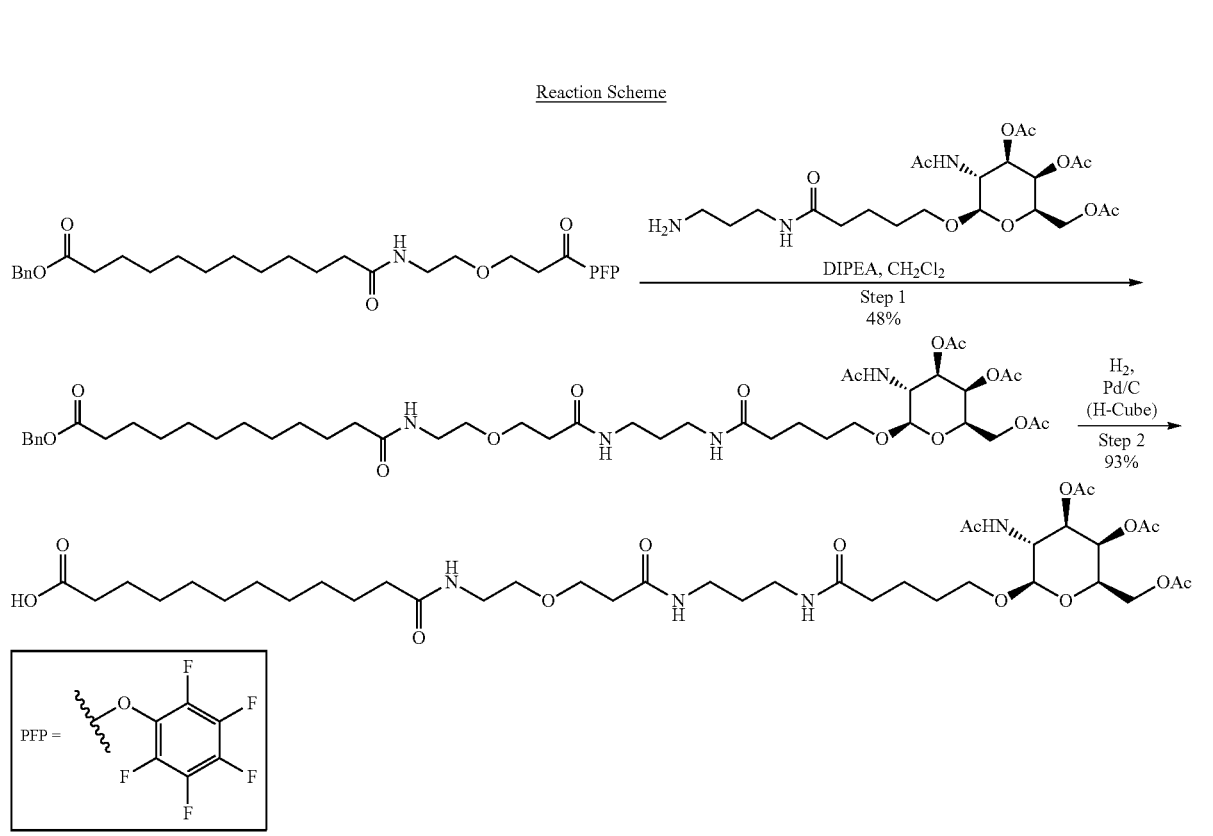

Step 1: Benzyl 5,11,18-trioxo-1-{[3,4,6-tri-O-acetyl-2-(acetylamino)-2-deoxy-β-D-galactopyranosyl]oxy}-14-oxa-6,10,17-triazanonacosan-29-oate N-(3-aminopropyl)-5-[3,4,6-tri-O-acetyl-2-(acetylamino)-2-deoxy-β-D-galactopyranosyl]oxy pentanamide acetate salt (159 mg, 0.264 mmol) was added to a solution of benzyl 12-oxo-12-({2-[3-oxo-3-(pentafluorophenoxy)propoxy]ethyl}amino)dodecanoate (164 mg, 0.291 mmol) and N,N-diisopropylethylamine (200 uL, 1.32 mmol) in dichloromethane (5 mL) and the reaction was stirred at ambient temperature for 16 h. The reaction mixture was concentrated and the resultant residue was taken up in heptane and concentrated (3×10 ml). The resultant residue was purified by silica gel chromatography (0-10% methanol in dichloromethane) to afford the title compound as colorless glass (116 mg, 48%). LCMS (m/z) for $C_{48}H_{72}N_4O_{15}^+$ (M+H)$^+$ 921.8; retention time=0.91 min (UPLC 1.3 min run).

Step 2: Example 36. 10% Pd/C (25 mg, wet) was added under nitrogen to a solution of benzyl5,11,18-trioxo-1-{[3, 4,6-tri-O-acetyl-2-(acetylamino)-2-deoxy-β-D-galactopyranosyl]oxy}-14-oxa-6,10,17-triazanonacosan-29-oate (196 mg, 0.213 mmol) in methanol (5 mL). The reaction was placed in the HelCat under 50 psi hydrogen and stirred at ambient temperature for 16 h. The head space was purged with nitrogen (×3) and the solution was filtered through a 0.2 um nylon syringe filter. The filter was washed with methanol and the combined filtrates were concentrated to afford the title compound as a colorless glass which was then dissolved in a mixture of acetonitrile and water (1:1, 20 mL) and freeze dried to afford a white solid (165 mg, 93%). $^1$H NMR (400 MHz, CD$_3$OD) δ ppm 8.01-7.91 (m, 1H), 5.33 (d, 1H), 5.06 (m, 1H), 4.55 (d, 1H), 4.19-3.98 (m, 4H), 3.91-3.84 (m, 1H), 3.76-3.67 (m, 2H), 3.57-3.47 (m, 4H), 3.25-3.18 (m, 4H), 2.44 (t, 2H), 2.30-2.16 (m, 6H), 2.14 (s, 3H), 2.02 (s, 3H), 1.95 (s, 3H), 1.93 (s, 3H), 1.73-1.54 (m, 10H), 1.39-1.28 (m, 12H). LCMS (m/z) for $C_{39}H_{67}N_4O_{15}^+$ (M+H)$^+$ 831.8; retention time=1.30 min (UPLC 3.0 min run.

Example 37. Synthesis of Oligonucleotides

Synthesis of various oligonucleotides is described herein. The two digits following the decimal after the WV oligonucleotide designation indicate a batch number. For example, WV-7107.03 indicates batch 03 of WV-7107.

Example 37A. Synthesis of WV-7107 and WV-6558

WV-6558 which has the sequence 5'-Mod001L001Aeo*SGeom5CeoTeoTeo*RC*ST*ST*SG*RT*SC*SC*RA*SG*SC*RTeoTeoTeoAeo*S Teo-3' (SEQ ID NO: 1136) is a GalNAc conjugate of WV-7107 which has the sequence 5'-L001Aeo*SGeom5CeoTeoTeo*RC*ST*ST*SG*RT*SC*SC*RA*SG*SC*RTeoTeoTeoAeo*STeo-3'. (SEQ ID NO: 1142). The GalNAc conjugation step is performed on WV-7107 to make WV-6558.

Solid Phase Synthesis of WV-7107:

Synthesis of WV-7107 was performed on an ÄKTA OP100 synthesizer (GE healthcare) using a 6.0 cm diameter stainless steel column reactor on a 3300 μmol scale using CPG support (Loading 72 umol/g). The process consists of five steps; detritylation, coupling, capping 1, oxidation/thiolation and capping 2. Detritylation was performed using 3% DCA in toluene with a UV watch command set at 436 nm. Following detritylation, at least 4 column volumes (CV) of ACN was used to wash off the detritylation reagent.

All phosphoramidite and activator solutions (CMIMT and ETT) were prepared and dried over 3A molecular sieves for at least 4 hours prior to synthesis.

Stereo-defined amidite coupling was performed using 0.2 M amidite solutions and 0.6 M CMIMT. All amidites were dissolved in ACN except dC-L and dC-D amidites which were dissolved in isobutyronitrile (IBN). Stereo-defined MOE amidites were dissolved in 20% IBN/ACN v/v. CMIMT was dissolved in ACN. Using 4 equivalents, coupling was performed by mixing 40% (by volume) of the respective amidite solution with 67% of the CMIMT activator in-line prior to addition to the column. The coupling mixture was then recirculated for a minimum of 10 minutes to maximize the coupling efficiency.

Standard stereorandom amidite coupling was performed using 0.2 M amidite solutions and 0.6 M ETT in ACN. MOE-T amidite was dissolved 20% IBN/ACN v/v. Using 4 equivalents, coupling was performed by mixing 40% (by volume) of the respective amidite solution with 60% of the ETT activator in-line prior to addition to the column. The coupling mixture was then recirculated for a minimum of 6 minutes to maximize the coupling efficiency.

After coupling in both instances, the column was washed with 2CV of ACN.

For stereo-defined couplings, the column was then treated with Capping 1 solution (Acetic Anhydride, Lutidine, ACN) mixture for 1 CV to in 4 minutes acetylate the Chiral axillary amine. Following this step the column was washed with ACN for at least 2 CV. Thiolation was then performed with 0.2 M Xanthane Hydride in pyridine with a contact time of 6 min for 2 CV. After a 2 CV thiolation wash step using ACN, capping 2 was performed using 0.5 CV of Capping A and Capping B reagents mixed inline (1:1) followed by a 2 CV ACN wash.

For stereorandom coupling cycles, there is no Capping 1 step. Oxidation was performed using 50 mM Iodine in/Pyridine/H2O (9:1) for 2.5 min and 3.5 equivalents. After a 2CV ACN wash, capping 2 was performed using 0.5 CV of Capping A and Capping B reagents mixed inline (1:1) followed by a 2 CV ACN wash.

Cleavage and Deprotection of WV-7107:

67% (or 2200 μmop of the material synthesized above was used in this step. The DPSE protecting groups on WV-7107 were removed by treating the oligo bound solid support with a 1M solution of TEA.HF made by mixing DMSO, Water, TEA and TEA.3HF in a v/v ratio of 39:8:1:2.5, to make a 100 mL solution per mmol of oligo. The mixture was then shaken at 25° C. for 6 hours in an incubator shaker. The mixture was cooled (ice bath) then 200 mL of aqueous ammonia per mmol of oligo added. The mixture was then shaken at 45° C. for 16 hours. The mixture was then filtered (0.2-1.2 μm filters) and the cake rinsed with water. The filtrate liquor was obtained and analyzed by UPLC and a purity of 30.8% FLP obtained. Quantitation was done using a Nano Drop one spectrophotometer (Thermo Scientific) and a yield of about 101,200 OD/mmol obtained.

Purification and Desalting of WV-7107:

The crude WV-7107 loaded on to an Agilent Load & Lock column (5 cm×32 cm) packed with Source 15Q (GE healthcare). Purification was performed on an ÄKTA 150 Pure (GE Healthcare) using 20 mM NaOH and 2.5 M NaCl as eluents. Fractions were analyzed and pooled to obtain material with a purity ≥70%. The purified material was then desalted on 2K re-generated cellulose membranes followed by lyophilization to obtain WV-7107 as a white powder. This material was then used for conjugation experiments.

Example 37B. Synthesis of WV-6558

Protocol for GalNAc Conjugation
Precursor material: WV-7107.03
Final Conjugated product: WV-6558.03
Reagents for Conjugation

TABLE 2

| Aqueous Oligonucleotide Solution | | | | | |
|---|---|---|---|---|---|
| Oligonucleotide/ Reagents | MW | Equivalent to Oligonucleotide | mg | μL | μmole |
| WV-7107.03 | 7191.7 | 1 | 400 | — | 55.62 |
| Tri-antennary GalNAc Lot: GL-N12-26 | 2005 | 1.6 | 178.4 | — | 88.99 |
| HATU P/N Sigma 445460 Lot: MKBV8272V | 382 | 1.4 | 29.75 | — | 77.87 |
| DIEA P/N Sigma 387649 Lot: SHBG2052V | 129 | 10.0 | — | 98.83 | 556.2 |
| Acetonitrile | — | — | — | 4000 | — |

| Oligonucleotide/Solvent | Conc (mg/mL) | Total volume (mL) | Total mg |
|---|---|---|---|
| WV-7107.01 in water | 50 | 8 | 400 |

Weighed 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy) pentanamido)propyl)amino)-3-oxopropoxy)methyl)-5,11,18-trioxo-14-oxa-6,10,17-triazanonacosan-29-oic acid (1.6 eq), and HATU (1.4 eq.) and transferred to a 50 ml plastic tube. Dissolved the material in anhydrous acetonitrile then add DIEA (d=0.742) (10 eq) into the tube. The clear mixture was stirred for 20 min at 37° C. Reconstituted the lyophilized WV-7107 sample with 8 mL water to a concentration at 50 mg/mL. Then the GalNac mixture was added to sample WV-7107 and stirred for 60 min at 37° C. The progress of the reaction was monitored by UPLC. The reaction is complete after 1 h of incubation. The solution was concentrated under vacuum (by speed vac) to remove acetonitrile and the resultant GalNAc-conjugated oligo was treated with concentrated Ammonium hydroxide (5 mL) for deprotection by incubating for 1 h at 37° C. The formation of the final product WV-6558 was confirmed by UPLC and Mass Spectrometry. The conjugated samples were purified by anion exchange chromatography. Observed Mass: 8802.4 (Deconvoluted), Target Mass: 8801.6.

Example 37C. Synthesis of WV-9542

Protocol for PFE Conjugation
Precursor material: WV-7107.02
Final Conjugated product: WV-9542.01
Reagents for Conjugation

TABLE 2

| Aqueous Oligonucleotide Solution | | | | | |
|---|---|---|---|---|---|
| Oligonucleotide/ Reagents | MW | Equivalent to Oligonucleotide | mg | µL | µmole |
| WV-7107.02 | 7191.7 | 1 | 1700 | — | 236.38 |
| Tri-antennary PFE ASGPR ligand Lot: GL-N12-58 | 2065.8 | 1.6 | 781.3 | — | 378.21 |
| HATU P/N Sigma 445460 Lot: MKBV8272V | 382 | 1.2 | 108.36 | — | 283.66 |
| DIEA P/N Sigma 387649 Lot: SHBG2052V | 129 | 10.0 | 304.93 | 420.02 | 2363.84 |
| DMF | — | — | — | 13000 | — |

| Oligonucleotide/Solvent | Conc (mg/mL) | Total volume (mL) | Total mg |
|---|---|---|---|
| WV-7107.01 in water | 60 | 13 | 1800 |

Weighed Tri-antennary PFE ASGPR ligand (18,18-bis (17-(((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-(((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid) (1.6 eq), and HATU (1.2 eq.) and transferred to a 50 mL tube. Dissolved the material in anhydrous Dimethylformamide then add DIEA (d=0.742) (10 eq) into the tube. The solution was sonicated till it became clear, and it was stirred for 20 min at 37° C. Reconstituted WV-7107 sample with 13 mL water. Then the Tri-antennary PFE ligand mixture was added to sample WV-7107 and stirred for 1 hr at 37° C. The progress of the reaction was monitored by UPLC. The reaction was incomplete after 1 hr incubation. Second addition of Tri-antennary PFE ligand (1.2 eq) and HATU (1 eq) were weighed out and dissolved in 5 mL DMF with DIEA (15 eq). Incubated the ligand for 20 min at 37° C. for activation. Then added the activated ligand to the reaction mixture and incubated for 1 hr at 37° C. The reaction completed and the formation of the final product WV-9542 was confirmed by UPLC and Mass Spectrometry. The conjugated samples were purified by anion exchange chromatography. Observed Mass: 8837.6 (Deconvoluted), Target Mass: 8837.6.

Example 37D. Synthesis of WV-9543

Protocol for PFE Conjugation
Precursor material: WV-7107.02
Final Conjugated product: WV-9543.01
Reagents for Conjugation

TABLE 2

| Aqueous Oligonucleotide Solution | | | | | |
|---|---|---|---|---|---|
| Oligonucleotide/ Reagents | MW | Equivalent to Oligonucleotide | mg | µL | µmole |
| WV-7107.02 | 7191.7 | 1 | 90 | — | 12.51 |
| Bis-antennary GalNAc Lot: PF-07075575 | 1418.59 | 2 | 35.5 | — | 25.03 |
| HATU P/N Sigma 445460 Lot: MKBV8272V | 382 | 1.8 | 8.6 | — | 22.53 |
| DIEA P/N Sigma 387649 Lot: SHBG2052V | 129 | 10.0 | 16.14 | 22.24 | 125.14 |
| Dimethylformamide | — | — | — | 1500 | — |

| Oligonucleotide/Solvent | Conc (mg/mL) | Total volume (mL) | Total mg |
|---|---|---|---|
| WV-7107.01 in water | 60 | 1.5 | 90 |

Weighed the Bis-antennary GalNAc (1-(((2R,3R,4R,5R,6R)-3-acetamido-4,5-diacetoxy-6-(acetoxymethyl)tetrahydro-2H-pyran-2-yl)oxy)-16-((3-((3-(5-(((2R,3R,4R,5R,6R)-3-acetamido-4,5-diacetoxy-6-(acetoxymethyl) tetrahydro-2H-pyran-2-yl)oxy)pentanamido)propyl)amino)-3-oxopropoxy)methyl)-5,11,18-trioxo-14-oxa-6,10,17-triazanonacosan-29-oic acid) (2.0 eq), and HATU (1.8 eq) and transferred to a 50 mL tube. Dissolved the material in anhydrous Dimethylformamide (1.5 mL) then add DIEA (d=0.742) (10 eq) into the tube. The solution was sonicated till it became clear, and it was stirred for 20 min at 37° C. Reconstituted WV-7107 sample with 1.5 mL water. Then the Bis-antennary GalNAc mixture was added to sample WV-7107 and stirred for 1 hr at 37° C. The progress of the reaction was monitored by UPLC. The reaction was completed after 1 hr incubation. The mixture was treated with concentrated Ammonium hydroxide (2 mL) for deprotection by incubating for 1 h at 37° C. Formation of the final product WV-9543 was confirmed by UPLC and Mass Spectrometry. The conjugated samples were purified by anion exchange chromatography. Observed Mass: 8342.6 (Deconvoluted), Target Mass: 8340.1.

Example 37E. Synthesis of WV-9544

Protocol for PFE Conjugation
Precursor material: WV-7107.02
Final Conjugated product: WV-9544.01
Reagents for Conjugation

TABLE 2

| Aqueous Oligonucleotide Solution | | | | | |
|---|---|---|---|---|---|
| Oligonucleotide/Reagents | MW | Equivalent to Oligonucleotide | mg | µL | µmole |
| WV-7107.02 | 7191.7 | 1 | 90 | — | 12.51 |
| Bis-antennary PFE ASGPR ligand Lot: PF-07075667 | 1190.39 | 2 | 29.8 | — | 25.03 |
| HATU P/N Sigma 445460 Lot: MKBV8272V | 382 | 1.8 | 8.6 | — | 22.53 |
| DIEA P/N Sigma 387649 Lot: SHBG2052V | 129 | 10.0 | 16.14 | 22.24 | 125.14 |
| Dimethylformamide | — | — | — | 1500 | — |

| Oligonucleotide/Solvent | Conc (mg/mL) | Total volume (mL) | Total mg |
|---|---|---|---|
| WV-7107.01 in water | 60 | 1.5 | 90 |

Weighed the Bis-antennary PFE ASGPR ligand (18-(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid) (2.0 eq), and HATU (1.8 eq) and transferred to a 50 mL tube. Dissolved the material in anhydrous Dimethylformamide (1.5 mL) then add DIEA (d=0.742) (10 eq) into the tube. The solution was sonicated till it became clear, and it was stirred for 20 min at 37° C. Reconstituted WV-7107 sample with 1.5 mL water. Then the Bis-antennary PFE ASGPR ligand mixture was added to sample WV-7107 and stirred for 1 hr at 37° C. The progress of the reaction was monitored by UPLC. The reaction was completed after 1 hr incubation. Formation of the final product WV-9544 was confirmed by UPLC and Mass Spectrometry. The conjugated samples were purified by anion exchange chromatography. Observed Mass: 8367.2 (Deconvoluted), Target Mass: 8364.1.

Example 37F. Synthesis of WV-9545

Protocol for PFE Conjugation
Precursor material: WV-7107.02
Final Conjugated product: WV-9545.01
Reagents for Conjugation

TABLE 2

| Aqueous Oligonucleotide Solution | | | | | |
|---|---|---|---|---|---|
| Oligonucleotide/Reagents | MW | Equivalent to Oligonucleotide | mg | µL | µmole |
| WV-7107.02 | 7191.7 | 1 | 90 | — | 12.51 |
| Mono GalNAc Lot: PF-07075574 | 830.97 | 2 | 20.8 | — | 25.03 |
| HATU P/N Sigma 445460 Lot: MKBV8272V | 382 | 1.8 | 8.6 | — | 22.53 |
| DIEA P/N Sigma 387649 Lot: SHBG2052V | 129 | 10.0 | 16.14 | 22.24 | 125.14 |
| Dimethylformamide | — | — | — | 1500 | — |

| Oligonucleotide/Solvent | Conc (mg/mL) | Total volume (mL) | Total mg |
|---|---|---|---|
| WV-7107.01 in water | 60 | 1.5 | 90 |

Weighed the Mono GalNAc (1-(((2R,3R,4R,5R,6R)-3-acetamido-4,5-diacetoxy-6-(acetoxymethyl)tetrahydro-2H-pyran-2-yl)oxy)-5,11,18-trioxo-14-oxa-6,10,17-triazanonacosan-29-oic acid) (2.0 eq), and HATU (1.8 eq) and transferred to a 50 mL tube. Dissolved the material in anhydrous Dimethylformamide (1.5 mL) then add DIEA (d=0.742) (10 eq) into the tube. The solution was sonicated till it became clear, and it was stirred for 20 min at 37° C. Reconstituted WV-7107 sample with 1.5 mL water. Then the Mono GalNAc ligand mixture was added to sample WV-7107 and stirred for 1 hr at 37° C. The progress of the reaction was monitored by UPLC. The reaction was completed after 1 hr incubation. The mixture was treated with concentrated Ammonium hydroxide (2 mL) for deprotection by incubating for 1 h at 37° C. Formation of the final product WV-9545 was confirmed by UPLC and Mass Spectrometry. The conjugated samples were purified by anion exchange chromatography. Observed Mass: 7881.3 (Deconvoluted), Target Mass: 7878.6.

Example 37G. Synthesis of WV-9546

Protocol for PFE Conjugation
Precursor material: WV-7107.02
Final Conjugated product: WV-9546.01
Reagents for Conjugation

TABLE 2

| Aqueous Oligonucleotide Solution | | | | | |
|---|---|---|---|---|---|
| Oligonucleotide/Reagents | MW | Equivalent to Oligonucleotide | mg | µL | µmole |
| WV-7107.02 | 7191.7 | 1 | 90 | — | 12.51 |
| Mono PFE ASGPR ligand Lot: PF-07075666 | 716.87 | 2 | 17.9 | — | 25.03 |
| HATU P/N Sigma 445460 Lot: MKBV8272V | 382 | 1.8 | 8.6 | — | 22.53 |
| DIEA P/N Sigma 387649 Lot: SHBG2052V | 129 | 10.0 | 16.14 | 22.24 | 125.14 |
| Dimethylformamide | — | — | — | 1500 | — |

| Oligonucleotide/Solvent | Conc (mg/mL) | Total volume (mL) | Total mg |
|---|---|---|---|
| WV-7107.01 in water | 60 | 1.5 | 90 |

Weighed the Mono PFE ASGPR ligand (1-((1S,2R,3R,4R,5S)-4-acetamido-2,3-dihydroxy-6,8-dioxabicyclo[3.2.1]

octan-1-yl)-7,13,20-trioxo-2,16-dioxa-8,12,19-triazahentriacontan-31-oic acid) (2.0 eq), and HATU (1.8 eq) and transferred to a 50 mL tube. Dissolved the material in anhydrous Dimethylformamide (1.5 mL) then add DIEA (d=0.742) (10 eq) into the tube. The solution was sonicated till it became clear, and it was stirred for 20 min at 37° C. Reconstituted WV-7107 sample with 1.5 mL water. Then the Mono GalNAc ligand mixture was added to sample WV-7107 and stirred for 1 hr at 37° C. The progress of the reaction was monitored by UPLC. The reaction was completed after 1 hr incubation. Formation of the final product WV-9546 was confirmed by UPLC and Mass Spectrometry. The conjugated samples were purified by anion exchange chromatography. Observed Mass: 7893.1 (Deconvoluted), Target Mass: 7890.6.

Example 37H. IEX Purification Condition

For sample WV-9542

| Buffer A | 20 mM Sodium Hydroxide | |
|---|---|---|
| Buffer B | 2.5 N sodium chloride in 20 mM Sodium hydroxide | |
| Column | 2.5 cm × 33 cm Source 15Q | |
| Gradient | % B | Column Vol (160 mL) |
| | 0 | 2 |
| | 0-15 | 2 |
| | 15 | 1 |
| | 15-90 | 15 |
| | 100 | 1 |

For sample WV-6558, WV-9542- WV-9546

| Buffer A | 20 mM Sodium Hydroxide | |
|---|---|---|
| Buffer B | 2.5 N sodium chloride in 20 mM Sodium hydroxide | |
| Column | 2.0 cm × 10 cm Source 15Q | |
| Gradient | % B | Column Vol (160 mL) |
| | 0 | 2 |
| | 0-20 | 5 |
| | 20 | 1 |
| | 20-90 | 15 |
| | 100 | 1 |

Example 38. Synthesis of Ligand

Synthesis of 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic acid

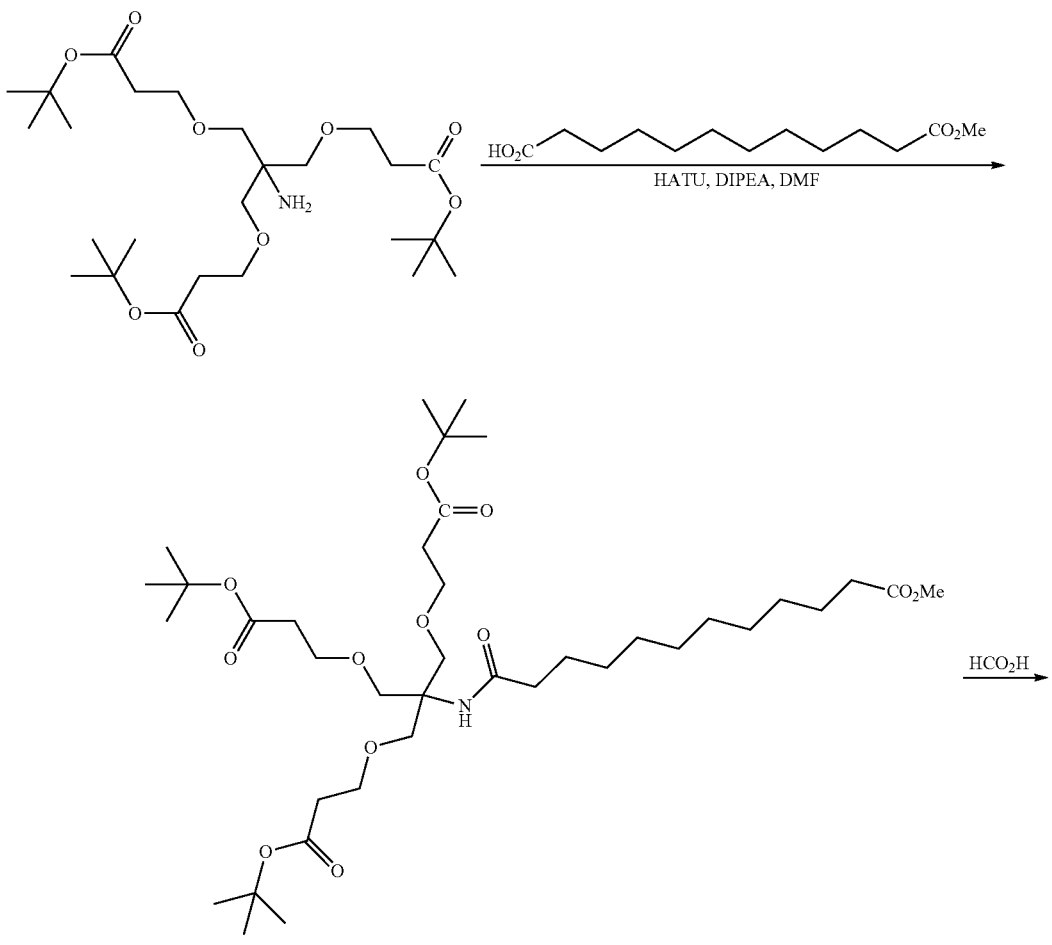

71%

-continued
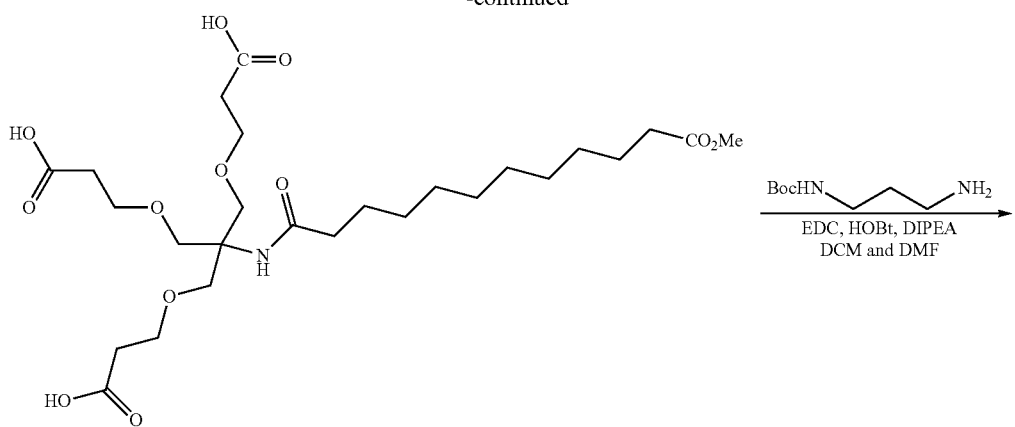
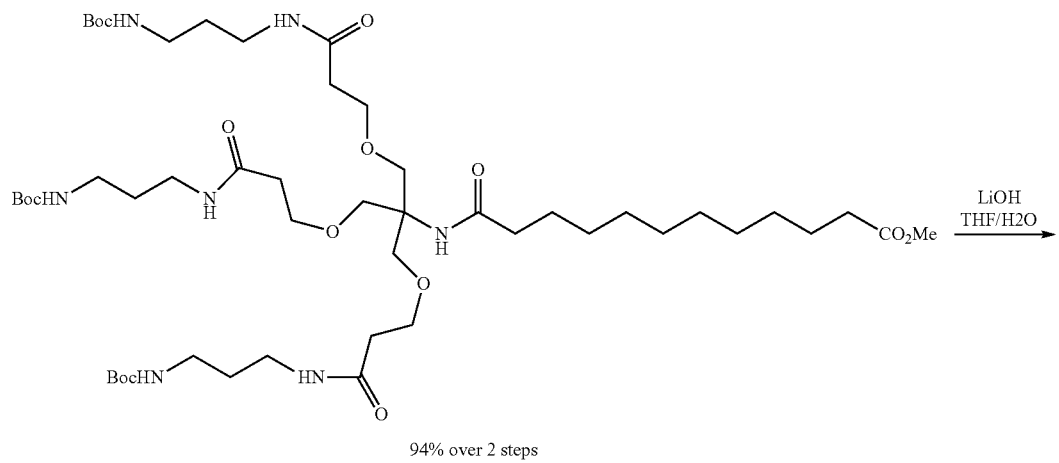
94% over 2 steps
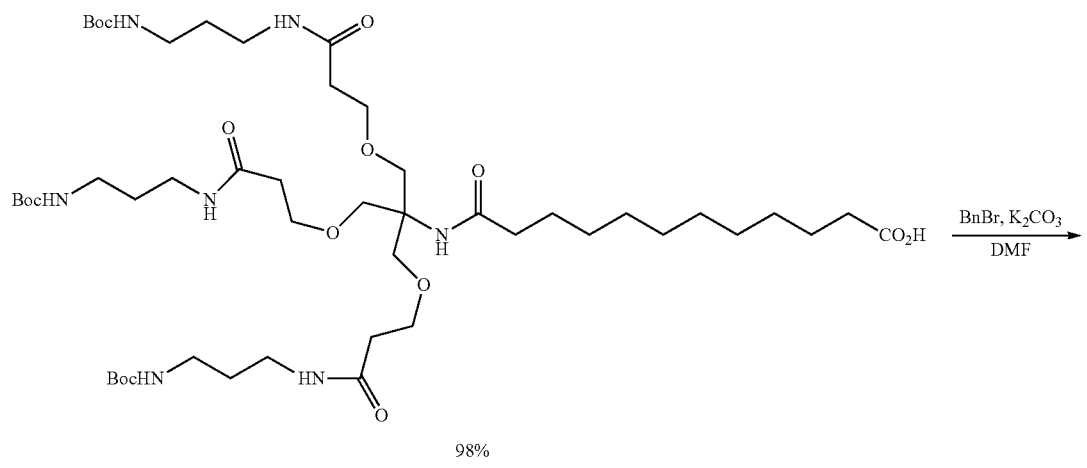
98%

-continued
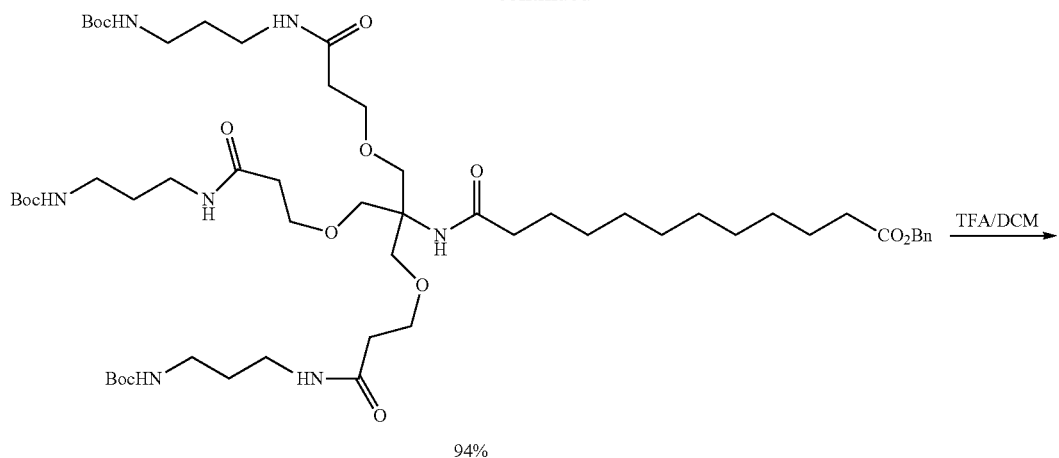
94%
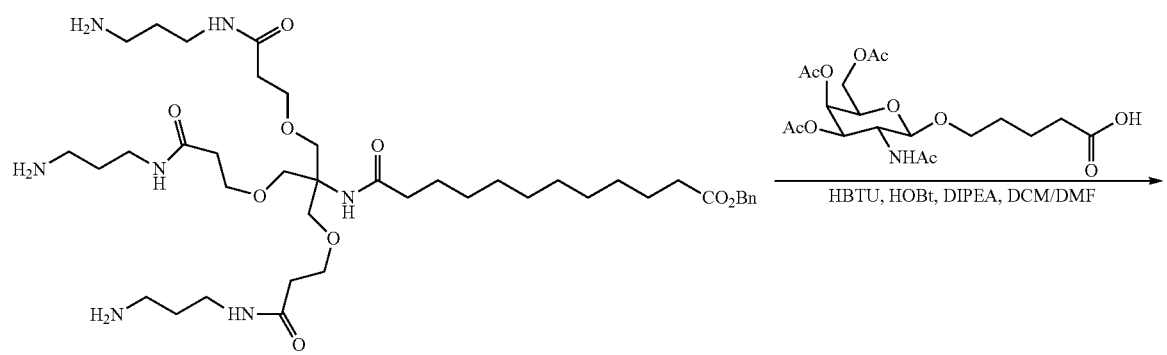
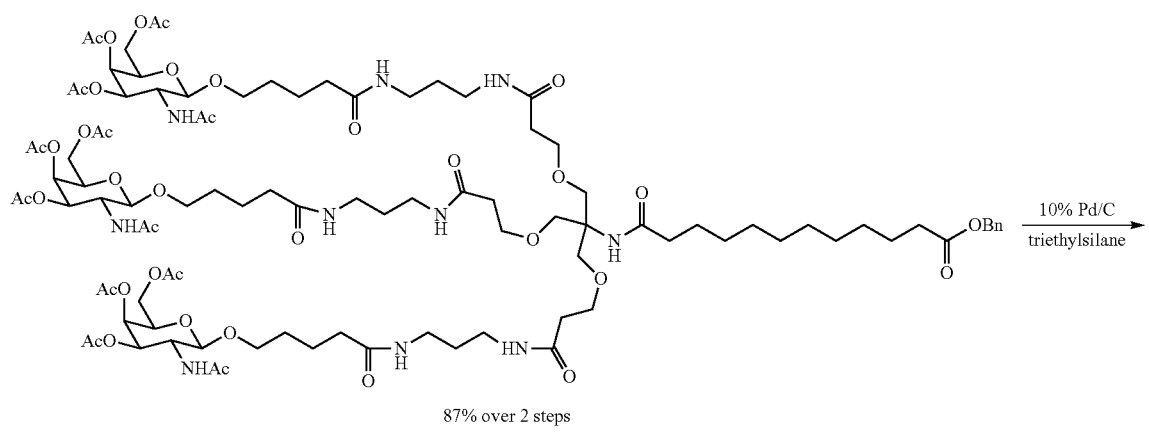
87% over 2 steps

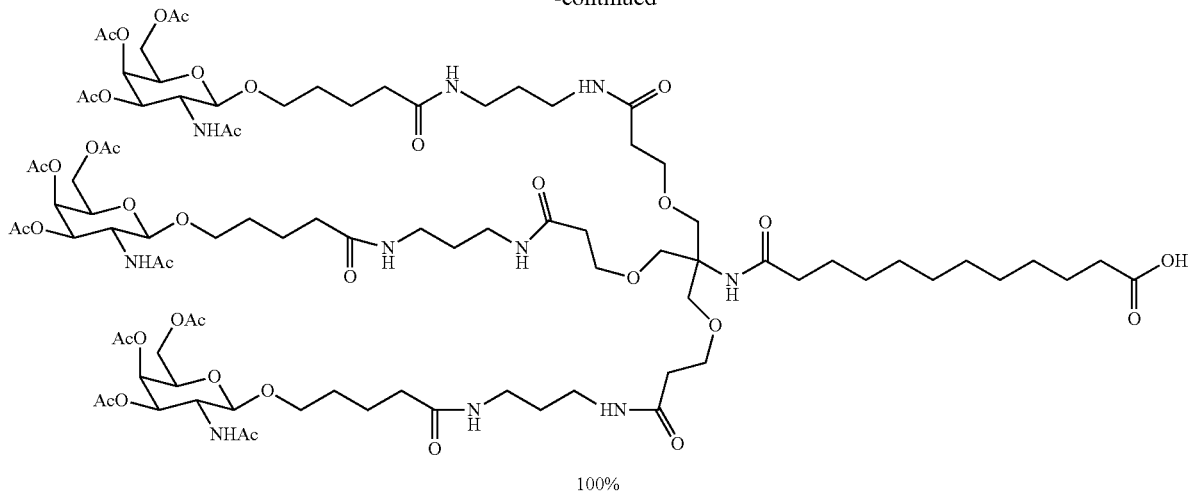

100%

Step 1: To a solution of di-tert-butyl 3,3'-((2-amino-2-((3-(tert-butoxy)-3-oxopropoxy)methyl)propane-1,3-diyl)bis(oxy))dipropanoate (5.0 g, 9.89 mmol) and 12-methoxy-12-oxododecanoic acid (2.416 g, 9.89 mmol) in DMF (45 mL) was added HATU (3.76 g, 9.89 mmol) and DIPEA (2.58 ml, 14.83 mmol). The reaction mixture was stirred at room temperature for 5 hrs. Solvent was concentrated under reduced pressure, and diluted with brine, extracted with EtOAc, dried over anhydrous sodium sulfate, and concentrated to give a residue, which was purified by ISCO (120 g gold silica gel cartridge) eluting with 10% EtOAc in hexane to 40% EtOAc in hexane to give di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.13 g, 7.01 mmol, 70.9% yield) as a colorless oil. $^1$H NMR (400 MHz, Chloroform-d) δ 6.03 (s, 1H), 3.74-3.61 (m, 15H), 2.45 (t, J=6.3 Hz, 6H), 2.31 (td, J=7.5, 3.9 Hz, 2H), 2.19-2.10 (m, 2H), 1.64-1.59 (m, 4H), 1.46 (s, 27H), 1.32-1.24 (m, 12H); MS (ESI), 732.6 (M+H)+.

Step 2: A solution of di-tert-butyl 3,3'-((2-((3-(tert-butoxy)-3-oxopropoxy)methyl)-2-(12-methoxy-12-oxododecanamido)propane-1,3-diyl)bis(oxy))dipropanoate (5.0 g, 6.83 mmol) in formic acid (50 mL) was stirred at room temperature for 48 hrs. Solvent was evaporated under reduced pressure, co-evaporated with toluene (3×) to give a white solid, which was dried under high vacuum for 2 days. LC-MS and H NMR showed the reaction is not complete. The crude product was redissolved in formic acid (50 mL). The reaction mixture was stirred at room temperature for 24 hrs. LC-MS showed the reaction was complete. Solvent was evaporated under reduced pressure, co-evaporated with toluene (3×), dried over high vacuum to give 3,3'-((2-((2-carboxyethoxy)methyl)-2-(12-methoxy-12-oxododecanamido)propane-1,3-diyl)bis(oxy))dipropanoic acid (4.00 g) as a white solid. MS (ESI): 562.4 (M−H)⁻.

Step 3: A solution of 3,3'-((2-((2-carboxyethoxy)methyl)-2-(12-methoxy-12-oxododecanamido)propane-1,3-diyl)bis(oxy))dipropanoic acid (3.85 g, 6.83 mmol) and HOBt (3.88 g, 28.7 mmol) in DCM (60 mL) and DMF (15 mL) at 0° C. was added tert-butyl (3-aminopropyl)carbamate (4.76 g, 27.3 mmol), EDAC HCl salt (5.24 g, 27.3 mmol) and DIPEA (8.33 ml, 47.8 mmol). The reaction mixture was stirred at 0° C. for 15 minutes and at room temperature for 20 hrs. LC-MS showed the reaction was not complete. t-Butyl (3-aminopropyl) carbamate (1.59 g, 9.12 mmol) and EDC HCl salt (1.75 g, 9.13 mol) was added into the reaction mixture. The reaction mixture was continually stirred at room temperature for 4 hrs. Solvent was evaporated to give a residue, which was dissolved in EtOAc (300 mL), washed with water (1×), saturated sodium bicarbonate (2×), 10% citric acid (2×) and water, dried over sodium sulfate, and concentrated to give a residue which was purified by ISCO (80 g gold cartridge) eluting with DCM to 30% MeOH in DCM to give methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.61 g, 6.40 mmol, 94% yield over 2 steps) as a white solid. MS (ESI): 1033.5 (M+H)+.

Step 4: To a solution of methyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.56 g, 6.35 mmol) in THF (75 mL) was added aq. LiOH (0.457 g, 19.06 mmol) in water (25 mL). The mixture was stirred at room temperature for overnight. LC-MS showed the reaction was completed. Solvent was evaporated, acidified using 1 N HCl (45 mL), extracted with DCM (3×), dried over anhydrous sodium sulfate, concentrated to give 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol, 98% yield) as a white solid. MS (ESI): 1019.6 (M+H)⁺.

Step 5: To a solution of 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oic acid (6.31 g, 6.20 mmol) and (bromomethyl)benzene (1.272 g, 7.44 mmol) in DMF (40 mL) was added K₂CO₃ (2.57 g, 18.59 mmol). The mixture was stirred at 40° C. for 4 hrs and at room temperature for overnight. Solvent was evaporated under reduced pressure. The reaction mixture was diluted with EtOAc, washed with water, dried over anhydrous sodium sulfate, concentrated under reduced pressure to give a residue, which was purified by ISCO (80 g cartridge) eluting with DCM to 30% MeOH in DCM to give benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (6.41 g, 5.78 mmol, 93% yield) as a colorless oil. $^1$H NMR (400 MHz, DMSO-d₆) δ 7.80 (t, J=5.7 Hz, 3H), 7.39-7.30 (m, 5H), 6.95 (s, 1H), 6.74 (t, J=5.8 Hz, 3H), 5.07 (s, 2H), 3.53 (J, J=7.3 Hz, 6H), 3.51 (s, 6H), 3.02 (q, J=6.7 Hz, 6H), 2.94-2.85 (m, 6H), 2.29 (dt, J=26.1, 6.9 Hz, 8H), 2.02 (q, J=9.7, 8.6 Hz, 2H), 1.56-1.39 (m, 10H), 1.35 (s, 27H), 1.20 (brs, 14H); MS (ESI): 1019.6 (M+H)+.

Step 6: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazaoctacosan-28-oate (2.42 g, 2.183 mmol) in DCM (40 mL) was added 2,2,2-trifluoroacetic acid (8 ml, 105 mmol). The reaction mixture was stirred at room temperature for overnight. Solvent was evaporated under reduced pressure, co-evaporated with toluene (2×), triturated with ether, dried under high vacuum for overnight. Directly use TFA salt for next step.

Step 7: To a solution of 5-(((2R,3R,4R,5R,6R)-3-acetamido-4,5-diacetoxy-6-(acetoxymethyl)tetrahydro-2H-pyran-2-yl)oxy)pentanoic acid (3.91 g, 8.73 mmol), HBTU (3.48 g, 9.17 mmol) and HOBT (1.239 g, 9.17 mmol) in DCM (25 mL) was added DIPEA (6.08 ml, 34.9 mmol) followed by benzyl 12-((1,19-diamino-10-((3-((3-aminopropyl)amino)-3-oxopropoxy)methyl)-5,15-dioxo-8,12-dioxa-4,16-diazanonadecan-10-yl)amino)-12-oxododecanoate (1.764 g, 2.183 mmol) in DMF (4.0 mL). The mixture was stirred at room temperature for 5 hrs. Solvent was evaporated under reduced pressure to give a residue, which was purified by ISCO (40 g gold column) eluting with 5% MeOH in DCM for 5 column value to remove HOBt followed by 5% to 30% MeOH in DCM to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic benzyl ester (3.98 g, 87% yield) as a white solid. $^1$H NMR (400 MHz, DMSO-d6) δ 7.82-7.74 (m, 6H), 7.69 (t, J=5.6 Hz, 3H), 7.33-7.27 (m, 5H), 6.94 (s, 1H), 5.16 (d, J=3.4 Hz, 3H), 5.03 (s, 2H), 4.92 (dd, J=11.2, 3.4 Hz, 3H), 4.43 (d, J=8.4 Hz, 3H), 4.02-3.95 (m, 9H), 3.82 (dt, J=11.2, 8.8 Hz, 3H), 3.65 (dt, J=10.5, 5.6 Hz, 3H), 3.51-3.44 (m, 12H), 3.36 (dt, J=9.6, 6.0 Hz, 3H), 3.01-2.95 (m, 12H), 2.29 (t, J=7.4 Hz, 2H), 2.23 (t, J=6.3 Hz, 6H), 2.05 (s, 9H), 1.99 (t, J=7.0 Hz, 8H), 1.94 (s, 9H), 1.84 (s, 9H), 1.72 (s, 9H), 1.50-1.14 (m, 34H); MS (ESI): 1049.0 (M/2+H)+.

Step 8: To a round bottom flask flushed with Ar was added 10% Pd/C (165 mg, 0.835 mmol) and EtOAc (15 mL). A solution of Benzyl protected tris-GalNAc (1.75 g, 0.835 mmol) in methanol (15 mL) was added followed by triethylsilane (2.67 ml, 16.70 mmol) dropwise. The mixture was stirred at room temperature for 3 hrs. LC-MS showed the reaction was complete, diluted with EtOAc, and filtered through celite, washed with 20% MeOH in EtOAc, concentrated under reduced pressure to give 1-(((2R,3R,4R,5R,6R)-3-acetamido-4,5-diacetoxy-6-(acetoxymethyl)tetrahydro-2H-pyran-2-yl)oxy)-16,16-bis((3-((3-(5-(((2R,3R,4R,5R,6R)-3-acetamido-4,5-diacetoxy-6-(acetoxymethyl)tetrahydro-2H-pyran-2-yl)oxy)pentanamido)propyl)amino)-3-oxopropoxy)methyl)-5,11,18-trioxo-14-oxa-6,10,17-triazanonacosan-29-oic acid (1.67 g, 0.832 mmol, 100% yield) as a white solid. $^1$H NMR (400 MHz, DMSO-d$_6$) δ 11.95 (s, 1H), 7.83-7.74 (m, 6H), 7.69 (t, J=5.7 Hz, 3H), 6.93 (s, 1H), 5.16 (d, J=3.4 Hz, 3H), 4.92 (dd, J=11.2, 3.4 Hz, 3H), 4.43 (d, J=8.4 Hz, 3H), 4.01-3.94 (m, 9H), 3.82 (dt, J=11.3, 8.8 Hz, 3H), 3.66 (dt, J=10.7, 5.6 Hz, 3H), 3.54-3.43 (m, 12H), 3.41-3.33 (m, 3H), 3.03-2.94 (m, 12H), 2.24 (t, J=7.4 Hz, 10H), 2.14 (t, J=7.4 Hz, 2H), 2.06 (s, 9H), 2.00 (t, J=7.2 Hz, 8H), 1.95 (s, 9H), 1.84 (s, 9H), 1.73 (s, 9H), 1.51-1.14 (m, 34H). MS (ESI): 1003.8 (M/2+H)+.

Example 39. Synthesis of Ligand

Synthesis of 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic

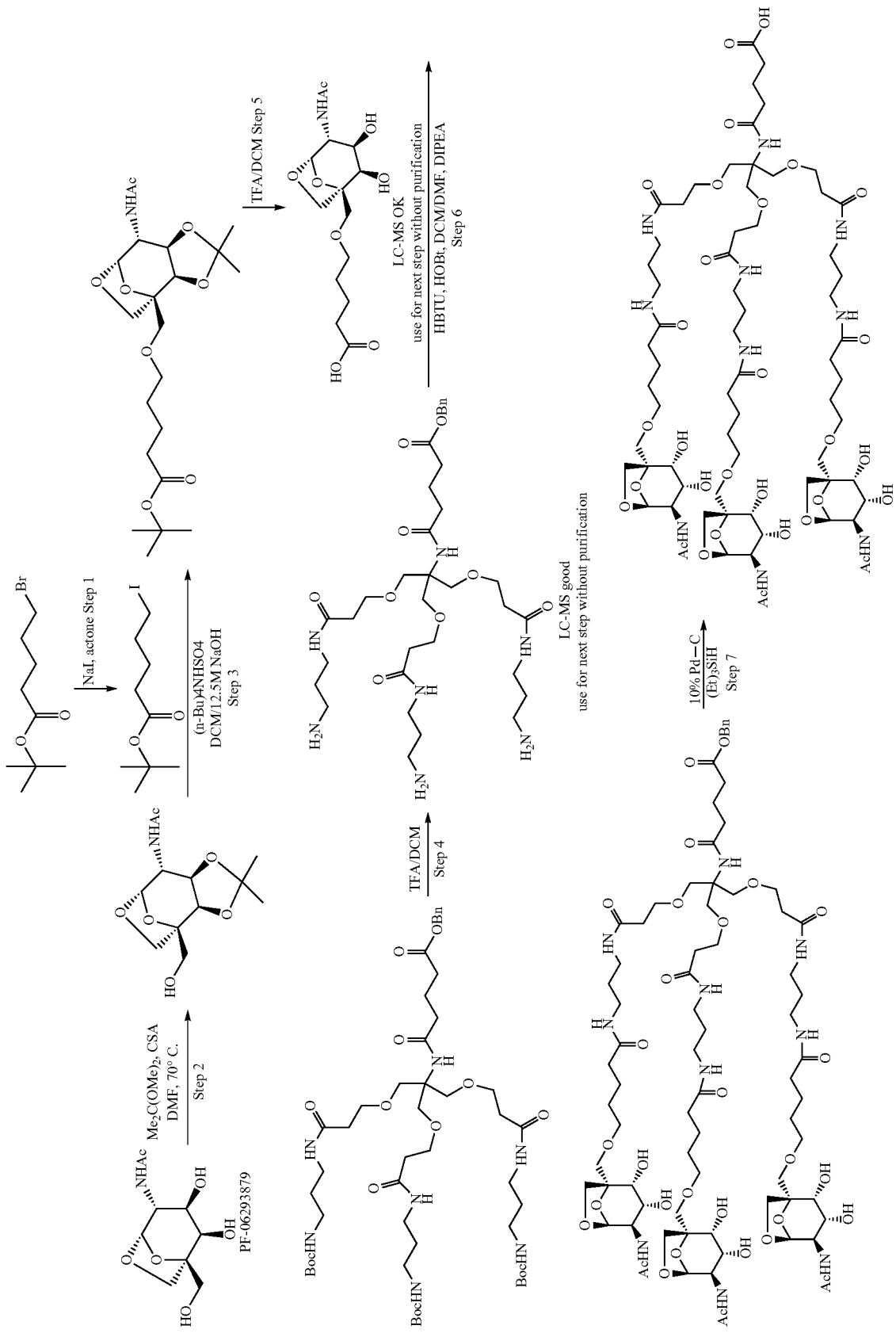

Step 1: To a solution of tert-butyl 5-bromopentanoate (4.0 g, 16.87 mmol) in acetone (80 mL) was added NaI (7.59 g, 50.6 mmol). The reaction mixture was stirred at 57° C. for 2 hrs, filtered, and washed with EtOAc. Solvent was evaporated under reduced pressure to give a residue, which was dissolved in EtOAc, washed with water, brine, dried over $Na_2SO_4$, concentrated to give a residue, which was purified by ISCO (40 g column) eluting with 20% EtOAc in hexane to 50% EtOAc in hexane to give tert-butyl 5-iodopentanoate 6 (4.54 g, 15.98 mmol, 95% yield) as a yellow oil. $^1H$ NMR (500 MHz, Chloroform-d) δ 3.19 (t, J=6.9 Hz, 2H), 2.24 (t, J=7.3 Hz, 2H), 1.86 (p, J=7.1 Hz, 2H), 1.70 (p, J=7.4 Hz, 2H), 1.45 (s, 9H).

Step 2: To a solution of N-((1S,2R,3R,4R,5S)-2,3-dihydroxy-1-(hydroxymethyl)-6,8-dioxabicyclo[3.2.1]octan-4-yl)acetamide (600 mg, 2.57 mmol) in DMF (15 mL) was added 2,2-dimethoxypropane (2087 µl, 17.03 mmol) followed by (+/−)-camphor-10-sulphonic acid (264 mg, 1.135 mmol). The reaction mixture was stirred at 70° C. for 24 hrs. The reaction mixture was cooled down to room temperature, and then methanol (2.5 mL) was added. The reaction mixture was stirred at room temperature for 30 minutes and neutralized with TEA (0.10 mL). The solvent was evaporated and the residue was coevaporated with toluene. The residue was purified by ISCO (24 g gold) eluting with EtOAc to 10% MeOH in EtOAc to give N-((3aR,4S,7S,8R,8aR)-4-(hydroxymethyl)-2,2-dimethylhexahydro-4,7-epoxy[1,3]dioxolo[4,5-d]oxepin-8-yl)acetamide 7 (666 mg, 2.437 mmol, 95% yield). $^1H$ NMR (500 MHz, DMSO-$d_6$) δ 8.09 (d, J=8.1 Hz, 1H), 5.15-5.05 (m, 2H), 4.26 (d, J=5.8 Hz, 1H), 4.09 (dd, J=7.3, 5.8 Hz, 1H), 3.80-3.60 (m, 5H), 1.83 (s, 3H), 1.37 (s, 3H), 1.26 (s, 3H); MS, 274.3 (M+H)+.

Step 3: To a solution of tert-butyl 5-iodopentanoate (1310 mg, 4.61 mmol) and N-((3aR,4S,7S,8R,8aR)-4-(hydroxymethyl)-2,2-dimethylhexahydro-4,7-epoxy[1,3]dioxolo[4,5-d]oxepin-8-yl)acetamide 7 (420 mg, 1.537 mmol) in DCM (10.5 mL) was added tetrabutylammonium hydrogensulfate (783 mg, 2.305 mmol) followed by 12.5 M sodium hydroxide solution (7 mL). The reaction mixture was stirred at room temperature for 24 hrs. The reaction mixture was diluted with DCM and water, extracted with DCM (2×). The organic layer was washed with 1 N HCl solution, and dried over sodium sulfate. Solvent was concentrated under reduce pressure to give a residue. The resulting crude material was added ethyl acetate (30 mL) and sonicated for 5 minutes. The result precipitate was filtered, washed with ethyl acetate (10 mL×2). LC_MS showed the filter doesn't contain desired product and was tetrabutylammonium salt. The filtrate was concentrated under reduced pressure to give a residue, which was purified by ISCO (40 g silica gel gold cartridge) eluting with 50% EtOAc in hexane to EtOAc to give tert-butyl 5-(((3aR,4S,7S,8R,8aR)-8-acetamido-2,2-dimethylhexahydro-4,7-epoxy[1,3]dioxolo[4,5-d]oxepin-4-yl)methoxy)pentanoate (0.470 g, 1.094 mmol, 71.2% yield) as a yellowish oil. $^1H$ NMR (500 MHz, Chloroform-d) δ 5.56 (d, J=9.1 Hz, 1H), 4.21 (d, J=5.9 Hz, 1H), 4.12 (dtd, J=7.7, 3.8, 1.7 Hz, 1H), 3.99 (t, J=6.3 Hz, 1H), 3.90 (d, J=9.5 Hz, 1H), 3.77 (d, J=2.0 Hz, 2H), 3.67 (d, J=9.5 Hz, 1H), 3.52 (ddt, J=30.5, 9.2, 5.8 Hz, 2H), 2.23 (t, J=7.1 Hz, 2H), 2.03 (d, J=14.5 Hz, 3H), 1.65-1.55 (m, 7H), 1.44 (s, 9H), 1.35 (s, 3H); MS, 452.4 (M+Na)+.

Step 4: To a solution of benzyl 15,15-bis(13,13-dimethyl-5,11-dioxo-2,12-dioxa-6,10-diazatetradecyl)-2,2-dimethyl-4,10,17-trioxo-3,13-dioxa-5,9,16-triazahenicosan-21-oate (0.168 g, 0.166 mmol) in DCM (3 mL) was added TFA (3 mL). The reaction mixture was stirred at room temperature for 3 hrs. LC-MS showed the reaction was completed. Solvent was evaporated under reduced pressure to give benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate as a colorless oil. MS, 710.5 (M+H)+. Directly use for next step without purification.

Step 5: To a solution of tert-butyl 5-(((3aR,4S,7S,8R,8aR)-8-acetamido-2,2-dimethylhexahydro-4,7-epoxy[1,3]dioxolo[4,5-d]oxepin-4-yl)methoxy)pentanoate (285 mg, 0.664 mmol) in DCM (5 mL) was added TFA (5 mL) was stirred at room temperature for 4 hrs. LC-MS showed the reaction was complete. Solvent was evaporated to give 5-(((1S,2R,3R,4R,5S)-4-acetamido-2,3-dihydroxy-6,8-dioxabicyclo[3.2.1]octan-1-yl)methoxy)pentanoic acid. MS (ESI): 334.3 (M+H)+. Directly use for next step without purification.

Step 6: To a solution of 5-(((1S,2R,3R,4R,5S)-4-acetamido-2,3-dihydroxy-6,8-dioxabicyclo[3.2.1]octan-1-yl)methoxy)pentanoic acid (221 mg, 0.664 mmol) in DCM (10 mL) was added DIPEA (2313 µl, 13.28 mmol), HBTU (208 mg, 0.548 mmol), HOBT (67.3 mg, 0.498 mmol), a solution of benzyl 5-((1,19-diamino-10-((3-((3-aminopropyl)amino)-3-oxopropoxy)methyl)-5,15-dioxo-8,12-dioxa-4,16-diazanonadecan-10-yl)amino)-5-oxopentanoate (118 mg, 0.166 mmol) (GL08-02) in DMF (3.0 mL) and DCM (5.0 mL). The reaction mixture was stirred at room temperature for overnight. LC-MS showed the desired product. Solvent was evaporated under reduced pressure to give a residue, which was purified by ISCO (24 g gold cartridge) eluting with DCM to 80% MeOH in DCM to give benzyl 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oate (272 mg, 0.164 mmol, 99% yield) (product @ tube 30 to 42 (40% MeOH in DCM to 60% MeOH in DCM) $^1H$ NMR (500 MHz, DMSO-$d_6$) δ 7.89 (d, J=7.8 Hz, 3H), 7.81 (t, J=5.7 Hz, 3H), 7.75 (s, 3H), 7.34 (q, J=7.5, 6.9 Hz, 5H), 7.05 (s, 1H), 5.07 (s, 5H), 4.83 (d, J=5.3 Hz, 3H), 4.56 (d, J=7.1 Hz, 3H), 3.73 (dd, J=23.3, 9.2 Hz, 6H), 3.64 (d, J=7.0 Hz, 6H), 3.58-3.35 (m, 27H), 3.02 (p, J=6.2 Hz, 12H), 2.33 (t, J=7.6 Hz, 2H), 2.26 (t, J=6.4 Hz, 6H), 2.10 (t, J=7.6 Hz, 2H), 2.04 (t, J=7.4 Hz, 6H), 1.82 (s, 9H), 1.72 (q, J=7.6 Hz, 2H), 1.52-1.39 (m, 18H); MS (ESI), 1656.3 (M+H)$^+$.

Step 7: To a solution of benzyl 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatracosan-24-oate (270 mg, 0.163 mmol) in EtOAc (10 mL) was added 10% Pd—C (50 mg), and MeOH (5.0 mL), and triethylsilane (1042 µl, 6.52 mmol). The reaction mixture was stirred at room temperature for 1 hr, filtered, and concentrated to give 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatracosan-24-oic acid (246 mg, 0.157 mmol, 96% yield) as a white solid. $^1H$ NMR (500 MHz, DMSO-$d_6$) δ 11.99 (brs, 1H), 7.89 (d, J=7.9 Hz, 3H), 7.82 (t, J=5.4 Hz, 3H), 7.75 (t, J=5.7 Hz, 3H), 7.03 (s, 1H), 5.07 (d, J=1.6 Hz, 3H), 4.83 (brs, 3H), 4.56 (brs, 3H), 3.79-3.68 (m, 6H), 3.64 (d, J=7.2 Hz, 6H), 3.58-3.34 (m, 27H), 3.02 (p, J=6.3 Hz, 12H), 2.27 (t, J=6.4 Hz, 6H), 2.17 (t, J=7.5 Hz, 2H), 2.08 (t, J=7.5 Hz, 2H), 2.04 (t, J=7.3 Hz, 6H), 1.82 (s, 9H), 1.65 (p, J=7.5 Hz, 2H), 1.54-1.40 (m, 18H); MS(ESI), 1566.3 (M+H)+.

Example 40. Synthesis of Ligand

Synthesis of 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid

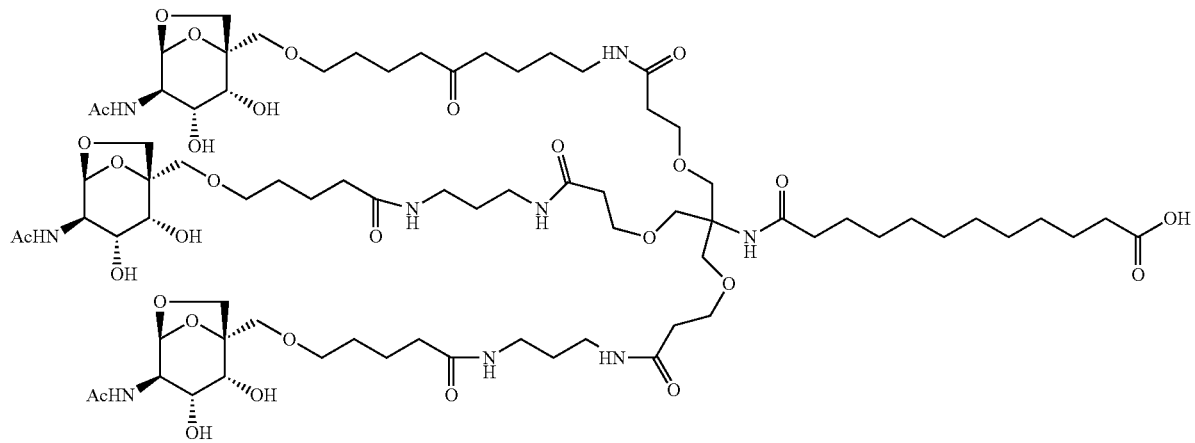 [SMILES: CC(=O)N[C@H]1[C@H]2OC[C@](COCCCCC(=O)CCCCNC(=O)CCOCC(COCCC(=O)NCCCNC(=O)CCCCOC[C@@]34CO[C@@H](O3)[C@H](NC(C)=O)[C@@H](O)[C@H]4O)(COCCC(=O)NCCCNC(=O)CCCCOC[C@@]34CO[C@@H](O3)[C@H](NC(C)=O)[C@@H](O)[C@H]4O)NC(=O)CCCCCCCCCCC(=O)O)(O2)[C@H](O)[C@@H]1O]

18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazahentriacontan-31-oic acid was synthesized using the same procedure as 18,18-bis(17-((1S,2R,3R,4R,5S)-4-acetamido-2,3-dihydroxy-6,8-dioxabicyclo[3.2.1]octan-1-yl)-5,11-dioxo-2,16-dioxa-6,10-diazaheptadecyl)-1-((1S,2R,3R,4R,5S)-4-acetamido-2,3-dihydroxy-6,8-dioxabicyclo[3.2.1]octan-1-yl)-7,13,20-trioxo-2,16-dioxa-8,12,19-triazatetracosan-24-oic acid. $^1$H NMR (400 MHz, DMSO-$d_6$) δ 7.90 (d, J=7.8 Hz, 3H), 7.83 (t, J=5.7 Hz, 3H), 7.76 (t, J=5.7 Hz, 3H), 6.98 (d, J=6.2 Hz, 1H), 5.09 (s, 3H), 3.81-3.69 (m, 6H), 3.69-3.62 (m, 6H), 3.62-3.40 (m, 24H), 3.04 (p, J=6.1 Hz, 9H), 2.28 (t, J=6.4 Hz, 4H), 2.18 (t, J=7.3 Hz, 2H), 2.06 (t, J=7.7 Hz, 6H), 1.84 (s, 6H), 1.48 (tq, J=14.9, 7.4 Hz, 16H), 1.23 (s, 8H). MS(ESI), 1664.0 (M+H)$^+$.

EQUIVALENTS

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the disclosure. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited, for example, in claimed inventions, if any, the means are not intended to be limited to the means disclosed herein for performing the recited function, but are intended to cover in scope any means, known now or later developed, for performing the recited function.

Use of ordinal terms such as "first", "second", "third", etc., in claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, use of these terms in the specification does not by itself connote any required priority, precedence, or order. Neither does use of any such terms indicate number of elements in described (including claimed) inventions.

The foregoing written specification is sufficient to enable one skilled in the art to practice any invention described in the present disclosure. The present disclosure is not to be limited in scope by examples provided, which are intended as illustrations of one or more aspects of described inventions and other functionally equivalent embodiments are within the scope of described inventions. Various modifications of described inventions in addition to those shown and described herein will become apparent to those skilled in the art from the foregoing description and fall within the scope of described inventions. Advantages and objects of described inventions are not necessarily encompassed by each embodiment of described inventions.

The foregoing written specification is considered to be sufficient to enable one skilled in the art to practice the invention. The present disclosure is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended Embodiments. The advantages and objects of the invention are not necessarily encompassed by each embodiment of the invention.

Throughout this application, various publications are referenced. The disclosures of these publications in their entireties are hereby incorporated by reference into this application for all purposes.

EMBODIMENTS
1. A compound having the Formula O1:
$$Y^1\text{-}L^1\text{-}(Z^{10})_{za} \qquad \text{O1}$$
or a pharmaceutically acceptable salt of said compound wherein Y¹ is an oligonucleotide targeting PNPLA3;
za is 1, 2, or 3; and
L¹ is a compound of Formula L11, L12, L13, L43, L44, L45, L46, L47, L48, L49, L50, L51, L52, L53 or L54 wherein the connection sites with $Y^1$ and $Z^{10}$ are indicated:
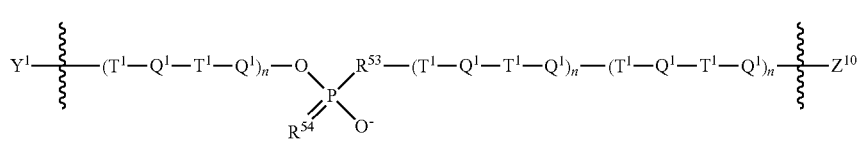
L11
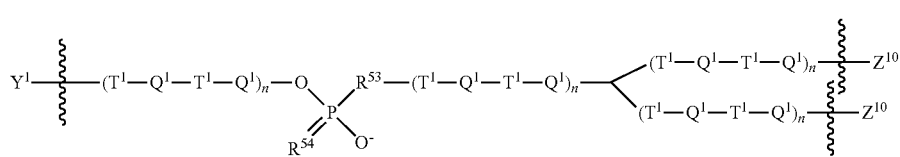
L12
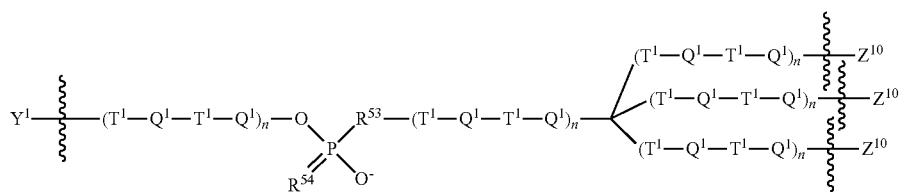
L13
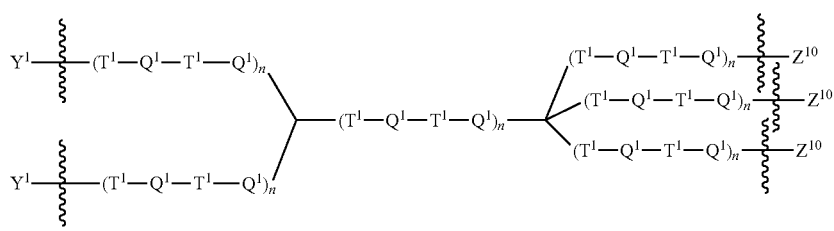
L43
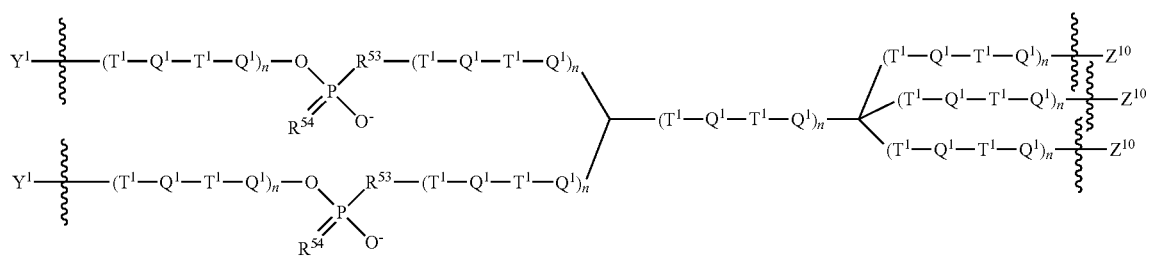
L44
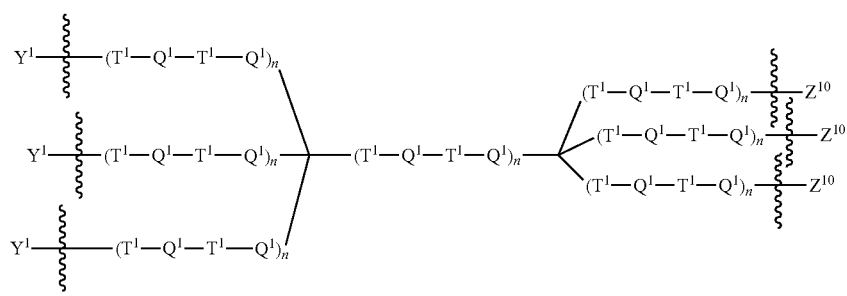
L45

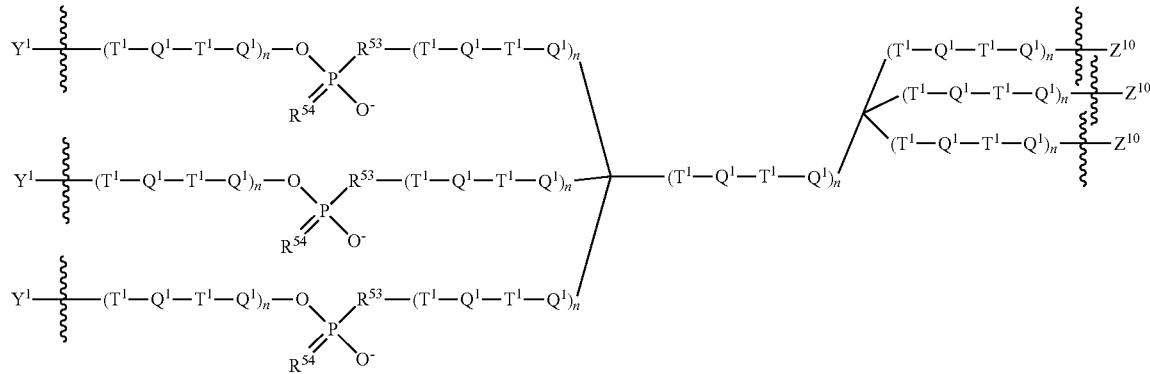
L46
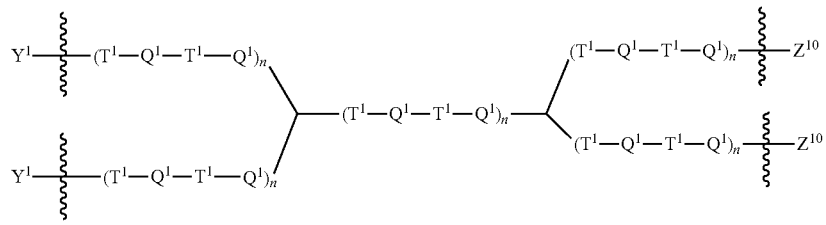
L47
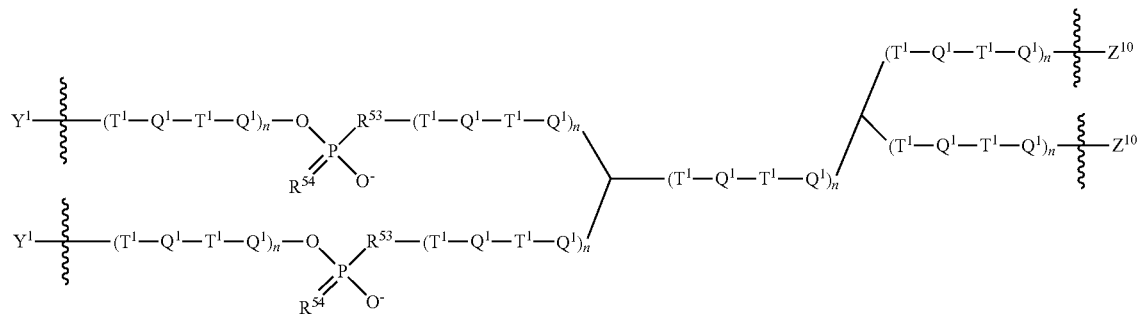
L48
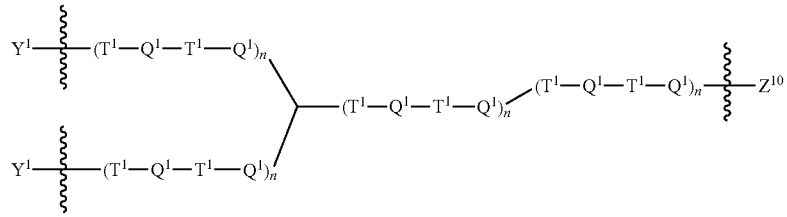
L49
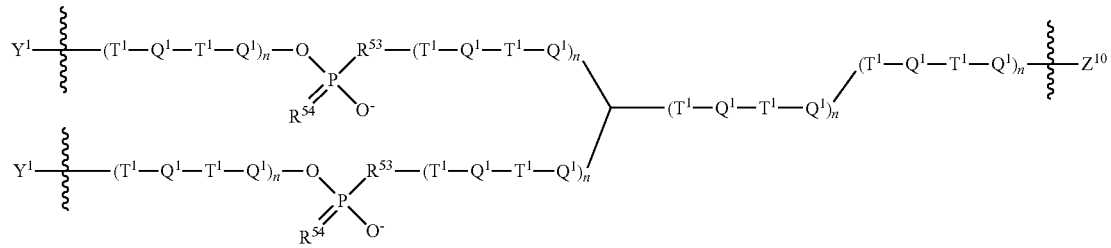
L50

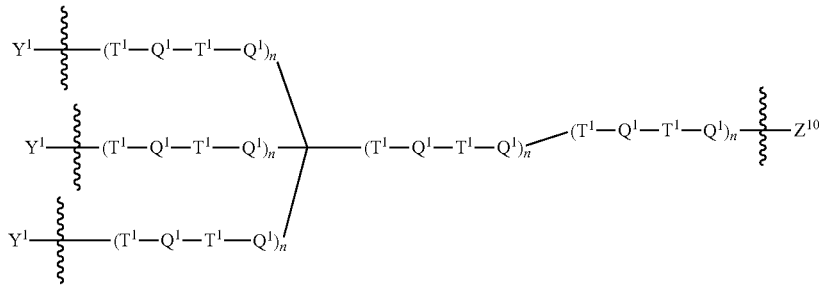
L51
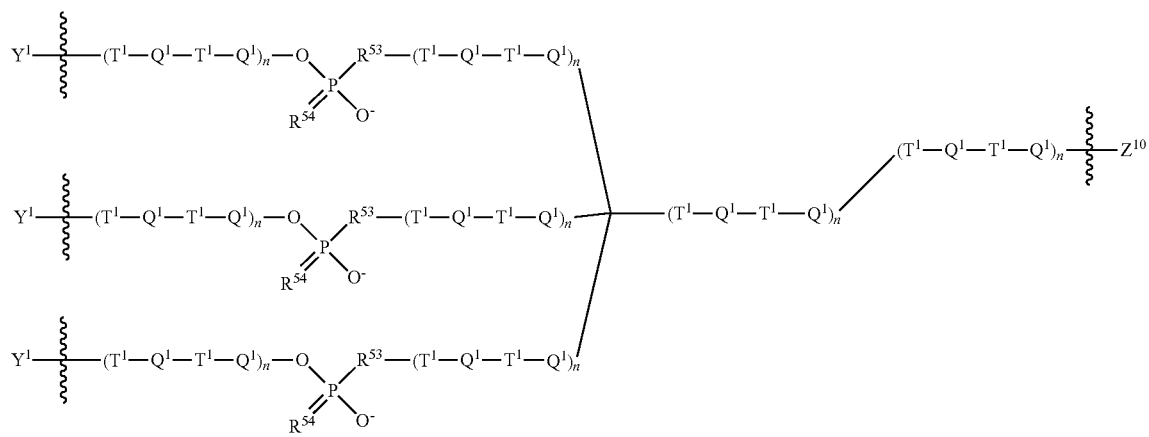
L52
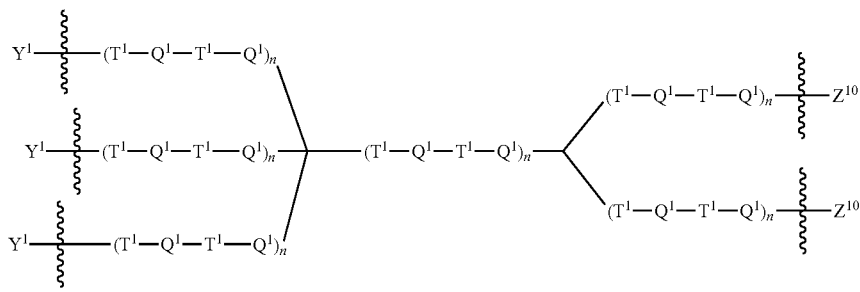
L53
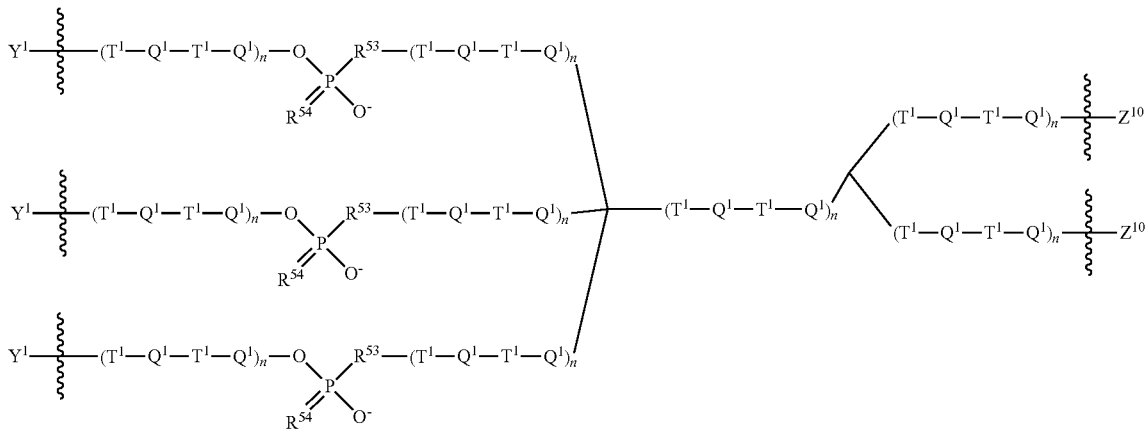
L54 wherein each T¹ is independently absent or is alkylene, alkenylene, or alkynylene, wherein one or more —CH₂— groups of the alkylene, alkenylene, or alkynylene may each independently be replaced with a heteroatom group independently selected from —O—, —S—, and —N(R⁴⁹)— wherein the heteroatom groups are separated by at least 2 carbon atoms;

each Q¹ is independently absent or is —C(O)—, —C(O)—NR⁴⁹—, —NR⁴⁹—C(O)—, —O—C(O)—NR⁴⁹—, —NR⁴⁹—C(O)—O—, —CH₂—, —NR⁴⁹C(O)NR⁴⁹—, a bivalent heteroaryl group, or a heteroatom group selected from —O—, —S—, —S—S—, —S(O)—, —S(O)₂—, and —NR⁴⁹—, wherein at least two carbon atoms separate the heteroatom groups —O—, —S—, —S—S—, —S(O)—, —S(O)₂— and —NR⁴⁹— from any other heteroatom group, or a structure of the formula:

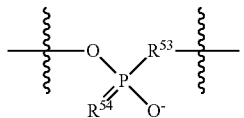

wherein R⁵³ is —O or —NH—, and R⁵⁴ is —O or —S;

each R⁴⁹ is independently —H, —(C₁-C₂₀)alkyl, or —(C₃-C₆)cycloalkyl wherein one to six —CH₂— groups of the alkyl or cycloalkyl separated by at least two carbon atoms may be replaced with —O—, —S—, or —N(R⁴⁹ᵃ)—, and —CH₃ of the alkyl may be replaced with a heteroatom group selected from —N(R⁴⁹ᵃ)₂, —OR⁴⁹ᵃ, and —S(R⁴⁹ᵃ) wherein the heteroatom groups are separated by at least 2 carbon atoms; and wherein the alkyl and cycloalkyl may be substituted with halo atoms and wherein each R⁴⁹ᵃ is independently —H, —(C₁-C₆)alkyl, or —(C₃-C₆)cycloalkyl;

R⁵³ is —O or —NH;

R⁵⁴ is —O or —S;

each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; wherein if n is greater than 0, each T¹ and each Q¹ of each (T¹-Q¹-T¹-Q¹) is independently selected; and each Z¹⁰ is independently a compound of Formula Z12, Z13, Z14, Z15, Z16, Z17, Z18, Z19, Z20, or Z21, or a geometrical or position isomer thereof, wherein the connection site with L¹ is indicated:

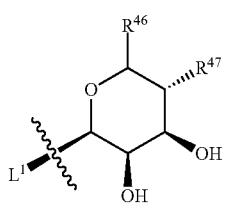

Z12

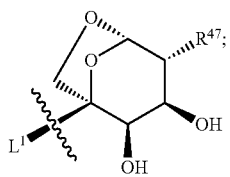

Z13

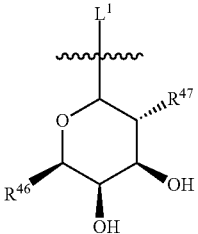

Z16 wherein each R⁴⁶ is independently —CN, —CH₂—CN, —C≡CH, —CH₂—N₃, —CH₂—NH₂, —CH₂—N(R⁵²)—S(O)₂—R⁵¹, —CH₂—CO₂H, —CO₂H, —CH₂—OH, —CH₂—SH, —CH=CH—R⁵¹, —CH₂—R⁵¹, —CH₂—S—R⁵¹, —CH₂—N(R⁵²)—R⁵', —CH₂—N(R⁵²)—C(O)—R⁵¹, —CH₂—N(R⁵²)—C(O)—O—R⁵¹, —CH₂—N(R⁵²)—C(O)—N(R⁵²)—R⁵¹, —CH₂—O—R⁵¹, —CH₂—O—C(O)—R⁵¹, —CH₂—O—C(O)—N(R⁵²)—R⁵¹, —CH₂—O—C(O)—O—R⁵¹, —CH₂—S(O)—R⁵¹, —CH₂—S(O)₂—R⁵¹, —CH₂—S(O)₂—N(R⁵²)—R⁵¹, —C(O)—NH₂, —C(O)—O—R⁵¹, —C(O)—N(R⁵²)—R⁵¹, or aryl or heteroaryl, wherein the aryl or heteroaryl is optionally substituted with R⁵¹ each R⁴⁷ is independently —OH, —N₃, —N(R⁴⁸)₂—N(R⁴⁸)—C(O)—R⁴⁸, —N(R⁴⁸)—C(O)—N(R⁴⁸)₂, —N(R⁴⁸)—C(O)—OR⁴⁸, —N(R⁴⁸)—S(O)₂—R⁴⁸, tetrazole, or triazole, wherein the tetrazole and triazole are optionally substituted with R⁴⁸;

each R⁴⁸ is independently —H, —(C₁-C₅)alkyl, halo-substituted (C₁-C₅)alkyl, halo substituted —(C₃-C₆)cycloalkyl, —(C₁-C₅)alkenyl, —(C₁-C₅)alkynyl, halo substituted —(C₁-C₅)alkenyl, halo substituted —(C₁-C₅)alkynyl, or —(C₃-C₆)cycloalkyl, wherein a —CH₂— group of the alkyl or cycloalkyl may each be independently replaced with a heteroatom group selected from —O—, —S—, and —N(R⁵²)— and —CH₃ of the alkyl may each be independently replaced with a heteroatom group selected from —N(R⁵²)₂, —OR⁵², and —S(R⁵²) wherein the heteroatom groups are separated by at least 2 carbon atoms;

each R⁵¹ is independently —H, —(C₃-C₂₀)cycloalkyl, —(C₁-C₆₀)alkenyl, —(C₁-C₆₀)alkynyl, or —(C₁-C₆₀)alkyl wherein one to six —CH₂— groups of the cycloalkyl or one to 20 —CH₂— groups of the alkyl may each be independently replaced with heteroatoms independently selected from —O—, —S—, and —N(R⁴⁹)— wherein the heteroatoms are separated by at least two carbon atoms, and —CH₃ of the alkyl may each be independently replaced with a heteroatom group selected from —N(R⁴⁹)₂, —OR⁴⁹, and —S(R⁴⁹) wherein the heteroatom groups are separated by at least 2 carbon atoms, and wherein the alkyl, alkenyl, alkynyl, and cycloalkyl may be substituted with halo atoms; and each R⁵² is independently —H, —(C₁-C₂₀)alkyl, —(C₁-C₂₀)alkenyl, —(C₁-C₂₀)alkynyl, or —(C₃-C₆)cycloalkyl wherein one to six —CH₂— groups of the alkyl or cycloalkyl separated by at least two carbon atoms may each be independently replaced with a heteroatom independently selected from —O—, —S—, or —N(R⁴⁹)—, and —CH₃ of the alkyl may each be independently replaced with a heteroatom group selected from —N(R⁴⁹)₂, —OR⁴⁹, and —S(R⁴⁹) wherein the heteroatom groups are separated by at least 2 carbon atoms; and wherein the alkyl, alkenyl, alkynyl, and cycloalkyl may be substituted with halo atoms.

2. The compound of any one of the preceding embodiments, wherein Y¹ comprises at least 15 bases.

3. The compound of any one of the preceding embodiments, wherein the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

4. The compound of any one of the preceding embodiments, wherein $Y^1$ comprises at least 1 phosphodiester internucleotidic linkage.

5. The compound of any one of the preceding embodiments, wherein $Y^1$ comprises at least 1 chirally controlled modified internucleotidic linkage.

6. The compound of any one of the preceding embodiments, $Y^1$ comprises at least 1 chirally controlled modified internucleotidic linkage which is a chirally controlled phosphorothioate.

7. The compound of any one of the preceding embodiments, wherein $Y^1$ comprises at least 1 chirally controlled modified internucleotidic linkage which is a chirally controlled phosphorothioate in the Sp configuration.

8. The compound of any one of the preceding embodiments, wherein $Y^1$ comprises at least 1 chirally controlled modified internucleotidic linkage which is a chirally controlled phosphorothioate in the Rp configuration.

9. The compound of any one of the preceding embodiments, wherein $Y^1$, wherein the chirally controlled modified internucleotidic linkage or chirally controlled phosphorothioate comprises a phosphorus chiral center which has a diastereopurity of at least 70% within the composition.

10. The compound of any one of the preceding embodiments, wherein $Y^1$, wherein the chirally controlled modified internucleotidic linkage or chirally controlled phosphorothioate comprises a phosphorus chiral center which has a diastereopurity of at least 70%, 75%, 80%, 85%, 90%, 91%, 92%, 93%, 94%, 95%, 96%, 97%, 98%, 99% or 99.5%.

11. The compound of any one of the preceding embodiments, wherein $Y^1$ comprises at least 1 sugar modification.

12. The compound of any one of the preceding embodiments, $Y^1$ comprises at least 1 base modification.

13. The compound of any one of the preceding embodiments, wherein $Y^1$ further comprises a pattern of backbone linkages.

14. The compound of any one of the preceding embodiments, wherein $Y^1$ further comprises a pattern of backbone chiral centers.

15. The compound of any one of the preceding embodiments, wherein $Y^1$ further comprises a pattern of chemical modifications.

16. The compound of any one of the preceding embodiments, wherein $Y^1$ further comprises a pattern of backbone linkages, a pattern of backbone chiral centers, and a pattern of chemical modifications.

17. The compound of any one of the preceding embodiments, wherein the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of any oligonucleotide listed in Table 1A.

18. The compound of any one of the preceding embodiments, wherein the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of an oligonucleotide listed in Table 1A the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

19. The compound of any one of the preceding embodiments, wherein the oligonucleotide is capable of mediating a decrease in the expression, level and/or activity of a PNPLA3 target gene or a gene product thereof.

20. The compound of any one of the preceding embodiments, wherein the oligonucleotide is capable of mediating a decrease in the expression, level and/or activity of a PNPLA3 target gene or a gene product thereof via a mechanism mediated by RNaseH, steric hindrance and/or RNA interference.

21. The compound of any one of the preceding embodiments wherein:
each $T^1$ is independently absent or is alkylene, wherein one or more —$CH_2$— groups of the alkylene, may each independently be replaced with a heteroatom group independently selected from —O—, and —N($R^{49}$)— wherein the heteroatom groups are separated by at least 2 carbon atoms;
each $Q^1$ is independently absent or is —C(O), —C(O)—$NR^{49}$, —$NR^{49}$—C(O), or a heteroatom group selected from —O—, and —$NR^{49}$, wherein at least two carbon atoms separate the heteroatom groups —O— and —$NR^{49}$ from any other heteroatom group;
each $R^{49}$ is independently —H, —($C_1$-$C_6$)alkyl, or —($C_3$-$C_6$)cycloalkyl wherein the alkyl and cycloalkyl may be substituted with halo atoms;
each n is independently 0, 1, 2, 3 or 4; wherein if n is greater than 0, each $T^1$ and each $Q^1$ of each ($T^1$-$Q^1$-$T^1$-$Q^1$) is independently selected;
each $R^{46}$ is —$CH_2$—OH;
each $R^{47}$ is —N($R^{48}$)—C(O)—$R^{48}$; and
each $R^{48}$ is independently —H, or —($C_1$-$C_5$)alkyl.

22. A compound having the Formula O2:

$$Y^1\text{-}L^2\text{-}(Z^{11})_{za} \qquad \text{O2}$$

or a pharmaceutically acceptable salt thereof wherein $Y^1$ is an oligonucleotide targets PNPLA3;
za is 1, 2, or 3;
$L^2$ is a linking group; and
$Z^{11}$ is a compound of Formula (B), wherein connection site with $L^2$ is indicated:

(B)

each $R^{47}$ is independently —OH, —N($R^{48}$)$_2$, —N($R^{48}$)—C(O)—$R^{48}$, —N($R^{48}$)—C(O)—N($R^{48}$)$_2$, —N($R^{48}$)—C(O)—O$R^{48}$, —N($R^{48}$)—S(O)$_2$—$R^{48}$, tetrazole, or triazole, wherein the tetrazole and triazole are optionally substituted with $R^{48}$;
each $R^{48}$ is independently —H, —($C_1$-$C_5$)alkyl, halo-substituted —($C_1$-$C_5$)alkyl, halo substituted —($C_3$-$C_6$)cycloalkyl, —($C_1$-$C_5$)alkenyl, —($C_1$-$C_5$)alkynyl, halo substituted —($C_1$-$C_5$)alkenyl, halo substituted —($C_1$-$C_5$)alkynyl, or —($C_3$-$C_6$)cycloalkyl, wherein a —$CH_2$— group of the alkyl or cycloalkyl may each be independently replaced with a heteroatom group selected from —O—, —S—, and —N(R$^{52}$)— and —CH$_3$ of the alkyl may each be independently replaced with a heteroatom group selected from —N(R$^{52}$)$_2$, —OR$^{52}$, and —S(R$^{52}$) wherein the heteroatom groups are separated by at least 2 carbon atoms;

each R$^{49}$ is independently —H, —(C$_1$-C$_{20}$)alkyl, or —(C$_3$-C$_6$)cycloalkyl wherein one to six —CH$_2$— groups of the alkyl or cycloalkyl separated by at least two carbon atoms may be replaced with —O—, —S—, or —N(R$^{49a}$)—, and —CH$_3$ of the alkyl may be replaced with a heteroatom group selected from —N(R$^{49a}$)$_2$, —OR$^{49a}$, and —S(R$^{49a}$) wherein the heteroatom groups are separated by at least 2 carbon atoms; and wherein the alkyl and cycloalkyl may be substituted with halo atoms and wherein each R$^{49a}$ is independently —H, —(C$_1$-C$_6$)alkyl, or —(C$_3$-C$_6$)cycloalkyl;

each R$^{52}$ is independently —H, —(C$_1$-C$_{20}$)alkyl, —(C$_1$-C$_{20}$)alkenyl, —(C$_1$-C$_{20}$)alkynyl, or —(C$_3$-C$_6$)cycloalkyl wherein one to six —CH$_2$— groups of the alkyl or cycloalkyl separated by at least two carbon atoms may each be independently replaced with a heteroatom independently selected from —O—, —S—, or —N(R$^{49}$)—, and —CH$_3$ of the alkyl may each be independently replaced with a heteroatom group selected from —N(R$^{49}$)$_2$, —OR$^{49}$, and —S(R$^{49}$) wherein the heteroatom groups are separated by at least 2 carbon atoms; and wherein the alkyl, alkenyl, alkynyl, and cycloalkyl may be substituted with halo atoms.

23. The compound of any one of the preceding claims, wherein L$^2$ is a compound of Formula L1, L2, L3, L4, L5, L6, L7, L8, L9, L10, L11, L12, L13 or L14, wherein connection sites with Y$^1$ and Z$^{11}$ are indicated:

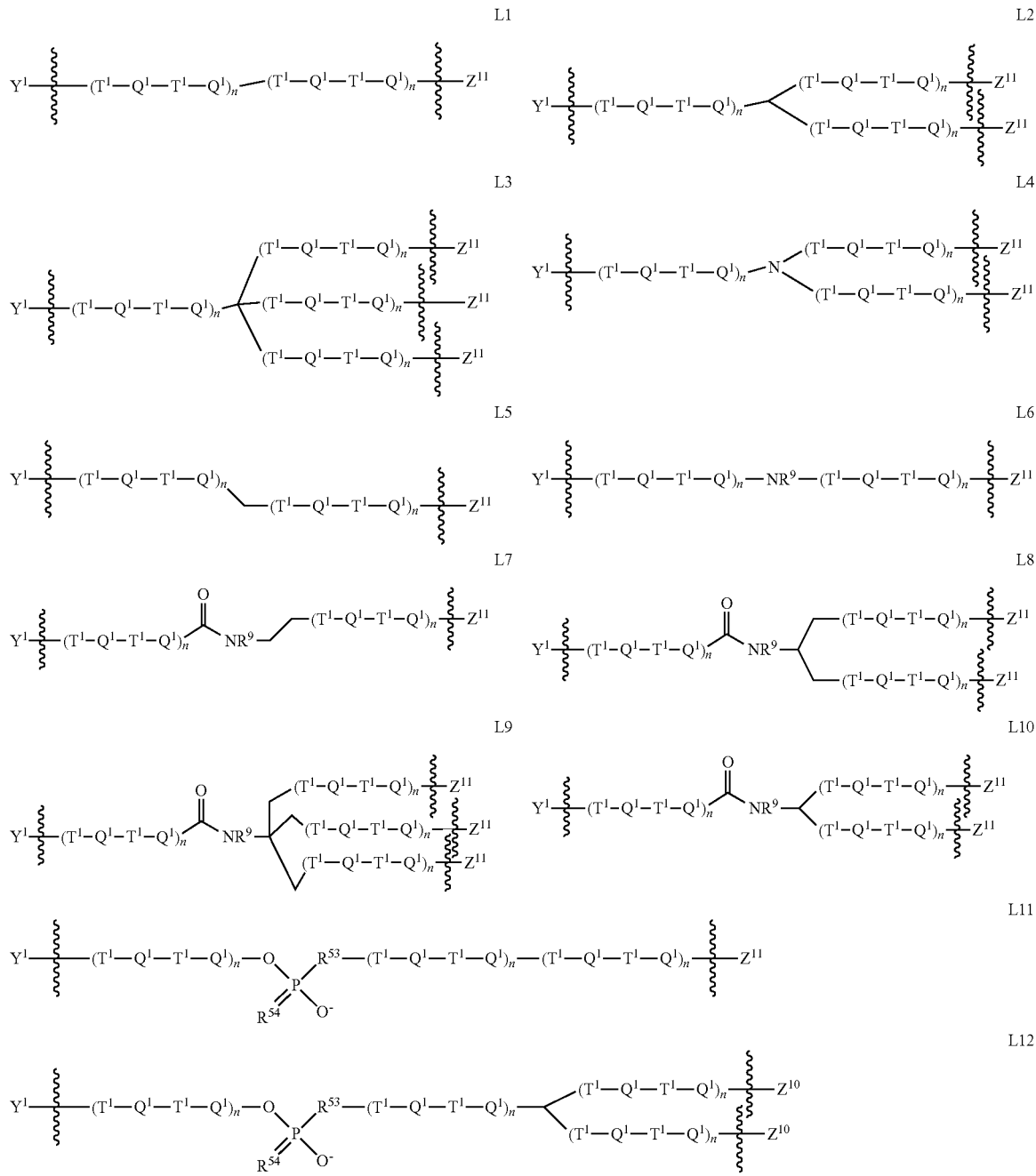

-continued

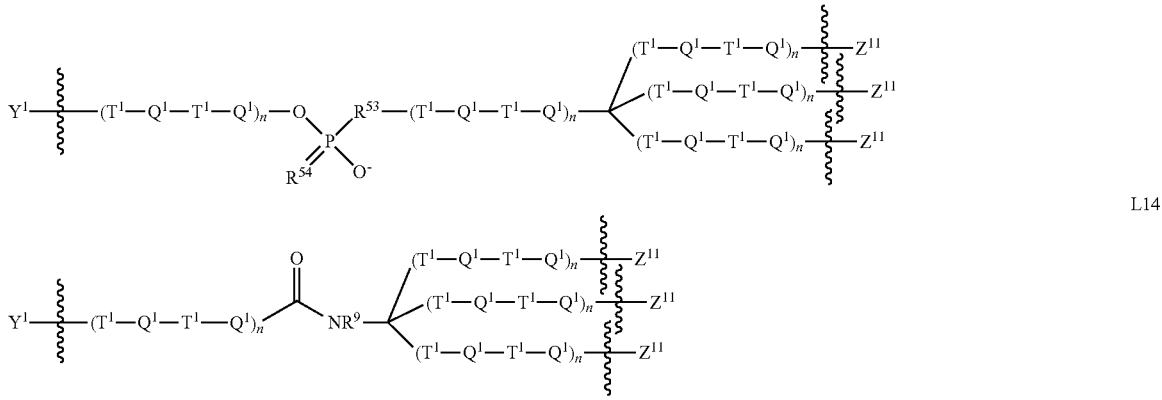

L13

L14 wherein each $T^1$ is independently absent or is alkylene, alkenylene, or alkynylene, wherein one or more —$CH_2$— groups of the alkylene, alkenylene, or alkynylene may each independently be replaced with a heteroatom group independently selected from —O—, —S—, and —N($R^{49}$)— wherein the heteroatom groups are separated by at least 2 carbon atoms;

each $Q^1$ is independently absent or is —C(O)—, —C(O)—$NR^{49}$—, —$NR^{49}$—C(O)—, —O—C(O)—$NR^{49}$—, —$NR^{49}$—C(O)—O—, —$CH_2$—, —$NR^{49}$C(O)$NR^{49}$—, a bivalent heteroaryl group, or a heteroatom group selected from —O—, —S—, —S—S—, —S(O)—, —$S(O)_2$—, and —$NR^{49}$—, wherein at least two carbon atoms separate the heteroatom groups —O—, —S—, —S—S—, —S(O)—, —$S(O)_2$— and —$NR^{49}$— from any other heteroatom group, or a structure of the formula:

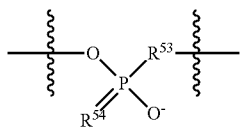

wherein $R^{53}$ is —O or —NH, and $R^{54}$ is —O or —S;

each $R^{49}$ is independently —H, —($C_1$-$C_{20}$)alkyl, or —($C_3$-$C_6$)cycloalkyl wherein one to six —$CH_2$— groups of the alkyl or cycloalkyl separated by at least two carbon atoms may be replaced with —O—, —S—, or —N($R^{49a}$)—, and —$CH_3$ of the alkyl may be replaced with a heteroatom group selected from —N($R^{49a}$)$_2$, —$OR^{49a}$, and —S($R^{49a}$) wherein the heteroatom groups are separated by at least 2 carbon atoms; and wherein the alkyl and cycloalkyl may be substituted with halo atoms; and wherein each $R^{49a}$ is independently —H, —($C_1$-$C_6$)alkyl, or —($C_3$-$C_6$)cycloalkyl;

$R^{53}$ is —O or —NH;
$R^{54}$ is —O or —S; and
each n is independently 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40; wherein if n is greater than 0, each $T^1$ and each $Q^1$ of each ($T^1$-$Q^1$-$T^1$-$Q^1$) is independently selected.

24. The compound of any one of the preceding embodiments, wherein $Y^1$ comprises at least 15 bases.

25. The compound of any one of the preceding embodiments, wherein the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

26. The compound of any one of the preceding embodiments, wherein $Y^1$ comprises at least 1 phosphodiester internucleotidic linkage.

27. The compound of any one of the preceding embodiments, wherein $Y^1$ comprises at least 1 chirally controlled modified internucleotidic linkage.

28. The compound of any one of the preceding embodiments, $Y^1$ comprises at least 1 chirally controlled modified internucleotidic linkage which is a chirally controlled phosphorothioate.

29. The compound of any one of the preceding embodiments, wherein $Y^1$ comprises at least 1 chirally controlled modified internucleotidic linkage which is a chirally controlled phosphorothioate in the Sp configuration.

30. The compound of any one of the preceding embodiments, wherein $Y^1$ comprises at least 1 chirally controlled modified internucleotidic linkage which is a chirally controlled phosphorothioate in the Rp configuration.

31. The compound of any one of the preceding embodiments, wherein $Y^1$, wherein the chirally controlled modified internucleotidic linkage or chirally controlled phosphorothioate comprises a phosphorus chiral center which has a diastereopurity of at least 70% within the composition.

32. The compound of any one of the preceding embodiments, wherein $Y^1$, wherein the chirally controlled modified internucleotidic linkage or chirally controlled phosphorothioate comprises a phosphorus chiral center which has a diastereopurity of at least 70%, 75%, 80%, 85%, 90%, 91%, 92%, 93%, 94%, 95%, 96%, 97%, 98%, 99% or 99.5%.

33. The compound of any one of the preceding embodiments, wherein $Y^1$ comprises at least 1 sugar modification.

34. The compound of any one of the preceding embodiments, wherein $Y^1$ comprises at least 1 base modification.

35. The compound of any one of the preceding embodiments, wherein the pattern of backbone linkages of the oligonucleotide is the pattern of backbone linkages of any oligonucleotide listed in Table 1A.

36. The compound of any one of the preceding embodiments, wherein the pattern of backbone chiral centers of the oligonucleotide is the pattern of backbone chiral centers of any oligonucleotide listed in Table 1A.

37. The compound of any one of the preceding embodiments, wherein the pattern of chemical modifications of the oligonucleotide is the pattern of chemical modifications of any oligonucleotide listed in Table 1A.

38. The compound of any one of the preceding embodiments, wherein the pattern of backbone linkages, the pattern of backbone chiral centers, and/or the pattern of chemical modifications of the oligonucleotide are the pattern of backbone linkages, the pattern of backbone chiral centers, and/or the pattern of chemical modifications of the oligonucleotide of any oligonucleotide listed in Table 1A.

39. The compound of any one of the preceding embodiments, wherein the pattern of backbone linkages, the pattern of backbone chiral centers, and the pattern of chemical modifications of the oligonucleotide are the pattern of backbone linkages, the pattern of backbone chiral centers, and/or the pattern of chemical modifications of the oligonucleotide of any oligonucleotide listed in Table 1A.

40. The compound of any one of the preceding embodiments, wherein the pattern of backbone linkages, the pattern of backbone chiral centers, and the pattern of chemical modifications of the oligonucleotide are the pattern of backbone linkages, the pattern of backbone chiral centers, and/or the pattern of chemical modifications of $Y^1$ is that of an oligonucleotide listed in Table 1A and the base sequence of $Y^1$ comprises or is the base sequence of any PNPLA3 oligonucleotide listed in Table 1A, or the base sequence of $Y^1$ comprises 15 contiguous bases of the sequence of any PNPLA3 oligonucleotide listed in Table 1A.

41. The compound of any one of the preceding embodiments, wherein the oligonucleotide is capable of mediating a decrease in the expression, level and/or activity of a PNPLA3 target gene or a gene product thereof.

42. The compound of any one of the preceding embodiments, wherein the oligonucleotide is capable of mediating a decrease in the expression, level and/or activity of a PNPLA3 target gene or a gene product thereof via a mechanism mediated by RNaseH, steric hindrance and/or RNA interference.

43. The compound of any one of the preceding embodiments wherein:
each $R^{47}$ is —N($R^{48}$)—C(O)—$R^{48}$; and
each $R^{48}$ is independently —H, or —($C_1$-$C_5$)alkyl.

44. The compound of any one of the preceding embodiments wherein:
each $T^1$ is independently absent or is alkylene, wherein one or more —$CH_2$— groups of the alkylene, may each independently be replaced with a heteroatom group independently selected from —O—, and —N($R^{49}$)— wherein the heteroatom groups are separated by at least 2 carbon atoms;
each $Q^1$ is independently absent or is C(O), C(O)—$NR^{49}$, $NR^{49}$—C(O), or a heteroatom group selected from O, and $NR^{49}$, wherein at least two carbon atoms separate the heteroatom groups 0 and $NR^{49}$ from any other heteroatom group;
each $R^{49}$ is independently —H, —($C_1$-$C_6$)alkyl, or —($C_3$-$C_6$)cycloalkyl wherein the alkyl and cycloalkyl may be substituted with halo atoms;
each n is independently 0, 1, 2, 3 or 4; wherein if n is greater than 0, each $T^1$ and each $Q^1$ of each $T^1$-$Q^1$-$T^1$-$Q^1$) is independently selected.

45. A composition comprising a compound comprising: (a) an oligonucleotide capable of targeting PNPLA3; (b) a linking group; and (c) 1, 2, or 3 moieties independently selected from $Z^{10}$ and $Z^{11}$; wherein the linking group links the oligonucleotide and the 1, 2 or 3 moieties, and wherein:
each $Z^{10}$ is independently a compound of Formula Z12, Z13, Z14, Z15, Z16, Z17, Z18, Z19, Z20, or Z21, or a geometrical or position isomer thereof, wherein the connection site with $L^1$ is indicated:

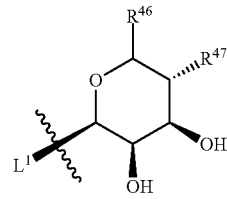

Z12

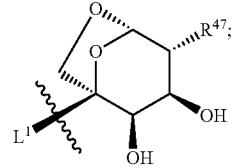

Z13

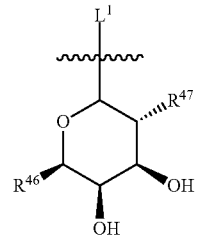

Z16 wherein each $R^{46}$ is independently —CN, —$CH_2$—CN, —C≡CH, —$CH_2$—$N_3$, —$CH_2$—$NH_2$, —$CH_2$—N($R^{52}$)—S(O)$_2$—$R^{51}$, —$CH_2$—$CO_2$H, —$CO_2$H, —$CH_2$—OH, —$CH_2$—SH, —CH=CH—$R^{51}$, —$CH_2$—$R^{51}$, —$CH_2$—S—$R^{51}$, —$CH_2$—N($R^{52}$)—$R^{5'}$, —$CH_2$—N($R^{52}$)—C(O)—$R^{51}$, —$CH_2$—N($R^{52}$)—C(O)—O—$R^{51}$, —$CH_2$—N($R^{52}$)—C(O)—N($R^{52}$)—$R^{51}$, —$CH_2$—O—$R^{51}$, —$CH_2$—O—C(O)—$R^{51}$, —$CH_2$—O—C(O)—N($R^{52}$)—$R^{51}$, —$CH_2$—O—C(O)—O—$R^{51}$, —$CH_2$—S(O)—$R^{51}$, —$CH_2$—S(O)$_2$—$R^{51}$, —$CH_2$—S(O)$_2$—N($R^{52}$)—$R^{51}$, —C(O)—$NH_2$, —C(O)—O—$R^{51}$, —C(O)—N($R^{52}$)—$R^{51}$, or aryl or heteroaryl, wherein the aryl or heteroaryl is optionally substituted with $R^{51}$ each $R^{47}$ is independently —OH, —$N_3$, —N($R^{48}$)$_2$—N($R^{48}$)—C(O)—$R^{48}$, —N($R^{48}$)—C(O)—N($R^{48}$)$_2$, —N($R^{48}$)—C(O)—$OR^{48}$, —N($R^{48}$)—S(O)$_2$—$R^{48}$, tetrazole, or triazole, wherein the tetrazole and triazole are optionally substituted with $R^{48}$;

each $R^{48}$ is independently —H, —($C_1$-$C_5$)alkyl, halo-substituted ($C_1$-$C_5$)alkyl, halo substituted —($C_3$-$C_6$)cycloalkyl, —($C_1$-$C_5$)alkenyl, —($C_1$-$C_5$)alkynyl, halo substituted —($C_1$-$C_5$)alkenyl, halo substituted —($C_1$-$C_5$)alkynyl, or —($C_3$-$C_6$)cycloalkyl, wherein a —$CH_2$— group of the alkyl or cycloalkyl may each be independently replaced with a heteroatom group selected from —O—, —S—, and —N($R^{52}$)— and —$CH_3$ of the alkyl may each be independently replaced with a heteroatom group selected from —N($R^{52}$)$_2$, —$OR^{52}$, and —S($R^{52}$) wherein the heteroatom groups are separated by at least 2 carbon atoms;

each $R^{51}$ is independently —H, —($C_3$-$C_{20}$)cycloalkyl, —($C_1$-$C_{60}$)alkenyl, —($C_1$-$C_{60}$)alkynyl, or —($C_1$-$C_{60}$)alkyl wherein one to six —$CH_2$— groups of the cycloalkyl or one to 20 —$CH_2$— groups of the alkyl may each be independently replaced with heteroatoms independently selected from —O—, —S—, and —N($R^{49}$)— wherein the heteroatoms are separated by at least two carbon atoms, and —$CH_3$ of the alkyl may each be independently replaced with a heteroatom group selected from —N($R^{49}$)$_2$, —O$R^{49}$, and —S($R^{49}$) wherein the heteroatom groups are separated by at least 2 carbon atoms, and wherein the alkyl, alkenyl, alkynyl, and cycloalkyl may be substituted with halo atoms; and each $R^{52}$ is independently —H, —($C_1$-$C_{20}$)alkyl, —($C_1$-$C_{20}$)alkynyl, or —($C_3$-$C_6$)cycloalkyl wherein one to six —$CH_2$— groups of the alkyl or cycloalkyl separated by at least two carbon atoms may each be independently replaced with a heteroatom independently selected from —O—, —S—, or —N($R^{49}$)—, and —$CH_3$ of the alkyl may each be independently replaced with a heteroatom group selected from —N($R^{49}$)$_2$, —O$R^{49}$, and —S($R^{49}$) wherein the heteroatom groups are separated by at least 2 carbon atoms; and wherein the alkyl, alkenyl, alkynyl, and cycloalkyl may be substituted with halo atoms;

each $R^{49}$ is independently —H, —($C_1$-$C_{20}$)alkyl, or —($C_3$-$C_6$)cycloalkyl wherein one to six —$CH_2$— groups of the alkyl or cycloalkyl separated by at least two carbon atoms may be replaced with —O—, —S—, or —N($R^{49a}$)—, and —$CH_3$ of the alkyl may be replaced with a heteroatom group selected from —N($R^{49a}$)$_2$, and —S($R^{49a}$) wherein the heteroatom groups are separated by at least 2 carbon atoms; and wherein the alkyl and cycloalkyl may be substituted with halo atoms and wherein each $R^{49a}$ is independently —H, —($C_1$-$C_6$)alkyl, or —($C_3$-$C_6$)cycloalkyl;

each $R^{49a}$ is independently —H, —($C_1$-$C_6$)alkyl, or —($C_3$-$C_6$)cycloalkyl;

and $Z^{11}$ is a compound of Formula (B), wherein connection site with $L^2$ is indicated:

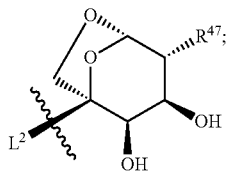

(B)

each $R^{47}$ is independently —OH, —$N_3$, —N($R^{48}$)$_2$, —N($R^{48}$)—C(O)—$R^{48}$, —N($R^{48}$)—C(O)—N($R^{48}$)$_2$, —N($R^{48}$)—C(O)—O$R^{48}$, —N($R^{48}$)—S(O)$_2$—$R^{48}$, tetrazole, or triazole, wherein the tetrazole and triazole are optionally substituted with $R^{48}$;

each $R^{48}$ is independently —H, —($C_1$-$C_5$)alkyl, halo-substituted —($C_1$-$C_5$)alkyl, halo substituted —($C_3$-$C_6$) cycloalkyl, —($C_1$-$C_5$)alkenyl, —($C_1$-$C_5$)alkynyl, halo substituted —($C_1$-$C_5$)alkenyl, halo substituted —($C_1$-$C_5$)alkynyl, or —($C_3$-$C_6$)cycloalkyl, wherein a —$CH_2$— group of the alkyl or cycloalkyl may each be independently replaced with a heteroatom group selected from —O—, —S—, and —N($R^{52}$)— and —$CH_3$ of the alkyl may each be independently replaced with a heteroatom group selected from —N($R^{52}$)$_2$, —O$R^{52}$, and —S($R^{52}$) wherein the heteroatom groups are separated by at least 2 carbon atoms;

each $R^{49}$ is independently —H, —($C_1$-$C_{20}$)alkyl, or —($C_3$-$C_6$)cycloalkyl wherein one to six —$CH_2$— groups of the alkyl or cycloalkyl separated by at least two carbon atoms may be replaced with —O—, —S—, or —N($R^{49a}$)—, and —$CH_3$ of the alkyl may be replaced with a heteroatom group selected from —N($R^{49a}$)$_2$, —O$R^{49a}$, and —S($R^{49a}$) wherein the heteroatom groups are separated by at least 2 carbon atoms; and wherein the alkyl and cycloalkyl may be substituted with halo atoms and wherein each $R^{49a}$ is independently —H, —($C_1$-$C_6$)alkyl, or —($C_3$-$C_6$)cycloalkyl;

each $R^{52}$ is independently —H, —($C_1$-$C_{20}$)alkyl, —($C_1$-$C_{20}$)alkenyl, —($C_1$-$C_{20}$)alkynyl, or —($C_3$-$C_6$)cycloalkyl wherein one to six —$CH_2$— groups of the alkyl or cycloalkyl separated by at least two carbon atoms may each be independently replaced with a heteroatom independently selected from —O—, —S—, or —N($R^{49}$)—, and —$CH_3$ of the alkyl may each be independently replaced with a heteroatom group selected from —N($R^{49}$)$_2$, —O$R^{49}$, and —S($R^{49}$) wherein the heteroatom groups are separated by at least 2 carbon atoms; and wherein the alkyl, alkenyl, alkynyl, and cycloalkyl may be substituted with halo atoms.

47. A chirally controlled PNPLA3 oligonucleotide composition comprising oligonucleotides of a particular oligonucleotide type characterized by:
a) a common base sequence and length, wherein the base sequence is complementary to a PNPLA3 target gene;
b) a common pattern of backbone linkages;
c) a common pattern of backbone chiral centers, wherein the common pattern of backbone chiral centers comprises at least one internucleotidic linkage comprising a chirally controlled chiral center;
which composition is chirally controlled in that it is enriched, relative to a substantially racemic preparation of oligonucleotides having the same common base sequence and length, for oligonucleotides of the particular oligonucleotide type; and
wherein the oligonucleotide composition is capable of decreasing the expression, level and/or activity of a PNPLA3 target gene or a gene product thereof.

48. The compound of any one of the preceding embodiments, wherein the oligonucleotides are capable of capable of decreasing the expression, level and/or activity of a PNPLA3 target gene or a gene product thereof via a mechanism mediated by RNaseH, steric hindrance and/or RNA interference.

49. A composition comprising a compound of any one of the preceding embodiments.

50. A composition comprising an PNPLA3 oligonucleotide which is a single-stranded RNAi agent, wherein the single-stranded RNAi agent is complementary or substantially complementary to a PNPLA3 target RNA sequence,
has a length of about 15 to about 49 nucleotides, and
is capable of directing target-specific RNA interference,
wherein the single-stranded RNAi agent comprises at least one non-natural base, sugar, and/or internucleotidic linkage, and
wherein the composition is capable of decreasing the expression, level and/or activity of a PNPLA3 target gene or a gene product thereof.

51. The composition of any one of the preceding embodiments, wherein the oligonucleotide or oligonucleotides further comprise a bridged bicyclic ketal 52. The composition of any one of the preceding embodiments, wherein $R^{CD}$ is

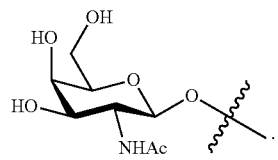

53. The composition of any one of the preceding embodiments, wherein $R^{CD}$ is
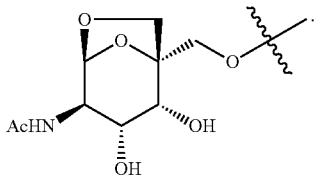 [SMILES: *OC[C@@]12CO[C@@H](O1)[C@H](NC(C)=O)[C@@H](O)[C@H]2O]
54. The composition of any one of the preceding embodiments, wherein $R^{CD}$ is of such a structure that $R^{CD}$—H is
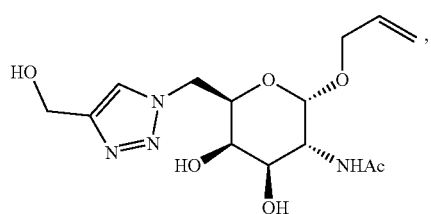
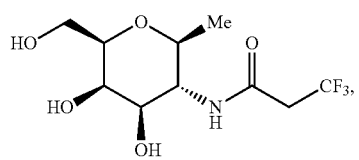
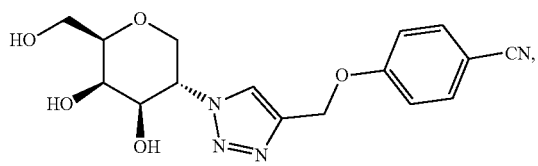
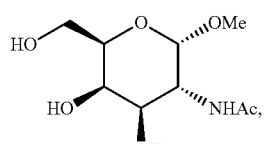
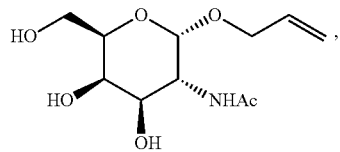
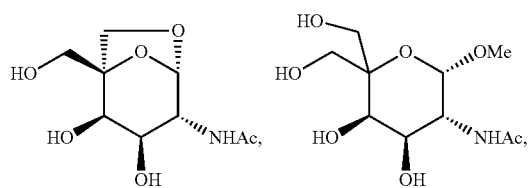
-continued
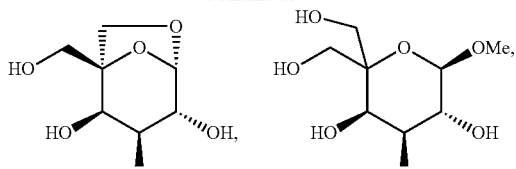
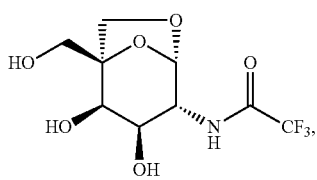
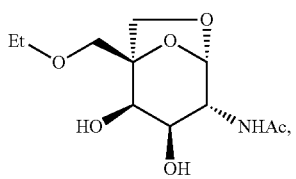
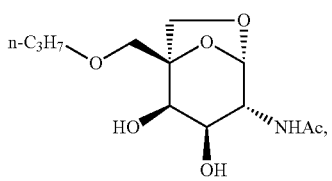
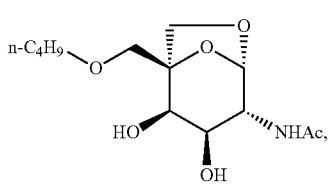
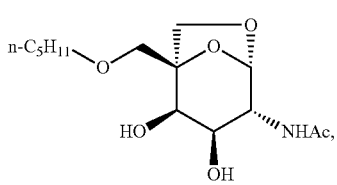
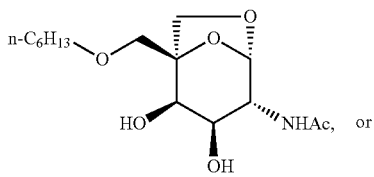 or -continued
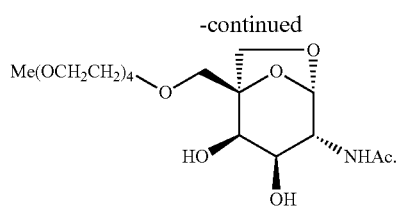
55. The composition of any one of the preceding embodiments, wherein $R^{CD}$ is connected to the oligonucleotide or oligonucleotides through a linker.
56. The composition of any one of the preceding embodiments, wherein the linker is $L^M$.
57. The composition of any one of the preceding embodiments, wherein the linker has the structure of
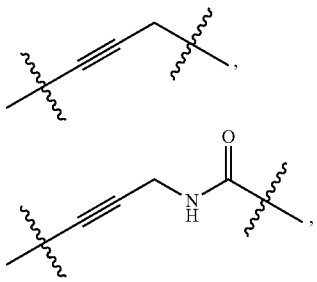
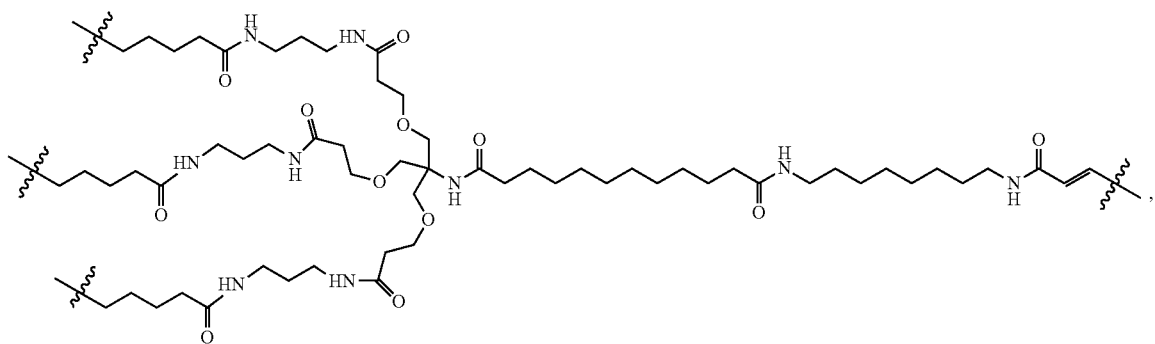
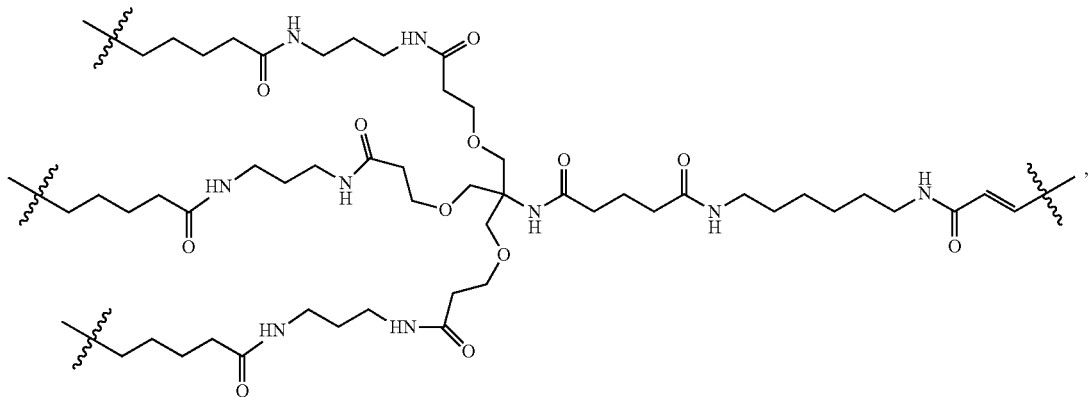
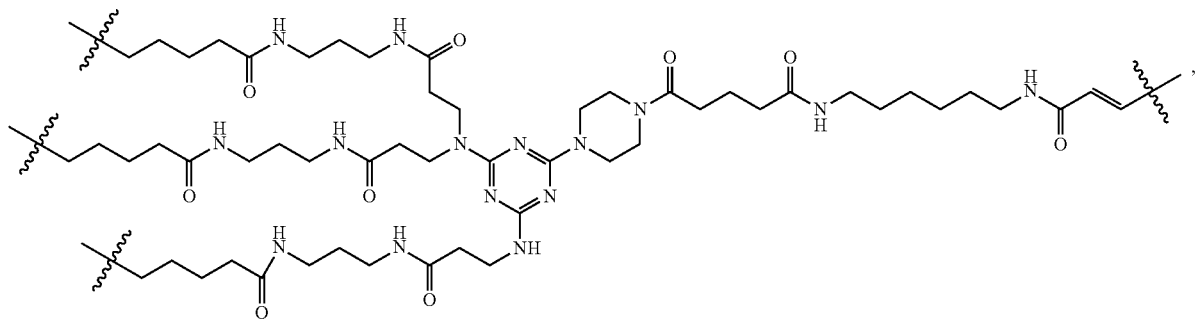

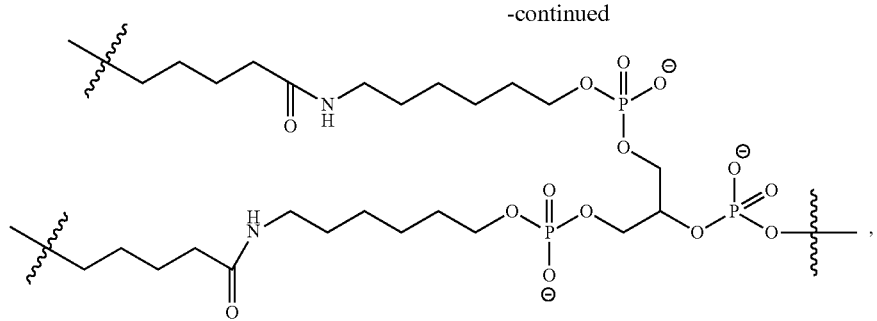
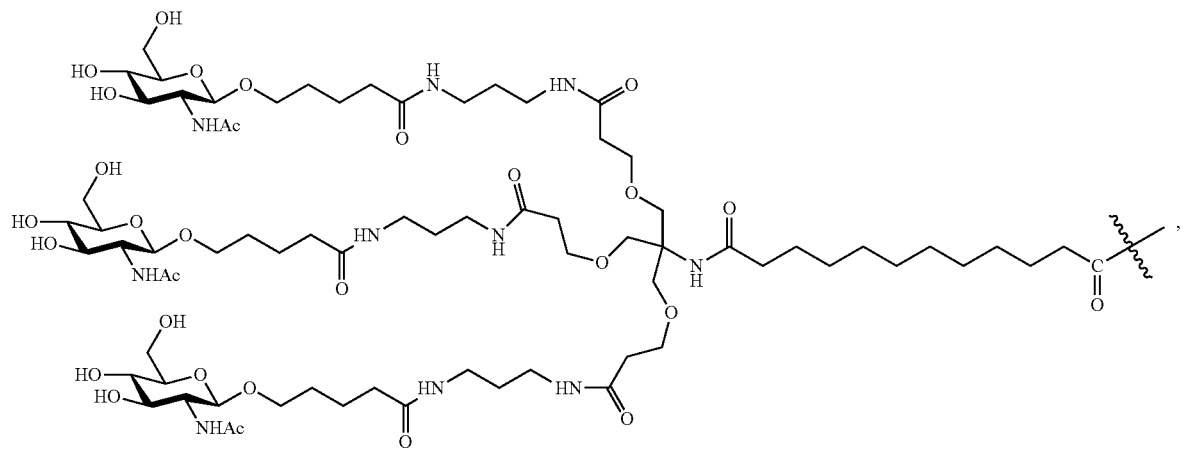
58. The composition of any one of the preceding embodiments, wherein $R^{CD}$ is selected from:

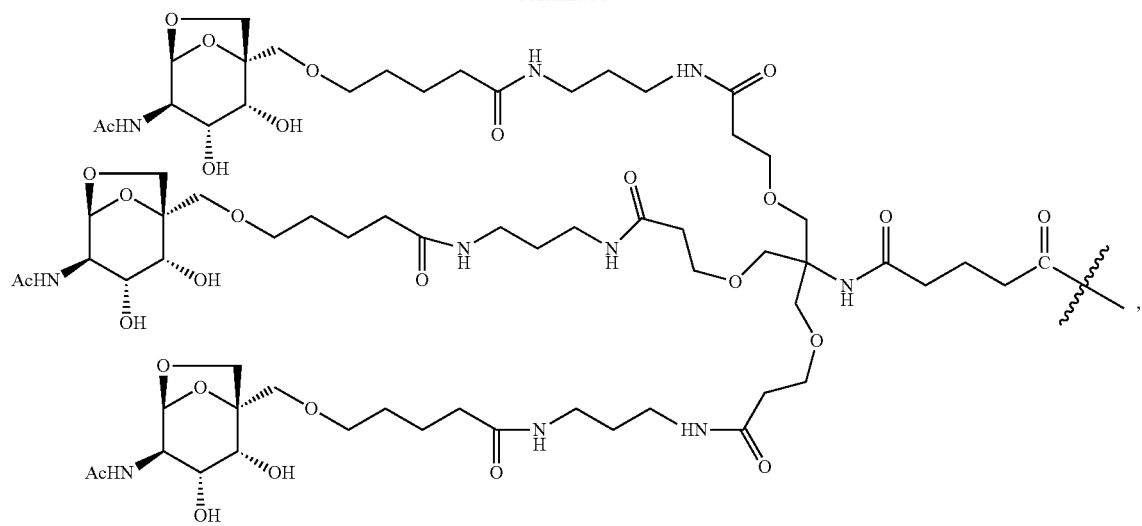
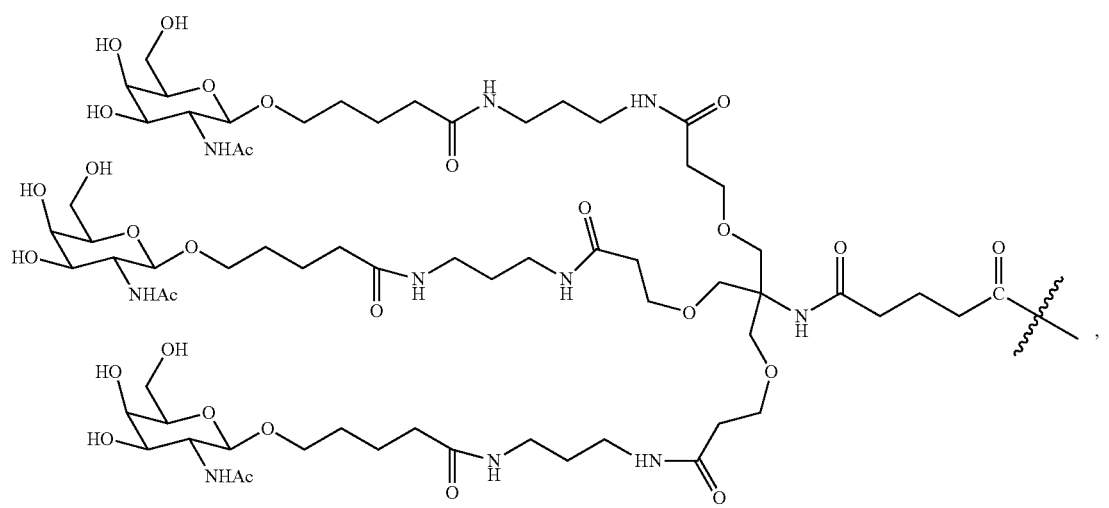
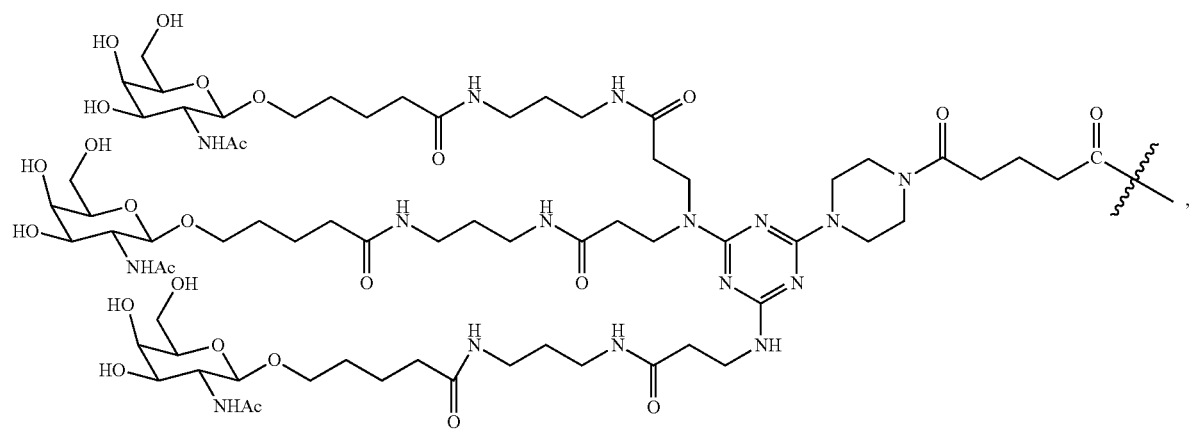

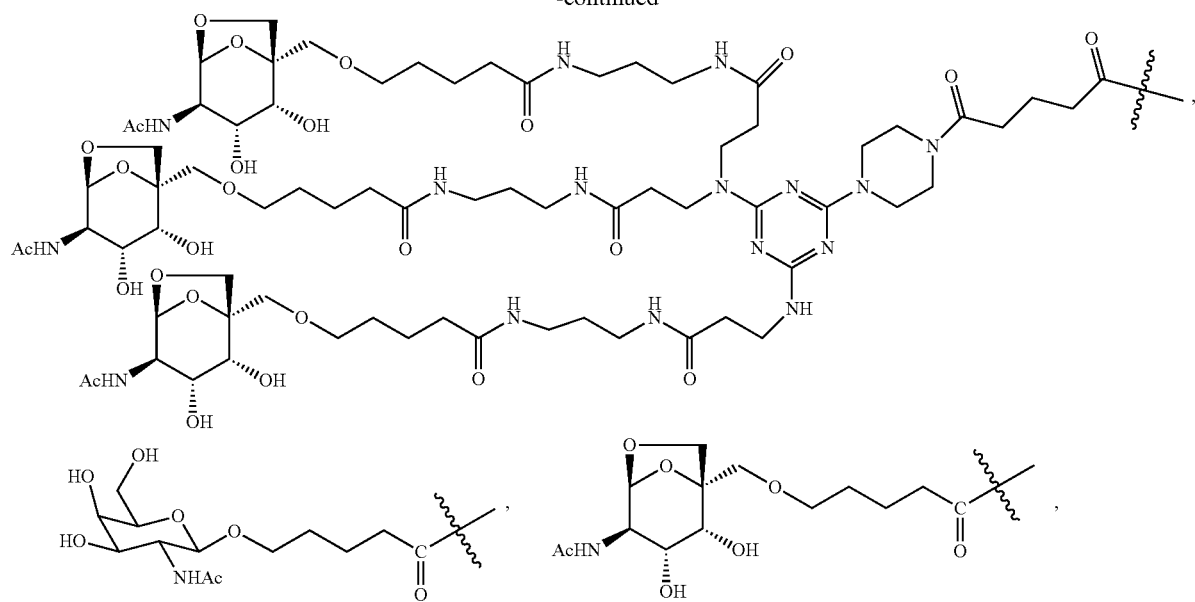
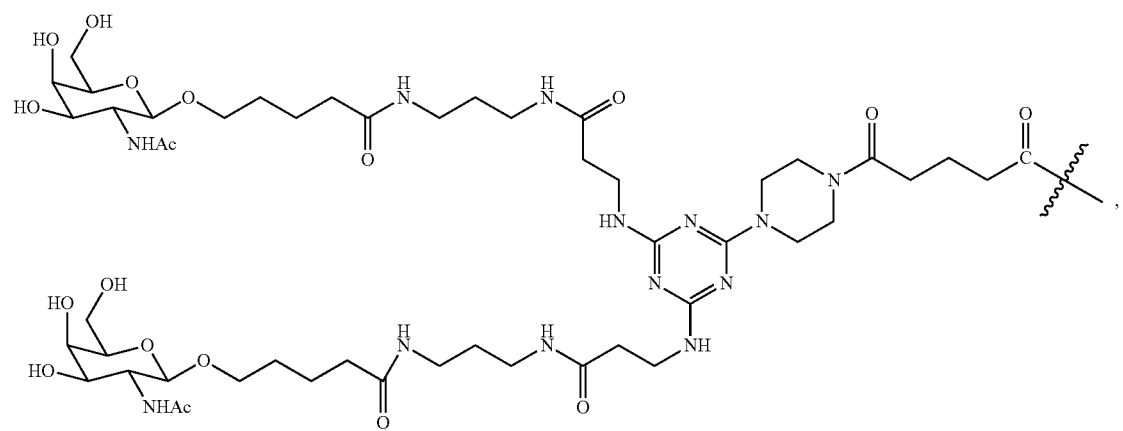
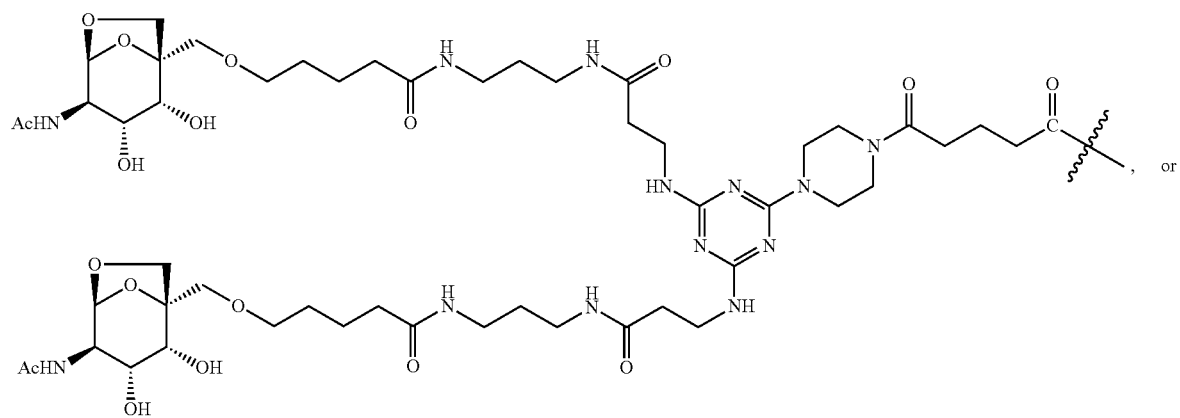

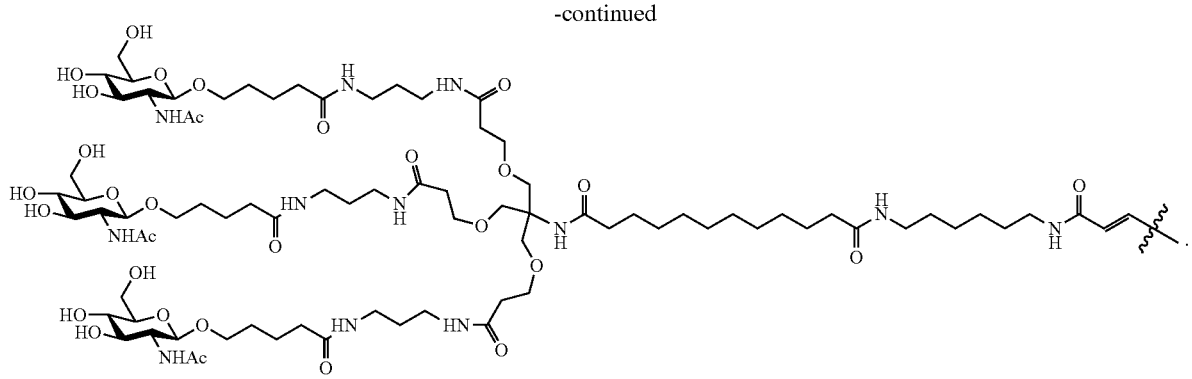

60. A pharmaceutical composition comprising a composition of any one of the preceding embodiments in a therapeutically effective amount, in admixture with at least one pharmaceutically acceptable excipient.

61. The composition of any one of the preceding embodiments further comprising at least one additional pharmaceutical agent selected from the group consisting of an anti-inflammatory agent, an anti-diabetic agent, and a cholesterol/lipid modulating agent.

62. The composition of any one of the preceding embodiments wherein said additional pharmaceutical agent is selected from the group consisting of an acetyl-CoA carboxylase-(ACC) inhibitor, a diacylglycerol O-acyltransferase 1 (DGAT-1) inhibitor, a diacylglycerol O-acyltransferase 2 (DGAT-2) inhibitor, monoacylglycerol O-acyltransferase inhibitors, a phosphodiesterase (PDE)-10 inhibitor, an AMPK activator, a sulfonylurea, a meglitinide, an α-amylase inhibitor, an α-glucoside hydrolase inhibitor, an α-glucosidase inhibitor, a PPARγ agonist, a PPAR α/γ agonist, a biguanide, a glucagon-like peptide 1 (GLP-1) modulator, liraglutide, albiglutide, exenatide, albiglutide, lixisenatide, dulaglutide, semaglutide, a protein tyrosine phosphatase-1B (PTP-1B) inhibitor, SIRT-1 activator, a dipeptidyl peptidase IV (DPP-IV) inhibitor, an insulin secreatagogue, a fatty acid oxidation inhibitor, an A2 antagonist, a c-jun amino-terminal kinase (JNK) inhibitor, glucokinase activators (GKa), insulin, an insulin mimetic, a glycogen phosphorylase inhibitor, a VPAC2 receptor agonist, SGLT2 inhibitors, a glucagon receptor modulator, GPR119 modulators, FGF21 derivatives or analogs, TGR5 receptor modulators, GPBAR1 receptor modulators, GPR40 agonists, GPR120 modulators, high affinity nicotinic acid receptor (HM74A) activators, SGLT1 inhibitors, inhibitors or modulators of carnitine palmitoyl transferase enzymes, inhibitors of fructose 1,6-diphosphatase, inhibitors of aldose reductase, mineralocorticoid receptor inhibitors, inhibitors of TORC2, inhibitors of CCR2 and/or CCR5, inhibitors of PKC isoforms (e.g. PKCα, PKCβ, PKCγ), inhibitors of fatty acid synthetase, inhibitors of serine palmitoyl transferase, modulators of GPR81, GPR39, GPR43, GPR41, GPR105, Kv1.3, retinol binding protein 4, glucocorticoid receptor, somatostatin receptors, inhibitors or modulators of PDHK2 or PDHK4, inhibitors of MAP4K4, modulators of IL1 family including IL1beta, HMG-CoA reductase inhibitors, squalene synthetase inhibitors, fibrates, bile acid sequestrants, ACAT inhibitors, MTP inhibitors, lipooxygenase inhibitors, cholesterol absorption inhibitors, PCSK9 modulators, cholesteryl ester transfer protein inhibitors and modulators of RXRalpha.

63. The composition of any one of the preceding embodiments further comprising at least one additional pharmaceutical agent selected from the group consisting of cystamine or a pharmaceutically acceptable salt thereof, cystamine or a pharmaceutically acceptable salt thereof, an anti-oxidant compound, lecithin, vitamin B complex, a bile salt preparations, an antagonists of Cannabinoid-1 (CB1) receptor, an inverse agonists of Cannabinoid-1 (CB1) receptor, a peroxisome proliferator-activated receptor) activity regulators, a benzothiazepine or benzothiepine compound, an RNA antisense construct to inhibit protein tyrosine phosphatase PTPRU, a heteroatom-linked substituted piperidine and derivatives thereof, an azacyclopentane derivative capable of inhibiting stearoyl-coenzyme alpha delta-9 desaturase, acylamide compound having secretagogue or inducer activity of adiponectin, a quaternary ammonium compound, Glatiramer acetate, pentraxin proteins, a HMG-CoA reductase inhibitor, n-acetyl cysteine, isoflavone compound, a macrolide antibiotic, a galectin inhibitor, an antibody, or any combination of thereof.

64. A method for the reduction of at least one point in severity of nonalcoholic fatty liver disease or nonalcoholic steatohepatitis grading scoring systems, reduction of the level of serum markers of nonalcoholic steatohepatitis activity, reduction of nonalcoholic steatohepatitis disease activity or reduction in the medical consequences of nonalcoholic steatohepatitis in humans comprising the step of administering to a human in need of such reduction a therapeutically effective amount of a composition of any one of the preceding embodiments to a patient in need thereof.

65. A method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma in humans comprising the step of administering to a human in need of such treatment a therapeutically effective amount of a composition of any one of the preceding embodiments to a patient in need thereof.

66. A method for treating hyperlipidemia, Type I diabetes, Type II diabetes mellitus, idiopathic Type I diabetes (Type Ib), latent autoimmune diabetes in adults (LADA), early-onset Type 2 diabetes (EOD), youth-onset atypical diabetes (YOAD), maturity onset diabetes of the young (MODY), malnutrition-related diabetes, gestational diabetes, coronary heart disease, ischemic stroke, restenosis after angioplasty, peripheral vascular disease, intermittent claudication, myocardial infarction, dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, transient ischemic attacks, stroke, vascular restenosis, hyperglycemia, hyperinsulinemia, hypertriglyceridemia, insulin resistance, impaired glucose metabolism, erectile dysfunction, skin and connective tissue disorders, foot ulcerations and ulcerative colitis, endothelial dysfunction and impaired vascular compliance, hyper apo B lipoproteinemia, Alzheimer's, schizophrenia, impaired cognition, inflammatory bowel disease, ulcerative colitis, Crohn's disease, and irritable bowel syndrome, non-alcoholic steatohepatitis (NASH), or non-alcoholic fatty liver disease (NAFLD), in humans comprising the step of administering to a human in need of such treatment a therapeutically effective amount of a composition of any one of the preceding embodiments to a patient in need thereof.

67. A method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma in humans comprising the step of administering to a human in need of such treatment a therapeutically effective amount of two separate pharmaceutical compositions comprising a. a first composition of any one of the preceding embodiments; and c. a second composition comprising at least one additional pharmaceutical agent selected from the group consisting of an anti-inflammatory agent, an anti-diabetic agent, and a cholesterol/lipid modulating agent and at least one pharmaceutically acceptable excipient.

68. The method any one of the preceding embodiments wherein said first composition and said second composition are administered simultaneously.

69. The method any one of the preceding embodiments wherein said first composition and said second composition are administered sequentially and in any order.

70. A method for reducing portal hypertension, hepatic protein synthetic capability, hyperbilirubinemia, or encephalopathy in humans comprising the step of administering to a human in need of such treatment a therapeutically effective amount of a composition of any one of the preceding embodiments to a patient in need thereof.

71. A method of decreasing the expression, activity and/or level of a PNPLA3 target gene or a gene product thereof in a cell, comprising the step of contacting the cell with a compound or composition of any one of the preceding embodiments.

72. A method of decreasing the expression, activity and/or level of a PNPLA3 target gene or a gene product thereof in a patient, comprising the step of contacting the cell with a compound or composition of any one of the preceding embodiments.

The invention claimed is:

1. A composition comprising oligonucleotides of a particular oligonucleotide type characterized by:
   a) a common base sequence;
   b) a common pattern of backbone linkages;
   c) a common pattern of backbone chiral centers;
   wherein the oligonucleotide comprises at least one internucleotidic linkage comprising a linkage phosphorus in the Sp configuration;
   wherein the composition is chirally controlled in that it is enriched, relative to a substantially racemic preparation of oligonucleotides having the same common base sequence, for oligonucleotides of the particular oligonucleotide type;
   wherein the oligonucleotide targets PNPLA3; and
   wherein the common base sequence has over 50% identity with TACUGUAGAAAGGCAUGAATU (SEQ ID NO: 153), wherein each U can be optionally and independently replaced with T.

2. The composition of claim 1, wherein oligonucleotides of the plurality share:
   the same linkage phosphorus stereochemistry independently at five or more chiral internucleotidic linkages ("chirally controlled internucleotidic linkages");
   wherein at least about 10% of all oligonucleotides in the composition that share the common base sequence are oligonucleotides of the plurality; and
   wherein the common base sequence is complementary to a portion of the base sequence of an PNPLA3 transcript, wherein the portion comprises 15 or more nucleobases.

3. The composition of claim 2, wherein oligonucleotides of the plurality share the same linkage phosphorus stereochemistry independently at five or more chiral internucleotidic linkages, and about 50%-100% of all oligonucleotides in the composition that share the common base sequence are oligonucleotides of the plurality.

4. The composition of claim 2, wherein oligonucleotides of the plurality share the same linkage phosphorus stereochemistry independently at each phosphorothioate internucleotidic linkage.

5. The composition of claim 2, wherein oligonucleotides of the plurality are of the same constitution.

6. The composition of claim 4, wherein the composition is a liquid composition.

7. The composition of claim 2, wherein oligonucleotides of the plurality each independently comprise a targeting moiety ($R^{CD}$).

8. The composition of claim 7, wherein $R^{CD}$ is

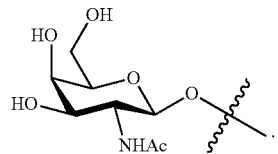

9. The composition of claim 7, wherein $R^{CD}$ is connected to the oligonucleotide or oligonucleotides through a linker.

10. The composition of claim 9, wherein the linker has the structure of

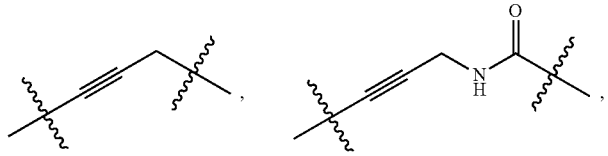

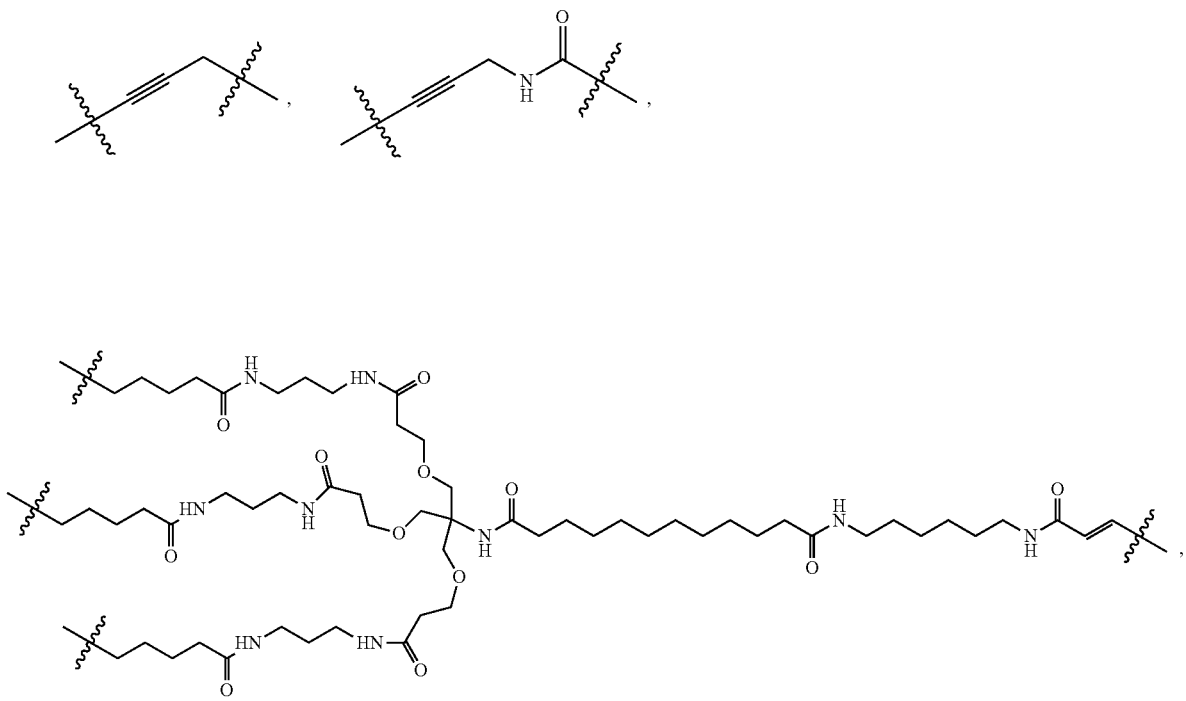

1211
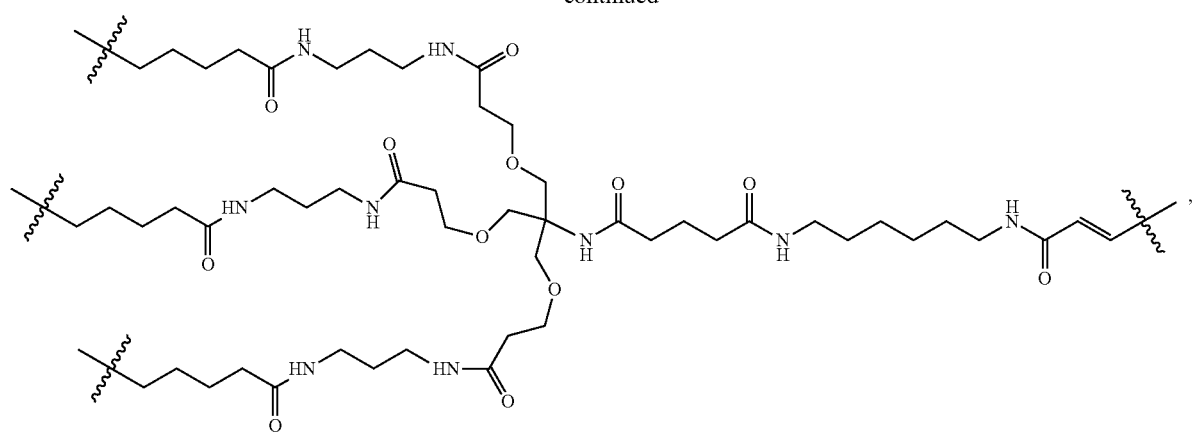
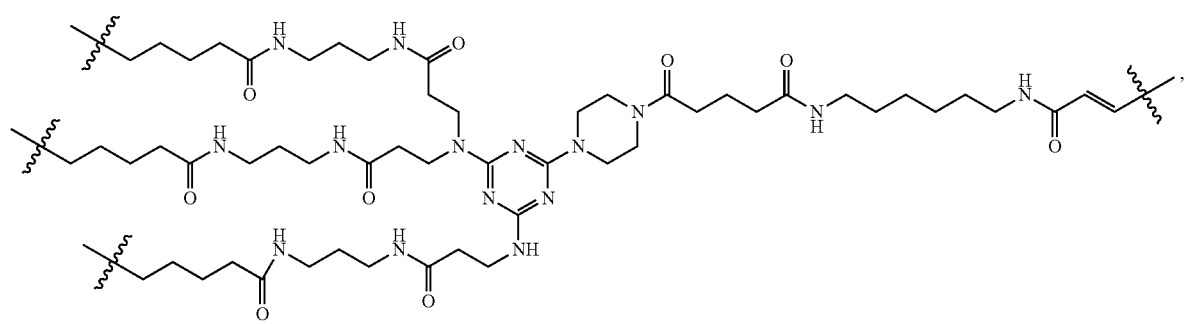
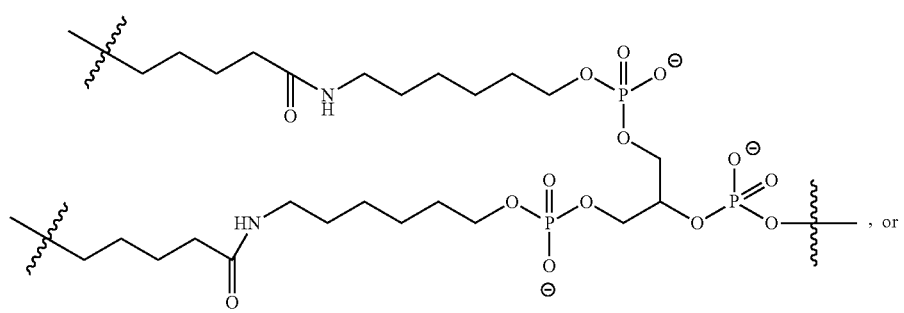
, or
1212
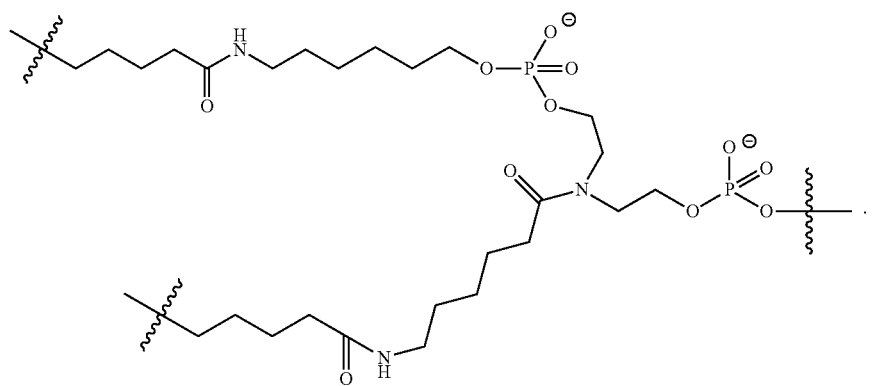 [SMILES: *CCCCC(=O)NCCCCCCOP(=O)([O-])OCCN(CCOP(=O)([O-])O*)C(=O)CCCCCNC(=O)CCCC*]
.

11. The composition of claim 7, wherein $R^{CD}$ is selected from:
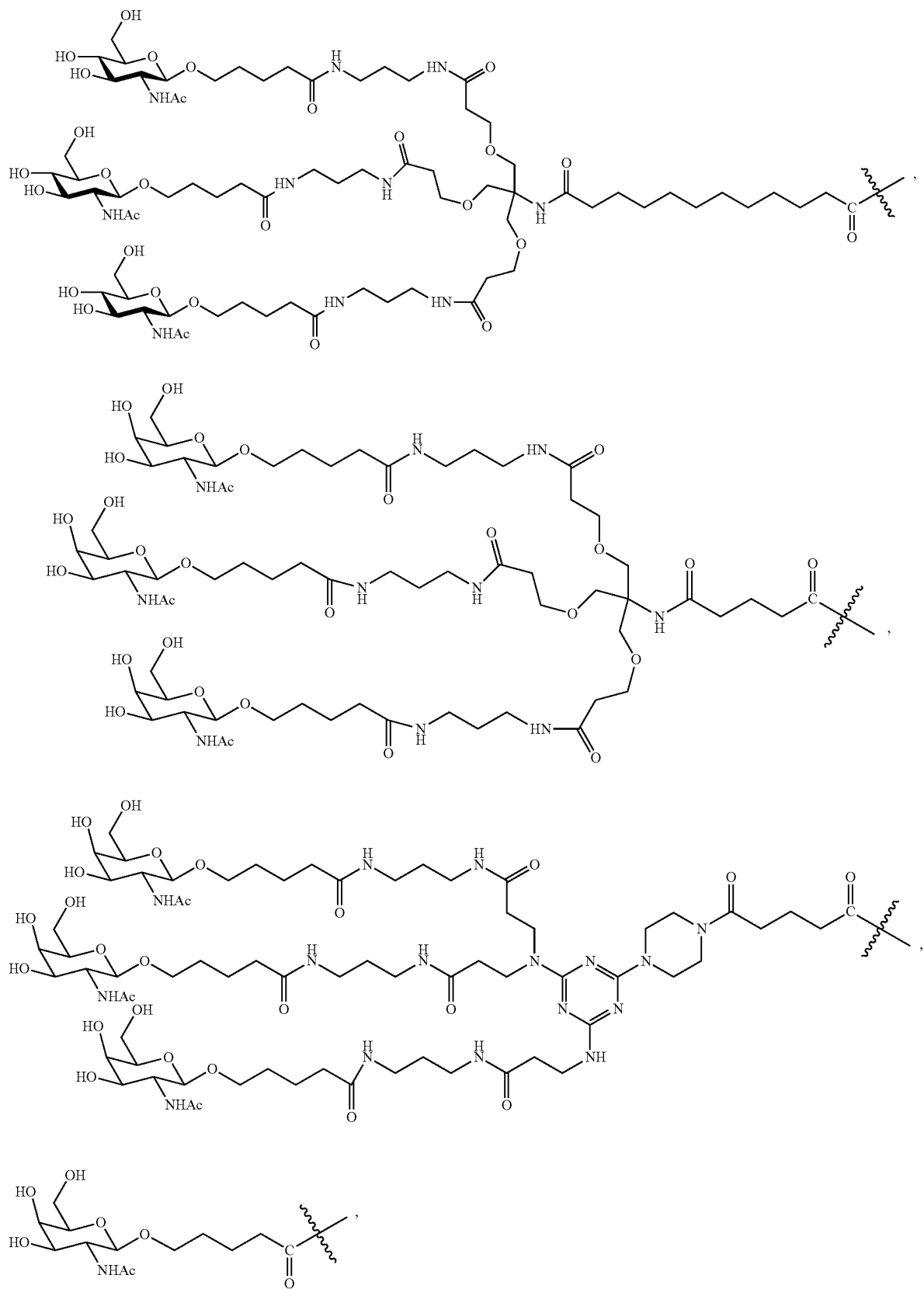

-continued

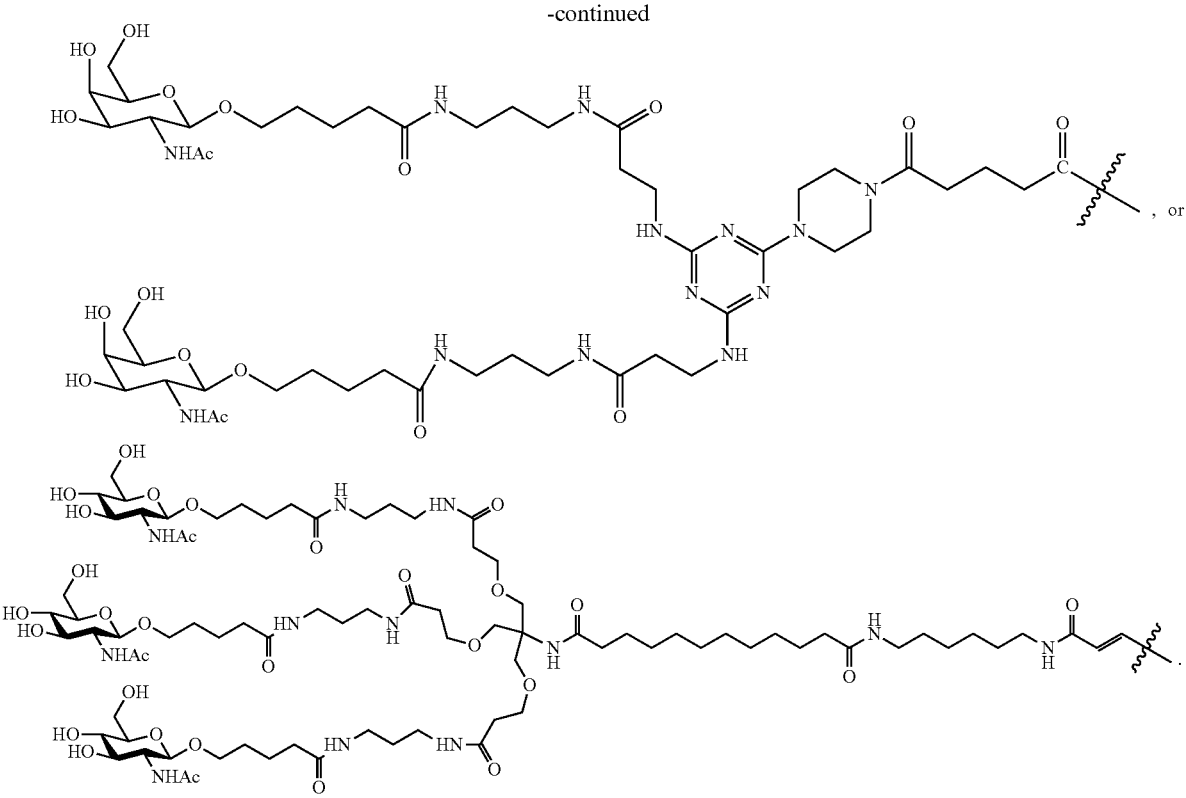

12. A method for treating fatty liver, nonalcoholic fatty liver disease, nonalcoholic steatohepatitis, nonalcoholic steatohepatitis with liver fibrosis, nonalcoholic steatohepatitis with cirrhosis, or nonalcoholic steatohepatitis with cirrhosis and hepatocellular carcinoma in humans comprising the step of administering to a human in need of such treatment a therapeutically effective amount of a composition of claim 2.

13. The composition of claim 1, wherein the common base sequence has over 60% identity with TACUGUA-GAAAGGCAUGAAUU (SEQ ID NO: 153), wherein each U can be optionally and independently be replaced with T.

14. The composition of claim 1, wherein the common base sequence has over 70% identity with TACUGUA-GAAAGGCAUGAAUU (SEQ ID NO: 153), wherein each U can be optionally and independently replaced with T.

15. The composition of claim 1, wherein the common base sequence has over 80% identity with TACUGUA-GAAAGGCAUGAAUU (SEQ ID NO: 153), wherein each U can be optionally and independently replaced with T.

* * * * *